United States Patent
Alcazar et al.

(10) Patent No.: US 11,802,111 B2
(45) Date of Patent: Oct. 31, 2023

(54) CYCLOBUTYL AMIDE MONOACYLGLYCEROL LIPASE MODULATORS

(71) Applicant: Janssen Pharmaceutica NV, Beerse (BE)

(72) Inventors: Jesus Alcazar, Toledo (ES); Michael K. Ameriks, San Diego, CA (US); Cynthia B. Berry, Poway, CA (US); Pablo Garcia-Reynaga, San Diego, CA (US); Brian Ngo Laforteza, San Diego, CA (US); Andrew V. Samant, Cardiff, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/480,493

(22) Filed: Sep. 21, 2021

(65) Prior Publication Data

US 2022/0089538 A1    Mar. 24, 2022

Related U.S. Application Data

(60) Provisional application No. 63/081,475, filed on Sep. 22, 2020.

(51) Int. Cl.
| | |
|---|---|
| *C07D 205/12* | (2006.01) |
| *C07D 401/04* | (2006.01) |
| *C07D 401/10* | (2006.01) |
| *C07D 403/04* | (2006.01) |
| *C07D 471/04* | (2006.01) |

(52) U.S. Cl.
CPC ......... *C07D 205/12* (2013.01); *C07D 401/04* (2013.01); *C07D 401/10* (2013.01); *C07D 403/04* (2013.01); *C07D 471/04* (2013.01)

(58) Field of Classification Search
CPC .. C07D 205/12; C07D 401/04; C07D 401/10; C07D 403/04; C07D 471/04
See application file for complete search history.

(56) References Cited

U.S. PATENT DOCUMENTS

2019/0152917 A1    5/2019    Malamas et al.

FOREIGN PATENT DOCUMENTS

| WO | 2018134695 A1 | 7/2018 |
|---|---|---|
| WO | 2018134698 A1 | 7/2018 |

OTHER PUBLICATIONS

Ahn et al., "Enzymatic Pathways That Regulate Endocannabinoid Signaling in the Nervous System", Chem Rev., 2008, p. 1687-1707, vol. 108, No. 5.
Alhouayek et al., "Increasing endogenous 2-arachidonoylglycerol levels counteracts colitis and related systemic inflammation", FASEB J., Aug. 2011, 2711-2721, vol. 25, No. 8.
Bedse et al., "Functional Redundancy Between Canonical Endocannabinoid Signaling Systems in the Modulation of Anxiety", Biol Psychiatry, Oct. 1, 2017, 488-499, vol. 82, No. 7.
Bedse et al., "Therapeutic endocannabinoid augmentation for mood and anxiety disorders: comparative profiling of FAAH, MAGL and dual inhibitors", Transl Psychiatry, Apr. 26, 2018, 92, vol. 8, No. 1.
Benito et al., "Cannabinoid CB2 Receptors in Human Brain Inflammation", British Journal of Pharmacology, 2008, 277-285, vol. 153.
Berge, S.M. et al., "Pharmaceutical Salts", J. Pharm. Sci., 1977, pp. 1-19, vol. 66 Issue 1.
Bernal-Chico et al., "Blockade of monoacylglycerol lipase inhibits oligodendrocyte excitotoxicity and prevents demyelination in vivo", Glia, Jan. 2015, 163-176, vol. 63, No. 1.
Buczynski and Parsons, "Quantification of brain endocannabinoid levels: methods, interpretations and pitfalls", Brit J Pharmacol, 2010, 423-442, vol. 160, No. 3.
Cavuoto et al., "The Expression of Receptors for Endocannabinoids in Human and Rodent Skeletal Muscle", Biochemical and Biophysical Research Communications, 2007, 105-110, vol. 364.
Chen et al., "Monoacylglycerol Lipase Is a Therapeutic Target for Alzheimer's Disease", Cell Rep., Nov. 29, 2012, 1329-1339, vol. 2, No. 5.
Chinnadurai et al, "Monoacylglycerol lipase inhibition as potential treatment for interstitial cystitis", Medical Hypotheses, Oct. 2019, 109321, vol. 131.
Christensen et al., "Efficacy and safety of the weight-loss drug rimonabant: a meta-analysis of randomised trials", The Lancet, 2007, 1706-1713, vol. 370.
Covey et al., "Inhibition of endocannabinoid degradation rectifies motivational and dopaminergic deficits in the Q175 mouse model of Huntington's disease", Neuropsychopharmacology, 2018, 2056-2063, vol. 43.

(Continued)

*Primary Examiner* — Rebecca L Anderson

(57) ABSTRACT

Compounds of Formula (I), and pharmaceutically acceptable salts, isotopes, N-oxides, solvates, and stereoisomers thereof, pharmaceutical compositions containing them, methods of making them, and methods of using them including methods for treating disease states, disorders, and conditions associated with MGL modulation, such as those associated with pain, psychiatric disorders, neurological disorders (including, but not limited to depression, major depressive disorder, treatment resistant depression, anxious depression, autism spectrum disorders, Asperger syndrome, and bipolar disorder), cancers and eye conditions:

(I)

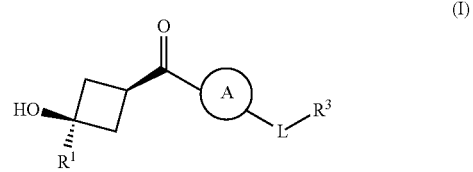

wherein $R^1$, Ⓐ, $R^3$, and L are as defined herein.

23 Claims, No Drawings

(56) References Cited

OTHER PUBLICATIONS

Curry et al., "Monoacylglycerol Lipase Inhibitors Reverse Paclitaxel-Induced Nociceptive Behavior and Proinflammatory Markers in a Mouse Model of Chemotherapy-Induced Neuropathy", J Pharmacol Exp Ther., Jul. 2018, 169-183, vol. 366, No. 1.

Devane et al., "Isolation and structure of a brain constituent that binds to the cannabinoid receptor", Science, 1992, 1946-1949, vol. 258.

Di Marzo et al., "Endocannabinoids and the regulation of their levels in health and disease", Curr Opin Lipidol, 2007, 129-140, vol. 18.

Di Marzo et al., "Plant, Synthetic, and Endogenous Cannabinoids in Medicine", Annu Rev Med., 2006, 553-574., vol. 57.

Dinh et al., "Brain monoglyceride lipase participating in endocannabinoid inactivation", Proc Natl Acad Sci USA, Aug. 6, 2002, 10819-10824, vol. 99, No. 16.

Folkes et al., "An endocannabinoid-regulated basolateral amygdala-nucleus accumbens circuit modulates sociability", J Clin Invest., 2020, 1728-1742., vol. 130, Issue 4.

Ghosh et al., "The monoacylglycerol lipase inhibitor JZL184 suppresses inflammatory pain in the mouse carrageenan model", Life Sci., Mar. 19, 2013, 498-505, vol. 92, No. 8-9.

Guindon et al., "Peripheral antinociceptive effects of inhibitors of monoacylglycerol lipase in a rat model of inflammatory pain", Br J Pharmacol., 2011, 1464-1478, vol. 163.

Hajrasouliha et al., "Endogenous cannabinoids contribute to remote ischemic preconditioning via cannabinoid CB2 receptors in the rat heart", Eur J Pharmacol, 2008, 246-252, vol. 579.

Hauer et al., "Glucocorticoid-endocannabinoid interaction in cardiac surgical patients: relationship to early cognitive dysfunction and late depression", Rev Neurosci., 2012, 681-690, vol. 23, No. 5-6.

Herkenam et al., "Cannabinoid receptor localization in brain", Proc. Nat. Acad. Sci., 1990, 1932-1936, vol. 87, No. 5.

Hernandez-Torres et al., "A Reversible and Selective Inhibitor of Monoacylglycerol Lipase Ameliorates Multiple Sclerosis", Angew Chem Int Ed Engl., Dec. 8, 2014, 13765-13770, vol. 53, No. 50.

Hill et al., "Circulating endocannabinoids and N-acyl ethanolamines are differentially regulated in major depression and following exposure to social stress", Psychoneuroendocrinology, Sep. 3, 2009, 1257-1262, vol. 34, No. 8.

Hill et al., "Reductions in circulating endocannabinoid levels in individuals with post-traumatic stress disorder following exposure to the World Trade Center attacks", Psychoneuroendocrinology, 2013, 2952-2961, vol. 38, No. 12.

Hill et al., "Serum Endocannabinoid Content is Altered in Females with Depressive Disorders: A Preliminary Report", Pharmacopsychiatry, Mar. 2008, 48-53, vol. 41, No. 2.

International Search Report and Written Opinion of PCT Application No. PCT/EP2021/075959 dated Dec. 23, 2021.

Jung et al., "Uncoupling of the endocannabinoid signalling complex in a mouse model of fragile X syndrome", Nature Communications, 2012, 1080., vol. 3.

Katz et al., "Endocannabinoid Degradation Inhibition Improves Neurobehavioral Function, Blood-Brain Barrier Integrity, and Neuroinflammation following Mild Traumatic Brain Injury", J Neurotrauma, Mar. 1, 2015, 297-306, vol. 32, Issue 5.

Kinsey et al., "Blockade of Endocannabinoid-Degrading Enzymes Attenuates Neuropathic Pain", J Pharmacol Exp Ther., Sep. 2009, 902-910, vol. 330, No. 3.

Ligresti et al., "From endocannabinoid profiling to 'endocannabinoid therapeutics'", Curr Opin Chem Biol., Jun. 2009, 321-331, vol. 13, No. 3.

Long et al., "Characterization of Monoacylglycerol Lipase Inhibition Reveals Differences in Central and Peripheral Endocannabinoid Metabolism", Chem Biol., Jul. 31, 2009, 744-753, vol. 16, No. 7.

Long et al., "Selective blockade of 2-arachidonoylglycerol hydrolysis produces cannabinoid behavioral effects", Nat Chem Biol., Jan. 2009, 37-44, vol. 5, No. 1.

Matsuda et al., "Structure of a cannabinoid recepter and functional expresion of the cloned cDNA", Nature, 1990, 561-564, vol. 346.

Mechoulam et al., "Identification of an endogenous 2-monoglyceride, present in canine gut, that binds to cannabinoid receptors", Biochem Pharmacol, 1995, 83-90, vol. 50.

Miller et al., "Controlled-deactivation cb1 receptor ligands as a novel strategy to lower intraocular pressure", Pharmaceuticals, 2018, 1-8, vol. 11, No. 50.

Mulvihill et al., "Therapeutic potential of monoacylglycerol lipase inhibitors", Life Sci., Mar. 19, 2013, 492-497, vol. 92, No. 8-9.

Munro et al., "Molecular characterization of a peripheral receptor for cannabinoids", Nature, 1993, 61-65, vol. 365.

Nithipatikom et al., "2-Arachidonoylglycerol: a novel inhibitor of androgen-independent prostate cancer cell invasion", Cancer Res., Dec. 15, 2004, 8826-8830, vol. 64, No. 24.

Nithipatikom et al., "A new class of inhibitors of 2-arachidonoylglycerol hydrolysis and invasion of prostate cancer cells", Biochem Biophys Res Commun., Jul. 15, 2005, 1028-1033, vol. 332, No. 4.

Nithipatikom et al., "Anti-proliferative effect of a putative endocannabinoid, 2-arachidonylglyceryl ether in prostate carcinoma cells", Prostaglandins Other Lipid Mediat., Feb. 9, 2011, 34-43, vol. 94, No. 1-2.

Nomura et al., "Endocannabinoid Hydrolysis Generates Brain Prostaglandins That Promote Neuroinflammation", Science, Nov. 11, 2011, 809-813, vol. 334, No. 6057.

Pacher et al., "Pleiotropic effects of the CB2 cannabinoid receptor activation on human monocyte migration implications for atherosclerosis and inflammatory diseases", Amer J Physiol, 2008, H1133-H1134, vol. 294.

Pasquarelli et al., "Contrasting effects of selective MAGL and FAAH inhibition on dopamine depletion and GDNF expression in a chronic MPTP mouse model of Parkinson's disease", Neurochem Int., Nov. 2017, 14-24, vol. 110.

Pasquarelli et al., "Evaluation of monoacylglycerol lipase as a therapeutic target in a transgenic mouse model of ALS", Neuropharmacology, Sep. 15, 2017, 157-169, vol. 124.

Patel et al., "The endocannabinoid system as a target for novel anxiolytic drugs", Neurosci Biobehav Rev., May 2017, 56-66, vol. 76, Part A.

Piomelli, "The molecular logic of endocannabinoid signalling", Nat Rev Neurosci, 2003, 873-884, vol. 4.

Piro et al., "A Dysregulated Endocannabinoid-Eicosanoid Network Supports Pathogenesis in a Mouse Model of Alzheimer's Disease", Cell Rep., Jun. 28, 2012, 617-623, vol. 1, No. 6.

Ramesh et al., "Blockade of Endocannabinoid Hydrolytic Enzymes Attenuates Precipitated Opioid Withdrawal Symptoms in Mice", J Pharmacol Exp Ther., Oct. 2011, 173-185, vol. 339, No. 1.

Schlosburg et al., "Chronic monoacylglycerol lipase blockade causes functional antagonism of the endocannabinoid system", Nat Neurosci., Sep. 13, 2010, 1113-1119, vol. 9.

Sticht et al., "Inhibition of monoacylglycerol lipase attenuates vomiting in Suncus murinus and 2-arachidonoyl glycerol attenuates nausea in rats", Br J Pharmacol., Apr. 2012, 2425-2435, vol. 165, No. 8.

Straiker et al., "Monoacylglycerol Lipase Limits the Duration of Endocannabinoid-Mediated Depolarization-Induced Suppression of Excitation in Autaptic Hippocampal Neurons", Mol Pharmacol., Dec. 2009, 1220-1227, vol. 76, No. 6.

Sugiura et al., "2-Arachidonoylgylcerol: A Possible Endogenous Cannabinoid Receptor Ligand in Brain", Biochem Biophys Res Commun, 1995, 89-97, vol. 215.

Sugiura et al., "Biosynthesis and degradation of anandamide and 2-arachidonoylglycerol and their possible physiological significance", Prostaglandins Leukot Essent Fatty Acid, Feb.-Mar. 2002, 173-192, vol. 66, No. 2-3.

Suguira et al., "Biochemistry, pharmacology and physiology of 2-arachidonoylglycerol, an endogenous cannabinoid receptor ligand", Prog Lipid Res, 2006, 405-446, vol. 45, No. 5.

(56) References Cited

OTHER PUBLICATIONS

Terrone et al., "Inhibition of monoacylglycerol lipase terminates diazepam-resistant status epilepticus in mice and its effects are potentiated by a ketogenic diet", Epilepsia, Jan. 2018, 79-91, vol. 59, No. 1.

Tuo et al., "Therapeutic Potential of Fatty Acid Amide Hydrolase, Monoacylglycerol Lipase, and N-Acylethanolamine Acid Amidase Inhibitors", J Med Chem., Jan. 12, 2017, 4-46, vol. 60, No. 1.

Von Ruden et al., "Inhibition of monoacylglycerol lipase mediates a cannabinoid 1-receptor dependent delay of kindling progression in mice", Neurobiol Dis., May 2015, 238-245, vol. 77.

Walter et al., "ATP Induces a Rapid and Pronounced Increase in 2-Arachidonoylglycerol Production by Astrocytes, a Response Limited by Monoacylglycerol Lipase", J Neurosci., Sep. 15, 2004, 8068-8074, vol. 24, No. 37.

Wang et al., "Treating a novel plasticity defect rescues episodic memory in Fragile X model mice", Mol Psychialry, 2018, 1798-1806, vol. 23, No. 8.

Wenzel et al., "Novel multi-target directed ligand-based strategies for reducing neuroinflammation in Alzheimer's disease", Life Sci., Aug. 15, 2018, 314-322, vol. 207.

Wilkerson et al., "The Selective Monoacylglycerol Lipase Inhibitor MJN110 Produces Opioid-Sparing Effects in a Mouse Neuropathic Pain Model", J Pharmacol Exp Ther., Apr. 2016, 145-156, vol. 357, No. 1.

Wilson et al., "A high-throughput-compatible assay for determining the activity of fatty acid amide hydrolase", Anal Biochem., Jul. 15, 2003, 270-275, vol. 318, No. 2.

Yi et al., "Reductions in circulating endocannabinoid 2-arachidonoylglycerol levels in healthy human subjects exposed to chronic stressors", Progress in Neuro-Psychopharmacology and Biological Psychiatry, 2016, 92-97, vol. 67, No. 3.

Zhang et al., "Inhibition of monoacylglycerol lipase prevents chronic traumatic encephalopathy-like neuropathology in a mouse model of repetitive mild closed head injury", J Cereb Blood Flow Metab., Mar. 31, 2015, 706, vol. 35, Issue No. 4.

CYCLOBUTYL AMIDE MONOACYLGLYCEROL LIPASE MODULATORS

CROSS-REFERENCE TO RELATED APPLICATIONS

This application claims priority to U.S. Provisional Application No. 63/081,475, filed Sep. 22, 2020, which is incorporated herein by reference in its entirety.

FIELD OF THE INVENTION

The present disclosure is related to certain chemical entities having MGL modulating properties, pharmaceutical compositions comprising these chemical entities, chemical processes for preparing these chemical entities and their use in the treatment of diseases, disorders, or conditions.

BACKGROUND OF THE INVENTION

*Cannabis sativa* and analogs of $\Delta^9$-tetrahydrocannabinol have been used since the days of folk medicine for therapeutic purposes. The endocannabinoid system consists of two G-protein coupled receptors, cannabinoid receptor type 1 (CB1) (Matsuda et al., *Nature*, 1990, 346, 561-4) and cannabinoid receptor type 2 (CB2) (Munro et al., *Nature*, 1993, 365, 61-5). CB1 receptor is one of the most abundant G-protein coupled receptor expressed in the brain (Herkenam et al., *Proc. Nat. Acad. Sci.*, 1990, 87 (5), 1932-1936). CB1 is also expressed peripherally in the liver, gastrointestinal tract, pancreas, adipose tissue, and skeletal muscles (Di Marzo et al., *Curr. Opin. Lipidol.*, 2007, 18, 129-140). CB2 is predominantly expressed in immune cells such as monocytes (Pacher et al., *Amer. J. Physiol.*, 2008, 294, H1133-H1134) and under certain conditions (inflammation) in the brain (Benito et al., *Brit. J. Pharmacol.*, 2008, 153, 277-285) and in skeletal (Cavuoto et al., *Biochem. Biophys. Res. Commun.*, 2007, 364, 105-110) and cardiac muscles (Hajrasouliha et al., *Eur. J. Pharmacol.*, 2008, 579, 246-252).

In 1992, N-arachidonoylethanolamine (AEA or anandamide) was found to be an endogenous ligand for cannabinoid receptors (Devane et al., *Science*, 1992, 258, 1946-9). Subsequently, 2-arachidonoylglycerol (2-AG) was also identified as an additional endogenous ligand for the cannabinoid receptors (Mechoulam et al., *Biochem. Pharmacol.*, 1995, 50, 83-90; Sugiura et al., *Biochem. Biophys. Res. Commun.*, 1995, 215, 89-97). Concentrations of 2-AG were reported to be at least 100 times higher than these of anandamide in the rat brain (Buczynski and Parsons, *Brit. J. Pharmacol.*, 2010, 160 (3), 423-42). Therefore 2-AG may play more essential physiological roles than anandamide in the brain endocannabinoid system (Sugiura et al. *Prostaglandins Leukot. Essent. Fatty Acids*, 2002, February-March, 66(2-3):173-92). The endocannabinoid 2-AG is a full agonist for CB1 and CB2 receptors, while anandamide is a partial agonist for both receptors (Suguira et al., *Prog. Lipid Res.*, 2006, 45(5):405-46). Unlike many classical neurotransmitters, endocannabinoids signal through a retrograde mechanism. They are synthesized on demand in postsynaptic neurons and then rapidly degraded following binding to presynaptic cannabinoid receptors (Ahn et al., *Chem. Rev.* 2008, 108(5):1687-707). Monoacylglycerol lipase (MGLL, also known as MAG lipase and MGL) is the serine hydrolase responsible for the degradation of 2-AG into arachidonic acid and glycerol in the central nervous system (Mechoulam et al., *Biochem. Pharmacol.*, 1995, 50, 83-90; Sugiura et al., *Biochem. Biophys. Res. Commun.*, 1995, 215, 89-97; Long et al., *Nat. Chem. Biol.*, 2009, 5(1):37-44; Schlosburg et al., *Nat. Neurosci.*, 2010, 13(9): 1113-9) and peripheral tissues (Long et al., *Chem. Biol.*, 2009, 16(7):744-53). Anandamide is hydrolyzed by fatty acid amide hydrolase (FAAH) (Piomelli, *Nat. Rev. Neurosci.*, 2003, 4, 873-884). MGL exists in both soluble and membrane bound forms (Dinh et al., *Proc. Natl. Acad. Sci. USA*, 2002, 99(16):10819-24). In the brain MGL is located in presynaptic neurons (Straiker et al., *Mol. Pharmacol.*, 2009, 76(6):1220-7) and astrocytes (Walter et al., *J. Neurosci.*, 2004, 24(37):8068-74) within regions associated with high CB1 receptor density. Compared to wild-type controls, genetic ablation of MGL expression produces 10-fold increase in brain 2-AG levels without affecting anandamide concentration (Schlosburg et al., *Nat. Neurosci.*, 2010, 13(9):1113-9).

Thus, MGL modulation offers an interesting strategy for potentiating the cannabinoid system. The primary advantage of this approach is that only brain regions where endocannabinoids are actively produced will be modulated, potentially minimizing the side effects associated with exogenous CB1 agonists. Pharmacological inactivation of MGL by covalent inhibitors in animals increase 2-AG content in brain and peripheral tissues and has been found to produce antinociceptive, anxiolytic and anti-inflammatory effects that are dependent on CB1 and/or CB2 receptors (Long et al., *Nat. Chem. Biol.*, 2009, 5(1):37-44; Ghosh et al., *Life Sci.*, 2013, 92(8-9):498-505; Bedse et al., *Biol. Psychiatry*, 2017, 82(7):488-499; Bernal-Chico et al., *Glia*, 2015, 63(1): 163-76; Patel et al., *Neurosci. Biobehav. Rev.*, 2017, 76(Pt A):56-66; Bedse et al., *Transl. Psychiatry*, 2018, 8(1):92). In addition to the role of MGL in terminating 2-AG signaling, MGL modulation, including MGL inhibition also promotes CB1/2-independent effects on neuroinflammation (Nomura et al., *Science*, 2011, 334(6057):809-13). MGL modulation, including MGL inhibition leads to reduction in proinflammatory prostanoid signaling in animal models of traumatic brain injury (Katz et al., *J. Neurotrauma*, 2015, 32(5):297-306; Zhang et al., *J. Cereb. Blood Flow Metab.*, 2015, 35(4):443-453), neurodegeneration including Alzheimer's disease (Piro et al., *Cell Rep.*, 2012, 1(6):617-23; Wenzel et al., *Life Sci.*, 2018, 207:314-322; Chen et al., *Cell Rep.*, 2012, 2(5):1329-39), Parkinson's disease (Nomura et al., *Science*, 2011, 334(6057), 809-13; Pasquarelli et al., *Neurochem. Int.*, 2017, 110:14-24), amyotrophic lateral sclerosis (Pasquarelli et al., *Neuropharmacology*, 2017, 124:157-169), multiple sclerosis (Hernadez-Torres et al., *Angew. Chem. Int. Ed. Engl.*, 2014, 53(50):13765-70; Bernal-Chico et al., *Glia*, 2015, 63(1):163-76), Huntington's disease (Covey et al., *Neuropsychopharmacology*, 2018, 43, 2056-2063), Tourette syndrome and status epilepticus (Terrone et al., *Epilepsia*, 2018, 59(1), 79-91; von Ruden et al., *Neurobiol. Dis.*, 2015, 77:238-45).

Therefore, by potentiating the cannabinoid system and attenuating proinflammatory cascades, MGL modulation, including MGL inhibition offers a compelling therapeutic approach for the treatment of a vast array of complex diseases. Importantly, MGL modulation, including MGL inhibition in animals does not produces the full spectrum of neurobehavioral effects observed with $\Delta^9$-tetrahydrocannabinol and other CB1 agonists (Tuo et al., *J. Med. Chem.*, 2017, 60(1), 4-46; Mulvihill et al., *Life Sci.*, 2013, 92(8-9), 492-7).

Endocannabinoid hypoactivity is a risk factor for the treatment of depression, anxiety, and post-traumatic stress disorders. Millennia of human use of *Cannabis sativa*, and a brief period in which humans were treated with the endocannabinoid antagonist, rimonabant, provide support for that hypothesis. 2-AG levels are decreased in individuals with major depression (Hill et al., *Pharmacopsychiatry*, 2008, 41(2): 48-53; Hill et al., *Psychoneuroendocrinology*, 2009, 34(8): 1257-1262). Low circulating 2-AG levels predict rates of depression (Hauer et al., *Rev. Neurosci.*, 2012, 23(5-6):681-90). Reduced circulating 2-AG has been found in patient with post-traumatic stress disorder (PTSD) (Hill et al., *Psychoneuroendocrinology*, 2013, 38 (12), 2952-2961). Healthy volunteers exposed to chronic stressors exhibited progressively diminished circulating 2-AG levels which correlated with the onset of reductions in measures of positive emotions (Yi et al., *Prog. Neuropsychopharmacol. Biol. Psychiatry*, 2016, 67 (3), 92-97). The CB1 receptor inverse agonist/antagonist Rimonabant has been withdrawn from the market due to the high incidence of severe depression and suicidal ideation (Christensen et al., *The Lancet*, 2007, 370, 1706-1713). Therefore, MGL modulators are potentially useful for the treatment of mood disorders, anxiety, PTSD, autism spectrum disorders, and Asperger syndrome (Folkes et al., *J Clin Invest.* 2020, 130(4):1728-1742, Jung et al., *Nat. Commun.*, 2012, 3, 1080; Wang et al., *Mol. Psychiatry*, 2018, 23(8): 1798-1806).

Cannabinoid receptor agonists are clinically used to treat pain, spasticity, emesis, and anorexia (Di Marzo, et al., *Annu. Rev. Med.*, 2006, 57:553-74; Ligresti et al., *Curr. Opin. Chem. Biol.*, 2009, 13(3):321-31). Therefore, MGL modulators, including MGL inhibitors are also potentially useful for these indications. MGL exerts CB1-dependant antinociceptive effects in animal models of noxious chemical, inflammatory, thermal, and neuropathic pain (Guindon et al., *Br. J. Pharmacol.*, 2011, 163(7):1464-78; Kinsey et al., *J. Pharmacol. Exp. Ther.*, 2009, 330(3):902-10; Long et al., *Nat. Chem. Biol.*, 2009, 5(1):37-44). MGL blockade reduces mechanical and acetone induced cold allodynia in mice subjected to chronic constriction injury of the sciatic nerve (Kinsey et al., *J. Pharmacol. Exp. Ther.*, 2009, 330 (3):902-10). MGL inhibition produces opiate-sparing events with diminished tolerance, constipation, and cannabimimetic side effects (Wilkerson et al., *J. Pharmacol. Exp. Ther.*, 2016, 357(1):145-56). MGL blockade is protective in model of inflammatory bowel disease (Alhouayek et al., *FASEB J.*, 2011, 25(8):2711-21). MGL inhibition also reverse paclitaxel-induced nociceptive behavior and proinflammatory markers in a mouse model of chemotherapy-induced neuropathy (Curry et al., *J. Pharmacol. Exp. Ther.*, 2018, 366(1):169-18). MGL inhibitors are also potentially useful for the treatment of chronic inflammatory condition of the urinary bladder like interstitial cystitis (Chinnadurai et al., *Med. Hypotheses* 2019, 131:109321).

Inhibition of 2-AG hydrolysis exerts anti-proliferative activity and reduction in prostate cancer cell invasiveness (Nithipatikom et al., *Cancer Res.*, 2004, 64(24):8826-30; Nithipatikom et al., *Biochem. Biophys. Res. Commun.*, 2005, 332(4):1028-33; Nithipatikom et al., *Prostaglandins Other Lipid Mediat.*, 2011, 94(1-2):34-43). MGL is upregulated in aggressive human cancer cells and primary tumors where it has a unique role of providing lipolytic sources of free fatty acids for synthesis of oncogenic signaling lipids that promote cancer aggressiveness. Thus, beyond the physiological roles of MGL in mediated endocannabinoid signaling, MGL in cancer plays a distinct role in modulating the fatty acid precursor pools for synthesis of protumorigenic signaling lipids in malignant human cancer cells.

MGL blockade shows anti-emetic and anti-nausea effects in a lithium chloride model of vomiting in shrews (Sticht et al., *Br. J. Pharmacol.*, 2012, 165(8):2425-35).

MGL modulators, including MGL inhibitors may have utility in modulating drug dependence of opiates. MGL blockade reduce the intensity of naloxone-precipitated morphine withdrawal symptoms in mice. MGL blockade also attenuated spontaneous withdrawal signs in morphine-dependent mice (Ramesh et al., *J. Pharmacol. Exp. Ther.*, 2011, 339(1):173-85).

MGL modulators are also potentially useful for the treatment of eye conditions, including but not limited to, glaucoma and disease states arising from elevated intraocular pressure (Miller et al., *Pharmaceuticals*, 2018, 11, 50).

SUMMARY OF THE INVENTION

Embodiments of the present disclosure relate to chemical entities, pharmaceutical compositions containing them, methods of making and purifying them, and methods for using them the treatment of diseases, disorders, and conditions associated with the MGL modulation. An additional embodiment is a method of treating a disease, disorder, or condition associated with the MGL modulation using a chemical entity as described herein.

Additional embodiments, features, and advantages of the invention will be apparent from the following detailed description and through practice of the invention.

Embodiments include compounds of Formula (I),

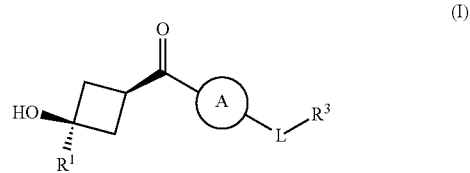

wherein
R$^1$ is C$_{1-4}$alkyl or C$_{1-4}$haloalkyl;

Ⓐ is

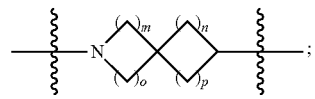

wherein m, n, o, and p are each independently 1 or 2; and wherein Ⓐ is optionally substituted with one, two, and three R$^2$ members;

wherein each R$^2$ is independently H, halo, OH, C$_{1-4}$alkyl, or OC$_{1-4}$alkyl;

L is a bond, C$_{1-4}$alkyl, C$_{1-4}$haloalkyl, or O; and

R$^3$ is:

(a) phenyl optionally substituted with one, two or three members each independently selected from halo, C$_{1-4}$alkyl, C$_{1-4}$haloalkyl, OC$_{1-4}$alkyl, OC$_{1-4}$haloalkyl, N(C$_{1-4}$alkyl)$_2$, pyrrolidinyl, C$_{3-6}$cycloalkyl, OC$_{3-6}$cycloalkyl, 1H-pyrazol-1-yl, and 1-methyl-1H-imidazol-4-yl;

(b) a 6-membered heteroaryl optionally substituted with one, two, or three members each independently selected from halo, C$_{1-4}$alkyl, C$_{1-4}$haloalkyl, OC$_{1-4}$alkyl, $OC_{1-4}$haloalkyl, $C_{3-6}$cycloalkyl, and $C_{3-6}$cycloalkyl substituted with $C_{1-4}$alkyl or $C_{1-4}$haloalkyl;

(c) a 5-membered heteroaryl optionally substituted with one, two, or three members each independently selected from $C_{1-4}$alkyl, $C_{1-4}$haloalkyl, $OC_{1-4}$alkyl, $OC_{1-4}$haloalkyl, and phenyl;

(d) a fused 5-6 heteroaryl or a fused 6-6 heteroaryl each optionally substituted with one, two, or three members each independently selected from halo, $C_{1-4}$alkyl, $C_{1-4}$haloalkyl, $OC_{1-4}$alkyl, and $OC_{1-4}$haloalkyl; or (e) 2,3-dihydro-1H-indenyl, 2,3-dihydrobenzofuranyl, 4,5,6,7-tetrahydropyrazolo[1,5-a]pyridinyl, 5,6,7,8-tetrahydroimidazo[1,2-a]pyridinyl, 5,6,7,8-tetrahydroimidazo[1,5-a]pyridinyl, or 6,7-dihydro-5H-cyclopenta[b]pyridinyl;

or a pharmaceutically acceptable salt, isotope, N-oxide, solvate, or stereoisomer thereof.

DETAILED DESCRIPTION OF THE INVENTION

As used herein, the terms "including," "containing," and "comprising" are used in their open, non-limiting sense.

Unless qualified specifically in particular instances of use, the term "alkyl" refers to a straight- or branched-chain alkyl group having from 1 to 8 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. "$C_{1-6}$alkyl" refers to a straight- or branched-chain alkyl group having from 1 to 6 carbon atoms in the chain. "$C_{1-4}$alkyl" refers to a straight- or branched-chain alkyl group having from 1 to 4 carbon atoms in the chain.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

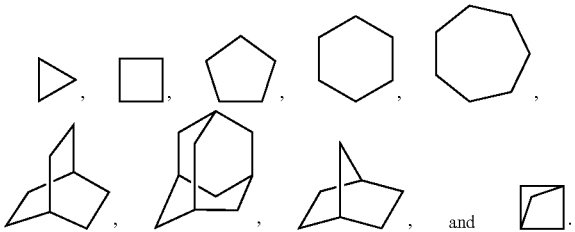

The term "halogen" or "halo" represents chlorine, fluorine, bromine, or iodine.

The term "haloalkyl" refers to a straight- or branched-chain alkyl group having from 1 to 6 carbon atoms in the chain optionally substituting hydrogens with halogens. The term "$C_{1-4}$ haloalkyl" refers to a straight- or branched-chain alkyl group having from 1 to 4 carbon atoms in the chain, optionally substituting one or more hydrogens with halogens. Examples of "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl ($CF(CF_3)_2$), and groups that in light of the ordinary skill in the art and the teachings provided herein would be considered equivalent to any one of the foregoing examples.

The term "aryl" refers to a monocyclic, aromatic carbocycle (ring structure having ring atoms that are all carbon) having 6 atoms per ring (carbon atoms in the aryl groups are sp2 hybridized). The term "phenyl" represents the following moiety:

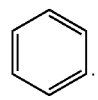

The term "heteroaryl" refers to an aromatic monocyclic or multicyclic ring system comprising 5 to 14 ring atoms, wherein from 1 to 4 of the ring atoms are independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is multicyclic and has 6 or 14 ring atoms and at least one nitrogen ring atom. A heteroaryl group is joined via a ring carbon atom and any nitrogen atom of a heteroaryl can be optionally oxidized to the corresponding N-oxide. The term "heteroaryl" also encompasses a heteroaryl group, as defined above, which has been fused to a benzene ring.

The term "5-membered heteroaryl" refers to a heteroaryl group, as defined above, which has 5 ring atoms. Non-limiting examples of illustrative 5-membered heteroaryls include:

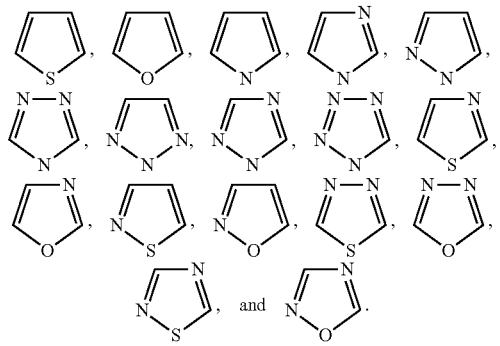

The term "6-membered heteroaryl" as used herein, refers to a heteroaryl group, as defined above, which has 6 ring atoms. Non-limiting examples of illustrative 6-membered heteroaryls include:

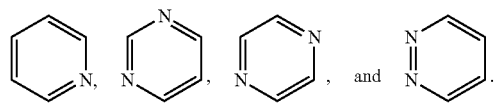

The terms "5,6-fused bicyclic heteroaryl" or "6,5-fused bicyclic heteroaryl" as used herein, refer to a heteroaryl group, as defined above, which has 9 ring atoms. Non-limiting examples of illustrative 5,6-fused bicyclic heteroaryls or 6,5-fused bicyclic heteroaryls include:

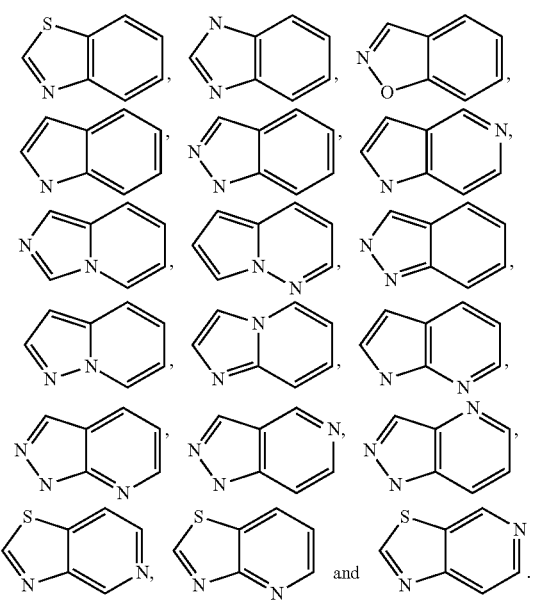

The term "6,6-fused bicyclic heteroaryl" as used herein, refers to a heteroaryl group, as defined above, which has 10 ring atoms. Non-limiting examples of illustrative 6,6-fused bicyclic heteroaryls include:

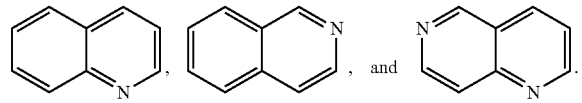

The term "heterocycloalkyl" as used herein, refers to a ring system which is non-aromatic, where 1 to 4 of the ring atoms are independently O, N or S and the remaining ring atoms are carbon atoms, which may optionally be fused to another ring (aromatic or heteroaromatic) spirocyclic with another ring (carbocyclic). Non-limiting examples of illustrative heterocycloalkyls include:

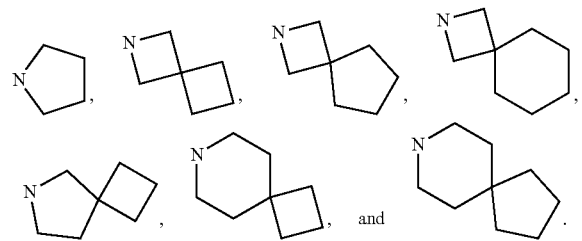

Those skilled in the art will recognize that the species of heteroaryl, heterocycloalkyl, cycloalkyl, and aryl groups listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

The term "variable point of attachment" means that a group is allowed to be attached at more than one alternative position in a structure. The attachment will always replace a hydrogen atom on one of the ring atoms. In other words, all permutations of bonding are represented by the single diagram, as shown in the illustrations below.

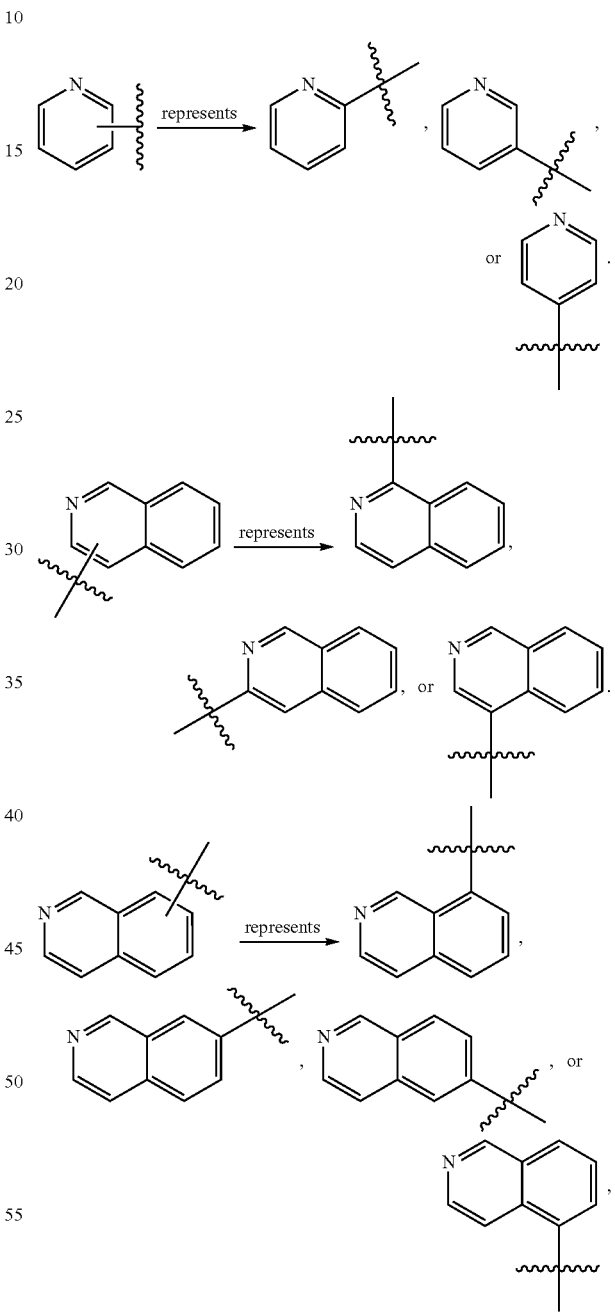

Those skilled in the art will recognize that that if more than one such substituent is present for a given ring, the bonding of each substituent is independent of all of the others. The groups listed or illustrated above are not exhaustive.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of such formula. The compounds described herein may possess one or more asymmetric centers; such compounds can therefore be produced as individual (R)- or (S)-stereoisomers or as mixtures thereof. Thus, any formula given herein is intended to represent a racemate, one or more of its enantiomeric forms, one or more of its diastereomeric forms, and mixtures thereof. Additionally, any formula given herein is intended to refer also to any one of: hydrates, solvates, polymorphs and of such compounds, and mixtures thereof, even if such forms are not listed explicitly.

The term "R" at a stereocenter designates that the stereocenter is purely of the R-configuration as defined in the art; likewise, the term "S" means that the stereocenter is purely of the S-configuration. As used herein, the term "RS" refers to a stereocenter that exists as a mixture of the R- and S-configurations.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Unlabeled stereocenters drawn without stereo bond designations are a mixture of the R- and S-configurations. For unlabeled stereocenters drawn with stereo bond designations, the absolute stereochemistry is as depicted.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of: for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number in an enriched form. Examples of isotopes that can be incorporated into the described compounds in a form that exceeds natural abundances include isotopes of hydrogen, carbon, nitrogen, oxygen, phosphorous, fluorine, chlorine, and iodine, such as $^2$H (or chemical symbol D), $^3$H (or chemical symbol T), $^{11}$C, $^{13}$C, $^{14}$C, $^{15}$N, $^{18}$O, $^{17}$O, $^{31}$P, $^{32}$P, $^{35}$S, $^{36}$Cl, and $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H, or D) may afford certain therapeutic advantages resulting from greater metabolic stability, for example increased in vivo half-life or reduced dosage requirements. Isotopically labeled compounds can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for such variable appearing elsewhere. In other words, where a variable appears more than once, the choice of the species from a specified list is independent of the choice of the species for the same variable elsewhere in the formula, unless stated otherwise.

The term $C_{n-m}$ alkyl refers to an aliphatic chain, whether straight or branched, with a total number N of carbon members in the chain that satisfies n≤N≤m, with m>n.

When the same plurality of substituents is assigned to various groups, the specific individual substituent assignment to each of such groups is meant to be independently made with respect to the specific individual substituent assignments to the remaining groups. By way of illustration, but not as a limitation, if each of groups Q and R can be H or F, the choice of H or F for Q is made independently of the choice of H or F for R, so the choice of assignment for Q does not determine or condition the choice of assignment for R, or vice-versa, unless it is expressly indicated otherwise. Illustrative claim recitation in this regard would read as "each of Q and R is independently H or F" or "each of Q and R is independently selected from the group consisting of H and F."

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

In another example, a zwitterionic compound would be encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well-established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds described herein are given explicitly herein. They are, however, part of the embodiments of this invention. No further examples in this regard are provided herein because the interactions and transformations in a given medium that lead to the various forms of a given compound are known by any one of ordinary skill in the art.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein.

Furthermore, when more than one assignment is given for any member or substituent, embodiments comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein.

The nomenclature "$C_i$-$C_j$" or "$C_{i-j}$" with j>i, when applied herein to a class of substituents, is meant to refer to embodiments for which each and every one of the number of carbon members, from i to j including i and j, is independently realized. By way of example, the term $C_1$-$C_3$ refers independently to embodiments that have one carbon member ($C_1$), embodiments that have two carbon members ($C_2$), and embodiments that have three carbon members ($C_3$).

A "pharmaceutically acceptable salt" is intended to mean a salt of an acid or base of a compound represented by Formula (I) that is non-toxic, biologically tolerable, or otherwise biologically suitable for administration to the subject. See, generally, S. M. Berge, et al., "Pharmaceutical Salts", *J. Pharm. Sci.*, 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response.

A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

Compounds of Formula (I) may contain at least one nitrogen of basic character, so desired pharmaceutically acceptable salts may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents.

Compounds of Formula (I) may contain a carboxylic acid moiety, a desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, piperazine, N-methyl-glucamine and tromethamine and inorganic salts derived from sodium, calcium, potassium, magnesium, manganese, iron, copper, zinc, aluminum, and lithium.

The compounds of the disclosure, including their pharmaceutically acceptable salts, whether alone or in combination, (collectively, "active agent" or "active agents") are useful as MGL-modulators in the methods described herein. Such methods for modulating MGL comprise the use of a therapeutically effective amount of a compound as described herein.

In some embodiments, the MGL modulator is an inhibitor and is used in a subject diagnosed with or suffering from a disease, disorder, or condition associated with MGL receptor activity, such as those described herein. Symptoms or disease states are intended to be included within the scope of "disease, disorder or condition."

Accordingly, the invention relates to methods of using the active agents described herein to treat a disease, disorder, or condition associated with MGL receptor activity in a subject diagnosed with or suffering therefrom. The term "treat" or "treating" as used herein is intended to refer to administration of an active agent or composition as described herein to a subject for the purpose of effecting a therapeutic or prophylactic benefit through modulation of MGL receptor activity. Treating includes reversing, ameliorating, alleviating, inhibiting the progress of, lessening the severity of, or preventing a disease, disorder, or condition, or one or more symptoms of such disease, disorder or condition associated with the MGL modulation. The term "subject" refers to a mammalian patient in need of such treatment, such as a human.

The term "composition" refers to a product that includes the specified ingredients in therapeutically effective amounts, as well as any product that results, directly, or indirectly, from combinations of the specified ingredients in the specified amounts.

The term "MGL inhibitor" is intended to encompass a compound that interacts with MGL to substantially reduce or eliminate its catalytic activity, thereby increasing the concentrations of its substrate(s). The term "MGL-modulated" is used to refer to the condition of being affected by the modulation of the MGL enzyme including the condition of being affected by the inhibition of the MGL enzyme. The disclosure is directed to methods for treating, ameliorating and/or preventing diseases, conditions, or disorders associated with pain (including inflammatory pain), and also psychiatric disorders, neurological disorders, cancers and eye conditions by the administration of therapeutically effective amounts of MGL modulators to subjects in need thereof.

The term "modulators" include both inhibitors and activators, where "inhibitors" refer to compounds that decrease, prevent, inactivate, desensitize, or down-regulate the MGL expression or activity, and "activators" are compounds that increase, activate, facilitate, sensitize, or up-regulate MGL expression or activity.

As used herein, unless otherwise noted, the term "affect" or "affected" (when referring to a disease, condition or disorder that is affected by inhibition of MGL) includes a reduction in the frequency and/or severity of one or more symptoms or manifestations of said disease, condition or disorder; and/or include the prevention of the development of one or more symptoms or manifestations of said disease, condition or disorder or the development of the disease, condition or disorder.

In treatment methods according to the present disclosure, a therapeutically effective amount of a compound as described herein is administered to a subject suffering from or diagnosed as having such a disease, disorder, or condition. A "therapeutically effective amount" means an amount or dose sufficient to generally bring about the desired therapeutic or prophylactic benefit in subjects in need of such treatment for the designated disease, disorder, or condition. Effective amounts or doses of the active agents described herein may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. For a 70-kg human, an illustrative range for a suitable dosage amount is from about 1 to 1000 mg/day in single or multiple dosage units (e.g., BID, TID, QID or as required by modality).

Once improvement of the subject's disease, disorder, or condition has occurred, the dose may be adjusted for preventive or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Subjects may, however, require intermittent treatment on a long-term basis upon any recurrence of symptoms.

In addition, the compounds described herein are envisaged for use alone, in combination with one or more of other compounds of the disclosure, or in combination with additional active ingredients in the treatment of the conditions discussed below. The additional active ingredients may be co-administered separately or together with a compound as described herein, or included with such an agent in a pharmaceutical composition described herein. In an illustrative embodiment, additional active ingredients are those that are known or discovered to be effective in the treatment of conditions, disorders, or diseases associated with the MGL modulation, such as another MGL inhibitor or a compound active against another target associated with the particular condition, disorder, or disease. The combination may serve to increase efficacy (e.g., by including in the combination a compound potentiating the potency or effectiveness of an agent), decrease one or more side effects, or decrease the required dose of the active agent.

When referring to inhibiting the target, an "effective amount" means an amount sufficient to affect MGL modulation.

The compounds described herein are envisaged for use, alone or in combination with one or more additional active ingredients, to formulate pharmaceutical compositions of the invention. A pharmaceutical composition of the invention comprises an active agent in accordance with the present disclosure.

Pharmaceutically acceptable excipients commonly used in pharmaceutical compositions are substances that are non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of such excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using pharmaceutically acceptable excipients and compounding techniques known or that become available to those of ordinary skill in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. The compositions may be formulated for any one of a plurality of administration routes, such as intravenous infusion, topical administration, or oral administration. Preferably, the compositions may be formulated for oral administration.

For oral administration, the active agents described herein can be provided in the form of tablets or capsules, or as a solution, emulsion, or suspension. To prepare the oral compositions, the active agents may be formulated to yield a dosage of, e.g., for a 70-kg human, an illustrative range for a suitable dosage amount is from about 1 to 1000 mg/day in single or multiple dosage units.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract or may be coated with an enteric coating.

Capsules for oral administration include hard and soft gelatin or (hydroxypropyl)methyl cellulose capsules. To prepare hard gelatin capsules, active ingredient(s) may be mixed with a solid, semi-solid, or liquid diluent. Liquids for oral administration may be in the form of suspensions, solutions, emulsions, or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents described herein may also be administered by non-oral routes. For example, compositions may be formulated for rectal administration as a suppository, enema or foam. For parenteral use, including intravenous, intramuscular, intraperitoneal, or subcutaneous routes, the agents described herein may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.01% to about 20% of drug to vehicle, preferably 0.1% to 10%. Another mode of administering the agents described herein may utilize a patch formulation to affect transdermal delivery.

Active agents may alternatively be administered in methods of treatment by inhalation, via the nasal or oral routes, e.g., in a spray formulation also containing a suitable carrier.

In a further embodiment is a method of treating a subject suffering from or diagnosed with a disease, disorder, or condition associated with MGL modulation, comprising administering to the subject in need of such treatment a therapeutically effective amount of the active agent.

The compounds of Formula (I) are useful in methods for treating, ameliorating and/or preventing a disease, a condition or a disorder that is affected by the inhibition of MGL. Such methods comprise administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

In particular, the compounds of Formula (I), or pharmaceutically acceptable salts, isotopes, N-oxides, solvates and stereoisomers thereof, are useful for treating, ameliorating and/or preventing diseases, conditions, or disorders causing pain, psychiatric disorders, neurological disorders, cancers, and eyes conditions. More particularly, the compounds of Formula (I), or pharmaceutically acceptable salts, isotopes, N-oxides, solvates and stereoisomers thereof, are useful for treating, ameliorating and/or preventing inflammatory pain, major depressive disorder, treatment resistant depression, anxious depression or bipolar disorder by administering to a subject in need thereof a therapeutically effective amount of a compound of Formula (I), or a pharmaceutically acceptable salt, isotope, N-oxide, solvate or stereoisomer thereof as herein defined.

1) Pain

Examples of inflammatory pain include, but are not limited to, pain due to a disease, condition, disorder, or a pain state including inflammatory bowel disease, visceral pain, migraine, post-operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache, or arachnoiditis.

One type of inflammatory pain is inflammatory hyperalgesia or hypersensitivity. Examples of inflammatory hyperalgesia include a disease, condition, disorder, or pain state including inflammation, osteoarthritis, rheumatoid arthritis, back pain, joint pain, abdominal pain, musculoskeletal diseases, skin diseases, post-operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity and/or dermal allergy, itch, eczema, pharyngitis, enteritis, irritable bowel syndrome, inflammatory bowel diseases including Crohn's Disease, ulcerative colitis, benign prostatic hypertrophy, and nasal hypersensitivity.

In another embodiment is a method for treating, ameliorating and/or preventing inflammatory visceral hyperalgesia in which an enhanced visceral irritability exists, comprising, consisting of, and/or consisting essentially of the step of administering to a subject in need of such treatment a therapeutically effective amount of a compound of Formula (I) or a pharmaceutically acceptable salt, isotope, N-oxide, solvate or stereoisomer thereof. In a further embodiment is a method for treating inflammatory somatic hyperalgesia in which a hypersensitivity to thermal, mechanical and/or chemical stimuli exists, comprising administering to a subject in need of such treatment a therapeutically effective amount of a compound of Formula (I) or a pharmaceutically acceptable salt, isotope, N-oxide, solvate or stereoisomer thereof.

A further embodiment is a method for treating, ameliorating and/or preventing neuropathic pain. Examples of a neuropathic pain include pain due to a disease, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngeal neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, vidian neuralgia or chemotherapy-induced neuropathy.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, disorder, or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

In a further embodiment is a method for treating, ameliorating and/or preventing neuropathic cold allodynia in which a hypersensitivity to a cooling stimuli exists, comprising administering to a subject in need of such treatment a therapeutically effective amount of a compound of Formula (I) or a pharmaceutically acceptable salt, isotope, N-oxide, solvate or stereoisomer thereof.

2) Psychiatric Disorders

Examples of psychiatric disorders include, but are not limited to, anxieties such as, social anxiety, post-traumatic stress disorder, phobias, social phobia, special phobias, panic disorder, obsessive-compulsive disorder, acute stress disorder, separation anxiety disorder, and generalized anxiety disorder, as well as depression such as, major depression, bipolar disorder, seasonal affective disorder, post-natal depression, manic depression, and bipolar depression, mood disorders and mood affective disorders that can be treated include, but are not limited to, bipolar disorder I depressed, hypomanic, manic and mixed form; bipolar disorder II; depressive disorders, such as single depressive episode or recurrent major depressive disorder, minor depressive disorder, treatment-resistant depression, anxious depression, bipolar disorder, depressive disorder with postpartum onset, depressive disorders with psychotic symptoms; persistent mood disorders, such as cyclothymia, dysthymia, euthymia; and premenstrual dysphoric disorder; psychoses and developmental disorders such as autism spectrum disorders, and Asperger syndrome. Examples of autism spectrum disorders include, but are not limited to, autistic disorder, pervasive developmental disorder not otherwise specified (PDD-NOS), Asperger's syndrome, Fragile X syndrome, Rett syndrome, childhood disintegrative disorder, Kanner's syndrome, Phelan McDermid Syndrome, Angelman syndrome, SCN2a related autism, SYNGAP related autism, Dub15q related autism, Dyrk1a related autism, GRIN2B related autism, Malan syndrome, ADNP syndrome, or tuberous sclerosis.

3) Neurological Disorders

Examples of neurological disorder include, but are not limited to, tremors, dyskinesias, dystonias, spasticity, Tourette's Syndrome; neuromyelitis optica, Parkinson's disease; Alzheimer's disease; senile dementia; Huntington's disease; Epilepsy/seizure disorders and sleep disorders.

4) Cancers:

Examples of cancers include, but are not limited to, benign skin tumors, prostate tumors, ovarian tumors, and cerebral tumors (glioblastomas, medulloepitheliomas, medulloblastomas, neuroblastomas, tumors of embryonic origin, astrocytomas, astroblastomas, ependymomas, oligodendrogliomas, neuroepitheliomas, epiphyseal tumor, ependymoblastomas, malignant meningiomas, sarcomatosis, malignant melanomas, schwannomas).

5) Eye Conditions

Examples of eye conditions include, but are not limited to, ocular hypertension, glaucoma, degeneration, and apoptosis of retinal ganglion cells and neuroretinal cells.

Other embodiments provide for a method for modulating MGL receptor activity, including when such receptor is in a subject, comprising exposing MGL receptor to a therapeutically effective amount of a compound as described herein.

Embodiments are compounds of Formula (I):

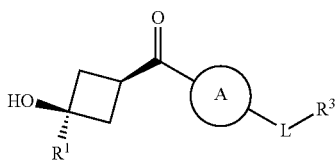
(I)

wherein
R$^1$ is C$_{1-4}$alkyl or C$_{1-4}$haloalkyl;

Ⓐ is

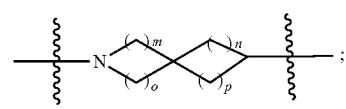
;

wherein m, n, o, and p are each independently 1 or 2; and wherein Ⓐ is optionally substituted with one, two, and three R$^2$ members;
wherein each R$^2$ independently H, halo, OH, C$_{1-4}$alkyl, or OC$_{1-4}$alkyl;

L is a bond, C$_{1-4}$alkyl, C$_{1-4}$haloalkyl, or O; and

R$^3$ is:

(a) phenyl optionally substituted with one, two or three members each independently selected from halo, C$_{1-4}$alkyl, C$_{1-4}$haloalkyl, OC$_{1-4}$alkyl, OC$_{1-4}$haloalkyl, N(C$_{1-4}$alkyl)$_2$, pyrrolidinyl, C$_{3-6}$cycloalkyl, OC$_{3-6}$cycloalkyl, 1H-pyrazol-1-yl, and 1-methyl-1H-imidazol-4-yl;

(b) a 6-membered heteroaryl optionally substituted with one, two, or three members each independently selected from halo, C$_{1-4}$alkyl, C$_{1-4}$haloalkyl, OC$_{1-4}$alkyl, OC$_{1-4}$haloalkyl, C$_{3-6}$cycloalkyl, and C$_{3-6}$cycloalkyl substituted with C$_{1-4}$alkyl or C$_{1-4}$haloalkyl;

(c) a 5-membered heteroaryl optionally substituted with one, two or three members each independently selected from C$_{1-4}$alkyl, C$_{1-4}$haloalkyl, OC$_{1-4}$alkyl, OC$_{1-4}$haloalkyl, and phenyl;

(d) a fused 5-6 heteroaryl or a fused 6-6 heteroaryl each optionally substituted with one, two, or three members each independently selected from halo, C$_{1-4}$alkyl, C$_{1-4}$haloalkyl, OC$_{1-4}$alkyl, and OC$_{1-4}$haloalkyl; or (e) 2,3-dihydro-1H-indenyl, 2,3-dihydrobenzofuranyl, 4,5,6,7-tetrahydropyrazolo[1,5-a]pyridinyl, 5,6,7,8-tetrahydroimidazo[1,2-a]pyridinyl, 5,6,7,8-tetrahydroimidazo[1,5-a]pyridinyl, or 6,7-dihydro-5H-cyclopenta[b]pyridinyl;

or a pharmaceutically acceptable salt, isotope, N-oxide, solvate, or stereoisomer thereof, or particularly, a pharmaceutically acceptable salt thereof.

In some embodiments are compounds of Formula (I-1),

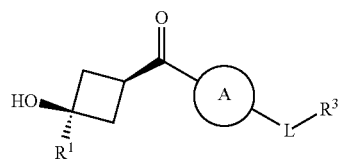
(I-1)

wherein
R$^1$ is C$_{1-4}$alkyl or C$_{1-4}$haloalkyl;

Ⓐ is

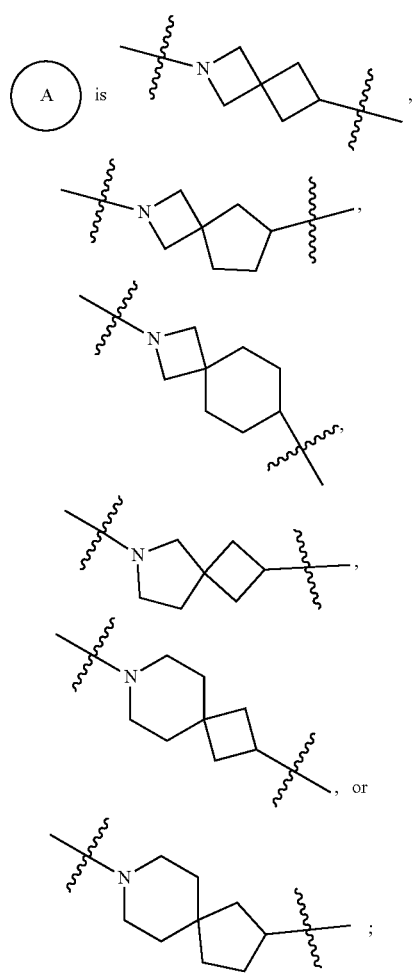

each optionally substituted with one, two, and three R$^2$ members;
wherein each R$^2$ is independently H, halo, OH, C$_{1-4}$alkyl, or OC$_{1-4}$alkyl;

L is a bond, CH$_2$, CF$_2$, CH(CH$_3$), or O; and

R$^3$ is:

(a) phenyl optionally substituted with one, two, or three members each independently selected from halo, C$_{1-4}$alkyl, C$_{1-4}$haloalkyl, OC$_{1-4}$alkyl, OC$_{1-4}$haloalkyl, N(C$_{1-4}$alkyl)$_2$, pyrrolidin-1-yl, 1H-pyrazol-1-yl, 1-methyl-1H-imidazol-4-yl, C$_{3-6}$cycloalkyl, and OC$_{3-6}$cycloalkyl;

(b) pyridinyl optionally substituted with one, two or three members each independently selected from C$_{1-4}$alkyl, C$_{1-4}$haloalkyl, OC$_{1-4}$alkyl, and OC$_{1-4}$haloalkyl; pyrazin-2-yl substituted with C$_{1-4}$alkyl; or pyrimidin-2-yl substituted with C$_{1-4}$alkyl or C$_{1-4}$haloalkyl;

(c) pyrazolyl, imidazolyl, or isoxazolyl, each optionally substituted with one or two members each independently selected from C$_{1-4}$alkyl and C$_{1-4}$haloalkyl;

(d) quinolinyl, isoquinolinyl, 1H-indazolyl, 2H-indazolyl, 1H-pyrrolo[2,3-b]pyridinyl, 1H-pyrrolo[3,2-c]pyridinyl, pyrrolo[1,2-b]pyridazinyl, 1H-pyrazolo[3,4-b]pyridinyl, pyrazolo[1,5-a]pyridinyl, imidazo[1,2-a]pyridinyl, imidazo[1,5-a]pyridinyl, or 1H-benzo[d]imidazolyl, each optionally substituted with one or two members each independently selected from halo, C$_{1-4}$alkyl, C$_{1-4}$haloalkyl, OC$_{1-4}$alkyl, and OC$_{1-4}$haloalkyl; or (e) 2,3-dihydro-1H-indenyl, 2,3-dihydrobenzofuranyl, 4,5,6,7-tetrahydropyrazolo[1,5-a]pyridinyl, 5,6,7,8-tetrahydroimidazo[1,2-a]pyridinyl, 5,6,7,8-tetrahydroimidazo[1,5-a]pyridinyl, or 6,7-dihydro-5H-cyclopenta[b]pyridinyl;

or a pharmaceutically acceptable salt, isotope, N-oxide, solvate, or stereoisomer thereof, or particularly, a pharmaceutically acceptable salt thereof.

In some embodiments are compounds of Formula (I-2),

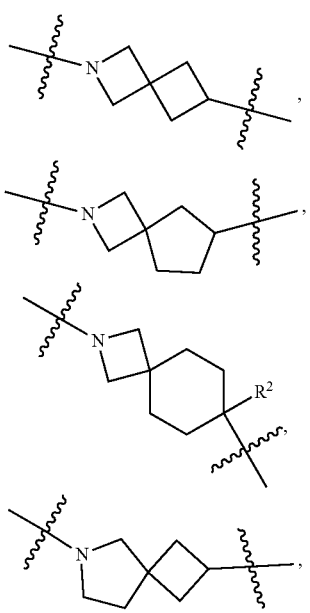
(I-2)

wherein
R$^1$ is C$_{1-4}$alkyl or C$_{1-4}$haloalkyl;

Ⓐ is

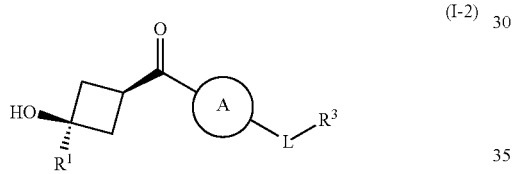

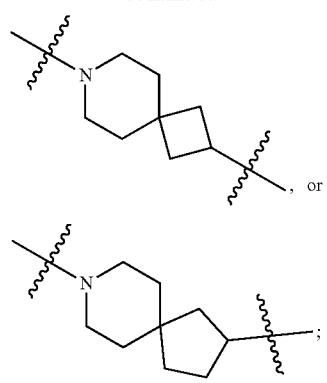

wherein R$^2$ is H, OH, or OCH$_3$;
L is a bond, CH$_2$, or O; and
R$^3$ is:

(a) phenyl optionally substituted with one or two members independently selected from halo, C$_{1-4}$alkyl, C$_{1-4}$haloalkyl, OC$_{1-4}$alkyl, OC$_{1-4}$haloalkyl, N(CH$_3$)$_2$, pyrrolidinyl, and C$_{3-6}$cycloalkyl; or

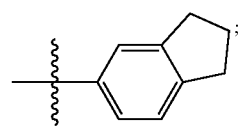

(b) pyridinyl optionally substituted with one member that is C$_{1-4}$alkyl, C$_{1-4}$haloalkyl, or OC$_{1-4}$alkyl;

(c)
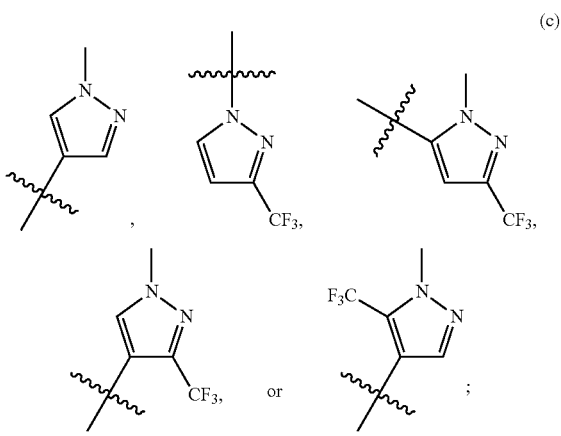

or
(d) quinolinyl, isoquinolinyl,

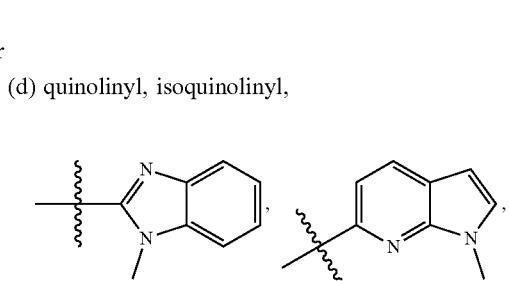

-continued

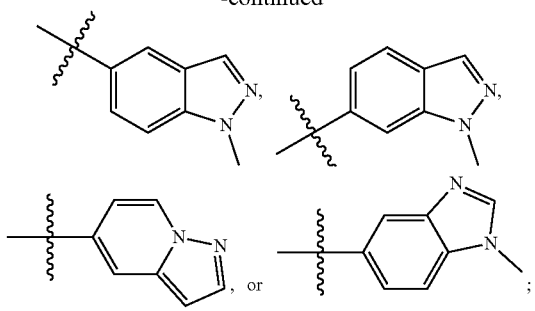

or a pharmaceutically acceptable salt, isotope, N-oxide, solvate, or stereoisomer thereof, or particularly, a pharmaceutically acceptable salt thereof.

In some embodiments of Formula (I), $R^1$ is $CH_3$. In some embodiments, $R^1$ is $CH_2CH_3$. In some embodiments, $R^1$ is $CF_2H$.

In some embodiments of Formula (I), Ⓐ is

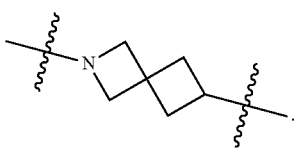 [SMILES: *C1CC2(C1)CN(*)C2]

In some embodiments, Ⓐ is

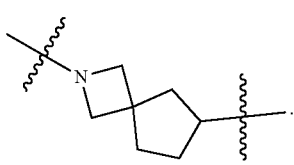 [SMILES: *C1CCC2(C1)CN(*)C2]

In some embodiments, Ⓐ is

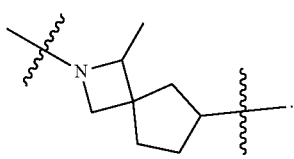 [SMILES: *C1CCC2(C1)CN(*)C2C]

In some embodiments, Ⓐ is

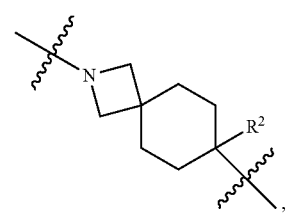

and $R^2$ is H, OH, $CH_3$, $CH_2CH_3$, $OCH_3$, or F. In some embodiments, Ⓐ is

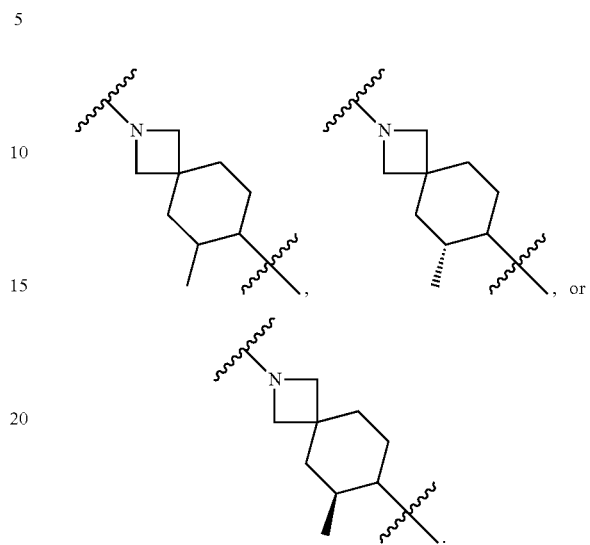

In some embodiments, Ⓐ is

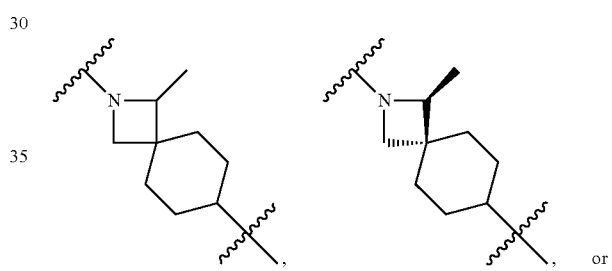

In some embodiments, Ⓐ is

In some embodiments, Ⓐ is

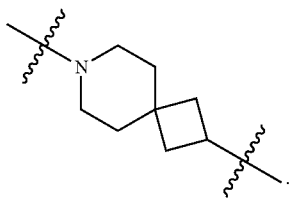 [SMILES: *C1CC2(CCN(*)CC2)C1]

In some embodiments, Ⓐ is

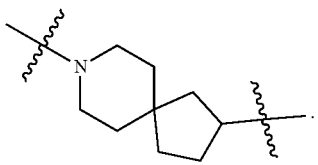 [SMILES: *C1CCC2(CCN(*)CC2)C1]

In some embodiments of Formula (I), $R^2$ is H. In some embodiments, $R^2$ is OH. In some embodiments, $R^2$ is $OCH_3$. In some embodiments, $R^2$ is $CH_3$. In some embodiments, $R^2$ is $CH_2CH_3$. In some embodiments, $R^2$ is F.

In some embodiments of Formula (I), L is a bond. In some embodiments, L is $CH_2$. In some embodiments, L is O. In some embodiments, L is $CH(CH_3)$. In some embodiments, L is $CF_2$.

In some embodiments of Formula (I), $R^3$ is phenyl optionally substituted with one two, or three members each independently selected from halo, $C_{1-4}$alkyl, $C_{1-4}$haloalkyl, $OC_{1-4}$alkyl, $OC_{1-4}$haloalkyl, $N(CH_3)_2$, pyrrolidin-1-yl, 1H-pyrazol-1-yl, 1-methyl-1H-imidazol-4-yl, $C_{3-6}$cycloalkyl, and $OC_{3-6}$cycloalkyl. In some embodiments, $R^3$ is phenyl substituted with one or two members independently selected from Cl, F, $CH_3$, $CH_2CH_3$, $CH(CH_3)_2$, $C(CH_3)_3$, $OCH_3$, $OCH_2CH_3$, $CHF_2$, $CF_3$, $CF_2CH_3$, $OCHF_2$, $OCF_3$, $N(CH_3)_2$, cyclopropyl, cyclobutyl, O-cyclopropyl, 1H-pyrazol-1-yl, pyrrolidin-1-yl, and 1-methyl-1H-imidazol-4-yl. In some embodiments, $R^3$ is phenyl, o-tolyl, m-tolyl, p-tolyl, 2-ethylphenyl, 3-ethylphenyl, 4-ethylphenyl, 2-isopropylphenyl, 3-isopropylphenyl, 4-isopropylphenyl, 2-(tert-butyl)phenyl, 3-(tert-butyl)phenyl, 4-(tert-butyl)phenyl, 3-(difluoromethyl)phenyl, 4-(difluoromethyl)phenyl, 2-(trifluoromethyl)phenyl, 3-(trifluoromethyl)phenyl, 4-(trifluoromethyl)phenyl, 3-(1,1-difluoroethyl)phenyl, 4-(1,1-difluoroethyl)phenyl, 2-methoxyphenyl, 3-methoxyphenyl, 4-methoxyphenyl, 3-(difluoromethoxy)phenyl, 4-(difluoromethoxy)phenyl, 2-(trifluoromethoxy)phenyl, 3-(trifluoromethoxy)phenyl, 4-(trifluoromethoxy)phenyl, 2-cyclopropylphenyl, 3-cyclopropylphenyl, 4-cyclopropylphenyl, 3-cyclobutylphenyl, 4-cyclopropoxyphenyl, 3-(1H-pyrazol-1-yl)phenyl, 4-(1H-pyrazol-1-yl)phenyl, 3-(1-methyl-1H-imidazol-4-yl)phenyl, or 3-(pyrrolidin-1-yl)phenyl. In some embodiments, $R^3$ is 2,4-dimethylphenyl, 2,6-dimethylphenyl, 3,5-dimethylphenyl, 3,4-dimethylphenyl, 2,3-dimethylphenyl, 3-ethyl-5-methylphenyl, 3-fluoro-4-methylphenyl, 2-fluoro-4-methylphenyl, 4-fluoro-3-methylphenyl, 3-fluoro-2-methylphenyl, 2-fluoro-6-methylphenyl, 3-fluoro-5-methylphenyl, 2-fluoro-5-methylphenyl, 5-fluoro-2-methylphenyl, 2-fluoro-3-methylphenyl, 4-fluoro-2-methylphenyl, 3-fluoro-5-isopropylphenyl, 4-chloro-2-methylphenyl, 4-chloro-3-methylphenyl, 2-chloro-5-methylphenyl, 3-chloro-4-methylphenyl, 3-chloro-2-methylphenyl, 4-chloro-3-ethylphenyl, 3-(difluoromethyl)-5-methylphenyl, 3-(difluoromethyl)-4-methylphenyl, 4-(difluoromethyl)-3-methylphenyl, 2-methyl-5-(trifluoromethyl)phenyl, 4-methyl-3-(trifluoromethyl)phenyl, 3-methyl-5-(trifluoromethyl)phenyl, 3-methyl-4-(trifluoromethyl)phenyl, 2-methyl-3-(trifluoromethyl)phenyl, 2-methyl-6-(trifluoromethyl)phenyl, 5-methyl-2-(trifluoromethyl)phenyl, 4-methyl-2-(trifluoromethyl)phenyl, 3-methyl-2-(trifluoromethyl)phenyl, 2-methyl-4-(trifluoromethyl)phenyl, 3-ethyl-5-(trifluoromethyl)phenyl, 2-isopropyl-3-(trifluoromethyl)phenyl, 3-isopropyl-2-(trifluoromethyl)phenyl, 3-fluoro-5-methoxyphenyl, 2-fluoro-3-methoxyphenyl, 4-fluoro-3-methoxyphenyl, 3-ethoxy-5-fluorophenyl, 3-chloro-5-methoxyphenyl, 4-chloro-3-methoxyphenyl, 2-chloro-3-methoxyphenyl, 2-methoxy-3-methylphenyl, 3-methoxy-5-methylphenyl, 3-methoxy-2-methylphenyl, 4-methoxy-3-methylphenyl, 3-methoxy-4-methylphenyl, 5-methoxy-2-methylphenyl, 3-ethyl-5-methoxyphenyl, 3-ethyl-2-methoxyphenyl, 3-(tert-butyl)-4-methoxyphenyl, 2-(difluoromethyl)-4-methoxyphenyl, 4-(difluoromethyl)-2-methoxyphenyl, 4-methoxy-2-(trifluoromethyl)phenyl, 3-ethoxy-4-methylphenyl, 3-ethoxy-2-methylphenyl, 3-isopropoxy-2-methylphenyl, 4-(difluoromethoxy)-2-methylphenyl, 3-(difluoromethoxy)-5-methylphenyl, 5-(difluoromethoxy)-2-methylphenyl, 3-(difluoromethoxy)-4-methylphenyl, 4-(difluoromethoxy)-3-methylphenyl, 2-methyl-4-(trifluoromethoxy)phenyl, 3-methyl-5-(trifluoromethoxy)phenyl, 4-methyl-3-(trifluoromethoxy)phenyl, 3-methyl-4-(trifluoromethoxy)phenyl, 4-methoxy-3-(trifluoromethyl)phenyl, 3-methoxy-5-(trifluoromethyl)phenyl, 3-methoxy-4-(trifluoromethyl)phenyl, 4-ethoxy-3-(trifluoromethyl)phenyl, 3-ethoxy-5-(trifluoromethoxy)phenyl, 3-chloro-5-(trifluoromethoxy)phenyl, 3-ethyl-5-(trifluoromethoxy)phenyl, 3-(dimethylamino)-5-(trifluoromethyl)phenyl, 3-(dimethylamino)-4-(trifluoromethyl)phenyl, 4-cyclopropyl-3-fluorophenyl, 3-cyclopropyl-2-fluorophenyl, 5-cyclopropyl-2-fluorophenyl, 3-cyclopropyl-4-fluorophenyl, 3-cyclopropyl-2-methylphenyl, 3-cyclopropyl-5-methylphenyl, 4-cyclopropyl-3-methylphenyl, 2-cyclopropyl-3-methylphenyl, 3-cyclopropyl-4-methylphenyl, 4-cyclopropyl-2-methylphenyl, 3-cyclopropyl-5-methoxyphenyl, 3-cyclopropyl-4-methoxyphenyl, 4-cyclopropyl-3-methoxyphenyl, 3-cyclopropoxy-2-methylphenyl, 3-fluoro-5-methoxy-4-methylphenyl, 2,5-difluoro-3-methoxyphenyl, or 2,3-difluoro-5-methoxyphenyl. In some embodiments, $R^3$ is

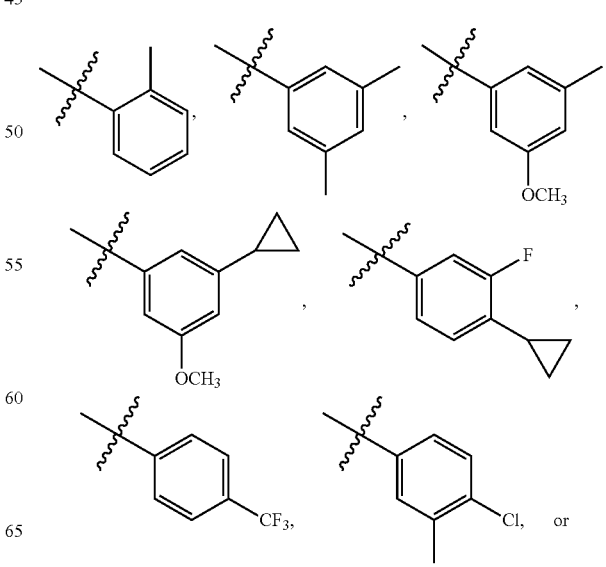

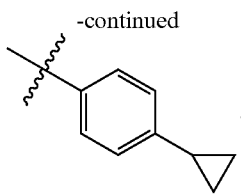

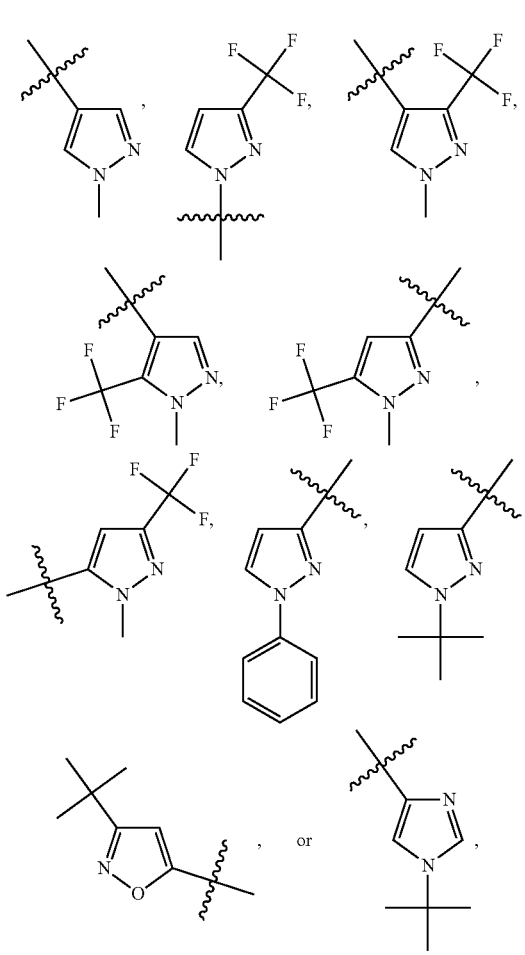

In some embodiments of Formula (I), $R^3$ is pyrazin-2-yl substituted with $C(CH_3)_3$; pyrimidin-2-yl substituted with $CF_3$ or $C(CH_3)_3$; or pyridinyl optionally substituted with one, two or three members each independently selected from Cl, F, $CH_3$, $CH_2CH_3$, $CH(CH_3)_2$, $C(CH_3)_3$, $CF_2H$, $CF_3$, $CF_2CH_3$, $OCH_3$, $OCH_2CH_3$, $OCH(CH_3)_2$, $OCF_2H$, $OCF_3$, cyclopropyl, and cyclopropyl substituted with $CH_3$ or $CF_3$. In some embodiments, $R^3$ is pyridin-2-yl, pyridin-3-yl, pyridin-4-yl, 4-(tert-butyl)pyridin-2-yl, 6-(tert-butyl)pyridin-2-yl, 2-(tert-butyl)pyridin-4-yl, 5-(difluoromethyl)pyridin-2-yl, 1,1-difluoroethyl)pyridin-2-yl, 4-(trifluoromethyl)pyridin-2-yl, 5-(trifluoromethyl)pyridin-2-yl, 6-(trifluoromethyl)pyridin-2-yl, 6-(trifluoromethyl)pyridin-3-yl, 6-methoxypyridin-2-yl, 5-(trifluoromethoxy)pyridin-2-yl, 6-(1-(trifluoromethyl)cyclopropyl)pyridin-2-yl, 3-fluoro-5-methylpyridin-2-yl, 3-fluoro-6-methylpyridin-2-yl, 5-ethyl-3-fluoropyridin-2-yl, 5-chloro-3-methylpyridin-2-yl, 3-chloro-5-methylpyridin-2-yl, 3-chloro-6-methylpyridin-2-yl, 5-chloro-6-methylpyridin-2-yl, 5-chloro-4-methoxypyridin-2-yl, 5-chloro-6-methoxypyridin-2-yl, 3-chloro-6-methoxypyridin-2-yl, 5-chloro-3-methoxypyridin-2-yl, 3-chloro-4-methoxypyridin-2-yl, 3,5-dimethylpyridin-2-yl, 3,6-dimethylpyridin-2-yl, 5,6-dimethylpyridin-2-yl, 6-isopropyl-5-methylpyridin-2-yl, 5-(difluoromethyl)-6-methylpyridin-2-yl, 5-(difluoromethyl)-6-ethylpyridin-2-yl, 6-(difluoromethyl)-5-ethylpyridin-2-yl, 3-(difluoromethyl)-6-ethylpyridin-2-yl, 3-fluoro-5-(trifluoromethyl)pyridin-2-yl, 6-methyl-4-(trifluoromethyl)pyridin-2-yl, 6-methyl-3-(trifluoromethyl)pyridin-2-yl, 3-methyl-5-(trifluoromethyl)pyridin-2-yl, 4-methyl-5-(trifluoromethyl)pyridin-2-yl, 6-methyl-5-(trifluoromethyl)pyridin-2-yl, 3-methyl-6-(trifluoromethyl)pyridin-2-yl, 5-methyl-6-(trifluoromethyl)pyridin-2-yl, 5-ethyl-6-(trifluoromethyl)pyridin-2-yl, 4,6-dimethyl-5-(trifluoromethyl)pyridin-2-yl, 3,6-dimethyl-5-(trifluoromethyl)pyridin-2-yl, 6-methoxy-5-methylpyridin-2-yl, 5-ethyl-6-methoxypyridin-2-yl, 5-cyclopropyl-6-methoxypyridin-2-yl, 4-methoxy-6-methylpyridin-2-yl, 6-isopropoxy-5-methylpyridin-2-yl, 6-methoxy-5-(trifluoromethyl)pyridin-2-yl, 6-ethoxy-5-(trifluoromethyl)pyridin-2-yl, 6-isopropoxy-5-(trifluoromethyl)pyridin-2-yl, 6-isopropoxy-4-methylpyridin-2-yl, 2-isopropoxy-3-methylpyridin-4-yl, 5-cyclopropylpyridin-2-yl, 6-(1-methylcyclopropyl)pyridin-2-yl, 5-(difluoromethoxy)-6-methylpyridin-2-yl, 6-(tert-butyl)pyrazin-2-yl, 4-(tert-butyl)pyrimidin-2-yl, or 5-(trifluoromethyl)pyrimidin-2-yl.

In some embodiments, $R^3$ is pyrazolyl, imidazolyl, triazolyl, isoxazolyl, oxazolyl, oxadiazolyl, tetrazolyl, isothiazolyl, thiazolyl, or thiadiazolyl, each optionally substituted with one, two or three members independently selected from $C_{1-4}$alkyl, $C_{1-4}$haloalkyl, $OC_{1-4}$alkyl, $OC_{1-4}$haloalkyl, and phenyl, or each optionally substituted with one or two members independently selected from $C_{1-4}$alkyl and $C_{1-4}$haloalkyl. In some embodiments, $R^3$ is pyrazolyl, imidazolyl, or isoxazolyl, each optionally substituted with one or two members each independently selected from $C_{1-4}$alkyl and $C_{1-4}$haloalkyl. In some embodiments, $R^3$ is In some embodiments, $R^3$ is 1H-indazolyl, 2H-indazolyl, 1H-pyrrolo[2,3-b]pyridinyl, 1H-pyrrolo[3,2-c]pyridinyl, pyrrolo[1,2-b]pyridazinyl, 1H-pyrazolo[3,4-b]pyridinyl, pyrazolo[1,5-a]pyridinyl, imidazo[1,2-a]pyridinyl, imidazo[1,5-a]pyridinyl, or 1H-benzo[d]imidazolyl, each optionally substituted with one, two, or three members each independently selected from halo, $C_{1-4}$alkyl, $C_{1-4}$haloalkyl, $OC_{1-4}$alkyl, and $OC_{1-4}$haloalkyl, or each optionally substituted with one or two members each independently selected from F, $CH_3$, $CH_2CH_3$, $CH(CH_3)_2$, $CF_3$, and $CH_2CF_3$. In some embodiments, $R^3$ is 1-methyl-1H-indazol-4-yl, 1-methyl-1H-indazol-5-yl, 1-methyl-1H-indazol-6-yl, 1-methyl-1H-indazol-7-yl, 1-isopropyl-1H-indazol-6-yl, 2-isopropyl-2H-indazol-6-yl, 1-(2,2,2-trifluoroethyl)-1H-indazol-6-yl, 7-fluoro-1-methyl-1H-indazol-6-yl, 5-fluoro-1-methyl-1H-indazol-6-yl, 4-fluoro-1-methyl-1H-indazol-6-yl, 1,3-dimethyl-1H-indazol-6-yl, 1,4-dimethyl-1H-indazol-6-yl, 1,5-dimethyl-1H-indazol-6-yl, 1H-pyrrolo[2,3-b]pyridin-1-yl, 1-methyl-1H-pyrrolo[2,3-b]pyridin-3-yl, 1-methyl-1H-pyrrolo[2,3-b]pyridin-5-yl, 1-methyl-1H-pyrrolo[2,3-b]pyridin-6-yl, 6-methyl-1H-pyrrolo[2,3-b]pyridin-1-yl, 2-methyl-1H-pyrrolo[2,3-b]pyridin-1-yl, 6-isopropyl-1H-pyrrolo[2,3-b]pyridin-1-yl, 1-isopropyl-1H-pyrrolo[2,3-b]pyridin-6-yl, 6-(trifluoromethyl)-1H-pyrrolo[2,3-b]pyridin-1-yl, 2-(trifluoromethyl)-1H-pyrrolo[2,3-b]pyridin-1-yl, difluoro(1-methyl-1H-pyrrolo[2,3-b]pyridin-6-yl, 1-(2,2,2-trifluoroethyl)-1H-pyrrolo[2,3-b]pyridin-6-yl, 1,2-dimethyl-1H-pyrrolo[2,3-b]pyridin-6-yl, 1,3-dimethyl-1H-pyrrolo[2,3-b]pyridin-6-yl, 1,4-dimethyl-1H-pyrrolo[2,3-b]pyridin-6- yl, 1,5-dimethyl-1H-pyrrolo[2,3-b]pyridin-6-yl, 3-fluoro-1-methyl-1H-pyrrolo[2,3-b]pyridin-6-yl, 1-ethyl-3-fluoro-1H-pyrrolo[2,3-b]pyridin-6-yl, 1-methyl-3-(trifluoromethyl)-1H-pyrrolo[2,3-b]pyridin-6-yl, 1-methyl-1H-pyrrolo[3,2-c]pyridin-6-yl, pyrrolo[1,2-b]pyridazin-3-yl, 1-methyl-1H-pyrazolo[3,4-b]pyridin-6-yl, pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl, imidazo[1,2-a]pyridin-2-yl, imidazo[1,2-a]pyridin-3-yl, imidazo[1,2-a]pyridin-5-yl, imidazo[1,2-a]pyridin-7-yl, imidazo[1,2-a]pyridin-8-yl, imidazo[1,5-a]pyridin-1-yl, 1-methyl-1H-benzo[d]imidazol-2-yl, or 1-methyl-1H-benzo[d]imidazol-5-yl.

In some embodiments, $R^3$ is a fused 6-6 heteroaryl optionally substituted with one, two, or three members each independently selected from halo, $C_{1-4}$alkyl, $C_{1-4}$haloalkyl, $OC_{1-4}$alkyl, and $OC_{1-4}$haloalkyl. In some embodiments, $R^3$ is quinolinyl or isoquinolinyl, each optionally substituted with one or two members independently selected from halo, $C_{1-4}$alkyl, $C_{1-4}$haloalkyl, $OC_{1-4}$alkyl, and $OC_{1-4}$haloalkyl. In some embodiments, $R^3$ is

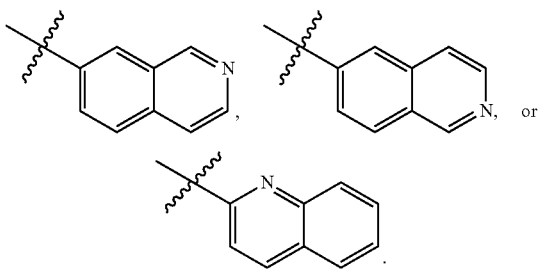

In some embodiments of Formula (I), $R^3$ is 6,7-dihydro-5H-cyclopenta[b]pyridin-2-yl, 5,6,7,8-tetrahydroimidazo[1,2-a]pyridin-2-yl, or 4,5,6,7-tetrahydropyrazolo[1,5-a]pyridin-2-yl.

In some embodiments of Formula (I), $R^3$ is

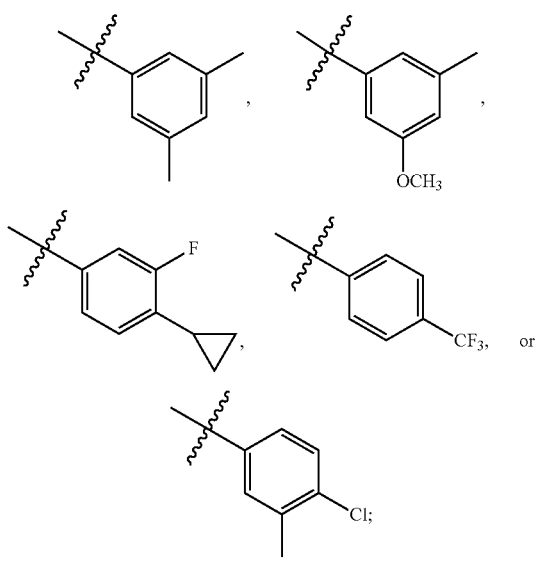

and A is

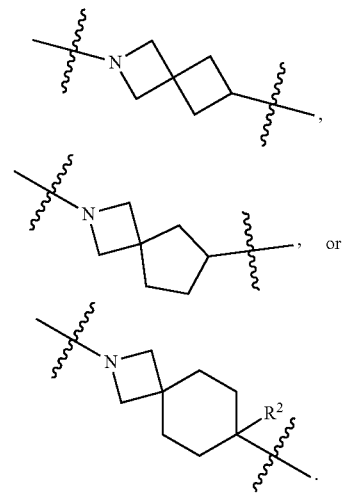

In some embodiments of Formula (I), L is a bond and A is

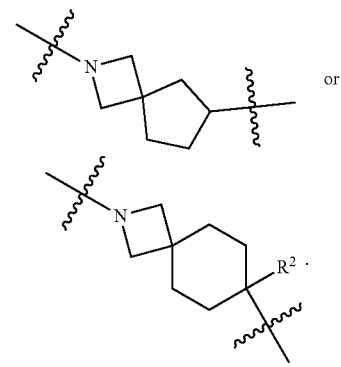

In some embodiments, L is a bond and $R^3$ is

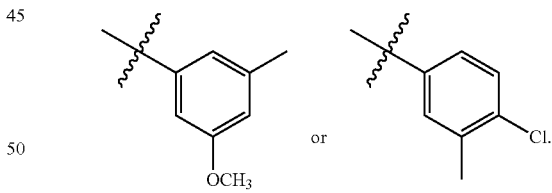

In some embodiments of Formula (I), $R^1$ is $CH_3$ and $R^2$ is H.

In some embodiments, the compound of Formula (I) is a compound in Table 1 or a single stereoisomer or mixture of stereoisomers thereof. Where stereochemistry in a chemical name includes a *S or *R stereochemical designation, the chemical name encompasses all compounds that are stereoisomeric at the designated center(s). Where an *S or *R is used in a chemical name, the chemical name provided refers to the compound with the absolute S or R stereochemistry as written or to a compound with any combination of S and R stereochemistry at those positions, or to mixtures thereof. For example, a compound name in Table 1 below with an *S designation refers to the S and R variations. A compound name in Table 1 below with two *S or *R designations refers to any one of the S/R, S/S, R/S, and S/S stereoisomers. Where the name includes a "(rac)" or racemic designation, the chemical name is intended to encompass a racemic mixture at that center or individual stereoisomers or mixtures thereof.

TABLE 1

| Entry | Compound Name |
|---|---|
| 1 | (6-(3-(tert-Butyl)phenyl)-2-azaspiro[3.3]heptan-2-yl)((1s,3s)-3-hydroxy-3-methylcyclobutyl)methanone; |
| 2 | (6-(4-(tert-Butyl)phenyl)-2-azaspiro[3.3]heptan-2-yl)((1s,3s)-3-hydroxy-3-methylcyclobutyl)methanone; |
| 3 | ((1s,3s)-3-Hydroxy-3-methylcyclobutyl)(6-(3-isopropylphenyl)-2-azaspiro[3.3]heptan-2-yl)methanone; |
| 4 | ((1s,3s)-3-Hydroxy-3-methylcyclobutyl)(6-(4-isopropylphenyl)-2-azaspiro[3.3]heptan-2-yl)methanone; |
| 5 | (6-(4-Cyclopropylphenyl)-2-azaspiro[3.3]heptan-2-yl)((1s,3s)-3-hydroxy-3-methylcyclobutyl)methanone; |
| 6 | ((1s,3s)-3-Hydroxy-3-methylcyclobutyl)(6-(4-methyl-3-(trifluoromethyl)phenyl)-2-azaspiro[3.3]heptan-2-yl)methanone; |
| 7 | (rac)-((1s,3s)-3-Hydroxy-3-methylcyclobutyl)(6-(2-methyl-3-(trifluoromethyl)phenyl)-2-azaspiro[3.4]octan-2-yl)methanone; |
| 8 | (rac)-((1s,3s)-3-Hydroxy-3-methylcyclobutyl)(6-(2-methyl-4-(trifluoromethyl)phenyl)-2-azaspiro[3.4]octan-2-yl)methanone; |
| 9 | (rac)-((1s,3s)-3-Hydroxy-3-methylcyclobutyl)(6-(2-methyl-4-(trifluoromethoxy)phenyl)-2-azaspiro[3.4]octan-2-yl)methanonemethanone; |
| 10 | (rac)-(6-(4-Chloro-2-methylphenyl)-2-azaspiro[3.4]octan-2-yl)((1s,3s)-3-hydroxy-3-methylcyclobutyl)methanone; |
| 11 | (rac)-(6-(3-Chloro-2-methylphenyl)-2-azaspiro[3.4]octan-2-yl)((1s,3s)-3-hydroxy-3-methylcyclobutyl)methanone; |
| 12 | (rac)-(6-(4-(Difluoromethyl)-3-methylphenyl)-2-azaspiro[3.4]octan-2-yl)((1s,3s)-3-hydroxy-3-methylcyclobutyl)methanone; |
| 13 | (rac)-((1s,3s)-3-Hydroxy-3-methylcyclobutyl)(6-(3-methoxy-2-methylphenyl)-2-azaspiro[3.4]octan-2-yl)methanone; |
| 14 | (rac)-(6-(2,4-Dimethylphenyl)-2-azaspiro[3.4]octan-2-yl)((1s,3s)-3-hydroxy-3-methylcyclobutyl)methanone; |
| 15 | (rac)-(6-(4-Chloro-3-ethylphenyl)-2-azaspiro[3.4]octan-2-yl)((1s,3s)-3-hydroxy-3-methylcyclobutyl)methanone; |
| 16 | (rac)-(6-(2,3-Dihydro-1H-inden-5-yl)-2-azaspiro[3.4]octan-2-yl)((1s,3s)-3-hydroxy-3-methylcyclobutyl)methanone; |
| 17 | (rac)-((1s,3s)-3-Hydroxy-3-methylcyclobutyl)(6-(3-methoxy-4-methylphenyl)-2-azaspiro[3.4]octan-2-yl)methanone; |
| 18 | ((1s,3*S)-3-Hydroxy-3-methylcyclobutyl)((*R)-6-(3-methoxy-4-methylphenyl)-2-azaspiro[3.4]octan-2-yl)methanone; |
| 19 | ((1s,3*R)-3-Hydroxy-3-methylcyclobutyl)((*S)-6-(3-methoxy-4-methylphenyl)-2-azaspiro[3.4]octan-2-yl)methanone; |
| 20 | (6-(3-Cyclopropylphenyl)-2-azaspiro[3.3]heptan-2-yl)((1s,3s)-3-hydroxy-3-methylcyclobutyl)methanone; |
| 21 | ((1s,3s)-3-Hydroxy-3-methylcyclobutyl)(6-(2-methyl-3-(trifluoromethyl)phenyl)-2-azaspiro[3.3]heptan-2-yl)methanone; |
| 22 | (7-(3-Chloro-4-methylphenyl)-2-azaspiro[3.5]nonan-2-yl)((1s,3s)-3-hydroxy-3-methylcyclobutyl)methanone; |
| 23 | ((1s,3s)-3-Hydroxy-3-methylcyclobutyl)(6-(4-methyl-3-(trifluoromethoxy)phenyl)-2-azaspiro[3.3]heptan-2-yl)methanone; |
| 24 | (rac)-(6-(3-Cyclopropyl-2-fluorophenyl)-2-azaspiro[3.4]octan-2-yl)((1s,3s)-3-hydroxy-3-methylcyclobutyl)methanone; |
| 25 | ((*R)-6-(3-Cyclopropyl-2-fluorophenyl)-2-azaspiro[3.4]octan-2-yl)((1s,3*S)-3-hydroxy-3-methylcyclobutyl)methanone; |
| 26 | ((*S)-6-(3-Cyclopropyl-2-fluorophenyl)-2-azaspiro[3.4]octan-2-yl)((1s,3*R)-3-hydroxy-3-methylcyclobutyl)methanone; |
| 27 | (6-(3-Cyclopropyl-4-methylphenyl)-2-azaspiro[3.3]heptan-2-yl)((1s,3s)-3-hydroxy-3-methylcyclobutyl)methanone; |
| 28 | (6-(4-Cyclopropyl-2-methylphenyl)-2-azaspiro[3.3]heptan-2-yl)((1s,3s)-3-hydroxy-3-methylcyclobutyl)methanone; |
| 29 | (rac)-(6-(6-(tert-Butyl)pyridin-2-yl)-2-azaspiro[3.4]octan-2-yl)((1s,3s)-3-hydroxy-3-methylcyclobutyl)methanone; |
| 30 | ((1s,3s)-3-Hydroxy-3-methylcyclobutyl)(6-(isoquinolin-7-yl)-2-azaspiro[3.3]heptan-2-yl)methanone; |
| 31 | ((1s,3s)-3-Hydroxy-3-methylcyclobutyl)(6-(isoquinolin-6-yl)-2-azaspiro[3.3]heptan-2-yl)methanone; |
| 32 | ((1s,3s)-3-Hydroxy-3-methylcyclobutyl)(6-(3-(pyrrolidin-1-yl)phenyl)-2-azaspiro[3.3]heptan-2-yl)methanone; |
| 33 | ((1s,3s)-3-Hydroxy-3-methylcyclobutyl)(6-(3-methyl-4-(trifluoromethyl)phenyl)-2-azaspiro[3.3]heptan-2-yl)methanone; |
| 34 | (6-(6-(tert-Butyl)pyridin-2-yl)-2-azaspiro[3.3]heptan-2-yl)((1s,3s)-3-hydroxy-3-methylcyclobutyl)methanone; |
| 35 | (rac)-((1s,3s)-3-Hydroxy-3-methylcyclobutyl)(6-(4-isopropylphenyl)-2-azaspiro[3.4]octan-2-yl)methanone; |
| 36 | ((1s,3s)-3-Hydroxy-3-methylcyclobutyl)(2-(3-isopropylphenyl)-6-azaspiro[3.4]octan-6-yl)methanone; |

TABLE 1-continued

| Entry | Compound Name |
|---|---|
| 37 | ((1s,3s)-3-Hydroxy-3-methylcyclobutyl)(7-phenyl-2-azaspiro[3.5]nonan-2-yl)methanone; |
| 38 | (rac)-(2-(3-(tert-Butyl)phenyl)-8-azaspiro[4.5]decan-8-yl)((1s,3s)-3-hydroxy-3-methylcyclobutyl)methanone; |
| 39 | (rac)-(2-(4-(tert-Butyl)phenyl)-8-azaspiro[4.5]decan-8-yl)((1s,3s)-3-hydroxy-3-methylcyclobutyl)methanone; |
| 40 | (rac)-((1s,3s)-3-Hydroxy-3-methylcyclobutyl)(6-(3-(trifluoromethoxy)phenyl)-2-azaspiro[3.4]octan-2-yl)methanone; |
| 41 | ((1s,3*S)-3-Hydroxy-3-methylcyclobutyl)((*R)-6-(3-(trifluoromethoxy)phenyl)-2-azaspiro[3.4]octan-2-yl)methanone; |
| 42 | ((1s,3*R)-3-Hydroxy-3-methylcyclobutyl)((*S)-6-(3-(trifluoromethoxy)phenyl)-2-azaspiro[3.4]octan-2-yl)methanone; |
| 43 | (rac)-(6-(3-(tert-Butyl)phenyl)-2-azaspiro[3.4]octan-2-yl)((1s,3s)-3-hydroxy-3-methylcyclobutyl)methanone; |
| 44 | ((*R)-6-(3-(tert-Butyl)phenyl)-2-azaspiro[3.4]octan-2-yl)((1s,3*S)-3-hydroxy-3-methylcyclobutyl)methanone; |
| 45 | ((*S)-6-(3-(tert-Butyl)phenyl)-2-azaspiro[3.4]octan-2-yl)((1s,3*R)-3-hydroxy-3-methylcyclobutyl)methanone; |
| 46 | (rac)-((1s,3s)-3-Hydroxy-3-methylcyclobutyl)(6-(3-isopropylphenyl)-2-azaspiro[3.4]octan-2-yl)methanone; |
| 47 | ((1s,3*S)-3-Hydroxy-3-methylcyclobutyl)((*R)-6-(3-isopropylphenyl)-2-azaspiro[3.4]octan-2-yl)methanone; |
| 48 | ((1s,3*R)-3-Hydroxy-3-methylcyclobutyl)((*S)-6-(3-isopropylphenyl)-2-azaspiro[3.4]octan-2-yl)methanone; |
| 49 | (rac)-(6-(4-Cyclopropylphenyl)-2-azaspiro[3.4]octan-2-yl)((1s,3s)-3-hydroxy-3-methylcyclobutyl)methanone; |
| 50 | ((*R)-6-(4-Cyclopropylphenyl)-2-azaspiro[3.4]octan-2-yl)((1s,3*S)-3-hydroxy-3-methylcyclobutyl)methanone; |
| 51 | ((*S)-6-(4-Cyclopropylphenyl)-2-azaspiro[3.4]octan-2-yl)((1s,3*R)-3-hydroxy-3-methylcyclobutyl)methanone; |
| 52 | (rac)-((1s,3s)-3-Hydroxy-3-methylcyclobutyl)(6-(4-(trifluoromethoxy)phenyl)-2-azaspiro[3.4]octan-2-yl)methanone; |
| 53 | ((1s,3*S)-3-Hydroxy-3-methylcyclobutyl)((*R)-6-(4-(trifluoromethoxy)phenyl)-2-azaspiro[3.4]octan-2-yl)methanone; |
| 54 | ((1s,3*R)-3-Hydroxy-3-methylcyclobutyl)((*S)-6-(4-(trifluoromethoxy)phenyl)-2-azaspiro[3.4]octan-2-yl)methanone; |
| 55 | (rac)-((1s,3s)-3-Hydroxy-3-methylcyclobutyl)(6-(4-(trifluoromethyl)phenyl)-2-azaspiro[3.4]octan-2-yl)methanone; |
| 56 | ((1s,3*S)-3-Hydroxy-3-methylcyclobutyl)((*R)-6-(4-(trifluoromethyl)phenyl)-2-azaspiro[3.4]octan-2-yl)methanone; |
| 57 | ((1s,3*R)-3-Hydroxy-3-methylcyclobutyl)((*S)-6-(4-(trifluoromethyl)phenyl)-2-azaspiro[3.4]octan-2-yl)methanone; |
| 58 | (rac)-(6-(3-Cyclopropylphenyl)-2-azaspiro[3.4]octan-2-yl)((1s,3s)-3-hydroxy-3-methylcyclobutyl)methanone; |
| 59 | ((*R)-6-(3-Cyclopropylphenyl)-2-azaspiro[3.4]octan-2-yl)((1s,3*S)-3-hydroxy-3-methylcyclobutyl)methanone; |
| 60 | ((*S)-6-(3-Cyclopropylphenyl)-2-azaspiro[3.4]octan-2-yl)((1s,3*R)-3-hydroxy-3-methylcyclobutyl)methanone; |
| 61 | (rac)-((1s,3s)-3-Hydroxy-3-methylcyclobutyl)(6-(3-(trifluoromethyl)phenyl)-2-azaspiro[3.4]octan-2-yl)methanone; |
| 62 | ((1s,3*S)-3-Hydroxy-3-methylcyclobutyl)((*R)-6-(3-(trifluoromethyl)phenyl)-2-azaspiro[3.4]octan-2-yl)methanone; |
| 63 | ((1s,3*R)-3-Hydroxy-3-methylcyclobutyl)((*S)-6-(3-(trifluoromethyl)phenyl)-2-azaspiro[3.4]octan-2-yl)methanone; |
| 64 | (rac)-(6-(3-Cyclobutylphenyl)-2-azaspiro[3.4]octan-2-yl)((1s,3s)-3-hydroxy-3-methylcyclobutyl)methanone; |
| 65 | (rac)-((1s,3s)-3-Hydroxy-3-methylcyclobutyl)(6-(4-methyl-3-(trifluoromethyl)phenyl)-2-azaspiro[3.4]octan-2-yl)methanone; |
| 66 | (rac)-((1s,3s)-3-Hydroxy-3-methylcyclobutyl)(6-(3-methyl-4-(trifluoromethoxy)phenyl)-2-azaspiro[3.4]octan-2-yl)methanone; |
| 67 | (rac)-((1s,3s)-3-Hydroxy-3-methylcyclobutyl)(6-(3-methyl-4-(trifluoromethyl)phenyl)-2-azaspiro[3.4]octan-2-yl)methanone; |
| 68 | (rac)-(6-(4-Chloro-3-methylphenyl)-2-azaspiro[3.4]octan-2-yl)((1s,3s)-3-hydroxy-3-methylcyclobutyl)methanone; |
| 69 | ((*R)-6-(4-Chloro-3-methylphenyl)-2-azaspiro[3.4]octan-2-yl)((1s,3*S)-3-hydroxy-3-methylcyclobutyl)methanone; |
| 70 | ((*S)-6-(4-Chloro-3-methylphenyl)-2-azaspiro[3.4]octan-2-yl)((1s,3*R)-3-hydroxy-3-methylcyclobutyl)methanone; |
| 71 | (rac)-(6-(3-Chloro-4-methylphenyl)-2-azaspiro[3.4]octan-2-yl)((1s,3s)-3-hydroxy-3-methylcyclobutyl)methanone; |
| 72 | (rac)-(6-(4-(Difluoromethoxy)-3-methylphenyl)-2-azaspiro[3.4]octan-2-yl)((1s,3s)-3-hydroxy-3-methylcyclobutyl)methanone; |
| 73 | ((*R)-6-(4-(Difluoromethoxy)-3-methylphenyl)-2-azaspiro[3.4]octan-2-yl)((1s,3*S)-3-hydroxy-3-methylcyclobutyl)methanone; |
| 74 | ((*S)-6-(4-(Difluoromethoxy)-3-methylphenyl)-2-azaspiro[3.4]octan-2-yl)((1s,3*R)-3-hydroxy-3-methylcyclobutyl)methanone; |
| 75 | (rac)-(6-(4-Cyclopropyl-2-methylphenyl)-2-azaspiro[3.4]octan-2-yl)((1s,3s)-3-hydroxy-3-methylcyclobutyl)methanone; |

TABLE 1-continued

| Entry | Compound Name |
|---|---|
| 76 | (rac)-((1s,3s)-3-Hydroxy-3-methylcyclobutyl)(6-(4-methoxy-3-methylphenyl)-2-azaspiro[3.4]octan-2-yl)methanone; |
| 77 | (rac)-((1s,3s)-3-Hydroxy-3-methylcyclobutyl)(6-(3-methyl-5-(trifluoromethyl)phenyl)-2-azaspiro[3.4]octan-2-yl)methanone; |
| 78 | (rac)-((1s,3s)-3-Hydroxy-3-methylcyclobutyl)(6-(2-methyl-5-(trifluoromethyl)phenyl)-2-azaspiro[3.4]octan-2-yl)methanone; |
| 79 | (rac)-(6-(2-Fluoro-3-methoxyphenyl)-2-azaspiro[3.4]octan-2-yl)((1s,3s)-3-hydroxy-3-methylcyclobutyl)methanone; |
| 80 | (rac)-((1s,3s)-3-Hydroxy-3-methylcyclobutyl)(6-(3-methoxy-5-methylphenyl)-2-azaspiro[3.4]octan-2-yl)methanone; |
| 81 | (rac)-(6-(5-Cyclopropyl-2-fluorophenyl)-2-azaspiro[3.4]octan-2-yl)((1s,3s)-3-hydroxy-3-methylcyclobutyl)methanone; |
| 82 | (rac)-(6-(3-(Difluoromethoxy)-4-methylphenyl)-2-azaspiro[3.4]octan-2-yl)((1s,3s)-3-hydroxy-3-methylcyclobutyl)methanone; |
| 83 | (rac)-(6-(4-(Difluoromethoxy)-2-methylphenyl)-2-azaspiro[3.4]octan-2-yl)((1s,3s)-3-hydroxy-3-methylcyclobutyl)methanone; |
| 84 | (rac)-(6-(3-(Difluoromethoxy)-5-methylphenyl)-2-azaspiro[3.4]octan-2-yl)((1s,3s)-3-hydroxy-3-methylcyclobutyl)methanone; |
| 85 | (rac)-(6-(5-(Difluoromethoxy)-2-methylphenyl)-2-azaspiro[3.4]octan-2-yl)((1s,3s)-3-hydroxy-3-methylcyclobutyl)methanone; |
| 86 | (rac)-(6-(3-Chloro-5-methoxyphenyl)-2-azaspiro[3.4]octan-2-yl)((1s,3s)-3-hydroxy-3-methylcyclobutyl)methanone; |
| 87 | (rac)-(6-(4-Chloro-3-methoxyphenyl)-2-azaspiro[3.4]octan-2-yl)((1s,3s)-3-hydroxy-3-methylcyclobutyl)methanone; |
| 88 | (rac)-((1s,3s)-3-Hydroxy-3-(trifluoromethyl)cyclobutyl)(6-(3-isopropylphenyl)-2-azaspiro[3.4]octan-2-yl)methanone; |
| 89 | (2-(3-(tert-Butyl)phenyl)-6-azaspiro[3.4]octan-6-yl)((1s,3s)-3-hydroxy-3-methylcyclobutyl)methanone; |
| 90 | (rac)-(6-(3-(1,1-Difluoroethyl)phenyl)-2-azaspiro[3.4]octan-2-yl)((1s,3s)-3-hydroxy-3-methylcyclobutyl)methanone; |
| 91 | (rac)-(6-(3-Ethylphenyl)-2-azaspiro[3.4]octan-2-yl)((1s,3s)-3-hydroxy-3-methylcyclobutyl)methanone; |
| 92 | (rac)-(6-(3-(Difluoromethyl)-4-methylphenyl)-2-azaspiro[3.4]octan-2-yl)((1s,3s)-3-hydroxy-3-methylcyclobutyl)methanone; |
| 93 | (rac)-((1s,3s)-3-Hydroxy-3-methylcyclobutyl)(6-(3-methyl-5-(trifluoromethoxy)phenyl)-2-azaspiro[3.4]octan-2-yl)methanone; |
| 94 | (rac)-(6-(3-(Difluoromethyl)-5-methylphenyl)-2-azaspiro[3.4]octan-2-yl)((1s,3s)-3-hydroxy-3-methylcyclobutyl)methanone; |
| 95 | (rac)-((1s,3s)-3-Hydroxy-3-methylcyclobutyl)(6-(2-methoxy-3-methylphenyl)-2-azaspiro[3.4]octan-2-yl)methanone; |
| 96 | (rac)-(6-(4-Ethylphenyl)-2-azaspiro[3.4]octan-2-yl)((1s,3s)-3-hydroxy-3-methylcyclobutyl)methanone; |
| 97 | (rac)-((1s,3s)-3-Hydroxy-3-methylcyclobutyl)(6-(pyrazolo[1,5-a]pyridin-5-yl)-2-azaspiro[3.4]octan-2-yl)methanone; |
| 98 | (rac)-(6-(2,6-Dimethylphenyl)-2-azaspiro[3.4]octan-2-yl)((1s,3s)-3-hydroxy-3-methylcyclobutyl)methanone; |
| 99 | (rac)-((1s,3s)-3-Hydroxy-3-methylcyclobutyl)(6-(1-methyl-1H-pyrazol-4-yl)-2-azaspiro[3.4]octan-2-yl)methanone; |
| 100 | (rac)-((1s,3s)-3-Hydroxy-3-methylcyclobutyl)(6-(1-methyl-3-(trifluoromethyl)-1H-pyrazol-4-yl)-2-azaspiro[3.4]octan-2-yl)methanone; |
| 101 | (rac)-((1s,3s)-3-Hydroxy-3-methylcyclobutyl)(6-(1-methyl-3-(trifluoromethyl)-1H-pyrazol-5-yl)-2-azaspiro[3.4]octan-2-yl)methanone; |
| 102 | (rac)-((1s,3s)-3-Hydroxy-3-methylcyclobutyl)(6-(1-methyl-1H-indazol-5-yl)-2-azaspiro[3.4]octan-2-yl)methanone; |
| 103 | (7-(4-Fluoro-3-methoxyphenyl)-2-azaspiro[3.5]nonan-2-yl)((1s,3s)-3-hydroxy-3-methylcyclobutyl)methanone; |
| 104 | (7-(3-Fluoro-5-methoxyphenyl)-2-azaspiro[3.5]nonan-2-yl)((1s,3s)-3-hydroxy-3-methylcyclobutyl)methanone; |
| 105 | ((1s,3s)-3-Hydroxy-3-methylcyclobutyl)(7-(4-methoxy-3-methylphenyl)-2-azaspiro[3.5]nonan-2-yl)methanone; |
| 106 | ((1s,3s)-3-Hydroxy-3-methylcyclobutyl)(7-(3-methoxy-2-methylphenyl)-2-azaspiro[3.5]nonan-2-yl)methanone; |
| 107 | (rac)-((1s,3s)-3-Hydroxy-3-methylcyclobutyl)(6-(4-methyl-3-(trifluoromethoxy)phenyl)-2-azaspiro[3.4]octan-2-yl)methanone; |
| 108 | (rac)-(6-(3-Cyclopropyl-4-fluorophenyl)-2-azaspiro[3.4]octan-2-yl)((1s,3s)-3-hydroxy-3-methylcyclobutyl)methanone; |
| 109 | (rac)-((1s,3s)-3-Hydroxy-3-methylcyclobutyl)(6-(1-methyl-5-(trifluoromethyl)-1H-pyrazol-4-yl)-2-azaspiro[3.4]octan-2-yl)methanone; |
| 110 | (rac)-((1s,3s)-3-Hydroxy-3-methylcyclobutyl)(6-(6-(trifluoromethyl)pyridin-2-yl)-2-azaspiro[3.4]octan-2-yl)methanone; |
| 111 | (rac)-((1s,3s)-3-Hydroxy-3-methylcyclobutyl)(6-(1-methyl-1H-benzo[d]imidazol-5-yl)-2-azaspiro[3.4]octan-2-yl)methanone; |
| 112 | (rac)-((1s,3s)-3-Hydroxy-3-methylcyclobutyl)(6-(1-methyl-1H-benzo[d]imidazol-2-yl)-2-azaspiro[3.4]octan-2-yl)methanone; |
| 113 | ((1s,3s)-3-Hydroxy-3-methylcyclobutyl)(7-(3-methoxy-4-(trifluoromethyl)phenyl)-2-azaspiro[3.5]nonan-2-yl)methanone; |
| 114 | ((1s,3s)-3-Hydroxy-3-methylcyclobutyl)(7-(4-methoxy-3-(trifluoromethyl)phenyl)-2-azaspiro[3.5]nonan-2-yl)methanone; |

TABLE 1-continued

| Entry | Compound Name |
|---|---|
| 115 | (7-(3-(Dimethylamino)-4-(trifluoromethyl)phenyl)-2-azaspiro[3.5]nonan-2-yl)((1s,3s)-3-hydroxy-3-methylcyclobutyl)methanone; |
| 116 | (7-(6-(tert-Butyl)pyridin-2-yl)-2-azaspiro[3.5]nonan-2-yl)((1s,3s)-3-hydroxy-3-methylcyclobutyl)methanone; |
| 117 | ((1s,3s)-3-Hydroxy-3-methylcyclobutyl)(7-(6-methoxypyridin-2-yl)-2-azaspiro[3.5]nonan-2-yl)methanone; |
| 118 | (7-(3-(tert-Butyl)-4-methoxyphenyl)-2-azaspiro[3.5]nonan-2-yl)((1s,3s)-3-hydroxy-3-methylcyclobutyl)methanone; |
| 119 | ((1s,3s)-3-Hydroxy-3-methylcyclobutyl)(7-(3-methoxy-5-(trifluoromethyl)phenyl)-2-azaspiro[3.5]nonan-2-yl)methanone; |
| 120 | (7-(3-Ethoxy-5-(trifluoromethyl)phenyl)-2-azaspiro[3.5]nonan-2-yl)((1s,3s)-3-hydroxy-3-methylcyclobutyl)methanone; |
| 121 | (7-(3-Ethyl-5-methylphenyl)-2-azaspiro[3.5]nonan-2-yl)((1s,3s)-3-hydroxy-3-methylcyclobutyl)methanone; |
| 122 | ((1s,3s)-3-Hydroxy-3-methylcyclobutyl)(7-(1-methyl-1H-indazol-5-yl)-2-azaspiro[3.5]nonan-2-yl)methanone; |
| 123 | (7-(3-(Dimethylamino)-5-(trifluoromethyl)phenyl)-2-azaspiro[3.5]nonan-2-yl)((1s,3s)-3-hydroxy-3-methylcyclobutyl)methanone; |
| 124 | ((1s,3s)-3-Hydroxy-3-methylcyclobutyl)(7-(quinolin-2-yl)-2-azaspiro[3.5]nonan-2-yl)methanone; |
| 125 | (rac)-(6-(3-Fluoro-5-isopropylphenyl)-2-azaspiro[3.4]octan-2-yl)((1s,3s)-3-hydroxy-3-methylcyclobutyl)methanone; |
| 126 | (rac)-(6-(3-(tert-Butyl)phenyl)-2-azaspiro[3.4]octan-2-yl)((1r,3s)-3-ethyl-3-hydroxycyclobutyl)methanone; |
| 127 | (7-(2,3-Dihydro-1H-inden-5-yl)-2-azaspiro[3.5]nonan-2-yl)((1s,3s)-3-hydroxy-3-methylcyclobutyl)methanone; |
| 128 | ((1s,3s)-3-Hydroxy-3-methylcyclobutyl)(7-(3-methoxy-5-methylphenyl)-2-azaspiro[3.5]nonan-2-yl)methanone; |
| 129 | ((1s,3s)-3-Hydroxy-3-methylcyclobutyl)(7-(3-methoxy-4-methylphenyl)-2-azaspiro[3.5]nonan-2-yl)methanone; |
| 130 | ((1s,3s)-3-Hydroxy-3-methylcyclobutyl)(7-(4-isopropylphenyl)-2-azaspiro[3.5]nonan-2-yl)methanone; |
| 131 | ((1s,3s)-3-Hydroxy-3-methylcyclobutyl)(7-(3-methoxyphenyl)-2-azaspiro[3.5]nonan-2-yl)methanone; |
| 132 | (7-(3-Ethoxyphenyl)-2-azaspiro[3.5]nonan-2-yl)((1s,3s)-3-hydroxy-3-methylcyclobutyl)methanone; |
| 133 | ((1s,3s)-3-Hydroxy-3-methylcyclobutyl)(7-(3-isopropylphenyl)-2-azaspiro[3.5]nonan-2-yl)methanone; |
| 134 | (7-(3,4-Dimethylphenyl)-2-azaspiro[3.5]nonan-2-yl)((1s,3s)-3-hydroxy-3-methylcyclobutyl)methanone; |
| 135 | (7-(3-(tert-Butyl)phenyl)-2-azaspiro[3.5]nonan-2-yl)((1s,3s)-3-hydroxy-3-methylcyclobutyl)methanone; |
| 136 | ((1s,3s)-3-Hydroxy-3-methylcyclobutyl)(7-(p-tolyl)-2-azaspiro[3.5]nonan-2-yl)methanone; |
| 137 | ((1s,3s)-3-Hydroxy-3-methylcyclobutyl)(7-(m-tolyl)-2-azaspiro[3.5]nonan-2-yl)methanone; |
| 138 | ((1s,3s)-3-Hydroxy-3-methylcyclobutyl)(7-(o-tolyl)-2-azaspiro[3.5]nonan-2-yl)methanone; |
| 139 | (7-(2-(tert-Butyl)pyridin-4-yl)-2-azaspiro[3.5]nonan-2-yl)((1s,3s)-3-hydroxy-3-methylcyclobutyl)methanone; |
| 140 | (7-(4-Cyclopropyl-3-methoxyphenyl)-2-azaspiro[3.5]nonan-2-yl)((1s,3s)-3-hydroxy-3-methylcyclobutyl)methanone; |
| 141 | (7-(3-Cyclopropyl-5-methoxyphenyl)-2-azaspiro[3.5]nonan-2-yl)((1s,3s)-3-hydroxy-3-methylcyclobutyl)methanone; |
| 142 | (7-(3-Cyclopropyl-4-methoxyphenyl)-2-azaspiro[3.5]nonan-2-yl)((1s,3s)-3-hydroxy-3-methylcyclobutyl)methanone; |
| 143 | (7-(3-Cyclopropyl-5-methylphenyl)-2-azaspiro[3.5]nonan-2-yl)((1s,3s)-3-hydroxy-3-methylcyclobutyl)methanone; |
| 144 | (7-(3-Ethyl-2-methoxyphenyl)-2-azaspiro[3.5]nonan-2-yl)((1s,3s)-3-hydroxy-3-methylcyclobutyl)methanone; |
| 145 | (7-(3-Ethyl-5-methoxyphenyl)-2-azaspiro[3.5]nonan-2-yl)((1s,3s)-3-hydroxy-3-methylcyclobutyl)methanone; |
| 146 | (7-(3-Ethyl-5-(trifluoromethyl)phenyl)-2-azaspiro[3.5]nonan-2-yl)((1s,3s)-3-hydroxy-3-methylcyclobutyl)methanone; |
| 147 | (7-(3,5-Dimethylphenyl)-2-azaspiro[3.5]nonan-2-yl)((1s,3s)-3-hydroxy-3-methylcyclobutyl)methanone; |
| 148 | (7-(3-Ethyl-5-(trifluoromethoxy)phenyl)-2-azaspiro[3.5]nonan-2-yl)((1s,3s)-3-hydroxy-3-methylcyclobutyl)methanone; |
| 149 | (7-(3-Chloro-5-(trifluoromethoxy)phenyl)-2-azaspiro[3.5]nonan-2-yl)((1s,3s)-3-hydroxy-3-methylcyclobutyl)methanone; |
| 150 | (7-(4-Ethoxy-3-(trifluoromethyl)phenyl)-2-azaspiro[3.5]nonan-2-yl)((1s,3s)-3-hydroxy-3-methylcyclobutyl)methanone; |
| 151 | ((1s,3s)-3-Hydroxy-3-methylcyclobutyl)(7-hydroxy-7-(3-isopropylphenyl)-2-azaspiro[3.5]nonan-2-yl)methanone; |
| 152 | (rac)-((1s,3s)-3-Hydroxy-3-methylcyclobutyl)(2-(4-(trifluoromethyl)phenyl)-8-azaspiro[4.5]decan-8-yl)methanone; |
| 153 | (2-(3-(tert-Butyl)phenyl)-7-azaspiro[3.5]nonan-7-yl)((1s,3s)-3-hydroxy-3-methylcyclobutyl)methanone; |

TABLE 1-continued

| Entry | Compound Name |
|---|---|
| 154 | (6-(3-Cyclopropyl-2-methylbenzyl)-2-azaspiro[3.3]heptan-2-yl)((1s,3s)-3-hydroxy-3-methylcyclobutyl)methanone; |
| 155 | ((1s,3s)-3-Hydroxy-3-methylcyclobutyl)(6-(2-methyl-3-(trifluoromethyl)benzyl)-2-azaspiro[3.3]heptan-2-yl)methanone; |
| 156 | (6-(2,3-Dimethylbenzyl)-2-azaspiro[3.3]heptan-2-yl)((1s,3s)-3-hydroxy-3-methylcyclobutyl)methanone; |
| 157 | (6-(3-(Difluoromethoxy)benzyl)-2-azaspiro[3.3]heptan-2-yl)((1s,3s)-3-hydroxy-3-methylcyclobutyl)methanone; |
| 158 | (6-(2-Ethylbenzyl)-2-azaspiro[3.3]heptan-2-yl)((1s,3s)-3-hydroxy-3-methylcyclobutyl)methanone; |
| 159 | ((1s,3s)-3-Hydroxy-3-methylcyclobutyl)(7-(3-methylbenzyl)-2-azaspiro[3.5]nonan-2-yl)methanone; |
| 160 | (7-(3-(Difluoromethoxy)benzyl)-2-azaspiro[3.5]nonan-2-yl)((1s,3s)-3-hydroxy-3-methylcyclobutyl)methanone; |
| 161 | (7-(4-(Difluoromethoxy)benzyl)-2-azaspiro[3.5]nonan-2-yl)((1s,3s)-3-hydroxy-3-methylcyclobutyl)methanone; |
| 162 | (7-(4-(Difluoromethyl)benzyl)-2-azaspiro[3.5]nonan-2-yl)((1s,3s)-3-hydroxy-3-methylcyclobutyl)methanone; |
| 163 | (7-(3-(Difluoromethyl)benzyl)-2-azaspiro[3.5]nonan-2-yl)((1s,3s)-3-hydroxy-3-methylcyclobutyl)methanone; |
| 164 | (6-Benzyl-2-azaspiro[3.3]heptan-2-yl)((1s,3s)-3-hydroxy-3-methylcyclobutyl)methanone; |
| 165 | ((1s,3s)-3-Hydroxy-3-methylcyclobutyl)(6-(3-methylbenzyl)-2-azaspiro[3.3]heptan-2-yl)methanone; |
| 166 | ((1s,3s)-3-Hydroxy-3-methylcyclobutyl)(6-(4-methylbenzyl)-2-azaspiro[3.3]heptan-2-yl)methanone; |
| 167 | ((1s,3s)-3-Hydroxy-3-methylcyclobutyl)(6-(pyridin-2-ylmethyl)-2-azaspiro[3.3]heptan-2-yl)methanone; |
| 168 | ((1s,3s)-3-Hydroxy-3-methylcyclobutyl)(6-(pyridin-3-ylmethyl)-2-azaspiro[3.3]heptan-2-yl)methanone; |
| 169 | (rac)-((1s,3s)-3-Hydroxy-3-methylcyclobutyl)(6-(4-methylbenzyl)-2-azaspiro[3.4]octan-2-yl)methanone; |
| 170 | (rac)-((1s,3s)-3-Hydroxy-3-methylcyclobutyl)(6-(4-isopropylbenzyl)-2-azaspiro[3.4]octan-2-yl)methanone; |
| 171 | (rac)-((1s,3s)-3-Hydroxy-3-methylcyclobutyl)(6-(4-(trifluoromethyl)benzyl)-2-azaspiro[3.4]octan-2-yl)methanone; |
| 172 | (2-Benzyl-7-azaspiro[3.5]nonan-7-yl)((1s,3s)-3-hydroxy-3-methylcyclobutyl)methanone; |
| 173 | ((1s,3s)-3-Hydroxy-3-methylcyclobutyl)(2-(4-methylbenzyl)-7-azaspiro[3.5]nonan-7-yl)methanone; |
| 174 | (rac)-((1s,3s)-3-Hydroxy-3-methylcyclobutyl)(6-(3-methylbenzyl)-2-azaspiro[3.4]octan-2-yl)methanone; |
| 175 | (rac)-((1s,3s)-3-Hydroxy-3-methylcyclobutyl)(6-(2-methylbenzyl)-2-azaspiro[3.4]octan-2-yl)methanone; |
| 176 | (rac)-((1s,3s)-3-Hydroxy-3-methylcyclobutyl)(6-(3-(trifluoromethyl)benzyl)-2-azaspiro[3.4]octan-2-yl)methanone; |
| 177 | ((1s,3*S)-3-Hydroxy-3-methylcyclobutyl)((*R)-6-(3-(trifluoromethyl)benzyl)-2-azaspiro[3.4]octan-2-yl)methanone; |
| 178 | ((1s,3*R)-3-Hydroxy-3-methylcyclobutyl)((*S)-6-(3-(trifluoromethyl)benzyl)-2-azaspiro[3.4]octan-2-yl)methanone; |
| 179 | (rac)-((1s,3s)-3-Hydroxy-3-methylcyclobutyl)(6-(4-(trifluoromethoxy)benzyl)-2-azaspiro[3.4]octan-2-yl)methanone; |
| 180 | (rac)-((1s,3s)-3-Hydroxy-3-methylcyclobutyl)(6-(3-(trifluoromethoxy)benzyl)-2-azaspiro[3.4]octan-2-yl)methanone; |
| 181 | (rac)-((1s,3s)-3-Hydroxy-3-methylcyclobutyl)(6-(3-isopropylbenzyl)-2-azaspiro[3.4]octan-2-yl)methanone; |
| 182 | (rac)-(6-(4-(Difluoromethyl)benzyl)-2-azaspiro[3.4]octan-2-yl)((1s,3s)-3-hydroxy-3-methylcyclobutyl)methanone; |
| 183 | (rac)-(6-(4-(Difluoromethoxy)benzyl)-2-azaspiro[3.4]octan-2-yl)((1s,3s)-3-hydroxy-3-methylcyclobutyl)methanone; |
| 184 | ((1s,3s)-3-Hydroxy-3-methylcyclobutyl)(6-(2-methylbenzyl)-2-azaspiro[3.3]heptan-2-yl)methanone; |
| 185 | ((1s,3s)-3-Hydroxy-3-methylcyclobutyl)(6-(4-isopropylbenzyl)-2-azaspiro[3.3]heptan-2-yl)methanone; |
| 186 | ((1s,3s)-3-Hydroxy-3-methylcyclobutyl)(6-(3-isopropylbenzyl)-2-azaspiro[3.3]heptan-2-yl)methanone; |
| 187 | ((1s,3s)-3-Hydroxy-3-methylcyclobutyl)(6-(2-isopropylbenzyl)-2-azaspiro[3.3]heptan-2-yl)methanone; |
| 188 | (6-(3,4-Dimethylbenzyl)-2-azaspiro[3.3]heptan-2-yl)((1s,3s)-3-hydroxy-3-methylcyclobutyl)methanone; |
| 189 | ((1s,3s)-3-Hydroxy-3-methylcyclobutyl)(6-(4-methyl-3-(trifluoromethyl)benzyl)-2-azaspiro[3.3]heptan-2-yl)methanone; |
| 190 | (6-((4-(tert-Butyl)pyridin-2-yl)methyl)-2-azaspiro[3.3]heptan-2-yl)((1s,3s)-3-hydroxy-3-methylcyclobutyl)methanone; |
| 191 | ((1s,3s)-3-Hydroxy-3-methylcyclobutyl)(6-((6-methoxypyridin-2-yl)methyl)-2-azaspiro[3.3]heptan-2-yl)methanone; |
| 192 | ((1s,3s)-3-Hydroxy-3-methylcyclobutyl)(6-(4-methoxybenzyl)-2-azaspiro[3.3]heptan-2-yl)methanone; |

TABLE 1-continued

| Entry | Compound Name |
|---|---|
| 193 | ((1s,3s)-3-Hydroxy-3-methylcyclobutyl)(6-(3-(trifluoromethyl)benzyl)-2-azaspiro[3.3]heptan-2-yl)methanone; |
| 194 | ((1s,3s)-3-Hydroxy-3-methylcyclobutyl)(6-(3-(trifluoromethoxy)benzyl)-2-azaspiro[3.3]heptan-2-yl)methanone; |
| 195 | ((1s,3s)-3-Hydroxy-3-methylcyclobutyl)(6-(4-(trifluoromethyl)benzyl)-2-azaspiro[3.3]heptan-2-yl)methanone; |
| 196 | ((1s,3s)-3-Hydroxy-3-methylcyclobutyl)(6-(2-(trifluoromethoxy)benzyl)-2-azaspiro[3.3]heptan-2-yl)methanone; |
| 197 | ((1s,3s)-3-Hydroxy-3-methylcyclobutyl)(6-(3-methoxybenzyl)-2-azaspiro[3.3]heptan-2-yl)methanone; |
| 198 | ((1s,3s)-3-Hydroxy-3-methylcyclobutyl)(6-(quinolin-2-ylmethyl)-2-azaspiro[3.3]heptan-2-yl)methanone; |
| 199 | ((1s,3s)-3-Hydroxy-3-methylcyclobutyl)(6-(2-(trifluoromethyl)benzyl)-2-azaspiro[3.3]heptan-2-yl)methanone; |
| 200 | (rac)-(6-(4-Cyclopropylbenzyl)-2-azaspiro[3.4]octan-2-yl)((1s,3s)-3-hydroxy-3-methylcyclobutyl)methanone; |
| 201 | (rac)-(6-(3-Cyclopropylbenzyl)-2-azaspiro[3.4]octan-2-yl)((1s,3s)-3-hydroxy-3-methylcyclobutyl)methanone; |
| 202 | (6-(4-Cyclopropyl-3-methylbenzyl)-2-azaspiro[3.3]heptan-2-yl)((1s,3s)-3-hydroxy-3-methylcyclobutyl)methanone; |
| 203 | (rac)-((1s,3s)-3-Hydroxy-3-methylcyclobutyl)(6-(2-methyl-4-(trifluoromethyl)benzyl)-2-azaspiro[3.4]octan-2-yl)methanone; |
| 204 | (rac)-((1s,3s)-3-Hydroxy-3-methylcyclobutyl)(6-(3-methyl-4-(trifluoromethyl)benzyl)-2-azaspiro[3.4]octan-2-yl)methanone; |
| 205 | (rac)-((1s,3s)-3-Hydroxy-3-methylcyclobutyl)(6-(4-methoxybenzyl)-2-azaspiro[3.4]octan-2-yl)methanone; |
| 206 | ((1s,3s)-3-Hydroxy-3-methylcyclobutyl)(6-(pyridin-4-ylmethyl)-2-azaspiro[3.3]heptan-2-yl)methanone; |
| 207 | (6-(2-Cyclopropyl-3-methylbenzyl)-2-azaspiro[3.3]heptan-2-yl)((1s,3s)-3-hydroxy-3-methylcyclobutyl)methanone; |
| 208 | (6-(2-(tert-Butyl)benzyl)-2-azaspiro[3.3]heptan-2-yl)((1s,3s)-3-hydroxy-3-methylcyclobutyl)methanone; |
| 209 | ((1s,3s)-3-Hydroxy-3-methylcyclobutyl)(6-(3-methyl-2-(trifluoromethyl)benzyl)-2-azaspiro[3.3]heptan-2-yl)methanone; |
| 210 | ((1s,3s)-3-Hydroxy-3-methylcyclobutyl)(6-(2-isopropyl-3-(trifluoromethyl)benzyl)-2-azaspiro[3.3]heptan-2-yl)methanone; |
| 211 | ((1s,3s)-3-Hydroxy-3-methylcyclobutyl)(6-(5-methyl-2-(trifluoromethyl)benzyl)-2-azaspiro[3.3]heptan-2-yl)methanone; |
| 212 | ((1s,3s)-3-Hydroxy-3-methylcyclobutyl)(6-(3-methyl-4-(trifluoromethyl)benzyl)-2-azaspiro[3.3]heptan-2-yl)methanone; |
| 213 | ((1s,3s)-3-Hydroxy-3-methylcyclobutyl)(6-(4-methyl-2-(trifluoromethyl)benzyl)-2-azaspiro[3.3]heptan-2-yl)methanone; |
| 214 | ((1s,3s)-3-Hydroxy-3-methylcyclobutyl)(6-((1-methyl-3-(trifluoromethyl)-1H-pyrazol-5-yl)methyl)-2-azaspiro[3.3]heptan-2-yl)methanone; |
| 215 | ((1s,3s)-3-Hydroxy-3-methylcyclobutyl)(6-((1-methyl-1H-indazol-6-yl)methyl)-2-azaspiro[3.3]heptan-2-yl)methanone; |
| 216 | ((1s,3s)-3-Hydroxy-3-methylcyclobutyl)(6-(2-methoxybenzyl)-2-azaspiro[3.3]heptan-2-yl)methanone; |
| 217 | ((1s,3s)-3-Hydroxy-3-methylcyclobutyl)(6-(4-methoxy-2-(trifluoromethyl)benzyl)-2-azaspiro[3.3]heptan-2-yl)methanone; |
| 218 | (6-(3-Cyclopropylbenzyl)-2-azaspiro[3.3]heptan-2-yl)((1s,3s)-3-hydroxy-3-methylcyclobutyl)methanone; |
| 219 | (6-(4-Cyclopropylbenzyl)-2-azaspiro[3.3]heptan-2-yl)((1s,3s)-3-hydroxy-3-methylcyclobutyl)methanone; |
| 220 | ((1s,3s)-3-Hydroxy-3-methylcyclobutyl)(6-(4-(trifluoromethoxy)benzyl)-2-azaspiro[3.3]heptan-2-yl)methanone; |
| 221 | (6-(4-(Difluoromethoxy)benzyl)-2-azaspiro[3.3]heptan-2-yl)((1s,3s)-3-hydroxy-3-methylcyclobutyl)methanone; |
| 222 | (6-(3-Ethylbenzyl)-2-azaspiro[3.3]heptan-2-yl)((1s,3s)-3-hydroxy-3-methylcyclobutyl)methanone; |
| 223 | ((1s,3s)-3-Hydroxy-3-methylcyclobutyl)(6-((6-(trifluoromethyl)pyridin-2-yl)methyl)-2-azaspiro[3.3]heptan-2-yl)methanone; |
| 224 | ((1s,3s)-3-Hydroxy-3-methylcyclobutyl)(6-((1-methyl-1H-pyrrolo[2,3-b]pyridin-6-yl)methyl)-2-azaspiro[3.3]heptan-2-yl)methanone; |
| 225 | ((1s,3s)-3-Hydroxy-3-methylcyclobutyl)(6-((1-methyl-3-(trifluoromethyl)-1H-pyrazol-4-yl)methyl)-2-azaspiro[3.3]heptan-2-yl)methanone; |
| 226 | ((1s,3s)-3-Hydroxy-3-methylcyclobutyl)(6-(2-methyl-6-(trifluoromethyl)benzyl)-2-azaspiro[3.3]heptan-2-yl)methanone; |
| 227 | (6-(3-Fluoro-2-methylbenzyl)-2-azaspiro[3.3]heptan-2-yl)((1s,3s)-3-hydroxy-3-methylcyclobutyl)methanone; |
| 228 | (6-(4-Fluoro-3-methylbenzyl)-2-azaspiro[3.3]heptan-2-yl)((1s,3s)-3-hydroxy-3-methylcyclobutyl)methanone; |
| 229 | (6-(3-Fluoro-4-methylbenzyl)-2-azaspiro[3.3]heptan-2-yl)((1s,3s)-3-hydroxy-3-methylcyclobutyl)methanone; |
| 230 | (6-(2-Fluoro-4-methylbenzyl)-2-azaspiro[3.3]heptan-2-yl)((1s,3s)-3-hydroxy-3-methylcyclobutyl)methanone; |
| 231 | (6-(3-(Difluoromethyl)benzyl)-2-azaspiro[3.3]heptan-2-yl)((1s,3s)-3-hydroxy-3-methylcyclobutyl)methanone; |

TABLE 1-continued

Entry Compound Name 232 (6-(4-(Difluoromethyl)benzyl)-2-azaspiro[3.3]heptan-2-yl)((1s,3s)-3-hydroxy-3-methylcyclobutyl)methanone;
233 (6-((6-(tert-Butyl)pyridin-2-yl)methyl)-2-azaspiro[3.3]heptan-2-yl)((1s,3s)-3-hydroxy-3-methylcyclobutyl)methanone;
234 (rac)-(6-Benzyl-2-azaspiro[3.4]octan-2-yl)((1s,3s)-3-hydroxy-3-methylcyclobutyl)methanone;
235 (7-Benzyl-2-azaspiro[3.5]nonan-2-yl)((1s,3s)-3-hydroxy-3-methylcyclobutyl)methanone;
236 ((1s,3s)-3-Hydroxy-3-methylcyclobutyl)(7-(2-methylbenzyl)-2-azaspiro[3.5]nonan-2-yl)methanone;
237 ((1s,3s)-3-Hydroxy-3-methylcyclobutyl)(6-((3-(trifluoromethyl)-1H-pyrazol-1-yl)methyl)-2-azaspiro[3.3]heptan-2-yl)methanone;
238 ((1s,3s)-3-Hydroxy-3-methylcyclobutyl)(6-(o-tolyloxy)-2-azaspiro[3.3]heptan-2-yl)methanone;
239 ((1s,3s)-3-Hydroxy-3-methylcyclobutyl)(7-(3-methyl-4-(trifluoromethyl)phenoxy)-2-azaspiro[3.5]nonan-2-yl)methanone;
240 (rac)-(6-(4-(tert-Butyl)phenoxy)-2-azaspiro[3.4]octan-2-yl)((1s,3s)-3-hydroxy-3-methylcyclobutyl)methanone;
241 ((1s,3s)-3-Hydroxy-3-methylcyclobutyl)(7-(3-isopropylphenoxy)-2-azaspiro[3.5]nonan-2-yl)methanone;
242 ((1s,3s)-3-Hydroxy-3-methylcyclobutyl)(7-(4-isopropylphenoxy)-2-azaspiro[3.5]nonan-2-yl)methanone;
243 (rac)-(6-(3-(tert-Butyl)phenoxy)-2-azaspiro[3.4]octan-2-yl)((1s,3s)-3-hydroxy-3-methylcyclobutyl)methanone;
244 (6-(3-(tert-Butyl)phenoxy)-2-azaspiro[3.3]heptan-2-yl)((1s,3s)-3-hydroxy-3-methylcyclobutyl)methanone;
245 ((1s,3s)-3-Hydroxy-3-methylcyclobutyl)(2-(p-tolyloxy)-7-azaspiro[3.5]nonan-7-yl)methanone;
246 (6-(4-(tert-Butyl)phenoxy)-2-azaspiro[3.3]heptan-2-yl)((1s,3s)-3-hydroxy-3-methylcyclobutyl)methanone;
247 ((1s,3s)-3-Hydroxy-3-methylcyclobutyl)(6-(3-methyl-4-(trifluoromethyl)phenoxy)-2-azaspiro[3.3]heptan-2-yl)methanone;
248 ((1s,3s)-3-Hydroxy-3-methylcyclobutyl)(6-(4-methyl-3-(trifluoromethyl)phenoxy)-2-azaspiro[3.3]heptan-2-yl)methanone;
249 ((1s,3s)-3-Hydroxy-3-methylcyclobutyl)(6-(2-methyl-4-(trifluoromethyl)phenoxy)-2-azaspiro[3.3]heptan-2-yl)methanone;
250 ((1s,3s)-3-Hydroxy-3-methylcyclobutyl)(6-(3-methyl-2-(trifluoromethyl)phenoxy)-2-azaspiro[3.3]heptan-2-yl)methanone;
251 ((1s,3s)-3-Hydroxy-3-methylcyclobutyl)(6-(3-isopropyl-2-(trifluoromethyl)phenoxy)-2-azaspiro[3.3]heptan-2-yl)methanone;
252 ((1s,3s)-3-Hydroxy-3-methylcyclobutyl)(6-(2-methyl-3-(trifluoromethyl)phenoxy)-2-azaspiro[3.3]heptan-2-yl)methanone;
253 (rac)-((1s,3s)-3-Hydroxy-3-methylcyclobutyl)(6-(2-methyl-3-(trifluoromethyl)phenoxy)-2-azaspiro[3.4]octan-2-yl)methanone;
254 (rac)-((1s,3s)-3-Hydroxy-3-methylcyclobutyl)(6-(3-methyl-4-(trifluoromethyl)phenoxy)-2-azaspiro[3.4]octan-2-yl)methanone;
255 (rac)-((1s,3s)-3-Hydroxy-3-methylcyclobutyl)(6-(2-methyl-4-(trifluoromethyl)phenoxy)-2-azaspiro[3.4]octan-2-yl)methanone;
256 (rac)-((1s,3s)-3-Hydroxy-3-methylcyclobutyl)(6-(4-methyl-3-(trifluoromethyl)phenoxy)-2-azaspiro[3.4]octan-2-yl)methanone;
257 (7-(3-(tert-Butyl)phenoxy)-2-azaspiro[3.5]nonan-2-yl)((1s,3s)-3-hydroxy-3-methylcyclobutyl)methanone;
258 ((1s,3s)-3-Hydroxy-3-methylcyclobutyl)(7-(2-methyl-4-(trifluoromethyl)phenoxy)-2-azaspiro[3.5]nonan-2-yl)methanone;
259 ((1s,3s)-3-Hydroxy-3-methylcyclobutyl)(7-(4-methyl-3-(trifluoromethyl)phenoxy)-2-azaspiro[3.5]nonan-2-yl)methanone;
260 (7-(4-(tert-Butyl)phenoxy)-2-azaspiro[3.5]nonan-2-yl)((1s,3s)-3-hydroxy-3-methylcyclobutyl)methanone;
261 (7-(4-Cyclopropylphenoxy)-2-azaspiro[3.5]nonan-2-yl)((1s,3s)-3-hydroxy-3-methylcyclobutyl)methanone;
262 ((1s,3s)-3-Hydroxy-3-methylcyclobutyl)(7-(4-(trifluoromethoxy)phenoxy)-2-azaspiro[3.5]nonan-2-yl)methanone;
263 ((1s,3s)-3-Hydroxy-3-methylcyclobutyl)(7-(3-(trifluoromethoxy)phenoxy)-2-azaspiro[3.5]nonan-2-yl)methanone;
264 (7-(3-Cyclopropylphenoxy)-2-azaspiro[3.5]nonan-2-yl)((1s,3s)-3-hydroxy-3-methylcyclobutyl)methanone;
265 ((1s,3s)-3-Hydroxy-3-methylcyclobutyl)(7-(2-isopropylphenoxy)-2-azaspiro[3.5]nonan-2-yl)methanone;
266 ((1s,3s)-3-Hydroxy-3-methylcyclobutyl)(7-(3-isopropylphenyl)-7-methoxy-2-azaspiro[3.5]nonan-2-yl)methanone;
267 ((1s,3s)-3-Hydroxy-3-methylcyclobutyl)(6-(3-methyl-5-(trifluoromethyl)phenyl)-2-azaspiro[3.3]heptan-2-yl)methanone;
268 ((1s,3s)-3-Hydroxy-3-methylcyclobutyl)(6-(1-methyl-1H-pyrrolo[2,3-b]pyridin-5-yl)-2-azaspiro[3.3]heptan-2-yl)methanone;
269 ((1s,3s)-3-Hydroxy-3-methylcyclobutyl)(6-(1-methyl-1H-pyrrolo[2,3-b]pyridin-6-yl)-2-azaspiro[3.3]heptan-2-yl)methanone;
270 (6-Benzyl-6-methoxy-2-azaspiro[3.3]heptan-2-yl)((1s,3s)-3-hydroxy-3-methylcyclobutyl)methanone;

TABLE 1-continued

| Entry | Compound Name |
|---|---|
| 271 | (6-(2-Cyclopropylbenzyl)-2-azaspiro[3.3]heptan-2-yl)((1s,3s)-3-hydroxy-3-methylcyclobutyl)methanone; |
| 272 | (6-(4-Cyclopropoxybenzyl)-2-azaspiro[3.3]heptan-2-yl)((1s,3s)-3-hydroxy-3-methylcyclobutyl)methanone; |
| 273 | (6-(4-Fluoro-2-methylbenzyl)-2-azaspiro[3.3]heptan-2-yl)((1s,3s)-3-hydroxy-3-methylcyclobutyl)methanone; |
| 274 | (6-(2-(Difluoromethyl)-4-methoxybenzyl)-2-azaspiro[3.3]heptan-2-yl)((1s,3s)-3-hydroxy-3-methylcyclobutyl)methanone; |
| 275 | (6-(4-(Difluoromethyl)-2-methoxybenzyl)-2-azaspiro[3.3]heptan-2-yl)((1s,3s)-3-hydroxy-3-methylcyclobutyl)methanone; |
| 276 | ((1s,3s)-3-Hydroxy-3-methylcyclobutyl)(6-(3-methoxy-4-(trifluoromethyl)benzyl)-2-azaspiro[3.3]heptan-2-yl)methanone; |
| 277 | ((1s,3s)-3-Hydroxy-3-methylcyclobutyl)(6-((5-methyl-6-(trifluoromethyl)pyridin-2-yl)methyl)-2-azaspiro[3.3]heptan-2-yl)methanone; |
| 278 | ((1s,3s)-3-Hydroxy-3-methylcyclobutyl)(6-((6-methyl-5-(trifluoromethyl)pyridin-2-yl)methyl)-2-azaspiro[3.3]heptan-2-yl)methanone; |
| 279 | ((1s,3s)-3-Hydroxy-3-methylcyclobutyl)(6-((6-isopropoxy-5-methylpyridin-2-yl)methyl)-2-azaspiro[3.3]heptan-2-yl)methanone; |
| 280 | (6-((5-(Difluoromethoxy)-6-methylpyridin-2-yl)methyl)-2-azaspiro[3.3]heptan-2-yl)((1s,3s)-3-hydroxy-3-methylcyclobutyl)methanone; |
| 281 | ((1s,3s)-3-Hydroxy-3-methylcyclobutyl)(6-((6-methoxy-5-(trifluoromethyl)pyridin-2-yl)methyl)-2-azaspiro[3.3]heptan-2-yl)methanone; |
| 282 | ((1s,3s)-3-Hydroxy-3-methylcyclobutyl)(6-((6-isopropoxy-5-(trifluoromethyl)pyridin-2-yl)methyl)-2-azaspiro[3.3]heptan-2-yl)methanone; |
| 283 | ((1s,3s)-3-Hydroxy-3-methylcyclobutyl)(6-((1-methyl-5-(trifluoromethyl)-1H-pyrazol-3-yl)methyl)-2-azaspiro[3.3]heptan-2-yl)methanone; |
| 284 | ((1s,3s)-3-Hydroxy-3-methylcyclobutyl)(6-(pyrazolo[1,5-a]pyridin-6-ylmethyl)-2-azaspiro[3.3]heptan-2-yl)methanone; |
| 285 | ((1s,3s)-3-Hydroxy-3-methylcyclobutyl)(6-(pyrazolo[1,5-a]pyridin-7-ylmethyl)-2-azaspiro[3.3]heptan-2-yl)methanone; |
| 286 | (6-((1H-Pyrrolo[2,3-b]pyridin-1-yl)methyl)-2-azaspiro[3.3]heptan-2-yl)((1s,3s)-3-hydroxy-3-methylcyclobutyl)methanone; |
| 287 | ((1s,3s)-3-Hydroxy-3-methylcyclobutyl)(6-((2-methyl-1H-pyrrolo[2,3-b]pyridin-1-yl)methyl)-2-azaspiro[3.3]heptan-2-yl)methanone; |
| 288 | ((1s,3s)-3-Hydroxy-3-methylcyclobutyl)(6-((6-methyl-1H-pyrrolo[2,3-b]pyridin-1-yl)methyl)-2-azaspiro[3.3]heptan-2-yl)methanone; |
| 289 | ((1s,3s)-3-Hydroxy-3-methylcyclobutyl)(6-((1-isopropyl-1H-pyrrolo[2,3-b]pyridin-6-yl)methyl)-2-azaspiro[3.3]heptan-2-yl)methanone; |
| 290 | ((1s,3s)-3-Hydroxy-3-methylcyclobutyl)(6-((6-isopropyl-1H-pyrrolo[2,3-b]pyridin-1-yl)methyl)-2-azaspiro[3.3]heptan-2-yl)methanone; |
| 291 | (6-((1,3-Dimethyl-1H-pyrrolo[2,3-b]pyridin-6-yl)methyl)-2-azaspiro[3.3]heptan-2-yl)((1s,3s)-3-hydroxy-3-methylcyclobutyl)methanone; |
| 292 | (6-((1,2-Dimethyl-1H-pyrrolo[2,3-b]pyridin-6-yl)methyl)-2-azaspiro[3.3]heptan-2-yl)((1s,3s)-3-hydroxy-3-methylcyclobutyl)methanone; |
| 293 | (6-((3-Fluoro-1-methyl-1H-pyrrolo[2,3-b]pyridin-6-yl)methyl)-2-azaspiro[3.3]heptan-2-yl)((1s,3s)-3-hydroxy-3-methylcyclobutyl)methanone; |
| 294 | ((1s,3s)-3-Hydroxy-3-methylcyclobutyl)(6-((2-(trifluoromethyl)-1H-pyrrolo[2,3-b]pyridin-1-yl)methyl)-2-azaspiro[3.3]heptan-2-yl)methanone; |
| 295 | ((1s,3s)-3-Hydroxy-3-methylcyclobutyl)(6-((6-(trifluoromethyl)-1H-pyrrolo[2,3-b]pyridin-1-yl)methyl)-2-azaspiro[3.3]heptan-2-yl)methanone; |
| 296 | ((1s,3s)-3-Hydroxy-3-methylcyclobutyl)(6-((1-methyl-3-(trifluoromethyl)-1H-pyrrolo[2,3-b]pyridin-6-yl)methyl)-2-azaspiro[3.3]heptan-2-yl)methanone; |
| 297 | ((1s,3s)-3-Hydroxy-3-methylcyclobutyl)(6-((1-(2,2,2-trifluoroethyl)-1H-pyrrolo[2,3-b]pyridin-6-yl)methyl)-2-azaspiro[3.3]heptan-2-yl)methanone; |
| 298 | ((1s,3s)-3-Hydroxy-3-methylcyclobutyl)(6-((1-methyl-1H-pyrrolo[3,2-c]pyridin-6-yl)methyl)-2-azaspiro[3.3]heptan-2-yl)methanone; |
| 299 | ((1s,3s)-3-Hydroxy-3-methylcyclobutyl)(6-((1-methyl-1H-indazol-7-yl)methyl)-2-azaspiro[3.3]heptan-2-yl)methanone; |
| 300 | (6-((1,4-Dimethyl-1H-indazol-6-yl)methyl)-2-azaspiro[3.3]heptan-2-yl)((1s,3s)-3-hydroxy-3-methylcyclobutyl)methanone; |
| 301 | (6-((1,5-Dimethyl-1H-indazol-6-yl)methyl)-2-azaspiro[3.3]heptan-2-yl)((1s,3s)-3-hydroxy-3-methylcyclobutyl)methanone; |
| 302 | (6-((1,3-Dimethyl-1H-indazol-6-yl)methyl)-2-azaspiro[3.3]heptan-2-yl)((1s,3s)-3-hydroxy-3-methylcyclobutyl)methanone; |
| 303 | (6-((4-Fluoro-1-methyl-1H-indazol-6-yl)methyl)-2-azaspiro[3.3]heptan-2-yl)((1s,3s)-3-hydroxy-3-methylcyclobutyl)methanone; |
| 304 | (6-((5-Fluoro-1-methyl-1H-indazol-6-yl)methyl)-2-azaspiro[3.3]heptan-2-yl)((1s,3s)-3-hydroxy-3-methylcyclobutyl)methanone; |
| 305 | (6-((7-Fluoro-1-methyl-1H-indazol-6-yl)methyl)-2-azaspiro[3.3]heptan-2-yl)((1s,3s)-3-hydroxy-3-methylcyclobutyl)methanone; |
| 306 | ((1s,3s)-3-Hydroxy-3-methylcyclobutyl)(6-((1-isopropyl-1H-indazol-6-yl)methyl)-2-azaspiro[3.3]heptan-2-yl)methanone; |
| 307 | ((1s,3s)-3-Hydroxy-3-methylcyclobutyl)(6-((1-(2,2,2-trifluoroethyl)-1H-indazol-6-yl)methyl)-2-azaspiro[3.3]heptan-2-yl)methanone; |
| 308 | ((1s,3s)-3-Hydroxy-3-methylcyclobutyl)(6-((2-isopropyl-2H-indazol-6-yl)methyl)-2-azaspiro[3.3]heptan-2-yl)methanone; |
| 309 | ((1s,3s)-3-Hydroxy-3-methylcyclobutyl)(6-((6-methyl-5-(trifluoromethyl)pyridin-2-yl)oxy)-2-azaspiro[3.3]heptan-2-yl)methanone; |

TABLE 1-continued

| Entry | Compound Name |
|---|---|
| 310 | ((1s,3*S)-3-Hydroxy-3-methylcyclobutyl)(6-((*R)-1-phenylethyl)-2-azaspiro[3.3]heptan-2-yl)methanone; |
| 311 | ((1s,3*R)-3-Hydroxy-3-methylcyclobutyl)(6-((*S)-1-phenylethyl)-2-azaspiro[3.3]heptan-2-yl)methanone; |
| 312 | ((1s,3*S)-3-Hydroxy-3-methylcyclobutyl)(6-((*R)-1-(6-methyl-5-(trifluoromethyl)pyridin-2-yl)ethyl)-2-azaspiro[3.3]heptan-2-yl)methanone; |
| 313 | ((1s,3*R)-3-Hydroxy-3-methylcyclobutyl)(6-((*S)-1-(6-methyl-5-(trifluoromethyl)pyridin-2-yl)ethyl)-2-azaspiro[3.3]heptan-2-yl)methanone; |
| 314 | ((1s,3*S)-3-Hydroxy-3-methylcyclobutyl)(6-((*R)-1-(1-methyl-1H-indazol-6-yl)ethyl)-2-azaspiro[3.3]heptan-2-yl)methanone; |
| 315 | ((1s,3*R)-3-Hydroxy-3-methylcyclobutyl)(6-((*S)-1-(1-methyl-1H-indazol-6-yl)ethyl)-2-azaspiro[3.3]heptan-2-yl)methanone; |
| 316 | (rac)-((1s,3s)-3-Hydroxy-3-methylcyclobutyl)(6-(1-(pyrazolo[1,5-a]pyridin-7-yl)ethyl)-2-azaspiro[3.3]heptan-2-yl)methanone; |
| 317 | (6-(Difluoro(1-methyl-1H-pyrrolo[2,3-b]pyridin-6-yl)methyl)-2-azaspiro[3.3]heptan-2-yl)((1s,3s)-3-hydroxy-3-methylcyclobutyl)methanone; |
| 318 | ((1s,3*S)-3-Hydroxy-3-methylcyclobutyl)((6*R)-6-(3-isopropylphenyl)-1-methyl-2-azaspiro[3.4]octan-2-yl)methanone; |
| 319 | (rac)-((1s,3s)-3-(Difluoromethyl)-3-hydroxycyclobutyl)(6-(3-isopropylphenyl)-2-azaspiro[3.4]octan-2-yl)methanone; |
| 320 | (rac)-(6-(4-(1,1-Difluoroethyl)phenyl)-2-azaspiro[3.4]octan-2-yl)((1s,3s)-3-hydroxy-3-methylcyclobutyl)methanone; |
| 321 | ((*S)-6-(2,4-Dimethylphenyl)-2-azaspiro[3.4]octan-2-yl)((1s,3*R)-3-hydroxy-3-methylcyclobutyl)methanone; |
| 322 | ((*R)-6-(2,4-Dimethylphenyl)-2-azaspiro[3.4]octan-2-yl)((1s,3*S)-3-hydroxy-3-methylcyclobutyl)methanone; |
| 323 | (rac)-(6-(2,3-Dihydrobenzofuran-6-yl)-2-azaspiro[3.4]octan-2-yl)((1s,3s)-3-hydroxy-3-methylcyclobutyl)methanone; |
| 324 | (rac)-((1s,3s)-3-Hydroxy-3-methylcyclobutyl)(6-(pyrazolo[1,5-a]pyridin-4-yl)-2-azaspiro[3.4]octan-2-yl)methanone; |
| 325 | (rac)-((1s,3s)-3-Hydroxy-3-methylcyclobutyl)(6-(pyrazolo[1,5-a]pyridin-2-yl)-2-azaspiro[3.4]octan-2-yl)methanone; |
| 326 | (rac)-((1s,3s)-3-Hydroxy-3-methylcyclobutyl)(6-(1-methyl-1H-indazol-4-yl)-2-azaspiro[3.4]octan-2-yl)methanone; |
| 327 | (rac)-((1s,3s)-3-Hydroxy-3-methylcyclobutyl)(6-(imidazo[1,2-a]pyridin-8-yl)-2-azaspiro[3.4]octan-2-yl)methanone; |
| 328 | (rac)-((1s,3s)-3-Hydroxy-3-methylcyclobutyl)(6-(imidazo[1,2-a]pyridin-7-yl)-2-azaspiro[3.4]octan-2-yl)methanone; |
| 329 | (rac)-((1s,3s)-3-Hydroxy-3-methylcyclobutyl)(6-(imidazo[1,5-a]pyridin-1-yl)-2-azaspiro[3.4]octan-2-yl)methanone; |
| 330 | (rac)-((1s,3s)-3-Hydroxy-3-methylcyclobutyl)(6-(5,6,7,8-tetrahydroimidazo[1,5-a]pyridin-1-yl)-2-azaspiro[3.4]octan-2-yl)methanone; |
| 331 | (rac)-((1s,3s)-3-Hydroxy-3-methylcyclobutyl)(6-(4,5,6,7-tetrahydropyrazolo[1,5-a]pyridin-2-yl)-2-azaspiro[3.4]octan-2-yl)methanone; |
| 332 | (rac)-(6-(3-Cyclopropyl-4-methylphenoxy)-2-azaspiro[3.4]octan-2-yl)((1s,3s)-3-hydroxy-3-methylcyclobutyl)methanone; |
| 333 | (rac)-(6-(3-Cyclopropyl-2-methylphenoxy)-2-azaspiro[3.4]octan-2-yl)((1s,3s)-3-hydroxy-3-methylcyclobutyl)methanone; |
| 334 | (rac)-(6-(3-Cyclopropyl-2-fluorophenoxy)-2-azaspiro[3.4]octan-2-yl)((1s,3s)-3-hydroxy-3-methylcyclobutyl)methanone; |
| 335 | (rac)-(6-(3-Cyclopropyl-4-fluorophenoxy)-2-azaspiro[3.4]octan-2-yl)((1s,3s)-3-hydroxy-3-methylcyclobutyl)methanone; |
| 336 | (rac)-((1s,3s)-3-Hydroxy-3-methylcyclobutyl)(6-((5-methyl-6-(trifluoromethyl)pyridin-2-yl)oxy)-2-azaspiro[3.4]octan-2-yl)methanone; |
| 337 | ((1s,3*S)-3-Hydroxy-3-methylcyclobutyl)((*R)-6-((*R)-1-phenylethyl)-2-azaspiro[3.4]octan-2-yl)methanone; |
| 338 | ((1s,3*R)-3-Hydroxy-3-methylcyclobutyl)((*S)-6-((*R)-1-phenylethyl)-2-azaspiro[3.4]octan-2-yl)methanone; |
| 339 | ((1s,3*R)-3-Hydroxy-3-methylcyclobutyl)((*S)-6-((*S)-1-phenylethyl)-2-azaspiro[3.4]octan-2-yl)methanone; |
| 340 | (7-Fluoro-7-phenyl-2-azaspiro[3.5]nonan-2-yl)((1s,3s)-3-hydroxy-3-methylcyclobutyl)methanone; |
| 341 | (7-Fluoro-7-(1-methyl-1H-pyrrolo[2,3-b]pyridin-6-yl)-2-azaspiro[3.5]nonan-2-yl)((1s,3s)-3-hydroxy-3-methylcyclobutyl)methanone; |
| 342 | ((1s,3s)-3-Hydroxy-3-methylcyclobutyl)(7-methoxy-7-phenyl-2-azaspiro[3.5]nonan-2-yl)methanone; |
| 343 | ((1s,3s)-3-Hydroxy-3-methylcyclobutyl)(7-methoxy-7-(o-tolyl)-2-azaspiro[3.5]nonan-2-yl)methanone; |
| 344 | (7-(3,5-Dimethylphenyl)-7-methoxy-2-azaspiro[3.5]nonan-2-yl)((1s,3s)-3-hydroxy-3-methylcyclobutyl)methanone; |
| 345 | ((1s,3s)-3-Hydroxy-3-methylcyclobutyl)(7-(3-(1-methyl-1H-imidazol-4-yl)phenyl)-2-azaspiro[3.5]nonan-2-yl)methanone; |
| 346 | (7-(4-(1H-Pyrazol-1-yl)phenyl)-2-azaspiro[3.5]nonan-2-yl)((1s,3s)-3-hydroxy-3-methylcyclobutyl)methanone; |
| 347 | (7-(3-(1H-Pyrazol-1-yl)phenyl)-2-azaspiro[3.5]nonan-2-yl)((1s,3s)-3-hydroxy-3-methylcyclobutyl)methanone; |
| 348 | ((1*S,4r,7*S)-7-(3,5-Dimethylphenyl)-1-methyl-2-azaspiro[3.5]nonan-2-yl)((1s,3*R)-3-hydroxy-3-methylcyclobutyl)methanone; |

TABLE 1-continued

| Entry | Compound Name |
|---|---|
| 349 | ((1*R,4r,7*R)-7-(3,5-Dimethylphenyl)-1-methyl-2-azaspiro[3.5]nonan-2-yl)((1s,3*S)-3-hydroxy-3-methylcyclobutyl)methanone; |
| 350 | ((1*S,4s,7*R)-7-(3,5-Dimethylphenyl)-1-methyl-2-azaspiro[3.5]nonan-2-yl)((1s,3*R)-3-hydroxy-3-methylcyclobutyl)methanone; |
| 351 | ((1*R,4s,7*S)-7-(3,5-Dimethylphenyl)-1-methyl-2-azaspiro[3.5]nonan-2-yl)((1s,3*S)-3-hydroxy-3-methylcyclobutyl)methanone; |
| 352 | (7-(3-Fluoro-5-methylphenyl)-2-azaspiro[3.5]nonan-2-yl)((1s,3s)-3-hydroxy-3-methylcyclobutyl)methanone; |
| 353 | (7-(4-Fluoro-3-methylphenyl)-2-azaspiro[3.5]nonan-2-yl)((1s,3s)-3-hydroxy-3-methylcyclobutyl)methanone; |
| 354 | (7-(2-Fluoro-5-methylphenyl)-2-azaspiro[3.5]nonan-2-yl)((1s,3s)-3-hydroxy-3-methylcyclobutyl)methanone; |
| 355 | (7-(2-Fluoro-3-methylphenyl)-2-azaspiro[3.5]nonan-2-yl)((1s,3s)-3-hydroxy-3-methylcyclobutyl)methanone; |
| 356 | (7-(2-Fluoro-6-methylphenyl)-2-azaspiro[3.5]nonan-2-yl)((1s,3s)-3-hydroxy-3-methylcyclobutyl)methanone; |
| 357 | (7-(4-Fluoro-2-methylphenyl)-2-azaspiro[3.5]nonan-2-yl)((1s,3s)-3-hydroxy-3-methylcyclobutyl)methanone; |
| 358 | (7-(5-Fluoro-2-methylphenyl)-2-azaspiro[3.5]nonan-2-yl)((1s,3s)-3-hydroxy-3-methylcyclobutyl)methanone; |
| 359 | (7-(3-Fluoro-2-methylphenyl)-2-azaspiro[3.5]nonan-2-yl)((1s,3s)-3-hydroxy-3-methylcyclobutyl)methanone; |
| 360 | (7-(3-Ethoxy-4-methylphenyl)-2-azaspiro[3.5]nonan-2-yl)((1s,3s)-3-hydroxy-3-methylcyclobutyl)methanone; |
| 361 | (7-(3-Ethoxy-2-methylphenyl)-2-azaspiro[3.5]nonan-2-yl)((1s,3s)-3-hydroxy-3-methylcyclobutyl)methanone; |
| 362 | ((1s,3s)-3-Hydroxy-3-methylcyclobutyl)(7-(3-isopropoxy-2-methylphenyl)-2-azaspiro[3.5]nonan-2-yl)methanone; |
| 363 | ((1s,3s)-3-Hydroxy-3-methylcyclobutyl)(7-(5-methoxy-2-methylphenyl)-2-azaspiro[3.5]nonan-2-yl)methanone; |
| 364 | (7-(3-Cyclopropoxy-2-methylphenyl)-2-azaspiro[3.5]nonan-2-yl)((1s,3s)-3-hydroxy-3-methylcyclobutyl)methanone; |
| 365 | (7-(3-Ethoxy-5-fluorophenyl)-2-azaspiro[3.5]nonan-2-yl)((1s,3s)-3-hydroxy-3-methylcyclobutyl)methanone; |
| 366 | (7-(2-Fluoro-3-methoxyphenyl)-2-azaspiro[3.5]nonan-2-yl)((1s,3s)-3-hydroxy-3-methylcyclobutyl)methanone; |
| 367 | (7-(2-Chloro-3-methoxyphenyl)-2-azaspiro[3.5]nonan-2-yl)((1s,3s)-3-hydroxy-3-methylcyclobutyl)methanone; |
| 368 | (7-(2,3-Difluoro-5-methoxyphenyl)-2-azaspiro[3.5]nonan-2-yl)((1s,3s)-3-hydroxy-3-methylcyclobutyl)methanone; |
| 369 | (7-(2,5-Difluoro-3-methoxyphenyl)-2-azaspiro[3.5]nonan-2-yl)((1s,3s)-3-hydroxy-3-methylcyclobutyl)methanone; |
| 370 | (7-(3-Fluoro-5-methoxy-4-methylphenyl)-2-azaspiro[3.5]nonan-2-yl)((1s,3s)-3-hydroxy-3-methylcyclobutyl)methanone; |
| 371 | ((1s,3s)-3-Hydroxy-3-methylcyclobutyl)(7-(6-(1-(trifluoromethyl)cyclopropyl)pyridin-2-yl)-2-azaspiro[3.5]nonan-2-yl)methanone; |
| 372 | ((1s,3s)-3-Hydroxy-3-methylcyclobutyl)(7-(6-(1-methylcyclopropyl)pyridin-2-yl)-2-azaspiro[3.5]nonan-2-yl)methanone; |
| 373 | ((1s,3s)-3-Hydroxy-3-methylcyclobutyl)(7-(6-isopropyl-5-methylpyridin-2-yl)-2-azaspiro[3.5]nonan-2-yl)methanone; |
| 374 | ((1s,3s)-3-Hydroxy-3-methylcyclobutyl)(7-(6-isopropoxy-4-methylpyridin-2-yl)-2-azaspiro[3.5]nonan-2-yl)methanone; |
| 375 | ((1s,3s)-3-Hydroxy-3-methylcyclobutyl)(7-(4-methoxy-6-methylpyridin-2-yl)-2-azaspiro[3.5]nonan-2-yl)methanone; |
| 376 | ((1s,3s)-3-Hydroxy-3-methylcyclobutyl)(7-(2-isopropoxy-3-methylpyridin-4-yl)-2-azaspiro[3.5]nonan-2-yl)methanone; |
| 377 | (7-(6-(tert-Butyl)pyrazin-2-yl)-2-azaspiro[3.5]nonan-2-yl)((1s,3s)-3-hydroxy-3-methylcyclobutyl)methanone; |
| 378 | (7-(4-(tert-Butyl)pyrimidin-2-yl)-2-azaspiro[3.5]nonan-2-yl)((1s,3s)-3-hydroxy-3-methylcyclobutyl)methanone; |
| 379 | (7-(1-(tert-Butyl)-1H-pyrazol-3-yl)-2-azaspiro[3.5]nonan-2-yl)((1s,3s)-3-hydroxy-3-methylcyclobutyl)methanone; |
| 380 | ((1s,3s)-3-Hydroxy-3-methylcyclobutyl)(7-(1-phenyl-1H-pyrazol-3-yl)-2-azaspiro[3.5]nonan-2-yl)methanone; |
| 381 | (7-(1-(tert-Butyl)-1H-imidazol-4-yl)-2-azaspiro[3.5]nonan-2-yl)((1s,3s)-3-hydroxy-3-methylcyclobutyl)methanone; |
| 382 | (7-(3-(tert-Butyl)isoxazol-5-yl)-2-azaspiro[3.5]nonan-2-yl)((1s,3s)-3-hydroxy-3-methylcyclobutyl)methanone; |
| 383 | ((1s,3s)-3-Hydroxy-3-methylcyclobutyl)(7-(1-methyl-1H-pyrrolo[2,3-b]pyridin-3-yl)-2-azaspiro[3.5]nonan-2-yl)methanone; |
| 384 | ((1s,3s)-3-Hydroxy-3-methylcyclobutyl)(7-(1-methyl-1H-pyrrolo[2,3-b]pyridin-6-yl)-2-azaspiro[3.5]nonan-2-yl)methanone; |
| 385 | ((1s,3s)-3-Hydroxy-3-methylcyclobutyl)(7-(1-isopropyl-1H-pyrrolo[2,3-b]pyridin-6-yl)-2-azaspiro[3.5]nonan-2-yl)methanone; |
| 386 | ((1s,3s)-3-Hydroxy-3-methylcyclobutyl)(7-(1-methyl-3-(trifluoromethyl)-1H-pyrrolo[2,3-b]pyridin-6-yl)-2-azaspiro[3.5]nonan-2-yl)methanone; |
| 387 | ((1s,3s)-3-Hydroxy-3-methylcyclobutyl)(7-(1-(2,2,2-trifluoroethyl)-1H-pyrrolo[2,3-b]pyridin-6-yl)-2-azaspiro[3.5]nonan-2-yl)methanone; |

TABLE 1-continued

| Entry | Compound Name |
|---|---|
| 388 | ((1s,3s)-3-Hydroxy-3-methylcyclobutyl)(7-(pyrazolo[1,5-a]pyridin-2-yl)-2-azaspiro[3.5]nonan-2-yl)methanone; |
| 389 | ((1s,3s)-3-Hydroxy-3-methylcyclobutyl)(7-(pyrazolo[1,5-a]pyridin-7-yl)-2-azaspiro[3.5]nonan-2-yl)methanone; |
| 390 | ((1s,3s)-3-Hydroxy-3-methylcyclobutyl)(7-(imidazo[1,2-a]pyridin-5-yl)-2-azaspiro[3.5]nonan-2-yl)methanone; |
| 391 | ((1s,3s)-3-Hydroxy-3-methylcyclobutyl)(7-(imidazo[1,2-a]pyridin-2-yl)-2-azaspiro[3.5]nonan-2-yl)methanone; |
| 392 | ((1s,3s)-3-Hydroxy-3-methylcyclobutyl)(7-(imidazo[1,2-a]pyridin-3-yl)-2-azaspiro[3.5]nonan-2-yl)methanone; |
| 393 | ((1s,3s)-3-Hydroxy-3-methylcyclobutyl)(7-(pyrrolo[1,2-b]pyridazin-3-yl)-2-azaspiro[3.5]nonan-2-yl)methanone; |
| 394 | ((1s,3s)-3-Hydroxy-3-methylcyclobutyl)(7-(pyrazolo[1,5-a]pyridin-3-yl)-2-azaspiro[3.5]nonan-2-yl)methanone; |
| 395 | ((1s,3s)-3-Hydroxy-3-methylcyclobutyl)(7-(4,5,6,7-tetrahydropyrazolo[1,5-a]pyridin-2-yl)-2-azaspiro[3.5]nonan-2-yl)methanone; |
| 396 | ((1s,3s)-3-Hydroxy-3-methylcyclobutyl)(7-(5,6,7,8-tetrahydroimidazo[1,2-a]pyridin-2-yl)-2-azaspiro[3.5]nonan-2-yl)methanone; |
| 397 | ((1s,3s)-3-Hydroxy-3-methylcyclobutyl)(7-(4-methylbenzyl)-2-azaspiro[3.5]nonan-2-yl)methanone; |
| 398 | (7-(2-Fluoro-3-methylbenzyl)-2-azaspiro[3.5]nonan-2-yl)((1s,3s)-3-hydroxy-3-methylcyclobutyl)methanone; |
| 399 | (7-(4-Fluoro-3-methylbenzyl)-2-azaspiro[3.5]nonan-2-yl)((1s,3s)-3-hydroxy-3-methylcyclobutyl)methanone; |
| 400 | (7-((1H-Pyrrolo[2,3-b]pyridin-1-yl)methyl)-2-azaspiro[3.5]nonan-2-yl)((1s,3s)-3-hydroxy-3-methylcyclobutyl)methanone; |
| 401 | ((1s,3s)-3-Hydroxy-3-methylcyclobutyl)(7-((1-methyl-1H-pyrrolo[2,3-b]pyridin-6-yl)methyl)-2-azaspiro[3.5]nonan-2-yl)methanone; |
| 402 | ((1s,3s)-3-Hydroxy-3-methylcyclobutyl)(7-((1-methyl-1H-indazol-6-yl)methyl)-2-azaspiro[3.5]nonan-2-yl)methanone; |
| 403 | ((1s,3s)-3-Hydroxy-3-methylcyclobutyl)(7-((1-methyl-1H-pyrazolo[3,4-b]pyridin-6-yl)methyl)-2-azaspiro[3.5]nonan-2-yl)methanone; |
| 404 | ((1s,3s)-3-Hydroxy-3-methylcyclobutyl)(7-(p-tolyloxy)-2-azaspiro[3.5]nonan-2-yl)methanone; |
| 405 | (7-(3,4-Dimethylphenoxy)-2-azaspiro[3.5]nonan-2-yl)((1s,3s)-3-hydroxy-3-methylcyclobutyl)methanone; |
| 406 | (7-(2,3-Dimethylphenoxy)-2-azaspiro[3.5]nonan-2-yl)((1s,3s)-3-hydroxy-3-methylcyclobutyl)methanone; |
| 407 | ((1s,3s)-3-Hydroxy-3-methylcyclobutyl)(7-(3-methoxy-5-methylphenoxy)-2-azaspiro[3.5]nonan-2-yl)methanone; |
| 408 | ((1s,3s)-3-Hydroxy-3-methylcyclobutyl)(7-(3-methoxy-4-methylphenoxy)-2-azaspiro[3.5]nonan-2-yl)methanone; |
| 409 | ((1s,3s)-3-Hydroxy-3-methylcyclobutyl)(7-(3-methoxy-2-methylphenoxy)-2-azaspiro[3.5]nonan-2-yl)methanone; |
| 410 | (7-(2-Chloro-5-methylphenoxy)-2-azaspiro[3.5]nonan-2-yl)((1s,3s)-3-hydroxy-3-methylcyclobutyl)methanone; |
| 411 | (7-(3-Chloro-4-methylphenoxy)-2-azaspiro[3.5]nonan-2-yl)((1s,3s)-3-hydroxy-3-methylcyclobutyl)methanone; |
| 412 | (7-(4-Chloro-2-methylphenoxy)-2-azaspiro[3.5]nonan-2-yl)((1s,3s)-3-hydroxy-3-methylcyclobutyl)methanone; |
| 413 | (7-(3-Chloro-2-methylphenoxy)-2-azaspiro[3.5]nonan-2-yl)((1s,3s)-3-hydroxy-3-methylcyclobutyl)methanone; |
| 414 | (7-(4-Chloro-3-methoxyphenoxy)-2-azaspiro[3.5]nonan-2-yl)((1s,3s)-3-hydroxy-3-methylcyclobutyl)methanone; |
| 415 | (7-(4-Cyclopropyl-3-fluorophenoxy)-2-azaspiro[3.5]nonan-2-yl)((1s,3s)-3-hydroxy-3-methylcyclobutyl)methanone; |
| 416 | ((1s,3s)-3-Hydroxy-3-methylcyclobutyl)(7-(2-methyl-5-(trifluoromethyl)phenoxy)-2-azaspiro[3.5]nonan-2-yl)methanone; |
| 417 | ((1s,3s)-3-Hydroxy-3-methylcyclobutyl)(7-((5-(trifluoromethyl)pyridin-2-yl)oxy)-2-azaspiro[3.5]nonan-2-yl)methanone; |
| 418 | ((1s,3s)-3-Hydroxy-3-methylcyclobutyl)(7-((4-(trifluoromethyl)pyridin-2-yl)oxy)-2-azaspiro[3.5]nonan-2-yl)methanone; |
| 419 | ((1s,3s)-3-Hydroxy-3-methylcyclobutyl)(7-methyl-7-((5-(trifluoromethyl)pyridin-2-yl)oxy)-2-azaspiro[3.5]nonan-2-yl)methanone; |
| 420 | (7-Ethyl-7-((5-(trifluoromethyl)pyridin-2-yl)oxy)-2-azaspiro[3.5]nonan-2-yl)((1s,3s)-3-hydroxy-3-methylcyclobutyl)methanone; |
| 421 | ((1s,3s)-3-Hydroxy-3-methylcyclobutyl)(7-((6-(trifluoromethyl)pyridin-2-yl)oxy)-2-azaspiro[3.5]nonan-2-yl)methanone; |
| 422 | (7-((5-(1,1-Difluoroethyl)pyridin-2-yl)oxy)-2-azaspiro[3.5]nonan-2-yl)((1s,3s)-3-hydroxy-3-methylcyclobutyl)methanone; |
| 423 | (7-((5-(Difluoromethyl)pyridin-2-yl)oxy)-2-azaspiro[3.5]nonan-2-yl)((1s,3s)-3-hydroxy-3-methylcyclobutyl)methanone; |
| 424 | ((1s,3s)-3-Hydroxy-3-methylcyclobutyl)(7-((6-(trifluoromethyl)pyridin-3-yl)oxy)-2-azaspiro[3.5]nonan-2-yl)methanone; |
| 425 | (7-((6-(tert-Butyl)pyridin-2-yl)oxy)-2-azaspiro[3.5]nonan-2-yl)((1s,3s)-3-hydroxy-3-methylcyclobutyl)methanone; |
| 426 | (7-((5-Cyclopropylpyridin-2-yl)oxy)-2-azaspiro[3.5]nonan-2-yl)((1s,3s)-3-hydroxy-3-methylcyclobutyl)methanone; |

TABLE 1-continued

| Entry | Compound Name |
|---|---|
| 427 | ((1s,3s)-3-Hydroxy-3-methylcyclobutyl)(7-((5-(trifluoromethoxy)pyridin-2-yl)oxy)-2-azaspiro[3.5]nonan-2-yl)methanone; |
| 428 | (7-((5,6-Dimethylpyridin-2-yl)oxy)-2-azaspiro[3.5]nonan-2-yl)((1s,3s)-3-hydroxy-3-methylcyclobutyl)methanone; |
| 429 | (7-((3,6-Dimethylpyridin-2-yl)oxy)-2-azaspiro[3.5]nonan-2-yl)((1s,3s)-3-hydroxy-3-methylcyclobutyl)methanone; |
| 430 | (7-((3,5-Dimethylpyridin-2-yl)oxy)-2-azaspiro[3.5]nonan-2-yl)((1s,3s)-3-hydroxy-3-methylcyclobutyl)methanone; |
| 431 | (7-((3-Fluoro-6-methylpyridin-2-yl)oxy)-2-azaspiro[3.5]nonan-2-yl)((1s,3s)-3-hydroxy-3-methylcyclobutyl)methanone; |
| 432 | (7-((3-Fluoro-5-methylpyridin-2-yl)oxy)-2-azaspiro[3.5]nonan-2-yl)((1s,3s)-3-hydroxy-3-methylcyclobutyl)methanone; |
| 433 | (7-((5-Ethyl-3-fluoropyridin-2-yl)oxy)-2-azaspiro[3.5]nonan-2-yl)((1s,3s)-3-hydroxy-3-methylcyclobutyl)methanone; |
| 434 | (7-((5-Chloro-6-methylpyridin-2-yl)oxy)-2-azaspiro[3.5]nonan-2-yl)((1s,3s)-3-hydroxy-3-methylcyclobutyl)methanone; |
| 435 | (7-((3-Chloro-6-methylpyridin-2-yl)oxy)-2-azaspiro[3.5]nonan-2-yl)((1s,3s)-3-hydroxy-3-methylcyclobutyl)methanone; |
| 436 | (7-((3-Chloro-5-methylpyridin-2-yl)oxy)-2-azaspiro[3.5]nonan-2-yl)((1s,3s)-3-hydroxy-3-methylcyclobutyl)methanone; |
| 437 | (7-((5-Chloro-3-methylpyridin-2-yl)oxy)-2-azaspiro[3.5]nonan-2-yl)((1s,3s)-3-hydroxy-3-methylcyclobutyl)methanone; |
| 438 | (7-((5-(Difluoromethyl)-6-methylpyridin-2-yl)oxy)-2-azaspiro[3.5]nonan-2-yl)((1s,3s)-3-hydroxy-3-methylcyclobutyl)methanone; |
| 439 | (7-((6-(Difluoromethyl)-5-ethylpyridin-2-yl)oxy)-2-azaspiro[3.5]nonan-2-yl)((1s,3s)-3-hydroxy-3-methylcyclobutyl)methanone; |
| 440 | (7-((5-(Difluoromethyl)-6-ethylpyridin-2-yl)oxy)-2-azaspiro[3.5]nonan-2-yl)((1s,3s)-3-hydroxy-3-methylcyclobutyl)methanone; |
| 441 | (7-((3-(Difluoromethyl)-6-ethylpyridin-2-yl)oxy)-2-azaspiro[3.5]nonan-2-yl)((1s,3s)-3-hydroxy-3-methylcyclobutyl)methanone; |
| 442 | ((1s,3s)-3-Hydroxy-3-methylcyclobutyl)(7-((4-methyl-5-(trifluoromethyl)pyridin-2-yl)oxy)-2-azaspiro[3.5]nonan-2-yl)methanone; |
| 443 | ((1s,3s)-3-Hydroxy-3-methylcyclobutyl)(7-((6-methyl-3-(trifluoromethyl)pyridin-2-yl)oxy)-2-azaspiro[3.5]nonan-2-yl)methanone; |
| 444 | ((1s,3*R)-3-Hydroxy-3-methylcyclobutyl)((6*S,7*S)-6-methyl-7-((6-methyl-5-(trifluoromethyl)pyridin-2-yl)oxy)-2-azaspiro[3.5]nonan-2-yl)methanone; |
| 445 | ((1s,3*S)-3-Hydroxy-3-methylcyclobutyl)((6*R,7*R)-6-methyl-7-((6-methyl-5-(trifluoromethyl)pyridin-2-yl)oxy)-2-azaspiro[3.5]nonan-2-yl)methanone; |
| 446 | ((1s,3s)-3-Hydroxy-3-methylcyclobutyl)(7-((3-methyl-5-(trifluoromethyl)pyridin-2-yl)oxy)-2-azaspiro[3.5]nonan-2-yl)methanone; |
| 447 | ((1s,3s)-3-Hydroxy-3-methylcyclobutyl)(7-((6-methyl-4-(trifluoromethyl)pyridin-2-yl)oxy)-2-azaspiro[3.5]nonan-2-yl)methanone; |
| 448 | ((1s,3s)-3-Hydroxy-3-methylcyclobutyl)(7-((6-methyl-5-(trifluoromethyl)pyridin-2-yl)oxy)-2-azaspiro[3.5]nonan-2-yl)methanone; |
| 449 | ((1s,3s)-3-Hydroxy-3-methylcyclobutyl)(7-((3-methyl-6-(trifluoromethyl)pyridin-2-yl)oxy)-2-azaspiro[3.5]nonan-2-yl)methanone; |
| 450 | (7-((5-Ethyl-6-(trifluoromethyl)pyridin-2-yl)oxy)-2-azaspiro[3.5]nonan-2-yl)((1s,3s)-3-hydroxy-3-methylcyclobutyl)methanone; |
| 451 | ((1s,3s)-3-Hydroxy-3-methylcyclobutyl)(7-((5-methyl-6-(trifluoromethyl)pyridin-2-yl)oxy)-2-azaspiro[3.5]nonan-2-yl)methanone; |
| 452 | ((1r,3s)-3-Ethyl-3-hydroxycyclobutyl)(7-((5-methyl-6-(trifluoromethyl)pyridin-2-yl)oxy)-2-azaspiro[3.5]nonan-2-yl)methanone; |
| 453 | ((1s,3s)-3-(Difluoromethyl)-3-hydroxycyclobutyl)(7-((5-methyl-6-(trifluoromethyl)pyridin-2-yl)oxy)-2-azaspiro[3.5]nonan-2-yl)methanone; |
| 454 | (7-((5-Ethyl-6-methoxypyridin-2-yl)oxy)-2-azaspiro[3.5]nonan-2-yl)((1s,3s)-3-hydroxy-3-methylcyclobutyl)methanone; |
| 455 | (7-((5-Cyclopropyl-6-methoxypyridin-2-yl)oxy)-2-azaspiro[3.5]nonan-2-yl)((1s,3s)-3-hydroxy-3-methylcyclobutyl)methanone; |
| 456 | ((1s,3s)-3-Hydroxy-3-methylcyclobutyl)(7-((6-methoxy-5-methylpyridin-2-yl)oxy)-2-azaspiro[3.5]nonan-2-yl)methanone; |
| 457 | (7-((3-Fluoro-5-(trifluoromethyl)pyridin-2-yl)oxy)-2-azaspiro[3.5]nonan-2-yl)((1s,3s)-3-hydroxy-3-methylcyclobutyl)methanone; |
| 458 | ((1s,3s)-3-Hydroxy-3-methylcyclobutyl)(7-((6-methoxy-5-(trifluoromethyl)pyridin-2-yl)oxy)-2-azaspiro[3.5]nonan-2-yl)methanone; |
| 459 | (7-((6-Ethoxy-5-(trifluoromethyl)pyridin-2-yl)oxy)-2-azaspiro[3.5]nonan-2-yl)((1s,3s)-3-hydroxy-3-methylcyclobutyl)methanone; |
| 460 | (7-((5-Chloro-4-methoxypyridin-2-yl)oxy)-2-azaspiro[3.5]nonan-2-yl)((1s,3s)-3-hydroxy-3-methylcyclobutyl)methanone; |
| 461 | (7-((5-Chloro-6-methoxypyridin-2-yl)oxy)-2-azaspiro[3.5]nonan-2-yl)((1s,3s)-3-hydroxy-3-methylcyclobutyl)methanone; |
| 462 | (7-((3-Chloro-6-methoxypyridin-2-yl)oxy)-2-azaspiro[3.5]nonan-2-yl)((1s,3s)-3-hydroxy-3-methylcyclobutyl)methanone; |
| 463 | (7-((5-Chloro-3-methoxypyridin-2-yl)oxy)-2-azaspiro[3.5]nonan-2-yl)((1s,3s)-3-hydroxy-3-methylcyclobutyl)methanone; |
| 464 | (7-((3-Chloro-4-methoxypyridin-2-yl)oxy)-2-azaspiro[3.5]nonan-2-yl)((1s,3s)-3-hydroxy-3-methylcyclobutyl)methanone; |
| 465 | (7-((4,6-Dimethyl-5-(trifluoromethyl)pyridin-2-yl)oxy)-2-azaspiro[3.5]nonan-2-yl)((1s,3s)-3-hydroxy-3-methylcyclobutyl)methanone; |

TABLE 1-continued

| Entry | Compound Name |
|---|---|
| 466 | (7-((3,6-Dimethyl-5-(trifluoromethyl)pyridin-2-yl)oxy)-2-azaspiro[3.5]nonan-2-yl)((1s,3s)-3-hydroxy-3-methylcyclobutyl)methanone; |
| 467 | ((1s,3s)-3-Hydroxy-3-methylcyclobutyl)(7-((5-(trifluoromethyl)pyrimidin-2-yl)oxy)-2-azaspiro[3.5]nonan-2-yl)methanone; |
| 468 | (7-((6,7-Dihydro-5H-cyclopenta[b]pyridin-2-yl)oxy)-2-azaspiro[3.5]nonan-2-yl)((1s,3s)-3-hydroxy-3-methylcyclobutyl)methanone; |
| 469 | ((1s,3s)-3-Hydroxy-3-methylcyclobutyl)(7-((1-methyl-1H-pyrrolo[2,3-b]pyridin-6-yl)oxy)-2-azaspiro[3.5]nonan-2-yl)methanone; |
| 470 | (7-((1,4-Dimethyl-1H-pyrrolo[2,3-b]pyridin-6-yl)oxy)-2-azaspiro[3.5]nonan-2-yl)((1s,3s)-3-hydroxy-3-methylcyclobutyl)methanone; |
| 471 | (7-((1,3-Dimethyl-1H-pyrrolo[2,3-b]pyridin-6-yl)oxy)-2-azaspiro[3.5]nonan-2-yl)((1s,3s)-3-hydroxy-3-methylcyclobutyl)methanone; |
| 472 | (7-((1,2-Dimethyl-1H-pyrrolo[2,3-b]pyridin-6-yl)oxy)-2-azaspiro[3.5]nonan-2-yl)((1s,3s)-3-hydroxy-3-methylcyclobutyl)methanone; |
| 473 | (7-((1,5-Dimethyl-1H-pyrrolo[2,3-b]pyridin-6-yl)oxy)-2-azaspiro[3.5]nonan-2-yl)((1s,3s)-3-hydroxy-3-methylcyclobutyl)methanone; |
| 474 | (7-((3-Fluoro-1-methyl-1H-pyrrolo[2,3-b]pyridin-6-yl)oxy)-2-azaspiro[3.5]nonan-2-yl)((1s,3s)-3-hydroxy-3-methylcyclobutyl)methanone; |
| 475 | (7-((1-Ethyl-3-fluoro-1H-pyrrolo[2,3-b]pyridin-6-yl)oxy)-2-azaspiro[3.5]nonan-2-yl)((1s,3s)-3-hydroxy-3-methylcyclobutyl)methanone; |
| 476 | ((1s,3s)-3-Hydroxy-3-methylcyclobutyl)(7-((1-methyl-3-(trifluoromethyl)-1H-pyrrolo[2,3-b]pyridin-6-yl)oxy)-2-azaspiro[3.5]nonan-2-yl)methanone; |
| 477 | ((1s,3s)-3-Hydroxy-3-methylcyclobutyl)(7-((1-methyl-1H-pyrazolo[3,4-b]pyridin-6-yl)oxy)-2-azaspiro[3.5]nonan-2-yl)methanone; |
| 478 | ((1s,3s)-3-Hydroxy-3-methylcyclobutyl)(2-(3-methoxy-5-methylphenyl)-7-azaspiro[3.5]nonan-7-yl)methanone; |
| 479 | ((1s,3s)-3-Hydroxy-3-methylcyclobutyl)(2-(2-methyl-4-(trifluoromethyl)phenoxy)-7-azaspiro[3.5]nonan-7-yl)methanone; |
| 480 | ((1s,3s)-3-Hydroxy-3-methylcyclobutyl)(2-(3-methyl-4-(trifluoromethyl)phenoxy)-7-azaspiro[3.5]nonan-7-yl)methanone; |
| 481 | ((1s,3s)-3-Hydroxy-3-methylcyclobutyl)(2-((3-methyl-5-(trifluoromethyl)pyridin-2-yl)oxy)-7-azaspiro[3.5]nonan-7-yl)methanone; and |
| 482 | ((1s,3s)-3-Hydroxy-3-methylcyclobutyl)(2-((6-methyl-5-(trifluoromethyl)pyridin-2-yl)oxy)-7-azaspiro[3.5]nonan-7-yl)methanone; | and pharmaceutically acceptable salts, isotopes, N-oxides, solvates, and stereoisomers thereof.

In another embodiment is a compound selected from the group consisting of:

((*S)-6-(3-Cyclopropyl-2-fluorophenyl)-2-azaspiro[3.4]octan-2-yl)((1s,3*R)-3-hydroxy-3-methylcyclobutyl)methanone;

((1s,3*R)-3-Hydroxy-3-methylcyclobutyl)((*S)-6-(4-(trifluoromethyl)phenyl)-2-azaspiro[3.4]octan-2-yl)methanone;

(7-(3,5-Dimethylphenyl)-2-azaspiro[3.5]nonan-2-yl)((1s,3s)-3-hydroxy-3-methylcyclobutyl)methanone;

((1s,3s)-3-Hydroxy-3-methylcyclobutyl)(7-(3-methoxy-5-methylphenyl)-2-azaspiro[3.5]nonan-2-yl)methanone; and ((*S)-6-(4-Chloro-3-methylphenyl)-2-azaspiro[3.4]octan-2-yl)((1s,3*R)-3-hydroxy-3-methylcyclobutyl)methanone;

and pharmaceutically acceptable salts, isotopes, N-oxides, solvates, and stereoisomers thereof.

In some embodiments, the compound of Formula (I) is a compound of Formula (IA):

wherein
L is a bond, $CH_2$, $CF_2$, $CH(CH_3)$, or O; and
$R^3$ is:
(a) phenyl optionally substituted with one or two members each independently selected from halo, $C_{1-4}$alkyl, $C_{1-4}$haloalkyl, $OC_{1-4}$alkyl, $OC_{1-4}$haloalkyl, pyrrolidinyl, cyclopropyl, and O-cyclopropyl;
(b) pyridinyl optionally substituted with one or two members each independently selected from $C_{1-4}$alkyl, $C_{1-4}$haloalkyl, $OC_{1-4}$alkyl, and $OC_{1-4}$alkyl;
(c) pyrazolyl substituted with one or two members each independently selected from $C_{1-4}$alkyl, and $C_{1-4}$haloalkyl; or
(d) quinolinyl, isoquinolinyl, 1H-pyrrolo[2,3-b]pyridinyl, 1H-indazolyl, 2H-indazolyl, pyrazolo[1,5-a]pyridinyl, or 1H-pyrrolo[3,2-c]pyridinyl, each optionally substituted with one or two members each independently selected from halo, $C_{1-4}$alkyl, and $C_{1-4}$haloalkyl;

or a pharmaceutically acceptable salt, isotope, N-oxide, solvate, or stereoisomer thereof.

In some embodiments, the compound of Formula (I) is a compound of Formula (IB):

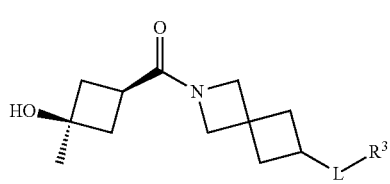

(IA)

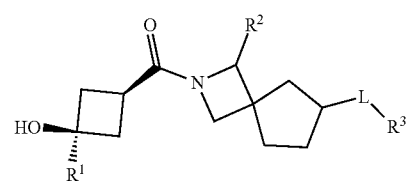

(IB)

wherein
L is a bond, CH$_2$, CH(CH$_3$) or O;
R$^1$ is CH$_3$, CH$_2$CH$_3$ or CF$_2$H;
R$^2$ is H or CH$_3$; and
R$^3$ is:
  (a) phenyl optionally substituted with one or two members each independently selected from halo, C$_{1-4}$alkyl, C$_{1-4}$haloalkyl, OC$_{1-4}$alkyl, OC$_{1-4}$haloalkyl, cyclopropyl, cyclobutyl, and cyclobutyl;
  (b) pyridinyl substituted with one or two members each independently selected from C$_{1-4}$alkyl and C$_{1-4}$haloalkyl;
  (c) pyrazolyl optionally substituted with one or two members each independently selected from C$_{1-4}$alkyl, and C$_{1-4}$haloalkyl;
  (d) pyrazolo[1,5-a]pyridinyl, 1H-indazolyl, 1H-benzo[d]imidazolyl, imidazo[1,2-a]pyridinyl, or imidazo[1,5-a]pyridinyl, each optionally substituted with one C$_{1-4}$alkyl member; or
  (e) 5,6,7,8-tetrahydroimidazo[1,5-a]pyridinyl, 4,5,6,7-tetrahydropyrazolo[1,5-a]pyridinyl, 3-dihydro-1H-indenyl, or 2,3-dihydrobenzofuranyl;
or a pharmaceutically acceptable salt, isotope, N-oxide, solvate, or stereoisomer thereof.

In some embodiments, the compound of Formula (I) is a compound of Formula (IC):

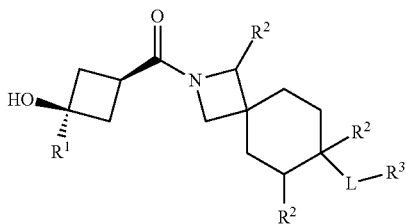

(IC)

wherein
L is a bond, CH$_2$ or O;
R$^2$ is H, F, OH, CH$_3$, CH$_2$CH$_3$, or OCH$_3$; and
R$^3$ is:
  (a) phenyl optionally substituted with one, two, or three members each independently selected from halo, C$_{1-4}$alkyl, C$_{1-4}$haloalkyl, OC$_{1-4}$alkyl, OC$_{1-4}$haloalkyl, N(CH$_3$)$_2$, cyclopropyl, O-cyclopropyl, 1-methyl-1H-imidazol-4-yl, and 1H-pyrazol-1-yl;
  (b) pyridinyl optionally substituted with one, two, or three members each independently selected from halo, C$_{1-4}$alkyl, C$_{1-4}$haloalkyl, OC$_{1-4}$alkyl, OC$_{1-4}$haloalkyl, cyclopropyl, and cyclopropyl substituted with CH$_3$ or CF$_3$;
  (c) 1H-pyrazolyl, 1H-imidazolyl, or isoxazolyl, each optionally substituted with C$_{1-4}$alkyl or phenyl;
  (d) quinolinyl, 1H-indazolyl, 1H-pyrrolo[2,3-b]pyridinyl, pyrrolo[1,2-b]pyridazinyl, pyrazolo[1,5-a]pyridinyl, 1H-pyrazolo[3,4-b]pyridinyl, or imidazo[1,2-a]pyridinyl, each optionally substituted with one or two members each independently selected from halo, C$_{1-4}$alkyl, and C$_{1-4}$haloalkyl;
  (e) 4,5,6,7-tetrahydropyrazolo[1,5-a]pyridinyl, 5,6,7,8-tetrahydroimidazo[1,2-a]pyridinyl, or 6,7-dihydro-5H-cyclopenta[b]pyridinyl;
or a pharmaceutically acceptable salt, isotope, N-oxide, solvate, or stereoisomer thereof.

In some embodiments, the compounds described herein include enantiomers and diastereomers of the compounds of Formula (I) (as well as Formulas (I-1), (I-2), (IA), (IB), and (IC), and those in Table 1). In some embodiments, the compounds described herein include pharmaceutically acceptable salts, N-oxides or solvates of the compounds of Formula (I) (as well as Formulas (I-1), (I-2), (IA), (IB), and (IC), and those in Table 1). In some embodiments, the compounds described herein include pharmaceutically acceptable prodrugs or pharmaceutically active metabolites of compounds of Formula (I) (as well as Formulas (I-1), (I-2), (IA), (IB), and (IC), and those in Table 1).

In some embodiments, the compounds described herein include isotopic variations of compounds of Formula (I) (as well as Formulas (I-1), (I-2), (IA), (IB), and (IC), and those in Table 1), such as, e.g., deuterated variations of such compounds, and pharmaceutically acceptable salts, N-oxides or solvates of such isotopic variations, and pharmaceutically acceptable prodrugs and pharmaceutically active metabolites of such compounds.

In an embodiment is a pharmaceutical composition comprising (A) a compound of Formula (I), or a pharmaceutically acceptable salt, isotope, N-oxide, solvate, or stereoisomer thereof, and (B) a pharmaceutically acceptable excipient. In some embodiments, the compound is selected from compounds from Table 1, of Formula (I-1), Formula (I-2), Formula (IA), Formula (IB), and Formula (IC), and pharmaceutically acceptable salts, isotopes, N-oxides, solvates, and stereoisomers thereof, and from pharmaceutically acceptable prodrugs and pharmaceutically active metabolites of such compounds. Encompassed within the scope of such pharmaceutical compositions are pharmaceutical compositions comprising at least one such compound.

An additional embodiment is a method of treating a disease, disorder, or condition mediated by MGL receptor activity in a subject in need thereof, comprising administering to the subject a therapeutically effective amount of a compound selected from compounds of Formula (I) and pharmaceutically acceptable salts, isotopes, N-oxides, solvates, and stereoisomers thereof. In some embodiments, the at least one compound is selected from compound of any one or more of Formulas (I-1), (I-2), (IA), (IB), and (IC)), and compounds in Table 1, and pharmaceutically acceptable salts, isotopes, N-oxides, solvates, and stereoisomers (e.g., enantiomers and diastereomers) thereof, and from pharmaceutically acceptable prodrugs and pharmaceutically active metabolites thereof. Encompassed within the scope of such methods are method comprising administering at least one such compound.

Exemplary compounds useful in methods described herein will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating.

Reactions may also be conducted in sealed pressure vessels above the normal reflux temperature of the solvent.

Abbreviations and acronyms used herein include the following:

TABLE 2

| Term | Acronym |
|---|---|
| Microliter | μL or uL |
| Acetonitrile | ACN, MeCN |
| Acetic acid | AcOH |
| Aqueous | aq |
| Atmosphere | atm |
| 2,2'-Bis(diphenylphosphino)-1,1'-binaphthyl | BINAP |
| tert-Butyloxycarbonyl | BOC or Boc |
| Mesylate[(di(1-adamantyl)-n-butylphosphine)-2-(2'-amino-1,1'-biphenyl)]palladium(II) | CataCXium ® A Pd G3 |
| Diatomaceous Earth | Celite ® |
| Diethylaminosulfur trifluoride | DAST |
| Dichloromethane | DCM |
| Diethyl azodicarboxylate | DEAD |
| Diisopropyl azodicarboxylate | DIAD |
| N-Ethyldiisopropylamine | DIPEA |
| 4-Dimethylaminopyridine | DMAP |
| 1,2-Dimethoxyethane | DME |
| Dimethylformamide | DMF |
| Dimethylsulfoxide | DMSO |
| 1-Ethyl-3-(3-dimethylaminopropyl)carbodiimide | EDC, EDAC or EDCI |
| Electrospray ionization | ESI |
| Diethyl ether | Ether, $Et_2O$ |
| Ethyl acetate | EtOAc |
| Ethanol | EtOH |
| Normal-phase silica gel chromatography | FCC |
| Grams | g |
| Hours | h, hr, hrs |
| 1-[Bis(dimethylamino)methylene]-1H-1,2,3-triazolo[4,5-b]pyridinium 3-oxide hexafluorophosphate | HATU |
| Hexamethylphosphoramide | HMPA |
| Hydroxybenzotriazole | HOBt |
| High-pressure liquid chromatography | HPLC |
| Hertz | Hz |
| Isopropanol | iPrOH, IPA |
| [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate | $(Ir[dF(CF_3)ppy]_2(dtbpy))PF_6$ |
| Liquid chromatography and mass spectrometry | LCMS |
| Lithium bis(trimethylsilyl)amide | LiHMDS |
| Molar | M |
| Mass to charge ratio | m/z |
| Methanol | MeOH |
| Milligrams | mg |
| Minute | min |
| Milliliter | mL |
| Millimoles | mmol |
| Mass spectrometry | MS |
| Sodium bis(trimethylsilyl)amide | NaHMDS |
| Normal | N |
| N-chlorosuccinimide | NCS |
| Nickel(II) chloride ethylene glycol dimethyl ether | $NiCl_2(DME)$ |
| Nuclear magnetic resonance | NMR |
| Acetate | OAc |
| Palladium on carbon | Pd/C |
| Bis(dibenzylideneacetone)palladium | $Pd(dba)_2$ |
| Tris(dibenzylideneacetone)dipalladium(0) | $Pd_2(dba)_3$ |
| [1,1'-Bis(diphenylphosphino)ferrocene]dichloropalladium(II) | $Pd(dppf)Cl_2$ |
| [1,1'-Bis(di-tert-butylphosphino)ferrocene]dichloropalladium(II) | $Pd(dtbpf)Cl_2$ |
| Palladium(II) acetate | $Pd(OAc)_2$ |
| Tetrakis(triphenylphosphine)palladium | $Pd(PPh_3)_4$ |
| Bis(tri-tert-butylphosphine)palladium | $Pd(t-Bu_3P)_2$ |
| Parts per million | ppm |
| Pounds per square inch | psi |
| Polytetrafluoroethylene | PTFE |
| Bromotripyrrolidinophosphonium hexafluorophosphate | PyBroP ® |
| Reverse Phase | RP |
| Retention time | Rt |
| Room temperature | rt |
| Saturated | sat |
| Supercritical Fluid Chromatography | SFC |
| 2,4,6-Tripropyl-1,3,5,2,4,6-trioxatriphosphorinane-2,4,6-trioxide | T3P ® |
| Triethylamine | TEA |
| Triethylsilane | TES |

TABLE 2-continued

| Term | Acronym |
|---|---|
| Trifluoroacetic acid | TFA |
| Trifluoroacetic anhydride | TFAA |
| Tetrahydrofuran | THF |
| Thin layer chromatography | TLC |
| N,N,N',N'-Tetramethylethylenediamine | TMEDA |
| Volume in milliliters of solvent per gram of substrate | V, or volumes |
| 2-Dicyclohexylphosphino-2',4',6'-triisopropylbiphenyl | XPhos |
| Chloro(2-dicyclohexylphosphino-2',4',6'-triisopropyl-1,1'-biphenyl)[2-(2'-amino-1,1'-biphenyl)]palladium(II) | XPhos Pd G2 |

Illustrative Synthetic Schemes

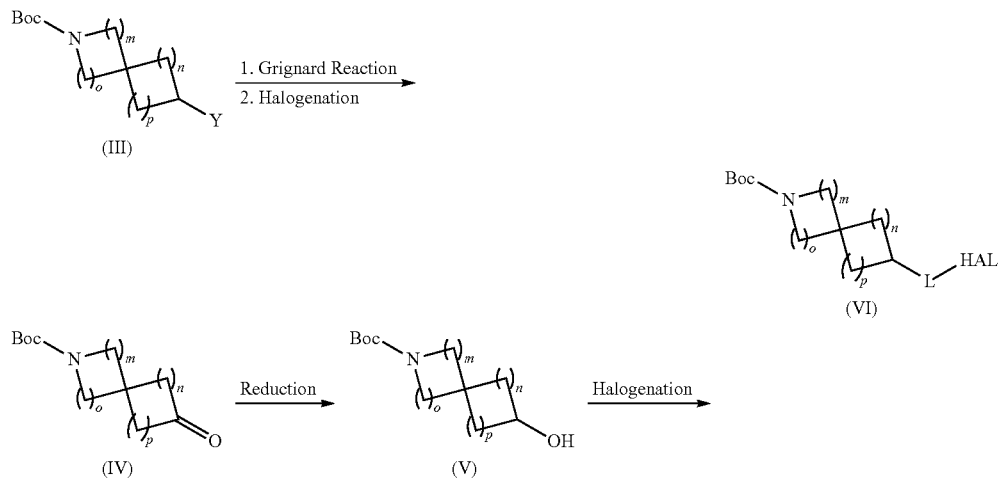

According to SCHEME 1, a compound of formula (VI), wherein m, n, o, and p are each independently 1, L is CH(CH$_3$), and HAL is I; is prepared in two steps from a compound of formula (III). In a first step, a compound of formula (III), wherein m, n, o, and p are each independently 1, and Y is CHO; is reacted under conventional Grignard reaction conditions in the presence of a commercially available or synthetically accessible organomagnesium halide methylmagnesium bromide and the like; with or without an additive such as cerium(III) chloride; in a suitable solvent such as THF, diethyl ether (Et$_2$O), and the like; at temperatures ranging from −78° C. to room temperature. In a second step, halogenation of the resulting alcohol, employing conditions known to one skilled in the art, for example, using iodine (I$_2$), employing an appropriate base such as imidazole; and triphenylphosphine (PPh$_3$); in a suitable solvent such as THF, and the like; at a temperature range of 0° C. to rt over a period of 1 h, provides compound of formula (VI), where L is CH(CH$_3$), and HAL is I.

Under conditions known to one skilled in the art, a commercially available or synthetically accessible compound of formula (IV), wherein m, o, and p are each independently 1 or 2, and n is 1; is reduced with a suitable reducing agent such as NaBH$_4$, LiAlH$_4$, LiBH$_4$, diisobutylaluminum hydride (DIBAL-H), and the like; in a suitable solvent such as tetrahydrofuran (THF), methanol (MeOH), ethanol (EtOH), and the like; at temperatures ranging from −78 to 0° C.; for a period of 30 min to 16 h; to provide a compound of formula (V). A compound of formula (V) is halogenated, employing conditions known to one skilled in the art, or as previously described, to provide a compound of formula (VI), where L is absent and HAL is I.

A compound of formula (V), where m and o are 1, and n and p are 2; and the ring with n and p is substituted with C$_{1-4}$alkyl; is prepared in two steps from a compound of formula (IV). In a first step, a compound of formula (IV) is reacted with a suitable base such as LiHMDS, and the like; an alkylating agent such as iodomethane, and the like; in a suitable solvent such as THF, and the like; at a temperature range of −78° C. to rt. In a second step, reduction with a suitable reducing agent, employing methods previously described; provides a compound of formula (V), where the ring with n and p is substituted with CH$_3$.

SCHEME 2

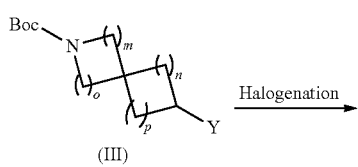

-continued

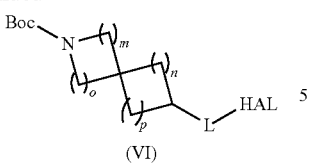

(VI)

According to SCHEME 2, a compound of formula (III), where m and o are 1 and n and p are 1 or 2, and Y is CH₂OH; is halogenated employing halogenation conditions known to one skilled in the art or as previously described such as I₂/PPh₃/imidazole or PPh₃/CBr₄; in a suitable solvent such as DCM, and the like; at a temperature of −78° C.; for a period of 1 hour; to provide a compound of formula (VI), where L is CH₂ and HAL is Br or I.

SCHEME 3

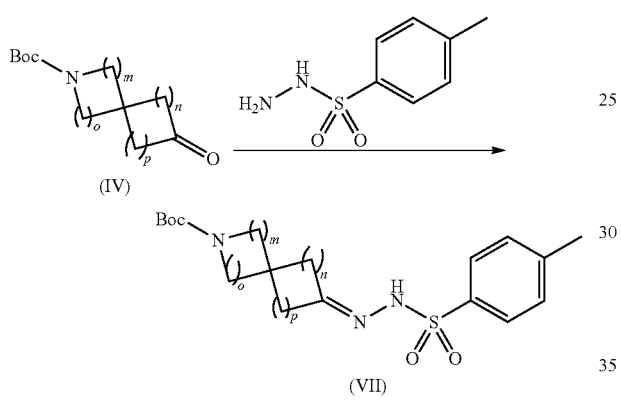

According to SCHEME 3, a compound of formula (IV), wherein m and p are each independently 1 or 2, and n and o are 1; is reacted with 4-methylbenzenesulfonhydrazide in a solvent such as 1,4-dioxane, THF, and the like; at 50 to 80° C. for 2-5 hours, to provide a compound of formula (VII).

SCHEME 4

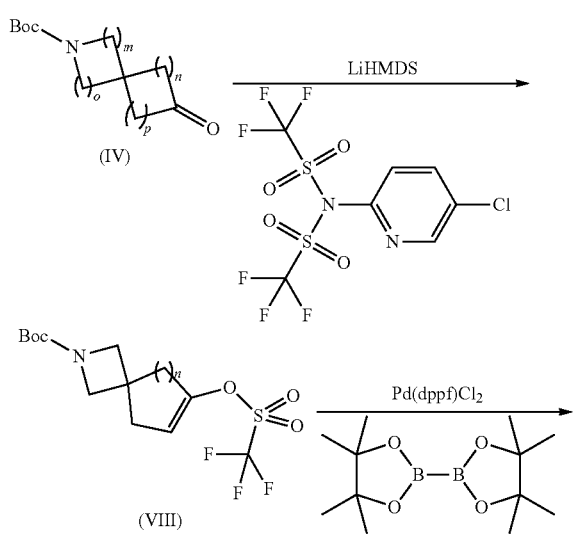

-continued

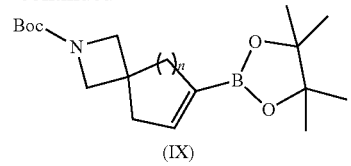

(IX)

According to SCHEME 4, a compound of formula (IV), wherein m and o is equal to 1, n is 1 or 2, and p is 2; is reacted with a suitable base such as LiHMDS, and the like; a suitable triflyl-donating reagent such as 2-[N,N-bis(trifluoromethanesulfonyl)amino]-5-chloropyridine (Comins' reagent); in a suitable solvent such as THF, and the like; at a temperature ranging from −78° C. to room temperature; for a period of up to 1 hour; to provide a compound of formula (VIII). A boronic ester compound of formula (IX) is prepared by reacting a triflate compound of formula (VIII), employing Miyaura borylation conditions known to one skilled in the art. For example, a compound of formula (VIII) is reacted with 4,4,4',4',5,5,5',5'-octamethyl-2,2'-bi(1,3,2-dioxaborolane) (bis(pinacolato)diboron, or B₂pin₂); a palladium catalyst such as Pd(dppf)Cl₂·CH₂Cl₂, and the like; a suitable base such as KOAc, and the like; in a solvent such as 1,4-dioxane, and the like; at a temperature of about 90° C.; for a period of 3 hours; to provide a compound of formula (IX).

SCHEME 5

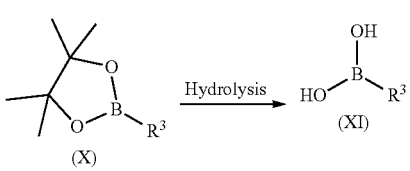

According to SCHEME 5, a compound of formula (V), where m and o are 1, and n and p are 2; is reacted with methanesulfonyl chloride; a suitable base such as Et₃N, and the like; in a solvent such as DCM, and the like; at room temperature; for a period of 16 hours; to provide tert-butyl 7-((methylsulfonyl)oxy)-2-azaspiro[3.5]nonane-2-carboxylate.

SCHEME 6

According to SCHEME 6, deprotection of a commercially available or synthetically accessible cyclic boronate ester compound of formula (X), where $R^3$ is as defined in claim 1, is achieved employing oxidative cleavage with aq. sodium periodate and acidic hydrolysis. For example, a boronic ester compound of formula (X), where $R^3$ is phenyl substituted with one or two members independently selected from the group consisting of: $C_{1-4}$alkyl, $C_{1-4}$haloalkyl, $OC_{1-4}$alkyl, and $OC_{1-4}$haloalkyl; is reacted with aq. $NaIO_4$; in a suitable solvent such as $THF/H_2O$; at room temperature; for a period of 30 minutes before adding HCl; for an additional 12 hours; to provide a compound of formula (XI).

SCHEME 7

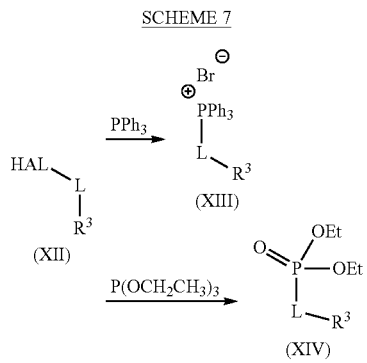

According to SCHEME 7, a commercially available or synthetically accessible benzyl or heterobenzyl bromide compound of formula (XII), where $R^3$ is as defined in claim 1, HAL is Br, and L is $CH_2$; is reacted with triphenylphosphine; in a suitable solvent such as toluene, and the like; at a temperature 90° C.; for a period of 12 hours; provides an aryl- or heteroaryltriphenylphosphonium compound of formula (XIII). A commercially available or synthetically accessible benzyl bromide compound of formula (XII), where $R^3$ is as defined in claim 1, HAL is Br, and L is $CH_2$; is reacted with a trialkyl phosphite such as triethyl phosphite, and the like; neat; at a temperature of about 100 to 110° C.; for a period of 12 hours; to provide a dialkyl arylphosphonate compound of formula (XIV). Elaboration of an dialkyl arylphosphonate compound of formula (XIV), employing Minisci reaction conditions known to one skilled in the art, for example, employing diethyl (pyridin-2-ylmethyl)phosphonate, sodium peroxydisulfate, pivalic acid, $H_2SO_4$, and $AgNO_3$ in MeCN and $H_2O$ at 80° C. for 1 hour; provides diethyl ((4-(tert-butyl)pyridin-2-yl)methyl)phosphonate.

SCHEME 8

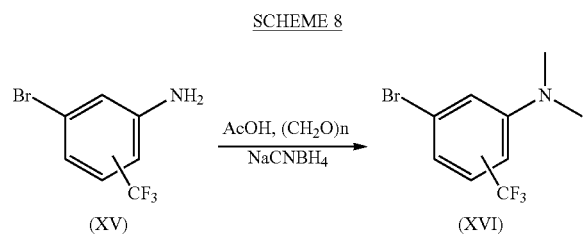

According to SCHEME 8, an aryl bromide compound of formula (XVI), is synthesized from a commercially available or synthetically accessible compound of formula (XV); employing AcOH; paraformaldehyde (($CH_2O)n$); in a suitable solvent such as MeCN, and the like; for a period of 30 minutes; at a temperature of 30° C.; followed by addition of a suitable reducing agent such as sodium cyanoborohydride, and the like; at a temperature of 35° C.; for 16 hours.

SCHEME 9

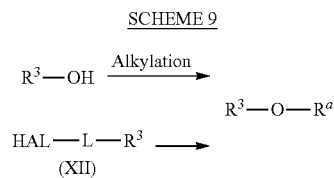

According to SCHEME 9, a commercially available or synthetically accessible compound of formula $R^3$—OH, wherein $R^3$ is a suitably substituted aryl or heteroaryl as defined in claim 1, is reacted with an alkylating agent such as methyl iodide, 2-iodopropane, 1,1,1-trifluoro-2-iodoethane, and the like; a suitable base such as $K_2CO_3$, $Cs_2CO_3$, NaH, and the like; in a suitable solvent such as $CH_3CN$, THF, DMSO, and the like; at temperatures ranging from room temperature to 35° C.; for a period of 4 to 16 hours; to provide a compound of formula $R^3$—O—$R^a$, where $R^a$ is $C_{1-4}$alkyl, $C_{1-4}$haloalkl, or $C_{3-6}$cycloalkyl. In a similar fashion, 6-bromo-1H-pyrrolo[2,3-b]pyridine is alkylated with MeI or 1,1,1-trifluoro-2-iodoethane, employing conditions previously described, to provide 6-bromo-1-methyl-1H-pyrrolo[2,3-b]pyridine and 6-bromo-1-(2,2,2-trifluoroethyl)-1H-pyrrolo[2,3-b]pyridine. 6-Bromo-2H-indazole is also alkylated employing methods described above with 2-iodopropane to provide 6-bromo-2-isopropyl-2H-indazole.

A compound of formula $R^3$—OH, such as 6-bromo-2-methylpyridin-3-ol, is treated with sodium 2-chloro-2,2-difluoroacetate; a base such as $Cs_2CO_3$, and the like; in a suitable solvent such as DMF, and the like; at a temperature of 65° C.; for a period of 40 hours; to provide 6-bromo-3-(difluoromethoxy)-2-methylpyridine.

A commercially available or synthetically accessible compound of formula (XII), where HAL is fluoro or chloro, L is absent and $R^3$ is an appropriately substituted pyridine; is reacted in an $S_NAr$ transformation with a commercially available or synthetically accessible alcohol of formula $R^a$—OH, where $R^a$ is $C_{1-4}$alkyl, $C_{1-4}$haloalkyl, or $C_{3-6}$cycloalkyl; a base such as KOtBu, NaH, $Cs_2CO_3$, and the like; in a suitable solvent such as DMF, THF, and the like; at temperatures ranging from 60-120° C.; for a period of 1-16 hours; to provide a compound of formula $R^3$—O—$R^a$. *It is noted that $R^3$ displays an additional halogen substituent not shown in formula $R^3$—O—$R^a$.

SCHEME 10

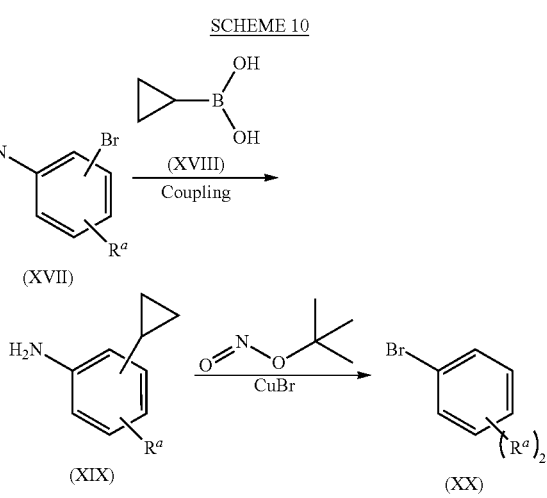

According to SCHEME 10, a compound of formula (XVII), where $R^a$ is $C_{1-4}$alkyl; is reacted in a metal-mediated cross coupling reaction to provide a compound of formula (XIX). For example, a compound of formula (XVII), is reacted with a commercially available or synthetically accessible suitably substituted aryl boronic acid such as cyclopropylboronic acid; in the presence of a palladium catalyst such as Pd(OAc)$_2$, bis(triphenylphosphine)palladium(II)chloride (PdCl$_2$(PPh$_3$)$_2$), bis(diphenylphosphino)ferrocene]dichloropalladium(II) complex with dichloromethane (PdCl$_2$(dppf).DCM), [1,1'-bis(diphenylphosphino)ferrocene]dichloropalladium(II) (PdCl$_2$(dppf)), tetrakis(triphenylphosphine)palladium(0) (Pd(PPh$_3$)$_4$), 2-dicyclohexylphosphino-2',6'-diisopropoxy-1,1'-biphenyl)[2-(2'-amino-1,1'-biphenyl)]palladium(II) methanesulfonate (RuPhos-Pd-G3), and the like; a phosphine ligand such as PPh$_3$; base such as potassium phosphate, Na$_2$CO$_3$, Cs$_2$CO$_3$, and the like; in a suitable solvent such as ACN, water, 1,4-dioxane, toluene, or a mixture thereof; at a temperature ranging from 70° C.-120° C.; for a period ranging from 2 h to 48 h, using conventional or microwave heating, to provide a compound of formula (XIX). Diazotization of an arylamine compound of formula (XIX); followed by reaction of the formed diazonium salt with a brominating agent such as CuBr, and the like; employing Sandmeyer reaction conditions; provides a compound of formula (XX). For example, a compound of formula (XIX) is reacted with tert-butyl nitrite; CuBr; in a suitable solvent such as acetonitrile, and the like; at a temperature of about 60° C.; for a period of about 1.5 hours; to provide a compound of formula (XX), where $R^a$ is independently cyclopropyl and $C_{1-4}$alkyl.

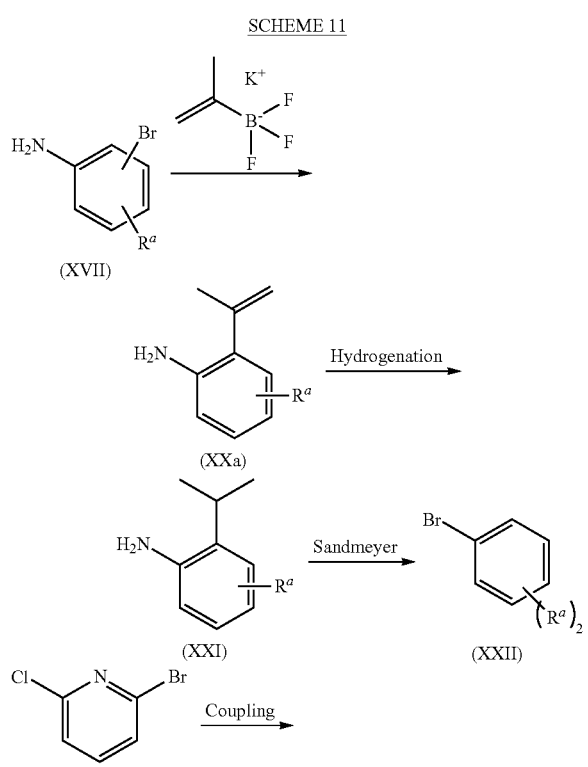

SCHEME 11

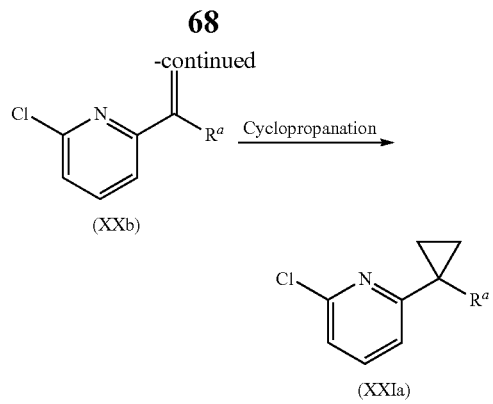

According to SCHEME 11, a compound of formula (XVII), where $R^a$ is $C_{1-4}$haloalkyl, is reacted in a Suzuki-Miyaura cross-coupling reaction with an alkyltrifluoroborate to provide a compound of formula (XXa). For example, 2-bromo-3-(trifluoromethyl) aniline is reacted with potassium trifluoro(prop-1-en-2-yl)borate; a base such as Cs$_2$CO$_3$, Na$_2$CO$_3$, TEA, and the like; a palladium catalyst such as Pd(dppf)Cl$_2$, Pd(dppf)Cl$_2$·CH$_2$Cl$_2$, and the like; in a suitable solvent such as EtOH, 1,4-dioxane, H$_2$O, or a mixture thereof; at a temperature of about 85° C. to 100° C.; for a period of 2 to 16 hours; to provide 2-(prop-1-en-2-yl)-3-(trifluoromethyl)aniline. In a similar fashion, 2-bromo-6-chloropyridine is reacted with potassium trifluoro(prop-1-en-2-yl)borate or 4,4,6-trimethyl-2-(3,3,3-trifluoroprop-1-en-2-yl)-1,3,2-dioxaborinane, employing conditions as described above to provide compounds of formula (XXb), where $R^a$ is $C_{1-4}$alkyl or $C_{1-4}$haloalkyl.

A compound of formula (XXa), where $R^a$ is $C_{1-4}$haloalkyl, is reduced under hydrogenation conditions known to one skilled in the art to provide a compound of formula (XXI). For example, reaction of 2-(prop-1-en-2-yl)-3-(trifluoromethyl)aniline with AcOH; in a suitable solvent such as ethanol, and the like; a catalyst such as PtO$_2$, and the like; under 50 psi of H$_2$; at a temperature of 60° C.; for a period of 24 hours; provides 2-isopropyl-3-(trifluoromethyl)aniline. A compound of formula (XXI), where $R^a$ is $C_{1-4}$haloalkyl, is reacted under Sandmeyer conditions as previously described, to provide a compound of formula (XXII), where $R^a$ is independently $C_{1-4}$alkyl and $C_{1-4}$haloalkyl.

A compound of formula (XXb), where $R^a$ is $C_{1-4}$alkyl or $C_{1-4}$haloalkyl, is reacted with a cyclopropanation reagent such as trimethylsulphoxonium or methyldiphenylsulfonium tetrafluoroborate; a base such as KOtBu, LiHMDS, and the like; in a solvent such as DMSO, THF, and the like; at temperatures ranging from −70° C. to rt; for a period of 3-16 h; to provide a compound of formula (XXIa).

SCHEME 12

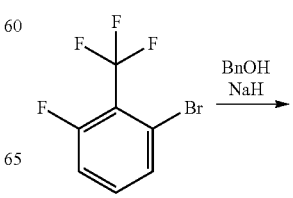

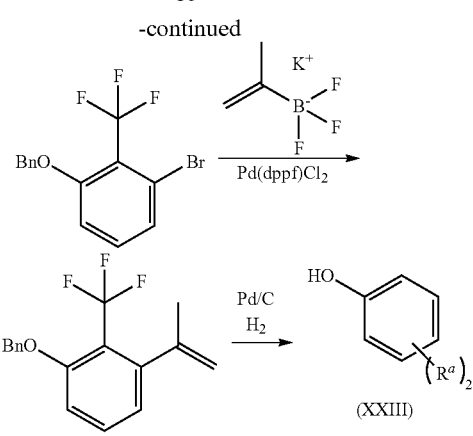

(XXIII)

According to SCHEME 12, 1-bromo-3-fluoro-2-(trifluoromethyl)benzene is reacted with benzyl alcohol, a suitable base such as sodium hydride, and the like; in a suitable solvent such as DMF, and the like; at room temperature; for a period of 12 hours; to provide 1-(benzyloxy)-3-bromo-2-(trifluoromethyl)benzene. 1-(Benzyloxy)-3-bromo-2-(trifluoromethyl)benzene is reacted in a Suzuki-Miyaura cross-coupling reaction as previously described with potassium trifluoro(prop-1-en-2-yl)borate, to provide 1-(benzyloxy)-3-(prop-1-en-2-yl)-2-(trifluoromethyl)benzene. 1-(Benzyloxy)-3-(prop-1-en-2-yl)-2-(trifluoromethyl)benzene is reacted under hydrogenation conditions such as with a palladium catalyst such as Pd/C; in a suitable solvent such as EtOH; under 50 psi of $H_2$; at a temperature of 60° C.; for a period of 20 hours; to provide a compound of formula (XXIII), where $R^a$ is independently $C_{1-4}$alkyl and $C_{1-4}$haloalkyl.

SCHEME 13

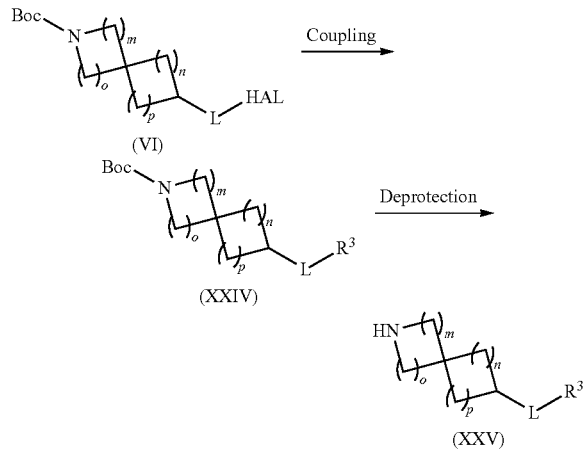

According to SCHEME 13, a compound of formula (VI), wherein L is absent or CH(CH₃), HAL is I, m is 1, o is 1 or 2; n and p are each independently 1 or 2; is reacted in a metal mediated cross coupling reaction with an appropriately substituted commercially available or synthetically accessible aryl or heteroaryl halide, aryl or heteroaryl boronic acid, or aryl or heteroaryl organomagnesium halide; in flow or in batch; using a suitable catalyst such as palladium (II) acetate, bis(dibenzylideneacetone)palladium, cobalt (II) bromide, cobalt (II) acetylacetonate, nickel(II) acetylacetonate, nickel(II) iodide, and the like; and a ligand such as dicyclohexyl(2',6'-diisopropoxy-[1,1'-biphenyl]-2-yl)phosphine (RuPhos), 2-dicyclohexylphosphino-2',4',6'-triisopropylbiphenyl (XPhos), N,N,N',N'-tetramethylethylenediamine, (1R,2R)-2-aminocyclohexanol and the like; with no base or an appropriate base such a sodium hexamethyldisilazide (NaHMDS) and the like; in a suitable solvent such as THF, over a period of 1-14 h; at a temperature range of 0-70° C. to provide a compound of formula (XXIV), where $R^3$ is as defined in claim 1. A compound of formula (XXIV), where the aryl $R^3$ displays a halogen substituent, is elaborated by reaction with 2,4,6-trimethyl-1,3,5,2,4,6-trioxatriborinane; a palladium catalyst such as Pd(dppf)Cl₂·CH₂Cl₂, and the like; a suitable base such as K₂CO₃, and the like; in a solvent such as 1,4-dioxane, H₂O, or a mixture thereof; at a temperature of about 120° C.; for a period of 48 hours; to provide a compound of formula (XXIV), where the halogen is now a CH₃ substituent.

Deprotection of the tert-butyl carbamate on a compound of formula (XXIV) is achieved under conditions known to one skilled in the art. For example, reaction with an acid such as TFA, HCl, and the like, in a suitable solvent such as DCM, 1,4-dioxane, and the like, at room temperature, for a period of 1-6 hr, provides a compound of formula (XXV), where L is absent or CH(CH₃) and $R^3$ is as defined in claim 1.

SCHEME 14

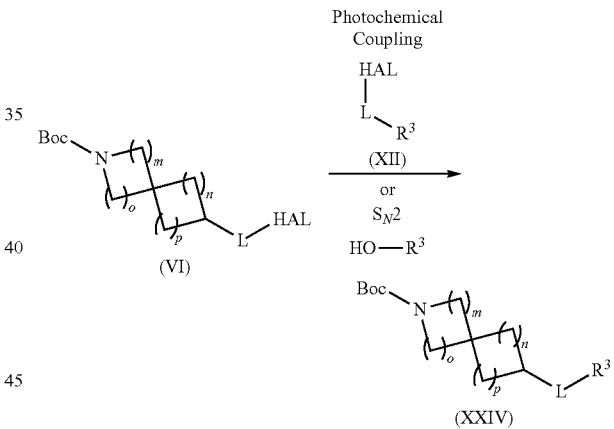

According to SCHEME 14, a compound of formula (VI), where m and o are 1 or 2, n and p are 1, HAL is Br, and L is absent or CH₂; is reacted under photochemical cross-coupling conditions in the presence of a commercially available or synthetically accessible appropriately substituted aryl or heteroaryl halide of formula (XII), where HAL is Br, L is absent or CH₂, and $R^3$ is as defined in claim 1; with a photocatalyst such as (Ir[dF(CF₃)ppy]₂(dtbpy))PF₆, and the like; a cross-coupling catalyst such as nickel(II) chloride ethylene glycol dimethyl ether complex (NiCl₂(DME)), and the like; a ligand such as 4,4'-di-tert-butyl-2,2'-bipyridine, and the like; a base such as 2,6-dimethylpyridine or potassium carbonate, and the like; a suitable additive such as tris(trimethylsilyl)silane or tris(trimethylsilyl)silanol, and the like; a suitable solvent such as 1,2-dimethoxyethane (DME) or dimethyl sulfoxide (DMSO), ethylene glycol dimethyl ether, and the like; under irradiation from light of wavelength 425 or 450 nm; at room temperature; to provide a compound of formula (XXIV), where L is absent or CH₂, and R³ is as defined in claim 1. Wherein the R³ moiety on a compound of formula (XXIV) is substituted with a halogen such as Br, further elaboration of the R³ group is achieved employing photochemical cross coupling methods as described above with potassium trifluoro(isopropyl)borate, to afford a compound of formula (XXIV) where the Br is replaced with an isopropyl. In a similar fashion, wherein the R³ moiety on a compound of formula (XXIV) is substituted with a halogen such as Br, further elaboration of the R³ group is achieved in a metal mediated cross coupling reaction with 2,4,6-trimethyl-1,3,5,2,4,6-trioxatriborinane, employing methods known to one skilled in the art or as previously described, to afford a compound of formula (XXIV) where the Br is now a CH₃ substituent.

Alternately, a compound of formula (VI), where m and o are 1, n and p are 1 or 2, L is absent, and HAL is iodo or bromo; is reacted with a nucleophile such as R³—OH, where R³ is a suitably substituted aryl such as o-cresol, and the like; a base such as cesium carbonate, and the like; in a solvent such as DMF, and the like; at a temperature of about 80° C.; for a period of about 12-18 h; to provide a compound of formula (XXIV), where L is O. In a similar manner, a compound of formula (VI), where m and o are 1, n and p are 1 or 2, L is CH₂, and HAL is iodo or bromo; is reacted with a nucleophile such as 3-(trifluoromethyl)-1H-pyrazole, and the like; a base such as cesium carbonate, and the like; in a solvent such as DMF, and the like; at a temperature of about 80° C.; for a period of about 12-18 h; to provide a compound of formula (XXIV), where L is CH₂.

(XII), where L is absent, HAL is Br, and R³ is a suitably substituted aryl; in a suitable solvent such as THF, diethyl ether (Et₂O), and the like; at temperatures ranging from −78° C. to room temperature; to provide a compound of formula (XXVI) where R³ is as defined in claim 1. Where a compound of formula (XXVI) displays a bromine substituent, further elaboration of the aryl R³ is achieved by reaction with 2,4,6-trimethyl-1,3,5,2,4,6-trioxatriborinane; a suitable palladium catalyst such as Pd(dppf)Cl₂·CH₂Cl₂, and the like; a suitable base such as K₂CO₃, and the like; in a solvent such as 1,4-dioxane, H₂O, or a mixture thereof; at a temperature of about 120° C.; for a period of 48 hours; to provide a compound of formula (XXVI), where the bromine is now a CH₃ substituent.

Alternatively, a compound of formula (IV), where n, m, o, p are each independently 1 or 2, is reacted with a commercially available or synthetically accessible suitably substituted aryl halide of formula R³—X, where R³ is as defined in claim 1, and X is I or Br; n-BuLi; in a suitable solvent such as THF, and the like; at temperatures ranging from −78° C. to room temperature; for a period of 2 to 8 hrs; to provide a compound of formula (XXVI). Where a compound of formula (XXVI) displays a bromine substituent, further elaboration of the aryl R³ is achieved by metal mediated coupling reaction with a boronic acid such as cyclopropylboronic acid; a catalyst such as CataCXium® A Pd G3, and the like; a base such as potassium phosphate, and the like; in a suitable solvent such as toluene, water, or a mixture thereof; a temperatures ranging from 70° C. to 100° C.; for

SCHEME 15

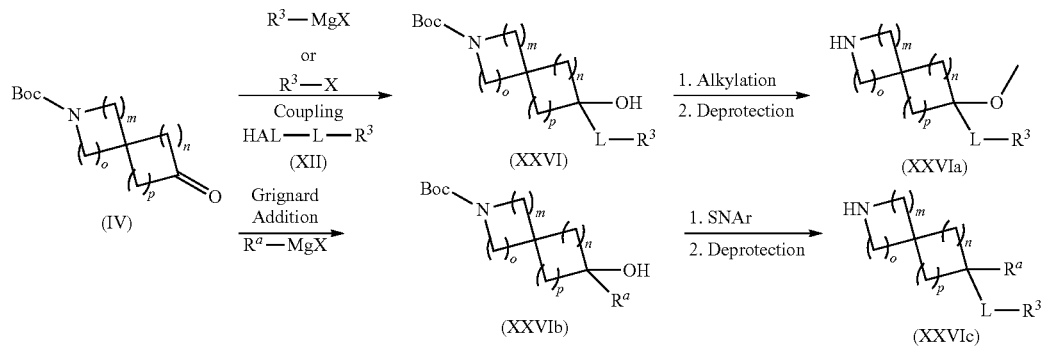

According to SCHEME 15, a compound of formula (IV), where n, m, o, p are each independently 1 or 2, is reacted under conventional Grignard reaction conditions in the presence of a commercially available or synthetically accessible organomagnesium halide of formula R³MgX, where R³ is as defined in claim 1, and X is Br or Cl, such as phenylmagnesium bromide, 3-isopropylphenylmagnesium bromide, 4-isopropylphenylmagnesium bromide, 3-tert-butylphenylmagnesium bromide, 4-tert-butylphenylmagnesium bromide, benzylmagnesium chloride, and the like; with or without an additive such as cerium(III) chloride; in a suitable solvent such as THF, diethyl ether (Et₂O), and the like; at temperatures ranging from −78° C. to room temperature; to provide a compound of formula (XXVI) wherein L is absent or CH₂, and R³ is as defined in claim 1.

A compound of formula (IV), where n, m, o, p are 1, is reacted with a Grignard reagent generated from a turbo Grignard reagent such as iPrMgCl·LiCl and a commercially available or synthetically accessible compound of formula a period of 12-18 hours; to provide a compound of formula (XXVI) where the bromine is now a cyclopropyl substituent.

A compound of formula (XXVIa), where L is absent or CH₂, is prepared in two steps from a compound of formula (XXVI). In a first step, alkylation of a compound of formula (XXVI) with a suitable alkylating agent such as MeI, and the like; a suitable base such as NaH; in a suitable solvent such as DMF, and the like; at temperatures ranging from 0° C. to room temperature; affords the —O— alkylated compound which in a second step is subsequently deprotected employing conditions previously described; to afford a compound of formula (XXVIa).

A compound of formula (IV), where n, m, o, p are each independently 1 or 2, is reacted under conventional Grignard reaction conditions in the presence of a commercially available or synthetically accessible organomagnesium halide of formula R^a MgX, where R^a is C₁₋₄alkyl, and X is Br or Cl, such as methylmagnesium bromide, ethylmagnesium bromide, and the like; employing conditions known to one skilled in the art or as previously described to afford a compound of formula (XXVIb). A compound of formula (XXIVb) is reacted with a commercially available or synthetically accessible halo pyridine in an S$_N$Ar addition reaction, employing methods known to one skilled in the art or as previously described, followed by deprotection under conditions previously described to afford a compound of formula (XXVIc) where L is O and R$^a$ is C$_{1-4}$alkyl.

SCHEME 16

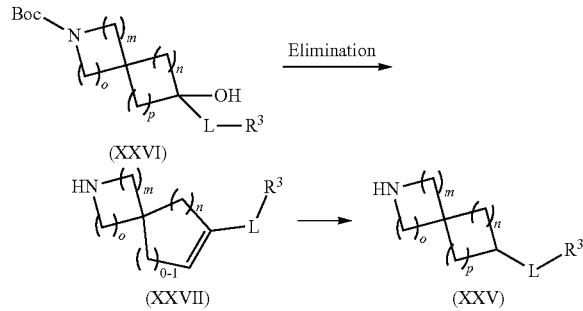

According to SCHEME 16, a compound of formula (XXVI), where L is absent, and R$^3$ is as defined in claim 1; is reacted under acidic ionic reduction conditions such as TFA, using triethylsilane (TES); at a temperature of about room temperature; for a period of 1-4 hours; which may eliminate the alcohol and cleave the tert-butoxycarbonyl group to provide a compound of formula (XXVII). It may also occur that under acidic ionic reduction conditions as described above that a compound of formula (XXVI), where m, and o are 1, n and p are 1 or 2; provides a compound of formula (XXV) directly.

In a similar fashion, a compound of formula (XXVI), where m, n, and o are 1, p is 1 or 2, L is absent, and R$^3$ is as defined in claim 1; is reacted under elimination conditions employing a dehydrating agent such as the Burgess reagent, and the like; to eliminate the alcohol and provide a compound of formula (XXVII). Reduction of the double bond is achieved employing hydrogenation conditions known to one skilled in the art, or as previously described. For example, using a catalyst such as PtO$_2$, Hz, in a suitable solvent such as EtOH, and the like. Deprotection of the tert-butyl carbamate is achieved under conditions known to one skilled in the art, or as previously described to provide a compound of formula (XXV). A compound of formula (XXV) is also prepared in two steps from a compound of formula (XXVII, where XXVII still has the Boc protecting group), instead by first deprotection then followed by hydrogenation of the double bond.

When a compound of formula (XXVI), where L is absent, and R$^3$ is phenyl substituted with CF$_2$CH$_3$, is reacted under acidic ionic reduction conditions such as TFA, using triethylsilane (TES) as previously described, a compound of formula (XXV) is afforded, where R$^3$ is phenyl substituted with CH$_2$CH$_3$.

SCHEME 17

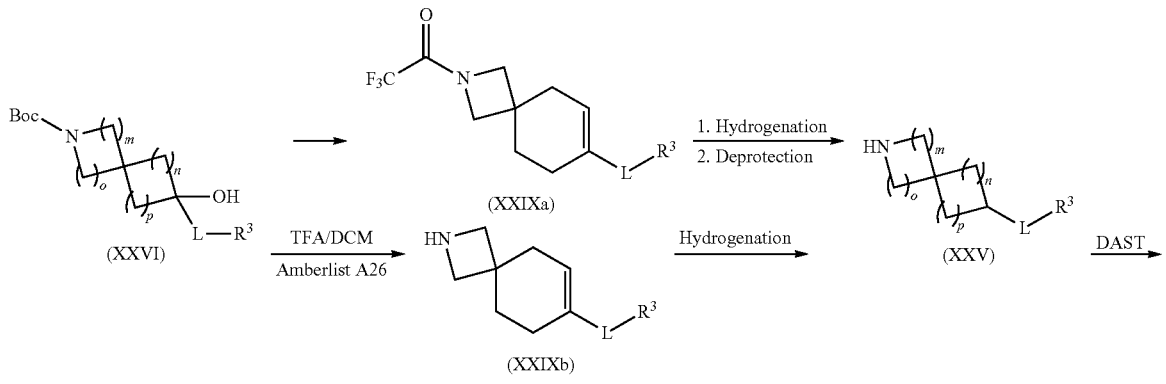

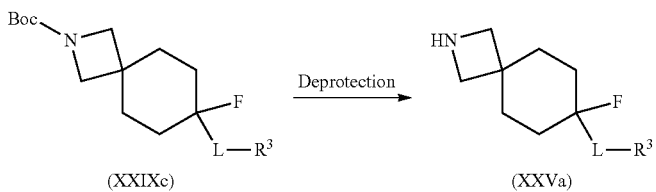

According to SCHEME 17, a compound of formula (XXVI), where m and o are 1, n and p are 2, L is CH$_2$, and R$^3$ is as defined in claim 1; is then dehydrated in the presence of trifluoroacetic acid and trifluoroacetic anhydride to afford a trifluoroacetate amide compound of formula (XXIXa). A compound of formula (XXIXa) is reduced employing hydrogenation conditions known to one skilled in the art or as previously described; and deprotection of the trifluoroacetate employing potassium carbonate, at elevated temperatures, provides a compound of formula (XXV). A compound of formula (XXVI), where m and o are 1, n and p are 2, L is absent, and R$^3$ is as defined in claim 1; is reacted with TFA in a suitable solvent such as DCM, and the like, at 60° C., for a period of 30 minutes; followed by the addition of Amberlist A26; to provide a compound of formula (XXIXb). Subsequent hydrogenation of a compound of formula (XXIXb), employing a palladium catalyst such as Pd/C, under H$_2$, in a suitable solvent such as MeOH, at a temperature of 50° C., for a period of 1 hr, provides a compound of formula (XXV), where m and o are 1, n and p are 2.

A compound of formula (XXVI), where m and o are 1, n and p are 2, L is absent and R$^3$ is as described in claim 1, is fluorinated with DAST; in a suitable solvent such as DCM, and the like; at temperatures ranging from of −78° C. to rt; for a period of 1-2 h; to provide a compound of formula (XXIXc). Cleavage of the BOC protecting group is achieved employing methods known to one skilled in the art or using 2,6-dimethylpyridine; and trimethylsilyl trifluoromethanesulfonate; at rt for 1.5 h; to afford a compound of formula (XXVa).

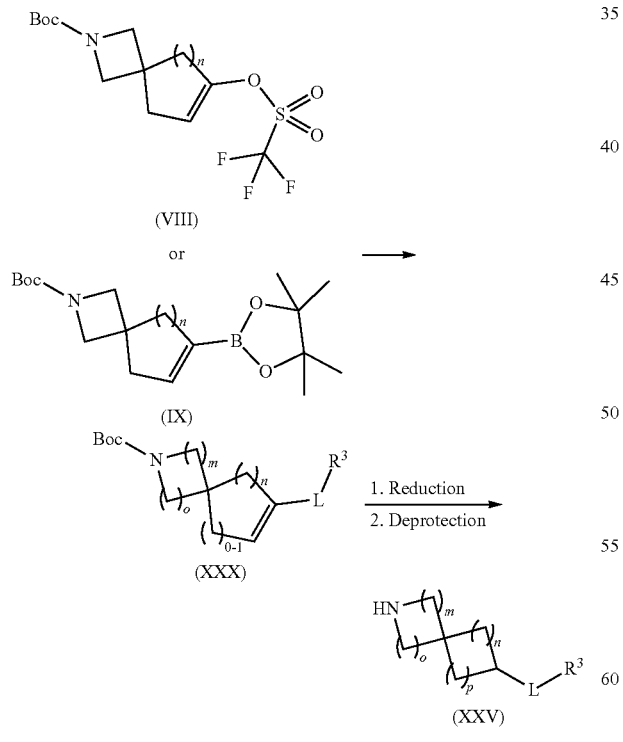

SCHEME 18

According to SCHEME 18, a compound of formula (VIII), where n is 1 or 2; is reacted in a metal mediated cross coupling reaction with a commercially available or synthetically accessible appropriately substituted aryl or heteroaryl boronic acid of formula R$^3$—B(OH)$_2$ (or pinacol boronic ester and boronate ester), where R$^3$ is as defined in claim 1; in the presence of a palladium catalyst such as PdCl$_2$(dtbpf), Pd(PPh$_3$)$_4$, bis(triphenylphosphine)palladium(II)chloride (PdCl$_2$(PPh$_3$)$_2$), bis(diphenylphosphino)ferrocene]dichloropalladium(II) complex with dichloromethane, (2-dicyclohexylphosphino-2',6'-diisopropoxy-1,1'-biphenyl)[2-(2'-amino-1,1'-biphenyl)]palladium(II) methanesulfonate (RuPhos Pd G3), [1,1'-bis(diphenylphosphino)ferrocene]dichloropalladium(II) (Pd(dppf)Cl$_2$), XPhos Pd G2, Pd(dppf)Cl$_2$, CataXCiumA Pd G3, and the like; a base such as KF, K$_3$PO$_4$, aq. Na$_2$CO$_3$, Cs$_2$CO$_3$, and the like; in a suitable solvent such as 1,4-dioxane, dimethylformamide (DMF), acetonitrile (ACN), water, or a mixture thereof; at temperatures ranging from 60 to 120° C.; for a period of about 16 to 48 hours to provide a compound of formula (XXX), where L is absent.

Where a compound of formula (XXX), where L is absent, has an R$^3$ substituent displaying a free OH moiety, further elaboration of the aryl R$^3$ is achieved by reaction with an alkylating agent such as ethyl iodide; a suitable base such as K$_3$PO$_4$, and the like; in a solvent such as ACN, and the like; at room temperature; for a period of 16 hours; to provide an compound of formula (XXX), where the OH is now OEt.

A compound of formula (IX), where n equals 1 or 2, is reacted with an appropriately substituted commercially available or synthetically accessible aryl or heteroaryl halide of formula R$^3$-HAL, where HAL is I or Br, and R$^3$ is as defined in claim 1, employing a suitable base such as Cs$_2$CO$_3$, K$_3$PO$_4$, and the like; a catalyst/ligand system such as CataCXium® A-Pd-G3, Pd(dppf)Cl$_2$, Pd(dppf)$_2$Cl$_2$·CH$_2$Cl$_2$, and the like; in a suitable solvent such as THF, 2-methyl-2-butanol, and the like; at a temperature of about 90 to 110° C.; for a period of about 2-4 hours; to provide a compound of formula (XXX), where L is absent.

Where a compound of formula (XXX) displays a bromine substituent, further elaboration of the aryl R$^3$ is achieved by metal mediated coupling reaction with a boronic acid or boronic ester such as cyclopropylboronic acid or trifluoro (vinyl)borate; a catalyst such as Pd(dtbpf)Cl$_2$, CataCXium® A Pd G3, and the like; a base such as CsF, potassium phosphate, and the like; in a suitable solvent such as 1,4-dioxane, toluene, water, or a mixture thereof; a temperatures ranging from 70° C. to 100° C.; for a period of 12-18 hours; to provide a compound of formula (XXX) where the bromine is now a vinyl or cyclopropyl substituent.

A compound of formula (XXV) is prepared in two steps from a compound of formula (XXX). In a first step, reduction of the double bond is achieved employing hydrogenation conditions known to one skilled in the art, or as previously described. Subsequent deprotection of the BOC protecting group is achieved employing deprotection conditions known to one skilled in the art, or as previously described.

SCHEME 19

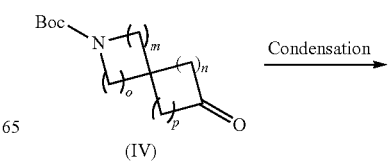

-continued

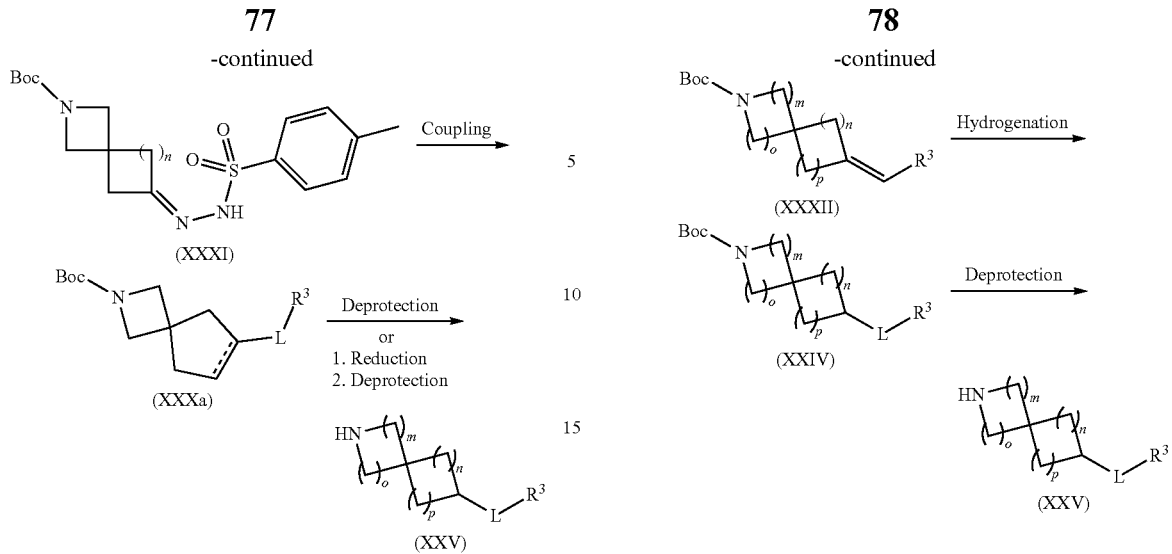

According to SCHEME 19, a compound of formula (IV), where m, o, and p are 1, and n is 1 or 2; is reacted with 4-methylbenzenesulfonhydrazide; in a suitable solvent such as 1,4-dioxane, and the like; at a temperature of about 80° C.; for a period of 2-5 h; to provide a compound of formula (XXXI). A compound of formula (XXXI), where n is 2, is reacted in a coupling reaction with an appropriately substituted aryl or heteroaryl boronic acid of formula $R^3$—$B(OH)_2$ (or pinacol boronic ester and boronate ester), where $R^3$ is as defined in claim 1; or an appropriately substituted aryl or heteroaryl halide of formula $R^3$-HAL, where HAL is I or Br, and $R^3$ is as defined in claim 1, employing methods previously described, to provide a compound of formula (XXXa), where ==== is a single or double bond, and L is absent. A compound of formula (XXXa), where ==== is a single bond, is deprotected employing methods known to one skilled in the art, or as previously described, to provide a compound of formula (XXV), where m, o, and p are 1, n is 2, L is absent, and $R^3$ is as defined in claim 1.

A compound of formula (XXXa), where ==== is a single or a double bond, L is absent, and $R^3$ is substituted with Br, is further elaborated by metal mediated coupling reaction employing conditions previously described, with 2,4,6-trimethyl-1,3,5,2,4,6-trioxatriborinane or potassium trifluoro (prop-1-en-2-yl)borate. Wherein a compound of (XXXa), where ==== is a double bond, L is absent, and/or $R^3$ is substituted with a vinyl group, is reduced with a suitable reducing agent known to one skilled in the art or as previously described to provide a compound of formula (XXXa), where ==== is a single bond, and the vinyl is now ethyl. Deprotection of a compound of formula (XXXa), employing conditions known to one skilled in the art, or as previously described affords a compound of formula (XXV), where L is absent.

According to SCHEME 20, a compound of formula (IV), where m and o are 1, and n and p are independently 1 or 2, is reacted with a commercially available or synthetically accessible Wittig type reagent of formula (XIII) or formula (XIV) where L is $CH_2$ and $R^3$ is as defined in claim 1, such as (3-methylbenzyl)triphenylphosphonium chloride, diethyl 4-(trifluoromethoxy)benzylphosphonate, diethyl 3-methylbenzylphosphonate, diethyl 4-bromobenzylphosphonate, and the like; a base such as NaH, n-butyllithium, and the like; in an organic solvent such as DMSO, THF, toluene, ether, and the like; to provide a compound of formula (XXXII). A compound of formula (XXXII), where $R^3$ is 2-bromophenyl is reacted with 2,4,6-trimethyl-1,3,5,2,4,6-trioxatriborinane, using a base such as $K_3PO_4$, and the like; a ligand/catalyst system such as Pd(dtbpf)$Cl_2$, and the like; in a solvent such as 1,4-dioxane, and the like; at 120° C.; for a period of 16 hours; affords a compound of formula (XXXII), where $R^3$ is 2-methylphenyl.

A compound of formula (XXXII) is reduced employing hydrogenation conditions in the presence of a palladium catalyst, including but not limited to, $PtO_2$, Pd/C, Pd(dppf)$Cl_2$ or Pd(PPh$_3$)$_4$; in a suitable solvent or solvent system such as ethyl acetate, methanol, dioxane/water, and the like; to provide a compound of formula (XXIV), where L is $CH_2$.

A compound of formula (XXIV) where L is $CH_2$ and $R^3$ is 4-bromophenyl, is reacted with cyclopropylboronic acid, a base such as potassium phosphate, and the like; and a catalyst such as CataCXium® A Pd G3, and the like; to provide a compound of formula (XXIV), where $R^3$ is 4-cyclopropylphenyl.

Deprotection of the tert-butyl carbamate on a compound of formula (XXIV) is achieved under conditions known to one skilled in the art. For example, reaction with an acid such as TFA, HCl, and the like, in a suitable solvent such as DCM, 1,4-dioxane, and the like, at room temperature, for a period of 1-6 hr, provides a compound of formula (XXV), where L is $CH_2$.

SCHEME 20

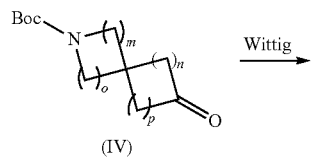

SCHEME 21

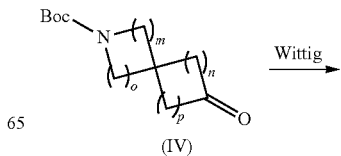

-continued

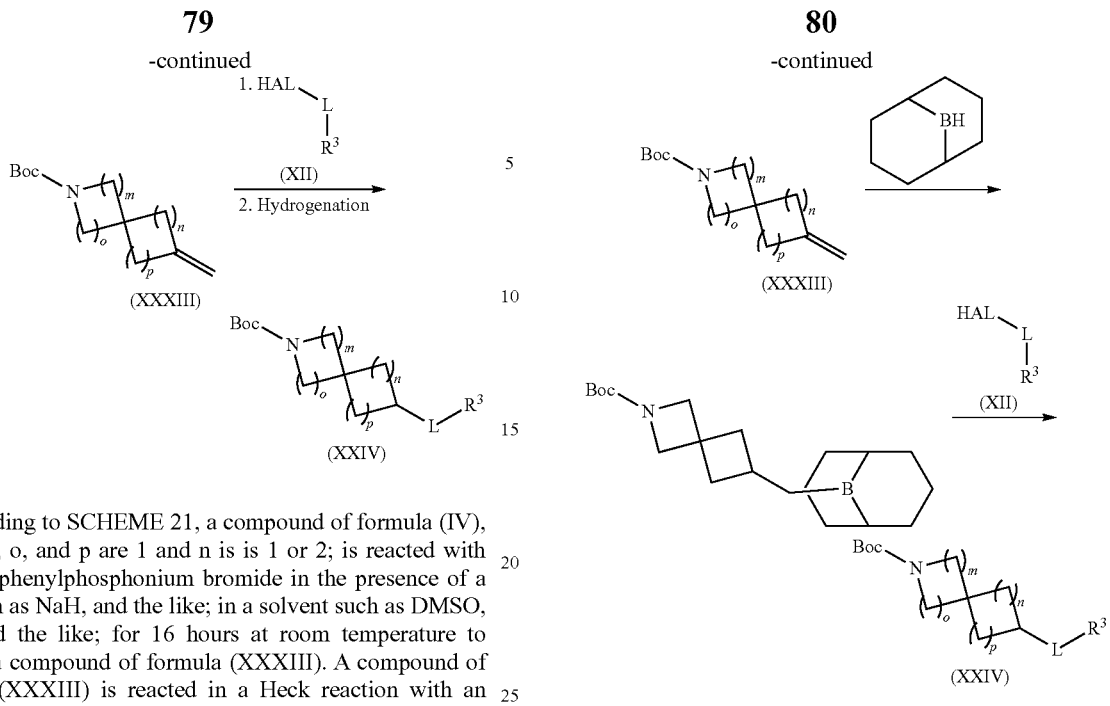

According to SCHEME 21, a compound of formula (IV), where m, o, and p are 1 and n is is 1 or 2; is reacted with methyltriphenylphosphonium bromide in the presence of a base such as NaH, and the like; in a solvent such as DMSO, THF, and the like; for 16 hours at room temperature to provide a compound of formula (XXXIII). A compound of formula (XXXIII) is reacted in a Heck reaction with an appropriately substituted commercially available or synthetically accessible aryl halide of formula (XII), where HAL is Br, L is absent, and $R^3$ is as defined in claim 1; using a catalyst such as Pd(OAc)$_2$, and the like; a ligand such as tri-o-tolylphosphine, and the like; a base such as TEA, and the like; in a solvent such as DMF, and the like; at a temperature of 130° C.; for a period of 12 hours. Subsequent hydrogenation of the double bond is achieved employing conditions known to one skilled in the art or as previously described; to provide a compound of formula (XXIV), where L is CH$_2$. In an alternate method, reduction of the double bond is also achieved employing a reducing agent such as BH$_3$.THF, in a suitable solvent such as THF, to afford a compound of formula (XXIV), where L is CH$_2$.

Wherein a compound of formula (XXIV) displays a bromine substituent on the aryl or heteroaryl $R^3$, further elaboration of the $R^3$ is achieved in a coupling reaction with 2,4,6-trimethyl-1,3,5,2,4,6-trioxatriborinane; a suitable palladium catalyst such as Pd(dppf)Cl$_2$·CH$_2$Cl$_2$, employing conditions previously described, to afford a compound of formula (XXIV), where the bromine is now a CH$_3$ substituent.

Wherein the $R^3$ moiety on compound of formula (XXIV) is an appropriately substituted halo pyridine (where the halogen is F or Cl) further functionalization of the $R^3$ is achieved under S$_N$Ar reaction conditions, for example, in a suitable alcohol solvent such as MeOH, iPrOH, and the like; a base such as NaH, MeONa, and the like; at an elevated temperature such as 60° C. to 80° C.; provides a compound of formula (XXIV), where the F or Cl on the pyridine is replaced with O—C$_{1-4}$alkyl.

SCHEME 22

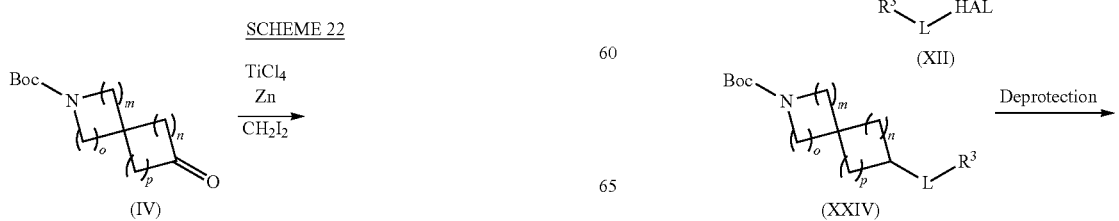

According to SCHEME 22, a compound of formula (IV) where m, n, o, and p are 1; is reacted with TiCl$_4$, zinc dust, and CH$_2$I$_2$, in a solvent such as THF, and the like; at room temperature; for a period of 12 hours; to provide a compound of formula (XXXIII). A compound of formula (XXXIII) is reacted with 9-borabicyclo[3.3.1]nonane; in THF; at temperatures ranging from −78° C. to 65° C.; for a period 16 hours; to provide tert-butyl 6-((9-borabicyclo[3.3.1]nonan-9-yl)methyl)-2-azaspiro[3.3]heptane-2-carboxylate. tert-Butyl 6-((9-borabicyclo[3.3.1]nonan-9-yl)methyl)-2-azaspiro[3.3]heptane-2-carboxylate is coupled with an appropriately substituted commercially available or synthetically accessible aryl halide of formula (XII), where L is absent and HAL is Br, using a catalyst such as Pd(dppf)Cl$_2$·CH$_2$Cl$_2$, and the like; a base such as Cs$_2$CO$_3$, and the like; in a suitable solvent such as DMF, and the like; at a temperature of about 65° C.; for a period of 16 hours; to provide a compound of formula (XXIV), where L is absent and $R^3$ is as defined in claim 1.

SCHEME 23

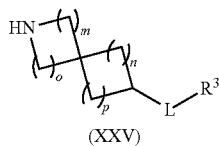

(XXV)

According to SCHEME 23, a compound of formula (V), wherein m, n, o, and p are each independently 1 or 2, and the ring with n and p is optionally substituted with $C_{1-4}$alkyl; is reacted in a Mitsunobu reaction with a commercially available or synthetically accessible phenol compound of formula (XXXIV), where $R^3$ is as defined in claim 1. For example, a compound of formula (V), where m, n, o, and p are each independently 1 or 2; is reacted with compound of formula (XXXIV; $PPh_3$; a suitable activating agent such as DEAD, DCAD, DIAD, DBAD, and the like; in a suitable solvent such as THF, DMF, and the like; at temperatures ranging from room temperature to about 50° C.; to provide a compound of formula (XXIV), where L is O.

A compound of formula (V), where m, n, o, and p are each independently 1 or 2 and the ring with n and p is optionally substituted with $C_{1-4}$alkyl; is reacted in a copper-catalyzed arylation reaction with a commercially available or synthetically accessible aryl iodide of formula (XII), where L is absent and HAL is I, to provide a compound of formula (XXIV), where L is O. For example, a compound of formula (V), where m, n, o, and p are each independently 1 or 2; is reacted with cuprous iodide; a ligand such as 3,4,7,8-tetramethyl-1,10-phenanthroline, and the like; and a base such as cesium carbonate, and the like; an aryl iodide of formula (XII), where L is absent and HAL is I; in a suitable solvent such as toluene, dioxane, and the like; at elevated temperatures up to 110° C.; to provide a compound of formula (XXIV). Deprotection of the tert-butyl carbamate on a compound of formula (XXIV) is achieved under conditions known to one skilled in the art to provide a compound of formula (XXV), where L is O.

A compound of formula (V) wherein m, n, o, and p are each independently 1 or 2 and the ring with n and p is optionally substituted with $C_{1-4}$alkyl; is reacted in a metal mediated coupling reaction with a commercially available or synthetically accessible aryl or heteroaryl halide of formula (XII), where $R^3$ is as defined in claim 1, L is absent, and HAL is Br; a palladium catalyst such as $Pd_2(dba)_3$, and the like; a chiral diphosphine ligand such as BINAP, and the like; a suitable base such as t-BuOK, and the like; in a suitable solvent such as toluene; at temperatures up to 110° C.; employing conventional or microwave heating; to afford a compound of formula (XXIV) where L is O.

A compound of formula (V) wherein m, n, o, and p are for 2 and the ring with n and p is optionally substituted with $C_{1-4}$alkyl; is reacted in an SNAr addition reaction with a suitably substituted commercially available or synthetically accessible 2-halopyridine compound of formula (XII), wherein L is absent, HAL is Cl, employing methods known to one skilled in the art or as previously described, to afford a compound of formula (XXIV) wherein L is O.

Wherein the $R^3$ moiety on a compound of formula (XXIV) is substituted with a halogen such as Br, further elaboration of the $R^3$ group is achieved by reaction with cyclopropylboronic acid, potassium trifluoro(vinyl)borate, and the like; under metal-mediated cross coupling reaction conditions known to one skilled in the art or as previously described to afford a compound of formula (XXIV) wherein the Br is replaced with a cyclopropyl and vinyl, respectively. Reduction of the vinyl substituent is achieved employing hydrogenation conditions known to one skilled in the art or as previously described to provide a compound of formula (XXIV) where the vinyl is reduced to an ethyl.

Wherein the $R^3$ moiety on a compound of formula (XXIV) is substituted with a halogen such as Br, further elaboration of the $R^3$ group is achieved by a transition-metal-catalyzed$gross-coupling reaction with an organozinc reagent such as diethylzinc, and the like; a palladium catalyst such as $Pd(t-Bu_3P)_2$, and the like; in a suitable solvent such as THF, toluene, or a mixture thereof; at temperatures ranging from rt to 60° C.; to provide a compound wherein the Br is replaced with ethyl.

SCHEME 24

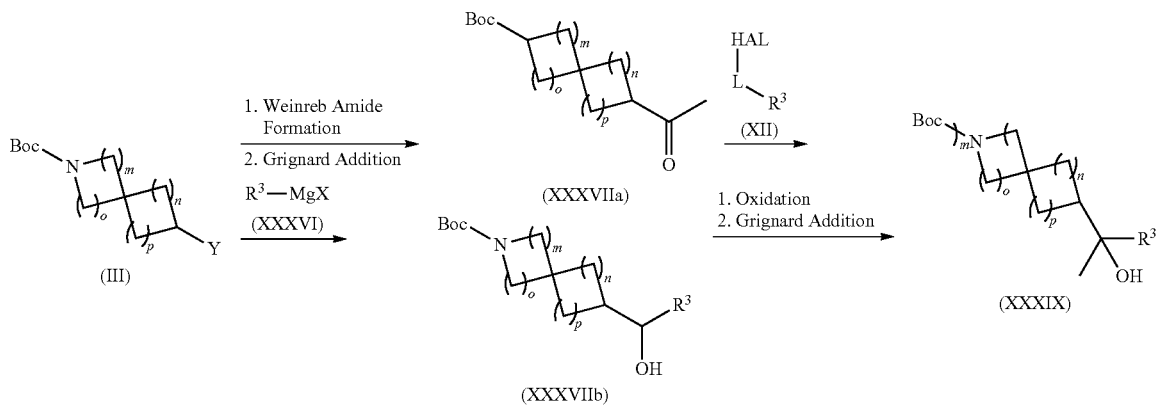

According to SCHEME 24, a compound of formula (III), wherein m, n, o, and p are each independently 1 or 2, and Y is $CO_2H$, is converted to the corresponding Weinreb amide employing methods known to one skilled in the art, for example, by reaction with N,O-dimethylhydroxylamine hydrochloride; DIPEA; HATU; in a suitable solvent such as DMF, and the like; at room temperature; for a period of 1 to 3 hrs. Subsequent reaction of the Weinreb amide in a Grignard addition with methylmagnesium bromide, employing conditions previously described, affords a compound of formula (XXXVIIa). A compound of formula (XXXVIIa) is reacted with a commercially available or synthetically accessible suitably substituted aryl halide of formula $R^3$-L-

HAL, where $R^3$ is as defined in claim 1, L is absent, and X is Br; n-BuLi; in a suitable solvent such as THF, and the like; at temperatures ranging from -78° C. to room temperature; for a period of 2 to 8 hrs; to provide a compound of formula (XXXIX).

A compound of formula (III), wherein m, n, o, and p are each independently 1 or 2, and Y is CHO, is reacted under Grignard reaction conditions in the presence of a commercially available or synthetically accessible organomagnesium halide of formula (XXXVI), where $R^3$ is as defined in claim 1, and X is Br or Cl (such as phenylmagnesium bromide, and the like); employing conditions known to one skilled in the art or as previously described, to provide a compound of formula (XXXVIIb). Oxidation a compound of formula (XXXVIIb) to a ketone is achieved employing conditions known to one skilled in the art, for example, DMP (Dess-Martin periodinane), $SO_3$-pyridine, Swern conditions [$(COCl)_2$, DMSO, $Et_3N$], PCC, and the like; in a solvent such as EtOAc, DMSO, DCM, and the like; at temperatures ranging from about -78° C. to room temperature (about 23° C.). In a preferred method, oxidation with Dess-Martin periodinane, in DCM, at 20° C. for 1 to 4 hours. The corresponding ketone is reacted employing conventional Grignard reaction conditions in the presence of an organo-magnesium halide such as methylmagnesium bromide, and the like; in in a suitable solvent such as $Et_2O$, THF, or a mixture thereof, at a temperature ranging from -40° C. to rt; to provide a compound of formula (XXXIX). The order in which the $R^3$ moiety is installed is also that the first Grignard employs methylmagnesium bromide and the second Grignard addition employs an organo-magnesium halide compound of formula (XXXVI), to provide a compound of formula (XXXIX).

example, hydrogenation of a compound of formula (XLa) under an atmosphere of hydrogen gas ($H_2$) in the presence of a catalyst such as palladium on carbon (Pd/C), $PtO_2$, and the like; in a suitable solvent such as ethyl acetate (EtOAc), EtOH, and the like, provides a compound of formula (XXV) where L is $CH(CH_3)$.

A compound of formula (XXXIX) is reacted under dehydration conditions such as with $SOCl_2$/pyridine, in a suitable solvent such as DCM and the like, to provide a compound of formula (XLb). Subsequent hydrogenation and deprotection of a compound of formula (XLb), employing conditions previously described, provides a compound of formula (XXV) where L is $CH(CH_3)$.

SCHEME 26

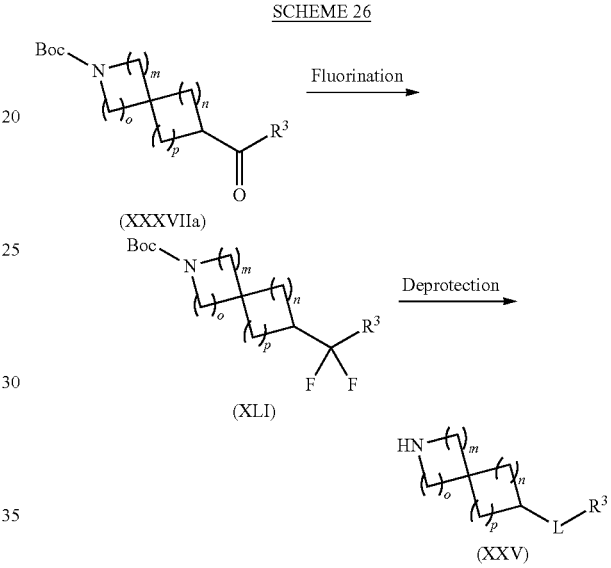

SCHEME 25

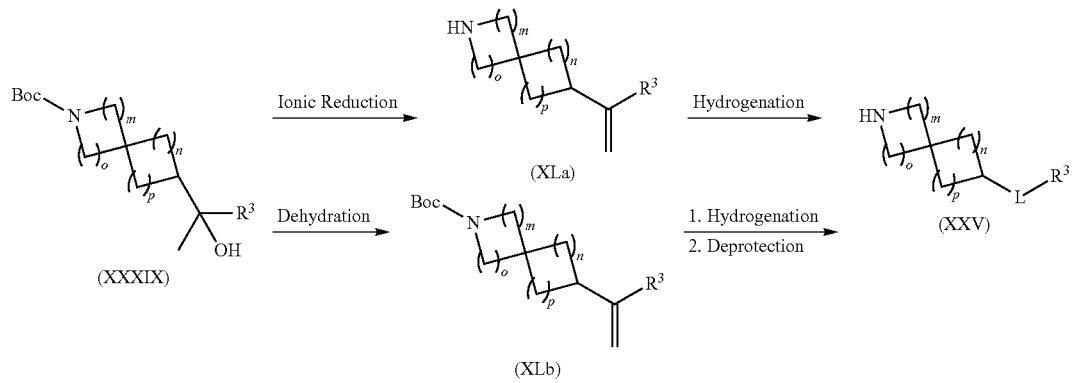

According to SCHEME 25, a compound of formula (XXXIX) is reacted under acidic ionic reduction conditions such as TFA, using triethylsilane (TES), employing methods known to one skilled in the art or as previously described, to eliminate the alcohol and cleave the tert-butoxycarbonyl group providing an alkene compound of formula (XLa). A compound of formula (XLa) is reduced under hydrogenation conditions known to one skilled in the art or as previously described, to provide a compound of formula (XXV). For According to SCHEME 26, difluorination of a compound of formula (XXXVIIa), where $R^3$ is as defined in claim 1, is achieved employing diethylaminosulfur trifluoride (DAST); in a suitable solvent such as DCM, and the like; at a temperature of room temperature; for a period of 1 h; to provide a compound of formula (XLI). Deprotection of a compound of formula (XLI) using conditions known to those skilled in the art or as previously described, provides a compound of formula (XXV), where L is $CF_2$.

SCHEME 27

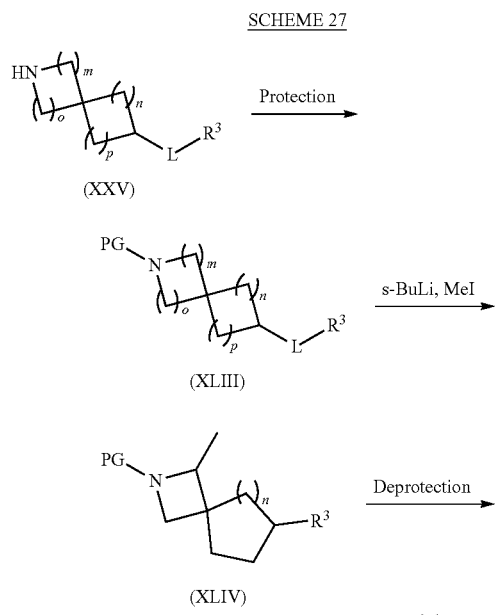

SCHEME 28

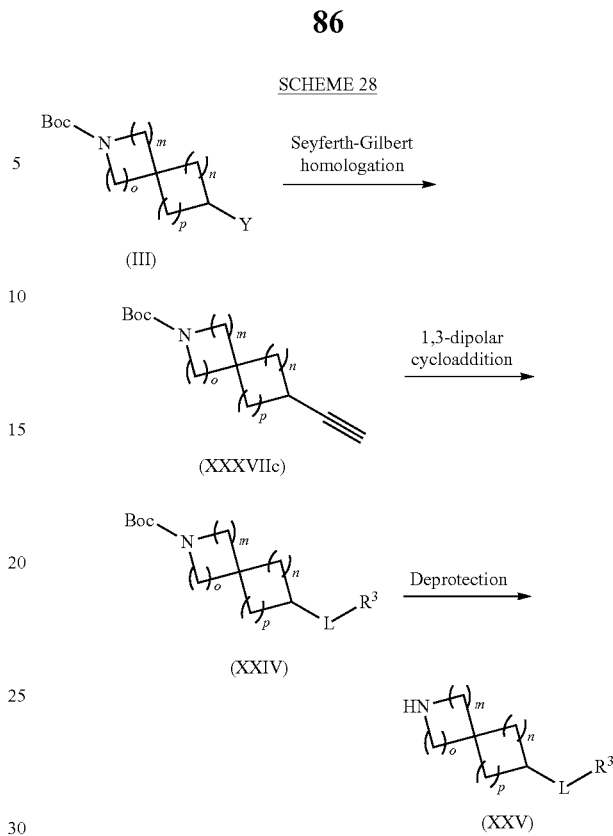

According to SCHEME 27, a compound of formula (XXV), wherein m and o are 1, p is 2, n is 1 or 2, L is absent, and R³ is as defined in claim 1, is reacted with sodium hypochlorite; potassium O-tert-butyl carbonodithioate (commercially available or synthetically accessible); and a base such as NaOH, and the like; in a solvent such as water, and the like; at room temperature; for a period of 12 hours; to provide a compound of formula (XLIII), where PG is tert-butoxythiocarbonyl (Botc). Lithiation of a compound of formula (XLIII) with s-BuLi; and TMEDA; in a suitable solvent such as Et₂O, and the like; at a temperature of −70° C. for 30 min; followed by alkylation with iodomethane; at rt; for a period of 10 h, provides a compound of formula (XLIV), where n is 1 or 2. Deprotection of a compound of formula (XLIV) using conditions known to those skilled in the art or as previously described provides a compound of formula (XXV), where L is absent and the ring formed with m and o is substituted with CH₃.

According to SCHEME 28, a compound of formula (III), wherein m and o are 1, p and n are 2, and Y is CHO, is reacted in a Seyferth-Gilbert homologation reaction with dimethyl (diazomethyl)phosphonate carbanion (Ohira-Bestmann reagent; which is formed in situ from dimethyl (1-diazo-2-oxopropyl)phosphonate); a base such as K₂CO₃, and the like; in a solvent such as MeOH, and the like; to provide a compound of formula (XXXVIIc). A compound of formula (XXXVIIc) is reacted in a 1,3-dipolar cycloaddition reaction with a N-hydroxyl imidoyl chloride compound (formed by reaction with an aldehyde such as pivalaldehyde with hydroxylamine hydrochloride in a suitable solvent such as EtOH followed by chlorination with N-chlorosuccinimide); a suitable base such as TEA, and the like; at rt; for a period of 16 h; to provide a compound of formula (XXIV), where L is absent and R³ is 3-(tert-butyl)isoxazol-5-yl. Deprotection of the BOC protecting group is achieved employing methods previously described to provide a compound of formula (XXV) where L is absent.

SCHEME 29

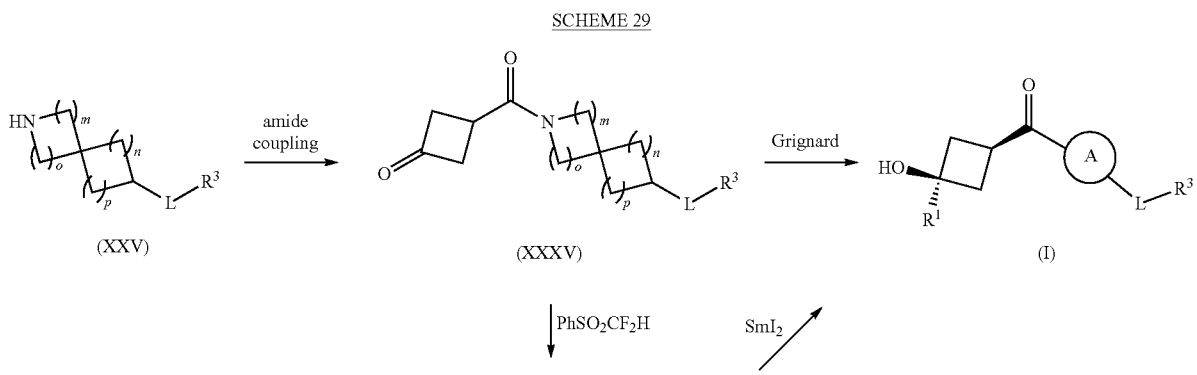

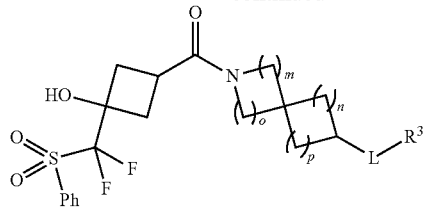

(XLII)

According to SCHEME 29, a compound of formula (XXV) (as well as XXVa, XXVIa, and XXVIc); where m, n, o, and p are each independently 1 or 2, L is absent, and R³ is 3-(tert-butyl)phenyl, is reacted in an amide coupling with a commercially available or synthetically accessible acid such as 3-oxocyclobutanecarboxylic acid; a suitable coupling agent such as COMU, HBTU, HATU, and the like; in a suitable solvent such as DCM, THF, DMF and the like, optionally in the presence of a tertiary amine such as N-methylmorpholine, N-ethyldiisopropylamine (DIEA, DIPEA), or triethylamine (TEA); at a temperature ranging from about 0° C. to rt; to provide a compound of formula (XXXV). A compound of formula (XXXV), where L is absent, is reacted in a Grignard reaction with ethylmagnesium bromide, employing conditions known to one skilled in the art or as previously described to provide a compound of Formula (I), where A is

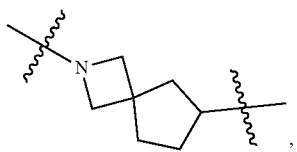 [SMILES: *C1CCC2(C1)CN(*)C2]

L is absent, R¹ is ethyl, and R³ is 3-(tert-butyl)phenyl.

A compound of formula (XXXV), where m and o are 1, and n and p are each independently 1 or 2, L is absent or O, and R³ is as described in claim 1, is treated with ((difluoromethyl)sulfonyl)benzene; LiHMDS; in a solvent such as THF, and the like; at a temperature of −78° C.; for a period of 2-3 hours; to provide a compound of formula (XLII). A compound of formula (XLII) is subjected to samarium(II) iodide; and hexamethylphosphoramide (HMPA); in THF; at a temperature of 0° C. to rt; for a period of 16-72 hours; to provide a compound of Formula (I), where L is absent or O, and R¹ is CF₂H.

SCHEME 30

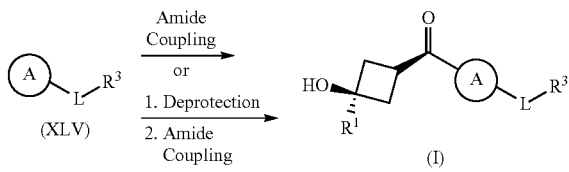

According to SCHEME 30, a compound of formula (XLV) (which encompasses formulas XXV, XXVa, XXVIa, and XXVIc), where Ⓐ is

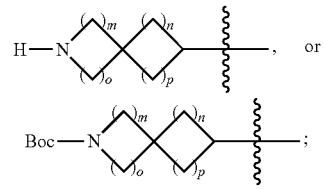

wherein m, n, o, and p are each independently 1 or 2; wherein Ⓐ is optionally substituted with one, two, and three members selected from H, halo, OH, C₁₋₄alkyl, and OC₁₋₄alkyl; L is absent, CH₂, CF₂, CH(CH₃) or O; and R³ is as defined in claim 1; is reacted employing conventional amide bond forming techniques with an acid such as (1s,3s)-3-hydroxy-3-methylcyclobutanecarboxylic acid, and the like; under coupling reaction conditions which are well known to those skilled in the art (such as HATU (1-[bis(dimethylamino)methylene]-1H-1,2,3-triazolo[4,5-b]pyridinium 3-oxide hexafluorophosphate), BOP (benzotriazol-1-yloxy-tris(dimethylamino)phosphonium hexafluorophosphate), or conversion of the acid to an acid chloride). For example, reaction of a compound of formula (XXV), where m, n, o, and p are each independently 1 or 2; L is absent, CH₂ or O; and R³ is as defined in claim 1; with (1s,3s)-3-hydroxy-3-methylcyclobutanecarboxylic acid, where the acid is activated with an appropriate activating reagent, for example a carbodiimide, such as N,N'-dicyclohexylcarbodiimide (DCC) or 1-ethyl-3-(3-dimethylaminopropyl)carbodiimide (EDC, EDAC or EDCI) optionally in the presence of hydroxybenzotriazole (HOBt) and/or a catalyst such as 4-dimethylaminopyridine (DMAP); a halotriaminophosphonium salt such as (benzotriazol-1-yloxy)tris(dimethylamino)phosphonium hexafluorophosphate (BOP), or bromotripyrrolidinophosphonium hexafluorophosphate (PyBroP®)); a suitable pyridinium salt such as 2-chloro-1-methyl pyridinium chloride; or another suitable coupling agent such as N,N,N',N'-tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxid hexafluorophosphate (HATU), 2,4,6-tripropyl-1,3,5,2,4,6-trioxatriphosphorinane-2,4,6-trioxide (T3P®) and the like. Coupling reactions are conducted in a suitable solvent such as DCM, THF, DMF and the like, optionally in the presence of a tertiary amine such as N-methylmorpholine, N-ethyldiisopropylamine (DIPEA), or triethylamine (TEA), at a temperature ranging from 0° C. to rt, to provide a compound of Formula (I).

A compound of Formula (I), where Ⓐ is

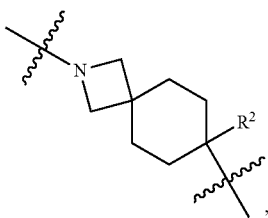

and $R^2$ is OH, $OCH_3$, $CH_3$, $CH_2CH_3$, or F; is prepared in two steps from a compound of formula (XLV), where Ⓐ is

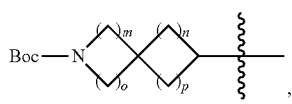

m, and o, are 1; n, and p are 2; L is absent; and $R^3$ is as defined in claim 1; by first deprotection of the tert-butyl carbamate, followed by amide bond coupling with (1s,3s)-3-hydroxy-3-methylcyclobutane-1-carboxylic acid, employing methods previously described.

A compound of Formula (I), where Ⓐ is

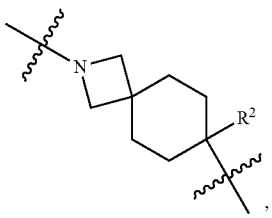

and $R^2$ is $OCH_3$; is prepared by coupling a compound of formula (XXVIa) with (1s,3s)-3-hydroxy-3-methylcyclobutane-1-carboxylic acid, employing amide bond coupling methods previously described.

Compounds of Formula (I) may be converted to their corresponding salts using methods known to one of ordinary skill in the art. For example, an amine of Formula (I) is treated with trifluoroacetic acid, HCl, or citric acid in a solvent such as $Et_2O$, $CH_2Cl_2$, THF, MeOH, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds described herein have at least one chiral center, they may accordingly exist as enantiomers. Where the compounds possess two or more chiral centers, they may additionally exist as diastereomers. It is to be understood that all such isomers and mixtures thereof are encompassed within the scope of the present disclosure.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via 1/16" PTFE tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

METHOD A. An Agilent HPLC with an Xterra Prep RP18 column (5 μM, 30×100 or 50×150 mm) or an)(Bridge C18 OBD column (5 μM, 30×100, 50×100, or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

METHOD B. A Shimadzu LC-8A Series HPLC with an Inertsil ODS-3 column (3 μm, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

METHOD C. A Shimadzu LC-8A Series HPLC with an XBridge C18 OBD column (5 μm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

METHOD D. A Gilson HPLC with an XBridge C18 column (5 μm, 100×50 mm), mobile phase of 5-99% ACN in 20 mM NH$_4$OH over 10 min and then hold at 99 ACN for 2 min, at a flow rate of 80 mL/min.

or

METHOD E. An ACCQ Prep HPLC with an XBridge C18 OBD column (5 μM, 30×100, or 50×100 mm), mobile phase of 5% ACN in H$_2$O (both with 0.05% TFA) was held for 1 min, then a gradient of 5-95% ACN over 12 min, then held at 95% ACN for 2 min, with a flow rate of 80 mL/min.

or

METHOD F. An Agilent HPLC with an Xterra Prep RP18 column (5 μM, 30×100 or 50×150 mm) or an)(Bridge C18 OBD column (5 μM, 30×100, 50×100, or 50×150 mm), and a mobile phase of 5% ACN in H$_2$O (both with 0.05% TFA) was held for 2 min, then a gradient of 5-99% ACN over 15 min, then held at 99% ACN for 5 min, with a flow rate of 40 or 80 mL/min.

Preparative supercritical fluid high performance liquid chromatography (SFC) was performed either on a Jasco preparative SFC system, an APS 1010 system from Berger instruments, or an SFC-PICLAB-PREP 200 (PIC SOLUTION, Avignon, France). The separations were conducted at 100 to 150 bar with a flow rate ranging from 40 to 60 mL/min. The column was heated to 35 to 40° C.

Mass spectra (MS) were obtained on an Agilent series 1100 MSD using electrospray ionization (ESI) in positive mode unless otherwise indicated. Calculated (calcd.) mass corresponds to the exact mass. Bromine has main two isotopes, $^{79}$Br and $^{81}$Br in an approximately 1:1 ratio, which means that a compound containing 1 bromine atom will have two peaks in the molecular ion region, corresponding to both isotopes. Observed mass spectrometry data are reported as either M+1 for the $^{79}$Br or M+2 for the $^{81}$Br.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad, dd=doublet of doublets, dt=doublet of triplets, td=triplet of doublets. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 17.1 (CambridgeSoft Corp., Cambridge, MA) or OEMetaChem V1.4.0.4 (Open Eye).

Compounds designated as *R or *S are enantiopure compounds where the absolute configuration was not determined.

Intermediate 1: tert-Butyl 2-iodo-8-azaspiro[4.5]decane-8-carboxylate

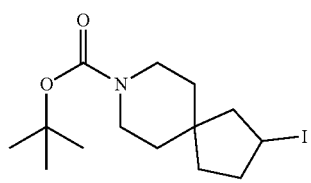 [SMILES: CC(C)(C)OC(=O)N1CCC2(CCC(I)C2)CC1]

Step A: tert-Butyl 2-hydroxy-8-azaspiro[4.5]decane-8-carboxylate. NaBH$_4$ (239 mg, 6.32 mmol) was added to a solution of tert-butyl 2-oxo-8-azaspiro[4.5]decane-8-carboxylate (800 mg, 3.16 mmol) in MeOH (60 mL) at 0° C. The reaction mixture was stirred at rt for 6 h. The solvent was evaporated under reduced pressure, and the residue was re-dissolved in EtOAc and washed with 0.1 N HCl and brine. The organic phase was separated, dried, filtered and evaporated under reduced pressure to afford the title compound that was used without further purification in the next step (841 mg, 100% yield). MS (ESI): mass calcd. for C$_{14}$H$_{25}$NO$_3$, 255.2; m/z found, 256.2 [M+H]$^+$.

Step B: tert-Butyl 2-iodo-8-azaspiro[4.5]decane-8-carboxylate. I2 (962 mg, 3.79 mmol) was added to a solution of tert-butyl 2-hydroxy-8-azaspiro[4.5]decane-8-carboxylate (807 mg, 3.16 mmol), imidazole (323 mg, 4.74 mmol), and PPh$_3$ (995 mg, 3.79 mmol) in THF (5.9 mL) at 0° C. The reaction mixture was stirred for 1 h at rt. Excess I2 was quenched with 10% Na$_2$S$_2$O$_3$. The aqueous phase was extracted with EtOAc and the combined organics were dried over MgSO$_4$. Solids were removed by filtration and the solvent was evaporated under reduced pressure. The residue was purified by flash column chromatography (FCC) (EtOAc in heptane 0-15%) affording the title compound as a colorless oil (719 mg, 62% yield). MS (ESI): mass calcd. for C$_{14}$H$_{25}$INO$_2$, 365.2; m/z found, 366.1 [M+H]$^+$.

Intermediate 2: tert-Butyl 6-iodo-2-azaspiro[3.4]octane-2-carboxylate

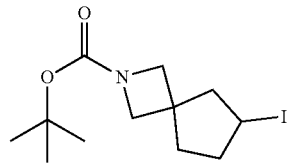 [SMILES: CC(C)(C)OC(=O)N1CC2(CCC(I)C2)C1]

The title compound was prepared in a manner analogous to Intermediate 1, Step B using tert-butyl 6-hydroxy-2-azaspiro[3.4]octane-2-carboxylate instead of tert-butyl 2-hydroxy-8-azaspiro[4.5]decane-8-carboxylate. MS (ESI): mass calcd. for C$_{12}$H$_{20}$INO$_2$, 337.2; m/z found, 338.1 [M+H]$^+$.

Intermediate 3: tert-Butyl 6-iodo-2-azaspiro[3.3]heptane-2-carboxylate

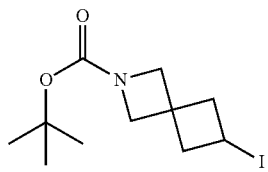

The title compound was prepared in a manner analogous to Intermediate 1, Step B using tert-butyl 6-hydroxy-2-azaspiro[3.3]heptane-2-carboxylate instead of tert-butyl 2-hydroxy-8-azaspiro[4.5]decane-8-carboxylate. MS (ESI): mass calcd. for C$_{11}$H$_{18}$INO$_2$, 323.0; m/z found, 267.9 [M+2H-tBu]$^+$.

Intermediate 4: tert-Butyl 6-(bromomethyl)-2-azaspiro[3.3]heptane-2-carboxylate

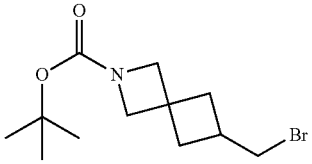 [SMILES: CC(C)(C)OC(=O)N1CC2(CC(CBr)C2)C1]

tert-Butyl 6-(hydroxymethyl)-2-azaspiro[3.3]heptane-2-carboxylate (300 mg, 1.32 mmol), PPh$_3$ (519 mg, 1.98 mmol), CBr$_4$ (657 mg, 1.98 mmol) and DCM (10 mL) were combined and cooled to −78° C. The reaction mixture was stirred at −78° C. for 1 hour. The reaction mixture was quenched with the sat. NH$_4$Cl and extracted with EtOAc. The combined organic extracts were washed with brine, dried over Na$_2$SO$_4$, filtered, and concentrated under pressure to give the crude product, which was purified by FCC (SiO$_2$, 0-20% EtOAc in ether) to afford desired product (185 mg, 48%) as a white solid. $^1$H NMR (400 MHz, CDCl$_3$) δ 3.94 (s, 2H), 3.84 (s, 2H), 3.38 (d, J=7.2 Hz, 2H), 2.64-2.48 (m, 1H), 2.37-2.28 (m, 2H), 1.99-1.86 (m, 2H), 1.43 (s, 9H).

Intermediate 5: tert-Butyl 6-(2-tosylhydraziney-lidene)-2-azaspiro[3.4]octane-2-carboxylate

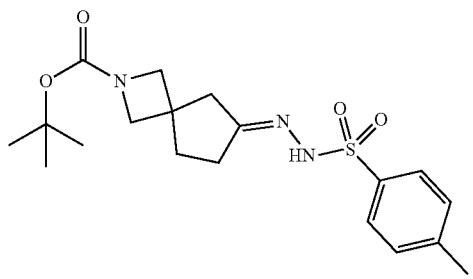 [SMILES: Cc1ccc(S(=O)(=O)N/N=C2\CCC3(C2)CN(C(=O)OC(C)(C)C)C3)cc1]

2-Boc-6-oxo-2-azapiro[3.4]octane (1.0 g, 4.39 mmol) and 4-methylbenzenesulfonyl hydrazide (0.84 g, 4.39 mmol) were taken up in THF (15 mL). This was stirred at 50° C. for 4 h. The reaction was cooled to rt before adding Na$_2$SO$_4$ and filtering off the solids. The crude mixture was concentrated under reduced pressure to provide a white solid in quantitative yield which was used as is in the next step. MS (ESI): mass calcd. for C$_{19}$H$_{27}$N$_3$O$_4$S, 393.2; m/z found, 394.2 [M+H]$^+$.

Intermediate 6: tert-Butyl 2-(2-tosylhydraziney-lidene)-6-azaspiro[3.4]octane-6-carboxylate

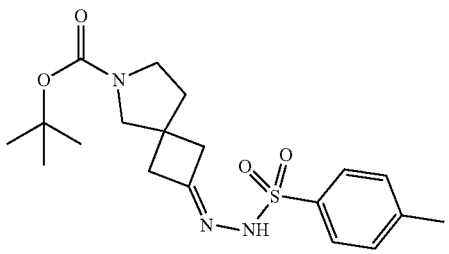 [SMILES: Cc1ccc(S(=O)(=O)NN=C2CC3(CCN(C(=O)OC(C)(C)C)C3)C2)cc1]

The title compound was prepared in a manner analogous to Intermediate 5 using tert-butyl 2-oxo-6-azaspiro[3.4]octane-6-carboxylate instead of 2-Boc-6-oxo-2-azapiro[3.4]octane.

Intermediate 7: tert-Butyl 6-(((trifluoromethyl)sulfonyl)oxy)-2-azaspiro[3.4]oct-6-ene-2-carboxylate

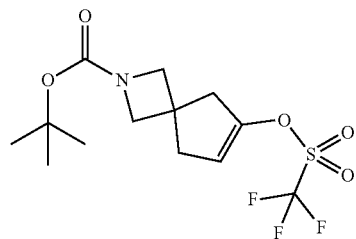 [SMILES: CC(C)(C)OC(=O)N1CC2(CC=C(OS(=O)(=O)C(F)(F)F)C2)C1]

To a solution of tert-butyl 6-oxo-2-azaspiro[3.4]octane-2-carboxylate (1.5 g, 6.66 mmol) in THF (16.6 mL) at −78° C. was added LiHMDS (1.06 M in THF, 9.12 mL, 9.12 mmol) dropwise via syringe and the reaction stirred at −78° C. for 1 h. A solution of 2-[N,N-bis(trifluoromethanesulfonyl)amino]-5-chloropyridine (3.07 g, 7.82 mmol) in THF (1.7 mL) was then added dropwise, and the reaction stirred at −78° C. for an additional 1 h before removing the cold bath and allowing the mixture to warm to rt for 30 min. The reaction was quenched with H$_2$O and the aqueous layer extracted with EtOAc. The combined organics were washed with brine, dried over Na$_2$SO$_4$, filtered, and concentrated in vacuo. The crude residue was purified via FCC (SiO$_2$, 0-50% EtOAc in hexanes) to afford the title compound as a white solid (1.89 g, 79% yield). MS (ESI): mass calcd. for C$_{13}$H$_{18}$F$_3$NO$_5$S, 357.1; m/z found, 302.0 [M-tBu+2H]$^+$. $^1$H NMR (500 MHz, Chloroform-d) δ 5.79 (t, J=1.9 Hz, 1H), 3.96 (d, J=8.7 Hz, 2H), 3.86 (d, J=8.7 Hz, 2H), 2.65-2.61 (m, 2H), 2.31-2.26 (m, 2H), 1.44 (s, 9H).

Intermediate 8: tert-Butyl 7-(((trifluoromethyl)sulfonyl)oxy)-2-azaspiro[3.5]non-6-ene-2-carboxylate

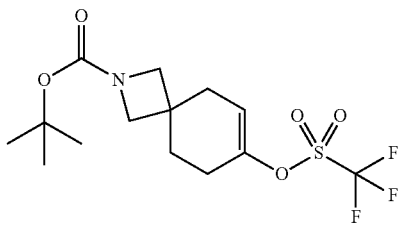 [SMILES: CC(C)(C)OC(=O)N1CC2(CC=C(OS(=O)(=O)C(F)(F)F)CC2)C1]

The title compound was prepared in a manner analogous to Intermediate 7 using tert-butyl 7-oxo-2-azaspiro[3.5]nonane-2-carboxylate instead of tert-butyl 6-oxo-2-azaspiro[3.4]octane-2-carboxylate. $^1$H NMR (400 MHz, CDCl$_3$) δ 5.71 (s, 1H), 3.75-3.62 (m, 4H), 2.47-2.38 (m, 4H), 1.96 (t, J=6.3 Hz, 2H), 1.44 (s, 9H).

Intermediate 9: tert-Butyl 6-(4,4,5,5-tetramethyl-1,3,2-dioxaborolan-2-yl)-2-azaspiro[3.4]oct-6-ene-2-carboxylate

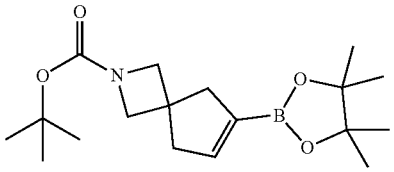 [SMILES: CC(C)(C)OC(=O)N1CC2(CC=C(B3OC(C)(C)C(C)(C)O3)C2)C1]

tert-Butyl 6-(((trifluoromethyl)sulfonyl)oxy)-2-azaspiro[3.4]oct-6-ene-2-carboxylate (Intermediate 7, 1.0 g, 2.80 mmol) was added to a solution of 4,4,4',4',5,5,5',5'-octamethyl-2,2'-bi(1,3,2-dioxaborolane) (853 mg, 3.36 mmol), KOAc (824 mg, 8.40 mmol), and 1,4-dioxane (20 mL). The resultant mixture was sparged with argon for 5 minutes, treated with Pd(dppf)Cl$_2$·CH$_2$Cl$_2$ (114 mg, 0.140 mmol), and stirred while heating at 90° C. for 3 hours before cooling to rt. The reaction mixture was concentrated under reduced pressure. The resulting residue was purified by FCC (SiO$_2$, 5-25% EtOAc in ether) to afford the title compound (1.0 g, 93%) as a white solid. MS (ESI): mass calcd. for C$_{18}$H$_{30}$BNO$_4$, 335.2; m/z found, 280.2, [M+2H-tBu]$^+$.

Intermediate 10: tert-butyl 7-(4,4,5,5-tetramethyl-1,3,2-dioxaborolan-2-yl)-2-azaspiro[3.5]non-6-ene-2-carboxylate

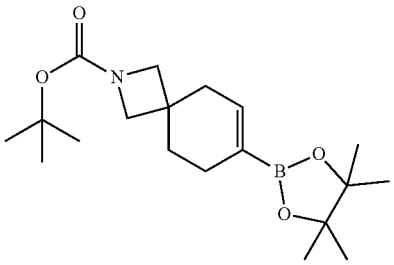 [SMILES: CC(C)(C)OC(=O)N1CC2(CC=C(B3OC(C)(C)C(C)(C)O3)CC2)C1]

The title compound was prepared in a manner analogous to Intermediate 9 using tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7). MS (ESI): mass calcd. for C$_{19}$H$_{32}$BNO$_4$, 349.2; m/z found, 294.4 [M+2H-tBu]t$^+$. $^1$H NMR (400 MHz, CDCl$_3$) δ 6.51-6.41 (m, 1H), 3.68-3.53 (m, 4H), 2.34-2.26 (m, 2H), 2.24-2.15 (m, 2H), 1.73 (t, J=6.3 Hz, 2H), 1.43 (s, 9H), 1.26 (s, 12H).

Intermediate 11: tert-Butyl 7-((methylsulfonyl)oxy)-2-azaspiro[3.5]nonane-2-carboxylate

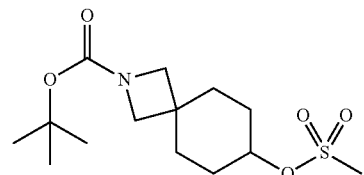

Methanesulfonyl chloride (690 mg, 6.02 mmol) was added to a 0° C. solution of tert-butyl 7-hydroxy-2-azaspiro[3.5]nonane-2-carboxylate (500 mg, 2.07 mmol) and TEA (0.87 mL, 6.2 mmol) in DCM (10 mL) under N$_2$. The resultant mixture was stirred at rt for 16 hours. The mixture was poured into sat. NaHCO$_3$ and extracted with DCM. The combined organic extracts were dried over Na$_2$SO$_4$, filtered, and concentrated under reduced pressure to afford the crude product, which was used in the next step without further purification. MS (ESI): mass calcd. for C$_{14}$H$_{25}$NO$_5$S, 319.2; m/z found, 263.9 [M+2H-tBu]$^+$.

Intermediate 12: (4-(Difluoromethoxy)-2-methylphenyl)boronic acid

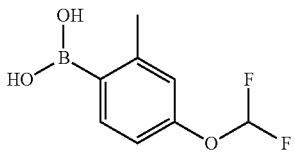

NaIO$_4$ (416 mg, 1.94 mmol) was added to a solution consisting of 2-(4-(difluoromethoxy)-2-methylphenyl)-4,4,5,5-tetramethyl-1,3,2-dioxaborolane (184 mg, 0.648 mmol) and THF/H$_2$O (4:1, 5 mL). The resultant mixture was stirred at rt for 30 minutes, then treated with 1M HCl (0.65 mL, 0.648 mmol). The resultant mixture was stirred at rt for 12 hours. The reaction mixture was poured it into H$_2$O (50 mL), the pH was adjusted to pH ~3, and extracted with EtOAc. The combined organic extracts were dried over Na$_2$SO$_4$, filtered, and concentrated under reduced pressure to afford the title compound (110 mg, 84%) as a light-yellow solid. $^1$H NMR (400 MHz, CDCl$_3$) δ 8.18 (d, J=8.0 Hz, 1H), 7.06-7.01 (m, 2H), 6.73-6.52 (m, 1H), 2.80 (s, 3H), 2.54 (s, 2H).

Intermediate 13: (3-(Difluoromethoxy)-5-methylphenyl)boronic acid

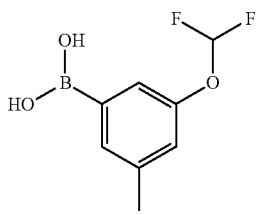

The title compound was prepared in a manner analogous to Intermediate 12 using 2-(3-(difluoromethoxy)-5-methylphenyl)-4,4,5,5-tetramethyl-1,3,2-dioxaborolane instead of 2-(4-(difluoromethoxy)-2-methylphenyl)-4,4,5,5-tetramethyl-1,3,2-dioxaborolane. $^1$H NMR (400 MHz, CDCl$_3$) δ 7.85 (s, 1H), 7.73 (d, J=2.0 Hz, 1H), 7.19 (s, 1H), 6.61 (t, J=74.0 Hz, 1H), 2.50 (s, 3H).

Intermediate 14:
(5-(Difluoromethoxy)-2-methylphenyl)boronic acid

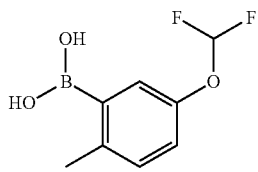

The title compound was prepared in a manner analogous to Intermediate 12 using 2-(5-(difluoromethoxy)-2-methylphenyl)-4,4,5,5-tetramethyl-1,3,2-dioxaborolane instead of 2-(4-(difluoromethoxy)-2-methylphenyl)-4,4,5,5-tetramethyl-1,3,2-dioxaborolane. $^1$H NMR (400 MHz, CDCl$_3$) δ 7.94 (d, J=2.8 Hz, 1H), 7.31-7.27 (m, 1H), 7.25-7.21 (m, 1H), 6.55 (t, J=73.6 Hz, 1H), 2.79 (s, 3H).

Intermediate 15:
(4-Isopropylbenzyl)triphenylphosphonium bromide

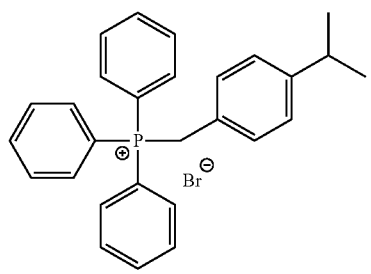 [SMILES: CC(C)c1ccc(C[P+](c2ccccc2)(c2ccccc2)c2ccccc2)cc1 ; [Br-]]

1-(Bromomethyl)-4-isopropylbenzene (1.0 g, 4.69 mmol), PPh$_3$ (1.8 g, 7.04 mmol), and toluene (20 mL) were combined and stirred at 90° C. for 12 hours to give a white suspension. The reaction was then cooled to rt and the suspension isolated via filtration. The filter cake was washed with toluene before drying under reduced pressure to afford the title compound (2.1 g, 94%) as a white solid. $^1$H NMR (400 MHz, CDCl$_3$) δ 7.80-7.69 (m, 9H), 7.66-7.59 (m, 6H), 7.01-6.94 (m, 4H), 5.34 (d, J=14.0 Hz, 2H), 2.85-2.75 (m, 1H), 1.17 (s, 3H), 1.15 (s, 3H).

Intermediate 16:
(4-Trifluoromethylbenzyl)triphenylphosphonium bromide

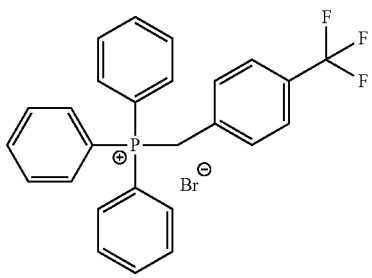 [SMILES: FC(F)(F)c1ccc(C[P+](c2ccccc2)(c2ccccc2)c2ccccc2)cc1 ; [Br-]]

The title compound was prepared in a manner analogous to Intermediate 15 using 1-(bromomethyl)-4-(trifluoromethyl)benzene instead of 1-(bromomethyl)-4-isopropylbenzene. $^1$H NMR (400 MHz, CDCl$_3$) δ 7.78-7.64 (m, 9H), 7.59-7.49 (m, 6H), 7.24-7.15 (m, 3H), 7.12-7.05 (m, 1H), 5.70 (s, 1H), 5.67 (s, 1H); $^{19}$F NMR (376 MHz, CDCl$_3$) δ −62.74 (s, 3F); $^{31}$P NMR (162 MHz, CDCl$_3$) δ 23.86 (br s, 1P).

Intermediate 17:
(3-(Difluoromethoxy)benzyl)triphenylphosphonium bromide

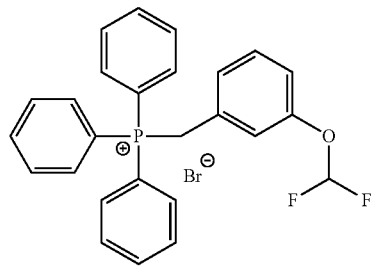 [SMILES: FC(F)Oc1cccc(C[P+](c2ccccc2)(c2ccccc2)c2ccccc2)c1 ; [Br-]]

The title compound was prepared in a manner analogous to Intermediate 15 using 1-(bromomethyl)-3-(difluoromethoxy)benzene instead of 1-(bromomethyl)-4-isopropylbenzene. MS (ESI): mass calcd. for C$_{26}$H$_{22}$F$_2$OPBr, 498.1; m/z found, 419.1 [M+H—Br]$^+$. $^1$H NMR (400 MHz, DMSO-d$_6$) δ 7.97-7.62 (m, 15H), 7.35-7.26 (m, 1H), 7.20-6.81 (m, 3H), 6.74 (s, 1H), 5.21 (d, J=15.8 Hz, 2H).

Intermediate 18:
3-(Difluoromethyl)benzyl)triphenylphosphonium bromide

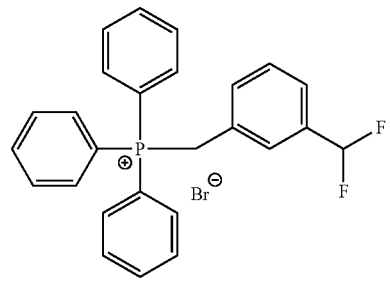 [SMILES: FC(F)c1cccc(C[P+](c2ccccc2)(c2ccccc2)c2ccccc2)c1 ; [Br-]]

The title compound was prepared in a manner analogous to Intermediate 15 using 1-(bromomethyl)-3-(difluoromethyl)benzene instead of 1-(bromomethyl)-4-isopropylbenzene.

Intermediate 19:
(4-(Difluoromethoxy)benzyl)triphenylphosphonium bromide

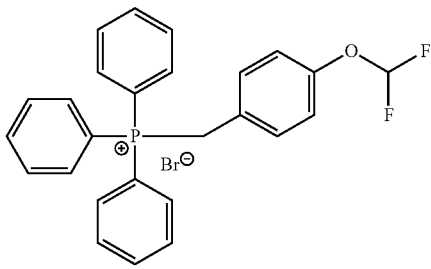 [SMILES: FC(F)Oc1ccc(C[P+](c2ccccc2)(c2ccccc2)c2ccccc2)cc1 ; [Br-]]

The title compound was prepared in a manner analogous to Intermediate 15 using 1-(bromomethyl)-4-(difluoromethoxy)benzene instead of 1-(bromomethyl)-4-isopropylbenzene.

Intermediate 20:
(4-(Difluoromethyl)benzyl)triphenylphosphonium bromide

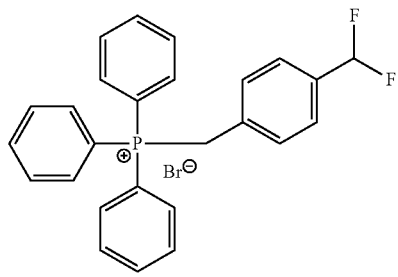 [SMILES: FC(F)c1ccc(C[P+](c2ccccc2)(c2ccccc2)c2ccccc2)cc1 ; [Br-]]

The title compound was prepared in a manner analogous to Intermediate 15 using 1-(bromomethyl)-4-(difluoromethyl)benzene instead of 1-(bromomethyl)-4-isopropylbenzene. MS (ESI): mass calcd. for $C_{26}H_{22}BrF_2P$, 482.1; m/z found, 403.1 [M-Br]$^+$. $^1$H NMR (400 MHz, DMSO-d$_6$) δ 7.98-7.63 (m, 15H), 7.44 (d, J=7.8 Hz, 2H), 7.22-6.82 (m, 3H), 5.30 (d, J=16.1 Hz, 2H).

Intermediate 21:
(2-Bromobenzyl)triphenylphosphonium bromide

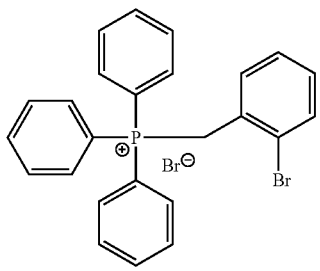 [SMILES: Brc1ccccc1C[P+](c1ccccc1)(c1ccccc1)c1ccccc1 ; [Br-]]

The title compound was prepared in a manner analogous to Intermediate 15 using 1-bromo-2-(bromomethyl)benzene instead of 1-(bromomethyl)-4-isopropylbenzene. MS (ESI): mass calcd. for $C_{25}H_{21}Br_2P$, 431.1; m/z found, 433.1 [M+H]$^+$. $^1$H NMR (400 MHz, DMSO-d$_6$) δ 8.05-7.89 (m, 3H), 7.85-7.51 (m, 12H), 7.38-7.05 (m, 4H), 5.16 (d, J=14.8 Hz, 2H).

Intermediate 22:
Triphenyl(pyridin-2-ylmethyl)phosphonium bromide

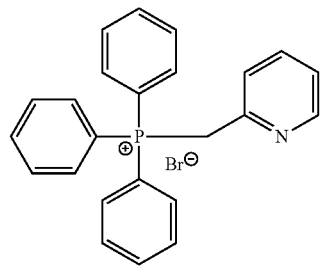 [SMILES: c1ccc([P+](Cc2ccccn2)(c2ccccc2)c2ccccc2)cc1 ; [Br-]]

The title compound was prepared in a manner analogous to Intermediate 15 using 2-(bromomethyl)pyridine hydrobromide instead of 1-(bromomethyl)-4-isopropylbenzene. $^1$H NMR (400 MHz, CDCl$_3$) δ 8.60-8.40 (m, 3H), 8.04 (br s, 1H), 7.94-7.81 (m, 8H), 7.77-7.65 (m, 7H), 6.55 (d, J=15.6 Hz, 2H).

Intermediate 23:
Triphenyl(pyridin-3-ylmethyl)phosphonium bromide

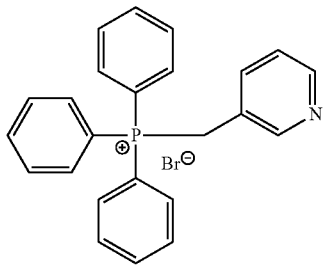 [SMILES: c1ccc([P+](Cc2cccnc2)(c2ccccc2)c2ccccc2)cc1 ; [Br-]]

The title compound was prepared in a manner analogous to Intermediate 15 using 3-(bromomethyl)pyridine hydrobromide instead of 1-(bromomethyl)-4-isopropylbenzene. $^1$H NMR (400 MHz, CDCl$_3$) δ 8.85-8.79 (m, 2H), 8.66 (d, J=5.6 Hz, 1H), 7.97-7.91 (m, 1H), 7.89-7.79 (m, 9H), 7.73-7.65 (m, 6H), 6.34 (d, J=15.2 Hz, 2H).

Intermediate 24: Diethyl 4-(trifluoromethoxy)benzylphosphonate

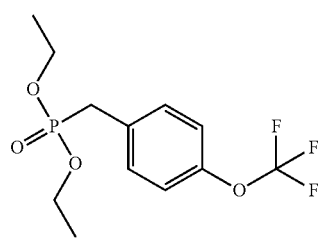 [SMILES: CCOP(=O)(Cc1ccc(OC(F)(F)F)cc1)OCC]

1-(Bromomethyl)-4-(trifluoromethoxy)benzene (500 mg, 0.938 mmol) and triethyl phosphite (710 mg, 4.27 mmol) were combined and the mixture was heated at 105° C. under nitrogen for 12 hours. The cooled, crude reaction mixture (890 mg) was used in the next step without further purification.

Intermediate 25: Diethyl 3-(trifluoromethoxy)benzylphosphonate

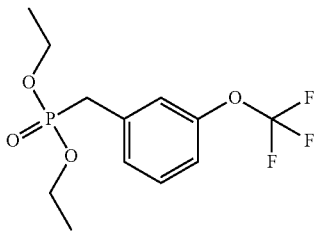 [SMILES: CCOP(=O)(Cc1cccc(OC(F)(F)F)c1)OCC]

The title compound was prepared in a manner analogous to Intermediate 24 using 1-(bromomethyl)-3-(trifluoromethoxy)benzene instead of 1-(bromomethyl)-4-(trifluoromethoxy)benzene.

Intermediate 26: Diethyl (3-isopropylbenzyl)phosphonate

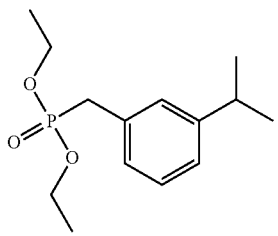 [SMILES: CCOP(=O)(Cc1cccc(C(C)C)c1)OCC]

The title compound was prepared in a manner analogous to Intermediate 24 using 1-(bromomethyl)-3-isopropylbenzene instead of 1-(bromomethyl)-4-(trifluoromethoxy)benzene.

Intermediate 27: Diethyl (4-(difluoromethyl)benzyl)phosphonate

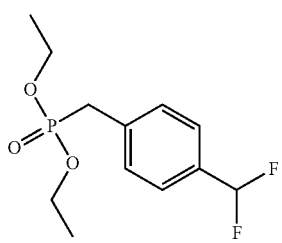 [SMILES: CCOP(=O)(Cc1ccc(C(F)F)cc1)OCC]

The title compound was prepared in a manner analogous to Intermediate 24 using 1-(bromomethyl)-4-(difluoromethyl)benzene instead of 1-(bromomethyl)-4-(trifluoromethoxy)benzene.

Intermediate 28: Diethyl (4-(difluoromethoxy)benzyl)phosphonate

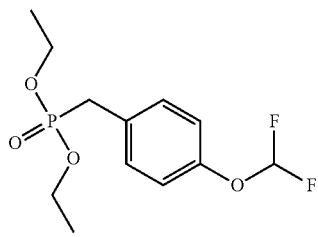 [SMILES: CCOP(=O)(Cc1ccc(OC(F)F)cc1)OCC]

The title compound was prepared in a manner analogous to Intermediate 24 using 1-(bromomethyl)-4-(difluoromethoxy)benzene instead of 1-(bromomethyl)-4-(trifluoromethoxy)benzene.

Intermediate 29: Diethyl 2-isopropylbenzylphosphonate

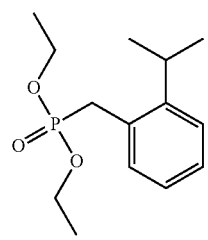 [SMILES: CCOP(=O)(Cc1ccccc1C(C)C)OCC]

The title compound was prepared in a manner analogous to Intermediate 24 using 1-(bromomethyl)-2-isopropylbenzene instead of 1-(bromomethyl)-4-(trifluoromethoxy)benzene. MS (ESI): mass calcd. for $C_{14}H_{23}O_3P$, 270.1; m/z found, 271.1 [M+H]$^+$.

Intermediate 30: Diethyl 3,4-dimethylbenzylphosphonate

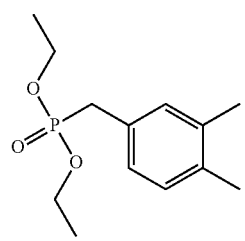 [SMILES: CCOP(=O)(Cc1ccc(C)c(C)c1)OCC]

The title compound was prepared in a manner analogous to Intermediate 24 using 4-(chloromethyl)-1,2-dimethylbenzene instead of 1-(bromomethyl)-4-(trifluoromethoxy)benzene. MS (ESI): mass calcd. for $C_{13}H_{21}O_3P$, 256.1; m/z found, 257.0 [M+H]$^+$.

Intermediate 31: Diethyl 4-methyl-3-(trifluoromethyl)benzylphosphonate

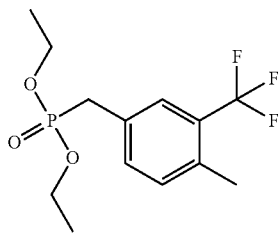 [SMILES: CCOP(=O)(Cc1ccc(C)c(C(F)(F)F)c1)OCC]

The title compound was prepared in a manner analogous to Intermediate 24 using 4-(bromomethyl)-1-methyl-2-(trifluoromethyl)benzene instead of 1-(bromomethyl)-4-(trifluoromethoxy)benzene. MS (ESI): mass calcd. for $C_{13}H_{18}F_3O_3P$, 310.1; m/z found, 310.9 $[M+H]^+$.

Intermediate 32: Diethyl ((4-(tert-butyl)pyridin-2-yl)methyl)phosphonate

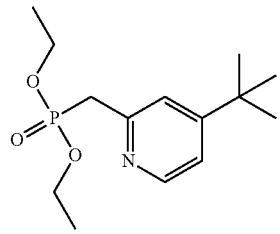 [SMILES: CCOP(=O)(Cc1cc(C(C)(C)C)ccn1)OCC]

Step A: Diethyl (pyridin-2-ylmethyl)phosphonate. 2-(Bromomethyl)pyridine (4.1 g, 16.2 mmol) and triethyl phosphite (10 mL, 60.0 mmol) were combined and stirred while heating at 160° C. under $N_2$ for 2 hours. The mixture was cooled to rt and purified by FCC ($SiO_2$, 0-10% EtOAc in ether) to afford the title compound (1.8 g, 52%) as a yellow oil. MS (ESI): mass calcd. for $C_{10}H_{16}NO_3P$, 229.2; m/z found, 229.9 $[M+H]^+$.

Step B: Diethyl ((4-(tert-butyl)pyridin-2-yl)methyl)phosphonate. A solution of sodium peroxydisulfate (1.4 g, 5.88 mmol) in $H_2O$ (5 mL) was added dropwise to a mixture of pivalic acid (602 mg, 5.89 mmol), diethyl (pyridin-2-ylmethyl)phosphonate (1.8 g, 7.78 mmol), $H_2SO_4$ (763 mg, 7.78 mmol), $AgNO_3$ (200 mg, 1.18 mmol), MeCN (10 mL), and $H_2O$ (10 mL) at 80° C. The resultant mixture was stirred at 80° C. for 1 hour before it was cooled to rt, diluted with sat. $NH_4Cl$, and extracted with EtOAc. The combined organic extracts were washed with brine, dried over $Na_2SO_4$, filtered, and concentrated under reduced pressure to afford the title compound (1.3 g, crude) as a red oil, which was used in the next step without further purification. MS (ESI): mass calcd. for $C_{14}H_{24}NO_3P$, 285.1; m/z found, 285.9 $[M+H]^+$.

Intermediate 33: Diethyl ((6-methoxypyridin-2-yl)methyl)phosphonate

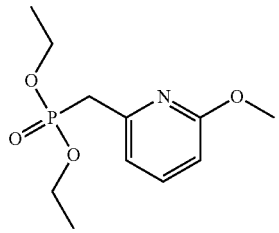 [SMILES: CCOP(=O)(Cc1cccc(OC)n1)OCC]

The title compound was prepared in a manner analogous to Intermediate 24 using 2-(bromomethyl)-6-methoxypyridine instead of 1-(bromomethyl)-4-(trifluoromethoxy)benzene. MS (ESI): mass calcd. for $C_{11}H_{18}NO_4P$, 259.1; m/z found, 259.9 $[M+H]^+$.

Intermediate 34: Diethyl 2-(trifluoromethoxy)benzylphosphonate

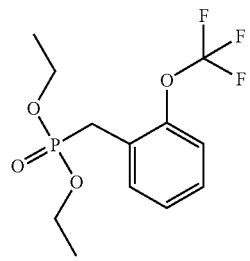 [SMILES: CCOP(=O)(Cc1ccccc1OC(F)(F)F)OCC]

The title compound was prepared in a manner analogous to Intermediate 24 using 1-(bromomethyl)-2-(trifluoromethoxy)benzene instead of 1-(bromomethyl)-4-(trifluoromethoxy)benzene.

Intermediate 35: Diethyl (quinolin-2-ylmethyl)phosphonate

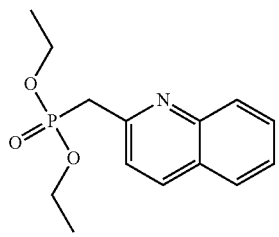 [SMILES: CCOP(=O)(Cc1ccc2ccccc2n1)OCC]

The title compound was prepared in a manner analogous to Intermediate 24 using 2-(chloromethyl)quinoline hydrochloride instead of 1-(bromomethyl)-4-(trifluoromethoxy) benzene.

Intermediate 36: Diethyl 2-(trifluoromethyl)benzylphosphonate

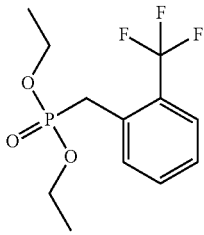 [SMILES: CCOP(=O)(Cc1ccccc1C(F)(F)F)OCC]

The title compound was prepared in a manner analogous to Intermediate 24 using 1-(bromomethyl)-2-(trifluoromethyl)benzene instead of 1-(bromomethyl)-4-(trifluoromethoxy)benzene.

Intermediate 37: Diethyl 4-bromo-3-methylbenzylphosphonate

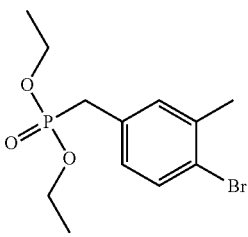 [SMILES: CCOP(=O)(Cc1ccc(Br)c(C)c1)OCC]

The title compound was prepared in a manner analogous to Intermediate 24 using 1-bromo-4-(bromomethyl)-2-methylbenzene instead of 1-(bromomethyl)-4-(trifluoromethoxy)benzene. MS (ESI): mass calcd. for $C_{12}H_{18}BrO_3P$, 320.0; m/z found, 320.7 $[M+H]^+$.

Intermediate 38: 3-Bromo-N,N-dimethyl-5-(trifluoromethyl)aniline

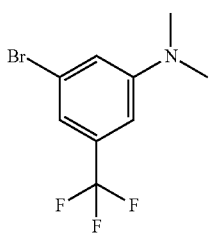

AcOH (3.0 mL, 52.0 mmol) was added to a mixture of 3-bromo-5-(trifluoromethyl)aniline (2.0 g, 8.0 mmol) and paraformaldehyde $((CH_2O)_n)$ (1.3 g, 42.0 mmol) in MeCN (15 mL). The reaction mixture was stirred for 30 minutes at 30° C. before sodium cyanoborohydride (1.0 g, 16.5 mmol) was added to the mixture. The reaction mixture was stirred at 35° C. for 16 hours. The product was poured into water and extracted with DCM. The combined organic extracts were washed with brine, dried over $Na_2SO_4$, filtered, and concentrated under reduced pressure. The resulting residue was purified by FCC ($SiO_2$, 0-5% EtOAc in ether) to afford the title compound (2.1 g, 93%) as a colorless oil. MS (ESI): mass calcd. for $C_9H_9BrF_3N$ 267.0; m/z found, 267.8 $[M+H]^+$.

Intermediate 39: 5-Bromo-N,N-dimethyl-2-(trifluoromethyl)aniline

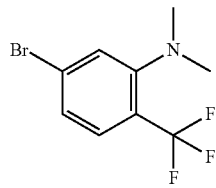

The title compound was prepared in a manner analogous to Intermediate 38 using 5-bromo-2-(trifluoromethyl)aniline instead of 3-bromo-5-(trifluoromethyl)aniline. MS (ESI): mass calcd. for $C_9H_9BrF_3N$, 267.0; m/z found, 267.8 $[M+H]^+$.

Intermediate 40: 4-Bromo-2-(tert-butyl)-1-methoxybenzene

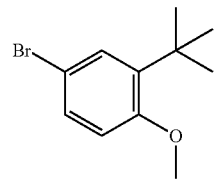

Iodomethane (3.33 g, 23.5 mmol) was added to a solution of 4-bromo-2-(tert-butyl)phenol (200 mg, 0.873 mmol) and $Cs_2CO_3$ (569 mg, 1.75 mmol) in $CH_3CN$ (10 mL). The resultant mixture was stirred at rt for 16 hours. The reaction mixture was poured into sat. $NaHCO_3$ and extracted with EtOAc. The combined organic extracts were dried over $Na_2SO_4$, filtered, and concentrated under reduced pressure. The resulting residue was purified by FCC ($SiO_2$, 0-5% EtOAc in ether) to afford the title compound (220 mg) as a colorless oil. $^1H$ NMR (400 MHz, $CDCl_3$) δ 7.36 (d, J=2.5 Hz, 1H), 7.30-7.27 (m, 1H), 6.77-6.73 (m, 1H), 3.82 (s, 3H), 1.36 (s, 9H).

Intermediate 41: 1-Bromo-2-cyclopropyl-3-methylbenzene

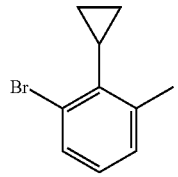

Step A: 2-Cyclopropyl-3-methylaniline. 2-Bromo-3-methylaniline (500 mg, 2.69 mmol), cyclopropylboronic acid (300 mg, 3.49 mmol), potassium phosphate (2.00 g, 9.41 mmol), $Pd(OAc)_2$ (30 mg, 0.134 mmol), $PPh_3$ (70 mg, 0.269 mmol), toluene (10 mL) and H$_2$O (1 mL) were combined. The resultant mixture was stirred while heating at 100° C. for 16 hours before cooling to rt. The reaction mixture was concentrated under reduced pressure. The resulting residue was purified by FCC (SiO$_2$, 0-10% EtOAc in ether) to afford the title compound (243 mg, 61%) as a light-yellow oil. $^1$H NMR (400 MHz, CDCl$_3$) δ 6.97-6.91 (m, 1H), 6.57 (d, J=7.2 Hz, 1H), 6.53 (d, J=7.6 Hz, 1H), 4.02 (br s, 2H), 2.38 (s, 3H), 1.55-1.50 (m, 1H), 1.05-0.98 (m, 2H), 0.60-0.54 (m, 2H).

Step B: 1-Bromo-2-cyclopropyl-3-methylbenzene. tert-Butyl nitrite (2.3 mL, 19.0 mmol) was added to a 0° C. solution of 2-cyclopropyl-3-methylaniline (1.4 g, 9.51 mmol) and CuBr (2.7 g, 19.0 mmol) in ACN (20 mL). The resultant mixture was stirred at 60° C. for 1.5 hours under N$_2$. The reaction mixture was cooled to rt, poured into H$_2$O, and extracted with EtOAc. The combined organic extracts were washed with brine, dried over Na$_2$SO$_4$, filtered, and concentrated under reduced pressure. The resulting residue was purified by FCC (SiO$_2$, 0-10% EtOAc in ether) to afford the title compound (425 mg, 21%) as colorless oil. $^1$H NMR (400 MHz, CDCl$_3$) δ 7.39 (d, J=8.0 Hz, 1H), 7.08 (d, J=7.2 Hz, 1H), 6.99-6.93 (m, 1H), 2.45 (s, 3H), 1.78-1.68 (m, 1H), 1.15-1.08 (m, 2H), 0.68-0.61 (m, 2H).

Intermediate 42:
1-Bromo-3-cyclopropyl-2-methylbenzene

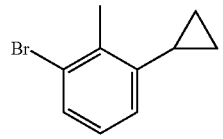

The title compound was prepared in a manner analogous to Intermediate 41 using 3-bromo-2-methylaniline instead of 2-bromo-3-methylaniline in Step A. $^1$H NMR (400 MHz, CDCl$_3$) δ 7.42-7.36 (m, 1H), 7.02-6.92 (m, 2H), 2.53 (s, 3H), 1.97-1.81 (m, 1H), 0.99-0.90 (m, 2H), 0.65-0.59 (m, 2H).

Intermediate 43:
1-Bromo-2-isopropyl-3-(trifluoromethyl)benzene

Step A: 2-(Prop-1-en-2-yl)-3-(trifluoromethyl)aniline. 2-Bromo-3-(trifluoromethyl) aniline (1.0 g, 4.17 mmol), potassium trifluoro(prop-1-en-2-yl)borate (930 mg, 6.25 mmol), Na$_2$CO$_3$ (1.8 g, 16.7 mmol), Pd(dppf)Cl$_2$ (610 mg, 6.25 mmol), 1,4-dioxane (8 mL), and H$_2$O (2 mL) were combined. The reaction mixture was stirred at 100° C. for 12 hours. The reaction mixture was cooled, quenched with H$_2$O and extracted with EtOAc. The combined organic extracts were washed with brine, dried over Na$_2$SO$_4$, filtered, and concentrated under reduced pressure. The resulting residue was purified by FCC (SiO$_2$, 0-50% EtOAc in ether) to afford the title compound (820 mg, 98%) as a brown oil. $^1$H NMR (400 MHz, CDCl$_3$) δ 7.21-7.12 (m, 1H), 7.22-7.12 (m, 1H), 7.07 (s, 1H), 6.96-6.84 (m, 2H), 5.43 (s, 1H), 4.99 (s, 1H), 2.11-1.99 (m, 3H).

Step B: 2-Isopropyl-3-(trifluoromethyl)aniline. 2-(Prop-1-en-2-yl)-3-(trifluoromethyl)aniline (800 mg, 3.98 mmol), AcOH (478 mg, 7.95 mmol), EtOH (10 mL), and PtO$_2$ (300 mg, 1.32 mmol) were combined. The resultant mixture was stirred under H$_2$ (50 psi) at 60° C. for 24 hours. The suspension was filtered through a pad of Celite® and the pad was washed with EtOH. The filtrate was concentrated under reduced pressure. The resulting residue was purified by FCC (SiO$_2$, 0-10% EtOAc in ether) to afford the title compound (400 mg, 50%) as a yellow oil. MS (ESI): mass calcd. for C$_{10}$H$_{12}$F$_3$N, 203.1; m/z found, 204.2 [M+H]$^+$. $^1$H NMR (400 MHz, CDCl$_3$) δ 7.06 (d, J=4.0 Hz, 2H), 6.83-6.78 (m, 1H), 3.59-3.48 (m, 1H), 1.40 (s, 3H), 1.38 (s, 3H). $^{19}$F NMR (376 MHz, CDCl$_3$) δ −58.28 (br s, 3F).

Step C: 1-Bromo-2-isopropyl-3-(trifluoromethyl)benzene. tert-Butyl nitrite (0.47 mL, 3.94 mmol) was added to a 0° C. solution of 2-isopropyl-3-(trifluoromethyl)aniline (400 mg, 1.97 mmol) and CuBr (565 mg, 3.94 mmol) in ACN (10 mL). The resultant mixture was stirred at 60° C. for 1 hour under Na before cooling to rt. The reaction mixture was poured into H$_2$O and extracted with EtOAc. The combined organic extracts were washed with brine, dried over Na$_2$SO$_4$, filtered, and concentrated under reduced pressure. The resulting residue was purified by FCC (SiO$_2$, 0-10% EtOAc in ether) to afford the title compound (220 mg, 42%) as yellow oil. $^1$H NMR (400 MHz, CDCl$_3$) δ 7.73 (d, J=8.0 Hz, 1H), 7.61 (d, J=8.0 Hz, 1H), 7.12 (t, J=8.0 Hz, 1H), 3.68-3.47 (m, 1H), 1.49 (d, J=7.2 Hz, 6H). $^{19}$F NMR (376 MHz, CDCl$_3$) δ −58.45 (s, 3F).

Intermediate 44: 6-Bromo-1-methyl-1H-pyrrolo[2,3-b]pyridine

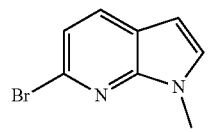

6-bromo-1H-pyrrolo[2,3-b]pyridine (500 mg, 2.54 mmol) was added to a 0° C. solution of NaH (152 mg, 60% in mineral oil, 3.81 mmol) in DMF (15 mL). The resultant mixture was stirred for 1 hour at rt and then treated with iodomethane (2.1 g, 15.0 mmol). The resulting mixture was stirred for 4 hours at rt. The reaction mixture was quenched with NH$_3$·H$_2$O (2 mL), poured into NH$_4$Cl, and extracted with EtOAc. The combined organic extracts were washed with brine, dried over Na$_2$SO$_4$, filtered, and concentrated under reduced pressure. The resulting residue was purified by FCC (SiO$_2$, 0-10% EtOAc in ether) to afford the title compound (487 mg, 91%) as light yellow oil.

Intermediate 45: 3-Isopropyl-2-(trifluoromethyl)phenol

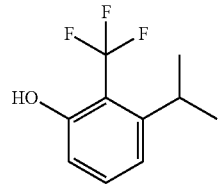

Step A: 1-(Benzyloxy)-3-bromo-2-(trifluoromethyl)benzene. Benzyl alcohol (534 mg, 4.94 mmol) was added to 0° C. solution of NaH (214 mg, 60% in mineral oil, 5.35 mmol) in DMF (10 mL). The resultant mixture was stirred at 0° C. for 30 minutes, then treated with a solution of 1-bromo-3-fluoro-2-(trifluoromethyl)benzene (1.0 g, 4.12 mmol) in DMF (10 mL) at 0° C. The resultant mixture was stirred for 12 hours with gradual warming to rt. The reaction mixture was quenched with sat. NH$_4$Cl and extracted with EtOAc. The combined organic extracts were washed with brine, dried over Na$_2$SO$_4$, filtered, and concentrated under reduced pressure. The resulting residue was purified by FCC (SiO$_2$, 0-30% EtOAc in ether) to afford the title compound (1.2 g) as colorless oil. $^1$H NMR (400 MHz, CDCl$_3$) δ 7.47-7.25 (m, 6H), 7.24-7.17 (m, 1H), 6.98 (d, J=8.4 Hz, 1H), 5.18-5.09 (m, 2H).

Step B: 1-(Benzyloxy)-3-(prop-1-en-2-yl)-2-(trifluoromethyl)benzene. 1-(Benzyloxy)-3-bromo-2-(trifluoromethyl)benzene (1.2 g, 3.62 mmol), trifluoro(prop-1-en-2-yl)borate (592 mg, 5.44 mmol), Na$_2$CO$_3$ (1.5 g, 14.5 mmol), Pd(dppf)Cl$_2$ (530 mg, 0.730 mmol), 1,4-dioxane (8 mL), and H$_2$O (2 mL) were combined. The reaction mixture was stirred at 100° C. for 12 hours. The reaction mixture was cooled, quenched with H$_2$O and extracted with EtOAc. The combined organic extracts were washed with brine, dried over Na$_2$SO$_4$, filtered, and concentrated under reduced pressure. The resulting residue was purified by FCC (SiO$_2$, 0-50% EtOAc in ether) to afford the title compound (600 mg, 57%) as a brown oil.

Step C: 3-Isopropyl-2-(trifluoromethyl)phenol. Pd/C (50 mg, 10% wet, 47.2 umol) was added to a mixture of 1-(benzyloxy)-3-(prop-1-en-2-yl)-2-(trifluoromethyl)benzene (600 mg, 2.05 mmol) in EtOH (5 mL). The resultant mixture was stirred under H$_2$ (50 psi) at 60° C. for 20 hours. The suspension was filtered through a pad of Celite® and the pad washed with EtOAc. The filtrate was concentrated under reduced pressure to afford the title product (140 mg, 33%) as a colorless oil. $^1$H NMR (400 MHz, CDCl$_3$) δ 7.36 (s, 1H), 7.03 (d, J=8.0 Hz, 1H), 6.80 (d, J=8.4 Hz, 1H), 6.08 (s, 1H), 3.35-3.27 (m, 1H), 1.25 (d, J=6.8 Hz, 6H).

Intermediate 46: 6-Bromo-1-(2,2,2-trifluoroethyl)-1H-pyrrolo[2,3-b]pyridine

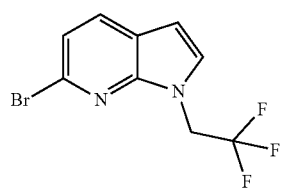 [SMILES: FC(F)(F)Cn1ccc2ccc(Br)nc21]

The title compound was prepared in a manner analogous to Intermediate 44 using 1,1,1-trifluoro-2-iodoethane instead of iodomethane. MS (ESI): mass calcd. for C$_9$H$_6$BrF$_3$N$_2$, 278.0; m/z found, 278.7 [M+H]$^+$. $^1$H NMR (400 MHz, CDCl$_3$) δ 7.81-7.77 (m, 1H), 7.30-7.27 (m, 1H), 7.26-7.24 (m, 1H), 6.59-6.55 (m, 1H), 4.94-4.82 (m, 2H).

Intermediate 47: 6-Bromo-1-isopropyl-1H-pyrrolo[2,3-b]pyridine

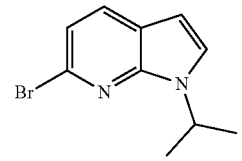

The title compound was prepared in a manner analogous to Intermediate 44 using 2-iodopropane instead of iodomethane. MS (ESI): mass calcd. for C$_{10}$H$_{11}$BrN$_2$, 238.0; m/z found, 238.8 [M+H]$^+$. $^1$H NMR (400 MHz, CDCl$_3$) δ 7.76-7.66 (m, 1H), 7.29-7.21 (m, 1H), 7.20-7.11 (m, 1H), 6.46-6.38 (m, 1H), 5.21-5.08 (m, 1H), 1.50-1.44 (m, 6H).

Intermediate 48: 6-Bromo-1-(2,2,2-trifluoroethyl)-1H-indazole

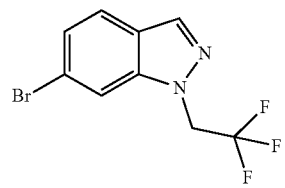 [SMILES: FC(F)(F)Cn1ncc2ccc(Br)cc21]

Cesium carbonate (5.0 g, 15.2 mmol) was added to a solution of 6-bromo-1H-indazole (1.0 g, 5.08 mmol) in DMF (10 mL). The reaction mixture was stirred for 16 hours at rt, then treated with 1,1,1-trifluoro-2-iodoethane (2.1 g, 10.2 mmol). The reaction mixture was stirred for 16 hours at rt. The reaction mixture was quenched with water and extracted with EtOAc. The combined organic extracts were washed with brine, dried over Na$_2$SO$_4$, filtered, and concentrated under reduced pressure. The resulting residue was purified by FCC (SiO$_2$, 0-100% EtOAc in ether) to afford the title compound (730 mg, 51% yield) as a light-yellow solid. MS (ESI): mass calcd. for C$_9$H$_6$BrF$_3$N$_2$, 278.0; m/z found, 278.8 [M+H]$^+$. $^1$H NMR (400 MHz, CDCl$_3$) δ 8.06 (d, J=0.8 Hz, 1H), 7.68-7.60 (m, 2H), 7.35 (dd, J=8.4, 1.6 Hz, 1H), 4.98-4.86 (m, 2H).

Intermediate 49: 6-Bromo-1-methyl-3-(trifluoromethyl)-1H-pyrrolo[2,3-b]pyridine

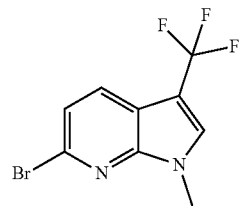

The title compound was prepared in a manner analogous to Intermediate 44 using 6-bromo-3-(trifluoromethyl)-1H-pyrrolo[2,3-b]pyridine instead of 6-bromo-1H-pyrrolo[2,3-b]pyridine. MS (ESI): mass calcd. for C$_9$H$_6$BrF$_3$N$_2$, 278.0; m/z found, 278.8 [M+H]$^+$. $^1$H NMR (400 MHz, CDCl$_3$) δ 7.80 (d, J=8.0 Hz, 1H), 7.43 (s, 1H), 7.27 (d, J=8.0 Hz, 1H), 3.84 (s, 3H).

Intermediate 50: 6-Bromo-2-isopropyl-2H-indazole

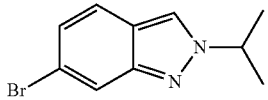

2-Iodopropane (520 mg, 3.06 mmol) was added dropwise to a solution of 6-bromo-2H-indazole (500 mg, 2.54 mmol) and K$_2$CO$_3$ (525 mg, 3.80 mmol) in DMSO (5 mL). The resultant mixture was stirred 16 hours at rt. The mixture was quenched with water and extracted with EtOAc. The combined organic extracts were dried over Na$_2$SO$_4$, filtered, and concentrated under reduced pressure. The resulting reside was purified by FCC (SiO$_2$, 0-50% EtOAc in ether) to give the title compound (200 mg, 29% yield) as a colorless oil. MS (ESI): mass calcd. for C$_{10}$H$_{11}$BrN$_2$, 238.0; m/z found, 238.8 [M+H]$^+$. $^1$H NMR (400 MHz, CDCl$_3$) δ 7.94-7.84 (m, 2H), 7.53-7.47 (m, 1H), 7.15-7.09 (m, 1H), 4.80-4.70 (m, 1H), 1.65-1.60 (m, 6H).

Intermediate 51:
6-Bromo-1,4-dimethyl-1H-indazole

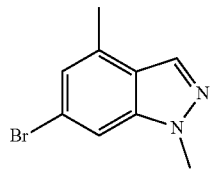

The title compound was prepared in a manner analogous to Intermediate 50 using 6-bromo-4-methyl-1H-indazole instead of 6-bromo-2H-indazole and iodomethane instead of 2-iodopropane. MS (ESI): mass calcd. for C$_9$H$_9$BrN$_2$, 224.0; m/z found, 224.8 [M+H]$^+$. $^1$H NMR (400 MHz, CDCl$_3$) δ 7.95 (s, 1H), 7.41 (s, 1H), 7.05 (s, 1H), 4.03 (s, 3H), 2.57 (s, 3H).

Intermediate 52:
6-Bromo-7-fluoro-1-methyl-1H-indazole

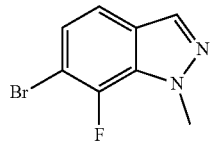

The title compound was prepared in a manner analogous to Intermediate 50 using 6-bromo-7-fluoro-1H-indazole instead of 6-bromo-2H-indazole; and iodomethane instead of 2-iodopropane. MS (ESI): mass calcd. for C$_8$H$_6$BrFN$_2$, 228.0; m/z found, 228.7 [M+H]$^+$. $^1$H NMR (400 MHz, CDCl$_3$) δ 7.96-7.92 (m, 1H), 7.36-7.32 (m, 1H), 7.23-7.18 (m, 1H), 4.26-4.24 (m, 3H).

Intermediate 53: 6-Chloro-1,2-dimethyl-1H-pyrrolo[2,3-b]pyridine

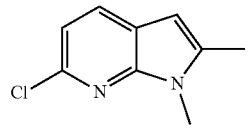

The title compound was prepared in a manner analogous to Intermediate 44 using 6-chloro-2-methyl-1H-pyrrolo[2,3-b]pyridine instead of 6-bromo-1H-pyrrolo[2,3-b]pyridine. MS (ESI): mass calcd. for C$_9$H$_9$ClN$_2$, 180.0; m/z found, 180.8 [M+H]$^+$. $^1$H NMR (400 MHz, CDCl$_3$) δ 7.70 (d, J=8.0 Hz, 1H), 7.04-6.97 (m, 1H), 6.19 (s, 1H), 3.79-3.73 (m, 3H), 2.44 (s, 3H).

Intermediate 54: 6-Chloro-1,3-dimethyl-1H-pyrrolo[2,3-b]pyridine

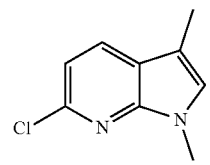

The title compound was prepared in a manner analogous to Intermediate 44 using 6-chloro-3-methyl-1H-pyrrolo[2,3-b]pyridine instead of 6-bromo-1H-pyrrolo[2,3-b]pyridine. MS (ESI): mass calcd. for C$_9$H$_9$ClN$_2$, 180.0; m/z found, 180.9 [M+H]$^+$.

Intermediate 55:
6-Bromo-3-(difluoromethoxy)-2-methylpyridine

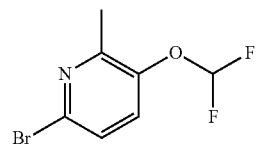

Sodium 2-chloro-2,2-difluoroacetate (2.6 g, 17.0 mmol) was added to 6-bromo-2-methylpyridin-3-ol (800 mg, 4.26 mmol) and Cs$_2$CO$_3$ (5.5 g, 17.0 mmol) in DMF (10 mL). The reaction mixture was stirred at 65° C. for 40 hours. The reaction mixture was cooled, then quenched with water. The resulting suspension was filtered, and the filtrate was extracted with EtOAc. The combined organic extracts were washed with brine, dried over Na$_2$SO$_4$, filtered, and concentrated under reduced pressure. The resulting residue was purified by FCC (SiO$_2$, 0-90% EtOAc in ether) to afford the title compound (440 mg, 43% yield) as a colorless oil. MS (ESI): mass calcd. for C$_7$H$_6$BrF$_2$NO, 237.0; m/z found, 237.7 [M+H]⁺. ¹H NMR (400 MHz, CDCl₃) δ 7.36-7.29 (m, 2H), 6.74-6.32 (m, 1H), 2.52 (s, 3H).

Intermediate 56: Diethyl ((1-methyl-5-(trifluoromethyl)-1H-pyrazol-3-yl)methyl)phosphonate

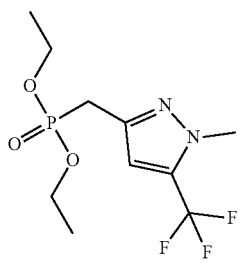 [SMILES: CCOP(=O)(Cc1cc(C(F)(F)F)n(C)n1)OCC]

The title compound was prepared in a manner analogous to Intermediate 24 using 3-(chloromethyl)-1-methyl-5-(trifluoromethyl)-1H-pyrazole instead of 1-(bromomethyl)-4-(trifluoromethoxy)benzene. MS (ESI): mass calcd. for C₁₀H₁₆F₃N₂O₃P, 300.1; m/z found, 300.9 [M+H]⁺.

Intermediate 57: 4-(3-Bromophenyl)-1-methyl-1H-imidazole

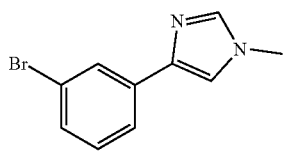

The title compound was prepared in a manner analogous to Intermediate 44 using 4-(3-bromophenyl)-1H-imidazole instead of 6-bromo-1H-pyrrolo[2,3-b]pyridine. MS (ESI): mass calcd. for C₁₀H₉BrN₂, 236.0; m/z found, 237.0 [M+H]⁺. ¹H NMR (400 MHz, CDCl₃) δ 7.94-7.90 (m, 1H), 7.70-7.66 (m, 1H), 7.47 (s, 1H), 7.38-7.33 (m, 1H), 7.26-7.18 (m, 2H), 3.74 (s, 3H).

Intermediate 58: 1-Bromo-3-cyclopropoxy-2-methylbenzene

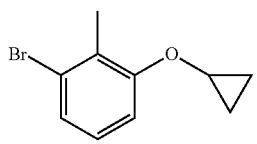

A mixture of 3-bromo-2-methylphenol (2.0 g, 10.7 mmol), bromocyclopropane (10.4 g, 86.0 mmol), CsOH·H₂O (1.8 g, 10.7 mmol), and potassium iodide (266 mg, 1.60 mmol), in DMA (20 mL) was stirred at 130° C. for 16 hours. The reaction mixture was cooled, then poured into water and extracted with EtOAc. The combined organic extracts were washed with water, dried over Na₂SO₄, filtered, and concentrated under reduced pressure. The resulting residue was purified by FCC (SiO₂, 0-10% EtOAc in ether) to afford the title compound (480 mg, 20% yield) as a yellow solid. MS (ESI): mass calcd. for C₁₀H₁₁BrO, 226.0; m/z found, 227.3 [M+H]⁺. ¹H NMR (400 MHz, CDCl₃) δ 7.18-7.14 (m, 2H), 7.05-7.00 (m, 1H), 3.76-3.70 (m, 1H), 2.26 (s, 3H), 0.82-0.76 (m, 4H).

Intermediate 59: 2-Chloro-6-(1-methylcyclopropyl)pyridine

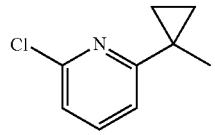

Step A: 2-Chloro-6-(prop-1-en-2-yl)pyridine. Potassium trifluoro(prop-1-en-2-yl)borate (8.5 g, 57.2 mmol) was added to a solution of 2-bromo-6-chloropyridine (10 g, 52.0 mmol) in ethanol (150 mL). The resultant mixture was sparged with Ar for 5 min, then treated with Pd(dppf)Cl₂·CH₂Cl₂ (2.1 g, 2.60 mmol) and Et₃N (22 mL, 156 mmol). The reaction mixture was stirred at 85° C. for 16 hours. The reaction mixture was cooled to rt and filtered through a pad of Celite® and washed with EtOAc. The resulting filtrate was concentrated under reduced pressure. The resulting residue was purified by FCC (SiO₂, 0-10% EtOAc in ether) to afford the title compound (6.0 g, crude) as a yellow oil. MS (ESI): mass calcd. for C₈H₈ClN, 153.0; m/z found, 153.8 [M+H]⁺.

Step B: 2-Chloro-6-(1-methylcyclopropyl)pyridine. Potassium tert-butoxide (6.6 g, 58.6 mmol) was added to a solution of trimethylsulphoxonium iodide (13 g, 58.6 mmol) in DMSO (20 mL) and THF (20 mL). The resultant mixture was stirred at rt for 30 min before a solution of 2-chloro-6-(prop-1-en-2-yl)pyridine (6.0 g, 39.1 mmol) in THF (20 mL) was added. The resultant mixture was stirred at rt for 16 hours. The reaction mixture was quenched with sat. aq. NH₄Cl and extracted with EtOAc. The combined organic extracts were washed with brine, dried over Na₂SO₄, filtered, and concentrated under reduced pressure. The resulting residue was purified by FCC (SiO₂, 0-5% EtOAc in ether) to afford the title compound (680 mg, 7% yield) as a yellow oil. MS (ESI): mass calcd. for C₉H₁₀ClN, 167.1; m/z found, 168.1 [M+H]⁺.

Intermediate 60: 2-Chloro-6-(1-(trifluoromethyl)cyclopropyl)pyridine

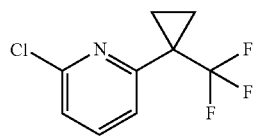 [SMILES: FC(F)(F)C1(c2cccc(Cl)n2)CC1]

Step A: 2-Chloro-6-(3,3,3-trifluoroprop-1-en-2-yl)pyridine. 2-Bromo-6-chloropyridine (2.0 g, 10.4 mol), 4,4,6-trimethyl-2-(3,3,3-trifluoroprop-1-en-2-yl)-1,3,2-dioxaborinane (2.3 g, 10.4 mmol), and Cs₂CO₃ (10 g, 31.3 mmol) were dissolved 1,4-dioxane (30 mL) and H₂O (6 mL). The resultant mixture was sparged with N₂ for 5 min, then treated with Pd(dppf)Cl₂ (760 mg, 1.04 mmol). The mixture was sparged with N₂ for another 5 min, then stirred at 95° C. for 1.5 hours. The reaction mixture was cooled and quenched with water and extracted with EtOAc. The combined organic extracts were dried over Na$_2$SO$_4$, filtered, and concentrated under reduced pressure. The resulting residue was purified by FCC (SiO$_2$, 0-5% EtOAc in ether) to afford the title compound (1.7 g, 58% yield) as a yellow oil. MS (ESI): mass calcd. for C$_8$H$_5$ClF$_3$N, 207.0; m/z found, 208.1 [M+H]$^+$. $^1$H NMR (400 MHz, CDCl$_3$) δ 7.73-7.66 (m, 1H), 7.42 (d, J=7.9 Hz, 1H), 7.32 (d, J=7.9 Hz, 1H), 6.75-6.71 (m, 1H), 6.20-6.16 (m, 1H).

Step B: 2-Chloro-6-(1-(trifluoromethyl)cyclopropyl)pyridine. LiHMDS (13 mL, 1 M in THF, 13.0 mmol) was added dropwise to a −70° C. solution of 2-chloro-6-(3,3,3-trifluoroprop-1-en-2-yl)pyridine (900 mg, 4.34 mmol) and methyldiphenylsulfonium tetrafluoroborate (1.9 g, 6.49 mmol) in THF (100 mL). The resultant mixture was stirred at −70° C. for 3 hours before it was quenched with sat. aq. NH$_4$Cl and extracted with EtOAc. The combined organic extracts were washed with brine, dried over Na$_2$SO$_4$, filtered, and concentrated under reduced pressure. The resulting residue was purified by FCC (SiO$_2$, 0-5% EtOAc in ether) to afford the title compound (700 mg, 71% yield) as a yellow oil. MS (ESI): mass calcd. for C$_9$H$_7$ClF$_3$N, 221.0; m/z found, 222.1 [M+H]$^+$.

Intermediate 61: 3-Chloropyrrolo[1,2-b]pyridazine

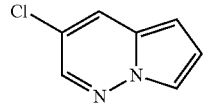

1H-pyrrol-1-amine (5.0 g, 60.9 mmol) was dissolved in MeOH (120 mL) and AcOH (40 mL). 2-Chloromalonaldehyde (7.8 g, 73.0 mmol) was added, and the resulting mixture was stirred at rt for 30 min. The mixture was then heated to 90° C. for 1 hour. The reaction mixture was cooled, concentrated under reduced pressure, diluted with sat. aq. NaHCO$_3$ and extracted with EtOAc. The combined organic extracts were dried over Na$_2$SO$_4$, filtered, and concentrated under reduced pressure. The resulting residue was purified by FCC (SiO$_2$, 0-10% EtOAc in ether) to afford the title compound (900 mg, 9% yield) as a red solid. MS (ESI): mass calcd. for C$_7$H$_5$ClN$_2$, 152.0; m/z found, 153.1 [M+H]$^+$.

Intermediate 62: 1-Bromo-3-isopropoxy-2-methylbenzene

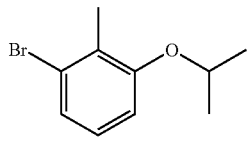

The title compound was prepared in a manner analogous to Intermediate 50 using 3-bromo-2-methylphenol instead of 6-bromo-2H-indazole. $^1$H NMR (400 MHz, CDCl$_3$) δ 7.16-7.10 (m, 2H), 6.80 (d, J=8.1 Hz, 1H), 4.55-4.44 (m, 1H), 2.34 (s, 3H), 1.34 (d, J=6.1 Hz, 6H).

Intermediate 63: 4-Bromo-2-isopropoxy-3-methylpyridine

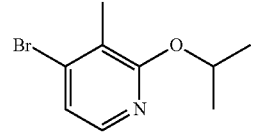

Potassium tert-butoxide (591 mg, 5.26 mmol) was added to a mixture of 4-bromo-2-fluoro-3-methylpyridine (500 mg, 2.63 mmol) and propan-2-ol (4.0 mL, 53.0 mmol). The resultant mixture was stirred at 80° C. for 16 hours. The mixture was cooled to rt and concentrated under reduced pressure. The resulting residue was purified by FCC (SiO$_2$, 0-50% EtOAc in ether) to afford the title compound (550 mg, 89% yield) as a white oil. MS (ESI): mass calcd. for C$_9$H$_{12}$BrNO, 229.0; m/z found, 231.8 [M+H]$^+$.

Intermediate 64: 2-Bromo-6-isopropoxy-4-methylpyridine

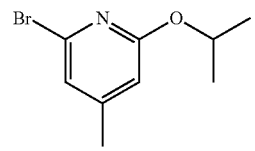

The title compound was prepared in a manner analogous to Intermediate 63 using 2-bromo-6-fluoro-4-methylpyridine instead of 4-bromo-2-fluoro-3-methylpyridine. MS (ESI): mass calcd. for C$_9$H$_{12}$BrNO, 229.0; m/z found, 229.7 [M+H]$^+$.

Intermediate 65: 1-Bromo-2,3-difluoro-5-methoxybenzene

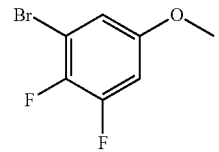

Step A: 2-Bromo-3,4-difluoro-6-methoxyaniline. Br$_2$ (200 µL, 3.64 mmol) was added to a solution of 4,5-difluoro-2-methoxyaniline (500 mg, 3.14 mmol) in AcOH (5 mL). The reaction mixture was stirred at rt for 16 hours. The reaction was quenched with sat. aq. Na$_2$S$_2$O$_3$ and the pH was adjusted to 7-8 by addition of sat. aq. K$_2$CO$_3$. The organics were extracted with EtOAc and the combined organic layers were washed with brine, dried over Na$_2$SO$_4$, and concentrated under reduced pressure. The resulting residue was purified by FCC (SiO$_2$, 0-10% EtOAc in ether) provided the title compound (510 mg, 65% yield) as a yellow solid. MS (ESI): mass calcd. for C$_7$H$_6$BrF$_2$NO, 237.0; m/z found, 237.6 [M+H]$^+$. $^1$H NMR (400 MHz, CDCl$_3$) δ 6.65 (dd, J=12.0, 7.2 Hz, 1H), 4.07 (br s, 2H), 3.85 (s, 3H).

Step B: 1-Bromo-2,3-difluoro-5-methoxybenzene. Isopentyl nitrite (0.87 mL, 6.46 mmol) was added a solution of 2-bromo-3,4-difluoro-6-methoxyaniline (510 mg, 2.14 mmol) in THF (10 mL). The reaction mixture was stirred at 70° C. for 16 hours. The reaction mixture was to rt and concentrating in vacuo. The resulting residue was dissolved in EtOAc and washed with sat. aq. NaHCO$_3$ and brine. The organic layers were concentrated under reduced pressure. The resulting residue was purified by FCC (SiO$_2$, 0-10% EtOAc in ether) to afford the title compound (120 mg, 25% yield) as a yellow oil. $^1$H NMR (400 MHz, CDCl$_3$) δ 6.88-6.82 (m, 1H), 6.75-6.65 (m, 1H), 3.78 (s, 3H).

Intermediate 66: (2-Fluoro-3-methylbenzyl)triphenylphosphonium bromide

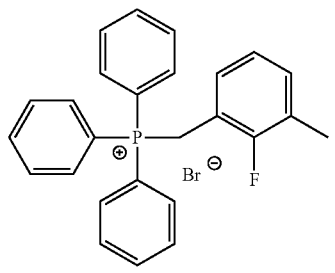 [SMILES: Cc1cccc(C[P+](c2ccccc2)(c2ccccc2)c2ccccc2)c1F ; [Br-]]

The title compound was prepared in a manner analogous to Intermediate 15 using 1-(bromomethyl)-2-fluoro-3-methylbenzene instead of 1-(bromomethyl)-4-isopropylbenzene. MS (ESI): mass calcd. for C$_{26}$H$_{23}$FPBr, 464.1; m/z found, 385.1 [M-Br]$^+$. $^1$H NMR (400 MHz, DMSO-d$_6$) δ 7.96-7.87 (m, 3H), 7.79-7.65 (m, 12H), 7.28-7.20 (m, 1H), 7.00-6.87 (m, 2H), 5.13 (d, J=15.1 Hz, 2H), 2.02 (s, 3H).

Intermediate 67: (4-Fluoro-3-methylbenzyl)triphenylphosphonium bromide

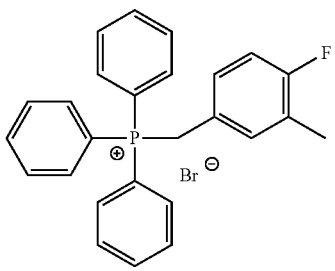 [SMILES: Cc1cc(C[P+](c2ccccc2)(c2ccccc2)c2ccccc2)ccc1F ; [Br-]]

The title compound was prepared in a manner analogous to Intermediate 15 using 4-(bromomethyl)-1-fluoro-2-methylbenzene instead of 1-(bromomethyl)-4-isopropylbenzene. MS (ESI): mass calcd. for C$_{26}$H$_{23}$FPBr, 464.1; m/z found, 385.0 [M-Br]$^+$. $^1$H NMR (400 MHz, DMSO-d$_6$) δ 7.98-7.85 (m, 3H), 7.81-7.65 (m, 12H), 7.07-6.99 (m, 1H), 6.95-6.86 (m, 1H), 6.78-6.70 (m, 1H), 5.21 (d, J=15.3 Hz, 2H), 2.00 (s, 3H).

Intermediate 68: ((1-Methyl-1H-pyrrolo[2,3-b]pyridin-6-yl)methyl)triphenylphosphonium bromide

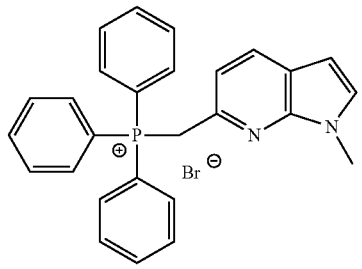 [SMILES: Cn1ccc2ccc(C[P+](c3ccccc3)(c3ccccc3)c3ccccc3)nc21 ; [Br-]]

Step A: 6-(Bromomethyl)-1-methyl-1H-pyrrolo[2,3-b]pyridine. PBr$_3$ (0.77 mL, 8.20 mmol) was added to a 0° C. solution of (1-methyl-1H-pyrrolo[2,3-b]pyridin-6-yl)methanol (1.2 g, 7.40 mmol) in DCM (15 mL). The reaction mixture was stirred at rt for 16 hours before it was quenched with water and extracted with DCM. The combined organic extracts were dried over Na$_2$SO$_4$, filtered, and concentrated under reduced pressure. The resulting residue was purified by FCC (SiO$_2$, 0-30% EtOAc in ether) to afford the title compound (1.1 g, 61% yield) as a clear oil. MS (ESI): mass calcd. for C$_9$H$_9$BrN$_2$, 224.0; m/z found, 226.9 [M+H]$^+$.

Step B: ((1-Methyl-1H-pyrrolo[2,3-b]pyridin-6-yl)methyl)triphenylphosphonium bromide. The title compound was prepared in a manner analogous to Intermediate 15 using 6-(bromomethyl)-1-methyl-1H-pyrrolo[2,3-b]pyridine instead of 1-(bromomethyl)-4-isopropylbenzene. MS (ESI): mass calcd. for C$_{27}$H$_{24}$N$_2$PBr, 486.1; m/z found, 407.1 [M−Br]$^+$. $^1$H NMR (400 MHz, DMSO-d$_6$) δ 7.93-7.77 (m, 10H), 7.75-7.64 (m, 6H), 7.44 (d, J=3.3 Hz, 1H), 7.08 (d, J=8.0 Hz, 1H), 6.40 (d, J=3.5 Hz, 1H), 5.56 (d, J=15.4 Hz, 2H), 3.41 (s, 3H).

Intermediate 69: ((1-Methyl-1H-indazol-6-yl)methyl)triphenylphosphonium bromide

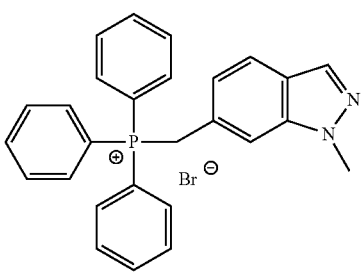 [SMILES: Cn1ncc2ccc(C[P+](c3ccccc3)(c3ccccc3)c3ccccc3)cc21 ; [Br-]]

The title compound was prepared in a manner analogous to Intermediate 15 using 6-(bromomethyl)-1-methyl-1H-indazole instead of 1-(bromomethyl)-4-isopropylbenzene. MS (ESI): mass calcd. for C$_{27}$H$_{24}$N$_2$PBr, 486.1; m/z found, 407.5 [M−Br]$^+$.

Intermediate 70: tert-Butyl 7-(bromomethyl)-2-azaspiro[3.5]nonane-2-carboxylate

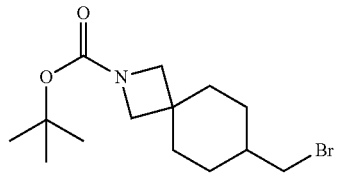 [SMILES: CC(C)(C)OC(=O)N1CC2(CCC(CBr)CC2)C1]

The title compound was prepared in a manner analogous to Intermediate 4 using tert-butyl 7-(hydroxymethyl)-2-azaspiro[3.5]nonane-2-carboxylate instead of tert-butyl 6-(hydroxymethyl)-2-azaspiro[3.3]heptane-2-carboxylate. MS (ESI): mass calcd. for $C_{14}H_{24}BrNO_2$, 317.1; m/z found, 262.0 [M-$C_2H_8$+H]$^+$. $^1$H NMR (400 MHz, CDCl$_3$) δ 3.58 (d, J=11.9 Hz, 4H), 3.27 (d, J=6.3 Hz, 2H), 1.90 (br s, 2H), 1.87-1.79 (m, 2H), 1.61-1.54 (m, 1H), 1.48 (d, J=3.1 Hz, 1H), 1.44 (s, 9H), 1.42 (d, J=3.3 Hz, 1H), 1.09-0.97 (m, 2H).

Intermediate 71: tert-Butyl 7-(iodomethyl)-2-azaspiro[3.5]nonane-2-carboxylate

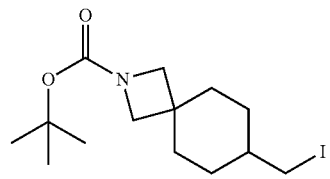 [SMILES: CC(C)(C)OC(=O)N1CC2(CCC(CI)CC2)C1]

The title compound was prepared in a manner analogous to Intermediate 1, Step B using tert-butyl 7-(hydroxymethyl)-2-azaspiro[3.5]nonane-2-carboxylate instead of tert-butyl 2-hydroxy-8-azaspiro[4.5]decane-8-carboxylate. MS (ESI): mass calcd. for $C_{14}H_{24}INO_2$, 365.1; m/z found, 309.9 [M-$C_2H_8$+H]$^+$. $^1$H NMR (400 MHz, CDCl$_3$) δ 3.55 (d, J=12.0 Hz, 4H), 3.06 (d, J=4.0 Hz, 2H), 1.91-1.77 (m, 4H), 1.50-1.33 (m, 12H), 1.03-0.89 (m, 2H).

Intermediate 72: tert-Butyl 6-methylene-2-azaspiro[3.3]heptane-2-carboxylate

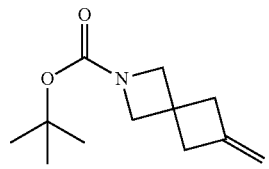

TiCl$_4$ (7.8 mL, 1M in DCM, 7.81 mmol) was added dropwise to a mixture of zinc dust (2.1 g, 31.8 mmol) and CH$_2$I$_2$ (3.1 g, 10.6 mmol) in THF (20 mL). The resultant mixture was stirred at rt for 15 minutes then treated with a solution of tert-butyl 6-oxo-2-azaspiro[3.3]heptane-2-carboxylate (1.5 g, 7.10 mmol) in THF (10 mL) dropwise. The resulting mixture was stirred at rt for 12 hours. The reaction mixture was poured into sat. NH$_4$Cl and extracted with EtOAc. The combined organic extracts were washed with brine, dried over Na$_2$SO$_4$, filtered, and concentrated under reduced pressure. The resulting residue was purified by FCC (SiO$_2$, 0-10% EtOAc in ether) to afford the title compound (607 mg) as a colorless oil.

Intermediate 73: 6-Bromo-3-fluoro-1-methyl-1H-pyrrolo[2,3-b]pyridine

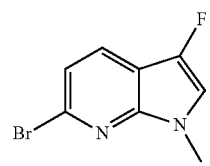

Step A: 6-Bromo-3-fluoro-1H-pyrrolo[2,3-b]pyridine. Selectfluor (6.5 g, 18.3 mmol) was added to a solution of 6-bromo-1H-pyrrolo[2,3-b]pyridine (3.0 g, 5.08 mmol) in MeCN (50 mL) and DMF (20 mL). The resulting mixture was stirred at 0° C. for 3 h. The reaction mixture was warmed to room temperature, poured into H$_2$O and extracted with DCM. The combined organic extracts were dried over Na$_2$SO$_4$, filtered, and concentrated under reduced pressure. The resulting residue was purified by FCC (SiO$_2$, 0-20% EtOAc in ether). The compound was further subjected to RP HPLC (34-64% CH$_3$CN in H$_2$O with 0.225% HCOOH) to afford the title compound (280 mg, 19% yield) as a white solid. MS (ESI): mass calcd. for $C_7H_4BrFN_2$, 214.0; m/z found, 214.8 [M+H]$^+$.

Step B: 6-Bromo-3-fluoro-1-methyl-1H-pyrrolo[2,3-b]pyridine. The title compound was prepared in a manner analogous to Intermediate 44 using 6-bromo-3-fluoro-1H-pyrrolo[2,3-b]pyridine instead of 6-bromo-1H-pyrrolo[2,3-b]pyridine. MS (ESI): mass calcd. for $C_8H_6BrFN_2$, 227.9; m/z found, 228.7 [M+H]$^+$. $^1$H NMR (400 MHz, CDCl$_3$) δ 7.76 (d, J=8.0 Hz, 1H), 7.23-7.18 (m, 1H), 6.90 (d, J=2.4 Hz, 1H), 3.80 (s, 3H).

Intermediate 74: tert-Butyl 6-acetyl-2-azaspiro[3.3]heptane-2-carboxylate

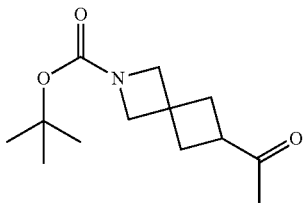 [SMILES: CC(=O)C1CC2(C1)CN(C(=O)OC(C)(C)C)C2]

Step A: tert-Butyl 6-(methoxy(methyl)carbamoyl)-2-azaspiro[3.3]heptane-2-carboxylate. HATU (1.58 g, 4.16 mmol) was added to a solution of 2-(tert-butoxycarbonyl)-2-azaspiro[3.3]heptane-6-carboxylic acid (500 mg, 2.07 mmol), N,O-dimethylhydroxylamine hydrochloride (242 mg, 2.48 mmol), and DIPEA (1.8 mL, 10.4 mmol) in DMF (10 mL). The resultant mixture was stirred at rt for 2 h before being poured into sat. aq. NaHCO$_3$ and extracted with EtOAc. The combined organic extracts were washed with sat. aq. NaHCO$_3$ and brine, dried over Na$_2$SO$_4$, filtered, and concentrated under reduced pressure. The resulting residue was purified by FCC (SiO$_2$, 0-50% EtOAc in ether) to afford the title compound (560 mg, 95% yield) as a yellow oil. MS (ESI): mass calcd. for $C_{14}H_{24}N_2O_4$, 284.2; m/z found, 228.9 [M+2H-tBu]$^+$. $^1$H NMR (400 MHz, CDCl$_3$) δ 3.96 (s, 2H), 3.85 (s, 2H), 3.65 (s, 3H), 3.34 (s, 1H), 3.17 (s, 3H), 2.52-2.42 (m, 2H), 2.39-2.29 (m, 2H), 1.43 (s, 9H).

Step B: tert-Butyl 6-acetyl-2-azaspiro[3.3]heptane-2-carboxylate. Methylmagnesium bromide (4.0 mL, 4.05 mmol, 1 M in THF) was added to a 0° C. solution of tert-butyl 6-(methoxy(methyl)carbamoyl)-2-azaspiro[3.3]heptane-2-carboxylate (560 mg, 1.97 mmol) in THF (5 mL). The resulting mixture was stirred at rt for 16 h before being quenched with sat. aq. NH$_4$Cl and extracted with EtOAc. The combined organic layers were washed with sat. aq. NaHCO$_3$, dried over Na$_2$SO$_4$, filtered, and concentrated under reduced pressure. The resulting residue was purified by FCC (SiO$_2$, 0-50% EtOAc in ether) to give the title compound (370 mg, 79% yield) as a yellow oil. MS (ESI): mass calcd. for $C_{13}H_{21}NO_3$, 239.2; m/z found, 183.8 [M+2H-tBu]$^+$. $^1$H NMR (400 MHz, CDCl$_3$) δ 3.94 (s, 2H), 3.81 (s, 2H), 3.19-3.07 (m, 1H), 2.41-2.29 (m, 4H), 2.10 (s, 3H), 1.43 (s, 9H).

Intermediate 75: Potassium O-tert-butyl carbonodithioate

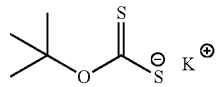

Carbon disulfide (5.0 g, 66.0 mmol) was added dropwise to a 0° C. solution of potassium t-butoxide (7.4 g, 66.0 mmol) in dry THF (100 mL) under N$_2$. The resultant mixture was stirred at rt for 12 h. The suspension was filtered, and the filter cake was washed with 2-isopropoxypropane before drying under reduced pressure to afford the title compound (10.2 g, 82% yield) as a yellow solid, which was used in the next step without further purification.

Intermediate 76: 6-Chloro-3-(difluoromethyl)-2-methylpyridine

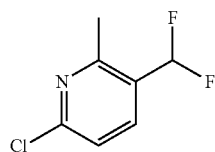

Diethylaminosulfur trifluoride (1.7 mL, 12.9 mmol) was added in portions to a 0° C. solution of 6-chloro-2-methylnicotinaldehyde (500 mg, 3.21 mmol) in DCM (10 mL). The resultant mixture was stirred for 16 h with gradual warming to rt. The reaction mixture was quenched with sat. aq. NaHCO$_3$ and extracted with DCM. The combined organic extracts were washed with brine, dried over Na$_2$SO$_4$, filtered, and concentrated under reduced pressure. The resulting residue was purified by FCC (SiO$_2$, 0-50% EtOAc in ether) to afford the title compound (450 mg, 76% yield) as a yellow oil. MS (ESI): mass calcd. for $C_7H_6ClF_2N$, 177.0; m/z found, 178.1 [M+H]$^+$.

Intermediate 77: 2-Bromo-6-chloro-3-(difluoromethyl)pyridine

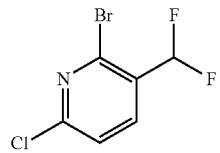 [SMILES: FC(F)c1ccc(Cl)nc1Br]

The title compound was prepared in a manner analogous to Intermediate 76 using 2-bromo-6-chloronicotinaldehyde instead of 6-chloro-2-methylnicotinaldehyde. MS (ESI): mass calcd. for $C_6H_3BrClF_2N$, 240.9; m/z found, 241.7 [M+H]$^+$.

Intermediate 78: 6-Fluoro-1-methyl-1H-pyrrolo[2,3-b]pyridine

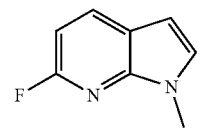

The title compound was prepared in a manner analogous to Intermediate 44 using 6-fluoro-1H-pyrrolo[2,3-b]pyridine instead of 6-bromo-1H-pyrrolo[2,3-b]pyridine. MS (ESI): mass calcd. for $C_8H_7FN_2$, 150.1; m/z found, 151.1 [M+H]$^+$.

Intermediate 79: 6-Chloro-1-methyl-3-(trifluoromethyl)-1H-pyrrolo[2,3-b]pyridine

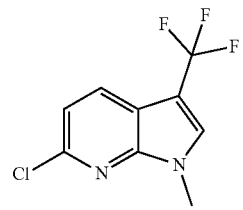

The title compound was prepared in a manner analogous to Intermediate 44 using 6-chloro-3-(trifluoromethyl)-1H-pyrrolo[2,3-b]pyridine instead of 6-bromo-1H-pyrrolo[2,3-b]pyridine. MS (ESI): mass calcd. for $C_9H_6ClF_3N_2$, 234.0; m/z found, 234.8 [M+H]$^+$.

Intermediate 80: 6-Bromo-2,4-dimethyl-3-(trifluoromethyl)pyridine

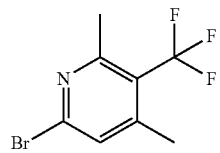

Step A: 2,4-Dimethyl-3-(trifluoromethyl)pyridine. K₂CO₃ (4.0 g, 12.0 mmol) was added to a solution of 2,4-dichloro-3-(trifluoromethyl)pyridine (2.0 g, 9.30 mmol) and 2,4,6-trimethyl-1,3,5,2,4,6-trioxatriborinane (7.7 mL, 27.8 mmol) in 1,4-dioxane (30 mL) and H₂O (6 mL). The mixture was sparged with N₂ for 5 min, then treated with Pd(dppf)Cl₂·CH₂Cl₂ (1.2 g, 1.50 mmol). The reaction mixture was stirred at 120° C. for 16 h under N₂. The reaction mixture was cooled to rt and poured into water and 1 M aq. HCl and extracted with DCM. The aqueous phase was adjusted to pH 10 with 1 M aq. NaOH and extracted with DCM. The combined organic extracts were dried over Na₂SO₄, filtered, and concentrated under reduced pressure to afford the title compound (1.6 g), which was used in the next step without further purification. MS (ESI): mass calcd. for C₈H₈F₃N, 175.1; m/z found, 175.9 [M+H]⁺.

Step B: 2,4-Dimethyl-3-(trifluoromethyl)pyridine 1-oxide. 3-Chlorobenzoperoxoic acid (3.2 g, 18.5 mmol) was added to a solution of 2,4-dimethyl-3-(trifluoromethyl)pyridine (1.6 g, 9.26 mmol) in DCM (150 mL). The reaction mixture was stirred at rt for 16 h before being diluted with DCM and washed with sat. aq. Na₂SO₃ and sat. aq. Na₂CO₃. The organic layers were dried over Na₂SO₄, filtered, and concentrated under reduced pressure to give the title compound (2.3 g, crude) as a yellow oil, which was used in the next step without further purification. MS (ESI): mass calcd. for C₈H₈F₃NO, 191.1; m/z found, 192.0 [M+H]⁺.

Step C: 6-Bromo-2,4-dimethyl-3-(trifluoromethyl)pyridine. POBr₃ (9.4 g, 33.0 mmol) was added to a solution of 2,4-dimethyl-3-(trifluoromethyl)pyridine 1-oxide (2.1 g, crude) in toluene (100 mL). The reaction mixture was stirred at 80° C. for 3 h before being cooled to rt. The reaction mixture was slowly poured into water and adjusted to pH 8 with sat. aq. NaHCO₃. The mixture was extracted with DCM and the combined organic layers were dried over Na₂SO₄, filtered, and concentrated under reduced pressure. The resulting residue was purified by FCC (SiO₂, 0-10% EtOAc in ether) to afford the title compound (300 mg, 5% yield) as a yellow oil. MS (ESI): mass calcd. for C₈H₇BrF₃N, 253.0; m/z found, 255.8 [M+H]⁺.

Intermediate 81:
6-Bromo-3,6-dimethyl-5-(trifluoromethyl)pyridine

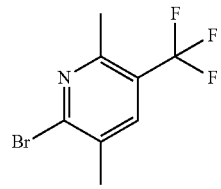

The title compound was prepared in a manner analogous to Intermediate 80 using 2,5-dibromo-3-(trifluoromethyl)pyridine instead of 2,4-dichloro-3-(trifluoromethyl)pyridine in Step A. MS (ESI): mass calcd. for C₈H₇BrF₃N, 253.0; m/z found, 253.6 [M+H]⁺.

Intermediate 82: 6-Chloro-1,4-dimethyl-1H-pyrrolo[2,3-b]pyridine

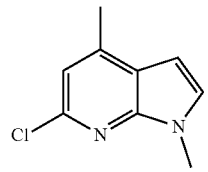

Step A: 4-Bromo-6-chloro-1-methyl-1H-pyrrolo[2,3-b]pyridine. The title compound was prepared in a manner analogous to Intermediate 44 using 4-bromo-6-chloro-1H-pyrrolo[2,3-b]pyridine instead of 6-bromo-1H-pyrrolo[2,3-b]pyridine. MS (ESI): mass calcd. for C₈H₆BrClN₂, 243.9; m/z found, 245.7 [M+H]⁺. ¹H NMR (400 MHz, CDCl₃) δ 7.30 (s, 1H), 7.21 (d, J=3.6 Hz, 1H), 6.49 (d, J=3.2 Hz, 1H), 3.87 (s, 3H).

Step B: 6-Chloro-1,4-dimethyl-1H-pyrrolo[2,3-b]pyridine. Pd(dppf)Cl₂·CH₂Cl₂ (424 mg, 0.519 mmol) was added to a solution of 4-bromo-6-chloro-1-methyl-1H-pyrrolo[2,3-b]pyridine (580 mg, 3.46 mmol), 2,4,6-trimethyl-1,3,5,2,4,6-trioxatriborinane (522 mg, 4.16 mmol), and Cs₂CO₃ (3.40 g, 10.4 mmol) in H₂O (10 mL) and dioxane (2.5 mL) under N₂. The reaction mixture was stirred at 110° C. for 1.5 h. The reaction mixture was cooled to rt and quenched with water and extracted with EtOAc. The organic layers were dried over Na₂SO₄, filtered, and concentrated under reduced pressure. The resulting residue was purified by FCC (SiO₂, 0-10% EtOAc in ether) to afford the title compound (230 mg, 64% yield) as a light-yellow oil. MS (ESI): mass calcd. for C₉H₉ClN₂, 180.0; m/z found, 180.9 [M+H]⁺.

Intermediate 83: 6-Chloro-1,5-dimethyl-1H-pyrrolo[2,3-b]pyridine

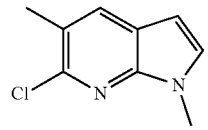

The title compound was prepared in a manner analogous to Intermediate 44 using 6-chloro-5-methyl-1H-pyrrolo[2,3-b]pyridine instead of 6-bromo-1H-pyrrolo[2,3-b]pyridine. MS (ESI): mass calcd. for C₉H₉ClN₂, 180.0; m/z found, 180.8 [M+H]⁺. ¹H NMR (400 MHz, CDCl₃) δ 7.75 (s, 1H), 7.12 (d, J=4.0 Hz, 1H), 6.37 (d, J=4.0 Hz, 1H), 3.85 (s, 3H), 2.45 (s, 3H).

Intermediate 84: 6-Chloro-3-fluoro-1-methyl-1H-pyrrolo[2,3-b]pyridine

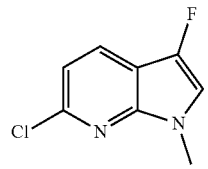

The title compound was prepared in a manner analogous to Intermediate 44 using 6-chloro-3-fluoro-1H-pyrrolo[2,3-b]pyridine instead of 6-bromo-1H-pyrrolo[2,3-b]pyridine. $^1$H NMR (400 MHz, CDCl$_3$) δ 7.86 (d, J=8.3 Hz, 1H), 7.08 (d, J=8.3 Hz, 1H), 6.92 (d, J=2.5 Hz, 1H), 3.81 (s, 3H).

Intermediate 85: 6-Bromo-1-ethyl-3-fluoro-1H-pyrrolo[2,3-b]pyridine

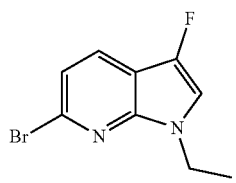

The title compound was prepared in a manner analogous to Intermediate 44 using 6-bromo-3-fluoro-1H-pyrrolo[2,3-b]pyridine (from Intermediate 73, Step A) instead of 6-bromo-1H-pyrrolo[2,3-b]pyridine and iodoethane instead of iodomethane. MS (ESI): mass calcd. for C$_9$H$_8$BrFN$_2$, 242.0; m/z found, 242.8 [M+H]$^+$. $^1$H NMR (400 MHz, CDCl$_3$) δ 7.77 (d, J=8.0 Hz, 1H), 7.22 (d, J=8.0 Hz, 1H), 6.97 (d, J=2.4 Hz, 1H), 4.28 (q, J=7.2 Hz, 2H), 1.44 (t, J=7.2 Hz, 3H).

Example 1

(6-(3-(tert-Butyl)phenyl)-2-azaspiro[3.3]heptan-2-yl)((1s,3s)-3-hydroxy-3-methylcyclobutyl)methanone

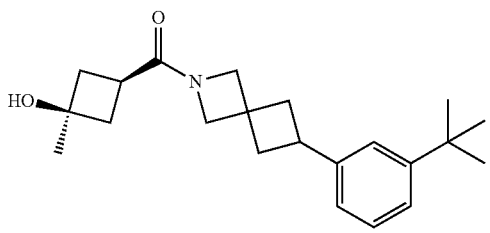 [SMILES: CC(C)(C)c1cccc(C2CC3(C2)CN(C(=O)[C@H]2C[C@@](C)(O)C2)C3)c1]

Step A: tert-Butyl 6-(3-(tert-butyl)phenyl)-2-azaspiro[3.3]heptane-2-carboxylate. (3-(tert-Butyl)phenyl)boronic acid (330 mg, 1.86 mmol), (1R,2R)-2-aminocyclohexanol (21 mg, 0.186 mmol), nickel(II) iodide (58 mg, 0.186 mmol), and IPA (10 mL) were combined. The resultant mixture was stirred at rt for 30 minutes under N$_2$, then treated with NaHMDS (1.86 mL, 1.86 mmol, 1M in THF). The resultant mixture was stirred at rt for 10 minutes under N$_2$, then treated with a solution of tert-butyl 6-iodo-2-azaspiro[3.3]heptane-2-carboxylate (Intermediate 3, 300 mg, 0.928 mmol) in IPA (5 mL). The resultant mixture was stirred at 70° C. for 14 hours under N$_2$ before cooling to rt. The reaction mixture was concentrated under reduced pressure and purified by FCC (SiO$_2$, 0-10% EtOAc in ether) to afford the title compound (275 mg, 90%) as a colorless oil. MS (ESI): mass calcd. for C$_{21}$H$_{31}$NO$_2$, 329.2; m/z found, 274.2 [M+2H-tBu]$^+$.

Step B: 6-(3-(tert-Butyl)phenyl)-2-azaspiro[3.3]heptane. tert-Butyl 6-(3-(tert-butyl)phenyl)-2-azaspiro[3.3]heptane-2-carboxylate (275 mg, 0.537 mmol), TFA (2 mL), and DCM (4 mL) were combined. The resultant mixture was stirred at rt for 1 hour. The reaction mixture was concentrated under reduced pressure to afford the title compound (300 mg, crude), which was used in the next step without further purification. MS (ESI): mass calcd. for C$_{16}$H$_{23}$N, 229.2; m/z found, 230.2 [M+H]$^+$.

Step C: (6-(3-(tert-Butyl)phenyl)-2-azaspiro[3.3]heptan-2-yl)((1s,3s)-3-hydroxy-3-methylcyclobutyl)methanone. HATU (219 mg, 0.576 mmol) was added to solution of (1s,3s)-3-hydroxy-3-methylcyclobutanecarboxylic acid (50 mg, 0.384 mmol), 6-(3-(tert-butyl)phenyl)-2-azaspiro[3.3]heptane (300 mg, 0.874 mmol, crude) and DIPEA (199 mg, 1.54 mmol) in DMF (4 mL). The resultant mixture was stirred at rt for 12 hours. The reaction mixture was poured into H$_2$O and extracted with EtOAc. The combined organic extracts were washed with brine, dried over Na$_2$SO$_4$, filtered, and concentrated under reduced pressure. The resulting residue was purified by preparative HPLC (Phenomenex Gemini NX-C18, 75 mm×30 mm×3 μm, 48% to 78% (v/v) CH$_3$CN and H$_2$O with 0.05% NH$_3$+10 mM NH$_4$HCO$_3$) to afford the title compound (64 mg, 47%) as a white solid. MS (ESI): mass calcd. for C$_{22}$H$_{31}$NO$_2$, 341.2; m/z found, 342.2 [M+H]$^+$. $^1$H NMR (400 MHz, CDCl$_3$) δ 7.30-7.27 (m, 2H), 7.18 (s, 1H), 7.03-7.01 (m, 1H), 4.25 (s, 1H), 4.17 (s, 1H), 4.02 (s, 1H), 3.99-3.87 (m, 2H), 3.51-3.35 (m, 1H), 2.74-2.57 (m, 3H), 2.41-2.22 (m, 6H), 1.37 (d, J=5.2 Hz, 3H), 1.33 (s, 9H)

Example 2

(6-(4-(tert-Butyl)phenyl)-2-azaspiro[3.3]heptan-2-yl)((1s,3s)-3-hydroxy-3-methylcyclobutyl)methanone

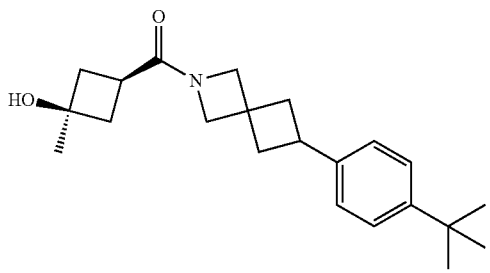 [SMILES: CC(C)(C)c1ccc(C2CC3(C2)CN(C(=O)[C@H]2C[C@@](C)(O)C2)C3)cc1]

The title compound was prepared in a manner analogous to Example 1 using (4-(tert-butyl)phenyl)boronic acid instead of (3-(tert-butyl)phenyl)boronic acid in Step A. MS (ESI): mass calcd. for C$_{22}$H$_{31}$NO$_2$, 341.2; m/z found, 342.2 [M+H]$^+$. $^1$H NMR (400 MHz, CDCl$_3$) δ 7.33 (d, J=8.0 Hz, 2H), 7.11 (d, J=8.0 Hz, 2H), 4.22 (s, 1H), 4.14 (s, 1H), 4.00 (s, 1H), 3.93 (s, 1H), 3.89 (br s, 1H), 3.47-3.32 (m, 1H), 2.73-2.55 (m, 3H), 2.37-2.21 (m, 6H), 1.35 (d, J=4.4 Hz, 3H), 1.31 (s, 9H).

Example 3

((1s,3s)-3-Hydroxy-3-methylcyclobutyl)(6-(3-isopropylphenyl)-2-azaspiro[3.3]heptan-2-yl)methanone

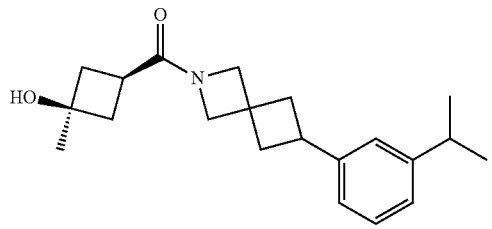 [SMILES: CC(C)c1cccc(C2CC3(C2)CN(C(=O)[C@H]2C[C@@](C)(O)C2)C3)c1]

The title compound was prepared in a manner analogous to Example 1 using (3-isopropylphenyl)boronic acid instead of (3-(tert-butyl)phenyl)boronic acid in Step A. MS (ESI): mass calcd. for $C_{21}H_{29}NO_2$, 327.2; m/z found, 328.2 [M+H]$^+$. $^1$H NMR (400 MHz, CDCl$_3$) δ 7.26-7.21 (m, 1H), 7.07 (d, J=7.6 Hz, 1H), 7.04-6.97 (m, 2H), 4.23 (s, 1H), 4.15 (s, 1H), 4.00 (s, 1H), 3.94 (s, 1H), 3.90 (s, 1H), 3.49-3.33 (m, 1H), 2.95-2.82 (m, 1H), 2.74-2.55 (m, 3H), 2.38-2.21 (m, 6H), 1.35 (d, J=4.8 Hz, 3H), 1.24 (d, J=6.8 Hz, 6H).

Example 4

((1s,3s)-3-Hydroxy-3-methylcyclobutyl)(6-(4-isopropylphenyl)-2-azaspiro[3.3]heptan-2-yl)methanone

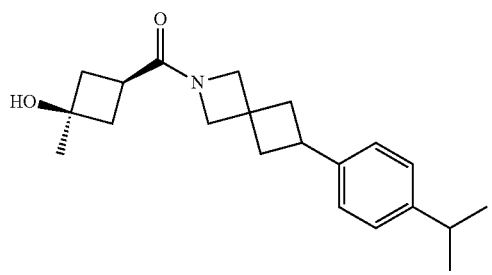 [SMILES: CC(C)c1ccc(C2CC3(C2)CN(C(=O)[C@H]2C[C@@](C)(O)C2)C3)cc1]

The title compound was prepared in a manner analogous to Example 1 using (4-isopropylphenyl)boronic acid instead of (3-(tert-butyl)phenyl)boronic acid in Step A. MS (ESI): mass calcd. for $C_{21}H_{29}NO_2$, 327.2; m/z found, 328.2 [M+H]$^+$. $^1$H NMR (400 MHz, CDCl$_3$) δ 7.20-7.15 (m, 2H), 7.13-7.07 (m, 2H), 4.22 (s, 1H), 4.14 (s, 1H), 4.00 (s, 1H), 3.93 (s, 1H), 3.88 (s, 1H), 3.48-3.31 (m, 1H), 2.94-3.82 (m, 1H), 2.75-2.54 (m, 3H), 2.38-2.20 (m, 6H), 1.34 (d, J=4.8 Hz, 3H), 1.24 (d, J=7.2 Hz, 6H).

Example 5

(6-(4-Cyclopropylphenyl)-2-azaspiro[3.3]heptan-2-yl)((1s,3s)-3-hydroxy-3-methylcyclobutyl)methanone

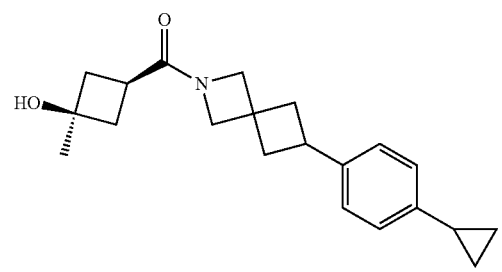 [SMILES: C[C@]1(O)C[C@@H](C(=O)N2CC3(CC(c4ccc(C5CC5)cc4)C3)C2)C1]

The title compound was prepared in a manner analogous to Example 1 using (4-cyclopropylphenyl)boronic acid instead of (3-(tert-butyl)phenyl)boronic acid in Step A. MS (ESI): mass calcd. for $C_{11}H_{27}NO_2$, 325.2; m/z found, 326.1 [M+H]$^+$. $^1$H NMR (400 MHz, CDCl$_3$) δ 7.11-6.99 (m, 4H), 4.22 (s, 1H), 4.14 (s, 1H), 4.00 (s, 1H), 3.93 (s, 1H), 3.83 (s, 1H), 3.45-3.31 (m, 1H), 2.74-2.53 (m, 3H), 2.39-2.19 (m, 6H), 1.92-1.83 (m, 1H), 1.36 (d, J=4.8 Hz, 3H), 0.97-0.91 (m, 2H), 0.70-0.64 (m, 2H).

Example 6

((1s,3s)-3-Hydroxy-3-methylcyclobutyl)(6-(4-methyl-3-(trifluoromethyl)phenyl)-2-azaspiro[3.3]heptan-2-yl)methanone

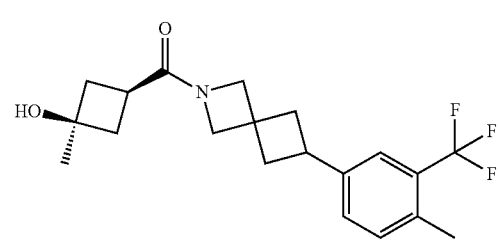 [SMILES: Cc1ccc(C2CC3(C2)CN(C(=O)[C@H]2C[C@@](C)(O)C2)C3)cc1C(F)(F)F]

The title compound was prepared in a manner analogous to Example 1 using (4-methyl-3-(trifluoromethyl)phenyl)boronic acid instead of (3-(tert-butyl)phenyl)boronic acid in Step A. MS (ESI): mass calcd. for $C_{20}H_{24}F_3NO_2$, 367.2; m/z found, 368.1 [M+H]$^+$. $^1$H NMR (400 MHz, CDCl$_3$) δ 7.38 (d, J=4.0 Hz, 1H), 7.21 (d, J=2.4 Hz, 2H), 4.23 (s, 1H), 4.15 (s, 1H), 4.01 (s, 1H), 3.94 (s, 1H), 3.78 (s, 1H), 3.50-3.35 (m, 1H), 2.74-2.57 (m, 3H), 2.44 (d, J=1.6 Hz, 3H), 2.35-2.21 (m, 6H), 1.35 (d, J=4.4 Hz, 3H).

Example 7

(rac)-((1s,3s)-3-Hydroxy-3-methylcyclobutyl)(6-(2-methyl-3-(trifluoromethyl)phenyl)-2-azaspiro[3.4]octan-2-yl)methanone

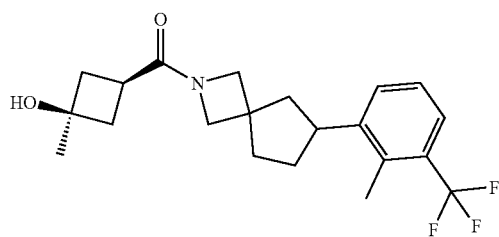 [SMILES: Cc1c(C2CCC3(C2)CN(C(=O)[C@H]2C[C@@](C)(O)C2)C3)cccc1C(F)(F)F]

Step A: (rac)-tert-Butyl 6-hydroxy-6-(2-methyl-3-(trifluoromethyl)phenyl)-2-azaspiro[3.4]octane-2-carboxylate. n-BuLi (0.46 mL, 2.5 M in hexane, 1.15 mmol) was added to a solution consisting of 1-bromo-2-methyl-3-(trifluoromethyl)benzene (255 mg, 1.07 mmol) and anhydrous THF (2 mL). The resultant mixture was stirred at −78° C. for 1 h before tert-butyl 6-oxo-2-azaspiro[3.4]octane-2-carboxylate (200 mg, 0.89 mmol) in anhydrous THF (2 mL) was added. The resultant mixture was stirred at −78° C. for 4 hours. The reaction mixture was quenched with sat. NH$_4$Cl and extracted with EtOAc. The combined organic extracts were washed with brine, dried over Na$_2$SO$_4$, filtered, and concentrated under reduced pressure. The resulting residue was purified by FCC (SiO$_2$, 0-50% EtOAc in ether) to afford the title compound (102 mg, 26%) as a colorless oil. MS (ESI): mass calcd. for C$_{20}$H$_{26}$F$_3$NO$_3$, 385.2; m/z found, 371.0 [M+2H+MeCN-tBu]$^+$.

Step B: (rac)-6-(2-Methyl-3-(trifluoromethyl)phenyl)-2-azaspiro[3.4]oct-5-ene trifluoroacetate. TES (92 mg, 0.794 mmol) was added to a solution of tert-butyl 6-hydroxy-6-(2-methyl-3-(trifluoromethyl)phenyl)-2-azaspiro[3.4]octane-2-carboxylate (102 mg, 0.265 mmol) in TFA (3 mL). The resultant mixture was stirred at rt for 2 hours before being concentrated under reduced pressure to give the crude product (92 mg, 85%), which was used for the next step without purification. MS (ESI): mass calcd. for C$_{15}$H$_{16}$F$_3$N, 267.1; m/z found, 267.9 [M+H]$^+$.

Step C: (rac)-((1s,3s)-3-Hydroxy-3-methylcyclobutyl)(6-(2-methyl-3-(trifluoromethyl)phenyl)-2-azaspiro[3.4]oct-5-en-2-yl)methanone. HATU (153 mg, 0.401 mmol) was added to a solution of 6-(2-methyl-3-(trifluoromethyl)phenyl)-2-azaspiro[3.4]oct-5-ene trifluoroacetate (102 mg, 0.267 mmol), (1s,3s)-3-hydroxy-3-methylcyclobutanecarboxylic acid (35 mg, 0.267 mmol) and DIPEA (138 mg, 1.07 mmol) in DMF (4 mL). The resultant mixture was stirred at rt for 17 h. The reaction mixture was quenched with H$_2$O and extracted with EtOAc. The combined organic extracts were washed with brine, dried over Na$_2$SO$_4$, filtered, and concentrated under reduced pressure to give the crude product which was purified by FCC (SiO$_2$, 0-25% MeOH in DCM) to afford the title compound (98 mg, 73%) as a colorless oil. MS (ESI): mass calcd. for C$_{21}$H$_4$F$_3$NO$_2$, 379.2; m/z found, 380.0 [M+H]$^+$.

Step D: (rac)-((1s,3s)-3-Hydroxy-3-methylcyclobutyl)(6-(2-methyl-3-(trifluoromethyl)phenyl)-2-azaspiro[3.4]octan-2-yl)methanone. ((1s,3s)-3-Hydroxy-3-methylcyclobutyl)(6-(2-methyl-3-(trifluoromethyl)phenyl)-2-azaspiro[3.4]oct-5-en-2-yl)methanone (98 mg, 0.200 mmol), wet Pd/C (10 mg, 10 wt. %, 0.090 mmol), and MeOH (3 mL) were combined. The resultant mixture was stirred under H$_2$ (15 psi) at rt for 2 hours. The reaction mixture was concentrated under reduced pressure. The resulting residue was purified by preparative HPLC (Welch Xtimate C18, 150 mm×30 mm×5 um, 50% to 80% (v/v) CH$_3$CN and water with 0.05% NH$_3$) to afford the title compound (41 mg, 54%) as a white solid. MS (ESI): mass calcd. for C$_{21}$H$_{26}$F$_3$NO$_2$, 381.2; m/z found, 382.1 [M+H]$^+$. $^1$H NMR (400 MHz, CDCl$_3$) δ 7.50 (d, J=8.0 Hz, 1H), 7.39 (t, J=7.2 Hz, 1H), 7.29-7.27 (m, 1H), 4.07-3.85 (m, 5H), 3.46-3.30 (m, 1H), 2.73-2.66 (m, 1H), 2.45-2.40 (m, 3H), 2.33-2.78 (m, 5H), 2.20-1.99 (m, 3H), 1.95-1.82 (m, 1H), 1.77-1.68 (m, 1H), 1.36 (s, 3H).

Example 8

(rac)-((1s,3s)-3-Hydroxy-3-methylcyclobutyl)(6-(2-methyl-4-(trifluoromethyl)phenyl)-2-azaspiro[3.4]octan-2-yl)methanone

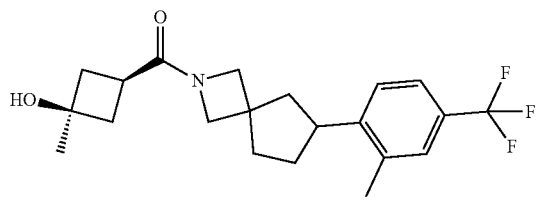 [SMILES: Cc1cc(C(F)(F)F)ccc1C1CCC2(C1)CN(C(=O)[C@H]1C[C@@](C)(O)C1)C2]

The title compound was prepared in a manner analogous to Example 7 using 1-bromo-2-methyl-4-(trifluoromethyl)benzene instead of 1-bromo-2-methyl-3-(trifluoromethyl)benzene in Step A. MS (ESI): mass calcd. for C$_{21}$H$_{26}$F$_3$NO$_2$, 381.2; m/z found, 382.1 [M+H]$^+$. $^1$H NMR (400 MHz, CDCl$_3$) δ 7.47-7.34 (m, 2H), 7.32-7.28 (m, 1H), 4.10-3.85 (m, 5H), 3.40-3.26 (m, 1H), 2.73-2.66 (m, 1H), 2.39 (s, 3H), 2.35-2.24 (m, 5H), 2.18-1.99 (m, 3H), 1.94-1.83 (m, 1H), 1.77-1.71 (m, 1H), 1.39-1.34 (s, 3H).

Example 9

(rac)-((1s,3s)-3-Hydroxy-3-methylcyclobutyl)(6-(2-methyl-4-(trifluoromethoxy)phenyl)-2-azaspiro[3.4]octan-2-yl)methanonemethanone

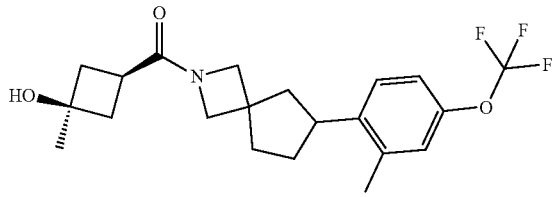 [SMILES: Cc1cc(OC(F)(F)F)ccc1C1CCC2(C1)CN(C(=O)[C@H]1C[C@@](C)(O)C1)C2]

The title compound was prepared in a manner analogous to Example 7 using 1-bromo-2-methyl-4-(trifluoromethoxy)benzene instead of 1-bromo-2-methyl-3-(trifluoromethyl)benzene in Step A. MS (ESI): mass calcd. for C$_{21}$H$_{26}$F$_3$NO$_3$, 397.2; m/z found, 398.1 [M+H]$^+$. $^1$H NMR (400 MHz, CDCl$_3$) δ 7.19 (t, J=8.0 Hz, 1H), 7.05-6.93 (m, 2H), 4.10-3.77 (m, 5H), 3.35-3.19 (m, 1H), 2.73-2.66 (m, 1H), 2.44-2.21 (m, 8H), 2.18-1.96 (m, 3H), 1.94-1.79 (m, 1H), 1.74-1.68 (m, 1H), 1.36 (s, 3H).

Example 10

(rac)-(6-(4-Chloro-2-methylphenyl)-2-azaspiro[3.4]octan-2-yl)((1s,3s)-3-hydroxy-3-methylcyclobutyl)methanone

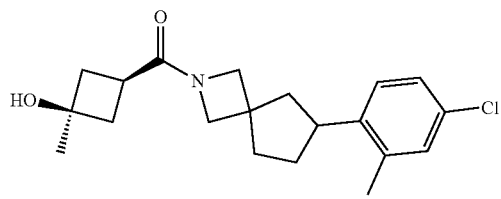 [SMILES: Cc1cc(Cl)ccc1C1CCC2(C1)CN(C(=O)[C@H]1C[C@@](C)(O)C1)C2]

The title compound was prepared in a manner analogous to Example 7 using 1-bromo-4-chloro-2-methylbenzene instead of 1-bromo-2-methyl-3-(trifluoromethyl)benzene in Step A. MS (ESI): mass calcd. for $C_{20}H_{26}ClNO_2$, 347.2; m/z found, 348.0 [M+H]$^+$. $^1$H NMR (400 MHz, CDCl$_3$) δ 7.16-7.05 (m, 3H), 4.02 (d, J=6.4 Hz, 1H), 3.98 (s, 1H), 3.95 (d, J=1.6 Hz, 1H), 3.90 (s, 1H), 3.87-3.67 (m, 1H), 3.30-3.16 (m, 1H), 2.73-2.63 (m, 1H), 2.36-2.24 (m, 7H), 2.15-1.94 (m, 3H), 1.89-1.76 (m, 1H), 1.73-1.63 (m, 2H), 1.35 (s, 3H).

Example 11

(rac)-(6-(3-Chloro-2-methylphenyl)-2-azaspiro[3.4]octan-2-yl)((1s,3s)-3-hydroxy-3-methylcyclobutyl)methanone

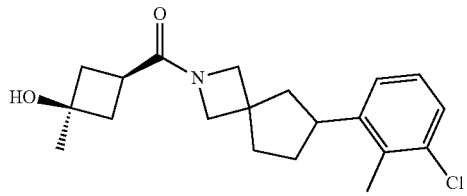 [SMILES: Cc1c(Cl)cccc1C1CCC2(C1)CN(C(=O)[C@H]1C[C@@](C)(O)C1)C2]

The title compound was prepared in a manner analogous to Example 7 using 1-bromo-3-chloro-2-methylbenzene instead of 1-bromo-2-methyl-3-(trifluoromethyl)benzene in Step A. MS (ESI): mass calcd. for $C_{20}H_{26}ClNO_2$, 347.2; m/z found, 348.1 [M+H]$^+$. $^1$H NMR (400 MHz, CDCl$_3$) δ 7.25-7.21 (m, 1H), 7.13-7.07 (m, 2H), 4.03-3.98 (m, 2H), 3.95 (d, J=1.6 Hz, 1H), 3.91 (s, 1H), 3.80 (br s, 1H), 3.39-3.25 (m, 1H), 2.73-2.64 (m, 1H), 2.38 (d, J=2.4 Hz, 3H), 2.34-2.23 (m, 5H), 2.17-1.95 (m, 3H), 1.92-1.80 (m, 1H), 1.75-1.63 (m, 1H), 1.35 (s, 3H).

Example 12

(rac)-(6-(4-(Difluoromethyl)-3-methylphenyl)-2-azaspiro[3.4]octan-2-yl)((1s,3s)-3-hydroxy-3-methylcyclobutyl)methanone

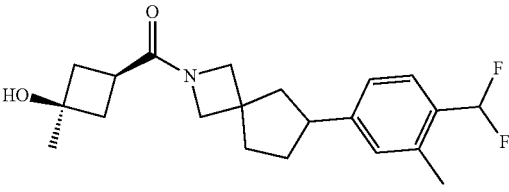 [SMILES: Cc1cc(C2CCC3(C2)CN(C(=O)[C@H]2C[C@@](C)(O)C2)C3)ccc1C(F)F]

The title compound was prepared in a manner analogous to Example 7 using 1-bromo-3-methyl-4-(difluoromethyl)benzene instead of 1-bromo-2-methyl-3-(trifluoromethyl)benzene in Step A. MS (ESI): mass calcd. for $C_{21}H_{27}F_2NO_2$, 363.2; m/z found, 364.3 [M+H]$^+$. $^1$H NMR (400 MHz, CDCl$_3$) δ 7.43 (d, J=7.6 Hz, 1H), 7.10 (d, J=8.0 Hz, 1H), 7.06 (s, 1H), 6.89-6.57 (t, J=55.6 Hz, 1H), 4.05-3.80 (m, 5H), 3.19-3.01 (m, 1H), 2.76-2.64 (m, 1H), 2.42 (s, 3H), 2.38-2.23 (m, 5H), 2.21-1.83 (m, 4H), 1.80-1.68 (m, 1H), 1.36 (s, 3H).

Example 13

(rac)-((1s,3s)-3-Hydroxy-3-methylcyclobutyl)(6-(3-methoxy-2-methylphenyl)-2-azaspiro[3.4]octan-2-yl)methanone

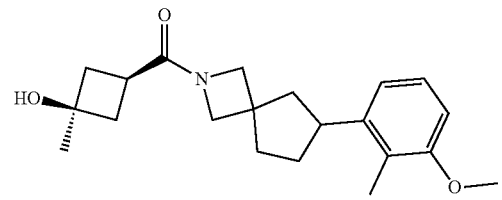 [SMILES: COc1cccc(C2CCC3(C2)CN(C(=O)[C@H]2C[C@@](C)(O)C2)C3)c1C]

The title compound was prepared in a manner analogous to Example 7 using 1-bromo-3-methoxy-2-methylbenzene instead of 1-bromo-2-methyl-3-(trifluoromethyl)benzene in Step A. MS (ESI): mass calcd. for $C_{21}H_{29}NO_3$, 343.2; m/z found, 344.2 [M+H]$^+$. $^1$H NMR (400 MHz, CDCl$_3$) δ 7.18-7.11 (m, 1H), 6.86-6.80 (m, 1H), 6.73 (d, J=8.0 Hz, 1H), 4.01 (d, J=3.2 Hz, 1H), 3.98 (s, 1H), 3.95 (s, 1H), 3.91 (s, 1H), 3.86 (br s, 1H), 3.82 (s, 3H), 3.39-3.25 (m, 1H), 2.74-2.65 (m, 1H), 2.36-2.21 (m, 5H), 2.19 (d, J=1.2 Hz, 3H), 2.15-1.80 (m, 4H), 1.76-1.67 (m, 1H), 1.35 (s, 3H).

Example 14

(rac)-(6-(2,4-Dimethylphenyl)-2-azaspiro[3.4]octan-2-yl)((1s,3s)-3-hydroxy-3-methylcyclobutyl)methanone

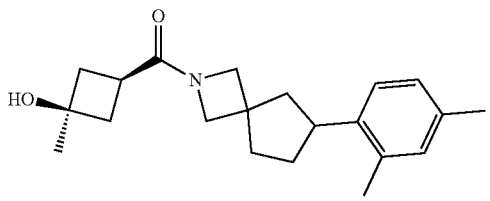 [SMILES: Cc1ccc(C2CCC3(C2)CN(C(=O)[C@H]2C[C@@](C)(O)C2)C3)c(C)c1]

The title compound was prepared in a manner analogous to Example 7 (Steps A, B, and C only) using 1-bromo-2,4-dimethylbenzene instead of 1-bromo-2-methyl-3-(trifluoromethyl)benzene in Step A. MS (ESI): mass calcd. for $C_{21}H_{29}NO_2$, 327.2; m/z found, 328.1 [M+H]+. 1H NMR (400 MHz, CDCl3) δ 7.11-7.05 (m, 1H), 7.01-6.95 (m, 2H), 4.05-3.86 (m, 5H), 3.32-3.18 (m, 1H), 2.73-2.65 (m, 1H), 2.34-2.24 (m, 11H), 2.12-1.94 (m, 3H), 1.92-1.79 (m, 1H), 1.73-1.66 (m, 1H), 1.35 (s, 3H).

Example 15

(rac)-(6-(4-Chloro-3-ethylphenyl)-2-azaspiro[3.4]octan-2-yl)((1s,3s)-3-hydroxy-3-methylcyclobutyl)methanone

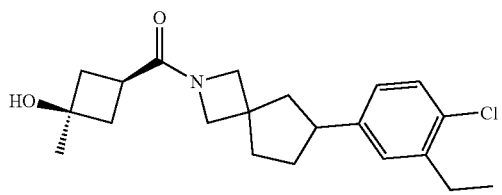 [SMILES: CCc1cc(C2CCC3(C2)CN(C(=O)[C@H]2C[C@@](C)(O)C2)C3)ccc1Cl]

The title compound was prepared in a manner analogous to Example 7 (Steps A, B, and C only) using 1-bromo-4-chloro-3-ethylbenzene instead of 1-bromo-2-methyl-3-(trifluoromethyl)benzene in Step A. MS (ESI): mass calcd. for $C_{21}H_{28}ClNO_2$, 361.2; m/z found, 362.1 [M+H]+. 1H NMR (400 MHz, CDCl3) δ 7.26-7.24 (m, 1H), 7.07-7.04 (m, 1H), 6.96 (d, J=8.4 Hz, 1H), 4.04-3.89 (m, 5H), 3.14-2.99 (m, 1H), 2.78-2.67 (m, 3H), 2.37-2.22 (m, 6H), 2.19-1.95 (m, 3H), 1.93-1.81 (m, 1H), 1.36 (s, 3H), 1.25-1.20 (m, 3H).

Example 16

(rac)-(6-(2,3-Dihydro-1H-inden-5-yl)-2-azaspiro[3.4]octan-2-yl)((1s,3s)-3-hydroxy-3-methylcyclobutyl)methanone

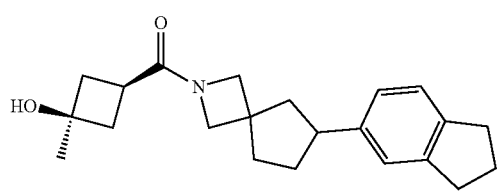 [SMILES: C[C@]1(O)C[C@@H](C(=O)N2CC3(CCC(c4ccc5c(c4)CCC5)C3)C2)C1]

The title compound was prepared in a manner analogous to Example 7 (Steps A, B, and C only) using 5-bromo-2,3-dihydro-1H-indene instead of 1-bromo-2-methyl-3-(trifluoromethyl)benzene in Step A. MS (ESI): mass calcd. for $C_{22}H_{29}NO_2$, 339.2; m/z found, 340.1 [M+H]+. 1H NMR (400 MHz, CDCl3) δ 7.16 (d, J=7.6 Hz, 1H), 7.09 (s, 1H), 6.98 (d, J=7.6 Hz, 1H), 4.03 (s, 1H), 3.99-3.87 (m, 4H), 3.15-3.00 (m, 1H), 2.89 (dt, J=3.2, 7.2 Hz, 4H), 2.74-2.65 (m, 1H), 2.36-2.23 (m, 5H), 2.16-1.73 (m, 7H), 1.36 (s, 3H).

Example 17

(rac)-((1s,3s)-3-Hydroxy-3-methylcyclobutyl)(6-(3-methoxy-4-methylphenyl)-2-azaspiro[3.4]octan-2-yl)methanone

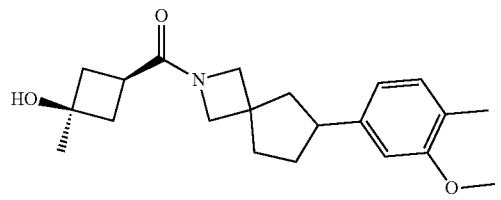 [SMILES: COc1cc(C2CCC3(C2)CN(C(=O)[C@H]2C[C@@](C)(O)C2)C3)ccc1C]

The title compound was prepared in a manner analogous to Example 7 (Steps A, B, and C only) using 4-bromo-2-methoxy-1-methylbenzene instead of 1-bromo-2-methyl-3-(trifluoromethyl)benzene in Step A. MS (ESI): mass calcd. for $C_{21}H_{29}NO_3$, 343.2; m/z found, 344.2 [M+H]+. 1H NMR (400 MHz, CDCl3) δ 7.05 (d, J=6.0 Hz, 1H), 6.70 (d, J=7.6 Hz, 1H), 6.66 (d, J=4.0 Hz, 1H), 4.02 (s, 1H), 3.99-3.95 (m, 2H), 3.90 (d, J=3.6 Hz, 1H), 3.82 (d, J=1.2 Hz, 4H), 3.13-3.02 (m, 1H), 2.74-2.64 (m, 1H), 2.35-2.28 (m, 3H), 2.27-2.22 (m, 2H), 2.18 (s, 3H), 2.13-1.83 (m, 4H), 1.79-1.66 (m, 1H), 1.35 (s, 3H).

Example 18

((1s,3*S)-3-Hydroxy-3-methylcyclobutyl)((*R)-6-(3-methoxy-4-methylphenyl)-2-azaspiro[3.4]octan-2-yl)methanone

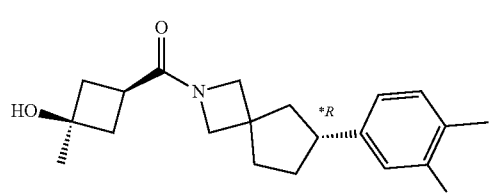

The title compound was prepared via separation of (rac)-((1s,3s)-3-hydroxy-3-methylcyclobutyl)(6-(3-methoxy-4-methylphenyl)-2-azaspiro[3.4]octan-2-yl)methanone (Example 17) by supercritical fluid chromatography (SFC) (Stationary phase: AD-H (2×25 cm); Mobile phase: 20% IPA/CO2; Rt=3.17 min). MS (ESI): mass calcd. for $C_{21}H_{29}NO_3$, 343.2; m/z found, 344.2 [M+H]+. 1H NMR (500 MHz, Chloroform-d) δ 7.07-7.02 (m, 1H), 6.73-6.67 (m, 1H), 6.65 (dd, J=4.9, 1.6 Hz, 1H), 4.06 (d, J=7.3 Hz, 1H), 4.03-3.93 (m, 3H), 3.93-3.86 (m, 1H), 3.82 (d, J=1.4

Hz, 3H), 3.15-2.99 (m, 1H), 2.66 (p, J=7.4 Hz, 1H), 2.35-2.25 (m, 5H), 2.18 (s, 3H), 2.16-1.86 (m, 4H), 1.79-1.67 (m, 1H), 1.35 (s, 3H).

Example 19

((1s,3*R)-3-Hydroxy-3-methylcyclobutyl)((*S)-6-(3-methoxy-4-methylphenyl)-2-azaspiro[3.4]octan-2-yl)methanone

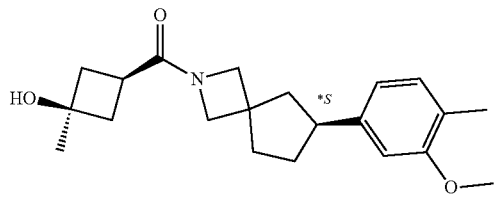 [SMILES: COc1cc([C@H]2CCC3(C2)CN(C(=O)[C@H]2C[C@@](C)(O)C2)C3)ccc1C]

The title compound was prepared via separation of (rac)-((1s,3s)-3-hydroxy-3-methylcyclobutyl)(6-(3-methoxy-4-methylphenyl)-2-azaspiro[3.4]octan-2-yl)methanone (Example 17) by SFC (Stationary phase: AD-H (2×25 cm); Mobile phase: 20% IPA/CO$_2$; Rt=3.51 min). MS (ESI): mass calcd. for C$_{21}$H$_{29}$NO$_3$, 343.2; m/z found, 344.3 [M+H]$^+$. $^1$H NMR (500 MHz, Chloroform-d) δ 7.08-7.02 (m, 1H), 6.72-6.67 (m, 1H), 6.65 (dd, J=4.9, 1.6 Hz, 1H), 4.09-3.93 (m, 4H), 3.93-3.86 (m, 1H), 3.82 (d, J=1.4 Hz, 3H), 3.15-3.00 (m, 1H), 2.70-2.62 (m, 1H), 2.35-2.24 (m, 5H), 2.18 (s, 3H), 2.16-1.84 (m, 4H), 1.78-1.66 (m, 1H), 1.35 (s, 3H).

Example 20

(6-(3-Cyclopropylphenyl)-2-azaspiro[3.3]heptan-2-yl)((1s,3s)-3-hydroxy-3-methylcyclobutyl)methanone

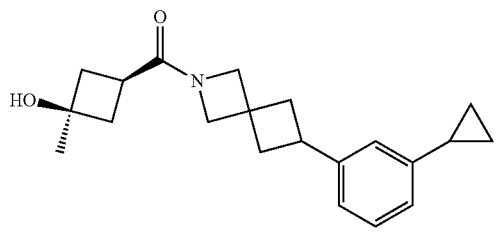 [SMILES: C[C@]1(O)C[C@@H](C(=O)N2CC3(CC(c4cccc(C5CC5)c4)C3)C2)C1]

The title compound was prepared in a manner analogous to Example 7 (Steps A, B, and C only) using tert-butyl 6-oxo-2-azaspiro[3.3]heptane-2-carboxylate instead of tert-butyl 6-oxo-2-azaspiro[3.4]octane-2-carboxylate and 1-bromo-3-cyclopropylbenzene instead of 1-bromo-2-methyl-3-(trifluoromethyl)benzene in Step A. MS (ESI): mass calcd. for C$_{21}$H$_{27}$NO$_2$, 325.2; m/z found, 326.2 [M+H]$^+$. $^1$H NMR (400 MHz, DMSO-d$_6$) δ 7.22-7.08 (m, 1H), 6.96 (d, J=7.6 Hz, 1H), 6.91 (br s, 1H), 6.85 (d, J=7.6 Hz, 1H), 5.02 (br s, 1H), 4.17 (s, 1H), 3.95 (d, J=2.0 Hz, 2H), 3.74 (s, 1H), 3.34-3.24 (m, 2H), 2.60-2.51 (m, 2H), 2.27-2.16 (m, 2H), 2.08 (br s, 2H), 2.03-1.93 (m, 2H), 1.92-1.83 (m, 1H), 1.23 (d, J=6.4 Hz, 3H), 0.98-0.84 (m, 2H), 0.70-0.57 (m, 2H).

Example 21

((1s,3s)-3-Hydroxy-3-methylcyclobutyl)(6-(2-methyl-3-(trifluoromethyl)phenyl)-2-azaspiro[3.3]heptan-2-yl)methanone

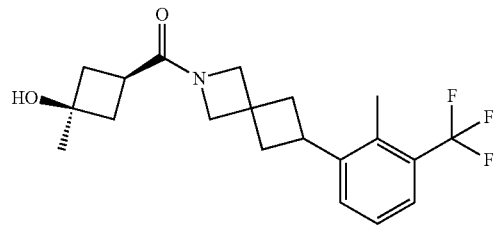 [SMILES: Cc1c(C2CC3(C2)CN(C(=O)[C@H]2C[C@@](C)(O)C2)C3)cccc1C(F)(F)F]

The title compound was prepared in a manner analogous to Example 7 using tert-butyl 6-oxo-2-azaspiro[3.3]heptane-2-carboxylate instead of tert-butyl 6-oxo-2-azaspiro[3.4]octane-2-carboxylate in Step A. MS (ESI): mass calcd. for C$_{20}$H$_{24}$F$_3$NO$_2$, 367.2; m/z found, 368.1 [M+H]$^+$. $^1$H NMR (400 MHz, CDCl$_3$) δ 7.50 (d, J=7.6 Hz, 1H), 7.35-7.30 (m, 1H), 7.29-7.26 (m, 1H), 4.28 (s, 1H), 4.19 (s, 1H), 4.00 (s, 1H), 3.93 (s, 1H), 3.87 (br s, 1H), 3.64-3.48 (m, 1H), 2.75-2.60 (m, 3H), 2.38-2.21 (m, 9H), 1.35 (d, J=6.0 Hz, 3H).

Example 22

(7-(3-Chloro-4-methylphenyl)-2-azaspiro[3.5]nonan-2-yl)((1s,3s)-3-hydroxy-3-methylcyclobutyl)methanone

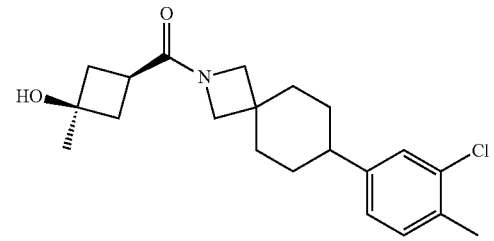 [SMILES: Cc1ccc(C2CCC3(CC2)CN(C(=O)[C@H]2C[C@@](C)(O)C2)C3)cc1Cl]

The title compound was prepared in a manner analogous to Example 7 (Steps A, B, and C only) using tert-butyl-7-oxo-2-azaspiro[3.5]nonane-2-carboxylate instead of tert-butyl 6-oxo-2-azaspiro[3.4]octane-2-carboxylate and 2-chloro-4-iodotoluene instead of 1-bromo-2-methyl-3-(trifluoromethyl)benzene in Step A. MS (ESI): mass calcd. for C$_{21}$H$_{28}$ClNO$_2$, 361.2; m/z found, 362.1 [M+H]$^+$. $^1$H NMR (400 MHz, CDCl$_3$) δ 7.14 (d, J=7.3 Hz, 2H), 6.96 (dd, J=7.8, 1.5 Hz, 1H), 3.83 (br s, 2H), 3.76 (s, 1H), 3.73 (s, 1H), 3.68 (s, 1H), 2.77-2.63 (m, 1H), 2.49-2.21 (m, 8H), 1.99 (d, J=12.6 Hz, 2H), 1.91-1.79 (m, 2H), 1.63-1.53 (m, 2H), 1.47-1.29 (m, 5H).

Example 23

((1s,3s)-3-Hydroxy-3-methylcyclobutyl)(6-(4-methyl-3-(trifluoromethoxy)phenyl)-2-azaspiro[3.3]heptan-2-yl)methanone

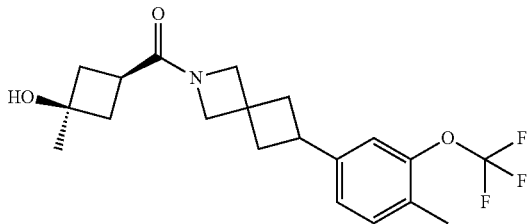 [SMILES: Cc1ccc(C2CC3(C2)CN(C(=O)[C@H]2C[C@@](C)(O)C2)C3)cc1OC(F)(F)F]

Step A: tert-Butyl 6-(4-bromo-3-(trifluoromethoxy)phenyl)-6-hydroxy-2-azaspiro[3.3]heptane-2-carboxylate. Isopropylmagnesium lithium chloride (1.3M in THF, 0.95 mL, 1.23 mmol) was added dropwise to a −78° C. solution of 1-bromo-4-iodo-2-(trifluoromethoxy)benzene (417 mg, 1.14 mmol) in THF (5 mL). The resultant mixture was stirred at −78° C. for 1 hour then treated with a solution of tert-butyl 6-oxo-2-azaspiro[3.3]heptane-2-carboxylate (200 mg, 0.947 mmol) in THF (5 mL). The reaction mixture was stirred for 2 hours. The reaction mixture was quenched with sat. $NH_4Cl$ and extracted with EtOAc. The combined organic extracts were washed with brine, dried over $Na_2SO_4$, filtered, and concentrated under reduced pressure. The resulting residue was purified by FCC ($SiO_2$, 0-50% EtOAc in ether) to afford the title compound (216 mg, 48%) as a white solid. MS (ESI): mass calcd. for $C_{18}H_{21}BrF_3NO_4$, 451.1; m/z found, 395.8 [M+2H-tBu]$^+$. $^1$H NMR (400 MHz, CDCl$_3$) δ 7.64 (d, J=8.4 Hz, 1H), 7.36 (d, J=1.6 Hz, 1H), 7.23-7.21 (m, 1H), 4.10 (s, 2H), 3.86 (s, 2H), 3.30 (s, 1H), 2.74-2.68 (m, 2H), 2.60-2.54 (m, 2H), 1.44 (s, 9H).

Step B: tert-Butyl 6-hydroxy-6-(4-methyl-3-(trifluoromethoxy)phenyl)-2-azaspiro[3.3]heptane-2-carboxylate. tert-Butyl 6-(4-bromo-3-(trifluoromethoxy)phenyl)-6-hydroxy-2-azaspiro[3.3]heptane-2-carboxylate (160 mg, 0.354 mmol), 2,4,6-trimethyl-1,3,5,2,4,6-trioxatriborinane (50% in THF, 355 mg, 1.42 mmol) and $K_2CO_3$ (147 mg, 1.06 mmol) were dissolved in 1,4-dioxane (5 mL) and $H_2O$ (0.5 mL). The resultant mixture was sparged with $N_2$ for 5 minutes and then treated with Pd(dppf)Cl$_2$·CH$_2$Cl$_2$ (29 mg, 0.035 mmol). The mixture was sparged with $N_2$ for another 5 minutes and then stirred while heating at 120° C. for 48 hours. The reaction mixture was concentrated under reduced pressure. The resulting residue was purified by FCC ($SiO_2$, 0-25% EtOAc in ether) to afford the title compound (140 mg, 94%) as a white solid. MS (ESI): mass calcd. for $C_{19}H_{24}F_3NO_4$, 387.2; m/z found, 332.1 [M+2H-tBu]$^+$. $^1$H NMR (400 MHz, CDCl$_3$) δ 7.26-7.20 (m, 3H), 4.08 (s, 2H), 3.83 (s, 2H), 2.76-2.70 (m, 2H), 2.59-2.52 (m, 2H), 2.32 (s, 3H), 1.44 (s, 9H).

Step C: 6-(4-Methyl-3-(trifluoromethoxy)phenyl)-2-azaspiro[3.3]heptane. tert-Butyl 6-hydroxy-6-(4-methyl-3-(trifluoromethoxy)phenyl)-2-azaspiro[3.3]heptane-2-carboxylate (140 mg, 0.332 mmol) and TFA (5 mL) were combined. The resultant mixture was stirred for 20 min before treating with TES (116 mg, 0.996 mmol) and stirring for 2 hours. The reaction mixture was concentrated under reduced pressure to afford the title compound (125 mg, 98%) as brown oil, which was used in the next step without further purification. MS (ESI): mass calcd. for $C_{14}H_{16}F_3NO$, 271.1; m/z found, 272.1 [M+H]$^+$.

Step D: ((1s,3s)-3-Hydroxy-3-methylcyclobutyl)(6-(4-methyl-3-(trifluoromethoxy)phenyl)-2-azaspiro[3.3]heptan-2-yl)methanone. HATU (140 mg, 0.369 mmol) was added to a solution of (1s,3s)-3-hydroxy-3-methylcyclobutanecarboxylic acid (40 mg, 0.307 mmol), 6-(4-methyl-3-(trifluoromethoxy)phenyl)-2-azaspiro[3.3]heptane (125 mg, crude) and DIPEA (0.25 mL, 1.54 mmol) in DMF (10 mL). The resultant mixture was stirred at rt overnight. The reaction mixture was diluted with EtOAc and $H_2O$ and extracted with EtOAc. The combined organic extracts were washed with brine, dried over $Na_2SO_4$, filtered, and concentrated under reduced pressure. The resulting residue was purified by preparative HPLC (Waters Xbridge BEH C18, 100 mm×30 mm×10 μm column, 35% to 75% (v/v) CH$_3$CN and H$_2$O with 0.05% NH$_3$) to afford the title compound (31 mg, 26%) as a white solid. MS (ESI): mass calcd. for $C_{20}H_{24}F_3NO_3$, 383.2; m/z found, 384.1 [M+H]$^+$. $^1$H NMR (400 MHz, CDCl$_3$) δ 7.18 (d, J=7.6 Hz, 1H), 7.03-6.96 (m, 2H), 4.23 (s, 1H), 4.15 (s, 1H), 4.01 (s, 1H), 3.94 (s, 1H), 3.86 (br s, 1H), 3.48-3.33 (m, 1H), 2.73-2.56 (m, 3H), 2.37-2.22 (m, 9H), 1.36 (d, J=4.8 Hz, 3H).

Example 24

(rac)-(6-(3-Cyclopropyl-2-fluorophenyl)-2-azaspiro[3.4]octan-2-yl)((1s,3s)-3-hydroxy-3-methylcyclobutyl)methanone

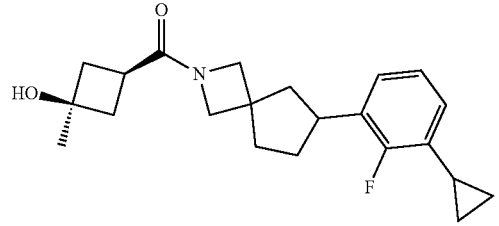 [SMILES: C[C@]1(O)C[C@@H](C(=O)N2CC3(CCC(c4cccc(C5CC5)c4F)C3)C2)C1]

Step A: (rac)-tert-Butyl 6-(3-bromo-2-fluorophenyl)-6-hydroxy-2-azaspiro[3.4]octane-2-carboxylate. n-BuLi (0.85 mL, 2.5M in hexane, 2.13 mmol) was added to a solution of 1,3-dibromo-2-fluorobenzene (443 mg, 2.13 mmol) in anhydrous THF (5 mL). The resultant mixture was stirred at −78° C. for 30 minutes before tert-butyl 6-oxo-2-azaspiro[3.3]heptane-2-carboxylate (300 mg, 1.42 mmol) in anhydrous THF (5 mL) was added. The resultant mixture was stirred at −78° C. for 2 h. The reaction mixture was quenched with sat. NH$_4$Cl and extracted with EtOAc. The combined organic extracts were washed with brine, dried over Na$_2$SO$_4$, filtered, and concentrated under reduced pressure. The resulting residue was purified by FCC (SiO$_2$, 0-50% EtOAc in ether) to afford the title compound (300 mg, 47%) as a colorless oil. MS (ESI): mass calcd. for $C_{18}H_{23}BrFNO_3$, 399.1; m/z found, 343.8 [M+2H-tBu]$^+$.

Step B: (rac)-tert-Butyl 6-(3-cyclopropyl-2-fluorophenyl)-6-hydroxy-2-azaspiro[3.4]octane-2-carboxylate. A mixture of tert-butyl 6-(3-bromo-2-fluorophenyl)-6-hydroxy-2-azaspiro[3.4]octane-2-carboxylate (300 mg, 0.749 mmol), cyclopropylboronic acid (129 mg, 1.50 mmol), potassium phosphate (477 mg, 2.25 mmol), CataCXium® A Pd G3 (54.6 mg, 0.075 mmol), toluene (5 mL), and H$_2$O (2 mL) was heated to 90° C. and stirred overnight. The reaction mixture was concentrated under reduced pressure and purified by FCC (SiO$_2$, 0-50% EtOAc in ether) to afford the title compound (196 mg, 73%) as a light-yellow oil. MS (ESI): mass calcd. for C$_{21}$H$_{28}$FNO$_3$, 361.2; m/z found, 288.0 [M-tBu-OH]$^+$.

Step C: (rac)-6-(3-Cyclopropyl-2-fluorophenyl)-2-azaspiro[3.4]oct-5-ene. tert-Butyl 6-(3-cyclopropyl-2-fluorophenyl)-6-hydroxy-2-azaspiro[3.4]octane-2-carboxylate (196 mg, 0.225 mmol) and TFA (4 mL) were stirred for 20 min before treating with TES (78 mg, 0.675 mmol) and stirring for another 2 hours. The reaction mixture was concentrated under reduced pressure to afford the crude product (196 mg) as brown oil, which was used in the next step without further purification.

Step D: (rac)-(6-(3-Cyclopropyl-2-fluorophenyl)-2-azaspiro[3.4]oct-5-en-2-yl)((1s,3s)-3-hydroxy-3-methylcyclobutyl)methanone. HATU (233 mg, 0.614 mmol) was added to a solution of (1s,3s)-3-hydroxy-3-methylcyclobutanecarboxylic acid (53 mg, 0.409 mmol), 6-(3-cyclopropyl-2-fluorophenyl)-2-azaspiro[3.4]oct-5-ene (190 mg, 0.610 mmol) and DIPEA (0.34 mL, 2.04 mmol) in DMF (6 mL). The resultant mixture was stirred at rt overnight. The reaction mixture was diluted with EtOAc, quenched with sat. NH$_4$Cl, and extracted with EtOAc. The combined organic extracts were washed with brine, dried over Na$_2$SO$_4$, filtered, and concentrated under reduced pressure. The resulting residue was purified by FCC (SiO$_2$, 0-10% MeOH in DCM) to afford the title compound (200 mg, 25%) as a colorless oil. MS (ESI): mass calcd. for C$_{22}$H$_{26}$FNO$_2$, 355.2; m/z found, 356.2 [M+H]$^+$.

Step E: (rac)-(6-(3-Cyclopropyl-2-fluorophenyl)-2-azaspiro[3.4]octan-2-yl)((1s,3s)-3-hydroxy-3-methylcyclobutyl)methanone. A mixture of (6-(3-cyclopropyl-2-fluorophenyl)-2-azaspiro[3.4]oct-5-en-2-yl)((1s,3s)-3-hydroxy-3-methylcyclobutyl)methanone (300 mg, 1.00 mmol), PtO$_2$ (22.8 mg, 0.100 mmol), and EtOAc (10 mL) was purged with H$_2$ and stirred at room temperature under H$_2$ (15 psi) for 1 h. The suspension was filtered through a pad of Celite® and the pad washed with EtOAc. The filtrate was concentrated under reduced pressure. The resulting residue was purified by preparative HPLC (Boston Prime C18, 150 mm×30 mm×5 μm column, 51% to 81% (v/v) CH$_3$CN and H$_2$O with 0.05% NH$_3$) to afford the title compound (50 mg, 24%) as a white solid. MS (ESI): mass calcd. for C$_{22}$H$_{28}$FNO$_2$, 357.2; m/z found, 358.2 [M+H]$^+$. $^1$H NMR (400 MHz, CDCl$_3$) δ 7.03-6.92 (m, 2H), 6.79-6.69 (m, 1H), 4.14 (d, J=8.4 Hz, 1H), 4.03 (s, 1H), 3.99 (d, J=4.4 Hz, 1H), 3.97-3.94 (m, 1H), 3.93-3.88 (m, 1H), 3.39-3.27 (m, 1H), 2.71-2.64 (m, 1H), 2.36-2.24 (m, 5H), 2.15-1.92 (m, 5H), 1.84-1.71 (m, 1H), 1.36 (s, 3H), 1.01-0.94 (m, 2H), 0.73-0.67 (m, 2H).

Example 25

((*R)-6-(3-Cyclopropyl-2-fluorophenyl)-2-azaspiro[3.4]octan-2-yl)((1s,3*S)-3-hydroxy-3-methylcyclobutyl)methanone

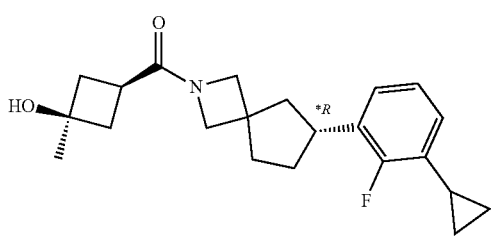 [SMILES: C[C@]1(O)C[C@@H](C(=O)N2CC3(CC[C@@H](c4cccc(C5CC5)c4F)C3)C2)C1]

The title compound was prepared via separation of (rac)-(6-(3-cyclopropyl-2-fluorophenyl)-2-azaspiro[3.4]octan-2-yl)((1s,3s)-3-hydroxy-3-methylcyclobutyl)methanone (Example 24) by SFC (Stationary phase: AD-H (3×25 cm); Mobile phase: 20% IPA/CO$_2$; Rt=6.90 min). MS (ESI): mass calcd. for C$_{22}$H$_{28}$FNO$_2$, 357.2; m/z found, 357.8 [M+H]$^+$. $^1$H NMR (500 MHz, Chloroform-d) δ 7.00-6.93 (m, 2H), 6.76-6.70 (m, 1H), 4.04-3.87 (m, 5H), 3.38-3.26 (m, 1H), 2.71-2.63 (m, 1H), 2.34-2.23 (m, 5H), 2.17-2.01 (m, 3H), 2.02-1.89 (m, 2H), 1.82-1.70 (m, 1H), 1.35 (s, 3H), 1.01-0.92 (m, 2H), 0.72-0.66 (m, 2H).

Example 26

((*S)-6-(3-Cyclopropyl-2-fluorophenyl)-2-azaspiro[3.4]octan-2-yl)((1s,3*R)-3-hydroxy-3-methylcyclobutyl)methanone

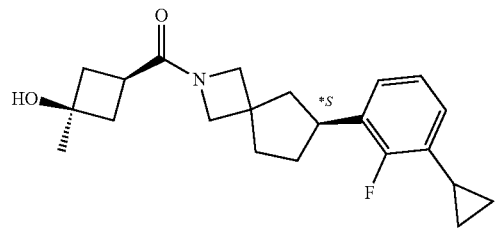 [SMILES: C[C@]1(O)C[C@@H](C(=O)N2CC3(CC[C@H](c4cccc(C5CC5)c4F)C3)C2)C1]

The title compound was prepared via separation of (rac)-(6-(3-cyclopropyl-2-fluorophenyl)-2-azaspiro[3.4]octan-2-yl)((1s,3s)-3-hydroxy-3-methylcyclobutyl)methanone (Example 24) by SFC (Stationary phase: AD-H (3×25 cm); Mobile phase: 20% IPA/CO$_2$; Rt=10.30 min). MS (ESI): mass calcd. for C$_{22}$H$_{28}$FNO$_2$, 357.2; m/z found, 357.8 [M+H]$^+$. $^1$H NMR (500 MHz, Chloroform-d) δ 7.00-6.93 (m, 2H), 6.77-6.69 (m, 1H), 4.05-3.87 (m, 5H), 3.37-3.27 (m, 1H), 2.70-2.62 (m, 1H), 2.34-2.23 (m, 5H), 2.18-2.02 (m, 3H), 2.02-1.89 (m, 2H), 1.82-1.70 (m, 1H), 1.35 (s, 3H), 1.01-0.92 (m, 2H), 0.72-0.66 (m, 2H).

Example 27

(6-(3-Cyclopropyl-4-methylphenyl)-2-azaspiro[3.3]heptan-2-yl)((1s,3s)-3-hydroxy-3-methylcyclobutyl)methanone

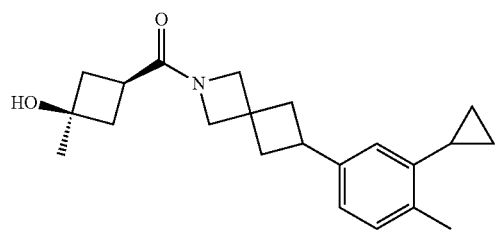 [SMILES: Cc1ccc(C2CC3(C2)CN(C(=O)[C@H]2C[C@@](C)(O)C2)C3)cc1C1CC1]

The title compound was prepared in a manner analogous to Example 24 (Steps A, B, C, and D only) using tert-butyl 6-oxo-2-azaspiro[3.3]heptane-2-carboxylate instead of tert-butyl 6-oxo-2-azaspiro[3.4]octane-2-carboxylate and 2-bromo-4-iodo-1-methylbenzene instead of 1,3-dibromo-2-fluorobenzene in Step A. MS (ESI): mass calcd. for C$_{22}$H$_{29}$NO$_2$, 339.2; m/z found, 340.2 [M+H]$^+$. $^1$H NMR (400 MHz, CDCl$_3$) δ 7.08 (d, J=7.6 Hz, 1H), 6.91 (d, J=6.8 Hz, 1H), 6.77 (s, 1H), 4.21 (s, 1H), 4.13 (s, 1H), 3.99 (s, 1H), 3.95-3.85 (m, 2H), 3.43-3.27 (m, 1H), 2.74-2.51 (m, 3H), 2.38 (s, 3H), 2.33-2.20 (m, 6H), 1.91-1.82 (m, 1H), 1.35 (d, J=4.8 Hz, 3H), 0.96-0.88 (m, 2H), 0.65-0.59 (m, 2H).

Example 28

(6-(4-Cyclopropyl-2-methylphenyl)-2-azaspiro[3.3]heptan-2-yl)((1s,3s)-3-hydroxy-3-methylcyclobutyl)methanone

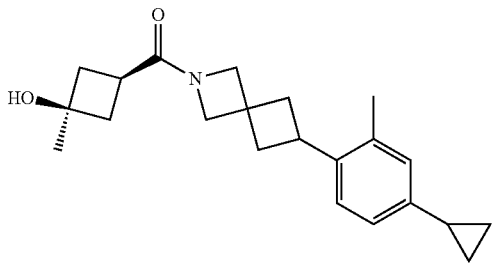 [SMILES: Cc1cc(C2CC2)ccc1C1CC2(C1)CN(C(=O)[C@H]1C[C@@](C)(O)C1)C2]

The title compound was prepared in a manner analogous to Example 24 (Steps A, B, C, and D only) using tert-butyl 6-oxo-2-azaspiro[3.3]heptane-2-carboxylate instead of tert-butyl 6-oxo-2-azaspiro[3.4]octane-2-carboxylate and 4-bromo-1-iodo-2-fluorobenzene instead of 1,3-dibromo-2-fluorobenzene in Step A. MS (ESI): mass calcd. for C$_{22}$H$_{29}$NO$_2$, 339.2; m/z found, 340.1 [M+H]$^+$. $^1$H NMR (400 MHz, CDCl$_3$) δ 7.03 (dd, J=5.6, 7.6 Hz, 1H), 6.88 (d, J=8.0 Hz, 1H), 6.84 (s, 1H), 4.24 (s, 1H), 4.15 (s, 1H), 4.05-3.96 (m, 2H), 3.91 (s, 1H), 3.55-3.40 (m, 1H), 2.73-2.53 (m, 3H), 2.34-2.22 (m, 6H), 2.19 (d, J=2.8 Hz, 3H), 1.88-1.80 (m, 1H), 1.35 (d, J=5.6 Hz, 3H), 0.95-0.88 (m, 2H), 0.65 (q, J=5.2 Hz, 2H).

Example 29

(rac)-(6-(6-(tert-Butyl)pyridin-2-yl)-2-azaspiro[3.4]octan-2-yl)((1s,3s)-3-hydroxy-3-methylcyclobutyl)methanone

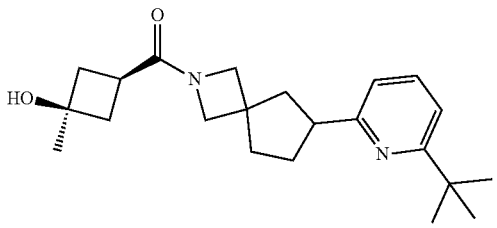

Step A: (rac)-tert-Butyl 6-(6-(tert-butyl)pyridin-2-yl)-6-hydroxy-2-azaspiro[3.4]octane-2-carboxylate. n-BuLi (2.5M in hexane, 1.15 mL, 2.89 mmol) was added dropwise to a −78° C. solution of 2-bromo-6-(tert-butyl)pyridine (570 mg, 2.66 mmol) in THF (4 mL). The resultant mixture was stirred for 2 hours before treating with a solution of tert-butyl 6-oxo-2-azaspiro[3.4]octane-2-carboxylate (500 mg, 2.22 mmol) in THF (1 mL). The reaction mixture was stirred for another 30 min before being warmed to rt and stirring overnight. The reaction mixture was diluted with EtOAc and quenched with sat. NH$_4$Cl, then extracted with EtOAc. The combined organic extracts were washed with brine, dried over Na$_2$SO$_4$, filtered, and concentrated under reduced pressure. The resulting residue was purified by FCC (SiO$_2$, 20-30% EtOAc in ether) to afford the title compound (220 mg, 25%) as colorless oil. MS (ESI): mass calcd. for C$_{21}$H$_{32}$N$_2$O$_3$, 360.2; m/z found, 361.2 [M+H]$^+$, $^1$H NMR (400 MHz, CDCl$_3$) δ 7.65 (t, J=7.6 Hz, 1H), 7.25 (d, J=7.6 Hz, 1H), 7.10 (d, J=7.6 Hz, 1H), 5.79 (br s, 1H), 4.14-4.07 (m, 1H), 3.95 (d, J=8.8 Hz, 1H), 3.92 (s, 2H), 2.41-2.30 (m, 1H), 2.28-2.18 (m, 2H), 2.15-2.00 (m, 3H), 1.46 (s, 9H), 1.38 (s, 9H).

Step B: (rac)-tert-Butyl 6-(6-(tert-butyl)pyridin-2-yl)-2-azaspiro[3.4]oct-5-ene-2-carboxylate. Burgess reagent (218 mg, 0.915 mmol) was added to a solution of tert-butyl 6-(6-(tert-butyl)pyridin-2-yl)-6-hydroxy-2-azaspiro[3.4]octane-2-carboxylate (220 mg, 0.610 mmol) in toluene (5 mL). The resultant mixture was heated to 120° C. and stirred overnight before being cooled to rt, poured into sat. NaHCO$_3$; and extracted with EtOAc. The combined organic extracts were washed with brine, dried over Na$_2$SO$_4$, filtered, and concentrated under reduced pressure. The resulting residue was purified by FCC (SiO$_2$, 0-7% EtOAc in ether) to afford the title compound (167 mg, 73%) as colorless oil. MS (ESI): mass calcd. for C$_{21}$H$_{30}$N$_2$O$_2$, 342.2; m/z found, 343.2 [M+H]$^+$. $^1$H NMR (400 MHz, CDCl$_3$) δ 7.60-7.51 (m, 1H), 7.22-7.11 (m, 2H), 6.70 (s, 1H), 4.07-3.87 (m, 4H), 3.08 (d, J=1.6 Hz, 1H), 2.87-2.81 (m, 2H), 2.33 (t, J=7.2 Hz, 1H), 1.49-1.44 (m, 9H), 1.39-1.34 (m, 9H).

Step C: (rac)-tert-Butyl 6-(6-(tert-butyl)pyridin-2-yl)-2-azaspiro[3.4]octane-2-carboxylate. A mixture of tert-butyl 6-(6-(tert-butyl)pyridin-2-yl)-2-azaspiro[3.4]oct-5-ene-2-carboxylate (160 mg, 0.428 mmol), PtO$_2$ (50 mg, 0.220 mmol), and EtOH (5 mL) was purged with H$_2$ and stirred at room-temperature under H$_2$ (15 psi) for 1 h. The mixture was filtered through a pad of Celite® and the pad washed with EtOAc. The filtrate was concentrated under reduced pressure to afford the crude product (140 mg, 70%) as colorless oil, which was used in the next step without further purification. MS (ESI): mass calcd. for C$_{21}$H$_{32}$N$_2$O$_2$, 344.3; m/z found, 345.5 [M+H]$^+$.

Step D: (rac)-6-(6-(tert-Butyl)pyridin-2-yl)-2-azaspiro[3.4]octane. A mixture of tert-butyl 6-(6-(tert-butyl)pyridin-2-yl)-2-azaspiro[3.4]octane-2-carboxylate (130 mg, 0.377 mmol), TFA (0.8 mL), and DCM (4 mL) was stirred at rt for 1 hour. The reaction mixture was concentrated under reduced pressure to afford the crude product (130 mg) as light-yellow oil, which was used in the next step without further purification. MS (ESI): mass calcd. for C$_{16}$H$_{24}$N$_2$, 244.2; m/z found, 245.2 [M+H]$^+$.

Step E: (rac)-(6-(6-(tert-Butyl)pyridin-2-yl)-2-azaspiro[3.4]octan-2-yl)((1s,3s)-3-hydroxy-3-methylcyclobutyl)methanone. HATU (129 mg, 0.338 mmol) was added to a solution of (1s,3s)-3-hydroxy-3-methylcyclobutanecarboxylic acid (40 mg, 0.307 mmol), 6-(6-(tert-butyl)pyridin-2-yl)-2-azaspiro[3.4]octane (130 mg, 0.363 mmol) and DIPEA (0.25 mL, 1.54 mmol) in DMF (5 mL). The resultant mixture was stirred at rt overnight. The reaction mixture was diluted with EtOAc, quenched with sat. NH$_4$Cl, and extracted with EtOAc. The combined organic extracts were washed with brine, dried over Na$_2$SO$_4$, filtered, and concentrated under reduced pressure. The resulting residue was purified by preparative HPLC (Boston Green ODS 150×30 mm×5 µm column, 30% to 60% (v/v) CH$_3$CN and H$_2$O with 0.225% HCOOH) to afford the title compound (37 mg, 34%) as a yellow syrupy solid. MS (ESI): mass calcd. for $C_{22}H_{32}N_2O_2$, 356.2; m/z found, 357.2 [M+H]$^+$. $^1$H NMR (400 MHz, MeOD) δ 7.57 (br s, 1H), 7.34-6.89 (m, 2H), 4.19-3.86 (m, 4H), 2.75-2.63 (m, 1H), 2.36-1.85 (m, 11H), 1.36 (d, J=2.4 Hz, 12H).

Example 30

((1s,3s)-3-Hydroxy-3-methylcyclobutyl)(6-(isoquinolin-7-yl)-2-azaspiro[3.3]heptan-2-yl)methanone

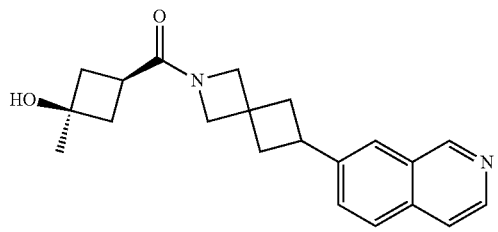 [SMILES: C[C@]1(O)C[C@@H](C(=O)N2CC3(CC(c4ccc5ccncc5c4)C3)C2)C1]

The title compound was prepared in a manner analogous to Example 29 using tert-butyl 6-oxo-2-azaspiro[3.3]heptane-2-carboxylate instead of tert-butyl 6-oxo-2-azaspiro[3.4]octane-2-carboxylate and 7-bromoisoquinoline instead of 2-bromo-6-(tert-butyl)pyridine in Step A. MS (ESI): mass calcd. for $C_{21}H_{24}N_2O_2$, 336.2; m/z found, 337.2 [M+H]$^+$. $^1$H NMR (400 MHz, CDCl$_3$) δ 9.22 (s, 1H), 8.51 (d, J=5.2 Hz, 1H), 7.79 (d, J=8.4 Hz, 1H), 7.72 (s, 1H), 7.63 (d, J=5.6 Hz, 1H), 7.54 (d, J=8.0 Hz, 1H), 4.29 (s, 1H), 4.21 (s, 1H), 4.05 (s, 1H), 3.99 (s, 1H), 3.82 (br s, 1H), 3.64 (td, J=8.8, 18.0 Hz, 1H), 2.81-2.62 (m, 3H), 2.51-2.26 (m, 6H), 1.37 (d, J=7.2 Hz, 3H).

Example 31

((1s,3s)-3-Hydroxy-3-methylcyclobutyl)(6-(isoquinolin-6-yl)-2-azaspiro[3.3]heptan-2-yl)methanone

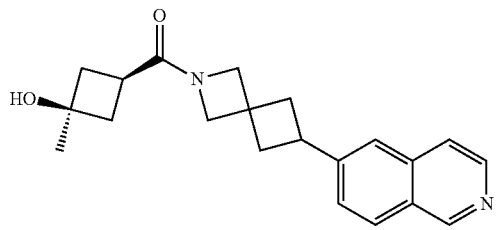 [SMILES: C[C@]1(O)C[C@@H](C(=O)N2CC3(CC(c4ccc5cnccc5c4)C3)C2)C1]

The title compound was prepared in a manner analogous to Example 29 using tert-butyl 6-oxo-2-azaspiro[3.3]heptane-2-carboxylate instead of tert-butyl 6-oxo-2-azaspiro[3.4]octane-2-carboxylate and 6-bromoisoquinoline instead of 2-bromo-6-(tert-butyl)pyridine in Step A. MS (ESI): mass calcd. for $C_{21}H_{24}N_2O_2$, 336.2; m/z found, 337.1 [M+H]$^+$. $^1$H NMR (400 MHz, CDCl$_3$) δ 9.23 (s, 1H), 8.52 (d, J=5.6 Hz, 1H), 7.94 (d, J=8.8 Hz, 1H), 7.61 (d, J=5.6 Hz, 1H), 7.57 (s, 1H), 7.44 (dd, J=1.6, 8.8 Hz, 1H), 4.29 (s, 1H), 4.21 (s, 1H), 4.05 (s, 1H), 3.99 (s, 1H), 3.83-3.56 (m, 2H), 2.80-2.63 (m, 3H), 2.53-2.39 (m, 2H), 2.39-2.21 (m, 4H), 1.37 (d, J=6.8 Hz, 3H).

Example 32

((1s,3s)-3-Hydroxy-3-methylcyclobutyl)(6-(3-(pyrrolidin-1-yl)phenyl)-2-azaspiro[3.3]heptan-2-yl)methanone

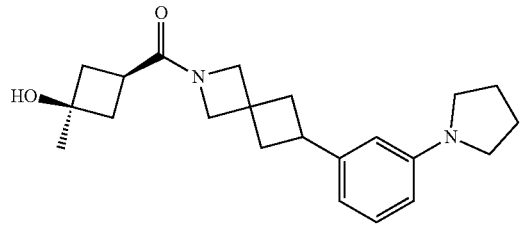 [SMILES: C[C@]1(O)C[C@@H](C(=O)N2CC3(CC(c4cccc(N5CCCC5)c4)C3)C2)C1]

The title compound was prepared in a manner analogous to Example 29 using tert-butyl 6-oxo-2-azaspiro[3.3]heptane-2-carboxylate instead of tert-butyl 6-oxo-2-azaspiro[3.4]octane-2-carboxylate and 1-(3-bromophenyl)pyrrolidine instead of 2-bromo-6-(tert-butyl)pyridine in Step A. MS (ESI): mass calcd. for $C_{22}H_{30}N_2O_2$, 354.2; m/z found, 355.3 [M+H]$^+$. $^1$H NMR (400 MHz, CDCl$_3$) δ 7.21-7.13 (m, 1H), 6.48 (d, J=7.2 Hz, 1H), 6.42 (d, J=8.0 Hz, 1H), 6.33 (br s, 1H), 4.21 (s, 1H), 4.14 (s, 1H), 4.00 (s, 1H), 3.94 (s, 1H), 3.91 (br s, 1H), 3.46-3.32 (m, 1H), 3.32-3.23 (m, 4H), 2.74-2.53 (m, 3H), 2.39-2.20 (m, 6H), 2.05-1.95 (m, 4H), 1.35 (d, J=5.2 Hz, 3H).

Example 33

((1s,3s)-3-Hydroxy-3-methylcyclobutyl)(6-(3-methyl-4-(trifluoromethyl)phenyl)-2-azaspiro[3.3]heptan-2-yl)methanone

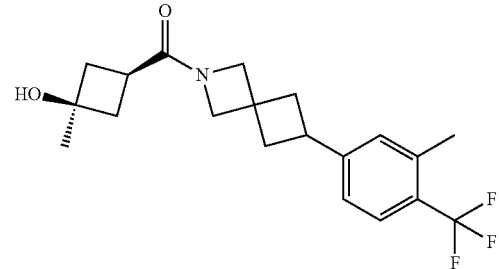 [SMILES: Cc1cc(C2CC3(C2)CN(C(=O)[C@H]2C[C@@](C)(O)C2)C3)ccc1C(F)(F)F]

The title compound was prepared in a manner analogous to Example 29 using tert-butyl 6-oxo-2-azaspiro[3.3]heptane-2-carboxylate instead of tert-butyl 6-oxo-2-azaspiro[3.4]octane-2-carboxylate and 4-bromo-2-methyl-1-(trifluoromethyl)benzene instead of 2-bromo-6-(tert-butyl)pyridine in Step A. MS (ESI): mass calcd. for $C_{20}H_{24}F_3NO_2$, 367.2; m/z found, 368.1 [M+H]$^+$. $^1$H NMR (400 MHz, CDCl$_3$) δ 7.54 (d, J=8.4 Hz, 1H), 7.08-7.04 (m, 2H), 4.24 (s, 1H), 4.16 (s, 1H), 4.02 (s, 1H), 3.95 (s, 1H), 3.51-3.37 (m, 1H), 2.72-2.59 (m, 3H), 2.47 (s, 3H), 2.38-2.23 (m, 6H), 1.36 (d, J=5.2 Hz, 3H).

Example 34

(6-(6-(tert-Butyl)pyridin-2-yl)-2-azaspiro[3.3]heptan-2-yl)((1s,3s)-3-hydroxy-3-methylcyclobutyl)methanone

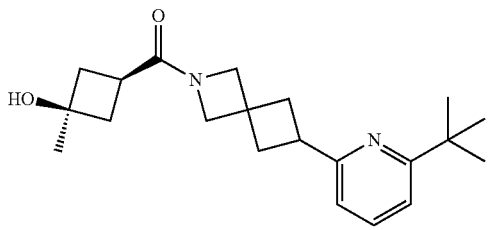 [SMILES: CC(C)(C)c1cccc(C2CC3(C2)CN(C(=O)[C@H]2C[C@@](C)(O)C2)C3)n1]

The title compound was prepared in a manner analogous to Example 29 using tert-butyl 6-oxo-2-azaspiro[3.3]heptane-2-carboxylate instead of tert-butyl 6-oxo-2-azaspiro[3.4]octane-2-carboxylate in Step A. MS (ESI): mass calcd. for $C_{11}H_{30}N_2O_2$, 342.2; m/z found, 343.1 [M+H]+. 1H NMR (400 MHz, MeOD) δ 7.54 (t, J=7.6 Hz, 1H), 7.19 (d, J=7.6 Hz, 1H), 6.94 (d, J=7.6 Hz, 1H), 4.25 (s, 1H), 4.14 (s, 1H), 4.07 (s, 1H), 3.96 (s, 1H), 3.54-3.45 (m, 1H), 2.73-2.48 (m, 5H), 2.29-2.12 (m, 4H), 1.35 (d, J=1.2 Hz, 12H).

Example 35

(rac)-((1s,3s)-3-Hydroxy-3-methylcyclobutyl)(6-(4-isopropylphenyl)-2-azaspiro[3.4]octan-2-yl)methanone

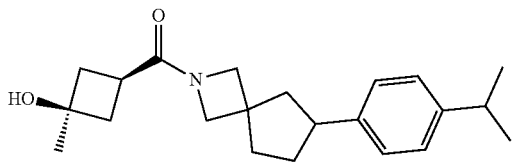 [SMILES: CC(C)c1ccc(C2CCC3(C2)CN(C(=O)[C@H]2C[C@@](C)(O)C2)C3)cc1]

Step A: (rac)-tert-Butyl 6-hydroxy-6-(4-isopropylphenyl)-2-azaspiro[3.4]octane-2-carboxylate. In an oven-dried flask under $N_2$, 2-Boc-6-oxo-2-azaspiro[3.4]octane (100 mg, 0.444 mmol) was taken up in anhydrous THF (2.2 mL) and cooled to −78° C. 4-Isopropylphenylmagnesium bromide (0.5M in THF, 1.3 mL) was added dropwise. This was allowed to warm to rt and stirred 2 h before being quenched with sat. aq. NH4Cl and extracted with EtOAc. The combined organic layers were dried over Na2SO4, filtered, and concentrated under reduced pressure. Purification via FCC (SiO2, 0-100% EtOAc in hexane) provided the title compound (54 mg, 35% yield). MS (ESI): mass calcd. for $C_{21}H_{31}NO_3$, 345.2; m/z found, 272.1 [M-tBu-OH+H]+.

Step B: (rac)-6-(4-Isopropylphenyl)-2-azaspiro[3.4]octane trifluoroacetate. tert-Butyl 6-hydroxy-6-(4-isopropylphenyl)-2-azaspiro[3.4]octane-2-carboxylate (54 mg, 0.156 mmol) was taken up in TFA (0.5 mL) and stirred for 5 min at rt. TES (76 μL) was added and this was stirred for 1 h at rt before concentrating under reduced pressure. The title compound was used without further purification in the next step. MS (ESI): mass calcd. for $C_{16}H_{23}N$, 229.2; m/z found, 230.2 [M+H]+.

Step C: (rac)-((1s,3s)-3-Hydroxy-3-methylcyclobutyl)(6-(4-isopropylphenyl)-2-azaspiro[3.4]octan-2-yl)methanone. 6-(4-Isopropylphenyl)-2-azaspiro[3.4]octane trifluoroacetate (20 mg, 0.058 mmol) and (1s,3s)-3-hydroxy-3-methylcyclobutane-1-carboxylic acid (8 mg, 0.064 mmol) were taken up in DMF (0.6 mL). DIPEA (30 μL, 0.175 mmol) and HATU (27 mg, 0.070 mmol) were added and the reaction was stirred at rt for 3 h. The reaction mixture was filtered through a PTFE filter with MeOH and purified via reverse phase (RP) HPLC (5-95% MeCN in 20 mM NH4OH in water) to afford the title compound (19 mg, 95% yield). MS (ESI): mass calcd. for $C_{22}H_{31}NO_2$, 341.2; m/z found, 342.2 [M+H]+. 1H NMR (400 MHz, Chloroform-d) δ 7.16 (d, J=8.3 Hz, 2H), 7.12 (d, J=8.3 Hz, 2H), 4.05-3.85 (m, 4H), 3.16-2.98 (m, 1H), 2.88 (kept, J=6.9 Hz, 1H), 2.71-2.61 (m, 1H), 2.35-2.23 (m, 5H), 2.19-1.82 (m, 4H), 1.80-1.63 (m, 1H), 1.35 (s, 3H), 1.24 (d, J=6.9 Hz, 6H).

Example 36

((1s,3s)-3-Hydroxy-3-methylcyclobutyl)(2-(3-isopropylphenyl)-6-azaspiro[3.4]octan-6-yl)methanone

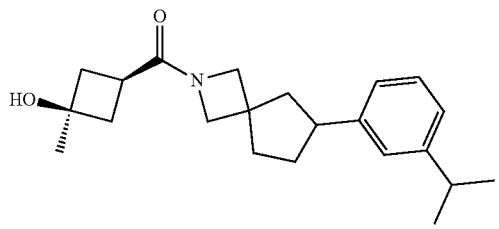 [SMILES: CC(C)c1cccc(C2CCC3(C2)CN(C(=O)[C@H]2C[C@@](C)(O)C2)C3)c1]

The title compound was prepared in a manner analogous to Example 35 using tert-butyl 2-oxo-6-azaspiro[3.4]octane-6-carboxylate instead of 2-Boc-6-oxo-2-azaspiro[3.4]octane and 3-isopropylphenylmagnesium bromide instead of 4-isopropylphenylmagnesium bromide in Step A. MS (ESI): mass calcd. for $C_{22}H_{31}NO_2$, 341.2; m/z found, 342.3 [M+H]+. 1H NMR (400 MHz, Chloroform-d) δ 7.23 (dd, J=7.7, 3.7 Hz, 1H), 7.10-7.05 (m, 1H), 7.03 (t, J=5.2 Hz, 2H), 3.68-3.27 (m, 5H), 2.94-2.70 (m, 2H), 2.45-2.26 (m, 6H), 2.26-2.08 (m, 3H), 2.08-1.80 (m, 2H), 1.37 (d, J=4.5 Hz, 3H), 1.25 (dd, J=6.9, 1.6 Hz, 6H).

Example 37

((1s,3s)-3-Hydroxy-3-methylcyclobutyl)(7-phenyl-2-azaspiro[3.5]nonan-2-yl)methanone

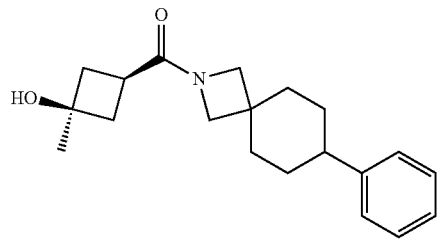

The title compound was prepared in a manner analogous to Example 35 using tert-butyl 7-oxo-2-azaspiro[3.5]nonane-2-carboxylate instead of 2-Boc-6-oxo-2-azaspiro

[3.4]octane and phenylmagnesium bromide instead of 4-isopropylphenylmagnesium bromide in Step A. MS (ESI): mass calcd. for $C_{20}H_{27}NO_2$, 313.2; m/z found, 314.2 [M+H]$^+$. $^1$H NMR (400 MHz, methanol-$d_4$) δ 7.31-7.06 (m, 5H), 3.93 (s, 1H), 3.80 (s, 1H), 3.74 (s, 1H), 3.61 (s, 1H), 2.70 (m, 1H), 2.55-2.41 (m, 1H), 2.31-2.13 (m, 4H), 2.05-1.94 (m, 2H), 1.81 (d, J=13.9 Hz, 2H), 1.65 (m, 2H), 1.58-1.42 (m, 2H), 1.36 (d, J=4.6 Hz, 3H).

Example 38

(rac)-(2-(3-(tert-Butyl)phenyl)-8-azaspiro[4.5]decan-8-yl)((1s,3s)-3-hydroxy-3-methylcyclobutyl)methanone

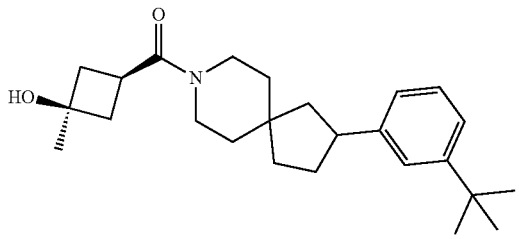 [SMILES: CC(C)(C)c1cccc(C2CCC3(CCN(C(=O)[C@H]4C[C@@](C)(O)C4)CC3)C2)c1]

The title compound was prepared in a manner analogous to Example 35 using tert-butyl 2-oxo-8-azaspiro[4.5]decane-8-carboxylate instead of 2-Boc-6-oxo-2-azaspiro[3.4]octane and 3-tert-butylphenylmagnesium bromide instead of 4-isopropylphenylmagnesium bromide in Step A. MS (ESI): mass calcd. for $C_{25}H_{37}NO_2$, 383.3; m/z found, 384.3 [M+H]$^+$. $^1$H NMR (400 MHz, Chloroform-d) δ 7.27-7.19 (m, 3H), 7.09-7.02 (m, 1H), 3.67-3.50 (m, 2H), 3.44-3.28 (m, 2H), 3.23-3.08 (m, 1H), 2.96-2.82 (m, 1H), 2.57 (s, 1H), 2.40-2.25 (m, 4H), 2.17-2.00 (m, 2H), 1.82-1.69 (m, 2H), 1.69-1.45 (m, 6H), 1.39 (s, 3H), 1.32 (s, 9H).

Example 39

(rac)-(2-(4-(tert-Butyl)phenyl)-8-azaspiro[4.5]decan-8-yl)((1s,3s)-3-hydroxy-3-methylcyclobutyl)methanone

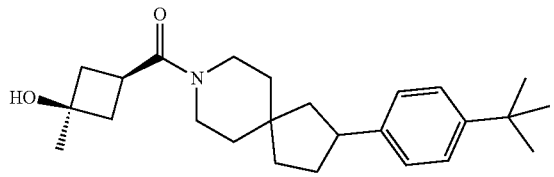 [SMILES: CC(C)(C)c1ccc(C2CCC3(CCN(C(=O)[C@H]4C[C@@](C)(O)C4)CC3)C2)cc1]

The title compound was prepared in a manner analogous to Example 35 using tert-butyl 2-oxo-8-azaspiro[4.5]decane-8-carboxylate instead of 2-Boc-6-oxo-2-azaspiro[3.4]octane and 4-tert-butylphenylmagnesium bromide instead of 4-isopropylphenylmagnesium bromide in Step A. MS (ESI): mass calcd. for $C_{25}H_{37}NO_2$, 383.3; m/z found, 384.3 [M+H]$^+$. $^1$H NMR (400 MHz, Chloroform-d) δ 7.34-7.29 (m, 2H), 7.19-7.14 (m, 2H), 3.66-3.50 (m, 2H), 3.40-3.28 (m, 2H), 3.18-3.06 (m, 1H), 2.96-2.82 (m, 1H), 2.56 (s, 1H), 2.39-2.25 (m, 4H), 2.15-1.97 (m, 2H), 1.82-1.65 (m, 2H), 1.66-1.45 (m, 6H), 1.39 (s, 3H), 1.31 (s, 9H).

Example 40

(rac)-((1s,3s)-3-Hydroxy-3-methylcyclobutyl)(6-(3-(trifluoromethoxy)phenyl)-2-azaspiro[3.4]octan-2-yl)methanone

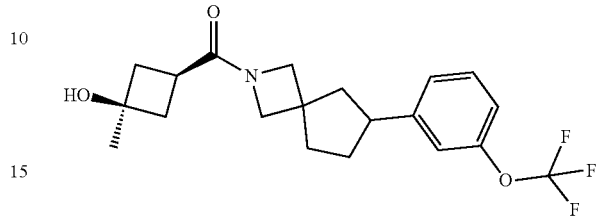

Step A: (rac)-tert-Butyl 6-(3-(trifluoromethoxy)phenyl)-2-azaspiro[3.4]octane-2-carboxylate. Potassium carbonate (132 mg, 0.953 mmol) and 3-(trifluoromethoxy)phenylboronic acid (200 mg, 0.953 mmol) were taken up in 1,4-dioxane (1.3 mL). To this was added tert-butyl 6-(2-tosyl-hydrazineylidene)-2-azaspiro[3.4]octane-2-carboxylate (Intermediate 5, 250 mg, 0.635 mmol) and the reaction was stirred at 110° C. for 10 h. The reaction was cooled to rt, and brine was added. The organic components were extracted with DCM. Purification via FCC (SiO$_2$, 0-20% EtOAc in hexanes) provided the title compound (122 mg, 52% yield). MS (ESI): mass calcd. for $C_{19}H_{24}F_3NO_3$ 371.2; m/z found, 316.1 [M+2H-tBu]$^+$.

Step B: (rac)-6-(3-(Trifluoromethoxy)phenyl)-2-azaspiro[3.4]octane hydrochloride. To tert-butyl 6-(3-(trifluoromethoxy)phenyl)-2-azaspiro[3.4]octane-2-carboxylate (122 mg, 0.328 mmol) in MeOH (0.3 mL) was added HCl in 1,4-dioxane (4M, 0.7 mL). This was heated to 45° C. for 1 hour before cooling and concentrating under reduced pressure. The title compound was used without further purification in the next step. MS (ESI): mass calcd. for $C_{14}H_{16}F_3NO$ 271.2; m/z found, 272.2 [M+H]$^+$.

Step C: (rac)-((1s,3s)-3-Hydroxy-3-methylcyclobutyl)(6-(3-(trifluoromethoxy)phenyl)-2-azaspiro[3.4]octan-2-yl)methanone. 6-(3-(Trifluoromethoxy)phenyl)-2-azaspiro[3.4]octane hydrochloride was taken up in DMF (1.6 mL) and to this was added (1s,3s)-3-hydroxy-3-methylcyclobutane-1-carboxylic acid (47 mg, 0.345 mmol), DIPEA (0.17 mL, 0.985 mmol), and HATU (141 mg, 0.361 mmol). This was stirred at rt for 16 hours. The reaction mixture was filtered through a PTFE filter with MeOH and purified via RP HPLC (5-95% ACN in 20 mM NH$_4$OH in water) to afford the title compound (84 mg, 67% yield). MS (ESI): mass calcd. for $C_{20}H_{24}F_3NO_3$, 383.2; m/z found, 384.2 [M+H]$^+$. $^1$H NMR (400 MHz, Chloroform-d) δ 7.31 (t, J=7.9 Hz, 1H), 7.14-7.09 (m, 1H), 7.07-7.01 (m, 2H), 3.96 (t, J=21.8 Hz, 4H), 3.11 (s, 1H), 2.85 (s, 1H), 2.65 (p, J=7.4 Hz, 1H), 2.29 (d, J=7.4 Hz, 5H), 2.22-2.10 (m, 1H), 2.10-1.94 (m, 2H), 1.94-1.78 (m, 1H), 1.71 (p, J=9.3 Hz, 2H), 1.35 (s, 3H).

Example 41

((1s,3*S)-3-Hydroxy-3-methylcyclobutyl)((*R)-6-
(3-(trifluoromethoxy)phenyl)-2-azaspiro[3.4]octan-
2-yl)methanone

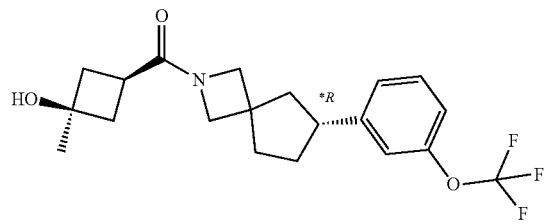 [SMILES: C[C@]1(O)C[C@@H](C(=O)N2CC3(CC[C@@H](c4cccc(OC(F)(F)F)c4)C3)C2)C1]

The title compound was prepared via separation of (rac)-((1s,3s)-3-hydroxy-3-methylcyclobutyl)(6-(3-(trifluoromethoxy)phenyl)-2-azaspiro[3.4]octan-2-yl)methanone (Example 40) by SFC (Stationary phase: AD-H (2×15 cm); Mobile phase: 45% MeOH/CO$_2$; Rt=1.69 min). MS (ESI): mass calcd. for C$_{20}$H$_{24}$F$_3$NO$_3$, 383.2; m/z found, 384.2 [M+H]$^+$. $^1$H NMR (400 MHz, Chloroform-d) δ 7.30 (t, J=7.9 Hz, 1H), 7.11 (dd, J=8.0, 1.4 Hz, 1H), 7.07-7.00 (m, 2H), 4.13 (s, 1H), 4.04-3.85 (m, 4H), 3.19-3.02 (m, 1H), 2.69-2.58 (m, 1H), 2.38-2.23 (m, 5H), 2.23-1.93 (m, 3H), 1.87 (td, J=13.4, 10.4 Hz, 1H), 1.78-1.63 (m, 1H), 1.35 (s, 3H).

Example 42

((1s,3*R)-3-Hydroxy-3-methylcyclobutyl)((*S)-6-
(3-(trifluoromethoxy)phenyl)-2-azaspiro[3.4]octan-
2-yl)methanone

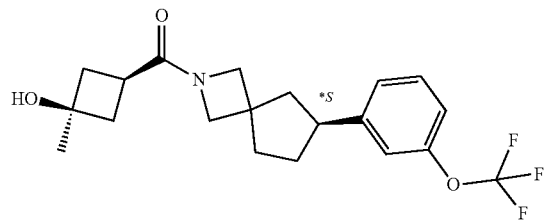 [SMILES: C[C@]1(O)C[C@@H](C(=O)N2CC3(CC[C@H](c4cccc(OC(F)(F)F)c4)C3)C2)C1]

The title compound was prepared via separation of (rac)-((1s,3s)-3-hydroxy-3-methylcyclobutyl)(6-(3-(trifluoromethoxy)phenyl)-2-azaspiro[3.4]octan-2-yl)methanone (Example 40) by SFC (Stationary phase: AD-H (2×15 cm); Mobile phase: 45% MeOH/CO$_2$; Rt=4.73 min). MS (ESI): mass calcd. for C$_{20}$H$_{24}$F$_3$NO$_3$, 383.2; m/z found, 384.2 [M+H]$^+$. $^1$H NMR (400 MHz, Chloroform-d) δ 7.30 (t, J=7.9 Hz, 1H), 7.14-7.09 (m, 1H), 7.07-7.00 (m, 2H), 4.22 (s, 1H), 4.05-3.84 (m, 4H), 3.19-3.02 (m, 1H), 2.68-2.58 (m, 1H), 2.37-2.22 (m, 5H), 2.22-1.93 (m, 3H), 1.87 (td, J=13.4, 10.5 Hz, 1H), 1.78-1.63 (m, 1H), 1.35 (s, 3H).

Example 43

(rac)-(6-(3-(tert-Butyl)phenyl)-2-azaspiro[3.4]octan-
2-yl)((1s,3s)-3-hydroxy-3-methylcyclobutyl)metha-
none

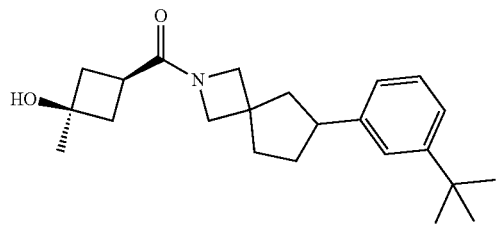 [SMILES: CC(C)(C)c1cccc(C2CCC3(C2)CN(C(=O)[C@H]2C[C@@](C)(O)C2)C3)c1]

The title compound was prepared in a manner analogous to Example 40 using (3-(tert-butyl)phenyl)boronic acid instead of 3-(trifluoromethoxy)phenylboronic acid in Step A. MS (ESI): mass calcd. for C$_{23}$H$_{33}$NO$_2$, 355.3; m/z found, 356.3 [M+H]$^+$. $^1$H NMR (400 MHz, Chloroform-d) δ 7.25-7.22 (m, 2H), 7.21 (s, 1H), 7.05-6.99 (m, 1H), 4.06-3.86 (m, 5H), 3.18-3.02 (m, 1H), 2.68 (tt, J=8.0, 6.5 Hz, 1H), 2.38-2.22 (m, 5H), 2.22-1.85 (m, 4H), 1.81-1.70 (m, 1H), 1.35 (s, 3H), 1.32 (d, J=1.0 Hz, 9H).

Example 44

((*R)-6-(3-(tert-Butyl)phenyl)-2-azaspiro[3.4]octan-
2-yl)((1s,3*S)-3-hydroxy-3-methylcyclobutyl)
methanone

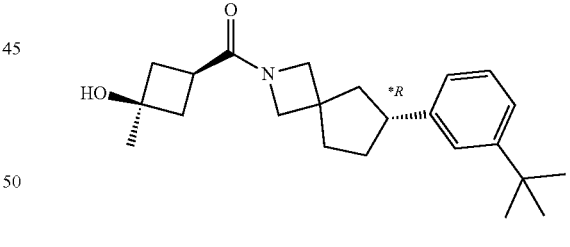

The title compound was prepared via separation of (rac)-(6-(3-(tert-butyl)phenyl)-2-azaspiro[3.4]octan-2-yl)((1s,3s)-3-hydroxy-3-methylcyclobutyl)methanone (Example 43) by SFC (Stationary phase: AD-H (3×25 cm); Mobile phase: 15% MeOH/CO$_2$; Rt=7.31 min). MS (ESI): mass calcd. for C$_{23}$H$_{33}$NO$_2$, 355.3; m/z found, 356.2 [M+H]$^+$. $^1$H NMR (500 MHz, Chloroform-d) δ 7.25-7.22 (m, 2H), 7.21 (s, 1H), 7.04-6.98 (m, 1H), 4.07-3.84 (m, 4H), 3.38-2.88 (m, 2H), 2.67 (p, J=7.4 Hz, 1H), 2.29 (d, J=7.5 Hz, 5H), 2.20-1.83 (m, 4H), 1.74 (s, 1H), 1.35 (s, 3H), 1.32 (s, 9H).

Example 45

((*S)-6-(3-(tert-Butyl)phenyl)-2-azaspiro[3.4]octan-2-yl)((1s,3*R)-3-hydroxy-3-methylcyclobutyl)methanone

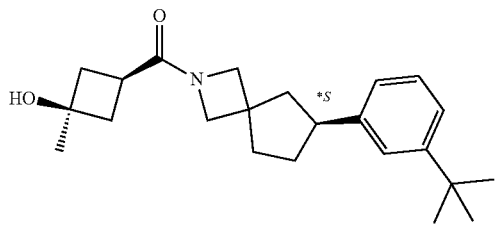 [SMILES: CC(C)(C)c1cccc([C@H]2CCC3(C2)CN(C(=O)[C@H]2C[C@@](C)(O)C2)C3)c1]

The title compound was prepared via separation of (rac)-(6-(3-(tert-butyl)phenyl)-2-azaspiro[3.4]octan-2-yl)((1s,3s)-3-hydroxy-3-methylcyclobutyl)methanone (Example 43) by SFC (Stationary phase: AD-H (3×25 cm); Mobile phase: 15% MeOH/CO$_2$; Rt=8.44 min). MS (ESI): mass calcd. for C$_{23}$H$_{33}$NO$_2$, 355.3; m/z found, 356.2 [M+H]$^+$. $^1$H NMR (500 MHz, Chloroform-d) δ 7.25-7.22 (m, 2H), 7.21 (s, 1H), 7.04-6.99 (m, 1H), 4.07-3.88 (m, 4H), 3.32-3.00 (m, 2H), 2.71-2.60 (m, 1H), 2.29 (d, J=7.5 Hz, 5H), 2.20-1.83 (m, 4H), 1.81-1.68 (m, 1H), 1.35 (s, 3H), 1.32 (s, 9H).

Example 46

(rac)-((1s,3s)-3-Hydroxy-3-methylcyclobutyl)(6-(3-isopropylphenyl)-2-azaspiro[3.4]octan-2-yl)methanone

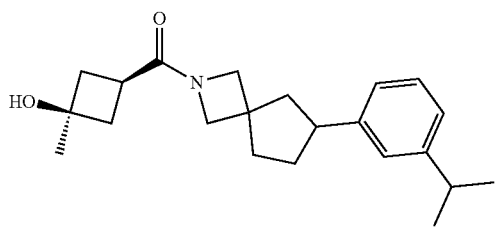 [SMILES: CC(C)c1cccc(C2CCC3(C2)CN(C(=O)[C@H]2C[C@@](C)(O)C2)C3)c1]

The title compound was prepared in a manner analogous to Example 40 using (3-isopropylphenyl)boronic acid instead of 3-(trifluoromethoxy)phenylboronic acid in Step A. MS (ESI): mass calcd. for C$_{22}$H$_{31}$NO$_2$, 341.2; m/z found, 342.2 [M+H]$^+$. $^1$H NMR (400 MHz, Chloroform-d) δ 7.23 (t, J=7.6 Hz, 1H), 7.09-6.99 (m, 3H), 3.97 (dd, J=25.7, 21.0 Hz, 4H), 3.09 (tt, J=18.4, 9.9 Hz, 1H), 2.88 (hept, J=6.9 Hz, 1H), 2.71-2.59 (m, 1H), 2.37-2.24 (m, 5H), 2.20-1.82 (m, 4H), 1.82-1.66 (m, 1H), 1.35 (s, 3H), 1.25 (d, J=6.9 Hz, 6H).

Example 47

((1s,3*S)-3-Hydroxy-3-methylcyclobutyl)((*R)-6-(3-isopropylphenyl)-2-azaspiro[3.4]octan-2-yl)methanone

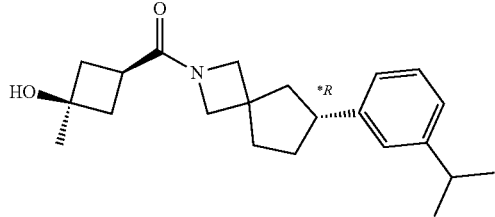 [SMILES: CC(C)c1cccc([C@@H]2CCC3(C2)CN(C(=O)[C@H]2C[C@@](C)(O)C2)C3)c1]

The title compound was prepared via separation of (rac)-((1s,3s)-3-hydroxy-3-methylcyclobutyl)(6-(3-isopropylphenyl)-2-azaspiro[3.4]octan-2-yl)methanone (Example 46) by SFC (Stationary phase: Chiralpak IA, 5 um 250×21 mm; Mobile phase: 10% MeOH:IPA (1:1) with 0.2% isopropylamine, 90% CO$_2$; Rt=15.07 min). MS (ESI): mass calcd. for C$_{22}$H$_{31}$NO$_2$, 341.2; m/z found, 342.3 [M+H]$^+$. $^1$H NMR (400 MHz, Chloroform-d) δ 7.22 (t, J=7.6 Hz, 1H), 7.12-6.95 (m, 3H), 4.30 (s, 1H), 4.14-3.80 (m, 4H), 3.08 (dt, J=17.4, 8.9 Hz, 1H), 2.88 (p, J=7.0 Hz, 1H), 2.64 (p, J=7.7 Hz, 1H), 2.41-2.21 (m, 5H), 2.21-1.82 (m, 4H), 1.74 (dq, J=14.2, 8.4 Hz, 1H), 1.35 (s, 3H), 1.24 (d, J=7.0 Hz, 6H).

Example 48

((1s,3*R)-3-Hydroxy-3-methylcyclobutyl)((*S)-6-(3-isopropylphenyl)-2-azaspiro[3.4]octan-2-yl)methanone

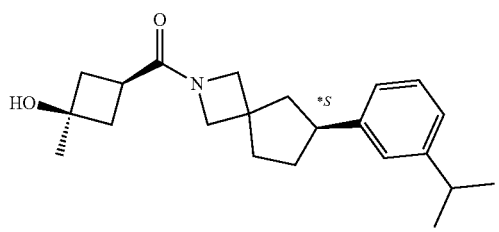 [SMILES: CC(C)c1cccc([C@H]2CCC3(C2)CN(C(=O)[C@H]2C[C@@](C)(O)C2)C3)c1]

The title compound was prepared via separation of (rac)-((1s,3s)-3-hydroxy-3-methylcyclobutyl)(6-(3-isopropylphenyl)-2-azaspiro[3.4]octan-2-yl)methanone (Example 46) by SFC (Stationary phase: Chiralpak IA, 5 um 250×21 mm; Mobile phase: 10% MeOH:IPA (1:1) with 0.2% isopropylamine, 90% CO$_2$; Rt=18.03 min). MS (ESI): mass calcd. for C$_{22}$H$_{31}$NO$_2$, 341.2; m/z found, 342.3 [M+H]$^+$. $^1$H NMR (400 MHz, Chloroform-d) δ 7.23 (t, J=8.1 Hz, 1H), 7.14-6.94 (m, 3H), 4.26-3.66 (m, 4H), 3.09 (dp, J=17.9, 9.0 Hz, 1H), 2.88 (p, J=7.0 Hz, 1H), 2.66 (p, J=7.5 Hz, 1H), 2.30 (t, J=6.8 Hz, 5H), 2.21-1.82 (m, 4H), 1.82-1.65 (m, 1H), 1.35 (s, 3H), 1.25 (d, J=7.0 Hz, 6H).

Example 49

(rac)-(6-(4-Cyclopropylphenyl)-2-azaspiro[3.4]oc-tan-2-yl)((1s,3s)-3-hydroxy-3-methylcyclobutyl)methanone

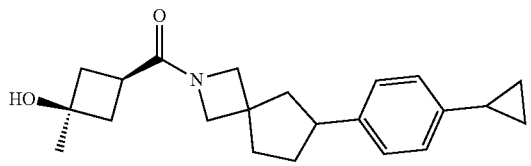 [SMILES: C[C@]1(O)C[C@@H](C(=O)N2CC3(CCC(c4ccc(C5CC5)cc4)C3)C2)C1]

The title compound was prepared in a manner analogous to Example 40 using (4-cyclopropylphenyl)boronic acid instead of 3-(trifluoromethoxy)phenylboronic acid in Step A. MS (ESI): mass calcd. for C₂₂H₂₉NO₂, 339.2; m/z found, 340.3 [M+H]⁺. ¹H NMR (400 MHz, Chloroform-d) δ 7.11-7.05 (m, 2H), 7.03-6.98 (m, 2H), 3.95 (d, J=20.5 Hz, 4H), 3.06 (dt, J=14.5, 7.3 Hz, 1H), 2.67 (tt, J=7.9, 6.7 Hz, 1H), 2.52 (s, 1H), 2.35-2.21 (m, 5H), 2.16-1.91 (m, 3H), 1.86 (tt, J=8.4, 5.0 Hz, 2H), 1.76-1.64 (m, 1H), 1.35 (s, 3H), 0.97-0.90 (m, 2H), 0.68-0.61 (m, 2H).

Example 50

((S)-6-(4-Cyclopropylphenyl)-2-azaspiro[3.4]octan-2-yl)((1s,3R)-3-hydroxy-3-methylcyclobutyl)methanone

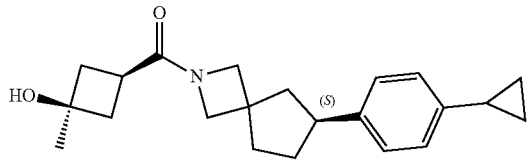

The title compound was prepared via separation of (rac)-(6-(4-cyclopropylphenyl)-2-azaspiro[3.4]octan-2-yl)((1s,3s)-3-hydroxy-3-methylcyclobutyl)methanone (Example 49) by SFC (Stationary phase: Lux-3 Cellulose Sum 250×21 mm; Mobile phase: 10% MeOH/CO₂; Rt=11.04 min). MS (ESI): mass calcd. for C₂₂H₂₉NO₂, 339.2; m/z found, 340.2 [M+H]⁺. ¹H NMR (500 MHz, Chloroform-d) δ 7.08 (dd, J=8.1, 1.5 Hz, 2H), 7.01 (dd, J=8.2, 1.1 Hz, 2H), 4.00 (s, 1H), 3.99-3.92 (m, 3H), 3.92-3.83 (m, 1H), 3.13-2.99 (m, 1H), 2.71-2.62 (m, 1H), 2.34-2.19 (m, 5H), 2.16-1.92 (m, 3H), 1.92-1.81 (m, 2H), 1.75-1.64 (m, 1H), 1.35 (s, 3H), 0.96-0.90 (m, 2H), 0.66 (dt, J=6.5, 4.6 Hz, 2H).

Example 51

((R)-6-(4-Cyclopropylphenyl)-2-azaspiro[3.4]octan-2-yl)((1s,3S)-3-hydroxy-3-methylcyclobutyl)methanone

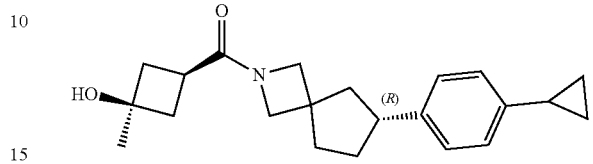

The title compound was prepared via separation of (rac)-(6-(4-cyclopropylphenyl)-2-azaspiro[3.4]octan-2-yl)((1s,3s)-3-hydroxy-3-methylcyclobutyl)methanone (Example 49) by SFC (Stationary phase: Lux-3 Cellulose Sum 250×21 mm; Mobile phase: 10% MeOH/CO₂; Rt=11.93 min). MS (ESI): mass calcd. for C₂₂H₂₉NO₂, 339.2; m/z found, 340.3 [M+H]⁺. ¹H NMR (500 MHz, Chloroform-d) δ 7.08 (dd, J=8.1, 1.5 Hz, 2H), 7.01 (dd, J=8.2, 1.1 Hz, 2H), 4.00 (s, 1H), 3.99-3.92 (m, 2H), 3.92-3.85 (m, 1H), 3.13-2.99 (m, 1H), 2.67 (tt, J=8.1, 6.5 Hz, 1H), 2.34-2.22 (m, 5H), 2.17-1.91 (m, 3H), 1.91-1.81 (m, 2H), 1.80-1.62 (m, 1H), 1.35 (s, 3H), 0.97-0.89 (m, 2H), 0.66 (dt, J=6.5, 4.6 Hz, 2H).

Example 52

(rac)-((1s,3s)-3-Hydroxy-3-methylcyclobutyl)(6-(4-(trifluoromethoxy)phenyl)-2-azaspiro[3.4]octan-2-yl)methanone

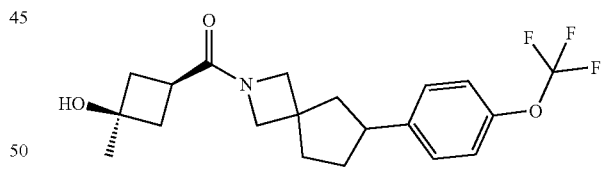

The title compound was prepared in a manner analogous to Example 40 using (4-(trifluoromethoxy)phenyl)boronic acid instead of 3-(trifluoromethoxy)phenylboronic acid in Step A. MS (ESI): mass calcd. for C₂₀H₂₄F₃NO₃, 383.2; m/z found, 384.2 [M+H]⁺. ¹H NMR (400 MHz, Chloroform-d) δ 7.23-7.17 (m, 2H), 7.17-7.09 (m, 2H), 4.07-3.85 (m, 4H), 3.18-3.02 (m, 1H), 2.65 (p, J=7.5 Hz, 1H), 2.37-2.24 (m, 5H), 2.21-1.94 (m, 3H), 1.93-1.79 (m, 1H), 1.76-1.62 (m, 1H), 1.35 (s, 3H).

Example 53

((1s,3*S)-3-Hydroxy-3-methylcyclobutyl)((*R)-6-(4-(trifluoromethoxy)phenyl)-2-azaspiro[3.4]octan-2-yl)methanone

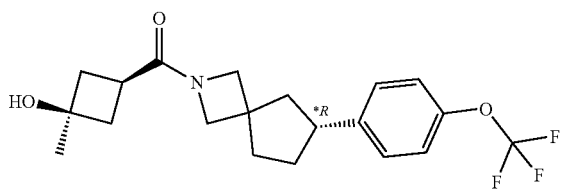 [SMILES: C[C@]1(O)C[C@@H](C(=O)N2CC3(CC[C@@H](c4ccc(OC(F)(F)F)cc4)C3)C2)C1]

The title compound was prepared via separation of (rac)-((1s,3s)-3-hydroxy-3-methylcyclobutyl)(6-(4-(trifluoromethoxy)phenyl)-2-azaspiro[3.4]octan-2-yl)methanone (Example 52) by SFC (Stationary phase: AD-H 2×25 cm; Mobile phase: 15% EtOH/CO$_2$; Rt=6.97 min). MS (ESI): mass calcd. for C$_{20}$H$_{24}$F$_3$NO$_3$, 383.2; m/z found, 384.2 [M+H]$^+$. $^1$H NMR (400 MHz, Chloroform-d) δ 7.20 (d, J=8.5 Hz, 2H), 7.17-7.10 (m, 2H), 4.06-3.85 (m, 5H), 3.20-3.01 (m, 1H), 2.71-2.62 (m, 1H), 2.38-2.22 (m, 5H), 2.22-1.92 (m, 3H), 1.94-1.79 (m, 1H), 1.77-1.63 (m, 1H), 1.35 (s, 3H).

Example 54

((1s,3*R)-3-Hydroxy-3-methylcyclobutyl)((*S)-6-(4-(trifluoromethoxy)phenyl)-2-azaspiro[3.4]octan-2-yl)methanone

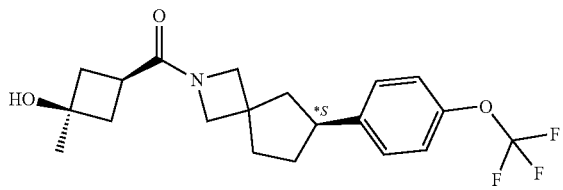 [SMILES: C[C@]1(O)C[C@@H](C(=O)N2CC3(CC[C@H](c4ccc(OC(F)(F)F)cc4)C3)C2)C1]

The title compound was prepared via separation of (rac)-((1s,3s)-3-hydroxy-3-methylcyclobutyl)(6-(4-(trifluoromethoxy)phenyl)-2-azaspiro[3.4]octan-2-yl)methanone (Example 52) by SFC (Stationary phase: AD-H 2×25 cm; Mobile phase: 15% EtOH/CO$_2$; Rt=8.71 min). MS (ESI): mass calcd. for C$_{20}$H$_{24}$F$_3$NO$_3$, 383.2; m/z found, 384.2 [M+H]$^+$. $^1$H NMR (400 MHz, Chloroform-d) δ 7.20 (d, J=8.5 Hz, 2H), 7.16-7.10 (m, 2H), 4.08-3.85 (m, 5H), 3.19-3.01 (m, 1H), 2.71-2.60 (m, 1H), 2.37-2.24 (m, 5H), 2.22-1.94 (m, 3H), 1.94-1.79 (m, 1H), 1.77-1.63 (m, 1H), 1.35 (s, 3H).

Example 55

(rac)-((1s,3s)-3-Hydroxy-3-methylcyclobutyl)(6-(4-(trifluoromethyl)phenyl)-2-azaspiro[3.4]octan-2-yl)methanone

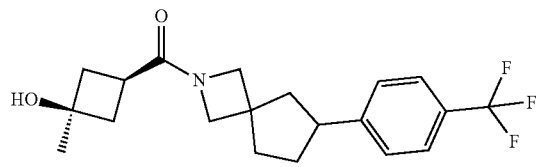 [SMILES: C[C@]1(O)C[C@@H](C(=O)N2CC3(CCC(c4ccc(C(F)(F)F)cc4)C3)C2)C1]

The title compound was prepared in a manner analogous to Example 40 using (4-(trifluoromethyl)phenyl)boronic acid instead of 3-(trifluoromethoxy)phenylboronic acid in Step A. MS (ESI): mass calcd. for C$_{20}$H$_{24}$F$_3$NO$_2$, 367.2; m/z found, 368.2 [M+H]$^+$. $^1$H NMR (400 MHz, Chloroform-d) δ 7.54 (d, J=8.1 Hz, 2H), 7.30 (d, J=7.9 Hz, 2H), 4.19-4.07 (m, 1H), 4.07-3.86 (m, 4H), 3.23-3.07 (m, 1H), 2.63 (dt, J=8.3, 7.1 Hz, 1H), 2.39-2.23 (m, 5H), 2.23-2.11 (m, 1H), 2.11-1.95 (m, 2H), 1.95-1.82 (m, 1H), 1.80-1.65 (m, 1H), 1.35 (s, 3H).

Example 56

((1s,3*S)-3-Hydroxy-3-methylcyclobutyl)((*R)-6-(4-(trifluoromethyl)phenyl)-2-azaspiro[3.4]octan-2-yl)methanone

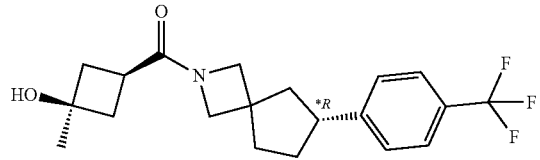 [SMILES: C[C@]1(O)C[C@@H](C(=O)N2CC3(CC[C@@H](c4ccc(C(F)(F)F)cc4)C3)C2)C1]

The title compound was prepared via separation of (rac)-((1s,3s)-3-hydroxy-3-methylcyclobutyl)(6-(4-(trifluoromethyl)phenyl)-2-azaspiro[3.4]octan-2-yl)methanone (Example 55) by SFC (Stationary phase: AD-H 2×25 cm; Mobile phase: 15% iPrOH/CO$_2$; Rt=4.95 min). MS (ESI): mass calcd. for C$_{20}$H$_{24}$F$_3$NO$_2$, 367.2; m/z found, 368.1 [M+H]$^+$. $^1$H NMR (400 MHz, Chloroform-d) δ 7.54 (d, J=8.1 Hz, 2H), 7.30 (d, J=8.0 Hz, 2H), 4.08-3.86 (m, 5H), 3.25-3.06 (m, 1H), 2.72-2.59 (m, 1H), 2.39-2.32 (m, 1H), 2.33-2.25 (m, 4H), 2.22-1.96 (m, 3H), 1.96-1.83 (m, 1H), 1.81-1.65 (m, 1H), 1.35 (s, 3H).

Example 57

((1s,3*R)-3-Hydroxy-3-methylcyclobutyl)((*S)-6-(4-(trifluoromethyl)phenyl)-2-azaspiro[3.4]octan-2-yl)methanone

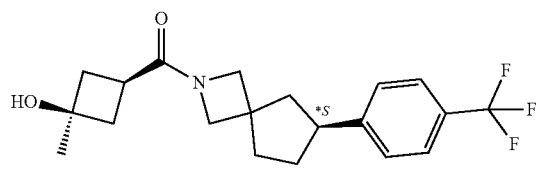 [SMILES: C[C@]1(O)C[C@@H](C(=O)N2CC3(CC[C@H](c4ccc(C(F)(F)F)cc4)C3)C2)C1]

The title compound was prepared via separation of (rac)-((1s,3s)-3-hydroxy-3-methylcyclobutyl)(6-(4-(trifluoromethyl)phenyl)-2-azaspiro[3.4]octan-2-yl)methanone (Example 55) by SFC (Stationary phase: AD-H 2×25 cm; Mobile phase: 15% iPrOH/CO$_2$; Rt=5.66 min). MS (ESI): mass calcd. for C$_{20}$H$_{24}$F$_3$NO$_2$, 367.2; m/z found, 368.1 [M+H]$^+$. $^1$H NMR (400 MHz, Chloroform-d) δ 7.54 (d, J=8.1 Hz, 2H), 7.29 (d, J=8.0 Hz, 2H), 4.26 (s, 1H), 4.05-3.86 (m, 4H), 3.22-3.07 (m, 1H), 2.68-2.57 (m, 1H), 2.39-2.22 (m, 5H), 2.22-1.95 (m, 3H), 1.97-1.81 (m, 1H), 1.80-1.65 (m, 1H), 1.34 (s, 3H).

Example 58

(rac)-(6-(3-Cyclopropylphenyl)-2-azaspiro[3.4]octan-2-yl)((1s,3s)-3-hydroxy-3-methylcyclobutyl)methanone

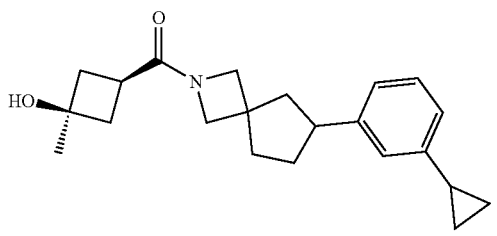 [SMILES: C[C@]1(O)C[C@@H](C(=O)N2CC3(CCC(c4cccc(C5CC5)c4)C3)C2)C1]

The title compound was prepared in a manner analogous to Example 40 using (3-cyclopropylphenyl)boronic acid instead of 3-(trifluoromethoxy)phenylboronic acid in Step A. MS (ESI): mass calcd. for C$_{22}$H$_{29}$NO$_2$, 339.2; m/z found, 340.3 [M+H]$^+$. $^1$H NMR (400 MHz, Chloroform-d) δ 7.18 (td, J=7.6, 1.1 Hz, 1H), 6.97 (dt, J=7.8, 1.2 Hz, 1H), 6.93 (q, J=1.6 Hz, 1H), 6.88 (dt, J=7.6, 1.4 Hz, 1H), 4.14-4.03 (m, 1H), 4.03-3.86 (m, 4H), 3.15-2.97 (m, 1H), 2.66 (pd, J=7.4, 1.4 Hz, 1H), 2.29 (d, J=7.5 Hz, 5H), 2.17-1.79 (m, 5H), 1.79-1.63 (m, 1H), 1.35 (s, 3H), 1.00-0.90 (m, 2H), 0.73-0.63 (m, 2H).

Example 59

((*R)-6-(3-Cyclopropylphenyl)-2-azaspiro[3.4]octan-2-yl)((1s,3*S)-3-hydroxy-3-methylcyclobutyl)methanone

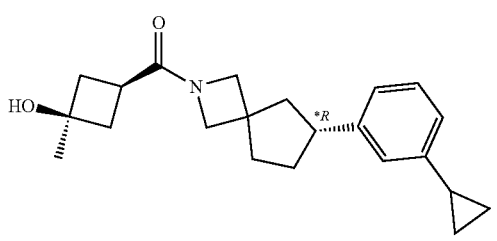 [SMILES: C[C@]1(O)C[C@@H](C(=O)N2CC3(CC[C@@H](c4cccc(C5CC5)c4)C3)C2)C1]

The title compound was prepared via separation of (rac)-(6-(3-cyclopropylphenyl)-2-azaspiro[3.4]octan-2-yl)((1s,3s)-3-hydroxy-3-methylcyclobutyl)methanone (Example 58) by SFC (Stationary phase: Chiralpak IC 5 um 250×21 mm; Mobile phase: 18% MeOHIPA (1:1) with 0.2% isopropylamine, 82% CO$_2$; Rt=9.48 min). MS (ESI): mass calcd. for C$_{22}$H$_{29}$NO$_2$, 339.2; m/z found, 340.3 [M+H]$^+$. $^1$H NMR (400 MHz, Chloroform-d) δ 7.23-7.14 (m, 1H), 7.00-6.95 (m, 1H), 6.94-6.91 (m, 1H), 6.92-6.84 (m, 1H), 4.05-3.85 (m, 4H), 3.15-2.97 (m, 1H), 2.67 (p, J=7.4 Hz, 1H), 2.36-2.22 (m, 5H), 2.19-1.92 (m, 4H), 1.92-1.82 (m, 2H), 1.78-1.65 (m, 1H), 1.35 (s, 3H), 0.99-0.91 (m, 2H), 0.73-0.63 (m, 2H).

Example 60

((*S)-6-(3-Cyclopropylphenyl)-2-azaspiro[3.4]octan-2-yl)((1s,3*R)-3-hydroxy-3-methylcyclobutyl)methanone

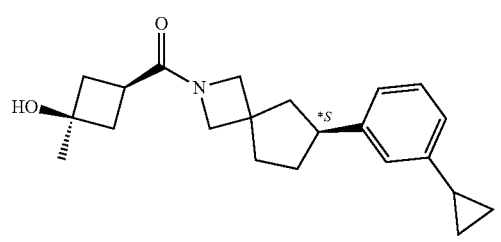 [SMILES: C[C@]1(O)C[C@@H](C(=O)N2CC3(CC[C@H](c4cccc(C5CC5)c4)C3)C2)C1]

The title compound was prepared via separation of (rac)-(6-(3-cyclopropylphenyl)-2-azaspiro[3.4]octan-2-yl)((1s,3s)-3-hydroxy-3-methylcyclobutyl)methanone (Example 58) by SFC (Stationary phase: Chiralpak IC 5 um 250×21 mm; Mobile phase: 18% MeOHIPA (1:1) with 0.2% isopropylamine, 82% CO$_2$; Rt=10.28 min). MS (ESI): mass calcd. for C$_{22}$H$_{29}$NO$_2$, 339.2; m/z found, 340.3 [M+H]$^+$. $^1$H NMR (400 MHz, Chloroform-d) δ 7.21-7.14 (m, 1H), 6.97 (d, J=7.7 Hz, 1H), 6.94-6.90 (m, 1H), 6.88 (d, J=7.7 Hz, 1H), 4.06-3.83 (m, 4H), 3.15-2.97 (m, 1H), 2.67 (p, J=7.3 Hz, 1H), 2.35-2.22 (m, 5H), 2.18-1.92 (m, 3H), 1.92-1.82 (m, 2H), 1.80-1.64 (m, 1H), 1.35 (s, 3H), 0.99-0.92 (m, 2H), 0.73-0.63 (m, 2H).

Example 61

(rac)-((1s,3s)-3-Hydroxy-3-methylcyclobutyl)(6-(3-(trifluoromethyl)phenyl)-2-azaspiro[3.4]octan-2-yl)methanone

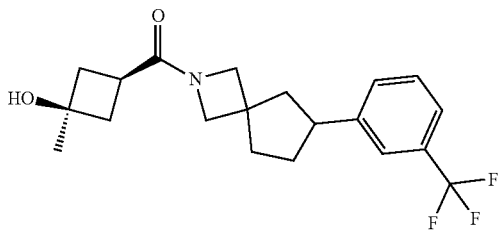 [SMILES: C[C@]1(O)C[C@@H](C(=O)N2CC3(CCC(c4cccc(C(F)(F)F)c4)C3)C2)C1]

The title compound was prepared in a manner analogous to Example 40 using 3-(trifluoromethyl)phenylboronic acid instead of 3-(trifluoromethoxy)phenylboronic acid in Step A. MS (ESI): mass calcd. for C$_{20}$H$_{24}$F$_3$NO$_2$, 367.2; m/z found, 368.2 [M+H]$^+$. $^1$H NMR (400 MHz, Chloroform-d) δ 7.49-7.35 (m, 4H), 4.08-3.87 (m, 5H), 3.24-3.05 (m, 1H), 2.72-2.60 (m, 1H), 2.41-2.32 (m, 1H), 2.32-2.23 (m, 4H), 2.23-1.96 (m, 3H), 1.90 (td, J=13.4, 10.5 Hz, 1H), 1.80-1.67 (m, 1H), 1.35 (s, 3H).

Example 62

((1s,3*S)-3-Hydroxy-3-methylcyclobutyl)((*R)-6-(3-(trifluoromethyl)phenyl)-2-azaspiro[3.4]octan-2-yl)methanone

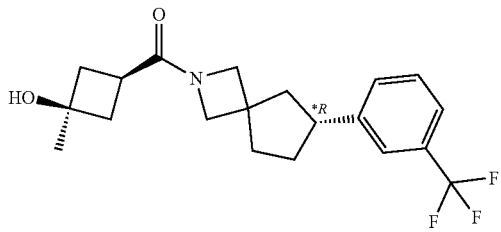 [SMILES: C[C@]1(O)C[C@@H](C(=O)N2CC3(CC[C@@H](c4cccc(C(F)(F)F)c4)C3)C2)C1]

The title compound was prepared via separation of (rac)-((1s,3s)-3-hydroxy-3-methylcyclobutyl)(6-(3-(trifluoromethyl)phenyl)-2-azaspiro[3.4]octan-2-yl)methanone (Example 61) by SFC (Stationary phase: Chiralpak IA 5 um 250×21 mm; Mobile phase: 25% MeOH with 0.2% TEA, 75% $CO_2$; Rt=1.75 min). MS (ESI): mass calcd. for $C_{20}H_{24}F_3NO_2$, 367.2; m/z found, 368.2 [M+H]$^+$. $^1$H NMR (400 MHz, Chloroform-d) δ 7.48-7.35 (m, 4H), 4.16-3.85 (m, 5H), 3.24-3.05 (m, 1H), 2.72-2.59 (m, 1H), 2.41-2.31 (m, 1H), 2.32-2.26 (m, 4H), 2.24-2.12 (m, 1H), 2.12-1.97 (m, 2H), 1.99-1.81 (m, 1H), 1.82-1.65 (m, 1H), 1.35 (s, 3H).

Example 63

((1s,3*R)-3-Hydroxy-3-methylcyclobutyl)((*S)-6-(3-(trifluoromethyl)phenyl)-2-azaspiro[3.4]octan-2-yl)methanone

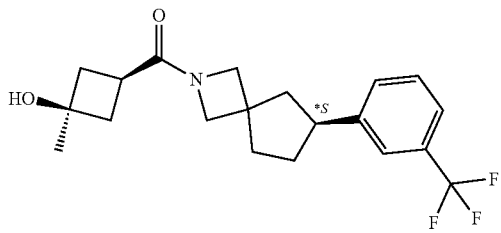 [SMILES: C[C@]1(O)C[C@@H](C(=O)N2CC3(CC[C@H](c4cccc(C(F)(F)F)c4)C3)C2)C1]

The title compound was prepared via separation of (rac)-((1s,3s)-3-hydroxy-3-methylcyclobutyl)(6-(3-(trifluoromethyl)phenyl)-2-azaspiro[3.4]octan-2-yl)methanone (Example 61) by SFC (Stationary phase: Chiralpak IA 5 um 250×21 mm; Mobile phase: 25% MeOH with 0.2% TEA, 75% $CO_2$; Rt=2.77 min). MS (ESI): mass calcd. for $C_{20}H_{24}F_3NO_2$, 367.2; m/z found, 368.2 [M+H]$^+$. $^1$H NMR (400 MHz, Chloroform-d) δ 7.49-7.35 (m, 4H), 4.17-3.87 (m, 5H), 3.25-3.07 (m, 1H), 2.71-2.60 (m, 1H), 2.41-2.33 (m, 1H), 2.35-2.26 (m, 4H), 2.24-2.13 (m, 1H), 2.13-1.97 (m, 2H), 1.99-1.83 (m, 1H), 1.81-1.66 (m, 1H), 1.36 (s, 3H).

Example 64

(rac)-(6-(3-Cyclobutylphenyl)-2-azaspiro[3.4]octan-2-yl)((1s,3s)-3-hydroxy-3-methylcyclobutyl)methanone

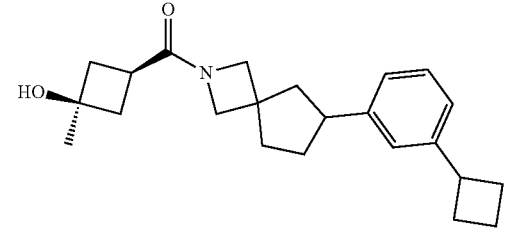 [SMILES: C[C@]1(O)C[C@@H](C(=O)N2CC3(CCC(c4cccc(C5CCC5)c4)C3)C2)C1]

The title compound was prepared in a manner analogous to Example 40 using (3-cyclobutylphenyl)boronic acid instead of 3-(trifluoromethoxy)phenylboronic acid in Step A. MS (ESI): mass calcd. for $C_{23}H_{31}NO_2$, 353.2; m/z found, 354.3 [M+H]$^+$. $^1$H NMR (400 MHz, Chloroform-d) δ 7.23 (t, J=7.5 Hz, 1H), 7.09-7.05 (m, 1H), 7.04-6.98 (m, 2H), 4.11 (d, J=7.3 Hz, 1H), 4.05-3.86 (m, 4H), 3.52 (p, J=8.7 Hz, 1H), 3.16-3.01 (m, 1H), 2.66 (p, J=7.4 Hz, 1H), 2.39-2.23 (m, 7H), 2.21-2.09 (m, 3H), 2.09-1.81 (m, 5H), 1.80-1.65 (m, 1H), 1.35 (s, 3H).

Example 65

(rac)-((1s,3s)-3-Hydroxy-3-methylcyclobutyl)(6-(4-methyl-3-(trifluoromethyl)phenyl)-2-azaspiro[3.4]octan-2-yl)methanone

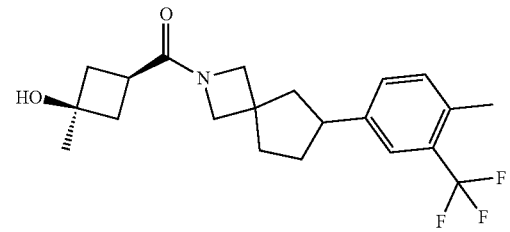 [SMILES: Cc1ccc(C2CCC3(C2)CN(C(=O)[C@H]2C[C@@](C)(O)C2)C3)cc1C(F)(F)F]

The title compound was prepared in a manner analogous to Example 40 using (4-methyl-3-(trifluoromethyl)phenyl)boronic acid instead of 3-(trifluoromethoxy)phenylboronic acid in Step A. MS (ESI): mass calcd. for $C_{21}H_{26}F_3NO_2$, 381.2; m/z found, 382.3 [M+H]$^+$. $^1$H NMR (400 MHz, Chloroform-d) δ 7.41 (s, 1H), 7.25-7.18 (m, 2H), 4.23 (s, 1H), 4.07-3.86 (m, 4H), 3.18-3.02 (m, 1H), 2.67 (p, J=7.4 Hz, 1H), 2.44 (q, J=1.9 Hz, 3H), 2.38-2.24 (m, 5H), 2.21-1.94 (m, 3H), 1.87 (td, J=13.3, 10.6 Hz, 1H), 1.78-1.64 (m, 1H), 1.36 (s, 3H).

Example 66

(rac)-((1s,3s)-3-Hydroxy-3-methylcyclobutyl)(6-(3-methyl-4-(trifluoromethoxy)phenyl)-2-azaspiro[3.4]octan-2-yl)methanone

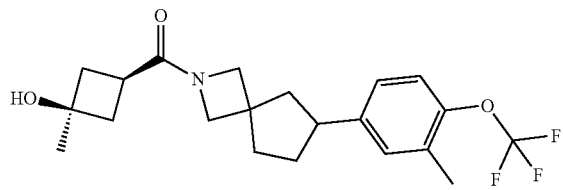 [SMILES: Cc1cc(C2CCC3(C2)CN(C(=O)[C@H]2C[C@@](C)(O)C2)C3)ccc1OC(F)(F)F]

The title compound was prepared in a manner analogous to Example 40 using (3-methyl-4-(trifluoromethoxy)phenyl)boronic acid instead of 3-(trifluoromethoxy)phenylboronic acid in Step A. MS (ESI): mass calcd. for $C_{21}H_{26}F_3NO_3$, 397.2; m/z found, 398.3 [M+H]$^+$. $^1$H NMR (400 MHz, Chloroform-d) δ 7.11 (dt, J=8.4, 1.5 Hz, 1H), 7.05 (d, J=2.0 Hz, 1H), 7.01 (dt, J=8.7, 1.6 Hz, 1H), 4.06-3.88 (m, 4H), 3.86 (d, J=4.1 Hz, 1H), 3.13-2.98 (m, 1H), 2.71-2.62 (m, 1H), 2.35-2.22 (m, 8H), 2.19-1.92 (m, 3H), 1.92-1.79 (m, 1H), 1.76-1.61 (m, 1H), 1.35 (s, 3H).

Example 67

(rac)-((1s,3s)-3-Hydroxy-3-methylcyclobutyl)(6-(3-methyl-4-(trifluoromethyl)phenyl)-2-azaspiro[3.4]octan-2-yl)methanone

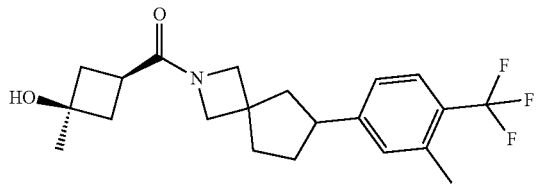 [SMILES: Cc1cc(C2CCC3(C2)CN(C(=O)[C@H]2C[C@@](C)(O)C2)C3)ccc1C(F)(F)F]

The title compound was prepared in a manner analogous to Example 40 using (3-methyl-4-(trifluoromethyl)phenyl)boronic acid instead of 3-(trifluoromethoxy)phenylboronic acid in Step A. MS (ESI): mass calcd. for $C_{21}H_{26}F_3NO_2$, 381.2; m/z found, 382.2 [M+H]$^+$. $^1$H NMR (400 MHz, Chloroform-d) δ 7.52 (d, J=8.0 Hz, 1H), 7.08 (d, J=8.3 Hz, 2H), 4.07-3.87 (m, 4H), 3.81 (s, 1H), 3.10 (dp, J=17.6, 8.5 Hz, 1H), 2.3-2.63 (m, 1H), 2.46 (d, J=2.1 Hz, 3H), 2.37-2.21 (m, 5H), 2.21-1.95 (m, 3H), 1.95-1.82 (m, 1H), 1.79-1.67 (m, 1H), 1.35 (s, 3H).

Example 68

(rac)-(6-(4-Chloro-3-methylphenyl)-2-azaspiro[3.4]octan-2-yl)((1s,3s)-3-hydroxy-3-methylcyclobutyl)methanone

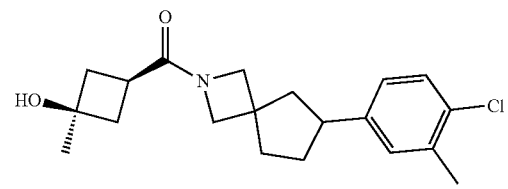 [SMILES: Cc1cc(C2CCC3(C2)CN(C(=O)[C@H]2C[C@@](C)(O)C2)C3)ccc1Cl]

The title compound was prepared in a manner analogous to Example 40 using (4-chloro-3-methylphenyl)boronic acid instead of 3-(trifluoromethoxy)phenylboronic acid in Step A. MS (ESI): mass calcd. for $C_{20}H_{26}ClNO_2$, 347.2; m/z found, 348.2 [M+H]$^+$. $^1$H NMR (400 MHz, Chloroform-d) δ 7.25 (dd, J=8.7, 1.3 Hz, 1H), 7.04 (d, J=2.2 Hz, 1H), 6.95 (dt, J=7.9, 1.7 Hz, 1H), 4.05-3.88 (m, 4H), 3.87 (d, J=4.4 Hz, 1H), 3.14-2.96 (m, 1H), 2.72-2.62 (m, 1H), 2.35 (s, 3H), 2.34-2.21 (m, 5H), 2.18-1.91 (m, 3H), 1.94-1.80 (m, 1H), 1.74-1.61 (m, 1H), 1.35 (s, 3H).

Example 69

((R)-6-(4-Chloro-3-methylphenyl)-2-azaspiro[3.4]octan-2-yl)((1s,3S)-3-hydroxy-3-methylcyclobutyl)methanone

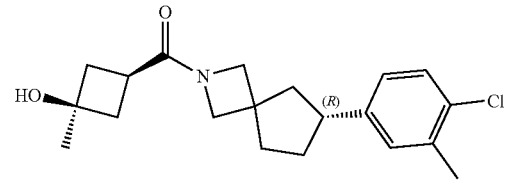

The title compound was prepared via separation of (rac)-(6-(4-chloro-3-methylphenyl)-2-azaspiro[3.4]octan-2-yl)((1s,3s)-3-hydroxy-3-methylcyclobutyl)methanone (Example 68) by SFC (Stationary phase: AD-H (2×25 cm); Mobile phase: 20% IPA/CO$_2$; Rt=8.95 min). MS (ESI): mass calcd. for $C_{20}H_{26}ClNO_2$, 347.2; m/z found, 348.2 [M+H]$^+$. $^1$H NMR (400 MHz, Chloroform-d) δ 7.30-7.22 (m, 1H), 7.08-7.04 (m, 1H), 7.00-6.92 (m, 1H), 4.08-3.87 (m, 5H), 3.14-2.96 (m, 1H), 2.68 (pd, J=7.4, 1.2 Hz, 1H), 2.36 (s, 3H), 2.37-2.24 (m, 5H), 2.19-1.94 (m, 3H), 1.94-1.80 (m, 1H), 1.76-1.64 (m, 1H), 1.37 (s, 3H).

Example 70

((S)-6-(4-Chloro-3-methylphenyl)-2-azaspiro[3.4]octan-2-yl)((1s,3R)-3-hydroxy-3-methylcyclobutyl)methanone

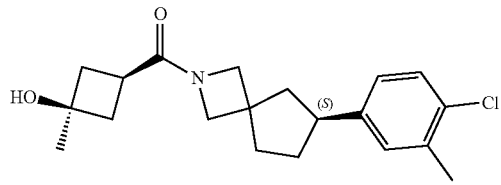

The title compound was prepared via separation of (rac)-(6-(4-chloro-3-methylphenyl)-2-azaspiro[3.4]octan-2-yl)((1s,3s)-3-hydroxy-3-methylcyclobutyl)methanone (Example 68) by SFC (Stationary phase: AD-H (2×25 cm); Mobile phase: 20% IPA/CO$_2$; Rt=11.75 min). MS (ESI): mass calcd. for C$_{20}$H$_{26}$ClNO$_2$, 347.2; m/z found, 348.2 [M+H]$^+$. $^1$H NMR (400 MHz, Chloroform-d) δ 7.28-7.20 (m, 1H), 7.06-7.02 (m, 1H), 6.98-6.90 (m, 1H), 4.09-3.84 (m, 5H), 3.12-2.94 (m, 1H), 2.66 (pd, J=7.4, 1.2 Hz, 1H), 2.35 (s, 3H), 2.35-2.22 (m, 5H), 2.18-1.92 (m, 3H), 1.87-1.78 (m, 1H), 1.74-1.61 (m, 1H), 1.35 (s, 3H).

Example 71

(rac)-(6-(3-Chloro-4-methylphenyl)-2-azaspiro[3.4]octan-2-yl)((1s,3s)-3-hydroxy-3-methylcyclobutyl)methanone

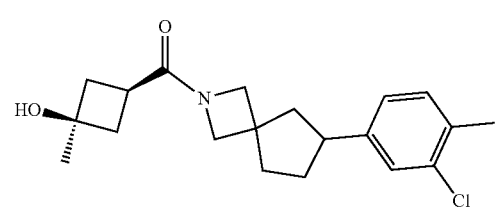 [SMILES: Cc1ccc(C2CCC3(C2)CN(C(=O)[C@H]2C[C@@](C)(O)C2)C3)cc1Cl]

The title compound was prepared in a manner analogous to Example 40 using (3-chloro-4-methylphenyl)boronic acid instead of 3-(trifluoromethoxy)phenylboronic acid in Step A. MS (ESI): mass calcd. for C$_{20}$H$_{26}$ClNO$_2$, 347.2; m/z found, 348.2 [M+H]$^+$. $^1$H NMR (500 MHz, Chloroform-d) δ 7.16 (t, J=1.4 Hz, 1H), 7.15-7.12 (m, 1H), 6.97 (dd, J=7.8, 1.8 Hz, 1H), 4.04-3.92 (m, 4H), 3.92-3.84 (m, 1H), 3.11-2.97 (m, 1H), 2.70-2.61 (m, 1H), 2.33 (s, 3H), 2.31-2.23 (m, 5H), 2.18-1.91 (m, 3H), 1.90-1.79 (m, 1H), 1.75-1.61 (m, 1H), 1.35 (s, 3H).

Example 72

(rac)-(6-(4-(Difluoromethoxy)-3-methylphenyl)-2-azaspiro[3.4]octan-2-yl)((1s,3s)-3-hydroxy-3-methylcyclobutyl)methanone

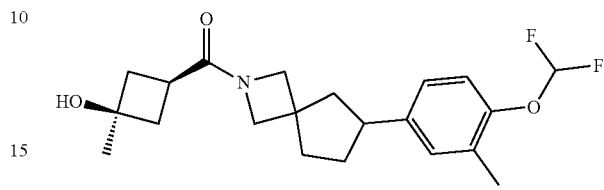

The title compound was prepared in a manner analogous to Example 40 using (4-(difluoromethoxy)-3-methylphenyl)boronic acid instead of 3-(trifluoromethoxy)phenylboronic acid in Step A. MS (ESI): mass calcd. for C$_{21}$H$_{27}$F$_2$NO$_3$, 379.2; m/z found, 380.2 [M+H]$^+$. $^1$H NMR (500 MHz, Chloroform-d) δ 7.06-7.02 (m, 1H), 6.99 (d, J=1.6 Hz, 2H), 6.46 (t, J=74.4 Hz, 1H), 4.06-3.92 (m, 4H), 3.92-3.85 (m, 1H), 3.11-2.98 (m, 1H), 2.66 (pd, J=7.4, 1.7 Hz, 1H), 2.35-2.27 (m, 5H), 2.27 (s, 3H), 2.19-1.93 (m, 3H), 1.90-1.79 (m, 1H), 1.74-1.63 (m, 1H), 1.35 (s, 3H).

Example 73

((*R)-6-(4-(Difluoromethoxy)-3-methylphenyl)-2-azaspiro[3.4]octan-2-yl)((1s,3*S)-3-hydroxy-3-methylcyclobutyl)methanone

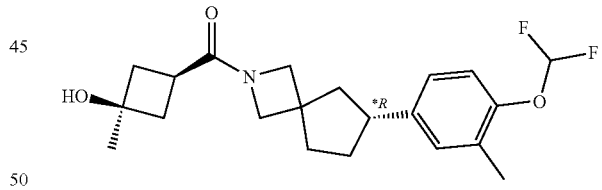

The title compound was prepared via separation of (rac)-(6-(4-(difluoromethoxy)-3-methylphenyl)-2-azaspiro[3.4]octan-2-yl)((1s,3s)-3-hydroxy-3-methylcyclobutyl)methanone (Example 72) by SFC (Stationary phase: OD-H (2×25 cm); Mobile phase: 15% IPA/CO$_2$; Rt=5.91 min). MS (ESI): mass calcd. for C$_{21}$H$_{27}$F$_2$NO$_3$, 379.2; m/z found, 380.3 [M+H]$^+$. $^1$H NMR (400 MHz, Chloroform-d) δ 7.04 (s, 1H), 7.01-6.97 (m, 2H), 6.46 (t, J=74.4 Hz, 1H), 4.20-4.09 (m, 1H), 4.04-3.85 (m, 4H), 3.13-2.95 (m, 1H), 2.68-2.60 (m, 1H), 2.34-2.27 (m, 5H), 2.26 (s, 3H), 2.17-1.91 (m, 3H), 1.90-1.79 (m, 1H), 1.75-1.61 (m, 1H), 1.35 (s, 3H).

Example 74

((*S)-6-(4-(Difluoromethoxy)-3-methylphenyl)-2-azaspiro[3.4]octan-2-yl)((1s,3*R)-3-hydroxy-3-methylcyclobutyl)methanone

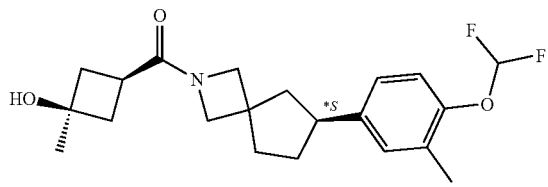 [SMILES: Cc1cc([C@H]2CCC3(C2)CN(C(=O)[C@H]2C[C@@](C)(O)C2)C3)ccc1OC(F)F]

The title compound was prepared via separation of (rac)-(6-(4-(difluoromethoxy)-3-methylphenyl)-2-azaspiro[3.4]octan-2-yl)((1s,3s)-3-hydroxy-3-methylcyclobutyl)methanone (Example 72) by SFC (Stationary phase: OD-H (2×25 cm); Mobile phase: 15% IPA/CO$_2$; Rt=6.70 min). MS (ESI): mass calcd. for C$_{21}$H$_{27}$F$_2$NO$_3$, 379.2; m/z found, 380.3 [M+H]$^+$. $^1$H NMR (400 MHz, Chloroform-d) δ 7.07-7.01 (m, 1H), 7.01-6.97 (m, 2H), 6.46 (t, J=74.4 Hz, 1H), 4.08-3.85 (m, 5H), 3.13-2.96 (m, 1H), 2.66 (pd, J=7.4, 1.4 Hz, 1H), 2.35-2.25 (m, 5H), 2.27 (s, 3H), 2.18-1.92 (m, 3H), 1.90-1.79 (m, 1H), 1.76-1.62 (m, 1H), 1.35 (s, 3H).

Example 75

(rac)-(6-(4-Cyclopropyl-2-methylphenyl)-2-azaspiro[3.4]octan-2-yl)((1s,3s)-3-hydroxy-3-methylcyclobutyl)methanone

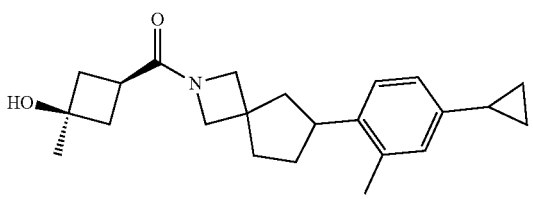 [SMILES: Cc1cc(C2CC2)ccc1C1CCC2(C1)CN(C(=O)[C@H]1C[C@@](C)(O)C1)C2]

The title compound was prepared in a manner analogous to Example 40 using (4-cyclopropyl-2-methylphenyl)boronic acid instead of 3-(trifluoromethoxy)phenylboronic acid in Step A. MS (ESI): mass calcd. for C$_{23}$H$_{31}$NO$_2$, 353.2; m/z found, 354.2 [M+H]$^+$. $^1$H NMR (400 MHz, Chloroform-d) δ 7.07 (t, J=7.4 Hz, 1H), 6.90-6.84 (m, 2H), 4.05-3.88 (m, 4H), 3.77 (d, J=3.4 Hz, 1H), 3.24 (dp, J=17.0, 8.6 Hz, 1H), 2.69 (tt, J=8.2, 6.2 Hz, 1H), 2.35-2.18 (m, 8H), 2.14-1.91 (m, 3H), 1.91-1.78 (m, 2H), 1.74-1.62 (m, 1H), 1.35 (s, 3H), 0.95-0.88 (m, 2H), 0.68-0.62 (m, 2H).

Example 76

(rac)-((1s,3s)-3-Hydroxy-3-methylcyclobutyl)(6-(4-methoxy-3-methylphenyl)-2-azaspiro[3.4]octan-2-yl)methanone

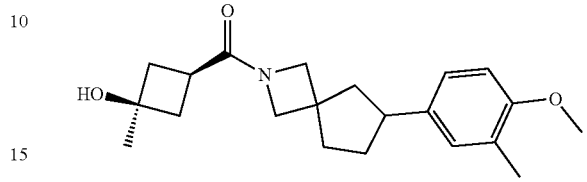

The title compound was prepared in a manner analogous to Example 40 using (4-methoxy-3-methylphenyl)boronic acid instead of 3-(trifluoromethoxy)phenylboronic acid in Step A. MS (ESI): mass calcd. for C$_{21}$H$_{29}$NO$_3$, 343.2; m/z found, 343.8 [M+H]$^+$. $^1$H NMR (400 MHz, Chloroform-d) δ 7.00-6.94 (m, 2H), 6.77-6.72 (m, 1H), 4.06-3.82 (m, 5H), 3.81 (s, 3H), 3.11-2.92 (m, 1H), 2.74-2.61 (m, 1H), 2.35-2.22 (m, 5H), 2.20 (s, 3H), 2.16-1.90 (m, 3H), 1.93-1.78 (m, 1H), 1.73-1.63 (m, 1H), 1.35 (s, 3H).

Example 77

(rac)-((1s,3s)-3-Hydroxy-3-methylcyclobutyl)(6-(3-methyl-5-(trifluoromethyl)phenyl)-2-azaspiro[3.4]octan-2-yl)methanone

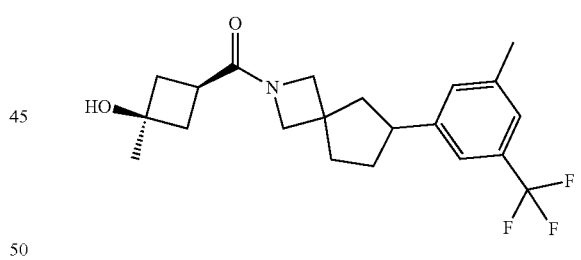

The title compound was prepared in a manner analogous to Example 40 using (3-methyl-5-(trifluoromethyl)phenyl)boronic acid instead of 3-(trifluoromethoxy)phenylboronic acid in Step A. MS (ESI): mass calcd. for C$_{21}$H$_{26}$F$_3$NO$_2$, 381.2; m/z found, 382.2 [M+H]$^+$. $^1$H NMR (500 MHz, Chloroform-d) δ 7.29-7.24 (m, 1H), 7.23 (s, 1H), 7.17 (s, 1H), 4.06-3.86 (m, 5H), 3.18-3.03 (m, 1H), 2.70-2.63 (m, 1H), 2.39 (s, 3H), 2.37-2.23 (m, 5H), 2.21-2.13 (m, 1H), 2.13-1.95 (m, 2H), 1.95-1.82 (m, 1H), 1.76-1.66 (m, 1H), 1.35 (s, 3H).

Example 78

(rac)-((1s,3s)-3-Hydroxy-3-methylcyclobutyl)(6-(2-methyl-5-(trifluoromethyl)phenyl)-2-azaspiro[3.4]octan-2-yl)methanone

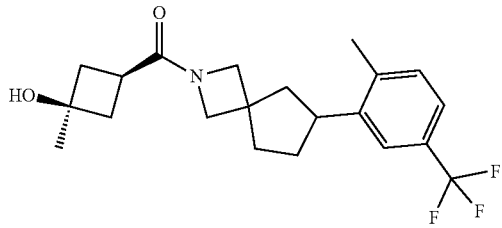 [SMILES: Cc1ccc(C(F)(F)F)cc1C1CCC2(C1)CN(C(=O)[C@H]1C[C@@](C)(O)C1)C2]

The title compound was prepared in a manner analogous to Example 40 using (2-methyl-5-(trifluoromethyl)phenyl)boronic acid instead of 3-(trifluoromethoxy)phenylboronic acid in Step A. MS (ESI): mass calcd. for $C_{21}H_{26}F_3NO_2$, 381.2; m/z found, 382.2 [M+H]$^+$. $^1$H NMR (500 MHz, Chloroform-d) δ 7.44-7.38 (m, 1H), 7.38-7.32 (m, 1H), 7.27-7.21 (m, 1H), 4.04 (q, J=8.3 Hz, 1H), 4.01-3.94 (m, 2H), 3.92 (s, 1H), 3.89-3.77 (m, 1H), 3.38-3.23 (m, 1H), 2.73-2.63 (m, 1H), 2.40-2.35 (m, 3H), 2.36-2.22 (m, 5H), 2.20-2.06 (m, 2H), 2.08-1.97 (m, 1H), 1.94-1.81 (m, 1H), 1.77-1.70 (m, 1H), 1.35 (s, 3H).

Example 79

(rac)-(6-(2-Fluoro-3-methoxyphenyl)-2-azaspiro[3.4]octan-2-yl)((1s,3s)-3-hydroxy-3-methylcyclobutyl)methanone

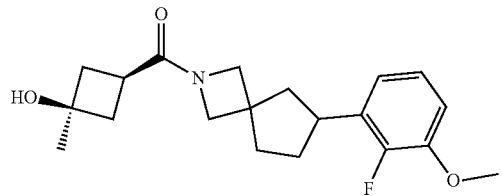 [SMILES: COc1cccc(C2CCC3(C2)CN(C(=O)[C@H]2C[C@@](C)(O)C2)C3)c1F]

The title compound was prepared in a manner analogous to Example 40 using (2-fluoro-3-methoxyphenyl)boronic acid instead of 3-(trifluoromethoxy)phenylboronic acid in Step A. MS (ESI): mass calcd. for $C_{20}H_{26}FNO_3$, 347.2; m/z found, 347.8 [M+H]$^+$. $^1$H NMR (600 MHz, Chloroform-d) δ 7.03-6.96 (m, 1H), 6.86-6.79 (m, 1H), 6.80-6.72 (m, 1H), 4.05-3.88 (m, 5H), 3.87 (s, 3H), 3.38-3.28 (m, 1H), 2.69-2.61 (m, 1H), 2.33-2.23 (m, 5H), 2.17-2.01 (m, 2H), 2.00-1.89 (m, 2H), 1.80-1.70 (m, 1H), 1.34 (s, 3H).

Example 80

(rac)-((1s,3s)-3-Hydroxy-3-methylcyclobutyl)(6-(3-methoxy-5-methylphenyl)-2-azaspiro[3.4]octan-2-yl)methanone

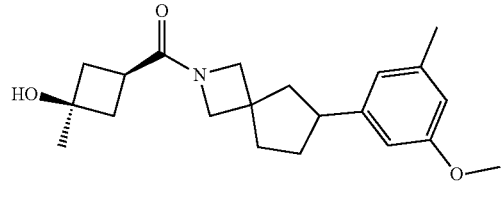 [SMILES: COc1cc(C)cc(C2CCC3(C2)CN(C(=O)[C@H]2C[C@@](C)(O)C2)C3)c1]

The title compound was prepared in a manner analogous to Example 40 using (3-methoxy-5-methylphenyl)boronic acid instead of 3-(trifluoromethoxy)phenylboronic acid in Step A. MS (ESI): mass calcd. for $C_{21}H_{29}NO_3$, 343.2; m/z found, 343.8 [M+H]$^-$. $^1$H NMR (600 MHz, Chloroform-d) δ 6.61 (d, J=2.2 Hz, 1H), 6.57-6.53 (m, 2H), 4.10 (d, J=12.5 Hz, 1H), 4.01 (s, 1H), 3.98-3.93 (m, 2H), 3.92-3.86 (m, 1H), 3.78 (d, J=2.5 Hz, 3H), 3.10-2.96 (m, 1H), 2.69-2.61 (m, 1H), 2.33-2.23 (m, 8H), 2.16-1.99 (m, 2H), 1.99-1.93 (m, 1H), 1.93-1.82 (m, 1H), 1.77-1.66 (m, 1H), 1.35 (s, 3H).

Example 81

(rac)-(6-(5-Cyclopropyl-2-fluorophenyl)-2-azaspiro[3.4]octan-2-yl)((1s,3s)-3-hydroxy-3-methylcyclobutyl)methanone

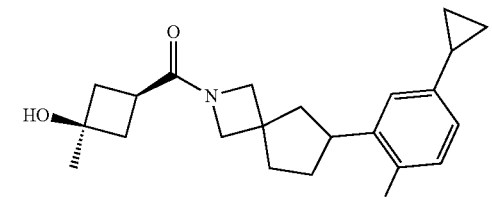

The title compound was prepared in a manner analogous to Example 40 using (5-cyclopropyl-2-fluorophenyl)boronic acid instead of 3-(trifluoromethoxy)phenylboronic acid in Step A. MS (ESI): mass calcd. for $C_{22}H_{28}FNO_2$, 357.2; m/z found, 357.8 [M+H]$^+$. $^1$H NMR (400 MHz, Chloroform-d) δ 6.94-6.80 (m, 3H), 4.11-3.85 (m, 5H), 3.32-3.17 (m, 1H), 2.66 (p, J=7.4 Hz, 1H), 2.34-2.20 (m, 5H), 2.16-2.00 (m, 2H), 2.00-1.87 (m, 2H), 1.90-1.78 (m, 1H), 1.80-1.68 (m, 1H), 1.35 (s, 3H), 0.96-0.89 (m, 2H), 0.66-0.57 (m, 2H).

Example 82

(rac)-(6-(3-(Difluoromethoxy)-4-methylphenyl)-2-azaspiro[3.4]octan-2-yl)((1s,3s)-3-hydroxy-3-methylcyclobutyl)methanone

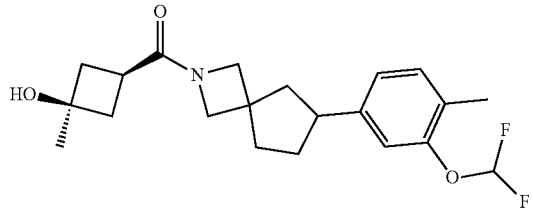 [SMILES: Cc1ccc(C2CCC3(C2)CN(C(=O)[C@H]2C[C@@](C)(O)C2)C3)cc1OC(F)F]

The title compound was prepared in a manner analogous to Example 40 using (3-(difluoromethoxy)-4-methylphenyl)boronic acid instead of 3-(trifluoromethoxy)phenylboronic acid in Step A. MS (ESI): mass calcd. for $C_{21}H_{27}F_2NO_3$, 379.2; m/z found, 380.4 $[M+H]^+$. $^1$H NMR (400 MHz, CDCl$_3$) δ 7.16 (d, J=8.0 Hz, 1H), 6.97 (dd, J=1.2, 8.0 Hz, 1H), 6.91 (s, 1H), 6.68-6.28 (m, 1H), 4.06-3.86 (m, 5H), 3.16-2.99 (m, 1H), 2.73-2.64 (m, 1H), 2.36-2.27 (m, 4H), 2.26 (s, 3H), 2.20-1.95 (m, 3H), 1.91-1.85 (m, 1H), 1.76-1.65 (m, 2H), 1.36 (s, 3H).

Example 83

(rac)-(6-(4-(Difluoromethoxy)-2-methylphenyl)-2-azaspiro[3.4]octan-2-yl)((1s,3s)-3-hydroxy-3-methylcyclobutyl)methanone

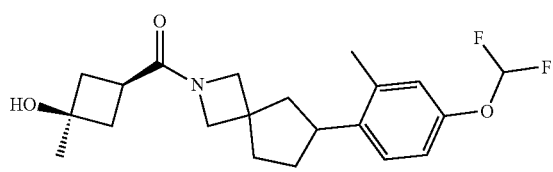 [SMILES: Cc1cc(OC(F)F)ccc1C1CCC2(C1)CN(C(=O)[C@H]1C[C@@](C)(O)C1)C2]

The title compound was prepared in a manner analogous to Example 40 using (4-(difluoromethoxy)-2-methylphenyl)boronic acid (Intermediate 12) instead of 3-(trifluoromethoxy)phenylboronic acid in Step A. MS (ESI): mass calcd. for $C_{21}H_{27}F_2NO_3$, 379.2; m/z found, 380.1 $[M+H]^+$. $^1$H NMR (400 MHz, CDCl$_3$) δ 7.16 (d, J=8.4 Hz, 1H), 6.97-6.87 (m, 2H), 6.47 (t, J=74.4 Hz, 1H), 4.09-3.86 (m, 4H), 3.24 (br s, 1H), 2.75-2.63 (m, 1H), 2.34-2.22 (m, 8H), 2.17-1.94 (m, 4H), 1.68-1.62 (m, 1H), 1.35 (s, 3H).

Example 84

(rac)-(6-(3-(Difluoromethoxy)-5-methylphenyl)-2-azaspiro[3.4]octan-2-yl)((1s,3s)-3-hydroxy-3-methylcyclobutyl)methanone

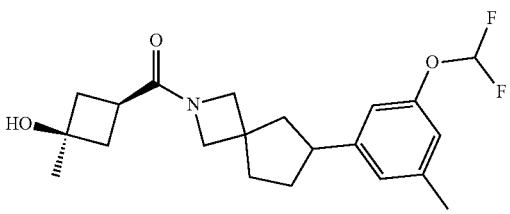 [SMILES: Cc1cc(OC(F)F)cc(C2CCC3(C2)CN(C(=O)[C@H]2C[C@@](C)(O)C2)C3)c1]

The title compound was prepared in a manner analogous to Example 40 using (3-(difluoromethoxy)-5-methylphenyl)boronic acid (Intermediate 13) instead of 3-(trifluoromethoxy)phenylboronic acid in Step A. MS (ESI): mass calcd. for $C_{21}H_{27}F_2NO_3$, 379.2; m/z found, 380.1 $[M+H]^+$. $^1$H NMR (400 MHz, CDCl$_3$) δ 6.86 (s, 1H), 6.77 (d, J=9.2 Hz, 2H), 6.49 (t, J=74.4 Hz, 1H), 4.05-3.81 (m, 5H), 3.15-3.00 (m, 1H), 2.70-2.65 (m, 1H), 2.39-2.23 (m, 8H), 2.19-1.82 (m, 4H), 1.78-1.64 (m, 1H), 1.36 (s, 3H).

Example 85

(rac)-(6-(5-(Difluoromethoxy)-2-methylphenyl)-2-azaspiro[3.4]octan-2-yl)((1s,3s)-3-hydroxy-3-methylcyclobutyl)methanone

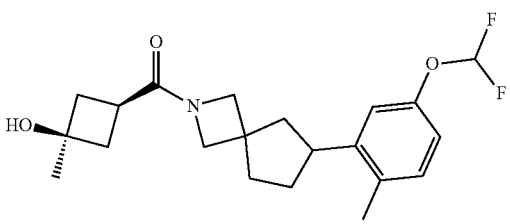 [SMILES: Cc1ccc(OC(F)F)cc1C1CCC2(C1)CN(C(=O)[C@H]1C[C@@](C)(O)C1)C2]

The title compound was prepared in a manner analogous to Example 40 using (5-(difluoromethoxy)-2-methylphenyl)boronic acid (Intermediate 14) instead of 3-(trifluoromethoxy)phenylboronic acid in Step A. MS (ESI): mass calcd. for $C_{21}H_{27}F_2NO_3$, 379.2; m/z found, 380.1 $[M+H]^+$. $^1$H NMR (400 MHz, CDCl$_3$) δ 7.13 (dd, J=3.2, 8.8 Hz, 1H), 6.94 (d, J=6.0 Hz, 1H), 6.87 (d, J=8.0 Hz, 1H), 6.47 (t, J=74.8 Hz, 1H), 4.07-3.89 (m, 4H), 3.36-3.18 (m, 1H), 2.69 (d, J=7.2 Hz, 1H), 2.43-2.20 (m, 8H), 2.19-1.76 (m, 5H), 1.36 (s, 3H).

Example 86

(rac)-(6-(3-Chloro-5-methoxyphenyl)-2-azaspiro[3.4]octan-2-yl)((1s,3s)-3-hydroxy-3-methylcyclobutyl)methanone

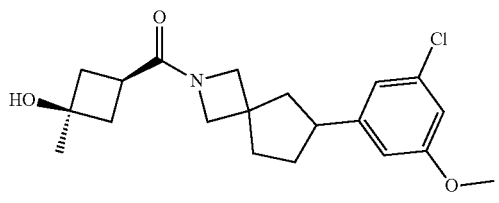 [SMILES: COc1cc(Cl)cc(C2CCC3(C2)CN(C(=O)[C@H]2C[C@@](C)(O)C2)C3)c1]

The title compound was prepared in a manner analogous to Example 40 using (3-chloro-5-methoxyphenyl)boronic acid instead of 3-(trifluoromethoxy)phenylboronic acid in Step A. MS (ESI): mass calcd. for $C_{20}H_{26}ClNO_3$, 363.2; m/z found, 364.1 [M+H]$^+$. $^1$H NMR (400 MHz, Chloroform-d) δ 6.78-6.75 (m, 1H), 6.73 (t, J=2.1 Hz, 1H), 6.61 (q, J=1.9 Hz, 1H), 4.10-3.83 (m, 5H), 3.78 (d, J=1.4 Hz, 3H), 3.12-2.94 (m, 1H), 2.72-2.58 (m, 1H), 2.35-2.23 (m, 5H), 2.17-1.91 (m, 3H), 1.93-1.78 (m, 1H), 1.77-1.63 (m, 1H), 1.35 (s, 3H).

Example 87

(rac)-(6-(4-Chloro-3-methoxyphenyl)-2-azaspiro[3.4]octan-2-yl)((1s,3s)-3-hydroxy-3-methylcyclobutyl)methanone

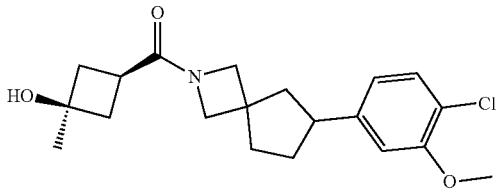 [SMILES: COc1cc(C2CCC3(C2)CN(C(=O)[C@H]2C[C@@](C)(O)C2)C3)ccc1Cl]

The title compound was prepared in a manner analogous to Example 40 using (4-chloro-3-methoxyphenyl)boronic acid instead of 3-(trifluoromethoxy)phenylboronic acid in Step A. MS (ESI): mass calcd. for $C_{20}H_{26}ClNO_3$, 363.2; m/z found, 364.1 [M+H]$^+$. $^1$H NMR (400 MHz, Chloroform-d) δ 7.26 (dd, J=7.9, 1.6 Hz, 1H), 6.76-6.69 (m, 2H), 4.15 (s, 1H), 4.06-3.92 (m, 3H), 3.94-3.83 (m, 4H), 3.15-2.98 (m, 1H), 2.64 (p, J=7.5 Hz, 1H), 2.36-2.21 (m, 4H), 2.20-1.92 (m, 4H), 1.93-1.78 (m, 1H), 1.76-1.63 (m, 1H), 1.34 (s, 3H).

Example 88

(rac)-((1s,3s)-3-Hydroxy-3-(trifluoromethyl)cyclobutyl)(6-(3-isopropylphenyl)-2-azaspiro[3.4]octan-2-yl)methanone

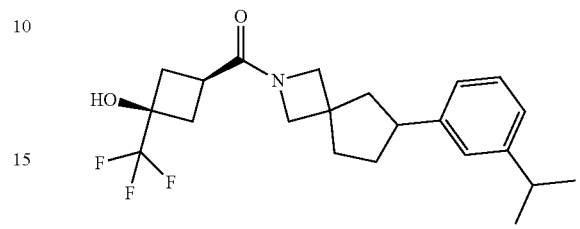

The title compound was prepared in a manner analogous to Example 40 using (3-isopropylphenyl)boronic acid instead of 3-(trifluoromethoxy)phenylboronic acid in Step A and (1s,3s)-3-hydroxy-3-(trifluoromethyl)cyclobutane-1-carboxylic acid instead of (1s,3s)-3-hydroxy-3-methylcyclobutane-1-carboxylic acid in Step C. MS (ESI): mass calcd. for $C_{22}H_{28}F_3NO_2$, 395.2; m/z found, 396.1 [M+H]$^+$. $^1$H NMR (400 MHz, Chloroform-d) δ 7.23 (t, J=7.6 Hz, 1H), 7.10-6.98 (m, 3H), 5.65 (d, J=15.0 Hz, 1H), 4.11-3.87 (m, 4H), 3.18-3.00 (m, 1H), 2.94-2.78 (m, 2H), 2.78-2.67 (m, 2H), 2.48-2.38 (m, 2H), 2.38-2.26 (m, 1H), 2.21-1.97 (m, 3H), 1.99-1.84 (m, 1H), 1.81-1.67 (m, 1H), 1.25 (dd, J=6.9, 0.7 Hz, 6H).

Example 89

(2-(3-(tert-Butyl)phenyl)-6-azaspiro[3.4]octan-6-yl)((1s,3s)-3-hydroxy-3-methylcyclobutyl)methanone

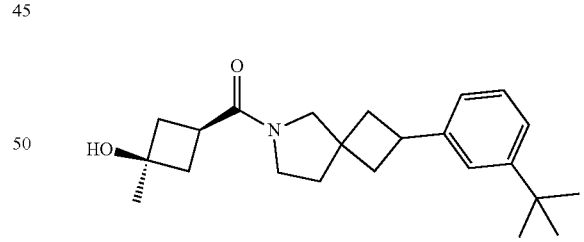

The title compound was prepared in a manner analogous to Example 40 using tert-butyl 2-(2-tosylhydrazineylidene)-6-azaspiro[3.4]octane-6-carboxylate (Intermediate 6) instead of tert-butyl 6-(2-tosylhydrazineylidene)-2-azaspiro[3.4]octane-2-carboxylate (Intermediate 5) and 3-tert-butylphenylboronic acid instead of 3-(trifluoromethoxy)phenylboronic acid in Step A. MS (ESI): mass calcd. for $C_{23}H_{33}NO_2$, 355.3; m/z found, 356.3 [M+H]$^+$. $^1$H NMR (400 MHz, Chloroform-d) δ 7.26-7.22 (m, 2H), 7.22-7.16 (m, 1H), 7.07-6.99 (m, 1H), 3.79-3.27 (m, 6H), 2.94-2.72 (m, 1H), 2.51-2.26 (m, 6H), 2.26-2.08 (m, 2H), 2.08-1.81 (m, 2H), 1.42-1.35 (m, 3H), 1.32 (d, J=1.8 Hz, 9H).

Example 90

(rac)-(6-(3-(1,1-Difluoroethyl)phenyl)-2-azaspiro[3.4]octan-2-yl)((1s,3s)-3-hydroxy-3-methylcyclobutyl)methanone

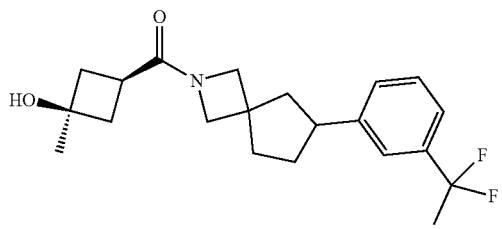 [SMILES: CC(F)(F)c1cccc(C2CCC3(C2)CN(C(=O)[C@H]2C[C@@](C)(O)C2)C3)c1]

Step A: (rac)-tert-Butyl 6-(3-(1,1-difluoroethyl)phenyl)-6-hydroxy-2-azaspiro[3.4]octane-2-carboxylate. n-BuLi (0.69 mL, 2.5M in hexane, 1.73 mmol) was added to a solution of 1-bromo-3-(1,1-difluoroethyl)benzene (353 mg, 1.60 mmol) and anhydrous THF (5 mL). The resultant mixture was stirred at −78° C. for 1 h before tert-butyl 6-oxo-2-azaspiro[3.4]octane-2-carboxylate (300 mg, 1.33 mmol) in anhydrous THF (5 mL) was added. The resultant mixture was stirred at −78° C. for 2 h. The reaction mixture was quenched with sat. NH$_4$Cl and extracted with EtOAc. The combined organic extracts were washed with brine, dried over Na$_2$SO$_4$, filtered, and concentrated under reduced pressure. The resulting residue was purified by FCC (SiO$_2$, 0-50% EtOAc in ether) to afford the title compound (270 mg, 36%) as a colorless oil. MS (ESI): mass calcd. for C$_{20}$H$_{27}$F$_2$NO$_3$, 367.2; m/z found, 353.1 (M+H+ACN-C2H8).

Step B: (rac)-6-(3-(1,1-Difluoroethyl)phenyl)-2-azaspiro[3.4]oct-5-ene. A mixture of tert-butyl 6-(3-(1,1-difluoroethyl)phenyl)-6-hydroxy-2-azaspiro[3.4]octane-2-carboxylate (200 mg, 0.54 mmol), TFA (2 mL) and DCM (2 mL) was stirred at rt for 1 hour. The reaction mixture was concentrated under reduced pressure to afford the crude product (200 mg) as brown oil, which was used in the next step without further purification.

Step C: (rac)-6-(3-(1,1-Difluoroethyl)phenyl)-2-azaspiro[3.4]octane. 6-(3-(1,1-Difluoroethyl)phenyl)-2-azaspiro[3.4]oct-5-ene (170 mg, 0.682 mmol), Pd/C (20 mg, 10 wt. %, 18.9 μmol) and MeOH (4 mL) were combined. The resultant mixture was stirred under H$_2$ (15 psi) at rt for 2 hours. The suspension was filtered through a pad of Celite® and the pad washed with EtOAc. The filtrate was concentrated under reduced pressure to afford the crude product (170 mg), which was used for the next step without purification. MS (ESI): mass calcd. for C$_{15}$H$_{19}$F$_2$N, 251.1; m/z found, 252.0 [M+H]$^+$.

Step D: (rac)-(6-(3-(1,1-Difluoroethyl)phenyl)-2-azaspiro[3.4]octan-2-yl)((1s,3s)-3-hydroxy-3-methylcyclobutyl)methanone. HATU (157 mg, 0.41 mmol) was added to a solution of 6-(3-(1,1-difluoroethyl)phenyl)-2-azaspiro[3.4]octane (102 mg, 0.28 mmol), (1s,3s)-3-hydroxy-3-methylcyclobutanecarboxylic acid (35.8 mg, 0.28 mmol), and DIPEA (142 mg, 1.10 mmol) in DMF (4 mL). The resultant mixture was stirred at rt for 17 hours. The reaction mixture was quenched with H$_2$O and extracted with EtOAc. The combined organic extracts were washed with brine, dried over Na$_2$SO$_4$, filtered, and concentrated under reduced pressure to give the crude product which was purified by preparative HPLC (Phenomenex Gemini-NX C18, 75×30 mm×3 μm, 42% to 72% (v/v) CH$_3$CN and water with 0.05% NH$_3$) to afford the title compound (21 mg, 21%) as a yellow solid. MS (ESI): mass calcd. for C$_{21}$H$_{27}$F$_2$NO$_2$, 363.2; m/z found, 364.2 [M+H]$^+$. $^1$H NMR (400 MHz, CDCl$_3$) δ 7.39-7.32 (m, 3H), 7.27-7.24 (m, 1H), 4.10-3.85 (m, 5H), 3.22-3.06 (m, 1H), 2.70 (p, J=7.2 Hz, 1H), 2.37-2.22 (m, 5H), 2.21-1.99 (m, 3H), 1.97-1.85 (m, 4H), 1.80-1.71 (m, 1H), 1.36 (s, 3H).

Example 91

(rac)-(6-(3-Ethylphenyl)-2-azaspiro[3.4]octan-2-yl)((1s,3s)-3-hydroxy-3-methylcyclobutyl)methanone

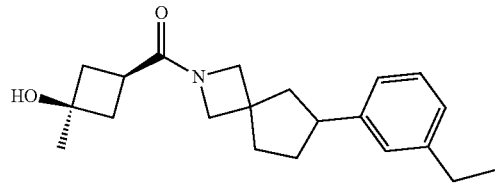 [SMILES: CCc1cccc(C2CCC3(C2)CN(C(=O)[C@H]2C[C@@](C)(O)C2)C3)c1]

Step A: (rac)-6-(3-Ethylphenyl)-2-azaspiro[3.4]octane. (rac)-tert-Butyl 6-(3-(1,1-difluoroethyl)phenyl)-6-hydroxy-2-azaspiro[3.4]octane-2-carboxylate (270 mg, 0.74 mmol) and TES (256 mg, 2.21 mmol) were stirred in TFA (4 mL) at rt for 2 h. The reaction mixture was concentrated under reduced pressure and the resulting title compound was used in next step without further purification. MS (ESI): mass calcd. for C$_{15}$H$_{21}$N, 215.2; m/z found, 216.0 [M+H]$^+$.

Step B: (rac)-(6-(3-Ethylphenyl)-2-azaspiro[3.4]octan-2-yl)((1s,3s)-3-hydroxy-3-methylcyclobutyl)methanone. HATU (234 mg, 0.62 mmol) was added to a solution of 6-(3-ethylphenyl)-2-azaspiro[3.4]octane (270 mg, 0.41 mmol), (1s,3s)-3-hydroxy-3-methylcyclobutanecarboxylic acid (53 mg, 0.41 mmol), and DIPEA (212 mg, 1.64 mmol) in DMF (4 mL). The resultant mixture was stirred at rt for 17 hours. The reaction mixture was quenched with H$_2$O and extracted with EtOAc. The combined organic extracts were washed with brine, dried over Na$_2$SO$_4$, filtered, and concentrated under reduced pressure. The resulting residue was purified by preparative HPLC (Phenomenex Gemini-NX C18, 75 mm×30 mm×3 μm, 42% to 72% (v/v) CH$_3$CN and water with 0.05% NH$_3$) to afford the title compound (31 mg, 22%) as a yellow solid. MS (ESI): mass calcd. for C$_{21}$H$_{29}$NO$_2$, 327.2; m/z found, 328.2 [M+H]$^+$. $^1$H NMR (400 MHz, CDCl$_3$) δ 7.28-7.20 (m, 2H), 7.07-7.00 (m, 2H), 4.14-3.70 (m, 5H), 2.98-3.20 (m, 1H), 2.77-2.59 (m, 3H), 2.40-2.22 (m, 4H), 2.19-1.85 (m, 4H), 1.84-1.63 (m, 3H), 1.36 (s, 3H), 1.24 (t, J=7.6 Hz, 2H).

Example 92

(rac)-(6-(3-(Difluoromethyl)-4-methylphenyl)-2-azaspiro[3.4]octan-2-yl)((1s,3s)-3-hydroxy-3-methylcyclobutyl)methanone

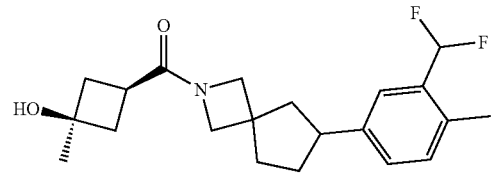 [SMILES: Cc1ccc(C2CCC3(C2)CN(C(=O)[C@H]2C[C@@](C)(O)C2)C3)cc1C(F)F]

The title compound was prepared in a manner analogous to Example 90 using 4-bromo-2-(difluoromethyl)-1-methylbenzene instead of 1-bromo-3-(1,1-difluoroethyl)benzene in Step A. MS (ESI): mass calcd. for $C_{21}H_{27}F_2NO_2$, 363.2; m/z found, 364.1 [M+H]$^+$. $^1$H NMR (400 MHz, CDCl$_3$) δ 7.34 (s, 1H), 7.22-7.13 (m, 2H), 6.75 (t, J=55.6 Hz, 1H), 3.98 (br s, 4H), 3.11 (br s, 1H), 2.77-2.63 (m, 1H), 2.40 (s, 3H), 2.35-2.24 (m, 5H), 2.19-1.86 (m, 4H), 1.80-1.67 (m, 1H), 1.36 (s, 3H).

Example 93

(rac)-((1s,3s)-3-Hydroxy-3-methylcyclobutyl)(6-(3-methyl-5-(trifluoromethoxy)phenyl)-2-azaspiro[3.4]octan-2-yl)methanone

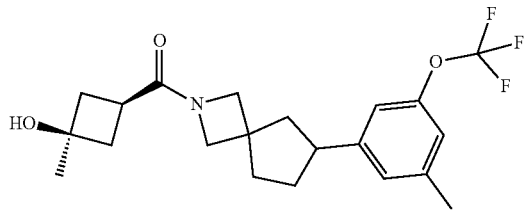 [SMILES: Cc1cc(OC(F)(F)F)cc(C2CCC3(C2)CN(C(=O)[C@H]2C[C@@](C)(O)C2)C3)c1]

The title compound was prepared in a manner analogous to Example 90 using 1-bromo-3-methyl-5-(trifluoromethoxy)benzene instead of 1-bromo-3-(1,1-difluoroethyl)benzene in Step A. MS (ESI): mass calcd. for $C_{21}H_{26}F_3NO_3$, 397.2; m/z found, 398.2 [M+H]$^+$. $^1$H NMR (400 MHz, CDCl$_3$) δ 6.93 (s, 1H), 6.87 (s, 1H), 6.83 (s, 1H), 4.04-3.99 (m, 1H), 3.99-3.94 (m, 2H), 3.93-3.86 (m, 1H), 3.83 (d, J=4.4 Hz, 1H), 3.15-2.99 (m, 1H), 2.73-2.64 (m, 1H), 2.35 (s, 3H), 2.33-2.22 (m, 5H), 2.18-1.96 (m, 3H), 1.92-1.81 (m, 1H), 1.75-1.66 (m, 1H), 1.35 (s, 3H).

Example 94

(rac)-(6-(3-(Difluoromethyl)-5-methylphenyl)-2-azaspiro[3.4]octan-2-yl)((1s,3s)-3-hydroxy-3-methylcyclobutyl)methanone

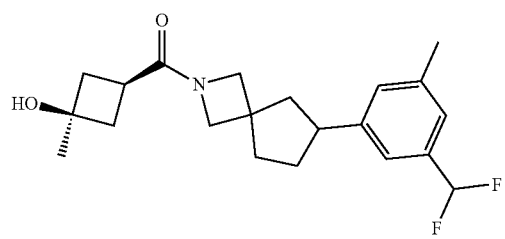 [SMILES: Cc1cc(C(F)F)cc(C2CCC3(C2)CN(C(=O)[C@H]2C[C@@](C)(O)C2)C3)c1]

The title compound was prepared in a manner analogous to Example 90 using 1-bromo-3-methyl-5-(difluoromethyl)benzene instead of 1-bromo-3-(1,1-difluoroethyl)benzene in Step A. MS (ESI): mass calcd. for $C_{21}H_{27}F_2NO_2$, 363.2; m/z found, 364.1 [M+H]$^+$. $^1$H NMR (400 MHz, CDCl$_3$) δ 7.19-7.10 (m, 3H), 6.73-6.45 (m, 1H), 4.07-3.87 (m, 4H), 3.19-3.04 (m, 1H), 2.74-2.63 (m, 1H), 2.38 (s, 3H), 2.34-2.25 (m, 4H), 2.18-1.84 (m, 4H), 1.80-1.67 (m, 2H), 1.36 (s, 3H).

Example 95

(rac)-((1s,3s)-3-Hydroxy-3-methylcyclobutyl)(6-(2-methoxy-3-methylphenyl)-2-azaspiro[3.4]octan-2-yl)methanone

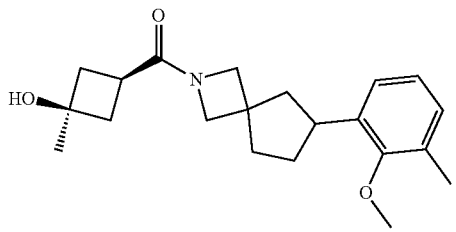 [SMILES: COc1c(C)cccc1C1CCC2(C1)CN(C(=O)[C@H]1C[C@@](C)(O)C1)C2]

The title compound was prepared in a manner analogous to Example 90 using 1-bromo-2-methoxy-3-methylbenzene instead of 1-bromo-3-(1,1-difluoroethyl)benzene in Step A. MS (ESI): mass calcd. for $C_{21}H_{29}NO_3$, 343.2; m/z found, 344.2 [M+H]$^+$. $^1$H NMR (400 MHz, CDCl$_3$) δ 7.08-6.96 (m, 3H), 4.03 (s, 1H), 3.98 (d, J=8.0 Hz, 2H), 3.92 (s, 1H), 3.83 (br s, 1H), 3.72 (s, 3H), 3.55-3.41 (m, 1H), 2.74-2.65 (m, 1H), 2.36-2.20 (m, 8H), 2.17-1.94 (m, 3H), 1.91-1.80 (m, 1H), 1.76-1.64 (m, 1H), 1.35 (s, 3H).

Example 96

(rac)-(6-(4-Ethylphenyl)-2-azaspiro[3.4]octan-2-yl)((1s,3s)-3-hydroxy-3-methylcyclobutyl)methanone

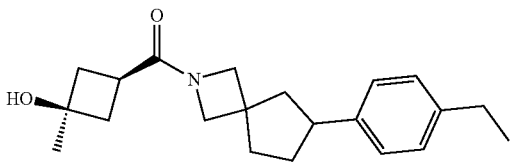 [SMILES: CCc1ccc(C2CCC3(C2)CN(C(=O)[C@H]2C[C@@](C)(O)C2)C3)cc1]

The title compound was prepared in a manner analogous to Example 90 using 1-bromo-4-(1,1-difluoroethyl)benzene instead of 1-bromo-3-(1,1-difluoroethyl)benzene in Step A. MS (ESI): mass calcd. for $C_{21}H_{29}NO_2$, 327.2; m/z found, 328.1 [M+H]$^+$. $^1$H NMR (400 MHz, CDCl$_3$) δ 7.17-7.10 (m, 4H), 4.21-4.04 (m, 1H), 4.02 (s, 1H), 4.00-3.95 (m, 2H), 3.94-3.87 (m, 1H), 3.15-3.01 (m, 1H), 2.70-2.60 (m, 3H), 2.35-2.27 (m, 5H), 2.16-1.86 (m, 5H), 1.39-1.33 (m, 3H), 1.23 (t, J=7.6 Hz, 3H).

Example 97

(rac)-((1s,3s)-3-Hydroxy-3-methylcyclobutyl)(6-(pyrazolo[1,5-a]pyridin-5-yl)-2-azaspiro[3.4]octan-2-yl)methanone

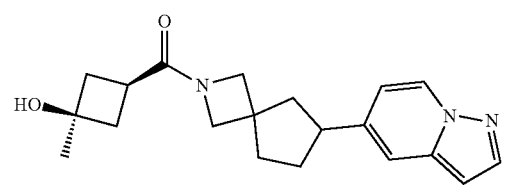 [SMILES: C[C@]1(O)C[C@@H](C(=O)N2CC3(CCC(c4ccn5nccc5c4)C3)C2)C1]

Step A: (rac)-tert-Butyl 6-(pyrazolo[1,5-a]pyridin-5-yl)-2-azaspiro[3.4]oct-6-ene-2-carboxylate. A microwave vial was charged with tert-butyl 6-(((trifluoromethyl)sulfonyl)oxy)-2-azaspiro[3.4]oct-6-ene-2-carboxylate (Intermediate 7, 50 mg, 0.140 mmol), XPhos Pd G2 (11 mg, 14.0 μmol), pyrazolo[1,5-a]pyridine-5-boronic acid pinacol ester (41 mg, 0.170 mmol), 1,4-dioxane (1.9 mL), and sat. aq. $Na_2CO_3$ (0.48 mL). The headspace was purged with vacuum/$N_2$ cycles (3×), the vial capped, and the reaction mixture irradiated in a microwave reactor at 110° C. for 30 min. After cooling to rt, the mixture was diluted with EtOAc and $H_2O$, the layers separated, and the aqueous layer extracted with EtOAc. The combined organic layers were washed with brine, dried over $Na_2SO_4$, filtered, and concentrated in vacuo. The crude residue was used in the next step without further purification. MS (ESI): mass calcd. for $C_{19}H_{23}N_3O_2$, 325.2; m/z found, 325.8 $[M]^+$.

Step B: (rac)-tert-Butyl 6-(pyrazolo[1,5-a]pyridin-5-yl)-2-azaspiro[3.4]octane-2-carboxylate. A crude mixture containing tert-butyl 6-(pyrazolo[1,5-a]pyridin-5-yl)-2-azaspiro[3.4]oct-6-ene-2-carboxylate (0.140 mmol) was dissolved in MeOH (1.5 mL) and 10% Pd/C (15 mg, 14.0 μmol) was added. The reaction was stirred under an atmosphere of $H_2$ for 3 h, then filtered through a pad of Celite®, eluting with EtOAc. The filtrate was concentrated in vacuo and the crude residue used in the next step without further purification. MS (ESI): mass calcd. for $C_{19}H_{25}N_3O_2$, 327.2; m/z found, 328.2 $[M+H]^+$.

Step C: (rac)-((1s,3s)-3-Hydroxy-3-methylcyclobutyl)(6-(pyrazolo[1,5-a]pyridin-5-yl)-2-azaspiro[3.4]octan-2-yl)methanone. A crude mixture containing tert-butyl 6-(pyrazolo[1,5-a]pyridin-5-yl)-2-azaspiro[3.4]octane-2-carboxylate (0.140 mmol) was dissolved in HCl in 1,4-dioxane (4M, 0.38 mL) and the mixture stirred at 45° C. for 1 h. The reaction was cooled to rt, the solvent removed in vacuo, and the residue re-dissolved in $CH_2Cl_2$ (1.4 mL). (1s,3s)-3-Hydroxy-3-methylcyclobutanecarboxylic acid (19.9 mg, 0.150 mmol) was added, followed by HATU (68.7 mg, 0.180 mmol) and DIPEA (96 μL, 0.560 mmol). After stirring at rt for 1 h, the solvent was removed in vacuo and the crude residue purified via RP HPLC (5-95% ACN in 20 mM $NH_4OH$ in water) to afford the title compound as a white foam (19.5 mg, 41% yield). MS (ESI): mass calcd. for $C_{20}H_{25}N_3O_2$, 339.2; m/z found, 340.2 $[M+H]^+$. $^1H$ NMR (600 MHz, Chloroform-d) δ 8.39 (d, J=7.2 Hz, 1H), 7.91 (d, J=2.3 Hz, 1H), 7.30 (s, 1H), 6.58 (dt, J=7.3, 2.1 Hz, 1H), 6.41 (s, 1H), 4.05-3.88 (m, 4H), 3.78-3.75 (m, 1H), 3.21-3.07 (m, 1H), 2.72-2.65 (m, 1H), 2.38-1.87 (m, 9H), 1.81-1.71 (m, 1H), 1.35 (d, J=2.2 Hz, 3H).

Example 98

(rac)-(6-(2,6-Dimethylphenyl)-2-azaspiro[3.4]octan-2-yl)((1s,3s)-3-hydroxy-3-methylcyclobutyl)methanone

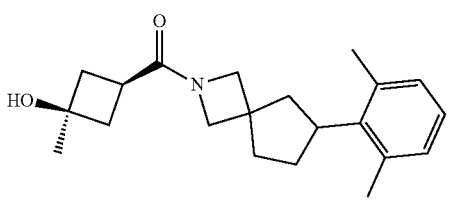 [SMILES: Cc1cccc(C)c1C1CCC2(C1)CN(C(=O)[C@H]1C[C@@](C)(O)C1)C2]

The title compound was prepared in a manner analogous to Example 97 using (2,6-dimethylphenyl)boronic acid instead of pyrazolo[1,5-a]pyridine-5-boronic acid pinacol ester and Pd(PPh3)4 instead of XPhos Pd G2 in Step A. MS (ESI): mass calcd. for $C_{21}H_{29}NO_2$, 327.2; m/z found, 328.2 $[M+H]^+$. $^1H$ NMR (400 MHz, $CDCl_3$) δ 7.04-6.97 (m, 3H), 4.09-3.97 (m, 4H), 3.90 (s, 1H), 3.66-3.52 (m, 1H), 2.76-2.65 (m, 1H), 2.36 (s, 6H), 2.31 (d, J=6.8 Hz, 4H), 2.20-1.99 (m, 6H), 1.36 (s, 3H).

Example 99

(rac)-((1s,3s)-3-Hydroxy-3-methylcyclobutyl)(6-(1-methyl-1H-pyrazol-4-yl)-2-azaspiro[3.4]octan-2-yl)methanone

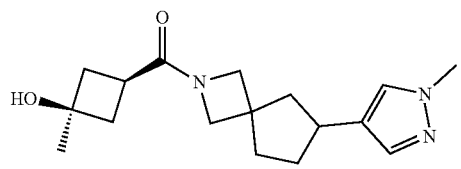 [SMILES: Cn1cc(C2CCC3(C2)CN(C(=O)[C@H]2C[C@@](C)(O)C2)C3)cn1]

The title compound was prepared in a manner analogous to Example 97 using (1-methyl-1H-pyrazol-4-yl)boronic acid instead of pyrazolo[1,5-c]pyridine-5-boronic acid pinacol ester and Pd(dppf)$Cl_2$ instead of XPhos Pd G2 in Step A. MS (ESI): mass calcd. for $C_{17}H_{25}N_3O_2$, 303.2; m/z found, 304.1 $[M+H]^+$. $^1H$ NMR (400 MHz, $CDCl_3$) δ 7.31 (s, 1H), 7.15-7.12 (m, 1H), 3.99-3.93 (m, 2H), 3.91 (s, 1H), 3.90-3.84 (m, 4H), 3.09-2.94 (m, 1H), 2.71-2.62 (m, 1H), 2.35-2.22 (m, 5H), 2.17-1.87 (m, 4H), 1.84-1.78 (m, 1H), 1.66-1.59 (m, 1H), 1.35 (s, 3H).

Example 100

(rac)-((1s,3s)-3-Hydroxy-3-methylcyclobutyl)(6-(1-methyl-3-(trifluoromethyl)-1H-pyrazol-4-yl)-2-azaspiro[3.4]octan-2-yl)methanone

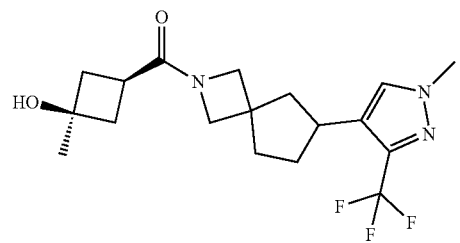 [SMILES: Cn1cc(C2CCC3(C2)CN(C(=O)[C@H]2C[C@@](C)(O)C2)C3)c(C(F)(F)F)n1]

The title compound was prepared in a manner analogous to Example 97 using (1-methyl-3-(trifluoromethyl)-1H-pyrazol-4-yl)boronic acid instead of pyrazolo[1,5-a]pyridine-5-boronic acid pinacol ester and Pd(dppf)$Cl_2$ instead of XPhos Pd G2 in Step A. MS (ESI): mass calcd. for $C_{18}H_{24}F_3N_3O_2$, 371.2; m/z found, 372.1 $[M+H]^+$. $^1H$ NMR (400 MHz, $CDCl_3$) δ 7.23-7.19 (m, 1H), 4.03-3.83 (m, 8H), 3.20-3.07 (m, 1H), 2.72-2.60 (m, 1H), 2.39-2.22 (m, 5H), 2.20-2.11 (m, 1H), 2.09-1.86 (m, 2H), 1.80-1.73 (m, 1H), 1.65-1.54 (m, 1H), 1.40-1.32 (m, 3H).

Example 101

(rac)-((1s,3s)-3-Hydroxy-3-methylcyclobutyl)(6-(1-methyl-3-(trifluoromethyl)-1H-pyrazol-5-yl)-2-azaspiro[3.4]octan-2-yl)methanone

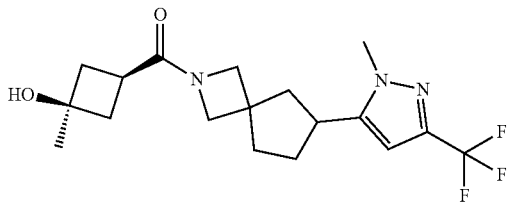 [SMILES: Cn1nc(C(F)(F)F)cc1C1CCC2(C1)CN(C(=O)[C@H]1C[C@@](C)(O)C1)C2]

The title compound was prepared in a manner analogous to Example 97 using (1-methyl-3-(trifluoromethyl)-1H-pyrazol-5-yl)boronic acid instead of pyrazolo[1,5-c]pyridine-5-boronic acid pinacol ester and CataCXium® A Pd G3 instead of XPhos Pd G2 in Step A. MS (ESI): mass calcd. for $C_{18}H_{24}F_3N_3O_2$, 371.2; m/z found, 372.1 [M+H]$^+$. $^1$H NMR (400 MHz, CDCl$_3$) δ 6.27 (d, J=8.2 Hz, 1H), 4.08-3.76 (m, 7H), 3.22-3.10 (m, 1H), 2.71-2.58 (m, 1H), 2.43-1.86 (m, 9H), 1.78-1.70 (m, 1H), 1.36 (s, 3H).

Example 102

(rac)-((1s,3s)-3-Hydroxy-3-methylcyclobutyl)(6-(1-methyl-1H-indazol-5-yl)-2-azaspiro[3.4]octan-2-yl)methanone

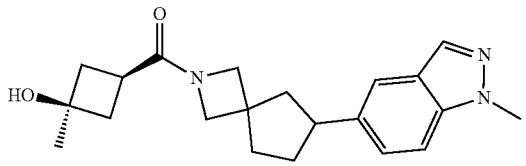 [SMILES: Cn1ncc2cc(C3CCC4(C3)CN(C(=O)[C@H]3C[C@@](C)(O)C3)C4)ccc21]

The title compound was prepared in a manner analogous to Example 97 using (1-methyl-1H-indazol-5-yl)boronic acid instead of pyrazolo[1,5-a]pyridine-5-boronic acid pinacol ester and Pd(dppf)Cl$_2$ instead of XPhos Pd G2 in Step A. MS (ESI): mass calcd. for $C_{21}H_{27}N_3O_2$, 353.2; m/z found, 354.1 [M+H]$^+$. $^1$H NMR (400 MHz, CDCl$_3$) δ 7.94-7.92 (m, 1H), 7.55-7.53 (m, 1H), 7.38-7.34 (m, 1H), 7.28-7.25 (m, 1H), 4.08 (s, 3H), 4.07-3.98 (m, 3H), 3.98-3.85 (m, 2H), 3.32-3.17 (m, 1H), 2.75-2.67 (m, 1H), 2.44-1.91 (m, 9H), 1.86-1.74 (m, 1H), 1.41-1.34 (m, 3H).

Example 103

(7-(4-Fluoro-3-methoxyphenyl)-2-azaspiro[3.5]nonan-2-yl)((1s,3s)-3-hydroxy-3-methylcyclobutyl)methanone

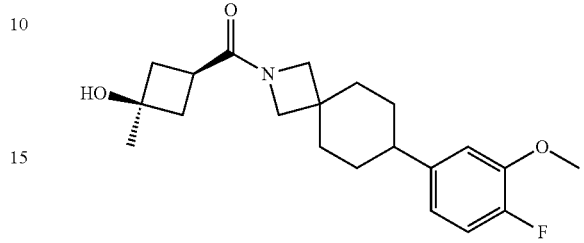

The title compound was prepared in a manner analogous to Example 97 using (4-fluoro-3-methoxyphenyl)boronic acid instead of pyrazolo[1,5-a]pyridine-5-boronic acid pinacol ester, tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7), and Pd(dppf)Cl$_2$ instead of XPhos Pd G2 in Step A. MS (ESI): mass calcd. for $C_{21}H_{28}FNO_3$, 361.2; m/z found, 362.1 [M+H]$^+$. $^1$H NMR (400 MHz, CDCl$_3$) δ 7.04-6.73 (m, 2H), 6.69 (ddd, J=2.0, 4.1, 8.2 Hz, 1H), 3.91-3.82 (m, 4H), 3.77 (d, J=9.8 Hz, 2H), 3.70 (s, 1H), 2.79-2.62 (m, 1H), 2.53-2.38 (m, 1H), 2.37-2.24 (m, 4H), 2.07-1.97 (m, 2H), 1.91-1.82 (m, 2H), 1.62 (dq, J=3.4, 13.1 Hz, 2H), 1.49-1.30 (m, 5H).

Example 104

(7-(3-Fluoro-5-methoxyphenyl)-2-azaspiro[3.5]nonan-2-yl)((1s,3s)-3-hydroxy-3-methylcyclobutyl)methanone

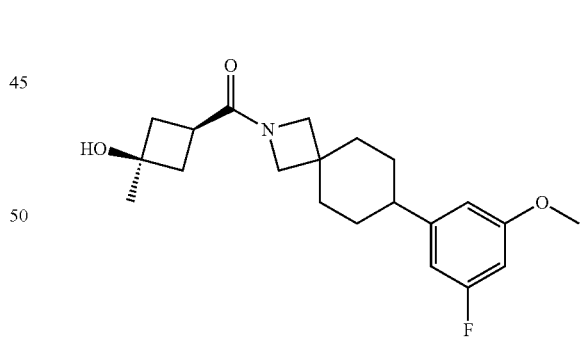

The title compound was prepared in a manner analogous to Example 97 using (3-fluoro-5-methoxyphenyl)boronic acid instead of pyrazolo[1,5-c]pyridine-5-boronic acid pinacol ester, tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7), and Pd(dppf)Cl$_2$ instead of XPhos Pd G2 in Step A. MS (ESI): mass calcd. for $C_{21}H_{28}FNO_3$, 361.2; m/z found, 362.1 [M+H]$^+$. $^1$H NMR (400 MHz, CDCl$_3$) δ 6.55-6.41 (m, 3H), 3.83 (s, 1H), 3.79 (s, 3H), 3.76 (d, J=6.8 Hz, 2H), 3.69 (s, 1H), 2.76-2.60 (m, 1H), 2.50-2.38 (m, 1H), 2.36-2.25 (m, 4H), 2.06-1.95 (m, 2H), 1.92-1.80 (m, 2H), 1.68-1.53 (m, 2H), 1.48-1.27 (m, 5H).

Example 105

((1s,3s)-3-Hydroxy-3-methylcyclobutyl)(7-(4-methoxy-3-methylphenyl)-2-azaspiro[3.5]nonan-2-yl)methanone

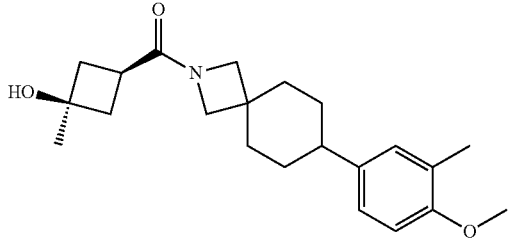 [SMILES: COc1ccc(C2CCC3(CC2)CN(C(=O)[C@H]2C[C@@](C)(O)C2)C3)cc1C]

The title compound was prepared in a manner analogous to Example 97 using (4-methoxy-3-methylphenyl)boronic acid instead of pyrazolo[1,5-c]pyridine-5-boronic acid pinacol ester, tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7), and Pd(dppf)Cl$_2$ instead of XPhos Pd G2 in Step A. MS (ESI): mass calcd. for C$_{22}$H$_{31}$NO$_3$, 357.2; m/z found, 358.2 [M+H]$^+$. $^1$H NMR (400 MHz, CDCl$_3$) δ 7.00-6.91 (m, 2H), 6.76 (d, J=7.9 Hz, 1H), 3.93 (br s, 1H), 3.87-3.65 (m, 7H), 2.80-2.65 (m, 1H), 2.51-2.24 (m, 5H), 2.21 (s, 3H), 2.03-1.93 (m, 2H), 1.90-1.78 (m, 2H), 1.64-1.55 (m, 2H), 1.48-1.30 (m, 5H).

Example 106

((1s,3s)-3-Hydroxy-3-methylcyclobutyl)(7-(3-methoxy-2-methylphenyl)-2-azaspiro[3.5]nonan-2-yl)methanone

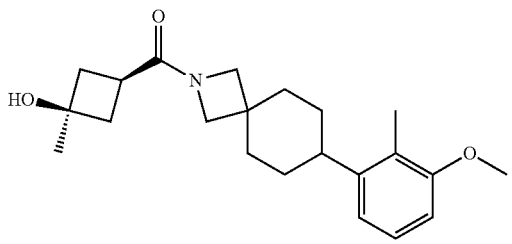 [SMILES: COc1cccc(C2CCC3(CC2)CN(C(=O)[C@H]2C[C@@](C)(O)C2)C3)c1C]

The title compound was prepared in a manner analogous to Example 97 using (3-methoxy-2-methylphenyl)boronic acid instead of pyrazolo[1,5-c]pyridine-5-boronic acid pinacol ester, tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7), and Pd(dppf)Cl$_2$ instead of XPhos Pd G2 in Step A. MS (ESI): mass calcd. for C$_{22}$H$_{31}$NO$_3$, 357.2; m/z found, 358.2 [M+H]$^+$. $^1$H NMR (400 MHz, CDCl$_3$) δ 7.20-7.10 (m, 1H), 6.84-6.69 (m, 2H), 3.87-3.68 (m, 7H), 2.79-2.65 (m, 2H), 2.38-2.25 (m, 4H), 2.19 (s, 3H), 2.02 (d, J=12.8 Hz, 2H), 1.86-1.74 (m, 2H), 1.66 (q, J=13.4 Hz, 2H), 1.51-1.32 (m, 5H).

Example 107

(rac)-((1s,3s)-3-Hydroxy-3-methylcyclobutyl)(6-(4-methyl-3-(trifluoromethoxy)phenyl)-2-azaspiro[3.4]octan-2-yl)methanone

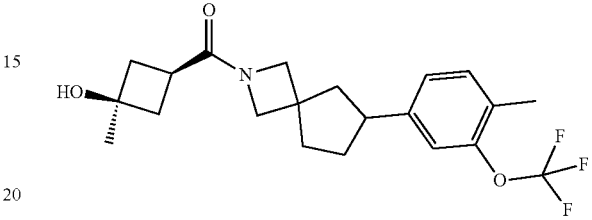

Step A: (rac)-tert-Butyl 6-(4-bromo-3-(trifluoromethoxy)phenyl)-2-azaspiro[3.4]oct-5-ene-2-carboxylate. tert-Butyl 6-(2-tosylhydrazineylidene)-2-azaspiro[3.4]octane-2-carboxylate (Intermediate 5, 2.22 mmol) in 1,4-dioxane (10 mL) was treated with 1-bromo-4-iodo-2-(trifluoromethoxy)benzene (896 mg, 2.44 mmol), t-BuOLi (444 mg, 5.55 mmol), XPhos (212 mg, 0.444 mmol), tris(dibenzylideneacetone)dipalladium(0) (Pd$_2$(dba)$_3$) (203 mg, 0.222 mmol) and 1,4-dioxane (5 mL). The resultant mixture was sparged with N$_2$ for 5 minutes and then stirred while heating at 110° C. overnight. After cooling to rt, the reaction mixture was diluted with H$_2$O, then extracted with EtOAc. The combined organic extracts were washed with brine, dried over Na$_2$SO$_4$, filtered, and concentrated under reduced pressure. The resulting residue was purified by FCC (SiO$_2$, 0-7% EtOAc in ether) to afford the title compound (280 mg, 25%) as brown oil. MS (ESI): mass calcd. for C$_{19}$H$_{21}$BrF$_3$NO$_3$, 447.1; m/z found, 392.0 [M+2H-tBu]$^+$. $^1$H NMR (400 MHz, CDCl$_3$) δ 7.57-7.53 (m, 1H), 7.05 (s, 1H), 6.94 (dd, J=2.0, 8.4 Hz, 1H), 5.76 (dd, J=2.0, 5.2 Hz, 1H), 3.97-3.89 (m, 4H), 2.81-2.64 (m, 2H), 2.32 (t, J=7.2 Hz, 1H), 1.94 (dd, J=5.6, 13.6 Hz, 1H), 1.45 (s, 9H).

Step B: (rac)-tert-Butyl 6-(4-methyl-3-(trifluoromethoxy)phenyl)-2-azaspiro[3.4]oct-5-ene-2-carboxylate. tert-Butyl 6-(4-bromo-3-(trifluoromethoxy)phenyl)-2-azaspiro[3.4]oct-5-ene-2-carboxylate (280 mg, 0.553 mmol), 2,4,6-trimethyl-1,3,5,2,4,6-trioxatriborinane (50% in THF, 555 mg, 2.21 mmol), and K$_2$CO$_3$ (229 mg, 1.66 mmol) were dissolved in dioxane (5 mL) and H$_2$O (0.5 mL). The resultant mixture was sparged with N$_2$ for 5 minutes and then treated with Pd(dppf)Cl$_2$·CH$_2$Cl$_2$ (45 mg, 0.055 mmol). The mixture was sparged with N$_2$ for another 5 minutes and then stirred while heating at 120° C. for 40 hours. After cooling to rt, the reaction mixture was concentrated under reduced pressure. The resulting residue was purified by FCC (SiO$_2$, 0-7% EtOAc in ether) to afford the title compound (210 mg, 78%) as brown oil. MS (ESI): mass calcd. for C$_{20}$H$_{24}$F$_3$NO$_3$, 383.2; m/z found, 328.0 [M+2H-tBu]$^+$. $^1$H NMR (400 MHz, CDCl$_3$) δ 7.26-7.14 (m, 2H), 6.96-6.93 (m, 1H), 5.80-5.73 (m, 1H), 4.04-3.92 (m, 4H), 2.81-2.61 (m, 2H), 2.38-2.25 (m, 4H), 1.99-1.90 (m, 1H), 1.45 (s, 9H).

Step C: (rac)-tert-Butyl 6-(4-methyl-3-(trifluoromethoxy)phenyl)-2-azaspiro[3.4]octane-2-carboxylate. A mixture of tert-butyl 6-(4-methyl-3-(trifluoromethoxy)phenyl)-2-azaspiro[3.4]oct-5-ene-2-carboxylate (210 mg, 0.433 mmol), wet Pd/C (50 mg, 0.047 mmol), and MeOH (10 mL) was purged with H₂ and then stirred at rt under H₂ (15 psi) for 30 hours. The mixture was filtered through a pad of Celite® and the pad washed with EtOAc. The filtrate was concentrated under reduced pressure to afford the crude product (150 mg, 71%) as a yellow oil, which was used in the next step without further purification. MS (ESI): mass calcd. for $C_{20}H_{26}F_3NO_3$, 385.2; m/z found, 330.2 [M+2H-tBu]⁺. ¹H NMR (400 MHz, CDCl₃) δ 7.18-7.12 (m, 1H), 7.07-6.98 (m, 2H), 3.91-3.78 (m, 4H), 3.13-3.01 (m, 1H), 2.34-2.27 (m, 3H), 2.17-1.90 (m, 4H), 1.88-1.79 (m, 1H), 1.72-1.63 (m, 1H), 1.47-1.44 (m, 9H).

Step D: (rac)-6-(4-Methyl-3-(trifluoromethoxy)phenyl)-2-azaspiro[3.4]octane. A mixture of tert-butyl 6-(4-methyl-3-(trifluoromethoxy)phenyl)-2-azaspiro[3.4]octane-2-carboxylate (150 mg, 0.309 mmol), TFA (0.5 mL), and DCM (5 mL) was stirred at rt for 1 hour. The reaction mixture was concentrated under reduced pressure to afford the crude product (150 mg) as a colorless oil, which was used in the next step without further purification. MS (ESI): mass calcd. for $C_{15}H_{18}F_3NO$, 285.1; m/z found, 286.1 [M+H]⁺.

Step E: (rac)-((1s,3s)-3-Hydroxy-3-methylcyclobutyl)(6-(4-methyl-3-(trifluoromethoxy)phenyl)-2-azaspiro[3.4]octan-2-yl)methanone. HATU (161 mg, 0.423 mmol) was added to a solution of (1s,3s)-3-hydroxy-3-methylcyclobutanecarboxylic acid (50 mg, 0.384 mmol), 6-(4-methyl-3-(trifluoromethoxy)phenyl)-2-azaspiro[3.4]octane (150 mg, crude), and DIPEA (0.32 mL, 1.92 mmol) in DMF (5 mL). The resultant mixture was stirred at rt overnight. The reaction mixture was diluted with EtOAc, quenched with sat. NH₄Cl, and extracted with EtOAc. The combined organic extracts were washed with brine, dried over Na₂SO₄, filtered, and concentrated under reduced pressure. The resulting residue was purified by preparative HPLC (Phenomenex Gemini-NX C18, 75×30 mm×3 μm column, 45% to 75% (v/v) CH₃CN and H₂O with 0.05% NH₃+10 mM NH₄HCO₃) to afford the title compound (32 mg, 21%) as a yellow solid. MS (ESI): mass calcd. for $C_{21}H_{26}F_3NO_3$, 397.2; m/z found, 398.1 [M+H]⁺. ¹H NMR (400 MHz, CDCl₃) δ 7.17 (d, J=7.6 Hz, 1H), 7.05-7.00 (m, 2H), 4.05-3.87 (m, 5H), 3.16-3.00 (m, 1H), 2.71-2.64 (m, 1H), 2.37-2.23 (m, 8H), 2.21-1.94 (m, 3H), 1.91-1.81 (m, 1H), 1.71-1.63 (m, 1H), 1.36 (s, 3H).

Example 108

(rac)-(6-(3-Cyclopropyl-4-fluorophenyl)-2-azaspiro[3.4]octan-2-yl)((1s,3s)-3-hydroxy-3-methylcyclobutyl)methanone

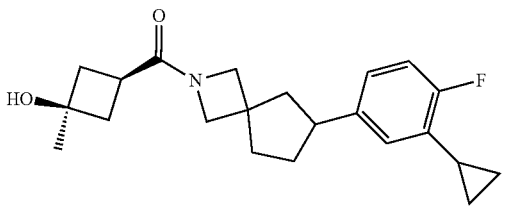 [SMILES: C[C@]1(O)C[C@@H](C(=O)N2CC3(CCC(c4ccc(F)c(C5CC5)c4)C3)C2)C1]

The title compound was prepared in a manner analogous to Example 107 using 2-bromo-1-fluoro-4-iodobenzene instead of 1-bromo-4-iodo-2-(trifluoromethoxy)benzene in Step A and cyclopropylboronic acid instead of 2,4,6-trimethyl-1,3,5,2,4,6-trioxatriborinane in Step B. MS (ESI): mass calcd. for $C_{22}H_{28}FNO_2$, 357.2; m/z found, 358.1 [M+H]⁺. ¹H NMR (400 MHz, CDCl₃) δ 6.93 (d, J=7.6 Hz, 2H), 6.71 (d, J=7.2 Hz, 1H), 4.08-3.85 (m, 5H), 3.10-2.94 (m, 1H), 2.74-2.63 (m, 1H), 2.36-2.22 (m, 5H), 2.17-1.92 (m, 4H), 1.89-1.77 (m, 1H), 1.73-1.64 (m, 1H), 1.36 (s, 3H), 1.00-0.93 (m, 2H), 0.75-0.68 (m, 2H).

Example 109

(rac)-((1s,3s)-3-Hydroxy-3-methylcyclobutyl)(6-(1-methyl-5-(trifluoromethyl)-1H-pyrazol-4-yl)-2-azaspiro[3.4]octan-2-yl)methanone

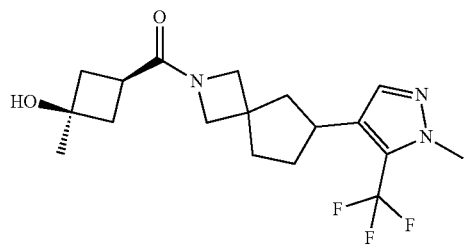 [SMILES: Cn1ncc(C2CCC3(C2)CN(C(=O)[C@H]2C[C@@](C)(O)C2)C3)c1C(F)(F)F]

Step A: (rac)-tert-Butyl 6-(1-methyl-5-(trifluoromethyl)-1H-pyrazol-4-yl)-2-azaspiro[3.4]oct-6-ene-2-carboxylate. tert-Butyl 6-(4,4,5,5-tetramethyl-1,3,2-dioxaborolan-2-yl)-2-azaspiro[3.4]oct-6-ene-2-carboxylate (Intermediate 9, 350 mg, 1.04 mmol), 4-bromo-1-methyl-5-(trifluoromethyl)-1H-pyrazole (287 mg, 1.25 mmol), Cs₂CO₃ (1.02 g, 3.13 mmol), and 2-methyl-2-butanol (10 mL) were combined. The resultant mixture was sparged with N₂ for 5 minutes and then treated with CataCXium® A Pd G3 (38 mg, 0.052 mmol). The mixture was sparged with N₂ for another 5 minutes and then stirred at 90° C. for 3 hours before cooling to rt. The reaction mixture was concentrated under reduced pressure. The resulting residue was purified by FCC (SiO₂, 5-25% EtOAc in ether) to afford the title compound (350 mg, crude) as a yellow oil. MS (ESI): mass calcd. for $C_{17}H_{22}F_3N_3O_2$, 357.2; m/z found, 302.1 [M+2H-tBu]⁺.

Step B: (rac)-tert-Butyl 6-(1-methyl-5-(trifluoromethyl)-1H-pyrazol-4-yl)-2-azaspiro[3.4]octane-2-carboxylate. tert-Butyl 6-(1-methyl-5-(trifluoromethyl)-1H-pyrazol-4-yl)-2-azaspiro[3.4]oct-6-ene-2-carboxylate (350 mg, 0.979 mmol), CH₃OH (10 mL), and dry Pd/C (150 mg, 10 wt. %) were combined. The resultant mixture was stirred under H₂ (15 psi) at rt for 16 hours. The suspension was filtered through a pad of Celite® and the pad washed with CH₃OH. The filtrate was concentrated under reduced pressure to afford the title compound (400 mg, crude) as a yellow oil. MS (ESI): mass calcd. for $C_{17}H_{24}F_3N_3O_2$, 359.2; m/z found, 304.1 [M+2H-tBu]⁺.

Step C: (rac)-6-(1-Methyl-5-(trifluoromethyl)-1H-pyrazol-4-yl)-2-azaspiro[3.4]octane. tert-Butyl 6-(1-methyl-5-(trifluoromethyl)-1H-pyrazol-4-yl)-2-azaspiro[3.4]octane-2-carboxylate (350 mg, 0.974 mmol) was added to a solution of TFA (3 mL) and DCM (6 mL). The reaction mixture was stirred at rt for 1 hour. The reaction mixture was concentrated under reduced pressure to afford the title compound (350 mg, crude, TFA salt) as a yellow oil, which was used in the next step without further purification. MS (ESI): mass calcd. for $C_{12}H_{16}F_3N_3$, 259.1; m/z found, 260.1 [M+H]⁺.

Step D: (rac)-((1s,3s)-3-Hydroxy-3-methylcyclobutyl)(6-(1-methyl-5-(trifluoromethyl)-1H-pyrazol-4-yl)-2-azaspiro[3.4]octan-2-yl)methanone. T₃P® (0.70 mL, 50% in EtOAc, 1.2 mmol) was added to a solution of 6-(1-methyl-5-(trifluoromethyl)-1H-pyrazol-4-yl)-2-azaspiro[3.4]octane (380 mg, crude, TFA salt), (1s,3s)-3-hydroxy-3-methylcyclobutanecarboxylic acid (100 mg, 0.768 mmol), and DIPEA (0.70 mL, 4.00 mmol) in DCM (6 mL). The reaction was stirred at rt for 16 hours. The reaction mixture was poured into H$_2$O and extracted with DCM. The combined organic extracts were dried over Na$_2$SO$_4$, filtered, and concentrated under reduced pressure. The resulting residue was purified by preparative HPLC (Phenomenex Gemini-NX C18 75×30×3 μm, 26% to 56% water (0.05% NH$_3$H$_2$O+10 mM NH$_4$HCO$_3$)-ACN)) to afford the title compound (85 mg). MS (ESI): mass calcd. for C$_{18}$H$_{24}$F$_3$N$_3$O$_2$, 371.2; m/z found, 372.1 [M+H]$^+$. $^1$H NMR (400 MHz, CDCl$_3$) δ 7.33 (d, J=7.3 Hz, 1H), 4.03-3.85 (m, 8H), 3.26-3.11 (m, 1H), 2.70-2.62 (m, 1H), 2.34-2.23 (m, 5H), 2.16-1.91 (m, 3H), 1.87-1.78 (m, 1H), 1.72-1.63 (m, 1H), 1.35 (s, 3H).

Example 110

(rac)-((1s,3s)-3-Hydroxy-3-methylcyclobutyl)(6-(6-(trifluoromethyl)pyridin-2-yl)-2-azaspiro[3.4]octan-2-yl)methanone

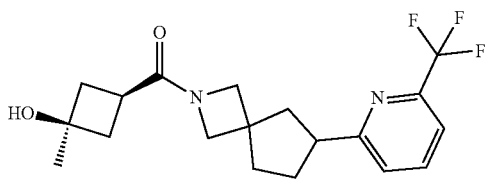 [SMILES: C[C@]1(O)C[C@@H](C(=O)N2CC3(CCC(c4cccc(C(F)(F)F)n4)C3)C2)C1]

The title compound was prepared in a manner analogous to Example 109 using 2-bromo-6-(trifluoromethyl)pyridine instead of 4-bromo-1-methyl-5-(trifluoromethyl)-1H-pyrazole in Step A. MS (ESI): mass calcd. for C$_{19}$H$_{23}$F$_3$N$_2$O$_2$, 368.2; m/z found, 369.1 [M+H]$^+$. $^1$H NMR (400 MHz, CDCl$_3$) δ 7.82-7.69 (m, 1H), 7.55-7.45 (m, 1H), 7.37-7.29 (m, 1H), 4.19-3.92 (m, 5H), 3.47-3.31 (m, 1H), 2.76-2.62 (m, 1H), 2.36-2.20 (m, 6H), 2.19-2.07 (m, 2H), 2.00-1.84 (m, 2H), 1.36 (s, 3H).

Example 111

(rac)-((1s,3s)-3-Hydroxy-3-methylcyclobutyl)(6-(1-methyl-1H-benzo[d]imidazol-5-yl)-2-azaspiro[3.4]octan-2-yl)methanone

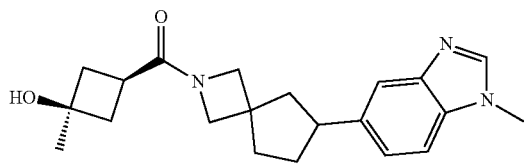 [SMILES: Cn1cnc2cc(C3CCC4(C3)CN(C(=O)[C@H]3C[C@@](C)(O)C3)C4)ccc21]

The title compound was prepared in a manner analogous to Example 109 using 5-bromo-1-methyl-1H-benzo[d]imidazole instead of 4-bromo-1-methyl-5-(trifluoromethyl)-1H-pyrazole in Step A. MS (ESI): mass calcd. for C$_{21}$H$_{27}$N$_3$O$_2$, 353.2; m/z found, 354.1 [M+H]$^+$. $^1$H NMR (400 MHz, MeOD) δ 8.06 (s, 1H), 7.53 (s, 1H), 7.46 (d, J=8.3 Hz, 1H), 7.26 (d, J=8.3 Hz, 1H), 4.13-4.04 (m, 2H), 3.98-3.88 (m, 2H), 3.88 (s, 3H), 3.30-3.21 (m, 1H), 2.76-2.64 (m, 1H), 2.41-2.33 (m, 1H), 2.25 (d, J=9.5 Hz, 2H), 2.21-1.95 (m, 6H), 1.88-1.73 (m, 1H), 1.36 (d, J=1.8 Hz, 3H).

Example 112

(rac)-((1s,3s)-3-Hydroxy-3-methylcyclobutyl)(6-(1-methyl-1H-benzo[d]imidazol-2-yl)-2-azaspiro[3.4]octan-2-yl)methanone

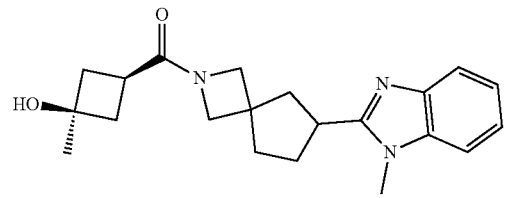 [SMILES: Cn1c(C2CCC3(C2)CN(C(=O)[C@H]2C[C@@](C)(O)C2)C3)nc2ccccc21]

The title compound was prepared in a manner analogous to Example 109 using 2-bromo-1-methyl-1H-benzo[d]imidazole instead of 4-bromo-1-methyl-5-(trifluoromethyl)-1H-pyrazole and Pd(dppf)Cl$_2$ instead of CataCXium® A Pd G3 in Step A. MS (ESI): mass calcd. for C$_{21}$H$_{27}$N$_3$O$_2$, 353.2; m/z found, 354.1 [M+H]$^+$. $^1$H NMR (400 MHz, CDCl$_3$) δ 7.75-7.69 (m, 1H), 7.33-7.28 (m, 1H), 7.27-7.21 (m, 2H), 4.20-3.90 (m, 5H), 3.76-3.72 (m, 3H), 3.51-3.37 (m, 1H), 2.70-2.62 (m, 1H), 2.54-2.44 (m, 1H), 2.39-2.09 (m, 8H), 2.05-2.00 (m, 1H), 1.37-1.33 (m, 3H).

Example 113

((1s,3s)-3-Hydroxy-3-methylcyclobutyl)(7-(3-methoxy-4-(trifluoromethyl)phenyl)-2-azaspiro[3.5]nonan-2-yl)methanone

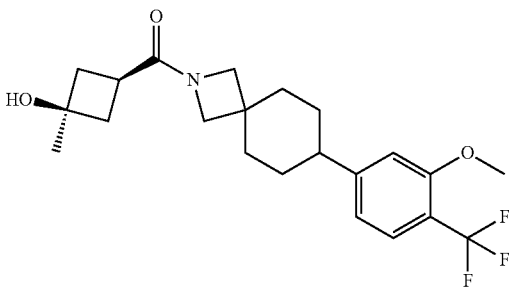 [SMILES: COc1cc(C2CCC3(CC2)CN(C(=O)[C@H]2C[C@@](C)(O)C2)C3)ccc1C(F)(F)F]

The title compound was prepared in a manner analogous to Example 109 using 4-bromo-2-methoxy-1-(trifluoromethyl)benzene instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for C$_{22}$H$_{28}$F$_3$NO$_3$, 411.2; m/z found, 412.1 [M+H]$^+$. $^1$H NMR (400 MHz, CDCl$_3$) δ 7.48 (d, J=8.0 Hz, 1H), 6.84-6.77 (m, 2H), 4.07-3.66 (m, 8H), 2.80-2.63 (m, 2H), 2.60-2.43 (m, 1H), 2.38-2.24 (m, 4H), 2.09-1.98 (m, 2H), 1.95-1.83 (m, 2H), 1.64 (dq, J=3.0, 13.1 Hz, 2H), 1.53-1.38 (m, 2H), 1.37 (s, 3H).

Example 114

((1s,3s)-3-Hydroxy-3-methylcyclobutyl)(7-(4-methoxy-3-(trifluoromethyl)phenyl)-2-azaspiro[3.5]nonan-2-yl)methanone

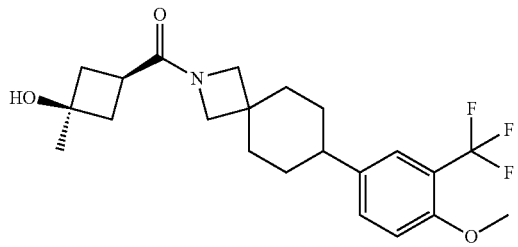 [SMILES: COc1ccc(C2CCC3(CC2)CN(C(=O)[C@H]2C[C@@](C)(O)C2)C3)cc1C(F)(F)F]

The title compound was prepared in a manner analogous to Example 109 using 4-bromo-1-methoxy-2-(trifluoromethyl)benzene instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{22}H_{28}F_3NO_3$, 411.2; m/z found, 412.1 [M+H]$^+$. $^1$H NMR (400 MHz, DMSO-$d_6$) δ 7.48 (d, J=8.5 Hz, 1H), 7.42 (s, 1H), 7.17 (d, J=8.5 Hz, 1H), 3.84 (s, 3H), 3.82 (s, 1H), 3.68 (s, 1H), 3.59 (s, 1H), 3.47 (s, 2H), 2.61-2.54 (m, 1H), 2.16-2.05 (m, 2H), 2.05-1.95 (m, 2H), 1.94-1.84 (m, 2H), 1.73-1.63 (m, 2H), 1.60-1.48 (m, 2H), 1.47-1.32 (m, 2H), 1.23 (d, J=2.5 Hz, 3H).

Example 115

(7-(3-(Dimethylamino)-4-(trifluoromethyl)phenyl)-2-azaspiro[3.5]nonan-2-yl)((1s,3s)-3-hydroxy-3-methylcyclobutyl)methanone

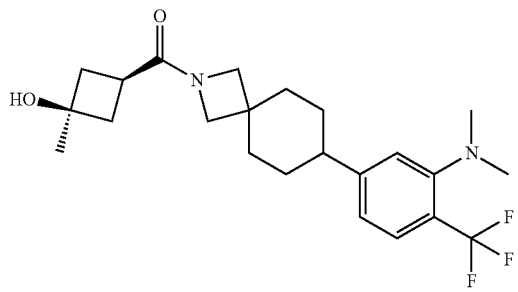 [SMILES: CN(C)c1cc(C2CCC3(CC2)CN(C(=O)[C@H]2C[C@@](C)(O)C2)C3)ccc1C(F)(F)F]

The title compound was prepared in a manner analogous to Example 109 using 5-bromo-N,N-dimethyl-2-(trifluoromethyl)aniline (Intermediate 39) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{23}H_{31}F_3N_2O_2$, 424.2; m/z found, 425.3 [M+H]$^+$. $^1$H NMR (400 MHz, CDCl$_3$) δ 7.57-7.45 (m, 1H), 7.11 (s, 1H), 7.01-6.89 (m, 1H), 3.92-3.62 (m, 4H), 2.83-2.64 (m, 7H), 2.57-2.44 (m, 1H), 2.38-2.22 (m, 4H), 2.10-1.98 (m, 2H), 1.95-1.81 (m, 2H), 1.72-1.56 (m, 2H), 1.53-1.40 (m, 2H), 1.37 (d, J=1.3 Hz, 3H).

Example 116

(7-(6-(tert-Butyl)pyridin-2-yl)-2-azaspiro[3.5]nonan-2-yl)((1s,3s)-3-hydroxy-3-methylcyclobutyl)methanone

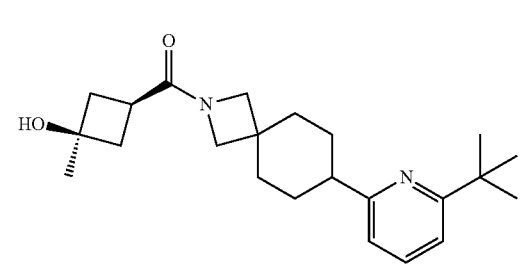

The title compound was prepared in a manner analogous to Example 109 using 2-bromo-6-(tert-butyl)pyridine instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{23}H_{34}N_2O_2$, 370.3; m/z found, 371.3 [M+H]$^+$. $^1$H NMR (400 MHz, CDCl$_3$) δ 7.50 (t, J=7.7 Hz, 1H), 7.12 (d, J=7.9 Hz, 1H), 6.88 (d, J=7.4 Hz, 1H), 3.98 (br s, 1H), 3.86-3.67 (m, 4H), 2.81-2.57 (m, 2H), 2.39-2.22 (m, 4H), 2.06-1.87 (m, 4H), 1.68-1.50 (m, 4H), 1.36 (d, J=1.9 Hz, 3H), 1.34 (d, J=3.6 Hz, 9H).

Example 117

((1s,3s)-3-Hydroxy-3-methylcyclobutyl)(7-(6-methoxypyridin-2-yl)-2-azaspiro[3.5]nonan-2-yl)methanone

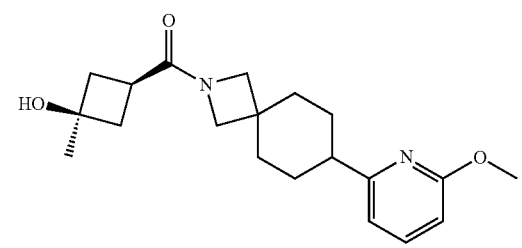 [SMILES: COc1cccc(C2CCC3(CC2)CN(C(=O)[C@H]2C[C@@](C)(O)C2)C3)n1]

The title compound was prepared in a manner analogous to Example 109 using 2-bromo-6-methoxypyridine instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{20}H_{28}N_2O_3$, 344.2; m/z found, 345.2 [M+H]$^+$. $^1$H NMR (400 MHz, CDCl$_3$) δ 7.52-7.44 (m, 1H), 6.73-6.64 (m, 1H), 6.60-6.49

(m, 1H), 3.97-3.65 (m, 7H), 2.79-2.64 (m, 1H), 2.62-2.50 (m, 1H), 2.39-2.22 (m, 4H), 2.08-1.81 (m, 4H), 1.70-1.47 (m, 4H), 1.36 (s, 3H).

Example 118

(7-(3-(tert-Butyl)-4-methoxyphenyl)-2-azaspiro[3.5]nonan-2-yl)((1s,3s)-3-hydroxy-3-methylcyclobutyl)methanone

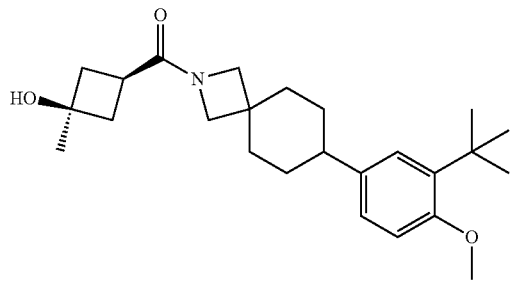 [SMILES: COc1ccc(C2CCC3(CC2)CN(C(=O)[C@H]2C[C@@](C)(O)C2)C3)cc1C(C)(C)C]

The title compound was prepared in a manner analogous to Example 109 using 4-bromo-2-(tert-butyl)-1-methoxybenzene (Intermediate 40) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{25}H_{37}NO_3$, 399.3; m/z found, 400.2 [M+H]$^+$. $^1$H NMR (400 MHz, DMSO-d$_6$) δ 7.06-6.95 (m, 2H), 6.90-6.83 (m, 1H), 5.01 (br s, 1H), 3.81-3.46 (m, 7H), 2.62-2.54 (m, 1H), 2.43-2.31 (m, 1H), 2.16-1.97 (m, 4H), 1.92-1.83 (m, 2H), 1.73-1.62 (m, 2H), 1.58-1.46 (m, 2H), 1.39-1.21 (m, 14H).

Example 119

((1s,3s)-3-Hydroxy-3-methylcyclobutyl)(7-(3-methoxy-5-(trifluoromethyl)phenyl)-2-azaspiro[3.5]nonan-2-yl)methanone

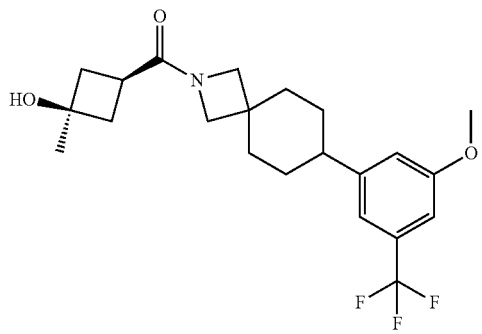 [SMILES: COc1cc(C2CCC3(CC2)CN(C(=O)[C@H]2C[C@@](C)(O)C2)C3)cc(C(F)(F)F)c1]

The title compound was prepared in a manner analogous to Example 109 using 1-bromo-3-methoxy-5-(trifluoromethyl)benzene instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{22}H_{28}F_3NO_3$, 411.2; m/z found, 412.1 [M+H]$^+$. $^1$H NMR (400 MHz, DMSO-d$_6$) δ 7.19-6.98 (m, 3H), 5.00 (d, J=5.8 Hz, 1H), 3.85-3.78 (m, 4H), 3.69 (s, 1H), 3.61 (s, 1H), 3.47 (s, 1H), 2.65-2.53 (m, 2H), 2.16-2.06 (m, 2H), 2.05-1.95 (m, 2H), 1.94-1.85 (m, 2H), 1.76-1.65 (m, 2H), 1.60-1.37 (m, 4H), 1.24 (d, J=2.5 Hz, 3H).

Example 120

(7-(3-Ethoxy-5-(trifluoromethyl)phenyl)-2-azaspiro[3.5]nonan-2-yl)((1s,3s)-3-hydroxy-3-methylcyclobutyl)methanone

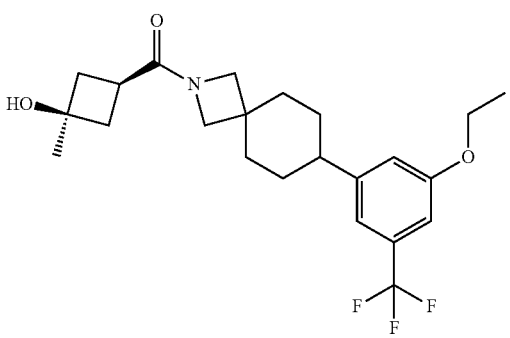 [SMILES: CCOc1cc(C2CCC3(CC2)CN(C(=O)[C@H]2C[C@@](C)(O)C2)C3)cc(C(F)(F)F)c1]

The title compound was prepared in a manner analogous to Example 109 using 1-bromo-3-ethoxy-5-(trifluoromethyl)benzene instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{23}H_{30}F_3NO_3$, 425.2; m/z found, 426.2 [M+H]$^+$. $^1$H NMR (400 MHz, DMSO-d$_6$) δ 7.20-6.92 (m, 3H), 5.00 (d, J=6.0 Hz, 1H), 4.09 (q, J=7.0 Hz, 2H), 3.82 (s, 1H), 3.69 (s, 1H), 3.60 (s, 1H), 3.47 (s, 1H), 2.63-2.53 (m, 2H), 2.17-2.06 (m, 2H), 2.05-1.96 (m, 2H), 1.94-1.85 (m, 2H), 1.76-1.65 (m, 2H), 1.61-1.40 (m, 4H), 1.32 (t, J=7.0 Hz, 3H), 1.24 (d, J=2.7 Hz, 3H).

Example 121

(7-(3-Ethyl-5-methylphenyl)-2-azaspiro[3.5]nonan-2-yl)((1s,3s)-3-hydroxy-3-methylcyclobutyl)methanone

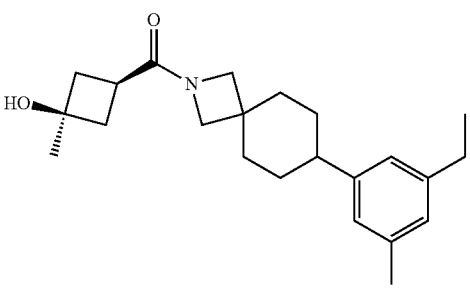 [SMILES: CCc1cc(C)cc(C2CCC3(CC2)CN(C(=O)[C@H]2C[C@@](C)(O)C2)C3)c1]

The title compound was prepared in a manner analogous to Example 109 using 1-bromo-3-ethyl-5-methylbenzene instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{23}H_{33}NO_2$, 355.3; m/z found, 356.2 [M+H]$^+$. $^1$H NMR (400 MHz, CDCl$_3$) δ 6.87 (s, 1H), 6.81 (s, 2H), 3.90-3.64 (m, 4H), 2.74-2.55 (m, 3H), 2.49-2.37 (m, 1H), 2.36-2.26 (m, 7H), 2.07-1.93 (m, 2H), 1.92-1.77 (m, 2H), 1.71-1.53 (m, 2H), 1.52-1.40 (m, 2H), 1.37 (s, 3H), 1.23 (t, J=7.5 Hz, 3H).

Example 122

((1s,3s)-3-Hydroxy-3-methylcyclobutyl)(7-(1-methyl-1H-indazol-5-yl)-2-azaspiro[3.5]nonan-2-yl)methanone

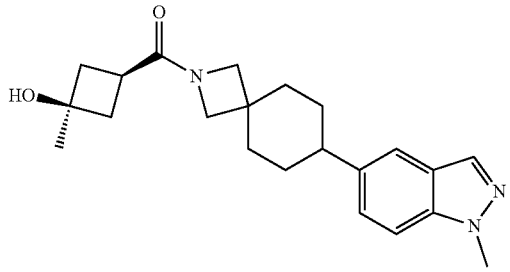 [SMILES: Cn1ncc2cc(C3CCC4(CC3)CN(C(=O)[C@H]3C[C@@](C)(O)C3)C4)ccc21]

The title compound was prepared in a manner analogous to Example 109 using 5-bromo-1-methyl-1H-indazole instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{22}H_{29}N_3O_2$, 367.2; m/z found, 368.1 [M+H]$^+$. $^1$H NMR (400 MHz, DMSO-d$_6$) δ 7.93 (s, 1H), 7.55-7.50 (m, 2H), 7.30-7.26 (m, 1H), 5.02-5.00 (m, 1H), 4.00 (s, 3H), 3.86-3.47 (m, 4H), 2.62-2.53 (m, 2H), 2.15-2.07 (m, 2H), 2.06-1.97 (m, 2H), 1.95-1.87 (m, 2H), 1.80-1.70 (m, 2H), 1.64-1.40 (m, 4H), 1.27-1.22 (m, 3H).

Example 123

(7-(3-(Dimethylamino)-5-(trifluoromethyl)phenyl)-2-azaspiro[3.5]nonan-2-yl)((1s,3s)-3-hydroxy-3-methylcyclobutyl)methanone

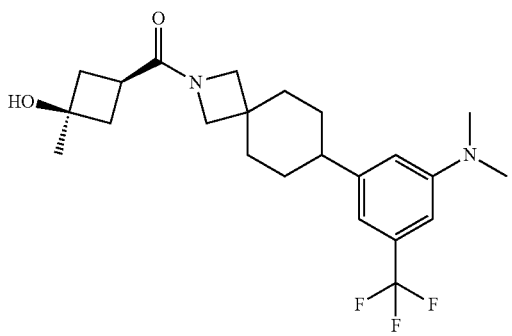 [SMILES: CN(C)c1cc(C2CCC3(CC2)CN(C(=O)[C@H]2C[C@@](C)(O)C2)C3)cc(C(F)(F)F)c1]

The title compound was prepared in a manner analogous to Example 109 using 3-bromo-5-(trifluoromethyl)aniline (Intermediate 38) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{23}H_{31}F_3N_2O_2$, 424.2; m/z found, 425.4 [M+H]$^+$. $^1$H NMR (400 MHz, CDCl$_3$) δ 6.75 (s, 2H), 6.64 (s, 1H), 3.87 (s, 1H), 3.80 (s, 1H), 3.76 (s, 1H), 3.70 (s, 1H), 3.00 (s, 6H), 2.78-2.64 (m, 1H), 2.55-2.43 (m, 1H), 2.39-2.22 (m, 4H), 2.06-1.98 (m, 2H), 1.94-1.85 (m, 2H), 1.68-1.58 (m, 2H), 1.52-1.40 (m, 2H), 1.37 (d, J=2.7 Hz, 3H).

Example 124

((1s,3s)-3-Hydroxy-3-methylcyclobutyl)(7-(quinolin-2-yl)-2-azaspiro[3.5]nonan-2-yl)methanone

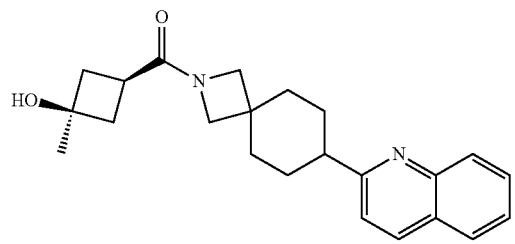 [SMILES: C[C@]1(O)C[C@@H](C(=O)N2CC3(CCC(c4ccc5ccccc5n4)CC3)C2)C1]

The title compound was prepared in a manner analogous to Example 109 using 2-bromoquinoline instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{23}H_{28}N_2O_2$, 364.2; m/z found, 365.2 [M+H]$^+$. $^1$H NMR (400 MHz, DMSO-d$_6$) δ 8.33-8.21 (m, 1H), 7.98-7.86 (m, 2H), 7.77-7.66 (m, 1H), 7.60-7.41 (m, 2H), 3.85 (s, 1H), 3.72 (s, 1H), 3.62 (s, 1H), 3.51 (s, 1H), 2.89-2.78 (m, 1H), 2.64-2.53 (m, 1H), 2.17-2.08 (m, 2H), 2.07-1.98 (m, 2H), 1.98-1.92 (m, 2H), 1.91-1.83 (m, 2H), 1.72-1.55 (m, 4H), 1.25 (s, 3H).

Example 125

(rac)-(6-(3-Fluoro-5-isopropylphenyl)-2-azaspiro[3.4]octan-2-yl)((1s,3s)-3-hydroxy-3-methylcyclobutyl)methanone

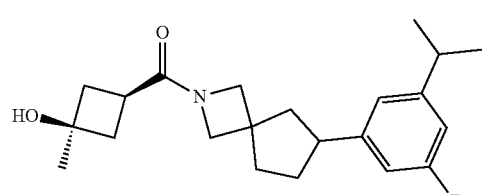

Step A: (rac)-tert-Butyl 6-(3-bromo-5-fluorophenyl)-2-azaspiro[3.4]octane-2-carboxylate. tert-Butyl 6-(2-tosylhydrazineylidene)-2-azaspiro[3.4]octane-2-carboxylate (Intermediate 5, 2.22 mmol) in 1,4-dioxane (5 mL) was treated with K₂CO₃ (460 mg, 3.33 mmol) and (3-bromo-5-fluorophenyl)boronic acid (728 mg, 3.33 mmol). This was heated to 110° C. for 12 h before being cooled to rt, quenched with sat. NH₄Cl, and extracted with EtOAc. The combined organic extracts were washed with brine, dried over Na₂SO₄, filtered, and concentrated under reduced pressure. The resulting residue was purified by FCC (SiO₂, 0-50% EtOAc in ether) to afford the title compound (400 mg) as a brown oil.

Step B: (rac)-tert-Butyl 6-(3-fluoro-5-(prop-1-en-2-yl) phenyl)-2-azaspiro[3.4]octane-2-carboxylate. tert-Butyl 6-(3-bromo-5-fluorophenyl)-2-azaspiro[3.4]octane-2-carboxylate (400 mg, 1.04 mmol), potassium trifluoro(prop-1-en-2-yl)borate (231 mg, 1.56 mmol), Na₂CO₃ (441 mg, 4.16 mmol), Pd(dppf)Cl₂ (152 mg, 0.21 mmol), 1,4-dioxane (4 mL), and THF (1 mL) were combined. The reaction mixture was stirred at 100° C. for 16 hours before being cooled to rt, quenched with H₂O, and extracted with EtOAc. The combined organic extracts were washed with brine, dried over Na₂SO₄, filtered, and concentrated under reduced pressure. The resulting residue was purified by FCC (SiO₂, 0-50% EtOAc in ether) to afford the title compound (200 mg, 49%) as a brown oil. MS (ESI): mass calcd. for C₂₁H₂₈BFNO₂, 345.2; m/z found, 331.1 [M+2H+MeCN-tBu]⁺.

Step C: (rac)-tert-Butyl 6-(3-ethyl-5-fluorophenyl)-2-azaspiro[3.4]octane-2-carboxylate. tert-Butyl 6-(3-fluoro-5-(prop-1-en-2-yl)phenyl)-2-azaspiro[3.4]octane-2-carboxylate (200 mg, 0.58 mmol), PtO₂ (50 mg, 0.22 mmol) and MeOH (4 mL) were combined. The resultant mixture was stirred under H₂ (15 psi) at rt for 2 hours. The suspension was filtered through a pad of Celite® and the pad washed with EtOAc. The filtrate was concentrated under reduced pressure to afford the title product (200 mg, crude) as a colorless oil. MS (ESI): mass calcd. for C₂₁H₃₀FNO₂, 347.2; m/z found, 333.0 [M+2H+MeCN-tBu]⁺.

Step D: (rac)-6-(3-Fluoro-5-isopropylphenyl)-2-azaspiro[3.4]octane. TFA (2 mL) was added to a solution of tert-butyl 6-(3-fluoro-5-isopropylphenyl)-6-hydroxy-2-azaspiro[3.4]octane-2-carboxylate (200 mg, 0.55 mmol) and DCM (2 mL). The resultant mixture was stirred at rt for 1 h. The reaction mixture was concentrated under reduced pressure to give the crude product (200 mg), which was used for the next step without purification. MS (ESI): mass calcd. for C₂₁H₃₀FNO₂, 247.2; m/z found, 248.2 [M+H]⁺.

Step E: (rac)-(6-(3-Fluoro-5-isopropylphenyl)-2-azaspiro [3.4]octan-2-yl)((1s,3s)-3-hydroxy-3-methylcyclobutyl) methanone. HATU (229 mg, 0.60 mmol) was added to a solution of 6-(3-fluoro-5-isopropylphenyl)-2-azaspiro[3.4] octane (200 mg, 0.55 mmol), (1s,3s)-3-hydroxy-3-methylcyclobutanecarboxylic acid (52 mg, 0.40 mmol), and DIPEA (208 mg, 1.61 mmol) in DMF (4 mL). The resultant mixture was stirred at rt for 17 h. The reaction mixture was quenched with H₂O and extracted with EtOAc. The combined organic extracts were washed with brine, dried over Na₂SO₄, filtered, and concentrated under reduced pressure. The resulting residue was purified by preparative HPLC (Boston Prime C18, 150×30 mm×5 um, 55% to 85% (v/v) CH₃CN and water with 0.05% NH₃) to afford the title compound (47 mg, 24%) as a yellow syrupy solid. MS (ESI): mass calcd. for C₂₂H₃₀FNO₂, 359.2; m/z found, 360.1 [M+H]⁺. ¹H NMR (400 MHz, CDCl₃) δ 6.82 (s, 1H), 6.78-6.75 (m, 1H), 6.73-6.70 (m, 1H), 4.12 (br s, 1H), 4.03 (s, 1H), 3.99-3.95 (m, 2H), 3.90 (d, J=2.4 Hz, 1H), 3.17-3.01 (m, 1H), 2.89-2.85 (m, 1H), 2.73-2.60 (m, 1H), 2.30 (d, J=7.6 Hz, 5H), 2.21-1.91 (m, 4H), 1.77-1.66 (m, 1H), 1.36 (s, 3H), 1.23 (d, J=6.8 Hz, 6H).

Example 126

(rac)-(6-(3-(tert-Butyl)phenyl)-2-azaspiro[3.4]octan-2-yl)((1r,3s)-3-ethyl-3-hydroxycyclobutyl)methanone

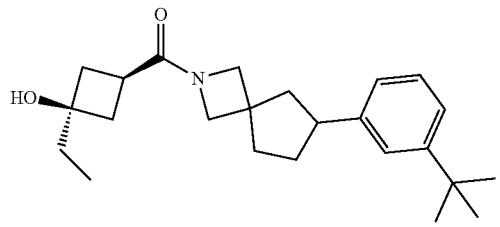 [SMILES: CC[C@]1(O)C[C@@H](C(=O)N2CC3(CCC(c4cccc(C(C)(C)C)c4)C3)C2)C1]

Step A: (rac)-tert-Butyl 6-(3-(tert-butyl)phenyl)-6-hydroxy-2-azaspiro[3.4]octane-2-carboxylate. In an oven-dried flask under N₂, 2-Boc-6-oxo-2-azaspiro[3.4]octane (100 mg, 0.444 mmol) was taken up in anhydrous THF (2.2 mL) and cooled to –78° C. 3-tert-Butylphenylmagnesium bromide (0.5M in THF, 0.9 mL) was added dropwise. This was allowed to warm to rt and stirred 1 h before being quenched with sat. aq. NH₄Cl and extracted with EtOAc. The combined organic layers were dried over Na₂SO₄, filtered, and concentrated under reduced pressure. Purification via FCC (SiO₂, 0-100% EtOAc in hexane) provided the title compound (67 mg, 42% yield). MS (ESI): mass calcd. for C₂₂H₃₃NO₃, 359.2; m/z found, 286.1 [M-tBu-OH+H]⁺.

Step B: (rac)-6-(3-(tert-Butyl)phenyl)-2-azaspiro[3.4]octane. tert-Butyl 6-(3-(tert-butyl)phenyl)-6-hydroxy-2-azaspiro[3.4]octane-2-carboxylate (67 mg, 0.186 mmol) was taken up in TFA (1.2 mL) and stirred for 5 min at rt. TES (90 μL, 0.559 mmol) was added and this was stirred for 1 h at rt before concentrating under reduced pressure. The title compound was used without further purification in the next step. MS (ESI): mass calcd. for C₁₇H₂₅N, 243.2; m/z found, 244.2 [M+H]⁺.

Step C: (rac)-3-(6-(3-(tert-Butyl)phenyl)-2-azaspiro[3.4] octane-2-carbonyl)cyclobutan-1-one. 6-(3-(tert-Butyl)phenyl)-2-azaspiro[3.4]octane (30 mg, 0.084 mmol) and 3-oxocyclobutanecarboxylic acid (11 mg, 0.092 mmol) were taken up in DCM (0.4 mL). DIPEA (43 μL, 0.252 mmol) and HATU (39 mg, 0.101 mmol) were added and the reaction was stirred at rt for 1 h. The reaction mixture was concentrated under reduced pressure. Purification via FCC (SiO₂, 0-70% EtOAc in hexane) provided the title compound (28 mg, 100% yield). MS (ESI): mass calcd. for C₂₂H₂₉NO₂, 339.2; m/z found, 340.2 [M+H]⁺.

Step D: (rac)-(6-(3-(tert-Butyl)phenyl)-2-azaspiro[3.4] octan-2-yl)((1r,3s)-3-ethyl-3-hydroxycyclobutyl)methanone. In an oven-dried flask under N₂, 3-(6-(3-(tert-butyl) phenyl)-2-azaspiro[3.4]octane-2-carbonyl)cyclobutan-1-one (28 mg, 0.082 mmol) was taken up in anhydrous THF (0.4 mL) and cooled to –78° C. Ethylmagnesium bromide (1M in THF, 0.12 mL) was added dropwise. This was allowed to warm to rt and stirred 1 h before re-cooling to –78° C. and adding another aliquot of ethylmagnesium bromide (0.12 mL). The reaction was allowed to warm to rt and stirred for 1.5 h before being quenched with sat. aq. NH₄Cl and extracted with EtOAc. The combined organic layers were dried over Na₂SO₄, filtered, and concentrated under reduced pressure. Purification via RP HPLC (5-95% MeCN in 20 mM NH₄OH in water) afforded the title compound (1.5 mg, 5% yield). MS (ESI): mass calcd. for C₂₄H₃₅NO₂, 369.3; m/z found, 370.3 [M+H]⁺. ¹H NMR (500 MHz, Chloroform-d) δ 7.25-7.22 (m, 2H), 7.21 (s, 1H), 7.04-6.99 (m, 1H), 4.06-3.85 (m, 4H), 3.18-3.01 (m, 1H), 2.67 (tt, J=8.4, 5.9 Hz, 1H), 2.32 (dd, J=12.7, 8.5 Hz, 3H), 2.17 (dd, J=12.8, 5.9 Hz, 3H), 2.09-1.85 (m, 3H), 1.85-1.67 (m, 2H), 1.59 (q, J=7.4 Hz, 2H), 1.32 (s, 9H), 0.93 (t, J=7.4 Hz, 3H).

Example 127

(7-(2,3-Dihydro-1H-inden-5-yl)-2-azaspiro[3.5] nonan-2-yl)((1s,3s)-3-hydroxy-3-methylcyclobutyl) methanone

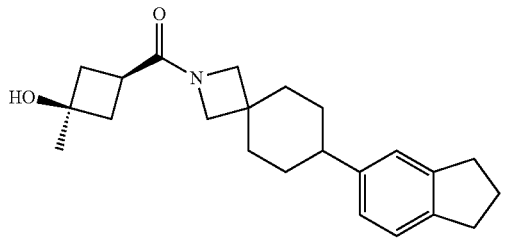 [SMILES: C[C@]1(O)C[C@@H](C(=O)N2CC3(CCC(c4ccc5c(c4)CCC5)CC3)C2)C1]

Step A: tert-Butyl 7-(2,3-dihydro-1H-inden-5-yl)-7-hydroxy-2-azaspiro[3.5]nonane-2-carboxylate. A mixture of magnesium turnings (99 mg, 4.1 mmol) and iodine (10 mg, 0.04 mmol) under N₂ was heated at 100° C. for 10 min. Anhydrous THF (4 mL) was added and a solution of 5-bromo-indan (807 mg, 4.1 mmol) in THF (1 mL) was added dropwise, keeping the mixture at reflux for 15 min. The mixture was cooled to rt, tert-butyl-7-oxo-2-azaspiro [3.5]nonane-2-carboxylate (200 mg, 0.8 mmol) in THF (1 mL) was added dropwise, and The reaction mixture was stirred at rt for 16 h. The reaction mixture was quenched with sat. aq. NH₄Cl and extracted with EtOAc and water. The organic phase was dried over MgSO₄, filtered, and concentrated in vacuo. The crude was purified via FCC (SiO₂, 0-50% EtOAc in heptane) to provide the title compound as a white solid (214 mg, 73% yield). MS (ESI): mass calcd. for C₂₂H₃₁NO₃, 357.2; m/z found, 258.1 [M+H-Boc]⁺. ¹H NMR (300 MHz, CDCl₃) δ 7.34 (s, 1H), 7.22 (d, J=4.6 Hz, 2H), 3.68 (s, 2H), 3.64 (s, 2H), 2.90 (dd, J=13.1, 6.8 Hz, 4H), 2.20-1.93 (m, 4H), 1.87-1.73 (m, 6H), 1.45 (s, 9H).

Step B: 7-(2,3-Dihydro-1H-inden-5-yl)-2-azaspiro[3.5] non-6-ene. TFA (0.55 mL, 7.2 mmol) was added to a solution of tert-butyl 7-(2,3-dihydro-1H-inden-5-yl)-7-hydroxy-2-azaspiro[3.5]nonane-2-carboxylate (214 mg, 0.6 mmol) in dichloroethane (4 mL). The reaction mixture was stirred at 60° C. for 30 min then treated with Amberlist A26 until pH around 7. The Amberlist was filtered and washed with MeOH. The filtrate was concentrated in vacuo to afford a pale orange oil which was used in the next step without further purification. MS (ESI): mass calcd. for C₁₇H₂₁N, 239.2; m/z found, 240.2 [M+H]⁺. ¹H NMR (300 MHz, CDCl₃) δ 7.18 (s, 1H), 7.15 (s, 2H), 5.97 (s, 1H), 3.56 (dd, J=19.2, 8.5 Hz, 4H), 2.95-2.82 (m, 4H), 2.49 (s, 4H), 2.36 (s, 2H), 2.13-1.92 (m, 3H).

Step C: 7-(2,3-Dihydro-1H-inden-5-yl)-2-azaspiro[3.5] nonane. A mixture of 7-(2,3-dihydro-1H-inden-5-yl)-2-azaspiro[3.5]non-6-ene (143 mg, 0.6 mmol), 10 wt % Pd/C (14.3 mg) and MeOH (3 mL) was stirred under H₂ at 50° C. for 1 h. The reaction mixture was filtered through Celite® and washed with MeOH. The filtrate was concentrated in vacuo to yield a beige solid which was used in the next step without further purification. MS (ESI): mass calcd. for C₁₇H₂₃N, 241.2; m/z found, 242.1 [M+H]⁺.

Step D: (7-(2,3-Dihydro-1H-inden-5-yl)-2-azaspiro[3.5] nonan-2-yl)((1s,3s)-3-hydroxy-3-methylcyclobutyl)methanone. A solution of 50 wt % T3P® in EtOAc (0.21 mL, 0.36 mmol,) and DIPEA (0.12 mL, 0.7 mmol) were added to a solution of (1s,3s)-3-hydroxy-3-methylcyclobutane-1-carboxylic acid (55 mg, 0.42 mmol) in DMF (2.2 mL). The reaction mixture was stirred for 10 min at rt, then a solution of 7-(2,3-dihydro-1H-inden-5-yl)-2-azaspiro[3.5]nonane (100 mg, 0.28 mmol) in DMF (1 mL) was added, and the reaction mixture was stirred at rt for 16 h. Sat. aq. NaHCO₃ was added and the mixture was extracted with EtOAc. The organic layers were dried over MgSO₄, filtered, and concentrated under reduced pressure. The mixture was purified via FCC (SiO₂, 0-20% 5% MeOH/DCM in DCM) to provide the title compound as a pale brown solid (56 mg, 53% yield). MS (ESI): mass calcd. for C₂₃H₃₁NO₂, 353.2; m/z found, 354.2 [M+H]⁺. ¹H NMR (400 MHz, CDCl₃) δ 7.15 (d, J=7.7 Hz, 1H), 7.05 (s, 1H), 6.94 (d, J=7.7 Hz, 1H), 3.83 (s, 1H), 3.80 (s, 1H), 3.77 (s, 1H), 3.73 (s, 1H), 3.68 (s, 1H), 2.95-2.78 (m, 4H), 2.78-2.63 (m, 1H), 2.51-2.40 (m, 1H), 2.37-2.21 (m, 4H), 2.12-2.03 (m, 2H), 1.99 (d, J=13.2 Hz, 2H), 1.90-1.80 (m, 2H), 1.68-1.52 (m, 3H), 1.51-1.37 (m, 1H), 1.35 (d, J=2.7 Hz, 3H).

Example 128

((1s,3s)-3-Hydroxy-3-methylcyclobutyl)(7-(3-methoxy-5-methylphenyl)-2-azaspiro[3.5]nonan-2-yl)methanone

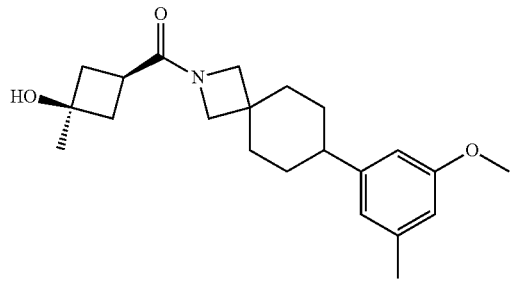 [SMILES: COc1cc(C)cc(C2CCC3(CC2)CN(C(=O)[C@H]2C[C@@](C)(O)C2)C3)c1]

The title compound was prepared in a manner analogous to Example 127 using 1-bromo-3-methoxy-5-methylbenzene instead of 5-bromo-indan in Step A. MS (ESI): mass calcd. for C₂₂H₃₁NO₃, 357.2; m/z found, 358.2 [M+H]⁺. ¹H NMR (400 MHz, CDCl₃) δ 6.59 (s, 1H), 6.56 (s, 1H), 6.52 (s, 1H), 3.84-3.67 (m, 8H), 2.80-2.62 (m, 1H), 2.48-2.37 (m, 1H), 2.37-2.28 (m, 5H), 2.28-2.20 (m, 2H), 1.99 (d, J=12.9 Hz, 2H), 1.92-1.80 (m, 2H), 1.69-1.53 (m, 2H), 1.50-1.36 (m, 2H), 1.35 (d, J=2.8 Hz, 3H).

Example 129

((1s,3s)-3-Hydroxy-3-methylcyclobutyl)(7-(3-methoxy-4-methylphenyl)-2-azaspiro[3.5]nonan-2-yl)methanone

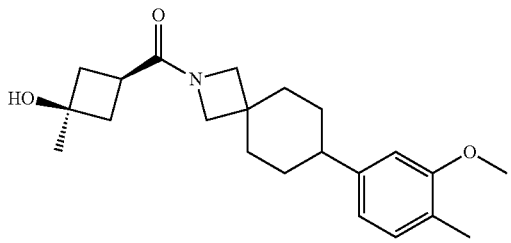 [SMILES: COc1cc(C2CCC3(CC2)CN(C(=O)[C@H]2C[C@@](C)(O)C2)C3)ccc1C]

The title compound was prepared in a manner analogous to Example 127 using 4-bromo-2-methoxy-1-methylbenzene instead of 5-bromo-indan in Step A. MS (ESI): mass calcd. for $C_{22}H_{31}NO_3$, 357.2; m/z found, 358.2 [M+H]$^+$. $^1$H NMR (400 MHz, CDCl$_3$) δ 7.05 (d, J=7.5 Hz, 1H), 6.67 (d, J=7.4 Hz, 1H), 6.63 (s, 1H), 3.83 (d, J=5.0 Hz, 4H), 3.78 (s, 1H), 3.73 (d, J=7.9 Hz, 2H), 3.69 (s, 1H), 2.78-2.66 (m, 1H), 2.46 (s, 1H), 2.38-2.29 (m, 2H), 2.28-2.20 (m, 2H), 2.18 (s, 3H), 2.00 (d, J=13.0 Hz, 2H), 1.88 (s, 2H), 1.62 (dd, J=19.7, 6.6 Hz, 2H), 1.45 (dd, J=22.3, 9.8 Hz, 2H), 1.36 (s, 3H).

Example 130

((1s,3s)-3-Hydroxy-3-methylcyclobutyl)(7-(4-isopropylphenyl)-2-azaspiro[3.5]nonan-2-yl)methanone

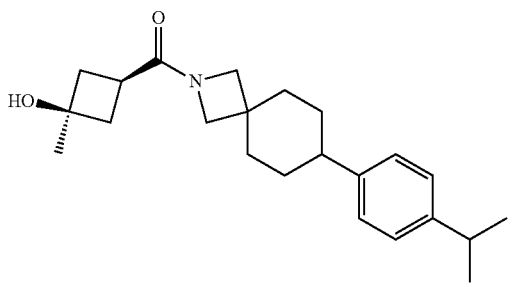 [SMILES: CC(C)c1ccc(C2CCC3(CC2)CN(C(=O)[C@H]2C[C@@](C)(O)C2)C3)cc1]

The title compound was prepared in a manner analogous to Example 127 using 1-bromo-4-isopropylbenzene instead of 5-bromo-indan in Step A. MS (ESI): mass calcd. for $C_{23}H_{33}NO_2$, 355.3; m/z found, 356.2 [M+H]$^+$. $^1$H NMR (400 MHz, CDCl$_3$) δ 7.15 (d, J=8.1 Hz, 2H), 7.09 (d, J=8.2 Hz, 2H), 3.78 (br s, 3H), 3.71 (br s, 2H), 2.87 (hept, J=6.9 Hz, 1H), 2.66 (br s, 1H), 2.44 (t, J=11.9 Hz, 1H), 2.36-2.26 (m, 4H), 1.98 (d, J=13.1 Hz, 2H), 1.90-1.81 (m, 2H), 1.60 (t, J=12.5 Hz, 2H), 1.49-1.34 (m, 5H), 1.24 (d, J=6.9 Hz, 6H).

Example 131

((1s,3s)-3-Hydroxy-3-methylcyclobutyl)(7-(3-methoxyphenyl)-2-azaspiro[3.5]nonan-2-yl)methanone

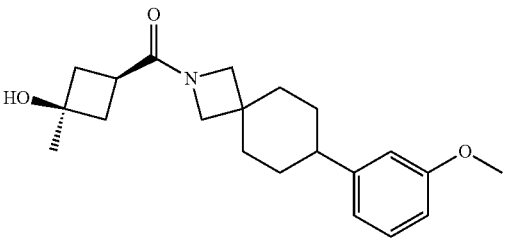 [SMILES: COc1cccc(C2CCC3(CC2)CN(C(=O)[C@H]2C[C@@](C)(O)C2)C3)c1]

The title compound was prepared in a manner analogous to Example 127 using 1-bromo-3-methoxybenzene instead of 5-bromo-indan in Step A. MS (ESI): mass calcd. for $C_{21}H_{29}NO_3$, 343.2; m/z found, 344.2 [M+H]$^+$. $^1$H NMR (400 MHz, CDCl$_3$) δ 7.21 (t, J=7.8 Hz, 1H), 6.79-6.69 (m, 3H), 3.88-3.51 (m, 8H), 2.67 (br s, 1H), 2.45 (t, J=11.8 Hz, 1H), 2.37-2.24 (m, 4H), 1.99 (d, J=12.9 Hz, 2H), 1.86 (d, J=12.6 Hz, 2H), 1.60 (t, J=12.1 Hz, 2H), 1.51-1.38 (m, 2H), 1.36 (s, 3H).

Example 132

(7-(3-Ethoxyphenyl)-2-azaspiro[3.5]nonan-2-yl)((1s,3s)-3-hydroxy-3-methylcyclobutyl)methanone

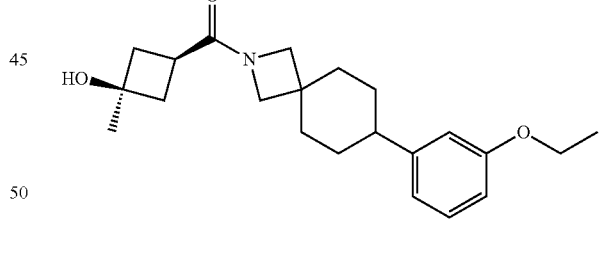

The title compound was prepared in a manner analogous to Example 127 using 1-bromo-3-ethoxybenzene instead of 5-bromo-indan in Step A. MS (ESI): mass calcd. for $C_{22}H_{31}NO_3$, 357.2; m/z found, 358.2 [M+H]$^+$. $^1$H NMR (400 MHz, CDCl$_3$) δ 7.20 (td, J=7.6, 1.3 Hz, 1H), 6.78-6.70 (m, 3H), 4.02 (q, J=7.0 Hz, 2H), 3.80 (s, 2H), 3.71 (s, 2H), 2.76-2.66 (m, 1H), 2.57-2.39 (m, 3H), 2.37-2.23 (m, 4H), 1.99 (d, J=13.1 Hz, 2H), 1.87 (d, J=11.7 Hz, 2H), 1.61 (td, J=13.0, 2.7 Hz, 2H), 1.48-1.38 (m, 4H), 1.36 (s, 3H).

Example 133

((1s,3s)-3-Hydroxy-3-methylcyclobutyl)(7-(3-isopropylphenyl)-2-azaspiro[3.5]nonan-2-yl)methanone

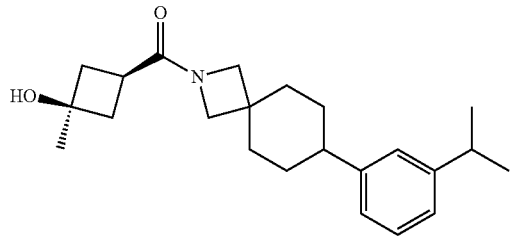 [SMILES: CC(C)c1cccc(C2CCC3(CC2)CN(C(=O)[C@H]2C[C@@](C)(O)C2)C3)c1]

The title compound was prepared in a manner analogous to Example 127 using 1-bromo-3-isopropylbenzene instead of 5-bromo-indan in Step A. MS (ESI): mass calcd. for $C_{23}H_{33}NO_2$, 355.3; m/z found, 356.2 [M+H]$^+$. $^1$H NMR (400 MHz, DMSO-d$_6$) δ 7.18 (t, J=7.5 Hz, 1H), 7.09-6.96 (m, 3H), 4.99 (d, J=3.5 Hz, 1H), 3.82 (s, 1H), 3.69 (s, 1H), 3.60 (s, 1H), 3.47 (s, 1H), 2.91-2.77 (m, 1H), 2.63-2.52 (m, 1H), 2.47-2.37 (m, 1H), 2.15-2.06 (m, 2H), 2.06-1.96 (m, 2H), 1.94-1.85 (m, 2H), 1.74-1.64 (m, 2H), 1.59-1.49 (m, 2H), 1.49-1.33 (m, 2H), 1.24 (d, J=3.8 Hz, 3H), 1.19 (d, J=6.9 Hz, 6H).

Example 134

(7-(3,4-Dimethylphenyl)-2-azaspiro[3.5]nonan-2-yl)((1s,3s)-3-hydroxy-3-methylcyclobutyl)methanone

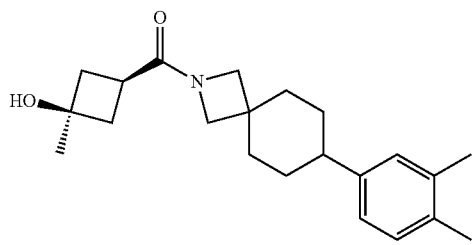 [SMILES: Cc1ccc(C2CCC3(CC2)CN(C(=O)[C@H]2C[C@@](C)(O)C2)C3)cc1C]

The title compound was prepared in a manner analogous to Example 127 using 4-bromo-1,2-dimethylbenzene instead of 5-bromo-indan in Step A. MS (ESI): mass calcd. for $C_{22}H_{31}NO_2$, 341.2; m/z found, 342.2 [M+H]$^+$. $^1$H NMR (400 MHz, CDCl$_3$) δ 7.06 (d, J=7.7 Hz, 1H), 6.94 (s, 1H), 6.91 (d, J=7.7 Hz, 1H), 3.83 (s, 2H), 3.77 (s, 1H), 3.73 (s, 1H), 3.68 (s, 1H), 2.78-2.64 (m, 1H), 2.47-2.36 (m, 1H), 2.36-2.26 (m, 4H), 2.25 (s, 3H), 2.23 (s, 3H), 1.98 (d, J=13.2 Hz, 2H), 1.91-1.78 (m, 2H), 1.62-1.53 (m, 2H), 1.50-1.38 (m, 2H), 1.35 (d, J=2.6 Hz, 3H).

Example 135

(7-(3-(tert-Butyl)phenyl)-2-azaspiro[3.5]nonan-2-yl)((1s,3s)-3-hydroxy-3-methylcyclobutyl)methanone

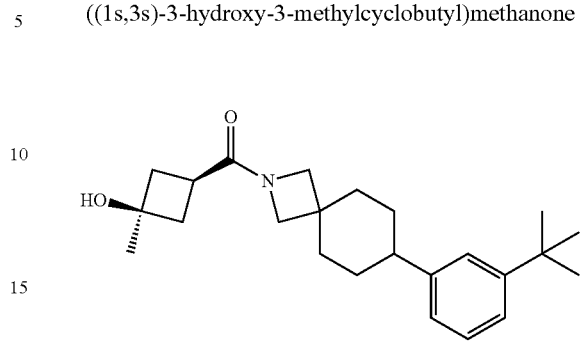

The title compound was prepared in a manner analogous to Example 127 using 1-bromo-3-(tert-butyl)benzene instead of 5-bromo-indan in Step A. MS (ESI): mass calcd. for $C_{24}H_{35}NO_2$, 369.3; m/z found, 370.2 [M+H]$^+$. $^1$H NMR (400 MHz, CDCl$_3$) δ 7.27-7.24 (m, 2H), 7.21 (s, 1H), 7.04-6.98 (m, 1H), 3.87 (s, 1H), 3.81 (s, 2H), 3.77 (s, 1H), 3.71 (s, 1H), 2.82-2.66 (m, 1H), 2.57-2.43 (m, 1H), 2.39-2.31 (m, 2H), 2.31-2.23 (m, 2H), 2.02 (d, J=13.2 Hz, 2H), 1.91 (s, 2H), 1.73-1.62 (m, 2H), 1.52-1.40 (m, 2H), 1.39-1.37 (m, 3H), 1.35-1.33 (m, 9H).

Example 136

((1s,3s)-3-Hydroxy-3-methylcyclobutyl)(7-(p-tolyl)-2-azaspiro[3.5]nonan-2-yl)methanone

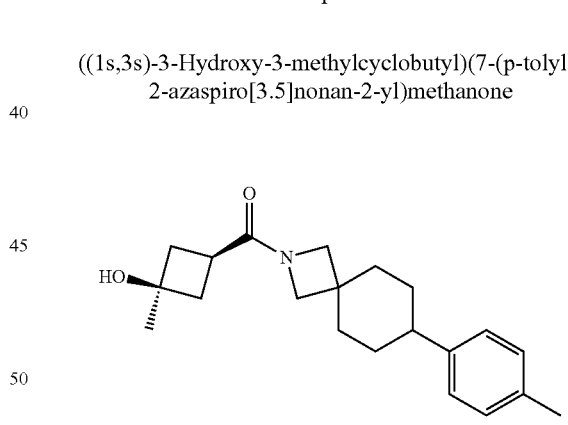

The title compound was prepared in a manner analogous to Example 127 using 1-bromo-4-methylbenzene instead of 5-bromo-indan in Step A. MS (ESI): mass calcd. for $C_{21}H_{29}NO_2$, 327.2; m/z found, 328.2 [M+H]$^+$. $^1$H NMR (400 MHz, DMSO-d$_6$) δ 7.06-6.96 (m, 4H), 4.92 (d, J=2.8 Hz, 1H), 3.74 (s, 1H), 3.61 (s, 1H), 3.51 (s, 1H), 3.40 (s, 1H), 2.56-2.46 (m, 1H), 2.33 (t, J=10.5 Hz, 1H), 2.18 (s, 3H), 2.09-1.99 (m, 2H), 1.99-1.88 (m, 2H), 1.81 (d, J=12.0 Hz, 2H), 1.60 (d, J=13.2 Hz, 2H), 1.53-1.42 (m, 2H), 1.39-1.26 (m, 2H), 1.17 (d, J=3.4 Hz, 3H).

Example 137

((1s,3s)-3-Hydroxy-3-methylcyclobutyl)(7-(m-tolyl)-2-azaspiro[3.5]nonan-2-yl)methanone

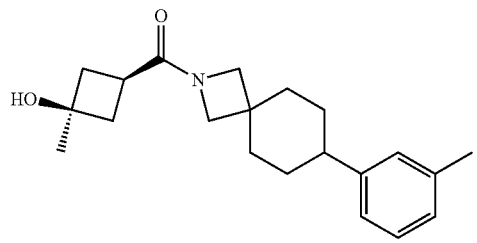 [SMILES: Cc1cccc(C2CCC3(CC2)CN(C(=O)[C@H]2C[C@@](C)(O)C2)C3)c1]

The title compound was prepared in a manner analogous to Example 127 using 1-bromo-3-methylbenzene instead of 5-bromo-indan in Step A. MS (ESI): mass calcd. for $C_{21}H_{29}NO_2$, 327.2; m/z found, 328.2 [M+H]$^+$. $^1$H NMR (400 MHz, DMSO-d$_6$) δ 7.15 (t, J=7.5 Hz, 1H), 7.02 (s, 1H), 7.01-6.94 (m, 2H), 5.00 (d, J=3.2 Hz, 1H), 3.81 (s, 1H), 3.68 (s, 1H), 3.59 (s, 1H), 3.47 (s, 1H), 2.63-2.52 (m, 1H), 2.46-2.35 (m, 1H), 2.27 (s, 3H), 2.14-2.07 (m, 2H), 2.05-1.96 (m, 2H), 1.93-1.85 (m, 2H), 1.73-1.64 (m, 2H), 1.59-1.48 (m, 2H), 1.47-1.34 (m, 2H), 1.24 (d, J=3.8 Hz, 3H).

Example 138

((1s,3s)-3-Hydroxy-3-methylcyclobutyl)(7-(o-tolyl)-2-azaspiro[3.5]nonan-2-yl)methanone

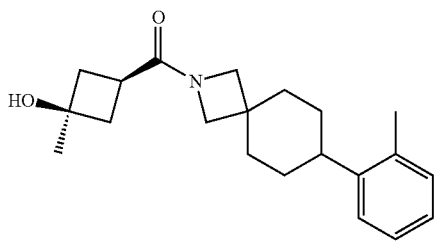 [SMILES: Cc1ccccc1C1CCC2(CC1)CN(C(=O)[C@H]1C[C@@](C)(O)C1)C2]

The title compound was prepared in a manner analogous to Example 127 using 1-bromo-2-methylbenzene instead of 5-bromo-indan in Step A. MS (ESI): mass calcd. for $C_{21}H_{29}NO_2$, 327.2; m/z found, 328.2 [M+H]$^+$. $^1$H NMR (400 MHz, DMSO-d$_6$) δ 7.19-7.09 (m, 3H), 7.08-7.00 (m, 1H), 4.99 (d, J=2.6 Hz, 1H), 3.83 (s, 1H), 3.69 (s, 1H), 3.61 (s, 1H), 3.48 (s, 1H), 2.71-2.52 (m, 2H), 2.28 (s, 3H), 2.16-2.07 (m, 2H), 2.06-1.96 (m, 2H), 1.95-1.82 (m, 2H), 1.70-1.51 (m, 4H), 1.48-1.32 (m, 2H), 1.24 (d, J=3.8 Hz, 3H).

Example 139

(7-(2-(tert-Butyl)pyridin-4-yl)-2-azaspiro[3.5]nonan-2-yl)((1s,3s)-3-hydroxy-3-methylcyclobutyl)methanone

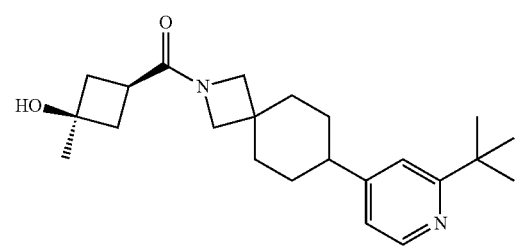

The title compound was prepared in a manner analogous to Example 127 using 4-bromo-2-(tert-butyl)pyridine instead of 5-bromo-indan in Step A. MS (ESI): mass calcd. for $C_{23}H_{34}N_2O_2$, 370.3; m/z found, 371.2 [M+H]$^+$. $^1$H NMR (400 MHz, CDCl$_3$) δ 8.46 (d, J=5.1 Hz, 1H), 7.12 (s, 1H), 6.89 (dt, J=4.9, 1.5 Hz, 1H), 3.89 (d, J=7.1 Hz, 1H), 3.84 (s, 1H), 3.77 (s, 1H), 3.75 (s, 1H), 3.69 (s, 1H), 2.76-2.61 (m, 1H), 2.52-2.40 (m, 1H), 2.36-2.23 (m, 4H), 2.02 (d, J=13.4 Hz, 2H), 1.93-1.81 (m, 2H), 1.62 (ddd, J=26.1, 13.1, 3.1 Hz, 2H), 1.52-1.39 (m, 2H), 1.38 (s, 12H).

Example 140

(7-(4-Cyclopropyl-3-methoxyphenyl)-2-azaspiro[3.5]nonan-2-yl)((1s,3s)-3-hydroxy-3-methylcyclobutyl)methanone

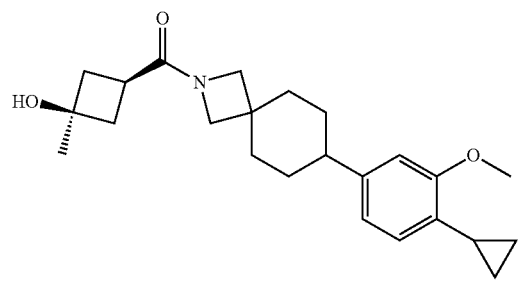 [SMILES: COc1cc(C2CCC3(CC2)CN(C(=O)[C@H]2C[C@@](C)(O)C2)C3)ccc1C1CC1]

Step A: tert-Butyl 7-(4-bromo-3-methoxyphenyl)-2-azaspiro[3.5]non-6-ene-2-carboxylate. 1-Bromo-4-iodo-2-methoxybenzene (700 mg, 2.24 mmol), tert-butyl 7-(4,4,5,5-tetramethyl-1,3,2-dioxaborolan-2-yl)-2-azaspiro[3.5]non-6-ene-2-carboxylate (Intermediate 10, 200 mg, 0.573 mmol) and K$_3$PO$_4$ (320 mg, 1.51 mmol) were dissolved in THF (15 mL). The resultant mixture was sparged with N$_2$ for 5 minutes and then treated with Pd(dppf)$_2$Cl$_2$·CH$_2$Cl$_2$ (42 mg, 0.051 mmol). The mixture was sparged with Ar for 5 minutes and then stirred while heating at 95° C. for 2 hours before cooling to rt. The reaction mixture was poured into water and extracted with EtOAc. The combined organic extracts were dried over Na$_2$SO$_4$, filtered, and concentrated under reduced pressure. The resulting residue was purified by FCC (SiO$_2$, 0-10% EtOAc in ether) to afford the title compound (230 mg, 94%) as a yellow oil. MS (ESI): mass calcd. for $C_{20}H_{26}BrNO_3$, 407.1; m/z found, 351.9 [M+2H-tBu]$^+$.

Step B: tert-Butyl 7-(4-cyclopropyl-3-methoxyphenyl)-2-azaspiro[3.5]non-6-ene-2-carboxylate. tert-Butyl 7-(4-bromo-3-methoxyphenyl)-2-azaspiro[3.5]non-6-ene-2-carboxylate (230 mg, 0.563 mmol), cyclopropylboronic acid (145 mg, 1.69 mmol) and $K_3PO_4$ (360 mg, 1.70 mmol) were dissolved in THF (10 mL). The resultant mixture was sparged with $N_2$ for 5 minutes and then treated with $Pd(dppf)_2Cl_2 \cdot CH_2Cl_2$ (50 mg, 0.061 mmol). The mixture was sparged with Ar for 5 minutes and then stirred while heating at 95° C. for 2 hours before cooling to rt. The reaction mixture was poured into water and extracted with EtOAc. The combined organic extracts were dried over $Na_2SO_4$, filtered, and concentrated under reduced pressure. The resulting residue was purified by FCC ($SiO_2$, 0-10% EtOAc in ether) to afford the title compound (150 mg, 68%) as a yellow oil. MS (ESI): mass calcd. for $C_{23}H_{31}NO_3$, 369.2; m/z found, 314.1 [M+2H-tBu]$^+$.

Step C: tert-Butyl 7-(4-cyclopropyl-3-methoxyphenyl)-2-azaspiro[3.5]nonane-2-carboxylate. tert-Butyl 7-(4-cyclopropyl-3-methoxyphenyl)-2-azaspiro[3.5]non-6-ene-2-carboxylate (150 mg, 0.406 mmol), EtOAc (15 mL), and wet 10 wt % Pd/C (200 mg) were combined. The resultant mixture was stirred under $H_2$ (15 psi) at rt for 1 hour. The suspension was filtered through a pad of Celite® and the pad washed with EtOAc. The filtrate was concentrated under reduced pressure to afford the title product (280 mg, crude) as a yellow oil, which was used in the next step without further purification.

Step D: 7-(4-Cyclopropyl-3-methoxyphenyl)-2-azaspiro[3.5]nonane. TFA (2 mL) was added to a solution of tert-butyl 7-(4-cyclopropyl-3-methoxyphenyl)-2-azaspiro[3.5]nonane-2-carboxylate (160 mg, crude) in DCM (10 mL). The resultant mixture was stirred at rt for 2 hours. The reaction mixture was concentrated under reduced pressure to afford the title compound (160 mg, crude) as a yellow oil, which was used in the next step without further purification.

Step E: (7-(4-Cyclopropyl-3-methoxyphenyl)-2-azaspiro[3.5]nonan-2-yl)((1s,3s)-3-hydroxy-3-methylcyclobutyl)methanone. $T_3P$® (300 mg, 0.471 mmol, 50 wt % in EtOAc) was added to a solution of 7-(4-cyclopropyl-3-methoxyphenyl)-2-azaspiro[3.5]nonane (160 mg, crude), (1s,3s)-3-hydroxy-3-methylcyclobutanecarboxylic acid (50 mg, 0.38 mmol), $Et_3N$ (0.30 mL, 2.2 mmol) and DCM (15 mL). The resultant mixture was stirred at rt for 2 hours. The reaction mixture was poured into water and extracted with DCM. The combined organic extracts were dried over $Na_2SO_4$, filtered, and concentrated under reduced pressure. The resulting residue was purified by SFC (DAICEL CHIRALCEL OD-H 250 mm×30 mm, 5 μm, isocratic elution: EtOH (containing 0.1% of 25% aq. $NH_3$): supercritical $CO_2$, 30%: 70% to 30%: 70% (v/v)). This afforded the title compound (15.5 mg) as a white solid. MS (ESI): mass calcd. for $C_{24}H_{33}NO_3$, 383.2; m/z found, 384.3 [M+H]$^+$. $^1$H NMR (400 MHz, $CDCl_3$) δ 6.80-6.74 (m, 1H), 6.72-6.63 (m, 2H), 3.87 (s, 3H), 3.86-3.69 (m, 4H), 2.79-2.64 (m, 1H), 2.52-2.39 (m, 1H), 2.37-2.22 (m, 4H), 2.19-2.08 (m, 1H), 2.04-1.96 (m, 2H), 1.92-1.82 (m, 2H), 1.61-1.54 (m, 2H), 1.50-1.34 (m, 5H), 0.94-0.87 (m, 2H), 0.68-0.57 (m, 2H).

Example 141

(7-(3-Cyclopropyl-5-methoxyphenyl)-2-azaspiro[3.5]nonan-2-yl)((1s,3s)-3-hydroxy-3-methylcyclobutyl)methanone

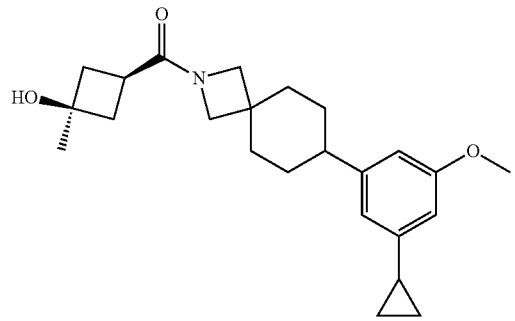 [SMILES: COc1cc(C2CC2)cc(C2CCC3(CC2)CN(C(=O)[C@H]2C[C@@](C)(O)C2)C3)c1]

The title compound was prepared in a manner analogous to Example 140 using 1,3-dibromo-5-methoxybenzene instead of 1-bromo-4-iodo-2-methoxybenzene in Step A. MS (ESI): mass calcd. for $C_{24}H_{33}NO_3$, 383.2; m/z found, 384.3 [M+H]$^+$. $^1$H NMR (400 MHz, $CDCl_3$) δ 6.55-6.48 (m, 2H), 6.46-6.41 (m, 1H), 3.86-3.68 (m, 7H), 2.80-2.65 (m, 1H), 2.49-2.22 (m, 5H), 2.04-1.96 (m, 2H), 1.92-1.79 (m, 3H), 1.60-1.53 (m, 2H), 1.52-1.29 (m, 5H), 1.01-0.88 (m, 2H), 0.74-0.64 (m, 2H).

Example 142

(7-(3-Cyclopropyl-4-methoxyphenyl)-2-azaspiro[3.5]nonan-2-yl)((1s,3s)-3-hydroxy-3-methylcyclobutyl)methanone

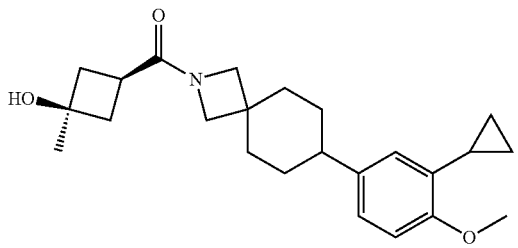 [SMILES: COc1ccc(C2CCC3(CC2)CN(C(=O)[C@H]2C[C@@](C)(O)C2)C3)cc1C1CC1]

The title compound was prepared in a manner analogous to Example 140 using 2-bromo-4-iodo-1-methoxybenzene instead of 1-bromo-4-iodo-2-methoxybenzene in Step A. MS (ESI): mass calcd. for $C_{24}H_{33}NO_3$, 383.2; m/z found, 384.4 [M+H]$^+$. $^1$H NMR (400 MHz, $CDCl_3$) δ 6.98-6.89 (m, 1H), 6.82-6.74 (m, 1H), 6.70-6.59 (m, 1H), 3.85 (s, 4H), 3.79-3.65 (m, 3H), 2.79-2.62 (m, 1H), 2.45-2.24 (m, 5H), 2.21-2.09 (m, 1H), 2.06-1.91 (m, 2H), 1.88-1.77 (m, 2H), 1.68-1.50 (m, 2H), 1.45-1.25 (m, 5H), 0.98-0.87 (m, 2H), 0.71-0.59 (m, 2H).

Example 143

(7-(3-Cyclopropyl-5-methylphenyl)-2-azaspiro[3.5]nonan-2-yl)((1s,3s)-3-hydroxy-3-methylcyclobutyl)methanone

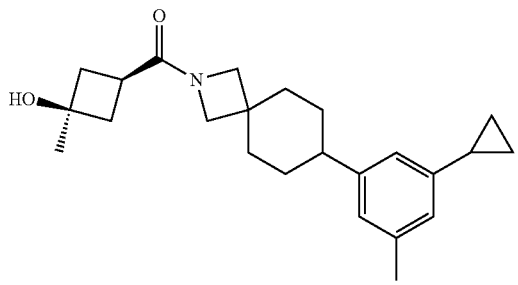 [SMILES: Cc1cc(C2CC2)cc(C2CCC3(CC2)CN(C(=O)[C@H]2C[C@@](C)(O)C2)C3)c1]

The title compound was prepared in a manner analogous to Example 140 using 1,3-dibromo-5-methylbenzene instead of 1-bromo-4-iodo-2-methoxybenzene in Step A and performing the hydrogenation (Step C) last. MS (ESI): mass calcd. for $C_{24}H_{33}NO_2$, 367.3; m/z found, 368.2 [M+H]$^+$. $^1$H NMR (400 MHz, CDCl$_3$) δ 6.77 (s, 1H), 6.71 (s, 2H), 4.16-3.95 (m, 1H), 3.86-3.67 (m, 4H), 2.79-2.62 (m, 1H), 2.48-2.36 (m, 1H), 2.35-2.24 (m, 7H), 1.99 (d, J=12.8 Hz, 2H), 1.88-1.81 (m, 3H), 1.69-1.52 (m, 2H), 1.48-1.34 (m, 5H), 0.99-0.87 (m, 2H), 0.74-0.55 (m, 2H).

Example 144

(7-(3-Ethyl-2-methoxyphenyl)-2-azaspiro[3.5]nonan-2-yl)((1s,3s)-3-hydroxy-3-methylcyclobutyl)methanone

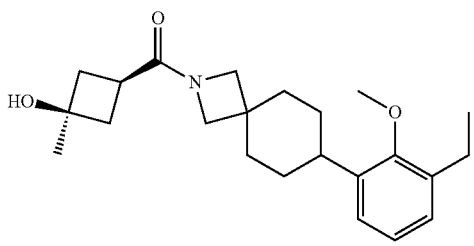 [SMILES: CCc1cccc(C2CCC3(CC2)CN(C(=O)[C@H]2C[C@@](C)(O)C2)C3)c1OC]

The title compound was prepared in a manner analogous to Example 140 using 1,3-dibromo-2-methoxybenzene instead of 1-bromo-4-iodo-2-methoxybenzene in Step A and potassium trifluoro(vinyl)borate instead of cyclopropylboronic acid in Step B. MS (ESI): mass calcd. for $C_{23}H_{33}NO_3$, 371.2; m/z found, 372.2 [M+H]$^+$. $^1$H NMR (400 MHz, DMSO-d$_6$) δ 7.17-6.82 (m, 3H), 5.10-4.89 (m, 1H), 3.84 (s, 1H), 3.74-3.54 (m, 5H), 3.48 (s, 1H), 2.89-2.74 (m, 1H), 2.67-2.54 (m, 3H), 2.18-1.84 (m, 6H), 1.70-1.31 (m, 6H), 1.24 (d, J=3.8 Hz, 3H), 1.16 (t, J=7.4 Hz, 3H).

Example 145

(7-(3-Ethyl-5-methoxyphenyl)-2-azaspiro[3.5]nonan-2-yl)((1s,3s)-3-hydroxy-3-methylcyclobutyl)methanone

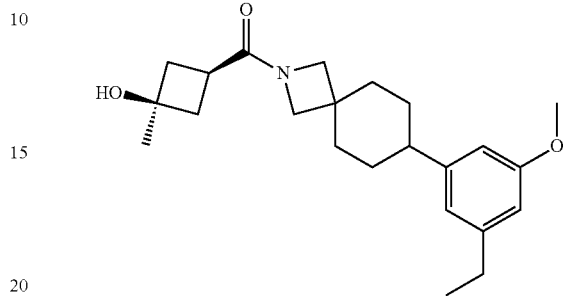

The title compound was prepared in a manner analogous to Example 140 using 1,3-dibromo-5-methoxybenzene instead of 1-bromo-4-iodo-2-methoxybenzene in Step A and potassium trifluoro(vinyl)borate instead of cyclopropylboronic acid in Step B. MS (ESI): mass calcd. for $C_{23}H_{33}NO_3$, 371.2; m/z found, 372.1 [M+H]$^+$. $^1$H NMR (400 MHz, DMSO-d$_6$) δ 6.63 (s, 1H), 6.57 (s, 2H), 5.00 (d, J=3.9 Hz, 1H), 3.81 (s, 1H), 3.71 (s, 3H), 3.68 (s, 1H), 3.59 (s, 1H), 3.47 (s, 1H), 2.63-2.51 (m, 3H), 2.44-2.30 (m, 1H), 2.17-2.06 (m, 2H), 2.05-1.95 (m, 2H), 1.92-1.84 (m, 2H), 1.73-1.63 (m, 2H), 1.58-1.48 (m, 2H), 1.47-1.33 (m, 2H), 1.24 (d, J=3.5 Hz, 3H), 1.15 (t, J=7.6 Hz, 3H).

Example 146

(7-(3-Ethyl-5-(trifluoromethyl)phenyl)-2-azaspiro[3.5]nonan-2-yl)((1s,3s)-3-hydroxy-3-methylcyclobutyl)methanone

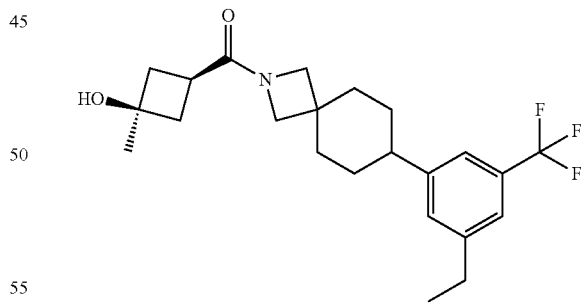

The title compound was prepared in a manner analogous to Example 140 using 1,3-dibromo-5-(trifluoromethyl)benzene instead of 1-bromo-4-iodo-2-methoxybenzene in Step A and potassium trifluoro(vinyl)borate instead of cyclopropylboronic acid in Step B. MS (ESI): mass calcd. for $C_{23}H_{30}F_3NO_2$, 409.2; m/z found, 410.2 [M+H]$^+$. $^1$H NMR (400 MHz, DMSO-d$_6$) δ 7.45-7.32 (m, 3H), 5.01 (br s, 1H), 3.84-3.47 (m, 4H), 2.70-2.62 (m, 2H), 2.61-2.54 (m, 2H), 2.17-2.06 (m, 2H), 2.05-1.98 (m, 2H), 1.94-1.87 (m, 2H), 1.75-1.66 (m, 2H), 1.61-1.41 (m, 4H), 1.28-1.16 (m, 6H).

Example 147

(7-(3,5-Dimethylphenyl)-2-azaspiro[3.5]nonan-2-yl)
((1s,3s)-3-hydroxy-3-methylcyclobutyl)methanone

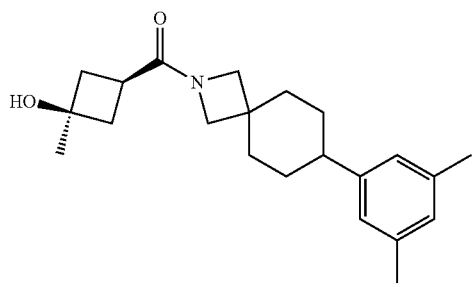 [SMILES: Cc1cc(C)cc(C2CCC3(CC2)CN(C(=O)[C@H]2C[C@@](C)(O)C2)C3)c1]

Step A: tert-Butyl 7-(3,5-dimethylphenyl)-2-azaspiro[3.5]non-6-ene-2-carboxylate. tert-Butyl 7-(((trifluoromethyl)sulfonyl)oxy)-2-azaspiro[3.5]non-6-ene-2-carboxylate (Intermediate 8, 300 mg, 0.618 mmol), (3,5-dimethylphenyl)boronic acid (140 mg, 0.933 mmol) and CsF (282 mg, 1.86 mmol) were dissolved in THF (10 mL). The resultant mixture was sparged with $N_2$ for 5 minutes and then treated with $Pd(dppf)_2Cl_2 \cdot CH_2Cl_2$ (51 mg, 0.062 mmol). The mixture was sparged with Ar for 5 minutes and then stirred at rt for 2 hours. The reaction mixture was poured into water and extracted with EtOAc. The combined organic extracts were dried over $Na_2SO_4$, filtered, and concentrated under reduced pressure. The resulting residue was purified by FCC ($SiO_2$, 0-10% EtOAc in ether) to afford the title compound (180 mg, 89%) as a colorless oil. MS (ESI): mass calcd. for $C_{21}H_{29}NO_2$, 327.2; m/z found, 272.0 [M+2H-tBu]$^+$.

Step B: 7-(3,5-Dimethylphenyl)-2-azaspiro[3.5]non-6-ene. TFA (1.5 mL) was added to a solution of tert-butyl 7-(3,5-dimethylphenyl)-2-azaspiro[3.5]non-6-ene-2-carboxylate (180 mg) in DCM (10 mL). The resultant mixture was stirred at rt for 2 hours. The reaction mixture was concentrated under reduced pressure to afford the title compound (180 mg, crude) as a yellow oil, which was used in the next step without further purification.

Step C: (7-(3,5-Dimethylphenyl)-2-azaspiro[3.5]non-6-en-2-yl)((cis)-3-hydroxy-3-methylcyclobutyl)methanone. $T_3P$® (0.5 mL, 0.80 mmol) was added to a solution of 7-(3,5-dimethylphenyl)-2-azaspiro[3.5]non-6-ene (180 mg, 0.53 mmol), (1s,3s)-3-hydroxy-3-methylcyclobutanecarboxylic acid (83 mg, 0.64 mmol) and TEA (0.4 mL, 2.9 mmol) in DCM (5 mL). The resultant mixture was stirred at rt for 2 hours. The reaction mixture was poured into water and extracted with DCM. The combined organic extracts were washed with brine, dried over $Na_2SO_4$, filtered, and concentrated under reduced pressure to give the crude product, which was used in the next step without further purification.

Step D: (7-(3,5-Dimethylphenyl)-2-azaspiro[3.5]nonan-2-yl)((1s,3s)-3-hydroxy-3-methylcyclobutyl)methanone. (7-(3,5-Dimethylphenyl)-2-azaspiro[3.5]non-6-en-2-yl)((cis)-3-hydroxy-3-methylcyclobutyl)methanone (200 mg, 0.589 mmol), EtOAc (15 mL), and wet 10 wt % Pd/C (200 mg) were combined. The resultant mixture was stirred under $H_2$ (15 psi) at rt for 1 hour. The suspension was filtered through a pad of Celite® and the pad washed with EtOAc. The filtrate was concentrated under reduced pressure. The resulting residue was purified by preparative HPLC (Boston Green ODS 150×30 mm×5 µm column, 55% to 85% (v/v) $CH_3CN$ and $H_2O$ with 0.225% HCOOH) to afford the title compound (36 mg, 18%) as a white solid. MS (ESI): mass calcd. for $C_{22}H_{31}NO_2$, 341.2; m/z found, 342.3 [M+H]$^+$. $^1H$ NMR (400 MHz, CDCl$_3$) δ 6.85 (s, 1H), 6.79 (s, 2H), 4.12 (br s, 1H), 3.94-3.63 (m, 4H), 2.81-2.59 (m, 1H), 2.49-2.20 (m, 11H), 2.04-1.96 (m, 2H), 1.90-1.79 (m, 2H), 1.69-1.54 (m, 2H), 1.52-1.40 (m, 2H), 1.37 (d, J=1.7 Hz, 3H).

Example 148

(7-(3-Ethyl-5-(trifluoromethoxy)phenyl)-2-azaspiro[3.5]nonan-2-yl)((1s,3s)-3-hydroxy-3-methylcyclobutyl)methanone

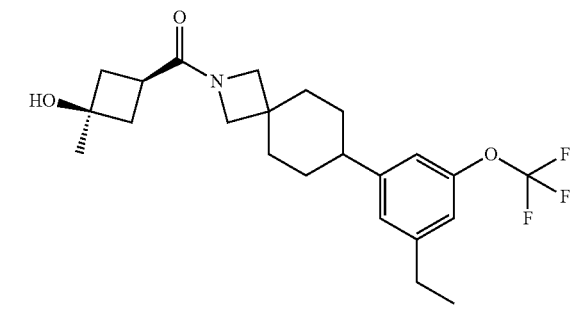 [SMILES: CCc1cc(OC(F)(F)F)cc(C2CCC3(CC2)CN(C(=O)[C@H]2C[C@@](C)(O)C2)C3)c1]

Step A: tert-Butyl 7-(3-chloro-5-(trifluoromethoxy)phenyl)-2-azaspiro[3.5]non-6-ene-2-carboxylate. tert-Butyl 7-(((trifluoromethyl)sulfonyl)oxy)-2-azaspiro[3.5]non-6-ene-2-carboxylate (Intermediate 8, 500 mg, 1.35 mmol), (3-chloro-5-(trifluoromethoxy)phenyl)boronic acid (485 mg, 2.02 mmol) and CsF (614 mg, 4.04 mmol) were dissolved in THF (10 mL). The resultant mixture was sparged with $N_2$ for 5 minutes and then treated with Pd(dppf)$Cl_2 \cdot CH_2Cl_2$ (110 mg, 0.135 mmol). The mixture was sparged with Ar for 5 minutes and stirred at rt for 2 hours. The reaction mixture was poured into water and and extracted with EtOAc. The combined organic extracts were dried over $Na_2SO_4$, filtered, and concentrated under reduced pressure. The resulting residue was purified by FCC ($SiO_2$, 0-25% EtOAc in ether) to afford the title compound (500 mg, 79%) as a white solid. MS (ESI): mass calcd. for $C_{20}H_{23}ClF_3NO_3$, 417.8; m/z found, 403.1 [M+2H+MeCN-tBu]$^+$.

Step B: tert-Butyl 7-(3-(trifluoromethoxy)-5-vinylphenyl)-2-azaspiro[3.5]non-6-ene-2-carboxylate. tert-Butyl 7-(3-chloro-5-(trifluoromethoxy)phenyl)-2-azaspiro[3.5]non-6-ene-2-carboxylate (250 mg, 0.598 mmol), potassium trifluoro(vinyl)borate (160 mg, 1.19 mmol), $K_3PO_4$ (317 mg, 1.49 mmol), 1,4-dioxane (6 mL), and $H_2O$ (1.5 mL) were combined. The resultant mixture was spared with Ar for 5 minutes and then treated with Pd(dtbpf)$Cl_2$ (39 mg, 0.060 mmol). The resultant mixture stirred and heated at 100° C. for 16 hours before cooling to rt. The mixture was quenched with water and extracted with EtOAc. The combined organic extracts were dried over $Na_2SO_4$, filtered, and concentrated under reduced pressure. The resulting residue was purified by FCC ($SiO_2$, 5-20% EtOAc in ether) to afford the title compound (209 mg, 83%) as a white solid. MS (ESI): mass calcd. for $C_{22}H_{26}F_3NO_3$, 409.2; m/z found, 395.1 [M+2H+MeCN-tBu]$^+$.

Step C: tert-Butyl 7-(3-ethyl-5-(trifluoromethoxy)phenyl)-2-azaspiro[3.5]nonane-2-carboxylate. tert-Butyl 7-(3-(trifluoromethoxy)-5-vinylphenyl)-2-azaspiro[3.5]non-6- ene-2-carboxylate (209 mg, 0.510 mmol), EtOAc (20 mL), and dry 10 wt % Pd/C (100 mg) were combined. The resultant mixture was stirred under $H_2$ (15 psi) at rt for 0.5 hour. The suspension was filtered through a pad of Celite® and the pad washed with EtOAc. The mixture was concentrated under reduced pressure to give the crude product (140 mg, 52%), which was used in the next step without further purification. MS (ESI): mass calcd. for $C_{22}H_{30}F_3NO_3$, 413.2; m/z found, 399.1 [M+2H+MeCN-tBu]$^+$.

Step D: 7-(3-Ethyl-5-(trifluoromethoxy)phenyl)-2-azaspiro[3.5]nonane. To a solution of tert-butyl 7-(3-ethyl-5-(trifluoromethoxy)phenyl)-2-azaspiro[3.5]nonane-2-carboxylate (140 mg, crude) in DCM (2 mL) was added TFA (4 mL). The reaction mixture was stirred at rt for 2 hours. The reaction mixture was concentrated under reduced pressure to give the crude product (140 mg) as yellow oil, which was used in the next step without further purification. MS (ESI): mass calcd. for $C_{17}H_{22}F_3NO$, 313.2; m/z found, 314.1 [M+H]$^+$.

Step E: (7-(3-Ethyl-5-(trifluoromethoxy)phenyl)-2-azaspiro[3.5]nonan-2-yl)((1s,3s)-3-hydroxy-3-methylcyclobutyl)methanone. $T_3P$® (0.40 mL, 50% in EtOAc, 0.67 mmol) was added to a 0° C. solution of 7-(3-ethyl-5-(trifluoromethoxy)phenyl)-2-azaspiro[3.5]nonane (140 mg, crude), (1s,3s)-3-hydroxy-3-methylcyclobutanecarboxylic acid (58 mg, 0.45 mmol) and TEA (0.73 mL, 5.4 mmol) in DCM (2 mL). The resultant mixture was stirred for 2 hours with gradual warming to rt. The mixture was poured into water and extracted with DCM. The combined organic extracts were dried over $Na_2SO_4$, filtered and concentrated under reduced pressure. The resulting residue was purified by preparative HPLC (Boston Green ODS 150×30 mm×5 μm column, 60% to 90% (v/v) $CH_3CN$ and $H_2O$ with 0.225% HCOOH) to afford the title compound (38 mg, 20%) as a yellow semi-solid. MS (ESI): mass calcd. for $C_{23}H_{30}F_3NO_3$, 425.2; m/z found, 426.1 [M+H]$^+$. $^1$H NMR (400 MHz, CDCl$_3$) δ 6.94 (s, 1H), 6.89 (s, 1H), 6.83 (s, 1H), 3.88-3.68 (m, 4H), 2.76-2.61 (m, 3H), 2.54-2.42 (m, 1H), 2.37-2.25 (m, 4H), 2.06-1.97 (m, 2H), 1.92-1.83 (m, 2H), 1.69-1.55 (m, 2H), 1.49-1.35 (m, 5H), 1.24 (t, J=7.6 Hz, 3H).

Example 149

(7-(3-Chloro-5-(trifluoromethoxy)phenyl)-2-azaspiro[3.5]nonan-2-yl)((1s,3s)-3-hydroxy-3-methylcyclobutyl)methanone

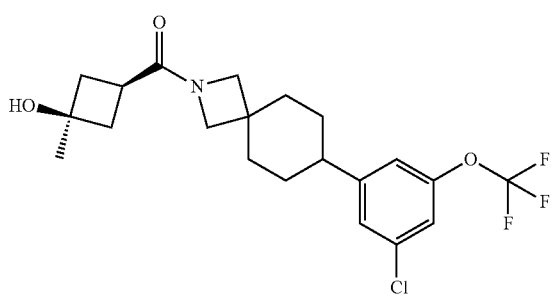 [SMILES: C[C@]1(O)C[C@@H](C(=O)N2CC3(CCC(c4cc(Cl)cc(OC(F)(F)F)c4)CC3)C2)C1]

Step A: tert-Butyl 7-(3-chloro-5-(trifluoromethoxy)phenyl)-2-azaspiro[3.5]nonane-2-carboxylate. tert-Butyl 7-(3-chloro-5-(trifluoromethoxy)phenyl)-2-azaspiro[3.5]non-6-ene-2-carboxylate (from Step A in Example 148, 200 mg, 0.479 mmol), EtOAc (15 mL) and PtO$_2$ (200 mg) were combined. The resultant mixture was stirred under $H_2$ (15 psi) at rt for 0.5 hours. The suspension was filtered through a pad of Celite® and the pad washed with EtOAc. The filtrate was concentrated under reduced pressure to afford the title product (200 mg, crude) as a colorless oil, which was used in the next step without further purification. MS (ESI): mass calcd. for $C_{20}H_{25}ClF_3NO_3$, 419.9; m/z found, 405.0 [M+2H+MeCN-tBu]$^+$.

Step B: 7-(3-Chloro-5-(trifluoromethoxy)phenyl)-2-azaspiro[3.5]nonane. To a solution of tert-butyl 7-(3-chloro-5-(trifluoromethoxy)phenyl)-2-azaspiro[3.5]nonane-2-carboxylate (200 mg, crude) in DCM (2 mL) was added TFA (4 mL). The reaction mixture was stirred at rt for 2 hours. The reaction mixture was concentrated under reduced pressure to give the crude product (202 mg) as yellow oil, which was used in the next step without further purification. MS (ESI): mass calcd. for $C_{15}H_{17}ClF_3NO$, 319.1; m/z found, 320.1 [M+H]$^+$.

Step C: (7-(3-Chloro-5-(trifluoromethoxy)phenyl)-2-azaspiro[3.5]nonan-2-yl)((1s,3s)-3-hydroxy-3-methylcyclobutyl)methanone. $T_3P$® (0.56 mL, 50 wt % in EtOAc, 0.94 mmol) was added to a 0° C. solution of 7-(3-chloro-5-(trifluoromethoxy)phenyl)-2-azaspiro[3.5]nonane (202 mg, 0.466 mmol), TEA (1.02 mL, 7.48 mmol), and (1s,3s)-3-hydroxy-3-methylcyclobutanecarboxylic acid (81 mg, 0.62 mmol) in DCM (5 mL). The resultant mixture was stirred for 2 hours with gradual warming to rt. The mixture was poured into water and extracted with DCM. The combined organic extracts were dried over $Na_2SO_4$, filtered, and concentrated under reduced pressure. The resulting residue was purified by preparative HPLC (Boston Green ODS 150×30 mm×5 μm column, 65% to 95% (v/v) $CH_3CN$ and $H_2O$ with 0.225% HCOOH) to afford the title compound (49 mg) as a white solid. MS (ESI): mass calcd. for $C_{21}H_{25}ClF_3NO_3$, 431.1; m/z found, 432.1 [M+H]$^+$. $^1$H NMR (400 MHz, CDCl$_3$) δ 7.15-7.04 (m, 2H), 6.92 (br s, 1H), 3.88-3.67 (m, 4H), 2.72-2.62 (m, 1H), 2.54-2.44 (m, 1H), 2.34-2.27 (m, 4H), 2.09-1.97 (m, 2H), 1.94-1.82 (m, 2H), 1.69-1.54 (m, 2H), 1.47-1.32 (m, 5H).

Example 150

(7-(4-Ethoxy-3-(trifluoromethyl)phenyl)-2-azaspiro[3.5]nonan-2-yl)((1s,3s)-3-hydroxy-3-methylcyclobutyl)methanone

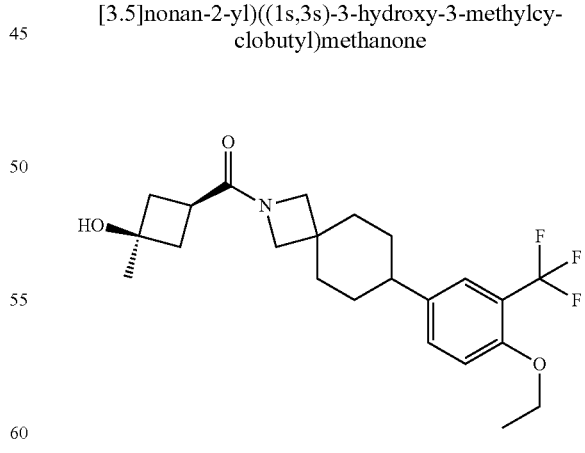

Step A: tert-Butyl 7-(4-hydroxy-3-(trifluoromethyl)phenyl)-2-azaspiro[3.5]non-6-ene-2-carboxylate. tert-Butyl 7-(((trifluoromethyl)sulfonyl)oxy)-2-azaspiro[3.5]non-6-ene-2-carboxylate (Intermediate 8, 300 mg, 0.808 mol), (4-hydroxy-3-(trifluoromethyl)phenyl)boronic acid (250 mg, 1.21 mmol) and CsF (368 mg, 2.42 mmol) were dissolved in THF (10 mL). The resultant mixture was sparged with $N_2$ for 5 minutes and then treated with Pd(dppf)$Cl_2 \cdot CH_2Cl_2$ (66 mg, 0.081 mmol). The mixture was sparged with Ar for 5 minutes and then stirred at rt for 2 hours. The reaction mixture was poured into water and extracted with EtOAc. The combined organic extracts were dried over $Na_2SO_4$, filtered, and concentrated under reduced pressure. The resulting residue was purified by FCC ($SiO_2$, 0-25% EtOAc in ether) to afford the title compound (300 mg, 94%) as a white solid. MS (ESI): mass calcd. for $C_{20}H_{24}F_3NO_3$, 383.2; m/z found, 328.1 [M+2H-tBu]$^+$.

Step B: tert-Butyl 7-(4-ethoxy-3-(trifluoromethyl)phenyl)-2-azaspiro[3.5]non-6-ene-2-carboxylate. Ethyl iodide (159 mg, 1.02 mmol) was added to a solution of tert-butyl 7-(4-hydroxy-3-(trifluoromethyl)phenyl)-2-azaspiro[3.5]non-6-ene-2-carboxylate (300 mg, 0.782 mmol) and $Cs_2CO_3$ (510 mg, 1.57 mmol) in $CH_3CN$ (10 mL). The resultant mixture was stirred at rt for 16 hours. The reaction mixture was poured into sat. $NaHCO_3$ and extracted with EtOAc. The combined organic extracts were dried over $Na_2SO_4$, filtered, and concentrated under reduced pressure to afford the title product (258 mg, 72%). MS (ESI): mass calcd. for $C_{22}H_{28}F_3NO_3$, 411.2; m/z found, 356.1 [M+2H-tBu]$^+$.

Step C: tert-Butyl 7-(4-ethoxy-3-(trifluoromethyl)phenyl)-2-azaspiro[3.5]nonane-2-carboxylate. tert-Butyl 7-(4-ethoxy-3-(trifluoromethyl)phenyl)-2-azaspiro[3.5]non-6-ene-2-carboxylate (258 mg, 0.627 mmol), EtOAc (20 mL), and dry 10 wt % Pd/C (100 mg) were combined. The resultant mixture was stirred under $H_2$ (15 psi) at rt for 0.5 hour. The suspension was filtered through a pad of Celite® and the pad washed with EtOAc. The mixture was concentrated under reduced pressure to give the crude product (190 mg, 71%), which was used in the next step without further purification. MS (ESI): mass calcd. for $C_{22}H_{30}F_3NO_3$, 413.2; m/z found, 399.1 [M+2H+MeCN-tBu]$^+$.

Step D: 7-(4-Ethoxy-3-(trifluoromethyl)phenyl)-2-azaspiro[3.5]nonane. To a solution of tert-butyl 7-(4-ethoxy-3-(trifluoromethyl)phenyl)-2-azaspiro[3.5]nonane-2-carboxylate (190 mg, crude) in DCM (1 mL) was added TFA (2 mL). The reaction mixture was stirred at rt for 2 hours. The reaction mixture was concentrated under reduced pressure to give the crude product (200 mg) as yellow solid, which was used in the next step without further purification. MS (ESI): mass calcd. for $C_{17}H_{22}F_3NO$, 313.2 m/z found, 314.1 [M+H]$^+$.

Step E: (7-(4-Ethoxy-3-(trifluoromethyl)phenyl)-2-azaspiro[3.5]nonan-2-yl)((1s,3s)-3-hydroxy-3-methylcyclobutyl)methanone. $T_3P®$ (0.57 mL, 50 wt % in EtOAc, 0.96 mmol) was added to a 0° C. solution of 7-(4-ethoxy-3-(trifluoromethyl)phenyl)-2-azaspiro[3.5]nonane (200 mg, crude), (1s,3s)-3-hydroxy-3-methylcyclobutanecarboxylic acid (83 mg, 0.64 mmol) and TEA (1.04 mL, 7.63 mmol) in DCM (3 mL). The resultant mixture was stirred for 2 hours with gradual warming to rt. The mixture was poured into water and extracted with DCM. The combined organic extracts were dried over $Na_2SO_4$, filtered, and concentrated under reduced pressure. The resulting residue was purified by preparative HPLC (Boston Green ODS 150×30 mm×5 μm column, 52% to 82% (v/v) $CH_3CN$ and $H_2O$ with 0.225% HCOOH) to afford the title compound (35 mg, 13%) as a white solid. MS (ESI): mass calcd. for $C_{23}H_{30}F_3NO_3$, 425.2; m/z found, 426.1 [M+H]$^+$. $^1H$ NMR (400 MHz, DMSO-$d_6$) δ 7.47-7.42 (m, 1H), 7.42-7.38 (m, 1H), 7.18-7.12 (m, 1H), 5.00 (s, 1H), 4.16-4.07 (m, 2H), 3.82-3.47 (m, 4H), 2.62-2.54 (m, 1H), 2.49-2.43 (m, 1H), 2.14-2.06 (m, 2H), 2.05-1.95 (m, 2H), 1.92-1.84 (m, 2H), 1.72-1.64 (m, 2H), 1.58-1.48 (m, 2H), 1.47-1.35 (m, 2H), 1.31 (t, J=6.9 Hz, 3H), 1.25-1.20 (m, 3H).

Example 151

((1s,3s)-3-Hydroxy-3-methylcyclobutyl)(7-hydroxy-7-(3-isopropylphenyl)-2-azaspiro[3.5]nonan-2-yl)methanone

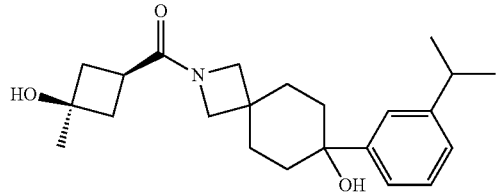 [SMILES: CC(C)c1cccc(C2(O)CCC3(CC2)CN(C(=O)[C@H]2C[C@@](C)(O)C2)C3)c1]

Step A: tert-Butyl 7-hydroxy-7-(3-isopropylphenyl)-2-azaspiro[3.5]nonane-2-carboxylate. In an oven-dried flask under $N_2$, tert-butyl 7-oxo-2-azaspiro[3.5]nonane-2-carboxylate (50 mg, 0.209 mmol) was taken up in anhydrous THF (1.0 mL) and cooled to 0° C. 3-Isopropylphenylmagnesium bromide (0.5M in THF, 0.63 mL) was added dropwise. This was allowed to warm to rt and stirred 2 h before adding additional Grignard reagent (0.3 mL). At 4 h, the reaction was quenched with sat. aq. $NH_4Cl$ and extracted with EtOAc. The combined organic layers were dried over $Na_2SO_4$, filtered, and concentrated under reduced pressure. Purification via FCC ($SiO_2$, 0-70% EtOAc in hexane) provided the title compound (12 mg, 16% yield). MS (ESI): mass calcd. for $C_{22}H_{33}NO_3$, 359.2; m/z found, 304.2 [M-tBu+2H]$^+$.

Step B: 7-(3-Isopropylphenyl)-2-azaspiro[3.5]nonan-7-ol. To tert-butyl 7-hydroxy-7-(3-isopropylphenyl)-2-azaspiro[3.5]nonane-2-carboxylate (12 mg, 0.033 mmol) was added HCl in EtOH (1.25M, 0.1 mL). This was heated to 45° C. for 2 hours before concentrating under reduced pressure. The title compound was used without further purification in the next step. MS (ESI): mass calcd. for $C_{17}H_{25}NO$ 259.2; m/z found, 260.3 [M+H]$^+$.

Step C: ((1s,3s)-3-Hydroxy-3-methylcyclobutyl)(7-hydroxy-7-(3-isopropylphenyl)-2-azaspiro[3.5]nonan-2-yl)methanone. 7-(3-Isopropylphenyl)-2-azaspiro[3.5]nonan-7-ol was taken up in DMF (0.3 mL) and to this was added (1s,3s)-3-hydroxy-3-methylcyclobutane-1-carboxylic acid (5 mg, 0.035 mmol), DIPEA (17 μL, 0.100 mmol), and HATU (14 mg, 0.037 mmol). This was stirred at rt for 1 hour. The reaction mixture was filtered through a PTFE filter with MeOH and purified via RP HPLC (5-95% ACN in 20 mM $NH_4OH$ in water) to afford the title compound (4 mg, 28% yield). MS (ESI): mass calcd. for $C_{23}H_{33}NO_3$, 371.2; m/z found, 372.3 [M+H]$^+$. $^1H$ NMR (500 MHz, Chloroform-d) δ 7.36-7.31 (m, 1H), 7.31-7.24 (m, 2H), 7.15 (dt, J=7.3, 1.7 Hz, 1H), 3.84 (s, 1H), 3.81 (s, 1H), 3.78 (d, J=3.1 Hz, 2H), 3.73 (s, 1H), 2.92 (kept, J=7.0 Hz, 1H), 2.76-2.65 (m, 1H), 2.35-2.23 (m, 4H), 2.13-2.01 (m, 2H), 1.92-1.77 (m, 6H), 1.52 (d, J=11.3 Hz, 1H), 1.38-1.33 (m, 3H), 1.26 (dd, J=7.0, 1.2 Hz, 6H).

Example 152

(rac)-((1s,3s)-3-Hydroxy-3-methylcyclobutyl)(2-(4-(trifluoromethyl)phenyl)-8-azaspiro[4.5]decan-8-yl)methanone

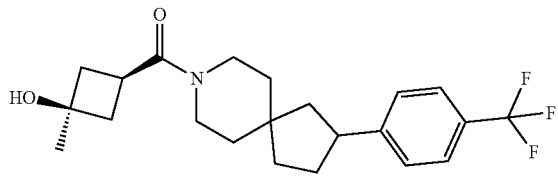 [SMILES: C[C@]1(O)C[C@@H](C(=O)N2CCC3(CCC(c4ccc(C(F)(F)F)cc4)C3)CC2)C1]

Step A: (rac)-tert-Butyl 2-(4-(trifluoromethyl)phenyl)-8-azaspiro[4.5]decane-8-carboxylate. A solution of tert-butyl 2-iodo-8-azaspiro[4.5]decane-8-carboxylate (Intermediate 1, 719 mg, 1.97 mmol) in THF (3.9 mL) was flowed through a column containing activated zinc at 40° C. (flow rate 0.5 mL/min). The outcoming solution was collected in a vial containing 4-bromobenzotrifluoride (0.18 mL, 1.31 mmol), Pd(dba)$_2$ (38 mg, 0.066 mmol) and XPhos (47 mg, 0.098 mmol). The reaction mixture was stirred at 50° C. for 4 h. Then, a 1:1 solution of sat. NH$_4$Cl and NH$_3$ (37% in water) was added and the mixture was extracted with EtOAc. The organic phase was separated, dried over Na$_2$SO$_4$, filtered and the solvent removed in vacuo. The residue was purified by FCC (SiO$_2$, 0-15% EtOAc in heptane) to afford the title compound as a yellow sticky oil (156 mg, 31% yield). MS (ESI): mass calcd. for $C_{21}H_{28}F_3NO_2$, 383.2; m/z found, 369.2 [M-tBu+2H+MeCN]$^+$.

Step B: (rac)-2-(4-(Trifluoromethyl)phenyl)-8-azaspiro[4.5]decane hydrochloride. To tert-butyl 2-(4-(trifluoromethyl)phenyl)-8-azaspiro[4.5]decane-8-carboxylate (10 mg, 0.026 mmol) in MeOH (52 µL) was added HCl in 1,4-dioxane (4M, 65 µL). This was heated to 45° C. for 1 h before concentrating under reduced pressure. The title compound was used without further purification in the next step. MS (ESI): mass calcd. for $C_{16}H_{20}F_3N$, 283.2; m/z found, 284.1 [M+H]$^+$.

Step C: (rac)-((1s,3s)-3-Hydroxy-3-methylcyclobutyl)(2-(4-(trifluoromethyl)phenyl)-8-azaspiro[4.5]decan-8-yl)methanone. 2-(4-(Trifluoromethyl)phenyl)-8-azaspiro[4.5]decane hydrochloride was taken up in DMF (0.3 mL) and to this was added (1s,3s)-3-hydroxy-3-methylcyclobutane-1-carboxylic acid (3.5 mg, 0.026 mmol), DIPEA (14 µL, 0.078 mmol), and HATU (11 mg, 0.029 mmol). This was stirred at rt for 1 hour. The reaction was filtered through a PTFE filter with MeOH and purified via RP HPLC (5-95% MeCN in 20 mM NH$_4$OH in water) to afford the title compound (9.5 mg, 92% yield). MS (ESI): mass calcd. for $C_{22}H_{28}F_3NO_2$, 395.2; m/z found, 396.2 [M+H]$^+$. $^1$H NMR (400 MHz, Chloroform-d) δ 7.54 (d, J=8.1 Hz, 2H), 7.33 (d, J=8.0 Hz, 2H), 3.71-3.53 (m, 2H), 3.37 (dt, J=11.2, 5.6 Hz, 2H), 3.20 (p, J=9.7 Hz, 1H), 2.89 (dq, J=8.0, 3.6 Hz, 2H), 2.39-2.26 (m, 4H), 2.20-2.01 (m, 2H), 1.83-1.66 (m, 2H), 1.61-1.42 (m, 6H), 1.39 (s, 3H).

Example 153

(2-(3-(tert-Butyl)phenyl)-7-azaspiro[3.5]nonan-7-yl)((1s,3s)-3-hydroxy-3-methylcyclobutyl)methanone

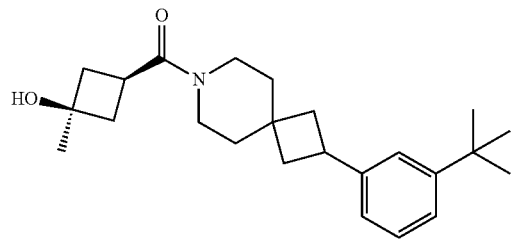 [SMILES: CC(C)(C)c1cccc(C2CC3(CCN(C(=O)[C@H]4C[C@@](C)(O)C4)CC3)C2)c1]

Step A: tert-Butyl 2-(3-(tert-butyl)phenyl)-7-azaspiro[3.5]nonane-7-carboxylate. NiCl$_2$(DME) (7.2 mg, 0.033 mmol) and 4,4'-di-tert-butyl-2,2'-bipyridine (10.6 mg, 0.039 mmol) were dissolved in DME and stirred for ten minutes. To a separate vessel were added tert-butyl 2-bromo-7-azaspiro[3.5]nonane-7-carboxylate (100 mg, 0.300 mmol), (Ir[dF(CF$_3$)ppy]$_2$(dtbpy))PF$_6$ (3.7 mg, 0.003 mmol), 2,6-dimethylpyridine (0.19 mL, 1.64 mmol), 1-bromo-3-tert-butylbenzene (105 mg, 0.490 mmol), and tris(trimethylsilyl)silane (0.20 mL, 0.660 mmol). The solution of nickel(II) complex was added to the second reaction vessel and the mixture was sparged with N$_2$ for 10 minutes, sealed with parafilm, and stirred overnight in a Pennoc 450 nm photoreactor (LED:100% power, fan:max, stirring:700 RPM). The reaction mixture was concentrated, dissolved in DCM, and purified via FCC (SiO$_2$, 0-30% EtOAc in hexanes) to yield a mixture of the desired product and silane byproducts (238 mg total mass). This mixture was carried on to the next step without further purification. MS (ESI): mass calcd. for $C_{23}H_{35}NO_2$ 357.3; m/z found, 302.1 [M-tBu+2H]$^+$.

Step B: (2-(3-(tert-Butyl)phenyl)-7-azaspiro[3.5]nonan-7-yl)((1s,3s)-3-hydroxy-3-methylcyclobutyl)methanone. A solution of tert-butyl 2-(3-(tert-butyl)phenyl)-7-azaspiro[3.5]nonane-7-carboxylate (58 mg, 0.162 mmol) in 4N HCl/dioxane (1.3 mL) was stirred at rt for 30 minutes and then concentrated. The residue was dissolved in DMF (1 mL) and (1s,3s)-3-hydroxy-3-methylcyclobutane-1-carboxylic acid (17.6 mg, 0.135 mmol), DIPEA (0.12 mL, 0.676 mmol), and HATU (79 mg, 0.203 mmol) were added. The reaction mixture was stirred at rt for 1 hour, then purified by RP HPLC (Gilson, 0-100% MeCN/water, NH$_4$OH modifier) to obtain the title compound (14.7 mg, 29% yield). MS (ESI): mass calcd. for $C_{24}H_{35}NO_2$, 369.3; m/z found, 370.3 [M+H]$^+$. $^1$H NMR (400 MHz, Chloroform-d) δ 7.11-7.00 (m, 3H), 6.89-6.83 (m, 1H), 3.45 (t, J=5.7 Hz, 1H), 3.40-3.29 (m, 2H), 3.21 (t, J=5.6 Hz, 1H), 3.09 (t, J=5.6 Hz, 1H), 2.80-2.63 (m, 1H), 2.14 (d, J=9.1 Hz, 6H), 1.76 (q, J=10.3, 9.7 Hz, 2H), 1.56 (d, J=5.8 Hz, 2H), 1.36 (d, J=5.8 Hz, 2H), 1.24-1.19 (m, 3H), 1.14 (s, 9H).

Example 154

(6-(3-Cyclopropyl-2-methylbenzyl)-2-azaspiro[3.3]heptan-2-yl)((1s,3s)-3-hydroxy-3-methylcyclobutyl)methanone

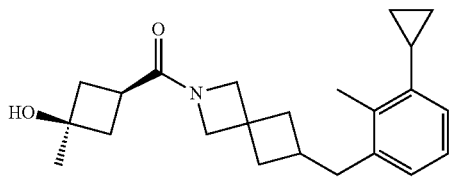 [SMILES: Cc1c(CC2CC3(C2)CN(C(=O)[C@H]2C[C@@](C)(O)C2)C3)cccc1C1CC1]

The title compound was prepared in a manner analogous to Example 153 using tert-butyl 6-(bromomethyl)-2-azaspiro[3.3]heptane-2-carboxylate (Intermediate 4) instead of tert-butyl 2-bromo-7-azaspiro[3.5]nonane-7-carboxylate and 1-bromo-3-cyclopropyl-2-methylbenzene (Intermediate 42) instead of 1-bromo-3-tert-butylbenzene in Step A. MS (ESI): mass calcd. for $C_{23}H_{31}NO_2$, 353.2; m/z found, 354.2 [M+H]$^+$. $^1$H NMR (400 MHz, CDCl$_3$) δ 7.06-7.00 (m, 1H), 6.91 (dd, J=7.6, 10.4 Hz, 2H), 4.14-3.85 (m, 4H), 2.71 (d, J=7.2 Hz, 2H), 2.67-2.60 (m, 1H), 2.45 (br s, 1H), 2.35 (s, 3H), 2.33-2.18 (m, 6H), 1.96-1.82 (m, 3H), 1.33 (s, 3H), 0.95-0.87 (m, 2H), 0.64-0.57 (m, 2H).

Example 155

((1s,3s)-3-Hydroxy-3-methylcyclobutyl)(6-(2-methyl-3-(trifluoromethyl)benzyl)-2-azaspiro[3.3]heptan-2-yl)methanone

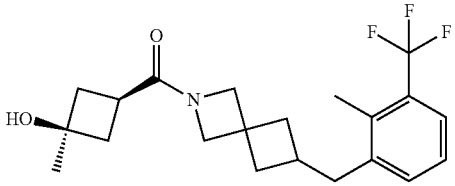 [SMILES: Cc1c(CC2CC3(C2)CN(C(=O)[C@H]2C[C@@](C)(O)C2)C3)cccc1C(F)(F)F]

The title compound was prepared in a manner analogous to Example 153 using tert-butyl 6-(bromomethyl)-2-azaspiro[3.3]heptane-2-carboxylate (Intermediate 4) instead of tert-butyl 2-bromo-7-azaspiro[3.5]nonane-7-carboxylate and 1-bromo-2-methyl-3-(trifluoromethyl)benzene instead of 1-bromo-3-tert-butylbenzene in Step A. MS (ESI): mass calcd. for $C_{21}H_{26}F_3NO_2$, 381.2; m/z found, 382.2 [M+H]$^+$. $^1$H NMR (400 MHz, CDCl$_3$) δ 7.53-7.48 (m, 1H), 7.25-7.17 (m, 2H), 4.09 (s, 1H), 4.02 (s, 1H), 3.99 (s, 1H), 3.94 (s, 1H), 3.83 (s, 1H), 2.77-2.73 (m, 2H), 2.69-2.60 (m, 1H), 2.54-2.40 (m, 1H), 2.38 (s, 3H), 2.35-2.19 (m, 6H), 2.00-1.88 (m, 2H), 1.34 (s, 3H).

Example 156

(6-(2,3-Dimethylbenzyl)-2-azaspiro[3.3]heptan-2-yl)((1s,3s)-3-hydroxy-3-methylcyclobutyl)methanone

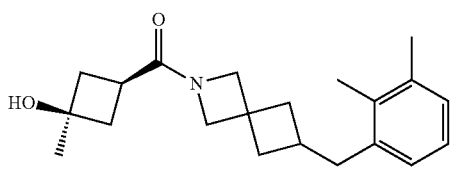

The title compound was prepared in a manner analogous to Example 153 using tert-butyl 6-(bromomethyl)-2-azaspiro[3.3]heptane-2-carboxylate (Intermediate 4) instead of tert-butyl 2-bromo-7-azaspiro[3.5]nonane-7-carboxylate and 1-bromo-2,3-dimethylbenzene instead of 1-bromo-3-tert-butylbenzene in Step A. MS (ESI): mass calcd. for $C_{21}H_{29}NO_2$, 327.2; m/z found, 328.2 [M+H]$^+$. $^1$H NMR (400 MHz, CDCl$_3$) δ 7.07-6.98 (m, 2H), 6.91-6.90 (m, 1H), 4.07 (s, 1H), 4.00 (s, 1H), 3.98 (s, 1H), 3.93 (s, 1H), 3.89 (s, 1H), 2.76-2.68 (m, 2H), 2.68-2.60 (m, 1H), 2.51-2.36 (m, 1H), 2.34-2.15 (m, 12H), 2.00-1.86 (m, 2H), 1.34 (s, 3H).

Example 157

(6-(3-(Difluoromethoxy)benzyl)-2-azaspiro[3.3]heptan-2-yl)((1s,3s)-3-hydroxy-3-methylcyclobutyl)methanone

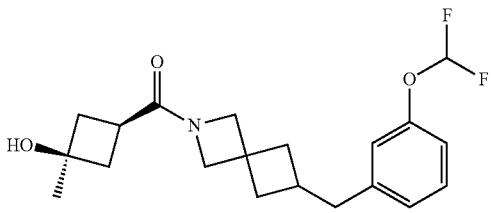 [SMILES: C[C@]1(O)C[C@@H](C(=O)N2CC3(CC(Cc4cccc(OC(F)F)c4)C3)C2)C1]

The title compound was prepared in a manner analogous to Example 153 using tert-butyl 6-(bromomethyl)-2-azaspiro[3.3]heptane-2-carboxylate (Intermediate 4) instead of tert-butyl 2-bromo-7-azaspiro[3.5]nonane-7-carboxylate and 1-bromo-3-(difluoromethoxy)benzene instead of 1-bromo-3-tert-butylbenzene in Step A. MS (ESI): mass calcd. for $C_{20}H_{25}F_2NO_3$, 365.2; m/z found, 366.1 [M+H]$^+$. $^1$H NMR (400 MHz, CDCl$_3$) δ 7.30-7.24 (m, 1H), 6.96 (d, J=8.0 Hz, 2H), 6.88 (s, 1H), 6.70-6.30 (t, J=74.0 Hz, 1H), 4.08 (s, 1H), 4.00 (s, 1H), 3.97 (s, 1H), 3.91 (s, 1H), 3.88 (br s, 1H), 2.73-2.60 (m, 3H), 2.52-2.35 (m, 1H), 2.34-2.18 (m, 6H), 1.99-1.85 (m, 2H), 1.34 (s, 3H).

Example 158

(6-(2-Ethylbenzyl)-2-azaspiro[3.3]heptan-2-yl)((1s,3s)-3-hydroxy-3-methylcyclobutyl)methanone

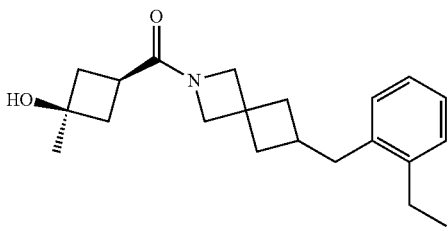 [SMILES: CCc1ccccc1CC1CC2(C1)CN(C(=O)[C@H]1C[C@@](C)(O)C1)C2]

The title compound was prepared in a manner analogous to Example 153 using tert-butyl 6-(bromomethyl)-2-azaspiro[3.3]heptane-2-carboxylate (Intermediate 4) instead of tert-butyl 2-bromo-7-azaspiro[3.5]nonane-7-carboxylate and 1-bromo-2-ethylbenzene instead of 1-bromo-3-tert-butylbenzene in Step A. MS (ESI): mass calcd. for $C_{21}H_{29}NO_2$, 327.2; m/z found, 328.1 $[M+H]^+$. $^1$H NMR (400 MHz, CDCl$_3$) δ 7.19-7.10 (m, 3H), 7.06-7.03 (m, 1H), 4.08 (s, 1H), 4.01 (s, 1H), 3.99-3.95 (m, 2H), 3.93 (s, 1H), 2.72-2.69 (m, 2H), 2.65-2.59 (m, 3H), 2.52-2.39 (m, 1H), 2.33-2.20 (m, 6H), 2.00-1.88 (m, 2H), 1.34 (s, 3H), 1.21 (t, J=7.6 Hz, 3H).

Example 159

((1s,3s)-3-Hydroxy-3-methylcyclobutyl)(7-(3-methylbenzyl)-2-azaspiro[3.5]nonan-2-yl)methanone

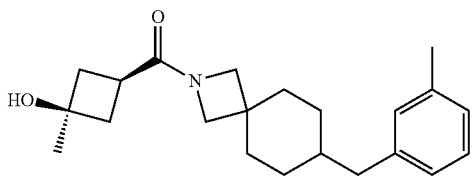 [SMILES: Cc1cccc(CC2CCC3(CC2)CN(C(=O)[C@H]2C[C@@](C)(O)C2)C3)c1]

Step A: tert-Butyl 7-(3-methylbenzylidene)-2-azaspiro[3.5]nonane-2-carboxylate. In an oven-dried flask under N$_2$, (3-methylbenzyl)triphenylphosphonium chloride (100 mg, 0.243 mmol) was taken up in anhydrous DMSO (1.0 mL). To this was added NaH (11 mg, 0.263 mmol) and this was stirred for 30 min at rt. tert-Butyl 7-oxo-2-azaspiro[3.5]nonane-2-carboxylate (50 mg, 0.203 mmol) was added and The reaction mixture was stirred at 80° C. for 16 h. The reaction was quenched with sat. aq. NH$_4$Cl and extracted with EtOAc. The combined organic layers were dried over Na$_2$SO$_4$, filtered, and concentrated under reduced pressure. Purification via FCC (SiO$_2$, 0-25% EtOAc in hexanes) provided the title compound (9 mg, 14% yield). MS (ESI): mass calcd. for $C_{21}H_{29}NO_2$, 327.2; m/z found, 272.2 $[M+2H-tBu]^+$.

Step B: tert-Butyl 7-(3-methylbenzyl)-2-azaspiro[3.5]nonane-2-carboxylate. tert-Butyl 7-(3-methylbenzylidene)-2-azaspiro[3.5]nonane-2-carboxylate (12 mg, 0.037 mmol) was taken up in EtOH (0.5 mL). Pd/C (4 mg, 0.004 mmol) was added and the reaction vessel was evacuated and left under H$_2$ to stir at rt for 45 min. The reaction mixture was filtered through Celite® with MeOH and concentrated under reduced pressure. The title compound was used without further purification in the next step. MS (ESI): mass calcd. for $C_{21}H_{31}NO_2$, 329.2; m/z found, 274.2 $[M+2H-tBu]^+$.

Step C: 7-(3-Methylbenzyl)-2-azaspiro[3.5]nonane. To tert-butyl 7-(3-methylbenzyl)-2-azaspiro[3.5]nonane-2-carboxylate (12 mg, 0.036 mmol) in MeOH (0.1 mL) was added HCl in 1,4-dioxane (4M, 0.3 mL). This was heated to 45° C. for 1 h before concentrating under reduced pressure. The title compound was used without further purification in the next step. MS (ESI): mass calcd. for $C_{16}H_{23}N$, 229.2; m/z found, 230.2 $[M+H]^+$.

Step D: ((1s,3s)-3-Hydroxy-3-methylcyclobutyl)(7-(3-methylbenzyl)-2-azaspiro[3.5]nonan-2-yl)methanone. 7-(3-Methylbenzyl)-2-azaspiro[3.5]nonane was taken up in DMF (0.4 mL) and to this was added (1s,3s)-3-hydroxy-3-methylcyclobutane-1-carboxylic acid (5.2 mg, 0.038 mmol), DIPEA (19 μL, 0.109 mmol), and HATU (16 mg, 0.040 mmol). This was stirred at rt for 16 h. The reaction was filtered through a PTFE filter with MeOH and purified via RP HPLC (5-95% MeCN in 20 mM NH$_4$OH in water) to afford the title compound (12 mg, 96% yield). MS (ESI): mass calcd. for $C_{22}H_{31}NO_2$, 341.2; m/z found, 342.3 $[M+H]^+$. $^1$H NMR (500 MHz, Chloroform-d) δ 7.16 (t, J=7.5 Hz, 1H), 7.02-6.98 (m, 1H), 6.96-6.88 (m, 2H), 3.98 (s, 1H), 3.66 (dd, J=31.3, 27.3 Hz, 4H), 2.73-2.59 (m, 1H), 2.43 (dd, J=7.2, 1.5 Hz, 2H), 2.32 (s, 3H), 2.31-2.22 (m, 4H), 1.87-1.80 (m, 2H), 1.70-1.61 (m, 2H), 1.54-1.35 (m, 3H), 1.34 (d, J=6.3 Hz, 3H), 1.02-0.86 (m, 2H).

Example 160

(7-(3-(Difluoromethoxy)benzyl)-2-azaspiro[3.5]nonan-2-yl)((1s,3s)-3-hydroxy-3-methylcyclobutyl)methanone

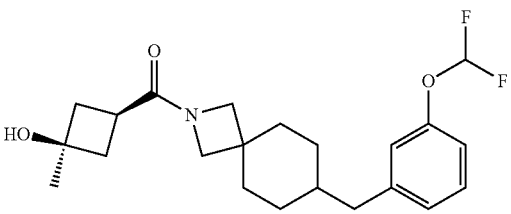 [SMILES: C[C@]1(O)C[C@@H](C(=O)N2CC3(CCC(Cc4cccc(OC(F)F)c4)CC3)C2)C1]

The title compound was prepared in a manner analogous to Example 159 using (3-(difluoromethoxy)benzyl)triphenylphosphonium bromide (Intermediate 17) instead of (3-methylbenzyl)triphenylphosphonium chloride in Step A. MS (ESI): mass calcd. for $C_{22}H_{29}F_2NO_3$, 393.2; m/z found, 394.1 $[M+H]^+$. $^1$H NMR (400 MHz, CDCl$_3$) δ 7.29-7.25 (m, 1H), 7.01-6.93 (m, 2H), 6.89 (s, 1H), 6.51 (t, J=76.0 Hz, 1H), 4.23-3.43 (m, 5H), 2.75-2.61 (m, 1H), 2.49 (d, J=7.0 Hz, 2H), 2.36-2.21 (m, 4H), 1.86 (d, J=13.2 Hz, 2H), 1.72-1.60 (m, 2H), 1.55-1.39 (m, 3H), 1.35 (d, J=4.3 Hz, 3H), 1.07-0.86 (m, 2H).

Example 161

(7-(4-(Difluoromethoxy)benzyl)-2-azaspiro[3.5]nonan-2-yl)((1s,3s)-3-hydroxy-3-methylcyclobutyl)methanone

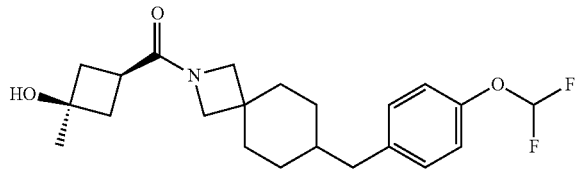 [SMILES: C[C@]1(O)C[C@@H](C(=O)N2CC3(CCC(Cc4ccc(OC(F)F)cc4)CC3)C2)C1]

The title compound was prepared in a manner analogous to Example 159 using (4-(difluoromethoxy)benzyl)triphenylphosphonium bromide (Intermediate 19) instead of (3-methylbenzyl)triphenylphosphonium chloride in Step A. MS (ESI): mass calcd. for $C_{22}H_{29}F_2NO_3$, 393.2; m/z found, 394.2 [M+H]$^+$. $^1$H NMR (400 MHz, DMSO-d$_6$) δ 7.22-7.11 (m, 2H), 7.17 (t, J=76.0 Hz, 1H), 7.10-7.02 (m, 2H), 3.85-3.55 (m, 4H) 2.58-2.52 (m, 1H), 2.43 (d, J=6.0 Hz, 2H), 2.13-2.02 (m, 2H), 2.02-1.92 (m, 2H), 1.76 (d, J=12.8 Hz, 2H), 1.58-1.46 (m, 2H), 1.46-1.38 (m, 1H), 1.38-1.27 (m, 2H), 1.22 (d, J=6.2 Hz, 3H), 1.02-0.79 (m, 2H).

Example 162

(7-(4-(Difluoromethyl)benzyl)-2-azaspiro[3.5]nonan-2-yl)((1s,3s)-3-hydroxy-3-methylcyclobutyl)methanone

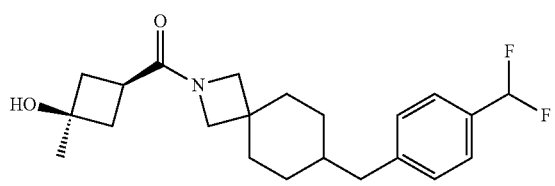 [SMILES: C[C@]1(O)C[C@@H](C(=O)N2CC3(CCC(Cc4ccc(C(F)F)cc4)CC3)C2)C1]

The title compound was prepared in a manner analogous to Example 159 using (4-(difluoromethyl)benzyl)triphenylphosphonium bromide (Intermediate 20) instead of (3-methylbenzyl)triphenylphosphonium chloride in Step A. MS (ESI): mass calcd. for $C_{22}H_{29}F_2NO_2$, 377.2; m/z found, 378.3 [M+H]$^+$. $^1$H NMR (400 MHz, CDCl$_3$) δ 7.51-7.33 (m, 2H), 7.31-7.13 (m, 2H), 6.63 (t, J=56.0 Hz, 1H), 3.98 (br s, 1H), 3.78-3.55 (m, 4H), 2.76-2.61 (m, 1H), 2.53 (d, J=5.8 Hz, 2H), 2.28 (s, 4H), 1.90-1.80 (m, 2H), 1.70-1.59 (m, 2H), 1.56-1.31 (m, 6H), 1.06-0.85 (m, 2H).

Example 163

(7-(3-(Difluoromethyl)benzyl)-2-azaspiro[3.5]nonan-2-yl)((1s,3s)-3-hydroxy-3-methylcyclobutyl)methanone

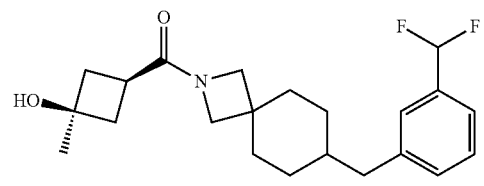 [SMILES: C[C@]1(O)C[C@@H](C(=O)N2CC3(CCC(Cc4cccc(C(F)F)c4)CC3)C2)C1]

The title compound was prepared in a manner analogous to Example 159 using (3-(difluoromethyl)benzyl)triphenylphosphonium bromide (Intermediate 18) instead of (3-methylbenzyl)triphenylphosphonium chloride in Step A. MS (ESI): mass calcd. for $C_{22}H_{29}F_2NO_2$, 377.2; m/z found, 378.2 [M+H]$^+$. $^1$H NMR (400 MHz, CDCl$_3$) δ 7.43-7.31 (m, 2H), 7.29-7.18 (m, 2H), 6.82-6.42 (m, 1H), 3.78-3.56 (m, 4H), 2.75-2.59 (m, 1H), 2.53 (d, J=7.0 Hz, 2H), 2.36-2.22 (m, 4H), 1.85 (d, J=13.1 Hz, 2H), 1.72-1.59 (m, 2H), 1.57-1.29 (m, 6H), 1.06-0.84 (m, 1H), 1.06-0.80 (m, 1H).

Example 164

(6-Benzyl-2-azaspiro[3.3]heptan-2-yl)((1s,3s)-3-hydroxy-3-methylcyclobutyl)methanone

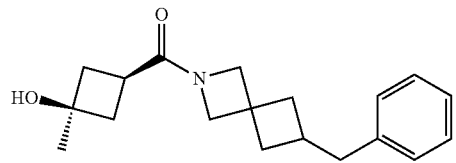 [SMILES: C[C@]1(O)C[C@@H](C(=O)N2CC3(CC(Cc4ccccc4)C3)C2)C1]

The title compound was prepared in a manner analogous to Example 159 using tert-butyl 6-oxo-2-azaspiro[3.3]heptane-2-carboxylate instead of tert-butyl 7-oxo-2-azaspiro[3.5]nonane-2-carboxylate and benzyltriphenylphosphonium chloride instead of (3-methylbenzyl)triphenylphosphonium chloride in Step A. MS (ESI): mass calcd. for $C_{19}H_{25}NO_2$, 299.2; m/z found, 300.1 [M+H]$^+$. $^1$H NMR (400 MHz, CDCl$_3$) δ 7.32-7.26 (m, 2H), 7.22-7.17 (m, 1H), 7.17-7.10 (m, 2H), 4.09-3.83 (m, 5H), 2.71-2.57 (m, 3H), 2.52-2.36 (m, 1H), 2.33-2.16 (m, 6H), 1.97-1.85 (m, 2H), 1.33 (s, 3H)

Example 165

((1s,3s)-3-Hydroxy-3-methylcyclobutyl)(6-(3-methylbenzyl)-2-azaspiro[3.3]heptan-2-yl)methanone

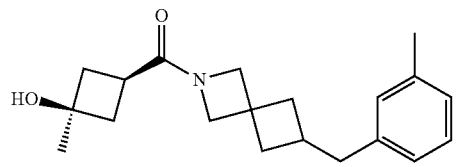 [SMILES: Cc1cccc(CC2CC3(C2)CN(C(=O)[C@H]2C[C@@](C)(O)C2)C3)c1]

The title compound was prepared in a manner analogous to Example 159 using tert-butyl 6-oxo-2-azaspiro[3.3]heptane-2-carboxylate instead of tert-butyl 7-oxo-2-azaspiro[3.5]nonane-2-carboxylate in Step A. MS (ESI): mass calcd. for $C_{20}H_{27}NO_2$, 313.2; m/z found, 314.1 [M+H]+. 1H NMR (400 MHz, CDCl3) δ 7.17 (t, J=7.2 Hz, 1H), 7.02 (d, J=7.6 Hz, 1H), 6.95-6.90 (m, 2H), 4.06 (s, 1H), 3.98 (d, J=11.2 Hz, 2H), 3.94-3.87 (m, 2H), 2.68-2.61 (m, 3H), 2.49-2.38 (m, 1H), 2.33 (s, 3H), 2.31-2.18 (m, 6H), 1.97-1.86 (m, 2H), 1.34 (d, J=1.2 Hz, 3H).

Example 166

((1s,3s)-3-Hydroxy-3-methylcyclobutyl)(6-(4-methylbenzyl)-2-azaspiro[3.3]heptan-2-yl)methanone

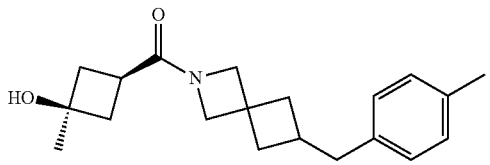 [SMILES: Cc1ccc(CC2CC3(C2)CN(C(=O)[C@H]2C[C@@](C)(O)C2)C3)cc1]

The title compound was prepared in a manner analogous to Example 159 using tert-butyl 6-oxo-2-azaspiro[3.3]heptane-2-carboxylate instead of tert-butyl 7-oxo-2-azaspiro[3.5]nonane-2-carboxylate and (4-methylbenzyl)triphenylphosphonium chloride instead of (3-methylbenzyl)triphenylphosphonium chloride in Step A. MS (ESI): mass calcd. for $C_{20}H_{27}NO_2$, 313.2; m/z found, 314.1 [M+H]+. 1H NMR (400 MHz, CDCl3) δ 7.12-7.06 (m, 2H), 7.02-6.97 (m, 2H), 4.05 (s, 1H), 3.98 (s, 1H), 3.95 (s, 1H), 3.90 (s, 1H), 3.85 (s, 1H), 2.68-2.59 (m, 3H), 2.48-2.34 (m, 1H), 2.31 (s, 3H), 2.30-2.17 (m, 6H), 1.97-1.84 (m, 2H), 1.33 (s, 3H).

Example 167

((1s,3s)-3-Hydroxy-3-methylcyclobutyl)(6-(pyridin-2-ylmethyl)-2-azaspiro[3.3]heptan-2-yl)methanone

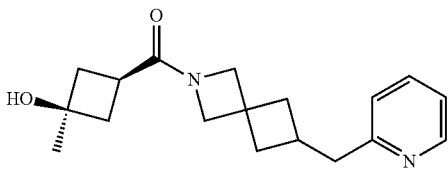 [SMILES: C[C@]1(O)C[C@@H](C(=O)N2CC3(CC(Cc4ccccn4)C3)C2)C1]

The title compound was prepared in a manner analogous to Example 159 using tert-butyl 6-oxo-2-azaspiro[3.3]heptane-2-carboxylate instead of tert-butyl 7-oxo-2-azaspiro[3.5]nonane-2-carboxylate and triphenyl(pyridin-2-ylmethyl)phosphonium bromide (Intermediate 22) instead of (3-methylbenzyl)triphenylphosphonium chloride in Step A. MS (ESI): mass calcd. for $C_{18}H_{24}N_2O_2$, 300.2; m/z found, 301.1 [M+H]+. 1H NMR (400 MHz, DMSO-d6) δ 8.45 (d, J=4.4 Hz, 1H), 7.70-7.64 (m, 1H), 7.67-7.15 (dt, J=1.6, 7.6 Hz, 2H), 5.03 (br s, 1H), 4.03 (s, 1H), 3.95 (s, 1H), 3.80 (s, 1H), 3.71 (s, 1H), 2.77 (d, J=7.6 Hz, 2H), 2.37-1.81 (m, 10H), 1.21 (d, J=2.0 Hz, 3H).

Example 168

((1s,3s)-3-Hydroxy-3-methylcyclobutyl)(6-(pyridin-3-ylmethyl)-2-azaspiro[3.3]heptan-2-yl)methanone

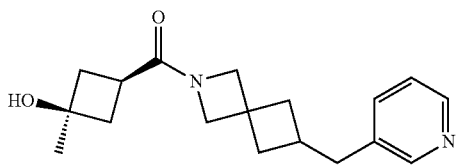 [SMILES: C[C@]1(O)C[C@@H](C(=O)N2CC3(CC(Cc4cccnc4)C3)C2)C1]

The title compound was prepared in a manner analogous to Example 159 using tert-butyl 6-oxo-2-azaspiro[3.3]heptane-2-carboxylate instead of tert-butyl 7-oxo-2-azaspiro[3.5]nonane-2-carboxylate and triphenyl(pyridin-3-ylmethyl)phosphonium bromide (Intermediate 23) instead of (3-methylbenzyl)triphenylphosphonium chloride in Step A. MS (ESI): mass calcd. for $C_{18}H_{24}N_2O_2$, 300.2; m/z found, 301.1 [M+H]+. 1H NMR (400 MHz, CDCl3) δ 8.46 (d, J=4.4 Hz, 1H), 8.39 (s, 1H), 7.42 (d, J=6.4 Hz, 1H), 7.24-7.18 (m, 1H), 4.07 (s, 1H), 4.00 (s, 1H), 3.96 (s, 1H), 3.91 (s, 1H), 3.82 (br s, 1H), 2.70-2.66 (m, 2H), 2.65-2.59 (m, 1H), 2.51-2.37 (m, 1H), 2.33-2.24 (m, 4H), 2.24-2.18 (m, 2H), 1.98-1.85 (m, 2H), 1.33 (s, 3H).

Example 169

(rac)-((1s,3s)-3-Hydroxy-3-methylcyclobutyl)(6-(4-methylbenzyl)-2-azaspiro[3.4]octan-2-yl)methanone

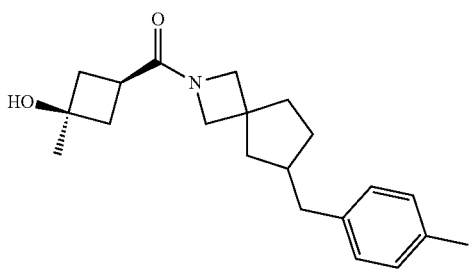 [SMILES: Cc1ccc(CC2CCC3(C2)CN(C(=O)[C@H]2C[C@@](C)(O)C2)C3)cc1]

The title compound was prepared in a manner analogous to Example 159 using tert-butyl 6-oxo-2-azaspiro[3.4]octane-2-carboxylate instead of tert-butyl 7-oxo-2-azaspiro[3.5]nonane-2-carboxylate and (4-methylbenzyl)triphenylphosphonium chloride instead of (3-methylbenzyl)triphenylphosphonium chloride in Step A. MS (ESI): mass calcd. for $C_{21}H_{29}NO_2$, 327.2; m/z found, 328.1 [M+H]+. 1H NMR (400 MHz, CDCl3) δ 7.11-7.07 (m, 2H), 7.05-7.01 (m, 2H), 3.92 (s, 1H), 3.89 (s, 1H), 3.87 (s, 1H), 3.84 (s, 1H), 3.77 (s, 1H), 2.69-2.50 (m, 3H), 2.32 (s, 3H), 2.30-2.11 (m, 5H), 1.99-1.74 (m, 4H), 1.53-1.42 (m, 1H), 1.40-1.25 (m, 4H).

Example 170

(rac)-((1s,3s)-3-Hydroxy-3-methylcyclobutyl)(6-(4-isopropylbenzyl)-2-azaspiro[3.4]octan-2-yl)methanone

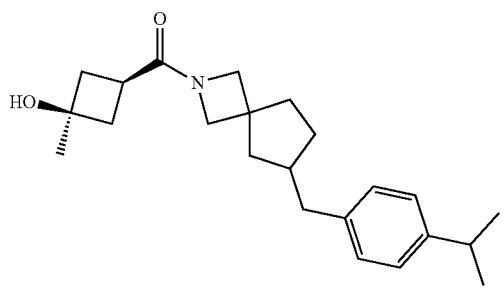 [SMILES: CC(C)c1ccc(CC2CCC3(C2)CN(C(=O)[C@H]2C[C@@](C)(O)C2)C3)cc1]

The title compound was prepared in a manner analogous to Example 159 using tert-butyl 6-oxo-2-azaspiro[3.4]octane-2-carboxylate instead of tert-butyl 7-oxo-2-azaspiro[3.5]nonane-2-carboxylate and (4-isopropylbenzyl)triphenylphosphonium bromide (Intermediate 15) instead of (3-methylbenzyl)triphenylphosphonium chloride in Step A. MS (ESI): mass calcd. for $C_{23}H_{33}NO_2$, 355.3; m/z found, 356.2 [M+H]$^+$. $^1$H NMR (400 MHz, CDCl$_3$) δ 7.17-7.10 (m, 2H), 7.08-7.03 (m, 2H), 4.00-3.83 (m, 4H), 3.77 (s, 1H), 2.93-2.82 (m, 1H), 2.68-2.52 (m, 3H), 2.31-2.15 (m, 5H), 1.99-1.78 (m, 4H), 1.53-1.34 (m, 2H), 1.33 (d, J=3.6 Hz, 3H), 1.24 (d, J=6.8 Hz, 6H).

Example 171

(rac)-((1s,3s)-3-Hydroxy-3-methylcyclobutyl)(6-(4-(trifluoromethyl)benzyl)-2-azaspiro[3.4]octan-2-yl)methanone

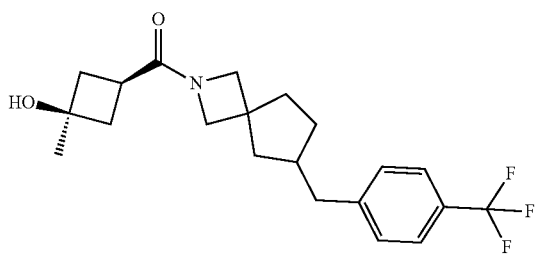 [SMILES: C[C@]1(O)C[C@@H](C(=O)N2CC3(CCC(Cc4ccc(C(F)(F)F)cc4)C3)C2)C1]

The title compound was prepared in a manner analogous to Example 159 using tert-butyl 6-oxo-2-azaspiro[3.4]octane-2-carboxylate instead of tert-butyl 7-oxo-2-azaspiro[3.5]nonane-2-carboxylate and (4-trifluoromethylbenzyl)triphenylphosphonium bromide (Intermediate 16) instead of (3-methylbenzyl)triphenylphosphonium chloride in Step A. MS (ESI): mass calcd. for $C_{21}H_{26}F_3NO_2$, 381.2; m/z found, 382.1 [M+H]$^+$. $^1$H NMR (400 MHz, CDCl$_3$) δ 7.54 (d, J=8.0 Hz, 2H), 7.27-7.26 (m, 1H), 7.26-7.24 (m, 1H), 3.95 (d, J=4.0 Hz, 1H), 3.93-3.89 (m, 2H), 3.87 (s, 1H), 3.79 (s, 1H), 2.72-2.61 (m, 3H), 2.34-2.15 (m, 5H), 2.02-1.76 (m, 4H), 1.55-1.42 (m, 1H), 1.40-1.25 (m, 4H).

Example 172

(2-Benzyl-7-azaspiro[3.5]nonan-7-yl)((1s,3s)-3-hydroxy-3-methylcyclobutyl)methanone

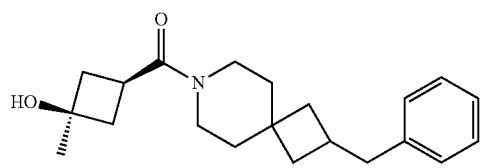 [SMILES: C[C@]1(O)C[C@@H](C(=O)N2CCC3(CC2)CC(Cc2ccccc2)C3)C1]

The title compound was prepared in a manner analogous to Example 159 using tert-butyl 2-oxo-7-azaspiro[3.5]nonane-7-carboxylate instead of tert-butyl 7-oxo-2-azaspiro[3.5]nonane-2-carboxylate, n-butyllithium instead of NaH, and benzyltriphenylphosphonium bromide instead of (3-methylbenzyl)triphenylphosphonium chloride in Step A. MS (ESI): mass calcd. for $C_{21}H_{29}NO_2$, 327.2; m/z found, 328.0 [M+H]$^+$. $^1$H NMR (400 MHz, Chloroform-d) δ 7.26 (s, 2H), 7.22-7.16 (m, 1H), 7.13 (d, J=7.5 Hz, 2H), 3.57-3.41 (m, 2H), 3.34-3.18 (m, 2H), 2.93-2.81 (m, 1H), 2.76-2.67 (m, 3H), 2.61-2.46 (m, 1H), 2.30 (d, J=7.9 Hz, 4H), 2.02-1.87 (m, 2H), 1.60-1.43 (m, 5H), 1.37 (s, 3H).

Example 173

((1s,3s)-3-Hydroxy-3-methylcyclobutyl)(2-(4-methylbenzyl)-7-azaspiro[3.5]nonan-7-yl)methanone

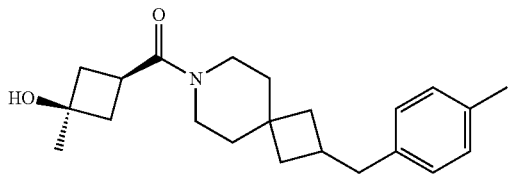 [SMILES: Cc1ccc(CC2CC3(CCN(C(=O)[C@H]4C[C@@](C)(O)C4)CC3)C2)cc1]

The title compound was prepared in a manner analogous to Example 159 using tert-butyl 2-oxo-7-azaspiro[3.5]nonane-7-carboxylate instead of tert-butyl 7-oxo-2-azaspiro[3.5]nonane-2-carboxylate, n-butyllithium instead of NaH, and (4-methylbenzyl)triphenylphosphonium bromide instead of (3-methylbenzyl)triphenylphosphonium chloride in Step A. MS (ESI): mass calcd. for $C_{22}H_{31}NO_2$, 341.2; m/z found, 342.1 [M+H]$^+$. $^1$H NMR (400 MHz, Chloroform-d) δ 7.00 (d, J=7.8 Hz, 2H), 6.98-6.89 (m, 2H), 3.49-3.31 (m, 2H), 3.23-3.11 (m, 2H), 2.96 (s, 1H), 2.76 (qd, J=8.0, 4.0 Hz, 1H), 2.66-2.54 (m, 2H), 2.51-2.33 (m, 1H), 2.22 (d, J=4.1 Hz, 7H), 1.93-1.82 (m, 2H), 1.51-1.33 (m, 6H), 1.29 (s, 3H).

Example 174: (rac)-((1s,3s)-3-Hydroxy-3-methylcyclobutyl)(6-(3-methylbenzyl)-2-azaspiro[3.4]octan-2-yl)methanone

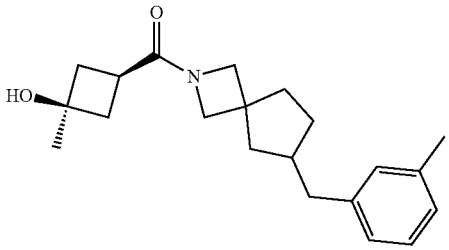 [SMILES: Cc1cccc(CC2CCC3(C2)CN(C(=O)[C@H]2C[C@@](C)(O)C2)C3)c1]

Step A: tert-Butyl 6-(3-methylbenzylidene)-2-azaspiro[3.4]octane-2-carboxylate. A solution of diethyl 3-methylbenzylphosphonate (968 mg, 4.00 mmol) in THF (5 mL) was added to a 0° C. solution of NaH (160 mg, 60 wt % in mineral oil, 4.00 mmol) and THF (5 mL) under $N_2$. The resultant mixture was stirred for 30 min before treating with a solution of tert-butyl 6-oxo-2-azaspiro[3.4]octane-2-carboxylate (300 mg, 1.33 mmol) and 15-crown-5 (880 mg, 4.00 mmol) in THF (5 mL). The reaction mixture was warmed to rt and stirred overnight. The reaction mixture was diluted with EtOAc, quenched with sat. $NH_4Cl$, and extracted with EtOAc. The combined organic extracts were washed with brine, dried over anhydrous $Na_2SO_4$, filtered, and concentrated under reduced pressure. The resulting residue was purified by FCC ($SiO_2$, 0-10% EtOAc in ether) to afford the title compound (150 mg, 36%) as colorless oil. MS (ESI): mass calcd. for $C_{20}H_{27}NO_2$, 313.2; m/z found, 258.0 [M+2H-tBu]$^+$. $^1$H NMR (400 MHz, CDCl$_3$) δ 7.25-7.20 (m, 1H), 7.12-7.06 (m, 2H), 7.01 (d, J=8.0 Hz, 1H), 6.34 (br s, 1H), 3.83-3.75 (m, 4H), 2.79 (s, 1H), 2.68 (s, 1H), 2.63 (t, J=7.2 Hz, 1H), 2.54 (t, J=7.6 Hz, 1H), 2.38-2.33 (m, 3H), 1.99 (t, J=7.2 Hz, 1H), 1.92-1.84 (m, 1H), 1.47-1.42 (m, 9H).

Step B: tert-Butyl 6-(3-methylbenzyl)-2-azaspiro[3.4]octane-2-carboxylate. tert-Butyl 6-(3-methylbenzylidene)-2-azaspiro[3.4]octane-2-carboxylate (210 mg, 0.670 mmol), 10 wt % wet Pd/C (50 mg), and MeOH (10 mL) were combined. The resultant mixture was stirred under H$_2$ (45 psi) at 60° C. for 48 hours before being cooled to rt and filtered through a pad of Celite®, washing with EtOAc. The filtrate was concentrated under reduced pressure to afford the crude product (170 mg, 80%) as a colorless oil, which was used in the next step without further purification. MS (ESI): mass calcd. for $C_{20}H_{29}NO_2$, 315.2; m/z found, 260.3 [M+2H-tBu]$^+$. $^1$H NMR (400 MHz, CDCl$_3$) δ 7.19-7.14 (m, 1H), 7.01 (d, J=7.6 Hz, 1H), 6.98-6.93 (m, 2H), 3.79 (s, 2H), 3.70 (s, 2H), 2.63-2.52 (m, 2H), 2.34 (s, 3H), 2.23-2.13 (m, 1H), 1.98-1.90 (m, 1H), 1.88-1.73 (m, 3H), 1.49-1.45 (m, 1H), 1.44 (s, 9H), 1.36-1.25 (m, 1H).

Step C: 6-(3-Methylbenzyl)-2-azaspiro[3.4]octane. A mixture of tert-butyl 6-(3-methylbenzyl)-2-azaspiro[3.4]octane-2-carboxylate (170 mg, 0.539 mmol), TFA (1.5 mL), and DCM (5 mL) was stirred at rt for 2 hours before being concentrated under reduced pressure to afford the crude product (150 mg, 85%) as a light-yellow oil, which was used in the next step without further purification. MS (ESI): mass calcd. for $C_{15}H_{21}N$, 215.2; m/z found, 216.2 [M+H]$^+$.

Step D: (rac)-((1s,3s)-3-Hydroxy-3-methylcyclobutyl)(6-(3-methylbenzyl)-2-azaspiro[3.4]octan-2-yl)methanone. HATU (140 mg, 0.368 mmol) was added to a solution of (1s,3s)-3-hydroxy-3-methylcyclobutanecarboxylic acid (40 mg, 0.307 mmol), 6-(3-methylbenzyl)-2-azaspiro[3.4]octane (150 mg, 0.455 mmol), and DIPEA (0.25 mL, 1.54 mmol) in DMF (5 mL). The resultant mixture was stirred at rt overnight. The reaction mixture was diluted with EtOAc and H$_2$O and extracted with EtOAc. The combined organic extracts were washed with brine, dried over Na$_2$SO$_4$, filtered, and concentrated under reduced pressure. The resulting residue was purified by preparative HPLC (Phenomenex Gemini-NX 150×30 mm×5 μm column, 52% to 82% (v/v) CH$_3$CN and H$_2$O with 0.05% NH$_3$) to afford the title compound (57.8 mg, 56%) as a white solid. MS (ESI): mass calcd. for $C_{21}H_{29}NO_2$, 327.2; m/z found, 328.2 [M+H]$^+$. $^1$H NMR (400 MHz, CDCl$_3$) δ 7.20-7.15 (m, 1H), 7.02 (d, J=7.6 Hz, 1H), 6.98-6.93 (m, 2H), 3.94 (s, 1H), 3.93 (s, 1H), 3.89 (s, 1H), 3.86 (s, 1H), 3.79 (s, 1H), 2.71-2.52 (m, 3H), 2.34 (s, 3H), 2.32-2.13 (m, 5H), 2.02-1.77 (m, 4H), 1.49 (ddd, J=9.2, 13.2, 17.2 Hz, 1H), 1.34 (d, J=4.0 Hz, 4H).

Example 175

(rac)-((1s,3s)-3-Hydroxy-3-methylcyclobutyl)(6-(2-methylbenzyl)-2-azaspiro[3.4]octan-2-yl)methanone

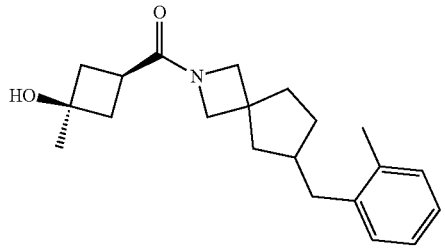 [SMILES: Cc1ccccc1CC1CCC2(C1)CN(C(=O)[C@H]1C[C@@](C)(O)C1)C2]

The title compound was prepared in a manner analogous to Example 174 using diethyl 2-methylbenzylphosphonate instead of diethyl 3-methylbenzylphosphonate in Step A. MS (ESI): mass calcd. for $C_{21}H_{29}NO_2$, 327.2; m/z found, 328.3 [M+H]$^+$. $^1$H NMR (400 MHz, CDCl$_3$) δ 7.15-7.08 (m, 4H), 3.96 (s, 1H), 3.90 (s, 1H), 3.86 (d, J=4.0 Hz, 2H), 3.78 (s, 1H), 2.71-2.59 (m, 3H), 2.32-2.27 (m, 5H), 2.24-2.17 (m, 3H), 2.04-1.76 (m, 5H), 1.55-1.48 (m, 1H), 1.33 (d, J=4.4 Hz, 3H).

Example 176

(rac)-((1s,3s)-3-Hydroxy-3-methylcyclobutyl)(6-(3-(trifluoromethyl)benzyl)-2-azaspiro[3.4]octan-2-yl)methanone

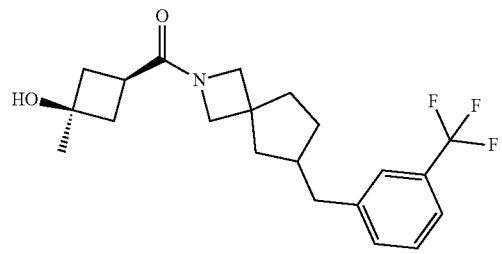 [SMILES: C[C@]1(O)C[C@@H](C(=O)N2CC3(CCC(Cc4cccc(C(F)(F)F)c4)C3)C2)C1]

The title compound was prepared in a manner analogous to Example 174 using diethyl (3-(trifluoromethyl)benzyl)phosphonate instead of diethyl 3-methylbenzylphosphonate in Step A. MS (ESI): mass calcd. for $C_{21}H_{26}F_3NO_2$, 381.2; m/z found, 382.1 [M+H]$^+$. $^1$H NMR (400 MHz, CDCl$_3$) δ 7.49-7.44 (m, 1H), 7.43-7.37 (m, 2H), 7.35-7.31 (m, 1H), 4.02 (s, 1H), 3.98-3.92 (m, 1H), 3.88 (d, J=8.4 Hz, 2H), 3.79 (s, 1H), 2.72-2.66 (m, 2H), 2.65-2.58 (m, 1H), 2.33-2.15 (m, 5H), 2.02-1.77 (m, 4H), 1.55-1.45 (m, 1H), 1.39-1.25 (m, 4H).

Example 177

((1s,3*S)-3-Hydroxy-3-methylcyclobutyl)((*R)-6-(3-(trifluoromethyl)benzyl)-2-azaspiro[3.4]octan-2-yl)methanone

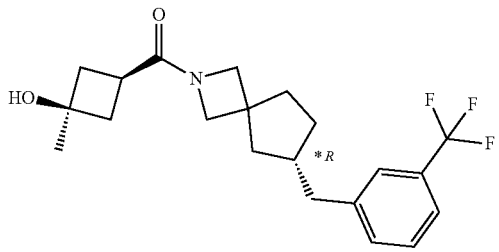

The title compound was prepared via separation of (rac)-((1s,3s)-3-hydroxy-3-methylcyclobutyl)(6-(3-(trifluoromethyl)benzyl)-2-azaspiro[3.4]octan-2-yl)methanone (Example 176) by SFC (Stationary phase: AD-H (3×25 cm); Mobile phase: 25% MeOH/CO$_2$; Rt=4.46 min). MS (ESI): mass calcd. for $C_{21}H_{26}F_3NO_2$, 381.2; m/z found, 382.2 [M+H]$^+$. $^1$H NMR (500 MHz, Chloroform-d) δ 7.45 (d, J=7.8 Hz, 1H), 7.42-7.35 (m, 2H), 7.32 (d, J=7.7 Hz, 1H), 4.13 (s, 1H), 3.97-3.90 (m, 1H), 3.86 (d, J=11.2 Hz, 2H), 3.77 (s, 1H), 2.73-2.64 (m, 2H), 2.64-2.56 (m, 1H), 2.31-2.23 (m, 4H), 2.23-2.13 (m, 1H), 2.05-1.75 (m, 4H), 1.54-1.41 (m, 1H), 1.39-1.25 (m, 4H).

Example 178

((1s,3*R)-3-Hydroxy-3-methylcyclobutyl)((*S)-6-(3-(trifluoromethyl)benzyl)-2-azaspiro[3.4]octan-2-yl)methanone

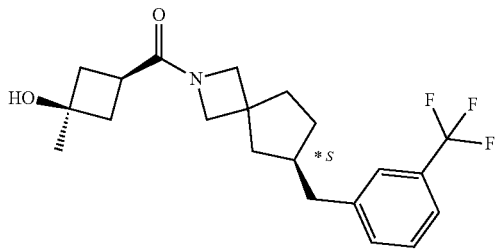

The title compound was prepared via separation of (rac)-((1s,3s)-3-hydroxy-3-methylcyclobutyl)(6-(3-(trifluoromethyl)benzyl)-2-azaspiro[3.4]octan-2-yl)methanone (Example 176) by SFC (Stationary phase: AD-H (3×25 cm); Mobile phase: 25% MeOH/CO$_2$; Rt=5.07 min). MS (ESI): mass calcd. for $C_{21}H_{26}F_3NO_2$, 381.2; m/z found, 382.3 [M+H]$^+$. $^1$H NMR (500 MHz, Chloroform-d) δ 7.45 (d, J=7.7 Hz, 1H), 7.42-7.35 (m, 2H), 7.31 (d, J=7.7 Hz, 1H), 4.21 (s, 1H), 3.98-3.71 (m, 4H), 2.78-2.63 (m, 2H), 2.64-2.52 (m, 1H), 2.39-2.05 (m, 5H), 2.02-1.71 (m, 4H), 1.54-1.40 (m, 1H), 1.39-1.25 (m, 4H).

Example 179

(rac)-((1s,3s)-3-Hydroxy-3-methylcyclobutyl)(6-(4-(trifluoromethoxy)benzyl)-2-azaspiro[3.4]octan-2-yl)methanone

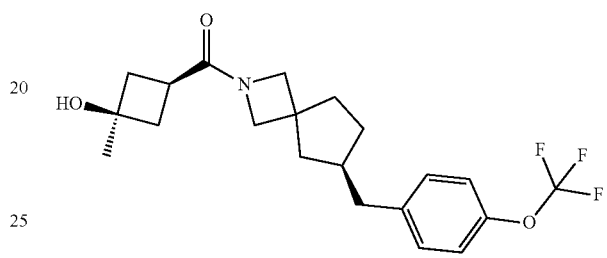

The title compound was prepared in a manner analogous to Example 174 using diethyl 4-(trifluoromethoxy)benzylphosphonate (Intermediate 24) instead of diethyl 3-methylbenzylphosphonate in Step A. MS (ESI): mass calcd. for $C_{21}H_{26}F_3NO_3$, 397.2; m/z found, 398.1 [M+H]$^+$. $^1$H NMR (400 MHz, CDCl$_3$) δ 7.19-7.11 (m, 4H), 3.98-3.91 (m, 1H), 3.89-3.87 (m, 3H), 3.79 (s, 1H), 2.70-2.57 (m, 3H), 2.34-2.12 (m, 5H), 2.03-1.76 (m, 4H), 1.53-1.43 (m, 1H), 1.38-1.27 (m, 4H).

Example 180

(rac)-((1s,3s)-3-Hydroxy-3-methylcyclobutyl)(6-(3-(trifluoromethoxy)benzyl)-2-azaspiro[3.4]octan-2-yl)methanone

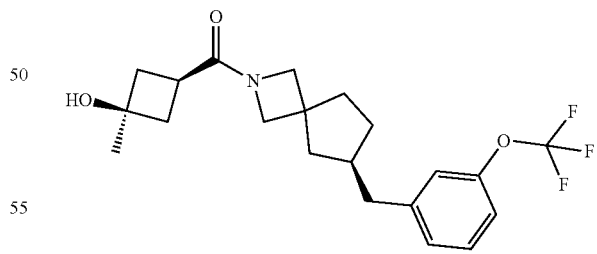

The title compound was prepared in a manner analogous to Example 174 using diethyl 3-(trifluoromethoxy)benzylphosphonate (Intermediate 25) instead of diethyl 3-methylbenzylphosphonate in Step A. MS (ESI): mass calcd. for $C_{21}H_{26}F_3NO_3$, 397.2; m/z found, 398.1 [M+H]$^+$. $^1$H NMR (400 MHz, CDCl$_3$) δ 7.33-7.28 (m, 1H), 7.10-7.04 (m, 2H), 7.01 (s, 1H), 3.97-3.91 (m, 1H), 3.89 (s, 1H), 3.88-3.84 (m, 2H), 3.79 (s, 1H), 2.71-2.60 (m, 3H), 2.34-2.13 (m, 5H), 2.03-1.77 (m, 4H), 1.54-1.43 (m, 1H), 1.39-1.25 (m, 4H).

Example 181

(rac)-((1s,3s)-3-Hydroxy-3-methylcyclobutyl)(6-(3-isopropylbenzyl)-2-azaspiro[3.4]octan-2-yl)methanone

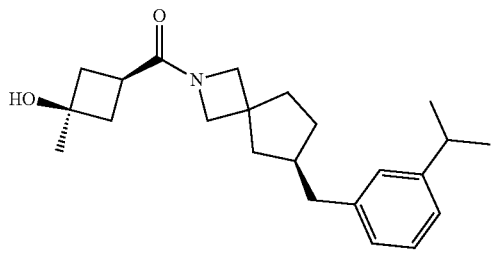 [SMILES: CC(C)c1cccc(C[C@@H]2CCC3(C2)CN(C(=O)[C@H]2C[C@@](C)(O)C2)C3)c1]

The title compound was prepared in a manner analogous to Example 174 using diethyl (3-isopropylbenzyl)phosphonate (Intermediate 26) instead of diethyl 3-methylbenzylphosphonate in Step A. MS (ESI): mass calcd. for $C_{23}H_{33}NO_2$, 355.3; m/z found, 356.2 [M+H]$^+$. $^1$H NMR (400 MHz, CDCl$_3$) δ 7.24-7.18 (m, 1H), 7.07 (d, J=7.6 Hz, 1H), 7.01-6.94 (m, 2H), 3.97-3.91 (m, 2H), 3.87 (d, J=10.4 Hz, 2H), 3.79 (s, 1H), 2.93-2.83 (m, 1H), 2.71-2.55 (m, 3H), 2.34-2.14 (m, 5H), 2.02-1.76 (m, 4H), 1.55-1.45 (m, 1H), 1.41-1.29 (m, 4H), 1.25 (d, J=7.2 Hz, 6H).

Example 182

(rac)-(6-(4-(Difluoromethyl)benzyl)-2-azaspiro[3.4]octan-2-yl)((1s,3s)-3-hydroxy-3-methylcyclobutyl)methanone

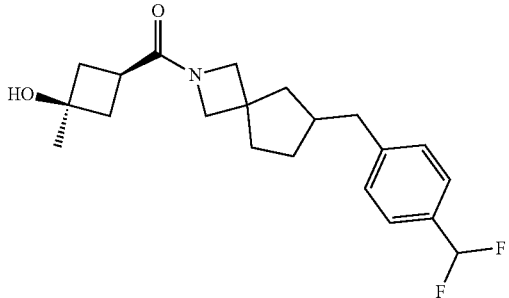 [SMILES: C[C@]1(O)C[C@@H](C(=O)N2CC3(CCC(Cc4ccc(C(F)F)cc4)C3)C2)C1]

The title compound was prepared in a manner analogous to Example 174 using diethyl (4-(difluoromethyl)benzyl)phosphonate (Intermediate 27) instead of diethyl 3-methylbenzylphosphonate in Step A. MS (ESI): mass calcd. for $C_{21}H_{27}F_2NO_2$, 363.2; m/z found, 364.2 [M+H]$^+$. $^1$H NMR (400 MHz, CDCl$_3$) δ 7.43 (d, J=8.0 Hz, 2H), 7.23 (d, J=7.6 Hz, 2H), 6.63 (t, J=56.0 Hz, 1H), 3.97-3.91 (m, 1H), 3.89 (s, 1H), 3.86 (s, 1H), 3.78 (s, 1H), 2.71-2.60 (m, 3H), 2.33-2.14 (m, 5H), 2.02-1.72 (m, 5H), 1.54-1.44 (m, 1H), 1.34 (d, J=3.6 Hz, 3H).

Example 183

(rac)-(6-(4-(Difluoromethoxy)benzyl)-2-azaspiro[3.4]octan-2-yl)((1s,3s)-3-hydroxy-3-methylcyclobutyl)methanone

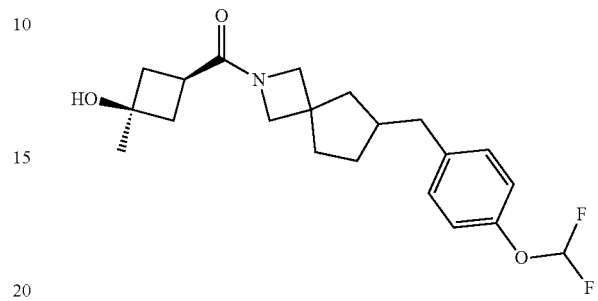

The title compound was prepared in a manner analogous to Example 174 using diethyl (4-(difluoromethoxy)benzyl)phosphonate (Intermediate 28) instead of diethyl 3-methylbenzylphosphonate in Step A. MS (ESI): mass calcd. for $C_{21}H_{27}F_2NO_3$, 379.2; m/z found, 380.1 [M+H]$^+$. $^1$H NMR (400 MHz, CDCl$_3$) δ 7.16-7.11 (m, 2H), 7.06-7.02 (m, 2H), 6.49 (t, J=76.0 Hz, 1H), 3.97-3.91 (m, 1H), 3.89 (s, 1H), 3.86 (s, 1H), 3.79 (s, 1H), 2.70-2.55 (m, 3H), 2.34-2.12 (m, 5H), 2.01-1.75 (m, 4H), 1.53-1.43 (m, 1H), 1.37-1.27 (m, 4H).

Example 184

((1s,3s)-3-Hydroxy-3-methylcyclobutyl)(6-(2-methylbenzyl)-2-azaspiro[3.3]heptan-2-yl)methanone

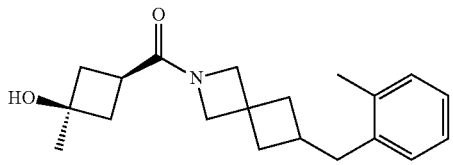 [SMILES: Cc1ccccc1CC1CC2(C1)CN(C(=O)[C@H]1C[C@@](C)(O)C1)C2]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl 2-methylbenzylphosphonate instead of diethyl 3-methylbenzylphosphonate in Step A. MS (ESI): mass calcd. for $C_{20}H_{27}NO_2$, 313.2; m/z found, 314.1 [M+H]$^+$. $^1$H NMR (400 MHz, CDCl$_3$) δ 7.16-7.09 (m, 3H), 7.06-7.01 (m, 1H), 4.07 (s, 1H), 4.00 (s, 1H), 3.97 (s, 1H), 3.92 (s, 1H), 3.82 (s, 1H), 2.71-2.60 (m, 3H), 2.54-2.39 (m, 1H), 2.34-2.25 (m, 7H), 2.25-2.17 (m, 2H), 1.99-1.86 (m, 2H), 1.33 (s, 3H).

Example 185

((1s,3s)-3-Hydroxy-3-methylcyclobutyl)(6-(4-isopropylbenzyl)-2-azaspiro[3.3]heptan-2-yl)methanone

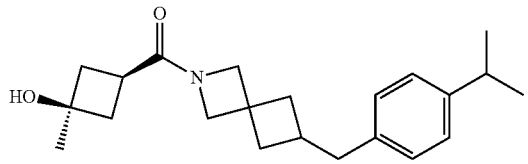 [SMILES: CC(C)c1ccc(CC2CC3(C2)CN(C(=O)[C@H]2C[C@@](C)(O)C2)C3)cc1]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl 4-isopropylbenzylphosphonate instead of diethyl 3-methylbenzylphosphonate in Step A. MS (ESI): mass calcd. for $C_{22}H_{31}NO_2$, 341.2; m/z found, 342.3 [M+H]$^+$. $^1$H NMR (400 MHz, DMSO-$d_6$) δ 7.12 (d, J=1.0 Hz, 2H), 7.05 (d, J=7.3 Hz, 2H), 3.92 (s, 1H), 3.79 (s, 1H), 3.71 (s, 1H), 2.91-2.77 (m, 1H), 2.57 (d, J=7.5 Hz, 3H), 2.32-2.30 (m, 2H), 2.18 (s, 2H), 2.09-2.01 (m, 2H), 1.99-1.92 (m, 2H), 1.88-1.80 (m, 2H), 1.23-1.20 (m, 3H), 1.17 (d, J=7.1 Hz, 6H).

Example 186

((1s,3s)-3-Hydroxy-3-methylcyclobutyl)(6-(3-isopropylbenzyl)-2-azaspiro[3.3]heptan-2-yl)methanone

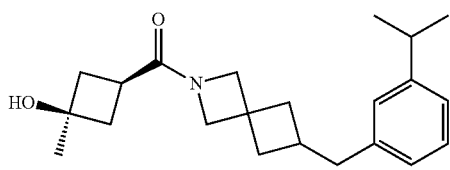 [SMILES: CC(C)c1cccc(CC2CC3(C2)CN(C(=O)[C@H]2C[C@@](C)(O)C2)C3)c1]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl 3-isopropylbenzylphosphonate (Intermediate 26) instead of diethyl 3-methylbenzylphosphonate in Step A. MS (ESI): mass calcd. for $C_{22}H_{31}NO_2$, 341.2; m/z found, 342.2 [M+H]$^+$. $^1$H NMR (400 MHz, CDCl$_3$) δ 7.23-7.18 (m, 1H), 7.07 (d, J=7.5 Hz, 1H), 6.98-6.90 (m, 2H), 4.07 (s, 1H), 4.00 (s, 1H), 3.96 (s, 1H), 3.92 (s, 1H), 2.88 (m, 2H), 2.71-2.58 (m, 3H), 2.51-2.38 (m, 1H), 2.26 (m, 5H), 1.99-1.86 (m, 2H), 1.34 (s, 3H), 1.25 (d, J=6.8 Hz, 6H).

Example 187

((1s,3s)-3-Hydroxy-3-methylcyclobutyl)(6-(2-isopropylbenzyl)-2-azaspiro[3.3]heptan-2-yl)methanone

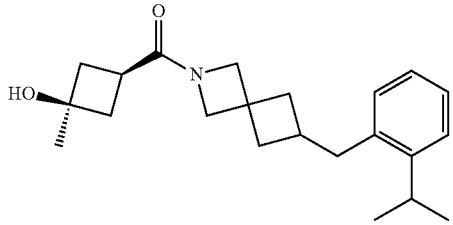 [SMILES: CC(C)c1ccccc1CC1CC2(C1)CN(C(=O)[C@H]1C[C@@](C)(O)C1)C2]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl 2-isopropylbenzylphosphonate (Intermediate 29) instead of diethyl 3-methylbenzylphosphonate in Step A. MS (ESI): mass calcd. for $C_{22}H_{31}NO_2$, 341.2; m/z found, 342.1 [M+H]$^+$. $^1$H NMR (400 MHz, DMSO-$d_6$) δ 7.26-7.22 (m, 1H), 7.18-7.12 (m, 1H), 7.06 (d, J=4.3 Hz, 2H), 4.03 (s, 1H), 3.95 (s, 1H), 3.81 (s, 1H), 3.73 (s, 1H), 3.14-3.02 (m, 1H), 2.67 (d, J=7.3 Hz, 2H), 2.49-2.43 (m, 1H), 2.30-2.26 (m, 1H), 2.22-2.15 (m, 2H), 2.10-2.02 (m, 2H), 2.00-1.93 (m, 2H), 1.90-1.83 (m, 2H), 1.22 (d, J=3.8 Hz, 3H), 1.16 (d, J=6.8 Hz, 6H).

Example 188

(6-(3,4-Dimethylbenzyl)-2-azaspiro[3.3]heptan-2-yl)((1s,3s)-3-hydroxy-3-methylcyclobutyl)methanone

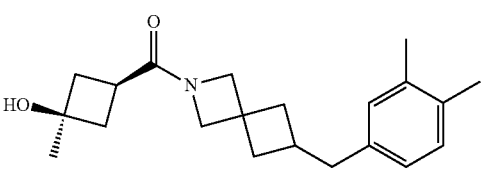

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl 3,4-dimethylbenzylphosphonate (Intermediate 30) instead of diethyl 3-methylbenzylphosphonate in Step A. MS (ESI): mass calcd. for $C_{21}H_{29}NO_2$, 327.2; m/z found, 328.2 [M+H]$^+$. $^1$H NMR (400 MHz, DMSO-$d_6$) δ 7.00 (d, J=7.6 Hz, 1H), 6.93-6.80 (m, 2H), 4.09-3.89 (m, 2H), 3.80-3.70 (m, 2H), 2.54 (s, 2H), 2.47-2.22 (m, 2H), 2.16 (d, J=5.6 Hz, 8H), 2.09-2.01 (m, 2H), 2.00-1.92 (m, 2H), 1.89-1.78 (m, 2H), 1.22 (d, J=2.9 Hz, 3H).

Example 189

((1s,3s)-3-Hydroxy-3-methylcyclobutyl)(6-(4-methyl-3-(trifluoromethyl)benzyl)-2-azaspiro[3.3]heptan-2-yl)methanone

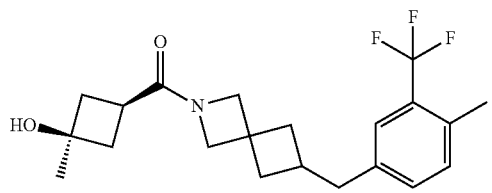 [SMILES: Cc1ccc(CC2CC3(C2)CN(C(=O)[C@H]2C[C@@](C)(O)C2)C3)cc1C(F)(F)F]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl 4-methyl-3-(trifluoromethyl)benzylphosphonate (Intermediate 31) instead of diethyl 3-methylbenzylphosphonate in Step A. MS (ESI): mass calcd. for $C_{21}H_{26}F_3NO_2$, 381.2; m/z found, 382.1 $[M+H]^+$. $^1$H NMR (400 MHz, DMSO-$d_6$) δ 7.42 (s, 1H), 7.36-7.29 (m, 2H), 4.01 (s, 1H), 3.93 (s, 1H), 3.79 (s, 1H), 3.74-3.70 (m, 1H), 2.66 (d, J=7.5 Hz, 2H), 2.49-2.43 (m, 1H), 2.38 (d, J=1.0 Hz, 3H), 2.35-2.26 (m, 1H), 2.20-2.12 (m, 2H), 2.10-2.02 (m, 2H), 1.99-1.92 (m, 2H), 1.89-1.79 (m, 2H), 1.22 (d, J=3.0 Hz, 3H).

Example 190

(6-((4-(tert-Butyl)pyridin-2-yl)methyl)-2-azaspiro[3.3]heptan-2-yl)((1s,3s)-3-hydroxy-3-methylcyclobutyl)methanone

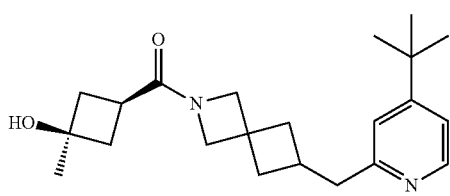 [SMILES: CC(C)(C)c1ccnc(CC2CC3(C2)CN(C(=O)[C@H]2C[C@@](C)(O)C2)C3)c1]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl ((4-(tert-butyl)pyridin-2-yl)methyl)phosphonate (Intermediate 32) instead of diethyl 3-methylbenzylphosphonate in Step A. MS (ESI): mass calcd. for $C_{22}H_{32}N_2O_2$, 356.2; m/z found, 357.3 $[M+H]^+$. $^1$H NMR (400 MHz, CDCl$_3$) δ 8.43 (d, J=4.9 Hz, 1H), 7.24-7.01 (m, 2H), 5.19 (s, 1H), 4.17-3.76 (m, 4H), 2.98-2.80 (m, 2H), 2.67-2.50 (m, 2H), 2.25 (d, J=7.5 Hz, 6H), 2.10-1.91 (m, 2H), 1.38-1.24 (m, 12H).

Example 191

((1s,3s)-3-Hydroxy-3-methylcyclobutyl)(6-((6-methoxypyridin-2-yl)methyl)-2-azaspiro[3.3]heptan-2-yl)methanone

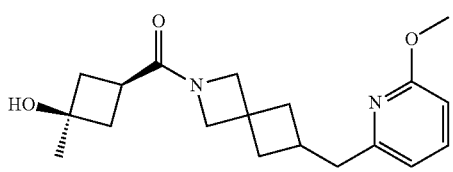 [SMILES: COc1cccc(CC2CC3(C2)CN(C(=O)[C@H]2C[C@@](C)(O)C2)C3)n1]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl ((6-methoxypyridin-2-yl)methyl)phosphonate (Intermediate 33) instead of diethyl 3-methylbenzylphosphonate in Step A. MS (ESI): mass calcd. for $C_{19}H_{26}N_2O_3$, 330.2; m/z found, 331.1 $[M+H]^+$. $^1$H NMR (400 MHz, DMSO-$d_6$) δ 7.59-7.55 (m, 1H), 6.76 (d, J=7.3 Hz, 1H), 6.59 (d, J=8.2 Hz, 1H), 5.00 (s, 1H), 4.03 (s, 1H), 3.95 (s, 1H), 3.80 (s, 4H), 3.71 (s, 1H), 2.68 (d, J=7.3 Hz, 2H), 2.49-2.42 (m, 2H), 2.28-2.18 (m, 2H), 2.11-2.01 (m, 2H), 1.99-1.86 (m, 4H), 1.22 (s, 3H).

Example 192: ((1s,3s)-3-Hydroxy-3-methylcyclobutyl)(6-(4-methoxybenzyl)-2-azaspiro[3.3]heptan-2-yl)methanone

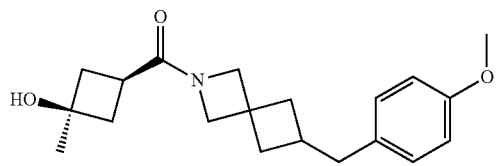 [SMILES: COc1ccc(CC2CC3(C2)CN(C(=O)[C@H]2C[C@@](C)(O)C2)C3)cc1]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl 4-methoxybenzylphosphonate instead of diethyl 3-methylbenzylphosphonate in Step A. MS (ESI): mass calcd. for $C_{20}H_{27}NO_3$, 329.2; m/z found, 330.2 $[M+H]^+$. $^1$H NMR (400 MHz, DMSO-$d_6$) δ 7.05 (d, J=8.4 Hz, 2H), 6.81 (d, J=8.4 Hz, 2H), 4.01 (s, 1H), 3.93 (s, 1H), 3.79 (s, 1H), 3.70 (s, 4H), 2.54 (d, J=7.5 Hz, 3H), 2.34-2.23 (m, 1H), 2.20-2.10 (m, 2H), 2.09-2.01 (m, 2H), 2.00-1.92 (m, 2H), 1.89-1.76 (m, 2H), 1.21 (d, J=2.4 Hz, 3H).

Example 193

((1s,3s)-3-Hydroxy-3-methylcyclobutyl)(6-(3-(trifluoromethyl)benzyl)-2-azaspiro[3.3]heptan-2-yl)methanone

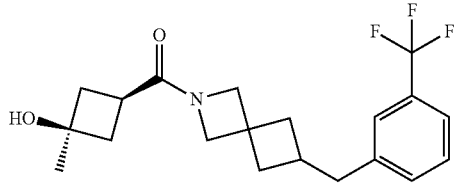 [SMILES: C[C@]1(O)C[C@@H](C(=O)N2CC3(CC(Cc4cccc(C(F)(F)F)c4)C3)C2)C1]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl 3-(trifluoromethyl)benzylphosphonate instead of diethyl 3-methylbenzylphosphonate in Step A. MS (ESI): mass calcd. for $C_{20}H_{24}F_3NO_2$, 367.2; m/z found, 368.1 [M+H]$^+$. $^1$H NMR (400 MHz, CDCl$_3$) δ 7.49-7.44 (m, 1H), 7.43-7.34 (m, 2H), 7.29 (d, J=7.6 Hz, 1H), 4.08 (s, 1H), 4.00 (s, 1H), 3.97 (s, 1H), 3.92 (s, 1H), 2.76-2.70 (m, 2H), 2.67-2.58 (m, 1H), 2.53-2.38 (m, 1H), 2.34-2.20 (m, 6H), 1.99-1.87 (m, 2H), 1.34 (d, J=1.2 Hz, 3H).

Example 194

((1s,3s)-3-Hydroxy-3-methylcyclobutyl)(6-(3-(trifluoromethoxy)benzyl)-2-azaspiro[3.3]heptan-2-yl)methanone

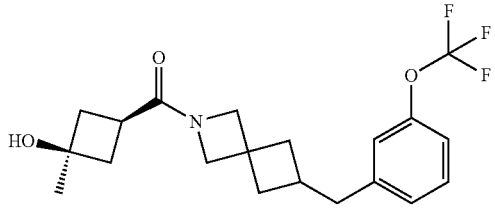 [SMILES: C[C@]1(O)C[C@@H](C(=O)N2CC3(CC(Cc4cccc(OC(F)(F)F)c4)C3)C2)C1]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl 3-(trifluoromethoxy)benzylphosphonate (Intermediate 25) instead of diethyl 3-methylbenzylphosphonate in Step A. MS (ESI): mass calcd. for $C_{20}H_{24}F_3NO_3$, 383.2; m/z found, 384.1 [M+H]$^+$. $^1$H NMR (400 MHz, CDCl$_3$) δ 7.32-7.27 (m, 1H), 7.04 (t, J=7.2 Hz, 2H), 6.95 (s, 1H), 4.17 (s, 1H), 4.07 (s, 1H), 3.99 (s, 1H), 3.95 (s, 1H), 3.90 (s, 1H), 2.69 (dd, J=3.2, 7.2 Hz, 2H), 2.60 (dt, J=3.2, 7.6 Hz, 1H), 2.50-2.38 (m, 1H), 2.26 (d, J=7.6 Hz, 6H), 1.97-1.85 (m, 2H), 1.34 (s, 3H).

Example 195

((1s,3s)-3-Hydroxy-3-methylcyclobutyl)(6-(4-(trifluoromethyl)benzyl)-2-azaspiro[3.3]heptan-2-yl)methanone

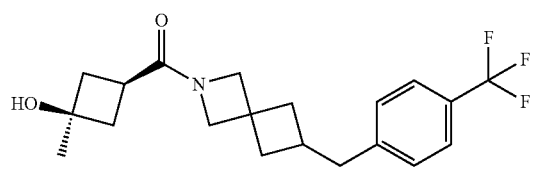 [SMILES: C[C@]1(O)C[C@@H](C(=O)N2CC3(CC(Cc4ccc(C(F)(F)F)cc4)C3)C2)C1]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl 4-(trifluoromethyl)benzylphosphonate instead of diethyl 3-methylbenzylphosphonate in Step A. MS (ESI): mass calcd. for $C_{20}H_{24}F_3NO_2$, 367.2; m/z found, 368.2 [M+H]$^+$. $^1$H NMR (400 MHz, CDCl$_3$) δ 7.54 (d, J=7.6 Hz, 2H), 7.22 (d, J=7.6 Hz, 2H), 4.08 (s, 1H), 4.01 (s, 1H), 3.97 (s, 1H), 3.93 (s, 1H), 2.77-2.70 (m, 2H), 2.64 (d, J=2.0 Hz, 1H), 2.52-2.39 (m, 1H), 2.34-2.21 (m, 6H), 1.98-1.87 (m, 2H), 1.34 (s, 3H).

Example 196

((1s,3s)-3-Hydroxy-3-methylcyclobutyl)(6-(2-(trifluoromethoxy)benzyl)-2-azaspiro[3.3]heptan-2-yl)methanone

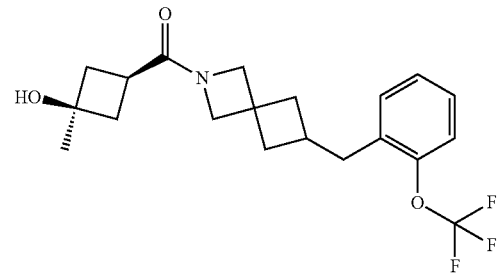 [SMILES: C[C@]1(O)C[C@@H](C(=O)N2CC3(CC(Cc4ccccc4OC(F)(F)F)C3)C2)C1]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl 2-(trifluoromethoxy)benzylphosphonate (Intermediate 34) instead of diethyl 3-methylbenzylphosphonate in Step A. MS (ESI): mass calcd. for $C_{20}H_{24}F_3NO_3$, 383.2; m/z found, 384.1 [M+H]$^+$. $^1$H NMR (400 MHz, CDCl$_3$) δ 7.25-7.16 (m, 4H), 4.07 (s, 1H), 4.01-3.98 (m, 2H), 3.92 (s, 1H), 3.85 (d, J=3.2 Hz, 1H), 2.75 (dd, J=1.2, 7.2 Hz, 2H), 2.68-2.61 (m, 1H), 2.45-2.41 (m, 1H), 2.34-2.20 (m, 6H), 1.98-1.88 (m, 2H), 1.34 (d, J=1.6 Hz, 3H).

Example 197

((1s,3s)-3-Hydroxy-3-methylcyclobutyl)(6-(3-methoxybenzyl)-2-azaspiro[3.3]heptan-2-yl)methanone

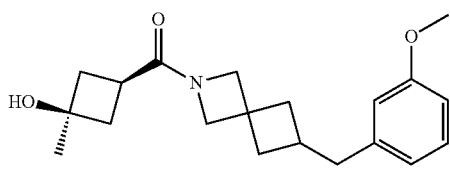 [SMILES: COc1cccc(CC2CC3(C2)CN(C(=O)[C@H]2C[C@@](C)(O)C2)C3)c1]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl 3-methoxybenzylphosphonate instead of diethyl 3-methylbenzylphosphonate in Step A. MS (ESI): mass calcd. for $C_{20}H_{27}NO_3$, 329.2; m/z found, 330.2 [M+H]$^+$. $^1$H NMR (400 MHz, CDCl$_3$) δ 7.22-7.18 (m, 1H), 6.79-6.69 (m, 2H), 6.66 (s, 1H), 4.06 (s, 1H), 3.99 (s, 1H), 3.97 (s, 1H), 3.91 (s, 1H), 3.80 (s, 3H), 2.69-2.59 (m, 3H), 2.50-2.37 (m, 1H), 2.33-2.19 (m, 6H), 1.97-1.86 (m, 2H), 1.34 (s, 3H).

Example 198

((1s,3s)-3-Hydroxy-3-methylcyclobutyl)(6-(quinolin-2-ylmethyl)-2-azaspiro[3.3]heptan-2-yl)methanone

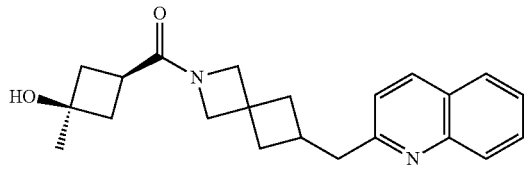 [SMILES: C[C@]1(O)C[C@@H](C(=O)N2CC3(CC(Cc4ccc5ccccc5n4)C3)C2)C1]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl (quinolin-2-ylmethyl)phosphonate (Intermediate 35) instead of diethyl 3-methylbenzylphosphonate in Step A. MS (ESI): mass calcd. for $C_{22}H_{26}N_2O_2$, 350.2; m/z found, 351.1 [M+H]$^+$. $^1$H NMR (400 MHz, MeOD) δ 8.26 (d, J=8.4 Hz, 1H), 7.98 (d, J=8.4 Hz, 1H), 7.89 (d, J=8.0 Hz, 1H), 7.74 (t, J=7.6 Hz, 1H), 7.58-7.52 (m, 1H), 7.41 (d, J=8.4 Hz, 1H), 4.17-3.86 (m, 4H), 3.05 (d, J=8.0 Hz, 2H), 2.74-2.55 (m, 2H), 2.31-2.26 (m, 2H), 2.25-2.03 (m, 6H), 1.34 (d, J=5.2 Hz, 3H).

Example 199

((1s,3s)-3-Hydroxy-3-methylcyclobutyl)(6-(2-(trifluoromethyl)benzyl)-2-azaspiro[3.3]heptan-2-yl)methanone

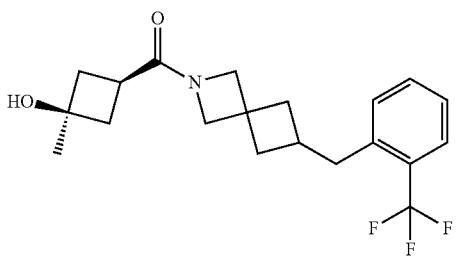 [SMILES: C[C@]1(O)C[C@@H](C(=O)N2CC3(CC(Cc4ccccc4C(F)(F)F)C3)C2)C1]

The title compound was prepared in a manner analogous to Example 174 using tert-butyl 6-oxo-2-azaspiro[3.3]heptane-2-carboxylate instead of tert-butyl 6-oxo-2-azaspiro[3.4]octane-2-carboxylate and diethyl 2-(trifluoromethyl)benzylphosphonate (Intermediate 36) instead of diethyl 3-methylbenzylphosphonate in Step A. MS (ESI): mass calcd. for $C_{20}H_{24}F_3NO_2$, 367.2; m/z found, 368.1 [M+H]$^+$. $^1$H NMR (400 MHz, CDCl$_3$) δ 7.63 (d, J=8.0 Hz, 1H), 7.52-7.45 (m, 1H), 7.33-7.28 (m, 1H), 7.26-7.20 (m, 1H), 4.14-3.85 (m, 5H), 2.88 (d, J=7.2 Hz, 2H), 7.70-2.60 (m, 1H), 2.59-2.42 (m, 1H), 2.33-2.20 (m, 6H), 2.03-1.91 (m, 2H), 1.36-1.32 (m, 3H).

Example 200

(rac)-(6-(4-Cyclopropylbenzyl)-2-azaspiro[3.4]octan-2-yl)((1s,3s)-3-hydroxy-3-methylcyclobutyl)methanone

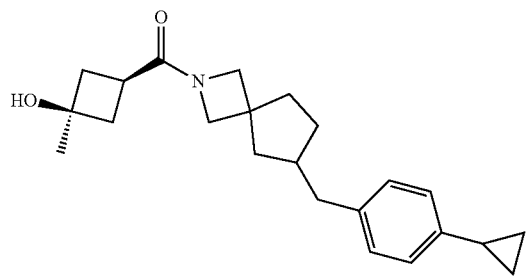 [SMILES: C[C@]1(O)C[C@@H](C(=O)N2CC3(CCC(Cc4ccc(C5CC5)cc4)C3)C2)C1]

Step A: tert-Butyl 6-(4-bromobenzylidene)-2-azaspiro[3.4]octane-2-carboxylate. A solution of diethyl 4-bromobenzylphosphonate (818 mg, 2.66 mmol) and THF (5 mL) was added to a 0° C. mixture of NaH (107 mg, 60 wt % in mineral oil, 2.66 mmol) and THF (5 mL) under N$_2$. The resultant mixture was stirred for 30 min before treating with a solution of tert-butyl 6-oxo-2-azaspiro[3.4]octane-2-carboxylate (200 mg, 0.888 mmol) and 15-crown-5 (587 mg, 2.66 mmol) in THF (5 mL). The reaction mixture was warmed to rt and stirred overnight before being quenched with sat. NH$_4$Cl and extracted with EtOAc. The combined organic extracts were washed with brine, dried over Na$_2$SO$_4$, filtered, and concentrated under reduced pressure. The resulting residue was purified by FCC (SiO$_2$, 0-7% EtOAc in ether) to afford the title compound (260 mg, 77%)

as colorless oil. $^1$H NMR (400 MHz, CDCl$_3$) δ 7.46-7.42 (m, 2H), 7.16-7.10 (m, 2H), 6.30 (br s, 1H), 3.86-3.78 (m, 4H), 2.76-2.66 (m, 2H), 2.61-2.50 (m, 2H), 2.00 (t, J=7.2 Hz, 1H), 1.90 (t, J=7.2 Hz, 1H), 1.45 (d, J=5.6 Hz, 9H).

Step B: (rac)-tert-Butyl 6-(4-bromobenzyl)-2-azaspiro[3.4]octane-2-carboxylate. A mixture of tert-butyl 6-(4-bromobenzylidene)-2-azaspiro[3.4]octane-2-carboxylate (180 mg, 0.476 mmol), PtO$_2$ (10.8 mg, 0.048 mmol) and EtOAc (10 mL) was purged with H$_2$ then stirred at rt under H$_2$ (15 psi) for 1 hour. The mixture was filtered through a pad of Celite® and the pad washed with EtOAc. The filtrate was concentrated under reduced pressure. The resulting residue was purified by FCC (SiO$_2$, 0-5% EtOAc in ether) to afford the title compound (128 mg, 66%) as colorless oil. MS (ESI): mass calcd. for C$_{19}$H$_{26}$BrNO$_2$, 379.1; m/z found 324.1 [M+2H-tBu]$^+$. $^1$H NMR (400 MHz, CDCl$_3$) δ 7.42-7.37 (m, 2H), 7.03 (d, J=8.4 Hz, 2H), 3.79 (s, 2H), 3.70 (s, 2H), 2.62-2.51 (m, 2H), 2.14 (td, J=8.0, 15.6 Hz, 1H), 1.98-1.71 (m, 4H), 1.47-1.40 (m, 11H).

Step C: (rac)-tert-Butyl 6-(4-cyclopropylbenzyl)-2-azaspiro[3.4]octane-2-carboxylate. A mixture of tert-butyl 6-(4-bromobenzyl)-2-azaspiro[3.4]octane-2-carboxylate (120 mg, 0.316 mmol), cyclopropylboronic acid (54 mg, 0.631 mmol), potassium phosphate (201 mg, 0.947 mmol), CataCXium® A Pd G3 (23 mg, 0.032 mmol), toluene (4 mL), and H$_2$O (2 mL) was heated to 100° C. and stirred overnight. The reaction mixture was cooled to rt and concentrated under reduced pressure. The resulting residue was purified by FCC (SiO$_2$, 0-5% EtOAc in ether) to afford the title compound (90 mg, 71%) as a light-yellow oil. MS (ESI): mass calcd. for C$_{22}$H$_{31}$NO$_2$, 341.2; m/z found, 286.0 [M+2H-tBu]$^+$. $^1$H NMR (400 MHz, CDCl$_3$) δ 7.05-7.02 (m, 2H), 7.00-6.97 (m, 2H), 3.78 (s, 2H), 3.69 (s, 2H), 2.62-2.50 (m, 2H), 2.20-2.10 (m, 1H), 1.97-1.71 (m, 6H), 1.43 (s, 9H), 1.33-1.25 (m, 1H), 0.96-0.90 (m, 2H), 0.70-0.64 (m, 2H).

Step D: (rac)-6-(4-Cyclopropylbenzyl)-2-azaspiro[3.4]octane. A mixture of tert-butyl 6-(4-cyclopropylbenzyl)-2-azaspiro[3.4]octane-2-carboxylate (90 mg, 0.264 mmol), TFA (1 mL) and DCM (2 mL) was stirred at rt for 1 hour. The reaction mixture was concentrated under reduced pressure to afford the crude product (90 mg, 96%) as a brown oil, which was used in the next step without further purification. MS (ESI): mass calcd. for C$_{17}$H$_{23}$N, 241.2; m/z found, 242.1 [M+H]$^+$.

Step E: (rac)-(6-(4-Cyclopropylbenzyl)-2-azaspiro[3.4]octan-2-yl)((1s,3s)-3-hydroxy-3-methylcyclobutyl)methanone. HATU (105 mg, 0.277 mmol) was added to a solution of (1s,3s)-3-hydroxy-3-methylcyclobutanecarboxylic acid (30 mg, 0.231 mmol), 6-(4-cyclopropylbenzyl)-2-azaspiro[3.4]octane (90 mg, 0.253 mmol), and DIPEA (0.19 mL, 1.15 mmol) in DMF (5 mL). The resultant mixture was stirred at rt overnight. The reaction mixture was diluted with EtOAc and H$_2$O and extracted with EtOAc. The combined organic extracts were washed with brine, dried over Na$_2$SO$_4$, filtered, and concentrated under reduced pressure. The resulting residue was purified by preparative HPLC (Phenomenex Gemini-NX 150×30 mm×5 μm column, 55% to 85% (v/v) CH$_3$CN and H$_2$O with 0.05% NH$_3$) to afford the title compound (42 mg, 51%) as a yellow syrupy solid. MS (ESI): mass calcd. for C$_{23}$H$_{31}$NO$_2$, 353.2; m/z found, 354.2 [M+H]$^+$. $^1$H NMR (400 MHz, CDCl$_3$) δ 7.05-7.01 (m, 2H), 7.01-6.97 (m, 2H), 3.98 (s, 1H), 3.95-3.89 (m, 1H), 3.88 (s, 1H), 3.85 (s, 1H), 3.78 (s, 1H), 2.69-2.50 (m, 3H), 2.33-2.11 (m, 5H), 1.99-1.75 (m, 5H), 1.53-1.42 (m, 1H), 1.39-1.25 (m, 4H), 0.97-0.91 (m, 2H), 0.69-0.64 (m, 2H).

Example 201

(rac)-(6-(3-Cyclopropylbenzyl)-2-azaspiro[3.4]octan-2-yl)((1s,3s)-3-hydroxy-3-methylcyclobutyl)methanone

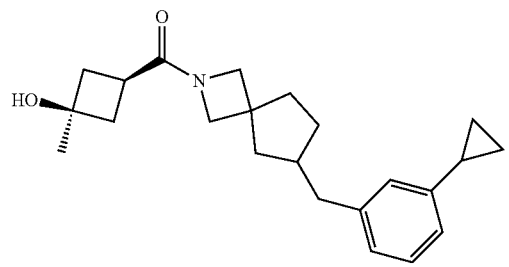 [SMILES: C[C@]1(O)C[C@@H](C(=O)N2CC3(CCC(Cc4cccc(C5CC5)c4)C3)C2)C1]

The title compound was prepared in a manner analogous to Example 200 using diethyl 3-bromobenzylphosphonate instead of diethyl 4-bromobenzylphosphonate in Step A. MS (ESI): mass calcd. for C$_{23}$H$_{31}$NO$_2$, 353.2; m/z found, 354.2 [M+H]$^+$. $^1$H NMR (400 MHz, CDCl$_3$) δ 7.19-7.14 (m, 1H), 6.95-6.86 (m, 3H), 3.96-3.91 (m, 1H), 3.89 (s, 1H), 3.86 (s, 1H), 3.79 (s, 1H), 2.71-2.51 (m, 3H), 2.34-2.12 (m, 5H), 2.01-1.75 (m, 5H), 1.54-1.43 (m, 1H), 1.40-1.25 (m, 4H), 0.99-0.93 (m, 2H), 0.71-0.66 (m, 2H).

Example 202

(6-(4-Cyclopropyl-3-methylbenzyl)-2-azaspiro[3.3]heptan-2-yl)((1s,3s)-3-hydroxy-3-methylcyclobutyl)methanone

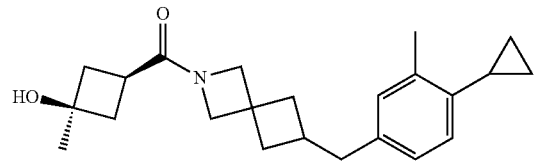 [SMILES: Cc1cc(CC2CC3(C2)CN(C(=O)[C@H]2C[C@@](C)(O)C2)C3)ccc1C1CC1]

The title compound was prepared in a manner analogous to Example 200 using tert-butyl 6-oxo-2-azaspiro[3.3]heptane-2-carboxylate instead of tert-butyl 6-oxo-2-azaspiro[3.4]octane-2-carboxylate and diethyl 4-bromo-3-methylbenzylphosphonate (Intermediate 37) instead of diethyl 4-bromobenzylphosphonate in Step A. MS (ESI): mass calcd. for C$_{23}$H$_{31}$NO$_2$, 353.2; m/z found, 354.2 [M+H]$^+$. $^1$H NMR (400 MHz, CDCl$_3$) δ 6.89-6.88 (m, 2H), 6.87-6.83 (m, 1H), 4.04 (s, 2H), 3.95 (s, 2H), 2.70-2.62 (m, 1H), 2.61 (d, J=7.3 Hz, 2H), 2.47-2.40 (m, 1H), 2.40 (s, 3H), 2.30-2.24 (m, 6H), 1.95-1.87 (m, 2H), 1.87-1.80 (m, 1H), 1.35 (s, 3H), 0.93-0.87 (m, 2H), 0.63-0.57 (m, 2H).

Example 203

(rac)-((1s,3s)-3-Hydroxy-3-methylcyclobutyl)(6-(2-methyl-4-(trifluoromethyl)benzyl)-2-azaspiro[3.4]octan-2-yl)methanone

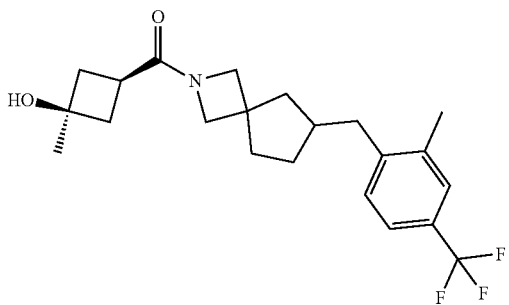 [SMILES: Cc1cc(C(F)(F)F)ccc1CC1CCC2(C1)CN(C(=O)[C@H]1C[C@@](C)(O)C1)C2]

Step A: tert-Butyl 6-methylene-2-azaspiro[3.4]octane-2-carboxylate. A solution of methyltriphenylphosphonium bromide (14.3 g, 40.0 mmol) in DMSO (30 ml) was added dropwise to a 0° C. mixture of NaH (692 mg, 60% in mineral oil, 17.3 mmol) and THF (120 mL). The resultant mixture was stirred at rt for 2 hours and then treated with a solution of tert-butyl 6-oxo-2-azaspiro[3.4]octane-2-carboxylate (3.0 g, 13.3 mmol) in THF (30 mL). The resultant mixture was stirred for another 16 hours at rt. The reaction mixture was quenched with sat. $NH_4Cl$ and extracted with EtOAc. The combined organic extracts were washed with brine, dried over $Na_2SO_4$, filtered, and concentrated under reduced pressure. The resulting residue was purified by FCC ($SiO_2$, 0-10% EtOAc in ether) to afford the title compound (2.6 g, 88%) as a light-yellow oil. $^1H$ NMR (400 MHz, $CDCl_3$) δ 4.98-4.77 (m, 2H), 3.83-3.66 (m, 4H), 2.47 (br s, 2H), 2.33 (t, J=6.4 Hz, 2H), 1.87 (t, J=7.4 Hz, 2H), 1.44 (s, 9H).

Step B: tert-Butyl 6-(2-methyl-4-(trifluoromethyl)benzylidene)-2-azaspiro[3.4]octane-2-carboxylate. tert-Butyl 6-methylene-2-azaspiro[3.4]octane-2-carboxylate (700 mg, 3.14 mmol), 1-bromo-2-methyl-4-(trifluoromethyl)benzene (823 mg, 3.44 mmol), TEA (793 mg, 7.84 mmol), tri-o-tolylphosphine (286 mg, 0.940 mmol), and DMF (5 mL) were combined. The resultant mixture was sparged with $N_2$ for 5 minutes and then treated with Pd(OAc)$_2$ (141 mg, 0.627 mmol). The mixture was sparged with $N_2$ for another 5 minutes and then stirred while heating at 130° C. for 12 hours. The reaction mixture was cooled to rt, quenched with water and brine, and extracted with EtOAc. The combined organic extracts were dried over $Na_2SO_4$, filtered, and concentrated under reduced pressure. The resulting residue was purified by FCC ($SiO_2$, 0-10% EtOAc in ether) to afford the title compound (900 mg, 65%) as a yellow oil. MS (ESI): mass calcd. for $C_{21}H_{26}F_3NO_2$, 381.2; m/z found, 367.1 [M+2H+MeCN-tBu]$^+$.

Step C: (rac)-tert-Butyl 6-(2-methyl-4-(trifluoromethyl)benzyl)-2-azaspiro[3.4]octane-2-carboxylate. tert-Butyl 6-(2-methyl-4-(trifluoromethyl)benzylidene)-2-azaspiro[3.4]octane-2-carboxylate (900 mg, 2.36 mmol), EtOH (10 mL), and wet PtO$_2$ (200 mg, 88.1 umol) were combined. The resultant mixture was stirred under H$_2$ (15 psi) at rt for 2 hours. The suspension was filtered through a pad of Celite® and the pad washed with EtOAc. The filtrate was concentrated under reduced pressure to afford the title product (900 mg, 86%) as yellow oil, which was used in the next step without further purification. MS (ESI): mass calcd. for $C_{21}H_{28}F_3NO_2$, 383.2; m/z found, 369.1 [M+2H+MeCN-tBu]$^+$.

Step D: (rac)-6-(2-Methyl-4-(trifluoromethyl)benzyl)-2-azaspiro[3.4]octane. tert-Butyl 6-(2-methyl-4-(trifluoromethyl)benzyl)-2-azaspiro[3.4]octane-2-carboxylate (400 mg, 1.04 mmol), DCM (10 mL) and TFA (2.5 mL) were combined. The resultant mixture was stirred at rt for 1 hour. The mixture was concentrated under reduced pressure to afford the title compound (400 mg, crude) as yellow oil, which was used in the next step without further purification. MS (ESI): mass calcd. for $C_{16}H_{20}F_3N$, 283.1; m/z found, 284.2 [M+H]$^+$.

Step E: (rac)-((1s,3s)-3-Hydroxy-3-methylcyclobutyl)(6-(2-methyl-4-(trifluoromethyl)benzyl)-2-azaspiro[3.4]octan-2-yl)methanone. HATU (316 mg, 0.830 mmol) was added to a solution of 6-(2-methyl-4-(trifluoromethyl)benzyl)-2-azaspiro[3.4]octane (400 mg, crude), (1s,3s)-3-hydroxy-3-methylcyclobutanecarboxylic acid (90 mg, 0.692 mmol), and DIPEA (447 mg, 3.46 mmol) in DMF (6 mL). The resultant mixture was stirred at rt for 12 hours. The reaction mixture was poured into brine:H$_2$O (1:1) and extracted with EtOAc. The combined organic extracts were dried over Na$_2$SO$_4$, filtered, and concentrated under reduced pressure. The resulting residue was purified by preparative HPLC (Boston Prime C18, 150 mm×30 mm×5 μm column, 55% to 85% (v/v) CH$_3$CN and H$_2$O with 0.05% NH$_3$+10 mM NH$_4$HCO$_3$)) to afford the title compound (238 mg, 87%) as a light-yellow syrupy solid. MS (ESI): mass calcd. for $C_{22}H_{28}F_3NO_2$, 395.2; m/z found, 396.2 [M+H]$^+$. $^1H$ NMR (400 MHz, CDCl$_3$) δ 7.42-7.34 (m, 2H), 7.20 (d, J=7.6 Hz, 1H), 4.03-3.74 (m, 4H), 2.72-2.61 (m, 3H), 2.35 (s, 3H), 2.32-2.16 (m, 5H), 2.06-1.80 (m, 4H), 1.58-1.45 (m, 1H), 1.43-1.26 (m, 4H).

Example 204

(rac)-((1s,3s)-3-Hydroxy-3-methylcyclobutyl)(6-(3-methyl-4-(trifluoromethyl)benzyl)-2-azaspiro[3.4]octan-2-yl)methanone

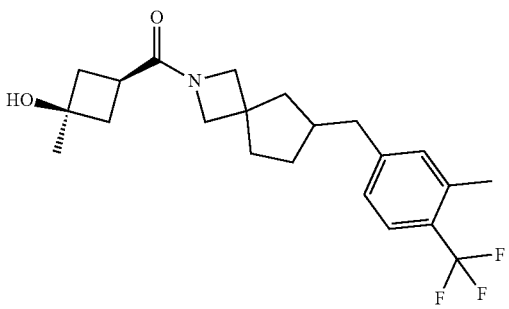 [SMILES: Cc1cc(CC2CCC3(C2)CN(C(=O)[C@H]2C[C@@](C)(O)C2)C3)ccc1C(F)(F)F]

The title compound was prepared in a manner analogous to Example 203 using 1-bromo-3-methyl-4-(trifluoromethyl)benzene instead of 1-bromo-2-methyl-4-(trifluoromethyl)benzene in Step A. MS (ESI): mass calcd. for $C_{22}H_{28}F_3NO_2$, 395.2; m/z found, 396.1 [M+H]$^+$. $^1H$ NMR (400 MHz, MeOD) δ 7.51 (d, J=8.0 Hz, 1H), 7.21-7.13 (m, 2H), 4.01 (s, 1H), 3.93 (s, 1H), 3.83 (s, 1H), 3.74 (s, 1H), 2.69-2.60 (m, 3H), 2.44 (d, J=1.2 Hz, 3H), 2.30-2.12 (m, 5H), 2.01-1.75 (m, 4H), 1.55-1.50 (m, 1H), 1.39-1.31 (m, 4H).

Example 205

(rac)-((1s,3s)-3-Hydroxy-3-methylcyclobutyl)(6-(4-methoxybenzyl)-2-azaspiro[3.4]octan-2-yl)methanone

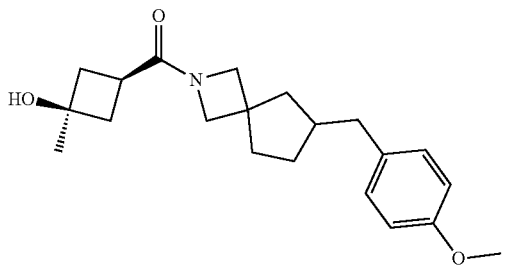 [SMILES: COc1ccc(CC2CCC3(C2)CN(C(=O)[C@H]2C[C@@](C)(O)C2)C3)cc1]

The title compound was prepared in a manner analogous to Example 203 using 1-bromo-4-methoxybenzene instead of 1-bromo-2-methyl-4-(trifluoromethyl)benzene in Step A. MS (ESI): mass calcd. for $C_{21}H_{29}NO_3$, 343.2; m/z found, 344.2 [M+H]$^+$. $^1$H NMR (400 MHz, CDCl$_3$) δ 7.06 (d, J=8.4 Hz, 2H), 6.83 (d, J=7.6 Hz, 2H), 4.01 (s, 1H), 3.93 (d, J=1.6 Hz, 1H), 3.87 (d, J=10.0 Hz, 2H), 3.81-3.77 (m, 4H), 2.68-2.50 (m, 3H), 2.33-2.13 (m, 5H), 2.00-1.75 (m, 5H), 1.60-1.40 (m, 1H), 1.34 (d, J=4.0 Hz, 3H).

Example 206

((1s,3s)-3-Hydroxy-3-methylcyclobutyl)(6-(pyridin-4-ylmethyl)-2-azaspiro[3.3]heptan-2-yl)methanone

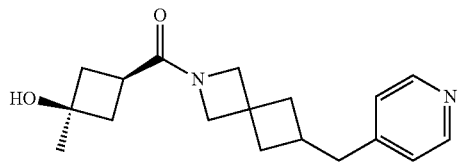 [SMILES: C[C@]1(O)C[C@@H](C(=O)N2CC3(CC(Cc4ccncc4)C3)C2)C1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 4-bromopyridine instead of 1-bromo-2-methyl-4-(trifluoromethyl)benzene in Step B. MS (ESI): mass calcd. for $C_{18}H_{24}N_2O_2$, 300.2; m/z found, 301.1 [M+H]$^+$. $^1$H NMR (400 MHz, DMSO-d$_6$) δ 8.45-8.41 (m, 2H), 7.18 (d, J=6.0 Hz, 2H), 4.99 (s, 1H), 4.03 (s, 1H), 3.95 (s, 1H), 3.80 (s, 1H), 3.72 (s, 1H), 2.65 (d, J=7.6 Hz, 2H), 2.47-2.31 (m, 2H), 2.25-2.14 (m, 2H), 2.10-1.80 (m, 6H), 1.22 (d, J=2.4 Hz, 3H).

Example 207

(6-(2-Cyclopropyl-3-methylbenzyl)-2-azaspiro[3.3]heptan-2-yl)((1s,3s)-3-hydroxy-3-methylcyclobutyl)methanone

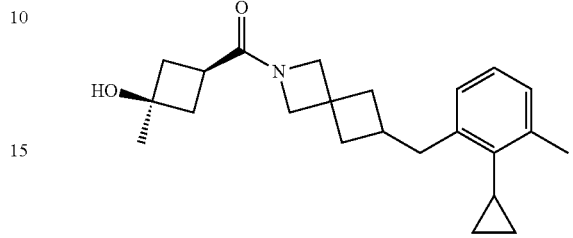

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-2-cyclopropyl-3-methylbenzene (Intermediate 41) instead of 1-bromo-2-methyl-4-(trifluoromethyl)benzene in Step B. MS (ESI): mass calcd. for $C_{23}H_{31}NO_2$, 353.2; m/z found, 354.2 [M+H]$^+$. $^1$H NMR (400 MHz, CDCl$_3$) δ 7.08-6.97 (m, 2H), 6.90 (d, J=6.8 Hz, 1H), 4.07-3.89 (m, 4H), 2.94 (d, J=7.2 Hz, 2H), 2.70-2.61 (m, 1H), 2.47 (br s, 1H), 2.42 (s, 3H), 2.33-2.26 (m, 4H), 2.23-2.18 (m, 2H), 1.92 (br s, 2H), 1.68-1.63 (m, 1H), 1.33 (s, 3H), 1.06-1.00 (m, 2H), 0.56-0.47 (m, 2H).

Example 208

(6-(2-(tert-Butyl)benzyl)-2-azaspiro[3.3]heptan-2-yl)((1s,3s)-3-hydroxy-3-methylcyclobutyl)methanone

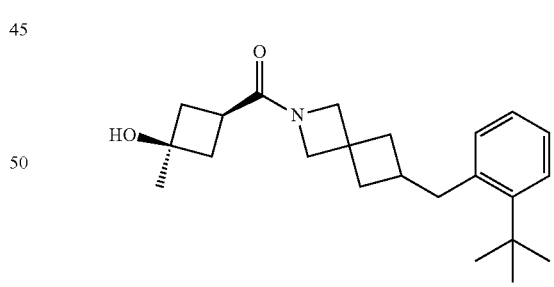

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-2-(tert-butyl)benzene instead of 1-bromo-2-methyl-4-(trifluoromethyl)benzene in Step B. MS (ESI): mass calcd. for $C_{23}H_{33}NO_2$, 355.3; m/z found, 356.3 [M+H]$^+$. $^1$H NMR (400 MHz, CDCl$_3$) δ 7.37 (d, J=4.8 Hz, 1H), 7.17-7.04 (m, 3H), 4.08 (s, 1H), 3.99 (d, J=10.8 Hz, 2H), 3.92 (br s, 2H), 2.96 (d, J=4.0 Hz, 2H), 2.69-2.58 (m, 1H), 2.44-2.21 (m, 7H), 2.08-1.95 (m, 2H), 1.39 (s, 9H), 1.34 (br s, 3H).

Example 209

((1s,3s)-3-Hydroxy-3-methylcyclobutyl)(6-(3-methyl-2-(trifluoromethyl)benzyl)-2-azaspiro[3.3]heptan-2-yl)methanone

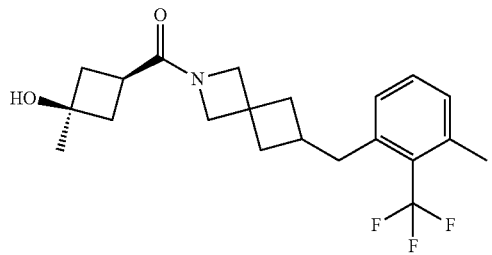 [SMILES: Cc1cccc(CC2CC3(C2)CN(C(=O)[C@H]2C[C@@](C)(O)C2)C3)c1C(F)(F)F]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-3-methyl-2-(trifluoromethyl)benzene instead of 1-bromo-2-methyl-4-(trifluoromethyl)benzene in Step B. MS (ESI): mass calcd. for $C_{21}H_{26}F_3NO_2$, 381.2; m/z found, 382.1 [M+H]$^+$. $^1$H NMR (400 MHz, CDCl$_3$) δ 7.32-7.27 (m, 1H), 7.12 (d, J=7.2 Hz, 1H), 7.02 (d, J=7.2 Hz, 1H), 4.15-3.83 (m, 5H), 2.88 (d, J=5.6 Hz, 2H), 2.6-2.55 (m, 1H), 2.53-2.36 (m, 4H), 2.31-2.16 (m, 6H), 1.95-1.87 (m, 2H), 1.34 (s, 3H).

Example 210

((1s,3s)-3-Hydroxy-3-methylcyclobutyl)(6-(2-isopropyl-3-(trifluoromethyl)benzyl)-2-azaspiro[3.3]heptan-2-yl)methanone

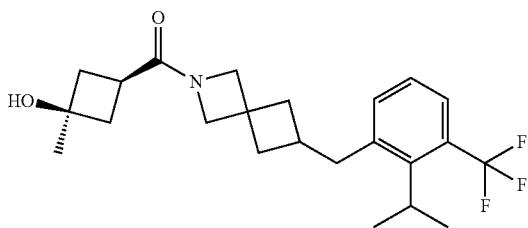 [SMILES: CC(C)c1c(CC2CC3(C2)CN(C(=O)[C@H]2C[C@@](C)(O)C2)C3)cccc1C(F)(F)F]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-2-isopropyl-3-(trifluoromethyl)benzene (Intermediate 43) instead of 1-bromo-2-methyl-4-(trifluoromethyl)benzene in Step B. MS (ESI): mass calcd. for $C_{23}H_{30}F_3NO_2$, 409.2; m/z found, 410.2 [M+H]$^+$. $^1$H NMR (400 MHz, CDCl$_3$) δ 7.49 (d, J=7.6 Hz, 1H), 7.24 (s, 1H), 7.22-7.15 (m, 1H), 4.11-3.90 (m, 4H), 3.60-3.47 (m, 1H), 2.92 (d, J=6.4 Hz, 2H), 2.69-2.59 (m, 1H), 2.41-2.17 (m, 7H), 2.00 (br s, 2H), 1.36 (s, 3H), 1.34 (d, J=2.8 Hz, 6H).

Example 211

((1s,3s)-3-Hydroxy-3-methylcyclobutyl)(6-(5-methyl-2-(trifluoromethyl)benzyl)-2-azaspiro[3.3]heptan-2-yl)methanone

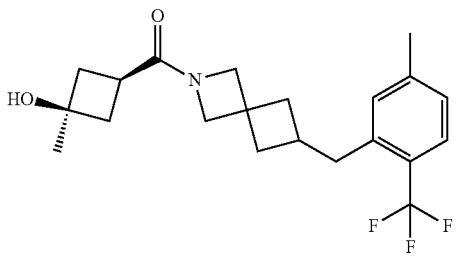 [SMILES: Cc1ccc(C(F)(F)F)c(CC2CC3(C2)CN(C(=O)[C@H]2C[C@@](C)(O)C2)C3)c1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 2-bromo-4-methyl-1-(trifluoromethyl)benzene instead of 1-bromo-2-methyl-4-(trifluoromethyl)benzene in Step B. MS (ESI): mass calcd. for $C_{21}H_{26}F_3NO_2$, 381.2; m/z found, 382.1 [M+H]$^+$. $^1$H NMR (400 MHz, CDCl$_3$) δ 7.50 (d, J=8.0 Hz, 1H), 7.09 (d, J=8.0 Hz, 1H), 7.04 (s, 1H), 4.09 (s, 1H), 4.01 (s, 1H), 3.99 (s, 1H), 3.93 (br s, 2H), 2.83 (d, J=6.8 Hz, 2H), 2.68-2.61 (m, 1H), 2.57-2.43 (m, 1H), 2.38 (s, 3H), 2.34-2.21 (m, 6H), 2.02-1.89 (m, 2H), 1.34 (d, J=2.4 Hz, 3H).

Example 212

((1s,3s)-3-Hydroxy-3-methylcyclobutyl)(6-(3-methyl-4-(trifluoromethyl)benzyl)-2-azaspiro[3.3]heptan-2-yl)methanone

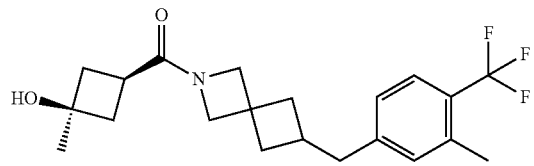 [SMILES: Cc1cc(CC2CC3(C2)CN(C(=O)[C@H]2C[C@@](C)(O)C2)C3)ccc1C(F)(F)F]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-3-methyl-4-(trifluoromethyl)benzene instead of 1-bromo-2-methyl-4-(trifluoromethyl)benzene in Step B. MS (ESI): mass calcd. for $C_{21}H_{26}F_3NO_2$, 381.2; m/z found, 382.1 [M+H]$^+$. $^1$H NMR (400 MHz, CDCl$_3$) δ 7.50 (d, J=8.0 Hz, 1H), 7.04-6.97 (m, 2H), 4.07 (s, 1H), 4.00 (s, 1H), 3.97 (s, 1H), 3.93 (s, 1H), 3.89 (d, J=2.8 Hz, 1H), 2.70-2.58 (m, 3H), 2.51-2.36 (m, 4H), 2.33-2.20 (m, 6H), 1.98-1.85 (m, 2H), 1.34 (s, 3H).

Example 213

((1s,3s)-3-Hydroxy-3-methylcyclobutyl)(6-(4-methyl-2-(trifluoromethyl)benzyl)-2-azaspiro[3.3]heptan-2-yl)methanone

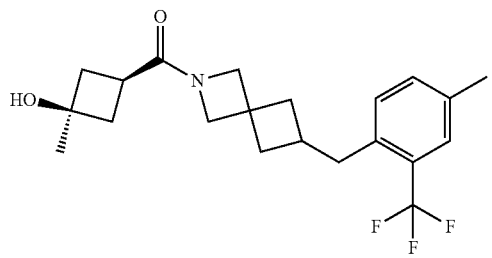 [SMILES: Cc1ccc(CC2CC3(C2)CN(C(=O)[C@H]2C[C@@](C)(O)C2)C3)c(C(F)(F)F)c1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-4-methyl-2-(trifluoromethyl)benzene instead of 1-bromo-2-methyl-4-(trifluoromethyl)benzene in Step B. MS (ESI): mass calcd. for $C_{21}H_{26}F_3NO_2$, 381.2; m/z found, 382.1 [M+H]$^+$. $^1$H NMR (400 MHz, CDCl$_3$) δ 7.43 (s, 1H), 7.25 (s, 1H), 7.13 (d, J=7.6 Hz, 1H), 4.08 (s, 1H), 3.99 (d, J=6.4 Hz, 2H), 3.95 (s, 1H), 3.92 (s, 1H), 2.83 (d, J=7.2 Hz, 2H), 2.67-2.60 (m, 1H), 2.56-2.40 (m, 1H), 2.37 (s, 3H), 2.33-2.20 (m, 6H), 2.00-1.88 (m, 2H), 1.34 (d, J=2.4 Hz, 3H).

Example 214

((1s,3s)-3-Hydroxy-3-methylcyclobutyl)(6-((1-methyl-3-(trifluoromethyl)-1H-pyrazol-5-yl)methyl)-2-azaspiro[3.3]heptan-2-yl)methanone

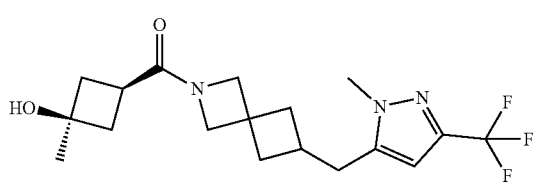 [SMILES: Cn1nc(C(F)(F)F)cc1CC1CC2(C1)CN(C(=O)[C@H]1C[C@@](C)(O)C1)C2]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 5-bromo-1-methyl-3-(trifluoromethyl)-1H-pyrazole instead of 1-bromo-2-methyl-4-(trifluoromethyl)benzene in Step B. MS (ESI): mass calcd. for $C_{18}H_{24}F_3N_3O_2$, 371.2; m/z found, 372.3 [M+H]$^+$. $^1$H NMR (400 MHz, CDCl$_3$) δ 6.21 (d, J=6.4 Hz, 1H), 4.13 (s, 1H), 4.05 (s, 1H), 3.99 (s, 1H), 3.94 (s, 1H), 3.89-3.85 (m, 1H), 3.82 (s, 3H), 2.69 (dd, J=3.2, 7.2 Hz, 2H), 2.66-2.47 (m, 2H), 2.46-2.40 (m, 2H), 2.31-2.24 (m, 4H), 2.00-1.89 (m, 2H), 1.35 (d, J=1.6 Hz, 3H).

Example 215

((1s,3s)-3-Hydroxy-3-methylcyclobutyl)(6-((1-methyl-1H-indazol-6-yl)methyl)-2-azaspiro[3.3]heptan-2-yl)methanone

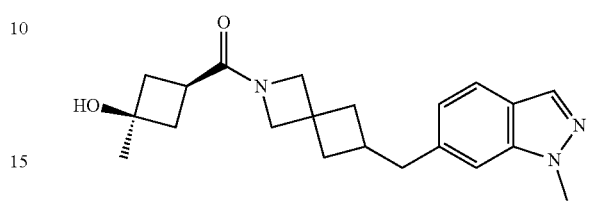

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-1-methyl-1H-indazole instead of 1-bromo-2-methyl-4-(trifluoromethyl)benzene in Step B. MS (ESI): mass calcd. for $C_{21}H_{27}N_3O_2$, 353.2; m/z found, 354.2 [M+H]$^+$. $^1$H NMR (400 MHz, CDCl$_3$) δ 7.92 (s, 1H), 7.62 (d, J=8.4 Hz, 1H), 7.09 (s, 1H), 6.94-6.90 (m, 1H), 4.16 (br s, 1H), 4.07 (s, 1H), 4.05 (s, 3H), 3.99 (d, J=8.8 Hz, 2H), 3.93 (s, 1H), 2.86-2.70 (m, 2H), 2.63-2.45 (m, 2H), 2.26 (d, J=7.2 Hz, 4H), 1.98-1.92 (m, 4H), 1.33 (s, 3H).

Example 216

((1s,3s)-3-Hydroxy-3-methylcyclobutyl)(6-(2-methoxybenzyl)-2-azaspiro[3.3]heptan-2-yl)methanone

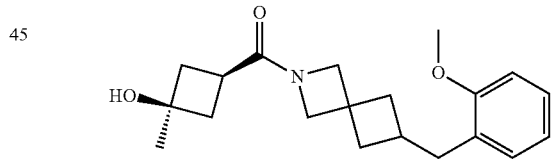

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-2-methoxybenzene instead of 1-bromo-2-methyl-4-(trifluoromethyl)benzene in Step B. MS (ESI): mass calcd. for $C_{20}H_{27}NO_3$, 329.2; m/z found, 330.2 [M+H]$^+$. $^1$H NMR (400 MHz, MeOD) δ 7.17-7.12 (m, 1H), 7.06-7.04 (m, 1H), 6.89 (d, J=8.0 Hz, 1H), 6.85-6.80 (m, 1H), 4.11 (s, 1H), 4.02 (s, 1H), 3.93 (s, 1H), 3.84 (s, 1H), 3.79 (s, 3H), 2.69-2.57 (m, 3H), 2.48-2.41 (m, 1H), 2.26-2.11 (m, 6H), 1.95-1.88 (m, 2H), 1.34 (d, J=3.2 Hz, 3H).

Example 217

((1s,3s)-3-Hydroxy-3-methylcyclobutyl)(6-(4-methoxy-2-(trifluoromethyl)benzyl)-2-azaspiro[3.3]heptan-2-yl)methanone

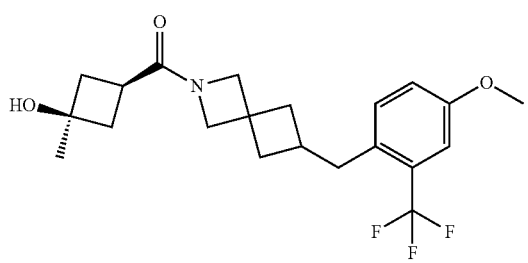 [SMILES: COc1ccc(CC2CC3(C2)CN(C(=O)[C@H]2C[C@@](C)(O)C2)C3)c(C(F)(F)F)c1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-4-methoxy-2-(trifluoromethyl)benzene instead of 1-bromo-2-methyl-4-(trifluoromethyl)benzene in Step B. MS (ESI): mass calcd. for $C_{21}H_{26}F_3NO_3$, 397.2; m/z found, 398.1 [M+H]$^+$. $^1$H NMR (400 MHz, CDCl$_3$) δ 7.17-7.15 (m, 1H), 7.14 (s, 1H), 6.99 (d, J=8.4 Hz, 1H), 4.08 (s, 1H), 4.00 (d, J=7.6 Hz, 2H), 3.90 (d, J=14.0 Hz, 2H), 3.83 (s, 3H), 2.80 (d, J=7.2 Hz, 2H), 2.68-2.60 (m, 1H), 2.51-2.39 (m, 1H), 2.33-2.21 (m, 6H), 1.98-1.88 (m, 2H), 1.34 (d, J=2.0 Hz, 3H).

Example 218

(6-(3-Cyclopropylbenzyl)-2-azaspiro[3.3]heptan-2-yl)((1s,3s)-3-hydroxy-3-methylcyclobutyl)methanone

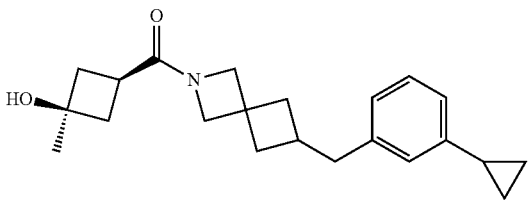 [SMILES: C[C@]1(O)C[C@@H](C(=O)N2CC3(CC(Cc4cccc(C5CC5)c4)C3)C2)C1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-3-cyclopropylbenzene instead of 1-bromo-2-methyl-4-(trifluoromethyl)benzene in Step B. MS (ESI): mass calcd. for $C_{22}H_{29}NO_2$, 339.2; m/z found, 340.2 [M+H]$^+$. $^1$H NMR (400 MHz, CDCl$_3$) δ 7.18-7.15 (m, 1H), 6.89 (d, J=8.0 Hz, 2H), 6.83 (s, 1H), 4.06 (s, 1H), 3.98 (d, J=11.6 Hz, 2H), 3.91 (s, 1H), 2.67-2.58 (m, 3H), 2.49-2.35 (m, 1H), 2.33-2.19 (m, 6H), 1.97-1.82 (m, 3H), 1.34 (d, J=1.2 Hz, 3H), 0.99-0.92 (m, 2H), 0.71-0.64 (m, 2H).

Example 219

(6-(4-Cyclopropylbenzyl)-2-azaspiro[3.3]heptan-2-yl)((1s,3s)-3-hydroxy-3-methylcyclobutyl)methanone

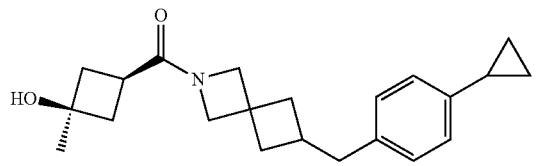 [SMILES: C[C@]1(O)C[C@@H](C(=O)N2CC3(CC(Cc4ccc(C5CC5)cc4)C3)C2)C1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-4-cyclopropylbenzene instead of 1-bromo-2-methyl-4-(trifluoromethyl)benzene in Step B. MS (ESI): mass calcd. for $C_{22}H_{29}NO_2$, 339.2; m/z found, 340.3 [M+H]$^+$. $^1$H NMR (400 MHz, CDCl$_3$) δ 6.99 (s, 4H), 4.08-3.87 (m, 4H), 2.63 (d, J=7.2 Hz, 3H), 2.30-2.22 (m, 5H), 1.99-1.78 (m, 5H), 1.34 (s, 3H), 1.00-0.91 (m, 2H), 0.71-0.64 (m, 2H).

Example 220

((1s,3s)-3-Hydroxy-3-methylcyclobutyl)(6-(4-(trifluoromethoxy)benzyl)-2-azaspiro[3.3]heptan-2-yl)methanone

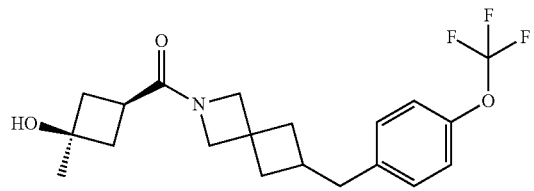 [SMILES: C[C@]1(O)C[C@@H](C(=O)N2CC3(CC(Cc4ccc(OC(F)(F)F)cc4)C3)C2)C1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-4-(trifluoromethoxy)benzene instead of 1-bromo-2-methyl-4-(trifluoromethyl)benzene in Step B. MS (ESI): mass calcd. for $C_{20}H_{24}F_3NO_3$, 383.2; m/z found, 384.2 [M+H]$^+$. $^1$H NMR (400 MHz, CDCl$_3$) δ 7.12 (s, 4H), 4.09-3.90 (m, 4H), 2.69-2.59 (m, 3H), 2.42 (br s, 1H), 2.31-2.19 (m, 6H), 1.95-1.86 (m, 2H), 1.33 (s, 3H).

Example 221

(6-(4-(Difluoromethoxy)benzyl)-2-azaspiro[3.3]heptan-2-yl)((1s,3s)-3-hydroxy-3-methylcyclobutyl)methanone

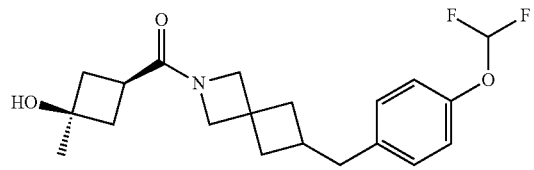 [SMILES: C[C@]1(O)C[C@@H](C(=O)N2CC3(CC(Cc4ccc(OC(F)F)cc4)C3)C2)C1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-4-(difluoromethoxy)benzene instead of 1-bromo-2-methyl-4-(trifluoromethyl)benzene in Step B. MS (ESI): mass calcd. for $C_{20}H_{25}F_2NO_3$, 365.2; m/z found, 366.1 $[M+H]^+$. $^1H$ NMR (400 MHz, CDCl$_3$) δ 7.13-7.07 (m, 2H), 7.06-6.99 (m, 2H), 6.67-6.27 (t, J=74.4 Hz, 1H), 4.10-3.87 (m, 4H), 2.68-2.58 (m, 3H), 2.33-2.17 (m, 7H), 1.95-1.82 (m, 2H), 1.33 (s, 3H).

Example 222

(6-(3-Ethylbenzyl)-2-azaspiro[3.3]heptan-2-yl)((1s,3s)-3-hydroxy-3-methylcyclobutyl)methanone

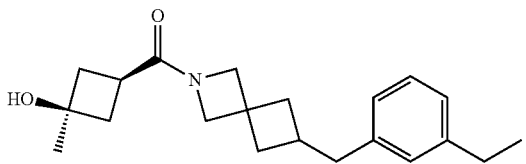 [SMILES: CCc1cccc(CC2CC3(C2)CN(C(=O)[C@H]2C[C@@](C)(O)C2)C3)c1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-3-ethylbenzene instead of 1-bromo-2-methyl-4-(trifluoromethyl)benzene in Step B. MS (ESI): mass calcd. for $C_{21}H_{29}NO_2$, 327.2; m/z found, 328.2 $[M+H]^+$. $^1H$ NMR (400 MHz, CDCl$_3$) δ 7.22-7.17 (m, 1H), 7.05 (d, J=8.0 Hz, 1H), 6.96-6.91 (m, 2H), 4.10-3.89 (m, 5H), 2.68-2.59 (m, 5H), 2.50-2.37 (m, 1H), 2.33-2.22 (m, 6H), 2.01-1.86 (m, 2H), 1.34 (d, J=1.2 Hz, 3H), 1.23 (t, J=7.6 Hz, 3H).

Example 223

((1s,3s)-3-Hydroxy-3-methylcyclobutyl)(6-((6-(trifluoromethyl)pyridin-2-yl)methyl)-2-azaspiro[3.3]heptan-2-yl)methanone

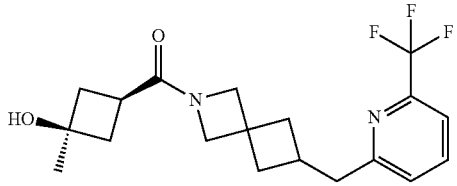 [SMILES: C[C@]1(O)C[C@@H](C(=O)N2CC3(CC(Cc4cccc(C(F)(F)F)n4)C3)C2)C1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 2-bromo-6-(trifluoromethyl)pyridine instead of 1-bromo-2-methyl-4-(trifluoromethyl)benzene in Step B. MS (ESI): mass calcd. for $C_{19}H_{23}F_3N_2O_2$, 368.2; m/z found, 369.1 $[M+H]^+$. $^1H$ NMR (400 MHz, MeOD) δ 7.94-7.90 (m, 1H), 7.61 (d, J=7.6 Hz, 1H), 7.47 (d, J=7.6 Hz, 1H), 4.16 (s, 1H), 4.05 (s, 1H), 3.97 (s, 1H), 3.86 (s, 1H), 2.94 (d, J=7.6 Hz, 2H), 2.68-2.58 (m, 2H), 2.35-2.27 (m, 2H), 2.26-2.12 (m, 4H), 2.06-1.99 (m, 2H), 1.35 (d, J=2.0 Hz, 3H).

Example 224

((1s,3s)-3-Hydroxy-3-methylcyclobutyl)(6-((1-methyl-1H-pyrrolo[2,3-b]pyridin-6-yl)methyl)-2-azaspiro[3.3]heptan-2-yl)methanone

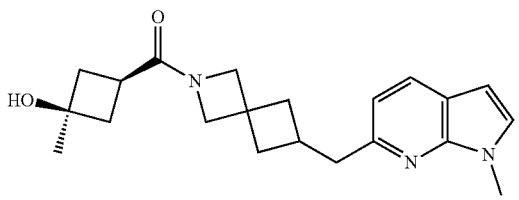 [SMILES: Cn1ccc2ccc(CC3CC4(C3)CN(C(=O)[C@H]3C[C@@](C)(O)C3)C4)nc21]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-1-methyl-1H-pyrrolo[2,3-b]pyridine (Intermediate 44) instead of 1-bromo-2-methyl-4-(trifluoromethyl)benzene in Step B. MS (ESI): mass calcd. for $C_{21}H_{27}N_3O_2$, 353.2; m/z found, 354.1 $[M+H]^+$. $^1H$ NMR (400 MHz, CDCl$_3$) δ 7.79 (d, J=8.0 Hz, 1H), 7.11 (d, J=3.2 Hz, 1H), 6.84 (d, J=7.6 Hz, 1H), 6.40 (d, J=3.2 Hz, 1H), 4.07 (s, 1H), 4.02-3.91 (m, 4H), 3.89-3.84 (m, 3H), 2.94 (dd, J=1.6, 7.6 Hz, 2H), 2.72-2.60 (m, 2H), 2.29-2.22 (m, 4H), 2.09-1.99 (m, 2H), 1.73 (br s, 2H), 1.34 (d, J=2.4 Hz, 3H).

Example 225

((1s,3s)-3-Hydroxy-3-methylcyclobutyl)(6-((1-methyl-3-(trifluoromethyl)-1H-pyrazol-4-yl)methyl)-2-azaspiro[3.3]heptan-2-yl)methanone

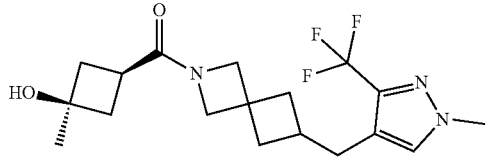 [SMILES: Cn1cc(CC2CC3(C2)CN(C(=O)[C@H]2C[C@@](C)(O)C2)C3)c(C(F)(F)F)n1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 4-bromo-1-methyl-3-(trifluoromethyl)-1H-pyrazole instead of 1-bromo-2-methyl-4-(trifluoromethyl)benzene in Step B. MS (ESI): mass calcd. for $C_{18}H_{24}F_3N_3O_2$, 371.2; m/z found, 372.1 $[M+H]^+$. $^1H$ NMR (400 MHz, CDCl$_3$) δ 7.16 (s, 1H), 4.08 (s, 1H), 4.00 (d, J=11.2 Hz, 3H), 3.90 (s, 4H), 2.65-2.56 (m, 3H), 2.41-2.24 (m, 7H), 1.92-1.82 (m, 2H), 1.34 (s, 3H).

Example 226

((1s,3s)-3-Hydroxy-3-methylcyclobutyl)(6-(2-methyl-6-(trifluoromethyl)benzyl)-2-azaspiro[3.3]heptan-2-yl)methanone

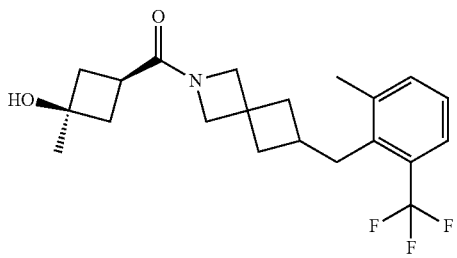 [SMILES: Cc1cccc(C(F)(F)F)c1CC1CC2(C1)CN(C(=O)[C@H]1C[C@@](C)(O)C1)C2]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 2-bromo-1-methyl-3-(trifluoromethyl)benzene instead of 1-bromo-2-methyl-4-(trifluoromethyl)benzene in Step B. MS (ESI): mass calcd. for $C_{21}H_{26}F_3NO_2$, 381.2; m/z found, 382.1 [M+H]$^+$. $^1$H NMR (400 MHz, CDCl$_3$) δ 7.49 (d, J=7.6 Hz, 1H), 7.34 (d, J=8.0 Hz, 1H), 7.23-7.16 (m, 1H), 4.06 (s, 1H), 3.98 (s, 1H), 3.96 (s, 1H), 3.92 (br s, 1H), 3.89 (s, 1H), 2.91 (d, J=5.2 Hz, 2H), 2.69-2.58 (m, 1H), 2.44-2.19 (m, 10H), 2.07-1.93 (m, 2H), 1.34 (d, J=4.0 Hz, 3H).

Example 227

(6-(3-Fluoro-2-methylbenzyl)-2-azaspiro[3.3]heptan-2-yl)((1s,3s)-3-hydroxy-3-methylcyclobutyl)methanone

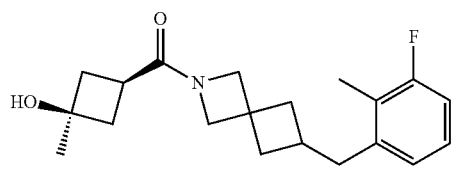 [SMILES: Cc1c(F)cccc1CC1CC2(C1)CN(C(=O)[C@H]1C[C@@](C)(O)C1)C2]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-3-fluoro-2-methylbenzene instead of 1-bromo-2-methyl-4-(trifluoromethyl)benzene in Step B. MS (ESI): mass calcd. for $C_{20}H_{26}FNO_2$, 331.2; m/z found, 332.1 [M+H]$^+$. $^1$H NMR (400 MHz, CDCl$_3$) δ 7.11-7.03 (m, 1H), 6.88 (t, J=9.2 Hz, 1H), 6.83 (d, J=7.2 Hz, 1H), 4.08 (s, 1H), 3.99 (d, J=12.4 Hz, 2H), 3.93-3.91 (m, 1H), 2.69 (dd, J=4.4, 7.2 Hz, 2H), 2.66-2.60 (m, 1H), 2.51-2.37 (m, 1H), 2.34-2.22 (m, 6H), 2.18 (d, J=1.6 Hz, 3H), 1.97-1.87 (m, 2H), 1.34 (s, 3H).

Example 228

(6-(4-Fluoro-3-methylbenzyl)-2-azaspiro[3.3]heptan-2-yl)((1s,3s)-3-hydroxy-3-methylcyclobutyl)methanone

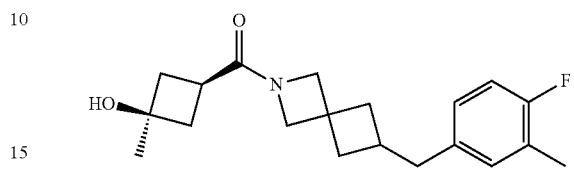

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 4-bromo-1-fluoro-2-methylbenzene instead of 1-bromo-2-methyl-4-(trifluoromethyl)benzene in Step B. MS (ESI): mass calcd. for $C_{20}H_{26}FNO_2$, 331.2; m/z found, 332.1 [M+H]$^+$. $^1$H NMR (400 MHz, CDCl$_3$) δ 6.95-6.82 (m, 3H), 4.07 (s, 1H), 4.00 (s, 1H), 3.96 (s, 1H), 3.91 (s, 1H), 3.84 (br s, 1H), 2.69-2.57 (m, 3H), 2.47-2.34 (m, 1H), 2.32-2.18 (m, 9H), 1.95-1.84 (m, 2H), 1.34 (s, 3H).

Example 229

(6-(3-Fluoro-4-methylbenzyl)-2-azaspiro[3.3]heptan-2-yl)((1s,3s)-3-hydroxy-3-methylcyclobutyl)methanone

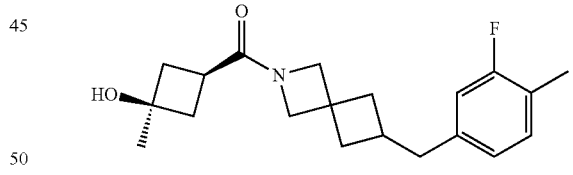

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 5-bromo-1-fluoro-2-methylbenzene instead of 1-bromo-2-methyl-4-(trifluoromethyl)benzene in Step B. MS (ESI): mass calcd. for $C_{20}H_{26}FNO_2$, 331.2; m/z found, 332.1 [M+H]$^+$. $^1$H NMR (400 MHz, CDCl$_3$) δ 7.07 (t, J=8.0 Hz, 1H), 6.80-6.72 (m, 2H), 4.06 (s, 1H), 3.98 (d, J=11.2 Hz, 2H), 3.90 (s, 1H), 2.66-2.56 (m, 3H), 2.50-2.38 (m, 1H), 2.28-2.22 (m, 8H), 1.98-1.81 (m, 3H), 1.34 (s, 3H).

Example 230

(6-(2-Fluoro-4-methylbenzyl)-2-azaspiro[3.3]heptan-2-yl)((1s,3s)-3-hydroxy-3-methylcyclobutyl)methanone

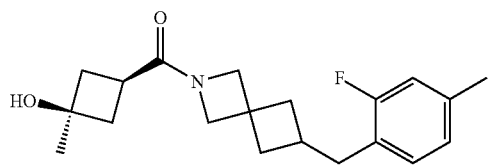 [SMILES: Cc1ccc(CC2CC3(C2)CN(C(=O)[C@H]2C[C@@](C)(O)C2)C3)c(F)c1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 2-bromo-1-fluoro-5-methylbenzene instead of 1-bromo-2-methyl-4-(trifluoromethyl)benzene in Step B. MS (ESI): mass calcd. for $C_{20}H_{26}FNO_2$, 331.2; m/z found, 332.1 [M+H]$^+$. $^1$H NMR (400 MHz, CDCl$_3$) δ 7.01-6.94 (m, 1H), 6.89-6.79 (m, 2H), 4.07-3.89 (m, 5H), 2.68-2.60 (m, 3H), 2.49-2.37 (m, 1H), 2.32 (s, 3H), 2.30-2.20 (m, 6H), 1.96-1.86 (m, 2H), 1.34 (d, J=1.2 Hz, 3H).

Example 231

(6-(3-(Difluoromethyl)benzyl)-2-azaspiro[3.3]heptan-2-yl)((1s,3s)-3-hydroxy-3-methylcyclobutyl)methanone

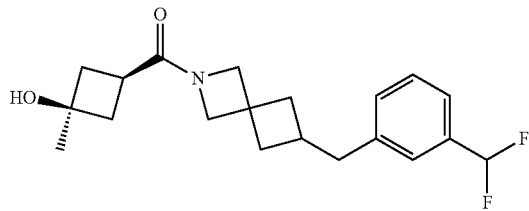 [SMILES: C[C@]1(O)C[C@@H](C(=O)N2CC3(CC(Cc4cccc(C(F)F)c4)C3)C2)C1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-3-(difluoromethyl)benzene instead of 1-bromo-2-methyl-4-(trifluoromethyl)benzene in Step B. MS (ESI): mass calcd. for $C_{20}H_{25}F_2NO_2$, 349.2; m/z found, 350.1 [M+H]$^+$. $^1$H NMR (400 MHz, CDCl$_3$) δ 7.40-7.32 (m, 2H), 7.26-7.21 (m, 2H), 6.77-6.47 (m, 1H), 4.07 (s, 1H), 3.98 (d, J=13.2 Hz, 2H), 3.92 (s, 2H), 2.74-2.71 (m, 2H), 2.68-2.59 (m, 1H), 2.53-2.38 (m, 1H), 2.31-2.20 (m, 6H), 1.99-1.86 (m, 2H), 1.34 (d, J=1.2 Hz, 3H).

Example 232

(6-(4-(Difluoromethyl)benzyl)-2-azaspiro[3.3]heptan-2-yl)((1s,3s)-3-hydroxy-3-methylcyclobutyl)methanone

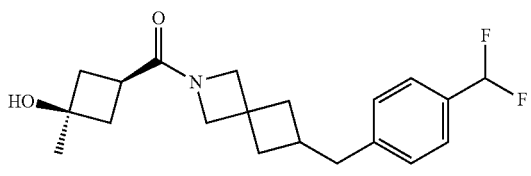 [SMILES: C[C@]1(O)C[C@@H](C(=O)N2CC3(CC(Cc4ccc(C(F)F)cc4)C3)C2)C1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-4-(difluoromethyl)benzene instead of 1-bromo-2-methyl-4-(trifluoromethyl)benzene in Step B. MS (ESI): mass calcd. for $C_{20}H_{25}F_2NO_2$, 349.2; m/z found, 350.1 [M+H]$^+$. $^1$H NMR (400 MHz, CDCl$_3$) δ 7.42 (d, J=8.0 Hz, 2H), 7.19 (d, J=8.0 Hz, 2H), 6.79-6.46 (m, 1H), 4.07 (s, 1H), 4.02-3.98 (m, 2H), 3.96 (s, 1H), 3.92 (s, 1H), 2.74-2.70 (m, 2H), 2.65-2.58 (m, 1H), 2.52-2.38 (m, 1H), 2.31-2.23 (m, 6H), 1.97-1.86 (m, 2H), 1.34 (s, 3H).

Example 233

(6-((6-(tert-Butyl)pyridin-2-yl)methyl)-2-azaspiro[3.3]heptan-2-yl)((1s,3s)-3-hydroxy-3-methylcyclobutyl)methanone

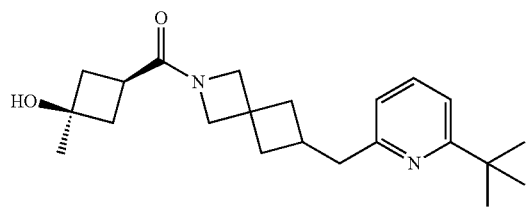 [SMILES: CC(C)(C)c1cccc(CC2CC3(C2)CN(C(=O)[C@H]2C[C@@](C)(O)C2)C3)n1]

Step A: tert-Butyl 6-methylene-2-azaspiro[3.3]heptane-2-carboxylate. TiCl$_4$ (7.8 mL, 1M in DCM, 7.81 mmol) was added dropwise to a mixture of zinc dust (2.1 g, 31.8 mmol) and CH$_2$I$_2$ (3.1 g, 10.6 mmol) in THF (20 mL) at rt. The resultant mixture was stirred at rt for 15 minutes then treated with a solution of tert-butyl 6-oxo-2-azaspiro[3.3]heptane-2-carboxylate (1.5 g, 7.1 mmol) in THF (10 mL) dropwise. The resulting mixture was stirred at rt for 12 hours. The reaction mixture was poured into sat. NH$_4$Cl and extracted with EtOAc. The combined organic extracts were washed with brine, dried over Na$_2$SO$_4$, filtered, and concentrated under reduced pressure. The resulting residue was purified by FCC (SiO$_2$, 0-10% EtOAc in ether) to afford the title compound (607 mg) as a colorless oil.

Step B: tert-Butyl 6-((9-borabicyclo[3.3.1]nonan-9-yl)methyl)-2-azaspiro[3.3]heptane-2-carboxylate. tert-Butyl 6-methylene-2-azaspiro[3.3]heptane-2-carboxylate (200 mg, 0.956 mmol) was cooled to −78° C. and treated with 9-borabicyclo[3.3.1]nonane (1.4 mL, 0.5M in THF) dropwise. The suspension was allowed to warm to rt for 1 hour then stirred at 65° C. for 16 hours before cooling to rt. The mixture was concentrated under reduced pressure at rt then diluted with H₂O (1 mL). The mixture was used in the next step without further purification.

Step C: tert-Butyl 6-((6-(tert-butyl)pyridin-2-yl)methyl)-2-azaspiro[3.3]heptane-2-carboxylate. tert-Butyl 6-(bicyclo[3.3.1]nonan-9-ylmethyl)-2-azaspiro[3.3]heptane-2-carboxylate solution (3 mL) was added dropwise to a solution of 2-bromo-6-(tert-butyl)pyridine (512 mg, 2.39 mmol), Pd(dppf)Cl₂·CH₂Cl₂ (48 mg, 0.059 mmol) and Cs₂CO₃ (2.3 g, 7.12 mmol) in DMF (10 mL). The resultant mixture was stirred at 65° C. for 16 hours under N₂ before cooling to rt and concentrating under reduced pressure. The mixture was diluted with water and extracted with DCM. The combined organic extracts were dried over Na₂SO₄, filtered, and concentrated under reduced pressure. The resulting residue was purified by FCC (SiO₂, 0-10% EtOAc in ether) to afford the title compound (230 mg).

Step D: 6-((6-tert-Butyl)pyridin-2-yl)methyl)-2-azaspiro[3.3]heptane. TFA (2 mL) was added to a 0° C. solution of tert-butyl 6-((6-(tert-butyl)pyridin-2-yl)methyl)-2-azaspiro[3.3]heptane-2-carboxylate (230 mg, 0.668 mmol) in DCM (2 mL). The resultant mixture was stirred at rt for 2 hours. The mixture was concentrated under reduced pressure to afford the title compound (100 mg, crude) as a colorless oil, which was used in the next step without further purification. MS (ESI): mass calcd. for $C_{16}H_{24}N_2$, 244.2; m/z found, 244.9 [M+H]⁺.

Step E: (6-((6-(tert-Butyl)pyridin-2-yl)methyl)-2-azaspiro[3.3]heptan-2-yl)((1s,3s)-3-hydroxy-3-methylcyclobutyl)methanone. HATU (233 mg, 0.614 mmol) was added to a solution of 6-((6-tert-butyl)pyridin-2-yl)methyl)-2-azaspiro[3.3]heptane (100 mg, crude), (1s,3s)-3-hydroxy-3-methylcyclobutanecarboxylic acid (59 mg, 0.450 mmol) and DIPEA (0.34 mL, 2.05 mmol) in DMF (5 mL). The resultant mixture was stirred at rt for 12 hours. The reaction mixture was poured into H₂O and extracted with EtOAc. The combined organic extracts were dried over Na₂SO₄, filtered, and concentrated under reduced pressure. The resulting residue was purified by preparative HPLC (Venusil ASB Phenyl, 150 mm×30 mm×5 μm column, 14% to 44% (v/v) CH₃CN and aqueous HCl (0.006 N)) to afford the title compound (16 mg, 60%) as a white solid. MS (ESI): mass calcd. for $C_{22}H_{32}N_2O_2$, 356.2; m/z found, 357.2 [M+H]⁺. ¹H NMR (400 MHz, DMSO-d₆) δ 8.38 (s, 1H), 7.81-7.67 (m, 2H), 4.04 (s, 1H), 3.98 (s, 1H), 3.81 (s, 1H), 3.76 (s, 1H), 3.33 (s, 3H), 2.20 (s, 2H), 2.09-1.93 (m, 7H), 1.49 (s, 9H), 1.22 (d, J=2.9 Hz, 3H).

Example 234

(rac)-(6-Benzyl-2-azaspiro[3.4]octan-2-yl)((1s,3s)-3-hydroxy-3-methylcyclobutyl)methanone

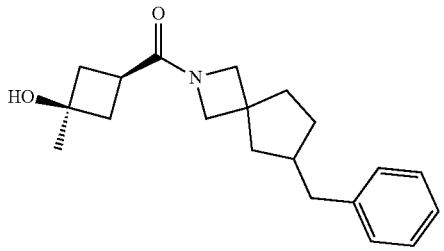 [SMILES: C[C@]1(O)C[C@@H](C(=O)N2CC3(CCC(Cc4ccccc4)C3)C2)C1]

Step A: (rac)-tert-Butyl 6-benzyl-2-azaspiro[3.4]octane-2-carboxylate. A solution of benzylzinc bromide (1.5 mL, 0.593 mmol, 0.4M in THF) was added to tert-butyl 6-iodo-2-azaspiro[3.4]octane-2-carboxylate (Intermediate 2, 100 mg, 0.297 mmol), cobalt(II) bromide (6.5 mg, 0.030 mmol), and zinc (1.9 mg, 0.030 mmol). The reaction mixture was stirred at 50° C. for 6 h before cooling to rt. The reaction was diluted with NH₄Cl/NH₃ (20%) and extracted with EtOAc. The organic phase was separated, dried over MgSO₄, filtered and the solvent removed in vacuo. The residue was purified by FCC (SiO₂, 0-20% EtOAc in heptane) followed by RP HPLC (25-60% ACN in 0.25% NH₄HCO₃ solution in water) to afford the title compound as a colorless, sticky oil (19 mg, 21% yield). ¹H NMR (400 MHz, CDCl₃) δ 7.17-7.11 (m, 1H), 7.10-6.98 (m, 1H), 3.66 (s, 2H), 2.55-2.40 (m, 2H), 2.14-1.94 (m, 1H), 1.86-1.60 (m, 4H), 1.37-1.29 (m, 10H), 1.23-1.17 (m, 3H), 0.78-0.72 (m, 2H).

Step B: (rac)-6-Benzyl-2-azaspiro[3.4]octane hydrochloride. To tert-butyl 6-benzyl-2-azaspiro[3.4]octane-2-carboxylate (10 mg, 0.033 mmol) in MeOH (52 μL) was added HCl in 1,4-dioxane (4M, 83 μL). This was heated to 45° C. for 1 h before concentrating under reduced pressure. The title compound was used without further purification in the next step. MS (ESI): mass calcd. for $C_{14}H_{19}N$, 201.2; m/z found, 202.1 [M+H]⁺.

Step C: (rac)-(6-Benzyl-2-azaspiro[3.4]octan-2-yl)((1s,3s)-3-hydroxy-3-methylcyclobutyl)methanone. 6-Benzyl-2-azaspiro[3.4]octane hydrochloride was taken up in DMF (0.3 mL) and to this was added (1s,3s)-3-hydroxy-3-methylcyclobutane-1-carboxylic acid (4.5 mg, 0.033 mmol), DIPEA (17 μL, 0.100 mmol), and HATU (14 mg, 0.036 mmol). This was stirred at rt for 1 hour. The reaction was filtered through a PTFE filter with MeOH and purified via RP HPLC (5-95% MeCN in 20 mM NH₄OH in water) to afford the title compound (7.5 mg, 72% yield). MS (ESI): mass calcd. for $C_{20}H_{27}NO_2$, 313.2; m/z found, 314.2 [M+H]⁺. ¹H NMR (400 MHz, Chloroform-d) δ 7.30-7.24 (m, 2H), 7.22-7.16 (m, 1H), 7.16-7.11 (m, 2H), 4.10-3.71 (m, 5H), 2.70-2.54 (m, 3H), 2.34-2.10 (m, 5H), 2.00-1.73 (m, 4H), 1.55-1.42 (m, 1H), 1.40-1.27 (m, 4H).

Example 235

(7-Benzyl-2-azaspiro[3.5]nonan-2-yl)((1s,3s)-3-hydroxy-3-methylcyclobutyl)methanone

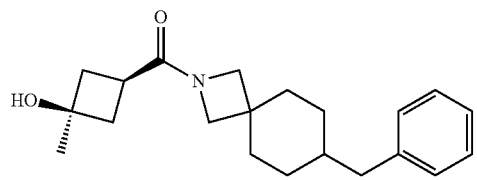

Step A: tert-Butyl 7-benzyl-7-hydroxy-2-azaspiro[3.5]nonane-2-carboxylate. Benzylmagnesium chloride (2M in THF, 0.94 mL, 1.88 mmol) was added dropwise to a mixture of cerium(III) chloride (463 mg, 1.88 mmol) and dry THF (6 mL) under N₂ at 0° C. The reaction mixture was stirred at rt for 2 h. tert-Butyl-7-oxo-2-azaspiro[3.5]nonane-2-carboxylate (150 mg, 0.6 mmol) was added at 0° C., and the reaction mixture was stirred at rt for 16 h. Water was added and the mixture was filtered through Celite®, and the solvent removed in vacuo. The crude residue was purified via FCC (SiO₂, 0-60% EtOAc in heptane) to provide the title compound as a white solid (209 mg, 99% yield). MS (ESI): mass calcd. for $C_{20}H_{29}NO_3$, 331.2; m/z found, 276.2 [M+2H-tBu]$^+$.

Step B: 1-(7-Benzyl-2-azaspiro[3.5]non-6-en-2-yl)-2,2,2-trifluoroethan-1-one. TFA (0.55 mL, 7.2 mmol) and trifluoroacetic anhydride (TFAA) (0.35 mL, 2.5 mmol) were added to a solution of tert-butyl 7-benzyl-7-hydroxy-2-azaspiro[3.5]nonane-2-carboxylate (214 mg, 0.6 mmol) in dichloroethane (4 mL). The reaction mixture was stirred at 60° C. for 16 h then treated with Amberlist A26 until pH around 7. The Amberlist was filtered and washed with MeOH. The filtrate was concentrated in vacuo to afford a pale orange oil which was used in the next step without further purification (188 mg, 99% yield). MS (ESI): mass calcd. for $C_{17}H_{18}F_3NO$, 309.1; m/z found, 310.1 [M+H]$^+$.

Step C: 1-(7-Benzyl-2-azaspiro[3.5]nonan-2-yl)-2,2,2-trifluoroethan-1-one. A mixture of 1-(7-benzyl-2-azaspiro[3.5]non-6-en-2-yl)-2,2,2-trifluoroethan-1-one (189 mg, 0.609 mmol), 10 wt % Pd/C (60 mg), and MeOH (4 mL) was stirred under $H_2$ at rt for 4 h. The reaction mixture was filtered through Celite® and washed with MeOH. The filtrate was concentrated in vacuo and used in the next step without further purification. MS (ESI): mass calcd. for $C_{17}H_{20}F_3NO$, 311.2; m/z found, 312.1 [M+H]$^+$.

Step D: 7-Benzyl-2-azaspiro[3.5]nonane. Potassium carbonate (97 mg, 0.7 mmol) was added to a solution of 1-(7-benzyl-2-aza-spiro[3.5]non-2-yl)-2,2,2-trifluoroethan-1-one (110 mg, 0.35 mmol) in MeOH (3 mL). The reaction mixture was stirred at 70° C. for 1.5 h before the solvent was removed in vacuo to give a pale-yellow solid. The product was used in the next step without further purification (75 mg, 99% yield). MS (ESI): mass calcd. for $C_{15}H_{21}N$, 215.2; m/z found, 216.2 [M+H]$^+$.

Step E: (7-Benzyl-2-azaspiro[3.5]nonan-2-yl)((1s,3s)-3-hydroxy-3-methylcyclobutyl)methanone. 50 wt % T3P® in EtOAc (0.27 mL, 0.453 mmol) and DIPEA (0.15 mL, 0.871 mmol) were added to a solution of (1s,3s)-3-hydroxy-3-methylcyclobutane-1-carboxylic acid (50 mg, 0.383 mmol) in DMF (2.0 mL). The reaction mixture was stirred for 10 min at rt, then a solution of 7-benzyl-2-azaspiro[3.5]nonane (75 mg, 0.348 mmol) in DMF (1 mL) was added, and the reaction mixture was stirred at rt for 16 h. Sat. aq. NaHCO$_3$ was added and the mixture was extracted with EtOAc. The organic layers were dried over MgSO$_4$, filtered, and concentrated under reduced pressure. The mixture was purified via FCC (SiO$_2$, 0-60% 5% MeOH/DCM in DCM) to provide the title compound as a white solid (45 mg, 37% yield). MS (ESI): mass calcd. for $C_{21}H_{29}NO_2$, 327.2; m/z found, 328.1 [M+H]$^+$. $^1$H NMR (400 MHz, DMSO-d$_6$) δ 7.33-7.22 (m, 2H), 7.22-7.09 (m, 3H), 4.97 (d, J=3.3 Hz, 1H), 3.69 (s, 1H), 3.62 (s, 1H), 3.47 (s, 1H), 3.40 (s, 1H), 2.44 (d, J=6.9 Hz, 2H), 2.13-2.03 (m, 2H), 2.03-1.92 (m, 2H), 1.76 (d, J=13.0 Hz, 2H), 1.58-1.48 (m, 2H), 1.48-1.39 (m, 1H), 1.34 (t, J=12.2 Hz, 2H), 1.22 (d, J=6.4 Hz, 3H), 1.02-0.85 (m, 2H).

Example 236

((1s,3s)-3-Hydroxy-3-methylcyclobutyl)(7-(2-methylbenzyl)-2-azaspiro[3.5]nonan-2-yl)methanone

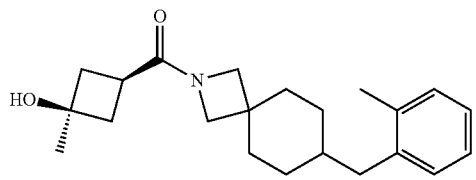 [SMILES: Cc1ccccc1CC1CCC2(CC1)CN(C(=O)[C@H]1C[C@@](C)(O)C1)C2]

Step A: tert-Butyl 7-(2-bromobenzylidene)-2-azaspiro[3.5]nonane-2-carboxylate. NaH (43 mg, 60 wt % in mineral oil, 1.10 mmol) was added to a mixture of (2-bromobenzyl)triphenylphosphonium bromide (Intermediate 21, 642 mg, 1.25 mmol) and DMSO (10 mL) and stirred at rt for 1 hour. tert-Butyl 7-oxo-2-azaspiro[3.5]nonane-2-carboxylate (200 mg, 0.836 mmol) was added to above solution and the resultant mixture was stirred at 80° C. for 12 hours before cooling to rt. The mixture was poured into water and extracted with EtOAc. The combined organic extracts were washed with brine, dried over Na$_2$SO$_4$, filtered, and concentrated under reduced pressure. The resulting residue was purified by FCC (SiO$_2$, 0-25% EtOAc in ether) to afford the title compound (120 mg, 37%) as a colorless oil. MS (ESI): mass calcd. for $C_{20}H_{26}BrNO_2$, 391.1; m/z found, 336.1 [M+2H-tBu]$^+$.

Step B: tert-Butyl 7-(2-methylbenzylidene)-2-azaspiro[3.5]nonane-2-carboxylate. tert-Butyl 7-(2-bromobenzylidene)-2-azaspiro[3.5]nonane-2-carboxylate (100 mg, 0.255 mmol), 2,4,6-trimethyl-1,3,5,2,4,6-trioxatriborinane (96 mg, 0.770 mmol) and K$_3$PO$_4$ (162 mg, 0.763 mmol) were taken up in 1,4-dioxane (10 mL). The resultant mixture was sparged with Ar for 5 minutes and then treated with Pd(dtbpf)Cl$_2$ (17 mg, 0.026 mmol). The resultant mixture was stirred while heating at 120° C. via microwave irradiation for 16 hours before cooling to rt. The reaction mixture was concentrated under reduced pressure. The resulting residue was purified by FCC (SiO$_2$, 0-25% EtOAc in ether) to afford the title compound (90 mg, 84%) as a white solid. MS (ESI): mass calcd. for $C_{21}H_{29}NO_2$, 327.2; m/z found, 272.2 [M+2H-tBu]$^+$.

Step C: tert-butyl 7-(2-methylbenzyl)-2-azaspiro[3.5]nonane-2-carboxylate. tert-Butyl 7-(2-methylbenzylidene)-2-azaspiro[3.5]nonane-2-carboxylate (90 mg, 0.28 mmol), EtOAc (5 mL), and wet 10 wt % Pd/C (100 mg) were combined. The resultant mixture was stirred under H$_2$ (15 psi) at rt for 1 hour. The suspension was filtered through a pad of Celite® and the pad washed with EtOAc. The filtrate was concentrated under reduced pressure to afford the title product (70 mg, crude) as a yellow oil, which was carried on without further purification. MS (ESI): mass calcd. for $C_{21}H_{31}NO_2$, 329.2; m/z found, 274.1 [M+2H-tBu]$^+$.

Step D: 7-(2-Methylbenzyl)-2-azaspiro[3.5]nonane. TFA (1.5 mL) was added to a solution of tert-butyl 7-(2-methylbenzyl)-2-azaspiro[3.5]nonane-2-carboxylate (70 mg, 0.21 mmol) in DCM (3 mL). The resultant mixture was stirred at rt for 1.5 hours. The reaction mixture was concentrated under reduced pressure to afford the title compound (80 mg, crude) as a yellow oil, which was used in the next step without further purification. MS (ESI): mass calcd. for $C_{16}H_{23}N$, 229.2; m/z found, 230.2 [M+H]$^+$.

Step E: ((1s,3s)-3-Hydroxy-3-methylcyclobutyl)(7-(2-methylbenzyl)-2-azaspiro[3.5]nonan-2-yl)methanone.

HATU (159 mg, 0.418 mmol) was added to a solution of (1s,3s)-3-hydroxy-3-methylcyclobutanecarboxylic acid (54 mg, 0.418 mmol), 7-(2-methylbenzyl)-2-azaspiro[3.5]nonane (80 mg, crude), and DIPEA (0.31 mL, 1.8 mmol) in DMF (8 mL). The resultant mixture was stirred at rt for 12 hours. The reaction mixture was poured into H$_2$O and extracted with EtOAc. The combined organic extracts were washed with brine, dried over Na$_2$SO$_4$, filtered, and concentrated under reduced pressure to give the crude product. The crude product was purified by preparative HPLC (Boston Prime C18 150×30 mm×5 um column, 55% to 85% (v/v) MeCN and water with 0.05% NH$_3$+10 mM NH$_4$HCO$_3$) to afford the title compound (22 mg, 18%). MS (ESI): mass calcd. for $C_{22}H_{31}NO_2$, 341.2; m/z found, 342.2 [M+H]$^+$. $^1$H NMR (400 MHz, CDCl$_3$) δ 7.20-6.99 (m, 4H), 4.30 (d, J=17.1 Hz, 1H), 3.78-3.57 (m, 4H), 2.74-2.58 (m, 1H), 2.48 (d, J=7.0 Hz, 2H), 2.36-2.24 (m, 7H), 2.14 (s, 1H), 1.85 (d, J=13.1 Hz, 2H), 1.68 (t, J=9.8 Hz, 2H), 1.51-1.44 (m, 1H), 1.42-1.38 (m, 1H), 1.35 (d, J=6.0 Hz, 3H), 1.09-0.90 (m, 2H).

Example 237

((1s,3s)-3-Hydroxy-3-methylcyclobutyl)(6-((3-(trifluoromethyl)-1H-pyrazol-1-yl)methyl)-2-azaspiro[3.3]heptan-2-yl)methanone

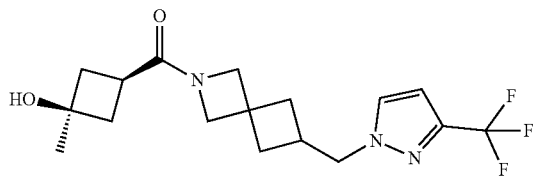 [SMILES: C[C@]1(O)C[C@@H](C(=O)N2CC3(CC(Cn4ccc(C(F)(F)F)n4)C3)C2)C1]

Step A: tert-Butyl 6-((3-(trifluoromethyl)-1H-pyrazol-1-yl)methyl)-2-azaspiro[3.3]heptane-2-carboxylate. A mixture of tert-butyl 6-(bromomethyl)-2-azaspiro[3.3]heptane-2-carboxylate (Intermediate 4, 150 mg, 0.517 mmol), 3-(trifluoromethyl)-1H-pyrazole (106 mg, 0.775 mmol), cesium carbonate (337 mg, 1.03 mmol) and DMF (5 mL) were combined. The resultant mixture was stirred while heating to 80° C. overnight. The reaction mixture was cooled to rt, diluted with H$_2$O, and extracted with EtOAc. The combined organic extracts were washed with brine, dried over Na$_2$SO$_4$, filtered, and concentrated under reduced pressure. The resulting residue was purified by FCC (SiO$_2$, 0-50% EtOAc in ether) to afford the title compound (100 mg, 27%) as a yellow solid. MS (ESI): mass calcd. for C$_{16}$H$_{22}$F$_3$N$_3$O$_2$, 345.2; m/z found, 346.2 [M+H]$^+$. $^1$H NMR (400 MHz, CD$_3$OD) δ 7.73 (d, J=1.2 Hz, 1H), 6.57 (d, J=2.4 Hz, 1H), 4.23-4.13 (m, 2H), 3.96-3.75 (m, 4H), 2.70 (td, J=7.6, 15.6 Hz, 1H), 2.32-2.23 (m, 2H), 2.07-1.99 (m, 2H), 1.42 (s, 9H).

Step B: 6-((3-(Trifluoromethyl)-1H-pyrazol-1-yl)methyl)-2-azaspiro[3.3]heptane. A mixture of tert-butyl 6-((3-(trifluoromethyl)-1H-pyrazol-1-yl)methyl)-2-azaspiro[3.3]heptane-2-carboxylate (100 mg, 0.141 mmol), TFA (0.5 mL) and DCM (5 mL) was stirred at rt for 1 hour. The reaction mixture was concentrated under reduced pressure to afford the title compound (100 mg, crude) as colorless oil, which was used in the next step without further purification. MS (ESI): mass calcd. for C$_{11}$H$_{14}$F$_3$N$_3$, 245.1; m/z found, 246.0 [M+H]$^+$.

Step C: ((1s,3s)-3-Hydroxy-3-methylcyclobutyl)(6-((3-(trifluoromethyl)-1H-pyrazol-1-yl)methyl)-2-azaspiro[3.3]heptan-2-yl)methanone. HATU (145 mg, 0.380 mmol) was added to a solution of (1s,3s)-3-hydroxy-3-methylcyclobutanecarboxylic acid (45 mg, 0.346 mmol), 6-((3-(trifluoromethyl)-1H-pyrazol-1-yl)methyl)-2-azaspiro[3.3]heptane (100 mg, crude) and DIPEA (0.29 mL, 1.73 mmol) in DMF (5 mL). The resultant mixture was stirred at rt overnight. The reaction mixture was diluted with EtOAc, quenched with sat. NH$_4$Cl, and extracted with EtOAc. The combined organic extracts were washed with brine, dried over Na$_2$SO$_4$, filtered, and concentrated under reduced pressure. The resulting residue was purified by preparative HPLC (Phenomenex Gemini-NX C18, 75 mm×30 mm×3 μm column, 30% to 60% (v/v) CH$_3$CN and H$_2$O with 0.05% NH$_3$+10 mM NH$_4$HCO$_3$) to afford the title compound (29 mg, 22%) as colourless syrupy solid. MS (ESI): mass calcd. for C$_{17}$H$_{22}$F$_3$N$_3$O$_2$, 357.2; m/z found, 358.2 [M+H]$^+$. $^1$H NMR (400 MHz, MeOD) δ 7.74 (d, J=1.2 Hz, 1H), 6.60-6.55 (m, 1H), 4.22-4.16 (m, 3H), 4.05-3.94 (m, 2H), 3.85 (s, 1H), 2.76-2.57 (m, 2H), 2.33-2.12 (m, 6H), 2.10-2.02 (m, 2H), 1.34 (s, 3H).

Example 238

((1s,3s)-3-Hydroxy-3-methylcyclobutyl)(6-(o-tolyloxy)-2-azaspiro[3.3]heptan-2-yl)methanone

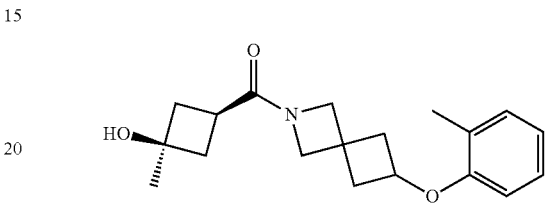

The title compound was prepared in a manner analogous to Example 237 using tert-butyl 6-iodo-2-azaspiro[3.3]heptane-2-carboxylate (Intermediate 3) instead of tert-butyl 6-(bromomethyl)-2-azaspiro[3.3]heptane-2-carboxylate (Intermediate 4) and o-cresol instead of 3-(trifluoromethyl)-1H-pyrazole in Step A. MS (ESI): mass calcd. for C$_{19}$H$_{25}$NO$_3$, 315.2; m/z found, 316.1 [M+H]$^+$. $^1$H NMR (400 MHz, CDCl$_3$) δ 7.16-7.07 (m, 2H), 6.90-6.81 (m, 1H), 6.63-6.57 (m, 1H), 4.64-4.53 (m, 1H), 4.15 (s, 1H), 4.11 (s, 1H), 4.06 (s, 1H), 4.03 (s, 1H), 3.86 (br s, 1H), 2.78-2.60 (m, 3H), 2.43-2.22 (m, 6H), 2.20 (s, 3H), 1.35 (d, J=2.0 Hz, 3H).

Example 239

((1s,3s)-3-Hydroxy-3-methylcyclobutyl)(7-(3-methyl-4-(trifluoromethyl)phenoxy)-2-azaspiro[3.5]nonan-2-yl)methanone

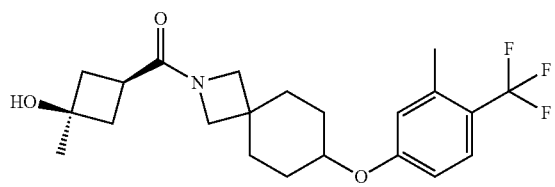 [SMILES: Cc1cc(OC2CCC3(CC2)CN(C(=O)[C@H]2C[C@@](C)(O)C2)C3)ccc1C(F)(F)F]

The title compound was prepared in a manner analogous to Example 237 using tert-butyl 7-((methylsulfonyl)oxy)-2-azaspiro[3.5]nonane-2-carboxylate (Intermediate 11) instead of tert-butyl 6-(bromomethyl)-2-azaspiro[3.3]heptane-2-carboxylate (Intermediate 4) and 3-methyl-4-(trifluoromethyl)phenol instead of 3-(trifluoromethyl)-1H-pyrazole in Step A. MS (ESI): mass calcd. for C$_{22}$H$_{28}$F$_3$NO$_3$, 411.2; m/z found, 412.1 [M+H]$^+$. $^1$H NMR (400 MHz, DMSO-d$_6$) δ 7.54 (d, J=8.8 Hz, 1H), 6.99 (s, 1H), 6.93-6.88 (m, 1H), 5.03-5.01 (m, 1H), 4.52-4.43 (m, 1H), 3.75 (d, J=6.0 Hz, 2H), 3.52 (d, J=4.5 Hz, 2H), 2.60-2.53 (m, 1H), 2.39 (s, 3H), 2.14-1.96 (m, 4H), 1.89-1.77 (m, 4H), 1.65-1.44 (m, 4H), 1.24 (s, 3H).

Example 240

(rac)-(6-(4-(tert-Butyl)phenoxy)-2-azaspiro[3.4]octan-2-yl)((1s,3s)-3-hydroxy-3-methylcyclobutyl)methanone

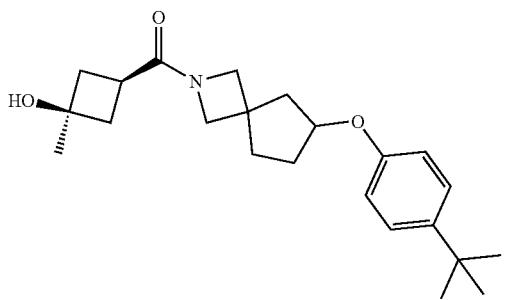 [SMILES: CC(C)(C)c1ccc(OC2CCC3(C2)CN(C(=O)[C@H]2C[C@@](C)(O)C2)C3)cc1]

Step A: (rac)-tert-Butyl 6-(4-(tert-butyl)phenoxy)-2-azaspiro[3.4]octane-2-carboxylate. In an oven-dried vial under $N_2$, (rac)-2-Boc-6-hydroxy-2-azaspiro[3.4]octane (85 mg, 0.374 mmol), cuprous iodide (1.8 mg, 0.009 mmol), 3,4,7,8-tetramethyl-1,10-phenanthroline (4.5 mg, 0.019 mmol), cesium carbonate (123 mg, 0.374 mmol), and 3 Å molecular sieves (25 mg) were combined. To this was added 1-tert-butyl-4-iodobenzene (34 µL, 0.187 mmol) and anhydrous toluene (0.1 mL). The reaction was stirred and heated at 100° C. for 20 h. After cooling to rt, the reaction was filtered through Celite® with EtOAc and concentrated in vacuo. Purification via FCC ($SiO_2$, 0-50% EtOAc in hexane) provided the title compound (14 mg, 21% yield). MS (ESI): mass calcd. for $C_{22}H_{33}NO_3$ 359.2; m/z found, 304.2 [M+2H-tBu]$^+$.

Step B: (rac)-6-(4-(tert-Butyl)phenoxy)-2-azaspiro[3.4]octane. To tert-butyl 6-(4-(tert-butyl)phenoxy)-2-azaspiro[3.4]octane-2-carboxylate (14 mg, 0.039 mmol) was added HCl in EtOH (1.25M, 0.1 mL). This was heated to 45° C. for 5 h before concentrating under reduced pressure. The title compound was used without further purification in the next step. MS (ESI): mass calcd. for $C_{17}H_{25}NO$ 259.2; m/z found, 260.2 [M+H]$^+$.

Step C: (rac)-(6-(4-(tert-Butyl)phenoxy)-2-azaspiro[3.4]octan-2-yl)((1s,3s)-3-hydroxy-3-methylcyclobutyl)methanone. 6-(4-(tert-Butyl)phenoxy)-2-azaspiro[3.4]octane was taken up in DMF (0.4 mL) and to this was added (1s,3s)-3-hydroxy-3-methylcyclobutane-1-carboxylic acid (5.5 mg, 0.041 mmol), DIPEA (20 µL, 0.117 mmol), and HATU (17 mg, 0.043 mmol). This was stirred at rt for 1 hour. The reaction mixture was filtered through a PTFE filter with MeOH and purified via RP HPLC (5-95% ACN in 20 mM $NH_4OH$ in water) to afford the title compound (10 mg, 69% yield). MS (ESI): mass calcd. for $C_{23}H_{33}NO_3$ 371.2; m/z found, 372.3 [M+H]$^+$. $^1$H NMR (400 MHz, Chloroform-d) δ 7.31-7.24 (m, 2H), 6.80-6.70 (m, 2H), 4.82-4.73 (m, 1H), 4.11-3.87 (m, 5H), 2.70-2.60 (m, 1H), 2.34-2.14 (m, 5H), 2.16-1.82 (m, 5H), 1.34 (s, 3H), 1.29 (d, J=2.6 Hz, 9H).

Example 241

((1s,3s)-3-Hydroxy-3-methylcyclobutyl)(7-(3-isopropylphenoxy)-2-azaspiro[3.5]nonan-2-yl)methanone

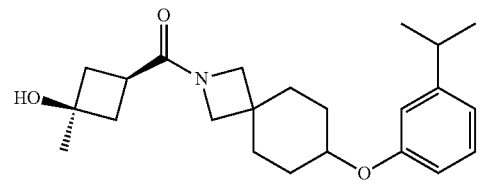 [SMILES: CC(C)c1cccc(OC2CCC3(CC2)CN(C(=O)[C@H]2C[C@@](C)(O)C2)C3)c1]

Step A: tert-Butyl 7-(3-isopropylphenoxy)-2-azaspiro[3.5]nonane-2-carboxylate. In an oven-dried vial under $N_2$, 2-Boc-7-hydroxy-2-azaspiro[3.5]nonane (50 mg, 0.207 mmol) and 3-isopropylphenol (34 mg, 0.249 mmol) were taken up in anhydrous THF (1.0 mL). To this was added DIAD (50 µL, 0.249 mmol) and PPh$_3$ (67 mg, 0.249 mmol). The reaction was stirred and heated at 60° C. for 4 h. The reaction was quenched with water and the organic layers were extracted with DCM. Purification via FCC ($SiO_2$, 0-15% EtOAc in hexane) provided the title compound (56 mg, 75% yield). MS (ESI): mass calcd. for $C_{22}H_{33}NO_3$ 359.2; m/z found, 304.2 [M+2H-tBu]$^+$.

Step B: 7-(3-Isopropylphenoxy)-2-azaspiro[3.5]nonane. To tert-butyl 7-(3-isopropylphenoxy)-2-azaspiro[3.5]nonane-2-carboxylate (27 mg, 0.075 mmol) was added HCl in EtOH (1.25M, 0.1 mL). This was heated to 45° C. for 1.5 hour before concentrating under reduced pressure. The title compound was used without further purification in the next step. MS (ESI): mass calcd. for $C_{17}H_{25}NO$ 259.2; m/z found, 260.2 [M+H]$^+$.

Step C: ((1s,3s)-3-Hydroxy-3-methylcyclobutyl)(7-(3-isopropylphenoxy)-2-azaspiro[3.5]nonan-2-yl)methanone. 7-(3-Isopropylphenoxy)-2-azaspiro[3.5]nonane was taken up in DMF (0.5 mL) and to this was added (1s,3s)-3-hydroxy-3-methylcyclobutane-1-carboxylic acid (11 mg, 0.079 mmol), DIPEA (39 µL, 0.225 mmol), and HATU (32 mg, 0.083 mmol). This was stirred at rt for 1.5 hours. The reaction mixture was filtered through a PTFE filter with MeOH and purified via RP HPLC (5-95% ACN in 20 mM $NH_4OH$ in water) to afford the title compound (16 mg, 57% yield). MS (ESI): mass calcd. for $C_{23}H_{33}NO_3$ 371.2; m/z found, 372.3 [M+H]$^+$. $^1$H NMR (500 MHz, Chloroform-d) δ 7.18 (td, J=7.9, 2.7 Hz, 1H), 6.84-6.78 (m, 1H), 6.75 (q, J=2.2 Hz, 1H), 6.71-6.67 (m, 1H), 4.33-4.24 (m, 1H), 3.99 (d, J=13.7 Hz, 1H), 3.77 (d, J=5.5 Hz, 2H), 3.71 (d, J=8.8 Hz, 2H), 2.91-2.80 (m, 1H), 2.72-2.63 (m, 1H), 2.34-2.24 (m, 4H), 2.02-1.91 (m, 2H), 1.90-1.85 (m, 2H), 1.72-1.57 (m, 4H), 1.35 (d, J=2.2 Hz, 3H), 1.23 (dd, J=6.9, 0.8 Hz, 6H).

Example 242

((1s,3s)-3-Hydroxy-3-methylcyclobutyl)(7-(4-isopropylphenoxy)-2-azaspiro[3.5]nonan-2-yl)methanone

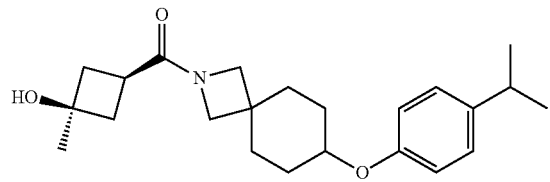 [SMILES: CC(C)c1ccc(OC2CCC3(CC2)CN(C(=O)[C@H]2C[C@@](C)(O)C2)C3)cc1]

The title compound was prepared in a manner analogous to Example 241 using 4-isopropylphenol instead of 3-isopropylphenol in Step A. MS (ESI): mass calcd. for $C_{23}H_{33}NO_3$, 371.2; m/z found, 372.3 [M+H]$^+$. $^1$H NMR (500 MHz, Chloroform-d) δ 7.14-7.09 (m, 2H), 6.83-6.78 (m, 2H), 4.29-4.19 (m, 1H), 4.11 (d, J=12.7 Hz, 1H), 3.76 (d, J=5.5 Hz, 2H), 3.71 (d, J=8.8 Hz, 2H), 2.90-2.78 (m, 1H), 2.66 (h, J=7.4 Hz, 1H), 2.29 (dd, J=7.5, 2.2 Hz, 4H), 2.00-1.90 (m, 2H), 1.90-1.78 (m, 2H), 1.69-1.54 (m, 4H), 1.35 (d, J=2.4 Hz, 3H), 1.22 (dd, J=6.9, 1.0 Hz, 6H).

Example 243

(rac)-(6-(3-(tert-Butyl)phenoxy)-2-azaspiro[3.4]octan-2-yl)((1s,3s)-3-hydroxy-3-methylcyclobutyl)methanone

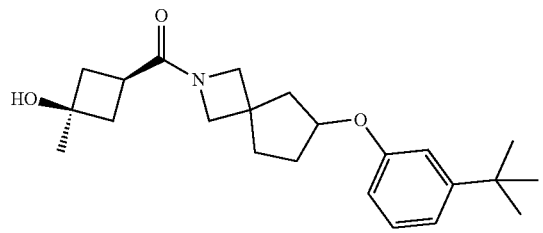 [SMILES: CC(C)(C)c1cccc(OC2CCC3(C2)CN(C(=O)[C@H]2C[C@@](C)(O)C2)C3)c1]

The title compound was prepared in a manner analogous to Example 241 using (rac)-2-Boc-6-hydroxy-2-azaspiro[3.4]octane instead of 2-Boc-7-hydroxy-2-azaspiro[3.5]nonane and 3-tert-butylphenol instead of 3-isopropylphenol in Step A. MS (ESI): mass calcd. for $C_{23}H_{33}NO_3$, 371.2; m/z found, 372.3 [M+H]$^+$. $^1$H NMR (400 MHz, Chloroform-d) δ 7.24-7.16 (m, 1H), 7.00-6.94 (m, 1H), 6.85 (t, J=2.2 Hz, 1H), 6.66-6.59 (m, 1H), 4.84-4.76 (m, 1H), 4.11-4.01 (m, 1H), 4.01-3.88 (m, 4H), 2.70-2.61 (m, 1H), 2.35-2.16 (m, 5H), 2.16-2.02 (m, 3H), 2.02-1.80 (m, 2H), 1.34 (s, 3H), 1.30 (d, J=3.7 Hz, 9H).

Example 244

(6-(3-(tert-Butyl)phenoxy)-2-azaspiro[3.3]heptan-2-yl)((1s,3s)-3-hydroxy-3-methylcyclobutyl)methanone

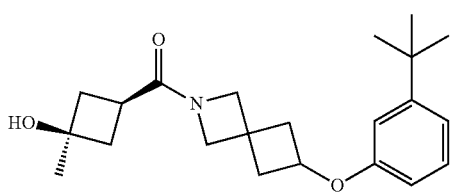 [SMILES: CC(C)(C)c1cccc(OC2CC3(C2)CN(C(=O)[C@H]2C[C@@](C)(O)C2)C3)c1]

The title compound was prepared in a manner analogous to Example 241 using tert-butyl 6-hydroxy-2-azaspiro[3.3]heptane-2-carboxylate instead of 2-Boc-7-hydroxy-2-azaspiro[3.5]nonane and 3-tert-butylphenol instead of 3-isopropylphenol in Step A. MS (ESI): mass calcd. for $C_{22}H_{31}NO_3$, 357.2; m/z found, 358.3 [M+H]$^+$. $^1$H NMR (500 MHz, Chloroform-d) δ 7.24-7.16 (m, 1H), 7.02-6.96 (m, 1H), 6.84 (t, J=2.2 Hz, 1H), 6.59-6.52 (m, 1H), 4.65-4.53 (m, 1H), 4.13 (d, J=25.4 Hz, 2H), 4.04 (d, J=21.1 Hz, 2H), 3.85 (d, J=5.2 Hz, 1H), 2.79-2.67 (m, 2H), 2.67-2.59 (m, 1H), 2.45-2.33 (m, 2H), 2.33-2.22 (m, 4H), 1.35 (d, J=3.0 Hz, 3H), 1.30 (d, J=0.9 Hz, 9H).

Example 245

((1s,3s)-3-Hydroxy-3-methylcyclobutyl)(2-(p-tolyloxy)-7-azaspiro[3.5]nonan-7-yl)methanone

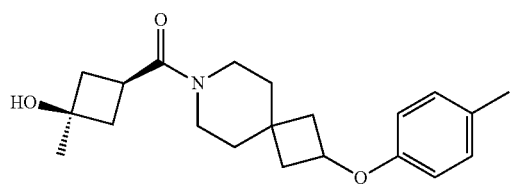 [SMILES: Cc1ccc(OC2CC3(CCN(C(=O)[C@H]4C[C@@](C)(O)C4)CC3)C2)cc1]

The title compound was prepared in a manner analogous to Example 241 using tert-butyl 2-hydroxy-7-azaspiro[3.5]nonane-7-carboxylate instead of 2-Boc-7-hydroxy-2-azaspiro[3.5]nonane and p-cresol instead of 3-isopropylphenol in Step A. MS (ESI): mass calcd. for $C_{21}H_{29}NO_3$, 343.2; m/z found, 344.2 [M+H]$^+$. $^1$H NMR (400 MHz, Chloroform-d) δ 7.11-7.04 (m, 2H), 6.75-6.67 (m, 2H), 4.75-4.62 (m, 1H), 3.56 (d, J=24.2 Hz, 2H), 3.33 (d, J=22.4 Hz, 2H), 2.89 (q, J=8.0 Hz, 1H), 2.34 (dt, J=8.2, 2.4 Hz, 6H), 2.30 (s, 3H), 1.99 (s, 3H), 1.64 (dd, J=6.9, 4.4 Hz, 4H), 1.41 (s, 3H).

Example 246

(6-(4-(tert-Butyl)phenoxy)-2-azaspiro[3.3]heptan-2-yl)((1s,3s)-3-hydroxy-3-methylcyclobutyl)methanone

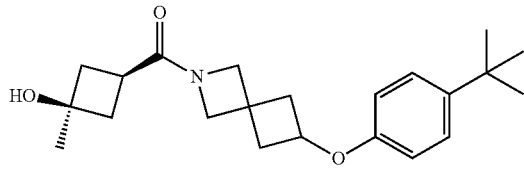 [SMILES: CC(C)(C)c1ccc(OC2CC3(C2)CN(C(=O)[C@H]2C[C@@](C)(O)C2)C3)cc1]

The title compound was prepared in a manner analogous to Example 241 using tert-butyl 6-hydroxy-2-azaspiro[3.3]heptane-2-carboxylate instead of 2-Boc-7-hydroxy-2-azaspiro[3.5]nonane and 4-tert-butylphenol instead of 3-isopropylphenol in Step A. MS (ESI): mass calcd. for $C_{22}H_{31}NO_3$, 357.2; m/z found, 358.2 [M+H]$^+$. $^1$H NMR (400 MHz, CDCl$_3$) δ 7.29 (dd, J=2.0, 8.4 Hz, 2H), 6.72 (dd, J=2.0, 8.8 Hz, 2H), 4.70-4.44 (m, 1H), 4.15 (s, 1H), 4.11 (s, 1H), 4.07 (s, 1H), 4.03 (s, 1H), 2.79-2.61 (m, 3H), 2.44-2.20 (m, 6H), 1.35 (d, J=2.0 Hz, 3H), 1.30 (s, 9H).

Example 247

((1s,3s)-3-Hydroxy-3-methylcyclobutyl)(6-(3-methyl-4-(trifluoromethyl)phenoxy)-2-azaspiro[3.3]heptan-2-yl)methanone

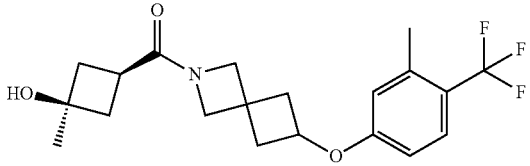 [SMILES: Cc1cc(OC2CC3(C2)CN(C(=O)[C@H]2C[C@@](C)(O)C2)C3)ccc1C(F)(F)F]

The title compound was prepared in a manner analogous to Example 241 using tert-butyl 6-hydroxy-2-azaspiro[3.3]heptane-2-carboxylate instead of 2-Boc-7-hydroxy-2-azaspiro[3.5]nonane and 3-methyl-4-(trifluoromethyl)phenol instead of 3-isopropylphenol in Step A. MS (ESI): mass calcd. for $C_{20}H_{24}F_3NO_3$, 383.2; m/z found, 384.2 [M+H]$^+$. $^1$H NMR (400 MHz, CDCl$_3$) δ 7.51 (d, J=8.4 Hz, 1H), 6.67 (s, 1H), 6.61 (d, J=4.8 Hz, 1H), 4.68-4.60 (m, 1H), 4.17 (s, 1H), 4.12 (s, 1H), 4.08 (s, 1H), 4.04 (s, 1H), 2.81-2.70 (m, 2H), 2.69-2.59 (m, 1H), 2.44 (s, 3H), 2.42-2.21 (m, 6H), 1.36 (d, J=2.0 Hz, 3H).

Example 248

((1s,3s)-3-Hydroxy-3-methylcyclobutyl)(6-(4-methyl-3-(trifluoromethyl)phenoxy)-2-azaspiro[3.3]heptan-2-yl)methanone

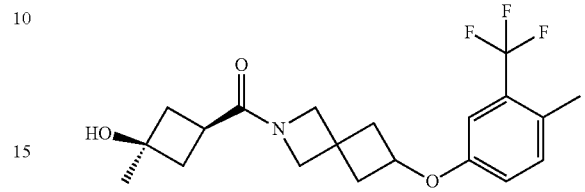

The title compound was prepared in a manner analogous to Example 241 using tert-butyl 6-hydroxy-2-azaspiro[3.3]heptane-2-carboxylate instead of 2-Boc-7-hydroxy-2-azaspiro[3.5]nonane and 4-methyl-3-(trifluoromethyl)phenol instead of 3-isopropylphenol in Step A. MS (ESI): mass calcd. for $C_{20}H_{24}F_3NO_3$, 383.2; m/z found, 384.3 [M+H]$^+$. $^1$H NMR (400 MHz, CDCl$_3$) δ 7.17 (d, J=8.0 Hz, 1H), 7.01 (dd, J=2.8, 9.6 Hz, 1H), 6.85-6.79 (m, 1H), 4.67-4.54 (m, 1H), 4.16 (s, 1H), 4.11 (s, 1H), 4.07 (s, 1H), 4.03 (s, 1H), 3.82 (br s, 1H), 2.79-2.70 (m, 2H), 2.69-2.59 (m, 1H), 2.43-2.21 (m, 9H), 1.35 (d, J=2.0 Hz, 3H).

Example 249

((1s,3s)-3-Hydroxy-3-methylcyclobutyl)(6-(2-methyl-4-(trifluoromethyl)phenoxy)-2-azaspiro[3.3]heptan-2-yl)methanone

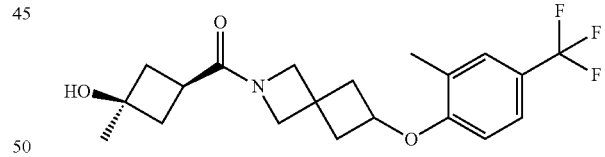

The title compound was prepared in a manner analogous to Example 241 using tert-butyl 6-hydroxy-2-azaspiro[3.3]heptane-2-carboxylate instead of 2-Boc-7-hydroxy-2-azaspiro[3.5]nonane and 2-methyl-4-(trifluoromethyl)phenol instead of 3-isopropylphenol in Step A. MS (ESI): mass calcd. for $C_{20}H_{24}F_3NO_3$, 383.2; m/z found, 384.2 [M+H]$^+$. $^1$H NMR (400 MHz, CDCl$_3$) δ 7.44-7.36 (m, 2H), 6.64 (t, J=8.8 Hz, 1H), 4.70-4.58 (m, 1H), 4.17 (s, 1H), 4.13 (s, 1H), 4.09 (s, 1H), 4.06 (s, 1H), 3.76 (br s, 1H), 2.84-2.73 (m, 2H), 2.70-2.61 (m, 1H), 2.51-2.20 (m, 9H), 1.36 (d, J=2.4 Hz, 3H).

Example 250

((1s,3s)-3-Hydroxy-3-methylcyclobutyl)(6-(3-methyl-2-(trifluoromethyl)phenoxy)-2-azaspiro[3.3]heptan-2-yl)methanone

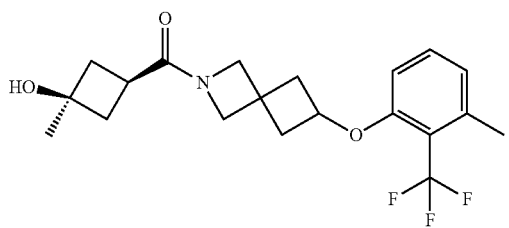 [SMILES: Cc1cccc(OC2CC3(C2)CN(C(=O)[C@H]2C[C@@](C)(O)C2)C3)c1C(F)(F)F]

The title compound was prepared in a manner analogous to Example 241 using tert-butyl 6-hydroxy-2-azaspiro[3.3]heptane-2-carboxylate instead of 2-Boc-7-hydroxy-2-azaspiro[3.5]nonane and 3-methyl-2-(trifluoromethyl)phenol instead of 3-isopropylphenol in Step A. MS (ESI): mass calcd. for $C_{20}H_{24}F_3NO_3$, 383.2; m/z found, 384.1 [M+H]$^+$. $^1$H NMR (400 MHz, CDCl$_3$) δ 7.27 (s, 1H), 6.83 (d, J=8.0 Hz, 1H), 6.64-6.58 (m, 1H), 4.70-4.58 (m, 1H), 4.16-4.10 (m, 2H), 4.04 (d, J=3.6 Hz, 2H), 3.87 (d, J=4.4 Hz, 1H), 2.76-2.68 (m, 2H), 2.67-2.60 (m, 1H), 2.47 (d, J=3.6 Hz, 3H), 2.43-2.35 (m, 2H), 2.33-2.21 (m, 4H), 1.35 (s, 3H).

Example 251

((1s,3s)-3-Hydroxy-3-methylcyclobutyl)(6-(3-isopropyl-2-(trifluoromethyl)phenoxy)-2-azaspiro[3.3]heptan-2-yl)methanone

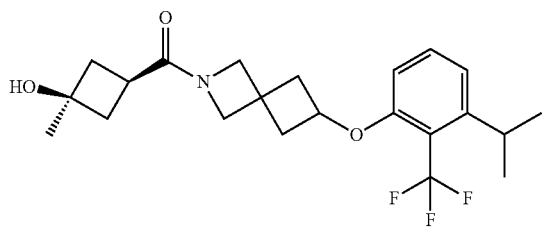 [SMILES: CC(C)c1cccc(OC2CC3(C2)CN(C(=O)[C@H]2C[C@@](C)(O)C2)C3)c1C(F)(F)F]

The title compound was prepared in a manner analogous to Example 241 using tert-butyl 6-hydroxy-2-azaspiro[3.3]heptane-2-carboxylate instead of 2-Boc-7-hydroxy-2-azaspiro[3.5]nonane and 3-isopropyl-2-(trifluoromethyl)phenol (Intermediate 45) instead of 3-isopropylphenol in Step A. MS (ESI): mass calcd. for $C_{22}H_{28}F_3NO_3$, 411.2; m/z found, 412.1 [M+H]$^+$. $^1$H NMR (400 MHz, CDCl$_3$) δ 7.45-7.30 (m, 1H), 7.05 (d, J=8.0 Hz, 1H), 6.60 (d, J=8.4 Hz, 1H), 4.64 (br s, 1H), 4.18-4.02 (m, 4H), 3.5-3.4 (m, 1H), 2.8-2.7 (m, 2H), 2.69-2.61 (m, 1H), 2.43 (br s, 2H), 2.35-2.28 (m, 2H), 2.27-2.21 (m, 2H), 1.35 (s, 3H), 1.24 (d, J=6.8 Hz, 6H).

Example 252

((1s,3s)-3-Hydroxy-3-methylcyclobutyl)(6-(2-methyl-3-(trifluoromethyl)phenoxy)-2-azaspiro[3.3]heptan-2-yl)methanone

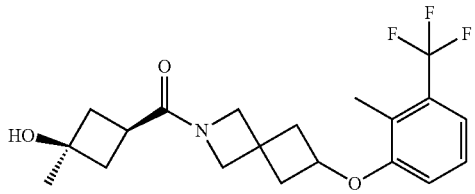 [SMILES: Cc1c(OC2CC3(C2)CN(C(=O)[C@H]2C[C@@](C)(O)C2)C3)cccc1C(F)(F)F]

The title compound was prepared in a manner analogous to Example 241 using tert-butyl 6-hydroxy-2-azaspiro[3.3]heptane-2-carboxylate instead of 2-Boc-7-hydroxy-2-azaspiro[3.5]nonane and 2-methyl-3-(trifluoromethyl)phenol instead of 3-isopropylphenol in Step A. MS (ESI): mass calcd. for $C_{20}H_{24}F_3NO_3$, 383.2; m/z found, 384.1 [M+H]$^+$. $^1$H NMR (400 MHz, CDCl$_3$) δ 7.24-7.16 (m, 2H), 6.77 (br s, 1H), 4.67-4.53 (m, 1H), 4.18-4.03 (m, 4H), 2.76 (br s, 2H), 2.69-2.59 (m, 1H), 2.39 (br s, 2H), 2.33-2.21 (m, 7H), 1.35 (s, 3H).

Example 253

(rac)-((1s,3s)-3-Hydroxy-3-methylcyclobutyl)(6-(2-methyl-3-(trifluoromethyl)phenoxy)-2-azaspiro[3.4]octan-2-yl)methanone

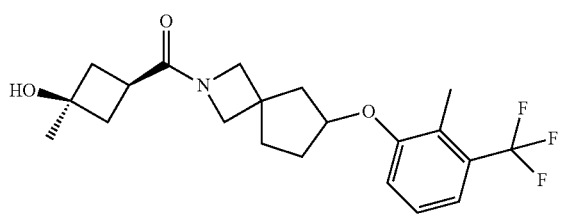 [SMILES: Cc1c(OC2CCC3(C2)CN(C(=O)[C@H]2C[C@@](C)(O)C2)C3)cccc1C(F)(F)F]

The title compound was prepared in a manner analogous to Example 241 using (rac)-2-Boc-6-hydroxy-2-azaspiro[3.4]octane instead of 2-Boc-7-hydroxy-2-azaspiro[3.5]nonane and 2-methyl-3-(trifluoromethyl)phenol instead of 3-isopropylphenol in Step A. MS (ESI): mass calcd. for $C_{21}H_{26}F_3NO_3$, 397.2; m/z found, 398.1 [M+H]$^+$. $^1$H NMR (400 MHz, CDCl$_3$) δ 7.24-7.18 (m, 2H), 6.96-6.89 (m, 1H), 4.87-4.81 (m, 1H), 4.13-3.90 (m, 5H), 2.70-2.62 (m, 1H), 2.33-2.23 (m, 8H), 2.19-2.08 (m, 3H), 2.00-1.90 (m, 2H), 1.35 (s, 3H).

Example 254: (rac)-((1s,3s)-3-Hydroxy-3-methylcyclobutyl)(6-(3-methyl-4-(trifluoromethyl)phenoxy)-2-azaspiro[3.4]octan-2-yl)methanone

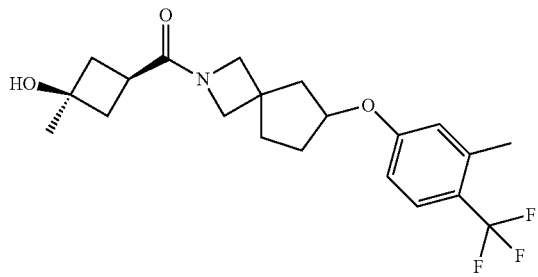 [SMILES: Cc1cc(OC2CCC3(C2)CN(C(=O)[C@H]2C[C@@](C)(O)C2)C3)ccc1C(F)(F)F]

The title compound was prepared in a manner analogous to Example 241 using (rac)-2-Boc-6-hydroxy-2-azaspiro[3.4]octane instead of 2-Boc-7-hydroxy-2-azaspiro[3.5]nonane and 3-methyl-4-(trifluoromethyl)phenol instead of 3-isopropylphenol in Step A. MS (ESI): mass calcd. for $C_{21}H_{26}F_3NO_3$, 397.2; m/z found, 398.1 [M+H]$^+$. $^1$H NMR (400 MHz, CDCl$_3$) δ 7.51 (d, J=8.8 Hz, 1H), 6.71 (s, 1H), 6.67 (d, J=8.8 Hz, 1H), 4.85 (br s, 1H), 4.11-3.89 (m, 4H), 2.72-2.63 (m, 1H), 2.44 (s, 3H), 2.36-2.05 (m, 8H), 1.93 (br s, 2H), 1.35 (s, 3H).

Example 255

(rac)-((1s,3s)-3-Hydroxy-3-methylcyclobutyl)(6-(2-methyl-4-(trifluoromethyl)phenoxy)-2-azaspiro[3.4]octan-2-yl)methanone

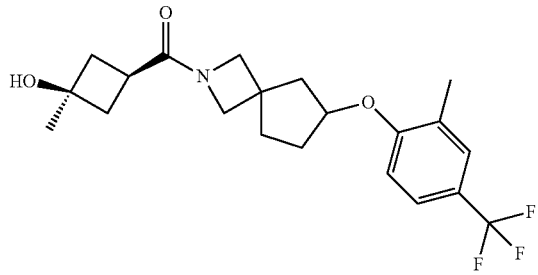 [SMILES: Cc1cc(C(F)(F)F)ccc1OC1CCC2(C1)CN(C(=O)[C@H]1C[C@@](C)(O)C1)C2]

The title compound was prepared in a manner analogous to Example 241 using (rac)-2-Boc-6-hydroxy-2-azaspiro[3.4]octane instead of 2-Boc-7-hydroxy-2-azaspiro[3.5]nonane and 2-methyl-4-(trifluoromethyl)phenol instead of 3-isopropylphenol in Step A. MS (ESI): mass calcd. for $C_{21}H_{26}F_3NO_3$, 397.2; m/z found, 398.1 [M+H]$^+$. $^1$H NMR (400 MHz, CDCl$_3$) δ 7.39 (br s, 2H), 6.80-6.76 (m, 1H), 4.87 (br s, 1H), 4.13-3.88 (m, 4H), 2.66 (br s, 1H), 2.35-2.23 (m, 5H), 2.20 (s, 3H), 2.18-2.08 (m, 3H), 2.04-1.86 (m, 2H), 1.35 (s, 3H).

Example 256

(rac)-((1s,3s)-3-Hydroxy-3-methylcyclobutyl)(6-(4-methyl-3-(trifluoromethyl)phenoxy)-2-azaspiro[3.4]octan-2-yl)methanone

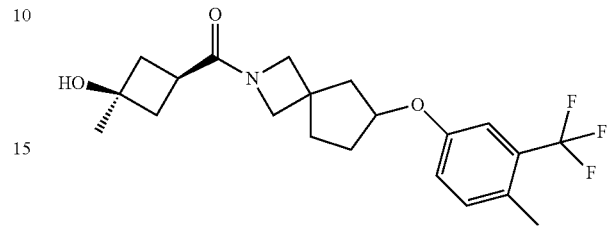

The title compound was prepared in a manner analogous to Example 241 using (rac)-2-Boc-6-hydroxy-2-azaspiro[3.4]octane instead of 2-Boc-7-hydroxy-2-azaspiro[3.5]nonane and 4-methyl-3-(trifluoromethyl)phenol instead of 3-isopropylphenol in Step A. MS (ESI): mass calcd. for $C_{21}H_{26}F_3NO_3$, 397.2; m/z found, 398.1 [M+H]$^+$. $^1$H NMR (400 MHz, CDCl$_3$) δ 7.17 (t, J=8.0 Hz, 1H), 7.07-7.05 (m, 1H), 6.87 (d, J=8.4 Hz, 1H), 4.82-4.80 (m, 1H), 4.11-3.89 (m, 5H), 2.72-2.62 (m, 1H), 2.40 (br s, 3H), 2.34-2.18 (m, 5H), 2.17-2.05 (m, 3H), 1.99-1.86 (m, 2H), 1.35 (s, 3H).

Example 257

(7-(3-(tert-Butyl)phenoxy)-2-azaspiro[3.5]nonan-2-yl)((1s,3s)-3-hydroxy-3-methylcyclobutyl)methanone

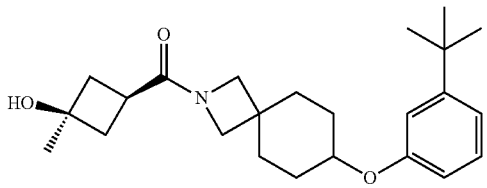 [SMILES: CC(C)(C)c1cccc(OC2CCC3(CC2)CN(C(=O)[C@H]2C[C@@](C)(O)C2)C3)c1]

The title compound was prepared in a manner analogous to Example 241 using 3-tert-butylphenol instead of 3-isopropylphenol in Step A. MS (ESI): mass calcd. for $C_{24}H_{35}NO_3$, 385.3; m/z found, 386.2 [M+H]$^+$. $^1$H NMR (400 MHz, DMSO-d$_6$) δ 7.21-7.14 (m, 1H), 6.95-6.90 (m, 1H), 6.87-6.84 (m, 1H), 6.77-6.70 (m, 1H), 5.00 (s, 1H), 4.39-4.30 (m, 1H), 3.74 (d, J=8.9 Hz, 2H), 3.51 (d, J=7.5 Hz, 2H), 2.58-2.53 (m, 1H), 2.13-2.06 (m, 2H), 2.03-1.95 (m, 2H), 1.86-1.77 (m, 4H), 1.63-1.40 (m, 4H), 1.27-1.21 (m, 12H).

Example 258

((1s,3s)-3-Hydroxy-3-methylcyclobutyl)(7-(2-methyl-4-(trifluoromethyl)phenoxy)-2-azaspiro[3.5]nonan-2-yl)methanone

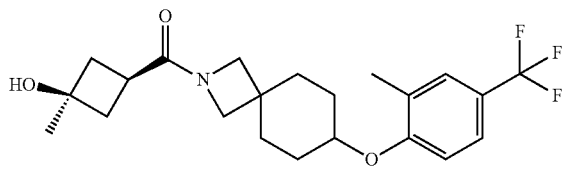 [SMILES: Cc1cc(C(F)(F)F)ccc1OC1CCC2(CC1)CN(C(=O)[C@H]1C[C@@](C)(O)C1)C2]

The title compound was prepared in a manner analogous to Example 241 using 2-methyl-4-(trifluoromethyl)phenol instead of 3-isopropylphenol in Step A. MS (ESI): mass calcd. for $C_{22}H_{28}F_3NO_3$, 411.2; m/z found, 412.1 [M+H]$^+$. $^1$H NMR (400 MHz, DMSO-d$_6$) δ 7.51-7.44 (m, 2H), 7.17-7.10 (m, 1H), 5.02-4.98 (m, 1H), 4.57-4.47 (m, 1H), 3.77-3.74 (m, 2H), 3.53 (s, 2H), 2.59-2.52 (m, 1H), 2.20-2.17 (m, 3H), 2.13-2.06 (m, 2H), 2.03-1.96 (m, 2H), 1.87-1.77 (m, 4H), 1.66-1.53 (m, 4H), 1.23 (s, 3H).

Example 259

((1s,3s)-3-Hydroxy-3-methylcyclobutyl)(7-(4-methyl-3-(trifluoromethyl)phenoxy)-2-azaspiro[3.5]nonan-2-yl)methanone

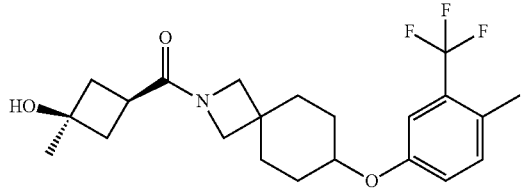 [SMILES: Cc1ccc(OC2CCC3(CC2)CN(C(=O)[C@H]2C[C@@](C)(O)C2)C3)cc1C(F)(F)F]

The title compound was prepared in a manner analogous to Example 241 using 4-methyl-3-(trifluoromethyl)phenol instead of 3-isopropylphenol in Step A. MS (ESI): mass calcd. for $C_{22}H_{28}F_3NO_3$, 411.2; m/z found, 412.2 [M+H]$^+$. $^1$H NMR (400 MHz, DMSO-d$_6$) δ 7.33 (d, J=8.3 Hz, 1H), 7.17-7.11 (m, 2H), 5.01-4.98 (m, 1H), 4.47-4.39 (m, 1H), 3.74 (d, J=6.3 Hz, 2H), 3.51 (d, J=5.0 Hz, 2H), 2.54-2.54 (m, 1H), 2.36-2.33 (m, 3H), 2.12-2.05 (m, 2H), 2.02-1.96 (m, 2H), 1.85-1.76 (m, 4H), 1.62-1.44 (m, 4H), 1.23 (s, 3H).

Example 260

(7-(4-(tert-Butyl)phenoxy)-2-azaspiro[3.5]nonan-2-yl)((1s,3s)-3-hydroxy-3-methylcyclobutyl)methanone

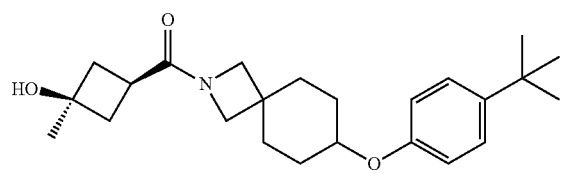 [SMILES: CC(C)(C)c1ccc(OC2CCC3(CC2)CN(C(=O)[C@H]2C[C@@](C)(O)C2)C3)cc1]

The title compound was prepared in a manner analogous to Example 241 using 4-tert-butylphenol instead of 3-isopropylphenol in Step A. MS (ESI): mass calcd. for $C_{24}H_{35}NO_3$, 385.3; m/z found, 386.4 [M+H]$^+$. $^1$H NMR (400 MHz, Chloroform-d) δ 7.31-7.23 (m, 2H), 6.84-6.78 (m, 2H), 4.30-4.19 (m, 1H), 4.10 (d, J=8.5 Hz, 1H), 3.76 (d, J=4.3 Hz, 2H), 3.71 (d, J=6.8 Hz, 2H), 2.73-2.59 (m, 1H), 2.29 (dd, J=7.5, 1.7 Hz, 4H), 2.02-1.90 (m, 2H), 1.92-1.77 (m, 2H), 1.72-1.53 (m, 4H), 1.35 (d, J=1.9 Hz, 3H), 1.29 (d, J=0.8 Hz, 9H).

Example 261

(7-(4-Cyclopropylphenoxy)-2-azaspiro[3.5]nonan-2-yl)((1s,3s)-3-hydroxy-3-methylcyclobutyl)methanone

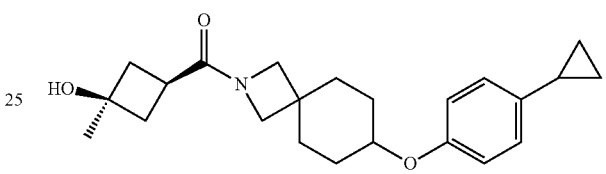

The title compound was prepared in a manner analogous to Example 241 using 4-cyclopropylphenol instead of 3-isopropylphenol in Step A. MS (ESI): mass calcd. for $C_{23}H_{31}NO_3$, 369.2; m/z found, 370.3 [M+H]$^+$. $^1$H NMR (400 MHz, Chloroform-d) δ 7.01-6.94 (m, 2H), 6.81-6.74 (m, 2H), 4.29-4.08 (m, 2H), 3.76 (d, J=4.0 Hz, 2H), 3.70 (d, J=6.6 Hz, 2H), 2.70-2.59 (m, 1H), 2.35-2.22 (m, 4H), 2.07 (s, 1H), 2.01-1.89 (m, 2H), 1.90-1.73 (m, 3H), 1.71-1.52 (m, 3H), 1.34 (d, J=2.0 Hz, 3H), 0.94-0.83 (m, 2H), 0.65-0.55 (m, 2H).

Example 262

((1s,3s)-3-Hydroxy-3-methylcyclobutyl)(7-(4-(trifluoromethoxy)phenoxy)-2-azaspiro[3.5]nonan-2-yl)methanone

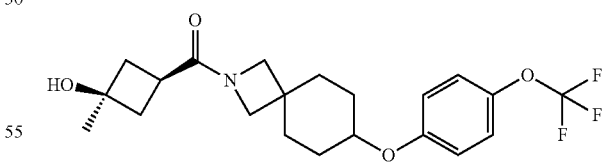

The title compound was prepared in a manner analogous to Example 241 using 4-trifluoromethoxyphenol instead of 3-isopropylphenol in Step A. MS (ESI): mass calcd. for $C_{21}H_{26}F_3NO_4$, 413.2; m/z found, 414.2 [M+H]$^+$. $^1$H NMR (400 MHz, Chloroform-d) δ 7.15-7.08 (m, 2H), 6.89-6.83 (m, 2H), 4.32-4.20 (m, 1H), 4.11-3.93 (m, 1H), 3.77 (d, J=2.9 Hz, 2H), 3.71 (d, J=5.6 Hz, 2H), 2.73-2.60 (m, 1H), 2.36-2.22 (m, 4H), 2.02-1.90 (m, 2H), 1.90-1.76 (m, 2H), 1.73-1.54 (m, 4H), 1.35 (d, J=1.6 Hz, 3H).

Example 263

((1s,3s)-3-Hydroxy-3-methylcyclobutyl)(7-(3-(trifluoromethoxy)phenoxy)-2-azaspiro[3.5]nonan-2-yl)methanone

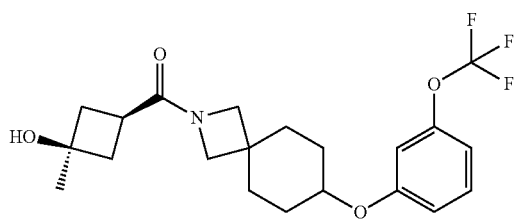 [SMILES: C[C@]1(O)C[C@@H](C(=O)N2CC3(CCC(Oc4cccc(OC(F)(F)F)c4)CC3)C2)C1]

The title compound was prepared in a manner analogous to Example 241 using 3-trifluoromethoxyphenol instead of 3-isopropylphenol in Step A. MS (ESI): mass calcd. for $C_{21}H_{26}F_3NO_4$, 413.2; m/z found, 414.2 [M+H]$^+$. $^1$H NMR (400 MHz, Chloroform-d) δ 7.29-7.23 (m, 1H), 6.83-6.76 (m, 2H), 6.75-6.70 (m, 1H), 4.35-4.23 (m, 1H), 3.99-3.85 (m, 1H), 3.78 (d, J=1.9 Hz, 2H), 3.72 (d, J=4.8 Hz, 2H), 2.72-2.61 (m, 1H), 2.36-2.21 (m, 4H), 2.03-1.90 (m, 2H), 1.90-1.79 (m, 2H), 1.73-1.57 (m, 4H), 1.35 (d, J=1.3 Hz, 3H).

Example 264

(7-(3-Cyclopropylphenoxy)-2-azaspiro[3.5]nonan-2-yl)((1s,3s)-3-hydroxy-3-methylcyclobutyl)methanone

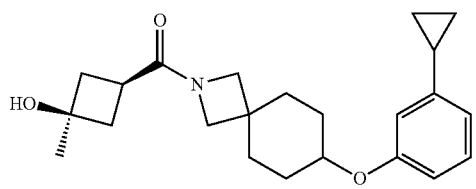 [SMILES: C[C@]1(O)C[C@@H](C(=O)N2CC3(CCC(Oc4cccc(C5CC5)c4)CC3)C2)C1]

The title compound was prepared in a manner analogous to Example 241 using 3-cyclopropylphenol instead of 3-isopropylphenol in Step A. MS (ESI): mass calcd. for $C_{23}H_{31}NO_3$, 369.2; m/z found, 370.3 [M+H]$^+$. $^1$H NMR (400 MHz, Chloroform-d) δ 7.14 (td, J=7.9, 2.0 Hz, 1H), 6.69-6.63 (m, 2H), 6.62-6.58 (m, 1H), 4.33-4.22 (m, 1H), 4.02 (s, 1H), 3.77 (d, J=3.7 Hz, 2H), 3.71 (d, J=6.3 Hz, 2H), 2.72-2.61 (m, 1H), 2.36-2.22 (m, 4H), 2.03-1.89 (m, 2H), 1.89-1.75 (m, 3H), 1.73-1.53 (m, 4H), 1.35 (d, J=1.9 Hz, 3H), 0.99-0.88 (m, 2H), 0.72-0.63 (m, 2H).

Example 265

((1s,3s)-3-Hydroxy-3-methylcyclobutyl)(7-(2-isopropylphenoxy)-2-azaspiro[3.5]nonan-2-yl)methanone

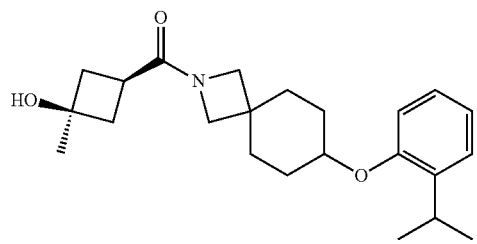 [SMILES: CC(C)c1ccccc1OC1CCC2(CC1)CN(C(=O)[C@H]1C[C@@](C)(O)C1)C2]

The title compound was prepared in a manner analogous to Example 241 using 2-isopropylphenol instead of 3-isopropylphenol in Step A. MS (ESI): mass calcd. for $C_{23}H_{33}NO_3$, 371.2; m/z found, 372.2 [M+H]$^+$. $^1$H NMR (500 MHz, Chloroform-d) δ 7.24-7.18 (m, 1H), 7.14-7.08 (m, 1H), 6.94-6.87 (m, 1H), 6.85-6.78 (m, 1H), 4.37-4.28 (m, 1H), 4.07 (s, 1H), 3.78 (d, J=6.0 Hz, 2H), 3.72 (d, J=3.8 Hz, 2H), 3.35-3.24 (m, 1H), 2.72-2.61 (m, 1H), 2.30 (d, J=7.5 Hz, 4H), 2.01-1.90 (m, 2H), 1.91-1.80 (m, 2H), 1.78-1.59 (m, 4H), 1.35 (s, 3H), 1.21 (d, J=6.9 Hz, 6H).

Example 266

((1s,3s)-3-Hydroxy-3-methylcyclobutyl)(7-(3-isopropylphenyl)-7-methoxy-2-azaspiro[3.5]nonan-2-yl)methanone

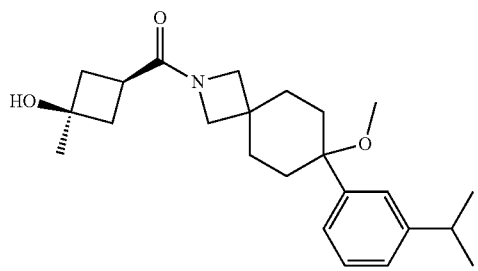 [SMILES: COC1(c2cccc(C(C)C)c2)CCC2(CC1)CN(C(=O)[C@H]1C[C@@](C)(O)C1)C2]

Step A: tert-Butyl 7-(3-isopropylphenyl)-7-methoxy-2-azaspiro[3.5]nonane-2-carboxylate. tert-Butyl 7-hydroxy-7-(3-isopropylphenyl)-2-azaspiro[3.5]nonane-2-carboxylate (from Step A in Example 151, 50 mg, 0.139 mmol) was taken up in anhydrous DMF (0.7 mL) in an oven-dried flask. This was placed under a N$_2$ atmosphere and cooled to 0° C. NaH (6.7 mg, 0.167 mmol) was added and the reaction was stirred for 10 minutes at 0° C. Iodomethane (13 μL, 0.209 mmol) was added and the reaction was allowed to warm to rt and stirred 1 h at which time another aliquot of iodomethane (13 μL, 0.209 mmol) was added. The reaction was stirred for 2 hours before being quenched with water and extracted with EtOAc. The crude mixture was dried over NaSO$_4$, filtered, concentrated in vacuo and purified via FCC (SiO$_2$, 0-40% EtOAc in hexanes) to provide the title compound (25 mg, 48% yield). MS (ESI): mass calcd. for $C_{23}H_{35}NO_3$ 373.3; m/z found, 318.2 [M+2H-tBu]$^+$.

Step B: 7-(3-Isopropylphenyl)-7-methoxy-2-azaspiro[3.5]nonane. To tert-butyl 7-(3-isopropylphenyl)-7-methoxy-2-azaspiro[3.5]nonane-2-carboxylate (25 mg, 0.067 mmol) was added HCl in EtOH (1.25M, 0.4 mL). This was heated to 45° C. for 1 hour before concentrating under reduced pressure. The title compound was used without purification in the next step.

Step C: ((1s,3s)-3-Hydroxy-3-methylcyclobutyl)(7-(3-isopropylphenyl)-7-methoxy-2-azaspiro[3.5]nonan-2-yl)methanone. 7-(3-Isopropylphenyl)-7-methoxy-2-azaspiro[3.5]nonane (0.067 mmol) was taken up in DMF (0.6 mL) and to this was added (1s,3s)-3-hydroxy-3-methylcyclobutane-1-carboxylic acid (9 mg, 0.070 mmol), DIPEA (35 µL, 0.201 mmol), and HATU (28 mg, 0.074 mmol). This was stirred at rt for 16 hours. The reaction mixture was filtered through a PTFE filter with MeOH and purified via RP HPLC (5-95% ACN in 20 mM NH$_4$OH in water) to afford the title compound (14 mg, 54% yield over 2 steps). MS (ESI): mass calcd. for $C_{24}H_{35}NO_3$, 385.3; m/z found, 386.3 [M+H]$^+$. $^1$H NMR (400 MHz, Chloroform-d) δ 7.27 (t, J=7.6 Hz, 1H), 7.25-7.22 (m, 1H), 7.19-7.12 (m, 2H), 3.95 (d, J=12.5 Hz, 1H), 3.82-3.69 (m, 4H), 2.95 (d, J=1.6 Hz, 3H), 2.94-2.84 (m, 1H), 2.73-2.64 (m, 1H), 2.35-2.23 (m, 4H), 2.09-1.89 (m, 4H), 1.80-1.73 (m, 2H), 1.71-1.58 (m, 2H), 1.35 (d, J=3.9 Hz, 3H), 1.25 (d, J=6.9 Hz, 6H).

Example 267

((1s,3s)-3-Hydroxy-3-methylcyclobutyl)(6-(3-methyl-5-(trifluoromethyl)phenyl)-2-azaspiro[3.3]heptan-2-yl)methanone

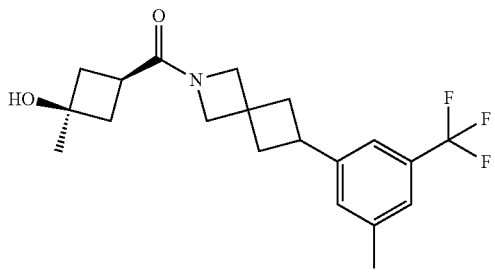 [SMILES: Cc1cc(C2CC3(C2)CN(C(=O)[C@H]2C[C@@](C)(O)C2)C3)cc(C(F)(F)F)c1]

The title compound was prepared in a manner analogous to Example 29 using tert-butyl 6-oxo-2-azaspiro[3.3]heptane-2-carboxylate instead of tert-butyl 6-oxo-2-azaspiro[3.4]octane-2-carboxylate and 1-bromo-3-methyl-5-(trifluoromethyl)benzene instead of 2-bromo-6-(tert-butyl)pyridine in Step A. MS (ESI): mass calcd. for $C_{20}H_{24}F_3NO_2$, 367.2; m/z found, 368.0 [M+H]$^+$. $^1$H NMR (400 MHz, CDCl$_3$) δ 7.27 (s, 1H), 7.23-7.10 (m, 2H), 4.24 (s, 1H), 4.16 (s, 1H), 4.11-3.86 (m, 3H), 3.46-3.42 (m, 1H), 2.72-2.56 (m, 3H), 2.42-2.37 (m, 3H), 2.36-2.24 (m, 6H), 1.36 (d, J=5.2 Hz, 3H).

Example 268

((1s,3s)-3-Hydroxy-3-methylcyclobutyl)(6-(1-methyl-1H-pyrrolo[2,3-b]pyridin-5-yl)-2-azaspiro[3.3]heptan-2-yl)methanone

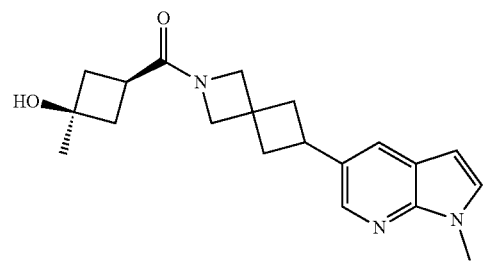 [SMILES: Cn1ccc2cc(C3CC4(C3)CN(C(=O)[C@H]3C[C@@](C)(O)C3)C4)cnc21]

The title compound was prepared in a manner analogous to Example 153 using tert-butyl 6-iodo-2-azaspiro[3.3]heptane-2-carboxylate (Intermediate 3) instead of tert-butyl 2-bromo-7-azaspiro[3.5]nonane-7-carboxylate and 5-bromo-1-methyl-1H-pyrrolo[2,3-b]pyridine instead of 1-bromo-3-tert-butylbenzene in Step A. MS (ESI): mass calcd. for $C_{20}H_{25}N_3O_2$, 339.2; m/z found, 340.3 [M+H]$^+$. $^1$H NMR (400 MHz, CDCl$_3$) δ 8.18-8.11 (m, 1H), 7.75-7.67 (m, 1H), 7.20-7.13 (m, 1H), 6.42-6.35 (m, 1H), 4.28-4.21 (m, 1H), 4.19-4.13 (m, 1H), 4.11-4.00 (m, 2H), 3.98-3.93 (m, 1H), 3.90-3.82 (m, 3H), 3.61-3.44 (m, 1H), 2.72-2.57 (m, 3H), 2.42-2.25 (m, 6H), 1.38-1.30 (m, 3H).

Example 269

((1s,3s)-3-Hydroxy-3-methylcyclobutyl)(6-(1-methyl-1H-pyrrolo[2,3-b]pyridin-6-yl)-2-azaspiro[3.3]heptan-2-yl)methanone

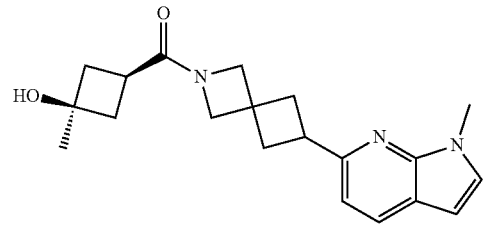 [SMILES: Cn1ccc2ccc(C3CC4(C3)CN(C(=O)[C@H]3C[C@@](C)(O)C3)C4)nc21]

The title compound was prepared in a manner analogous to Example 29 using tert-butyl 6-oxo-2-azaspiro[3.3]heptane-2-carboxylate instead of tert-butyl 6-oxo-2-azaspiro[3.4]octane-2-carboxylate and 6-bromo-1-methyl-1H-pyrrolo[2,3-b]pyridine (Intermediate 44) instead of 2-bromo-6-(tert-butyl)pyridine in Step A. MS (ESI): mass calcd. for $C_{20}H_{25}N_3O_2$, 339.2; m/z found, 340.2 [M+H]$^+$. $^1$H NMR (400 MHz, CDCl$_3$) δ 7.77 (d, J=8.0 Hz, 1H), 7.11 (d, J=3.2 Hz, 1H), 6.93-6.80 (m, 1H), 6.44-6.34 (m, 1H), 4.26 (br s, 1H), 4.19 (s, 1H), 4.11 (d, J=3.2 Hz, 2H), 4.06 (s, 1H), 3.86 (s, 3H), 3.63-3.47 (m, 1H), 2.69-2.55 (m, 5H), 2.36-2.23 (m, 4H), 1.34 (d, J=5.6 Hz, 3H).

Example 270

(6-Benzyl-6-methoxy-2-azaspiro[3.3]heptan-2-yl)
((1s,3s)-3-hydroxy-3-methylcyclobutyl)methanone

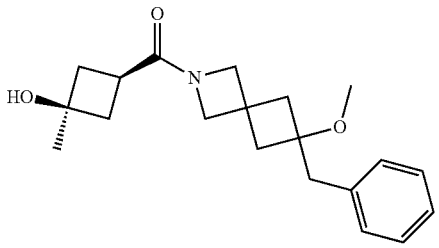 [SMILES: COC1(Cc2ccccc2)CC2(CN(C(=O)[C@H]3C[C@@](C)(O)C3)C2)C1]

Step A: tert-Butyl 6-benzyl-6-hydroxy-2-azaspiro[3.3]heptane-2-carboxylate. In an oven-dried flask under N$_2$, tert-butyl 6-oxo-2-azaspiro[3.3]heptane-2-carboxylate (100 mg, 0.464 mmol) was taken up in THF (2.3 mL) and cooled to 0° C. Benzylmagnesium chloride (0.35 mL, 2 M in THF, 0.696 mmol) was added dropwise. The reaction was allowed to warm to rt and stirred for 1.5 hours. The reaction mixture was quenched with sat. aq. NH$_4$Cl and extracted with EtOAc. The combined organic layers were dried over Na$_2$SO$_4$, filtered, and concentrated under reduced pressure. Purification by FCC (SiO$_2$, 0-80% EtOAc in hexanes) provided the title compound (44 mg, 31% yield). MS (ESI): mass calcd. for C$_{18}$H$_{25}$NO$_3$, 303.2; m/z found, 248.2 [M+2H-tBu]$^+$.

Step B: tert-Butyl 6-benzyl-6-methoxy-2-azaspiro[3.3]heptane-2-carboxylate. Under an atmosphere of N$_2$, tert-butyl 6-benzyl-6-hydroxy-2-azaspiro[3.3]heptane-2-carboxylate (44 mg, 0.145 mmol) was taken up in DMF (0.7 mL) and cooled to 0° C. NaH (7.0 mg, 0.174 mmol) was added to the reaction mixture and the reaction mixture was stirred for 10 min. Iodomethane (14 μL, 0.218 mmol) was added and the reaction was allowed to warm to rt and stirred for 3 hours. The reaction was quenched with water and extracted with EtOAc. The combined organic layers were dried over Na$_2$SO$_4$, filtered, and concentrated under reduced pressure. Purification by FCC (SiO$_2$, 0-40% EtOAc in hexanes) provided the title compound (33 mg, 72% yield). MS (ESI): mass calcd. for C$_{19}$H$_{27}$NO$_3$, 317.2; m/z found, 262.2 [M+2H-tBu]$^+$.

Step C: 6-Benzyl-6-methoxy-2-azaspiro[3.3]heptane. To tert-butyl 6-benzyl-6-methoxy-2-azaspiro[3.3]heptane-2-carboxylate (16 mg, 0.050 mmol) was added HCl (1.25M in EtOH, 0.4 mL). The reaction was heated to 45° C. for 1 hour. The reaction mixture was concentrated under reduced pressure to afford the title compound which was used without further purification in the next step. MS (ESI): mass calcd. for C$_{14}$H$_{19}$NO, 217.1; m/z found, 218.2 [M+H]$^+$.

Step D: 6-Benzyl-6-methoxy-2-azaspiro[3.3]heptan-2-yl)((1s,3s)-3-hydroxy-3-methylcyclobutyl)methanone. To a solution of 6-benzyl-6-methoxy-2-azaspiro[3.3]heptane in DMF (0.5 mL) was added (1s,3s)-3-hydroxy-3-methylcyclobutane-1-carboxylic acid (7.0 mg, 0.053 mmol), DIPEA (26 μL, 0.151 mmol), and HATU (21 mg, 0.055 mmol). The reaction mixture was stirred at rt for 1 hour. The reaction mixture was filtered through a PTFE filter and washed with MeOH and purified via RP HPLC (5-95% ACN in 20 mM NH$_4$OH in water) to afford the title compound (10 mg, 69% yield). MS (ESI): mass calcd. for C$_{20}$H$_{27}$NO$_3$, 329.2; m/z found, 330.2 [M+H]$^+$. $^1$H NMR (400 MHz, CDCl$_3$) δ 7.34-7.21 (m, 3H), 7.21-7.14 (m, 2H), 4.03 (s, 1H), 3.94 (s, 2H), 3.81 (d, J=9.3 Hz, 2H), 3.25 (d, J=1.8 Hz, 3H), 2.82 (d, J=3.4 Hz, 2H), 2.64-2.49 (m, 1H), 2.32-2.17 (m, 8H), 1.33 (d, J=2.3 Hz, 3H).

Example 271

(6-(2-Cyclopropylbenzyl)-2-azaspiro[3.3]heptan-2-yl)((1s,3s)-3-hydroxy-3-methylcyclobutyl)methanone

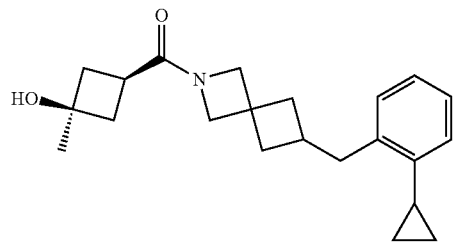 [SMILES: C[C@]1(O)C[C@@H](C(=O)N2CC3(CC(Cc4ccccc4C4CC4)C3)C2)C1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-2-cyclopropylbenzene instead of 1-bromo-2-methyl-4-(trifluoromethyl)benzene in Step B. MS (ESI): mass calcd. for C$_{22}$H$_{29}$NO$_2$, 339.2; m/z found, 340.1 [M+H]$^+$. $^1$H NMR (400 MHz, CDCl$_3$) δ 7.15-7.09 (m, 2H), 7.07-7.02 (m, 1H), 6.97-6.92 (m, 1H), 4.21 (br s, 1H), 4.08 (s, 1H), 4.00 (d, J=10.4 Hz, 2H), 3.93 (s, 1H), 2.90-2.85 (m, 2H), 2.65-2.49 (m, 2H), 2.34-2.31 (m, 1H), 2.30-2.24 (m, 5H), 2.06 (br s, 1H), 1.99-1.95 (m, 1H), 1.92-1.86 (m, 1H), 1.35 (s, 3H), 0.96-0.91 (m, 2H), 0.69-0.62 (m, 2H).

Example 272

(6-(4-Cyclopropoxybenzyl)-2-azaspiro[3.3]heptan-2-yl)((1s,3s)-3-hydroxy-3-methylcyclobutyl)methanone

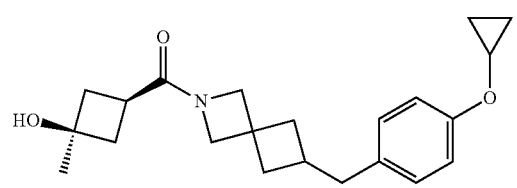 [SMILES: C[C@]1(O)C[C@@H](C(=O)N2CC3(CC(Cc4ccc(OC5CC5)cc4)C3)C2)C1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-4-cyclopropoxybenzene instead of 1-bromo-2-methyl-4-(trifluoromethyl)benzene in Step B. MS (ESI): mass calcd. for C$_{22}$H$_{29}$NO$_3$, 355.2; m/z found, 356.2 [M+H]$^+$. $^1$H NMR (400 MHz, CDCl$_3$) δ 7.05-6.99 (m, 2H), 6.98-6.93 (m, 2H), 4.10 (br s, 1H), 4.07-3.88 (m, 4H), 3.74-3.67 (m, 1H), 2.66-2.57 (m, 3H), 2.47-2.33 (m, 1H), 2.31-2.21 (m, 6H), 1.93-1.82 (m, 2H), 1.34 (s, 3H), 0.78-0.74 (m, 4H).

Example 273

(6-(4-Fluoro-2-methylbenzyl)-2-azaspiro[3.3]heptan-2-yl)((1s,3s)-3-hydroxy-3-methylcyclobutyl)methanone

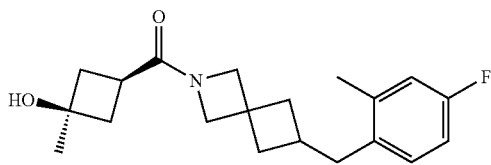 [SMILES: Cc1cc(F)ccc1CC1CC2(C1)CN(C(=O)[C@H]1C[C@@](C)(O)C1)C2]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-4-fluoro-2-methylbenzene instead of 1-bromo-2-methyl-4-(trifluoromethyl)benzene in Step B. MS (ESI): mass calcd. for $C_{20}H_{26}FNO_2$, 331.2; m/z found, 332.1 [M+H]$^+$. $^1$H NMR (400 MHz, CDCl$_3$) δ 6.99-6.94 (m, 1H), 6.88-6.76 (m, 2H), 4.12-4.06 (m, 2H), 4.02-3.95 (m, 2H), 3.94-3.91 (m, 1H), 2.66-2.59 (m, 3H), 2.49-2.37 (m, 1H), 2.33-2.25 (m, 8H), 1.96-1.84 (m, 3H), 1.34 (s, 3H).

Example 274

(6-(2-(Difluoromethyl)-4-methoxybenzyl)-2-azaspiro[3.3]heptan-2-yl)((1s,3s)-3-hydroxy-3-methylcyclobutyl)methanone

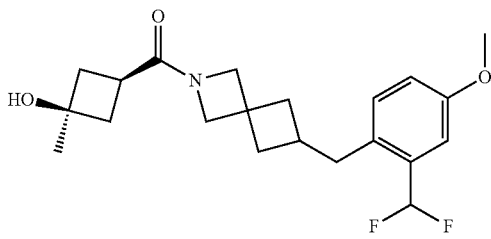 [SMILES: COc1ccc(CC2CC3(C2)CN(C(=O)[C@H]2C[C@@](C)(O)C2)C3)c(C(F)F)c1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-2-(difluoromethyl)-4-methoxybenzene instead of 1-bromo-2-methyl-4-(trifluoromethyl)benzene in Step B. MS (ESI): mass calcd. for $C_{21}H_{27}F_2NO_3$, 379.2; m/z found, 380.2 [M+H]$^+$. $^1$H NMR (400 MHz, CDCl$_3$) δ 7.11-7.05 (m, 2H), 6.97-6.90 (m, 1H), 6.87-6.56 (m, 1H), 4.10-3.89 (m, 5H), 3.82 (s, 3H), 2.74 (d, J=7.2 Hz, 2H), 2.69-2.57 (m, 1H), 2.53-2.35 (m, 1H), 2.32-2.19 (m, 6H), 2.00-1.82 (m, 2H), 1.37-1.31 (m, 3H).

Example 275

(6-(4-(Difluoromethyl)-2-methoxybenzyl)-2-azaspiro[3.3]heptan-2-yl)((1s,3s)-3-hydroxy-3-methylcyclobutyl)methanone

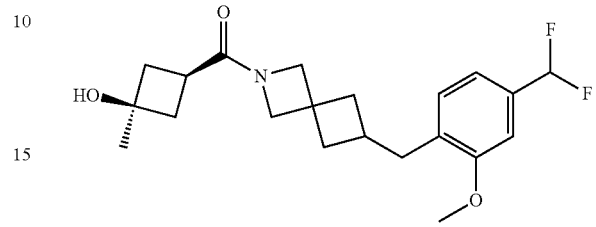

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 1-bromo-4-(difluoromethyl)-2-methoxybenzene instead of 1-bromo-2-methyl-4-(trifluoromethyl)benzene in Step B. MS (ESI): mass calcd. for $C_{21}H_{27}F_2NO_3$, 379.2; m/z found, 380.1 [M+H]$^+$. $^1$H NMR (400 MHz, CDCl$_3$) δ 7.12-7.07 (m, 1H), 7.02-6.95 (m, 2H), 6.76-6.43 (m, 1H), 4.30-4.11 (m, 1H), 4.07-3.97 (m, 2H), 3.97-3.90 (m, 2H), 3.85 (s, 3H), 2.73-2.66 (m, 2H), 2.64-2.54 (m, 1H), 2.52-2.38 (m, 1H), 2.29-2.19 (m, 6H), 1.97-1.81 (m, 2H), 1.34 (s, 3H).

Example 276

((1s,3s)-3-Hydroxy-3-methylcyclobutyl)(6-(3-methoxy-4-(trifluoromethyl)benzyl)-2-azaspiro[3.3]heptan-2-yl)methanone

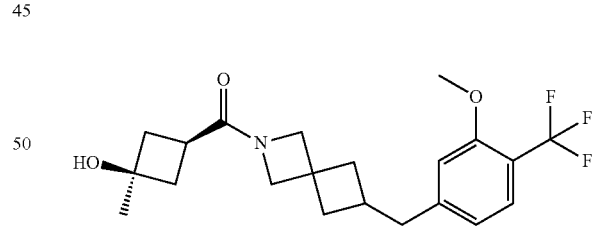

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 4-bromo-2-methoxy-1-(trifluoromethyl)benzene instead of 1-bromo-2-methyl-4-(trifluoromethyl)benzene in Step B. MS (ESI): mass calcd. for $C_{21}H_{26}F_3NO_3$, 397.2; m/z found, 398.1 [M+H]$^+$. $^1$H NMR (400 MHz, CDCl$_3$) δ 7.46 (d, J=7.8 Hz, 1H), 6.78-6.71 (m, 2H), 4.08 (s, 1H), 4.05-3.92 (m, 4H), 3.89 (s, 3H), 2.75-2.69 (m, 2H), 2.66-2.56 (m, 1H), 2.51-2.37 (m, 1H), 2.35-2.20 (m, 6H), 2.01-1.86 (m, 2H), 1.34 (s, 3H).

Example 277

((1s,3s)-3-Hydroxy-3-methylcyclobutyl)(6-((5-methyl-6-(trifluoromethyl)pyridin-2-yl)methyl)-2-azaspiro[3.3]heptan-2-yl)methanone

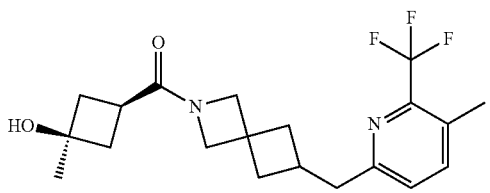 [SMILES: Cc1ccc(CC2CC3(C2)CN(C(=O)[C@H]2C[C@@](C)(O)C2)C3)nc1C(F)(F)F]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-chloro-3-methyl-2-(trifluoromethyl)pyridine instead of 1-bromo-2-methyl-4-(trifluoromethyl)benzene in Step B. MS (ESI): mass calcd. for $C_{20}H_{25}F_3N_2O_2$, 382.2; m/z found, 383.1 [M+H]$^+$. $^1$H NMR (400 MHz, CDCl$_3$) δ 7.56-7.50 (m, 1H), 7.14 (d, J=8.0 Hz, 1H), 4.26-3.79 (m, 5H), 2.87 (d, J=7.6 Hz, 2H), 2.68-2.53 (m, 2H), 2.45 (s, 3H), 2.35-2.20 (m, 6H), 2.04-1.93 (m, 2H), 1.34 (s, 3H).

Example 278

((1s,3s)-3-Hydroxy-3-methylcyclobutyl)(6-((6-methyl-5-(trifluoromethyl)pyridin-2-yl)methyl)-2-azaspiro[3.3]heptan-2-yl)methanone

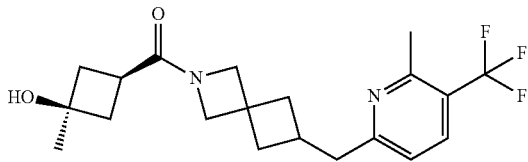 [SMILES: Cc1nc(CC2CC3(C2)CN(C(=O)[C@H]2C[C@@](C)(O)C2)C3)ccc1C(F)(F)F]

Step A: tert-Butyl 6-((6-chloro-5-(trifluoromethyl)pyridin-2-yl)methylene)-2-azaspiro[3.3]heptane-2-carboxylate. Pd(OAc)$_2$ (42 mg, 0.185 mmol) and tri-o-tolylphosphine (85 mg, 0.278 mmol) were added to a solution of 2,6-dichloro-3-(trifluoromethyl)pyridine (200 mg, 0.926 mmol), tert-butyl 6-methylene-2-azaspiro[3.3]heptane-2-carboxylate (Intermediate 72, 194 mg, 0.926 mmol), and TEA (0.3 mL, 2.32 mmol) in DMF (5 mL) under N$_2$. The resultant mixture was stirred at 120° C. for 12 h before being cooled to rt, quenched with water, and extracted with EtOAc. The combined organic layers were dried over Na$_2$SO$_4$, filtered, and concentrated under reduced pressure. The resulting residue was purified by FCC (SiO$_2$, 0-10% EtOAc in ether) to afford the title compound (177 mg, 47% yield) as a light-yellow solid. MS (ESI): mass calcd. for $C_{18}H_{20}ClF_3N_2O_2$, 388.1; m/z found, 332.8 [M+2H-tBu]$^+$. $^1$H NMR (400 MHz, CDCl$_3$) δ 7.94-7.82 (m, 1H), 7.10-6.98 (m, 1H), 6.28 (br s, 1H), 4.07-3.92 (m, 4H), 3.41 (br s, 2H), 3.12 (br s, 2H), 1.45 (s, 9H).

Step B: tert-Butyl 6-((6-methyl-5-(trifluoromethyl)pyridin-2-yl)methylene)-2-azaspiro[3.3]heptane-2-carboxylate. Pd(dppf)Cl$_2$ (30 mg, 0.040 mmol) was added to a solution of tert-butyl 6-((6-chloro-5-(trifluoromethyl)pyridin-2-yl)methylene)-2-azaspiro[3.3]heptane-2-carboxylate (157 mg, 0.404 mmol), 2,4,6-trimethyl-1,3,5,2,4,6-trioxatriborinane (152 mg, 0.606 mmol) and Cs$_2$CO$_3$ (395 mg, 1.21 mmol) in 1,4-dioxane (16 mL) and H$_2$O (4 mL) under N$_2$. The resultant mixture was stirred at 120° C. for 2 h before being cooled to rt. The suspension was filtered through a pad of Celite® and the pad was washed with EtOAc. The filtrate was washed with water and brine, dried over Na$_2$SO$_4$, filtered, and concentrated under reduced pressure. The resulting residue was purified by FCC (SiO$_2$, 0-10% EtOAc in ether) to afford the title compound (100 mg, 63% yield) as a light-yellow solid. MS (ESI): mass calcd. for $C_{19}H_{23}F_3N_2O_2$, 368.2; m/z found, 369.0 [M+H]$^+$.

Step C: tert-Butyl 6-((6-methyl-5-(trifluoromethyl)pyridin-2-yl)methyl)-2-azaspiro[3.3]heptane-2-carboxylate. PtO$_2$ (93 mg, 0.407 mmol) was added to a solution of tert-butyl 6-((6-methyl-5-(trifluoromethyl)pyridin-2-yl)methylene)-2-azaspiro[3.3]heptane-2-carboxylate (100 mg, 0.271 mmol) in EtOH (5 mL). The resulting mixture was evacuated and filled with H$_2$ and stirred under H$_2$ (15 psi) at rt for 1.5 h. The suspension was filtered through a pad of Celite® and the filtrate was concentrated under reduced pressure to afford the title compound (80 mg, crude), which used in the next step without further purification.

Step D: 6-((6-Methyl-5-(trifluoromethyl)pyridin-2-yl)methyl)-2-azaspiro[3.3]heptane. TFA (1 mL, 13.1 mmol) was added to a solution of tert-butyl 6-((6-methyl-5-(trifluoromethyl)pyridin-2-yl)methyl)-2-azaspiro[3.3]heptane-2-carboxylate (80 mg, 0.216 mmol) in DCM (6 mL). The resultant mixture was stirred at rt for 2 h before being concentrated under reduced pressure. The resulting residue was taken up in 25% aq. NH$_3$ (5 mL) and extracted with DCM. The combined organic extracts were dried over Na$_2$SO$_4$, filtered, and concentrated under reduced pressure to afford the title compound (79 mg), which was used in the next step without further purification.

Step E: ((1s,3s)-3-Hydroxy-3-methylcyclobutyl)(6-((6-methyl-5-(trifluoromethyl)pyridin-2-yl)methyl)-2-azaspiro[3.3]heptan-2-yl)methanone. DIPEA (0.28 mL, 1.46 mmol) was added to a solution of HATU (222 mg, 0.585 mmol), 6-((6-methyl-5-(trifluoromethyl)pyridin-2-yl)methyl)-2-azaspiro[3.3]heptane (79 mg, 0.292 mmol) and (1s,3s)-3-hydroxy-3-methylcyclobutanecarboxylic acid (46 mg, 0.351 mmol) in DMF (5 mL). The resultant mixture was stirred at rt for 3 h. Purification (RP HPLC (35-65% CH$_3$CN in H$_2$O with 0.05% NH$_3$ and 10 mM NH$_4$HCO$_3$)) afforded the title compound (12 mg, 11% yield) as a light-yellow solid. MS (ESI): mass calcd. for $C_{20}H_{25}F_3N_2O_2$, 382.2; m/z found, 383.3 [M+H]$^+$. $^1$H NMR (400 MHz, CDCl$_3$) δ 7.78 (d, J=8.0 Hz, 1H), 6.99 (d, J=8.0 Hz, 1H), 4.08 (s, 1H), 4.03-3.89 (m, 4H), 2.91-2.83 (m, 2H), 2.67 (s, 3H), 2.65-2.56 (m, 2H), 2.35-2.20 (m, 6H), 2.03-1.92 (m, 2H), 1.34 (s, 3H).

Example 279

((1s,3s)-3-Hydroxy-3-methylcyclobutyl)(6-((6-isopropoxy-5-methylpyridin-2-yl)methyl)-2-azaspiro[3.3]heptan-2-yl)methanone

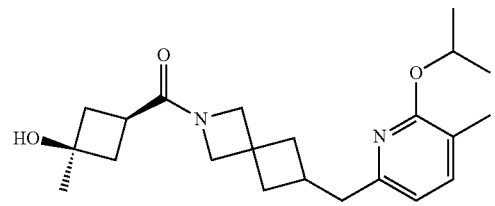 [SMILES: Cc1ccc(CC2CC3(C2)CN(C(=O)[C@H]2C[C@@](C)(O)C2)C3)nc1OC(C)C]

Step A: tert-Butyl 6-((6-fluoro-5-methylpyridin-2-yl)methylene)-2-azaspiro[3.3]heptane-2-carboxylate. Pd(OAc)$_2$ (47 mg, 0.211 mmol) and tri-o-tolylphosphine (96 mg, 0.316 mmol) were added to a solution of 6-bromo-2-fluoro-3-methylpyridine (200 mg, 1.05 mmol), tert-butyl 6-methylene-2-azaspiro[3.3]heptane-2-carboxylate (Intermediate 72, 220 mg, 1.05 mmol), and TEA (0.34 mL, 2.63 mmol) in DMF (5 mL) under N$_2$. The resultant mixture was stirred at 120° C. for 12 h before being cooled to rt and filtered. The filtrate was extracted with EtOAc and the combined organic extracts were washed with water and brine, dried over Na$_2$SO$_4$, filtered, and concentrated under reduced pressure. The resulting residue was purified by FCC (SiO$_2$, 0-10% EtOAc in ether) to afford the title compound (179 mg, 34% yield) as a yellow oil. MS (ESI): mass calcd. for C$_{18}$H$_{23}$FN$_2$O$_2$, 318.4; m/z found, 262.9 [M+2H-tBu]$^+$.

Step B: tert-Butyl 6-((6-fluoro-5-methylpyridin-2-yl)methyl)-2-azaspiro[3.3]heptane-2-carboxylate. PtO$_2$ (137 mg, 0.603 mmol) was added to a solution of tert-butyl 6-((6-fluoro-5-methylpyridin-2-yl)methylene)-2-azaspiro[3.3]heptane-2-carboxylate (128 mg, 0.402 mmol) in EtOH (5 mL). The resulting mixture was evacuated and filled with H$_2$ and stirred under H$_2$ (15 psi) at rt for 1.5 h. The suspension was filtered through a pad of Celite® and the filtrate was concentrated under reduced pressure to afford the title compound (130 mg, crude), which was used in the next step without further purification.

Step C: tert-Butyl 6-((6-isopropoxy-5-methylpyridin-2-yl)methyl)-2-azaspiro[3.3]heptane-2-carboxylate. Sodium hydride (163 mg, 60% in mineral oil, 4.06 mmol) was added to iPrOH (3 mL). The resulting mixture was stirred at 70° C. for 1 h, then treated with tert-butyl 6-((6-fluoro-5-methylpyridin-2-yl)methyl)-2-azaspiro[3.3]heptane-2-carboxylate (130 mg, crude) in iPrOH (1 mL) dropwise. The resultant mixture was stirred at 70° C. overnight. The reaction mixture was cooled, quenched with water and extracted with EtOAc. The combined organic extracts were washed with water and brine, dried over Na$_2$SO$_4$, filtered, and concentrated under reduced pressure. The resulting residue was purified by FCC (SiO$_2$, 0-10% EtOAc in ether) to afford the title compound (50 mg, 34% yield) as a yellow oil. MS (ESI): mass calcd. for C$_{21}$H$_{32}$N$_2$O$_3$, 360.2; m/z found, 361.5 [M+H]$^+$.

Step D: 6-((6-Isopropoxy-5-methylpyridin-2-yl)methyl)-2-azaspiro[3.3]heptane. TFA (1 mL, 13.1 mmol) was added to a solution of tert-butyl 6-((6-isopropoxy-5-methylpyridin-2-yl)methyl)-2-azaspiro[3.3]heptane-2-carboxylate (49 mg, 0.136 mmol) in DCM (6 mL). The resultant mixture was stirred at rt for 2 h. The reaction mixture was concentrated under reduced pressure. The resulting residue was taken up in 25% aq. NH$_3$ (5 mL) and extracted with DCM. The combined organic extracts were concentrated under reduced pressure to give the title compound (34 mg) which was used in the next step without further purification.

Step E: ((1s,3s)-3-Hydroxy-3-methylcyclobutyl)(6-((6-isopropoxy-5-methylpyridin-2-yl)methyl)-2-azaspiro[3.3]heptan-2-yl)methanone. DIPEA (0.11 mL, 0.653 mmol) was added to a solution of HATU (99 mg, 0.261 mmol), 6-((6-isopropoxy-5-methylpyridin-2-yl)methyl)-2-azaspiro[3.3]heptane (34 mg, 0.131 mmol) and (1s,3s)-3-hydroxy-3-methylcyclobutanecarboxylic acid (20 mg, 0.157 mmol) in DMF (5 mL). The resultant mixture was stirred at rt for 3 h. The reaction mixture was quenched with water and extracted with EtOAc. The combined organic extracts were washed with water and brine, dried over Na$_2$SO$_4$, filtered, and concentrated under reduced pressure. The resulting residue was purified by RP HPLC (35-65% CH$_3$CN in H$_2$O with 0.05% NH$_3$ and 10 mM NH$_4$HCO$_3$). The product was further subjected to SFC (Stationary phase: OD-H (250×30 mm); Mobile phase: 15% EtOH containing 0.1% of 25% aq. NH$_3$/CO$_2$) to afford the title compound (12 mg, 54% yield) as a white solid. MS (ESI): mass calcd. for C$_{22}$H$_{32}$N$_2$O$_3$, 372.2; m/z found, 373.5 [M+H]$^+$. $^1$H NMR (400 MHz, CDCl$_3$) δ 7.23 (d, J=7.2 Hz, 1H), 6.49 (d, J=7.2 Hz, 1H), 5.36-5.24 (m, 1H), 4.07 (s, 1H), 4.07-3.90 (m, 4H), 2.71-2.66 (m, 2H), 2.65-2.50 (m, 2H), 2.34-2.21 (m, 6H), 2.11 (s, 3H), 2.04-1.91 (m, 2H), 1.37-1.31 (m, 9H).

Example 280

(6-((5-(Difluoromethoxy)-6-methylpyridin-2-yl)methyl)-2-azaspiro[3.3]heptan-2-yl)((1s,3s)-3-hydroxy-3-methylcyclobutyl)methanone

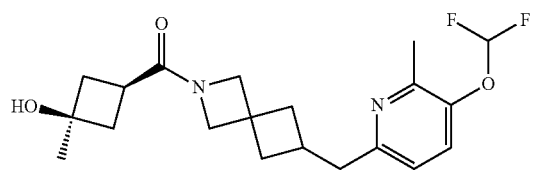 [SMILES: Cc1nc(CC2CC3(C2)CN(C(=O)[C@H]2C[C@@](C)(O)C2)C3)ccc1OC(F)F]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-3-(difluoromethoxy)-2-methylpyridine (Intermediate 55) instead of 1-bromo-2-methyl-4-(trifluoromethyl)benzene in Step B. MS (ESI): mass calcd. for C$_{20}$H$_{26}$F$_2$N$_2$O$_3$, 380.2; m/z found, 381.1 [M+H]$^+$. $^1$H NMR (400 MHz, CDCl$_3$) δ 7.32 (d, J=8.0 Hz, 1H), 6.90 (d, J=8.4 Hz, 1H), 6.72-6.29 (m, 1H), 4.09-3.89 (m, 5H), 2.81 (d, J=7.6 Hz, 2H), 2.68-2.52 (m, 2H), 2.50 (s, 3H), 2.34-2.19 (m, 6H), 2.03-1.90 (m, 2H), 1.34 (s, 3H).

Example 281

((1s,3s)-3-Hydroxy-3-methylcyclobutyl)(6-((6-methoxy-5-(trifluoromethyl)pyridin-2-yl)methyl)-2-azaspiro[3.3]heptan-2-yl)methanone

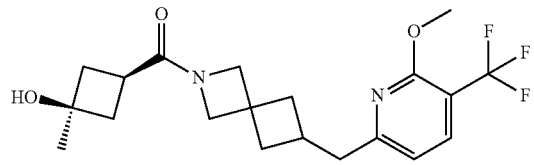 [SMILES: COc1nc(CC2CC3(C2)CN(C(=O)[C@H]2C[C@@](C)(O)C2)C3)ccc1C(F)(F)F]

Step A: tert-Butyl 6-((6-chloro-5-(trifluoromethyl)pyridin-2-yl)methyl)-2-azaspiro[3.3]heptane-2-carboxylate.

PtO$_2$ (200 mg, 0.880 mmol) was added to a solution of tert-butyl 6-((6-chloro-5-(trifluoromethyl)pyridin-2-yl)methylene)-2-azaspiro[3.3]heptane-2-carboxylate (from Example 278, Step A) (460 mg, 1.18 mmol) in EtOH (10 mL). The resultant mixture was stirred under H$_2$ (15 psi) at rt for 1 h. The reaction mixture was filtered through a pad of Celite® and the pad was washed with EtOH. The filtrate was concentrated under reduced pressure to afford the title compound (440 mg, 83% yield) as a yellow oil. MS (ESI): mass calcd. for C$_{18}$H$_{22}$ClF$_3$N$_2$O$_2$, 390.1; m/z found, 334.9 [M+2H-tBu]$^+$.

Step B: tert-Butyl 6-((6-methoxy-5-(trifluoromethyl)pyridin-2-yl)methyl)-2-azaspiro[3.3]heptane-2-carboxylate. MeONa (200 mg, 3.70 mmol) was added to a solution of tert-butyl 6-((6-chloro-5-(trifluoromethyl)pyridin-2-yl)methyl)-2-azaspiro[3.3]heptane-2-carboxylate (150 mg, 0.384 mmol) in MeOH (5 mL). The resultant mixture was stirred at 80° C. for 12 h. The reaction mixture was cooled, quenched with water and extracted with EtOAc. The combined organic extracts were dried over $Na_2SO_4$, filtered, and concentrated under reduced pressure to give the title compound (180 mg, 86% yield) as a yellow solid, which was used in the next step without further purification. MS (ESI): mass calcd. for $C_{19}H_{25}F_3N_2O_3$, 386.2; m/z found, 330.9 [M+2H-tBu]+.

Step C: 6-((6-Methoxy-5-(trifluoromethyl)pyridin-2-yl)methyl)-2-azaspiro[3.3]heptane. TFA (0.4 mL, 5.40 mmol) was added to a solution of tert-butyl 6-((6-methoxy-5-(trifluoromethyl)pyridin-2-yl)methyl)-2-azaspiro[3.3]heptane-2-carboxylate (180 mg, 0.466 mmol) in DCM (4 mL). The resultant mixture was stirred at rt for 2 h. The reaction mixture was concentrated under reduced pressure and the resulting residue was taken up in water, adjusted to pH 8 with sat. aq. $NaHCO_3$ and extracted with DCM. The combined organic extracts were dried over $Na_2SO_4$, filtered, and concentrated under reduced pressure to give the title compound (140 mg, 95% yield) as a yellow oil. MS (ESI): mass calcd. for $C_{14}H_{17}F_3N_2O$, 286.1; m/z found, 286.9 [M+H]+.

Step D: ((1s,3s)-3-Hydroxy-3-methylcyclobutyl)(6-((6-methoxy-5-(trifluoromethyl)pyridin-2-yl)methyl)-2-azaspiro[3.3]heptan-2-yl)methanone. HATU (295 mg, 0.776 mmol) was added to a solution of (1s,3s)-3-hydroxy-3-methylcyclobutanecarboxylic acid (75 mg, 0.580 mmol) and DIPEA (0.35 mL, 1.97 mmol) in DMF (2 mL). The resultant mixture was stirred at rt for 5 min, then treated with 6-((6-methoxy-5-(trifluoromethyl)pyridin-2-yl)methyl)-2-azaspiro[3.3]heptane (110 mg, 0.384 mmol). The resulting mixture was stirred at rt for 2 h. The reaction mixture was quenched with water and extracted with EtOAc. The combined organic extracts were dried over $Na_2SO_4$, filtered, and concentrated under reduced pressure. The resulting residue was purified by RP HPLC (40-70% $CH_3CN$ in $H_2O$ with 0.05% $NH_3$ and 10 mM $NH_4HCO_3$). The title compound was further subjected to SFC (Stationary phase: AS-H (250×30 mm); Mobile phase: 10% EtOH containing 0.1% of 25% aq. $NH_3/CO_2$) to give the title compound (41 mg, 26% yield) as a white solid. MS (ESI): mass calcd. for $C_{20}H_{25}F_3N_2O_3$, 398.2; m/z found, 399.2 [M+H]+. $^1$H NMR (400 MHz, $CDCl_3$) δ 7.73 (d, J=8.0 Hz, 1H), 6.71 (d, J=8.0 Hz, 1H), 4.14-4.08 (m, 1H), 4.08-3.96 (m, 6H), 3.96-3.92 (m, 1H), 2.84-2.76 (m, 2H), 2.68-2.54 (m, 2H), 2.41-2.18 (m, 6H), 2.06-1.94 (m, 2H), 1.34 (s, 3H).

Example 282

((1s,3s)-3-Hydroxy-3-methylcyclobutyl)(6-((6-isopropoxy-5-(trifluoromethyl)pyridin-2-yl)methyl)-2-azaspiro[3.3]heptan-2-yl)methanone

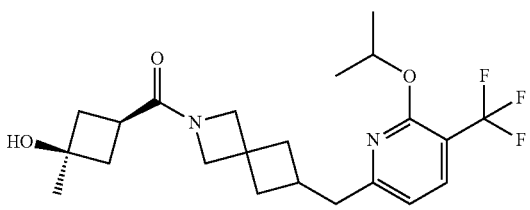 [SMILES: CC(C)Oc1nc(CC2CC3(C2)CN(C(=O)[C@H]2C[C@@](C)(O)C2)C3)ccc1C(F)(F)F]

The title compound was prepared in a manner analogous to Example 279 using 6-chloro-2-fluoro-3-(trifluoromethyl)pyridine instead of 6-bromo-2-fluoro-3-methylpyridine in Step A. MS (ESI): mass calcd. for $C_{22}H_{29}F_3N_2O_3$, 426.2; m/z found, 427.1 [M+H]+. $^1$H NMR (400 MHz, $CDCl_3$) δ 7.70 (d, J=7.6 Hz, 1H), 6.65 (d, J=7.6 Hz, 1H), 5.48-5.31 (m, 1H), 4.16-3.92 (m, 5H), 2.77 (d, J=6.8 Hz, 2H), 2.68-2.51 (m, 2H), 2.38-2.23 (m, 6H), 2.06-1.91 (m, 2H), 1.41-1.30 (m, 9H).

Example 283

((1s,3s)-3-Hydroxy-3-methylcyclobutyl)(6-((1-methyl-5-(trifluoromethyl)-1H-pyrazol-3-yl)methyl)-2-azaspiro[3.3]heptan-2-yl)methanone

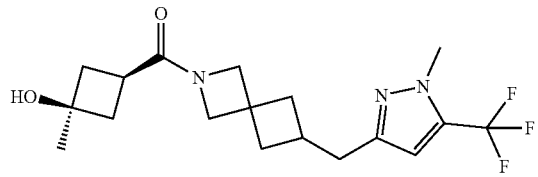 [SMILES: Cn1nc(CC2CC3(C2)CN(C(=O)[C@H]2C[C@@](C)(O)C2)C3)cc1C(F)(F)F]

The title compound was prepared in a manner analogous to Example 174 using diethyl ((1-methyl-5-(trifluoromethyl)-1H-pyrazol-3-yl)methyl)phosphonate (Intermediate 56) instead of diethyl 3-methylbenzylphosphonate in Step A. MS (ESI): mass calcd. for $C_{18}H_{24}F_3N_3O_2$, 371.2; m/z found, 372.2 [M+H]+. $^1$H NMR (400 MHz, $CDCl_3$) δ 6.31 (s, 1H), 4.06 (s, 1H), 4.01-3.93 (m, 3H), 3.92-3.86 (m, 4H), 2.71-2.56 (m, 3H), 2.52-2.38 (m, 1H), 2.34-2.18 (m, 6H), 2.00-1.84 (m, 2H), 1.32 (s, 3H).

Example 284

((1s,3s)-3-Hydroxy-3-methylcyclobutyl)(6-(pyrazolo[1,5-c]pyridin-6-ylmethyl)-2-azaspiro[3.3]heptan-2-yl)methanone

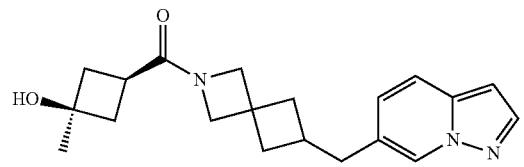 [SMILES: C[C@]1(O)C[C@@H](C(=O)N2CC3(CC(Cc4ccc5ccnn5c4)C3)C2)C1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromopyrazolo[1,5-c]pyridine instead of 1-bromo-2-methyl-4-(trifluoromethyl)benzene in Step B. MS (ESI): mass calcd. for $C_{20}H_{25}N_3O_2$, 339.2; m/z found, 340.1 [M+H]+. $^1$H NMR (400 MHz, $CDCl_3$) δ 8.23 (s, 1H), 7.94-7.87 (m, 1H), 7.50-7.43 (m, 1H), 6.90 (d, J=9.2 Hz, 1H), 6.53-6.43 (m, 1H), 4.09 (s, 1H), 4.04-3.96 (m, 3H), 3.92 (s, 1H), 2.73-2.58 (m, 3H), 2.56-2.40 (m, 1H), 2.36-2.20 (m, 6H), 2.03-1.88 (m, 2H), 1.34 (s, 3H).

Example 285

((1s,3s)-3-Hydroxy-3-methylcyclobutyl)(6-(pyrazolo[1,5-c]pyridin-7-ylmethyl)-2-azaspiro[3.3]heptan-2-yl)methanone

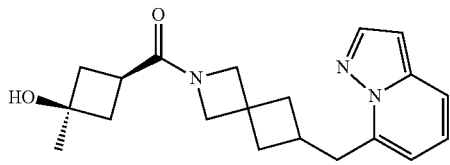 [SMILES: C[C@]1(O)C[C@@H](C(=O)N2CC3(CC(Cc4cccc5ccnn45)C3)C2)C1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 7-bromopyrazolo[1,5-c]pyridine instead of 1-bromo-2-methyl-4-(trifluoromethyl)benzene in Step B. MS (ESI): mass calcd. for $C_{20}H_{25}N_3O_2$, 339.2; m/z found, 340.2 [M+H]$^+$. $^1$H NMR (400 MHz, CDCl$_3$) δ 7.97-7.91 (m, 1H), 7.48-7.40 (m, 1H), 7.08-6.99 (m, 1H), 6.54-6.50 (m, 1H), 6.50-6.45 (m, 1H), 4.46-4.35 (m, 1H), 4.07-4.03 (m, 1H), 4.01-3.96 (m, 2H), 3.92-3.88 (m, 1H), 3.23-3.16 (m, 2H), 2.89-2.77 (m, 1H), 2.60-2.49 (m, 1H), 2.49-2.27 (m, 4H), 2.27-2.15 (m, 4H), 1.33-1.28 (m, 3H).

Example 286

(6-((1H-Pyrrolo[2,3-b]pyridin-1-yl)methyl)-2-azaspiro[3.3]heptan-2-yl)((1s,3s)-3-hydroxy-3-methylcyclobutyl)methanone

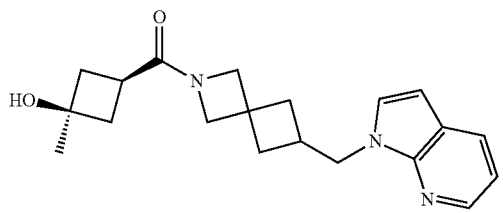 [SMILES: C[C@]1(O)C[C@@H](C(=O)N2CC3(CC(Cn4ccc5cccnc54)C3)C2)C1]

The title compound was prepared in a manner analogous to Example 237 using 1H-pyrrolo[2,3-b]pyridine instead of 3-(trifluoromethyl)-1H-pyrazole and sodium hydride instead of cesium carbonate in Step A. MS (ESI): mass calcd. for $C_{20}H_{25}N_3O_2$, 339.2; m/z found, 340.1 [M+H]$^+$. $^1$H NMR (400 MHz, CDCl$_3$) δ 8.33-8.23 (m, 1H), 7.92-7.84 (m, 1H), 7.16-7.10 (m, 1H), 7.07-6.99 (m, 1H), 6.45-6.38 (m, 1H), 4.59 (br s, 1H), 4.32-4.19 (m, 2H), 4.04-3.83 (m, 4H), 2.93-2.78 (m, 1H), 2.77-2.63 (m, 1H), 2.58-2.44 (m, 1H), 2.31-2.24 (m, 2H), 2.23-2.17 (m, 3H), 2.07-1.94 (m, 2H), 1.35-1.27 (m, 3H).

Example 287

((1s,3s)-3-Hydroxy-3-methylcyclobutyl)(6-((2-methyl-1H-pyrrolo[2,3-b]pyridin-1-yl)methyl)-2-azaspiro[3.3]heptan-2-yl)methanone

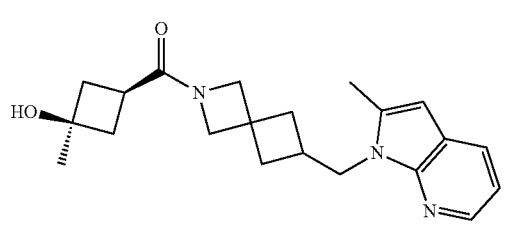 [SMILES: Cc1cc2cccnc2n1CC1CC2(C1)CN(C(=O)[C@H]1C[C@@](C)(O)C1)C2]

The title compound was prepared in a manner analogous to Example 237 using 2-methyl-1H-pyrrolo[2,3-b]pyridine instead of 3-(trifluoromethyl)-1H-pyrazole and sodium hydride instead of cesium carbonate in Step A. MS (ESI): mass calcd. for $C_{21}H_{27}N_3O_2$, 353.2; m/z found, 354.1 [M+H]$^+$. $^1$H NMR (400 MHz, CDCl$_3$) δ 8.23-8.12 (m, 1H), 7.79-7.69 (m, 1H), 7.04-6.90 (m, 1H), 6.22-6.10 (m, 1H), 4.32-4.12 (m, 3H), 4.07-3.84 (m, 4H), 2.75-2.61 (m, 1H), 2.60-2.49 (m, 1H), 2.42 (s, 3H), 2.25-2.20 (m, 4H), 2.19-2.13 (m, 2H), 2.11-2.01 (m, 2H), 1.36-1.27 (m, 3H).

Example 288

((1s,3s)-3-Hydroxy-3-methylcyclobutyl)(6-((6-methyl-1H-pyrrolo[2,3-b]pyridin-1-yl)methyl)-2-azaspiro[3.3]heptan-2-yl)methanone

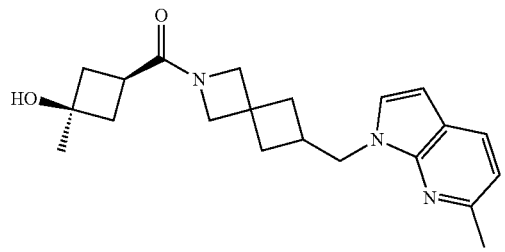 [SMILES: Cc1ccc2ccn(CC3CC4(C3)CN(C(=O)[C@H]3C[C@@](C)(O)C3)C4)c2n1]

The title compound was prepared in a manner analogous to Example 237 using 6-methyl-1H-pyrrolo[2,3-b]pyridine instead of 3-(trifluoromethyl)-1H-pyrazole and sodium hydride instead of cesium carbonate in Step A. MS (ESI): mass calcd. for $C_{21}H_{27}N_3O_2$, 353.2; m/z found, 354.5 [M+H]$^+$. $^1$H NMR (400 MHz, CDCl$_3$) δ 7.77 (d, J=8.0 Hz, 1H), 7.06 (d, J=2.8 Hz, 1H), 6.92 (d, J=7.2 Hz, 1H), 6.41-6.35 (m, 1H), 4.27 (d, J=7.2 Hz, 2H), 4.07-3.91 (m, 4H), 2.77-2.68 (m, 1H), 2.64-2.56 (m, 4H), 2.32-2.20 (m, 7H), 2.13-2.04 (m, 2H), 1.36-1.30 (m, 3H).

Example 289

((1s,3s)-3-Hydroxy-3-methylcyclobutyl)(6-((1-isopropyl-1H-pyrrolo[2,3-b]pyridin-6-yl)methyl)-2-azaspiro[3.3]heptan-2-yl)methanone

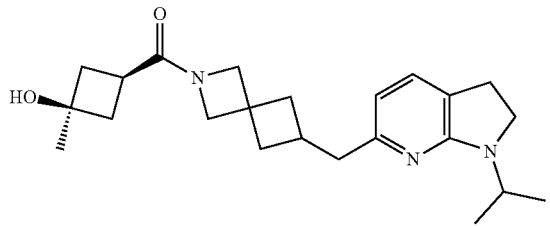 [SMILES: CC(C)N1CCc2ccc(CC3CC4(C3)CN(C(=O)[C@H]3C[C@@](C)(O)C3)C4)nc21]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-1-isopropyl-1H-pyrrolo[2,3-b]pyridine (Intermediate 47) instead of 1-bromo-2-methyl-4-(trifluoromethyl)benzene in Step B. MS (ESI): mass calcd. for $C_{23}H_{31}N_3O_2$, 381.2; m/z found, 382.2 $[M+H]^+$. $^1$H NMR (400 MHz, CDCl$_3$) δ 7.78 (d, J=8.0 Hz, 1H), 7.25 (d, J=3.6 Hz, 1H), 6.83 (d, J=8.0 Hz, 1H), 6.41 (d, J=3.2 Hz, 1H), 5.26-5.10 (m, 1H), 4.16 (s, 1H), 4.09-3.90 (m, 4H), 2.92 (d, J=7.6 Hz, 2H), 2.74-2.53 (m, 2H), 2.35-2.21 (m, 6H), 2.10-2.02 (m, 2H), 1.51 (d, J=6.8 Hz, 6H), 1.34 (s, 3H).

Example 290

((1s,3s)-3-Hydroxy-3-methylcyclobutyl)(6-((6-isopropyl-1H-pyrrolo[2,3-b]pyridin-1-yl)methyl)-2-azaspiro[3.3]heptan-2-yl)methanone

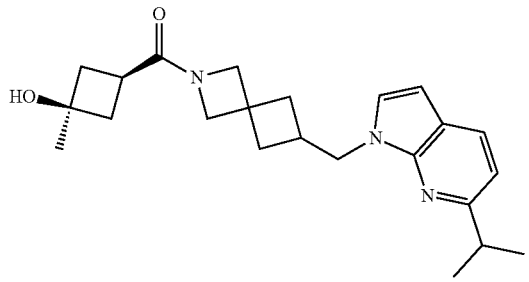 [SMILES: CC(C)c1ccc2ccn(CC3CC4(C3)CN(C(=O)[C@H]3C[C@@](C)(O)C3)C4)c2n1]

Step A: tert-Butyl 6-((6-bromo-1H-pyrrolo[2,3-b]pyridin-1-yl)methyl)-2-azaspiro[3.3]heptane-2-carboxylate. Sodium hydride (200 mg, 60% in mineral oil, 5.00 mmol) was added to a solution of 6-bromo-1H-pyrrolo[2,3-b]pyridine (300 mg, 1.52 mmol) in DMF (8 mL) under N$_2$. The resultant mixture was stirred at 40° C. for 30 min, then treated with tert-butyl 6-(bromomethyl)-2-azaspiro[3.3]heptane-2-carboxylate (Intermediate 4, 443 mg, 1.53 mmol) in DMF (2 mL). The resultant mixture was stirred at 40° C. for 12 h under N$_2$. The reaction mixture was cooled, quenched with water and extracted with EtOAc. The combined organic extracts were dried over Na$_2$SO$_4$, filtered, and concentrated under reduced pressure. The resulting residue was purified by FCC (SiO$_2$, 0-50% EtOAc in ether) to give the title compound (320 mg, 47% yield) as a white solid. MS (ESI): mass calcd. for $C_{19}H_{24}BrN_3O_2$, 405.1; m/z found, 349.8 $[M+2H-tBu]^+$.

Step B: tert-Butyl 6-((6-isopropyl-1H-pyrrolo[2,3-b]pyridin-1-yl)methyl)-2-azaspiro[3.3]heptane-2-carboxylate. NiCl$_2$(DME) (22 mg, 0.100 mmol) and 4,4'-di-tert-butyl-2,2'-bipyridine (32 mg, 0.120 mmol) were taken up in DMA (2 mL). The resulting mixture was stirred for 10 min under N$_2$, then treated with tert-butyl 6-((6-bromo-1H-pyrrolo[2,3-b]pyridin-1-yl)methyl)-2-azaspiro[3.3]heptane-2-carboxylate (320 mg, 0.788 mmol), potassium trifluoro(isopropyl)borate (128 mg, 0.853 mmol), (Ir[dF(CF$_3$)ppy]z(dtbpy))PF$_6$ (22 mg, 0.020 mmol) and 2,6-dimethylpyridine (0.22 mL, 1.90 mmol) in 1,4-dioxane (88 μL). The resultant mixture was sparged with N$_2$ then stirred at rt under 425 nm blue light overnight. The resultant mixture was poured into water and extracted with EtOAc. The combined organic extracts were dried over Na$_2$SO$_4$, filtered, and concentrated under reduced pressure. The resulting residue was purified by FCC (SiO$_2$, 0-50% EtOAc in ether) to afford the title compound (50 mg, 14% yield) as a light-yellow oil. MS (ESI): mass calcd. for $C_{22}H_{31}N_3O_2$, 369.2; m/z found, 370.1 $[M+H]^+$.

Step C: 1-(2-Azaspiro[3.3]heptan-6-ylmethyl)-6-isopropyl-1H-pyrrolo[2,3-b]pyridine. TFA (0.20 mL, 2.70 mmol) was added to a solution of tert-butyl 6-((6-isopropyl-1H-pyrrolo[2,3-b]pyridin-1-yl)methyl)-2-azaspiro[3.3]heptane-2-carboxylate (70 mg, 0.190 mmol) in DCM (1 mL). The resultant mixture was stirred at rt for 2 h before being concentrated under reduced pressure. The residue was taken up in water, adjusted to pH 8 with sat. aq. NaHCO$_3$ and extracted with DCM. The combined organic extracts were dried over Na$_2$SO$_4$, filtered, and concentrated under reduced pressure to provide the title compound (60 mg) as a yellow oil. MS (ESI): mass calcd. for $C_{17}H_{23}N_3$, 269.2; m/z found, 270.0 $[M+H]^+$.

Step D: ((1s,3s)-3-Hydroxy-3-methylcyclobutyl)(6-((6-isopropyl-1H-pyrrolo[2,3-b]pyridin-1-yl)methyl)-2-azaspiro[3.3]heptan-2-yl)methanone. HATU (160 mg, 0.421 mmol) was added to a solution of 1-(2-azaspiro[3.3]heptan-6-ylmethyl)-6-isopropyl-1H-pyrrolo[2,3-b]pyridine (50 mg, 0.190 mmol), (1s,3s)-3-hydroxy-3-methylcyclobutanecarboxylic acid (38 mg, 0.290 mmol) and DIPEA (0.20 mL, 1.10 mmol) in DMF (1 mL). The resultant mixture was stirred at rt for 2 h before being quenched with water and extracted with EtOAc. The combined organic extracts were washed with brine, dried over Na$_2$SO$_4$, filtered, and concentrated under reduced pressure to give crude product, which purified by RP HPLC (37-67% CH$_3$CN in H$_2$O with 0.05% NH$_3$) to afford the title compound (13 mg, 15% yield) as a yellow solid. MS (ESI): mass calcd. for $C_{23}H_{31}N_3O_2$, 381.2; m/z found, 382.2 $[M+H]^+$. $^1$H NMR (400 MHz, CDCl$_3$) δ 7.82-7.77 (m, 1H), 7.09-7.05 (m, 1H), 6.97-6.93 (m, 1H), 6.41-6.36 (m, 1H), 4.32-4.25 (m, 2H), 4.12-4.02 (m, 3H), 3.99-3.89 (m, 2H), 3.17-3.09 (m, 1H), 2.76-2.66 (m, 1H), 2.65-2.55 (m, 1H), 2.31-2.22 (m, 6H), 2.15-2.03 (m, 2H), 1.37-1.32 (m, 9H).

Example 291

(6-((1,3-Dimethyl-1H-pyrrolo[2,3-b]pyridin-6-yl)methyl)-2-azaspiro[3.3]heptan-2-yl)((1s,3s)-3-hydroxy-3-methylcyclobutyl)methanone

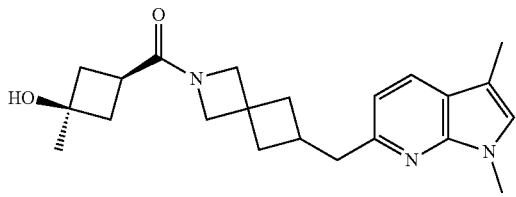

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-chloro-1,3-dimethyl-1H-pyrrolo[2,3-b]pyridine (Intermediate 54) instead of 1-bromo-2-methyl-4-(trifluoromethyl)benzene in Step B. MS (ESI): mass calcd. for $C_{22}H_{29}N_3O_2$, 367.2; m/z found, 368.2 [M+H]$^+$. $^1$H NMR (400 MHz, CDCl$_3$) δ 7.73 (d, J=8.0 Hz, 1H), 6.87 (s, 1H), 6.82 (d, J=8.0 Hz, 1H), 4.07 (s, 1H), 4.04-3.95 (m, 3H), 3.92 (s, 1H), 3.80 (s, 3H), 2.93 (d, J=7.6 Hz, 2H), 2.74-2.55 (m, 2H), 2.35-2.16 (m, 9H), 2.09-1.93 (m, 2H), 1.40-1.28 (m, 3H).

Example 292

(6-((1,2-Dimethyl-1H-pyrrolo[2,3-b]pyridin-6-yl)methyl)-2-azaspiro[3.3]heptan-2-yl)((1s,3s)-3-hydroxy-3-methylcyclobutyl)methanone

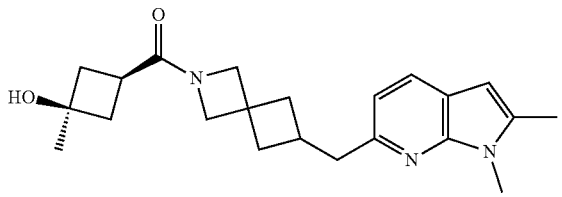 [SMILES: Cc1cc2ccc(CC3CC4(C3)CN(C(=O)[C@H]3C[C@@](C)(O)C3)C4)nc2n1C]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-chloro-1,2-dimethyl-1H-pyrrolo[2,3-b]pyridine (Intermediate 53) instead of 1-bromo-2-methyl-4-(trifluoromethyl)benzene in Step B. MS (ESI): mass calcd. for $C_{22}H_{29}N_3O_2$, 367.2; m/z found, 368.2 [M+H]$^+$. $^1$H NMR (400 MHz, CDCl$_3$) δ 7.66 (d, J=7.6 Hz, 1H), 6.79 (d, J=7.6 Hz, 1H), 6.14 (s, 1H), 4.12-3.86 (m, 5H), 3.76 (s, 3H), 2.91 (d, J=7.6 Hz, 2H), 2.74-2.56 (m, 2H), 2.44 (s, 3H), 2.36-2.19 (m, 6H), 2.09-1.97 (m, 2H), 1.37-1.32 (m, 3H).

Example 293

(6-((3-Fluoro-1-methyl-1H-pyrrolo[2,3-b]pyridin-6-yl)methyl)-2-azaspiro[3.3]heptan-2-yl)((1s,3s)-3-hydroxy-3-methylcyclobutyl)methanone

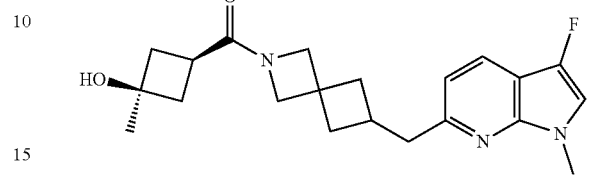

Step A: tert-Butyl 6-((3-fluoro-1-methyl-1H-pyrrolo[2,3-b]pyridin-6-yl)methylene)-2-azaspiro[3.3]heptane-2-carboxylate. Pd(OAc)$_2$ (58 mg, 0.258 mmol) and tri-o-tolylphosphine (112 mg, 0.368 mmol) were added to a solution of 6-bromo-3-fluoro-1-methyl-1H-pyrrolo[2,3-b]pyridine (Intermediate 73, 280 mg, 1.22 mmol), tert-butyl 6-methylene-2-azaspiro[3.3]heptane-2-carboxylate (Intermediate 72, 257 mg, 1.23 mmol), and TEA (0.41 mL, 3.17 mmol) in DMF (2 mL) under N$_2$. The resultant mixture was stirred at 120° C. for 12 h. The reaction mixture was cooled, poured into sat. aq. NaHCO$_3$ and extracted with EtOAc. The combined organic extracts were washed with brine, dried over Na$_2$SO$_4$, filtered, and concentrated under reduced pressure. The resulting residue was purified by FCC (SiO$_2$, 0-33% EtOAc in ether) to afford the title compound (280 mg, 44% yield) as a yellow solid. MS (ESI): mass calcd. for $C_{20}H_{24}FN_3O_2$, 357.2; m/z found, 358.0 [M+H]$^+$. $^1$H NMR (400 MHz, CDCl$_3$) δ 7.87-7.79 (m, 1H), 6.95-6.86 (m, 2H), 6.42-6.29 (m, 1H), 4.06-3.98 (m, 4H), 3.79 (s, 3H), 3.49-3.43 (m, 2H), 3.14-3.06 (m, 2H), 1.45 (s, 9H).

Step B: tert-Butyl 6-((3-fluoro-1-methyl-1H-pyrrolo[2,3-b]pyridin-6-yl)methyl)-2-azaspiro[3.3]heptane-2-carboxylate. BH$_3$.THF (1.1 mL, 1 M in THF, 1.10 mmol) was added dropwise to a 0° C. solution of tert-butyl 6-((3-fluoro-1-methyl-1H-pyrrolo[2,3-b]pyridin-6-yl)methylene)-2-azaspiro[3.3]heptane-2-carboxylate (130 mg, 0.364 mmol) in THF (2 mL). The resultant mixture was stirred at rt overnight then quenched with AcOH (0.65 mL, 1.08 mmol). The resulting mixture was stirred at rt for 1 h, then treated with sat. aq. NaHCO$_3$ and extracted with EtOAc. The combined organic extracts were washed with brine, dried over Na$_2$SO$_4$, filtered, and concentrated under reduced pressure to afford the title compound (130 mg) as a yellow oil, which was used in the next step without further purification.

Step C: 6-((2-Azaspiro[3.3]heptan-6-yl)methyl)-3-fluoro-1-methyl-1H-pyrrolo[2,3-b]pyridine. TFA (0.50 mL, 6.70 mmol) was added to a solution of tert-butyl 6-((3-fluoro-1-methyl-1H-pyrrolo[2,3-b]pyridin-6-yl)methyl)-2-azaspiro[3.3]heptane-2-carboxylate (260 mg, 0.723 mmol) in DCM (2.5 mL). The resulting mixture was stirred at rt for 1 h then concentrated under reduced pressure. The resulting residue was taken up in EtOAc, washed with sat. aq. NaHCO$_3$ and brine, dried over Na$_2$SO$_4$, filtered, and concentrated under reduced pressure to give the title compound (170 mg) as a yellow oil, which was used in the next step without further purification.

Step D: (6-((3-Fluoro-1-methyl-1H-pyrrolo[2,3-b]pyridin-6-yl)methyl)-2-azaspiro[3.3]heptan-2-yl)((1s,3s)-3-hydroxy-3-methylcyclobutyl)methanone. T$_3$P® (0.6 mL, 0.998 mmol, 50% in EtOAc) was added to a solution of 6-((2-azaspiro[3.3]heptan-6-yl)methyl)-3-fluoro-1-methyl-1H-pyrrolo[2,3-b]pyridine (170 mg), (1s,3s)-3-hydroxy-3-methylcyclobutanecarboxylic acid (85 mg, 0.653 mmol) and DIPEA (0.6 mL, 3.36 mmol) in DCM (2 mL). The resultant mixture was stirred at rt for 2 h. The reaction mixture was poured into H$_2$O and extracted with DCM. The combined organic extracts were dried over Na$_2$SO$_4$, filtered, and concentrated under reduced pressure. The resulting residue was purified by RP HPLC (35-65% CH$_3$CN in H$_2$O with 0.05% NH$_3$ and 10 mM (NH$_4$HCO$_3$). The title compound was further subjected to SFC (Stationary phase: AD (250×30 mm); Mobile phase: 40% EtOH containing 0.1% of 25% aq. NH$_3$/CO$_2$) to afford the title compound (56 mg, 23% yield) as an off-white solid. MS (ESI): mass calcd. for C$_{21}$H$_{26}$FN$_3$O$_2$, 371.2; m/z found, 372.2 [M+H]$^+$. $^1$H NMR (400 MHz, CDCl$_3$) δ 7.81 (d, J=8.0 Hz, 1H), 6.89-6.82 (m, 2H), 4.10-3.90 (m, 5H), 3.80 (s, 3H), 2.95-2.88 (m, 2H), 2.73-2.57 (m, 2H), 2.35-2.20 (m, 6H), 2.08-1.97 (m, 2H), 1.37-1.31 (m, 3H).

Example 294

((1s,3s)-3-Hydroxy-3-methylcyclobutyl)(6-((2-(trifluoromethyl)-1H-pyrrolo[2,3-b]pyridin-1-yl)methyl)-2-azaspiro[3.3]heptan-2-yl)methanone

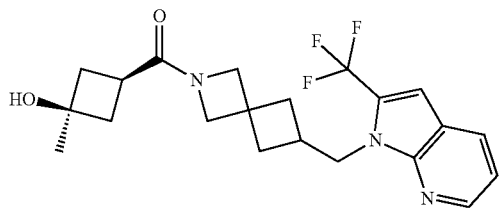 [SMILES: C[C@]1(O)C[C@@H](C(=O)N2CC3(CC(Cn4c(C(F)(F)F)cc5cccnc54)C3)C2)C1]

The title compound was prepared in a manner analogous to Example 237 using 2-(trifluoromethyl)-1H-pyrrolo[2,3-b]pyridine instead of 3-(trifluoromethyl)-1H-pyrazole and sodium hydride instead of cesium carbonate in Step A. MS (ESI): mass calcd. for C$_{21}$H$_{24}$F$_3$N$_3$O$_2$, 407.2; m/z found, 408.3 [M+H]$^+$. $^1$H NMR (400 MHz, CDCl$_3$) δ 8.50-8.38 (m, 1H), 8.03-7.95 (m, 1H), 7.21-7.11 (m, 1H), 6.90 (s, 1H), 4.48-4.33 (m, 2H), 4.14-4.08 (m, 1H), 4.05 (s, 2H), 4.02-3.91 (m, 2H), 2.93-2.73 (m, 1H), 2.69-2.50 (m, 1H), 2.36-2.08 (m, 8H), 1.38-1.28 (m, 3H).

Example 295

((1s,3s)-3-Hydroxy-3-methylcyclobutyl)(6-((6-(trifluoromethyl)-1H-pyrrolo[2,3-b]pyridin-1-yl)methyl)-2-azaspiro[3.3]heptan-2-yl)methanone

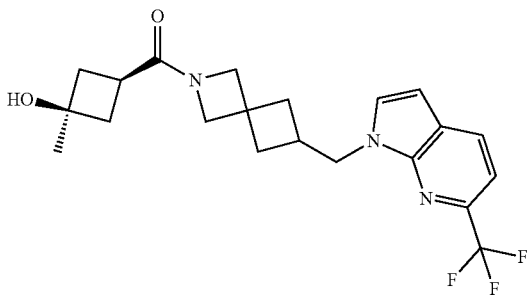 [SMILES: C[C@]1(O)C[C@@H](C(=O)N2CC3(CC(Cn4ccc5ccc(C(F)(F)F)nc54)C3)C2)C1]

The title compound was prepared in a manner analogous to Example 237 using 6-(trifluoromethyl)-1H-pyrrolo[2,3-b]pyridine instead of 3-(trifluoromethyl)-1H-pyrazole and sodium hydride instead of cesium carbonate in Step A. MS (ESI): mass calcd. for C$_{21}$H$_{24}$F$_3$N$_3$O$_2$, 407.2; m/z found, 408.5 [M+H]$^+$. $^1$H NMR (400 MHz, CDCl$_3$) δ 8.05-7.99 (m, 1H), 7.49-7.42 (m, 1H), 7.36-7.31 (m, 1H), 6.57-6.51 (m, 1H), 4.39-4.27 (m, 2H), 4.15-4.04 (m, 2H), 4.01-3.89 (m, 3H), 2.80-2.56 (m, 2H), 2.33-2.20 (m, 6H), 2.14-1.97 (m, 2H), 1.38-1.31 (m, 3H).

Example 296

((1s,3s)-3-Hydroxy-3-methylcyclobutyl)(6-((1-methyl-3-(trifluoromethyl)-1H-pyrrolo[2,3-b]pyridin-6-yl)methyl)-2-azaspiro[3.3]heptan-2-yl)methanone

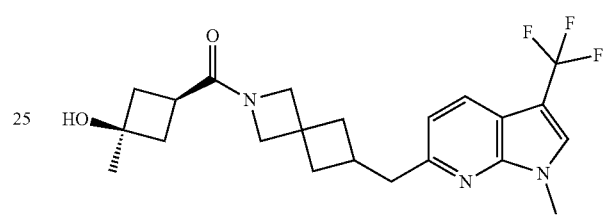

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-1-methyl-3-(trifluoromethyl)-1H-pyrrolo[2,3-b]pyridine (Intermediate 49) instead of 1-bromo-2-methyl-4-(trifluoromethyl)benzene in Step B. MS (ESI): mass calcd. for C$_{22}$H$_{26}$F$_3$N$_3$O$_2$, 421.2; m/z found, 422.5 [M+H]$^+$. $^1$H NMR (400 MHz, CDCl$_3$) δ 7.92 (d, J=8.0 Hz, 1H), 7.48 (s, 1H), 6.98 (d, J=8.0 Hz, 1H), 4.26 (s, 1H), 4.08 (s, 1H), 4.03-3.97 (m, 2H), 3.93 (s, 1H), 3.89 (s, 3H), 3.03-2.89 (m, 2H), 2.75-2.51 (m, 2H), 2.40-2.21 (m, 6H), 2.04-1.92 (m, 2H), 1.44-1.21 (m, 3H).

Example 297

((1s,3s)-3-Hydroxy-3-methylcyclobutyl)(6-((1-(2,2,2-trifluoroethyl)-1H-pyrrolo[2,3-b]pyridin-6-yl)methyl)-2-azaspiro[3.3]heptan-2-yl)methanone

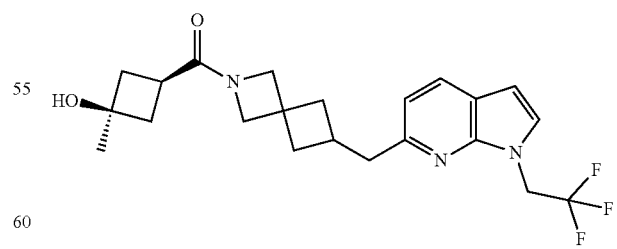

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-1-(2,2,2-trifluoroethyl)-1H-pyrrolo[2,3-b]pyridine (Intermediate 46)

instead of 1-bromo-2-methyl-4-(trifluoromethyl)benzene in Step B. MS (ESI): mass calcd. for $C_{22}H_{26}F_3N_3O_2$, 421.2; m/z found, 422.1 [M+H]$^+$. $^1$H NMR (400 MHz, CDCl$_3$) δ 7.90-7.77 (m, 1H), 7.27-7.17 (m, 1H), 6.95-6.86 (m, 1H), 6.60-6.47 (m, 1H), 5.03-4.80 (m, 2H), 4.24 (br s, 1H), 4.16-3.88 (m, 4H), 3.05-2.84 (m, 2H), 2.75-2.52 (m, 2H), 2.35-2.23 (m, 6H), 2.10-1.95 (m, 2H), 1.34 (br s, 3H).

Example 298

((1s,3s)-3-Hydroxy-3-methylcyclobutyl)(6-((1-methyl-1H-pyrrolo[3,2-c]pyridin-6-yl)methyl)-2-azaspiro[3.3]heptan-2-yl)methanone

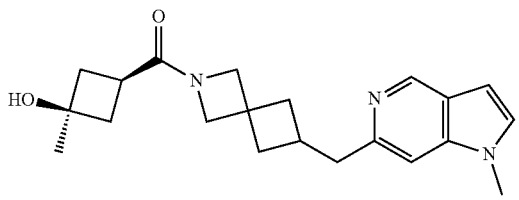 [SMILES: Cn1ccc2cnc(CC3CC4(C3)CN(C(=O)[C@H]3C[C@@](C)(O)C3)C4)cc21]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-1-methyl-1H-pyrrolo[3,2-c]pyridine instead of 1-bromo-2-methyl-4-(trifluoromethyl)benzene in Step B. MS (ESI): mass calcd. for $C_{21}H_{27}N_3O_2$, 353.2; m/z found, 354.1 [M+H]$^+$. $^1$H NMR (400 MHz, CDCl$_3$) δ 8.80 (s, 1H), 7.03 (d, J=3.2 Hz, 1H), 6.99 (s, 1H), 6.54 (d, J=3.2 Hz, 1H), 4.08-4.06 (m, 1H), 4.00-3.98 (m, 2H), 3.93-3.90 (m, 1H), 3.78 (s, 3H), 2.97-2.92 (m, 2H), 2.75-2.61 (m, 2H), 2.30-2.23 (m, 6H), 2.04-2.00 (m, 2H), 1.34-1.33 (m, 3H).

Example 299

((1s,3s)-3-Hydroxy-3-methylcyclobutyl)(6-((1-methyl-1H-indazol-7-yl)methyl)-2-azaspiro[3.3]heptan-2-yl)methanone

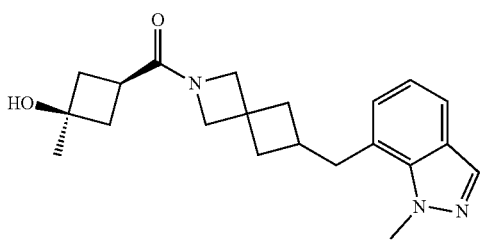 [SMILES: Cn1ncc2cccc(CC3CC4(C3)CN(C(=O)[C@H]3C[C@@](C)(O)C3)C4)c21]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 7-bromo-1-methyl-1H-indazole instead of 1-bromo-2-methyl-4-(trifluoromethyl)benzene in Step B. MS (ESI): mass calcd. for $C_{21}H_{27}N_3O_2$, 353.2; m/z found, 354.2 [M+H]$^+$. $^1$H NMR (400 MHz, CDCl$_3$) δ 7.94 (s, 1H), 7.60-7.56 (m, 1H), 7.05-7.00 (m, 2H), 4.27 (s, 3H), 4.09 (s, 1H), 4.04-3.96 (m, 3H), 3.93 (s, 1H), 3.17 (d, J=8.0 Hz, 2H), 2.67-2.49 (m, 2H), 2.38-2.30 (m, 2H), 2.29-2.21 (m, 4H), 2.06-1.94 (m, 2H), 1.34 (s, 3H).

Example 300

(6-((1,4-Dimethyl-1H-indazol-6-yl)methyl)-2-azaspiro[3.3]heptan-2-yl)((1s,3s)-3-hydroxy-3-methylcyclobutyl)methanone

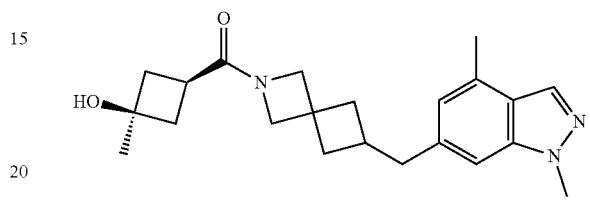

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-1,4-dimethyl-1H-indazole (Intermediate 51) instead of 1-bromo-2-methyl-4-(trifluoromethyl)benzene in Step B. MS (ESI): mass calcd. for $C_{22}H_{29}N_3O_2$, 367.2; m/z found, 368.2 [M+H]$^+$. $^1$H NMR (400 MHz, CDCl$_3$) δ 7.92 (s, 1H), 6.90 (s, 1H), 6.67 (s, 1H), 4.50 (s, 1H), 4.05 (s, 1H), 4.02 (s, 3H), 3.99-3.91 (m, 3H), 2.79-2.72 (m, 2H), 2.65-2.38 (m, 5H), 2.33-2.19 (m, 6H), 2.00-1.88 (m, 2H), 1.36-1.31 (m, 3H).

Example 301

(6-((1,5-Dimethyl-1H-indazol-6-yl)methyl)-2-azaspiro[3.3]heptan-2-yl)((1s,3s)-3-hydroxy-3-methylcyclobutyl)methanone

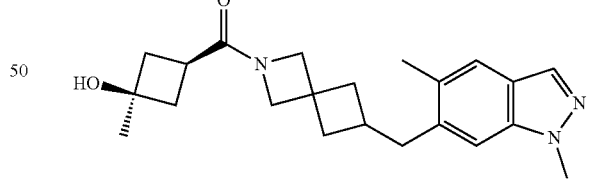

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-1,5-dimethyl-1H-indazole instead of 1-bromo-2-methyl-4-(trifluoromethyl)benzene in Step B. MS (ESI): mass calcd. for $C_{22}H_{29}N_3O_2$, 367.2; m/z found, 368.5 [M+H]$^+$. $^1$H NMR (400 MHz, CDCl$_3$) δ 7.85 (s, 1H), 7.47 (s, 1H), 7.03 (s, 1H), 4.16-4.08 (m, 2H), 4.05-4.02 (m, 4H), 4.01-3.93 (m, 2H), 2.86-2.77 (m, 2H), 2.70-2.48 (m, 2H), 2.39-2.31 (m, 5H), 2.29-2.23 (m, 4H), 2.05-1.96 (m, 2H), 1.34 (s, 3H).

Example 302

(6-((1,3-Dimethyl-1H-indazol-6-yl)methyl)-2-azaspiro[3.3]heptan-2-yl)((1s,3s)-3-hydroxy-3-methylcyclobutyl)methanone

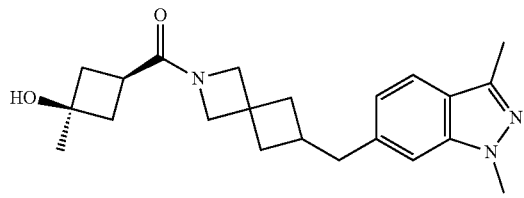 [SMILES: Cc1nn(C)c2cc(CC3CC4(C3)CN(C(=O)[C@H]3C[C@@](C)(O)C3)C4)ccc12]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-1,3-dimethyl-1H-indazole instead of 1-bromo-2-methyl-4-(trifluoromethyl)benzene in Step B. MS (ESI): mass calcd. for $C_{22}H_{29}N_3O_2$, 367.2; m/z found, 368.2 [M+H]$^+$. $^1$H NMR (400 MHz, CDCl$_3$) δ 7.54 (d, J=8.0 Hz, 1H), 7.03 (s, 1H), 6.91-6.86 (m, 1H), 4.07 (s, 1H), 4.03-3.95 (m, 6H), 3.94 (s, 1H), 2.85-2.78 (m, 2H), 2.67-2.59 (m, 1H), 2.56-2.44 (m, 4H), 2.33-2.21 (m, 6H), 2.03-1.90 (m, 2H), 1.36-1.32 (m, 3H).

Example 303

(6-((4-Fluoro-1-methyl-1H-indazol-6-yl)methyl)-2-azaspiro[3.3]heptan-2-yl)((1s,3s)-3-hydroxy-3-methylcyclobutyl)methanone

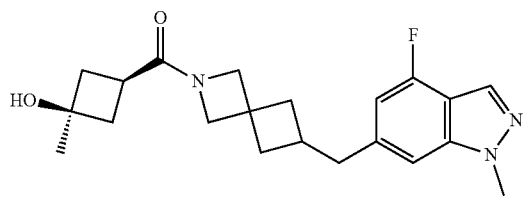 [SMILES: Cn1ncc2c(F)cc(CC3CC4(C3)CN(C(=O)[C@H]3C[C@@](C)(O)C3)C4)cc21]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-4-fluoro-1-methyl-1H-indazole instead of 1-bromo-2-methyl-4-(trifluoromethyl)benzene in Step B. MS (ESI): mass calcd. for $C_{21}H_{26}FN_3O_2$, 371.2; m/z found, 372.5 [M+H]$^+$. $^1$H NMR (400 MHz, CDCl$_3$) δ 7.98 (s, 1H), 6.88 (s, 1H), 6.56 (d, J=10.8 Hz, 1H), 4.09-3.92 (m, 8H), 2.85-2.76 (m, 2H), 2.68-2.57 (m, 1H), 2.55-2.41 (m, 1H), 2.36-2.19 (m, 6H), 2.01-1.91 (m, 2H), 1.34 (s, 3H).

Example 304

(6-((5-Fluoro-1-methyl-1H-indazol-6-yl)methyl)-2-azaspiro[3.3]heptan-2-yl)((1s,3s)-3-hydroxy-3-methylcyclobutyl)methanone

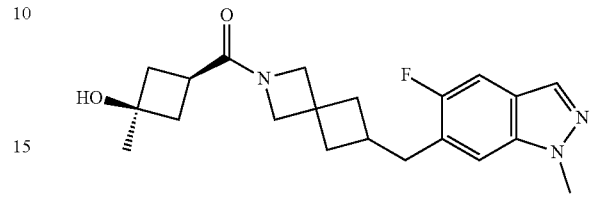

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-5-fluoro-1-methyl-1H-indazole instead of 1-bromo-2-methyl-4-(trifluoromethyl)benzene in Step B. MS (ESI): mass calcd. for $C_{21}H_{26}FN_3O_2$, 371.2; m/z found, 372.1 [M+H]$^+$. $^1$H NMR (400 MHz, CDCl$_3$) δ 7.88 (s, 1H), 7.32-7.27 (m, 1H), 7.10-7.04 (m, 1H), 4.29 (br s, 1H), 4.09-4.02 (m, 4H), 4.01-3.90 (m, 3H), 2.86-2.77 (m, 2H), 2.64-2.45 (m, 2H), 2.32-2.23 (m, 6H), 2.02-1.89 (m, 2H), 1.37-1.30 (m, 3H).

Example 305

(6-((7-Fluoro-1-methyl-1H-indazol-6-yl)methyl)-2-azaspiro[3.3]heptan-2-yl)((1s,3s)-3-hydroxy-3-methylcyclobutyl)methanone

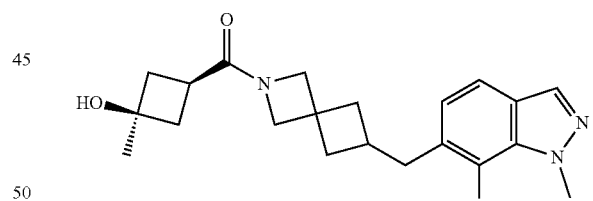

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-7-fluoro-1-methyl-1H-indazole (Intermediate 52) instead of 1-bromo-2-methyl-4-(trifluoromethyl)benzene in Step B. MS (ESI): mass calcd. for $C_{21}H_{26}FN_3O_2$, 371.2; m/z found, 372.2 [M+H]$^+$. $^1$H NMR (400 MHz, CDCl$_3$) δ 7.90 (d, J=2.4 Hz, 1H), 7.39-7.33 (m, 1H), 6.86-6.79 (m, 1H), 4.24 (s, 3H), 4.06 (s, 1H), 3.99 (s, 3H), 3.94 (s, 1H), 2.87-2.79 (m, 2H), 2.67-2.58 (m, 1H), 2.57-2.42 (m, 1H), 2.33-2.20 (m, 6H), 2.04-1.91 (m, 2H), 1.36-1.32 (m, 3H).

Example 306

((1s,3s)-3-Hydroxy-3-methylcyclobutyl)(6-((1-isopropyl-1H-indazol-6-yl)methyl)-2-azaspiro[3.3]heptan-2-yl)methanone

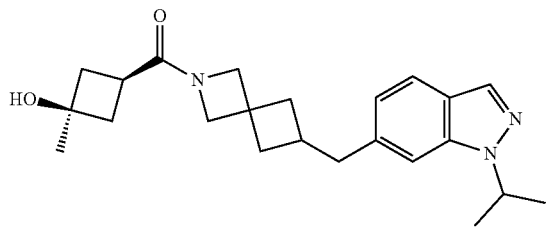 [SMILES: CC(C)n1ncc2ccc(CC3CC4(C3)CN(C(=O)[C@H]3C[C@@](C)(O)C3)C4)cc21]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-1-isopropyl-1H-indazole instead of 1-bromo-2-methyl-4-(trifluoromethyl)benzene in Step B. MS (ESI): mass calcd. for $C_{23}H_{31}N_3O_2$, 381.2; m/z found, 382.2 [M+H]$^+$. $^1$H NMR (400 MHz, CDCl$_3$) δ 7.95 (s, 1H), 7.62 (d, J=8.4 Hz, 1H), 7.14 (s, 1H), 6.91 (d, J=8.4 Hz, 1H), 4.87-4.78 (m, 1H), 4.11-4.05 (m, 2H), 4.03-3.92 (m, 3H), 2.85-2.79 (m, 2H), 2.67-2.57 (m, 1H), 2.57-2.43 (m, 1H), 2.36-2.19 (m, 6H), 2.03-1.90 (m, 2H), 1.59 (d, J=6.8 Hz, 6H), 1.37-1.31 (m, 3H).

Example 307

((1s,3s)-3-Hydroxy-3-methylcyclobutyl)(6-((1-(2,2,2-trifluoroethyl)-1H-indazol-6-yl)methyl)-2-azaspiro[3.3]heptan-2-yl)methanone

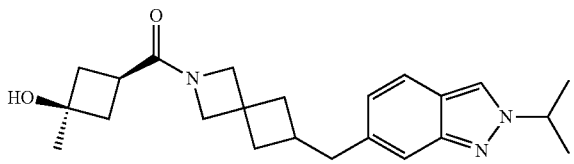 [SMILES: CC(C)n1cc2ccc(CC3CC4(C3)CN(C(=O)[C@H]3C[C@@](C)(O)C3)C4)cc2n1]

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-1-(2,2,2-trifluoroethyl)-1H-indazole (Intermediate 48) instead of 1-bromo-2-methyl-4-(trifluoromethyl)benzene in Step B. MS (ESI): mass calcd. for $C_{22}H_{26}F_3N_3O_2$, 421.2; m/z found, 422.1 [M+H]$^+$. $^1$H NMR (400 MHz, CDCl$_3$) δ 8.02 (s, 1H), 7.65 (d, J=8.4 Hz, 1H), 7.14 (s, 1H), 6.99 (d, J=8.4 Hz, 1H), 4.98-4.88 (m, 2H), 4.31-4.18 (m, 1H), 4.10-3.89 (m, 4H), 2.83 (d, J=7.2 Hz, 2H), 2.64-2.41 (m, 2H), 2.33-2.22 (m, 6H), 2.01-1.88 (m, 2H), 1.36-1.31 (m, 3H).

Example 308: ((1s,3s)-3-Hydroxy-3-methylcyclobutyl)(6-((2-isopropyl-2H-indazol-6-yl)methyl)-2-azaspiro[3.3]heptan-2-yl)methanone

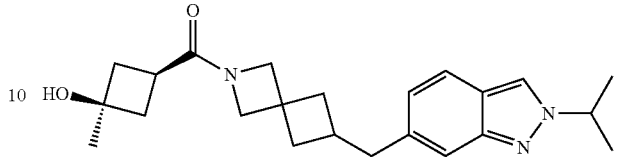

The title compound was prepared in a manner analogous to Example 203 using tert-butyl 6-oxo-2-azaspiro[3.3]heptane-2-carboxylate instead of tert-butyl 6-oxo-2-azaspiro[3.4]octane-2-carboxylate in Step A and 6-bromo-2-isopropyl-1H-indazole (Intermediate 50) instead of 1-bromo-2-methyl-4-(trifluoromethyl)benzene in Step B. MS (ESI): mass calcd. for $C_{23}H_{31}N_3O_2$, 381.2; m/z found, 382.3 [M+H]$^+$. $^1$H NMR (400 MHz, CDCl$_3$) δ 7.88 (s, 1H), 7.53 (d, J=8.4 Hz, 1H), 7.39 (s, 1H), 6.83 (d, J=8.8 Hz, 1H), 4.80-4.69 (m, 1H), 4.29-4.00 (m, 2H), 3.98-3.94 (m, 2H), 3.88 (s, 1H), 2.80-2.69 (m, 2H), 2.65-2.55 (m, 1H), 2.54-2.40 (m, 1H), 2.31-2.19 (m, 6H), 1.99-1.92 (m, 2H), 1.62 (d, J=6.8 Hz, 6H), 1.36-1.28 (m, 3H).

Example 309

((1s,3s)-3-Hydroxy-3-methylcyclobutyl)(6-((6-methyl-5-(trifluoromethyl)pyridin-2-yl)oxy)-2-azaspiro[3.3]heptan-2-yl)methanone

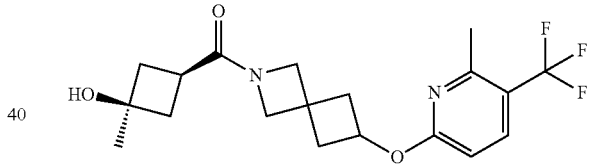

Step A: tert-Butyl 6-((6-methyl-5-(trifluoromethyl)pyridin-2-yl)oxy)-2-azaspiro[3.3]heptane-2-carboxylate. tert-Butyl 6-hydroxy-2-azaspiro[3.3]heptane-2-carboxylate (229 mg, 1.07 mmol) and t-BuOK (138 mg, 1.23 mmol) were added to a solution of 6-chloro-2-methyl-3-(trifluoromethyl)pyridine (200 mg, 1.02 mmol) in DMF (5 mL). The resulting mixture was stirred at rt for 2 h. The reaction mixture was diluted with EtOAc and washed with sat. aq. NH$_4$Cl. The aqueous phase was extracted with EtOAc and the combined organic extracts were washed with brine, dried over Na$_2$SO$_4$, filtered, and concentrated under reduced pressure. The resulting residue was purified by FCC (SiO$_2$, 0-20% EtOAc in ether) to afford the title compound (240 mg, 63% yield) as a yellow oil. MS (ESI): mass calcd. for $C_{18}H_{23}F_3N_2O_3$, 372.2; m/z found, 316.9 [M+2H-tBu]$^+$. $^1$H NMR (400 MHz, CDCl$_3$) δ 7.73 (d, J=8.8 Hz, 1H), 6.54 (d, J=8.8 Hz, 1H), 5.21-5.03 (m, 1H), 4.01 (s, 2H), 3.93 (s, 2H), 2.80-2.67 (m, 2H), 2.57 (s, 3H), 2.37-2.25 (m, 2H), 1.44 (s, 9H).

Step B: 6-((6-Methyl-5-(trifluoromethyl)pyridin-2-yl)oxy)-2-azaspiro[3.3]heptane. TFA (1.5 mL, 19.6 mmol) was added to a solution of tert-butyl 6-((6-methyl-5-(trifluoromethyl)pyridin-2-yl)oxy)-2-azaspiro[3.3]heptane-2-carboxylate (240 mg, 0.644 mmol) in DCM (5 mL). The resulting mixture was stirred at rt for 1 h. The reaction mixture was concentrated under reduced pressure and the resulting residue was taken up in DCM, washed with sat. aq. $Na_2CO_3$ and extracted with DCM. The combined organic extracts were washed with brine, dried over $Na_2SO_4$, filtered, and concentrated under reduced pressure to afford the title compound (175 mg) as a yellow oil, which was used in the next step without further purification.

Step C: ((1s,3s)-3-Hydroxy-3-methylcyclobutyl)(6-((6-methyl-5-(trifluoromethyl)pyridin-2-yl)oxy)-2-azaspiro[3.3]heptan-2-yl)methanone. $T_3P$® (0.6 mL, 0.964 mmol, 50% in EtOAc) was added to a solution of 6-((6-methyl-5-(trifluoromethyl)pyridin-2-yl)oxy)-2-azaspiro[3.3]heptane (175 mg, crude), (1s,3s)-3-hydroxy-3-methylcyclobutanecarboxylic acid (84 mg, 0.642 mmol), and DIPEA (0.6 mL, 3.21 mmol) in DCM (2 mL). The resultant mixture was stirred at rt for 4 h.

The reaction mixture was poured into $H_2O$ and extracted with DCM. The combined organic extracts were dried over $Na_2SO_4$, filtered, and concentrated under reduced pressure. The resulting residue was purified by RP HPLC (35-65% $CH_3CN$ in $H_2O$ with 0.05% $NH_3$ and 10 mM $NH_4HCO_3$). The title compound was further subjected to SFC (Stationary phase: AD (250×30 mm); Mobile phase: 30% EtOH containing 0.1% of 25% aq. $NH_3/CO_2$) to afford the title compound (31 mg, 12% yield) as a brown solid. MS (ESI): mass calcd. for $C_{19}H_{23}F_3N_2O_3$, 384.2; m/z found, 385.1 $[M+H]^+$. $^1H$ NMR (400 MHz, $CDCl_3$) δ 7.74 (d, J=8.4 Hz, 1H), 6.60-6.50 (m, 1H), 5.25-5.07 (m, 1H), 4.19 (s, 1H), 4.13-4.00 (m, 4H), 2.84-2.70 (m, 2H), 2.68-2.60 (m, 1H), 2.59-2.54 (m, 3H), 2.40-2.27 (m, 6H), 1.40-1.32 (m, 3H).

Example 310

((1s,3*S)-3-Hydroxy-3-methylcyclobutyl)(6-((*R)-1-phenylethyl)-2-azaspiro[3.3]heptan-2-yl)methanone

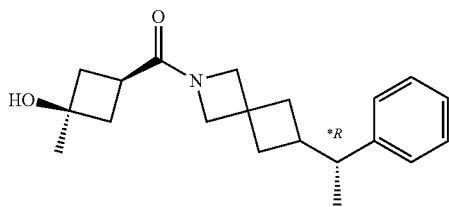 [SMILES: C[C@@H](c1ccccc1)C1CC2(C1)CN(C(=O)[C@H]1C[C@@](C)(O)C1)C2]

Step A: tert-Butyl 6-(hydroxy(phenyl)methyl)-2-azaspiro[3.3]heptane-2-carboxylate. Phenylmagnesium bromide (0.58 mL, 2.8 M in THF, 1.62 mmol) was added dropwise to a 0° C. solution of tert-butyl 6-formyl-2-azaspiro[3.3]heptane-2-carboxylate (300 mg, 1.33 mmol) in THF (5 mL). The resultant mixture was stirred for 4 h at rt. The reaction mixture was quenched with sat. aq. $NH_4Cl$ and extracted with EtOAc. The combined organic extracts were washed with brine, dried over $Na_2SO_4$, filtered, and concentrated under reduced pressure. The resulting residue was purified by FCC ($SiO_2$, 0-30% EtOAc in ether) to afford the title compound (366 mg, 72% yield) as a colorless oil. MS (ESI): mass calcd. for $C_{18}H_{25}NO_3$, 303.2; m/z found, 248.0 $[M+2H-tBu]^+$. $^1H$ NMR (400 MHz, $CDCl_3$) δ 7.39-7.28 (m, 5H), 4.53 (d, J=7.3 Hz, 1H), 3.96-3.76 (m, 4H), 3.50 (s, 1H), 2.54-2.39 (m, 1H), 2.30-2.15 (m, 2H), 2.07-1.96 (m, 2H), 1.43 (s, 9H).

Step B: tert-Butyl 6-benzoyl-2-azaspiro[3.3]heptane-2-carboxylate. A mixture of tert-butyl 6-(hydroxy(phenyl)methyl)-2-azaspiro[3.3]heptane-2-carboxylate (366 mg, 1.21 mmol) and Dess-Martin periodinane (1.54 g, 3.63 mmol) in DCM (20 mL) was stirred at rt for 1 h. The reaction mixture was quenched with sat. aq. $Na_2SO_3$ and extracted with DCM. The combined organic extracts were washed with sat. aq. $NaHCO_3$, dried over $Na_2SO_4$, filtered, and concentrated under reduced pressure. The resulting reside was purified by FCC ($SiO_2$, 0-30% EtOAc in ether) to yield the title compound (320 mg, 82% yield) as a yellow solid. MS (ESI): mass calcd. for $C_{18}H_{23}NO_3$, 301.2; m/z found, 245.9 $[M+2H-tBu]^+$. $^1H$ NMR (400 MHz, $CDCl_3$) δ 7.94-7.81 (m, 2H), 7.63-7.53 (m, 1H), 7.50-7.42 (m, 2H), 4.02 (s, 2H), 3.92-3.79 (m, 3H), 2.62-2.45 (m, 4H), 1.44 (s, 9H).

Step C: tert-Butyl 6-(1-hydroxy-1-phenylethyl)-2-azaspiro[3.3]heptane-2-carboxylate. Methylmagnesium bromide (100 µL, 3 M in THF, 0.300 mmol) was added dropwise to a 0° C. solution of tert-butyl 6-benzoyl-2-azaspiro[3.3]heptane-2-carboxylate (50 mg, 0.166 mmol) in THF (2 mL). The resultant mixture was stirred for 2 h at rt. The reaction mixture was quenched with EtOAc and $H_2O$. The organic phase was washed with sat. aq. $NH_4Cl$ and the combined aqueous phase was extracted with EtOAc. The combined organic extracts were washed with brine, dried over $Na_2SO_4$, filtered, and concentrated under reduced pressure. The resulting residue was purified by FCC ($SiO_2$, 0-30% EtOAc in ether) to afford the title compound (52 mg, 65% yield) as a colorless oil. MS (ESI): mass calcd. for $C_{19}H_{27}NO_3$, 317.2; m/z found, 261.9 $[M+2H-tBu]^+$. $^1H$ NMR (400 MHz, $CDCl_3$) δ 7.33-7.05 (m, 5H), 3.88-3.70 (m, 2H), 3.68-3.56 (m, 2H), 3.38-3.34 (m, 1H), 2.52-2.33 (m, 1H), 2.21-1.88 (m, 4H), 1.37-1.26 (m, 12H).

Step D: 6-(1-Phenylvinyl)-2-azaspiro[3.3]heptane. TES (0.78 mL, 4.92 mmol) and TFA (0.20 mL, 2.69 mmol) were added to a solution of tert-butyl 6-(1-hydroxy-1-phenylethyl)-2-azaspiro[3.3]heptane-2-carboxylate (52 mg, 0.164 mmol) in DCM (1 mL) under $N_2$. The resulting mixture was stirred at rt for 16 h. The reaction mixture was concentrated under reduced pressure. The resulting residue was taken up in EtOAc, washed with sat. aq. $NaHCO_3$, dried over $Na_2SO_4$, filtered, and concentrated under reduced pressure to afford the title compound (33 mg) as a yellow oil, which was used in the next step without further purification.

Step E: 6-(1-Phenylethyl)-2-azaspiro[3.3]heptane. $PtO_2$ (163 mg, 0.718 mmol) was added to a solution of 6-(1-phenylvinyl)-2-azaspiro[3.3]heptane (95 mg, 0.477 mmol) in EtOH (10 mL). The flask was evacuated and filled with $H_2$ and the mixture stirred under $H_2$ (15 psi) at rt for 1.5 h. The suspension was filtered through a pad of Celite® and the filtrate was concentrated under reduced pressure to afford the title compound (95 mg) as a white solid, which was used in the next step without further purification.

Step F: (rac)-((1s,3s)-3-Hydroxy-3-methylcyclobutyl)(6-(1-phenylethyl)-2-azaspiro[3.3]heptan-2-yl)methanone. $T_3P$® (0.42 mL, 0.712 mmol, 50% in EtOAc) was added to a solution of 6-(1-phenylethyl)-2-azaspiro[3.3]heptane (95 mg, crude), (1s,3s)-3-hydroxy-3-methylcyclobutanecarboxylic acid (62 mg, 0.476 mmol) and DIPEA (0.42 mL, 2.37 mmol) in DCM (2 mL). The resultant mixture was stirred at rt for 2 h before being poured into $H_2O$ and extracted with DCM. The combined organic extracts were dried over $Na_2SO_4$, filtered, and concentrated under reduced pressure. The resulting residue was purified by RP HPLC (35-65% $CH_3CN$ in $H_2O$ with 0.05% $NH_3$ and 10 mM $NH_4HCO_3$) to afford the title compound (53 mg, 35% yield) as a white solid. MS (ESI): mass calcd. for $C_{20}H_{27}NO_2$, 313.2; m/z found, 314.1 [M+H]⁺. ¹H NMR (400 MHz, CDCl₃) δ 7.28-7.21 (m, 2H), 7.21-7.15 (m, 1H), 7.11 (d, J=7.6 Hz, 2H), 4.10-3.77 (m, 5H), 2.67-2.45 (m, 2H), 2.41-2.13 (m, 6H), 2.08-1.84 (m, 2H), 1.83-1.76 (m, 1H), 1.32 (s, 3H), 1.14 (d, J=7.2 Hz, 3H).

Step G: ((1s,3*S)-3-Hydroxy-3-methylcyclobutyl)(6-((*R)-1-phenylethyl)-2-azaspiro[3.3]heptan-2-yl)methanone. The title compound was prepared via separation of (rac)-((1s,3s)-3-hydroxy-3-methylcyclobutyl)(6-(1-phenylethyl)-2-azaspiro[3.3]heptan-2-yl)methanone by chiral SFC (Stationary phase: OD-H (3×25 cm); Mobile phase: 20% EtOH containing 0.1% of 25% aq. NH₃/CO₂; Rt=3.66 min). MS (ESI): mass calcd. for C₂₀H₂₇NO₂, 313.2; m/z found, 314.1 [M+H]⁺. ¹H NMR (400 MHz, CDCl₃) δ 7.26-7.22 (m, 2H), 7.19-7.13 (m, 1H), 7.09 (d, J=7.2 Hz, 2H), 4.09-3.76 (m, 5H), 2.65-2.43 (m, 2H), 2.39-2.15 (m, 6H), 2.01-1.83 (m, 2H), 1.74-1.67 (m, 1H), 1.30 (s, 3H), 1.13 (d, J=6.8 Hz, 3H).

Example 311

((1s,3*R)-3-Hydroxy-3-methylcyclobutyl)(6-((*S)-1-phenylethyl)-2-azaspiro[3.3]heptan-2-yl)methanone

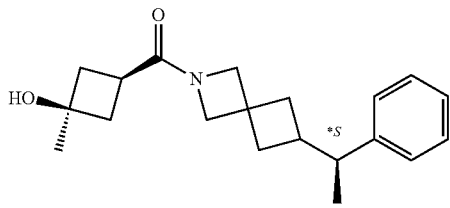 [SMILES: C[C@H](c1ccccc1)C1CC2(C1)CN(C(=O)[C@H]1C[C@@](C)(O)C1)C2]

The title compound was prepared via separation of (rac)-((1s,3s)-3-hydroxy-3-methylcyclobutyl)(6-(1-phenylethyl)-2-azaspiro[3.3]heptan-2-yl)methanone (Example 310, Step F) by chiral SFC (Stationary phase: OD-H (3×25 cm); Mobile phase: 20% EtOH containing 0.1% of 25% aq. NH₃/CO₂; Rt=3.94 min). MS (ESI): mass calcd. for C₂₀H₂₇NO₂, 313.2; m/z found, 314.1 [M+H]⁺. ¹H NMR (400 MHz, CDCl₃) δ 7.26-7.21 (m, 2H), 7.20-7.13 (m, 1H), 7.09 (d, J=7.6 Hz, 2H), 4.09-3.75 (m, 5H), 2.66-2.42 (m, 2H), 2.39-2.14 (m, 6H), 2.02-1.83 (m, 2H), 1.77-1.68 (m, 1H), 1.30 (s, 3H), 1.13 (d, J=6.8 Hz, 3H).

Example 312

((1s,3*S)-3-Hydroxy-3-methylcyclobutyl)(6-((*R)-1-(6-methyl-5-(trifluoromethyl)pyridin-2-yl)ethyl)-2-azaspiro[3.3]heptan-2-yl)methanone

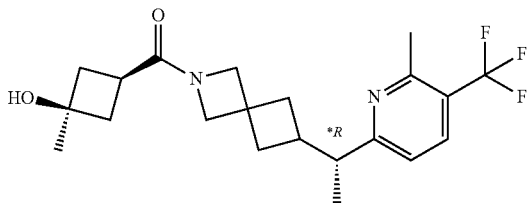 [SMILES: Cc1nc([C@H](C)C2CC3(C2)CN(C(=O)[C@H]2C[C@@](C)(O)C2)C3)ccc1C(F)(F)F]

Step A: tert-Butyl 6-(1-hydroxyethyl)-2-azaspiro[3.3]heptane-2-carboxylate. Methylmagnesium bromide (0.52 mL, 3.0 M in THF, 1.56 mmol) was added dropwise to a 0° C. solution of tert-butyl 6-formyl-2-azaspiro[3.3]heptane-2-carboxylate (260 mg, 1.15 mmol) in THF (10 mL) under N₂. The resultant mixture was warmed to rt and stirred for 6 h before being poured into water and extracted with EtOAc. The combined organic extracts were dried over Na₂SO₄, filtered, and concentrated under reduced pressure. The resulting residue was purified by FCC (SiO₂, 0-20% EtOAc in ether) to afford the title compound (270 mg, 97% yield) as a yellow solid. MS (ESI): mass calcd. for C₁₃H₂₃NO₃ 241.2; m/z found, 185.9 [M+2H-tBu]⁺. ¹H NMR (400 MHz, CDCl₃) δ 3.92 (s, 2H), 3.83-3.76 (m, 2H), 3.70-3.59 (m, 1H), 2.30-1.99 (m, 4H), 1.90-1.81 (m, 1H), 1.43 (s, 9H), 1.14-1.05 (m, 3H).

Step B: tert-Butyl 6-(1-iodoethyl)-2-azaspiro[3.3]heptane-2-carboxylate. 12 (430 mg, 1.69 mmol) was added to a solution of PPh₃ (440 mg, 1.68 mmol) and imidazole (235 mg, 3.45 mmol) in DCM (10 mL) at 0° C. under N₂. The resultant mixture was stirred at 0° C. for 5 min. tert-Butyl 6-(1-hydroxyethyl)-2-azaspiro[3.3]heptane-2-carboxylate (270 mg, 1.12 mmol) in DCM (2 mL) was added and the resultant mixture was stirred at rt for 3 h. The crude reaction was poured into water and extracted with EtOAc. The combined organic extracts were dried over Na₂SO₄, filtered, and concentrated under reduced pressure. The resulting residue was purified by FCC (SiO₂, 0-20% EtOAc in ether) to afford the title compound (220 mg, 43% yield) as a white solid. MS (ESI): mass calcd. for C₁₃H₂₂INO₂, 351.1; m/z found, 295.8 [M+2H-tBu]⁺.

Step C: tert-Butyl 6-(1-(6-chloro-5-(trifluoromethyl)pyridin-2-yl)ethyl)-2-azaspiro[3.3]heptane-2-carboxylate. NiCl₂(DME) (5.0 mg, 0.023 mmol) and 4,4'-di-tert-butyl-2,2'-bipyridine (6.0 mg, 0.022 mmol) were taken up in DME (3 mL). The resultant mixture was stirred for 10 min under N₂, then treated with 2,6-dichloro-3-(trifluoromethyl)pyridine (90 mg, 0.420 mmol), tert-butyl 6-(1-iodoethyl)-2-azaspiro[3.3]heptane-2-carboxylate (220 mg, 0.626 mmol), and (Ir[dF(CF₃)ppy]₂(dtbpy))PF₆ (50 mg, 0.045 mmol). The resultant mixture was treated with Na₂CO₃ (135 mg, 1.26 mmol) and tris(trimethylsilyl)silane (155 mg, 0.623 mmol), sparged with N₂, and stirred at rt under 425 nm blue light for 16 h. The resultant mixture was poured into water and extracted with EtOAc. The combined organic extracts were dried over Na₂SO₄, filtered, and concentrated under reduced pressure. The resulting residue was purified by FCC (SiO₂, 0-20% EtOAc in ether) to afford the title compound (110 mg, 37% yield) as a yellow solid. MS (ESI): mass calcd. for C₁₉H₂₄ClF₃N₂O₂, 404.2; m/z found, 348.9 [M+2H-tBu]⁺. ¹H NMR (400 MHz, CDCl₃) δ 7.77 (d, J=8.0 Hz, 1H), 6.99 (d, J=8.0 Hz, 1H), 3.86-3.71 (m, 3H), 3.67-3.63 (m, 2H), 2.70-2.59 (m, 1H), 2.31-2.21 (m, 2H), 1.95-1.77 (m, 2H), 1.29 (s, 9H), 1.07 (d, J=6.8 Hz, 3H).

Step D: tert-Butyl 6-(1-(6-methyl-5-(trifluoromethyl)pyridin-2-yl)ethyl)-2-azaspiro[3.3]heptane-2-carboxylate. K₂CO₃ (107 mg, 0.774 mmol) was added to a mixture of tert-butyl 6-(1-(6-chloro-5-(trifluoromethyl)pyridin-2-yl)ethyl)-2-azaspiro[3.3]heptane-2-carboxylate (100 mg, 0.247 mmol) and 2,4,6-trimethyl-1,3,5,2,4,6-trioxatriborinane (150 μL, 0.537 mmol) in 1,4-dioxane (2 mL) and H₂O (0.4 mL). The resulting mixture was sparged with N₂ for 5 min, then treated with Pd(dppf)Cl₂·CH₂Cl₂ (35 mg, 0.043 mmol). The resultant mixture was stirred at 120° C. for 16 h under N₂ before being poured into water and extracted with EtOAc. The combined organic extracts were dried over Na₂SO₄, filtered, and concentrated under reduced pressure. The resulting residue was purified by FCC (SiO₂, 0-20% EtOAc in ether) to afford the title compound (50 mg, 48% yield) as a yellow oil. MS (ESI): mass calcd. for $C_{20}H_{27}F_3N_2O_2$, 384.2; m/z found, 328.9 [M+2H-tBu]$^+$.

Step E: 6-(1-(6-Methyl-5-(trifluoromethyl)pyridin-2-yl)ethyl)-2-azaspiro[3.3]heptane. TFA (0.15 mL, 2.00 mmol) was added to a solution of tert-butyl 6-(1-(6-methyl-5-(trifluoromethyl)pyridin-2-yl)ethyl)-2-azaspiro[3.3]heptane-2-carboxylate (50 mg, 0.130 mmol) in DCM (2 mL). The resultant mixture was stirred at rt for 2 h before concentrating under reduced pressure. The residue was taken up in water, adjusted to pH 10 with sat. aq. NaHCO$_3$ and extracted with DCM. The combined organic extracts were dried over Na$_2$SO$_4$, filtered, and concentrated under reduced pressure to give the title product (50 mg) as a yellow oil. MS (ESI): mass calcd. for $C_{15}H_{19}F_3N_2$, 284.2; m/z found, 285.0 [M+H]$^+$.

Step F: (rac)-((1s,3s)-3-Hydroxy-3-methylcyclobutyl)(6-(1-(6-methyl-5-(trifluoromethyl)pyridin-2-yl)ethyl)-2-azaspiro[3.3]heptan-2-yl)methanone. HATU (72 mg, 0.190 mmol) was added to a solution of 6-(1-(6-methyl-5-(trifluoromethyl)pyridin-2-yl)ethyl)-2-azaspiro[3.3]heptane (50 mg, 0.180 mmol), (1s,3s)-3-hydroxy-3-methylcyclobutanecarboxylic acid (25 mg, 0.190 mmol) and DIPEA (96 µL, 0.540 mmol) in DMF (1 mL). The resultant mixture was stirred at rt for 2 h before being quenched with H$_2$O and extracted with EtOAc. The combined organic extracts were dried over Na$_2$SO$_4$, filtered, and concentrated under reduced pressure. The resulting residue was purified by FCC (SiO$_2$, 0-65% EtOAc in ether) to afford the title compound (27 mg, 30% yield) as a light-yellow solid.

Step G: ((1s,3*S)-3-Hydroxy-3-methylcyclobutyl)(6-((*R)-1-(6-methyl-5-(trifluoromethyl)pyridin-2-yl)ethyl)-2-azaspiro[3.3]heptan-2-yl)methanone. The title compound was prepared via separation of (rac)-((1s,3s)-3-hydroxy-3-methylcyclobutyl)(6-(1-(6-methyl-5-(trifluoromethyl)pyridin-2-yl)ethyl)-2-azaspiro[3.3]heptan-2-yl)methanone by chiral SFC (Stationary phase: AD-S (3×25 cm); Mobile phase: 25-75% EtOH containing 0.1% of 25% aq. NH$_3$/CO$_2$; Rt=4.62 min). MS (ESI): mass calcd. for $C_{21}H_{27}F_3N_2O_2$, 396.2; m/z found, 397.2 [M+H]$^+$. $^1$H NMR (400 MHz, CDCl$_3$) δ 7.84-7.70 (m, 1H), 7.02-6.91 (m, 1H), 4.13-3.83 (m, 5H), 2.82-2.72 (m, 1H), 2.67 (s, 3H), 2.65-2.57 (m, 1H), 2.51-2.34 (m, 2H), 2.33-2.17 (m, 4H), 2.07-1.92 (m, 2H), 1.89-1.78 (m, 1H), 1.34 (s, 3H), 1.20 (d, J=6.8 Hz, 3H).

Example 313

((1s,3*R)-3-Hydroxy-3-methylcyclobutyl)(6-((*S)-1-(6-methyl-5-(trifluoromethyl)pyridin-2-yl)ethyl)-2-azaspiro[3.3]heptan-2-yl)methanone

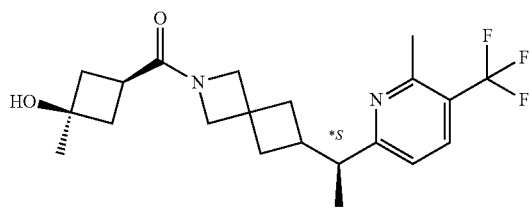 [SMILES: Cc1nc([C@@H](C)C2CC3(C2)CN(C(=O)[C@H]2C[C@@](C)(O)C2)C3)ccc1C(F)(F)F]

The title compound was prepared via separation of (rac)-((1s,3s)-3-hydroxy-3-methylcyclobutyl)(6-(1-(6-methyl-5-(trifluoromethyl)pyridin-2-yl)ethyl)-2-azaspiro[3.3]heptan-2-yl)methanone (Example 312, Step F) by chiral SFC (Stationary phase: AD-S (3×25 cm); Mobile phase: 25-75% EtOH containing 0.1% of 25% aq. NH$_3$/CO$_2$; Rt=6.48 min). MS (ESI): mass calcd. for $C_{21}H_{27}F_3N_2O_2$, 396.2; m/z found, 397.2 [M+H]$^+$. $^1$H NMR (400 MHz, CDCl$_3$) δ 7.84-7.73 (m, 1H), 7.03-6.92 (m, 1H), 4.15-3.82 (m, 5H), 2.84-2.73 (m, 1H), 2.67 (s, 3H), 2.65-2.58 (m, 1H), 2.51-2.35 (m, 2H), 2.33-2.14 (m, 4H), 2.09-1.91 (m, 2H), 1.89-1.80 (m, 1H), 1.34 (s, 3H), 1.20 (d, J=6.8 Hz, 3H).

Example 314

((1s,3*S)-3-Hydroxy-3-methylcyclobutyl)(6-((*R)-1-(1-methyl-1H-indazol-6-yl)ethyl)-2-azaspiro[3.3]heptan-2-yl)methanone

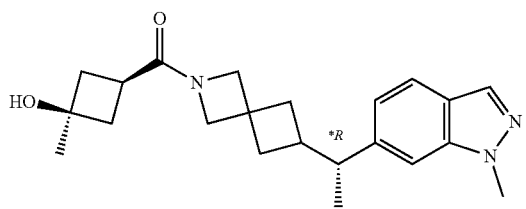 [SMILES: C[C@@H](c1ccc2cnn(C)c2c1)C1CC2(C1)CN(C(=O)[C@H]1C[C@@](C)(O)C1)C2]

Step A: (rac)-((1s,3s)-3-Hydroxy-3-methylcyclobutyl)(6-(1-(1-methyl-1H-indazol-6-yl)ethyl)-2-azaspiro[3.3]heptan-2-yl)methanone. The title compound was prepared in a manner analogous to Example 7 using tert-butyl 6-acetyl-2-azaspiro[3.3]heptane-2-carboxylate (Intermediate 74) instead of tert-butyl 6-oxo-2-azaspiro[3.4]octane-2-carboxylate and 6-bromo-1-methyl-1H-indazole instead of 1-bromo-2-methyl-3-(trifluoromethyl)benzene in Step A.

Step B: ((1s,3*S)-3-Hydroxy-3-methylcyclobutyl)(6-((*R)-1-(1-methyl-1H-indazol-6-yl)ethyl)-2-azaspiro[3.3]heptan-2-yl)methanone. The title compound was prepared via separation of (rac)-((1s,3s)-3-hydroxy-3-methylcyclobutyl)(6-(1-(1-methyl-1H-indazol-6-yl)ethyl)-2-azaspiro[3.3]heptan-2-yl)methanone by chiral SFC (Stationary phase: OJ-H (3×25 cm); Mobile phase: 20% EtOH containing 0.1% of 25% aq. NH$_3$/CO$_2$; Rt=2.07 min). MS (ESI): mass calcd. for $C_{22}H_{29}N_3O_2$, 367.2; m/z found, 368.2 [M+H]$^+$. $^1$H NMR (400 MHz, CDCl$_3$) δ 7.92 (s, 1H), 7.63 (d, J=8.4 Hz, 1H), 7.11 (s, 1H), 6.95 (d, J=8.4 Hz, 1H), 4.13-3.84 (m, 8H), 2.76-2.56 (m, 2H), 2.47-2.33 (m, 2H), 2.31-2.17 (m, 4H), 2.05-1.91 (m, 2H), 1.87-1.79 (m, 1H), 1.34 (s, 3H), 1.24 (d, J=6.8 Hz, 3H).

Example 315

((1s,3*R)-3-Hydroxy-3-methylcyclobutyl)(6-((*S)-1-(1-methyl-1H-indazol-6-yl)ethyl)-2-azaspiro[3.3]heptan-2-yl)methanone

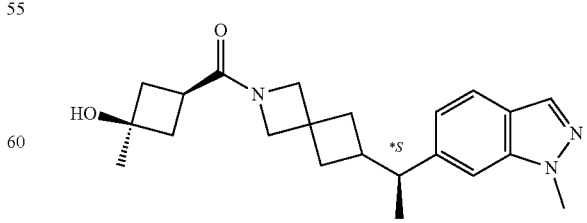

The title compound was prepared via separation of (rac)-((1s,3s)-3-hydroxy-3-methylcyclobutyl)(6-(1-(1-methyl-1H-indazol-6-yl)ethyl)-2-azaspiro[3.3]heptan-2-yl)methanone (Example 314, Step A) by chiral SFC (Stationary phase: OJ-H (3×25 cm); Mobile phase: 20% EtOH containing 0.1% of 25% aq. NH$_3$/CO$_2$; Rt=2.23 min). MS (ESI): mass calcd. for C$_{22}$H$_{29}$N$_3$O$_2$, 367.2; m/z found, 368.2 [M+H]$^+$. $^1$H NMR (400 MHz, CDCl$_3$) δ 7.92 (s, 1H), 7.63 (d, J=8.4 Hz, 1H), 7.11 (s, 1H), 6.95 (d, J=8.0 Hz, 1H), 4.13-3.83 (m, 8H), 2.76-2.54 (m, 2H), 2.47-2.18 (m, 6H), 2.06-1.91 (m, 2H), 1.87-1.82 (m, 1H), 1.34 (s, 3H), 1.24 (d, J=7.2 Hz, 3H).

Example 316

(rac)-((1s,3s)-3-Hydroxy-3-methylcyclobutyl)(6-(1-(pyrazolo[1,5-a]pyridin-7-yl)ethyl)-2-azaspiro[3.3]heptan-2-yl)methanone

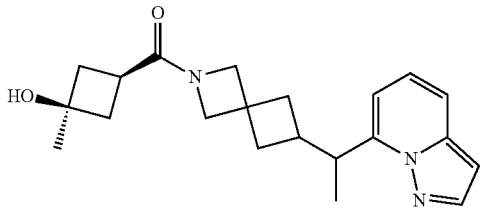 [SMILES: CC(c1cccc2ccnn12)C1CC2(C1)CN(C(=O)[C@H]1C[C@@](C)(O)C1)C2]

The title compound was prepared in a manner analogous to Example 29 using tert-butyl 6-acetyl-2-azaspiro[3.3]heptane-2-carboxylate (Intermediate 74) instead of tert-butyl 6-oxo-2-azaspiro[3.4]octane-2-carboxylate and 7-bromopyrazolo[1,5-a]pyridine instead of 2-bromo-6-(tert-butyl)pyridine in Step A and using SOCl$_2$/pyridine instead of Burgess reagent in Step B. MS (ESI): mass calcd. for C$_{21}$H$_{27}$N$_3$O$_2$, 353.2; m/z found, 354.1 [M+H]$^+$. $^1$H NMR (400 MHz, CDCl$_3$) δ 8.00-7.94 (m, 1H), 7.44 (d, J=8.8 Hz, 1H), 7.14-7.03 (m, 1H), 6.57-6.54 (m, 1H), 6.53-6.45 (m, 1H), 4.15-3.92 (m, 4H), 3.91-3.84 (m, 1H), 3.82-3.72 (m, 1H), 2.75-2.57 (m, 2H), 2.51-2.34 (m, 1H), 2.33-2.17 (m, 5H), 2.10-2.00 (m, 1H), 1.97-1.85 (m, 1H), 1.34 (s, 3H), 1.33-1.28 (m, 3H).

Example 317

(6-(Difluoro(1-methyl-1H-pyrrolo[2,3-b]pyridin-6-yl)methyl)-2-azaspiro[3.3]heptan-2-yl)((1s,3s)-3-hydroxy-3-methylcyclobutyl)methanone

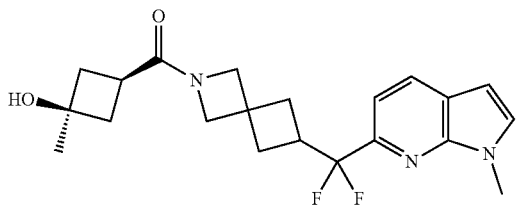 [SMILES: Cn1ccc2ccc(C(F)(F)C3CC4(C3)CN(C(=O)[C@H]3C[C@@](C)(O)C3)C4)nc21]

Step A: tert-Butyl 6-(hydroxy(l-methyl-1H-pyrrolo[2,3-b]pyridin-6-yl)methyl)-2-azaspiro[3.3]heptane-2-carboxylate. n-BuLi (1.6 mL, 2.5 M in hexanes, 4.03 mmol) was added dropwise to a −78° C. solution of 6-bromo-1-methyl-1H-pyrrolo[2,3-b]pyridine (Intermediate 44, 788 mg, 3.73 mmol) in THF (10 mL). The resultant mixture was stirred for 30 min before being treated with a solution of tert-butyl 6-formyl-2-azaspiro[3.3]heptane-2-carboxylate (700 mg, 3.11 mmol) in THF (5 mL). The resultant mixture was stirred at −78° C. for 2 h. The reaction mixture was diluted with EtOAc, quenched with sat. aq. NH$_4$Cl and extracted with EtOAc. The combined organic extracts were washed with brine, dried over Na$_2$SO$_4$, filtered, and concentrated under reduced pressure. The resulting residue was purified by FCC (SiO$_2$, 0-30% EtOAc in ether) to afford the title compound (623 mg, 50% yield) as a white solid. MS (ESI): mass calcd. for C$_{20}$H$_{27}$N$_3$O$_3$, 357.2; m/z found, 358.1 [M+H]$^+$. $^1$H NMR (400 MHz, CDCl$_3$) δ 7.87 (d, J=8.0 Hz, 1H), 7.17 (d, J=3.2 Hz, 1H), 6.91 (d, J=8.0 Hz, 1H), 6.45 (d, J=3.6 Hz, 1H), 4.72 (d, J=4.4 Hz, 1H), 4.59 (br s, 1H), 3.89 (s, 3H), 3.88-3.80 (m, 4H), 2.62-2.48 (m, 1H), 2.38-2.29 (m, 1H), 2.24-2.10 (m, 2H), 2.01-1.89 (m, 1H), 1.43 (s, 9H).

Step B: tert-Butyl 6-(1-methyl-1H-pyrrolo[2,3-b]pyridine-6-carbonyl)-2-azaspiro[3.3]heptane-2-carboxylate. tert-Butyl 6-(hydroxy(l-methyl-1H-pyrrolo[2,3-b]pyridin-6-yl)methyl)-2-azaspiro[3.3]heptane-2-carboxylate (623 mg, 1.74 mmol) and Dess-Martin periodinane (2.22 g, 5.23 mmol) in DCM (10 mL) were stirred at rt for 1 h. The reaction mixture was quenched with sat. aq. Na$_2$SO$_3$ and extracted with DCM. The combined organic extracts were washed with sat. aq. NaHCO$_3$, dried over Na$_2$SO$_4$, filtered, and concentrated under reduced pressure. The resulting residue was purified by FCC (SiO$_2$, 0-25% EtOAc in ether) to yield the title compound (550 mg, 76% yield) as a white solid. MS (ESI): mass calcd. for C$_{20}$H$_{25}$N$_3$O$_3$, 355.2; m/z found, 356.1 [M+H]$^+$. $^1$H NMR (400 MHz, CDCl$_3$) δ 8.03-7.94 (m, 1H), 7.92-7.86 (m, 1H), 7.39 (d, J=3.2 Hz, 1H), 6.52 (d, J=3.2 Hz, 1H), 4.57-4.44 (m, 1H), 4.07 (s, 2H), 3.94 (s, 3H), 3.88 (s, 2H), 2.60-2.51 (m, 4H), 1.44 (s, 9H).

Step C: tert-Butyl 6-(difluoro(1-methyl-1H-pyrrolo[2,3-b]pyridin-6-yl)methyl)-2-azaspiro[3.3]heptane-2-carboxylate. Bis(2-methoxyethyl)aminosulphur trifluoride (0.34 mL, 1.82 mmol) was added dropwise to a −70° C. solution of tert-butyl 6-(1-methyl-1H-pyrrolo[2,3-b]pyridine-6-carbonyl)-2-azaspiro[3.3]heptane-2-carboxylate (380 mg, 1.07 mmol) in DCM (2 mL) under N$_2$. The resulting mixture was stirred at 70° C. for 72 h. The reaction mixture was cooled to 0° C., diluted with DCM, quenched with sat. aq. NaHCO$_3$ and extracted with DCM. The combined organic extracts were washed with brine, dried over Na$_2$SO$_4$, filtered, and concentrated under reduced pressure. The resulting residue was purified by FCC (SiO$_2$, 0-10% EtOAc in ether) to afford the title compound (33 mg, 7% yield) as a yellow solid. MS (ESI): mass calcd. for C$_{20}$H$_{25}$F$_2$N$_3$O$_2$, 377.2; m/z found, 322.0 [M+2H-tBu]$^+$. $^1$H NMR (400 MHz, CDCl$_3$) δ 7.96 (d, J=8.0 Hz, 1H), 7.38 (d, J=8.0 Hz, 1H), 7.28 (d, J=3.6 Hz, 1H), 6.49 (d, J=3.6 Hz, 1H), 3.95 (s, 2H), 3.90-3.87 (m, 5H), 3.42-3.26 (m, 1H), 2.50-2.41 (m, 2H), 2.36-2.27 (m, 2H), 1.44 (s, 9H).

Step D: 6-(Difluoro(2-azaspiro[3.3]heptan-6-yl)methyl)-1-methyl-1H-pyrrolo[2,3-b]pyridine. TFA (0.5 mL, 6.54 mmol) was added to a 0° C. solution of tert-butyl 6-(difluoro (1-methyl-1H-pyrrolo[2,3-b]pyridin-6-yl)methyl)-2-azaspiro[3.3]heptane-2-carboxylate (43 mg, 0.110 mmol) in DCM (2 mL). The resultant mixture was stirred for 1 h, then gradually warmed to rt. The reaction mixture was concentrated under reduced pressure and the resulting was taken up in DCM, washed with sat. aq. Na$_2$CO$_3$ and extracted with DCM. The combined organic extracts were washed with brine, dried over Na$_2$SO$_4$, filtered, and concentrated under reduced pressure to afford the title compound (31 mg) as a yellow oil, which was used in the next step without further purification.

Step E: (6-(Difluoro(1-methyl-1H-pyrrolo[2,3-b]pyridin-6-yl)methyl)-2-azaspiro[3.3]heptan-2-yl)((1s,3s)-3-hydroxy-3-methylcyclobutyl)methanone. T₃P® (0.10 mL, 0.168 mmol, 50% in EtOAc) was added to a solution of 6-(difluoro(2-azaspiro[3.3]heptan-6-yl)methyl)-1-methyl-1H-pyrrolo[2,3-b]pyridine (33 mg), (1s,3s)-3-hydroxy-3-methylcyclobutanecarboxylic acid (16 mg, 0.119 mmol) and DIPEA (0.10 mL, 0.565 mmol) in DCM (2 mL). The resulting mixture was stirred at rt for 2 h before being poured into H₂O and extracted with DCM. The combined organic extracts were dried over Na₂SO₄, filtered, and concentrated under reduced pressure. The resulting residue was purified by RP HPLC (34-64% CH₃CN in H₂O with 0.05% NH₃ and 10 mM NH₄HCO₃) to afford the title compound (13 mg, 27% yield) as an off-white solid. MS (ESI): mass calcd. for $C_{21}H_{25}F_2N_3O_2$, 389.2; m/z found, 390.1 [M+H]⁺. ¹H NMR (400 MHz, CDCl₃) δ 7.97 (d, J=8.4 Hz, 1H), 7.43-7.35 (m, 1H), 7.30-7.27 (m, 1H), 6.49 (d, J=3.2 Hz, 1H), 4.18-3.95 (m, 5H), 3.88 (s, 3H), 3.49-3.27 (m, 1H), 2.70-2.59 (m, 1H), 2.55-2.44 (m, 2H), 2.42-2.33 (m, 2H), 2.32-2.21 (m, 4H), 1.35 (s, 3H).

Example 318

((1s,3*S)-3-Hydroxy-3-methylcyclobutyl)((6*R)-6-(3-isopropylphenyl)-1-methyl-2-azaspiro[3.4]octan-2-yl)methanone

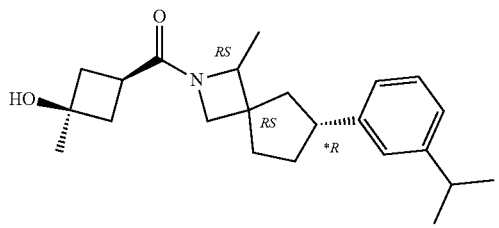 [SMILES: CC(C)c1cccc([C@@H]2CCC3(C2)CN(C(=O)[C@H]2C[C@@](C)(O)C2)C3C)c1]

Step A: O-tert-Butyl 6-(3-isopropylphenyl)-2-azaspiro[3.4]octane-2-carbothioate. Sodium hypochlorite (3.3 mL, 4.14 mmol) was added to a solution of 6-(3-isopropylphenyl)-2-azaspiro[3.4]octane (intermediate from Example 46, 750 mg, 3.27 mmol), potassium O-tert-butyl carbonodithioate (Intermediate 75, 924 mg, 4.91 mmol) and NaOH (4.4 mL, 0.1 N in water) in water (30 mL). The resultant mixture was stirred at rt for 12 h before being quenched with brine and extracted with DCM. The combined organic extracts were dried over Na₂SO₄, filtered, and concentrated under reduced pressure. The resulting residue was purified by FCC (SiO₂, 0-10% EtOAc in ether) to afford the title compound (240 mg, 18% yield) as a colorless oil. MS (ESI): mass calcd. for $C_{21}H_{31}NOS$, 345.2; m/z found, 331.1 [M+2H+MeCN-tBu]⁺.

Step B: O-(tert-Butyl) (*R)-6-(3-isopropylphenyl)-2-azaspiro[3.4]octane-2-carbothioate. The title compound was prepared via separation of O-tert-butyl 6-(3-isopropylphenyl)-2-azaspiro[3.4]octane-2-carbothioate by chiral SFC (Stationary phase: OJ-H (3×25 cm); Mobile phase: 15% EtOH containing 0.1% of 25% aq. NH₃/CO₂; Rt=2.26 min). MS (ESI): mass calcd. for $C_{21}H_{31}NOS$, 345.2; m/z found, 290.0 [M+2H-tBu]⁺.

Step C: O-(tert-Butyl) (6*R)-6-(3-isopropylphenyl)-1-methyl-2-azaspiro[3.4]octane-2-carbothioate. s-BuLi (0.5 mL, 1.3 M in hexane, 0.650 mmol) was added dropwise to a −70° C. solution of O-(tert-butyl) (*R)-6-(3-isopropylphenyl)-2-azaspiro[3.4]octane-2-carbothioate (100 mg, 0.289 mmol) and TMEDA (68 mg, 0.590 mmol) in Et₂O (2 mL) under N₂. The reaction mixture was stirred at −70° C. for 30 min, then treated with a solution of iodomethane (120 mg, 0.845 mmol) in Et₂O (1 mL). The resultant mixture was stirred at −70° C. for 30 min then rt for 10 h. The reaction mixture was quenched with 25% aq. NH₃ and sat. aq. NH₄Cl and extracted with EtOAc. The combined organic extracts were washed with brine, dried over Na₂SO₄, filtered, and concentrated under reduced pressure. The resulting residue was purified by FCC (SiO₂, 0-7% EtOAc in ether) to afford the title compound (50 mg, 43% yield) as a light-yellow oil. MS (ESI): mass calcd. for $C_{22}H_{33}NOS$, 359.2; m/z found, 304.1 [M+2H-tBu]⁺. ¹H NMR (400 MHz, CDCl₃) δ 7.23-7.09 (m, 1H), 7.03-6.90 (m, 3H), 4.21-4.02 (m, 1H), 3.95-3.68 (m, 2H), 3.08-2.88 (m, 1H), 2.85-2.75 (m, 1H), 2.44-2.14 (m, 1H), 2.11-1.85 (m, 3H), 1.84-1.63 (m, 2H), 1.62-1.53 (m, 10H), 1.34-1.23 (m, 2H), 1.17 (d, J=6.8 Hz, 6H).

Step D: (6*R)-6-(3-Isopropylphenyl)-1-methyl-2-azaspiro[3.4]octane. TFA (0.1 mL, 1.40 mmol) was added to a solution of O-(tert-butyl) (6*R)-6-(3-isopropylphenyl)-1-methyl-2-azaspiro[3.4]octane-2-carbothioate (50 mg, 0.140 mmol) in DCM (1 mL). The reaction was stirred at rt for 4 h before being concentrated under reduced pressure. The resulting residue was dissolved in water, adjusted to pH 10 with aq. sat. NaHCO₃, and extracted with EtOAc. The combined organic extracts were washed with brine, dried over Na₂SO₄, filtered, and concentrated under reduced pressure to give the title compound (35 mg) as a yellow oil. MS (ESI): mass calcd. for $C_{17}H_{25}N$, 243.2; m/z found, 244.1 [M+H]⁺.

Step E: ((1s,3*S)-3-Hydroxy-3-methylcyclobutyl)((6*R)-6-(3-isopropylphenyl)-1-methyl-2-azaspiro[3.4]octan-2-yl)methanone. HATU (65 mg, 0.170 mmol) was added to a solution of (6*R)-6-(3-isopropylphenyl)-1-methyl-2-azaspiro[3.4]octane (35 mg, crude), (1s,3s)-3-hydroxy-3-methylcyclobutanecarboxylic acid (23 mg, 0.180 mmol) and DIPEA (75 µL, 0.430 mmol) in DMF (1 mL). The resultant mixture was stirred at rt for 2 h before being quenched with H₂O and extracted with EtOAc. The combined organic extracts were washed with brine, dried over Na₂SO₄, filtered, and concentrated under reduced pressure. The resulting residue was purified by RP HPLC (60-90% MeCN in H₂O with 0.05% 25% aq. NH₃) to afford the title compound (6 mg, 11% yield) as a brown oil. MS (ESI): mass calcd. for $C_{23}H_{33}NO_2$, 355.3; m/z found, 356.4 [M+H]⁺. ¹H NMR (400 MHz, CD3OD) δ 7.21-7.12 (m, 1H), 7.09-6.97 (m, 3H), 4.60 (br s, 1H), 4.40-4.10 (m, 1H), 4.03-3.85 (m, 1H), 3.81-3.72 (m, 1H), 3.12-2.94 (m, 1H), 2.91-2.77 (m, 1H), 2.74-2.55 (m, 1H), 2.46-1.92 (m, 8H), 1.89-1.56 (m, 2H), 1.43-1.31 (m, 6H), 1.24-1.16 (m, 6H).

Example 319

(rac)-((1s,3s)-3-(Difluoromethyl)-3-hydroxycyclobutyl)(6-(3-isopropylphenyl)-2-azaspiro[3.4]octan-2-yl)methanone

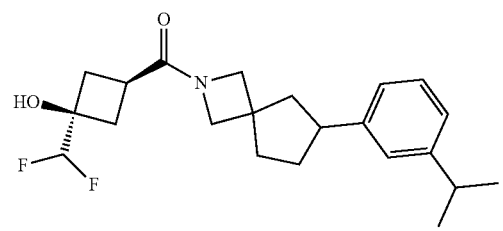 [SMILES: CC(C)c1cccc(C2CCC3(C2)CN(C(=O)[C@H]2C[C@](O)(C(F)F)C2)C3)c1]

Step A: 3-(6-(3-Isopropylphenyl)-2-azaspiro[3.4]octane-2-carbonyl)cyclobutan-1-one. tert-Butyl 6-(3-isopropylphenyl)-2-azaspiro[3.4]octane-2-carboxylate (intermediate from Example 46, 100 mg, 0.304 mmol) was taken up in HCl (1.25 M in EtOH, 1.9 mL, 2.43 mmol). The reaction mixture was stirred at 45° C. for 1 h before being concentrated under reduced pressure. The resulting residue was taken up in DCM (1.5 mL). To this was added 3-oxocyclobutanecarboxylic acid (37 mg, 0.319 mmol), DIPEA (0.16 mL, 0.911 mmol), and HATU (127 mg, 0.334 mmol). The reaction mixture was stirred at rt for 16 hours before being concentrated under reduced pressure. The resulting residue was purified by FCC (SiO$_2$, 0-100% EtOAc in hexanes) to provide the title compound (69 mg, 70% yield). MS (ESI): mass calcd. for $C_{21}H_{27}NO_2$, 325.2; m/z found, 326.2 [M+H]$^+$.

Step B: (3-(Difluoro(phenylsulfonyl)methyl)-3-hydroxycyclobutyl)(6-(3-isopropylphenyl)-2-azaspiro[3.4]octan-2-yl)methanone. In an oven-dried flask under N$_2$, 3-(6-(3-isopropylphenyl)-2-azaspiro[3.4]octane-2-carbonyl)cyclobutan-1-one (68 mg, 0.209 mmol) and ((difluoromethyl)sulfonyl)benzene (32 µL, 0.209 mmol) were taken up in THF (1 mL) and cooled −78° C. To the reaction mixture was added LiHMDS (0.42 mL, 1 M in THF, 0.418 mmol) and the reaction was stirred for 2.5 h at −78° C. After warming to rt, the reaction was quenched with sat. aq. NH$_4$Cl and extracted with EtOAc. The combined organic extracts were dried over Na$_2$SO$_4$, filtered, and concentrated under reduced pressure. Purification by FCC (SiO$_2$, 0-100% EtOAc in hexanes) provided the title compound (67 mg, 62% yield). MS (ESI): mass calcd. for $C_{28}H_{33}F_2NO_4S$, 517.2; m/z found, 518.2 [M+H]$^+$.

Step C: (rac)-((1s,3s)-3-(Difluoromethyl)-3-hydroxycyclobutyl)(6-(3-isopropylphenyl)-2-azaspiro[3.4]octan-2-yl)methanone. (3-(Difluoro(phenylsulfonyl)methyl)-3-hydroxycyclobutyl)(6-(3-isopropylphenyl)-2-azaspiro[3.4]octan-2-yl)methanone (30 mg, 0.058 mmol) was placed under N$_2$ at 0° C. To this was added hexamethylphosphoramide (0.20 mL, 0.058 mmol). Samarium(II) iodide (5.8 mL, 0.1 M in THF, 0.580 mmol) was added dropwise to the mixture and the reaction was stirred for 72 hours at rt. The reaction was quenched with sat. aq. NH$_4$Cl and extracted with EtOAc. The combined organic layers were dried over Na$_2$SO$_4$, filtered, and concentrated under reduced pressure. Purification by RP HPLC (5-95% ACN in 20 mM NH$_4$OH in water) provided the title compound (2.5 mg, 11% yield). MS (ESI): mass calcd. for $C_{22}H_{29}F_2NO_2$, 377.2; m/z found, 378.2 [M+H]$^+$. $^1$H NMR (400 MHz, CDCl$_3$) δ 7.23 (t, J=7.8 Hz, 1H), 7.10-6.99 (m, 3H), 5.67 (t, J=56.6 Hz, 1H), 4.91 (d, J=7.5 Hz, 1H), 4.06-3.88 (m, 4H), 3.18-3.02 (m, 1H), 2.94-2.76 (m, 2H), 2.72-2.61 (m, 2H), 2.38-2.27 (m, 1H), 2.25-2.14 (m, 3H), 2.16-1.97 (m, 2H), 1.99-1.85 (m, 1H), 1.83-1.69 (m, 1H), 1.25 (d, J=6.9 Hz, 6H).

Example 320

(rac)-(6-(4-(1,1-Difluoroethyl)phenyl)-2-azaspiro[3.4]octan-2-yl)((1s,3s)-3-hydroxy-3-methylcyclobutyl)methanone

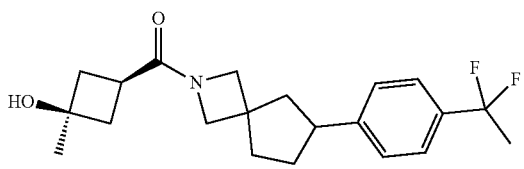 [SMILES: CC(F)(F)c1ccc(C2CCC3(C2)CN(C(=O)[C@H]2C[C@@](C)(O)C2)C3)cc1]

The title compound was prepared in a manner analogous to Example 29 using 1-bromo-4-(1,1-difluoroethyl)benzene instead of 2-bromo-6-(tert-butyl)pyridine in Step A. MS (ESI): mass calcd. for $C_{21}H_{27}F_2NO_2$, 363.2; m/z found, 364.1 [M+H]$^+$. $^1$H NMR (400 MHz, CDCl$_3$) δ 7.50-7.45 (m, 2H), 7.30 (s, 2H), 4.06 (s, 1H), 4.04-3.98 (m, 2H), 3.95-3.90 (m, 2H), 3.26-3.10 (m, 1H), 2.75-2.70 (m, 1H), 2.42-2.28 (m, 5H), 2.25-2.04 (m, 3H), 2.00-1.90 (m, 4H), 1.83-1.73 (m, 1H), 1.39 (s, 3H).

Example 321

((*S)-6-(2,4-Dimethylphenyl)-2-azaspiro[3.4]octan-2-yl)((1s,3*R)-3-hydroxy-3-methylcyclobutyl)methanone

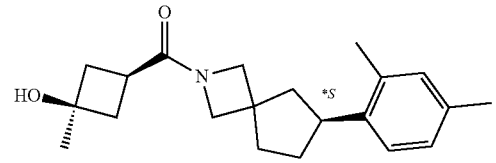 [SMILES: Cc1ccc([C@H]2CCC3(C2)CN(C(=O)[C@H]2C[C@@](C)(O)C2)C3)c(C)c1]

The title compound was prepared via separation of (rac)-(6-(2,4-dimethylphenyl)-2-azaspiro[3.4]octan-2-yl)((1s,3s)-3-hydroxy-3-methylcyclobutyl)methanone (Example 14) by chiral SFC (Stationary phase: IG (2×25 cm); Mobile phase: 40% MeOH/CO$_2$; Rt=9.00 min). MS (ESI): mass calcd. for $C_{21}H_{29}NO_2$, 327.2; m/z found, 328.3 [M+H]$^+$. $^1$H NMR (400 MHz, CDCl$_3$) δ 7.12-7.03 (m, 1H), 7.01-6.94 (m, 2H), 4.05-3.85 (m, 5H), 3.34-3.16 (m, 1H), 2.72-2.63 (m, 1H), 2.35-2.19 (m, 11H), 2.14-1.92 (m, 3H), 1.94-1.77 (m, 1H), 1.76-1.62 (m, 1H), 1.35 (s, 3H).

Example 322

((*R)-6-(2,4-Dimethylphenyl)-2-azaspiro[3.4]octan-2-yl)((1s,3*S)-3-hydroxy-3-methylcyclobutyl)methanone

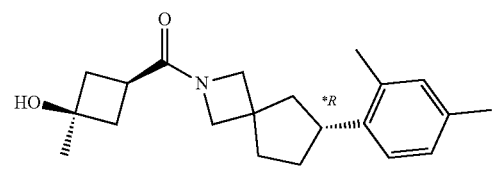 [SMILES: Cc1ccc([C@@H]2CCC3(C2)CN(C(=O)[C@H]2C[C@@](C)(O)C2)C3)c(C)c1]

The title compound was prepared via separation of (rac)-(6-(2,4-dimethylphenyl)-2-azaspiro[3.4]octan-2-yl)((1s,3s)-3-hydroxy-3-methylcyclobutyl)methanone (Example 14) by chiral SFC (Stationary phase: IG (2×25 cm); Mobile phase: 40% MeOH/CO$_2$; Rt=6.64 min). MS (ESI): mass calcd. for $C_{21}H_{29}NO_2$, 327.2; m/z found, 328.3 [M+H]$^+$. $^1$H NMR (400 MHz, CDCl$_3$) δ 7.12-7.03 (m, 1H), 7.01-6.94 (m, 2H), 4.04-3.84 (m, 5H), 3.32-3.17 (m, 1H), 2.72-2.62 (m, 1H), 2.35-2.18 (m, 11H), 2.14-1.93 (m, 3H), 1.94-1.77 (m, 1H), 1.75-1.61 (m, 1H), 1.35 (s, 3H).

Example 323

(rac)-(6-(2,3-Dihydrobenzofuran-6-yl)-2-azaspiro[3.4]octan-2-yl)((1s,3s)-3-hydroxy-3-methylcyclobutyl)methanone

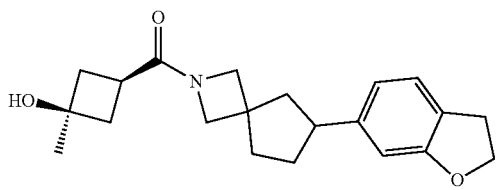 [SMILES: C[C@]1(O)C[C@@H](C(=O)N2CC3(CCC(c4ccc5c(c4)OCC5)C3)C2)C1]

The title compound was prepared in a manner analogous to Example 40 using (2,3-dihydrobenzofuran-6-yl)boronic acid instead of 3-(trifluoromethoxy)phenylboronic acid in Step A. MS (ESI): mass calcd. for $C_{21}H_{27}NO_3$, 341.2; m/z found, 342.3 [M+H]$^+$. $^1$H NMR (400 MHz, CDCl$_3$) δ 7.13-7.06 (m, 1H), 6.71-6.64 (m, 1H), 6.66-6.60 (m, 1H), 4.55 (td, J=8.7, 1.5 Hz, 2H), 4.11 (d, J=5.2 Hz, 1H), 4.02-3.91 (m, 3H), 3.91-3.84 (m, 1H), 3.21-3.11 (m, 2H), 3.14-2.95 (m, 1H), 2.65 (p, J=7.4 Hz, 1H), 2.34-2.21 (m, 5H), 2.17-1.91 (m, 3H), 1.93-1.79 (m, 1H), 1.76-1.61 (m, 1H), 1.34 (s, 3H).

Example 324

(rac)-((1s,3s)-3-Hydroxy-3-methylcyclobutyl)(6-(pyrazolo[1,5-c]pyridin-4-yl)-2-azaspiro[3.4]octan-2-yl)methanone

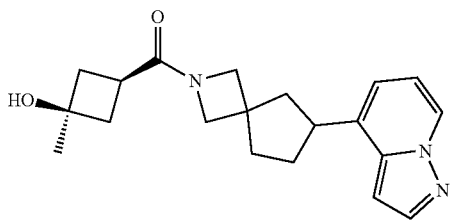 [SMILES: C[C@]1(O)C[C@@H](C(=O)N2CC3(CCC(c4cccn5nccc45)C3)C2)C1]

The title compound was prepared in a manner analogous to Example 109 using 4-bromopyrazolo[1,5-c]pyridine instead of 4-bromo-1-methyl-5-(trifluoromethyl)-1H-pyrazole in Step A. MS (ESI): mass calcd. for $C_{20}H_{25}N_3O_2$, 339.2; m/z found, 340.1 [M+H]$^+$. $^1$H NMR (400 MHz, CDCl$_3$) δ 8.37 (d, J=7.0 Hz, 1H), 7.97-7.92 (m, 1H), 6.95-6.88 (m, 1H), 6.75-6.68 (m, 1H), 6.52-6.46 (m, 1H), 4.11-3.87 (m, 5H), 3.46-3.33 (m, 1H), 2.73-2.62 (m, 1H), 2.45-2.00 (m, 9H), 1.96-1.85 (m, 1H), 1.42-1.30 (m, 3H).

Example 325

(rac)-((1s,3s)-3-Hydroxy-3-methylcyclobutyl)(6-(pyrazolo[1,5-c]pyridin-2-yl)-2-azaspiro[3.4]octan-2-yl)methanone

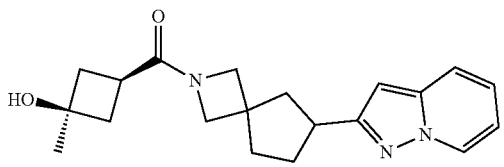 [SMILES: C[C@]1(O)C[C@@H](C(=O)N2CC3(CCC(c4cc5ccccn5n4)C3)C2)C1]

The title compound was prepared in a manner analogous to Example 109 using 2-chloropyrazolo[1,5-c]pyridine instead of 4-bromo-1-methyl-5-(trifluoromethyl)-1H-pyrazole in Step A. MS (ESI): mass calcd. for $C_{20}H_{25}N_3O_2$, 339.2; m/z found, 340.2 [M+H]$^+$. $^1$H NMR (400 MHz, CDCl$_3$) δ 8.39-8.33 (m, 1H), 7.45-7.40 (m, 1H), 7.09-7.03 (m, 1H), 6.71-6.66 (m, 1H), 6.27 (s, 1H), 4.07-3.89 (m, 5H), 3.47-3.34 (m, 1H), 2.72-2.62 (m, 1H), 2.43-1.88 (m, 10H), 1.35 (d, J=3.8 Hz, 3H).

Example 326

(rac)-((1s,3s)-3-Hydroxy-3-methylcyclobutyl)(6-(1-methyl-1H-indazol-4-yl)-2-azaspiro[3.4]octan-2-yl)methanone

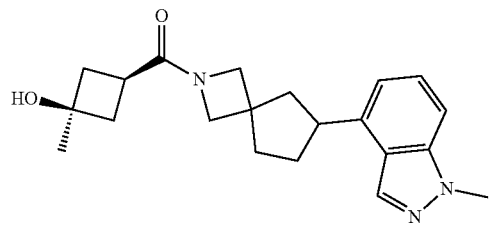 [SMILES: Cn1ncc2c(C3CCC4(C3)CN(C(=O)[C@H]3C[C@@](C)(O)C3)C4)cccc21]

The title compound was prepared in a manner analogous to Example 97 using (1-methyl-1H-indazol-4-yl)boronic acid instead of pyrazolo[1,5-c]pyridine-5-boronic acid pinacol ester and Pd(dppf)Cl$_2$ instead of XPhos Pd G2 in Step A. MS (ESI): mass calcd. for $C_{21}H_{27}N_3O_2$, 353.2; m/z found, 354.1 [M+H]$^+$. $^1$H NMR (400 MHz, CDCl$_3$) δ 8.02-7.96 (m, 1H), 7.37-7.30 (m, 1H), 7.27-7.23 (m, 1H), 6.99-6.93 (m, 1H), 4.13-3.92 (m, 8H), 3.62-3.49 (m, 1H), 2.74-2.64 (m, 1H), 2.48-1.90 (m, 10H), 1.40-1.32 (m, 3H).

Example 327

(rac)-((1s,3s)-3-Hydroxy-3-methylcyclobutyl)(6-(imidazo[1,2-c]pyridin-8-yl)-2-azaspiro[3.4]octan-2-yl)methanone

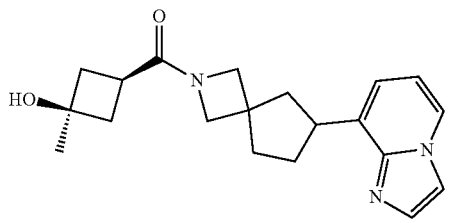 [SMILES: C[C@]1(O)C[C@@H](C(=O)N2CC3(CCC(c4cccn5ccnc45)C3)C2)C1]

The title compound was prepared in a manner analogous to Example 109 using 8-bromoimidazo[1,2-a]pyridine instead of 4-bromo-1-methyl-5-(trifluoromethyl)-1H-pyrazole and XPhos Pd G2 instead of CataCXium® A Pd G3 in Step A. MS (ESI): mass calcd. for $C_{20}H_{25}N_3O_2$, 339.2; m/z found, 340.2 [M+H]$^+$. $^1$H NMR (600 MHz, CDCl$_3$) δ 8.02 (dt, J=6.7, 1.3 Hz, 1H), 7.61 (d, J=1.3 Hz, 1H), 7.58 (dd, J=2.7, 1.3 Hz, 1H), 6.99-6.93 (m, 1H), 6.73 (dt, J=13.4, 6.9 Hz, 1H), 4.09-4.02 (m, 1H), 4.02-3.95 (m, 2H), 3.85 (s, 1H), 3.82-3.69 (m, 1H), 2.69 (tt, J=8.3, 6.1 Hz, 1H), 2.50-2.41 (m, 1H), 2.35-2.20 (m, 6H), 2.18-2.10 (m, 1H), 2.09-2.01 (m, 2H), 1.98-1.83 (m, 1H), 1.35 (d, J=3.5 Hz, 3H).

Example 328

(rac)-((1s,3s)-3-Hydroxy-3-methylcyclobutyl)(6-(imidazo[1,2-a]pyridin-7-yl)-2-azaspiro[3.4]octan-2-yl)methanone

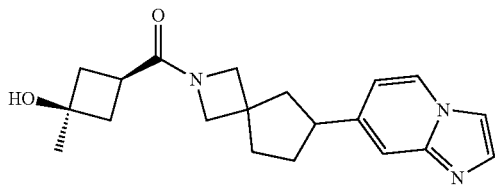 [SMILES: C[C@]1(O)C[C@@H](C(=O)N2CC3(CCC(c4ccn5ccnc5c4)C3)C2)C1]

The title compound was prepared in a manner analogous to Example 109 using 7-bromoimidazo[1,2-a]pyridine instead of 4-bromo-1-methyl-5-(trifluoromethyl)-1H-pyrazole in Step A. MS (ESI): mass calcd. for $C_{20}H_{25}N_3O_2$, 339.2; m/z found, 340.1 [M+H]$^+$. $^1$H NMR (400 MHz, CDCl$_3$) δ 8.10-8.02 (m, 1H), 7.59 (s, 1H), 7.52 (s, 1H), 7.40 (s, 1H), 6.67-6.61 (m, 1H), 4.09-3.86 (m, 5H), 3.24-3.08 (m, 1H), 2.73-2.62 (m, 1H), 2.41-1.88 (m, 9H), 1.82-1.70 (m, 1H), 1.36 (s, 3H).

Example 329

(rac)-((1s,3s)-3-Hydroxy-3-methylcyclobutyl)(6-(imidazo[1,5-a]pyridin-1-yl)-2-azaspiro[3.4]octan-2-yl)methanone

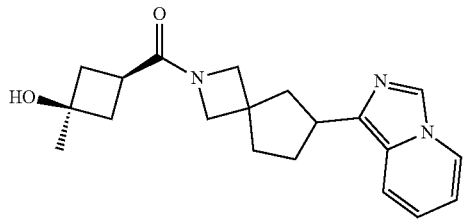 [SMILES: C[C@]1(O)C[C@@H](C(=O)N2CC3(CCC(c4ncn5ccccc45)C3)C2)C1]

The title compound was prepared in a manner analogous to Example 109 using 1-bromoimidazo[1,5-a]pyridine instead of 4-bromo-1-methyl-5-(trifluoromethyl)-1H-pyrazole in Step A. MS (ESI): mass calcd. for $C_{20}H_{25}N_3O_2$, 339.2; m/z found, 340.1 [M+H]$^+$. $^1$H NMR (400 MHz, CDCl$_3$) δ 8.04 (s, 1H), 7.84 (d, J=7.2 Hz, 1H), 7.42-7.34 (m, 1H), 6.67-6.58 (m, 1H), 6.55-6.47 (m, 1H), 4.15-3.85 (m, 5H), 3.60-3.43 (m, 1H), 2.79-2.68 (m, 1H), 2.40-1.94 (m, 10H), 1.37 (s, 3H).

Example 330

(rac)-((1s,3s)-3-Hydroxy-3-methylcyclobutyl)(6-(5,6,7,8-tetrahydroimidazo[1,5-a]pyridin-1-yl)-2-azaspiro[3.4]octan-2-yl)methanone

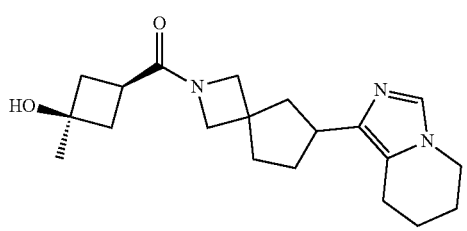 [SMILES: C[C@]1(O)C[C@@H](C(=O)N2CC3(CCC(c4ncn5c4CCCC5)C3)C2)C1]

Step A: tert-Butyl 6-(5,6,7,8-tetrahydroimidazo[1,5-c]pyridin-1-yl)-2-azaspiro[3.4]octane-2-carboxylate. tert-Butyl 6-(imidazo[1,5-c]pyridin-1-yl)-2-azaspiro[3.4]oct-6-ene-2-carboxylate (from Example 329, 200 mg, crude), MeOH (10 mL), ammonia hydrate (2 mL), and wet Pd/C (200 mg, 10 wt. %) were combined. The resultant mixture was stirred under H$_2$ (15 psi) at rt for 16 h. The suspension was filtered through a pad of Celite® and the pad was washed with MeOH. The filtrate was concentrated under reduced pressure to afford the title compound (200 mg, crude) as a yellow oil. MS (ESI): mass calcd. for $C_{19}H_{29}N_3O_2$, 331.2; m/z found, 332.1 [M+H]$^+$.

Step B: 1-(2-Azaspiro[3.4]octan-6-yl)-5,6,7,8-tetrahydroimidazo[1,5-a]pyridine. TFA (3 mL, 39.2 mmol) was added to a solution of tert-butyl 6-(5,6,7,8-tetrahydroimidazo[1,5-a]pyridin-1-yl)-2-azaspiro[3.4]octane-2-carboxylate (200 mg, 0.603 mmol) in DCM (6 mL). The reaction mixture was stirred at rt for 14 h before being concentrated under reduced pressure to afford the title compound (220 mg, TFA salt) as a yellow oil, which was used in the next step without further purification.

Step C: (rac)-((1s,3s)-3-Hydroxy-3-methylcyclobutyl)(6-(5,6,7,8-tetrahydroimidazo[1,5-a]pyridin-1-yl)-2-azaspiro[3.4]octan-2-yl)methanone. T$_3$P® (0.57 mL, 50% in EtOAc, 0.960 mmol) was added to a solution of 1-(2-azaspiro[3.4]octan-6-yl)-5,6,7,8-tetrahydroimidazo[1,5-a]pyridine (220 mg, crude), (1s,3s)-3-hydroxy-3-methylcyclobutanecarboxylic acid (80 mg, 0.620 mmol) and DIPEA (0.56 mL, 3.2 mmol) in DCM (6 mL). The reaction was stirred at rt for 1 h before being poured into H$_2$O and extracted with DCM. The combined organic extracts were dried over Na$_2$SO$_4$, filtered, and concentrated under reduced pressure. The resulting residue was purified by RP HPLC (22-52% CH$_3$CN in H$_2$O with 0.05% NH$_3$+10 mM NH$_4$HCO$_3$). The product was further subjected to SFC (Stationary phase: AD (250×30 mm); Mobile phase: 40% MeOH containing 0.1% of 25% aq. NH$_3$/CO$_2$) to provide the title compound (81 mg, 38% yield). MS (ESI): mass calcd. for $C_{20}H_{29}N_3O_2$, 343.2; m/z found, 344.4 [M+H]$^+$. $^1$H NMR (400 MHz, CDCl$_3$) δ 7.33-7.30 (m, 1H), 4.11-3.83 (m, 7H), 3.12-2.98 (m, 1H), 2.74-2.63 (m, 3H), 2.34-2.22 (m, 4H), 2.16-2.04 (m, 3H), 2.00-1.86 (m, 7H), 1.35 (s, 3H).

Example 331

(rac)-((1s,3s)-3-Hydroxy-3-methylcyclobutyl)(6-(4,5,6,7-tetrahydropyrazolo[1,5-a]pyridin-2-yl)-2-azaspiro[3.4]octan-2-yl)methanone

The title compound was recovered as a byproduct from the synthesis of (rac)-((1s,3s)-3-hydroxy-3-methylcyclobutyl)(6-(pyrazolo[1,5-a]pyridin-2-yl)-2-azaspiro[3.4]octan-2-yl)methanone (Example 325). MS (ESI): mass calcd. for $C_{20}H_{29}N_3O_2$, 343.2; m/z found, 344.1 [M+H]$^+$. $^1$H NMR (400 MHz, CDCl$_3$) δ 5.78-5.73 (m, 1H), 4.13-3.82 (m, 7H), 3.21-3.09 (m, 1H), 2.75 (t, J=6.4 Hz, 2H), 2.71-2.63 (m, 1H), 2.35-2.21 (m, 5H), 2.16-2.06 (m, 1H), 2.05-1.78 (m, 8H), 1.35 (s, 3H).

Example 332

(rac)-(6-(3-Cyclopropyl-4-methylphenoxy)-2-azaspiro[3.4]octan-2-yl)((1s,3s)-3-hydroxy-3-methylcyclobutyl)methanone

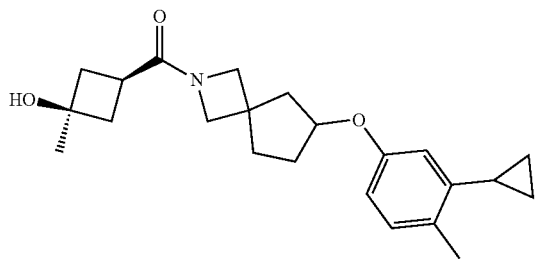 [SMILES: Cc1ccc(OC2CCC3(C2)CN(C(=O)[C@H]2C[C@@](C)(O)C2)C3)cc1C1CC1]

Step A: tert-Butyl 6-(3-bromo-4-methylphenoxy)-2-azaspiro[3.4]octane-2-carboxylate. PPh$_3$ (631 mg, 2.41 mmol) was added to a solution of 3-bromo-4-methylphenol (300 mg, 1.60 mmol) and tert-butyl 6-hydroxy-2-azaspiro[3.4]octane-2-carboxylate (365 mg, 1.60 mmol) in THF (12 mL) under N$_2$. The reaction was cooled to 0° C. before DIAD (0.48 mL, 2.41 mmol) was added. The resultant mixture was stirred at rt for 16 hours before being poured into water and extracted with EtOAc. The combined organic layers were washed with brine, dried over Na$_2$SO$_4$, filtered, and concentrated under reduced pressure. The resulting residue was purified by FCC (SiO$_2$, 10-25% EtOAc in ether) to afford the title compound (200 mg, 31% yield) as an oil. MS (ESI): mass calcd. for C$_{19}$H$_{26}$BrNO$_3$, 395.1; m/z found, 340.1 [M+2H-tBu]$^+$.

Step B: tert-Butyl 6-(3-cyclopropyl-4-methylphenoxy)-2-azaspiro[3.4]octane-2-carboxylate. A solution of tert-butyl 6-(3-bromo-4-methylphenoxy)-2-azaspiro[3.4]octane-2-carboxylate (200 mg, 0.505 mmol), cyclopropylboronic acid (173 mg, 2.00 mmol) and K$_3$PO$_4$ (428 mg, 2.00 mmol) in 1,4-dioxane (5 mL) and H$_2$O (1 mL) was sparged with Ar for 5 min, then treated with Pd(dppf)Cl$_2$·CH$_2$Cl$_2$ (41 mg, 0.050 mmol). The resultant mixture was sparged with Ar for another 5 min, then stirred at 100° C. for 2 h before cooling to rt. The suspension was filtered through a pad of Celite® and the pad was washed with EtOAc. The filtrate was diluted with water and extracted with EtOAc. The combined organic extracts were dried over Na$_2$SO$_4$, filtered, and concentrated under reduced pressure. The resulting residue was purified by FCC (SiO$_2$, 10-20% EtOAc in ether) to afford the title compound (120 mg, 66% yield) as a yellow oil. MS (ESI): mass calcd. for C$_{22}$H$_{31}$NO$_3$, 357.2; m/z found, 302.2 [M+2H-tBu]$^+$.

Step C: 6-(3-Cyclopropyl-4-methylphenoxy)-2-azaspiro[3.4]octane. TFA (1 mL, 13.1 mmol) was added to a solution of tert-butyl 6-(3-cyclopropyl-4-methylphenoxy)-2-azaspiro[3.4]octane-2-carboxylate (120 mg, 0.336 mmol) in DCM (3 mL). The resultant mixture was stirred at rt for 24 h. The mixture was concentrated to give the title compound (100 mg, TFA salt), which was used in the next step without further purification. MS (ESI): mass calcd. for C$_{17}$H$_{23}$NO, 257.2; m/z found, 258.2 [M+H]$^+$.

Step D: (rac)-(6-(3-Cyclopropyl-4-methylphenoxy)-2-azaspiro[3.4]octan-2-yl)((1s,3s)-3-hydroxy-3-methylcyclobutyl)methanone. T$_3$P® (0.3 mL, 50% in EtOAc, 0.470 mmol) was added to a solution of 6-(3-cyclopropyl-4-methylphenoxy)-2-azaspiro[3.4]octane (100 mg, 0.270 mmol, TFA salt), (1s,3s)-3-hydroxy-3-methylcyclobutanecarboxylic acid (51 mg, 0.392 mmol) and DIPEA (0.3 mL, 1.81 mmol) in CH$_2$Cl$_2$ (5 mL). The resultant mixture was stirred at rt for 12 h. The reaction mixture was poured into H$_2$O and extracted with EtOAc. The combined organic extracts were dried over Na$_2$SO$_4$, filtered, and concentrated under reduced pressure. The resulting residue was purified by RP HPLC (55-85% CH$_3$CN in H$_2$O with 0.225% HCOOH). The title compound was further subjected to SFC (Stationary phase: OJ-H (250 mm×30 mm); Mobile phase: 20% MeOH containing 0.1% of 25% aq. NH$_3$/CO$_2$) to afford the title compound (20 mg, 25% yield). MS (ESI): mass calcd. for C$_{23}$H$_{31}$NO$_3$, 369.2; m/z found, 370.1 [M+H]$^+$. $^1$H NMR (400 MHz, CDCl$_3$) δ 7.09-6.97 (m, 1H), 6.61-6.50 (m, 1H), 6.45 (s, 1H), 4.76 (s, 1H), 4.19-3.87 (m, 4H), 2.72-2.58 (m, 1H), 2.43-2.33 (m, 3H), 2.31-2.25 (m, 3H), 2.22-1.99 (m, 5H), 1.98-1.80 (m, 3H), 1.35 (s, 3H), 1.03-0.84 (m, 2H), 0.69-0.53 (m, 2H).

Example 333

(rac)-(6-(3-Cyclopropyl-2-methylphenoxy)-2-azaspiro[3.4]octan-2-yl)((1s,3s)-3-hydroxy-3-methylcyclobutyl)methanone

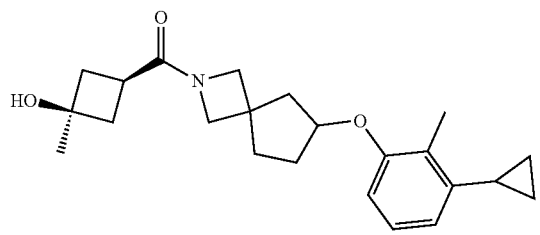 [SMILES: Cc1c(OC2CCC3(C2)CN(C(=O)[C@H]2C[C@@](C)(O)C2)C3)cccc1C1CC1]

The title compound was prepared in a manner analogous to Example 332 using 3-bromo-2-methylphenol instead of 3-bromo-4-methylphenol in Step A. MS (ESI): mass calcd. for C$_{23}$H$_{31}$NO$_3$, 369.2; m/z found, 370.2 [M+H]$^+$. $^1$H NMR (400 MHz, CDCl$_3$) δ 7.11-6.98 (m, 1H), 6.68-6.58 (m, 2H), 4.85-4.76 (m, 1H), 4.17-4.03 (m, 1H), 4.03-3.90 (m, 3H), 2.69-2.64 (m, 1H), 2.36-2.22 (m, 8H), 2.21-2.03 (m, 3H), 2.03-1.95 (m, 1H), 1.95-1.83 (m, 2H), 1.35 (s, 3H), 0.96-0.85 (m, 2H), 0.66-0.58 (m, 2H).

Example 334

(rac)-(6-(3-Cyclopropyl-2-fluorophenoxy)-2-azaspiro[3.4]octan-2-yl)((1s,3s)-3-hydroxy-3-methylcyclobutyl)methanone

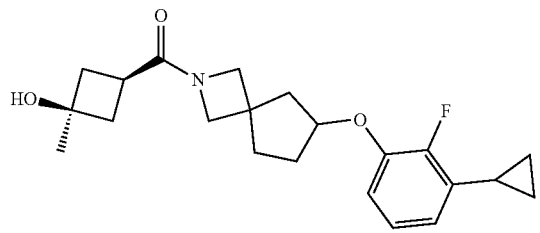 [SMILES: C[C@]1(O)C[C@@H](C(=O)N2CC3(CCC(Oc4cccc(C5CC5)c4F)C3)C2)C1]

The title compound was prepared in a manner analogous to Example 332 using 3-bromo-2-fluorophenol instead of 3-bromo-4-methylphenol in Step A. MS (ESI): mass calcd.

for C$_{22}$H$_{28}$FNO$_3$, 373.2; m/z found, 374.2 [M+H]$^+$. $^1$H NMR (400 MHz, CDCl$_3$) δ 6.98-6.84 (m, 1H), 6.75-6.63 (m, 1H), 6.51-6.38 (m, 1H), 4.89-4.75 (m, 1H), 4.22-3.86 (m, 4H), 2.73-2.60 (m, 1H), 2.33-2.24 (m, 5H), 2.23-2.14 (m, 1H), 2.13-2.06 (m, 2H), 2.06-1.95 (m, 2H), 1.95-1.83 (m, 1H), 1.42-1.31 (m, 3H), 1.02-0.93 (m, 2H), 0.75-0.66 (m, 2H).

Example 335

(rac)-(6-(3-Cyclopropyl-4-fluorophenoxy)-2-azaspiro[3.4]octan-2-yl)((1s,3s)-3-hydroxy-3-methylcyclobutyl)methanone

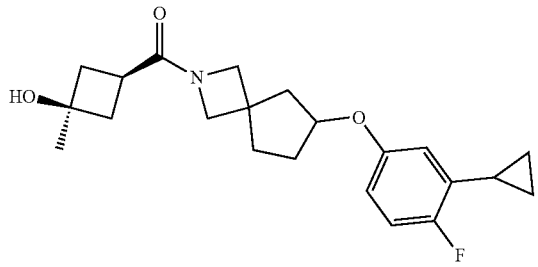 [SMILES: C[C@]1(O)C[C@@H](C(=O)N2CC3(CCC(Oc4ccc(F)c(C5CC5)c4)C3)C2)C1]

The title compound was prepared in a manner analogous to Example 332 using 3-bromo-4-fluorophenol instead of 3-bromo-4-methylphenol in Step A. MS (ESI): mass calcd. for C$_{22}$H$_{28}$FNO$_3$, 373.2; m/z found, 374.1 [M+H]$^+$. $^1$H NMR (400 MHz, CDCl$_3$) δ 6.94-6.82 (m, 1H), 6.57-6.47 (m, 1H), 6.32 (dd, J=6.1, 3.0 Hz, 1H), 4.71 (s, 1H), 4.10-3.86 (m, 4H), 2.71-2.59 (m, 1H), 2.32-2.25 (m, 4H), 2.19-2.02 (m, 5H), 1.95-1.82 (m, 2H), 1.35 (s, 3H), 1.02-0.92 (m, 2H), 0.69 (m, 2H).

Example 336

(rac)-((1s,3s)-3-Hydroxy-3-methylcyclobutyl)(6-((5-methyl-6-(trifluoromethyl)pyridin-2-yl)oxy)-2-azaspiro[3.4]octan-2-yl)methanone

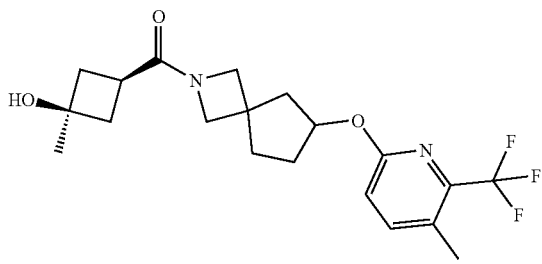 [SMILES: Cc1ccc(OC2CCC3(C2)CN(C(=O)[C@H]2C[C@@](C)(O)C2)C3)nc1C(F)(F)F]

The title compound was prepared in a manner analogous to Example 309 using tert-butyl 6-hydroxy-2-azaspiro[3.4]octane-2-carboxylate instead of tert-butyl 6-hydroxy-2-azaspiro[3.3]heptane-2-carboxylate and 6-chloro-3-methyl-2-(trifluoromethyl)pyridine instead of 6-chloro-2-methyl-3-(trifluoromethyl)pyridine in Step A. MS (ESI): mass calcd. for C$_{20}$H$_{25}$F$_3$N$_2$O$_3$, 398.2; m/z found, 399.2 [M+H]$^+$. $^1$H NMR (400 MHz, CDCl$_3$) δ 7.47 (dd, J=8.4, 3.4 Hz, 1H), 6.73 (d, J=8.4 Hz, 1H), 5.46-5.36 (m, 1H), 4.07-3.86 (m, 5H), 2.70-2.60 (m, 1H), 2.41-2.35 (m, 3H), 2.34-2.23 (m, 4H), 2.23-2.04 (m, 4H), 1.92-1.79 (m, 2H), 1.34 (s, 3H).

Example 337

((1s,3*S)-3-Hydroxy-3-methylcyclobutyl)((*R)-6-((*R)-1-phenylethyl)-2-azaspiro[3.4]octan-2-yl)methanone

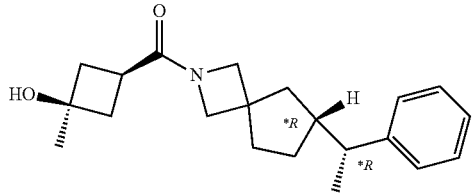 [SMILES: C[C@@H](c1ccccc1)[C@@H]1CCC2(C1)CN(C(=O)[C@H]1C[C@@](C)(O)C1)C2]

The title compound was prepared in a manner analogous to Example 97 using 4,4,5,5-tetramethyl-2-(1-phenylvinyl)-1,3,2-dioxaborolane instead of pyrazolo[1,5-a]pyridine-5-boronic acid pinacol ester and Pd(dppf)Cl$_2$ instead of XPhos Pd G2 in Step A. The final racemic compound was separated via chiral SFC (Stationary phase: OJ-H (3×25 cm); Mobile phase: 10% EtOH/CO$_2$; Rt=1.59 min) to provide the title compound. MS (ESI): mass calcd. for C$_{21}$H$_{29}$NO$_2$, 327.2; m/z found, 328.3 [M+H]$^+$. $^1$H NMR (400 MHz, CDCl$_3$) δ 7.33-7.27 (m, 2H), 7.23-7.12 (m, 3H), 3.91-3.68 (m, 5H), 2.66-2.57 (m, 1H), 2.48-2.38 (m, 1H), 2.32-1.78 (m, 8H), 1.68-1.63 (m, 1H), 1.43-1.28 (m, 5H), 1.25 (d, J=6.9 Hz, 3H).

Example 338

((1s,3*R)-3-Hydroxy-3-methylcyclobutyl)((*S)-6-((*R)-1-phenylethyl)-2-azaspiro[3.4]octan-2-yl)methanone

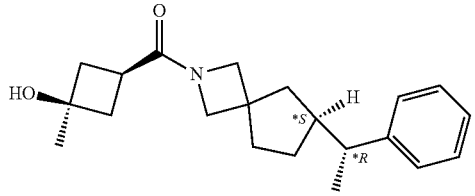 [SMILES: C[C@@H](c1ccccc1)[C@H]1CCC2(C1)CN(C(=O)[C@H]1C[C@@](C)(O)C1)C2]

The title compound was prepared in a manner analogous to Example 97 using 4,4,5,5-tetramethyl-2-(1-phenylvinyl)-1,3,2-dioxaborolane instead of pyrazolo[1,5-c]pyridine-5-boronic acid pinacol ester and Pd(dppf)Cl$_2$ instead of XPhos Pd G2 in Step A. The final racemic compound was separated via chiral SFC (Stationary phase: OJ-H (3×25 cm); Mobile phase: 10% EtOH/CO$_2$; Rt=1.86 min) to provide the title compound. MS (ESI): mass calcd. for C$_{21}$H$_{29}$NO$_2$, 327.2; m/z found, 328.2 [M+H]$^+$. $^1$H NMR (400 MHz, CDCl$_3$) δ 7.34-7.27 (m, 2H), 7.23-7.10 (m, 3H), 4.05-3.77 (m, 5H), 2.71-2.62 (m, 1H), 2.51-2.41 (m, 1H), 2.36-2.22 (m, 4H), 2.19-2.01 (m, 2H), 1.85-1.73 (m, 2H), 1.60-1.41 (m, 2H), 1.35 (s, 3H), 1.25 (d, J=6.9 Hz, 3H), 1.22-1.11 (m, 1H).

Example 339

((1s,3*R)-3-Hydroxy-3-methylcyclobutyl)((*S)-6-((*S)-1-phenylethyl)-2-azaspiro[3.4]octan-2-yl)methanone

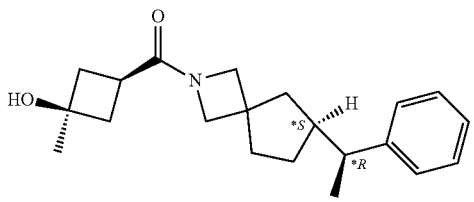 [SMILES: C[C@H](c1ccccc1)[C@H]1CCC2(C1)CN(C(=O)[C@H]1C[C@@](C)(O)C1)C2]

The title compound was prepared in a manner analogous to Example 97 using 4,4,5,5-tetramethyl-2-(1-phenylvinyl)-1,3,2-dioxaborolane instead of pyrazolo[1,5-a]pyridine-5-boronic acid pinacol ester and Pd(dppf)Cl$_2$ instead of XPhos Pd G2 in Step A. The final racemic compound was separated via chiral SFC (Stationary phase: OJ-H (3×25 cm); Mobile phase: 10% EtOH/CO$_2$; Rt=2.01 min) to provide the title compound. MS (ESI): mass calcd. for C$_{21}$H$_{29}$NO$_2$, 327.2; m/z found, 328.1 [M+H]$^+$. $^1$H NMR (400 MHz, CDCl$_3$) δ 7.32-7.27 (m, 2H), 7.22-7.12 (m, 3H), 4.04-3.76 (m, 5H), 2.71-2.62 (m, 1H), 2.51-2.41 (m, 1H), 2.35-2.21 (m, 4H), 2.19-2.01 (m, 2H), 1.86-1.73 (m, 2H), 1.59-1.40 (m, 2H), 1.35 (s, 3H), 1.25 (d, J=7.0 Hz, 3H), 1.22-1.12 (m, 1H).

Example 340

(7-Fluoro-7-phenyl-2-azaspiro[3.5]nonan-2-yl)((1s,3s)-3-hydroxy-3-methylcyclobutyl)methanone

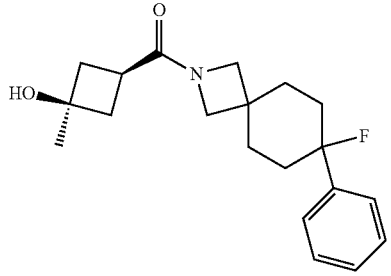 [SMILES: C[C@]1(O)C[C@@H](C(=O)N2CC3(CCC(F)(c4ccccc4)CC3)C2)C1]

Step A: tert-Butyl 7-fluoro-7-phenyl-2-azaspiro[3.5]nonane-2-carboxylate. In an oven-dried flask under N$_2$, tert-butyl 7-hydroxy-7-phenyl-2-azaspiro[3.5]nonane-2-carboxylate (intermediate from Example 37, 49 mg, 0.154 mmol) was taken up in DCM (1.5 mL) and cooled to −78° C. To this was added diethylaminosulfur trifluoride (25 μL, 0.185 mmol) and the resulting solution was stirred at −78° C. for 30 min, then allowed to warm to rt and stirred 1 h. The reaction was quenched with sat. aq. NaHCO$_3$ and filtered through a Bond Elut™ filter with DCM. Purification by FCC (SiO$_2$, 0-15% EtOAc in hexanes) provided the title compound (11 mg, 22% yield). MS (ESI): mass calcd. for C$_{19}$H$_{26}$FNO$_2$, 319.2; m/z found, 264.2 [M+2H-tBu]$^+$.

Step B: 7-Fluoro-7-phenyl-2-azaspiro[3.5]nonane. tert-Butyl 7-fluoro-7-phenyl-2-azaspiro[3.5]nonane-2-carboxylate (11 mg, 0.034 mmol) was taken up in DCM (0.23 mL). 2,6-Dimethylpyridine (8.0 μL, 0.069 mmol) and trimethylsilyl trifluoromethanesulfonate (13 μL, 0.069 mmol) were added and the reaction was stirred at rt for 1.5 h. The reaction was concentrated under a stream of N$_2$ at rt and carried on without purification. MS (ESI): mass calcd. for C$_{14}$H$_{18}$FN, 219.1; m/z found, 220.2 [M+H]$^+$.

Step C: (7-Fluoro-7-phenyl-2-azaspiro[3.5]nonan-2-yl)((1s,3s)-3-hydroxy-3-methylcyclobutyl)methanone. 7-Fluoro-7-phenyl-2-azaspiro[3.5]nonane (7.5 mg, 0.034 mmol) and (1s,3s)-3-hydroxy-3-methylcyclobutanecarboxylic acid (4.7 mg, 0.036 mmol) were taken up in DMF (0.34 mL). To this was added DIPEA (30 μL, 0.171 mmol) and HATU (14 mg, 0.036 mmol) and the reaction was stirred at rt for 30 min. The reaction mixture was filtered through a PTFE filter with MeOH and purified by RP HPLC (5-95% ACN in water containing 20 mM NH$_4$OH) provided the title compound (7 mg, 62% yield). MS (ESI): mass calcd. for C$_{20}$H$_{26}$FNO$_2$, 331.2; m/z found, 332.2 [M+H]$^+$. $^1$H NMR (500 MHz, CDCl$_3$) δ 7.40-7.32 (m, 4H), 7.34-7.26 (m, 1H), 3.90-3.72 (m, 5H), 2.75-2.65 (m, 1H), 2.36-2.24 (m, 4H), 2.10-1.97 (m, 4H), 1.91-1.72 (m, 4H), 1.36 (s, 3H).

Example 341

(7-Fluoro-7-(1-methyl-1H-pyrrolo[2,3-b]pyridin-6-yl)-2-azaspiro[3.5]nonan-2-yl)((1s,3s)-3-hydroxy-3-methylcyclobutyl)methanone

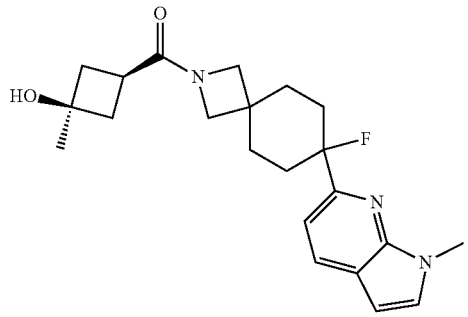 [SMILES: Cn1ccc2ccc(C3(F)CCC4(CC3)CN(C(=O)[C@H]3C[C@@](C)(O)C3)C4)nc21]

Step A: tert-Butyl 7-hydroxy-7-(1-methyl-1H-pyrrolo[2,3-b]pyridin-6-yl)-2-azaspiro[3.5]nonane-2-carboxylate.
n-BuLi (2.5 M in THF, 2.8 mL, 7.10 mmol) was added dropwise to a −70° C. solution of 6-bromo-1-methyl-1H-pyrrolo[2,3-b]pyridine (Intermediate 44, 1.0 g, 4.70 mmol) in THF (15 mL) under N$_2$. The reaction mixture was stirred for 30 min then treated with tert-butyl 7-oxo-2-azaspiro[3.5]nonane-2-carboxylate (1.1 g, 4.70 mmol) in THF (5 mL) at −70° C. The resultant mixture was stirred at −70° C. for 2 h before being quenched with sat. aq. NH$_4$Cl and extracted with EtOAc. The combined organic extracts were washed with brine, dried over Na$_2$SO$_4$, filtered, and concentrated under reduced pressure. The resulting residue was purified by FCC (SiO$_2$, 0-50% EtOAc in ether) to afford the title compound (1.5 g, 80% yield) as a colorless oil. MS (ESI): mass calcd. for C$_{21}$H$_{29}$N$_3$O$_3$, 371.2; m/z found, 372.5 [M+H]$^+$.

Step B: tert-Butyl 7-fluoro-7-(1-methyl-1H-pyrrolo[2,3-b]pyridin-6-yl)-2-azaspiro[3.5]nonane-2-carboxylate.
Diethylaminosulfur trifluoride (0.36 mL, 2.69 mmol) was added portionwise to a 0° C. solution of tert-butyl 7-hydroxy-7-(1-methyl-1H-pyrrolo[2,3-b]pyridin-6-yl)-2-azaspiro[3.5]nonane-2-carboxylate (500 mg, 1.35 mmol) in DCM (10 mL). The resultant mixture was stirred for 2 h with gradual warming to rt before being quenched with sat. aq.

NaHCO$_3$ and extracted with DCM. The combined organic extracts were washed with brine, dried over Na$_2$SO$_4$, filtered, and concentrated under reduced pressure. The resulting residue was purified by FCC (SiO$_2$, 10-50% EtOAc in ether) to afford the title compound (240 mg, 44% yield) as a white oil. MS (ESI): mass calcd. for C$_{21}$H$_{28}$FN$_3$O$_2$, 373.2; m/z found, 374.5 [M+H]$^+$.

Step C: 6-(7-Fluoro-2-azaspiro[3.5]nonan-7-yl)-1-methyl-1H-pyrrolo[2,3-b]pyridine. TFA (0.40 mL, 5.40 mmol) was added to a solution of tert-butyl 7-fluoro-7-(1-methyl-1H-pyrrolo[2,3-b]pyridin-6-yl)-2-azaspiro[3.5]nonane-2-carboxylate (240 mg, 0.643 mmol) in DCM (4 mL). The reaction mixture was stirred at rt for 30 min before being concentrated under reduced pressure to give the title compound (240 mg), which was used in the next step without further purification. MS (ESI): mass calcd. for C$_{16}$H$_{20}$FN$_3$, 273.2; m/z found, 274.0 [M+H]$^+$.

Step D: (7-Fluoro-7-(1-methyl-1H-pyrrolo[2,3-b]pyridin-6-yl)-2-azaspiro[3.5]nonan-2-yl)((1s,3s)-3-hydroxy-3-methylcyclobutyl)methanone. T$_3$P® (0.37 mL, 50% in EtOAc, 0.620 mmol) was added to solution of 6-(7-fluoro-2-azaspiro[3.5]nonan-7-yl)-1-methyl-1H-pyrrolo[2,3-b]pyridine (240 mg, 0.620 mmol), (1s,3s)-3-hydroxy-3-methylcyclobutanecarboxylic acid (81 mg, 0.620 mmol) and TEA (0.86 mL, 6.20 mmol) in DCM (5 mL). The resultant mixture was stirred at rt for 2 h then poured into H$_2$O and extracted with DCM. The combined organic extracts were dried over Na$_2$SO$_4$, filtered, and concentrated under reduced pressure. The resulting residue was purified by RP HPLC (41-71% CH$_3$CN in H$_2$O with 0.225% HCOOH) to afford the title compound (20 mg, 8% yield) as a white solid. MS (ESI): mass calcd. for C$_{22}$H$_{28}$FN$_3$O$_2$, 385.2; m/z found, 386.2 [M+H]$^+$. $^1$H NMR (400 MHz, CDCl$_3$) δ 7.93-7.84 (m, 1H), 7.33-7.27 (m, 1H), 7.18-7.15 (m, 1H), 6.44-6.40 (m, 1H), 3.92 (s, 1H), 3.88-3.79 (m, 6H), 3.75 (s, 1H), 2.81-2.66 (m, 1H), 2.39-2.14 (m, 6H), 2.08-1.95 (m, 4H), 1.93-1.83 (m, 2H), 1.35 (s, 3H).

Example 342

((1s,3s)-3-Hydroxy-3-methylcyclobutyl)(7-methoxy-7-phenyl-2-azaspiro[3.5]nonan-2-yl)methanone

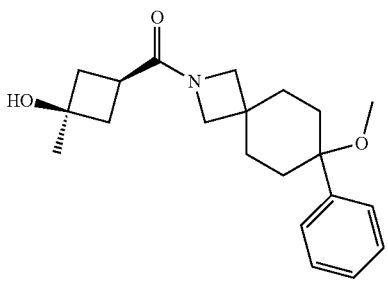 [SMILES: COC1(c2ccccc2)CCC2(CC1)CN(C(=O)[C@H]1C[C@@](C)(O)C1)C2]

The title compound was prepared in a manner analogous to Example 270 using tert-butyl 7-oxo-2-azaspiro[3.5]nonane-2-carboxylate instead of tert-butyl 6-oxo-2-azaspiro[3.3]heptane-2-carboxylate and phenylmagnesium bromide instead of benzylmagnesium chloride in Step A. MS (ESI): mass calcd. for C$_{21}$H$_{29}$NO$_3$, 343.2; m/z found, 344.3 [M+H]$^+$. $^1$H NMR (400 MHz, CDCl$_3$) δ 7.40-7.32 (m, 4H), 7.30-7.24 (m, 1H), 4.06 (d, J=13.4 Hz, 1H), 3.77 (d, J=11.0 Hz, 2H), 3.72 (d, J=6.4 Hz, 2H), 2.94 (d, J=1.3 Hz, 3H), 2.73-2.61 (m, 1H), 2.33-2.23 (m, 4H), 2.08-1.85 (m, 4H), 1.78-1.56 (m, 4H), 1.35 (d, J=4.1 Hz, 3H).

Example 343

((1s,3s)-3-Hydroxy-3-methylcyclobutyl)(7-methoxy-7-(o-tolyl)-2-azaspiro[3.5]nonan-2-yl)methanone

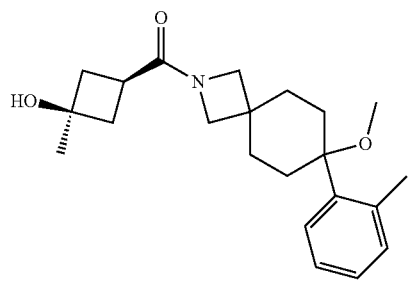 [SMILES: COC1(c2ccccc2C)CCC2(CC1)CN(C(=O)[C@H]1C[C@@](C)(O)C1)C2]

The title compound was prepared in a manner analogous to Example 270 using tert-butyl 7-oxo-2-azaspiro[3.5]nonane-2-carboxylate instead of tert-butyl 6-oxo-2-azaspiro[3.3]heptane-2-carboxylate and o-tolylmagnesium bromide instead of benzylmagnesium chloride in Step A. MS (ESI): mass calcd. for C$_{22}$H$_{31}$NO$_3$, 357.2; m/z found, 358.3 [M+H]$^+$. $^1$H NMR (400 MHz, CDCl$_3$) δ 7.23-7.10 (m, 4H), 4.03 (s, 1H), 3.80-3.67 (m, 4H), 2.93 (d, J=1.7 Hz, 3H), 2.73-2.63 (m, 1H), 2.54 (d, J=2.2 Hz, 3H), 2.34-2.18 (m, 6H), 2.07-1.90 (m, 2H), 1.78-1.69 (m, 2H), 1.68-1.51 (m, 2H), 1.35 (d, J=4.3 Hz, 3H).

Example 344

(7-(3,5-Dimethylphenyl)-7-methoxy-2-azaspiro[3.5]nonan-2-yl)((1s,3s)-3-hydroxy-3-methylcyclobutyl)methanone

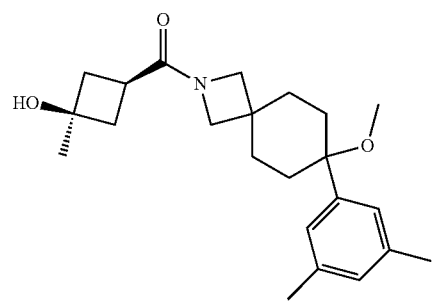 [SMILES: COC1(c2cc(C)cc(C)c2)CCC2(CC1)CN(C(=O)[C@H]1C[C@@](C)(O)C1)C2]

Step A: tert-Butyl 7-(3,5-dimethylphenyl)-7-hydroxy-2-azaspiro[3.5]nonane-2-carboxylate. (3,5-Dimethylphenyl)magnesium bromide (8.4 mL, 0.5 M in THF, 4.18 mmol) was added dropwise to a 0° C. solution of tert-butyl 7-oxo-2-azaspiro[3.5]nonane-2-carboxylate (500 mg, 2.09 mmol) in THF (10 mL) under N$_2$. The resultant mixture was stirred at 0° C. for 3 h before being quenched with sat. aq. NH$_4$Cl and extracted with EtOAc. The combined organic extracts were washed with brine, dried over Na$_2$SO$_4$, filtered, and concentrated under reduced pressure. The resulting residue was purified by FCC (SiO$_2$, 0-25% EtOAc in ether) to afford the title compound (400 mg, 55% yield) as a yellow oil. MS (ESI): mass calcd. for C$_{21}$H$_{31}$NO$_3$, 345.2; m/z found, 290.2 [M+2H-tBu]$^+$.

Step B: tert-Butyl 7-(3,5-dimethylphenyl)-7-methoxy-2-azaspiro[3.5]nonane-2-carboxylate. LiHMDS (5.8 mL, 1 M in THF, 5.80 mmol) was added to a 0° C. solution of tert-butyl 7-(3,5-dimethylphenyl)-7-hydroxy-2-azaspiro[3.5]nonane-2-carboxylate (400 mg, 1.16 mmol) in THF (10 mL) under N$_2$. The reaction mixture was stirred for 30 min at 0° C. before iodomethane (0.36 mL, 5.79 mmol) was added dropwise. The reaction mixture was stirred for 16 h at 60° C. After cooling to rt, the reaction mixture was poured into sat. aq. NH$_4$Cl and extracted with EtOAc. The combined organic extracts were dried over Na$_2$SO$_4$, filtered, and concentrated under reduced pressure. The resulting residue was purified by FCC (SiO$_2$, 0-20% EtOAc in ether). The title compound was subjected to RP HPLC (70-95% ACN in water with 0.225% HCOOH) to afford the title compound (90 mg, 26% yield). MS (ESI): mass calcd. for C$_{22}$H$_{33}$NO$_3$, 359.2; m/z found, 304.1 [M+2H-tBu]$^+$. $^1$H NMR (400 MHz, CDCl$_3$) δ 7.00 (s, 2H), 6.93 (s, 1H), 3.65 (d, J=11.8 Hz, 4H), 2.97 (s, 3H), 2.34 (s, 6H), 2.04-1.88 (m, 4H), 1.79-1.63 (m, 4H), 1.47 (s, 9H).

Step C: 7-(3,5-Dimethylphenyl)-7-methoxy-2-azaspiro[3.5]nonane. Trimethylsilyl trifluoromethanesulfonate (91 µL, 0.501 mmol) was added to a solution of tert-butyl dimethylphenyl)-7-methoxy-2-azaspiro[3.5]nonane-2-carboxylate (90 mg, 0.250 mmol) and 2,6-dimethylpyridine (58 µL, 0.501 mmol) in DCM (2 mL). The reaction mixture was stirred at rt for 1 hour before being concentrated under reduced pressure to give the title compound (70 mg, crude) as a yellow oil, which was used in the next step without further purification. MS (ESI): mass calcd. for C$_{17}$H$_{25}$NO, 259.2; m/z found, 260.2 [M+H]$^+$.

Step D: (7-(3,5-Dimethylphenyl)-7-methoxy-2-azaspiro[3.5]nonan-2-yl)((1s,3s)-3-hydroxy-3-methylcyclobutyl)methanone. T$_3$P® (0.24 mL, 50% in EtOAc, 0.403 mmol) was added to a 0° C. solution of 7-(3,5-dimethylphenyl)-7-methoxy-2-azaspiro[3.5]nonane (70 mg, crude), (1s,3s)-3-hydroxy-3-methylcyclobutanecarboxylic acid (35 mg, 0.269 mmol) and TEA (0.44 mL, 3.23 mmol) in DCM (3 mL). The resultant mixture was stirred for 1 hour with gradual warming to rt. The mixture was poured into water and extracted with DCM. The combined organic extracts were dried over Na$_2$SO$_4$, filtered, and concentrated under reduced pressure. The resulting residue was purified by RP HPLC (51-81% ACN in water with 0.225% HCOOH) to afford the title compound (26 mg, 25% yield) as a white solid. MS (ESI): mass calcd. for C$_{23}$H$_{33}$NO$_3$, 371.2; m/z found, 372.3 [M+H]$^+$. $^1$H NMR (400 MHz, DMSO-d$_6$) δ 6.97 (s, 2H), 6.88 (s, 1H), 3.80-3.46 (m, 4H), 2.84 (d, J=5.8 Hz, 3H), 2.58-2.52 (m, 1H), 2.26 (s, 6H), 2.13-2.05 (m, 2H), 2.03-1.96 (m, 2H), 1.88-1.73 (m, 4H), 1.68-1.60 (m, 4H), 1.23 (d, J=4.3 Hz, 3H).

Example 345

((1s,3s)-3-Hydroxy-3-methylcyclobutyl)(7-(3-(1-methyl-1H-imidazol-4-yl)phenyl)-2-azaspiro[3.5]nonan-2-yl)methanone

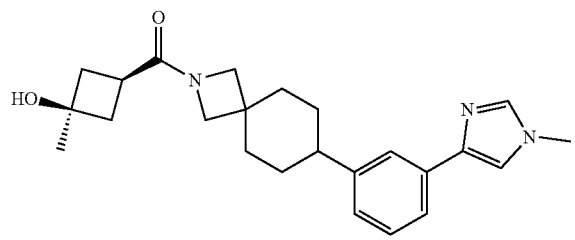 [SMILES: Cn1cnc(-c2cccc(C3CCC4(CC3)CN(C(=O)[C@H]3C[C@@](C)(O)C3)C4)c2)c1]

The title compound was prepared in a manner analogous to Example 109 using 4-(3-bromophenyl)-1-methyl-1H-imidazole (Intermediate 57) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for C$_{24}$H$_{31}$N$_3$O$_2$, 393.2; m/z found, 394.2 [M+H]$^+$. $^1$H NMR (400 MHz, CDCl$_3$) δ 7.72-7.65 (m, 1H), 7.57-7.48 (m, 2H), 7.33-7.29 (m, 1H), 7.21-7.18 (m, 1H), 7.10-7.04 (m, 1H), 3.86-3.70 (m, 7H), 2.78-2.67 (m, 1H), 2.59-2.49 (m, 1H), 2.39-2.26 (m, 4H), 2.05-1.99 (m, 2H), 1.96-1.90 (m, 2H), 1.68-1.48 (m, 4H), 1.38 (d, J=6.3 Hz, 3H).

Example 346

(7-(4-(1H-Pyrazol-1-yl)phenyl)-2-azaspiro[3.5]nonan-2-yl)((1s,3s)-3-hydroxy-3-methylcyclobutyl)methanone

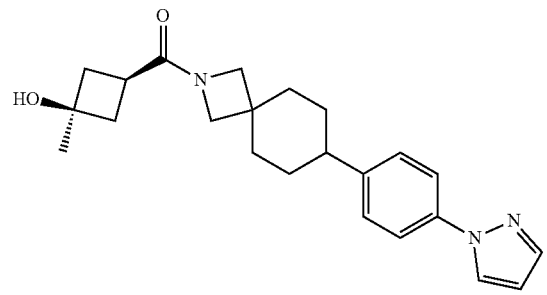 [SMILES: C[C@]1(O)C[C@@H](C(=O)N2CC3(CCC(c4ccc(-n5cccn5)cc4)CC3)C2)C1]

The title compound was prepared in a manner analogous to Example 97 using [4-(1H-pyrazol-1-yl)phenyl]boronic acid instead of pyrazolo[1,5-a]pyridine-5-boronic acid pinacol ester and tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7) in Step A. MS (ESI): mass calcd. for C$_{23}$H$_{29}$N$_3$O$_2$, 379.2; m/z found, 380.3 [M+H]$^+$. $^1$H NMR (600 MHz, CDCl$_3$) δ 7.90-7.88 (m, 1H), 7.71 (t, J=1.9 Hz, 1H), 7.63-7.60 (m, 2H), 7.26-7.23 (m, 2H), 6.47-6.43 (m, 1H), 3.85 (s, 1H), 3.79 (s, 1H), 3.75 (s, 2H), 3.70 (s, 1H), 2.77-2.66 (m, 1H), 2.58-2.47 (m, 1H), 2.36-2.29 (m, 2H), 2.29-2.22 (m, 2H), 2.05-1.99 (m, 2H), 1.94-1.85 (m, 2H), 1.70-1.58 (m, 2H), 1.52-1.37 (m, 2H), 1.36 (d, J=3.4 Hz, 3H).

Example 347

(7-(3-(1H-Pyrazol-1-yl)phenyl)-2-azaspiro[3.5]nonan-2-yl)((1s,3s)-3-hydroxy-3-methylcyclobutyl)methanone

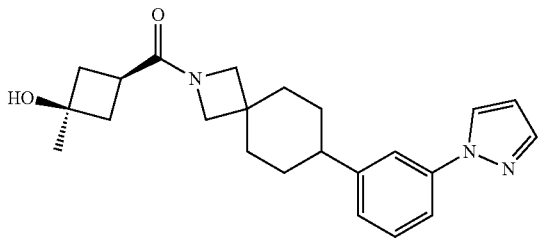 [SMILES: C[C@]1(O)C[C@@H](C(=O)N2CC3(CCC(c4cccc(-n5cccn5)c4)CC3)C2)C1]

The title compound was prepared in a manner analogous to Example 97 using 1-[3-(4,4,5,5-tetramethyl-1,3,2-dioxaborolan-2-yl)phenyl]-1H-pyrazole instead of pyrazolo[1,5-a]pyridine-5-boronic acid pinacol ester and tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7) in Step A. MS (ESI): mass calcd. for $C_{23}H_{29}N_3O_2$, 379.2; m/z found, 380.2 [M+H]$^+$. $^1$H NMR (600 MHz, CDCl$_3$) δ 7.94-7.90 (m, 1H), 7.75-7.70 (m, 1H), 7.59 (dt, J=13.0, 2.0 Hz, 1H), 7.49-7.42 (m, 1H), 7.37 (td, J=7.9, 2.7 Hz, 1H), 7.11 (dt, J=7.5, 1.3 Hz, 1H), 6.47 (td, J=2.6, 1.8 Hz, 1H), 3.84 (s, 1H), 3.78 (s, 1H), 3.75 (s, 2H), 3.70 (s, 1H), 2.75-2.67 (m, 1H), 2.61-2.51 (m, 1H), 2.35-2.29 (m, 2H), 2.29-2.23 (m, 2H), 2.05-1.99 (m, 2H), 1.96-1.88 (m, 2H), 1.69-1.61 (m, 2H), 1.56-1.42 (m, 2H), 1.36 (d, J=7.0 Hz, 3H).

Example 348

((1*S,4r,7*S)-7-(3,5-Dimethylphenyl)-1-methyl-2-azaspiro[3.5]nonan-2-yl)((1s,3*R)-3-hydroxy-3-methylcyclobutyl)methanone

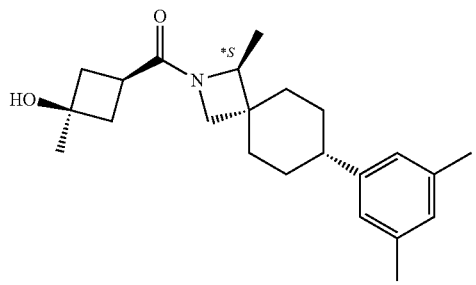 [SMILES: Cc1cc(C)cc([C@H]2CC[C@]3(CC2)CN(C(=O)[C@H]2C[C@@](C)(O)C2)[C@H]3C)c1]

Step A: 7-(3,5-Dimethylphenyl)-2-azaspiro[3.5]nonane. TES (11 mL, 69.0 mmol) was added to a solution of tert-butyl 7-(3,5-dimethylphenyl)-7-hydroxy-2-azaspiro[3.5]nonane-2-carboxylate (from Example 344, Step A, 1.2 g, 3.50 mmol) in DCM (30 mL) under N$_2$. TFA (4.0 mL, 54.0 mmol) was added, and the reaction mixture was stirred at rt for 16 h. The reaction mixture was diluted with DCM and adjusted to pH 8-9 with sat. aq. NaHCO$_3$. The mixture was extracted with DCM and the combined organic layers were dried over Na$_2$SO$_4$, filtered, and concentrated under reduced pressure to give the title compound (830 mg, 97% yield), which was used in the next step without further purification. MS (ESI): mass calcd. for $C_{16}H_{23}N$, 229.2; m/z found, 230.1 [M+H]$^+$.

Step B: O-tert-Butyl 7-(3,5-dimethylphenyl)-2-azaspiro[3.5]nonane-2-carbothioate. NaClO (3.2 mL, 4.30 mmol, 1.35 M) was added to a solution of 7-(3,5-dimethylphenyl)-2-azaspiro[3.5]nonane (630 mg) and potassium O-tert-butyl carbonodithioate (Intermediate 75, 920 mg, 4.88 mmol) in NaOH (4.3 mL, 0.430 mmol, 0.1 M in water) and H$_2$O (30 mL). The resultant mixture was stirred at rt for 16 h before being quenched with brine and extracted with DCM. The combined organic extracts were dried over Na$_2$SO$_4$, filtered, and concentrated under reduced pressure. The resulting residue was purified by FCC (SiO$_2$, 0-10% EtOAc in ether) to afford the title compound (200 mg) as a yellow solid. MS (ESI): mass calcd. for $C_{21}H_{31}NOS$, 345.2; m/z found, 290.0 [M+2H-tBu]$^+$.

Step C: O-tert-Butyl 7-(3,5-dimethylphenyl)-1-methyl-2-azaspiro[3.5]nonane-2-carbothioate. s-BuLi (1.0 mL, 1.3 M in hexane, 1.30 mmol) was added dropwise to a −70° C. solution of O-tert-butyl 7-(3,5-dimethylphenyl)-2-azaspiro[3.5]nonane-2-carbothioate (200 mg, 0.579 mmol) and TMEDA (136 mg, 1.17 mmol) in Et$_2$O (5 mL) under N$_2$. The reaction mixture was stirred at −70° C. for 30 min, then treated with iodomethane (240 mg, 1.69 mmol) in Et$_2$O (1 mL). The resultant mixture was stirred at −70° C. for 30 min, then rt for 10 h. The reaction mixture was quenched with H$_2$O, diluted with 25% aq. NH$_3$, and extracted with EtOAc. The combined organic extracts were washed with brine, dried over Na$_2$SO$_4$, filtered, and concentrated under reduced pressure. The resulting residue was purified by FCC (SiO$_2$, 0-7% EtOAc in ether) to afford the title compound (120 mg, 56% yield) as a light-yellow oil. MS (ESI): mass calcd. for $C_{22}H_{33}NOS$, 359.2; m/z found, 304.0 [M+2H-tBu]$^+$.

Step D: 7-(3,5-Dimethylphenyl)-1-methyl-2-azaspiro[3.5]nonane. TFA (0.30 mL, 4.10 mmol) was added to a solution of O-tert-butyl 7-(3,5-dimethylphenyl)-1-methyl-2-azaspiro[3.5]nonane-2-carbothioate (120 mg, 0.334 mmol) in DCM (5 mL). The reaction mixture was stirred at rt for 2 h before being concentrated under reduced pressure. The resulting residue was dissolved in water, adjusted to pH 10 with aq. sat. NaHCO$_3$, and extracted with DCM. The combined organic extracts were dried over Na$_2$SO$_4$, filtered, and concentrated under reduced pressure to give the title compound (90 mg, 96% yield) as a yellow oil. MS (ESI): mass calcd. for $C_{17}H_{25}N$, 243.2; m/z found, 244.1 [M+H]$^+$.

Step E: ((4s,7*S)-7-(3,5-Dimethylphenyl)-1-methyl-2-azaspiro[3.5]nonan-2-yl)((1s,3*S)-3-hydroxy-3-methylcyclobutyl)methanone and ((4r,7*R)-7-(3,5-Dimethylphenyl)-1-methyl-2-azaspiro[3.5]nonan-2-yl)((1s,3*S)-3-hydroxy-3-methylcyclobutyl)methanone. HATU (150 mg, 0.394 mmol) was added to a solution of 7-(3,5-dimethylphenyl)-1-methyl-2-azaspiro[3.5]nonane (90 mg, 0.370 mmol), (1s,3s)-3-hydroxy-3-methylcyclobutanecarboxylic acid (52 mg, 0.400 mmol) and DIPEA (0.19 mL, 1.08 mmol) in DMF (2 mL). The resultant mixture was stirred at rt for 2 h, then quenched with H$_2$O and extracted with EtOAc. The combined organic extracts were dried over Na$_2$SO$_4$, filtered, and concentrated under reduced pressure. The resulting residue was purified by RP HPLC (44-74% MeCN in water with 0.05% NH$_3$+10 mM NH$_4$HCO$_3$) to afford the title compounds: ((4s,7*S)-7-(3,5-dimethylphenyl)-1-methyl-2-azaspiro[3.5]nonan-2-yl)((1s,3*S)-3-hydroxy-3-methylcyclobutyl)methanone (32 mg, 24% yield). MS (ESI): mass calcd. for $C_{23}H_{33}NO_2$, 355.2; m/z found, 356.1 [M+H]$^+$. $^1$H NMR (400 MHz, CDCl$_3$) δ 6.83 (s, 1H), 6.77 (s, 2H), 4.19-3.98 (m, 1H), 3.71-3.48 (m, 2H), 2.79-2.55 (m, 1H), 2.49-2.35 (m, 2H), 2.31-2.24 (m, 10H), 2.18-1.94 (m, 3H), 1.71-1.57 (m, 1H), 1.52-1.42 (m, 5H), 1.41-1.38 (m, 1H), 1.33 (s, 4H). ((4r,7*R)-7-(3,5-dimethylphenyl)-1-methyl-2-azaspiro[3.5]nonan-2-yl)((1s,3*S)-3-hydroxy-3-methylcyclobutyl)methanone (30 mg, 23% yield). MS (ESI): mass calcd. for $C_{23}H_{33}NO_2$, 355.2; m/z found, 356.1 [M+H]$^+$. $^1$H NMR (400 MHz, CDCl$_3$) δ 6.85 (s, 1H), 6.79 (s, 2H), 4.01 (br s, 1H), 3.88-3.66 (m, 2H), 2.91-2.54 (m, 4H), 2.48-2.35 (m, 2H), 2.30 (s, 9H), 2.02-1.81 (m, 4H), 1.65-1.53 (m, 1H), 1.50-1.44 (m, 1H), 1.37 (s, 6H).

Step F: ((1*S,4r,7*S)-7-(3,5-Dimethylphenyl)-1-methyl-2-azaspiro[3.5]nonan-2-yl)((1s,3*R)-3-hydroxy-3-methylcyclobutyl)methanone. The title compound was prepared via separation of ((4r,7*R)-7-(3,5-dimethylphenyl)-1-methyl-2-azaspiro[3.5]nonan-2-yl)((1s,3*S)-3-hydroxy-3-methylcyclobutyl)methanone by chiral SFC (Stationary phase: AS (3×25 cm); Mobile phase: 15% EtOH containing 0.1% of 25% aq. NH$_3$/CO$_2$; Rt=1.74 min). MS (ESI): mass calcd. for $C_{23}H_{33}NO_2$, 355.3; m/z found, 356.3 [M+H]$^+$. $^1$H NMR (400 MHz, CDCl$_3$) δ 6.85 (s, 1H), 6.79 (s, 2H), 4.16-3.66 (m, 4H), 2.79-2.64 (m, 1H), 2.48-2.20 (m, 12H), 2.04-1.94 (m, 1H), 1.93-1.89 (m, 1H), 1.62-1.31 (m, 11H).

Example 349

((1*R,4r,7*R)-7-(3,5-Dimethylphenyl)-1-methyl-2-azaspiro[3.5]nonan-2-yl)((1s,3*S)-3-hydroxy-3-methylcyclobutyl)methanone

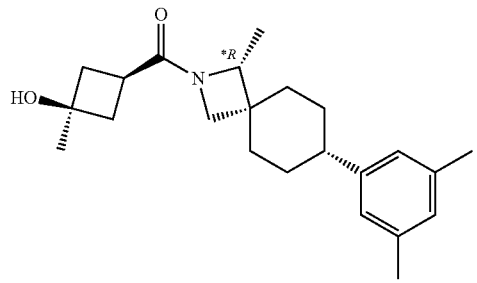 [SMILES: Cc1cc(C)cc([C@H]2CC[C@]3(CC2)CN(C(=O)[C@H]2C[C@@](C)(O)C2)[C@@H]3C)c1]

The title compound was prepared via separation of ((4r,7*R)-7-(3,5-dimethylphenyl)-1-methyl-2-azaspiro[3.5]nonan-2-yl)((1s,3*S)-3-hydroxy-3-methylcyclobutyl)methanone (Example 348, Step E) by chiral SFC (Stationary phase: AS (3×25 cm); Mobile phase: 15% EtOH containing 0.1% of 25% aq. NH$_3$/CO$_2$; Rt=1.40 min). MS (ESI): mass calcd. for $C_{23}H_{33}NO_2$, 355.3; m/z found, 356.3 [M+H]$^+$. $^1$H NMR (400 MHz, CDCl$_3$) δ 6.85 (s, 1H), 6.79 (s, 2H), 4.38-3.86 (m, 2H), 3.85-3.64 (m, 2H), 2.77-2.63 (m, 1H), 2.54-2.17 (m, 12H), 2.02-1.94 (m, 1H), 1.93-1.88 (m, 1H), 1.70-1.30 (m, 11H).

Example 350

((1*S,4s,7*R)-7-(3,5-Dimethylphenyl)-1-methyl-2-azaspiro[3.5]nonan-2-yl)((1s,3*R)-3-hydroxy-3-methylcyclobutyl)methanone

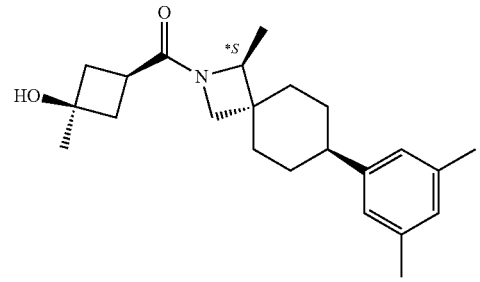 [SMILES: Cc1cc(C)cc([C@H]2CC[C@@]3(CC2)CN(C(=O)[C@H]2C[C@@](C)(O)C2)[C@H]3C)c1]

The title compound was prepared via separation of ((4s,7*S)-7-(3,5-dimethylphenyl)-1-methyl-2-azaspiro[3.5]nonan-2-yl)((1s,3*S)-3-hydroxy-3-methylcyclobutyl)methanone (Example 348, Step E) by chiral SFC (Stationary phase: AD (3×25 cm); Mobile phase: 25% EtOH containing 0.1% of 25% aq. NH$_3$/CO$_2$; Rt=3.72 min). MS (ESI): mass calcd. for $C_{23}H_{33}NO_2$, 355.3; m/z found, 356.2 [M+H]$^+$. $^1$H NMR (400 MHz, CDCl$_3$) δ 6.85 (s, 1H), 6.79 (s, 2H), 4.56-3.77 (m, 2H), 3.74-3.49 (m, 2H), 2.89-2.57 (m, 1H), 2.53-2.22 (m, 12H), 2.20-1.96 (m, 2H), 1.90-1.84 (m, 1H), 1.74-1.58 (m, 1H), 1.56-1.39 (m, 6H), 1.39-1.33 (m, 3H).

Example 351

((1*R,4s,7*S)-7-(3,5-Dimethylphenyl)-1-methyl-2-azaspiro[3.5]nonan-2-yl)((1s,3*S)-3-hydroxy-3-methylcyclobutyl)methanone

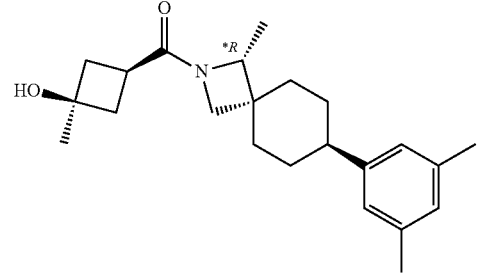 [SMILES: Cc1cc(C)cc([C@H]2CC[C@@]3(CC2)CN(C(=O)[C@H]2C[C@@](C)(O)C2)[C@@H]3C)c1]

The title compound was prepared via separation of ((4s,7*S)-7-(3,5-dimethylphenyl)-1-methyl-2-azaspiro[3.5]nonan-2-yl)((1s,3*S)-3-hydroxy-3-methylcyclobutyl)methanone (Example 348, Step E) by chiral SFC (Stationary phase: AD (3×25 cm); Mobile phase: 25% EtOH containing 0.1% of 25% aq. NH$_3$/CO$_2$; Rt=3.35 min). MS (ESI): mass calcd. for $C_{23}H_{33}NO_2$, 355.3; m/z found, 356.2 [M+H]$^+$. $^1$H NMR (400 MHz, CDCl$_3$) δ 6.85 (s, 1H), 6.79 (s, 2H), 4.28-3.86 (m, 2H), 3.77-3.47 (m, 2H), 2.84-2.57 (m, 1H), 2.50-2.19 (m, 12H), 2.18-2.07 (m, 1H), 2.06-1.97 (m, 1H), 1.89-1.83 (m, 1H), 1.72-1.59 (m, 1H), 1.55-1.39 (m, 6H), 1.37-1.34 (m, 3H).

Example 352

(7-(3-Fluoro-5-methylphenyl)-2-azaspiro[3.5]nonan-2-yl)((1s,3s)-3-hydroxy-3-methylcyclobutyl)methanone

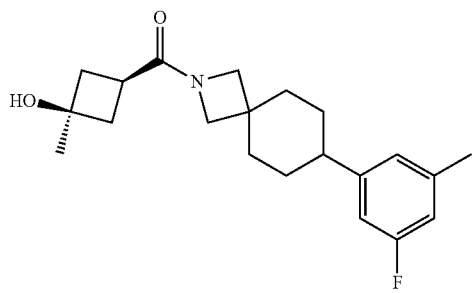 [SMILES: Cc1cc(F)cc(C2CCC3(CC2)CN(C(=O)[C@H]2C[C@@](C)(O)C2)C3)c1]

The title compound was prepared in a manner analogous to Example 109 using 1-bromo-3-fluoro-5-methylbenzene instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{21}H_{28}FNO_2$, 345.2; m/z found, 346.2 [M+H]$^+$. $^1$H NMR (400 MHz, DMSO-$d_6$) δ 6.88 (s, 1H), 6.86-6.79 (m, 2H), 5.03-4.98 (m, 1H), 3.81 (s, 1H), 3.68 (s, 1H), 3.58 (s, 1H), 3.47 (s, 1H), 2.60-2.53 (m, 1H), 2.48-2.39 (m, 1H), 2.28 (s, 3H), 2.14-2.06 (m, 2H), 2.05-1.96 (m, 2H), 1.93-1.84 (m, 2H), 1.72-1.64 (m, 2H), 1.57-1.48 (m, 2H), 1.48-1.34 (m, 2H), 1.27-1.21 (m, 3H).

Example 353

(7-(4-Fluoro-3-methylphenyl)-2-azaspiro[3.5]nonan-2-yl)((1s,3s)-3-hydroxy-3-methylcyclobutyl)methanone

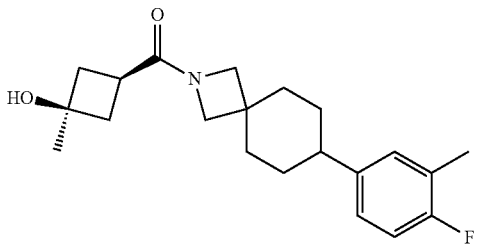 [SMILES: Cc1cc(C2CCC3(CC2)CN(C(=O)[C@H]2C[C@@](C)(O)C2)C3)ccc1F]

The title compound was prepared in a manner analogous to Example 97 using (4-fluoro-3-methylphenyl)boronic acid instead of pyrazolo[1,5-c]pyridine-5-boronic acid pinacol ester, tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7), and Pd(dppf)Cl$_2$ instead of XPhos Pd G2 in Step A. MS (ESI): mass calcd. for $C_{21}H_{28}FNO_2$, 345.2; m/z found, 346.1 [M+H]$^+$. $^1$H NMR (400 MHz, DMSO-$d_6$) δ 7.12-7.07 (m, 1H), 7.04-6.94 (m, 2H), 4.98 (d, J=4.6 Hz, 1H), 3.78 (s, 1H), 3.65 (s, 1H), 3.56 (s, 1H), 3.44 (s, 1H), 2.60-2.50 (m, 1H), 2.44-2.32 (m, 1H), 2.17 (s, 3H), 2.11-2.03 (m, 2H), 2.02-1.92 (m, 2H), 1.89-1.81 (m, 2H), 1.69-1.60 (m, 2H), 1.55-1.45 (m, 2H), 1.43-1.29 (m, 2H), 1.24-1.18 (m, 3H).

Example 354

(7-(2-Fluoro-5-methylphenyl)-2-azaspiro[3.5]nonan-2-yl)((1s,3s)-3-hydroxy-3-methylcyclobutyl)methanone

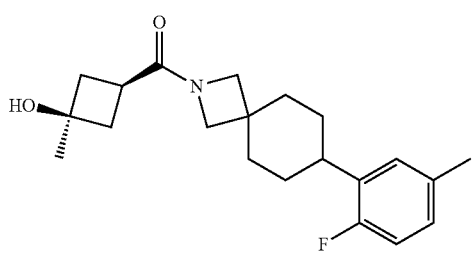 [SMILES: Cc1ccc(F)c(C2CCC3(CC2)CN(C(=O)[C@H]2C[C@@](C)(O)C2)C3)c1]

The title compound was prepared in a manner analogous to Example 97 using (2-fluoro-5-methylphenyl)boronic acid instead of pyrazolo[1,5-c]pyridine-5-boronic acid pinacol ester, tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7), and Pd(dppf)Cl$_2$ instead of XPhos Pd G2 in Step A. MS (ESI): mass calcd. for $C_{21}H_{28}FNO_2$, 345.2; m/z found, 346.1 [M+H]$^+$. $^1$H NMR (400 MHz, CDCl$_3$) δ 6.99-6.86 (m, 3H), 3.87-3.69 (m, 4H), 2.82-2.65 (m, 2H), 2.36-2.26 (m, 7H), 2.05-1.96 (m, 2H), 1.90-1.79 (m, 2H), 1.71-1.59 (m, 2H), 1.53-1.41 (m, 2H), 1.37 (d, J=2.1 Hz, 3H).

Example 355

(7-(2-Fluoro-3-methylphenyl)-2-azaspiro[3.5]nonan-2-yl)((1s,3s)-3-hydroxy-3-methylcyclobutyl)methanone

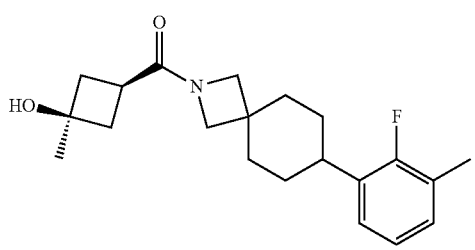 [SMILES: Cc1cccc(C2CCC3(CC2)CN(C(=O)[C@H]2C[C@@](C)(O)C2)C3)c1F]

The title compound was prepared in a manner analogous to Example 7 (switching steps C and D) using tert-butyl-7-oxo-2-azaspiro[3.5]nonane-2-carboxylate instead of tert-butyl 6-oxo-2-azaspiro[3.4]octane-2-carboxylate and 3-bromo-2-fluorotoluene instead of 1-bromo-2-methyl-3-(trifluoromethyl)benzene in Step A. MS (ESI): mass calcd. for $C_{21}H_{28}FNO_2$, 345.2; m/z found, 346.2 [M+H]$^+$. $^1$H NMR (400 MHz, CDCl$_3$) δ 7.05-6.92 (m, 3H), 3.87-3.63 (m, 5H), 2.86-2.73 (m, 1H), 2.75-2.63 (m, 1H), 2.37-2.20 (m, 7H), 2.04-1.94 (m, 2H), 1.90-1.77 (m, 2H), 1.71-1.57 (m, 2H), 1.54-1.37 (m, 2H), 1.35 (d, J=2.3 Hz, 3H).

Example 356

(7-(2-Fluoro-6-methylphenyl)-2-azaspiro[3.5]nonan-2-yl)((1s,3s)-3-hydroxy-3-methylcyclobutyl)methanone

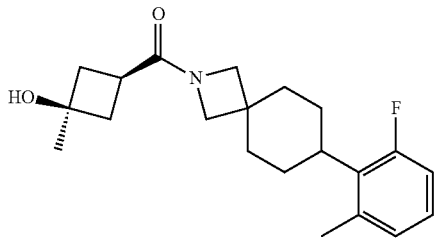 [SMILES: Cc1cccc(F)c1C1CCC2(CC1)CN(C(=O)[C@H]1C[C@@](C)(O)C1)C2]

The title compound was prepared in a manner analogous to Example 97 using (2-fluoro-6-methylphenyl)boronic acid instead of pyrazolo[1,5-a]pyridine-5-boronic acid pinacol ester, tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7), and Pd(dppf)Cl$_2$ instead of XPhos Pd G2 in Step A. MS (ESI): mass calcd. for C$_{21}$H$_{28}$FNO$_2$, 345.2; m/z found, 346.2 [M+H]$^+$. $^1$H NMR (400 MHz, CDCl$_3$) δ 7.08-7.01 (m, 1H), 6.95-6.90 (m, 1H), 6.84 (dd, J=11.8, 8.3 Hz, 1H), 3.89-3.68 (m, 4H), 2.80-2.68 (m, 2H), 2.37-2.24 (m, 7H), 2.03-1.82 (m, 4H), 1.74-1.65 (m, 2H), 1.63-1.53 (m, 2H), 1.37 (d, J=5.8 Hz, 3H).

Example 357

(7-(4-Fluoro-2-methylphenyl)-2-azaspiro[3.5]nonan-2-yl)((1s,3s)-3-hydroxy-3-methylcyclobutyl)methanone

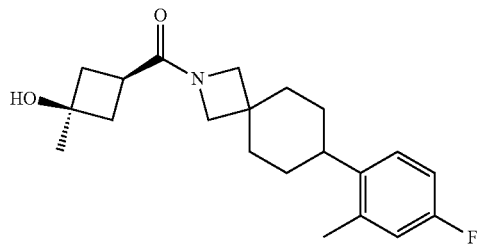 [SMILES: Cc1cc(F)ccc1C1CCC2(CC1)CN(C(=O)[C@H]1C[C@@](C)(O)C1)C2]

The title compound was prepared in a manner analogous to Example 97 using (4-fluoro-2-methylphenyl)boronic acid instead of pyrazolo[1,5-a]pyridine-5-boronic acid pinacol ester, tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7), and Pd(dppf)Cl$_2$ instead of XPhos Pd G2 in Step A. MS (ESI): mass calcd. for C$_{21}$H$_{28}$FNO$_2$, 345.2; m/z found, 346.1 [M+H]$^+$. $^1$H NMR (400 MHz, DMSO-d$_6$) δ 7.22-7.16 (m, 1H), 6.99-6.90 (m, 2H), 5.02-4.98 (m, 1H), 3.82 (s, 1H), 3.69 (s, 1H), 3.60 (s, 1H), 3.47 (s, 1H), 2.69-2.54 (m, 3H), 2.28 (s, 3H), 2.13-2.06 (m, 2H), 2.04-1.96 (m, 2H), 1.93-1.87 (m, 2H), 1.62-1.53 (m, 3H), 1.44-1.33 (m, 2H), 1.25-1.22 (m, 3H).

Example 358

(7-(5-Fluoro-2-methylphenyl)-2-azaspiro[3.5]nonan-2-yl)((1s,3s)-3-hydroxy-3-methylcyclobutyl)methanone

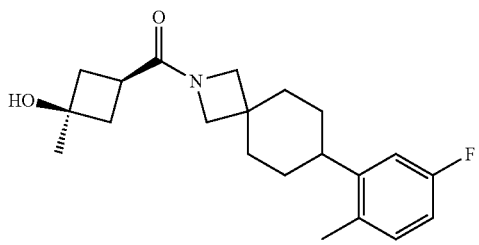 [SMILES: Cc1ccc(F)cc1C1CCC2(CC1)CN(C(=O)[C@H]1C[C@@](C)(O)C1)C2]

The title compound was prepared in a manner analogous to Example 97 using (5-fluoro-2-methylphenyl)borane instead of pyrazolo[1,5-c]pyridine-5-boronic acid pinacol ester, tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7), and Pd(dppf)Cl$_2$ instead of XPhos Pd G2 in Step A. MS (ESI): mass calcd. for C$_{21}$H$_{28}$FNO$_2$, 345.2; m/z found, 346.2 [M+H]$^+$. $^1$H NMR (400 MHz, DMSO-d$_6$) δ 7.18-7.10 (m, 1H), 7.04-6.96 (m, 1H), 6.92-6.83 (m, 1H), 5.06-4.95 (m, 1H), 3.83 (s, 1H), 3.69 (s, 1H), 3.61 (s, 1H), 3.48 (s, 1H), 2.68-2.53 (m, 2H), 2.24 (s, 3H), 2.15-2.06 (m, 2H), 2.05-1.96 (m, 2H), 1.95-1.86 (m, 2H), 1.67-1.52 (m, 4H), 1.47-1.33 (m, 2H), 1.29-1.20 (m, 3H).

Example 359

(7-(3-Fluoro-2-methylphenyl)-2-azaspiro[3.5]nonan-2-yl)((1s,3s)-3-hydroxy-3-methylcyclobutyl)methanone

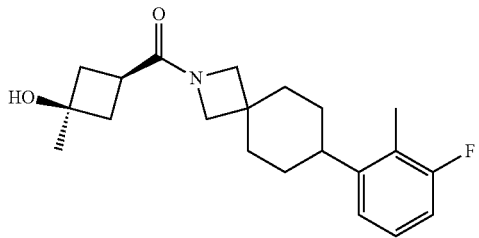 [SMILES: Cc1c(F)cccc1C1CCC2(CC1)CN(C(=O)[C@H]1C[C@@](C)(O)C1)C2]

The title compound was prepared in a manner analogous to Example 109 using 1-bromo-3-fluoro-2-methylbenzene instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for C$_{21}$H$_{28}$FNO$_2$, 345.2; m/z found, 346.1 [M+H]$^+$. $^1$H NMR (400 MHz, DMSO-d$_6$) δ 7.20-7.11 (m, 1H), 7.06-7.01 (m, 1H), 6.99-6.88 (m, 1H), 5.00 (d, J=3.1 Hz, 1H), 3.82 (s, 1H), 3.69 (s, 1H), 3.60 (s, 1H), 3.48 (s, 1H), 2.72-2.58 (m, 2H), 2.18 (d, J=2.0 Hz, 3H), 2.14-2.06 (m, 2H), 2.05-1.97 (m, 2H), 1.95-1.87 (m, 2H), 1.69-1.54 (m, 4H), 1.47-1.33 (m, 2H), 1.24 (d, J=2.7 Hz, 3H).

Example 360

(7-(3-Ethoxy-4-methylphenyl)-2-azaspiro[3.5]nonan-2-yl)((1s,3s)-3-hydroxy-3-methylcyclobutyl)methanone

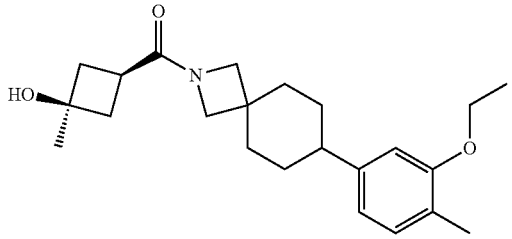 [SMILES: CCOc1cc(C2CCC3(CC2)CN(C(=O)[C@H]2C[C@@](C)(O)C2)C3)ccc1C]

The title compound was prepared in a manner analogous to Example 109 using 4-bromo-2-ethoxy-1-methylbenzene instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{23}H_{33}NO_3$, 371.2; m/z found, 372.3 [M+H]$^+$. $^1$H NMR (400 MHz, DMSO-$d_6$) δ 7.02-6.98 (m, 1H), 6.75-6.72 (m, 1H), 6.68-6.63 (m, 1H), 5.03-4.98 (m, 1H), 4.04-3.97 (m, 2H), 3.81 (s, 1H), 3.68 (s, 1H), 3.59 (s, 1H), 3.47 (s, 1H), 2.61-2.54 (m, 1H), 2.42-2.31 (m, 1H), 2.14-2.07 (m, 5H), 2.05-1.96 (m, 2H), 1.93-1.84 (m, 2H), 1.72-1.64 (m, 2H), 1.58-1.48 (m, 2H), 1.47-1.37 (m, 2H), 1.35-1.30 (m, 3H), 1.26-1.22 (m, 3H).

Example 361

(7-(3-Ethoxy-2-methylphenyl)-2-azaspiro[3.5]nonan-2-yl)((1s,3s)-3-hydroxy-3-methylcyclobutyl)methanone

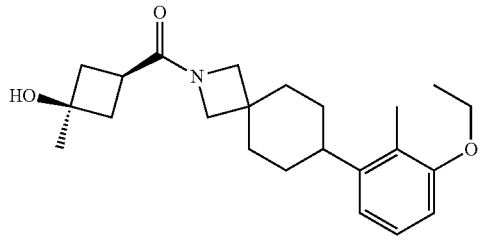 [SMILES: CCOc1cccc(C2CCC3(CC2)CN(C(=O)[C@H]2C[C@@](C)(O)C2)C3)c1C]

The title compound was prepared in a manner analogous to Example 109 using 1-bromo-3-ethoxy-2-methylbenzene instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{23}H_{33}NO_3$, 371.2; m/z found, 372.2 [M+H]$^+$. $^1$H NMR (400 MHz, DMSO-$d_6$) δ 7.10-7.04 (m, 1H), 6.80-6.73 (m, 2H), 5.01-4.99 (m, 1H), 3.97 (q, J=6.9 Hz, 2H), 3.84-3.46 (m, 4H), 2.70-2.52 (m, 2H), 2.14-2.07 (m, 5H), 2.05-1.97 (m, 2H), 1.93-1.85 (m, 2H), 1.65-1.53 (m, 4H), 1.44-1.30 (m, 5H), 1.26-1.21 (m, 3H).

Example 362

((1s,3s)-3-Hydroxy-3-methylcyclobutyl)(7-(3-isopropoxy-2-methylphenyl)-2-azaspiro[3.5]nonan-2-yl)methanone

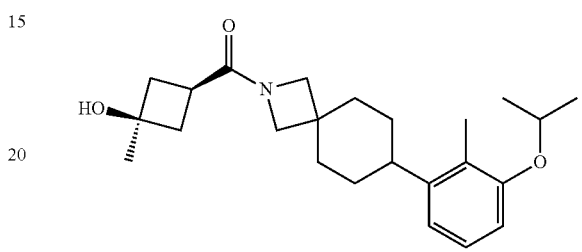

The title compound was prepared in a manner analogous to Example 109 using 1-bromo-3-isopropoxy-2-methylbenzene (Intermediate 62) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{24}H_{35}NO_3$, 385.3; m/z found, 386.2 [M+H]$^+$. $^1$H NMR (400 MHz, DMSO-$d_6$) δ 7.09-7.03 (m, 1H), 6.79-6.74 (m, 2H), 4.53-4.46 (m, 1H), 3.83-3.46 (m, 4H), 2.69-2.53 (m, 2H), 2.14-2.06 (m, 5H), 2.04-1.96 (m, 2H), 1.93-1.86 (m, 2H), 1.65-1.54 (m, 4H), 1.44-1.32 (m, 2H), 1.27-1.23 (m, 9H).

Example 363

((1s,3s)-3-Hydroxy-3-methylcyclobutyl)(7-(5-methoxy-2-methylphenyl)-2-azaspiro[3.5]nonan-2-yl)methanone

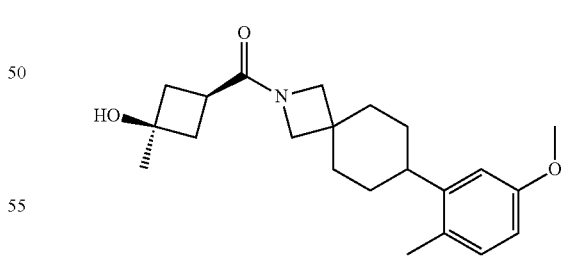

The title compound was prepared in a manner analogous to Example 109 using 2-bromo-4-methoxy-1-methylbenzene instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{22}H_{31}NO_3$, 357.2; m/z found, 358.2 [M+H]$^+$. $^1$H NMR (400 MHz, CDCl₃) δ 7.07 (dd, J=8.2, 5.7 Hz, 1H), 6.72-6.69 (m, 1H), 6.68-6.63 (m, 1H), 3.86-3.69 (m, 7H), 2.78-2.58 (m, 2H), 2.37-2.25 (m, 7H), 2.05-1.99 (m, 2H), 1.84-1.77 (m, 2H), 1.71-1.58 (m, 2H), 1.48-1.35 (m, 5H).

Example 364

(7-(3-Cyclopropoxy-2-methylphenyl)-2-azaspiro[3.5]nonan-2-yl)((1s,3s)-3-hydroxy-3-methylcyclobutyl)methanone

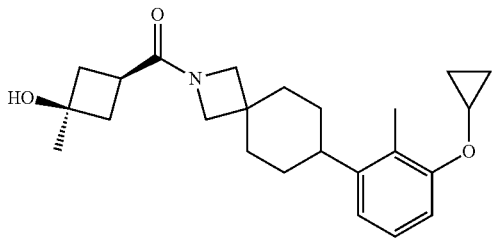 [SMILES: Cc1c(OC2CC2)cccc1C1CCC2(CC1)CN(C(=O)[C@H]1C[C@@](C)(O)C1)C2]

The title compound was prepared in a manner analogous to Example 109 using 1-bromo-3-cyclopropoxy-2-methylbenzene (Intermediate 58) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for C₂₄H₃₃NO₃, 383.2; m/z found, 384.2 [M+H]⁺. ¹H NMR (400 MHz, CDCl₃) δ 7.18-7.09 (m, 2H), 6.83-6.76 (m, 1H), 3.87-3.68 (m, 6H), 2.77-2.66 (m, 2H), 2.38-2.21 (m, 4H), 2.15-2.11 (m, 3H), 2.05-1.98 (m, 2H), 1.83-1.74 (m, 2H), 1.71-1.61 (m, 2H), 1.50-1.33 (m, 5H), 0.80-0.75 (m, 4H).

Example 365

(7-(3-Ethoxy-5-fluorophenyl)-2-azaspiro[3.5]nonan-2-yl)((1s,3s)-3-hydroxy-3-methylcyclobutyl)methanone

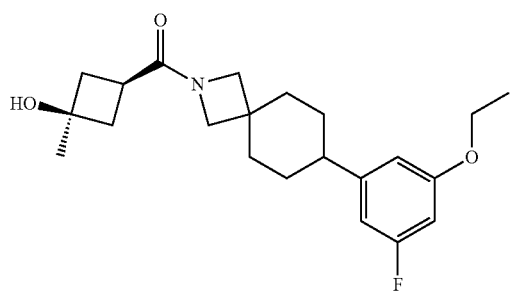 [SMILES: CCOc1cc(F)cc(C2CCC3(CC2)CN(C(=O)[C@H]2C[C@@](C)(O)C2)C3)c1]

The title compound was prepared in a manner analogous to Example 109 using 1-bromo-3-ethoxy-5-fluorobenzene instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for C₂₂H₃₀FNO₃, 375.2; m/z found, 376.2 [M+H]⁺. ¹H NMR (400 MHz, DMSO-d₆) δ 6.65-6.55 (m, 3H), 5.03-4.98 (m, 1H), 4.04-3.96 (m, 2H), 3.80 (s, 1H), 3.68 (s, 1H), 3.58 (s, 1H), 3.46 (s, 1H), 2.60-2.53 (m, 1H), 2.48-2.38 (m, 1H), 2.14-2.06 (m, 2H), 2.05-1.95 (m, 2H), 1.92-1.83 (m, 2H), 1.72-1.64 (m, 2H), 1.57-1.47 (m, 2H), 1.46-1.35 (m, 2H), 1.33-1.27 (m, 3H), 1.26-1.21 (m, 3H).

Example 366

(7-(2-Fluoro-3-methoxyphenyl)-2-azaspiro[3.5]nonan-2-yl)((1s,3s)-3-hydroxy-3-methylcyclobutyl)methanone

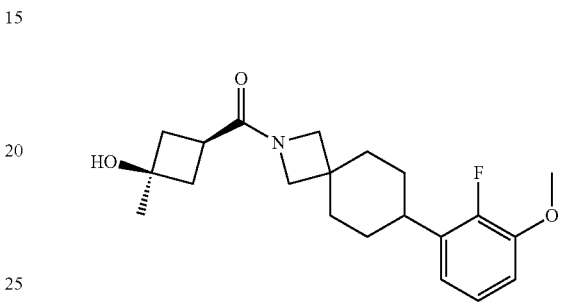

The title compound was prepared in a manner analogous to Example 97 2-(2-fluoro-3-methoxyphenyl)-4,4,5,5-tetramethyl-1,3,2-dioxaborolane instead of pyrazolo[1,5-a]pyridine-5-boronic acid pinacol ester, tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7), and Pd(dppf)Cl₂ instead of XPhos Pd G2 in Step A. MS (ESI): mass calcd. for C₂₁H₂₈FNO₃, 361.2; m/z found, 362.1 [M+H]⁺. ¹H NMR (400 MHz, DMSO-d₆) δ 7.09-7.02 (m, 1H), 7.01-6.94 (m, 1H), 6.88-6.80 (m, 1H), 5.03-4.96 (m, 1H), 3.83-3.81 (m, 1H), 3.81-3.78 (m, 3H), 3.68 (s, 1H), 3.59 (s, 1H), 3.47 (s, 1H), 2.81-2.70 (m, 1H), 2.61-2.52 (m, 1H), 2.15-2.06 (m, 2H), 2.05-1.95 (m, 2H), 1.94-1.85 (m, 2H), 1.70-1.61 (m, 2H), 1.61-1.51 (m, 2H), 1.50-1.37 (m, 2H), 1.27-1.20 (m, 3H).

Example 367

(7-(2-Chloro-3-methoxyphenyl)-2-azaspiro[3.5]nonan-2-yl)((1s,3s)-3-hydroxy-3-methylcyclobutyl)methanone

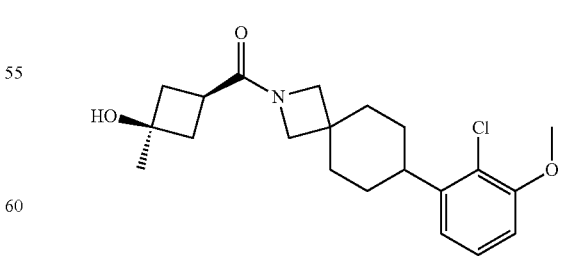

The title compound was prepared in a manner analogous to Example 97 (2-chloro-3-methoxyphenyl)boronic acid instead of pyrazolo[1,5-a]pyridine-5-boronic acid pinacol ester, tert-butyl 7-(((trifluoromethyl)sulfonyl)oxy)-2- azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7), and Pd(dppf)Cl$_2$ instead of XPhos Pd G2 in Step A. MS (ESI): mass calcd. for C$_{21}$H$_{28}$ClNO$_3$, 377.2; m/z found, 378.1 [M+H]$^+$. $^1$H NMR (400 MHz, CDCl$_3$) δ 7.23-7.17 (m, 1H), 6.86-6.79 (m, 2H), 3.91 (s, 3H), 3.85-3.69 (m, 4H), 3.09-2.98 (m, 1H), 2.76-2.66 (m, 1H), 2.36-2.23 (m, 4H), 2.06-1.98 (m, 2H), 1.93-1.83 (m, 2H), 1.74-1.63 (m, 2H), 1.46-1.31 (m, 5H).

Example 368

(7-(2,3-Difluoro-5-methoxyphenyl)-2-azaspiro[3.5]nonan-2-yl)((1s,3s)-3-hydroxy-3-methylcyclobutyl)methanone

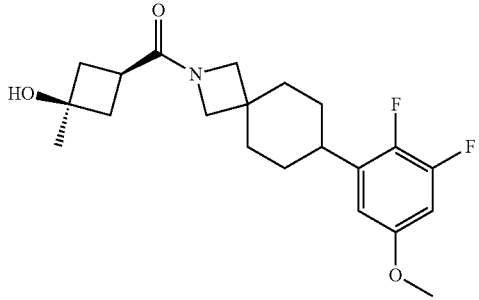 [SMILES: COc1cc(F)c(F)c(C2CCC3(CC2)CN(C(=O)[C@H]2C[C@@](C)(O)C2)C3)c1]

The title compound was prepared in a manner analogous to Example 109 using 1-bromo-2,3-difluoro-5-methoxybenzene (Intermediate 65) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for C$_{21}$H$_{27}$F$_2$NO$_3$, 379.2; m/z found, 380.3 [M+H]$^+$. $^1$H NMR (400 MHz, CDCl$_3$) δ 6.60-6.51 (m, 1H), 6.44 (s, 1H), 4.17 (br s, 1H), 3.89-3.81 (m, 1H), 3.78-3.74 (m, 5H), 3.72-3.65 (m, 1H), 2.89-2.75 (m, 1H), 2.74-2.60 (m, 1H), 2.35-2.27 (m, 4H), 2.04-1.98 (m, 2H), 1.89-1.81 (m, 2H), 1.72-1.58 (m, 2H), 1.50-1.39 (m, 2H), 1.37-1.33 (m, 3H).

Example 369

(7-(2,5-Difluoro-3-methoxyphenyl)-2-azaspiro[3.5]nonan-2-yl)((1s,3s)-3-hydroxy-3-methylcyclobutyl)methanone

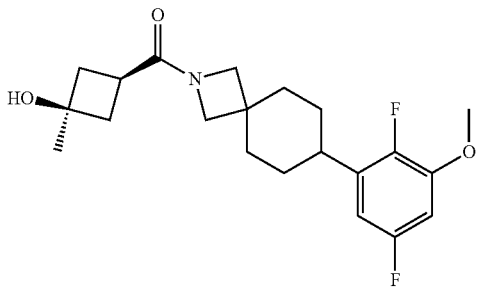 [SMILES: COc1cc(F)cc(C2CCC3(CC2)CN(C(=O)[C@H]2C[C@@](C)(O)C2)C3)c1F]

Step A: tert-Butyl 7-(3-bromo-2,5-difluorophenyl)-2-azaspiro[3.5]non-6-ene-2-carboxylate. tert-Butyl 7-(4,4,5,5-tetramethyl-1,3,2-dioxaborolan-2-yl)-2-azaspiro[3.5]non-6-ene-2-carboxylate (Intermediate 10, 300 mg, 0.859 mmol), 1,3-dibromo-2,5-difluorobenzene (1.17 g, 4.30 mmol) and Cs$_2$CO$_3$ (840 mg, 2.58 mmol) were dissolved in dioxane (10 mL) and H$_2$O (2 mL). The resultant mixture was sparged with N$_2$ for 5 min, then treated with Pd(dppf)Cl$_2$ (63 mg, 0.086 mmol). The mixture was sparged with Ar for 5 min, then stirred at 90° C. for 2 h. The reaction mixture was poured into water and extracted with EtOAc. The combined organic extracts were dried over Na$_2$SO$_4$, filtered, and concentrated under reduced pressure. The resulting residue was purified by FCC (SiO$_2$, 0-10% EtOAc in ether) to afford the title compound (220 mg, 50% yield) as a colorless oil. MS (ESI): mass calcd. for C$_{19}$H$_{22}$BrF$_2$NO$_2$, 413.1; m/z found, 360.0 [M+2H-tBu]$^+$.

Step B: tert-Butyl 7-(3-bromo-2,5-difluorophenyl)-2-azaspiro[3.5]nonane-2-carboxylate. tert-Butyl 7-(3-bromo-2,5-difluorophenyl)-2-azaspiro[3.5]non-6-ene-2-carboxylate (220 mg, 0.531 mmol) and PtO$_2$ (200 mg, 8.81 mmol) were taken up in EtOAc (10 mL) and stirred under H$_2$ (15 psi) at rt for 1 hour. The suspension was filtered through a pad of Celite® and the pad was washed with EtOAc. The filtrate was concentrated under reduced pressure to give the title compound (210 mg, crude), which was used in the next step without further purification. MS (ESI): mass calcd. for C$_{19}$H$_{24}$BrF$_2$NO$_2$, 415.1; m/z found, 359.8 [M+2H-tBu]$^+$.

Step C: tert-Butyl 7-(2,5-difluoro-3-(4,4,5,5-tetramethyl-1,3,2-dioxaborolan-2-yl)phenyl)-2-azaspiro[3.5]nonane-2-carboxylate. tert-Butyl 7-(3-bromo-2,5-difluorophenyl)-2-azaspiro[3.5]nonane-2-carboxylate (200 mg, 0.480 mmol), 4,4,4',4',5,5,5',5'-octamethyl-2,2'-bi(1,3,2-dioxaborolane) (183 mg, 0.721 mmol) and KOAc (95 mg, 0.968 mmol) were dissolved in 1,4-dioxane (6 mL). The resultant mixture was sparged with N$_2$ for 5 min, then treated with Pd(dppf)Cl$_2$ (35 mg, 0.048 mmol). The resultant mixture was sparged with N$_2$ for another 5 min, then stirred at 100° C. for 12 h before cooling to rt. The solids were filtered off and the filtrate was concentrated under reduced pressure. The resulting residue was purified by FCC (SiO$_2$, 0-10% EtOAc in ether) to afford the title compound (120 mg, 31% yield) as a colorless oil. MS (ESI): mass calcd. for C$_{25}$H$_{36}$BF$_2$NO$_4$, 463.3; m/z found, 326.2 [M+2H-tBu-C$_6$H$_{10}$]$^+$ (ionizes as carbamic acid and boronic acid).

Step D: tert-Butyl 7-(2,5-difluoro-3-hydroxyphenyl)-2-azaspiro[3.5]nonane-2-carboxylate. Oxone (174 mg, 1.04 mmol) and H$_2$O (2 mL) were added to a solution of tert-butyl difluoro-3-(4,4,5,5-tetramethyl-1,3,2-dioxaborolan-2-yl)phenyl)-2-azaspiro[3.5]nonane-2-carboxylate (120 mg, 0.259 mmol) in acetone (2 mL). The reaction mixture was stirred at rt for 5 h. The reaction mixture was poured into sat. aq. Na$_2$SO$_3$ and concentrated under reduced pressure. The resulting residue was purified by FCC (SiO$_2$, 0-20% EtOAc in ether) to afford the title compound (80 mg, 70% yield) as a grey solid. MS (ESI): mass calcd. for C$_{19}$H$_{25}$F$_2$NO$_3$, 353.2; m/z found, 298.1 [M+2H-tBu]$^+$.

Step E: tert-Butyl 7-(2,5-difluoro-3-methoxyphenyl)-2-azaspiro[3.5]nonane-2-carboxylate. Iodomethane (0.16 mL, 2.57 mmol) was added to a solution of tert-butyl 7-(2,5-difluoro-3-hydroxyphenyl)-2-azaspiro[3.5]nonane-2-carboxylate (110 mg, 0.311 mmol) and Cs$_2$CO$_3$ (203 mg, 0.623 mmol) in CH$_3$CN (5 mL). The resultant mixture was stirred at rt for 16 h before being poured into sat. aq. NaHCO$_3$ and extracted with EtOAc. The combined organic extracts were dried over Na$_2$SO$_4$, filtered, and concentrated under reduced pressure. The resulting residue was purified by FCC (SiO$_2$, 0-10% EtOAc in ether) to afford the title compound (70 mg, 52% yield) as a yellow oil. MS (ESI): mass calcd. for $C_{20}H_{27}F_2NO_3$, 367.2; m/z found, 311.9 [M+2H-tBu]$^+$.

Step F: 7-(2,5-Difluoro-3-methoxyphenyl)-2-azaspiro[3.5]nonane. TFA (2 mL, 26.1 mmol) was added to a solution of tert-butyl 7-(2,5-difluoro-3-methoxyphenyl)-2-azaspiro[3.5]nonane-2-carboxylate (70 mg, crude) in DCM (1 mL) at rt. The reaction mixture was stirred at rt for 1 hour before being concentrated under reduced pressure to give the title compound (80 mg, crude) as a yellow oil, which was used in the next step without further purification. MS (ESI): mass calcd. for $C_{15}H_{19}F_2NO$, 267.1; m/z found, 267.9 [M+H]$^+$.

Step G: (7-(2,5-Difluoro-3-methoxyphenyl)-2-azaspiro[3.5]nonan-2-yl)((1s,3s)-3-hydroxy-3-methylcyclobutyl)methanone. T$_3$P® (0.19 mL, 50% in EtOAc, 0.320 mmol) was added to a 0° C. solution of 7-(2,5-difluoro-3-methoxyphenyl)-2-azaspiro[3.5]nonane (80 mg, crude), (1s,3s)-3-hydroxy-3-methylcyclobutanecarboxylic acid (27 mg, 0.207 mmol) and TEA (0.35 mL, 2.57 mmol) in DCM (2 mL). The resultant mixture was stirred for 2 h with gradual warming to rt before being poured into water and extracted with DCM. The combined organic extracts were dried over Na$_2$SO$_4$, filtered, and concentrated under reduced pressure. The resulting residue was purified by RP HPLC (36-66% ACN in water containing 0.225% HCOOH) to afford the title compound (27 mg, 33% yield) as a white solid. MS (ESI): mass calcd. for $C_{21}H_{27}F_2NO_3$, 379.2; m/z found, 380.2 [M+H]$^+$. $^1$H NMR (400 MHz, CDCl$_3$) δ 6.58-6.52 (m, 1H), 6.48-6.40 (m, 1H), 3.87-3.82 (m, 4H), 3.78-3.74 (m, 2H), 3.69 (s, 1H), 2.90-2.79 (m, 1H), 2.76-2.64 (m, 1H), 2.36-2.24 (m, 4H), 2.05-1.94 (m, 2H), 1.88-1.79 (m, 2H), 1.71-1.58 (m, 2H), 1.48-1.35 (m, 5H).

Example 370

(7-(3-Fluoro-5-methoxy-4-methylphenyl)-2-azaspiro[3.5]nonan-2-yl)((1s,3s)-3-hydroxy-3-methylcyclobutyl)methanone

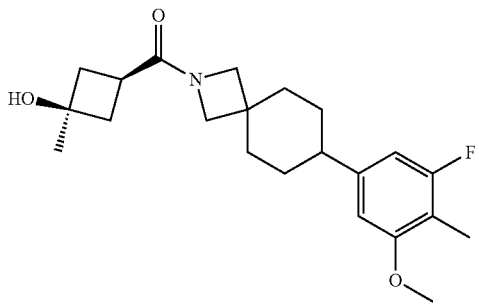 [SMILES: COc1cc(C2CCC3(CC2)CN(C(=O)[C@H]2C[C@@](C)(O)C2)C3)cc(F)c1C]

Step A: (4-Bromo-2-fluoro-6-methoxyphenyl)methanol. BH$_3$ (13 mL, 13.3 mmol, 1 M in THF) was added to a 0° C. solution of 4-bromo-2-fluoro-6-methoxybenzoic acid (1.1 g, 4.42 mmol) in THF (10 mL). The reaction mixture was stirred at rt for 16 h. The reaction was quenched with MeOH dropwise at 0° C. then concentrated to afford the title compound (1.0 g, crude), which was used in the next step without further purification.

Step B: tert-Butyl 7-(3-fluoro-4-(hydroxymethyl)-5-methoxyphenyl)-2-azaspiro[3.5]non-6-ene-2-carboxylate. Pd(dppf)Cl$_2$·CH$_2$Cl$_2$ (50 mg, 0.069 mmol) was added to a solution of (4-bromo-2-fluoro-6-methoxyphenyl)methanol (162 mg, 0.687 mmol), tert-butyl 7-(4,4,5,5-tetramethyl-1,3,2-dioxaborolan-2-yl)-2-azaspiro[3.5]non-6-ene-2-carboxylate (Intermediate 10, 200 mmol, 0.573 mmol) and K$_3$PO$_4$ (365 mg, 1.72 mmol) in dioxane (10 mL) and H$_2$O (2.5 mL) under N$_2$. The reaction mixture was stirred at 90° C. for 16 h. After cooling to rt, water was added, and the solids were filtered off. The filtrate was extracted with EtOAc, and the combined organic extracts were concentrated under reduced pressure. The resulting residue was purified by FCC (SiO$_2$, 0-30% EtOAc in ether) to afford the title compound (200 mg, 92% yield) as a white solid. MS (ESI): mass calcd. for $C_{21}H_{28}FNO_4$, 377.2; m/z found, 322.0 [M+2H-tBu]$^+$.

Step C: tert-Butyl 7-(3-fluoro-4-(hydroxymethyl)-5-methoxyphenyl)-2-azaspiro[3.5]nonane-2-carboxylate. Wet Pd/C (259 mg, 0.244 mmol) was added to a solution of tert-butyl 7-(3-fluoro-4-(hydroxymethyl)-5-methoxyphenyl)-2-azaspiro[3.5]non-6-ene-2-carboxylate (92 mg, 0.244 mmol) in MeOH (5 mL). The suspension was purged with H$_2$ and stirred under H$_2$ (15 psi) at rt for 2.5 h. The crude mixture was filtered, dried over Na$_2$SO$_4$, filtered, and concentrated under reduced pressure to afford the title compound (89 mg), which used in the next step without further purification. $^1$H NMR (400 MHz, CDCl$_3$) δ 6.53 (d, J=10.4 Hz, 1H), 6.50 (s, 1H), 4.72 (br s, 2H), 3.89 (s, 3H), 3.71-3.57 (m, 4H), 2.48-2.40 (m, 1H), 2.24 (br s, 1H), 2.02 (d, J=13.2 Hz, 2H), 1.94 (br s, 2H), 1.84 (d, J=11.6 Hz, 2H), 1.58-1.55 (m, 2H), 1.25 (s, 9H).

Step D: 7-(3-Fluoro-5-methoxy-4-methylphenyl)-2-azaspiro[3.5]nonane. TFA (0.21 mL, 2.80 mmol) was added to a solution of tert-butyl 7-(3-fluoro-4-(hydroxymethyl)-5-methoxyphenyl)-2-azaspiro[3.5]nonane-2-carboxylate (89 mg, 0.233 mmol) and TES (136 mg, 1.17 mmol) in DCM (2 mL) under N$_2$. The reaction mixture was stirred for 16 h at rt before being concentrated and quenched with 25% aq. NH$_3$. The crude mixture was extracted with DCM, dried over Na$_2$SO$_4$, filtered, and concentrated under reduced pressure to afford the title compound (89 mg, crude), which was used in the next step without further purification.

Step E: (7-(3-Fluoro-5-methoxy-4-methylphenyl)-2-azaspiro[3.5]nonan-2-yl)((1s,3s)-3-hydroxy-3-methylcyclobutyl)methanone. DIPEA (0.30 mL, 1.69 mmol) was added to a solution of HATU (257 mg, 0.676 mmol), 7-(3-fluoro-5-methoxy-4-methylphenyl)-2-azaspiro[3.5]nonane (89 mg, 0.338 mmol) and (1s,3s)-3-hydroxy-3-methylcyclobutanecarboxylic acid (53 mg, 0.406 mmol) in DMF (5 mL). The reaction mixture was stirred at rt for 3 h before being concentrated under reduced pressure. The resulting residue was purified by RP HPLC (45-75% MeCN in water containing 0.05% NH$_3$+10 mM NH$_4$HCO$_3$) to afford the title compound (25 mg, 19% yield) as a white solid. MS (ESI): mass calcd. for $C_{22}H_{30}FNO_3$, 375.2; m/z found, 376.2 [M+H]$^+$. $^1$H NMR (400 MHz, CDCl$_3$) δ 6.49 (d, J=10.4 Hz, 1H), 6.44 (s, 1H), 3.86-3.81 (m, 4H), 3.79-3.68 (m, 3H), 2.77-2.65 (m, 1H), 2.50-2.36 (m, 1H), 2.36-2.22 (m, 4H), 2.08 (s, 3H), 2.04-1.96 (m, 2H), 1.92-1.82 (m, 2H), 1.64-1.56 (m, 2H), 1.48-1.34 (m, 5H).

Example 371

((1s,3s)-3-Hydroxy-3-methylcyclobutyl)(7-(6-(1-(trifluoromethyl)cyclopropyl)pyridin-2-yl)-2-azaspiro[3.5]nonan-2-yl)methanone

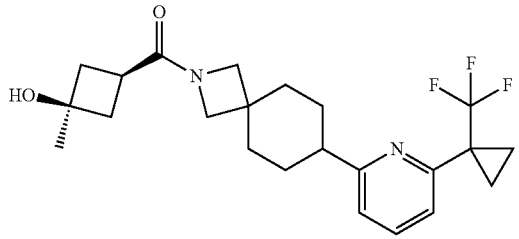 [SMILES: C[C@]1(O)C[C@@H](C(=O)N2CC3(CCC(c4cccc(C5(C(F)(F)F)CC5)n4)CC3)C2)C1]

The title compound was prepared in a manner analogous to Example 109 using 2-chloro-6-(1-(trifluoromethyl)cyclopropyl)pyridine (Intermediate 60) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{23}H_{29}F_3N_2O_2$, 422.2; m/z found, 423.1 [M+H]$^+$. $^1$H NMR (400 MHz, DMSO-$d_6$) δ 7.72 (m, 1H), 7.37-7.31 (m, 1H), 7.20 (d, J=7.7 Hz, 1H), 3.80 (s, 1H), 3.70 (s, 1H), 3.57 (s, 1H), 3.48 (s, 1H), 2.66-2.55 (m, 2H), 2.14-2.07 (m, 2H), 2.05-1.97 (m, 2H), 1.94-1.86 (m, 2H), 1.81-1.74 (m, 2H), 1.60-1.44 (m, 4H), 1.39 (s, 4H), 1.24 (d, J=2.4 Hz, 3H).

Example 372

((1s,3s)-3-Hydroxy-3-methylcyclobutyl)(7-(6-(1-methylcyclopropyl)pyridin-2-yl)-2-azaspiro[3.5]nonan-2-yl)methanone

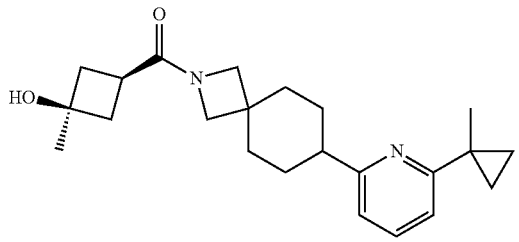 [SMILES: CC1(c2cccc(C3CCC4(CC3)CN(C(=O)[C@H]3C[C@@](C)(O)C3)C4)n2)CC1]

The title compound was prepared in a manner analogous to Example 109 using 2-chloro-6-(1-methylcyclopropyl)pyridine (Intermediate 59) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{23}H_{32}N_2O_2$, 368.2; m/z found, 369.2 [M+H]$^+$. $^1$H NMR (400 MHz, CDCl$_3$) δ 7.61-7.55 (m, 1H), 7.15 (dd, J=7.7, 1.9 Hz, 1H), 6.98 (d, J=7.6 Hz, 1H), 5.01 (s, 1H), 3.81-3.44 (m, 4H), 2.62-2.53 (m, 2H), 2.15-2.06 (m, 2H), 2.04-1.96 (m, 2H), 1.93-1.85 (m, 2H), 1.79-1.70 (m, 2H), 1.60-1.44 (m, 7H), 1.24 (d, J=3.1 Hz, 3H), 1.17-1.13 (m, 2H), 0.77-0.73 (m, 2H).

Example 373

((1s,3s)-3-Hydroxy-3-methylcyclobutyl)(7-(6-isopropyl-5-methylpyridin-2-yl)-2-azaspiro[3.5]nonan-2-yl)methanone

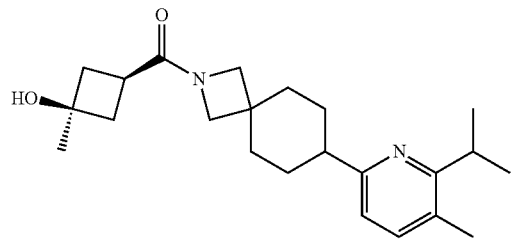 [SMILES: Cc1ccc(C2CCC3(CC2)CN(C(=O)[C@H]2C[C@@](C)(O)C2)C3)nc1C(C)C]

Step A: tert-Butyl 7-(6-chloro-5-methylpyridin-2-yl)-2-azaspiro[3.5]non-6-ene-2-carboxylate. K$_3$PO$_4$ (1.2 g, 5.70 mmol) was added to a mixture of tert-butyl 7-(4,4,5,5-tetramethyl-1,3,2-dioxaborolan-2-yl)-2-azaspiro[3.5]non-6-ene-2-carboxylate (Intermediate 10, 647 mg, 1.85 mmol) and 2,6-dichloro-3-methylpyridine (300 mg, 1.85 mmol) in THF (15 mL). The resultant mixture was sparged with N$_2$ for 5 min, then treated with Pd(dppf)Cl$_2$·CH$_2$Cl$_2$ (151 mg, 0.185 mmol). The mixture was sparged with N$_2$ for another 5 min, then stirred at 90° C. for 2 h before being poured into water and extracted with EtOAc. The combined organic extracts were dried over Na$_2$SO$_4$, filtered, and concentrated under reduced pressure. The resulting residue was purified by FCC (SiO$_2$, 0-10% EtOAc in ether) to afford the title compound (600 mg, 90% yield) as a colorless oil. MS (ESI): mass calcd. for $C_{19}H_{25}ClN_2O_2$, 348.2; m/z found, 348.9 [M+H]$^+$.

Step B: tert-Butyl 7-(5-methyl-6-(prop-1-en-2-yl)pyridin-2-yl)-2-azaspiro[3.5]non-6-ene-2-carboxylate. tert-Butyl 7-(6-chloro-5-methylpyridin-2-yl)-2-azaspiro[3.5]non-6-ene-2-carboxylate (130 mg, 0.373 mmol), 4,4,5,5-tetramethyl-2-(prop-1-en-2-yl)-1,3,2-dioxaborolane (63 mg, 0.380 mmol) and K$_3$PO$_4$ (242 mg, 1.14 mmol) were dissolved in THF (2 mL). The resultant mixture was sparged with N$_2$ for 5 minutes, then treated with Pd(dppf)Cl$_2$·CH$_2$Cl$_2$ (31 mg, 0.038 mmol). The mixture was sparged with N$_2$ for another 5 minutes, then stirred at 90° C. for 2 h. The reaction mixture was poured into water and extracted with EtOAc. The combined organic extracts were dried over Na$_2$SO$_4$, filtered, and concentrated under reduced pressure. The resulting residue was purified by FCC (SiO$_2$, 0-10% EtOAc in ether) to afford the title compound (110 mg, 83% yield) as a colorless oil. MS (ESI): mass calcd. for $C_{22}H_{30}N_2O_2$, 354.2; m/z found, 355.5 [M+H]$^+$.

Step C: tert-Butyl 7-(6-isopropyl-5-methylpyridin-2-yl)-2-azaspiro[3.5]nonane-2-carboxylate. tert-Butyl 7-(5-methyl-6-(prop-1-en-2-yl)pyridin-2-yl)-2-azaspiro[3.5]non-6-ene-2-carboxylate (150 mg, 0.406 mmol) and wet Pd/C (200 mg, 10 wt. %) were taken up in EtOAc (15 mL). The resultant mixture was stirred under H$_2$ (15 psi) at rt for 1 h. The suspension was filtered through a pad of Celite® and the pad was washed with EtOAc. The filtrate was concentrated under reduced pressure to afford the title compound (280 mg, crude) as a yellow oil, which was used in the next step without further purification.

Step D: 7-(6-Isopropyl-5-methylpyridin-2-yl)-2-azaspiro[3.5]nonane. TFA (1 mL, 13.1 mmol) was added to a solution of tert-butyl 7-(6-isopropyl-5-methylpyridin-2-yl)-2-azaspiro[3.5]nonane-2-carboxylate (110 mg, 0.307 mmol) in DCM (4 mL). The reaction mixture was stirred at rt for 2 h before being concentrated under reduced pressure to afford the title compound (110 mg), which was used in the next step without further purification.

Step E: ((1s,3s)-3-Hydroxy-3-methylcyclobutyl)(7-(6-isopropyl-5-methylpyridin-2-yl)-2-azaspiro[3.5]nonan-2-yl)methanone. T$_3$P® (0.40 mL, 50% in EtOAc, 0.650 mmol) was added to solution of 7-(6-isopropyl-5-methylpyridin-2-yl)-2-azaspiro[3.5]nonane (110 mg, 0.295 mmol), (1s,3s)-3-hydroxy-3-methylcyclobutanecarboxylic acid (58 mg, 0.450 mmol) and TEA (0.41 mL, 2.90 mmol) in DCM (10 mL). The resultant mixture was stirred at rt for 1.5 h before being poured into H$_2$O and extracted with DCM. The combined organic extracts were dried over Na$_2$SO$_4$, filtered, and concentrated under reduced pressure. The resulting residue was purified by RP HPLC (46-76% ACN in water containing 0.05% NH$_3$) to afford the title compound (39 mg, 35% yield) as a white solid. MS (ESI): mass calcd. for C$_{23}$H$_{34}$N$_2$O$_2$, 370.3; m/z found, 371.4 [M+H]$^+$. $^1$H NMR (400 MHz, DMSO-d$_6$) δ 7.35 (d, J=7.7 Hz, 1H), 6.90 (d, J=7.7 Hz, 1H), 4.97 (s, 1H), 3.76 (s, 1H), 3.66 (s, 1H), 3.53 (s, 1H), 3.45 (s, 1H), 3.19-3.11 (m, 1H), 2.61-2.49 (m, 2H), 2.21 (s, 3H), 2.12-2.03 (m, 2H), 2.01-1.93 (m, 2H), 1.91-1.82 (m, 2H), 1.79-1.70 (m, 2H), 1.58-1.37 (m, 4H), 1.21 (s, 3H), 1.14 (d, J=6.6 Hz, 6H).

Example 374

((1s,3s)-3-Hydroxy-3-methylcyclobutyl)(7-(6-isopropoxy-4-methylpyridin-2-yl)-2-azaspiro[3.5]nonan-2-yl)methanone

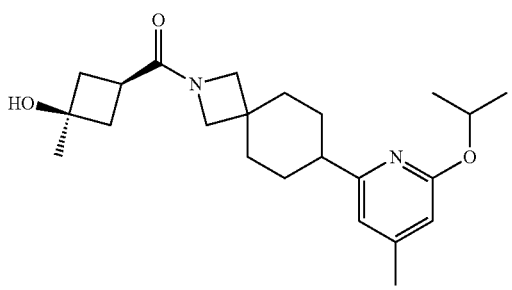 [SMILES: Cc1cc(OC(C)C)nc(C2CCC3(CC2)CN(C(=O)[C@H]2C[C@@](C)(O)C2)C3)c1]

The title compound was prepared in a manner analogous to Example 109 using 2-bromo-6-isopropoxy-4-methylpyridine (Intermediate 64) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for C$_{23}$H$_{34}$N$_2$O$_3$, 386.3; m/z found, 387.3 [M+H]$^+$. $^1$H NMR (400 MHz, DMSO-d$_6$) δ 6.60 (s, 1H), 6.36-6.32 (m, 1H), 5.23-5.14 (m, 1H), 5.00 (s, 1H), 3.78 (s, 1H), 3.69 (s, 1H), 3.54 (s, 1H), 3.46 (s, 1H), 2.63-2.54 (m, 1H), 2.48-2.39 (m, 1H), 2.20 (s, 3H), 2.14-2.06 (m, 2H), 2.03-1.96 (m, 2H), 1.92-1.85 (m, 2H), 1.81-1.71 (m, 2H), 1.59-1.41 (m, 4H), 1.28-1.22 (m, 9H).

Example 375

((1s,3s)-3-Hydroxy-3-methylcyclobutyl)(7-(4-methoxy-6-methylpyridin-2-yl)-2-azaspiro[3.5]nonan-2-yl)methanone

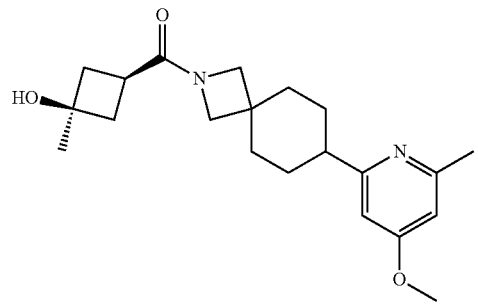 [SMILES: COc1cc(C)nc(C2CCC3(CC2)CN(C(=O)[C@H]2C[C@@](C)(O)C2)C3)c1]

The title compound was prepared in a manner analogous to Example 109 using 2-chloro-4-methoxy-6-methylpyridine instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for C$_{21}$H$_{30}$N$_2$O$_3$, 358.2; m/z found, 359.2 [M+H]$^+$. $^1$H NMR (400 MHz, DMSO-d$_6$) δ 6.68-6.54 (m, 2H), 5.01 (s, 1H), 3.80 (s, 1H), 3.82-3.79 (m, 1H), 3.78 (s, 3H), 3.69 (s, 1H), 3.57 (s, 1H), 3.47 (s, 1H), 2.64-2.54 (m, 1H), 2.36 (s, 3H), 2.16-2.07 (m, 2H), 2.04-1.96 (m, 1H), 2.04-1.96 (m, 1H), 1.93-1.85 (m, 2H), 1.77-1.68 (m, 2H), 1.59-1.42 (m, 4H), 1.24 (s, 3H).

Example 376

((1s,3s)-3-Hydroxy-3-methylcyclobutyl)(7-(2-isopropoxy-3-methylpyridin-4-yl)-2-azaspiro[3.5]nonan-2-yl)methanone

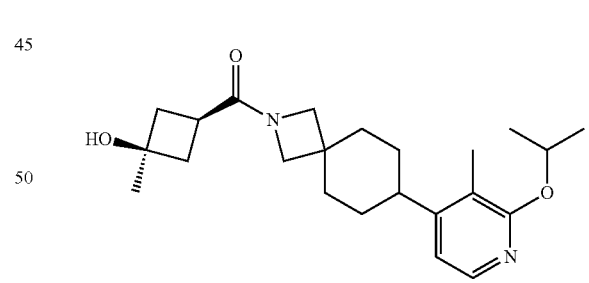

The title compound was prepared in a manner analogous to Example 109 using 4-bromo-2-isopropoxy-3-methylpyridine (Intermediate 63) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for C$_{23}$H$_{34}$N$_2$O$_3$, 386.3; m/z found, 387.2 [M+H]$^+$. $^1$H NMR (400 MHz, DMSO-d$_6$) δ 7.92-7.86 (m, 1H), 6.80-6.75 (m, 1H), 5.26-5.17 (m, 1H), 5.02-4.99 (m, 1H), 3.82 (s, 1H), 3.69 (s, 1H), 3.60 (s, 1H), 3.47 (s, 1H), 2.73-2.63 (m, 1H), 2.62-2.54 (m, 1H), 2.14-2.07 (m, 5H), 2.04-1.96 (m, 2H), 1.94-1.86 (m, 2H), 1.64-1.52 (m, 4H), 1.44-1.34 (m, 2H), 1.29-1.25 (m, 6H), 1.25-1.22 (m, 3H).

Example 377

(7-(6-(tert-Butyl)pyrazin-2-yl)-2-azaspiro[3.5]nonan-2-yl)((1s,3s)-3-hydroxy-3-methylcyclobutyl)methanone

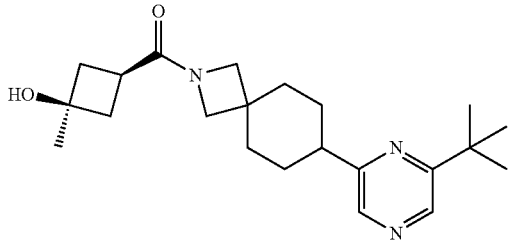 [SMILES: CC(C)(C)c1cncc(C2CCC3(CC2)CN(C(=O)[C@H]2C[C@@](C)(O)C2)C3)n1]

The title compound was prepared in a manner analogous to Example 109 using 2-bromo-6-(tert-butyl)pyrazine instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{22}H_{33}N_3O_2$, 371.3; m/z found, 372.3 [M+H]$^+$. $^1$H NMR (400 MHz, DMSO-d$_6$) δ 8.54 (s, 1H), 8.38 (s, 1H), 5.00 (s, 1H), 3.80 (s, 1H), 3.71 (s, 1H), 3.57 (s, 1H), 3.49 (s, 1H), 2.74-2.65 (m, 1H), 2.63-2.53 (m, 1H), 2.15-2.06 (m, 2H), 2.05-1.96 (m, 2H), 1.96-1.88 (m, 2H), 1.84-1.76 (m, 2H), 1.63-1.47 (m, 4H), 1.33 (s, 9H), 1.24 (s, 3H).

Example 378

(7-(4-(tert-Butyl)pyrimidin-2-yl)-2-azaspiro[3.5]nonan-2-yl)((1s,3s)-3-hydroxy-3-methylcyclobutyl)methanone

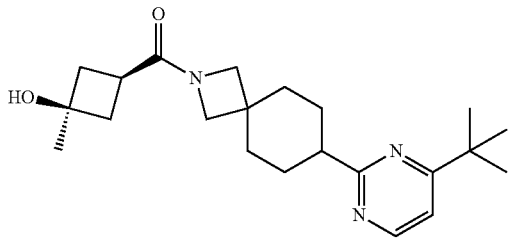 [SMILES: CC(C)(C)c1ccnc(C2CCC3(CC2)CN(C(=O)[C@H]2C[C@@](C)(O)C2)C3)n1]

The title compound was prepared in a manner analogous to Example 109 using 4-(tert-butyl)-2-chloropyrimidine instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{22}H_{33}N_3O_2$, 371.3; m/z found, 372.2 [M+H]$^+$. $^1$H NMR (400 MHz, CDCl$_3$) δ 8.55 (dd, J=5.3, 2.1 Hz, 1H), 7.12 (dd, J=5.4, 2.4 Hz, 1H), 3.90-3.66 (m, 4H), 2.95-2.63 (m, 2H), 2.37-2.22 (m, 5H), 2.10-1.92 (m, 4H), 1.74-1.60 (m, 4H), 1.37-1.32 (m, 12H).

Example 379

(7-(1-(tert-Butyl)-1H-pyrazol-3-yl)-2-azaspiro[3.5]nonan-2-yl)((1s,3s)-3-hydroxy-3-methylcyclobutyl)methanone

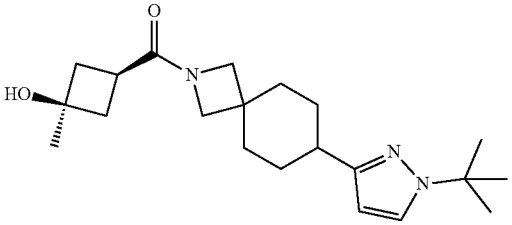 [SMILES: CC(C)(C)n1ccc(C2CCC3(CC2)CN(C(=O)[C@H]2C[C@@](C)(O)C2)C3)n1]

The title compound was prepared in a manner analogous to Example 109 using 3-bromo-1-(tert-butyl)-1H-pyrazole instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{21}H_{33}N_3O_2$, 359.3; m/z found, 360.2 [M+H]$^+$. $^1$H NMR (400 MHz, DMSO-d$_6$) δ 7.61 (d, J=2.3 Hz, 1H), 6.06-5.94 (m, 1H), 3.75 (s, 1H), 3.67 (s, 1H), 3.52 (s, 1H), 3.46 (s, 1H), 2.62-2.53 (m, 2H), 2.14-2.05 (m, 2H), 2.03-1.94 (m, 2H), 1.89-1.73 (m, 4H), 1.57-1.50 (m, 2H), 1.46 (s, 9H), 1.39-1.29 (m, 2H), 1.23 (s, 3H).

Example 380

((1s,3s)-3-Hydroxy-3-methylcyclobutyl)(7-(1-phenyl-1H-pyrazol-3-yl)-2-azaspiro[3.5]nonan-2-yl)methanone

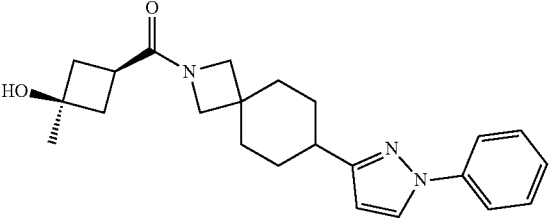 [SMILES: C[C@]1(O)C[C@@H](C(=O)N2CC3(CCC(c4ccn(-c5ccccc5)n4)CC3)C2)C1]

The title compound was prepared in a manner analogous to Example 97 using 1-phenyl-3-(4,4,5,5-tetramethyl-1,3,2-dioxaborolan-2-yl)-1H-pyrazole instead of pyrazolo[1,5-a]pyridine-5-boronic acid pinacol ester, tert-butyl 7-(((trifluoromethyl)sulfonyl)oxy)-2-azaspiro[3.5]non-6-ene-2-carboxylate (Intermediate 8) instead of tert-butyl 6-(((trifluoromethyl)sulfonyl)oxy)-2-azaspiro[3.4]oct-6-ene-2-carboxylate (Intermediate 7), and Pd(dppf)Cl$_2$ instead of XPhos Pd G2 in Step A. MS (ESI): mass calcd. for $C_{23}H_{29}N_3O_2$, 379.2; m/z found, 380.3 [M+H]$^+$. $^1$H NMR (400 MHz, DMSO-d$_6$) δ 8.42-8.30 (m, 1H), 7.78 (d, J=8.0 Hz, 2H), 7.52-7.40 (m, 2H), 7.31-7.19 (m, 1H), 6.42-6.34

(m, 1H), 5.00 (s, 1H), 3.79 (s, 1H), 3.70 (s, 1H), 3.55 (s, 1H), 3.48 (s, 1H), 2.69-2.52 (m, 2H), 2.15-2.06 (m, 2H), 2.05-1.96 (m, 2H), 1.94-1.81 (m, 4H), 1.63-1.38 (m, 4H), 1.24 (s, 3H).

Example 381

(7-(1-(tert-Butyl)-1H-imidazol-4-yl)-2-azaspiro[3.5]nonan-2-yl)((1s,3s)-3-hydroxy-3-methylcyclobutyl)methanone

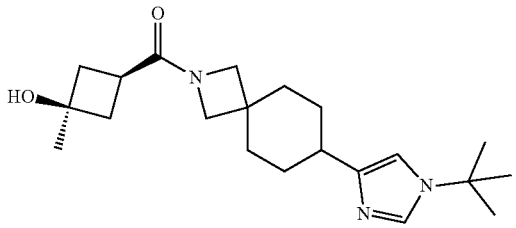 [SMILES: CC(C)(C)n1cnc(C2CCC3(CC2)CN(C(=O)[C@H]2C[C@@](C)(O)C2)C3)c1]

The title compound was prepared in a manner analogous to Example 109 using 4-bromo-1-(tert-butyl)-1H-imidazole instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{21}H_{33}N_3O_2$, 359.3; m/z found, 360.2 [M+H]$^+$. $^1$H NMR (400 MHz, DMSO-d$_6$) δ 7.57-7.54 (m, 1H), 6.98-6.94 (m, 1H), 5.03-4.99 (m, 1H), 3.75-3.66 (m, 2H), 3.48 (d, J=18.5 Hz, 2H), 2.60-2.53 (m, 1H), 2.40-2.30 (m, 1H), 2.13-2.05 (m, 2H), 2.03-1.95 (m, 2H), 1.87-1.79 (m, 4H), 1.55-1.48 (m, 2H), 1.45 (s, 9H), 1.37-1.26 (m, 2H), 1.23 (s, 3H).

Example 382

(7-(3-(tert-Butyl)isoxazol-5-yl)-2-azaspiro[3.5]nonan-2-yl)((1s,3s)-3-hydroxy-3-methylcyclobutyl)methanone

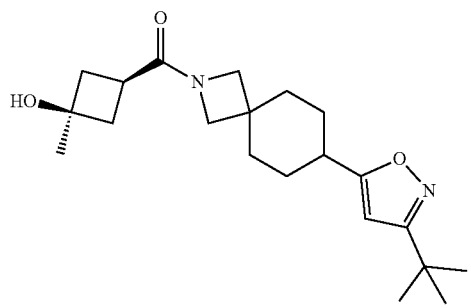 [SMILES: CC(C)(C)c1cc(C2CCC3(CC2)CN(C(=O)[C@H]2C[C@@](C)(O)C2)C3)on1]

Step A: tert-Butyl 7-ethynyl-2-azaspiro[3.5]nonane-2-carboxylate. Dimethyl (1-diazo-2-oxopropyl)phosphonate (948 mg, 4.94 mmol) was added in portions to a 0° C. solution of tert-butyl 7-formyl-2-azaspiro[3.5]nonane-2-carboxylate (500 mg, 1.97 mmol) and $K_2CO_3$ (818 mg, 5.92 mmol) in MeOH (10 mL). The resultant mixture was stirred at rt for 2 h before being poured into H$_2$O and extracted with DCM. The combined organic extracts were washed with brine, dried over Na$_2$SO$_4$, filtered, and concentrated under reduced pressure. The resulting residue was purified by FCC (SiO$_2$, 0-50% EtOAc in ether) to afford the title compound (450 mg, 91% yield) as a white oil. MS (ESI): mass calcd. for $C_{15}H_{23}NO_2$, 249.2; m/z found, 193.8 [M+2H-tBu]$^+$.

Step B: tert-Butyl 7-(3-(tert-butyl)isoxazol-5-yl)-2-azaspiro[3.5]nonane-2-carboxylate. Pyridine (0.32 mL, 4.00 mmol) was added to a mixture of pivalaldehyde (345 mg, 4.01 mmol) and NH$_2$OH·HCl (167 mg, 2.40 mmol) in EtOH (5 mL). The reaction mixture was stirred at 80° C. for 2 h. The reaction mixture was cooled to rt and concentrated under reduced pressure. The resulting residue was added to a mixture of N-chlorosuccinimide (321 mg, 2.40 mmol) in DCM (10 mL). The reaction mixture was stirred at rt for 2 h before tert-butyl 7-ethynyl-2-azaspiro[3.5]nonane-2-carboxylate (500 mg, 2.00 mmol) and TEA (0.56 mL, 4.02 mmol) were added. The reaction mixture was stirred at rt for 16 h before being poured into water and extracted with DCM. The combined organic extracts were dried over Na$_2$SO$_4$, filtered, and concentrated under reduced pressure. The resulting residue was purified by FCC (SiO$_2$, 0-50% EtOAc in ether) to afford the title compound (680 mg, 61% yield) as a yellow oil. MS (ESI): mass calcd. for $C_{20}H_{32}N_2O_3$, 348.2; m/z found, 293.4 [M+2H-tBu]$^+$.

Step C: 3-(tert-Butyl)-5-(2-azaspiro[3.5]nonan-7-yl)isoxazole. TFA (1 mL, 13.1 mmol) was added to a solution of tert-butyl 7-(3-(tert-butyl)isoxazol-5-yl)-2-azaspiro[3.5]nonane-2-carboxylate (680 mg, 1.95 mmol) in DCM (5 mL). The reaction mixture was stirred at rt for 2 h before being concentrated under reduced pressure to give the title compound (700 mg, crude), which was used in the next step without further purification. MS (ESI): mass calcd. for $C_{15}H_{24}N_2O$, 248.2; m/z found, 249.1 [M+H]$^+$.

Step D: (7-(3-(tert-Butyl)isoxazol-5-yl)-2-azaspiro[3.5]nonan-2-yl)((1s,3s)-3-hydroxy-3-methylcyclobutyl)methanone. T$_3$P® (1.2 mL, 50% in EtOAc, 2.00 mmol) was added to solution of 3-(tert-butyl)-5-(2-azaspiro[3.5]nonan-7-yl)isoxazole (700 mg, 1.93 mmol), (1s,3s)-3-hydroxy-3-methylcyclobutanecarboxylic acid (251 mg, 1.93 mmol) and TEA (2.7 mL, 19.0 mmol) in DCM (10 mL). The resultant mixture was stirred at rt for 2 h before being poured into H$_2$O and extracted with DCM. The combined organic extracts were dried over Na$_2$SO$_4$, filtered, and concentrated under reduced pressure. The resulting residue was purified by RP HPLC (35-65% CH$_3$CN in H$_2$O with 0.05% NH$_3$) to afford the title compound (39 mg, 6% yield) as a yellow solid. MS (ESI): mass calcd. for $C_{21}H_{32}N_2O_3$, 360.2; m/z found, 361.2 [M+H]$^+$. $^1$H NMR (400 MHz, DMSO-d$_6$) δ 6.28-6.20 (m, 1H), 4.99 (s, 1H), 3.80-3.64 (m, 2H), 3.57-3.44 (m, 2H), 2.76-2.66 (m, 1H), 2.60-2.53 (m, 1H), 2.14-2.05 (m, 2H), 2.03-1.95 (m, 2H), 1.92-1.80 (m, 4H), 1.61-1.48 (m, 2H), 1.47-1.34 (m, 2H), 1.24 (s, 12H).

Example 383

((1s,3s)-3-Hydroxy-3-methylcyclobutyl)(7-(1-methyl-1H-pyrrolo[2,3-b]pyridin-3-yl)-2-azaspiro[3.5]nonan-2-yl)methanone

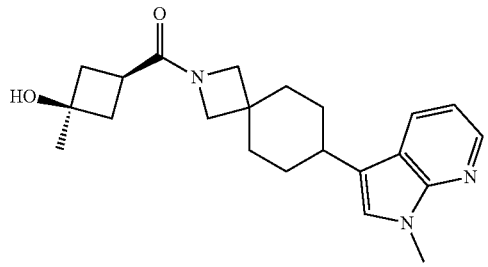 [SMILES: Cn1cc(C2CCC3(CC2)CN(C(=O)[C@H]2C[C@@](C)(O)C2)C3)c2cccnc21]

The title compound was prepared in a manner analogous to Example 109 using 3-bromo-1-methyl-1H-pyrrolo[2,3-b]pyridine instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{22}H_{29}N_3O_2$, 367.2; m/z found, 368.2 [M+H]$^+$. $^1$H NMR (400 MHz, CDCl$_3$) δ 8.34-8.31 (m, 1H), 7.91-7.86 (m, 1H), 7.06-7.00 (m, 1H), 6.92 (d, J=8.5 Hz, 1H), 3.86-3.71 (m, 7H), 2.84-2.66 (m, 2H), 2.33-2.27 (m, 4H), 2.11-1.98 (m, 4H), 1.75-1.63 (m, 2H), 1.56-1.42 (m, 2H), 1.37 (s, 3H).

Example 384

((1s,3s)-3-Hydroxy-3-methylcyclobutyl)(7-(1-methyl-1H-pyrrolo[2,3-b]pyridin-6-yl)-2-azaspiro[3.5]nonan-2-yl)methanone

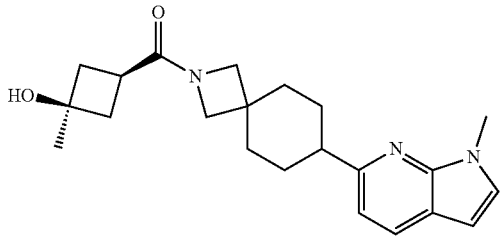 [SMILES: Cn1ccc2ccc(C3CCC4(CC3)CN(C(=O)[C@H]3C[C@@](C)(O)C3)C4)nc21]

The title compound was prepared in a manner analogous to Example 109 using 6-bromo-1-methyl-1H-pyrrolo[2,3-b]pyridine (Intermediate 44) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{22}H_{29}N_3O_2$, 367.2; m/z found, 368.2 [M+H]$^+$. $^1$H NMR (400 MHz, CDCl$_3$) δ 7.94-7.71 (m, 1H), 7.20-7.02 (m, 1H), 6.97-6.72 (m, 1H), 6.54-6.28 (m, 1H), 3.92-3.67 (m, 7H), 3.44 (br s, 1H), 2.87-2.59 (m, 2H), 2.44-2.21 (m, 4H), 2.12-1.91 (m, 4H), 1.78-1.54 (m, 4H), 1.37 (s, 3H).

Example 385

((1s,3s)-3-Hydroxy-3-methylcyclobutyl)(7-(1-isopropyl-1H-pyrrolo[2,3-b]pyridin-6-yl)-2-azaspiro[3.5]nonan-2-yl)methanone

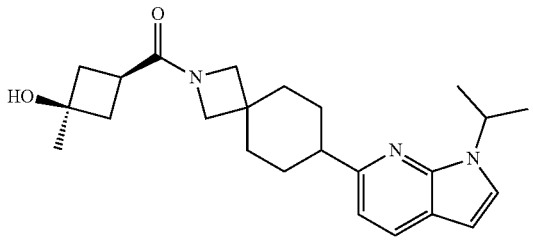 [SMILES: CC(C)n1ccc2ccc(C3CCC4(CC3)CN(C(=O)[C@H]3C[C@@](C)(O)C3)C4)nc21]

The title compound was prepared in a manner analogous to Example 109 using 6-bromo-1-isopropyl-1H-pyrrolo[2,3-b]pyridine (Intermediate 47) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{24}H_{33}N_3O_2$, 395.3; m/z found, 396.2 [M+H]$^+$. $^1$H NMR (400 MHz, DMSO-d$_6$) δ 7.83 (d, J=8.0 Hz, 1H), 7.55-7.52 (m, 1H), 6.96 (d, J=8.1 Hz, 1H), 6.40-6.37 (m, 1H), 5.12-4.93 (m, 2H), 3.83 (s, 1H), 3.71 (s, 1H), 3.60 (s, 1H), 3.49 (s, 1H), 2.71-2.66 (m, 1H), 2.63-2.54 (m, 1H), 2.14-2.08 (m, 2H), 2.04-1.98 (m, 2H), 1.96-1.90 (m, 2H), 1.87-1.81 (m, 2H), 1.64-1.54 (m, 4H), 1.46 (s, 3H), 1.45 (s, 3H), 1.26-1.23 (m, 3H).

Example 386

((1s,3s)-3-Hydroxy-3-methylcyclobutyl)(7-(1-methyl-3-(trifluoromethyl)-1H-pyrrolo[2,3-b]pyridin-6-yl)-2-azaspiro[3.5]nonan-2-yl)methanone

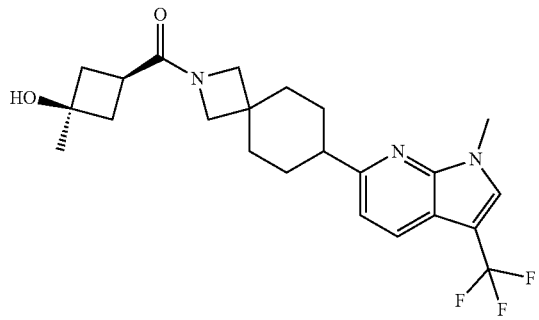 [SMILES: Cn1cc(C(F)(F)F)c2ccc(C3CCC4(CC3)CN(C(=O)[C@H]3C[C@@](C)(O)C3)C4)nc21]

The title compound was prepared in a manner analogous to Example 109 using 6-bromo-1-methyl-3-(trifluoromethyl)-1H-pyrrolo[2,3-b]pyridine (Intermediate 49) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{23}H_{28}F_3N_3O_2$, 435.2; m/z found, 436.1 [M+H]$^+$. $^1$H NMR (400 MHz, CDCl$_3$) δ 7.94 (d, J=8.0 Hz, 1H), 7.48 (s, 1H), 7.04 (d, J=8.0 Hz, 1H), 3.90 (s, 3H), 3.88 (s, 1H), 3.82 (s, 1H), 3.77 (s, 1H), 3.72 (s, 1H), 2.85-2.65 (m, 2H), 2.40-2.24 (m, 4H), 2.11-1.92 (m, 4H), 1.75-1.66 (m, 3H), 1.62-1.56 (m, 1H), 1.37 (s, 3H).

Example 387

((1s,3s)-3-Hydroxy-3-methylcyclobutyl)(7-(1-(2,2,2-trifluoroethyl)-1H-pyrrolo[2,3-b]pyridin-6-yl)-2-azaspiro[3.5]nonan-2-yl)methanone

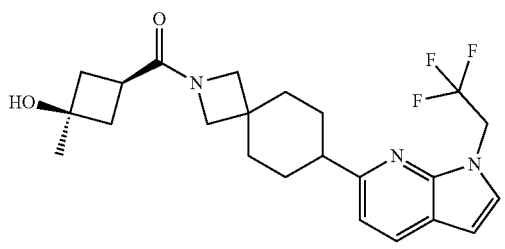 [SMILES: C[C@]1(O)C[C@@H](C(=O)N2CC3(CCC(c4ccc5ccn(CC(F)(F)F)c5n4)CC3)C2)C1]

The title compound was prepared in a manner analogous to Example 109 using 6-bromo-1-(2,2,2-trifluoroethyl)-1H-pyrrolo[2,3-b]pyridine (Intermediate 46) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for C$_{23}$H$_{28}$F$_3$N$_3$O$_2$, 435.2; m/z found, 436.2 [M+H]$^+$. $^1$H NMR (400 MHz, DMSO-d$_6$) δ 7.94-7.90 (m, 1H), 7.48 (d, J=3.5 Hz, 1H), 7.06 (d, J=8.0 Hz, 1H), 6.54-6.51 (m, 1H), 5.16-5.08 (m, 2H), 5.01 (s, 1H), 3.82 (s, 1H), 3.71 (s, 1H), 3.59 (s, 1H), 3.49 (s, 1H), 2.74-2.67 (m, 1H), 2.61-2.55 (m, 1H), 2.13-2.07 (m, 2H), 2.04-1.98 (m, 2H), 1.96-1.89 (m, 2H), 1.87-1.81 (m, 2H), 1.63-1.55 (m, 4H), 1.25-1.23 (m, 3H).

Example 388

((1s,3s)-3-Hydroxy-3-methylcyclobutyl)(7-(pyrazolo[1,5-c]pyridin-2-yl)-2-azaspiro[3.5]nonan-2-yl)methanone

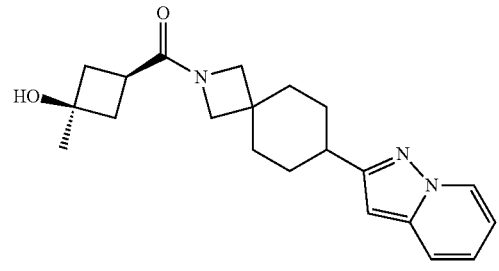 [SMILES: C[C@]1(O)C[C@@H](C(=O)N2CC3(CCC(c4cc5ccccn5n4)CC3)C2)C1]

The title compound was prepared in a manner analogous to Example 109 using 2-chloropyrazolo[1,5-a]pyridine instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for C$_{21}$H$_{27}$N$_3$O$_2$, 353.2; m/z found, 354.2 [M+H]$^+$. $^1$H NMR (400 MHz, DMSO-d$_6$) δ 8.58-8.51 (m, 1H), 7.59-7.53 (m, 1H), 7.17-7.09 (m, 1H), 6.81-6.74 (m, 1H), 6.39 (d, J=1.0 Hz, 1H), 5.01 (s, 1H), 3.79 (s, 1H), 3.70 (s, 1H), 3.55 (s, 1H), 3.49 (s, 1H), 2.78-2.68 (m, 1H), 2.62-2.53 (m, 1H), 2.15-2.05 (m, 2H), 2.04-1.95 (m, 2H), 1.95-1.82 (m, 4H), 1.64-1.45 (m, 4H), 1.23 (s, 3H).

Example 389

((1s,3s)-3-Hydroxy-3-methylcyclobutyl)(7-(pyrazolo[1,5-a]pyridin-7-yl)-2-azaspiro[3.5]nonan-2-yl)methanone

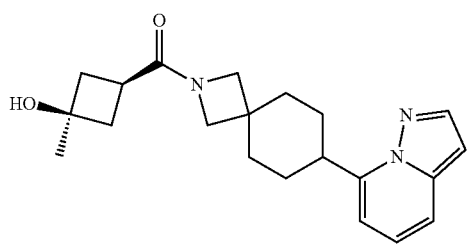 [SMILES: C[C@]1(O)C[C@@H](C(=O)N2CC3(CCC(c4cccc5ccnn45)CC3)C2)C1]

The title compound was prepared in a manner analogous to Example 109 using 7-bromopyrazolo[1,5-a]pyridine instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for C$_{21}$H$_{27}$N$_3$O$_2$, 353.2; m/z found, 354.3 [M+H]$^+$. $^1$H NMR (400 MHz, CDCl$_3$) δ 8.02-7.98 (m, 1H), 7.47 (d, J=8.8 Hz, 1H), 7.15-7.06 (m, 1H), 6.62-6.54 (m, 2H), 3.91-3.73 (m, 4H), 3.65-3.55 (m, 1H), 2.78-2.67 (m, 1H), 2.39-2.22 (m, 6H), 2.12-2.04 (m, 2H), 1.88-1.74 (m, 2H), 1.57-1.43 (m, 2H), 1.38 (s, 3H).

Example 390

((1s,3s)-3-Hydroxy-3-methylcyclobutyl)(7-(imidazo[1,2-c]pyridin-5-yl)-2-azaspiro[3.5]nonan-2-yl)methanone

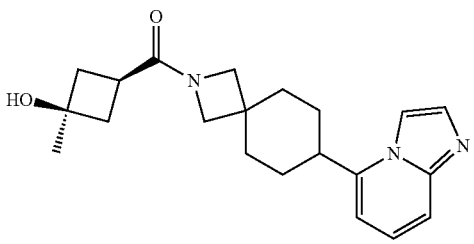 [SMILES: C[C@]1(O)C[C@@H](C(=O)N2CC3(CCC(c4cccc5nccn45)CC3)C2)C1]

The title compound was prepared in a manner analogous to Example 109 using 5-bromoimidazo[1,2-a]pyridine instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{21}H_{27}N_3O_2$, 353.2; m/z found, 354.1 [M+H]$^+$. $^1$H NMR (400 MHz, CDCl$_3$) δ 7.72-7.68 (m, 1H), 7.58-7.53 (m, 2H), 7.22-7.15 (m, 1H), 6.60 (dd, J=12.1, 7.0 Hz, 1H), 3.88-3.75 (m, 4H), 2.91-2.79 (m, 1H), 2.76-2.66 (m, 1H), 2.37-2.26 (m, 4H), 2.23-2.09 (m, 4H), 1.82-1.72 (m, 2H), 1.55-1.42 (m, 2H), 1.37 (s, 3H).

Example 391

((1s,3s)-3-Hydroxy-3-methylcyclobutyl)(7-(imidazo[1,2-c]pyridin-2-yl)-2-azaspiro[3.5]nonan-2-yl)methanone

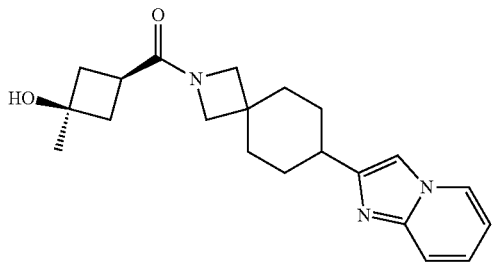 [SMILES: C[C@]1(O)C[C@@H](C(=O)N2CC3(CCC(c4cn5ccccc5n4)CC3)C2)C1]

The title compound was prepared in a manner analogous to Example 109 using 2-bromoimidazo[1,2-c]pyridine instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{21}H_{27}N_3O_2$, 353.2; m/z found, 354.1 [M+H]$^+$. $^1$H NMR (400 MHz, MeOD-d$_4$) δ 8.34 (d, J=6.8 Hz, 1H), 7.61 (d, J=3.0 Hz, 1H), 7.52-7.37 (m, 1H), 7.33-7.20 (m, 1H), 6.97-6.75 (m, 1H), 4.03-3.57 (m, 4H), 2.95-2.58 (m, 2H), 2.32-1.97 (m, 8H), 1.75-1.51 (m, 4H), 1.36 (s, 3H).

Example 392

((1s,3s)-3-Hydroxy-3-methylcyclobutyl)(7-(imidazo[1,2-c]pyridin-3-yl)-2-azaspiro[3.5]nonan-2-yl)methanone

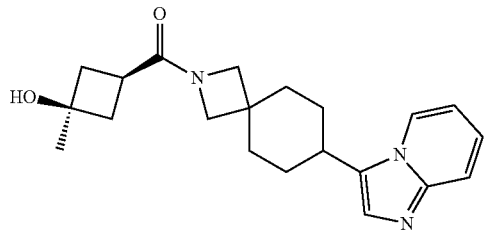 [SMILES: C[C@]1(O)C[C@@H](C(=O)N2CC3(CCC(c4cnc5ccccn45)CC3)C2)C1]

The title compound was prepared in a manner analogous to Example 109 using 3-bromoimidazo[1,2-c]pyridine instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{21}H_{27}N_3O_2$, 353.2; m/z found, 354.1 [M+H]$^+$. $^1$H NMR (400 MHz, CDCl$_3$) δ 7.95-7.91 (m, 1H), 7.62 (d, J=9.1 Hz, 1H), 7.39 (d, J=9.2 Hz, 1H), 7.19-7.13 (m, 1H), 6.83 (q, J=6.6 Hz, 1H), 3.88-3.72 (m, 5H), 2.88-2.77 (m, 1H), 2.77-2.65 (m, 1H), 2.36-2.26 (m, 4H), 2.16-2.04 (m, 4H), 1.78-1.73 (m, 2H), 1.59-1.47 (m, 2H), 1.37 (s, 3H).

Example 393

((1s,3s)-3-Hydroxy-3-methylcyclobutyl)(7-(pyrrolo[1,2-b]pyridazin-3-yl)-2-azaspiro[3.5]nonan-2-yl)methanone

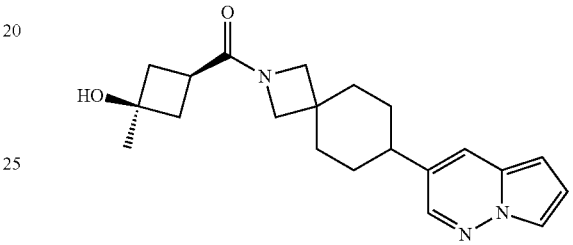

The title compound was prepared in a manner analogous to Example 109 using 3-chloropyrrolo[1,2-b]pyridazine (Intermediate 61) instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{21}H_{27}N_3O_2$, 353.2; m/z found, 354.4 [M+H]$^+$. $^1$H NMR (400 MHz, DMSO-d$_6$) δ 8.17-8.14 (m, 1H), 7.92-7.88 (m, 1H), 6.69-6.65 (m, 1H), 6.57 (dd, J=9.0, 4.3 Hz, 1H), 6.51-6.47 (m, 1H), 5.00 (s, 1H), 3.84-3.48 (m, 4H), 3.16-3.08 (m, 1H), 2.63-2.53 (m, 1H), 2.14-2.07 (m, 2H), 2.04-1.90 (m, 6H), 1.67-1.56 (m, 2H), 1.52-1.38 (m, 2H), 1.24 (s, 3H).

Example 394

((1s,3s)-3-Hydroxy-3-methylcyclobutyl)(7-(pyrazolo[1,5-c]pyridin-3-yl)-2-azaspiro[3.5]nonan-2-yl)methanone

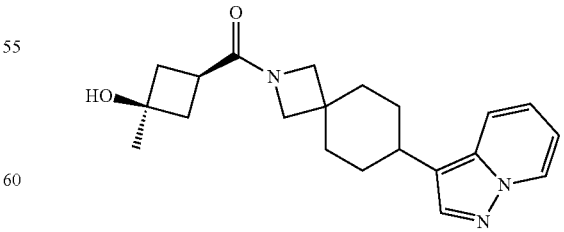

The title compound was prepared in a manner analogous to Example 109 using 3-bromopyrazolo[1,5-c]pyridine instead of 4-bromo-1-methyl-5-(trifluoromethyl)-1H-pyrazole and tert-butyl 7-(4,4,5,5-tetramethyl-1,3,2-dioxaborolan-2-yl)-2-azaspiro[3.5]non-6-ene-2-carboxylate (Intermediate 10) instead of tert-butyl 6-(4,4,5,5-tetramethyl-1,3,2-dioxaborolan-2-yl)-2-azaspiro[3.4]oct-6-ene-2-carboxylate (Intermediate 9) in Step A. MS (ESI): mass calcd. for $C_{21}H_{27}N_3O_2$, 353.2; m/z found, 354.2 [M+H]$^+$. $^1$H NMR (400 MHz, CDCl$_3$) δ 8.42 (d, J=7.0 Hz, 1H), 7.76 (d, J=6.4 Hz, 1H), 7.52-7.41 (m, 1H), 7.13-6.98 (m, 1H), 6.80-6.64 (m, 1H), 3.89-3.70 (m, 5H), 2.83-2.65 (m, 2H), 2.41-2.21 (m, 4H), 2.06-1.95 (m, 4H), 1.73-1.65 (m, 2H), 1.57-1.44 (m, 2H), 1.37 (s, 3H).

Example 395

((1s,3s)-3-Hydroxy-3-methylcyclobutyl)(7-(4,5,6,7-tetrahydropyrazolo[1,5-a]pyridin-2-yl)-2-azaspiro[3.5]nonan-2-yl)methanone

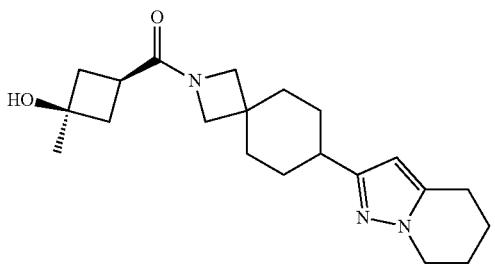 [SMILES: C[C@]1(O)C[C@@H](C(=O)N2CC3(CCC(c4cc5n(n4)CCCC5)CC3)C2)C1]

The title compound was recovered as a byproduct from the synthesis of ((1s,3s)-3-hydroxy-3-methylcyclobutyl)(7-(pyrazolo[1,5-c]pyridin-2-yl)-2-azaspiro[3.5]nonan-2-yl)methanone (Example 388). MS (ESI): mass calcd. for $C_{21}H_{31}N_3O_2$, 357.2; m/z found, 358.2 [M+H]$^+$. $^1$H NMR (400 MHz, DMSO-d$_6$) δ 5.75 (d, J=4.4 Hz, 1H), 3.93 (t, J=6.0 Hz, 2H), 3.76-3.66 (m, 2H), 3.51-3.45 (m, 3H), 2.66 (t, J=6.3 Hz, 2H), 2.59-2.53 (m, 1H), 2.46-2.39 (m, 1H), 2.13-2.05 (m, 2H), 2.03-1.96 (m, 2H), 1.94-1.87 (m, 2H), 1.84-1.70 (m, 6H), 1.54-1.45 (m, 2H), 1.41-1.30 (m, 2H), 1.23 (s, 3H).

Example 396

((1s,3s)-3-Hydroxy-3-methylcyclobutyl)(7-(5,6,7,8-tetrahydroimidazo[1,2-a]pyridin-2-yl)-2-azaspiro[3.5]nonan-2-yl)methanone

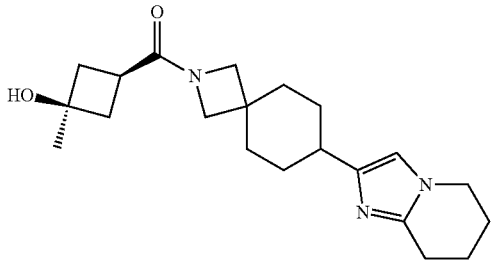 [SMILES: C[C@]1(O)C[C@@H](C(=O)N2CC3(CCC(c4cn5c(n4)CCCC5)CC3)C2)C1]

The title compound was recovered as a byproduct from the synthesis of ((1s,3s)-3-hydroxy-3-methylcyclobutyl)(7-(imidazo[1,2-c]pyridin-2-yl)-2-azaspiro[3.5]nonan-2-yl)methanone (Example 391). MS (ESI): mass calcd. for $C_{21}H_{31}N_3O_2$, 357.2; m/z found, 358.3 [M+H]$^+$. $^1$H NMR (400 MHz, CDCl$_3$) δ 6.46 (s, 1H), 3.99-3.56 (m, 7H), 2.89-2.79 (m, 2H), 2.76-2.62 (m, 1H), 2.55-2.43 (m, 1H), 2.40-2.15 (m, 5H), 2.07-1.90 (m, 7H), 1.65-1.52 (m, 2H), 1.44-1.33 (m, 5H).

Example 397

((1s,3s)-3-Hydroxy-3-methylcyclobutyl)(7-(4-methylbenzyl)-2-azaspiro[3.5]nonan-2-yl)methanone

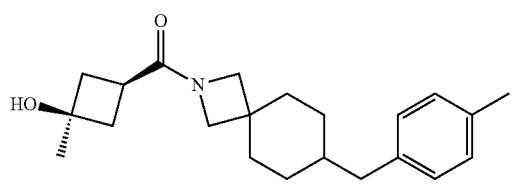 [SMILES: Cc1ccc(CC2CCC3(CC2)CN(C(=O)[C@H]2C[C@@](C)(O)C2)C3)cc1]

The title compound was prepared in a manner analogous to Example 174 using tert-butyl 7-oxo-2-azaspiro[3.5]nonane-2-carboxylate instead of tert-butyl 6-oxo-2-azaspiro[3.4]octane-2-carboxylate and diethyl 4-methylbenzylphosphonate instead of diethyl 3-methylbenzylphosphonate in Step A. MS (ESI): mass calcd. for $C_{22}H_{31}NO_2$, 341.2; m/z found, 342.1 [M+H]$^+$. $^1$H NMR (400 MHz, CDCl$_3$) δ 7.12-7.06 (m, 2H), 7.05-6.99 (m, 2H), 3.95 (s, 1H), 3.76-3.59 (m, 4H), 2.75-2.60 (m, 1H), 2.48-2.40 (m, 2H), 2.36-2.18 (m, 7H), 1.84 (d, J=13.0 Hz, 2H), 1.67-1.61 (m, 2H), 1.53-1.38 (m, 3H), 1.35 (d, J=4.9 Hz, 3H), 1.06-0.84 (m, 2H).

Example 398

(7-(2-Fluoro-3-methylbenzyl)-2-azaspiro[3.5]nonan-2-yl)((1s,3s)-3-hydroxy-3-methylcyclobutyl)methanone

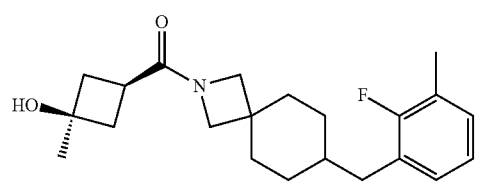 [SMILES: Cc1cccc(CC2CCC3(CC2)CN(C(=O)[C@H]2C[C@@](C)(O)C2)C3)c1F]

The title compound was prepared in a manner analogous to Example 159 using (2-fluoro-3-methylbenzyl)triphenylphosphonium bromide (Intermediate 66) instead of (3-methylbenzyl)triphenylphosphonium chloride in Step A. MS (ESI): mass calcd. for $C_{22}H_{30}FNO_2$, 359.2; m/z found, 360.1 [M+H]$^+$. $^1$H NMR (400 MHz, CDCl$_3$) δ 7.07-6.98 (m, 1H), 6.97-6.90 (m, 2H), 3.93 (d, J=5.2 Hz, 1H), 3.77-3.60 (m, 4H), 2.75-2.61 (m, 1H), 2.50 (d, J=7.2 Hz, 2H), 2.36-2.21 (m, 7H), 1.85 (d, J=13.4 Hz, 2H), 1.67-1.62 (m, 2H), 1.58-1.37 (m, 3H), 1.35 (d, J=5.2 Hz, 3H), 1.09-0.88 (m, 2H).

Example 399

(7-(4-Fluoro-3-methylbenzyl)-2-azaspiro[3.5]nonan-2-yl)((1s,3s)-3-hydroxy-3-methylcyclobutyl)methanone

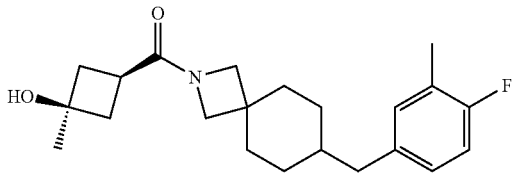 [SMILES: Cc1cc(CC2CCC3(CC2)CN(C(=O)[C@H]2C[C@@](C)(O)C2)C3)ccc1F]

The title compound was prepared in a manner analogous to Example 159 using (4-fluoro-3-methylbenzyl)triphenylphosphonium bromide (Intermediate 67) instead of (3-methylbenzyl)triphenylphosphonium chloride in Step A. MS (ESI): mass calcd. for $C_{22}H_{30}FNO_2$, 359.2; m/z found, 360.1 [M+H]$^+$. $^1$H NMR (400 MHz, CDCl$_3$) δ 6.94-6.84 (m, 3H), 4.03-3.95 (m, 1H), 3.76-3.59 (m, 4H), 2.74-2.60 (m, 1H), 2.41 (d, J=7.2 Hz, 2H), 2.36-2.22 (m, 7H), 1.88-1.81 (m, 2H), 1.69-1.60 (m, 2H), 1.51-1.38 (m, 3H), 1.35 (d, J=4.5 Hz, 3H), 1.02-0.84 (m, 2H).

Example 400

(7-((1H-Pyrrolo[2,3-b]pyridin-1-yl)methyl)-2-azaspiro[3.5]nonan-2-yl)((1s,3s)-3-hydroxy-3-methylcyclobutyl)methanone

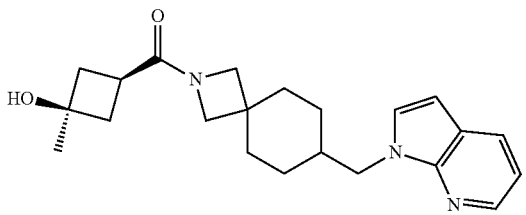 [SMILES: C[C@]1(O)C[C@@H](C(=O)N2CC3(CCC(Cn4ccc5cccnc54)CC3)C2)C1]

The title compound was prepared in a manner analogous to Example 237 using tert-butyl 7-(bromomethyl)-2-azaspiro[3.5]nonane-2-carboxylate (Intermediate 70) instead of tert-butyl 6-(bromomethyl)-2-azaspiro[3.3]heptane-2-carboxylate (Intermediate 4) and 1H-pyrrolo[2,3-b]pyridine instead of 3-(trifluoromethyl)-1H-pyrazole in Step A. MS (ESI): mass calcd. for $C_{22}H_{29}N_3O_2$, 367.2; m/z found, 368.5 [M+H]$^+$. $^1$H NMR (400 MHz, DMSO-d$_6$) δ 8.25-8.21 (m, 1H), 7.97-7.94 (m, 1H), 7.54-7.49 (m, 1H), 7.07 (dd, J=7.7, 4.6 Hz, 1H), 6.46 (m, 1H), 4.98 (br s, 1H), 4.10 (d, J=7.4 Hz, 2H), 3.71 (s, 1H), 3.62 (s, 1H), 3.49 (s, 1H), 3.40 (s, 1H), 2.59-2.53 (m, 1H), 2.13-2.04 (m, 2H), 2.03-1.94 (m, 2H), 1.91-1.73 (m, 3H), 1.45-1.28 (m, 4H), 1.23 (d, J=8.9 Hz, 3H), 1.09-0.94 (m, 2H).

Example 401

((1s,3s)-3-Hydroxy-3-methylcyclobutyl)(7-((1-methyl-1H-pyrrolo[2,3-b]pyridin-6-yl)methyl)-2-azaspiro[3.5]nonan-2-yl)methanone

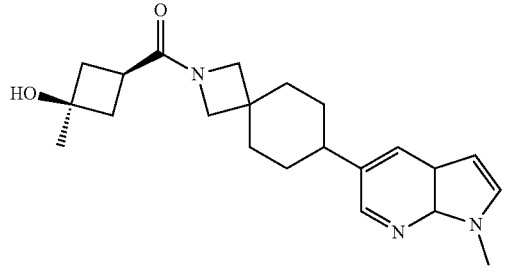 [SMILES: CN1C=CC2C=C(C3CCC4(CC3)CN(C(=O)[C@H]3C[C@@](C)(O)C3)C4)C=NC21]

The title compound was prepared in a manner analogous to Example 159 using ((1-methyl-1H-pyrrolo[2,3-b]pyridin-6-yl)methyl)triphenylphosphonium bromide (Intermediate 68) instead of (3-methylbenzyl)triphenylphosphonium chloride in Step A. MS (ESI): mass calcd. for $C_{23}H_{31}N_3O_2$, 381.2; m/z found, 382.2 [M+H]$^+$. $^1$H NMR (400 MHz, CDCl$_3$) δ 7.79 (dd, J=7.9, 1.2 Hz, 1H), 7.14-7.08 (m, 1H), 6.86 (dd, J=7.9, 2.6 Hz, 1H), 6.43-6.37 (m, 1H), 4.04 (br s, 1H), 3.87 (s, 3H), 3.75-3.61 (m, 4H), 2.74 (d, J=7.3 Hz, 2H), 2.72-2.61 (m, 1H), 2.34-2.23 (m, 4H), 1.90-1.85 (m, 2H), 1.81-1.76 (m, 1H), 1.74-1.64 (m, 2H), 1.51-1.38 (m, 2H), 1.35 (d, J=6.6 Hz, 3H), 1.13-0.95 (m, 2H).

Example 402

((1s,3s)-3-Hydroxy-3-methylcyclobutyl)(7-((1-methyl-1H-indazol-6-yl)methyl)-2-azaspiro[3.5]nonan-2-yl)methanone

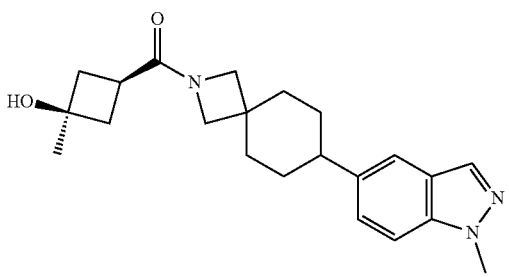 [SMILES: Cn1ncc2cc(C3CCC4(CC3)CN(C(=O)[C@H]3C[C@@](C)(O)C3)C4)ccc21]

The title compound was prepared in a manner analogous to Example 159 using ((1-methyl-1H-indazol-6-yl)methyl)triphenylphosphonium bromide (Intermediate 69) instead of (3-methylbenzyl)triphenylphosphonium chloride in Step A. MS (ESI): mass calcd. for $C_{23}H_{31}N_3O_2$, 381.2; m/z found, 382.3 [M+H]$^+$. $^1$H NMR (400 MHz, DMSO-d$_6$) δ 7.95 (s, 1H), 7.65-7.60 (m, 1H), 7.38-7.33 (m, 1H), 6.97-6.91 (m, 1H), 5.02-4.97 (m, 1H), 3.99 (s, 3H), 3.71 (s, 1H), 3.62 (s, 1H), 3.59 (s, 1H), 3.41-3.40 (m, 1H), 2.61-2.52 (m, 3H), 2.11-2.04 (m, 2H), 2.03-1.93 (m, 2H), 1.80-1.73 (m, 2H), 1.59-1.50 (m, 3H), 1.39-1.29 (m, 2H), 1.25-1.20 (m, 3H), 1.05-0.90 (m, 2H).

Example 403

((1s,3s)-3-Hydroxy-3-methylcyclobutyl)(7-((1-methyl-1H-pyrazolo[3,4-b]pyridin-6-yl)methyl)-2-azaspiro[3.5]nonan-2-yl)methanone

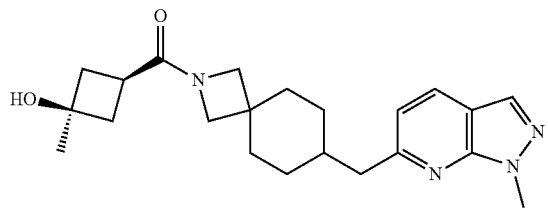 [SMILES: Cn1ncc2ccc(CC3CCC4(CC3)CN(C(=O)[C@H]3C[C@@](C)(O)C3)C4)nc21]

The title compound was prepared in a manner analogous to Example 153 using tert-butyl 7-(iodomethyl)-2-azaspiro[3.5]nonane-2-carboxylate (Intermediate 71) instead of tert-butyl 2-bromo-7-azaspiro[3.5]nonane-7-carboxylate and 6-bromo-1-methyl-1H-pyrazolo[3,4-b]pyridine instead of 1-bromo-3-tert-butylbenzene in Step A. MS (ESI): mass calcd. for $C_{22}H_{30}N_4O_2$, 382.2; m/z found, 383.2 [M+H]$^+$. $^1$H NMR (400 MHz, CDCl$_3$) δ 7.95-7.89 (m, 2H), 6.96-6.90 (m, 1H), 4.13 (s, 3H), 3.76-3.60 (m, 4H), 2.78 (d, J=7.2 Hz, 2H), 2.70-2.58 (m, 1H), 2.31-2.25 (m, 4H), 1.92-1.76 (m, 4H), 1.73-1.61 (m, 2H), 1.51-1.39 (m, 2H), 1.37-1.32 (m, 3H), 1.14-0.96 (m, 2H).

Example 404

((1s,3s)-3-Hydroxy-3-methylcyclobutyl)(7-(p-tolyloxy)-2-azaspiro[3.5]nonan-2-yl)methanone

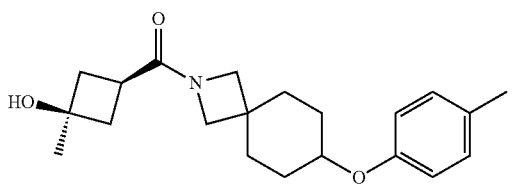 [SMILES: Cc1ccc(OC2CCC3(CC2)CN(C(=O)[C@H]2C[C@@](C)(O)C2)C3)cc1]

The title compound was prepared in a manner analogous to Example 241 using p-cresol instead of 3-isopropylphenol in Step A. MS (ESI): mass calcd. for $C_{21}H_{29}NO_3$, 343.2; m/z found, 344.3 [M+H]$^+$. $^1$H NMR (500 MHz, CDCl$_3$) δ 7.09-7.04 (m, 2H), 6.81-6.76 (m, 2H), 4.28-4.19 (m, 1H), 4.10 (d, J=12.8 Hz, 1H), 3.76 (d, J=5.5 Hz, 2H), 3.70 (d, J=8.9 Hz, 2H), 2.65 (h, J=7.4 Hz, 1H), 2.31-2.25 (m, 7H), 2.00-1.90 (m, 2H), 1.88-1.78 (m, 2H), 1.69-1.55 (m, 4H), 1.35 (d, J=2.5 Hz, 3H).

Example 405

(7-(3,4-Dimethylphenoxy)-2-azaspiro[3.5]nonan-2-yl)((1s,3s)-3-hydroxy-3-methylcyclobutyl)methanone

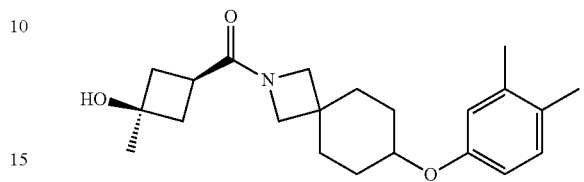

The title compound was prepared in a manner analogous to Example 241 using 3,4-dimethylphenol instead of 3-isopropylphenol in Step A. MS (ESI): mass calcd. for $C_{22}H_{31}NO_3$, 357.2; m/z found, 358.3 [M+H]$^+$. $^1$H NMR (400 MHz, CDCl$_3$) δ 7.01 (dd, J=8.2, 1.7 Hz, 1H), 6.70 (d, J=2.5 Hz, 1H), 6.63 (dd, J=8.2, 2.7 Hz, 1H), 4.28-4.19 (m, 1H), 4.09 (d, J=10.6 Hz, 1H), 3.76 (d, J=4.0 Hz, 2H), 3.70 (d, J=6.6 Hz, 2H), 2.73-2.59 (m, 1H), 2.32-2.25 (m, 4H), 2.22 (s, 3H), 2.18 (s, 3H), 2.00-1.89 (m, 2H), 1.89-1.78 (m, 2H), 1.70-1.54 (m, 4H), 1.35 (d, J=2.0 Hz, 3H).

Example 406

(7-(2,3-Dimethylphenoxy)-2-azaspiro[3.5]nonan-2-yl)((1s,3s)-3-hydroxy-3-methylcyclobutyl)methanone

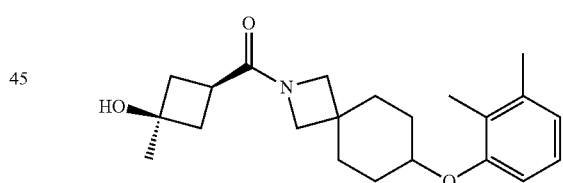

The title compound was prepared in a manner analogous to Example 241 using 2,3-dimethylphenol instead of 3-isopropylphenol in Step A. MS (ESI): mass calcd. for $C_{22}H_{31}NO_3$, 357.2; m/z found, 358.3 [M+H]$^+$. $^1$H NMR (500 MHz, CDCl$_3$) δ 7.05-6.97 (m, 1H), 6.77 (d, J=7.5 Hz, 1H), 6.70 (dd, J=8.3, 3.1 Hz, 1H), 4.31-4.23 (m, 1H), 3.92 (s, 1H), 3.78 (d, J=7.0 Hz, 2H), 3.72 (d, J=6.9 Hz, 2H), 2.74-2.62 (m, 1H), 2.34-2.24 (m, 7H), 2.14 (d, J=2.9 Hz, 3H), 2.00-1.90 (m, 2H), 1.89-1.77 (m, 2H), 1.74-1.57 (m, 4H), 1.35 (d, J=1.5 Hz, 3H).

Example 407

((1s,3s)-3-Hydroxy-3-methylcyclobutyl)(7-(3-methoxy-5-methylphenoxy)-2-azaspiro[3.5]nonan-2-yl)methanone

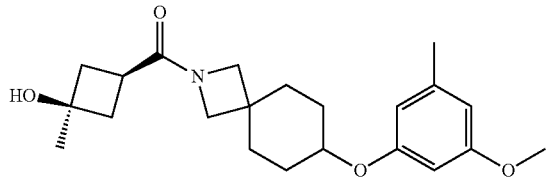 [SMILES: COc1cc(C)cc(OC2CCC3(CC2)CN(C(=O)[C@H]2C[C@@](C)(O)C2)C3)c1]

The title compound was prepared in a manner analogous to Example 241 using 3-methoxy-5-methylphenol instead of 3-isopropylphenol in Step A. MS (ESI): mass calcd. for $C_{22}H_{31}NO_4$, 373.2; m/z found, 374.2 [M+H]$_+$. $^1$H NMR (400 MHz, CDCl$_3$) δ 6.34-6.29 (m, 2H), 6.27-6.24 (m, 1H), 4.30-4.20 (m, 1H), 3.88 (d, J=8.1 Hz, 1H), 3.79-3.74 (m, 5H), 3.71 (d, J=6.0 Hz, 2H), 2.75-2.61 (m, 1H), 2.35-2.21 (m, 7H), 1.99-1.90 (m, 2H), 1.90-1.78 (m, 2H), 1.68-1.55 (m, 4H), 1.35 (d, J=1.7 Hz, 3H).

Example 408

((1s,3s)-3-Hydroxy-3-methylcyclobutyl)(7-(3-methoxy-4-methylphenoxy)-2-azaspiro[3.5]nonan-2-yl)methanone

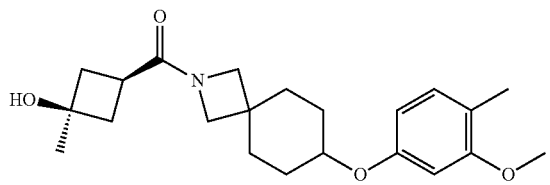 [SMILES: COc1cc(OC2CCC3(CC2)CN(C(=O)[C@H]2C[C@@](C)(O)C2)C3)ccc1C]

The title compound was prepared in a manner analogous to Example 241 using 3-methoxy-4-methylphenol instead of 3-isopropylphenol in Step A. MS (ESI): mass calcd. for $C_{22}H_{31}NO_4$, 373.2; m/z found, 374.2 [M+H]$^+$. $^1$H NMR (400 MHz, CDCl$_3$) δ 7.01-6.96 (m, 1H), 6.43-6.34 (m, 2H), 4.30-4.19 (m, 1H), 4.03 (s, 1H), 3.79 (s, 3H), 3.77 (d, J=5.0 Hz, 2H), 3.71 (d, J=7.7 Hz, 2H), 2.73-2.60 (m, 1H), 2.35-2.22 (m, 4H), 2.13 (s, 3H), 2.01-1.91 (m, 2H), 1.90-1.79 (m, 2H), 1.72-1.54 (m, 4H), 1.35 (d, J=1.9 Hz, 3H).

Example 409

((1s,3s)-3-Hydroxy-3-methylcyclobutyl)(7-(3-methoxy-2-methylphenoxy)-2-azaspiro[3.5]nonan-2-yl)methanone

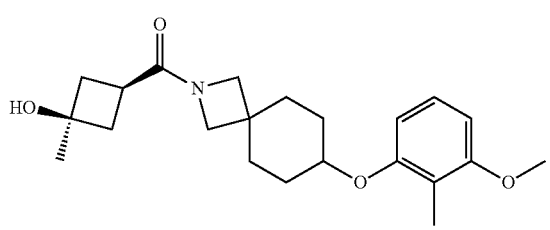 [SMILES: COc1cccc(OC2CCC3(CC2)CN(C(=O)[C@H]2C[C@@](C)(O)C2)C3)c1C]

The title compound was prepared in a manner analogous to Example 241 using 3-methoxy-2-methylphenol instead of 3-isopropylphenol in Step A. MS (ESI): mass calcd. for $C_{22}H_{31}NO_4$, 373.2; m/z found, 374.2 [M+H]$^+$. $^1$H NMR (400 MHz, CDCl$_3$) δ 7.07 (td, J=8.3, 3.7 Hz, 1H), 6.55-6.48 (m, 2H), 4.34-4.23 (m, 1H), 4.01 (s, 1H), 3.81 (d, J=1.0 Hz, 3H), 3.77 (d, J=5.1 Hz, 2H), 3.71 (d, J=5.2 Hz, 2H), 2.74-2.60 (m, 1H), 2.36-2.22 (m, 4H), 2.09 (d, J=2.1 Hz, 3H), 2.00-1.89 (m, 2H), 1.86-1.76 (m, 2H), 1.78-1.65 (m, 2H), 1.68-1.55 (m, 2H), 1.35 (d, J=1.2 Hz, 3H).

Example 410

(7-(2-Chloro-5-methylphenoxy)-2-azaspiro[3.5]nonan-2-yl)((1s,3s)-3-hydroxy-3-methylcyclobutyl)methanone

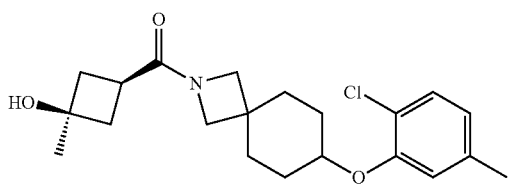 [SMILES: Cc1ccc(Cl)c(OC2CCC3(CC2)CN(C(=O)[C@H]2C[C@@](C)(O)C2)C3)c1]

The title compound was prepared in a manner analogous to Example 241 using 2-chloro-5-methylphenol instead of 3-isopropylphenol in Step A. MS (ESI): mass calcd. for $C_{21}H_{28}ClNO_3$, 377.2; m/z found, 378.2 [M+H]$^+$. $^1$H NMR (400 MHz, CDCl$_3$) δ 7.21 (d, J=8.0 Hz, 1H), 6.76-6.73 (m, 1H), 6.73-6.68 (m, 1H), 4.40-4.26 (m, 1H), 4.02 (d, J=8.3 Hz, 1H), 3.77 (d, J=5.4 Hz, 2H), 3.72 (d, J=6.6 Hz, 2H), 2.72-2.62 (m, 1H), 2.33-2.23 (m, 7H), 2.05-1.94 (m, 2H), 1.87-1.68 (m, 4H), 1.68-1.55 (m, 2H), 1.35 (d, J=1.9 Hz, 3H).

Example 411

(7-(3-Chloro-4-methylphenoxy)-2-azaspiro[3.5]nonan-2-yl)((1s,3s)-3-hydroxy-3-methylcyclobutyl)methanone

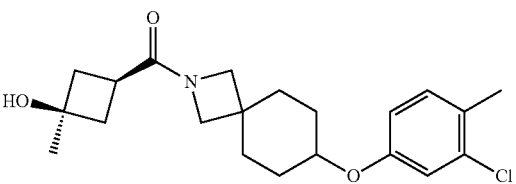 [SMILES: Cc1ccc(OC2CCC3(CC2)CN(C(=O)[C@H]2C[C@@](C)(O)C2)C3)cc1Cl]

The title compound was prepared in a manner analogous to Example 241 using 3-chloro-4-methylphenol instead of 3-isopropylphenol in Step A. MS (ESI): mass calcd. for $C_{21}H_{28}ClNO_3$, 377.2; m/z found, 378.2 [M+H]$^+$. $^1$H NMR (400 MHz, CDCl$_3$) δ 7.09 (dd, J=8.6, 1.5 Hz, 1H), 6.89 (d, J=2.6 Hz, 1H), 6.73-6.65 (m, 1H), 4.29-4.16 (m, 1H), 4.10 (d, J=8.9 Hz, 1H), 3.76 (d, J=1.9 Hz, 2H), 3.70 (d, J=4.8 Hz, 2H), 2.71-2.58 (m, 1H), 2.32-2.24 (m, 7H), 2.01-1.88 (m, 2H), 1.88-1.77 (m, 2H), 1.71-1.54 (m, 4H), 1.35 (d, J=1.7 Hz, 3H).

Example 412

(7-(4-Chloro-2-methylphenoxy)-2-azaspiro[3.5]nonan-2-yl)((1s,3s)-3-hydroxy-3-methylcyclobutyl)methanone

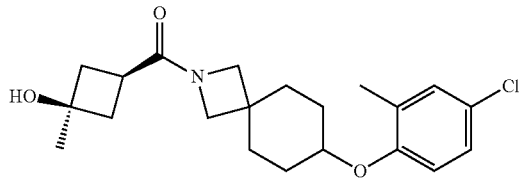 [SMILES: Cc1cc(Cl)ccc1OC1CCC2(CC1)CN(C(=O)[C@H]1C[C@@](C)(O)C1)C2]

The title compound was prepared in a manner analogous to Example 241 using 4-chloro-2-methylphenol instead of 3-isopropylphenol in Step A. MS (ESI): mass calcd. for $C_{21}H_{28}ClNO_3$, 377.2; m/z found, 378.2 [M+H]$^+$. $^1$H NMR (500 MHz, CDCl$_3$) δ 7.10 (d, J=2.7 Hz, 1H), 7.10-7.03 (m, 1H), 6.72 (dd, J=8.7, 3.7 Hz, 1H), 4.30-4.21 (m, 1H), 4.04 (d, J=2.9 Hz, 1H), 3.77 (d, J=3.3 Hz, 2H), 3.71 (d, J=3.9 Hz, 2H), 2.71-2.60 (m, 1H), 2.33-2.25 (m, 4H), 2.17 (d, J=2.8 Hz, 3H), 1.98-1.89 (m, 2H), 1.87-1.76 (m, 2H), 1.73-1.57 (m, 4H), 1.35 (s, 3H).

Example 413

(7-(3-Chloro-2-methylphenoxy)-2-azaspiro[3.5]nonan-2-yl)((1s,3s)-3-hydroxy-3-methylcyclobutyl)methanone

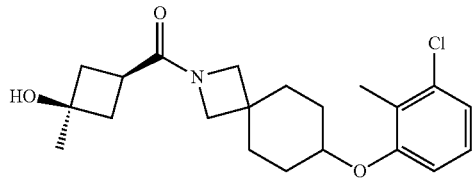 [SMILES: Cc1c(Cl)cccc1OC1CCC2(CC1)CN(C(=O)[C@H]1C[C@@](C)(O)C1)C2]

The title compound was prepared in a manner analogous to Example 241 using 3-chloro-2-methylphenol instead of 3-isopropylphenol in Step A. MS (ESI): mass calcd. for $C_{21}H_{28}ClNO_3$, 377.2; m/z found, 378.1 [M+H]$^+$. $^1$H NMR (400 MHz, CDCl$_3$) δ 7.09-6.99 (m, 1H), 6.99-6.92 (m, 1H), 6.77-6.69 (m, 1H), 4.35-4.23 (m, 1H), 3.97 (s, 1H), 3.78 (d, J=4.3 Hz, 2H), 3.72 (d, J=4.5 Hz, 2H), 2.72-2.62 (m, 1H), 2.36-2.25 (m, 4H), 2.26 (d, J=2.4 Hz, 3H), 2.01-1.88 (m, 2H), 1.90-1.76 (m, 2H), 1.76-1.58 (m, 4H), 1.35 (d, J=1.2 Hz, 3H).

Example 414

(7-(4-Chloro-3-methoxyphenoxy)-2-azaspiro[3.5]nonan-2-yl)((1s,3s)-3-hydroxy-3-methylcyclobutyl)methanone

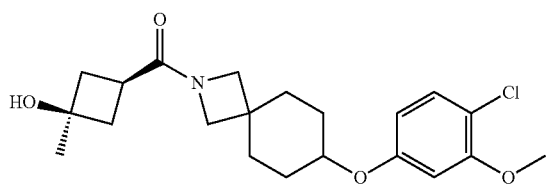

The title compound was prepared in a manner analogous to Example 241 using 4-chloro-3-methoxyphenol instead of 3-isopropylphenol in Step A. MS (ESI): mass calcd. for $C_{21}H_{28}ClNO_4$, 393.2; m/z found, 394.1 [M+H]$^+$. $^1$H NMR (400 MHz, CDCl$_3$) δ 7.22 (dd, J=8.7, 2.4 Hz, 1H), 6.49 (t, J=3.0 Hz, 1H), 6.45-6.37 (m, 1H), 4.30-4.21 (m, 1H), 3.88 (s, 1H), 3.86 (s, 3H), 3.77 (d, J=3.0 Hz, 2H), 3.72 (d, J=5.9 Hz, 2H), 2.74-2.61 (m, 1H), 2.34-2.21 (m, 4H), 2.01-1.90 (m, 2H), 1.91-1.79 (m, 2H), 1.69-1.56 (m, 4H), 1.35 (d, J=1.6 Hz, 3H).

Example 415

(7-(4-Cyclopropyl-3-fluorophenoxy)-2-azaspiro[3.5]nonan-2-yl)((1s,3s)-3-hydroxy-3-methylcyclobutyl)methanone

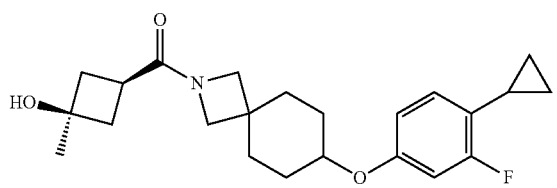 [SMILES: C[C@]1(O)C[C@@H](C(=O)N2CC3(CCC(Oc4ccc(C5CC5)c(F)c4)CC3)C2)C1]

The title compound was prepared in a manner analogous to Example 241 using 4-cyclopropyl-3-fluorophenol instead of 3-isopropylphenol in Step A. MS (ESI): mass calcd. for $C_{23}H_{30}FNO_3$, 387.2; m/z found, 388.2 [M+H]$^+$. $^1$H NMR (400 MHz, CDCl$_3$) δ 6.85-6.75 (m, 1H), 6.60-6.54 (m, 1H), 6.56-6.52 (m, 1H), 4.27-4.15 (m, 1H), 4.06 (d, J=8.4 Hz, 1H), 3.76 (d, J=1.9 Hz, 2H), 3.70 (d, J=4.8 Hz, 2H), 2.71-2.58 (m, 1H), 2.28 (dd, J=7.5, 1.4 Hz, 4H), 2.01-1.87 (m, 4H), 1.87-1.75 (m, 2H), 1.72-1.52 (m, 3H), 1.34 (d, J=1.6 Hz, 3H), 0.93-0.85 (m, 2H), 0.66-0.58 (m, 2H).

Example 416

((1s,3s)-3-Hydroxy-3-methylcyclobutyl)(7-(2-methyl-5-(trifluoromethyl)phenoxy)-2-azaspiro[3.5]nonan-2-yl)methanone

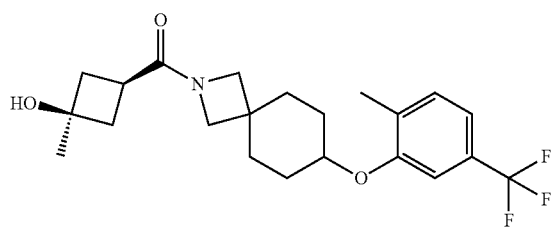 [SMILES: Cc1ccc(C(F)(F)F)cc1OC1CCC2(CC1)CN(C(=O)[C@H]1C[C@@](C)(O)C1)C2]

The title compound was prepared in a manner analogous to Example 241 using 2-methyl-5-(trifluoromethyl)phenol instead of 3-isopropylphenol in Step A. MS (ESI): mass calcd. for $C_{22}H_{28}F_3NO_3$, 411.2; m/z found, 412.2 [M+H]$^+$. $^1$H NMR (400 MHz, CDCl$_3$) δ 7.22 (d, J=7.8 Hz, 1H), 7.10 (d, J=7.8 Hz, 1H), 7.02-6.95 (m, 1H), 4.44-4.31 (m, 1H), 3.97 (d, J=3.8 Hz, 1H), 3.79 (s, 2H), 3.73 (s, 2H), 2.74-2.61 (m, 1H), 2.36-2.25 (m, 4H), 2.26-2.21 (m, 3H), 2.00-1.90 (m, 2H), 1.90-1.82 (m, 2H), 1.78-1.60 (m, 4H), 1.35 (s, 3H).

Example 417

((1s,3s)-3-Hydroxy-3-methylcyclobutyl)(7-((5-(trifluoromethyl)pyridin-2-yl)oxy)-2-azaspiro[3.5]nonan-2-yl)methanone

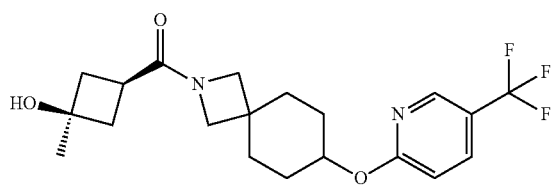 [SMILES: C[C@]1(O)C[C@@H](C(=O)N2CC3(CCC(Oc4ccc(C(F)(F)F)cn4)CC3)C2)C1]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-fluoro-5-(trifluoromethyl)pyridine instead of 6-chloro-2-methyl-3-(trifluoromethyl)pyridine in Step A. MS (ESI): mass calcd. for $C_{20}H_{25}F_3N_2O_3$, 398.2; m/z found, 399.2 [M+H]$^+$. $^1$H NMR (400 MHz, CDCl$_3$) δ 8.43-8.36 (m, 1H), 7.75 (dd, J=8.7, 2.6 Hz, 1H), 6.78-6.71 (m, 1H), 5.18-5.07 (m, 1H), 3.78 (d, J=6.1 Hz, 2H), 3.72 (d, J=9.3 Hz, 2H), 2.75-2.61 (m, 1H), 2.34-2.22 (m, 4H), 2.00-1.87 (m, 4H), 1.72-1.59 (m, 4H), 1.35 (s, 3H).

Example 418

((1s,3s)-3-Hydroxy-3-methylcyclobutyl)(7-((4-(trifluoromethyl)pyridin-2-yl)oxy)-2-azaspiro[3.5]nonan-2-yl)methanone

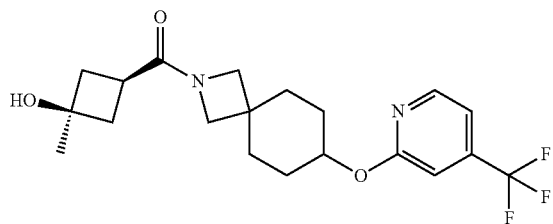 [SMILES: C[C@]1(O)C[C@@H](C(=O)N2CC3(CCC(Oc4cc(C(F)(F)F)ccn4)CC3)C2)C1]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-fluoro-4-(trifluoromethyl)pyridine instead of 6-chloro-2-methyl-3-(trifluoromethyl)pyridine in Step A. MS (ESI): mass calcd. for $C_{20}H_{25}F_3N_2O_3$, 398.2; m/z found, 399.2 [M+H]$^+$. $^1$H NMR (400 MHz, CDCl$_3$) δ 8.29-8.21 (m, 1H), 7.06-6.98 (m, 1H), 6.94-6.87 (m, 1H), 5.15-5.05 (m, 1H), 3.98 (d, J=7.8 Hz, 1H), 3.78 (d, J=6.5 Hz, 2H), 3.72 (d, J=9.5 Hz, 2H), 2.72-2.61 (m, 1H), 2.34-2.23 (m, 4H), 2.00-1.86 (m, 4H), 1.74-1.58 (m, 4H), 1.35 (d, J=2.0 Hz, 3H).

Example 419

((1s,3s)-3-Hydroxy-3-methylcyclobutyl)(7-methyl-7-((5-(trifluoromethyl)pyridin-2-yl)oxy)-2-azaspiro[3.5]nonan-2-yl)methanone

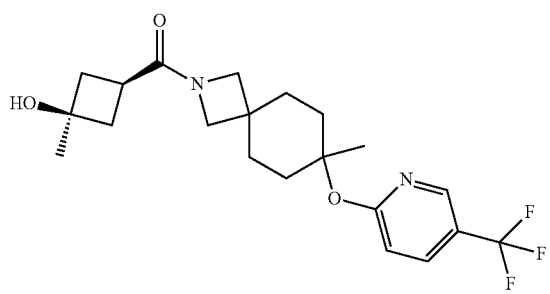 [SMILES: CC1(Oc2ccc(C(F)(F)F)cn2)CCC2(CC1)CN(C(=O)[C@H]1C[C@@](C)(O)C1)C2]

Step A: tert-Butyl 7-hydroxy-7-methyl-2-azaspiro[3.5]nonane-2-carboxylate. In an oven-dried flask under N$_2$, tert-butyl 7-oxo-2-azaspiro[3.5]nonane-2-carboxylate (200 mg, 0.811 mmol) was taken up in THF (4.0 mL) and cooled to −78° C. Methylmagnesium bromide (0.40 mL, 1.22 mmol) was added dropwise, and the reaction was stirred at −78° C. for 2 h. The reaction mixture was allowed to warm to rt before being quenched with sat. aq. NH$_4$Cl and extracted with EtOAc. The combined organic layers were dried over Na$_2$SO$_4$, filtered, and concentrated under reduced pressure. Purification by RP HPLC (5-95% ACN in water with 20 mM NH$_4$OH) provided the title compound (99 mg, 48% yield). MS (ESI): mass calcd. for $C_{14}H_{25}NO_3$, 255.2; m/z found, 200.2 [M+2H-tBu]$^+$.

Step B: tert-Butyl 7-methyl-7-((5-(trifluoromethyl)pyridin-2-yl)oxy)-2-azaspiro[3.5]nonane-2-carboxylate. Under N$_2$, NaH (31 mg, 60% in mineral oil, 0.783 mmol) was taken up in THF (0.8 mL) and cooled to 0° C. tert-Butyl 7-hydroxy-7-methyl-2-azaspiro[3.5]nonane-2-carboxylate (40 mg, 0.157 mmol) was added, and the reaction was stirred at rt for 30 min. 2-Fluoro-5-(trifluoromethyl)pyridine (29 μL, 0.235 mmol) was added. The reaction mixture was purged with N$_2$, and heated in a sealed tube at 90° C. for 16 h. After cooling to rt, the reaction was quenched with water and extracted with DCM. The combined organic layers were dried over Na$_2$SO$_4$, filtered, and concentrated under reduced pressure. Purification by FCC (SiO$_2$, 0-25% EtOAc in hexanes) provided the title compound (42 mg, 67% yield). MS (ESI): mass calcd. for $C_{20}H_{27}F_3N_2O_3$, 400.2; m/z found, 345.1 [M+2H-tBu]$^+$.

Step C: 7-Methyl-7-((5-(trifluoromethyl)pyridin-2-yl)oxy)-2-azaspiro[3.5]nonane. tert-Butyl 7-methyl-7-((5-(trifluoromethyl)pyridin-2-yl)oxy)-2-azaspiro[3.5]nonane-2-carboxylate (12 mg, 0.030 mmol) was taken up in DCM (0.2 mL). To this was added 2,6-dimethylpyridine (6.9 μL, 0.060 mmol) and trimethylsilyl trifluoromethanesulfonate (11 μL, 0.060 mmol) and the reaction was stirred at rt for 1 h. The reaction mixture was concentrated under a stream of N$_2$ at rt and carried on to the next step without purification. MS (ESI): mass calcd. for $C_{15}H_{19}F_3N_2O$, 300.1; m/z found, 301.2 [M+H]$^+$.

Step D: ((1s,3s)-3-Hydroxy-3-methylcyclobutyl)(7-methyl-7-((5-(trifluoromethyl)pyridin-2-yl)oxy)-2-azaspiro[3.5]nonan-2-yl)methanone. 7-Methyl-7-((5-(trifluoromethyl)pyridin-2-yl)oxy)-2-azaspiro[3.5]nonane (9 mg, 0.030 mmol) and (1s,3s)-3-hydroxy-3-methylcyclobutanecarboxylic acid (4 mg, 0.030 mmol) were taken up in DMF (0.3 mL). To the reaction mixture was added DIPEA (16 µL, 0.090 mmol) and HATU (11 mg, 0.030 mmol) and the reaction was stirred at rt for 45 min. The reaction mixture was filtered through a PTFE filter with MeOH and purified by RP HPLC (5-95% ACN in water with 20 mM NH$_4$OH) to provide the title compound (11 mg, 93% yield). MS (ESI): mass calcd. for C$_{21}$H$_{27}$F$_3$N$_2$O$_3$, 412.2; m/z found, 413.2 [M+H]$^+$. $^1$H NMR (400 MHz, CDCl$_3$) δ 8.41-8.33 (m, 1H), 7.72 (dt, J=8.7, 2.2 Hz, 1H), 6.73 (dd, J=8.7, 4.6 Hz, 1H), 3.94 (d, J=12.6 Hz, 1H), 3.80-3.63 (m, 4H), 2.74-2.59 (m, 1H), 2.51-2.37 (m, 2H), 2.34-2.20 (m, 4H), 1.84-1.63 (m, 4H), 1.61 (d, J=2.3 Hz, 3H), 1.55-1.39 (m, 2H), 1.34 (d, J=3.6 Hz, 3H).

Example 420

(7-Ethyl-7-((5-(trifluoromethyl)pyridin-2-yl)oxy)-2-azaspiro[3.5]nonan-2-yl)((1s,3s)-3-hydroxy-3-methylcyclobutyl)methanone

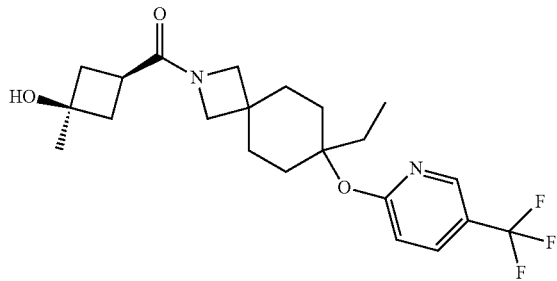 [SMILES: CCC1(Oc2ccc(C(F)(F)F)cn2)CCC2(CC1)CN(C(=O)[C@H]1C[C@@](C)(O)C1)C2]

The title compound was prepared in a manner analogous to Example 419 using ethylmagnesium bromide instead of methylmagnesium bromide in Step A. MS (ESI): mass calcd. for C$_{22}$H$_{29}$F$_3$N$_2$O$_3$, 426.2; m/z found, 427.2 [M+H]$^+$. $^1$H NMR (500 MHz, CDCl$_3$) δ 8.37-8.33 (m, 1H), 7.72 (dt, J=8.7, 2.6 Hz, 1H), 6.74 (dd, J=8.6, 6.3 Hz, 1H), 3.95 (d, J=19.1 Hz, 1H), 3.80-3.62 (m, 4H), 2.73-2.60 (m, 1H), 2.53-2.44 (m, 2H), 2.33-2.22 (m, 4H), 2.14-2.04 (m, 2H), 1.80-1.64 (m, 4H), 1.46-1.31 (m, 5H), 0.84-0.76 (m, 3H).

Example 421

((1s,3s)-3-Hydroxy-3-methylcyclobutyl)(7-((6-(trifluoromethyl)pyridin-2-yl)oxy)-2-azaspiro[3.5]nonan-2-yl)methanone

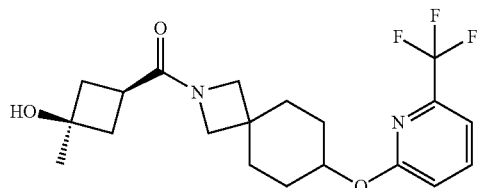

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-fluoro-6-(trifluoromethyl)pyridine instead of 6-chloro-2-methyl-3-(trifluoromethyl)pyridine in Step A. MS (ESI): mass calcd. for C$_{20}$H$_{25}$F$_3$N$_2$O$_3$, 398.2; m/z found, 399.2 [M+H]$^+$. $^1$H NMR (400 MHz, CDCl$_3$) δ 7.72-7.63 (m, 1H), 7.21 (d, J=7.3 Hz, 1H), 6.87-6.81 (m, 1H), 5.17-5.06 (m, 1H), 3.78 (d, J=5.5 Hz, 2H), 3.72 (d, J=7.5 Hz, 2H), 2.72-2.63 (m, 1H), 2.34-2.22 (m, 4H), 1.99-1.87 (m, 4H), 1.75-1.57 (m, 4H), 1.35 (s, 3H).

Example 422

(7-((5-(1,1-Difluoroethyl)pyridin-2-yl)oxy)-2-azaspiro[3.5]nonan-2-yl)((1s,3s)-3-hydroxy-3-methylcyclobutyl)methanone

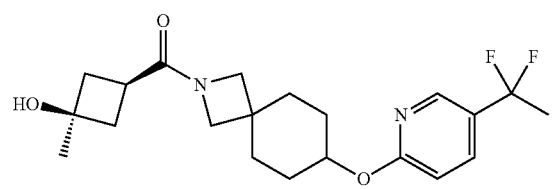 [SMILES: CC(F)(F)c1ccc(OC2CCC3(CC2)CN(C(=O)[C@H]2C[C@@](C)(O)C2)C3)nc1]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-chloro-5-(1,1-difluoroethyl)pyridine instead of 6-chloro-2-methyl-3-(trifluoromethyl)pyridine in Step A. MS (ESI): mass calcd. for C$_{21}$H$_{28}$F$_2$N$_2$O$_3$, 394.2; m/z found, 395.3 [M+H]$^+$. $^1$H NMR (400 MHz, CDCl$_3$) δ 8.30-8.24 (m, 1H), 7.71-7.63 (m, 1H), 6.71 (ddd, J=8.6, 4.1, 0.8 Hz, 1H), 5.13-5.04 (m, 1H), 3.99 (d, J=6.5 Hz, 1H), 3.78 (d, J=6.3 Hz, 2H), 3.72 (d, J=9.7 Hz, 2H), 2.72-2.61 (m, 1H), 2.34-2.23 (m, 4H), 1.99-1.86 (m, 7H), 1.72-1.56 (m, 4H), 1.35 (d, J=1.3 Hz, 3H).

Example 423

(7-((5-(Difluoromethyl)pyridin-2-yl)oxy)-2-azaspiro[3.5]nonan-2-yl)((1s,3s)-3-hydroxy-3-methylcyclobutyl)methanone

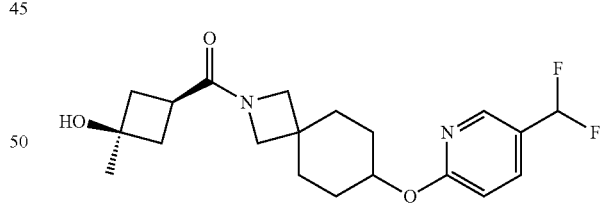

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-chloro-5-(difluoromethyl)pyridine instead of 6-chloro-2-methyl-3-(trifluoromethyl)pyridine in Step A. MS (ESI): mass calcd. for C$_{20}$H$_{26}$F$_2$N$_2$O$_3$, 380.2; m/z found, 381.2 [M+H]$^+$. $^1$H NMR (400 MHz, CDCl$_3$) δ 8.22 (t, J=2.2 Hz, 1H), 7.74-7.66 (m, 1H), 6.77-6.73 (m, 1H), 6.73-6.46 (m, 1H), 5.15-5.06 (m, 1H), 4.12 (d, J=8.2 Hz, 1H), 3.77 (d, J=6.3 Hz, 2H), 3.71 (d, J=9.6 Hz, 2H), 2.72-2.59 (m, 1H), 2.32-2.24 (m, 4H), 1.99-1.85 (m, 4H), 1.72-1.56 (m, 4H), 1.34 (d, J=1.4 Hz, 3H).

Example 424

((1s,3s)-3-Hydroxy-3-methylcyclobutyl)(7-((6-(trifluoromethyl)pyridin-3-yl)oxy)-2-azaspiro[3.5]nonan-2-yl)methanone

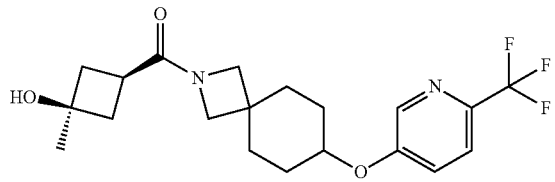 [SMILES: C[C@]1(O)C[C@@H](C(=O)N2CC3(CCC(Oc4ccc(C(F)(F)F)nc4)CC3)C2)C1]

The title compound was prepared in a manner analogous to Example 241 using 6-(trifluoromethyl)pyridin-3-ol instead of 3-isopropylphenol in Step A. MS (ESI): mass calcd. for $C_{20}H_{25}F_3N_2O_3$, 398.2; m/z found, 399.2 [M+H]$^+$. $^1$H NMR (500 MHz, CDCl$_3$) δ 8.35 (d, J=2.8 Hz, 1H), 7.60 (dd, J=8.7, 3.2 Hz, 1H), 7.28-7.23 (m, 1H), 4.48-4.39 (m, 1H), 3.82 (d, J=8.0 Hz, 1H), 3.79 (d, J=2.2 Hz, 2H), 3.73 (d, J=5.0 Hz, 2H), 2.73-2.62 (m, 1H), 2.35-2.23 (m, 4H), 2.02-1.84 (m, 4H), 1.77-1.61 (m, 4H), 1.35 (d, J=1.3 Hz, 3H).

Example 425

(7-((6-(tert-Butyl)pyridin-2-yl)oxy)-2-azaspiro[3.5]nonan-2-yl)((1s,3s)-3-hydroxy-3-methylcyclobutyl)methanone

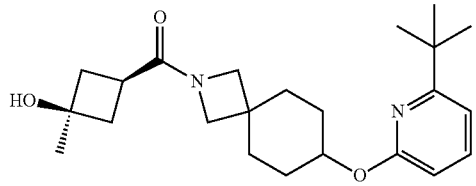 [SMILES: CC(C)(C)c1cccc(OC2CCC3(CC2)CN(C(=O)[C@H]2C[C@@](C)(O)C2)C3)n1]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-(tert-butyl)-6-chloropyridine instead of 6-chloro-2-methyl-3-(trifluoromethyl)pyridine in Step A. MS (ESI): mass calcd. for $C_{23}H_{34}N_2O_3$, 386.3; m/z found, 387.3 [M+H]$^+$. $^1$H NMR (400 MHz, CDCl$_3$) δ 7.51-7.45 (m, 1H), 6.87-6.80 (m, 1H), 6.51-6.43 (m, 1H), 5.16-5.04 (m, 1H), 3.97 (br s, 1H), 3.83-3.68 (m, 4H), 2.77-2.65 (m, 1H), 2.37-2.21 (m, 4H), 2.03-1.88 (m, 4H), 1.83-1.65 (m, 4H), 1.36 (s, 3H), 1.31 (s, 9H).

Example 426

(7-((5-Cyclopropylpyridin-2-yl)oxy)-2-azaspiro[3.5]nonan-2-yl)((1s,3s)-3-hydroxy-3-methylcyclobutyl)methanone

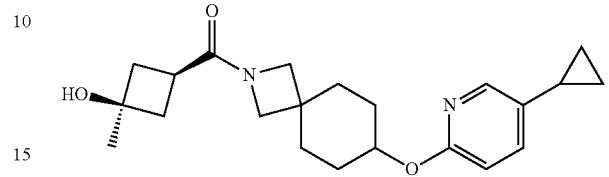

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 5-cyclopropyl-2-fluoropyridine instead of 6-chloro-2-methyl-3-(trifluoromethyl)pyridine in Step A. MS (ESI): mass calcd. for $C_{22}H_{30}N_2O_3$, 370.2; m/z found, 371.3 [M+H]$^+$. $^1$H NMR (400 MHz, CDCl$_3$) δ 7.95-7.89 (m, 1H), 7.22 (dd, J=8.5, 2.5 Hz, 1H), 6.57 (dd, J=8.5, 4.2 Hz, 1H), 5.04-4.95 (m, 1H), 4.11 (d, J=11.0 Hz, 1H), 3.76 (d, J=6.0 Hz, 2H), 3.70 (d, J=10.1 Hz, 2H), 2.72-2.59 (m, 1H), 2.28 (dd, J=7.4, 1.8 Hz, 4H), 1.98-1.84 (m, 4H), 1.87-1.75 (m, 1H), 1.70-1.50 (m, 4H), 1.34 (d, J=1.5 Hz, 3H), 0.96-0.86 (m, 2H), 0.64-0.55 (m, 2H).

Example 427

((1s,3s)-3-Hydroxy-3-methylcyclobutyl)(7-((5-(trifluoromethoxy)pyridin-2-yl)oxy)-2-azaspiro[3.5]nonan-2-yl)methanone

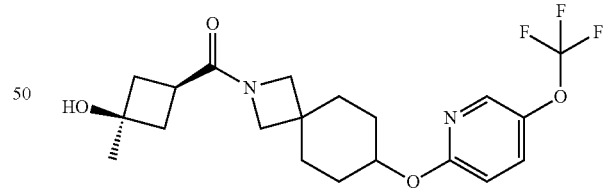

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-chloro-5-(trifluoromethoxy)pyridine instead of 6-chloro-2-methyl-3-(trifluoromethyl)pyridine in Step A. MS (ESI): mass calcd. for $C_{20}H_{25}F_3N_2O_4$, 414.2; m/z found, 415.2 [M+H]$^+$. $^1$H NMR (400 MHz, CDCl$_3$) δ 8.04 (t, J=3.6 Hz, 1H), 7.44 (ddt, J=8.9, 2.9, 0.9 Hz, 1H), 6.69 (dd, J=9.0, 4.5 Hz, 1H), 5.07-4.98 (m, 1H), 3.97 (d, J=6.2 Hz, 1H), 3.78 (d, J=6.4 Hz, 2H), 3.72 (d, J=9.8 Hz, 2H), 2.72-2.62 (m, 1H), 2.34-2.23 (m, 4H), 1.99-1.85 (m, 4H), 1.72-1.55 (m, 4H), 1.35 (s, 3H).

Example 428

(7-((5,6-Dimethylpyridin-2-yl)oxy)-2-azaspiro[3.5]nonan-2-yl)((1s,3s)-3-hydroxy-3-methylcyclobutyl)methanone

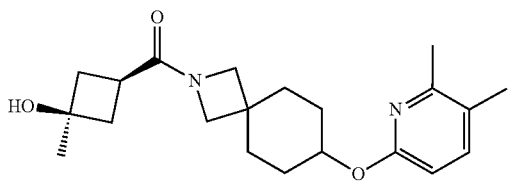 [SMILES: Cc1ccc(OC2CCC3(CC2)CN(C(=O)[C@H]2C[C@@](C)(O)C2)C3)nc1C]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 6-chloro-2,3-dimethylpyridine instead of 6-chloro-2-methyl-3-(trifluoromethyl)pyridine in Step A. MS (ESI): mass calcd. for $C_{21}H_{30}N_2O_3$, 358.2; m/z found, 359.3 [M+H]$^+$. $^1$H NMR (400 MHz, CDCl$_3$) δ 7.30-7.27 (m, 1H), 6.42 (dd, J=8.2, 3.0 Hz, 1H), 5.04-4.95 (m, 1H), 3.89 (d, J=5.9 Hz, 1H), 3.77 (d, J=5.7 Hz, 2H), 3.71 (d, J=8.4 Hz, 2H), 2.76-2.62 (m, 1H), 2.36 (d, J=1.5 Hz, 3H), 2.34-2.20 (m, 4H), 2.17 (s, 3H), 1.98-1.83 (m, 4H), 1.67-1.54 (m, 4H), 1.35 (s, 3H).

Example 429

(7-((3,6-Dimethylpyridin-2-yl)oxy)-2-azaspiro[3.5]nonan-2-yl)((1s,3s)-3-hydroxy-3-methylcyclobutyl)methanone

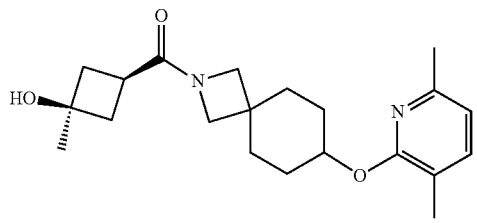 [SMILES: Cc1ccc(C)c(OC2CCC3(CC2)CN(C(=O)[C@H]2C[C@@](C)(O)C2)C3)n1]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-chloro-3,6-dimethylpyridine instead of 6-chloro-2-methyl-3-(trifluoromethyl)pyridine in Step A. MS (ESI): mass calcd. for $C_{21}H_{30}N_2O_3$, 358.2; m/z found, 359.3 [M+H]$^+$. $^1$H NMR (500 MHz, CDCl$_3$) δ 7.26-7.20 (m, 1H), 6.58 (d, J=7.2 Hz, 1H), 5.20-5.12 (m, 1H), 3.82 (d, J=2.5 Hz, 1H), 3.78 (d, J=4.6 Hz, 2H), 3.72 (d, J=5.1 Hz, 2H), 2.75-2.65 (m, 1H), 2.36 (s, 3H), 2.35-2.22 (m, 4H), 2.11 (d, J=4.7 Hz, 3H), 1.97-1.78 (m, 4H), 1.73-1.64 (m, 4H), 1.35 (s, 3H).

Example 430

(7-((3,5-Dimethylpyridin-2-yl)oxy)-2-azaspiro[3.5]nonan-2-yl)((1s,3s)-3-hydroxy-3-methylcyclobutyl)methanone

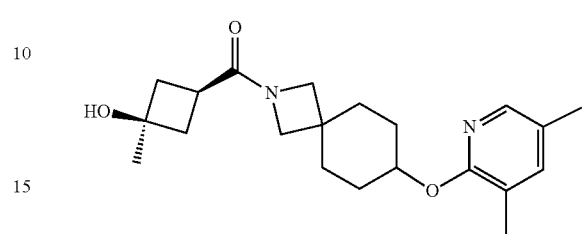

Step A: tert-Butyl 7-((3,5-dimethylpyridin-2-yl)oxy)-2-azaspiro[3.5]nonane-2-carboxylate. Pd$_2$(dba)$_3$ (59 mg, 0.064 mmol) was added to a solution of tert-butyl 7-hydroxy-2-azaspiro[3.5]nonane-2-carboxylate (311 mg, 1.29 mmol), 2-bromo-3,5-dimethylpyridine (200 mg, 1.08 mmol), (2,2'-bis(diphenylphosphino)-1,1'-binaphthyl) (BINAP) (27 mg, 0.043 mmol), and t-BuOK (169 mg, 1.51 mmol) in toluene (5 mL) under N$_2$. The reaction mixture was reacted under microwave irradiation at 110° C. for 2 h. The reaction mixture was cooled, diluted with water and extracted with EtOAc. The combined organic extracts were dried over Na$_2$SO$_4$, filtered, and concentrated under reduced pressure. The resulting residue was purified by FCC (SiO$_2$, 0-10% EtOAc in ether) to afford the title compound (130 mg, 28% yield) as a light-yellow oil. MS (ESI): mass calcd. for $C_{20}H_{30}N_2O_3$, 346.2; m/z found, 347.2 [M+H]$^+$.

Step B: 7-((3,5-Dimethylpyridin-2-yl)oxy)-2-azaspiro[3.5]nonane. TFA (1 mL, 13.1 mmol) was added to a solution of tert-butyl 7-((3,5-dimethylpyridin-2-yl)oxy)-2-azaspiro[3.5]nonane-2-carboxylate (130 mg, 0.375 mmol) in DCM (5 mL). The reaction mixture was stirred at rt for 1.5 hours before being concentrated under reduced pressure. The resulting residue was quenched with 25% aq. NH$_3$ and extracted with DCM. The combined organic extracts were concentrated under reduced pressure to afford the title compound (100 mg), which was used in the next step without further purification.

Step C: (7-((3,5-Dimethylpyridin-2-yl)oxy)-2-azaspiro[3.5]nonan-2-yl)((1s,3s)-3-hydroxy-3-methylcyclobutyl)methanone. HATU (309 mg, 0.812 mmol) was added to a solution of 7-((3,5-dimethylpyridin-2-yl)oxy)-2-azaspiro[3.5]nonane (100 mg, 0.406 mmol), (1s,3s)-3-hydroxy-3-methylcyclobutanecarboxylic acid (64 mg, 0.487 mmol) and DIPEA (0.36 mL, 2.03 mmol) in DMF (5 mL). The reaction mixture was stirred at rt for 3 h before being concentrated under reduced pressure. The resulting residue was purified by RP HPLC (38-68% MeCN in water with 0.05% NH$_3$+10 mM NH$_4$HCO$_3$) to afford the title compound (55 mg, 37% yield) as an off-white solid. MS (ESI): mass calcd. for $C_{21}H_{30}N_2O_3$, 358.2; m/z found, 359.3 [M+H]$^+$. $^1$H NMR (400 MHz, CDCl$_3$) δ 7.74 (s, 1H), 7.20 (s, 1H), 5.10-5.01 (m, 1H), 4.30 (br s, 1H), 3.81-3.68 (m, 4H), 2.70-2.60 (m, 1H), 2.34-2.24 (m, 4H), 2.19 (s, 3H), 2.15-2.10 (m, 3H), 1.97-1.80 (m, 4H), 1.74-1.58 (m, 4H), 1.35 (s, 3H).

Example 431

(7-((3-Fluoro-6-methylpyridin-2-yl)oxy)-2-azaspiro[3.5]nonan-2-yl)((1s,3s)-3-hydroxy-3-methylcyclobutyl)methanone

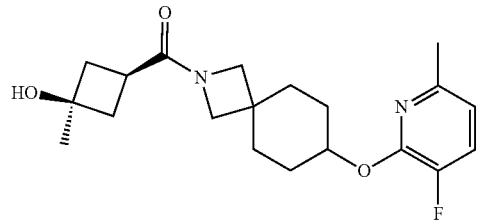 [SMILES: Cc1ccc(F)c(OC2CCC3(CC2)CN(C(=O)[C@H]2C[C@@](C)(O)C2)C3)n1]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-chloro-3-fluoro-6-picoline instead of 6-chloro-2-methyl-3-(trifluoromethyl)pyridine in Step A. MS (ESI): mass calcd. for $C_{20}H_{27}FN_2O_3$, 362.2; m/z found, 363.2 [M+H]$^+$. $^1$H NMR (400 MHz, CDCl$_3$) δ 7.17 (dd, J=10.3, 7.9 Hz, 1H), 6.65-6.57 (m, 1H), 5.22-5.12 (m, 1H), 3.87 (d, J=12.4 Hz, 1H), 3.78 (d, J=6.3 Hz, 2H), 3.73 (d, J=10.0 Hz, 2H), 2.76-2.63 (m, 1H), 2.37 (s, 3H), 2.35-2.20 (m, 4H), 2.02-1.86 (m, 4H), 1.76-1.60 (m, 4H), 1.35 (d, J=1.8 Hz, 3H).

Example 432

(7-((3-Fluoro-5-methylpyridin-2-yl)oxy)-2-azaspiro[3.5]nonan-2-yl)((1s,3s)-3-hydroxy-3-methylcyclobutyl)methanone

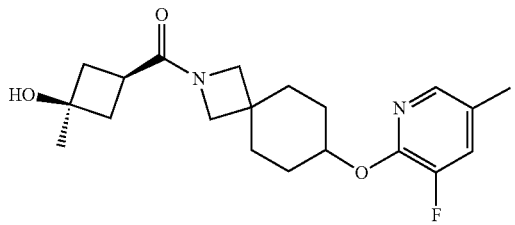 [SMILES: Cc1cnc(OC2CCC3(CC2)CN(C(=O)[C@H]2C[C@@](C)(O)C2)C3)c(F)c1]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2,3-difluoro-5-methylpyridine instead of 6-chloro-2-methyl-3-(trifluoromethyl)pyridine in Step A. MS (ESI): mass calcd. for $C_{20}H_{27}FN_2O_3$, 362.2; m/z found, 363.2 [M+H]$^+$. $^1$H NMR (400 MHz, CDCl$_3$) δ 7.71-7.64 (m, 1H), 7.14 (dd, J=11.0, 2.0 Hz, 1H), 5.14-5.03 (m, 1H), 4.03 (d, J=18.0 Hz, 1H), 3.77 (d, J=6.5 Hz, 2H), 3.71 (d, J=11.3 Hz, 2H), 2.71-2.61 (m, 1H), 2.35-2.24 (m, 4H), 2.24 (s, 3H), 2.01-1.85 (m, 4H), 1.73-1.59 (m, 4H), 1.34 (d, J=2.2 Hz, 3H).

Example 433

(7-((5-Ethyl-3-fluoropyridin-2-yl)oxy)-2-azaspiro[3.5]nonan-2-yl)((1s,3s)-3-hydroxy-3-methylcyclobutyl)methanone

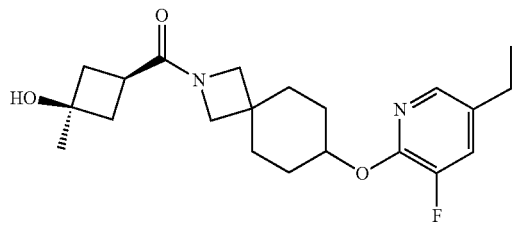 [SMILES: CCc1cnc(OC2CCC3(CC2)CN(C(=O)[C@H]2C[C@@](C)(O)C2)C3)c(F)c1]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 5-ethyl-2,3-difluoropyridine instead of 6-chloro-2-methyl-3-(trifluoromethyl)pyridine in Step A. MS (ESI): mass calcd. for $C_{21}H_{29}FN_2O_3$, 376.2; m/z found, 377.3 [M+H]$^+$. $^1$H NMR (500 MHz, CDCl$_3$) δ 7.70 (dd, J=5.2, 2.0 Hz, 1H), 7.17 (dd, J=11.0, 2.0 Hz, 1H), 5.14-5.04 (m, 1H), 4.05 (d, J=20.6 Hz, 1H), 3.77 (d, J=8.5 Hz, 2H), 3.71 (d, J=14.2 Hz, 2H), 2.71-2.61 (m, 1H), 2.60-2.52 (m, 2H), 2.32-2.23 (m, 4H), 2.01-1.87 (m, 4H), 1.73-1.60 (m, 4H), 1.34 (d, J=2.9 Hz, 3H), 1.20 (td, J=7.6, 0.9 Hz, 3H).

Example 434

(7-((5-Chloro-6-methylpyridin-2-yl)oxy)-2-azaspiro[3.5]nonan-2-yl)((1s,3s)-3-hydroxy-3-methylcyclobutyl)methanone

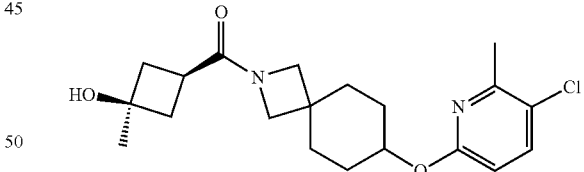

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 3,6-dichloro-2-methylpyridine instead of 6-chloro-2-methyl-3-(trifluoromethyl)pyridine in Step A. MS (ESI): mass calcd. for $C_{20}H_{27}ClN_2O_3$, 378.2; m/z found, 379.2 [M+H]$^+$. $^1$H NMR (400 MHz, CDCl$_3$) δ 7.44 (d, J=8.6 Hz, 1H), 6.46 (dd, J=8.6, 3.2 Hz, 1H), 5.07-4.96 (m, 1H), 3.97 (d, J=6.8 Hz, 1H), 3.77 (d, J=5.0 Hz, 2H), 3.71 (d, J=7.5 Hz, 2H), 2.73-2.61 (m, 1H), 2.47 (s, 3H), 2.34-2.22 (m, 4H), 1.98-1.83 (m, 4H), 1.71-1.53 (m, 4H), 1.35 (s, 3H).

Example 435

(7-((3-Chloro-6-methylpyridin-2-yl)oxy)-2-azaspiro[3.5]nonan-2-yl)((1s,3s)-3-hydroxy-3-methylcyclobutyl)methanone

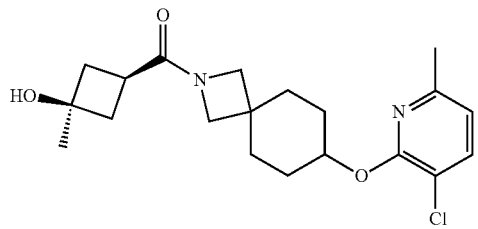 [SMILES: Cc1ccc(Cl)c(OC2CCC3(CC2)CN(C(=O)[C@H]2C[C@@](C)(O)C2)C3)n1]

The title compound was prepared in a manner analogous to Example 30 using tert-butyl 7-hydroxy-2-azaspiro[3.5]nonane-2-carboxylate instead of tert-butyl 6-hydroxy-2-azaspiro[3.3]heptane-2-carboxylate and 2,3-dichloro-6-methylpyridine instead of 6-chloro-2-methyl-3-(trifluoromethyl)pyridine in Step A. MS (ESI): mass calcd. for $C_{20}H_{27}ClN_2O_3$, 378.2; m/z found, 379.2 [M+H]$^+$. $^1$H NMR (400 MHz, CDCl$_3$) δ 7.46 (d, J=7.7 Hz, 1H), 6.63 (dd, J=7.8, 1.3 Hz, 1H), 5.23-5.11 (m, 1H), 4.12 (d, J=7.2 Hz, 1H), 3.78 (d, J=5.0 Hz, 2H), 3.72 (d, J=6.3 Hz, 2H), 2.73-2.60 (m, 1H), 2.38 (s, 3H), 2.29 (d, J=7.6 Hz, 4H), 1.98-1.91 (m, 2H), 1.93-1.79 (m, 2H), 1.79-1.60 (m, 4H), 1.35 (s, 3H).

Example 436

(7-((3-Chloro-5-methylpyridin-2-yl)oxy)-2-azaspiro[3.5]nonan-2-yl)((1s,3s)-3-hydroxy-3-methylcyclobutyl)methanone

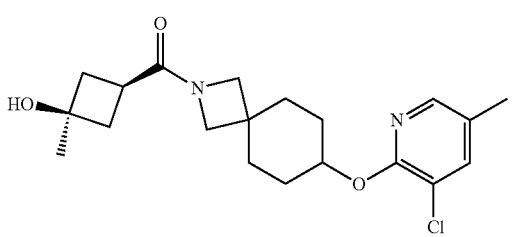 [SMILES: Cc1cnc(OC2CCC3(CC2)CN(C(=O)[C@H]2C[C@@](C)(O)C2)C3)c(Cl)c1]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2,3-dichloro-5-methylpyridine instead of 6-chloro-2-methyl-3-(trifluoromethyl)pyridine in Step A. MS (ESI): mass calcd. for $C_{20}H_{27}ClN_2O_3$, 378.2; m/z found, 379.2 [M+H]$^+$. $^1$H NMR (400 MHz, CDCl$_3$) δ 7.84-7.77 (m, 1H), 7.48-7.42 (m, 1H), 5.14-5.03 (m, 1H), 3.96 (s, 1H), 3.78 (d, J=5.5 Hz, 2H), 3.72 (d, J=8.1 Hz, 2H), 2.72-2.62 (m, 1H), 2.35-2.21 (m, 4H), 2.22 (s, 3H), 2.01-1.93 (m, 2H), 1.94-1.81 (m, 2H), 1.78-1.61 (m, 4H), 1.35 (d, J=1.3 Hz, 3H).

Example 437

(7-((5-Chloro-3-methylpyridin-2-yl)oxy)-2-azaspiro[3.5]nonan-2-yl)((1s,3s)-3-hydroxy-3-methylcyclobutyl)methanoneo

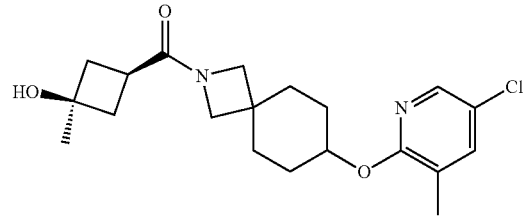 [SMILES: Cc1cc(Cl)cnc1OC1CCC2(CC1)CN(C(=O)[C@H]1C[C@@](C)(O)C1)C2]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2,5-dichloro-3-methylpyridine instead of 6-chloro-2-methyl-3-(trifluoromethyl)pyridine in Step A. MS (ESI): mass calcd. for $C_{20}H_{27}ClN_2O_3$, 378.2; m/z found, 379.2 [M+H]$^+$. $^1$H NMR (500 MHz, CDCl$_3$) δ 7.90-7.85 (m, 1H), 7.37-7.32 (m, 1H), 5.09-5.00 (m, J=3.6 Hz, 1H), 3.98 (s, 1H), 3.80-3.74 (m, 2H), 3.71 (d, J=7.6 Hz, 2H), 2.70-2.63 (m, 1H), 2.34-2.23 (m, 4H), 2.16-2.11 (m, 3H), 1.96-1.82 (m, 4H), 1.72-1.57 (m, 4H), 1.34 (s, 3H).

Example 438

(7-((5-(Difluoromethyl)-6-methylpyridin-2-yl)oxy)-2-azaspiro[3.5]nonan-2-yl)((1s,3s)-3-hydroxy-3-methylcyclobutyl)methanone

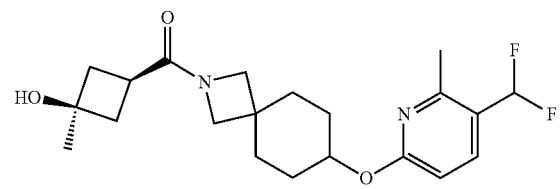 [SMILES: Cc1nc(OC2CCC3(CC2)CN(C(=O)[C@H]2C[C@@](C)(O)C2)C3)ccc1C(F)F]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 6-chloro-3-(difluoromethyl)-2-methylpyridine (Intermediate 76) instead of 6-chloro-2-methyl-3-(trifluoromethyl)pyridine in Step A. MS (ESI): mass calcd. for $C_{21}H_{28}F_2N_2O_3$, 394.2; m/z found, 395.1 [M+H]$^+$. $^1$H NMR (400 MHz, DMSO-d$_6$) δ 7.78 (d, J=8.5 Hz, 1H), 7.29-7.00 (m, 1H), 6.68 (d, J=8.3 Hz, 1H), 5.06-4.99 (m, 2H), 3.74 (d, J=12.8 Hz, 2H), 3.52 (d, J=10.8 Hz, 2H), 2.60-2.53 (m, 1H), 2.46 (s, 3H), 2.13-2.05 (m, 2H), 2.03-1.96 (m, 2H), 1.91-1.78 (m, 4H), 1.65-1.47 (m, 4H), 1.23 (s, 3H).

Example 439

(7-((6-(Difluoromethyl)-5-ethylpyridin-2-yl)oxy)-2-azaspiro[3.5]nonan-2-yl)((1s,3s)-3-hydroxy-3-methylcyclobutyl)methanone

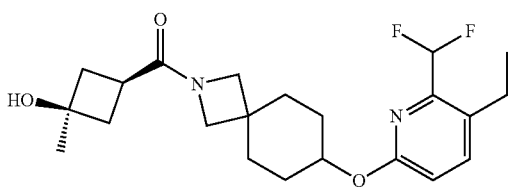 [SMILES: CCc1ccc(OC2CCC3(CC2)CN(C(=O)[C@H]2C[C@@](C)(O)C2)C3)nc1C(F)F]

Step A: tert-Butyl 7-((5-bromo-6-(difluoromethyl)pyridin-2-yl)oxy)-2-azaspiro[3.5]nonane-2-carboxylate. CsF (940 mg, 6.19 mmol) was added to a solution of tert-butyl 7-hydroxy-2-azaspiro[3.5]nonane-2-carboxylate (358 mg, 1.48 mmol) and 3-bromo-6-chloro-2-(difluoromethyl)pyridine (300 mg, 1.24 mmol) in DMSO (8 mL) under $N_2$. The reaction mixture was stirred for 16 h at 120° C. After cooling to rt, the reaction mixture was poured into brine and extracted with EtOAc. The combined organic extracts were washed brine, dried over $Na_2SO_4$, filtered, and concentrated under reduced pressure. The resulting residue was purified by FCC ($SiO_2$, 0-10% EtOAc in ether) to afford the title compound (140 mg, 24% yield) as a colorless oil. MS (ESI): mass calcd. for $C_{19}H_{25}BrF_2N_2O_3$, 446.1; m/z found, 393.1 [M+2H-tBu]$^+$.

Step B: tert-Butyl 7-((6-(difluoromethyl)-5-ethylpyridin-2-yl)oxy)-2-azaspiro[3.5]nonane-2-carboxylate. A mixture of tert-butyl 7-((5-bromo-6-(difluoromethyl)pyridin-2-yl)oxy)-2-azaspiro[3.5]nonane-2-carboxylate (100 mg, 0.224 mmol) and $Et_2Zn$ (0.67 mL, 1 M in toluene, 0.670 mmol) in THF (3 mL) was sparged with $N_2$ for 5 minutes, then treated with Pd(t-$Bu_3P)_2$ (23 mg, 0.045 mmol). The reaction mixture was stirred at 60° C. for 4 h before being quenched with sat. aq. $NH_4Cl$ and extracted with EtOAc. The organic layers were dried over $Na_2SO_4$, filtered, and concentrated under reduced pressure. The resulting residue was purified by FCC ($SiO_2$, 0-20% EtOAc in ether) to give the title compound (100 mg, 99% yield) as a yellow oil. MS (ESI): mass calcd. for $C_{21}H_{30}F_2N_2O_3$, 396.2; m/z found, 341.2 [M+2H-tBu]$^+$.

Step C: 7-((6-(Difluoromethyl)-5-ethylpyridin-2-yl)oxy)-2-azaspiro[3.5]nonane. TFA (1 mL, 13.1 mmol) was added to a solution of tert-butyl 7-((6-(difluoromethyl)-5-ethylpyridin-2-yl)oxy)-2-azaspiro[3.5]nonane-2-carboxylate (100 mg, 0.252 mmol) in DCM (4 mL). The reaction mixture was stirred at rt for 1 hour before being concentrated under reduced pressure to give the title compound (110 mg, crude) as a yellow oil, which was used in the next step without further purification. MS (ESI): mass calcd. for $C_{16}H_{22}F_2N_2O$, 296.2; m/z found, 297.2 [M+H]$^+$.

Step D: (7-((6-(Difluoromethyl)-5-ethylpyridin-2-yl)oxy)-2-azaspiro[3.5]nonan-2-yl)((1s,3s)-3-hydroxy-3-methylcyclobutyl)methanone. $T_3P$® (0.24 mL, 50% in EtOAc, 0.403 mmol) was added to a solution of 7-((6-(difluoromethyl)-5-ethylpyridin-2-yl)oxy)-2-azaspiro[3.5]nonane (110 mg), (1s,3s)-3-hydroxy-3-methylcyclobutanecarboxylic acid (70 mg, 0.538 mmol) and TEA (0.44 mL, 3.23 mmol) in DCM (3 mL). The resultant mixture was stirred for 1 hour at rt before being poured into water and extracted with DCM. The combined organic extracts were dried over $Na_2SO_4$, filtered, and concentrated under reduced pressure. The resulting residue was purified by RP HPLC (53-83% ACN in water with 0.225% HCOOH) to afford the title compound (44 mg, 39% yield) as a white solid. MS (ESI): mass calcd. for $C_{22}H_{30}F_2N_2O_3$, 408.2; m/z found, 409.2 [M+H]$^+$. $^1$H NMR (400 MHz, $CDCl_3$) δ 7.52 (d, J=8.3 Hz, 1H), 6.74 (dd, J=8.4, 3.1 Hz, 1H), 6.71-6.42 (m, 1H), 5.11-5.03 (m, 1H), 3.81-3.70 (m, 4H), 2.81-2.67 (m, 3H), 2.35-2.23 (m, 4H), 1.98-1.89 (m, 4H), 1.72-1.59 (m, 4H), 1.36 (s, 3H), 1.22 (t, J=7.5 Hz, 3H).

Example 440

(7-((5-(Difluoromethyl)-6-ethylpyridin-2-yl)oxy)-2-azaspiro[3.5]nonan-2-yl)((1s,3s)-3-hydroxy-3-methylcyclobutyl)methanone

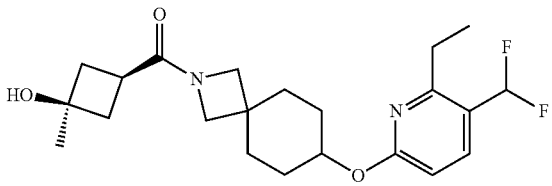 [SMILES: CCc1nc(OC2CCC3(CC2)CN(C(=O)[C@H]2C[C@@](C)(O)C2)C3)ccc1C(F)F]

Step A: tert-Butyl 7-((6-bromo-5-(difluoromethyl)pyridin-2-yl)oxy)-2-azaspiro[3.5]nonane-2-carboxylate and tert-Butyl 7-((6-chloro-3-(difluoromethyl)pyridin-2-yl)oxy)-2-azaspiro[3.5]nonane-2-carboxylate. Sodium hydride (198 mg, 60% in mineral oil, 4.95 mmol) was added in portions to a 0° C. solution of tert-butyl 7-hydroxy-2-azaspiro[3.5]nonane-2-carboxylate (239 mg, 0.990 mmol) in THF (5 mL). The resultant mixture was stirred for 30 min with gradual warming to rt, then treated with 2-bromo-6-chloro-3-(difluoromethyl)pyridine (Intermediate 77, 240 mg, 0.990 mmol). The resultant mixture was stirred at 90° C. for 16 h. After cooling to rt, the reaction mixture was quenched with $H_2O$ and extracted with EtOAc. The combined organic extracts were washed with brine, dried over $Na_2SO_4$, filtered, and concentrated under reduced pressure. The resulting residue was purified by FCC ($SiO_2$, 0-50% EtOAc in ether) to afford a mixture of the title compounds (300 mg). MS (ESI): mass calcd. for $C_{19}H_{25}BrF_2N_2O_3$ and $C_{19}H_{25}ClF_2N_2O_3$, 446.1 and 402.2; m/z found, 390.9 and 346.9 [M+2H-tBu]$^+$.

Step B: tert-Butyl 7-((5-(difluoromethyl)-6-vinylpyridin-2-yl)oxy)-2-azaspiro[3.5]nonane-2-carboxylate and tert-Butyl 7-((3-(difluoromethyl)-6-vinylpyridin-2-yl)oxy)-2-azaspiro[3.5]nonane-2-carboxylate. Potassium trifluoro(vinyl)borate (168 mg, 1.25 mmol), the mixture of tert-butyl 7-((6-bromo-5-(difluoromethyl)pyridin-2-yl)oxy)-2-azaspiro[3.5]nonane-2-carboxylate and tert-butyl 7-((6-chloro-3-(difluoromethyl)pyridin-2-yl)oxy)-2-azaspiro[3.5]nonane-2-carboxylate (280 mg), and $Cs_2CO_3$ (612 mg, 1.88 mmol) were dissolved in 1,4-dioxane (4 mL) and $H_2O$ (1 mL). The reaction mixture was sparged with $N_2$ for 5 min, then treated with $Pd(dppf)_2Cl_2$ (46 mg, 0.063 mmol). The resultant mixture was sparged with Ar for another 5 min, then stirred at 90° C. for 1 hour before being cooled to rt. The reaction mixture was poured into water and extracted with EtOAc. The combined organic extracts were dried over $Na_2SO_4$, filtered, and concentrated under reduced pressure. The resulting residue was purified by FCC ($SiO_2$, 0-50% EtOAc in ether) to afford a mixture of the title compounds (230 mg).

Step C: tert-Butyl 7-((5-(difluoromethyl)-6-ethylpyridin-2-yl)oxy)-2-azaspiro[3.5]nonane-2-carboxylate and tert-Butyl 7-((3-(difluoromethyl)-6-ethylpyridin-2-yl)oxy)-2-azaspiro[3.5]nonane-2-carboxylate. The mixture of tert-butyl 7-((5-(difluoromethyl)-6-vinylpyridin-2-yl)oxy)-2-azaspiro[3.5]nonane-2-carboxylate and tert-butyl 7-((3-(difluoromethyl)-6-ethylpyridin-2-yl)oxy)-2-azaspiro[3.5]nonane-2-carboxylate (180 mg) and wet Pd/C (97 mg, 0.046 mmol) were taken up in EtOAc (10 mL). The resultant mixture was stirred under $H_2$ (15 psi) at rt for 1 hour before the suspension was filtered through a pad of Celite® and the pad was washed with EtOAc. The filtrate was concentrated under reduced pressure to afford a mixture of the title compounds (180 mg), which was used in the next step without further purification.

Step D: 7-((5-(Difluoromethyl)-6-ethylpyridin-2-yl)oxy)-2-azaspiro[3.5]nonane and 7-((3-(Difluoromethyl)-6-ethylpyridin-2-yl)oxy)-2-azaspiro[3.5]nonane. TFA (0.3 mL, 3.92 mmol) was added to a solution of the mixture of tert-butyl 7-((5-(difluoromethyl)-6-ethylpyridin-2-yl)oxy)-2-azaspiro[3.5]nonane-2-carboxylate and tert-butyl 7-((3-(difluoromethyl)-6-ethylpyridin-2-yl)oxy)-2-azaspiro[3.5]nonane-2-carboxylate (180 mg) in DCM (3 mL). The reaction mixture was stirred at rt for 1 hour before being concentrated under reduced pressure to give a mixture of the title compounds (180 mg), which was used in the next step without further purification.

Step E: (7-((5-(Difluoromethyl)-6-ethylpyridin-2-yl)oxy)-2-azaspiro[3.5]nonan-2-yl)((1s,3s)-3-hydroxy-3-methylcyclobutyl)methanone. $T_3P$® (0.50 mL, 50% in EtOAc, 0.420 mmol) was added to a solution of the mixture of 7-((5-(difluoromethyl)-6-ethylpyridin-2-yl)oxy)-2-azaspiro[3.5]nonane and 7-((3-(difluoromethyl)-6-ethylpyridin-2-yl)oxy)-2-azaspiro[3.5]nonane (180 mg), (1s,3s)-3-hydroxy-3-methylcyclobutanecarboxylic acid (57 mg, 0.440 mmol) and TEA (0.60 mL, 4.30 mmol) in DCM (5 mL). The resultant mixture was stirred at rt for 2 h before being poured into $H_2O$ and extracted with DCM. The combined organic extracts were dried over $Na_2SO_4$, filtered, and concentrated under reduced pressure to afford crude product, which was purified by RP HPLC (45-75% $CH_3CN$ in $H_2O$ with 0.05% $NH_3$) to afford (7-((5-(difluoromethyl)-6-ethylpyridin-2-yl)oxy)-2-azaspiro[3.5]nonan-2-yl)((1s,3s)-3-hydroxy-3-methylcyclobutyl)methanone. MS (ESI): mass calcd. for $C_{22}H_{30}F_2N_2O_3$, 408.2; m/z found, 409.1 [M+H]$^+$. $^1$H NMR (400 MHz, DMSO-$d_6$) δ 7.80-7.76 (m, 1H), 7.33-7.02 (t, J=54.8, 1H), 6.71-6.65 (m, 1H), 5.08-5.00 (m, 1H), 4.99 (s, 1H), 3.80-3.71 (m, 2H), 3.58-3.48 (m, 2H), 2.84-2.71 (m, 2H), 2.58-2.53 (m, 1H), 2.14-2.06 (m, 2H), 2.04-1.96 (m, 2H), 1.94-1.80 (m, 4H), 1.66-1.49 (m, 4H), 1.25-1.21 (m, 4H), 1.20-1.17 (m, 2H).

Example 441

(7-((3-(Difluoromethyl)-6-ethylpyridin-2-yl)oxy)-2-azaspiro[3.5]nonan-2-yl)((1s,3s)-3-hydroxy-3-methylcyclobutyl)methanone

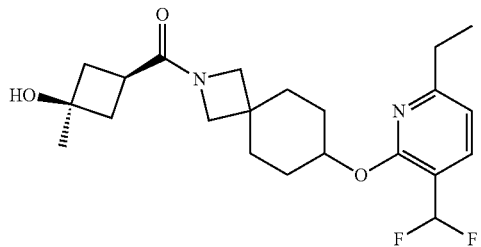 [SMILES: CCc1ccc(C(F)F)c(OC2CCC3(CC2)CN(C(=O)[C@H]2C[C@@](C)(O)C2)C3)n1]

The title compound was recovered from Example 440, Step E. MS (ESI): mass calcd. for $C_{22}H_{30}F_2N_2O_3$, 408.2; m/z found, 409.3 [M+H]$^+$. $^1$H NMR (400 MHz, DMSO-$d_6$) δ 7.83-7.78 (m, 1H), 7.15-6.84 (m, 2H), 5.21-5.09 (m, 1H), 5.06-4.95 (m, 1H), 3.79-3.67 (m, 2H), 3.52 (s, 2H), 2.76-2.64 (m, 2H), 2.59-2.53 (m, 1H), 2.13-2.06 (m, 2H), 2.03-1.96 (m, 2H), 1.88-1.75 (m, 4H), 1.69-1.56 (m, 4H), 1.25-1.21 (m, 4H), 1.21-1.18 (m, 2H).

Example 442

((1s,3s)-3-Hydroxy-3-methylcyclobutyl)(7-((4-methyl-5-(trifluoromethyl)pyridin-2-yl)oxy)-2-azaspiro[3.5]nonan-2-yl)methanone

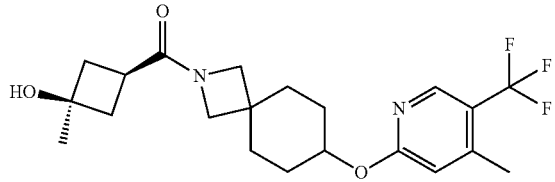 [SMILES: Cc1cc(OC2CCC3(CC2)CN(C(=O)[C@H]2C[C@@](C)(O)C2)C3)ncc1C(F)(F)F]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-chloro-4-methyl-5-(trifluoromethyl)pyridine instead of 6-chloro-2-methyl-3-(trifluoromethyl)pyridine in Step A. MS (ESI): mass calcd. for $C_{21}H_{27}F_3N_2O_3$, 412.2; m/z found, 413.2 [M+H]$^+$. $^1$H NMR (400 MHz, CDCl$_3$) δ 8.31 (d, J=3.7 Hz, 1H), 6.58 (d, J=4.6 Hz, 1H), 5.16-5.06 (m, 1H), 3.88 (d, J=3.6 Hz, 1H), 3.78 (d, J=5.9 Hz, 2H), 3.72 (d, J=9.1 Hz, 2H), 2.75-2.61 (m, 1H), 2.42-2.37 (m, 3H), 2.36-2.21 (m, 4H), 1.98-1.84 (m, 4H), 1.69-1.55 (m, 4H), 1.35 (s, 3H).

Example 443

((1s,3s)-3-Hydroxy-3-methylcyclobutyl)(7-((6-methyl-3-(trifluoromethyl)pyridin-2-yl)oxy)-2-azaspiro[3.5]nonan-2-yl)methanone

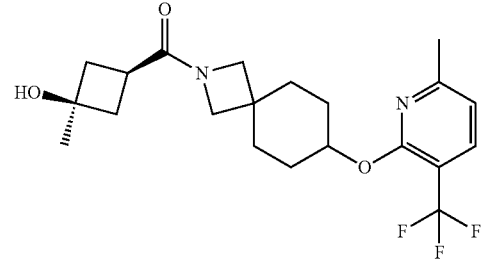 [SMILES: Cc1ccc(C(F)(F)F)c(OC2CCC3(CC2)CN(C(=O)[C@H]2C[C@@](C)(O)C2)C3)n1]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-chloro-6-methyl-3-(trifluoromethyl)pyridine instead of 6-chloro-2-methyl-3-(trifluoromethyl)pyridine in Step A. MS (ESI): mass calcd. for $C_{21}H_{27}F_3N_2O_3$, 412.2; m/z found, 413.2 [M+H]$^+$. $^1$H NMR (400 MHz, CDCl$_3$) δ 7.69 (d, J=7.6 Hz, 1H), 6.74 (d, J=7.6 Hz, 1H), 5.36-5.24 (m, 1H), 4.00 (s, 1H), 3.78 (d, J=2.6 Hz, 2H), 3.72 (d, J=4.1 Hz, 2H), 2.74-2.61 (m, 1H), 2.45 (s, 3H), 2.33-2.24 (m, 4H), 2.00-1.87 (m, 2H), 1.85-1.71 (m, 4H), 1.73-1.61 (m, 2H), 1.35 (s, 3H).

Example 444

((1s,3*R)-3-Hydroxy-3-methylcyclobutyl)((6*S,7*S)-6-methyl-7-((6-methyl-5-(trifluoromethyl)pyridin-2-yl)oxy)-2-azaspiro[3.5]nonan-2-yl)methanone

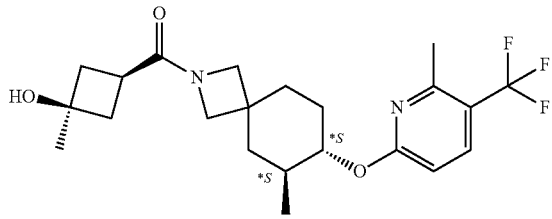 [SMILES: Cc1nc(O[C@H]2CCC3(C[C@@H]2C)CN(C(=O)[C@H]2C[C@@](C)(O)C2)C3)ccc1C(F)(F)F]

Step A: tert-Butyl 6-methyl-7-oxo-2-azaspiro[3.5]nonane-2-carboxylate. LiHMDS (9.2 mL, 1 M in hexane, 9.20 mmol) was added dropwise to a −78° C. solution of tert-butyl 7-oxo-2-azaspiro[3.5]nonane-2-carboxylate (2.0 g, 8.40 mmol) in THF (30 mL) under $N_2$. After stirring for 1 h, iodomethane (0.52 mL, 8.40 mmol) was added dropwise. The reaction mixture was stirred at rt for 2 h before being diluted with water and extracted with EtOAc. The combined organic extracts were washed with brine, dried over $Na_2SO_4$, filtered, and concentrated under reduced pressure. The resulting residue was purified by FCC ($SiO_2$, 0-30% EtOAc in ether) to afford the title compound (1.0 g, 47% yield). $^1$H NMR (400 MHz, CDCl$_3$) δ 3.87-3.75 (m, 2H), 3.59 (s, 2H), 2.42-2.25 (m, 3H), 2.24-2.12 (m, 2H), 1.86-1.75 (m, 1H), 1.54 (t, J=13.2 Hz, 1H), 1.39 (s, 9H), 0.97 (d, J=6.4 Hz, 3H).

Step B: tert-Butyl 7-hydroxy-6-methyl-2-azaspiro[3.5]nonane-2-carboxylate. NaBH$_4$ (300 mg, 7.93 mmol) was added in portions to a 0° C. solution of tert-butyl 6-methyl-7-oxo-2-azaspiro[3.5]nonane-2-carboxylate (1.0 g, 3.90 mmol) in MeOH (20 mL). The reaction mixture was stirred at rt for 1.5 h before being concentrated under reduced pressure. The resulting residue was purified by FCC ($SiO_2$, 25% EtOAc in ether) to give the title compound (900 mg, 89% yield) as a colorless oil.

Step C: tert-Butyl 6-methyl-7-((6-methyl-5-(trifluoromethyl)pyridin-2-yl)oxy)-2-azaspiro[3.5]nonane-2-carboxylate. tert-Butyl 7-hydroxy-2-azaspiro[3.5]nonane-2-carboxylate (500 mg, 1.96 mmol) was added to a mixture of NaH (400 mg, 60% in mineral oil, 10.0 mmol) in THF (15 mL) at 0° C. The reaction mixture was stirred at rt for 30 min before 6-chloro-2-methyl-3-(trifluoromethyl)pyridine (390 mg, 1.99 mmol) was added. The reaction mixture was stirred at 90° C. for 16 h. After cooling to rt, the reaction mixture was quenched with sat. aq. NH$_4$Cl and extracted with EtOAc. The organic extracts were combined, dried over Na$_2$SO$_4$, filtered, and concentrated under reduced pressure. The resulting residue was purified by FCC (SiO$_2$, 0-50% EtOAc in ether) to afford the title compound (800 mg, 97% yield) as a yellow oil. MS (ESI): mass calcd. for $C_{21}H_{29}F_3N_2O_3$, 414.2; m/z found, 359.1 [M+2H-tBu]$^+$.

Step D: tert-Butyl (6*R,7*R)-6-methyl-7-((6-methyl-5-(trifluoromethyl)pyridin-2-yl)oxy)-2-azaspiro[3.5]nonane-2-carboxylate and tert-Butyl (6*S,7*S)-6-methyl-7-((6-methyl-5-(trifluoromethyl)pyridin-2-yl)oxy)-2-azaspiro[3.5]nonane-2-carboxylate. tert-Butyl 6-methyl-7-((6-methyl-5-(trifluoromethyl)pyridin-2-yl)oxy)-2-azaspiro[3.5]nonane-2-carboxylate was separated by SFC (Stationary phase: AD (250×30 mm); Mobile phase: 25% EtOH containing 0.1% aq. NH$_3$/CO$_2$) to provide the title compounds:

tert-Butyl (6*R,7*R)-6-methyl-7-((6-methyl-5-(trifluoromethyl)pyridin-2-yl)oxy)-2-azaspiro[3.5]nonane-2-carboxylate. $^1$H NMR (400 MHz, CDCl$_3$) δ 7.70 (d, J=8.6 Hz, 1H), 6.52 (d, J=8.6 Hz, 1H), 4.74 (dt, J=10.5, 4.2 Hz, 1H), 3.72-3.63 (m, 2H), 3.59 (s, 2H), 2.54 (s, 3H), 2.20-2.08 (m, 1H), 2.02-1.89 (m, 2H), 1.77-1.56 (m, 2H), 1.44 (s, 9H), 1.39-1.20 (m, 2H), 0.95 (d, J=6.4 Hz, 3H).

tert-Butyl (6*S,7*S)-6-methyl-7-((6-methyl-5-(trifluoromethyl)pyridin-2-yl)oxy)-2-azaspiro[3.5]nonane-2-carboxylate. $^1$H NMR (400 MHz, CDCl$_3$) δ 7.70 (d, J=8.6 Hz, 1H), 6.52 (d, J=8.6 Hz, 1H), 4.74 (dt, J=10.5, 4.2 Hz, 1H), 3.72-3.63 (m, 2H), 3.59 (s, 2H), 2.54 (s, 3H), 2.20-2.08 (m, 1H), 2.02-1.89 (m, 2H), 1.77-1.56 (m, 2H), 1.44 (s, 9H), 1.39-1.20 (m, 2H), 0.95 (d, J=6.4 Hz, 3H).

Step E: (6*S,7*S)-6-Methyl-7-((6-methyl-5-(trifluoromethyl)pyridin-2-yl)oxy)-2-azaspiro[3.5]nonane. TFA (1 mL, 13.1 mmol) was added to a mixture of tert-butyl (6*S,7*S)-6-methyl-7-((6-methyl-5-(trifluoromethyl)pyridin-2-yl)oxy)-2-azaspiro[3.5]nonane-2-carboxylate (100 mg, 0.199 mmol) in DCM (4 mL). The reaction mixture was stirred at rt for 30 min before being concentrated under reduced pressure to afford the title compound (230 mg), which was used in the next step without further purification. MS (ESI): mass calcd. for $C_{16}H_{21}F_3N_2O$, 314.2; m/z found, 315.0 [M+H]$^+$.

Step F: ((1s,3*R)-3-Hydroxy-3-methylcyclobutyl)((6*S,7*S)-6-methyl-7-((6-methyl-5-(trifluoromethyl)pyridin-2-yl)oxy)-2-azaspiro[3.5]nonan-2-yl)methanone. T$_3$P® (0.64 mL, 50% in EtOAc, 1.10 mmol) was added to solution of (6*S,7*S)-6-methyl-7-((6-methyl-5-(trifluoromethyl)pyridin-2-yl)oxy)-2-azaspiro[3.5]nonane (230 mg, 0.537 mmol), (1s,3s)-3-hydroxy-3-methylcyclobutanecarboxylic acid (70 mg, 0.540 mmol) and TEA (0.75 mL, 5.40 mmol) in DCM (10 mL). The resultant mixture was stirred at rt for 2 h before being poured into H$_2$O and extracted with DCM. The combined organic extracts were dried over Na$_2$SO$_4$, filtered, and concentrated under reduced pressure. The resulting residue was purified by RP HPLC (35-65% CH$_3$CN in H$_2$O with 0.05% NH$_3$) to afford the title compound (102 mg, 44% yield). MS (ESI): mass calcd. for $C_{22}H_{29}F_3N_2O_3$, 426.2; m/z found, 427.1 [M+H]$^+$. $^1$H NMR (400 MHz, CDCl$_3$) δ 7.74 (d, J=8.7 Hz, 1H), 6.56 (dd, J=8.6, 3.7 Hz, 1H), 4.86-4.74 (m, 1H), 3.93 (br s, 1H), 3.89-3.82 (m, 1H), 3.81-3.75 (m, 2H), 3.71 (s, 1H), 2.77-2.65 (m, 1H), 2.58 (s, 3H), 2.39-2.25 (m, 4H), 2.24-2.15 (m, 1H), 2.03-1.91 (m, 2H), 1.84-1.62 (m, 2H), 1.49-1.24 (m, 5H), 1.04-0.95 (m, 3H).

Example 445

((1s,3*S)-3-Hydroxy-3-methylcyclobutyl)((6*R, 7*R)-6-methyl-7-((6-methyl-5-(trifluoromethyl)pyridin-2-yl)oxy)-2-azaspiro[3.5]nonan-2-yl)methanone

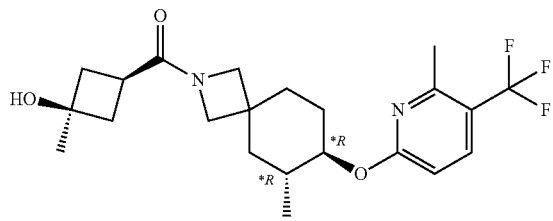 [SMILES: Cc1nc(O[C@@H]2CCC3(C[C@H]2C)CN(C(=O)[C@H]2C[C@@](C)(O)C2)C3)ccc1C(F)(F)F]

The title compound was prepared from tert-butyl (6*R, 7*R)-6-methyl-7-((6-methyl-5-(trifluoromethyl)pyridin-2-yl)oxy)-2-azaspiro[3.5]nonane-2-carboxylate (Example 444, Step D) following Example 444, Steps E and F. MS (ESI): mass calcd. for $C_{22}H_{29}F_3N_2O_3$, 426.2; m/z found, 427.1 [M+H]$^+$. $^1$H NMR (400 MHz, CDCl$_3$) δ 7.73 (d, J=8.6 Hz, 1H), 6.56 (dd, J=8.6, 3.5 Hz, 1H), 4.85-4.73 (m, 1H), 4.00 (br s, 1H), 3.90-3.81 (m, 1H), 3.80-3.74 (m, 2H), 3.71 (s, 1H), 2.78-2.63 (m, 1H), 2.58 (s, 3H), 2.39-2.13 (m, 5H), 2.03-1.90 (m, 2H), 1.82-1.61 (m, 2H), 1.54-1.19 (m, 5H), 1.04-0.94 (m, 3H).

Example 446

((1s,3s)-3-Hydroxy-3-methylcyclobutyl)(7-((3-methyl-5-(trifluoromethyl)pyridin-2-yl)oxy)-2-azaspiro[3.5]nonan-2-yl)methanone

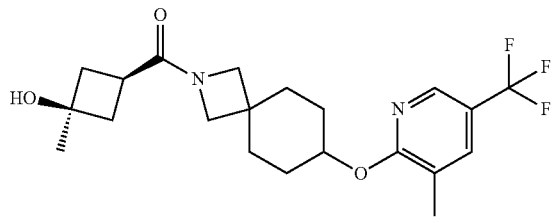

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-chloro-3-methyl-5-(trifluoromethyl)pyridine instead of 6-chloro-2-methyl-3-(trifluoromethyl)pyridine in Step A. MS (ESI): mass calcd. for $C_{21}H_{27}F_3N_2O_3$, 412.2; m/z found, 413.2 [M+H]$^1$. $^1$H NMR (400 MHz, CDCl$_3$) δ 8.25-8.20 (m, 1H), 7.58-7.54 (m, 1H), 5.22-5.13 (m, 1H), 3.90-3.85 (m, 1H), 3.79 (d, J=4.9 Hz, 2H), 3.73 (d, J=6.4 Hz, 2H), 2.73-2.63 (m, 1H), 2.35-2.23 (m, 4H), 2.20 (d, J=3.9 Hz, 3H), 1.99-1.84 (m, 4H), 1.76-1.60 (m, 4H), 1.35 (s, 3H).

Example 447

((1s,3s)-3-Hydroxy-3-methylcyclobutyl)(7-((6-methyl-4-(trifluoromethyl)pyridin-2-yl)oxy)-2-azaspiro[3.5]nonan-2-yl)methanone

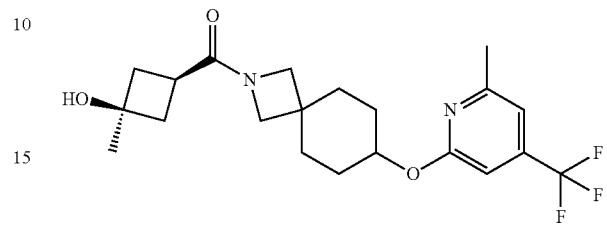

The title compound was prepared in a manner analogous to Example 309 using tert-butyl 7-hydroxy-2-azaspiro[3.5] nonane-2-carboxylate instead of tert-butyl 6-hydroxy-2-azaspiro[3.3]heptane-2-carboxylate and 2-chloro-6-methyl-4-(trifluoromethyl)pyridine instead of 6-chloro-2-methyl-3-(trifluoromethyl)pyridine in Step A. MS (ESI): mass calcd. for $C_{21}H_{27}F_3N_2O_3$, 412.2; m/z found, 413.3 [M+H]$^+$. $^1$H NMR (400 MHz, CDCl$_3$) δ 6.87 (s, 1H), 6.69 (d, J=3.9 Hz, 1H), 5.18-5.07 (m, 1H), 4.07 (d, J=8.6 Hz, 1H), 3.77 (d, J=5.2 Hz, 2H), 3.72 (d, J=7.2 Hz, 2H), 2.74-2.60 (m, 1H), 2.47 (s, 3H), 2.29 (dd, J=7.5, 1.6 Hz, 4H), 1.98-1.83 (m, 4H), 1.72-1.57 (m, 4H), 1.35 (d, J=1.4 Hz, 3H).

Example 448

((1s,3s)-3-Hydroxy-3-methylcyclobutyl)(7-((6-methyl-5-(trifluoromethyl)pyridin-2-yl)oxy)-2-azaspiro[3.5]nonan-2-yl)methanone

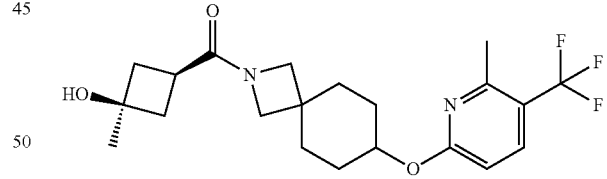

The title compound was prepared in a manner analogous to Example 309 using tert-butyl 7-hydroxy-2-azaspiro[3.5] nonane-2-carboxylate instead of tert-butyl 6-hydroxy-2-azaspiro[3.3]heptane-2-carboxylate in Step A. MS (ESI): mass calcd. for $C_{21}H_{27}F_3N_2O_3$, 412.2; m/z found, 413.1 [M+H]$^+$. $^1$H NMR (400 MHz, DMSO-d$_6$) δ 7.92 (d, J=8.8 Hz, 1H), 6.74 (d, J=8.6 Hz, 1H), 5.12-5.01 (m, 1H), 3.75 (d, J=12.5 Hz, 2H), 3.52 (d, J=10.7 Hz, 2H), 2.58-2.52 (m, 4H), 2.13-2.06 (m, 2H), 2.03-1.96 (m, 2H), 1.89-1.79 (m, 4H), 1.64-1.53 (m, 4H), 1.23 (s, 3H).

Example 449

((1s,3s)-3-Hydroxy-3-methylcyclobutyl)(7-((3-methyl-6-(trifluoromethyl)pyridin-2-yl)oxy)-2-azaspiro[3.5]nonan-2-yl)methanone

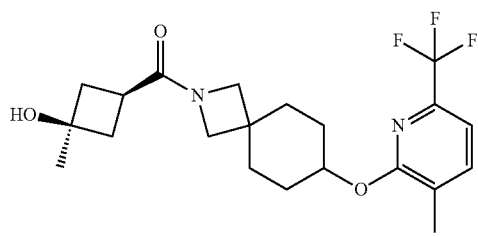 [SMILES: Cc1ccc(C(F)(F)F)nc1OC1CCC2(CC1)CN(C(=O)[C@H]1C[C@@](C)(O)C1)C2]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-chloro-3-methyl-6-(trifluoromethyl)pyridine instead of 6-chloro-2-methyl-3-(trifluoromethyl)pyridine in Step A. MS (ESI): mass calcd. for $C_{21}H_{27}F_3N_2O_3$, 412.2; m/z found, 413.2 [M+H]$^1$. $^1$H NMR (400 MHz, CDCl$_3$) δ 7.48 (d, J=7.3 Hz, 1H), 7.12 (d, J=7.3 Hz, 1H), 5.21-5.11 (m, 1H), 3.96 (d, J=5.8 Hz, 1H), 3.79 (d, J=3.8 Hz, 2H), 3.73 (d, J=4.1 Hz, 2H), 2.73-2.63 (m, 1H), 2.35-2.24 (m, 4H), 2.21 (d, J=3.2 Hz, 3H), 1.98-1.84 (m, 4H), 1.74-1.61 (m, 4H), 1.35 (s, 3H).

Example 450

(7-((5-Ethyl-6-(trifluoromethyl)pyridin-2-yl)oxy)-2-azaspiro[3.5]nonan-2-yl)((1s,3s)-3-hydroxy-3-methylcyclobutyl)methanone

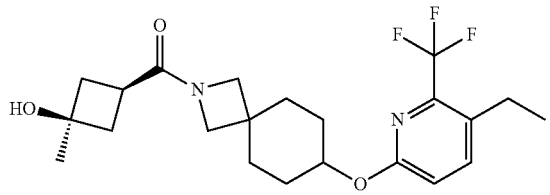 [SMILES: CCc1ccc(OC2CCC3(CC2)CN(C(=O)[C@H]2C[C@@](C)(O)C2)C3)nc1C(F)(F)F]

The title compound was prepared in a manner analogous to Example 439 using 3-bromo-6-chloro-2-(trifluoromethyl)pyridine instead of 3-bromo-6-chloro-2-(difluoromethyl)pyridine in Step A. MS (ESI): mass calcd. for $C_{22}H_{29}F_3N_2O_3$, 426.2; m/z found, 427.1 [M+H]$^+$. $^1$H NMR (400 MHz, CDCl$_3$) δ 7.58-7.52 (m, 1H), 6.84-6.77 (m, 1H), 5.12-5.04 (m, 1H), 3.93 (br s, 1H), 3.84-3.77 (m, 2H), 3.76-3.69 (m, 2H), 2.78-2.65 (m, 3H), 2.37-2.22 (m, 4H), 2.02-1.88 (m, 4H), 1.75-1.59 (m, 4H), 1.41-1.32 (m, 3H), 1.27-1.14 (m, 3H).

Example 451

((1s,3s)-3-Hydroxy-3-methylcyclobutyl)(7-((5-methyl-6-(trifluoromethyl)pyridin-2-yl)oxy)-2-azaspiro[3.5]nonan-2-yl)methanone

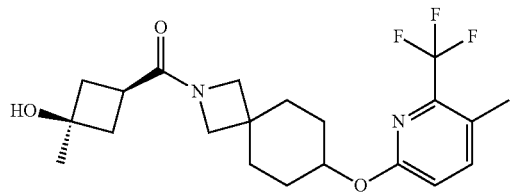 [SMILES: Cc1ccc(OC2CCC3(CC2)CN(C(=O)[C@H]2C[C@@](C)(O)C2)C3)nc1C(F)(F)F]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 6-chloro-3-methyl-2-(trifluoromethyl)pyridine instead of 6-chloro-2-methyl-3-(trifluoromethyl)pyridine in Step A. MS (ESI): mass calcd. for $C_{21}H_{27}F_3N_2O_3$, 412.2; m/z found, 413.2 [M+H]$^+$. $^1$H NMR (400 MHz, CDCl$_3$) δ 7.47 (d, J=8.4 Hz, 1H), 6.75 (dd, J=8.4, 3.1 Hz, 1H), 5.11-5.01 (m, 1H), 3.98 (s, 1H), 3.77 (d, J=5.9 Hz, 2H), 3.71 (d, J=7.6 Hz, 2H), 2.73-2.61 (m, 1H), 2.37 (q, J=2.2 Hz, 3H), 2.34-2.22 (m, 4H), 1.97-1.85 (m, 4H), 1.74-1.53 (m, 4H), 1.35 (s, 3H).

Example 452

((1r,3s)-3-Ethyl-3-hydroxycyclobutyl)(7-((5-methyl-6-(trifluoromethyl)pyridin-2-yl)oxy)-2-azaspiro[3.5]nonan-2-yl)methanone

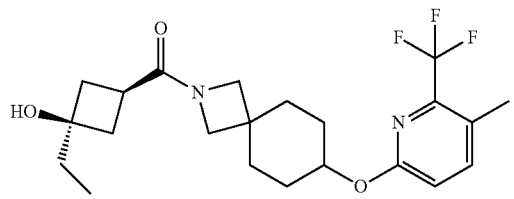 [SMILES: CC[C@]1(O)C[C@@H](C(=O)N2CC3(CCC(Oc4ccc(C)c(C(F)(F)F)n4)CC3)C2)C1]

In an oven-dried flask under N$_2$, 3-(7-((5-methyl-6-(trifluoromethyl)pyridin-2-yl)oxy)-2-azaspiro[3.5]nonane-2-carbonyl)cyclobutan-1-one (intermediate from Example 453, 19 mg, 0.048 mmol) was taken up in THF (0.24 mL) and cooled to −78° C. Ethylmagnesium bromide (24 μL, 3 M in Et$_2$O, 0.072 mmol) was added and the reaction mixture was allowed to warm to rt. The reaction mixture was stirred for 2 h, quenched with sat. aq. NH$_4$Cl and extracted with EtOAc. The organic layers were dried over Na$_2$SO$_4$, filtered, and concentrated under reduced pressure. Purification by RP HPLC (5-95% ACN in water with 20 mM NH$_4$OH) provided the title compound (3.1 mg, 15% yield). MS (ESI): mass calcd. for $C_{22}H_{29}F_3N_2O_3$, 426.2; m/z found, 427.2 [M+H]$^+$. $^1$H NMR (400 MHz, CDCl$_3$) δ 7.47 (d, J=8.4 Hz, 1H), 6.75 (dd, J=8.4, 3.8 Hz, 1H), 5.12-5.02 (m, 1H), 3.80-3.74 (m, 3H), 3.72 (d, J=7.6 Hz, 2H), 2.74-2.61 (m, 1H), 2.41-2.34 (m, 3H), 2.35-2.28 (m, 2H), 2.21-2.12 (m, 2H), 1.99-1.86 (m, 4H), 1.73-1.53 (m, 6H), 0.93 (t, J=7.4 Hz, 3H).

Example 453

((1s,3s)-3-(Difluoromethyl)-3-hydroxycyclobutyl)(7-((5-methyl-6-(trifluoromethyl)pyridin-2-yl)oxy)-2-azaspiro[3.5]nonan-2-yl)methanone

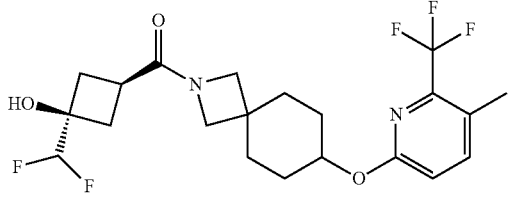 [SMILES: Cc1ccc(OC2CCC3(CC2)CN(C(=O)[C@H]2C[C@](O)(C(F)F)C2)C3)nc1C(F)(F)F]

The title compound was prepared in a manner analogous to Example 319 using tert-butyl 7-((5-methyl-6-(trifluoromethyl)pyridin-2-yl)oxy)-2-azaspiro[3.5]nonane-2-carboxylate (intermediate from Example 451) instead of tert-butyl 6-(3-isopropylphenyl)-2-azaspiro[3.4]octane-2-carboxylate in Step A. MS (ESI): mass calcd. for $C_{21}H_{25}F_5N_2O_3$, 448.2; m/z found, 449.2 [M+H]$^+$. $^1$H NMR (400 MHz, CDCl$_3$) δ 7.47 (d, J=8.4 Hz, 1H), 6.76 (dd, J=8.4, 2.4 Hz, 1H), 5.67 (t, J=56.7 Hz, 1H), 5.12-5.01 (m, 1H), 4.95 (s, 1H), 3.80 (d, J=5.2 Hz, 2H), 3.74 (d, J=7.2 Hz, 2H), 2.86-2.75 (m, 1H), 2.72-2.60 (m, 2H), 2.38 (q, J=2.2 Hz, 3H), 2.27-2.18 (m, 2H), 1.98-1.87 (m, 4H), 1.74-1.57 (m, 4H).

Example 454

(7-((5-Ethyl-6-methoxypyridin-2-yl)oxy)-2-azaspiro[3.5]nonan-2-yl)((1s,3s)-3-hydroxy-3-methylcyclobutyl)methanone

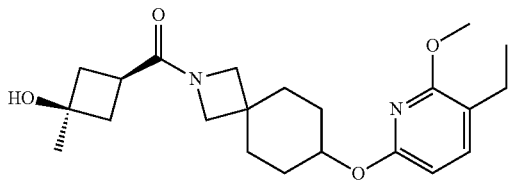 [SMILES: CCc1ccc(OC2CCC3(CC2)CN(C(=O)[C@H]2C[C@@](C)(O)C2)C3)nc1OC]

The title compound was prepared in a manner analogous to Example 440 using 3-bromo-6-chloro-2-methoxypyridine instead of 2-bromo-6-chloro-3-(difluoromethyl)pyridine in Step A and 4,4,5,5-tetramethyl-2-vinyl-1,3,2-dioxaborolane instead of potassium trifluoro(vinyl)borate in Step B. MS (ESI): mass calcd. for $C_{22}H_{32}N_2O_4$, 388.2; m/z found, 389.4 [M+H]$^+$. $^1$H NMR (400 MHz, DMSO-d$_6$) δ 7.42 (d, J=7.9 Hz, 1H), 6.24 (d, J=7.9 Hz, 1H), 5.01 (d, J=1.0 Hz, 1H), 4.90-4.81 (m, 1H), 3.83 (s, 3H), 3.74 (d, J=13.4 Hz, 2H), 3.51 (d, J=10.7 Hz, 2H), 2.59-2.53 (m, 1H), 2.44 (q, J=7.5 Hz, 2H), 2.14-2.05 (m, 2H), 2.03-1.95 (m, 2H), 1.91-1.79 (m, 4H), 1.63-1.46 (m, 4H), 1.23 (s, 3H), 1.07 (t, J=7.5 Hz, 3H).

Example 455

(7-((5-Cyclopropyl-6-methoxypyridin-2-yl)oxy)-2-azaspiro[3.5]nonan-2-yl)((1s,3s)-3-hydroxy-3-methylcyclobutyl)methanone

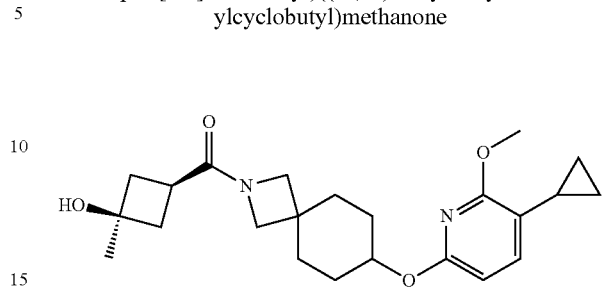

Step A: tert-Butyl 7-((5-bromo-6-methoxypyridin-2-yl)oxy)-2-azaspiro[3.5]nonane-2-carboxylate. NaH (1.8 g, 60% in mineral oil, 45.0 mmol) was added to a 0° C. solution of tert-butyl 7-hydroxy-2-azaspiro[3.5]nonane-2-carboxylate (2.6 g, 10.8 mmol) in THF (20 mL) under N$_2$. The reaction mixture was stirred for 30 min with gradual warming to rt. 3-Bromo-6-chloro-2-methoxypyridine (2.0 g, 8.99 mmol) was added dropwise to the reaction mixture at rt and the reaction was stirred for 16 h at 50° C. The reaction mixture was cooled, poured into sat. aq. NH$_4$Cl and extracted with EtOAc. The combined organic extracts were dried over Na$_2$SO$_4$, filtered, and concentrated under reduced pressure. The resulting residue was purified by FCC (SiO$_2$, 0-25% EtOAc in ether) to afford the title compound (620 mg, 16% yield) as a colorless oil. MS (ESI): mass calcd. for $C_{19}H_{27}BrN_2O_4$, 426.1; m/z found, 371.0 [M+2H-tBu]$^+$.

Step B: tert-Butyl 7-((5-cyclopropyl-6-methoxypyridin-2-yl)oxy)-2-azaspiro[3.5]nonane-2-carboxylate. tert-Butyl 7-((5-bromo-6-methoxypyridin-2-yl)oxy)-2-azaspiro[3.5]nonane-2-carboxylate (200 mg, 0.468 mmol), cyclopropylboronic acid (48 mg, 0.559 mmol) and K$_3$PO$_4$ (300 mg, 1.41 mmol) were dissolved in THF (10 mL). The resultant mixture was sparged with N$_2$ for 5 min, then treated with Pd(dppf)Cl$_2$·CH$_2$Cl$_2$ (38 mg, 0.047 mmol). The reaction mixture was sparged with Ar for another 5 min, then stirred at 90° C. for 2 h. After cooling to rt, the mixture was poured into water and extracted with EtOAc. The combined organic extracts were dried over Na$_2$SO$_4$, filtered, and concentrated under reduced pressure. The resulting residue was purified by FCC (SiO$_2$, 0-10% EtOAc in ether) to afford the title compound (100 mg, 51% yield) as a colorless oil. MS (ESI): mass calcd. for $C_{22}H_{32}N_2O_4$, 388.2; m/z found, 333.2 [M+2H-tBu]$^+$.

Step C: 7-((5-Cyclopropyl-6-methoxypyridin-2-yl)oxy)-2-azaspiro[3.5]nonane. TFA (1 mL, 13.1 mmol) was added to a solution of tert-butyl 7-((5-cyclopropyl-6-methoxypyridin-2-yl)oxy)-2-azaspiro[3.5]nonane-2-carboxylate (100 mg, 0.257 mmol) in DCM (1 mL). The reaction mixture was stirred at rt for 1 hour before being concentrated under reduced pressure to give the title compound (110 mg) as a yellow oil, which was used in the next step without further purification. MS (ESI): mass calcd. for $C_{17}H_{24}N_2O_2$, 288.2; m/z found, 289.3 [M+H]$^+$.

Step D: (7-((5-Cyclopropyl-6-methoxypyridin-2-yl)oxy)-2-azaspiro[3.5]nonan-2-yl)((1s,3s)-3-hydroxy-3-methylcyclobutyl)methanone. T$_3$P® (0.25 mL, 50% in EtOAc, 0.420 mmol) was added to a 0° C. solution of 7-((5-cyclopropyl-6-methoxypyridin-2-yl)oxy)-2-azaspiro[3.5]nonane (110 mg, crude), (1s,3s)-3-hydroxy-3 methylcyclobutanecarboxylic acid (53 mg, 0.407 mmol) and TEA (0.45 mL, 3.30 mmol) in DCM (5 mL). The resultant mixture was stirred for 1 hour with gradual warming to rt before being poured into water and extracted with DCM. The combined organic extracts were dried over Na$_2$SO$_4$, filtered, and concentrated under reduced pressure. The resulting residue was purified by RP HPLC (50-80% CH$_3$CN in water with 0.225% HCOOH). The product was subjected to SFC (Stationary phase: AD (250 mm×30 mm); Mobile phase: 30% IPA containing 0.1% NH$_3$/CO$_2$) to provide the title compound (16 mg, 15% yield) as a white solid. MS (ESI): mass calcd. for C$_{23}$H$_{32}$N$_2$O$_4$, 400.2; m/z found, 401.2 [M+H]$^+$. $^1$H NMR (400 MHz, DMSO-d$_6$) δ 7.16 (d, J=8.0 Hz, 1H), 6.21 (d, J=8.0 Hz, 1H), 4.99 (s, 1H), 4.90-4.83 (m, 1H), 3.85 (s, 3H), 3.73 (d, J=12.3 Hz, 2H), 3.51 (d, J=9.8 Hz, 2H), 2.59-2.54 (m, 1H), 2.14-2.05 (m, 2H), 2.03-1.95 (m, 2H), 1.89-1.77 (m, 5H), 1.63-1.45 (m, 4H), 1.23 (s, 3H), 0.84-0.77 (m, 2H), 0.57-0.50 (m, 2H).

Example 456

((1s,3s)-3-Hydroxy-3-methylcyclobutyl)(7-((6-methoxy-5-methylpyridin-2-yl)oxy)-2-azaspiro[3.5]nonan-2-yl)methanone

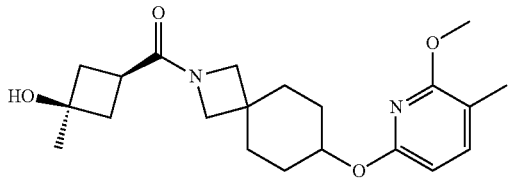 [SMILES: COc1nc(OC2CCC3(CC2)CN(C(=O)[C@H]2C[C@@](C)(O)C2)C3)ccc1C]

The title compound was prepared in a manner analogous to Example 455 using 2,4,6-trimethyl-1,3,5,2,4,6-trioxatriborinane instead of cyclopropylboronic acid in Step B. MS (ESI): mass calcd. for C$_{21}$H$_{30}$N$_2$O$_4$, 374.2; m/z found, 375.2 [M+H]$^+$. $^1$H NMR (400 MHz, DMSO-d$_6$) δ 7.41 (d, J=7.8 Hz, 1H), 6.23 (d, J=7.8 Hz, 1H), 5.00 (d, J=1.0 Hz, 1H), 4.90-4.81 (m, 1H), 3.83 (s, 3H), 3.74 (d, J=13.3 Hz, 2H), 3.52 (d, J=10.8 Hz, 2H), 2.60-2.54 (m, 1H), 2.14-2.07 (m, 2H), 2.05-1.97 (m, 5H), 1.91-1.79 (m, 4H), 1.63-1.46 (m, 4H), 1.24 (s, 3H).

Example 457

(7-((3-Fluoro-5-(trifluoromethyl)pyridin-2-yl)oxy)-2-azaspiro[3.5]nonan-2-yl)((1s,3s)-3-hydroxy-3-methylcyclobutyl)methanone

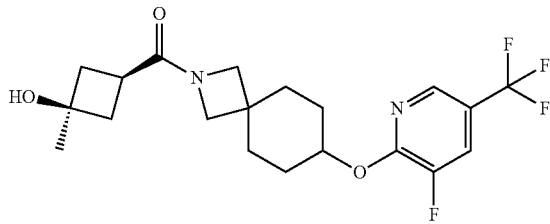 [SMILES: C[C@]1(O)C[C@@H](C(=O)N2CC3(CCC(Oc4ncc(C(F)(F)F)cc4F)CC3)C2)C1]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2,3-difluoro-5-(trifluoromethyl)pyridine instead of 6-chloro-2-methyl-3-(trifluoromethyl)pyridine in Step A. MS (ESI): mass calcd. for C$_{20}$H$_{24}$F$_4$N$_2$O$_3$, 416.2; m/z found, 417.2 [M+H]$^+$. $^1$H NMR (400 MHz, CDCl$_3$) δ 8.18 (ddd, J=4.4, 2.2, 1.1 Hz, 1H), 7.51 (dd, J=9.7, 2.1 Hz, 1H), 5.27-5.16 (m, 1H), 3.90 (d, J=8.7 Hz, 1H), 3.79 (d, J=6.1 Hz, 2H), 3.73 (d, J=9.6 Hz, 2H), 2.75-2.61 (m, 1H), 2.36-2.22 (m, 4H), 2.04-1.87 (m, 4H), 1.75-1.62 (m, 4H), 1.35 (d, J=1.6 Hz, 3H).

Example 458

((1s,3s)-3-Hydroxy-3-methylcyclobutyl)(7-((6-methoxy-5-(trifluoromethyl)pyridin-2-yl)oxy)-2-azaspiro[3.5]nonan-2-yl)methanone

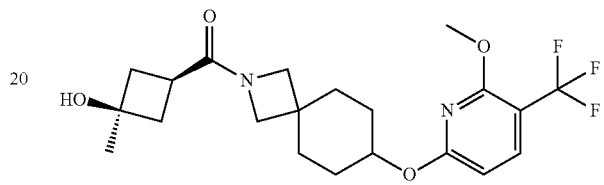

Step A: tert-Butyl 7-((6-chloro-5-(trifluoromethyl)pyridin-2-yl)oxy)-2-azaspiro[3.5]nonane-2-carboxylate. NaH (278 mg, 60% in mineral oil, 6.95 mmol) was added in portions to a 0° C. solution of tert-butyl 7-hydroxy-2-azaspiro[3.5]nonane-2-carboxylate (1.12 g, 4.64 mmol) in THF (10 mL). The reaction mixture was stirred for 30 min at 0° C., then treated with 2,6-dichloro-3-(trifluoromethyl)pyridine (500 mg, 2.32 mmol). The resultant mixture was stirred at rt for 16 h before being quenched with sat. aq. NH$_4$Cl and extracted with EtOAc. The combined organic extracts were washed with brine, dried over Na$_2$SO$_4$, filtered, and concentrated under reduced pressure. The resulting residue was purified by FCC (SiO$_2$, 0-50% EtOAc in ether) to afford the title compound (800 mg, 69% yield) as a white oil. MS (ESI): mass calcd. for C$_{19}$H$_{24}$ClF$_3$N$_2$O$_3$, 420.1; m/z found, 365.0 [M+2H-tBu]$^+$.

Step B: tert-Butyl 7-((6-methoxy-5-(trifluoromethyl)pyridin-2-yl)oxy)-2-azaspiro[3.5]nonane-2-carboxylate. MeONa (513 mg, 9.50 mmol) was added to a solution of tert-butyl 7-((6-chloro-5-(trifluoromethyl)pyridin-2-yl)oxy)-2-azaspiro[3.5]nonane-2-carboxylate (400 mg, 0.950 mmol) in MeOH (5 mL). The reaction mixture was stirred at 80° C. for 12 h before being quenched with water and extracted with EtOAc. The organic layers were dried over Na$_2$SO$_4$, filtered, and concentrated under reduced pressure. The resulting residue was purified by FCC (SiO$_2$, 0-50% EtOAc in ether) to afford the title compound (180 mg, 45% yield) as a white solid. MS (ESI): mass calcd. for C$_{20}$H$_{27}$F$_3$N$_2$O$_4$, 416.2; m/z found, 361.4 [M+2H-tBu]$^+$.

Step C: 7-((6-Methoxy-5-(trifluoromethyl)pyridin-2-yl)oxy)-2-azaspiro[3.5]nonane. TFA (0.3 mL, 4.30 mmol) was added to a solution of tert-butyl 7-((6-methoxy-5-(trifluoromethyl)pyridin-2-yl)oxy)-2-azaspiro[3.5]nonane-2-carboxylate (180 mg, 0.432 mmol) in DCM (3 mL). The reaction mixture was stirred at rt for 1 hour before being concentrated under reduced pressure to give the title compound (180 mg), which was used in the next step without further purification. MS (ESI): mass calcd. for C$_{15}$H$_{19}$F$_3$N$_2$O$_2$, 316.1; m/z found, 317.4 [M+H]$^+$.

Step D: ((1s,3s)-3-Hydroxy-3-methylcyclobutyl)(7-((6-methoxy-5-(trifluoromethyl)pyridin-2-yl)oxy)-2-azaspiro[3.5]nonan-2-yl)methanone. T$_3$P® (0.37 mL, 50% in EtOAc, 0.630 mmol) was added to solution of 7-((6-methoxy-5-(trifluoromethyl)pyridin-2-yl)oxy)-2-azaspiro[3.5]nonane (180 mg, 0.418 mmol), (1s,3s)-3-hydroxy-3-methylcyclobutanecarboxylic acid (109 mg, 0.840 mmol) and TEA (0.58 mL, 4.20 mmol) in DCM (5 mL). The resultant mixture was stirred at rt for 2 h before being poured into H$_2$O and extracted with DCM. The combined organic extracts were dried over Na$_2$SO$_4$, filtered, and concentrated under reduced pressure to afford crude product, which was purified by RP HPLC (55-85% CH$_3$CN in H$_2$O with 0.05% NH$_3$) to afford the title compound (129 mg, 72% yield). MS (ESI): mass calcd. for C$_{21}$H$_{27}$F$_3$N$_2$O$_4$, 428.2; m/z found, 429.3 [M+H]$^+$. $^1$H NMR (400 MHz, DMSO-d$_6$) δ 7.95-7.88 (m, 1H), 6.47-6.43 (m, 1H), 5.05-4.97 (m, 2H), 3.94 (s, 3H), 3.78-3.72 (m, 2H), 3.56-3.50 (m, 2H), 2.60-2.53 (m, 1H), 2.13-2.09 (m, 1H), 2.08-2.06 (m, 1H), 2.04-1.80 (m, 6H), 1.68-1.48 (m, 4H), 1.23 (s, 3H).

Example 459

(7-((6-Ethoxy-5-(trifluoromethyl)pyridin-2-yl)oxy)-2-azaspiro[3.5]nonan-2-yl)((1s,3s)-3-hydroxy-3-methylcyclobutyl)methanone

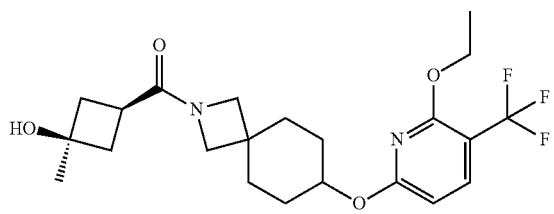 [SMILES: CCOc1nc(OC2CCC3(CC2)CN(C(=O)[C@H]2C[C@@](C)(O)C2)C3)ccc1C(F)(F)F]

The title compound was prepared in a manner analogous to Example 458; using EtONa instead of MeONa in Step B. MS (ESI): mass calcd. for C$_{22}$H$_{29}$F$_3$N$_2$O$_4$, 442.2; m/z found, 442.9 [M+H]$^+$. $^1$H NMR (400 MHz, DMSO-d$_6$) δ 7.94-7.87 (m, 1H), 6.45-6.39 (m, 1H), 5.02-4.93 (m, 2H), 4.46-4.37 (m, 2H), 3.78-3.71 (m, 2H), 3.57-3.48 (m, 2H), 2.60-2.53 (m, 1H), 2.14-2.05 (m, 2H), 2.04-1.95 (m, 2H), 1.94-1.80 (m, 4H), 1.67-1.51 (m, 4H), 1.35-1.29 (m, 3H), 1.23 (s, 3H).

Example 460

(7-((5-Chloro-4-methoxypyridin-2-yl)oxy)-2-azaspiro[3.5]nonan-2-yl)((1s,3s)-3-hydroxy-3-methylcyclobutyl)methanone

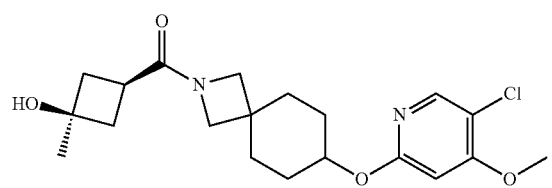 [SMILES: COc1cc(OC2CCC3(CC2)CN(C(=O)[C@H]2C[C@@](C)(O)C2)C3)ncc1Cl]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2,5-dichloro-4-methoxypyridine instead of 6-chloro-2-methyl-3-(trifluoromethyl)pyridine in Step A. MS (ESI): mass calcd. for C$_{20}$H$_{27}$ClN$_2$O$_4$, 394.2; m/z found, 395.2 [M+H]$^+$. $^1$H NMR (400 MHz, CDCl$_3$) δ 7.94 (d, J=3.5 Hz, 1H), 6.20 (d, J=5.6 Hz, 1H), 5.05-4.97 (m, 1H), 3.89 (s, 3H), 3.86 (d, J=4.7 Hz, 1H), 3.77 (d, J=6.4 Hz, 2H), 3.72 (d, J=10.6 Hz, 2H), 2.74-2.63 (m, 1H), 2.36-2.21 (m, 4H), 1.98-1.84 (m, 4H), 1.72-1.52 (m, 4H), 1.35 (d, J=1.4 Hz, 3H).

Example 461

(7-((5-Chloro-6-methoxypyridin-2-yl)oxy)-2-azaspiro[3.5]nonan-2-yl)((1s,3s)-3-hydroxy-3-methylcyclobutyl)methanone

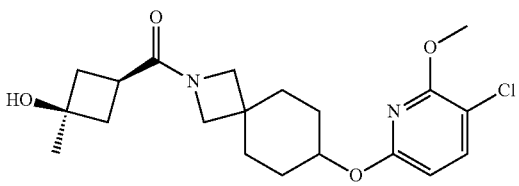 [SMILES: COc1nc(OC2CCC3(CC2)CN(C(=O)[C@H]2C[C@@](C)(O)C2)C3)ccc1Cl]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 3,6-dichloro-2-methoxypridine instead of 6-chloro-2-methyl-3-(trifluoromethyl)pyridine in Step A. MS (ESI): mass calcd. for C$_{20}$H$_{27}$ClN$_2$O$_4$, 394.2; m/z found, 395.2 [M+H]$^+$. $^1$H NMR (500 MHz, CDCl$_3$) δ 7.49 (dt, J=8.3, 2.5 Hz, 1H), 6.28-6.21 (m, 1H), 5.15-4.90 (m, 1H), 3.97-3.83 (m, 3H), 3.85-3.80 (m, 1H), 3.78 (dd, J=8.2, 5.5 Hz, 2H), 3.73 (dd, J=9.0, 5.0 Hz, 2H), 2.74-2.64 (m, 1H), 2.36-2.27 (m, 2H), 2.29-2.22 (m, 2H), 2.04-1.82 (m, 4H), 1.82-1.64 (m, 4H), 1.37-1.32 (m, 3H).

Example 462

(7-((3-Chloro-6-methoxypyridin-2-yl)oxy)-2-azaspiro[3.5]nonan-2-yl)((1s,3s)-3-hydroxy-3-methylcyclobutyl)methanone

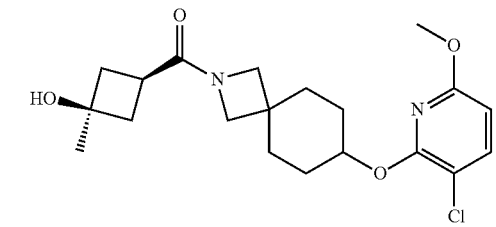 [SMILES: COc1ccc(Cl)c(OC2CCC3(CC2)CN(C(=O)[C@H]2C[C@@](C)(O)C2)C3)n1]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2,3-dichloro-6-methoxypyridine instead of 6-chloro-2-methyl-3-(trifluoromethyl)pyridine in Step A. MS (ESI): mass calcd. for C$_{20}$H$_{27}$ClN$_2$O$_4$, 394.2; m/z found, 395.2 [M+H]$^+$. $^1$H NMR (400 MHz, CDCl$_3$) δ 7.49 (dd, J=8.3, 2.0 Hz, 1H), 6.25 (dd, J=8.3, 1.6 Hz, 1H), 5.17-5.04 (m, 1H), 3.99-3.92 (m, 2H), 3.85 (s, 3H), 3.78 (d, J=6.7 Hz, 2H), 3.73 (d, J=6.8 Hz, 2H), 2.75-2.61 (m, 1H), 2.35-2.22 (m, 4H), 2.05-1.92 (m, 2H), 1.94-1.83 (m, 2H), 1.79-1.72 (m, 2H), 1.73-1.60 (m, 2H), 1.35 (d, J=1.4 Hz, 3H).

Example 463

(7-((5-Chloro-3-methoxypyridin-2-yl)oxy)-2-azaspiro[3.5]nonan-2-yl)((1s,3s)-3-hydroxy-3-methylcyclobutyl)methanone

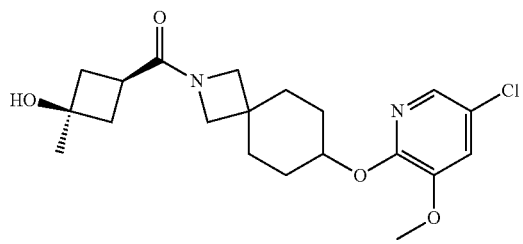 [SMILES: COc1cc(Cl)cnc1OC1CCC2(CC1)CN(C(=O)[C@H]1C[C@@](C)(O)C1)C2]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2,5-dichloro-3-methoxypyridine instead of 6-chloro-2-methyl-3-(trifluoromethyl)pyridine in Step A. MS (ESI): mass calcd. for $C_{20}H_{27}ClN_2O_4$, 394.2; m/z found, 395.2 [M+H]$^+$. $^1$H NMR (500 MHz, CDCl$_3$) δ 7.64 (dd, J=6.1, 2.2 Hz, 1H), 7.01 (t, J=2.0 Hz, 1H), 5.11-5.02 (m, 1H), 3.84 (s, 3H), 3.81 (d, J=14.2 Hz, 1H), 3.79-3.68 (m, 4H), 2.74-2.64 (m, 1H), 2.35-2.21 (m, 4H), 2.04-1.92 (m, 4H), 1.72-1.60 (m, 4H), 1.35 (d, J=2.6 Hz, 3H).

Example 464

(7-((3-Chloro-4-methoxypyridin-2-yl)oxy)-2-azaspiro[3.5]nonan-2-yl)((1s,3s)-3-hydroxy-3-methylcyclobutyl)methanone

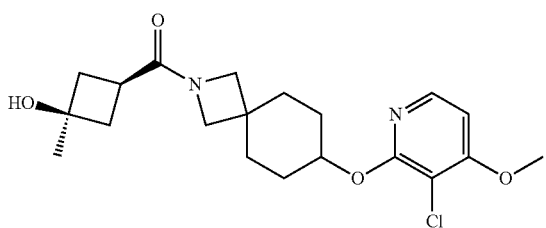 [SMILES: COc1ccnc(OC2CCC3(CC2)CN(C(=O)[C@H]2C[C@@](C)(O)C2)C3)c1Cl]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2,3-dichloro-4-methoxypyridine instead of 6-chloro-2-methyl-3-(trifluoromethyl)pyridine in Step A. MS (ESI): mass calcd. for $C_{20}H_{27}ClN_2O_4$, 394.2; m/z found, 395.1 [M+H]$^1$. $^1$H NMR (400 MHz, CDCl$_3$) δ 7.96-7.88 (m, 1H), 6.55-6.49 (m, 1H), 5.18-4.42 (m, 1H), 4.03-3.87 (m, 4H), 3.81-3.75 (m, 2H), 3.74-3.68 (m, 2H), 2.72-2.61 (m, 1H), 2.34-2.22 (m, 4H), 2.04-1.92 (m, 2H), 1.92-1.76 (m, 3H), 1.76-1.60 (m, 3H), 1.35 (s, 3H).

Example 465

(7-((4,6-Dimethyl-5-(trifluoromethyl)pyridin-2-yl)oxy)-2-azaspiro[3.5]nonan-2-yl)((1s,3s)-3-hydroxy-3-methylcyclobutyl)methanone

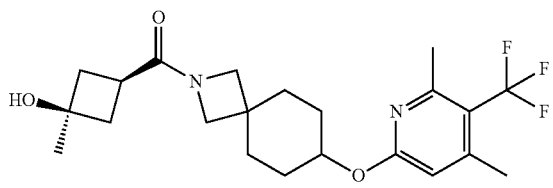 [SMILES: Cc1cc(OC2CCC3(CC2)CN(C(=O)[C@H]2C[C@@](C)(O)C2)C3)nc(C)c1C(F)(F)F]

The title compound was prepared in a manner analogous to Example 430 using 6-bromo-2,4-dimethyl-3-(trifluoromethyl)pyridine (Intermediate 80) instead of 2-bromo-3,5-dimethylpyridine in Step A. MS (ESI): mass calcd. for $C_{22}H_{29}F_3N_2O_3$, 426.2; m/z found, 427.2 [M+H]$^+$. $^1$H NMR (400 MHz, CDCl$_3$) δ 6.42-6.36 (m, 1H), 5.19-5.05 (m, 1H), 3.90 (br s, 1H), 3.81-3.76 (m, 2H), 3.75-3.70 (m, 2H), 2.77-2.64 (m, 1H), 2.63-2.52 (m, 3H), 2.43-2.37 (m, 3H), 2.36-2.21 (m, 4H), 2.00-1.84 (m, 4H), 1.75-1.54 (m, 4H), 1.36 (s, 3H).

Example 466

(7-((3,6-Dimethyl-5-(trifluoromethyl)pyridin-2-yl)oxy)-2-azaspiro[3.5]nonan-2-yl)((1s,3s)-3-hydroxy-3-methylcyclobutyl)methanone

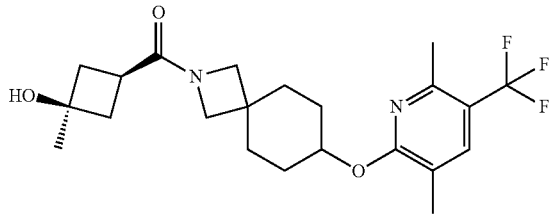 [SMILES: Cc1cc(C(F)(F)F)c(C)nc1OC1CCC2(CC1)CN(C(=O)[C@H]1C[C@@](C)(O)C1)C2]

The title compound was prepared in a manner analogous to Example 430 using 6-bromo-3,6-dimethyl-5-(trifluoromethyl)pyridine (Intermediate 81) instead of 2-bromo-3,5-dimethylpyridine in Step A. MS (ESI): mass calcd. for $C_{22}H_{29}F_3N_2O_3$, 426.2; m/z found, 427.2 [M+H]$^1$. $^1$H NMR (400 MHz, CDCl$_3$) δ 7.53 (s, 1H), 5.26-5.16 (m, 1H), 4.00 (br s, 1H), 3.84-3.71 (m, 4H), 2.75-2.64 (m, 1H), 2.52 (s, 3H), 2.36-2.24 (m, 4H), 2.17-2.13 (m, 3H), 1.99-1.83 (m, 4H), 1.75-1.63 (m, 4H), 1.36 (s, 3H).

Example 467

((1s,3s)-3-Hydroxy-3-methylcyclobutyl)(7-((5-(trifluoromethyl)pyrimidin-2-yl)oxy)-2-azaspiro[3.5]nonan-2-yl)methanone

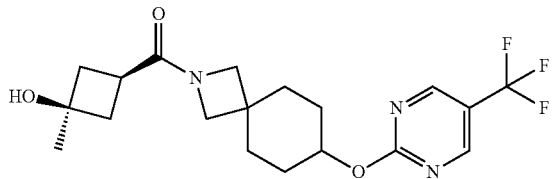

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 2-chloro-5-(trifluoromethyl)pyrimidine instead of 6-chloro-2-methyl-3-(trifluoromethyl)pyridine in Step A. MS (ESI): mass calcd. for $C_{19}H_{24}F_3N_3O_3$, 399.2; m/z found, 400.2 [M+H]⁺. ¹H NMR (400 MHz, CDCl₃) δ 8.76-8.70 (m, 2H), 5.20-5.07 (m, 1H), 3.88 (s, 1H), 3.79 (d, J=3.6 Hz, 2H), 3.73 (d, J=6.3 Hz, 2H), 2.75-2.60 (m, 1H), 2.36-2.22 (m, 4H), 2.05-1.87 (m, 4H), 1.82-1.62 (m, 4H), 1.35 (d, J=2.1 Hz, 3H).

Example 468

(7-((6,7-Dihydro-5H-cyclopenta[b]pyridin-2-yl)oxy)-2-azaspiro[3.5]nonan-2-yl)((1s,3s)-3-hydroxy-3-methylcyclobutyl)methanone

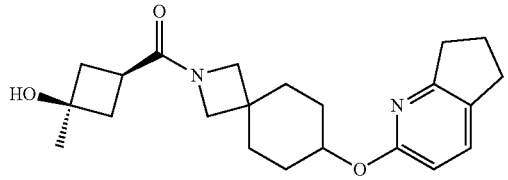 [SMILES: C[C@]1(O)C[C@@H](C(=O)N2CC3(CCC(Oc4ccc5c(n4)CCC5)CC3)C2)C1]

The title compound was prepared in a manner analogous to Example 430 using 2-chloro-6,7-dihydro-5H-cyclopenta[b]pyridine instead of 2-bromo-3,5-dimethylpyridine in Step A. MS (ESI): mass calcd. for $C_{22}H_{30}N_2O_3$, 370.2; m/z found, 371.2 [M+H]⁺. ¹H NMR (400 MHz, CDCl₃) δ 7.38 (d, J=8.0 Hz, 1H), 6.47-6.38 (m, 1H), 5.10-4.97 (m, 1H), 3.96 (br s, 1H), 3.82-3.65 (m, 4H), 2.95-2.76 (m, 4H), 2.75-2.62 (m, 1H), 2.37-2.21 (m, 4H), 2.16-2.04 (m, 2H), 2.00-1.83 (m, 4H), 1.73-1.56 (m, 4H), 1.36 (s, 3H).

Example 469

((1s,3s)-3-Hydroxy-3-methylcyclobutyl)(7-((1-methyl-1H-pyrrolo[2,3-b]pyridin-6-yl)oxy)-2-azaspiro[3.5]nonan-2-yl)methanone

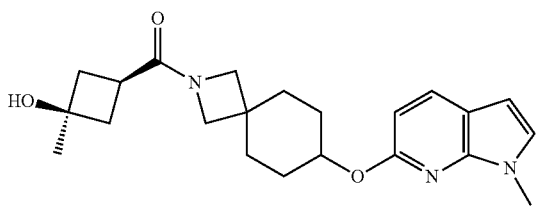 [SMILES: Cn1ccc2ccc(OC3CCC4(CC3)CN(C(=O)[C@H]3C[C@@](C)(O)C3)C4)nc21]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 6-fluoro-1-methyl-1H-pyrrolo[2,3-b]pyridine (Intermediate 78) instead of 6-chloro-2-methyl-3-(trifluoromethyl)pyridine in Step A. MS (ESI): mass calcd. for $C_{22}H_{29}N_3O_3$, 383.2; m/z found, 384.3 [M+H]⁺. ¹H NMR (400 MHz, DMSO-d₆) δ 7.81 (d, J=8.5 Hz, 1H), 7.22 (d, J=3.5 Hz, 1H), 6.46 (d, J=8.5 Hz, 1H), 6.33 (d, J=3.3 Hz, 1H), 5.10-5.02 (m, 1H), 3.77-3.70 (m, 5H), 3.56-3.51 (m, 2H), 2.61-2.53 (m, 1H), 2.14-2.07 (m, 2H), 2.04-1.96 (m, 2H), 1.95-1.82 (m, 4H), 1.67-1.51 (m, 4H), 1.24 (s, 3H).

Example 470

(7-((1,4-Dimethyl-1H-pyrrolo[2,3-b]pyridin-6-yl)oxy)-2-azaspiro[3.5]nonan-2-yl)((1s,3s)-3-hydroxy-3-methylcyclobutyl)methanone

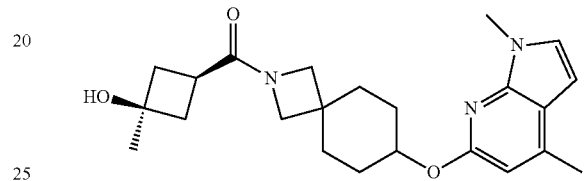

The title compound was prepared in a manner analogous to Example 430 using 6-chloro-1,4-dimethyl-1H-pyrrolo[2,3-b]pyridine (Intermediate 82) instead of 2-bromo-3,5-dimethylpyridine in Step A. MS (ESI): mass calcd. for $C_{23}H_{31}N_3O_3$, 397.2; m/z found, 398.2 [M+H]⁺. ¹H NMR (400 MHz, CDCl₃) δ 6.98-6.88 (m, 1H), 6.41-6.27 (m, 2H), 5.23-5.02 (m, 1H), 3.92 (br s, 1H), 3.85-3.72 (m, 7H), 2.79-2.66 (m, 1H), 2.47 (s, 3H), 2.38-2.22 (m, 4H), 2.03-1.90 (m, 4H), 1.77-1.68 (m, 4H), 1.36 (s, 3H).

Example 471

(7-((1,3-Dimethyl-1H-pyrrolo[2,3-b]pyridin-6-yl)oxy)-2-azaspiro[3.5]nonan-2-yl)((1s,3s)-3-hydroxy-3-methylcyclobutyl)methanone

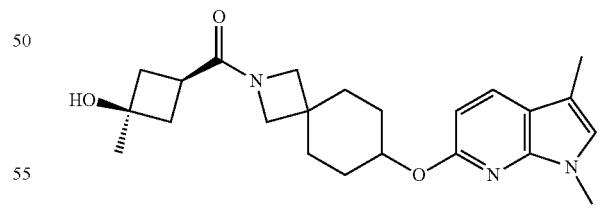

The title compound was prepared in a manner analogous to Example 430 using 6-chloro-1,3-dimethyl-1H-pyrrolo[2,3-b]pyridine (Intermediate 54) instead of 2-bromo-3,5-dimethylpyridine in Step A. MS (ESI): mass calcd. for $C_{23}H_{31}N_3O_3$, 397.2; m/z found, 398.0 [M+H]⁺. ¹H NMR (400 MHz, CDCl₃) δ 7.73 (d, J=8.4 Hz, 1H), 6.73 (s, 1H), 6.47 (d, J=8.4 Hz, 1H), 5.23-5.07 (m, 1H), 3.92-3.60 (m, 8H), 2.80-2.65 (m, 1H), 2.38-2.23 (m, 7H), 2.02-1.92 (m, 4H), 1.78-1.62 (m, 4H), 1.41-1.33 (m, 3H).

Example 472

(7-((1,2-Dimethyl-1H-pyrrolo[2,3-b]pyridin-6-yl)oxy)-2-azaspiro[3.5]nonan-2-yl)((1s,3s)-3-hydroxy-3-methylcyclobutyl)methanone

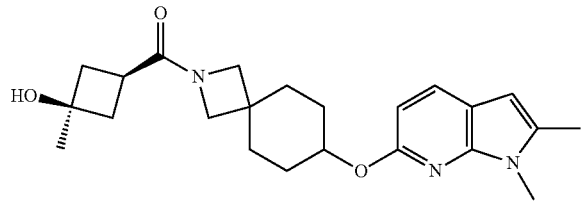 [SMILES: Cc1cc2ccc(OC3CCC4(CC3)CN(C(=O)[C@H]3C[C@@](C)(O)C3)C4)nc2n1C]

The title compound was prepared in a manner analogous to Example 430 using 6-chloro-1,2-dimethyl-1H-pyrrolo[2,3-b]pyridine (Intermediate 53) instead of 2-bromo-3,5-dimethylpyridine in Step A. MS (ESI): mass calcd. for $C_{23}H_{31}N_3O_3$, 397.2; m/z found, 398.2 [M+H]$^+$. $^1$H NMR (400 MHz, CDCl$_3$) δ 7.63 (d, J=8.4 Hz, 1H), 6.45-6.38 (m, 1H), 6.07 (s, 1H), 5.16-5.02 (m, 1H), 3.80-3.75 (m, 2H), 3.74-3.70 (m, 2H), 3.65 (s, 3H), 2.75-2.61 (m, 1H), 2.37 (s, 3H), 2.34-2.22 (m, 4H), 2.01-1.90 (m, 4H), 1.73-1.59 (m, 4H), 1.34 (s, 3H).

Example 473

(7-((1,5-Dimethyl-1H-pyrrolo[2,3-b]pyridin-6-yl)oxy)-2-azaspiro[3.5]nonan-2-yl)((1s,3s)-3-hydroxy-3-methylcyclobutyl)methanone

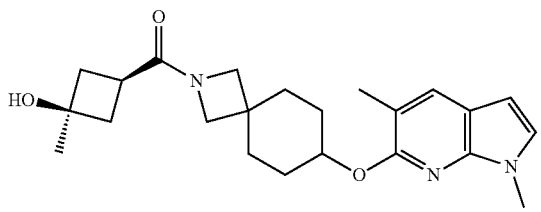 [SMILES: Cc1cc2ccn(C)c2nc1OC1CCC2(CC1)CN(C(=O)[C@H]1C[C@@](C)(O)C1)C2]

The title compound was prepared in a manner analogous to Example 430 using 6-chloro-1,5-dimethyl-1H-pyrrolo[2,3-b]pyridine (Intermediate 83) instead of 2-bromo-3,5-dimethylpyridine in Step A. MS (ESI): mass calcd. for $C_{23}H_{31}N_3O_3$, 397.2; m/z found, 398.3 [M+H]$^+$. $^1$H NMR (400 MHz, CDCl$_3$) δ 7.59 (s, 1H), 6.93-6.89 (m, 1H), 6.29 (d, J=3.2 Hz, 1H), 5.29-5.21 (m, 1H), 3.98 (s, 1H), 3.81 (s, 2H), 3.77-3.70 (m, 5H), 2.76-2.66 (m, 1H), 2.39-2.14 (m, 8H), 2.02-1.87 (m, 4H), 1.85-1.73 (m, 3H), 1.36 (s, 3H).

Example 474

(7-((3-Fluoro-1-methyl-1H-pyrrolo[2,3-b]pyridin-6-yl)oxy)-2-azaspiro[3.5]nonan-2-yl)((1s,3s)-3-hydroxy-3-methylcyclobutyl)methanone

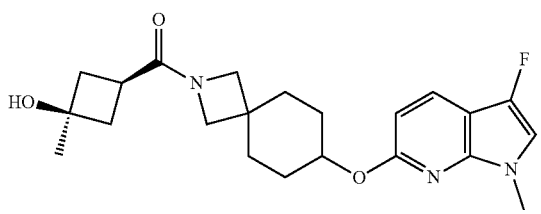 [SMILES: Cn1cc(F)c2ccc(OC3CCC4(CC3)CN(C(=O)[C@H]3C[C@@](C)(O)C3)C4)nc21]

The title compound was prepared in a manner analogous to Example 430 using 6-chloro-3-fluoro-1-methyl-1H-pyrrolo[2,3-b]pyridine (Intermediate 84) instead of 2-bromo-3,5-dimethylpyridine in Step A. MS (ESI): mass calcd. for $C_{22}H_{28}FN_3O_3$, 401.2; m/z found, 402.3 [M+H]$^+$. $^1$H NMR (400 MHz, DMSO-d$_6$) δ 7.86 (d, J=8.5 Hz, 1H), 7.22 (d, J=2.0 Hz, 1H), 6.53 (d, J=8.5 Hz, 1H), 5.10-4.97 (m, 2H), 3.76 (d, J=11.8 Hz, 2H), 3.66 (s, 3H), 3.54 (d, J=9.3 Hz, 2H), 2.62-2.54 (m, 1H), 2.16-1.83 (m, 8H), 1.68-1.51 (m, 4H), 1.24 (s, 3H).

Example 475

(7-((1-Ethyl-3-fluoro-1H-pyrrolo[2,3-b]pyridin-6-yl)oxy)-2-azaspiro[3.5]nonan-2-yl)((1s,3s)-3-hydroxy-3-methylcyclobutyl)methanone

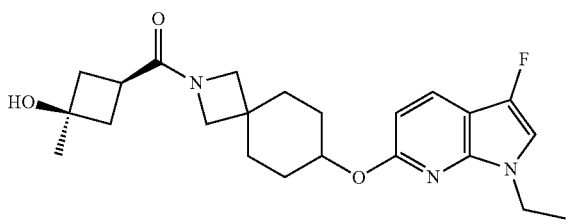 [SMILES: CCn1cc(F)c2ccc(OC3CCC4(CC3)CN(C(=O)[C@H]3C[C@@](C)(O)C3)C4)nc21]

The title compound was prepared in a manner analogous to Example 430 using 6-bromo-1-ethyl-3-fluoro-1H-pyrrolo[2,3-b]pyridine (Intermediate 85) instead of 2-bromo-3,5-dimethylpyridine in Step A. MS (ESI): mass calcd. for $C_{23}H_{30}FN_3O_3$, 415.2; m/z found, 416.0 [M+H]$^+$. $^1$H NMR (400 MHz, CDCl$_3$) δ 7.77 (d, J=8.4 Hz, 1H), 6.74 (d, J=2.0 Hz, 1H), 6.50 (d, J=8.4 Hz, 1H), 5.18-5.04 (m, 1H), 4.16 (q, J=7.2 Hz, 2H), 3.82-3.71 (m, 4H), 3.01 (br s, 1H), 2.77-2.65 (m, 1H), 2.38-2.21 (m, 4H), 2.01-1.87 (m, 4H), 1.77-1.64 (m, 4H), 1.41 (t, J=7.2 Hz, 3H), 1.38-1.33 (m, 3H).

Example 476

((1s,3s)-3-Hydroxy-3-methylcyclobutyl)(7-((1-methyl-3-(trifluoromethyl)-1H-pyrrolo[2,3-b]pyridin-6-yl)oxy)-2-azaspiro[3.5]nonan-2-yl)methanone

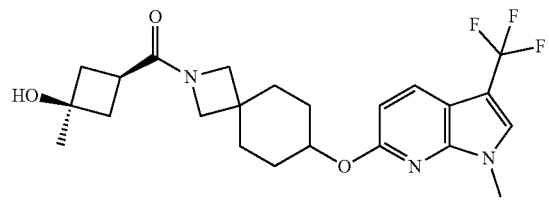 [SMILES: Cn1cc(C(F)(F)F)c2ccc(OC3CCC4(CC3)CN(C(=O)[C@H]3C[C@@](C)(O)C3)C4)nc21]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 6-chloro-1-methyl-3-(trifluoromethyl)-1H-pyrrolo[2,3-b]pyridine (Intermediate 79) instead of 6-chloro-2-methyl-3-(trifluoromethyl)pyridine in Step A. MS (ESI): mass calcd. for $C_{23}H_{28}F_3N_3O_3$, 451.2; m/z found, 452.2 [M+H]$^+$. $^1$H NMR (400 MHz, DMSO-d$_6$) δ 7.96-7.93 (m, 1H), 7.92-7.88 (m, 1H), 6.69-6.65 (m, 1H), 5.13-5.04 (m, 1H), 5.02-4.99 (m, 1H), 3.77 (s, 4H), 3.74 (s, 1H), 3.57-3.49 (m, 2H), 2.60-2.51 (m, 2H), 2.13-2.09 (m, 1H), 2.03-1.83 (m, 6H), 1.68-1.53 (m, 4H), 1.23 (s, 3H).

Example 477

((1s,3s)-3-Hydroxy-3-methylcyclobutyl)(7-((1-methyl-1H-pyrazolo[3,4-b]pyridin-6-yl)oxy)-2-azaspiro[3.5]nonan-2-yl)methanone

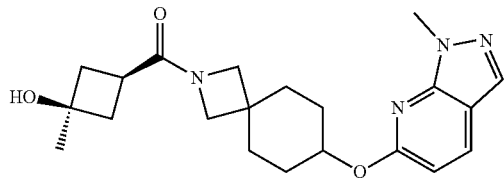 [SMILES: Cn1ncc2ccc(OC3CCC4(CC3)CN(C(=O)[C@H]3C[C@@](C)(O)C3)C4)nc21]

The title compound was prepared in a manner analogous to Example 309 using tert-butyl 7-hydroxy-2-azaspiro[3.5]nonane-2-carboxylate instead of tert-butyl 6-hydroxy-2-azaspiro[3.3]heptane-2-carboxylate and 6-chloro-1-methyl-1H-pyrazolo[3,4-b]pyridine instead of 6-chloro-2-methyl-3-(trifluoromethyl)pyridine in Step A. MS (ESI): mass calcd. for $C_{21}H_{28}N_4O_3$, 384.2; m/z found, 385.2 [M+H]$^+$. $^1$H NMR (400 MHz, CDCl$_3$) δ 7.85-7.79 (m, 2H), 6.51 (dd, J=8.6, 3.1 Hz, 1H), 5.27-5.17 (m, 1H), 4.00 (s, 3H), 3.97 (s, 1H), 3.80 (d, J=3.7 Hz, 2H), 3.74 (d, J=5.5 Hz, 2H), 2.73-2.63 (m, 1H), 2.35-2.23 (m, 4H), 2.03-1.89 (m, 4H), 1.77-1.62 (m, 4H), 1.35 (s, 3H).

Example 478

((1s,3s)-3-Hydroxy-3-methylcyclobutyl)(2-(3-methoxy-5-methylphenyl)-7-azaspiro[3.5]nonan-7-yl)methanone

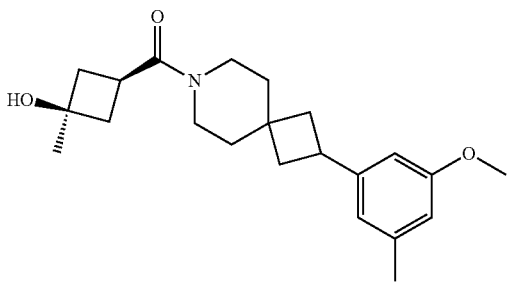 [SMILES: COc1cc(C)cc(C2CC3(CCN(C(=O)[C@H]4C[C@@](C)(O)C4)CC3)C2)c1]

Step A: tert-Butyl 2-(3-bromo-5-methoxyphenyl)-7-azaspiro[3.5]nonane-7-carboxylate. (3-Bromo-5-methoxyphenyl)boronic acid (657 mg, 2.85 mmol), (1R,2R)-2-aminocyclohexanol (26 mg, 0.227 mmol) and nickel(II) iodide (71 mg, 0.228 mmol) in IPA (5 mL) was stirred at rt for 30 min under N$_2$. NaHMDS (1.1 mL, 2 M in THF, 2.28 mmol) was added and the reaction mixture was stirred for 10 min under N$_2$. Finally, tert-butyl 2-iodo-7-azaspiro[3.5]nonane-7-carboxylate (400 mg, 1.14 mmol) in IPA (5 mL) was added to the reaction mixture and the reaction mixture was stirred at 70° C. for 16 h under N$_2$. After cooling to rt, the reaction mixture was triturated with sat. aq. NH$_4$Cl and extracted with DCM. The combined organic extracts were washed with brine, dried over Na$_2$SO$_4$, filtered, and concentrated under reduced pressure. The resulting residue was purified by RP HPLC (70-100% CH$_3$CN in H$_2$O with 0.05% NH$_3$) to afford the title compound (130 mg, 28% yield) as a yellow solid. MS (ESI): mass calcd. for $C_{20}H_{28}BrNO_3$, 409.1; m/z found, 353.9 [M+2H-tBu]$^+$.

Step B: tert-Butyl 2-(3-methoxy-5-methylphenyl)-7-azaspiro[3.5]nonane-7-carboxylate. tert-Butyl 2-(3-bromo-5-methoxyphenyl)-7-azaspiro[3.5]nonane-7-carboxylate (110 mg, 0.268 mmol), 2,4,6-trimethyl-1,3,5,2,4,6-trioxatriborinane (50 mg, 0.402 mmol) and K$_2$CO$_3$ (111 mg, 0.803 mmol) were taken up in 1,4-dioxane (3 mL) and H$_2$O (0.5 mL). The mixture was sparged with Ar for 5 min, then treated with Pd(dppf)Cl$_2$·CH$_2$Cl$_2$ (22 mg, 0.027 mmol). The mixture was sparged with Ar for another 5 min, then stirred at 90° C. for 1 h before cooling to rt. The reaction mixture was filtered through a pad of Celite® and the pad was washed with EtOAc. The filtrate was concentrated under reduced pressure. The resulting residue was purified by FCC (SiO$_2$, 0-50% EtOAc in ether) to afford the title compound (90 mg, 75% yield) as a white oil. MS (ESI): mass calcd. for $C_{21}H_{31}NO_3$, 345.2; m/z found, 290.4 [M+2H-tBu]$^+$.

Step C: 2-(3-Methoxy-5-methylphenyl)-7-azaspiro[3.5] nonane. TFA (0.15 mL, 2.00 mmol) was added to a solution of tert-butyl 2-(3-methoxy-5-methylphenyl)-7-azaspiro[3.5] nonane-7-carboxylate (90 mg, 0.260 mmol) in DCM (2 mL). The reaction mixture was stirred at rt for 1 hour before being concentrated under reduced pressure to give the title compound (100 mg, crude), which was used in the next step without further purification. MS (ESI): mass calcd. for $C_{16}H_{23}NO$, 245.2; m/z found, 246.0 [M+H]$^+$.

Step D: ((1s,3s)-3-Hydroxy-3-methylcyclobutyl)(2-(3-methoxy-5-methylphenyl)-7-azaspiro[3.5]nonan-7-yl) methanone. T$_3$P® (0.17 mL, 50% in EtOAc, 0.570 mmol) was added to solution of 2-(3-methoxy-5-methylphenyl)-7-azaspiro[3.5]nonane (100 mg, 0.278 mmol), (1s,3s)-3-hydroxy-3-methylcyclobutanecarboxylic acid (36 mg, 0.277 mmol) and TEA (0.39 mL, 2.80 mmol) in DCM (4 mL). The resultant mixture was stirred at rt for 30 min before being poured into H$_2$O and extracted with DCM. The combined organic extracts were dried over Na$_2$SO$_4$, filtered, and concentrated under reduced pressure. The resulting residue was purified by RP HPLC (40-70% CH$_3$CN in H$_2$O with 0.05% NH$_3$) to afford the title compound (32 mg, 32% yield). MS (ESI): mass calcd. for $C_{22}H_{31}NO_3$, 357.2; m/z found, 358.2 [M+H]$^+$. $^1$H NMR (400 MHz, DMSO-d$_6$) δ 6.63-6.60 (m, 1H), 6.56-6.53 (m, 2H), 4.97-4.90 (m, 1H), 3.71 (s, 3H), 3.49-3.38 (m, 2H), 3.33-3.30 (m, 2H), 3.24-3.16 (m, 1H), 2.89-2.73 (m, 1H), 2.27-2.24 (m, 3H), 2.23-2.17 (m, 2H), 2.16-2.09 (m, 2H), 2.08-1.99 (m, 2H), 1.85-1.77 (m, 2H), 1.65-1.56 (m, 2H), 1.47-1.37 (m, 2H), 1.30-1.22 (m, 3H).

Example 479

((1s,3s)-3-Hydroxy-3-methylcyclobutyl)(2-(2-methyl-4-(trifluoromethyl)phenoxy)-7-azaspiro[3.5] nonan-7-yl)methanone

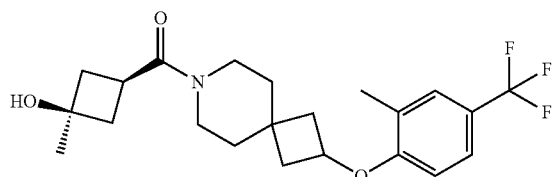

Step A: tert-Butyl 2-(2-bromo-4-(trifluoromethyl)phenoxy)-7-azaspiro[3.5]nonane-7-carboxylate. tert-Butyl 2-iodo-7-azaspiro[3.5]nonane-7-carboxylate (400 mg, 1.14 mmol), 2-bromo-4-(trifluoromethyl)phenol (250 mg, 1.04 mmol) and $Cs_2CO_3$ (676 mg, 2.08 mmol) were dissolved in MeCN (10 mL). The reaction mixture was stirred at 90° C. for 16 h before being cooled to rt. The reaction mixture was concentrated under reduced pressure. The resulting residue was purified by FCC ($SiO_2$, 0-50% EtOAc in ether) to afford the title compound (400 mg, 83% yield) as a white oil. MS (ESI): mass calcd. for $C_{20}H_{25}BrF_3NO_3$, 463.1; m/z found, 407.8 [M+2H-tBu]$^+$.

Step B: tert-Butyl 2-(2-methyl-4-(trifluoromethyl)phenoxy)-7-azaspiro[3.5]nonane-7-carboxylate. tert-Butyl 2-(2-bromo-4-(trifluoromethyl)phenoxy)-7-azaspiro[3.5]nonane-7-carboxylate (400 mg, 0.861 mmol), 2,4,6-trimethyl-1,3,5,2,4,6-trioxatriborinane (162 mg, 1.29 mmol) and $K_2CO_3$ (357 mg, 2.58 mmol) were taken up in 1,4-dioxane (5 mL) and $H_2O$ (1 mL). The reaction mixture was sparged with Ar for 5 min, then treated with $Pd(dppf)Cl_2 \cdot CH_2Cl_2$ (70 mg, 0.086 mmol). The reaction mixture was sparged with Ar for another 5 min, then stirred at 90° C. for 16 h before being cooled to rt. The reaction mixture was filtered through a pad of Celite® and the pad was washed with EtOAc. The filtrate was concentrated under reduced pressure. The resulting residue was purified by FCC ($SiO_2$, 0-50% EtOAc in ether) to afford the title compound (330 mg, 87% yield) as a yellow oil. MS (ESI): mass calcd. for $C_{21}H_{28}F_3NO_3$, 399.2; m/z found, 344.0 [M+2H-tBu]$^+$.

Step C: 2-(2-Methyl-4-(trifluoromethyl)phenoxy)-7-azaspiro[3.5]nonane. TFA (0.6 mL, 7.84 mmol) was added to a solution of tert-butyl 2-(2-methyl-4-(trifluoromethyl)phenoxy)-7-azaspiro[3.5]nonane-7-carboxylate (330 mg, 0.826 mmol) in DCM (6 mL). The reaction mixture was stirred at rt for 1 hour before being concentrated under reduced pressure to give the title compound (330 mg), which was used in the next step without further purification. MS (ESI): mass calcd. for $C_{16}H_{20}F_3NO$, 299.1; m/z found, 300.7 [M+H]$^+$.

Step D: ((1s,3s)-3-Hydroxy-3-methylcyclobutyl)(2-(2-methyl-4-(trifluoromethyl)phenoxy)-7-azaspiro[3.5]nonan-7-yl)methanone. $T_3P$® (0.70 mL, 50% in EtOAc, 1.20 mmol) was added to solution of 2-(2-methyl-4-(trifluoromethyl)phenoxy)-7-azaspiro[3.5]nonane (330 mg, 0.798 mmol), (1s,3s)-3-hydroxy-3-methylcyclobutanecarboxylic acid (208 mg, 1.60 mmol) and TEA (1.1 mL, 7.90 mmol) in DCM (5 mL). The resultant mixture was stirred at rt for 2 h before being poured into $H_2O$ and extracted with DCM. The combined organic extracts were dried over $Na_2SO_4$, filtered, and concentrated under reduced pressure. The resulting residue was purified by RP HPLC (60-90% $CH_3CN$ in $H_2O$ with 0.05% $NH_3$) to afford the title compound (151 mg, 46% yield) as a white solid. MS (ESI): mass calcd. for $C_{22}H_{28}F_3NO_3$, 411.2; m/z found, 412.2 [M+H]$^+$. $^1$H NMR (400 MHz, DMSO-d$_6$) δ 7.53-7.43 (m, 2H), 6.95-6.88 (m, 1H), 4.97-4.81 (m, 2H), 3.44-3.39 (m, 1H), 3.33-3.19 (m, 3H), 2.87-2.75 (m, 1H), 2.49-2.42 (m, 2H), 2.21 (s, 3H), 2.17-2.08 (m, 2H), 2.07-1.97 (m, 2H), 1.87-1.77 (m, 2H), 1.59-1.41 (m, 4H), 1.29-1.23 (m, 3H).

Example 480

((1s,3s)-3-Hydroxy-3-methylcyclobutyl)(2-(3-methyl-4-(trifluoromethyl)phenoxy)-7-azaspiro[3.5]nonan-7-yl)methanone

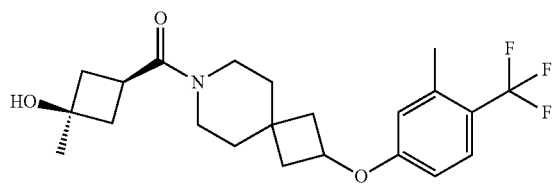 [SMILES: Cc1cc(OC2CC3(CCN(C(=O)[C@H]4C[C@@](C)(O)C4)CC3)C2)ccc1C(F)(F)F]

The title compound was prepared in a manner analogous to Example 479 using 3-bromo-4-(trifluoromethyl)phenol instead of 2-bromo-4-(trifluoromethyl)phenol in Step A. MS (ESI): mass calcd. for $C_{22}H_{28}F_3NO_3$, 411.2; m/z found, 412.1 [M+H]$^+$. $^1$H NMR (400 MHz, DMSO-d$_6$) δ 7.51 (d, J=8.8 Hz, 1H), 6.86 (s, 1H), 6.81-6.73 (m, 1H), 4.94-4.87 (m, 1H), 4.85-4.74 (m, 1H), 3.43-3.36 (m, 1H), 3.34-3.31 (m, 1H), 3.28 (s, 1H), 3.22-3.14 (m, 1H), 2.86-2.70 (m, 1H), 2.45-2.38 (m, 2H), 2.36 (s, 3H), 2.16-2.06 (m, 2H), 2.05-1.93 (m, 2H), 1.83-1.72 (m, 2H), 1.56-1.37 (m, 4H), 1.23 (d, J=6.4 Hz, 3H).

Example 481

((1s,3s)-3-Hydroxy-3-methylcyclobutyl)(2-((3-methyl-5-(trifluoromethyl)pyridin-2-yl)oxy)-7-azaspiro[3.5]nonan-7-yl)methanone

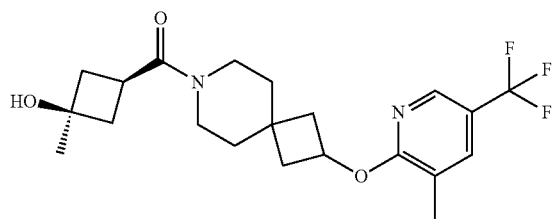 [SMILES: Cc1cc(C(F)(F)F)cnc1OC1CC2(CCN(C(=O)[C@H]3C[C@@](C)(O)C3)CC2)C1]

The title compound was prepared in a manner analogous to Example 479 using tert-butyl 2-hydroxy-7-azaspiro[3.5]nonane-7-carboxylate instead of tert-butyl 2-iodo-7-azaspiro[3.5]nonane-7-carboxylate and 3-bromo-2-chloro-5-(trifluoromethyl)pyridine instead of 2-bromo-4-(trifluoromethyl)phenol in Step A. MS (ESI): mass calcd. for $C_{21}H_{27}F_3N_2O_3$, 412.2; m/z found, 413.2 [M+H]$^+$. $^1$H NMR (400 MHz, CDCl$_3$) δ 8.24 (s, 1H), 7.58 (s, 1H), 5.34-5.24 (m, 1H), 3.66-3.46 (m, 2H), 3.42-3.24 (m, 2H), 2.96-2.83 (m, 1H), 2.55-2.44 (m, 2H), 2.39-2.28 (m, 4H), 2.24 (s, 3H), 2.02 (s, 1H), 2.01-1.89 (m, 2H), 1.68-1.59 (m, 4H), 1.39 (s, 3H).

Example 482

((1s,3s)-3-Hydroxy-3-methylcyclobutyl)(2-((6-methyl-5-(trifluoromethyl)pyridin-2-yl)oxy)-7-azaspiro[3.5]nonan-7-yl)methanone

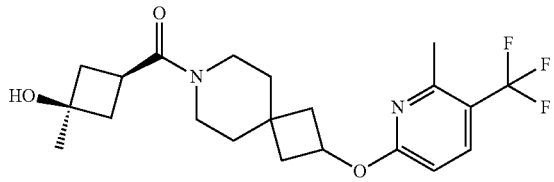 [SMILES: Cc1nc(OC2CC3(CCN(C(=O)[C@H]4C[C@@](C)(O)C4)CC3)C2)ccc1C(F)(F)F]

The title compound was prepared in a manner analogous to Example 309 using tert-butyl 2-hydroxy-7-azaspiro[3.5]nonane-7-carboxylate instead of tert-butyl 6-hydroxy-2-azaspiro[3.3]heptane-2-carboxylate in Step A. MS (ESI): mass calcd. for $C_{21}H_{27}F_3N_2O_3$, 412.2; m/z found, 413.2 [M+H]$^+$. $^1$H NMR (400 MHz, CDCl$_3$) δ 7.78-7.72 (m, 1H), 6.59-6.53 (m, 1H), 5.27-5.20 (m, 1H), 3.65-3.23 (m, 4H), 2.96-2.84 (m, 1H), 2.58 (s, 3H), 2.53-2.43 (m, 2H), 2.37-2.28 (m, 4H), 2.04-1.90 (m, 3H), 1.70-1.58 (m, 4H), 1.40 (s, 3H).

Biological Data

The assay used to measure the in vitro activity of MGL is adapted from the assay used for another serine hydrolase (FAAH) described in Wilson et al., 2003 (A high-throughput-compatible assay for determining the activity of fatty acid amide hydrolase. Wilson S J, Lovenberg T W, Barbier A J. Anal Biochem. 2003 Jul. 15; 318(2):270-5). The assay consists of combining endogenously expressed MGL from HeLa cells with test compounds, adding [glycerol-1,3-$^3$H]-oleyl glycerol, incubating for one hour, and then measuring the amount of cleaved [1,3-$^3$H]-glycerol that passes through an activated carbon filter. The amount of cleaved, tritiated glycerol passing through the carbon filter is proportional to the activity of the MGL enzyme in a particular well/test condition.

Standard conditions for this assay combine 300 nM [Glycerol-1,3-$^3$H]-oleoyl glycerol with human MGL from HeLa cells and test compounds for one hour, after which the reaction is filtered through activated carbon and tritium is measured in the flow through. The test compound concentration in screening mode is 10 μM, while the highest compound concentration in IC$_{50}$ assays is determined empirically. MGL is the predominant hydrolase in HeLa cells/cell homogenates.

TABLE 3

| Ex # | Compound Name | MGL IC$_{50}$ (nM) |
|---|---|---|
| 1 | (6-(3-(tert-Butyl)phenyl)-2-azaspiro[3.3]heptan-2-yl)((1s,3s)-3-hydroxy-3-methylcyclobutyl)methanone; | 9.9 |
| 2 | (6-(4-(tert-Butyl)phenyl)-2-azaspiro[3.3]heptan-2-yl)((1s,3s)-3-hydroxy-3-methylcyclobutyl)methanone; | 149 |
| 3 | ((1s,3s)-3-Hydroxy-3-methylcyclobutyl)(6-(3-isopropylphenyl)-2-azaspiro[3.3]heptan-2-yl)methanone; | 24 |
| 4 | ((1s,3s)-3-Hydroxy-3-methylcyclobutyl)(6-(4-isopropylphenyl)-2-azaspiro[3.3]heptan-2-yl)methanone; | 128 |
| 5 | (6-(4-Cyclopropylphenyl)-2-azaspiro[3.3]heptan-2-yl)((1s,3s)-3-hydroxy-3-methylcyclobutyl)methanone; | 292 |
| 6 | ((1s,3s)-3-Hydroxy-3-methylcyclobutyl)(6-(4-methyl-3-(trifluoromethyl)phenyl)-2-azaspiro[3.3]heptan-2-yl)methanone; | 31 |
| 7 | (rac)-((1s,3s)-3-Hydroxy-3-methylcyclobutyl)(6-(2-methyl-3-(trifluoromethyl)phenyl)-2-azaspiro[3.4]octan-2-yl)methanone; | 10 |
| 8 | (rac)-((1s,3s)-3-Hydroxy-3-methylcyclobutyl)(6-(2-methyl-4-(trifluoromethyl)phenyl)-2-azaspiro[3.4]octan-2-yl)methanone; | 5.0 |
| 9 | (rac)-((1s,3s)-3-Hydroxy-3-methylcyclobutyl)(6-(2-methyl-4-(trifluoromethoxy)phenyl)-2-azaspiro[3.4]octan-2-yl)methanone;methanone; | 3.4 |
| 10 | (rac)-(6-(4-Chloro-2-methylphenyl)-2-azaspiro[3.4]octan-2-yl)((1s,3s)-3-hydroxy-3-methylcyclobutyl)methanone; | 22 |
| 11 | (rac)-(6-(3-Chloro-2-methylphenyl)-2-azaspiro[3.4]octan-2-yl)((1s,3s)-3-hydroxy-3-methylcyclobutyl)methanone; | 37 |
| 12 | (rac)-(6-(4-(Difluoromethyl)-3-methylphenyl)-2-azaspiro[3.4]octan-2-yl)((1s,3s)-3-hydroxy-3-methylcyclobutyl)methanone; | 25 |
| 13 | (rac)-((1s,3s)-3-Hydroxy-3-methylcyclobutyl)(6-(3-methoxy-2-methylphenyl)-2-azaspiro[3.4]octan-2-yl)methanone; | 159 |
| 14 | (rac)-(6-(2,4-Dimethylphenyl)-2-azaspiro[3.4]octan-2-yl)((1s,3s)-3-hydroxy-3-methylcyclobutyl)methanone; | 26 |
| 15 | (rac)-(6-(4-Chloro-3-ethylphenyl)-2-azaspiro[3.4]octan-2-yl)((1s,3s)-3-hydroxy-3-methylcyclobutyl)methanone; | 6.0 |
| 16 | (rac)-(6-(2,3-Dihydro-1H-inden-5-yl)-2-azaspiro[3.4]octan-2-yl)((1s,3s)-3-hydroxy-3-methylcyclobutyl)methanone; | 10 |
| 17 | (rac)-((1s,3s)-3-Hydroxy-3-methylcyclobutyl)(6-(3-methoxy-4-methylphenyl)-2-azaspiro[3.4]octan-2-yl)methanone; | 46 |
| 18 | ((1s,3*S)-3-Hydroxy-3-methylcyclobutyl)((*R)-6-(3-methoxy-4-methylphenyl)-2-azaspiro[3.4]octan-2-yl)methanone; | 64 |
| 19 | ((1s,3*R)-3-Hydroxy-3-methylcyclobutyl)((*S)-6-(3-methoxy-4-methylphenyl)-2-azaspiro[3.4]octan-2-yl)methanone; | 67 |
| 20 | (6-(3-Cyclopropylphenyl)-2-azaspiro[3.3]heptan-2-yl)((1s,3s)-3-hydroxy-3-methylcyclobutyl)methanone; | 37 |
| 21 | ((1s,3s)-3-Hydroxy-3-methylcyclobutyl)(6-(2-methyl-3-(trifluoromethyl)phenyl)-2-azaspiro[3.3]heptan-2-yl)methanone; | 112 |

TABLE 3-continued

| Ex # | Compound Name | MGL IC$_{50}$ (nM) |
|---|---|---|
| 22 | (7-(3-Chloro-4-methylphenyl)-2-azaspiro[3.5]nonan-2-yl)((1s,3s)-3-hydroxy-3-methylcyclobutyl)methanone; | 12 |
| 23 | ((1s,3s)-3-Hydroxy-3-methylcyclobutyl)(6-(4-methyl-3-(trifluoromethoxy)phenyl)-2-azaspiro[3.3]heptan-2-yl)methanone; | 45 |
| 24 | (rac)-(6-(3-Cyclopropyl-2-fluorophenyl)-2-azaspiro[3.4]octan-2-yl)((1s,3s)-3-hydroxy-3-methylcyclobutyl)methanone; | 11 |
| 25 | ((*R)-6-(3-Cyclopropyl-2-fluorophenyl)-2-azaspiro[3.4]octan-2-yl)((1s,3*S)-3-hydroxy-3-methylcyclobutyl)methanone; | 4.0 |
| 26 | ((*S)-6-(3-Cyclopropyl-2-fluorophenyl)-2-azaspiro[3.4]octan-2-yl)((1s,3*R)-3-hydroxy-3-methylcyclobutyl)methanone; | 28 |
| 27 | (6-(3-Cyclopropyl-4-methylphenyl)-2-azaspiro[3.3]heptan-2-yl)((1s,3s)-3-hydroxy-3-methylcyclobutyl)methanone; | 47 |
| 28 | (6-(4-Cyclopropyl-2-methylphenyl)-2-azaspiro[3.3]heptan-2-yl)((1s,3s)-3-hydroxy-3-methylcyclobutyl)methanone; | 125 |
| 29 | (rac)-(6-(6-(tert-Butyl)pyridin-2-yl)-2-azaspiro[3.4]octan-2-yl)((1s,3s)-3-hydroxy-3-methylcyclobutyl)methanone; | 7.7 |
| 30 | ((1s,3s)-3-Hydroxy-3-methylcyclobutyl)(6-(isoquinolin-7-yl)-2-azaspiro[3.3]heptan-2-yl)methanone; | 1176 |
| 31 | ((1s,3s)-3-Hydroxy-3-methylcyclobutyl)(6-(isoquinolin-6-yl)-2-azaspiro[3.3]heptan-2-yl)methanone; | 1598 |
| 32 | ((1s,3s)-3-Hydroxy-3-methylcyclobutyl)(6-(3-(pyrrolidin-1-yl)phenyl)-2-azaspiro[3.3]heptan-2-yl)methanone; | 178 |
| 33 | ((1s,3s)-3-Hydroxy-3-methylcyclobutyl)(6-(3-methyl-4-(trifluoromethyl)phenyl)-2-azaspiro[3.3]heptan-2-yl)methanone; | 246 |
| 34 | (6-(6-(tert-Butyl)pyridin-2-yl)-2-azaspiro[3.3]heptan-2-yl)((1s,3s)-3-hydroxy-3-methylcyclobutyl)methanone; | 25 |
| 35 | (rac)-((1s,3s)-3-Hydroxy-3-methylcyclobutyl)(6-(4-isopropylphenyl)-2-azaspiro[3.4]octan-2-yl)methanone; | 15 |
| 36 | ((1s,3s)-3-Hydroxy-3-methylcyclobutyl)(2-(3-isopropylphenyl)-6-azaspiro[3.4]octan-6-yl)methanone; | 153 |
| 37 | ((1s,3s)-3-Hydroxy-3-methylcyclobutyl)(7-phenyl-2-azaspiro[3.5]nonan-2-yl)methanone; | 58 |
| 38 | (rac)-(2-(3-(tert-Butyl)phenyl)-8-azaspiro[4.5]decan-8-yl)((1s,3s)-3-hydroxy-3-methylcyclobutyl)methanone; | 20 |
| 39 | (rac)-(2-(4-(tert-Butyl)phenyl)-8-azaspiro[4.5]decan-8-yl)((1s,3s)-3-hydroxy-3-methylcyclobutyl)methanone; | 18 |
| 40 | (rac)-((1s,3s)-3-Hydroxy-3-methylcyclobutyl)(6-(3-(trifluoromethoxy)phenyl)-2-azaspiro[3.4]octan-2-yl)methanone; | 23 |
| 41 | ((1s,3*S)-3-Hydroxy-3-methylcyclobutyl)((*R)-6-(3-(trifluoromethoxy)phenyl)-2-azaspiro[3.4]octan-2-yl)methanone; | 23 |
| 42 | ((1s,3*R)-3-Hydroxy-3-methylcyclobutyl)((*S)-6-(3-(trifluoromethoxy)phenyl)-2-azaspiro[3.4]octan-2-yl)methanone; | 22 |
| 43 | (rac)-(6-(3-(tert-Butyl)phenyl)-2-azaspiro[3.4]octan-2-yl)((1s,3s)-3-hydroxy-3-methylcyclobutyl)methanone; | 6.9 |
| 44 | ((*R)-6-(3-(tert-Butyl)phenyl)-2-azaspiro[3.4]octan-2-yl)((1s,3*S)-3-hydroxy-3-methylcyclobutyl)methanone; | 9.8 |
| 45 | ((*S)-6-(3-(tert-Butyl)phenyl)-2-azaspiro[3.4]octan-2-yl)((1s,3*R)-3-hydroxy-3-methylcyclobutyl)methanone; | 11 |
| 46 | (rac)-((1s,3s)-3-Hydroxy-3-methylcyclobutyl)(6-(3-isopropylphenyl)-2-azaspiro[3.4]octan-2-yl)methanone; | 13 |
| 47 | ((1s,3*S)-3-Hydroxy-3-methylcyclobutyl)((*R)-6-(3-isopropylphenyl)-2-azaspiro[3.4]octan-2-yl)methanone; | 21 |
| 48 | ((1s,3*R)-3-Hydroxy-3-methylcyclobutyl)((*S)-6-(3-isopropylphenyl)-2-azaspiro[3.4]octan-2-yl)methanone; | 17 |
| 49 | (rac)-(6-(4-Cyclopropylphenyl)-2-azaspiro[3.4]octan-2-yl)((1s,3s)-3-hydroxy-3-methylcyclobutyl)methanone; | 14 |
| 50 | ((*R)-6-(4-Cyclopropylphenyl)-2-azaspiro[3.4]octan-2-yl)((1s,3*S)-3-hydroxy-3-methylcyclobutyl)methanone; | 9.7 |
| 51 | ((*S)-6-(4-Cyclopropylphenyl)-2-azaspiro[3.4]octan-2-yl)((1s,3*R)-3-hydroxy-3-methylcyclobutyl)methanone; | 5.5 |
| 52 | (rac)-((1s,3s)-3-Hydroxy-3-methylcyclobutyl)(6-(4-(trifluoromethoxy)phenyl)-2-azaspiro[3.4]octan-2-yl)methanone; | 16 |
| 53 | ((1s,3*S)-3-Hydroxy-3-methylcyclobutyl)((*R)-6-(4-(trifluoromethoxy)phenyl)-2-azaspiro[3.4]octan-2-yl)methanone; | 10 |
| 54 | ((1s,3*R)-3-Hydroxy-3-methylcyclobutyl)((*S)-6-(4-(trifluoromethoxy)phenyl)-2-azaspiro[3.4]octan-2-yl)methanone; | 10 |
| 55 | (rac)-((1s,3s)-3-Hydroxy-3-methylcyclobutyl)(6-(4-(trifluoromethyl)phenyl)-2-azaspiro[3.4]octan-2-yl)methanone; | 22 |
| 56 | ((1s,3*S)-3-Hydroxy-3-methylcyclobutyl)((*R)-6-(4-(trifluoromethyl)phenyl)-2-azaspiro[3.4]octan-2-yl)methanone; | 22 |
| 57 | ((1s,3*R)-3-Hydroxy-3-methylcyclobutyl)((*S)-6-(4-(trifluoromethyl)phenyl)-2-azaspiro[3.4]octan-2-yl)methanone; | 24 |
| 58 | (rac)-(6-(3-Cyclopropylphenyl)-2-azaspiro[3.4]octan-2-yl)((1s,3s)-3-hydroxy-3-methylcyclobutyl)methanone; | 41 |
| 59 | ((*R)-6-(3-Cyclopropylphenyl)-2-azaspiro[3.4]octan-2-yl)((1s,3*S)-3-hydroxy-3-methylcyclobutyl)methanone; | 37 |

TABLE 3-continued

| Ex # | Compound Name | MGL IC$_{50}$ (nM) |
|---|---|---|
| 60 | ((*S)-6-(3-Cyclopropylphenyl)-2-azaspiro[3.4]octan-2-yl)((1s,3*R)-3-hydroxy-3-methylcyclobutyl)methanone; | 25 |
| 61 | (rac)-((1s,3s)-3-Hydroxy-3-methylcyclobutyl)(6-(3-(trifluoromethyl)phenyl)-2-azaspiro[3.4]octan-2-yl)methanone; | 29 |
| 62 | ((1s,3*S)-3-Hydroxy-3-methylcyclobutyl)((*R)-6-(3-(trifluoromethyl)phenyl)-2-azaspiro[3.4]octan-2-yl)methanone; | 34 |
| 63 | ((1s,3*R)-3-Hydroxy-3-methylcyclobutyl)((*S)-6-(3-(trifluoromethyl)phenyl)-2-azaspiro[3.4]octan-2-yl)methanone; | 22 |
| 64 | (rac)-(6-(3-Cyclobutylphenyl)-2-azaspiro[3.4]octan-2-yl)((1s,3s)-3-hydroxy-3-methylcyclobutyl)methanone; | 14 |
| 65 | (rac)-((1s,3s)-3-Hydroxy-3-methylcyclobutyl)(6-(4-methyl-3-(trifluoromethyl)phenyl)-2-azaspiro[3.4]octan-2-yl)methanone; | 11 |
| 66 | (rac)-((1s,3s)-3-Hydroxy-3-methylcyclobutyl)(6-(3-methyl-4-(trifluoromethoxy)phenyl)-2-azaspiro[3.4]octan-2-yl)methanone; | 0.5 |
| 67 | (rac)-((1s,3s)-3-Hydroxy-3-methylcyclobutyl)(6-(3-methyl-4-(trifluoromethyl)phenyl)-2-azaspiro[3.4]octan-2-yl)methanone; | 1.7 |
| 68 | (rac)-(6-(4-Chloro-3-methylphenyl)-2-azaspiro[3.4]octan-2-yl)((1s,3s)-3-hydroxy-3-methylcyclobutyl)methanone; | 12 |
| 69 | ((*R)-6-(4-Chloro-3-methylphenyl)-2-azaspiro[3.4]octan-2-yl)((1s,3*S)-3-hydroxy-3-methylcyclobutyl)methanone; | 15 |
| 70 | ((*S)-6-(4-Chloro-3-methylphenyl)-2-azaspiro[3.4]octan-2-yl)((1s,3*R)-3-hydroxy-3-methylcyclobutyl)methanone; | 17 |
| 71 | (rac)-(6-(3-Chloro-4-methylphenyl)-2-azaspiro[3.4]octan-2-yl)((1s,3s)-3-hydroxy-3-methylcyclobutyl)methanone; | 15 |
| 72 | (rac)-(6-(4-(Difluoromethoxy)-3-methylphenyl)-2-azaspiro[3.4]octan-2-yl)((1s,3s)-3-hydroxy-3-methylcyclobutyl)methanone; | 4.6 |
| 73 | ((*R)-6-(4-(Difluoromethoxy)-3-methylphenyl)-2-azaspiro[3.4]octan-2-yl)((1s,3*S)-3-hydroxy-3-methylcyclobutyl)methanone; | 8.1 |
| 74 | ((*S)-6-(4-(Difluoromethoxy)-3-methylphenyl)-2-azaspiro[3.4]octan-2-yl)((1s,3*R)-3-hydroxy-3-methylcyclobutyl)methanone; | 6.8 |
| 75 | (rac)-(6-(4-Cyclopropyl-2-methylphenyl)-2-azaspiro[3.4]octan-2-yl)((1s,3s)-3-hydroxy-3-methylcyclobutyl)methanone; | 2.4 |
| 76 | (rac)-((1s,3s)-3-Hydroxy-3-methylcyclobutyl)(6-(4-methoxy-3-methylphenyl)-2-azaspiro[3.4]octan-2-yl)methanone; | 51 |
| 77 | (rac)-((1s,3s)-3-Hydroxy-3-methylcyclobutyl)(6-(3-methyl-5-(trifluoromethyl)phenyl)-2-azaspiro[3.4]octan-2-yl)methanone; | 12 |
| 78 | (rac)-((1s,3s)-3-Hydroxy-3-methylcyclobutyl)(6-(2-methyl-5-(trifluoromethyl)phenyl)-2-azaspiro[3.4]octan-2-yl)methanone; | 11 |
| 79 | (rac)-(6-(2-Fluoro-3-methoxyphenyl)-2-azaspiro[3.4]octan-2-yl)((1s,3s)-3-hydroxy-3-methylcyclobutyl)methanone; | 242 |
| 80 | (rac)-((1s,3s)-3-Hydroxy-3-methylcyclobutyl)(6-(3-methoxy-5-methylphenyl)-2-azaspiro[3.4]octan-2-yl)methanone; | 104 |
| 81 | (rac)-(6-(5-Cyclopropyl-2-fluorophenyl)-2-azaspiro[3.4]octan-2-yl)((1s,3s)-3-hydroxy-3-methylcyclobutyl)methanone; | 20 |
| 82 | (rac)-(6-(3-(Difluoromethoxy)-4-methylphenyl)-2-azaspiro[3.4]octan-2-yl)((1s,3s)-3-hydroxy-3-methylcyclobutyl)methanone; | 31 |
| 83 | (rac)-(6-(4-(Difluoromethoxy)-2-methylphenyl)-2-azaspiro[3.4]octan-2-yl)((1s,3s)-3-hydroxy-3-methylcyclobutyl)methanone; | 25 |
| 84 | (rac)-(6-(3-(Difluoromethoxy)-5-methylphenyl)-2-azaspiro[3.4]octan-2-yl)((1s,3s)-3-hydroxy-3-methylcyclobutyl)methanone; | 47 |
| 85 | (rac)-(6-(5-(Difluoromethoxy)-2-methylphenyl)-2-azaspiro[3.4]octan-2-yl)((1s,3s)-3-hydroxy-3-methylcyclobutyl)methanone; | 42 |
| 86 | (rac)-(6-(3-Chloro-5-methoxyphenyl)-2-azaspiro[3.4]octan-2-yl)((1s,3s)-3-hydroxy-3-methylcyclobutyl)methanone; | 42 |
| 87 | (rac)-(6-(4-Chloro-3-methoxyphenyl)-2-azaspiro[3.4]octan-2-yl)((1s,3s)-3-hydroxy-3-methylcyclobutyl)methanone; | 105 |
| 88 | (rac)-((1s,3s)-3-Hydroxy-3-(trifluoromethyl)cyclobutyl)(6-(3-isopropylphenyl)-2-azaspiro[3.4]octan-2-yl)methanone; | 59 |
| 89 | (2-(3-(tert-Butyl)phenyl)-6-azaspiro[3.4]octan-6-yl)((1s,3s)-3-hydroxy-3-methylcyclobutyl)methanone; | 126 |
| 90 | (rac)-(6-(3-(1,1-Difluoroethyl)phenyl)-2-azaspiro[3.4]octan-2-yl)((1s,3s)-3-hydroxy-3-methylcyclobutyl)methanone; | 64 |
| 91 | (rac)-(6-(3-Ethylphenyl)-2-azaspiro[3.4]octan-2-yl)((1s,3s)-3-hydroxy-3-methylcyclobutyl)methanone; | 58 |
| 92 | (rac)-(6-(3-(Difluoromethyl)-4-methylphenyl)-2-azaspiro[3.4]octan-2-yl)((1s,3s)-3-hydroxy-3-methylcyclobutyl)methanone; | 27 |
| 93 | (rac)-((1s,3s)-3-Hydroxy-3-methylcyclobutyl)(6-(3-methyl-5-(trifluoromethoxy)phenyl)-2-azaspiro[3.4]octan-2-yl)methanone; | 20 |
| 94 | (rac)-(6-(3-(Difluoromethyl)-5-methylphenyl)-2-azaspiro[3.4]octan-2-yl)((1s,3s)-3-hydroxy-3-methylcyclobutyl)methanone; | 60 |
| 95 | (rac)-((1s,3s)-3-Hydroxy-3-methylcyclobutyl)(6-(2-methoxy-3-methylphenyl)-2-azaspiro[3.4]octan-2-yl)methanone; | 290 |
| 96 | (rac)-(6-(4-Ethylphenyl)-2-azaspiro[3.4]octan-2-yl)((1s,3s)-3-hydroxy-3-methylcyclobutyl)methanone; | 18 |
| 97 | (rac)-((1s,3s)-3-Hydroxy-3-methylcyclobutyl)(6-(pyrazolo[1,5-a]pyridin-5-yl)-2-azaspiro[3.4]octan-2-yl)methanone; | 654 |

TABLE 3-continued

| Ex # | Compound Name | MGL IC$_{50}$ (nM) |
|---|---|---|
| 98 | (rac)-(6-(2,6-Dimethylphenyl)-2-azaspiro[3.4]octan-2-yl)((1s,3s)-3-hydroxy-3-methylcyclobutyl)methanone; | 292 |
| 99 | (rac)-((1s,3s)-3-Hydroxy-3-methylcyclobutyl)(6-(1-methyl-1H-pyrazol-4-yl)-2-azaspiro[3.4]octan-2-yl)methanone; | 5933 |
| 100 | (rac)-((1s,3s)-3-Hydroxy-3-methylcyclobutyl)(6-(1-methyl-3-(trifluoromethyl)-1H-pyrazol-4-yl)-2-azaspiro[3.4]octan-2-yl)methanone; | 8853 |
| 101 | (rac)-((1s,3s)-3-Hydroxy-3-methylcyclobutyl)(6-(1-methyl-3-(trifluoromethyl)-1H-pyrazol-5-yl)-2-azaspiro[3.4]octan-2-yl)methanone; | 753 |
| 102 | (rac)-((1s,3s)-3-Hydroxy-3-methylcyclobutyl)(6-(1-methyl-1H-indazol-5-yl)-2-azaspiro[3.4]octan-2-yl)methanone; | 301 |
| 103 | (7-(4-Fluoro-3-methoxyphenyl)-2-azaspiro[3.5]nonan-2-yl)((1s,3s)-3-hydroxy-3-methylcyclobutyl)methanone; | 99 |
| 104 | (7-(3-Fluoro-5-methoxyphenyl)-2-azaspiro[3.5]nonan-2-yl)((1s,3s)-3-hydroxy-3-methylcyclobutyl)methanone; | 26 |
| 105 | ((1s,3s)-3-Hydroxy-3-methylcyclobutyl)(7-(4-methoxy-3-methylphenyl)-2-azaspiro[3.5]nonan-2-yl)methanone; | 68 |
| 106 | ((1s,3s)-3-Hydroxy-3-methylcyclobutyl)(7-(3-methoxy-2-methylphenyl)-2-azaspiro[3.5]nonan-2-yl)methanone; | 30 |
| 107 | (rac)-((1s,3s)-3-Hydroxy-3-methylcyclobutyl)(6-(4-methyl-3-(trifluoromethoxy)phenyl)-2-azaspiro[3.4]octan-2-yl)methanone; | 7.4 |
| 108 | (rac)-(6-(3-Cyclopropyl-4-fluorophenyl)-2-azaspiro[3.4]octan-2-yl)((1s,3s)-3-hydroxy-3-methylcyclobutyl)methanone; | 14 |
| 109 | (rac)-((1s,3s)-3-Hydroxy-3-methylcyclobutyl)(6-(1-methyl-5-(trifluoromethyl)-1H-pyrazol-4-yl)-2-azaspiro[3.4]octan-2-yl)methanone; | 899 |
| 110 | (rac)-((1s,3s)-3-Hydroxy-3-methylcyclobutyl)(6-(6-(trifluoromethyl)pyridin-2-yl)-2-azaspiro[3.4]octan-2-yl)methanone; | 435 |
| 111 | (rac)-((1s,3s)-3-Hydroxy-3-methylcyclobutyl)(6-(1-methyl-1H-benzo[d]imidazol-5-yl)-2-azaspiro[3.4]octan-2-yl)methanone; | 949 |
| 112 | (rac)-((1s,3s)-3-Hydroxy-3-methylcyclobutyl)(6-(1-methyl-1H-benzo[d]imidazol-2-yl)-2-azaspiro[3.4]octan-2-yl)methanone; | 5535 |
| 113 | ((1s,3s)-3-Hydroxy-3-methylcyclobutyl)(7-(3-methoxy-4-(trifluoromethyl)phenyl)-2-azaspiro[3.5]nonan-2-yl)methanone; | 37 |
| 114 | ((1s,3s)-3-Hydroxy-3-methylcyclobutyl)(7-(4-methoxy-3-(trifluoromethyl)phenyl)-2-azaspiro[3.5]nonan-2-yl)methanone; | 65 |
| 115 | (7-(3-(Dimethylamino)-4-(trifluoromethyl)phenyl)-2-azaspiro[3.5]nonan-2-yl)((1s,3s)-3-hydroxy-3-methylcyclobutyl)methanone; | 17 |
| 116 | (7-(6-(tert-Butyl)pyridin-2-yl)-2-azaspiro[3.5]nonan-2-yl)((1s,3s)-3-hydroxy-3-methylcyclobutyl)methanone; | 4.4 |
| 117 | ((1s,3s)-3-Hydroxy-3-methylcyclobutyl)(7-(6-methoxypyridin-2-yl)-2-azaspiro[3.5]nonan-2-yl)methanone; | 420 |
| 118 | (7-(3-(tert-Butyl)-4-methoxyphenyl)-2-azaspiro[3.5]nonan-2-yl)((1s,3s)-3-hydroxy-3-methylcyclobutyl)methanone; | 20 |
| 119 | ((1s,3s)-3-Hydroxy-3-methylcyclobutyl)(7-(3-methoxy-5-(trifluoromethyl)phenyl)-2-azaspiro[3.5]nonan-2-yl)methanone; | 12 |
| 120 | (7-(3-Ethoxy-5-(trifluoromethyl)phenyl)-2-azaspiro[3.5]nonan-2-yl)((1s,3s)-3-hydroxy-3-methylcyclobutyl)methanone; | 141 |
| 121 | (7-(3-Ethyl-5-methylphenyl)-2-azaspiro[3.5]nonan-2-yl)((1s,3s)-3-hydroxy-3-methylcyclobutyl)methanone; | 7.4 |
| 122 | ((1s,3s)-3-Hydroxy-3-methylcyclobutyl)(7-(1-methyl-1H-indazol-5-yl)-2-azaspiro[3.5]nonan-2-yl)methanone; | 143 |
| 123 | (7-(3-(Dimethylamino)-5-(trifluoromethyl)phenyl)-2-azaspiro[3.5]nonan-2-yl)((1s,3s)-3-hydroxy-3-methylcyclobutyl)methanone; | 27 |
| 124 | ((1s,3s)-3-Hydroxy-3-methylcyclobutyl)(7-(quinolin-2-yl)-2-azaspiro[3.5]nonan-2-yl)methanone; | 227 |
| 125 | (rac)-(6-(3-Fluoro-5-isopropylphenyl)-2-azaspiro[3.4]octan-2-yl)((1s,3s)-3-hydroxy-3-methylcyclobutyl)methanone; | 8.3 |
| 126 | (rac)-(6-(3-(tert-Butyl)phenyl)-2-azaspiro[3.4]octan-2-yl)((1r,3s)-3-ethyl-3-hydroxycyclobutyl)methanone; | 7.5 |
| 127 | (7-(2,3-Dihydro-1H-inden-5-yl)-2-azaspiro[3.5]nonan-2-yl)((1s,3s)-3-hydroxy-3-methylcyclobutyl)methanone; | 14 |
| 128 | ((1s,3s)-3-Hydroxy-3-methylcyclobutyl)(7-(3-methoxy-5-methylphenyl)-2-azaspiro[3.5]nonan-2-yl)methanone; | 30 |
| 129 | ((1s,3s)-3-Hydroxy-3-methylcyclobutyl)(7-(3-methoxy-4-methylphenyl)-2-azaspiro[3.5]nonan-2-yl)methanone; | 25 |
| 130 | ((1s,3s)-3-Hydroxy-3-methylcyclobutyl)(7-(4-isopropylphenyl)-2-azaspiro[3.5]nonan-2-yl)methanone; | 17 |
| 131 | ((1s,3s)-3-Hydroxy-3-methylcyclobutyl)(7-(3-methoxyphenyl)-2-azaspiro[3.5]nonan-2-yl)methanone; | 32 |
| 132 | (7-(3-Ethoxyphenyl)-2-azaspiro[3.5]nonan-2-yl)((1s,3s)-3-hydroxy-3-methylcyclobutyl)methanone; | 41 |
| 133 | ((1s,3s)-3-Hydroxy-3-methylcyclobutyl)(7-(3-isopropylphenyl)-2-azaspiro[3.5]nonan-2-yl)methanone; | 8.2 |

TABLE 3-continued

| Ex # | Compound Name | MGL IC$_{50}$ (nM) |
|---|---|---|
| 134 | (7-(3,4-Dimethylphenyl)-2-azaspiro[3.5]nonan-2-yl)((1s,3s)-3-hydroxy-3-methylcyclobutyl)methanone; | 12 |
| 135 | (7-(3-(tert-Butyl)phenyl)-2-azaspiro[3.5]nonan-2-yl)((1s,3s)-3-hydroxy-3-methylcyclobutyl)methanone; | 2.1 |
| 136 | ((1s,3s)-3-Hydroxy-3-methylcyclobutyl)(7-(p-tolyl)-2-azaspiro[3.5]nonan-2-yl)methanone; | 35 |
| 137 | ((1s,3s)-3-Hydroxy-3-methylcyclobutyl)(7-(m-tolyl)-2-azaspiro[3.5]nonan-2-yl)methanone; | 38 |
| 138 | ((1s,3s)-3-Hydroxy-3-methylcyclobutyl)(7-(o-tolyl)-2-azaspiro[3.5]nonan-2-yl)methanone; | 47 |
| 139 | (7-(2-(tert-Butyl)pyridin-4-yl)-2-azaspiro[3.5]nonan-2-yl)((1s,3s)-3-hydroxy-3-methylcyclobutyl)methanone; | 167 |
| 140 | (7-(4-Cyclopropyl-3-methoxyphenyl)-2-azaspiro[3.5]nonan-2-yl)((1s,3s)-3-hydroxy-3-methylcyclobutyl)methanone; | 33 |
| 141 | (7-(3-Cyclopropyl-5-methoxyphenyl)-2-azaspiro[3.5]nonan-2-yl)((1s,3s)-3-hydroxy-3-methylcyclobutyl)methanone; | 20 |
| 142 | (7-(3-Cyclopropyl-4-methoxyphenyl)-2-azaspiro[3.5]nonan-2-yl)((1s,3s)-3-hydroxy-3-methylcyclobutyl)methanone; | 121 |
| 143 | (7-(3-Cyclopropyl-5-methylphenyl)-2-azaspiro[3.5]nonan-2-yl)((1s,3s)-3-hydroxy-3-methylcyclobutyl)methanone; | 4.5 |
| 144 | (7-(3-Ethyl-2-methoxyphenyl)-2-azaspiro[3.5]nonan-2-yl)((1s,3s)-3-hydroxy-3-methylcyclobutyl)methanone; | 16 |
| 145 | (7-(3-Ethyl-5-methoxyphenyl)-2-azaspiro[3.5]nonan-2-yl)((1s,3s)-3-hydroxy-3-methylcyclobutyl)methanone; | 31 |
| 146 | (7-(3-Ethyl-5-(trifluoromethyl)phenyl)-2-azaspiro[3.5]nonan-2-yl)((1s,3s)-3-hydroxy-3-methylcyclobutyl)methanone; | 4.6 |
| 147 | (7-(3,5-Dimethylphenyl)-2-azaspiro[3.5]nonan-2-yl)((1s,3s)-3-hydroxy-3-methylcyclobutyl)methanone; | 6.4 |
| 148 | (7-(3-Ethyl-5-(trifluoromethoxy)phenyl)-2-azaspiro[3.5]nonan-2-yl)((1s,3s)-3-hydroxy-3-methylcyclobutyl)methanone; | 9.4 |
| 149 | (7-(3-Chloro-5-(trifluoromethoxy)phenyl)-2-azaspiro[3.5]nonan-2-yl)((1s,3s)-3-hydroxy-3-methylcyclobutyl)methanone; | 1.7 |
| 150 | (7-(4-Ethoxy-3-(trifluoromethyl)phenyl)-2-azaspiro[3.5]nonan-2-yl)((1s,3s)-3-hydroxy-3-methylcyclobutyl)methanone; | 17 |
| 151 | ((1s,3s)-3-Hydroxy-3-methylcyclobutyl)(7-hydroxy-7-(3-isopropylphenyl)-2-azaspiro[3.5]nonan-2-yl)methanone; | 4.6 |
| 152 | (rac)-((1s,3s)-3-Hydroxy-3-methylcyclobutyl)(2-(4-(trifluoromethyl)phenyl)-8-azaspiro[4.5]decan-8-yl)methanone; | 3.3 |
| 153 | (2-(3-(tert-Butyl)phenyl)-7-azaspiro[3.5]nonan-7-yl)((1s,3s)-3-hydroxy-3-methylcyclobutyl)methanone; | 22 |
| 154 | (6-(3-Cyclopropyl-2-methylbenzyl)-2-azaspiro[3.3]heptan-2-yl)((1s,3s)-3-hydroxy-3-methylcyclobutyl)methanone; | 1.7 |
| 155 | ((1s,3s)-3-Hydroxy-3-methylcyclobutyl)(6-(2-methyl-3-(trifluoromethyl)benzyl)-2-azaspiro[3.3]heptan-2-yl)methanone; | 3.0 |
| 156 | (6-(2,3-Dimethylbenzyl)-2-azaspiro[3.3]heptan-2-yl)((1s,3s)-3-hydroxy-3-methylcyclobutyl)methanone; | 11 |
| 157 | (6-(3-(Difluoromethoxy)benzyl)-2-azaspiro[3.3]heptan-2-yl)((1s,3s)-3-hydroxy-3-methylcyclobutyl)methanone; | 29 |
| 158 | (6-(2-Ethylbenzyl)-2-azaspiro[3.3]heptan-2-yl)((1s,3s)-3-hydroxy-3-methylcyclobutyl)methanone; | 9.2 |
| 159 | ((1s,3s)-3-Hydroxy-3-methylcyclobutyl)(7-(3-methylbenzyl)-2-azaspiro[3.5]nonan-2-yl)methanone; | 31 |
| 160 | (7-(3-(Difluoromethoxy)benzyl)-2-azaspiro[3.5]nonan-2-yl)((1s,3s)-3-hydroxy-3-methylcyclobutyl)methanone; | 38 |
| 161 | (7-(4-(Difluoromethoxy)benzyl)-2-azaspiro[3.5]nonan-2-yl)((1s,3s)-3-hydroxy-3-methylcyclobutyl)methanone; | 19 |
| 162 | (7-(4-(Difluoromethyl)benzyl)-2-azaspiro[3.5]nonan-2-yl)((1s,3s)-3-hydroxy-3-methylcyclobutyl)methanone; | 29 |
| 163 | (7-(3-(Difluoromethyl)benzyl)-2-azaspiro[3.5]nonan-2-yl)((1s,3s)-3-hydroxy-3-methylcyclobutyl)methanone; | 61 |
| 164 | (6-Benzyl-2-azaspiro[3.3]heptan-2-yl)((1s,3s)-3-hydroxy-3-methylcyclobutyl)methanone; | 52 |
| 165 | ((1s,3s)-3-Hydroxy-3-methylcyclobutyl)(6-(3-methylbenzyl)-2-azaspiro[3.3]heptan-2-yl)methanone; | 21 |
| 166 | ((1s,3s)-3-Hydroxy-3-methylcyclobutyl)(6-(4-methylbenzyl)-2-azaspiro[3.3]heptan-2-yl)methanone; | 14 |
| 167 | ((1s,3s)-3-Hydroxy-3-methylcyclobutyl)(6-(pyridin-2-ylmethyl)-2-azaspiro[3.3]heptan-2-yl)methanone; | 1391 |
| 168 | ((1s,3s)-3-Hydroxy-3-methylcyclobutyl)(6-(pyridin-3-ylmethyl)-2-azaspiro[3.3]heptan-2-yl)methanone; | 1366 |
| 169 | (rac)-((1s,3s)-3-Hydroxy-3-methylcyclobutyl)(6-(4-methylbenzyl)-2-azaspiro[3.4]octan-2-yl)methanone; | 36 |
| 170 | (rac)-((1s,3s)-3-Hydroxy-3-methylcyclobutyl)(6-(4-isopropylbenzyl)-2-azaspiro[3.4]octan-2-yl)methanone; | 10 |
| 171 | (rac)-((1s,3s)-3-Hydroxy-3-methylcyclobutyl)(6-(4-(trifluoromethyl)benzyl)-2-azaspiro[3.4]octan-2-yl)methanone; | 6.8 |

TABLE 3-continued

| Ex # | Compound Name | MGL IC$_{50}$ (nM) |
|---|---|---|
| 172 | (2-Benzyl-7-azaspiro[3.5]nonan-7-yl)((1s,3s)-3-hydroxy-3-methylcyclobutyl)methanone; | 74 |
| 173 | ((1s,3s)-3-Hydroxy-3-methylcyclobutyl)(2-(4-methylbenzyl)-7-azaspiro[3.5]nonan-7-yl)methanone; | 28 |
| 174 | (rac)-((1s,3s)-3-Hydroxy-3-methylcyclobutyl)(6-(3-methylbenzyl)-2-azaspiro[3.4]octan-2-yl)methanone; | 23 |
| 175 | (rac)-((1s,3s)-3-Hydroxy-3-methylcyclobutyl)(6-(2-methylbenzyl)-2-azaspiro[3.4]octan-2-yl)methanone; | 43 |
| 176 | (rac)-((1s,3s)-3-Hydroxy-3-methylcyclobutyl)(6-(3-(trifluoromethyl)benzyl)-2-azaspiro[3.4]octan-2-yl)methanone; | 11 |
| 177 | ((1s,3*S)-3-Hydroxy-3-methylcyclobutyl)((*R)-6-(3-(trifluoromethyl)benzyl)-2-azaspiro[3.4]octan-2-yl)methanone; | 14 |
| 178 | ((1s,3*R)-3-Hydroxy-3-methylcyclobutyl)((*S)-6-(3-(trifluoromethyl)benzyl)-2-azaspiro[3.4]octan-2-yl)methanone; | 11 |
| 179 | (rac)-((1s,3s)-3-Hydroxy-3-methylcyclobutyl)(6-(4-(trifluoromethoxy)benzyl)-2-azaspiro[3.4]octan-2-yl)methanone; | 5.7 |
| 180 | (rac)-((1s,3s)-3-Hydroxy-3-methylcyclobutyl)(6-(3-(trifluoromethoxy)benzyl)-2-azaspiro[3.4]octan-2-yl)methanone; | 8.3 |
| 181 | (rac)-((1s,3s)-3-Hydroxy-3-methylcyclobutyl)(6-(3-isopropylbenzyl)-2-azaspiro[3.4]octan-2-yl)methanone; | 4.6 |
| 182 | (rac)-(6-(4-(Difluoromethyl)benzyl)-2-azaspiro[3.4]octan-2-yl)((1s,3s)-3-hydroxy-3-methylcyclobutyl)methanone; | 34 |
| 183 | (rac)-(6-(4-(Difluoromethoxy)benzyl)-2-azaspiro[3.4]octan-2-yl)((1s,3s)-3-hydroxy-3-methylcyclobutyl)methanone; | 48 |
| 184 | ((1s,3s)-3-Hydroxy-3-methylcyclobutyl)(6-(2-methylbenzyl)-2-azaspiro[3.3]heptan-2-yl)methanone; | 14 |
| 185 | ((1s,3s)-3-Hydroxy-3-methylcyclobutyl)(6-(4-isopropylbenzyl)-2-azaspiro[3.3]heptan-2-yl)methanone; | 2.3 |
| 186 | ((1s,3s)-3-Hydroxy-3-methylcyclobutyl)(6-(3-isopropylbenzyl)-2-azaspiro[3.3]heptan-2-yl)methanone; | 4.7 |
| 187 | ((1s,3s)-3-Hydroxy-3-methylcyclobutyl)(6-(2-isopropylbenzyl)-2-azaspiro[3.3]heptan-2-yl)methanone; | 12 |
| 188 | (6-(3,4-Dimethylbenzyl)-2-azaspiro[3.3]heptan-2-yl)((1s,3s)-3-hydroxy-3-methylcyclobutyl)methanone; | 4.3 |
| 189 | ((1s,3s)-3-Hydroxy-3-methylcyclobutyl)(6-(4-methyl-3-(trifluoromethyl)benzyl)-2-azaspiro[3.3]heptan-2-yl)methanone; | 3.5 |
| 190 | (6-((4-(tert-Butyl)pyridin-2-yl)methyl)-2-azaspiro[3.3]heptan-2-yl)((1s,3s)-3-hydroxy-3-methylcyclobutyl)methanone; | 73 |
| 191 | ((1s,3s)-3-Hydroxy-3-methylcyclobutyl)(6-((6-methoxypyridin-2-yl)methyl)-2-azaspiro[3.3]heptan-2-yl)methanone; | 159 |
| 192 | ((1s,3s)-3-Hydroxy-3-methylcyclobutyl)(6-(4-methoxybenzyl)-2-azaspiro[3.3]heptan-2-yl)methanone; | 22 |
| 193 | ((1s,3s)-3-Hydroxy-3-methylcyclobutyl)(6-(3-(trifluoromethyl)benzyl)-2-azaspiro[3.3]heptan-2-yl)methanone; | 5.8 |
| 194 | ((1s,3s)-3-Hydroxy-3-methylcyclobutyl)(6-(3-(trifluoromethoxy)benzyl)-2-azaspiro[3.3]heptan-2-yl)methanone; | 4.9 |
| 195 | ((1s,3s)-3-Hydroxy-3-methylcyclobutyl)(6-(4-(trifluoromethyl)benzyl)-2-azaspiro[3.3]heptan-2-yl)methanone; | 4.2 |
| 196 | ((1s,3s)-3-Hydroxy-3-methylcyclobutyl)(6-(2-(trifluoromethoxy)benzyl)-2-azaspiro[3.3]heptan-2-yl)methanone; | 2.8 |
| 197 | ((1s,3s)-3-Hydroxy-3-methylcyclobutyl)(6-(3-methoxybenzyl)-2-azaspiro[3.3]heptan-2-yl)methanone; | 64 |
| 198 | ((1s,3s)-3-Hydroxy-3-methylcyclobutyl)(6-(quinolin-2-ylmethyl)-2-azaspiro[3.3]heptan-2-yl)methanone; | 56 |
| 199 | ((1s,3s)-3-Hydroxy-3-methylcyclobutyl)(6-(2-(trifluoromethyl)benzyl)-2-azaspiro[3.3]heptan-2-yl)methanone; | 4.1 |
| 200 | (rac)-(6-(4-Cyclopropylbenzyl)-2-azaspiro[3.4]octan-2-yl)((1s,3s)-3-hydroxy-3-methylcyclobutyl)methanone; | 6.9 |
| 201 | (rac)-(6-(3-Cyclopropylbenzyl)-2-azaspiro[3.4]octan-2-yl)((1s,3s)-3-hydroxy-3-methylcyclobutyl)methanone; | 9.9 |
| 202 | (6-(4-Cyclopropyl-3-methylbenzyl)-2-azaspiro[3.3]heptan-2-yl)((1s,3s)-3-hydroxy-3-methylcyclobutyl)methanone; | 0.6 |
| 203 | (rac)-((1s,3s)-3-Hydroxy-3-methylcyclobutyl)(6-(2-methyl-4-(trifluoromethyl)benzyl)-2-azaspiro[3.4]octan-2-yl)methanone; | 7.8 |
| 204 | (rac)-((1s,3s)-3-Hydroxy-3-methylcyclobutyl)(6-(6-methyl-4-(trifluoromethyl)benzyl)-2-azaspiro[3.4]octan-2-yl)methanone; | 3.9 |
| 205 | (rac)-((1s,3s)-3-Hydroxy-3-methylcyclobutyl)(6-(4-methoxybenzyl)-2-azaspiro[3.4]octan-2-yl)methanone; | 76 |
| 206 | ((1s,3s)-3-Hydroxy-3-methylcyclobutyl)(6-(pyridin-4-ylmethyl)-2-azaspiro[3.3]heptan-2-yl)methanone; | 1137 |
| 207 | (6-(2-Cyclopropyl-3-methylbenzyl)-2-azaspiro[3.3]heptan-2-yl)((1s,3s)-3-hydroxy-3-methylcyclobutyl)methanone; | 1.7 |
| 208 | (6-(2-(tert-Butyl)benzyl)-2-azaspiro[3.3]heptan-2-yl)((1s,3s)-3-hydroxy-3-methylcyclobutyl)methanone; | 5.3 |
| 209 | ((1s,3s)-3-Hydroxy-3-methylcyclobutyl)(6-(3-methyl-2-(trifluoromethyl)benzyl)-2-azaspiro[3.3]heptan-2-yl)methanone; | 2.2 |

TABLE 3-continued

| Ex # | Compound Name | MGL IC$_{50}$ (nM) |
|---|---|---|
| 210 | ((1s,3s)-3-Hydroxy-3-methylcyclobutyl)(6-(2-isopropyl-3-(trifluoromethyl)benzyl)-2-azaspiro[3.3]heptan-2-yl)methanone; | 0.8 |
| 211 | ((1s,3s)-3-Hydroxy-3-methylcyclobutyl)(6-(5-methyl-2-(trifluoromethyl)benzyl)-2-azaspiro[3.3]heptan-2-yl)methanone; | 4.1 |
| 212 | ((1s,3s)-3-Hydroxy-3-methylcyclobutyl)(6-(3-methyl-4-(trifluoromethyl)benzyl)-2-azaspiro[3.3]heptan-2-yl)methanone; | 0.3 |
| 213 | ((1s,3s)-3-Hydroxy-3-methylcyclobutyl)(6-(4-methyl-2-(trifluoromethyl)benzyl)-2-azaspiro[3.3]heptan-2-yl)methanone; | 4.1 |
| 214 | ((1s,3s)-3-Hydroxy-3-methylcyclobutyl)(6-((1-methyl-3-(trifluoromethyl)-1H-pyrazol-5-yl)methyl)-2-azaspiro[3.3]heptan-2-yl)methanone; | 417 |
| 215 | ((1s,3s)-3-Hydroxy-3-methylcyclobutyl)(6-((1-methyl-1H-indazol-6-yl)methyl)-2-azaspiro[3.3]heptan-2-yl)methanone; | 43 |
| 216 | ((1s,3s)-3-Hydroxy-3-methylcyclobutyl)(6-(2-methoxybenzyl)-2-azaspiro[3.3]heptan-2-yl)methanone; | 12 |
| 217 | ((1s,3s)-3-Hydroxy-3-methylcyclobutyl)(6-(4-methoxy-2-(trifluoromethyl)benzyl)-2-azaspiro[3.3]heptan-2-yl)methanone; | 3.5 |
| 218 | (6-(3-Cyclopropylbenzyl)-2-azaspiro[3.3]heptan-2-yl)((1s,3s)-3-hydroxy-3-methylcyclobutyl)methanone; | 6.3 |
| 219 | (6-(4-Cyclopropylbenzyl)-2-azaspiro[3.3]heptan-2-yl)((1s,3s)-3-hydroxy-3-methylcyclobutyl)methanone; | 1.2 |
| 220 | ((1s,3s)-3-Hydroxy-3-methylcyclobutyl)(6-(4-(trifluoromethoxy)benzyl)-2-azaspiro[3.3]heptan-2-yl)methanone; | 1.1 |
| 221 | (6-(4-(Difluoromethoxy)benzyl)-2-azaspiro[3.3]heptan-2-yl)((1s,3s)-3-hydroxy-3-methylcyclobutyl)methanone; | 5.1 |
| 222 | (6-(3-Ethylbenzyl)-2-azaspiro[3.3]heptan-2-yl)((1s,3s)-3-hydroxy-3-methylcyclobutyl)methanone; | 5.1 |
| 223 | ((1s,3s)-3-Hydroxy-3-methylcyclobutyl)(6-((6-(trifluoromethyl)pyridin-2-yl)methyl)-2-azaspiro[3.3]heptan-2-yl)methanone; | 169 |
| 224 | ((1s,3s)-3-Hydroxy-3-methylcyclobutyl)(6-((1-methyl-1H-pyrrolo[2,3-b]pyridin-6-yl)methyl)-2-azaspiro[3.3]heptan-2-yl)methanone; | 27 |
| 225 | ((1s,3s)-3-Hydroxy-3-methylcyclobutyl)(6-((1-methyl-3-(trifluoromethyl)-1H-pyrazol-4-yl)methyl)-2-azaspiro[3.3]heptan-2-yl)methanone; | 119 |
| 226 | ((1s,3s)-3-Hydroxy-3-methylcyclobutyl)(6-(2-methyl-6-(trifluoromethyl)benzyl)-2-azaspiro[3.3]heptan-2-yl)methanone; | 2.1 |
| 227 | (6-(3-Fluoro-2-methylbenzyl)-2-azaspiro[3.3]heptan-2-yl)((1s,3s)-3-hydroxy-3-methylcyclobutyl)methanone; | 20 |
| 228 | (6-(4-Fluoro-3-methylbenzyl)-2-azaspiro[3.3]heptan-2-yl)((1s,3s)-3-hydroxy-3-methylcyclobutyl)methanone; | 15 |
| 229 | (6-(3-Fluoro-4-methylbenzyl)-2-azaspiro[3.3]heptan-2-yl)((1s,3s)-3-hydroxy-3-methylcyclobutyl)methanone; | 12 |
| 230 | (6-(2-Fluoro-4-methylbenzyl)-2-azaspiro[3.3]heptan-2-yl)((1s,3s)-3-hydroxy-3-methylcyclobutyl)methanone; | 6.4 |
| 231 | (6-(3-(Difluoromethyl)benzyl)-2-azaspiro[3.3]heptan-2-yl)((1s,3s)-3-hydroxy-3-methylcyclobutyl)methanone; | 14 |
| 232 | (6-(4-(Difluoromethyl)benzyl)-2-azaspiro[3.3]heptan-2-yl)((1s,3s)-3-hydroxy-3-methylcyclobutyl)methanone; | 11 |
| 233 | (6-((6-(tert-Butyl)pyridin-2-yl)methyl)-2-azaspiro[3.3]heptan-2-yl)((1s,3s)-3-hydroxy-3-methylcyclobutyl)methanone; | 273 |
| 234 | (rac)-(6-Benzyl-2-azaspiro[3.4]octan-2-yl)((1s,3s)-3-hydroxy-3-methylcyclobutyl)methanone; | 98 |
| 235 | (7-Benzyl-2-azaspiro[3.5]nonan-2-yl)((1s,3s)-3-hydroxy-3-methylcyclobutyl)methanone; | 40 |
| 236 | ((1s,3s)-3-Hydroxy-3-methylcyclobutyl)(7-(2-methylbenzyl)-2-azaspiro[3.5]nonan-2-yl)methanone; | 49 |
| 237 | ((1s,3s)-3-Hydroxy-3-methylcyclobutyl)(6-((3-(trifluoromethyl)-1H-pyrazol-1-yl)methyl)-2-azaspiro[3.3]heptan-2-yl)methanone; | 840 |
| 238 | ((1s,3s)-3-Hydroxy-3-methylcyclobutyl)(6-(o-tolyloxy)-2-azaspiro[3.3]heptan-2-yl)methanone; | 541 |
| 239 | ((1s,3s)-3-Hydroxy-3-methylcyclobutyl)(7-(3-methyl-4-(trifluoromethyl)phenoxy)-2-azaspiro[3.5]nonan-2-yl)methanone; | 0.4 |
| 240 | (rac)-(6-(4-(tert-Butyl)phenoxy)-2-azaspiro[3.4]octan-2-yl)((1s,3s)-3-hydroxy-3-methylcyclobutyl)methanone; | 122 |
| 241 | ((1s,3s)-3-Hydroxy-3-methylcyclobutyl)(7-(3-isopropylphenoxy)-2-azaspiro[3.5]nonan-2-yl)methanone; | 27 |
| 242 | ((1s,3s)-3-Hydroxy-3-methylcyclobutyl)(7-(4-isopropylphenoxy)-2-azaspiro[3.5]nonan-2-yl)methanone; | 6.3 |
| 243 | (rac)-(6-(3-(tert-Butyl)phenoxy)-2-azaspiro[3.4]octan-2-yl)((1s,3s)-3-hydroxy-3-methylcyclobutyl)methanone; | 26 |
| 244 | (6-(3-(tert-Butyl)phenoxy)-2-azaspiro[3.3]heptan-2-yl)((1s,3s)-3-hydroxy-3-methylcyclobutyl)methanone; | 63 |
| 245 | ((1s,3s)-3-Hydroxy-3-methylcyclobutyl)(2-(p-tolyloxy)-7-azaspiro[3.5]nonan-7-yl)methanone; | 329 |
| 246 | (6-(4-(tert-Butyl)phenoxy)-2-azaspiro[3.3]heptan-2-yl)((1s,3s)-3-hydroxy-3-methylcyclobutyl)methanone; | 84 |

TABLE 3-continued

| Ex # | Compound Name | MGL IC$_{50}$ (nM) |
|---|---|---|
| 247 | ((1s,3s)-3-Hydroxy-3-methylcyclobutyl)(6-(3-methyl-4-(trifluoromethyl)phenoxy)-2-azaspiro[3.3]heptan-2-yl)methanone; | 14 |
| 248 | ((1s,3s)-3-Hydroxy-3-methylcyclobutyl)(6-(4-methyl-3-(trifluoromethyl)phenoxy)-2-azaspiro[3.3]heptan-2-yl)methanone; | 114 |
| 249 | ((1s,3s)-3-Hydroxy-3-methylcyclobutyl)(6-(2-methyl-4-(trifluoromethyl)phenoxy)-2-azaspiro[3.3]heptan-2-yl)methanone; | 20 |
| 250 | ((1s,3s)-3-Hydroxy-3-methylcyclobutyl)(6-(3-methyl-2-(trifluoromethyl)phenoxy)-2-azaspiro[3.3]heptan-2-yl)methanone; | 35 |
| 251 | ((1s,3s)-3-Hydroxy-3-methylcyclobutyl)(6-(3-isopropyl-2-(trifluoromethyl)phenoxy)-2-azaspiro[3.3]heptan-2-yl)methanone; | 7.4 |
| 252 | ((1s,3s)-3-Hydroxy-3-methylcyclobutyl)(6-(2-methyl-3-(trifluoromethyl)phenoxy)-2-azaspiro[3.3]heptan-2-yl)methanone; | 47 |
| 253 | (rac)-((1s,3s)-3-Hydroxy-3-methylcyclobutyl)(6-(2-methyl-3-(trifluoromethyl)phenoxy)-2-azaspiro[3.4]octan-2-yl)methanone; | 26 |
| 254 | (rac)-((1s,3s)-3-Hydroxy-3-methylcyclobutyl)(6-(3-methyl-4-(trifluoromethyl)phenoxy)-2-azaspiro[3.4]octan-2-yl)methanone; | 21 |
| 255 | (rac)-((1s,3s)-3-Hydroxy-3-methylcyclobutyl)(6-(2-methyl-4-(trifluoromethyl)phenoxy)-2-azaspiro[3.4]octan-2-yl)methanone; | 15 |
| 256 | (rac)-((1s,3s)-3-Hydroxy-3-methylcyclobutyl)(6-(4-methyl-3-(trifluoromethyl)phenoxy)-2-azaspiro[3.4]octan-2-yl)methanone; | 74 |
| 257 | (7-(3-(tert-Butyl)phenoxy)-2-azaspiro[3.5]nonan-2-yl)((1s,3s)-3-hydroxy-3-methylcyclobutyl)methanone; | 8.1 |
| 258 | ((1s,3s)-3-Hydroxy-3-methylcyclobutyl)(7-(2-methyl-4-(trifluoromethyl)phenoxy)-2-azaspiro[3.5]nonan-2-yl)methanone; | 0.2 |
| 259 | ((1s,3s)-3-Hydroxy-3-methylcyclobutyl)(7-(4-methyl-3-(trifluoromethyl)phenoxy)-2-azaspiro[3.5]nonan-2-yl)methanone; | 3.0 |
| 260 | (7-(4-(tert-Butyl)phenoxy)-2-azaspiro[3.5]nonan-2-yl)((1s,3s)-3-hydroxy-3-methylcyclobutyl)methanone; | 10 |
| 261 | (7-(4-Cyclopropylphenoxy)-2-azaspiro[3.5]nonan-2-yl)((1s,3s)-3-hydroxy-3-methylcyclobutyl)methanone; | 7.2 |
| 262 | ((1s,3s)-3-Hydroxy-3-methylcyclobutyl)(7-(4-(trifluoromethoxy)phenoxy)-2-azaspiro[3.5]nonan-2-yl)methanone; | 3.2 |
| 263 | ((1s,3s)-3-Hydroxy-3-methylcyclobutyl)(7-(3-(trifluoromethoxy)phenoxy)-2-azaspiro[3.5]nonan-2-yl)methanone; | 12 |
| 264 | (7-(3-Cyclopropylphenoxy)-2-azaspiro[3.5]nonan-2-yl)((1s,3s)-3-hydroxy-3-methylcyclobutyl)methanone; | 32 |
| 265 | ((1s,3s)-3-Hydroxy-3-methylcyclobutyl)(7-(2-isopropylphenoxy)-2-azaspiro[3.5]nonan-2-yl)methanone; | 37 |
| 266 | ((1s,3s)-3-Hydroxy-3-methylcyclobutyl)(7-(3-isopropylphenyl)-7-methoxy-2-azaspiro[3.5]nonan-2-yl)methanone; | 1.2 |
| 267 | ((1s,3s)-3-Hydroxy-3-methylcyclobutyl)(6-(3-methyl-5-(trifluoromethyl)phenyl)-2-azaspiro[3.3]heptan-2-yl)methanone; | 65 |
| 268 | ((1s,3s)-3-Hydroxy-3-methylcyclobutyl)(6-(1-methyl-1H-pyrrolo[2,3-b]pyridin-5-yl)-2-azaspiro[3.3]heptan-2-yl)methanone; | 2398 |
| 269 | ((1s,3s)-3-Hydroxy-3-methylcyclobutyl)(6-(1-methyl-1H-pyrrolo[2,3-b]pyridin-6-yl)-2-azaspiro[3.3]heptan-2-yl)methanone; | 507 |
| 270 | (6-Benzyl-6-methoxy-2-azaspiro[3.3]heptan-2-yl)((1s,3s)-3-hydroxy-3-methylcyclobutyl)methanone; | 3292 |
| 271 | (6-(2-Cyclopropylbenzyl)-2-azaspiro[3.3]heptan-2-yl)((1s,3s)-3-hydroxy-3-methylcyclobutyl)methanone; | 3.6 |
| 272 | (6-(4-Cyclopropoxybenzyl)-2-azaspiro[3.3]heptan-2-yl)((1s,3s)-3-hydroxy-3-methylcyclobutyl)methanone; | 8.1 |
| 273 | (6-(4-Fluoro-2-methylbenzyl)-2-azaspiro[3.3]heptan-2-yl)((1s,3s)-3-hydroxy-3-methylcyclobutyl)methanone; | 9.9 |
| 274 | (6-(2-(Difluoromethyl)-4-methoxybenzyl)-2-azaspiro[3.3]heptan-2-yl)((1s,3s)-3-hydroxy-3-methylcyclobutyl)methanone; | 6.2 |
| 275 | (6-(4-(Difluoromethyl)-2-methoxybenzyl)-2-azaspiro[3.3]heptan-2-yl)((1s,3s)-3-hydroxy-3-methylcyclobutyl)methanone; | 0.44 |
| 276 | ((1s,3s)-3-Hydroxy-3-methylcyclobutyl)(6-(3-methoxy-4-(trifluoromethyl)benzyl)-2-azaspiro[3.3]heptan-2-yl)methanone; | 1.0 |
| 277 | ((1s,3s)-3-Hydroxy-3-methylcyclobutyl)(6-((5-methyl-6-(trifluoromethyl)pyridin-2-yl)methyl)-2-azaspiro[3.3]heptan-2-yl)methanone; | 18 |
| 278 | ((1s,3s)-3-Hydroxy-3-methylcyclobutyl)(6-((6-methyl-5-(trifluoromethyl)pyridin-2-yl)methyl)-2-azaspiro[3.3]heptan-2-yl)methanone; | 16 |
| 279 | ((1s,3s)-3-Hydroxy-3-methylcyclobutyl)(6-((6-isopropoxy-5-methylpyridin-2-yl)methyl)-2-azaspiro[3.3]heptan-2-yl)methanone; | 10 |
| 280 | (6-((5-(Difluoromethoxy)-6-methylpyridin-2-yl)methyl)-2-azaspiro[3.3]heptan-2-yl)((1s,3s)-3-hydroxy-3-methylcyclobutyl)methanone; | 37 |
| 281 | ((1s,3s)-3-Hydroxy-3-methylcyclobutyl)(6-((6-methoxy-5-(trifluoromethyl)pyridin-2-yl)methyl)-2-azaspiro[3.3]heptan-2-yl)methanone; | 1.2 |
| 282 | ((1s,3s)-3-Hydroxy-3-methylcyclobutyl)(6-((6-isopropoxy-5-(trifluoromethyl)pyridin-2-yl)methyl)-2-azaspiro[3.3]heptan-2-yl)methanone; | 1.0 |

TABLE 3-continued

| Ex # | Compound Name | MGL IC$_{50}$ (nM) |
|---|---|---|
| 283 | ((1s,3s)-3-Hydroxy-3-methylcyclobutyl)(6-((1-methyl-5-(trifluoromethyl)-1H-pyrazol-3-yl)methyl)-2-azaspiro[3.3]heptan-2-yl)methanone; | 116 |
| 284 | ((1s,3s)-3-Hydroxy-3-methylcyclobutyl)(6-(pyrazolo[1,5-a]pyridin-6-ylmethyl)-2-azaspiro[3.3]heptan-2-yl)methanone; | 122 |
| 285 | ((1s,3s)-3-Hydroxy-3-methylcyclobutyl)(6-(pyrazolo[1,5-a]pyridin-7-ylmethyl)-2-azaspiro[3.3]heptan-2-yl)methanone; | 47 |
| 286 | (6-((1H-Pyrrolo[2,3-b]pyridin-1-yl)methyl)-2-azaspiro[3.3]heptan-2-yl)((1s,3s)-3-hydroxy-3-methylcyclobutyl)methanone; | 90 |
| 287 | ((1s,3s)-3-Hydroxy-3-methylcyclobutyl)(6-((2-methyl-1H-pyrrolo[2,3-b]pyridin-1-yl)methyl)-2-azaspiro[3.3]heptan-2-yl)methanone; | 67 |
| 288 | ((1s,3s)-3-Hydroxy-3-methylcyclobutyl)(6-((6-methyl-1H-pyrrolo[2,3-b]pyridin-1-yl)methyl)-2-azaspiro[3.3]heptan-2-yl)methanone; | 26 |
| 289 | ((1s,3s)-3-Hydroxy-3-methylcyclobutyl)(6-((1-isopropyl-1H-pyrrolo[2,3-b]pyridin-6-yl)methyl)-2-azaspiro[3.3]heptan-2-yl)methanone; | 8.2 |
| 290 | ((1s,3s)-3-Hydroxy-3-methylcyclobutyl)(6-((6-isopropyl-1H-pyrrolo[2,3-b]pyridin-1-yl)methyl)-2-azaspiro[3.3]heptan-2-yl)methanone; | 16 |
| 291 | (6-((1,3-Dimethyl-1H-pyrrolo[2,3-b]pyridin-6-yl)methyl)-2-azaspiro[3.3]heptan-2-yl)((1s,3s)-3-hydroxy-3-methylcyclobutyl)methanone; | 3.8 |
| 292 | (6-((1,2-Dimethyl-1H-pyrrolo[2,3-b]pyridin-6-yl)methyl)-2-azaspiro[3.3]heptan-2-yl)((1s,3s)-3-hydroxy-3-methylcyclobutyl)methanone; | 19 |
| 293 | (6-((3-Fluoro-1-methyl-1H-pyrrolo[2,3-b]pyridin-6-yl)methyl)-2-azaspiro[3.3]heptan-2-yl)((1s,3s)-3-hydroxy-3-methylcyclobutyl)methanone; | 10 |
| 294 | ((1s,3s)-3-Hydroxy-3-methylcyclobutyl)(6-((2-(trifluoromethyl)-1H-pyrrolo[2,3-b]pyridin-1-yl)methyl)-2-azaspiro[3.3]heptan-2-yl)methanone; | 10 |
| 295 | ((1s,3s)-3-Hydroxy-3-methylcyclobutyl)(6-((6-(trifluoromethyl)-1H-pyrrolo[2,3-b]pyridin-1-yl)methyl)-2-azaspiro[3.3]heptan-2-yl)methanone; | 20 |
| 296 | ((1s,3s)-3-Hydroxy-3-methylcyclobutyl)(6-((1-methyl-3-(trifluoromethyl)-1H-pyrrolo[2,3-b]pyridin-6-yl)methyl)-2-azaspiro[3.3]heptan-2-yl)methanone; | 0.29 |
| 297 | ((1s,3s)-3-Hydroxy-3-methylcyclobutyl)(6-((1-(2,2,2-trifluoroethyl)-1H-pyrrolo[2,3-b]pyridin-6-yl)methyl)-2-azaspiro[3.3]heptan-2-yl)methanone; | 21 |
| 298 | ((1s,3s)-3-Hydroxy-3-methylcyclobutyl)(6-((1-methyl-1H-pyrrolo[3,2-c]pyridin-6-yl)methyl)-2-azaspiro[3.3]heptan-2-yl)methanone; | 775 |
| 299 | ((1s,3s)-3-Hydroxy-3-methylcyclobutyl)(6-((1-methyl-1H-indazol-7-yl)methyl)-2-azaspiro[3.3]heptan-2-yl)methanone; | 70 |
| 300 | (6-((1,4-Dimethyl-1H-indazol-6-yl)methyl)-2-azaspiro[3.3]heptan-2-yl)((1s,3s)-3-hydroxy-3-methylcyclobutyl)methanone; | 20 |
| 301 | (6-((1,5-Dimethyl-1H-indazol-6-yl)methyl)-2-azaspiro[3.3]heptan-2-yl)((1s,3s)-3-hydroxy-3-methylcyclobutyl)methanone; | 36 |
| 302 | (6-((1,3-Dimethyl-1H-indazol-6-yl)methyl)-2-azaspiro[3.3]heptan-2-yl)((1s,3s)-3-hydroxy-3-methylcyclobutyl)methanone; | 21 |
| 303 | (6-((4-Fluoro-1-methyl-1H-indazol-6-yl)methyl)-2-azaspiro[3.3]heptan-2-yl)((1s,3s)-3-hydroxy-3-methylcyclobutyl)methanone; | 29 |
| 304 | (6-((5-Fluoro-1-methyl-1H-indazol-6-yl)methyl)-2-azaspiro[3.3]heptan-2-yl)((1s,3s)-3-hydroxy-3-methylcyclobutyl)methanone; | 13 |
| 305 | (6-((7-Fluoro-1-methyl-1H-indazol-6-yl)methyl)-2-azaspiro[3.3Jheptan-2-yl)((1s,3s)-3-hydroxy-3-methylcyclobutyl)methanone; | 28 |
| 306 | ((1s,3s)-3-Hydroxy-3-methylcyclobutyl)(6-((1-isopropyl-1H-indazol-6-yl)methyl)-2-azaspiro[3.3]heptan-2-yl)methanone; | 23 |
| 307 | ((1s,3s)-3-Hydroxy-3-methylcyclobutyl)(6-((1-(2,2,2-trifluoroethyl)-1H-indazol-6-yl)methyl)-2-azaspiro[3.3]heptan-2-yl)methanone; | 431 |
| 308 | ((1s,3s)-3-Hydroxy-3-methylcyclobutyl)(6-((2-isopropyl-2H-indazol-6-yl)methyl)-2-azaspiro[3.3]heptan-2-yl)methanone; | 117 |
| 309 | ((1s,3s)-3-Hydroxy-3-methylcyclobutyl)(6-((6-methyl-5-(trifluoromethyl)pyridin-2-yl)oxy)-2-azaspiro[3.3]heptan-2-yl)methanone; | 130 |
| 310 | ((1s,3*S)-3-Hydroxy-3-methylcyclobutyl)(6-(((*R)-1-phenylethyl)-2-azaspiro[3.3]heptan-2-yl)methanone; | 33 |
| 311 | ((1s,3*R)-3-Hydroxy-3-methylcyclobutyl)(6-(((*S)-1-phenylethyl)-2-azaspiro[3.3]heptan-2-yl)methanone; | 77 |
| 312 | ((1s,3*S)-3-Hydroxy-3-methylcyclobutyl)(6-(((*R)-1-(6-methyl-5-(trifluoromethyl)pyridin-2-yl)ethyl)-2-azaspiro[3.3]heptan-2-yl)methanone; | 5.4 |
| 313 | ((1s,3*R)-3-Hydroxy-3-methylcyclobutyl)(6-(((*S)-1-(6-methyl-5-(trifluoromethyl)pyridin-2-yl)ethyl)-2-azaspiro[3.3]heptan-2-yl)methanone; | 52 |
| 314 | ((1s,3*S)-3-Hydroxy-3-methylcyclobutyl)(6-(((*R)-1-(1-methyl-1H-indazol-6-yl)ethyl)-2-azaspiro[3.3]heptan-2-yl)methanone; | 130 |

TABLE 3-continued

| Ex # | Compound Name | MGL IC$_{50}$ (nM) |
|---|---|---|
| 315 | ((1s,3*R)-3-Hydroxy-3-methylcyclobutyl)(6-((*S)-1-(1-methyl-1H-indazol-6-yl)ethyl)-2-azaspiro[3.3]heptan-2-yl)methanone; | 45 |
| 316 | (rac)-((1s,3s)-3-Hydroxy-3-methylcyclobutyl)(6-(1-(pyrazolo[1,5-a]pyridin-7-yl)ethyl)-2-azaspiro[3.3]heptan-2-yl)methanone; | 49 |
| 317 | (6-(Difluoro(1-methyl-1H-pyrrolo[2,3-b]pyridin-6-yl)methyl)-2-azaspiro[3.3]heptan-2-yl)((1s,3s)-3-hydroxy-3-methylcyclobutyl)methanone; | 69 |
| 318 | ((1s,3*S)-3-Hydroxy-3-methylcyclobutyl)((6*R)-6-(3-isopropylphenyl)-1-methyl-2-azaspiro[3.4]octan-2-yl)methanone; | 48 |
| 319 | (rac)-((1s,3s)-3-(Difluoromethyl)-3-hydroxycyclobutyl)(6-(3-isopropylphenyl)-2-azaspiro[3.4]octan-2-yl)methanone; | 38 |
| 320 | (rac)-(6-(4-(1,1-Difluoroethyl)phenyl)-2-azaspiro[3.4]octan-2-yl)((1s,3s)-3-hydroxy-3-methylcyclobutyl)methanone; | 18 |
| 321 | ((*S)-6-(2,4-Dimethylphenyl)-2-azaspiro[3.4]octan-2-yl)((1s,3*R)-3-hydroxy-3-methylcyclobutyl)methanone; | 36 |
| 322 | ((*R)-6-(2,4-Dimethylphenyl)-2-azaspiro[3.4]octan-2-yl)((1s,3*S)-3-hydroxy-3-methylcyclobutyl)methanone; | 64 |
| 323 | (rac)-(6-(2,3-Dihydrobenzofuran-6-yl)-2-azaspiro[3.4]octan-2-yl)((1s,3s)-3-hydroxy-3-methylcyclobutyl)methanone; | 166 |
| 324 | (rac)-((1s,3s)-3-Hydroxy-3-methylcyclobutyl)(6-(pyrazolo[1,5-a]pyridin-4-yl)-2-azaspiro[3.4]octan-2-yl)methanone; | 835 |
| 325 | (rac)-((1s,3s)-3-Hydroxy-3-methylcyclobutyl)(6-(pyrazolo[1,5-a]pyridin-2-yl)-2-azaspiro[3.4]octan-2-yl)methanone; | 348 |
| 326 | (rac)-((1s,3s)-3-Hydroxy-3-methylcyclobutyl)(6-(1-methyl-1H-indazol-4-yl)-2-azaspiro[3.4]octan-2-yl)methanone; | 185 |
| 327 | (rac)-((1s,3s)-3-Hydroxy-3-methylcyclobutyl)(6-(imidazo[1,2-a]pyridin-8-yl)-2-azaspiro[3.4]octan-2-yl)methanone; | 3091 |
| 328 | (rac)-((1s,3s)-3-Hydroxy-3-methylcyclobutyl)(6-(imidazo[1,2-a]pyridin-7-yl)-2-azaspiro[3.4]octan-2-yl)methanone; | 3706 |
| 329 | (rac)-((1s,3s)-3-Hydroxy-3-methylcyclobutyl)(6-(imidazo[1,5-a]pyridin-1-yl)-2-azaspiro[3.4]octan-2-yl)methanone; | 683 |
| 330 | (rac)-((1s,3s)-3-Hydroxy-3-methylcyclobutyl)(6-(5,6,7,8-tetrahydroimidazo[1,5-a]pyridin-1-yl)-2-azaspiro[3.4]octan-2-yl)methanone; | 2379 |
| 331 | (rac)-((1s,3s)-3-Hydroxy-3-methylcyclobutyl)(6-(4,5,6,7-tetrahydropyrazolo[1,5-a]pyridin-2-yl)-2-azaspiro[3.4]octan-2-yl)methanone; | 1023 |
| 332 | (rac)-(6-(3-Cyclopropyl-4-methylphenoxy)-2-azaspiro[3.4]octan-2-yl)((1s,3s)-3-hydroxy-3-methylcyclobutyl)methanone; | 136 |
| 333 | (rac)-(6-(3-Cyclopropyl-2-methylphenoxy)-2-azaspiro[3.4]octan-2-yl)((1s,3s)-3-hydroxy-3-methylcyclobutyl)methanone; | 37 |
| 334 | (rac)-(6-(3-Cyclopropyl-2-fluorophenoxy)-2-azaspiro[3.4]octan-2-yl)((1s,3s)-3-hydroxy-3-methylcyclobutyl)methanone; | 125 |
| 335 | (rac)-(6-(3-Cyclopropyl-4-fluorophenoxy)-2-azaspiro[3.4]octan-2-yl)((1s,3s)-3-hydroxy-3-methylcyclobutyl)methanone; | 116 |
| 336 | (rac)-((1s,3s)-3-Hydroxy-3-methylcyclobutyl)(6-((5-methyl-6-(trifluoromethyl)pyridin-2-yl)oxy)-2-azaspiro[3.4]octan-2-yl)methanone; | 91 |
| 337 | ((1s,3*S)-3-Hydroxy-3-methylcyclobutyl)((*R)-6-((*R)-1-phenylethyl)-2-azaspiro[3.4]octan-2-yl)methanone; | 149 |
| 338 | ((1s,3*R)-3-Hydroxy-3-methylcyclobutyl)((*S)-6-((*R)-1-phenylethyl)-2-azaspiro[3.4]octan-2-yl)methanone; | 60 |
| 339 | ((1s,3*R)-3-Hydroxy-3-methylcyclobutyl)((*S)-6-((*S)-1-phenylethyl)-2-azaspiro[3.4]octan-2-yl)methanone; | 48 |
| 340 | (7-Fluoro-7-phenyl-2-azaspiro[3.5]nonan-2-yl)((1s,3s)-3-hydroxy-3-methylcyclobutyl)methanone; | 288 |
| 341 | (7-Fluoro-7-(1-methyl-1H-pyrrolo[2,3-b]pyridin-6-yl)-2-azaspiro[3.5]nonan-2-yl)((1s,3s)-3-hydroxy-3-methylcyclobutyl)methanone; | 101 |
| 342 | ((1s,3s)-3-Hydroxy-3-methylcyclobutyl)(7-methoxy-7-phenyl-2-azaspiro[3.5]nonan-2-yl)methanone; | 40 |
| 343 | ((1s,3s)-3-Hydroxy-3-methylcyclobutyl)(7-methoxy-7-(o-tolyl)-2-azaspiro[3.5]nonan-2-yl)methanone; | 16 |
| 344 | (7-(3,5-Dimethylphenyl)-7-methoxy-2-azaspiro[3.5]nonan-2-yl)((1s,3s)-3-hydroxy-3-methylcyclobutyl)methanone; | 0.84 |
| 345 | ((1s,3s)-3-Hydroxy-3-methylcyclobutyl)(7-(3-(1-methyl-1H-imidazol-4-yl)phenyl)-2-azaspiro[3.5]nonan-2-yl)methanone; | 187 |
| 346 | (7-(4-(1H-Pyrazol-1-yl)phenyl)-2-azaspiro[3.5]nonan-2-yl)((1s,3s)-3-hydroxy-3-methylcyclobutyl)methanone; | 295 |
| 347 | (7-(3-(1H-Pyrazol-1-yl)phenyl)-2-azaspiro[3.5]nonan-2-yl)((1s,3s)-3-hydroxy-3-methylcyclobutyl)methanone; | 56 |
| 348 | ((1*S,4r,7*S)-7-(3,5-Dimethylphenyl)-1-methyl-2-azaspiro[3.5]nonan-2-yl)((1s,3*R)-3-hydroxy-3-methylcyclobutyl)methanone; | 326 |
| 349 | ((1*R,4r,7*R)-7-(3,5-Dimethylphenyl)-1-methyl-2-azaspiro[3.5]nonan-2-yl)((1s,3*S)-3-hydroxy-3-methylcyclobutyl)methanone; | 523 |
| 350 | ((1*S,4s,7*R)-7-(3,5-Dimethylphenyl)-1-methyl-2-azaspiro[3.5]nonan-2-yl)((1s,3*R)-3-hydroxy-3-methylcyclobutyl)methanone; | 34 |

TABLE 3-continued

| Ex # | Compound Name | MGL IC$_{50}$ (nM) |
|---|---|---|
| 351 | ((1*R,4s,7*S)-7-(3,5-Dimethylphenyl)-1-methyl-2-azaspiro[3.5]nonan-2-yl)((1s,3*S)-3-hydroxy-3-methylcyclobutyl)methanone; | 77 |
| 352 | (7-(3-Fluoro-5-methylphenyl)-2-azaspiro[3.5]nonan-2-yl)((1s,3s)-3-hydroxy-3-methylcyclobutyl)methanone; | 22 |
| 353 | (7-(4-Fluoro-3-methylphenyl)-2-azaspiro[3.5]nonan-2-yl)((1s,3s)-3-hydroxy-3-methylcyclobutyl)methanone; | 18 |
| 354 | (7-(2-Fluoro-5-methylphenyl)-2-azaspiro[3.5]nonan-2-yl)((1s,3s)-3-hydroxy-3-methylcyclobutyl)methanone; | 20 |
| 355 | (7-(2-Fluoro-3-methylphenyl)-2-azaspiro[3.5]nonan-2-yl)((1s,3s)-3-hydroxy-3-methylcyclobutyl)methanone; | 39 |
| 356 | (7-(2-Fluoro-6-methylphenyl)-2-azaspiro[3.5]nonan-2-yl)((1s,3s)-3-hydroxy-3-methylcyclobutyl)methanone; | 15 |
| 357 | (7-(4-Fluoro-2-methylphenyl)-2-azaspiro[3.5]nonan-2-yl)((1s,3s)-3-hydroxy-3-methylcyclobutyl)methanone; | 29 |
| 358 | (7-(5-Fluoro-2-methylphenyl)-2-azaspiro[3.5]nonan-2-yl)((1s,3s)-3-hydroxy-3-methylcyclobutyl)methanone; | 29 |
| 359 | (7-(3-Fluoro-2-methylphenyl)-2-azaspiro[3.5]nonan-2-yl)((1s,3s)-3-hydroxy-3-methylcyclobutyl)methanone; | 18 |
| 360 | (7-(3-Ethoxy-4-methylphenyl)-2-azaspiro[3.5]nonan-2-yl)((1s,3s)-3-hydroxy-3-methylcyclobutyl)methanone; | 36 |
| 361 | (7-(3-Ethoxy-2-methylphenyl)-2-azaspiro[3.5]nonan-2-yl)((1s,3s)-3-hydroxy-3-methylcyclobutyl)methanone; | 1.8 |
| 362 | ((1s,3s)-3-Hydroxy-3-methylcyclobutyl)(7-(3-isopropoxy-2-methylphenyl)-2-azaspiro[3.5]nonan-2-yl)methanone; | 1.5 |
| 363 | ((1s,3s)-3-Hydroxy-3-methylcyclobutyl)(7-(5-methoxy-2-methylphenyl)-2-azaspiro[3.5]nonan-2-yl)methanone; | 164 |
| 364 | (7-(3-Cyclopropoxy-2-methylphenyl)-2-azaspiro[3.5]nonan-2-yl)((1s,3s)-3-hydroxy-3-methylcyclobutyl)methanone; | 2.9 |
| 365 | (7-(3-Ethoxy-5-fluorophenyl)-2-azaspiro[3.5]nonan-2-yl)((1s,3s)-3-hydroxy-3-methylcyclobutyl)methanone; | 22 |
| 366 | (7-(2-Fluoro-3-methoxyphenyl)-2-azaspiro[3.5]nonan-2-yl)((1s,3s)-3-hydroxy-3-methylcyclobutyl)methanone; | 50 |
| 367 | (7-(2-Chloro-3-methoxyphenyl)-2-azaspiro[3.5]nonan-2-yl)((1s,3s)-3-hydroxy-3-methylcyclobutyl)methanone; | 40 |
| 368 | (7-(2,3-Difluoro-5-methoxyphenyl)-2-azaspiro[3.5]nonan-2-yl)((1s,3s)-3-hydroxy-3-methylcyclobutyl)methanone; | 59 |
| 369 | (7-(2,5-Difluoro-3-methoxyphenyl)-2-azaspiro[3.5]nonan-2-yl)((1s,3s)-3-hydroxy-3-methylcyclobutyl)methanone; | 35 |
| 370 | (7-(3-Fluoro-5-methoxy-4-methylphenyl)-2-azaspiro[3.5]nonan-2-yl)((1s,3s)-3-hydroxy-3-methylcyclobutyl)methanone; | 11 |
| 371 | ((1s,3s)-3-Hydroxy-3-methylcyclobutyl)(7-(6-(1-(trifluoromethyl)cyclopropyl)pyridin-2-yl)-2-azaspiro[3.5]nonan-2-yl)methanone; | 6.4 |
| 372 | ((1s,3s)-3-Hydroxy-3-methylcyclobutyl)(7-(6-(1-methylcyclopropyl)pyridin-2-yl)-2-azaspiro[3.5]nonan-2-yl)methanone; | 5.1 |
| 373 | ((1s,3s)-3-Hydroxy-3-methylcyclobutyl)(7-(6-isopropyl-5-methylpyridin-2-yl)-2-azaspiro[3.5]nonan-2-yl)methanone; | 2.4 |
| 374 | ((1s,3s)-3-Hydroxy-3-methylcyclobutyl)(7-(6-isopropoxy-4-methylpyridin-2-yl)-2-azaspiro[3.5]nonan-2-yl)methanone; | 9.3 |
| 375 | ((1s,3s)-3-Hydroxy-3-methylcyclobutyl)(7-(4-methoxy-6-methylpyridin-2-yl)-2-azaspiro[3.5]nonan-2-yl)methanone; | 231 |
| 376 | ((1s,3s)-3-Hydroxy-3-methylcyclobutyl)(7-(2-isopropoxy-3-methylpyridin-4-yl)-2-azaspiro[3.5]nonan-2-yl)methanone; | 17 |
| 377 | (7-(6-(tert-Butyl)pyrazin-2-yl)-2-azaspiro[3.5]nonan-2-yl)((1s,3s)-3-hydroxy-3-methylcyclobutyl)methanone; | 82 |
| 378 | (7-(4-(tert-Butyl)pyrimidin-2-yl)-2-azaspiro[3.5]nonan-2-yl)((1s,3s)-3-hydroxy-3-methylcyclobutyl)methanone; | 37 |
| 379 | (7-(1-(tert-Butyl)-1H-pyrazol-3-yl)-2-azaspiro[3.5]nonan-2-yl)((1s,3s)-3-hydroxy-3-methylcyclobutyl)methanone; | 56 |
| 380 | ((1s,3s)-3-Hydroxy-3-methylcyclobutyl)(7-(1-phenyl-1H-pyrazol-3-yl)-2-azaspiro[3.5]nonan-2-yl)methanone; | 23 |
| 381 | (7-(1-(tert-Butyl)-1H-imidazol-4-yl)-2-azaspiro[3.5]nonan-2-yl)((1s,3s)-3-hydroxy-3-methylcyclobutyl)methanone; | 1386 |
| 382 | (7-(3-(tert-Butyl)isoxazol-5-yl)-2-azaspiro[3.5]nonan-2-yl)((1s,3s)-3-hydroxy-3-methylcyclobutyl)methanone; | 178 |
| 383 | ((1s,3s)-3-Hydroxy-3-methylcyclobutyl)(7-(1-methyl-1H-pyrrolo[2,3-b]pyridin-3-yl)-2-azaspiro[3.5]nonan-2-yl)methanone; | 180 |
| 384 | ((1s,3s)-3-Hydroxy-3-methylcyclobutyl)(7-(1-methyl-1H-pyrrolo[2,3-b]pyridin-6-yl)-2-azaspiro[3.5]nonan-2-yl)methanone; | 97 |
| 385 | ((1s,3s)-3-Hydroxy-3-methylcyclobutyl)(7-(1-isopropyl-1H-pyrrolo[2,3-b]pyridin-6-yl)-2-azaspiro[3.5]nonan-2-yl)methanone; | 30 |
| 386 | ((1s,3s)-3-Hydroxy-3-methylcyclobutyl)(7-(1-methyl-3-(trifluoromethyl)-1H-pyrrolo[2,3-b]pyridin-6-yl)-2-azaspiro[3.5]nonan-2-yl)methanone; | 19 |
| 387 | ((1s,3s)-3-Hydroxy-3-methylcyclobutyl)(7-(1-(2,2,2-trifluoroethyl)-1H-pyrrolo[2,3-b]pyridin-6-yl)-2-azaspiro[3.5]nonan-2-yl)methanone; | 68 |

TABLE 3-continued

| Ex # | Compound Name | MGL IC$_{50}$ (nM) |
|---|---|---|
| 388 | ((1s,3s)-3-Hydroxy-3-methylcyclobutyl)(7-(pyrazolo[1,5-a]pyridin-2-yl)-2-azaspiro[3.5]nonan-2-yl)methanone; | 198 |
| 389 | ((1s,3s)-3-Hydroxy-3-methylcyclobutyl)(7-(pyrazolo[1,5-a]pyridin-7-yl)-2-azaspiro[3.5]nonan-2-yl)methanone; | 101 |
| 390 | ((1s,3s)-3-Hydroxy-3-methylcyclobutyl)(7-(imidazo[1,2-a]pyridin-5-yl)-2-azaspiro[3.5]nonan-2-yl)methanone; | 722 |
| 391 | ((1s,3s)-3-Hydroxy-3-methylcyclobutyl)(7-(imidazo[1,2-a]pyridin-2-yl)-2-azaspiro[3.5]nonan-2-yl)methanone; | 1269 |
| 392 | ((1s,3s)-3-Hydroxy-3-methylcyclobutyl)(7-(imidazo[1,2-a]pyridin-3-yl)-2-azaspiro[3.5]nonan-2-yl)methanone; | 790 |
| 393 | ((1s,3s)-3-Hydroxy-3-methylcyclobutyl)(7-(pyrrolo[1,2-b]pyridazin-3-yl)-2-azaspiro[3.5]nonan-2-yl)methanone; | 27 |
| 394 | ((1s,3s)-3-Hydroxy-3-methylcyclobutyl)(7-(pyrazolo[1,5-a]pyridin-3-yl)-2-azaspiro[3.5]nonan-2-yl)methanone; | 226 |
| 395 | ((1s,3s)-3-Hydroxy-3-methylcyclobutyl)(7-(4,5,6,7-tetrahydropyrazolo[1,5-a]pyridin-2-yl)-2-azaspiro[3.5]nonan-2-yl)methanone; | 354 |
| 396 | ((1s,3s)-3-Hydroxy-3-methylcyclobutyl)(7-(5,6,7,8-tetrahydroimidazo[1,2-a]pyridin-2-yl)-2-azaspiro[3.5]nonan-2-yl)methanone; | 7243 |
| 397 | ((1s,3s)-3-Hydroxy-3-methylcyclobutyl)(7-(4-methylbenzyl)-2-azaspiro[3.5]nonan-2-yl)methanone; | 16 |
| 398 | (7-(2-Fluoro-3-methylbenzyl)-2-azaspiro[3.5]nonan-2-yl)((1s,3s)-3-hydroxy-3-methylcyclobutyl)methanone; | 18 |
| 399 | (7-(4-Fluoro-3-methylbenzyl)-2-azaspiro[3.5]nonan-2-yl)((1s,3s)-3-hydroxy-3-methylcyclobutyl)methanone; | 19 |
| 400 | (7-((1H-Pyrrolo[2,3-b]pyridin-1-yl)methyl)-2-azaspiro[3.5]nonan-2-yl)((1s,3s)-3-hydroxy-3-methylcyclobutyl)methanone; | 311 |
| 401 | ((1s,3s)-3-Hydroxy-3-methylcyclobutyl)(7-((1-methyl-1H-pyrrolo[2,3-b]pyridin-6-yl)methyl)-2-azaspiro[3.5]nonan-2-yl)methanone; | 66 |
| 402 | ((1s,3s)-3-Hydroxy-3-methylcyclobutyl)(7-((1-methyl-1H-indazol-6-yl)methyl)-2-azaspiro[3.5]nonan-2-yl)methanone; | 185 |
| 403 | ((1s,3s)-3-Hydroxy-3-methylcyclobutyl)(7-((1-methyl-1H-pyrazolo[3,4-b]pyridin-6-yl)methyl)-2-azaspiro[3.5]nonan-2-yl)methanone; | 449 |
| 404 | ((1s,3s)-3-Hydroxy-3-methylcyclobutyl)(7-(p-tolyloxy)-2-azaspiro[3.5]nonan-2-yl)methanone; | 53 |
| 405 | (7-(3,4-Dimethylphenoxy)-2-azaspiro[3.5]nonan-2-yl)((1s,3s)-3-hydroxy-3-methylcyclobutyl)methanone; | 32 |
| 406 | (7-(2,3-Dimethylphenoxy)-2-azaspiro[3.5]nonan-2-yl)((1s,3s)-3-hydroxy-3-methylcyclobutyl)methanone; | 20 |
| 407 | ((1s,3s)-3-Hydroxy-3-methylcyclobutyl)(7-(3-methoxy-5-methylphenoxy)-2-azaspiro[3.5]nonan-2-yl)methanone; | 143 |
| 408 | ((1s,3s)-3-Hydroxy-3-methylcyclobutyl)(7-(3-methoxy-4-methylphenoxy)-2-azaspiro[3.5]nonan-2-yl)methanone; | 33 |
| 409 | ((1s,3s)-3-Hydroxy-3-methylcyclobutyl)(7-(3-methoxy-2-methylphenoxy)-2-azaspiro[3.5]nonan-2-yl)methanone; | 42 |
| 410 | (7-(2-Chloro-5-methylphenoxy)-2-azaspiro[3.5]nonan-2-yl)((1s,3s)-3-hydroxy-3-methylcyclobutyl)methanone; | 2.8 |
| 411 | (7-(3-Chloro-4-methylphenoxy)-2-azaspiro[3.5]nonan-2-yl)((1s,3s)-3-hydroxy-3-methylcyclobutyl)methanone; | 9.1 |
| 412 | (7-(4-Chloro-2-methylphenoxy)-2-azaspiro[3.5]nonan-2-yl)((1s,3s)-3-hydroxy-3-methylcyclobutyl)methanone; | 1.4 |
| 413 | (7-(3-Chloro-2-methylphenoxy)-2-azaspiro[3.5]nonan-2-yl)((1s,3s)-3-hydroxy-3-methylcyclobutyl)methanone; | 22 |
| 414 | (7-(4-Chloro-3-methoxyphenoxy)-2-azaspiro[3.5]nonan-2-yl)((1s,3s)-3-hydroxy-3-methylcyclobutyl)methanone; | 15 |
| 415 | (7-(4-Cyclopropyl-3-fluorophenoxy)-2-azaspiro[3.5]nonan-2-yl)((1s,3s)-3-hydroxy-3-methylcyclobutyl)methanone; | 3.3 |
| 416 | ((1s,3s)-3-Hydroxy-3-methylcyclobutyl)(7-(2-methyl-5-(trifluoromethyl)phenoxy)-2-azaspiro[3.5]nonan-2-yl)methanone; | 1.9 |
| 417 | ((1s,3s)-3-Hydroxy-3-methylcyclobutyl)(7-((5-(trifluoromethyl)pyridin-2-yl)oxy)-2-azaspiro[3.5]nonan-2-yl)methanone; | 29 |
| 418 | ((1s,3s)-3-Hydroxy-3-methylcyclobutyl)(7-((4-(trifluoromethyl)pyridin-2-yl)oxy)-2-azaspiro[3.5]nonan-2-yl)methanone; | 180 |
| 419 | ((1s,3s)-3-Hydroxy-3-methylcyclobutyl)(7-methyl-7-((5-(trifluoromethyl)pyridin-2-yl)oxy)-2-azaspiro[3.5]nonan-2-yl)methanone; | 12 |
| 420 | (7-Ethyl-7-((5-(trifluoromethyl)pyridin-2-yl)oxy)-2-azaspiro[3.5]nonan-2-yl)((1s,3s)-3-hydroxy-3-methylcyclobutyl)methanone; | 33 |
| 421 | ((1s,3s)-3-Hydroxy-3-methylcyclobutyl)(7-((6-(trifluoromethyl)pyridin-2-yl)oxy)-2-azaspiro[3.5]nonan-2-yl)methanone; | 84 |
| 422 | (7-((5-(1,1-Difluoroethyl)pyridin-2-yl)oxy)-2-azaspiro[3.5]nonan-2-yl)((1s,3s)-3-hydroxy-3-methylcyclobutyl)methanone; | 24 |
| 423 | (7-((5-(Difluoromethyl)pyridin-2-yl)oxy)-2-azaspiro[3.5]nonan-2-yl)((1s,3s)-3-hydroxy-3-methylcyclobutyl)methanone; | 188 |

TABLE 3-continued

| Ex # | Compound Name | MGL IC$_{50}$ (nM) |
|---|---|---|
| 424 | ((1s,3s)-3-Hydroxy-3-methylcyclobutyl)(7-((6-(trifluoromethyl)pyridin-3-yl)oxy)-2-azaspiro[3.5]nonan-2-yl)methanone; | 99 |
| 425 | (7-((6-(tert-Butyl)pyridin-2-yl)oxy)-2-azaspiro[3.5]nonan-2-yl)((1s,3s)-3-hydroxy-3-methylcyclobutyl)methanone; | 7.8 |
| 426 | (7-((5-Cyclopropylpyridin-2-yl)oxy)-2-azaspiro[3.5]nonan-2-yl)((1s,3s)-3-hydroxy-3-methylcyclobutyl)methanone; | 20 |
| 427 | ((1s,3s)-3-Hydroxy-3-methylcyclobutyl)(7-((5-(trifluoromethoxy)pyridin-2-yl)oxy)-2-azaspiro[3.5]nonan-2-yl)methanone; | 28 |
| 428 | (7-((5,6-Dimethylpyridin-2-yl)oxy)-2-azaspiro[3.5]nonan-2-yl)((1s,3s)-3-hydroxy-3-methylcyclobutyl)methanone; | 47 |
| 429 | (7-((3,6-Dimethylpyridin-2-yl)oxy)-2-azaspiro[3.5]nonan-2-yl)((1s,3s)-3-hydroxy-3-methylcyclobutyl)methanone; | 19 |
| 430 | (7-((3,5-Dimethylpyridin-2-yl)oxy)-2-azaspiro[3.5]nonan-2-yl)((1s,3s)-3-hydroxy-3-methylcyclobutyl)methanone; | 12 |
| 431 | (7-((3-Fluoro-6-methylpyridin-2-yl)oxy)-2-azaspiro[3.5]nonan-2-yl)((1s,3s)-3-hydroxy-3-methylcyclobutyl)methanone; | 97 |
| 432 | (7-((3-Fluoro-5-methylpyridin-2-yl)oxy)-2-azaspiro[3.5]nonan-2-yl)((1s,3s)-3-hydroxy-3-methylcyclobutyl)methanone; | 71 |
| 433 | (7-((5-Ethyl-3-fluoropyridin-2-yl)oxy)-2-azaspiro[3.5]nonan-2-yl)((1s,3s)-3-hydroxy-3-methylcyclobutyl)methanone; | 14 |
| 434 | (7-((5-Chloro-6-methylpyridin-2-yl)oxy)-2-azaspiro[3.5]nonan-2-yl)((1s,3s)-3-hydroxy-3-methylcyclobutyl)methanone; | 25 |
| 435 | (7-((3-Chloro-6-methylpyridin-2-yl)oxy)-2-azaspiro[3.5]nonan-2-yl)((1s,3s)-3-hydroxy-3-methylcyclobutyl)methanone; | 8.4 |
| 436 | (7-((3-Chloro-5-methylpyridin-2-yl)oxy)-2-azaspiro[3.5]nonan-2-yl)((1s,3s)-3-hydroxy-3-methylcyclobutyl)methanone; | 13 |
| 437 | (7-((5-Chloro-3-methylpyridin-2-yl)oxy)-2-azaspiro[3.5]nonan-2-yl)((1s,3s)-3-hydroxy-3-methylcyclobutyl)methanone; | 3.7 |
| 438 | (7-((5-(Difluoromethyl)-6-methylpyridin-2-yl)oxy)-2-azaspiro[3.5]nonan-2-yl)((1s,3s)-3-hydroxy-3-methylcyclobutyl)methanone; | 32 |
| 439 | (7-((6-(Difluoromethyl)-5-ethylpyridin-2-yl)oxy)-2-azaspiro[3.5]nonan-2-yl)((1s,3s)-3-hydroxy-3-methylcyclobutyl)methanone; | 1.8 |
| 440 | (7-((5-(Difluoromethyl)-6-ethylpyridin-2-yl)oxy)-2-azaspiro[3.5]nonan-2-yl)((1s,3s)-3-hydroxy-3-methylcyclobutyl)methanone; | 15 |
| 441 | (7-((3-(Difluoromethyl)-6-ethylpyridin-2-yl)oxy)-2-azaspiro[3.5]nonan-2-yl)((1s,3s)-3-hydroxy-3-methylcyclobutyl)methanone; | 14 |
| 442 | ((1s,3s)-3-Hydroxy-3-methylcyclobutyl)(7-((4-methyl-5-(trifluoromethyl)pyridin-2-yl)oxy)-2-azaspiro[3.5]nonan-2-yl)methanone; | 9.6 |
| 443 | ((1s,3s)-3-Hydroxy-3-methylcyclobutyl)(7-((6-methyl-3-(trifluoromethyl)pyridin-2-yl)oxy)-2-azaspiro[3.5]nonan-2-yl)methanone; | 17 |
| 444 | ((1s,3*R)-3-Hydroxy-3-methylcyclobutyl)((6*S,7*S)-6-methyl-7-((6-methyl-5-(trifluoromethyl)pyridin-2-yl)oxy)-2-azaspiro[3.5]nonan-2-yl)methanone; | 4.8 |
| 445 | ((1s,3*S)-3-Hydroxy-3-methylcyclobutyl)((6*R,7*R)-6-methyl-7-((6-methyl-5-(trifluoromethyl)pyridin-2-yl)oxy)-2-azaspiro[3.5]nonan-2-yl)methanone; | 33 |
| 446 | ((1s,3s)-3-Hydroxy-3-methylcyclobutyl)(7-((3-methyl-5-(trifluoromethyl)pyridin-2-yl)oxy)-2-azaspiro[3.5]nonan-2-yl)methanone; | 0.76 |
| 447 | ((1s,3s)-3-Hydroxy-3-methylcyclobutyl)(7-((6-methyl-4-(trifluoromethyl)pyridin-2-yl)oxy)-2-azaspiro[3.5]nonan-2-yl)methanone; | 110 |
| 448 | ((1s,3s)-3-Hydroxy-3-methylcyclobutyl)(7-((6-methyl-5-(trifluoromethyl)pyridin-2-yl)oxy)-2-azaspiro[3.5]nonan-2-yl)methanone; | 2.4 |
| 449 | ((1s,3s)-3-Hydroxy-3-methylcyclobutyl)(7-((3-methyl-6-(trifluoromethyl)pyridin-2-yl)oxy)-2-azaspiro[3.5]nonan-2-yl)methanone; | 8.5 |
| 450 | (7-((5-Ethyl-6-(trifluoromethyl)pyridin-2-yl)oxy)-2-azaspiro[3.5]nonan-2-yl)((1s,3s)-3-hydroxy-3-methylcyclobutyl)methanone; | 2.9 |
| 451 | ((1s,3s)-3-Hydroxy-3-methylcyclobutyl)(7-((5-methyl-6-(trifluoromethyl)pyridin-2-yl)oxy)-2-azaspiro[3.5]nonan-2-yl)methanone; | 8.2 |
| 452 | ((1r,3s)-3-Ethyl-3-hydroxycyclobutyl)(7-((5-methyl-6-(trifluoromethyl)pyridin-2-yl)oxy)-2-azaspiro[3.5]nonan-2-yl)methanone; | 20 |
| 453 | ((1s,3s)-3-(Difluoromethyl)-3-hydroxycyclobutyl)(7-((5-methyl-6-(trifluoromethyl)pyridin-2-yl)oxy)-2-azaspiro[3.5]nonan-2-yl)methanone; | 19 |
| 454 | (7-((5-Ethyl-6-methoxypyridin-2-yl)oxy)-2-azaspiro[3.5]nonan-2-yl)((1s,3s)-3-hydroxy-3-methylcyclobutyl)methanone; | 2.2 |

TABLE 3-continued

| Ex # | Compound Name | MGL IC$_{50}$ (nM) |
|---|---|---|
| 455 | (7-((5-Cyclopropyl-6-methoxypyridin-2-yl)oxy)-2-azaspiro[3.5]nonan-2-yl)((1s,3s)-3-hydroxy-3-methylcyclobutyl)methanone; | 1.3 |
| 456 | ((1s,3s)-3-Hydroxy-3-methylcyclobutyl)(7-((6-methoxy-5-methylpyridin-2-yl)oxy)-2-azaspiro[3.5]nonan-2-yl)methanone; | 19 |
| 457 | (7-((3-Fluoro-5-(trifluoromethyl)pyridin-2-yl)oxy)-2-azaspiro[3.5]nonan-2-yl)((1s,3s)-3-hydroxy-3-methylcyclobutyl)methanone; | 13 |
| 458 | ((1s,3s)-3-Hydroxy-3-methylcyclobutyl)(7-((6-methoxy-5-(trifluoromethyl)pyridin-2-yl)oxy)-2-azaspiro[3.5]nonan-2-yl)methanone; | 0.55 |
| 459 | (7-((6-Ethoxy-5-(trifluoromethyl)pyridin-2-yl)oxy)-2-azaspiro[3.5]nonan-2-yl)((1s,3s)-3-hydroxy-3-methylcyclobutyl)methanone; | 0.22 |
| 460 | (7-((5-Chloro-4-methoxypyridin-2-yl)oxy)-2-azaspiro[3.5]nonan-2-yl)((1s,3s)-3-hydroxy-3-methylcyclobutyl)methanone; | 142 |
| 461 | (7-((5-Chloro-6-methoxypyridin-2-yl)oxy)-2-azaspiro[3.5]nonan-2-yl)((1s,3s)-3-hydroxy-3-methylcyclobutyl)methanone; | 6.1 |
| 462 | (7-((3-Chloro-6-methoxypyridin-2-yl)oxy)-2-azaspiro[3.5]nonan-2-yl)((1s,3s)-3-hydroxy-3-methylcyclobutyl)methanone; | 6.8 |
| 463 | (7-((5-Chloro-3-methoxypyridin-2-yl)oxy)-2-azaspiro[3.5]nonan-2-yl)((1s,3s)-3-hydroxy-3-methylcyclobutyl)methanone; | 9.7 |
| 464 | (7-((3-Chloro-4-methoxypyridin-2-yl)oxy)-2-azaspiro[3.5]nonan-2-yl)((1s,3s)-3-hydroxy-3-methylcyclobutyl)methanone; | 81 |
| 465 | (7-((4,6-Dimethyl-5-(trifluoromethyl)pyridin-2-yl)oxy)-2-azaspiro[3.5]nonan-2-yl)((1s,3s)-3-hydroxy-3-methylcyclobutyl)methanone; | 2.7 |
| 466 | (7-((3,6-Dimethyl-5-(trifluoromethyl)pyridin-2-yl)oxy)-2-azaspiro[3.5]nonan-2-yl)((1s,3s)-3-hydroxy-3-methylcyclobutyl)methanone; | 0.10 |
| 467 | ((1s,3s)-3-Hydroxy-3-methylcyclobutyl)(7-((5-(trifluoromethyl)pyrimidin-2-yl)oxy)-2-azaspiro[3.5]nonan-2-yl)methanone; | 858 |
| 468 | (7-((6,7-Dihydro-5H-cyclopenta[b]pyridin-2-yl)oxy)-2-azaspiro[3.5]nonan-2-yl)((1s,3s)-3-hydroxy-3-methylcyclobutyl)methanone; | 29 |
| 469 | ((1s,3s)-3-Hydroxy-3-methylcyclobutyl)(7-((1-methyl-1H-pyrrolo[2,3-b]pyridin-6-yl)oxy)-2-azaspiro[3.5]nonan-2-yl)methanone; | 18 |
| 470 | (7-((1,4-Dimethyl-1H-pyrrolo[2,3-b]pyridin-6-yl)oxy)-2-azaspiro[3.5]nonan-2-yl)((1s,3s)-3-hydroxy-3-methylcyclobutyl)methanone; | 11 |
| 471 | (7-((1,3-Dimethyl-1H-pyrrolo[2,3-b]pyridin-6-yl)oxy)-2-azaspiro[3.5]nonan-2-yl)((1s,3s)-3-hydroxy-3-methylcyclobutyl)methanone; | 2.0 |
| 472 | (7-((1,2-Dimethyl-1H-pyrrolo[2,3-b]pyridin-6-yl)oxy)-2-azaspiro[3.5]nonan-2-yl)((1s,3s)-3-hydroxy-3-methylcyclobutyl)methanone; | 26 |
| 473 | (7-((1,5-Dimethyl-1H-pyrrolo[2,3-b]pyridin-6-yl)oxy)-2-azaspiro[3.5]nonan-2-yl)((1s,3s)-3-hydroxy-3-methylcyclobutyl)methanone; | 1.2 |
| 474 | (7-((3-Fluoro-1-methyl-1H-pyrrolo[2,3-b]pyridin-6-yl)oxy)-2-azaspiro[3.5]nonan-2-yl)((1s,3s)-3-hydroxy-3-methylcyclobutyl)methanone; | 5.5 |
| 475 | (7-((1-Ethyl-3-fluoro-1H-pyrrolo[2,3-b]pyridin-6-yl)oxy)-2-azaspiro[3.5]nonan-2-yl)((1s,3s)-3-hydroxy-3-methylcyclobutyl)methanone; | 4.6 |
| 476 | ((1s,3s)-3-Hydroxy-3-methylcyclobutyl)(7-((1-methyl-3-(trifluoromethyl)-1H-pyrrolo[2,3-b]pyridin-6-yl)oxy)-2-azaspiro[3.5]nonan-2-yl)methanone; | 1.4 |
| 477 | ((1s,3s)-3-Hydroxy-3-methylcyclobutyl)(7-((1-methyl-1H-pyrazolo[3,4-b]pyridin-6-yl)oxy)-2-azaspiro[3.5]nonan-2-yl)methanone; | 146 |
| 478 | ((1s,3s)-3-Hydroxy-3-methylcyclobutyl)(2-(3-methoxy-5-methylphenyl)-7-azaspiro[3.5]nonan-7-yl)methanone; | 203 |
| 479 | ((1s,3s)-3-Hydroxy-3-methylcyclobutyl)(2-(2-methyl-4-(trifluoromethyl)phenoxy)-7-azaspiro[3.5]nonan-7-yl)methanone; | 3.1 |
| 480 | ((1s,3s)-3-Hydroxy-3-methylcyclobutyl)(2-(3-methyl-4-(trifluoromethyl)phenoxy)-7-azaspiro[3.5]nonan-7-yl)methanone; | 5.8 |
| 481 | ((1s,3s)-3-Hydroxy-3-methylcyclobutyl)(2-((3-methyl-5-(trifluoromethyl)pyridin-2-yl)oxy)-7-azaspiro[3.5]nonan-7-yl)methanone; and | 15 |
| 482 | ((1s,3s)-3-Hydroxy-3-methylcyclobutyl)(2-((6-methyl-5-(trifluoromethyl)pyridin-2-yl)oxy)-7-azaspiro[3.5]nonan-7-yl)methanone; | 61 |

NT means Not tested.

What is claimed is:

1. A compound of Formula (I):

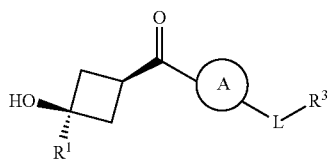
(I)

wherein $R^1$ is $C_{1-4}$alkyl or $C_{1-4}$haloalkyl;

Ⓐ is

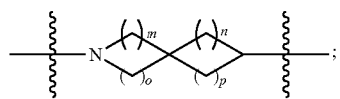

wherein m, n, o, and p are each independently 1 or 2; and wherein Ⓐ is optionally substituted with one, two, and three $R^2$ members;
  wherein each $R^2$ is independently H, halo, OH, $C_{1-4}$alkyl, or $OC_{1-4}$alkyl;

L is a bond, $C_{1-4}$alkyl, $C_{1-4}$haloalkyl, or O; and $R^3$ is:
  (a) phenyl optionally substituted with one, two or three members each independently selected from halo, $C_{1-4}$alkyl, $C_{1-4}$haloalkyl, $OC_{1-4}$alkyl, $OC_{1-4}$haloalkyl, $N(C_{1-4}$alkyl$)_2$, pyrrolidinyl, $C_{3-6}$cycloalkyl, $OC_{3-6}$cycloalkyl, 1H-pyrazol-1-yl, and 1-methyl-1H-imidazol-4-yl;
  (b) a 6-membered heteroaryl optionally substituted with one, two, or three members each independently selected from halo, $C_{1-4}$alkyl, $C_{1-4}$haloalkyl, $OC_{1-4}$alkyl, $OC_{1-4}$haloalkyl, $C_{3-6}$cycloalkyl, and $C_{3-6}$cycloalkyl substituted with $C_{1-4}$alkyl or $C_{1-4}$haloalkyl;
  (c) a 5-membered heteroaryl optionally substituted with one, two, or three members each independently selected from $C_{1-4}$alkyl, $C_{1-4}$haloalkyl, $OC_{1-4}$alkyl, $OC_{1-4}$haloalkyl, and phenyl;
  (d) a fused 5-6 heteroaryl or a fused 6-6 heteroaryl each optionally substituted with one, two, or three members each independently selected from halo, $C_{1-4}$alkyl, $C_{1-4}$haloalkyl, $OC_{1-4}$alkyl, and $OC_{1-4}$haloalkyl; or
  (e) 2,3-dihydro-1H-indenyl, 2,3-dihydrobenzofuranyl, 4,5,6,7-tetrahydropyrazolo[1,5-a]pyridinyl, 5,6,7,8-tetrahydroimidazo[1,2-a]pyridinyl, 5,6,7,8-tetrahydroimidazo[1,5-a]pyridinyl, or 6,7-dihydro-5H-cyclopenta[b]pyridinyl;

or a pharmaceutically acceptable salt, isotope, N-oxide, solvate, or stereoisomer thereof.

2. The compound of claim 1, wherein $R^1$ is $CH_3$, $CH_2CH_3$, or $CF_2H$.

3. The compound of claim 1, wherein Ⓐ is

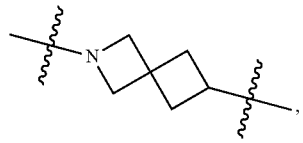

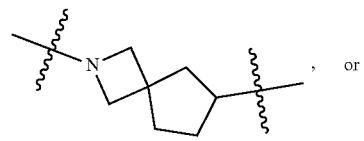
, or

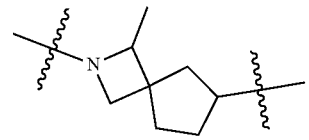
.

4. The compound of claim 1, wherein Ⓐ is

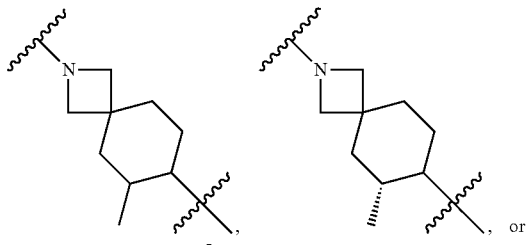
, or or Ⓐ is

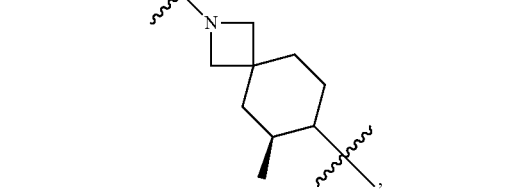

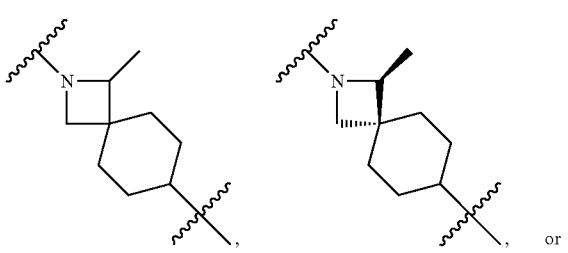
, or

5. The compound of claim 1, wherein (A) is

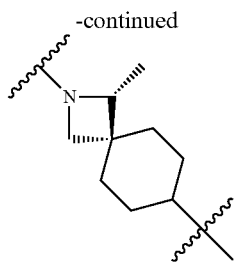

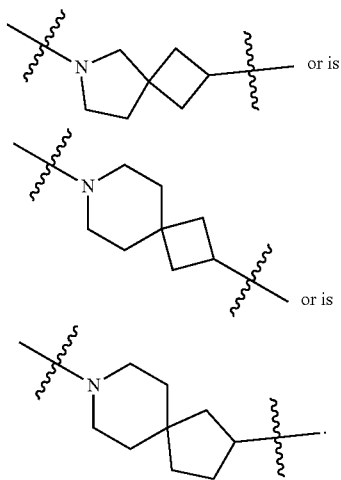

6. The compound of claim 1, wherein R² is H, or is OH, or is OCH₃, or is CH₃, or is CH₂CH₃, or is F.

7. The compound of claim 1, wherein R² is H, OH, OCH₃, CH₃, CH₂CH₃, or F, and (A) is

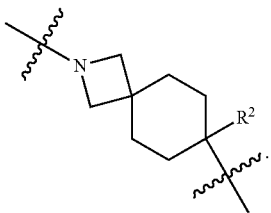

8. The compound of claim 1, wherein L is a bond, or is CH₂, or is CH(CH₃), or is CF₂, or is O.

9. The compound of claim 1, wherein R³ is:
phenyl optionally substituted with one two, or three members each independently selected from halo, $C_{1-4}$alkyl, $C_{1-4}$haloalkyl, $OC_{1-4}$alkyl, $OC_{1-4}$haloalkyl, $N(CH_3)_2$, pyrrolidin-1-yl, 1H-pyrazol-1-yl, 1-methyl-1H-imidazol-4-yl, $C_{3-6}$cycloalkyl, and $OC_{3-6}$cycloalkyl; or
phenyl substituted with one or two members independently selected from Cl, F, CH₃, CH₂CH₃, CH(CH₃)₂, C(CH₃)₃, OCH₃, OCH₂CH₃, CHF₂, CF₃, CF₂CH₃, OCHF₂, OCF₃, N(CH₃)₂, cyclopropyl, cyclobutyl, O-cyclopropyl 1H-pyrazol-1-yl, pyrrolidin-1-yl, and 1-methyl-1H-imidazol-4-yl; or phenyl, o-tolyl, m-tolyl, p-tolyl, 2-ethylphenyl, 3-ethylphenyl, 4-ethylphenyl, 2-isopropylphenyl, 3-isopropylphenyl, 4-isopropylphenyl, 2-(tert-butyl)phenyl, 3-(tert-butyl)phenyl, 4-(tert-butyl)phenyl, 3-(difluoromethyl)phenyl, 4-(difluoromethyl)phenyl, 2-(trifluoromethyl)phenyl, 3-(trifluoromethyl)phenyl, 4-(trifluoromethyl)phenyl, 3-(1,1-difluoroethyl)phenyl, 4-(1,1-difluoroethyl)phenyl, 2-methoxyphenyl, 3-methoxyphenyl, 4-methoxyphenyl, 3-(difluoromethoxy)phenyl, 4-(difluoromethoxy)phenyl, 2-(trifluoromethoxy)phenyl, 3-(trifluoromethoxy)phenyl, 4-(trifluoromethoxy)phenyl, 2-cyclopropylphenyl, 3-cyclopropylphenyl, 4-cyclopropylphenyl, 3-cyclobutylphenyl, 4-cyclopropoxyphenyl, 3-(1H-pyrazol-1-yl)phenyl, 4-(1H-pyrazol-1-yl)phenyl, 3-(1-methyl-1H-imidazol-4-yl)phenyl, or 3-(pyrrolidin-1-yl)phenyl; or
2,4-dimethylphenyl, 2,6-dimethylphenyl, 3,5-dimethylphenyl, 3,4-dimethylphenyl, 2,3-dimethylphenyl, 3-ethyl-5-methylphenyl, 3-fluoro-4-methylphenyl, 2-fluoro-4-methylphenyl, 4-fluoro-3-methylphenyl, 3-fluoro-2-methylphenyl, 2-fluoro-6-methylphenyl, 3-fluoro-5-methylphenyl, 2-fluoro-5-methylphenyl, 5-fluoro-2-methylphenyl, 2-fluoro-3-methylphenyl, 4-fluoro-2-methylphenyl, 3-fluoro-5-isopropylphenyl, 4-chloro-2-methylphenyl, 4-chloro-3-methylphenyl, 2-chloro-5-methylphenyl, 3-chloro-4-methylphenyl, 3-chloro-2-methylphenyl, 4-chloro-3-ethylphenyl, 3-(difluoromethyl)-5-methylphenyl, 3-(difluoromethyl)-4-methylphenyl, 4-(difluoromethyl)-3-methylphenyl, 2-methyl-5-(trifluoromethyl)phenyl, 4-methyl-3-(trifluoromethyl)phenyl, 3-methyl-5-(trifluoromethyl)phenyl, 3-methyl-4-(trifluoromethyl)phenyl, 2-methyl-3-(trifluoromethyl)phenyl, 2-methyl-6-(trifluoromethyl)phenyl, 5-methyl-2-(trifluoromethyl)phenyl, 4-methyl-2-(trifluoromethyl)phenyl, 3-methyl-2-(trifluoromethyl)phenyl, 2-methyl-4-(trifluoromethyl)phenyl, 3-ethyl-5-(trifluoromethyl)phenyl, 2-isopropyl-3-(trifluoromethyl)phenyl, 3-isopropyl-2-(trifluoromethyl)phenyl, 3-fluoro-5-methoxyphenyl, 2-fluoro-3-methoxyphenyl, 4-fluoro-3-methoxyphenyl, 3-ethoxy-5-fluorophenyl, 3-chloro-5-methoxyphenyl, 4-chloro-3-methoxyphenyl, 2-chloro-3-methoxyphenyl, 2-methoxy-3-methylphenyl, 3-methoxy-5-methylphenyl, 3-methoxy-2-methylphenyl, 4-methoxy-3-methylphenyl, 3-methoxy-4-methylphenyl, 5-methoxy-2-methylphenyl, 3-ethyl-5-methoxyphenyl, 3-ethyl-2-methoxyphenyl, 3-(tert-butyl)-4-methoxyphenyl, 2-(difluoromethyl)-4-methoxyphenyl, 4-(difluoromethyl)-2-methoxyphenyl, 4-methoxy-2-(trifluoromethyl)phenyl, 3-ethoxy-4-methylphenyl, 3-ethoxy-2-methylphenyl, 3-isopropoxy-2-methylphenyl, 4-(difluoromethoxy)-2-methylphenyl, 3-(difluoromethoxy)-5-methylphenyl, 5-(difluoromethoxy)-2-methylphenyl, 3-(difluoromethoxy)-4-methylphenyl, 4-(difluoromethoxy)-3-methylphenyl, 2-methyl-4-(trifluoromethoxy)phenyl, 3-methyl-5-(trifluoromethoxy)phenyl, 4-methyl-3-(trifluoromethoxy)phenyl, 3-methyl-4-(trifluoromethoxy)phenyl, 4-methoxy-3-(trifluoromethyl)phenyl, 3-methoxy-5-(trifluoromethyl)phenyl, 3-methoxy-4-(trifluoromethyl)phenyl, 4-ethoxy-3-(trifluoromethyl)phenyl, 3-ethoxy-5-(trifluoromethyl)phenyl, 3-chloro-5-(trifluoromethoxy)phenyl, 3-ethyl-5-(trifluoromethoxy)phenyl, 3-(dimethylamino)-5-(trifluoromethyl)phenyl, 3-(dimethylamino)-4-(trifluoromethyl)phenyl, 4-cyclopropyl-3- fluorophenyl, 3-cyclopropyl-2-fluorophenyl, 5-cyclopropyl-2-fluorophenyl, 3-cyclopropyl-4-fluorophenyl, 3-cyclopropyl-2-methylphenyl, 3-cyclopropyl-5-methylphenyl, 4-cyclopropyl-3-methylphenyl, 2-cyclopropyl-3-methylphenyl, 3-cyclopropyl-4-methylphenyl, 4-cyclopropyl-2-methylphenyl, 3-cyclopropyl-5-methoxyphenyl, 3-cyclopropyl-4-methoxyphenyl, 4-cyclopropyl-3-methoxyphenyl, 3-cyclopropoxy-2-methylphenyl, 3-fluoro-5-methoxy-4-methylphenyl, 2,5-difluoro-3-methoxyphenyl, or 2,3-difluoro-5-methoxyphenyl; or

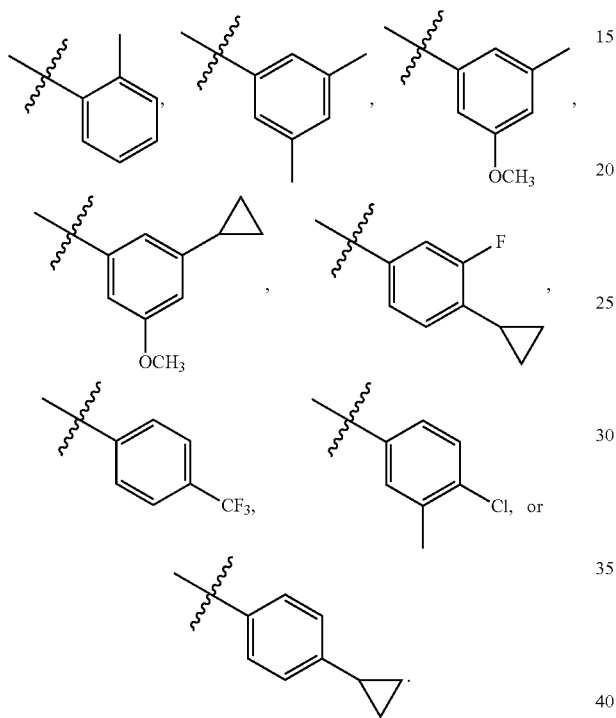

10. The compound of claim 1, wherein $R^3$ is:
pyrazin-2-yl substituted with $C(CH_3)_3$; pyrimidin-2-yl substituted with CF or $C(CH_3)_3$; or pyridine optionally substituted with one, two or three members each independently selected from Cl, F, $CH_3$, $CH_2CH_3$, $CH(CH_3)_2$, $C(CH_3)_3$, $CF_2H$, $CF_3$, $CF_2CH_3$, $OCH_3$, $OCH_2CH_3$, $OCH(CH_3)_2$, $OCF_2H$, $OCF_3$, cyclopropyl, and cyclopropyl substituted with $CH_3$ or $CF_3$; or pyridin-2-yl, pyridin-3-yl, pyridin-4-yl, 4-(tert-butyl)pyridin-2-yl, 6-(tert-butyl)pyridin-2-yl, 2-(tert-butyl)pyridin-4-yl, 5-(difluoromethyl)pyridin-2-yl, 1,1-difluoroethyl)pyridin-2-yl, 4-(trifluoromethyl)pyridin-2-yl, 5-(trifluoromethyl)pyridin-2-yl, 6-(trifluoromethyl)pyridin-2-yl, 6-(trifluoromethyl)pyridin-3-yl, 6-methoxypyridin-2-yl, 5-(trifluoromethoxy)pyridin-2-yl, 6-(1-(trifluoromethyl)cyclopropyl)pyridin-2-yl, 3-fluoro-5-methylpyridin-2-yl, 3-fluoro-6-methylpyridin-2-yl, 5-ethyl-3-fluoropyridin-2-yl, 5-chloro-3-methylpyridin-2-yl, 3-chloro-5-methylpyridin-2-yl, 3-chloro-6-methylpyridin-2-yl, 5-chloro-6-methylpyridin-2-yl, 5-chloro-4-methoxypyridin-2-yl, 5-chloro-6-methoxypyridin-2-yl, 3-chloro-6-methoxypyridin-2-yl, 5-chloro-3-methoxypyridin-2-yl, 3-chloro-4-methoxypyridin-2-yl, 3,5-dimethylpyridin-2-yl, 3,6-dimethylpyridin-2-yl, 5,6-dimethylpyridin-2-yl, 6-isopropyl-5-methylpyridin-2-yl, 5-(difluoromethyl)-6-methylpyridin-2-yl, 5-(difluoromethyl)-6-ethylpyridin-2-yl, 6-(difluoromethyl)-5-ethylpyridin-2-yl, 3-(difluoromethyl)-6-ethylpyridin-2-yl, 3-fluoro-5-(trifluoromethyl)pyridin-2-yl, 6-methyl-4-(trifluoromethyl)pyridin-2-yl, 6-methyl-3-(trifluoromethyl)pyridin-2-yl, 3-methyl-5-(trifluoromethyl)pyridin-2-yl, 4-methyl-5-(trifluoromethyl)pyridin-2-yl, 6-methyl-5-(trifluoromethyl)pyridin-2-yl, 3-methyl-6-(trifluoromethyl)pyridin-2-yl, 5-methyl-6-(trifluoromethyl)pyridin-2-yl, 5-ethyl-6-(trifluoromethyl)pyridin-2-yl, 4,6-dimethyl-5-(trifluoromethyl)pyridin-2-yl, 3,6-dimethyl-5-(trifluoromethyl)pyridin-2-yl, 6-methoxy-5-methylpyridin-2-yl, 5-ethyl-6-methoxypyridin-2-yl, 5-cyclopropyl-6-methoxypyridin-2-yl, 4-methoxy-6-methylpyridin-2-yl, 6-isopropoxy-5-methylpyridin-2-yl, 6-methoxy-5-(trifluoromethyl)pyridin-2-yl, 6-ethoxy-5-(trifluoromethyl)pyridin-2-yl, 6-isopropoxy-5-(trifluoromethyl)pyridin-2-yl, 6-isopropoxy-4-methylpyridin-2-yl, 2-isopropoxy-3-methylpyridin-4-yl, 5-cyclopropylpyridin-2-yl, 6-(1-methylcyclopropyl)pyridin-2-yl, 5-(difluoromethoxy)-6-methylpyridin-2-yl, 6-(tert-butyl)pyrazin-2-yl, 4-(tert-butyl)pyrimidin-2-yl, or 5-(trifluoromethyl)pyrimidin-2-yl; or pyrazolyl, imidazolyl, triazolyl, isoxazolyl, oxazolyl, oxadiazolyl, tetrazolyl, isothiazolyl, thiazolyl, or thiadiazolyl, each optionally substituted with one, two or three members independently selected from $C_{1-4}$alkyl, $C_{1-4}$haloalkyl, $OC_{1-4}$alkyl, $OC_{1-4}$haloalkyl, and phenyl, or each optionally substituted with one or two members independently selected from $C_{1-4}$ alkyl and $C_{1-4}$haloalkyl; or pyrazolyl, imidazolyl, or isoxazolyl, each optionally substituted with one or two members each independently selected from $C_{1-4}$alkyl and $C_{1-4}$haloalkyl; or

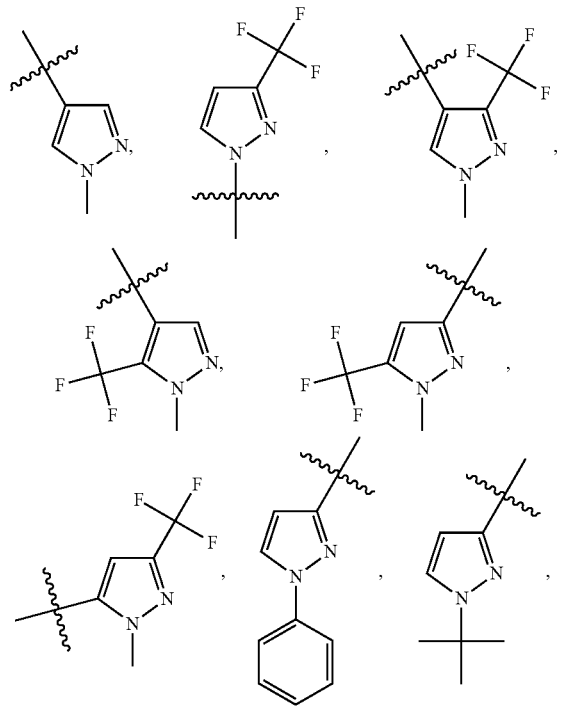

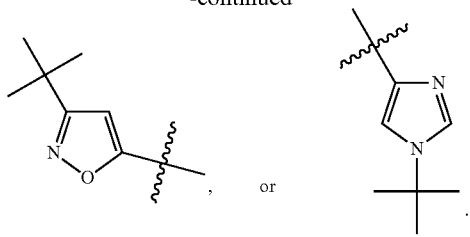

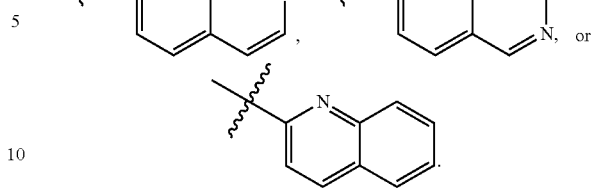

11. The compound of claim 1, wherein $R^3$ is:

1H-indazolyl, 2H-indazolyl, 1H-pyrrolo[2,3-b]pyridinyl, 1H-pyrrolo[3,2-c]pyridinyl, pyrrolo[1,2-b]pyridazinyl, 1H-pyrazolo[3,4-b]pyridinyl, pyrazolo[1,5-a]pyridinyl, imidazo[1,2-a]pyridinyl, imidazo[1,5-a]pyridinyl, 1H-benzo[d]imidazolyl, each optionally substituted with one, two, or three members each independently selected from halo, $C_{1-4}$alkyl, $C_{1-4}$haloalkyl, $OC_{1-4}$alkyl, and $OC_{1-4}$haloalkyl, or each optionally substituted with one or two members each independently selected from F, $CH_3$, $CH_2CH_3$, $CH(CH_3)_2$, $CF_3$, and $CH_2CF_3$; or 1-methyl-1H-indazol-4-yl, 1-methyl-1H-indazol-5-yl, 1-methyl-1H-indazol-6-yl, 1-methyl-1H-indazol-7-yl, 1-isopropyl-1H-indazol-6-yl, 2-isopropyl-2H-indazol-6-yl, 1-(2,2,2-trifluoroethyl)-1H-indazol-6-yl, 7-fluoro-1-methyl-1H-indazol-6-yl, 5-fluoro-1-methyl-1H-indazol-6-yl, 4-fluoro-1-methyl-1H-indazol-6-yl, 1,3-dimethyl-1H-indazol-6-yl, 1,4-dimethyl-1H-indazol-6-yl, 1,5-dimethyl-1H-indazol-6-yl, 1H-pyrrolo[2,3-b]pyridin-1-yl, 1-methyl-1H-pyrrolo[2,3-b]pyridin-3-yl, 1-methyl-1H-pyrrolo[2,3-b]pyridin-5-yl, 1-methyl-1H-pyrrolo[2,3-b]pyridin-6-yl, 6-methyl-1H-pyrrolo[2,3-b]pyridin-1-yl, 2-methyl-1H-pyrrolo[2,3-b]pyridin-1-yl, 6-isopropyl-1H-pyrrolo[2,3-b]pyridin-1-yl, 1-isopropyl-1H-pyrrolo[2,3-b]pyridin-6-yl, 6-(trifluoromethyl)-1H-pyrrolo[2,3-b]pyridin-1-yl, 2-(trifluoromethyl)-1H-pyrrolo[2,3-b]pyridin-1-yl, difluoro(1-methyl-1H-pyrrolo[2,3-b]pyridin-6-yl, 1-(2,2,2-trifluoroethyl)-1H-pyrrolo[2,3-b]pyridin-6-yl, 1,2-dimethyl-1H-pyrrolo[2,3-b]pyridin-6-yl, 1,3-dimethyl-1H-pyrrolo[2,3-b]pyridin-6-yl, 1,4-dimethyl-1H-pyrrolo[2,3-b]pyridin-6-yl, 1,5-dimethyl-1H-pyrrolo[2,3-b]pyridin-6-yl, 3-fluoro-1-methyl-1H-pyrrolo[2,3-b]pyridin-6-yl, 1-ethyl-3-fluoro-1H-pyrrolo[2,3-b]pyridin-6-yl, 1-methyl-3-(trifluoromethyl)-1H-pyrrolo[2,3-b]pyridin-6-yl, 1-methyl-1H-pyrrolo[3,2-c]pyridin-6-yl, pyrrolo[1,2-b]pyridazin-3-yl, 1-methyl-1H-pyrazolo[3,4-b]pyridin-6-yl, pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl, imidazo[1,2-a]pyridin-2-yl, imidazo[1,2-a]pyridin-3-yl, imidazo[1,2-a]pyridin-5-yl, imidazo[1,2-a]pyridin-7-yl, imidazo[1,2-a]pyridin-8-yl, imidazo[1,5-a]pyridin-1-yl, 1-methyl-1H-benzo[d]imidazol-2-yl, or 1-methyl-1H-benzo[d]imidazol-5-yl.

12. The compound of claim 1, wherein $R^3$ is:

a fused 6-6 heteroaryl optionally substituted with one, two, or three members each independently selected from halo, $C_{1-4}$alkyl, $C_{1-4}$haloalkyl, $OC_{1-4}$alkyl, and $OC_{1-4}$haloalkyl; or quinolinyl or isoquinolinyl, each optionally substituted with one or two members independently selected from halo $C_{1-4}$alkyl, $C_{1-4}$haloalkyl $OC_{1-4}$alkyl, and $OC_{1-4}$haloalkyl; or

13. The compound of claim 1, wherein $R^3$ is 6,7-dihydro-5H-cyclopenta[b]pyridin-2-yl, 5,6,7,8-tetrahydroimidazo[1,2-a]pyridin-2-yl, or 4,5,6,7-tetrahydropyrazolo[1,5-a]pyridin-2-yl.

14. The compound of claim 1, wherein $R^3$ is

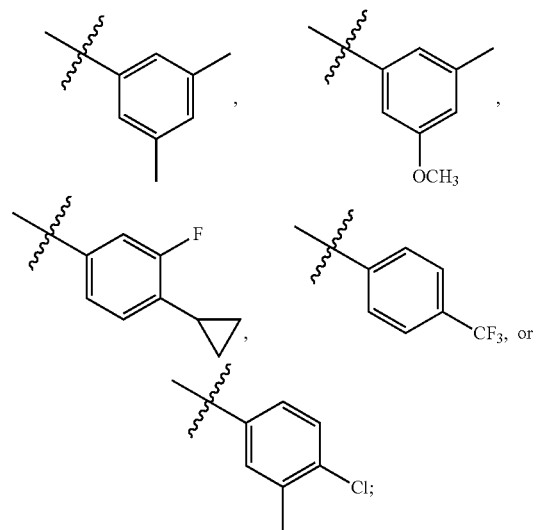

and A is

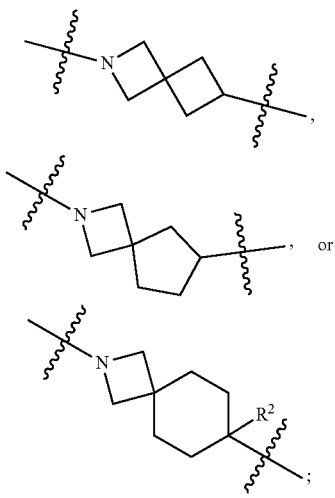

optionally wherein $R^1$ is $CH_3$, $CH_2CH_3$, or $CF_2H$.

15. The compound of claim 1, wherein
L is a bond; and
A is

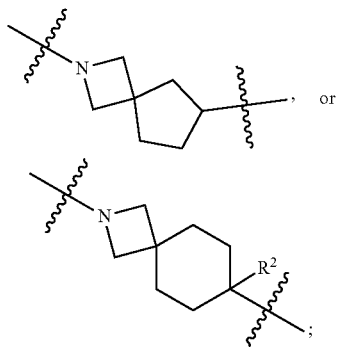

optionally wherein R¹ is CH₃, CH₂CH₃, or CF₂H.

16. The compound of claim 1, wherein
L is a bond; and
R³ is

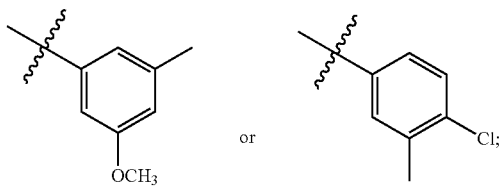

optionally wherein R¹ is CH₃, CH₂CH₃, or CF₂H.

17. The compound of claim 1, wherein R¹ is CH₃ and R² is H.

18. A compound selected from:
(6-(3-(tert-Butyl)phenyl)-2-azaspiro[3.3]heptan-2-yl)((1s,3s)-3-hydroxy-3-methylcyclobutyl)methanone;
(6-(4-(tert-Butyl)phenyl)-2-azaspiro[3.3]heptan-2-yl)((1s,3s)-3-hydroxy-3-methylcyclobutyl)methanone;
((1s,3s)-3-Hydroxy-3-methylcyclobutyl)(6-(3-isopropylphenyl)-2-azaspiro[3.3]heptan-2-yl)methanone;
((1s,3s)-3-Hydroxy-3-methylcyclobutyl)(6-(4-isopropylphenyl)-2-azaspiro[3.3]heptan-2-yl)methanone;
(6-(4-Cyclopropylphenyl)-2-azaspiro[3.3]heptan-2-yl)((1s,3s)-3-hydroxy-3-methylcyclobutyl)methanone;
((1s,3s)-3-Hydroxy-3-methylcyclobutyl)(6-(4-methyl-3-(trifluoromethyl)phenyl)-2-azaspiro[3.3]heptan-2-yl)methanone;
(rac)-((1s,3s)-3-Hydroxy-3-methylcyclobutyl)(6-(2-methyl-3-(trifluoromethyl)phenyl)-2-azaspiro[3.4]octan-2-yl)methanone;
(rac)-((1s,3s)-3-Hydroxy-3-methylcyclobutyl)(6-(2-methyl-4-(trifluoromethyl)phenyl)-2-azaspiro[3.4]octan-2-yl)methanone;
(rac)-((1s,3s)-3-Hydroxy-3-methylcyclobutyl)(6-(2-methyl-4-(trifluoromethoxy)phenyl)-2-azaspiro[3.4]octan-2-yl)methanonemethanone;
(rac)-(6-(4-Chloro-2-methylphenyl)-2-azaspiro[3.4]octan-2-yl)((1s,3s)-3-hydroxy-3-methylcyclobutyl)methanone;
(rac)-(6-(3-Chloro-2-methylphenyl)-2-azaspiro[3.4]octan-2-yl)((1s,3s)-3-hydroxy-3-methylcyclobutyl)methanone;
(rac)-(6-(4-(Difluoromethyl)-3-methylphenyl)-2-azaspiro[3.4]octan-2-yl)((1s,3s)-3-hydroxy-3-methylcyclobutyl)methanone;
(rac)-((1s,3s)-3-Hydroxy-3-methylcyclobutyl)(6-(3-methoxy-2-methylphenyl)-2-azaspiro[3.4]octan-2-yl)methanone;
(rac)-(6-(2,4-Dimethylphenyl)-2-azaspiro[3.4]octan-2-yl)((1s,3s)-3-hydroxy-3-methylcyclobutyl)methanone;
(rac)-(6-(4-Chloro-3-ethylphenyl)-2-azaspiro[3.4]octan-2-yl)((1s,3s)-3-hydroxy-3-methylcyclobutyl)methanone;
(rac)-(6-(2,3-Dihydro-1H-inden-5-yl)-2-azaspiro[3.4]octan-2-yl)((1s,3s)-3-hydroxy-3-methylcyclobutyl)methanone;
(rac)-((1s,3s)-3-Hydroxy-3-methylcyclobutyl)(6-(3-methoxy-4-methylphenyl)-2-azaspiro[3.4]octan-2-yl)methanone;
((1s,3*S)-3-Hydroxy-3-methylcyclobutyl)((*R)-6-(3-methoxy-4-methylphenyl)-2-azaspiro[3.4]octan-2-yl)methanone;
((1s,3*R)-3-Hydroxy-3-methylcyclobutyl)((*S)-6-(3-methoxy-4-methylphenyl)-2-azaspiro[3.4]octan-2-yl)methanone;
(6-(3-Cyclopropylphenyl)-2-azaspiro[3.3]heptan-2-yl)((1s,3s)-3-hydroxy-3-methylcyclobutyl)methanone;
((1s,3s)-3-Hydroxy-3-methylcyclobutyl)(6-(2-methyl-3-(trifluoromethyl)phenyl)-2-azaspiro[3.3]heptan-2-yl)methanone;
(7-(3-Chloro-4-methylphenyl)-2-azaspiro[3.5]nonan-2-yl)((1s,3s)-3-hydroxy-3-methylcyclobutyl)methanone;
((1s,3s)-3-Hydroxy-3-methylcyclobutyl)(6-(4-methyl-3-(trifluoromethoxy)phenyl)-2-azaspiro[3.3]heptan-2-yl)methanone;
(rac)-(6-(3-Cyclopropyl-2-fluorophenyl)-2-azaspiro[3.4]octan-2-yl)((1s,3s)-3-hydroxy-3-methylcyclobutyl)methanone;
((*R)-6-(3-Cyclopropyl-2-fluorophenyl)-2-azaspiro[3.4]octan-2-yl)((1s,3*S)-3-hydroxy-3-methylcyclobutyl)methanone;
((*S)-6-(3-Cyclopropyl-2-fluorophenyl)-2-azaspiro[3.4]octan-2-yl)((1s,3*R)-3-hydroxy-3-methylcyclobutyl)methanone;
(6-(3-Cyclopropyl-4-methylphenyl)-2-azaspiro[3.3]heptan-2-yl)((1s,3s)-3-hydroxy-3-methylcyclobutyl)methanone;
(6-(4-Cyclopropyl-2-methylphenyl)-2-azaspiro[3.3]heptan-2-yl)((1s,3s)-3-hydroxy-3-methylcyclobutyl)methanone;
(rac)-(6-(6-(tert-Butyl)pyridin-2-yl)-2-azaspiro[3.4]octan-2-yl)((1s,3s)-3-hydroxy-3-methylcyclobutyl)methanone;
((1s,3s)-3-Hydroxy-3-methylcyclobutyl)(6-(isoquinolin-7-yl)-2-azaspiro[3.3]heptan-2-yl)methanone;
((1s,3s)-3-Hydroxy-3-methylcyclobutyl)(6-(isoquinolin-6-yl)-2-azaspiro[3.3]heptan-2-yl)methanone;
((1s,3s)-3-Hydroxy-3-methylcyclobutyl)(6-(3-(pyrrolidin-1-yl)phenyl)-2-azaspiro[3.3]heptan-2-yl)methanone;
((1s,3s)-3-Hydroxy-3-methylcyclobutyl)(6-(3-methyl-4-(trifluoromethyl)phenyl)-2-azaspiro[3.3]heptan-2-yl)methanone;
(6-(6-(tert-Butyl)pyridin-2-yl)-2-azaspiro[3.3]heptan-2-yl)((1s,3s)-3-hydroxy-3-methylcyclobutyl)methanone;
(rac)-((1s,3s)-3-Hydroxy-3-methylcyclobutyl)(6-(4-isopropylphenyl)-2-azaspiro[3.4]octan-2-yl)methanone;
((1s,3s)-3-Hydroxy-3-methylcyclobutyl)(2-(3-isopropylphenyl)-6-azaspiro[3.4]octan-6-yl)methanone;

((1s,3s)-3-Hydroxy-3-methylcyclobutyl)(7-phenyl-2-azaspiro[3.5]nonan-2-yl)methanone;
(rac)-(2-(3-(tert-Butyl)phenyl)-8-azaspiro[4.5]decan-8-yl)((1s,3s)-3-hydroxy-3-methylcyclobutyl)methanone;
(rac)-(2-(4-(tert-Butyl)phenyl)-8-azaspiro[4.5]decan-8-yl)((1s,3s)-3-hydroxy-3-methylcyclobutyl)methanone;
(rac)-((1s,3s)-3-Hydroxy-3-methylcyclobutyl)(6-(3-(trifluoromethoxy)phenyl)-2-azaspiro[3.4]octan-2-yl)methanone;
((1s,3*S)-3-Hydroxy-3-methylcyclobutyl)((*R)-6-(3-(trifluoromethoxy)phenyl)-2-azaspiro[3.4]octan-2-yl)methanone;
((1s,3*R)-3-Hydroxy-3-methylcyclobutyl)((*S)-6-(3-(trifluoromethoxy)phenyl)-2-azaspiro[3.4]octan-2-yl)methanone;
(rac)-(6-(3-(tert-Butyl)phenyl)-2-azaspiro[3.4]octan-2-yl)((1s,3s)-3-hydroxy-3-methylcyclobutyl)methanone;
((*R)-6-(3-(tert-Butyl)phenyl)-2-azaspiro[3.4]octan-2-yl)((1s,3*S)-3-hydroxy-3-methylcyclobutyl)methanone;
((*S)-6-(3-(tert-Butyl)phenyl)-2-azaspiro[3.4]octan-2-yl)((1s,3*R)-3-hydroxy-3-methylcyclobutyl)methanone;
(rac)-((1s,3s)-3-Hydroxy-3-methylcyclobutyl)(6-(3-isopropylphenyl)-2-azaspiro[3.4]octan-2-yl)methanone;
((1s,3*S)-3-Hydroxy-3-methylcyclobutyl)((*R)-6-(3-isopropylphenyl)-2-azaspiro[3.4]octan-2-yl)methanone;
((1s,3*R)-3-Hydroxy-3-methylcyclobutyl)((*S)-6-(3-isopropylphenyl)-2-azaspiro[3.4]octan-2-yl)methanone;
(rac)-(6-(4-Cyclopropylphenyl)-2-azaspiro[3.4]octan-2-yl)((1s,3s)-3-hydroxy-3-methylcyclobutyl)methanone;
((*R)-6-(4-Cyclopropylphenyl)-2-azaspiro[3.4]octan-2-yl)((1s,3*S)-3-hydroxy-3-methylcyclobutyl)methanone;
((*S)-6-(4-Cyclopropylphenyl)-2-azaspiro[3.4]octan-2-yl)((1s,3*R)-3-hydroxy-3-methylcyclobutyl)methanone;
(rac)-((1s,3s)-3-Hydroxy-3-methylcyclobutyl)(6-(4-(trifluoromethoxy)phenyl)-2-azaspiro[3.4]octan-2-yl)methanone;
((1s,3*S)-3-Hydroxy-3-methylcyclobutyl)((*R)-6-(4-(trifluoromethoxy)phenyl)-2-azaspiro[3.4]octan-2-yl)methanone;
((1s,3*R)-3-Hydroxy-3-methylcyclobutyl)((*S)-6-(4-(trifluoromethoxy)phenyl)-2-azaspiro[3.4]octan-2-yl)methanone;
(rac)-((1s,3s)-3-Hydroxy-3-methylcyclobutyl)(6-(4-(trifluoromethyl)phenyl)-2-azaspiro[3.4]octan-2-yl)methanone;
((1s,3*S)-3-Hydroxy-3-methylcyclobutyl)((*R)-6-(4-(trifluoromethyl)phenyl)-2-azaspiro[3.4]octan-2-yl)methanone;
((1s,3*R)-3-Hydroxy-3-methylcyclobutyl)((*S)-6-(4-(trifluoromethyl)phenyl)-2-azaspiro[3.4]octan-2-yl)methanone;
(rac)-(6-(3-Cyclopropylphenyl)-2-azaspiro[3.4]octan-2-yl)((1s,3s)-3-hydroxy-3-methylcyclobutyl)methanone;
((*R)-6-(3-Cyclopropylphenyl)-2-azaspiro[3.4]octan-2-yl)((1s,3*S)-3-hydroxy-3-methylcyclobutyl)methanone;
((*S)-6-(3-Cyclopropylphenyl)-2-azaspiro[3.4]octan-2-yl)((1s,3*R)-3-hydroxy-3-methylcyclobutyl)methanone;
(rac)-((1s,3s)-3-Hydroxy-3-methylcyclobutyl)(6-(3-(trifluoromethyl)phenyl)-2-azaspiro[3.4]octan-2-yl)methanone;
((1s,3*S)-3-Hydroxy-3-methylcyclobutyl)((*R)-6-(3-(trifluoromethyl)phenyl)-2-azaspiro[3.4]octan-2-yl)methanone;
((1s,3*R)-3-Hydroxy-3-methylcyclobutyl)((*S)-6-(3-(trifluoromethyl)phenyl)-2-azaspiro[3.4]octan-2-yl)methanone;
(rac)-(6-(3-Cyclobutylphenyl)-2-azaspiro[3.4]octan-2-yl)((1s,3s)-3-hydroxy-3-methylcyclobutyl)methanone;
(rac)-((1s,3s)-3-Hydroxy-3-methylcyclobutyl)(6-(4-methyl-3-(trifluoromethyl)phenyl)-2-azaspiro[3.4]octan-2-yl)methanone;
(rac)-((1s,3s)-3-Hydroxy-3-methylcyclobutyl)(6-(3-methyl-4-(trifluoromethoxy)phenyl)-2-azaspiro[3.4]octan-2-yl)methanone;
(rac)-((1s,3s)-3-Hydroxy-3-methylcyclobutyl)(6-(3-methyl-4-(trifluoromethyl)phenyl)-2-azaspiro[3.4]octan-2-yl)methanone;
(rac)-(6-(4-Chloro-3-methylphenyl)-2-azaspiro[3.4]octan-2-yl)((1s,3s)-3-hydroxy-3-methylcyclobutyl)methanone;
((*R)-6-(4-Chloro-3-methylphenyl)-2-azaspiro[3.4]octan-2-yl)((1s,3*S)-3-hydroxy-3-methylcyclobutyl)methanone;
((*S)-6-(4-Chloro-3-methylphenyl)-2-azaspiro[3.4]octan-2-yl)((1s,3*R)-3-hydroxy-3-methylcyclobutyl)methanone;
(rac)-(6-(3-Chloro-4-methylphenyl)-2-azaspiro[3.4]octan-2-yl)((1s,3s)-3-hydroxy-3-methylcyclobutyl)methanone;
(rac)-(6-(4-(Difluoromethoxy)-3-methylphenyl)-2-azaspiro[3.4]octan-2-yl)((1s,3s)-3-hydroxy-3-methylcyclobutyl)methanone;
((*R)-6-(4-(Difluoromethoxy)-3-methylphenyl)-2-azaspiro[3.4]octan-2-yl)((1s,3*S)-3-hydroxy-3-methylcyclobutyl)methanone;
((*S)-6-(4-(Difluoromethoxy)-3-methylphenyl)-2-azaspiro[3.4]octan-2-yl)((1s,3*R)-3-hydroxy-3-methylcyclobutyl)methanone;
(rac)-(6-(4-Cyclopropyl-2-methylphenyl)-2-azaspiro[3.4]octan-2-yl)((1s,3s)-3-hydroxy-3-methylcyclobutyl)methanone;
(rac)-((1s,3s)-3-Hydroxy-3-methylcyclobutyl)(6-(4-methoxy-3-methylphenyl)-2-azaspiro[3.4]octan-2-yl)methanone;
(rac)-((1s,3s)-3-Hydroxy-3-methylcyclobutyl)(6-(3-methyl-5-(trifluoromethyl)phenyl)-2-azaspiro[3.4]octan-2-yl)methanone;
(rac)-((1s,3s)-3-Hydroxy-3-methylcyclobutyl)(6-(2-methyl-5-(trifluoromethyl)phenyl)-2-azaspiro[3.4]octan-2-yl)methanone;
(rac)-(6-(2-Fluoro-3-methoxyphenyl)-2-azaspiro[3.4]octan-2-yl)((1s,3s)-3-hydroxy-3-methylcyclobutyl)methanone;
(rac)-((1s,3s)-3-Hydroxy-3-methylcyclobutyl)(6-(3-methoxy-5-methylphenyl)-2-azaspiro[3.4]octan-2-yl)methanone;
(rac)-(6-(5-Cyclopropyl-2-fluorophenyl)-2-azaspiro[3.4]octan-2-yl)((1s,3s)-3-hydroxy-3-methylcyclobutyl)methanone;
(rac)-(6-(3-(Difluoromethoxy)-4-methylphenyl)-2-azaspiro[3.4]octan-2-yl)((1s,3s)-3-hydroxy-3-methylcyclobutyl)methanone;
(rac)-(6-(4-(Difluoromethoxy)-2-methylphenyl)-2-azaspiro[3.4]octan-2-yl)((1s,3s)-3-hydroxy-3-methylcyclobutyl)methanone;
(rac)-(6-(3-(Difluoromethoxy)-5-methylphenyl)-2-azaspiro[3.4]octan-2-yl)((1s,3s)-3-hydroxy-3-methylcyclobutyl)methanone;

(rac)-(6-(5-(Difluoromethoxy)-2-methylphenyl)-2-azaspiro[3.4]octan-2-yl)((1s,3s)-3-hydroxy-3-methylcyclobutyl)methanone;
(rac)-(6-(3-Chloro-5-methoxyphenyl)-2-azaspiro[3.4]octan-2-yl)((1s,3s)-3-hydroxy-3-methylcyclobutyl)methanone;
(rac)-(6-(4-Chloro-3-methoxyphenyl)-2-azaspiro[3.4]octan-2-yl)((1s,3s)-3-hydroxy-3-methylcyclobutyl)methanone;
(rac)-((1s,3s)-3-Hydroxy-3-(trifluoromethyl)cyclobutyl)(6-(3-isopropylphenyl)-2-azaspiro[3.4]octan-2-yl)methanone;
(2-(3-(tert-Butyl)phenyl)-6-azaspiro[3.4]octan-6-yl)((1s,3s)-3-hydroxy-3-methylcyclobutyl)methanone;
(rac)-(6-(3-(1,1-Difluoroethyl)phenyl)-2-azaspiro[3.4]octan-2-yl)((1s,3s)-3-hydroxy-3-methylcyclobutyl)methanone;
(rac)-(6-(3-Ethylphenyl)-2-azaspiro[3.4]octan-2-yl)((1s,3s)-3-hydroxy-3-methylcyclobutyl)methanone;
(rac)-(6-(3-(Difluoromethyl)-4-methylphenyl)-2-azaspiro[3.4]octan-2-yl)((1s,3s)-3-hydroxy-3-methylcyclobutyl)methanone;
(rac)-((1s,3s)-3-Hydroxy-3-methylcyclobutyl)(6-(3-methyl-5-(trifluoromethoxy)phenyl)-2-azaspiro[3.4]octan-2-yl)methanone;
(rac)-(6-(3-(Difluoromethyl)-5-methylphenyl)-2-azaspiro[3.4]octan-2-yl)((1s,3s)-3-hydroxy-3-methylcyclobutyl)methanone;
(rac)-((1s,3s)-3-Hydroxy-3-methylcyclobutyl)(6-(2-methoxy-3-methylphenyl)-2-azaspiro[3.4]octan-2-yl)methanone;
(rac)-(6-(4-Ethylphenyl)-2-azaspiro[3.4]octan-2-yl)((1s,3s)-3-hydroxy-3-methylcyclobutyl)methanone;
(rac)-((1s,3s)-3-Hydroxy-3-methylcyclobutyl)(6-(pyrazolo[1,5-a]pyridin-5-yl)-2-azaspiro[3.4]octan-2-yl)methanone;
(rac)-(6-(2,6-Dimethylphenyl)-2-azaspiro[3.4]octan-2-yl)((1s,3s)-3-hydroxy-3-methylcyclobutyl)methanone;
(rac)-((1s,3s)-3-Hydroxy-3-methylcyclobutyl)(6-(1-methyl-1H-pyrazol-4-yl)-2-azaspiro[3.4]octan-2-yl)methanone;
(rac)-((1s,3s)-3-Hydroxy-3-methylcyclobutyl)(6-(1-methyl-3-(trifluoromethyl)-1H-pyrazol-4-yl)-2-azaspiro[3.4]octan-2-yl)methanone;
(rac)-((1s,3s)-3-Hydroxy-3-methylcyclobutyl)(6-(1-methyl-3-(trifluoromethyl)-1H-pyrazol-5-yl)-2-azaspiro[3.4]octan-2-yl)methanone;
(rac)-((1s,3s)-3-Hydroxy-3-methylcyclobutyl)(6-(1-methyl-1H-indazol-5-yl)-2-azaspiro[3.4]octan-2-yl)methanone;
(7-(4-Fluoro-3-methoxyphenyl)-2-azaspiro[3.5]nonan-2-yl)((1s,3s)-3-hydroxy-3-methylcyclobutyl)methanone;
(7-(3-Fluoro-5-methoxyphenyl)-2-azaspiro[3.5]nonan-2-yl)((1s,3s)-3-hydroxy-3-methylcyclobutyl)methanone;
((1s,3s)-3-Hydroxy-3-methylcyclobutyl)(7-(4-methoxy-3-methylphenyl)-2-azaspiro[3.5]nonan-2-yl)methanone;
((1s,3s)-3-Hydroxy-3-methylcyclobutyl)(7-(3-methoxy-2-methylphenyl)-2-azaspiro[3.5]nonan-2-yl)methanone;
(rac)-((1s,3s)-3-Hydroxy-3-methylcyclobutyl)(6-(4-methyl-3-(trifluoromethoxy)phenyl)-2-azaspiro[3.4]octan-2-yl)methanone;
(rac)-(6-(3-Cyclopropyl-4-fluorophenyl)-2-azaspiro[3.4]octan-2-yl)((1s,3s)-3-hydroxy-3-methylcyclobutyl)methanone;
(rac)-((1s,3s)-3-Hydroxy-3-methylcyclobutyl)(6-(1-methyl-5-(trifluoromethyl)-1H-pyrazol-4-yl)-2-azaspiro[3.4]octan-2-yl)methanone;
(rac)-((1s,3s)-3-Hydroxy-3-methylcyclobutyl)(6-(6-(trifluoromethyl)pyridin-2-yl)-2-azaspiro[3.4]octan-2-yl)methanone;
(rac)-((1s,3s)-3-Hydroxy-3-methylcyclobutyl)(6-(1-methyl-1H-benzo[d]imidazol-5-yl)-2-azaspiro[3.4]octan-2-yl)methanone;
(rac)-((1s,3s)-3-Hydroxy-3-methylcyclobutyl)(6-(1-methyl-1H-benzo[d]imidazol-2-yl)-2-azaspiro[3.4]octan-2-yl)methanone;
((1s,3s)-3-Hydroxy-3-methylcyclobutyl)(7-(3-methoxy-4-(trifluoromethyl)phenyl)-2-azaspiro[3.5]nonan-2-yl)methanone;
((1s,3s)-3-Hydroxy-3-methylcyclobutyl)(7-(4-methoxy-3-(trifluoromethyl)phenyl)-2-azaspiro[3.5]nonan-2-yl)methanone;
(7-(3-(Dimethylamino)-4-(trifluoromethyl)phenyl)-2-azaspiro[3.5]nonan-2-yl)((1s,3s)-3-hydroxy-3-methylcyclobutyl)methanone;
(7-(6-(tert-Butyl)pyridin-2-yl)-2-azaspiro[3.5]nonan-2-yl)((1s,3s)-3-hydroxy-3-methylcyclobutyl)methanone;
((1s,3s)-3-Hydroxy-3-methylcyclobutyl)(7-(6-methoxypyridin-2-yl)-2-azaspiro[3.5]nonan-2-yl)methanone;
(7-(3-(tert-Butyl)-4-methoxyphenyl)-2-azaspiro[3.5]nonan-2-yl)((1s,3s)-3-hydroxy-3-methylcyclobutyl)methanone;
((1s,3s)-3-Hydroxy-3-methylcyclobutyl)(7-(3-methoxy-5-(trifluoromethyl)phenyl)-2-azaspiro[3.5]nonan-2-yl)methanone;
(7-(3-Ethoxy-5-(trifluoromethyl)phenyl)-2-azaspiro[3.5]nonan-2-yl)((1s,3s)-3-hydroxy-3-methylcyclobutyl)methanone;
(7-(3-Ethyl-5-methylphenyl)-2-azaspiro[3.5]nonan-2-yl)((1s,3s)-3-hydroxy-3-methylcyclobutyl)methanone;
((1s,3s)-3-Hydroxy-3-methylcyclobutyl)(7-(1-methyl-1H-indazol-5-yl)-2-azaspiro[3.5]nonan-2-yl)methanone;
(7-(3-(Dimethylamino)-5-(trifluoromethyl)phenyl)-2-azaspiro[3.5]nonan-2-yl)((1s,3s)-3-hydroxy-3-methylcyclobutyl)methanone;
((1s,3s)-3-Hydroxy-3-methylcyclobutyl)(7-(quinolin-2-yl)-2-azaspiro[3.5]nonan-2-yl)methanone;
(rac)-(6-(3-Fluoro-5-isopropylphenyl)-2-azaspiro[3.4]octan-2-yl)((1s,3s)-3-hydroxy-3-methylcyclobutyl)methanone;
(rac)-(6-(3-(tert-Butyl)phenyl)-2-azaspiro[3.4]octan-2-yl)((1r,3s)-3-ethyl-3-hydroxycyclobutyl)methanone;
(7-(2,3-Dihydro-1H-inden-5-yl)-2-azaspiro[3.5]nonan-2-yl)((1s,3s)-3-hydroxy-3-methylcyclobutyl)methanone;
((1s,3s)-3-Hydroxy-3-methylcyclobutyl)(7-(3-methoxy-5-methylphenyl)-2-azaspiro[3.5]nonan-2-yl)methanone;
((1s,3s)-3-Hydroxy-3-methylcyclobutyl)(7-(3-methoxy-4-methylphenyl)-2-azaspiro[3.5]nonan-2-yl)methanone;
((1s,3s)-3-Hydroxy-3-methylcyclobutyl)(7-(4-isopropylphenyl)-2-azaspiro[3.5]nonan-2-yl)methanone;
((1s,3s)-3-Hydroxy-3-methylcyclobutyl)(7-(3-methoxyphenyl)-2-azaspiro[3.5]nonan-2-yl)methanone;
(7-(3-Ethoxyphenyl)-2-azaspiro[3.5]nonan-2-yl)((1s,3s)-3-hydroxy-3-methylcyclobutyl)methanone;
((1s,3s)-3-Hydroxy-3-methylcyclobutyl)(7-(3-isopropylphenyl)-2-azaspiro[3.5]nonan-2-yl)methanone;
(7-(3,4-Dimethylphenyl)-2-azaspiro[3.5]nonan-2-yl)((1s,3s)-3-hydroxy-3-methylcyclobutyl)methanone;

(7-(3-(tert-Butyl)phenyl)-2-azaspiro[3.5]nonan-2-yl)((1s,3s)-3-hydroxy-3-methylcyclobutyl)methanone;
((1s,3s)-3-Hydroxy-3-methylcyclobutyl)(7-(p-tolyl)-2-azaspiro[3.5]nonan-2-yl)methanone;
((1s,3s)-3-Hydroxy-3-methylcyclobutyl)(7-(m-tolyl)-2-azaspiro[3.5]nonan-2-yl)methanone;
((1s,3s)-3-Hydroxy-3-methylcyclobutyl)(7-(o-tolyl)-2-azaspiro[3.5]nonan-2-yl)methanone;
(7-(2-(tert-Butyl)pyridin-4-yl)-2-azaspiro[3.5]nonan-2-yl)((1s,3s)-3-hydroxy-3-methylcyclobutyl)methanone;
(7-(4-Cyclopropyl-3-methoxyphenyl)-2-azaspiro[3.5]nonan-2-yl)((1s,3s)-3-hydroxy-3-methylcyclobutyl)methanone;
(7-(3-Cyclopropyl-5-methoxyphenyl)-2-azaspiro[3.5]nonan-2-yl)((1s,3s)-3-hydroxy-3-methylcyclobutyl)methanone;
(7-(3-Cyclopropyl-4-methoxyphenyl)-2-azaspiro[3.5]nonan-2-yl)((1s,3s)-3-hydroxy-3-methylcyclobutyl)methanone;
(7-(3-Cyclopropyl-5-methylphenyl)-2-azaspiro[3.5]nonan-2-yl)((1s,3s)-3-hydroxy-3-methylcyclobutyl)methanone;
(7-(3-Ethyl-2-methoxyphenyl)-2-azaspiro[3.5]nonan-2-yl)((1s,3s)-3-hydroxy-3-methylcyclobutyl)methanone;
(7-(3-Ethyl-5-methoxyphenyl)-2-azaspiro[3.5]nonan-2-yl)((1s,3s)-3-hydroxy-3-methylcyclobutyl)methanone;
(7-(3-Ethyl-5-(trifluoromethyl)phenyl)-2-azaspiro[3.5]nonan-2-yl)((1s,3s)-3-hydroxy-3-methylcyclobutyl)methanone;
(7-(3,5-Dimethylphenyl)-2-azaspiro[3.5]nonan-2-yl)((1s,3s)-3-hydroxy-3-methylcyclobutyl)methanone;
(7-(3-Ethyl-5-(trifluoromethoxy)phenyl)-2-azaspiro[3.5]nonan-2-yl)((1s,3s)-3-hydroxy-3-methylcyclobutyl)methanone;
(7-(3-Chloro-5-(trifluoromethoxy)phenyl)-2-azaspiro[3.5]nonan-2-yl)((1s,3s)-3-hydroxy-3-methylcyclobutyl)methanone;
(7-(4-Ethoxy-3-(trifluoromethyl)phenyl)-2-azaspiro[3.5]nonan-2-yl)((1s,3s)-3-hydroxy-3-methylcyclobutyl)methanone;
((1s,3s)-3-Hydroxy-3-methylcyclobutyl)(7-hydroxy-7-(3-isopropylphenyl)-2-azaspiro[3.5]nonan-2-yl)methanone;
(rac)-((1s,3s)-3-Hydroxy-3-methylcyclobutyl)(2-(4-(trifluoromethyl)phenyl)-8-azaspiro[4.5]decan-8-yl)methanone;
(2-(3-(tert-Butyl)phenyl)-7-azaspiro[3.5]nonan-7-yl)((1s,3s)-3-hydroxy-3-methylcyclobutyl)methanone;
(6-(3-Cyclopropyl-2-methylbenzyl)-2-azaspiro[3.3]heptan-2-yl)((1s,3s)-3-hydroxy-3-methylcyclobutyl)methanone;
((1s,3s)-3-Hydroxy-3-methylcyclobutyl)(6-(2-methyl-3-(trifluoromethyl)benzyl)-2-azaspiro[3.3]heptan-2-yl)methanone;
(6-(2,3-Dimethylbenzyl)-2-azaspiro[3.3]heptan-2-yl)((1s,3s)-3-hydroxy-3-methylcyclobutyl)methanone;
(6-(3-(Difluoromethoxy)benzyl)-2-azaspiro[3.3]heptan-2-yl)((1s,3s)-3-hydroxy-3-methylcyclobutyl)methanone;
(6-(2-Ethylbenzyl)-2-azaspiro[3.3]heptan-2-yl)((1s,3s)-3-hydroxy-3-methylcyclobutyl)methanone;
((1s,3s)-3-Hydroxy-3-methylcyclobutyl)(7-(3-methylbenzyl)-2-azaspiro[3.5]nonan-2-yl)methanone;
(7-(3-(Difluoromethoxy)benzyl)-2-azaspiro[3.5]nonan-2-yl)((1s,3s)-3-hydroxy-3-methylcyclobutyl)methanone;
(7-(4-(Difluoromethoxy)benzyl)-2-azaspiro[3.5]nonan-2-yl)((1s,3s)-3-hydroxy-3-methylcyclobutyl)methanone;
(7-(4-(Difluoromethyl)benzyl)-2-azaspiro[3.5]nonan-2-yl)((1s,3s)-3-hydroxy-3-methylcyclobutyl)methanone;
(7-(3-(Difluoromethyl)benzyl)-2-azaspiro[3.5]nonan-2-yl)((1s,3s)-3-hydroxy-3-methylcyclobutyl)methanone;
(6-Benzyl-2-azaspiro[3.3]heptan-2-yl)((1s,3s)-3-hydroxy-3-methylcyclobutyl)methanone;
((1s,3s)-3-Hydroxy-3-methylcyclobutyl)(6-(3-methylbenzyl)-2-azaspiro[3.3]heptan-2-yl)methanone;
((1s,3s)-3-Hydroxy-3-methylcyclobutyl)(6-(4-methylbenzyl)-2-azaspiro[3.3]heptan-2-yl)methanone;
((1s,3s)-3-Hydroxy-3-methylcyclobutyl)(6-(pyridin-2-ylmethyl)-2-azaspiro[3.3]heptan-2-yl)methanone;
((1s,3s)-3-Hydroxy-3-methylcyclobutyl)(6-(pyridin-3-ylmethyl)-2-azaspiro[3.3]heptan-2-yl)methanone;
(rac)-((1s,3s)-3-Hydroxy-3-methylcyclobutyl)(6-(4-methylbenzyl)-2-azaspiro[3.4]octan-2-yl)methanone;
(rac)-((1s,3s)-3-Hydroxy-3-methylcyclobutyl)(6-(4-isopropylbenzyl)-2-azaspiro[3.4]octan-2-yl)methanone;
(rac)-((1s,3s)-3-Hydroxy-3-methylcyclobutyl)(6-(4-(trifluoromethyl)benzyl)-2-azaspiro[3.4]octan-2-yl)methanone;
(2-Benzyl-7-azaspiro[3.5]nonan-7-yl)((1s,3s)-3-hydroxy-3-methylcyclobutyl)methanone;
((1s,3s)-3-Hydroxy-3-methylcyclobutyl)(2-(4-methylbenzyl)-7-azaspiro[3.5]nonan-7-yl)methanone;
(rac)-((1s,3s)-3-Hydroxy-3-methylcyclobutyl)(6-(3-methylbenzyl)-2-azaspiro[3.4]octan-2-yl)methanone;
(rac)-((1s,3s)-3-Hydroxy-3-methylcyclobutyl)(6-(2-methylbenzyl)-2-azaspiro[3.4]octan-2-yl)methanone;
(rac)-((1s,3s)-3-Hydroxy-3-methylcyclobutyl)(6-(3-(trifluoromethyl)benzyl)-2-azaspiro[3.4]octan-2-yl)methanone;
((1s,3*S)-3-Hydroxy-3-methylcyclobutyl)((*R)-6-(3-(trifluoromethyl)benzyl)-2-azaspiro[3.4]octan-2-yl)methanone;
((1s,3*R)-3-Hydroxy-3-methylcyclobutyl)((*S)-6-(3-(trifluoromethyl)benzyl)-2-azaspiro[3.4]octan-2-yl)methanone;
(rac)-((1s,3s)-3-Hydroxy-3-methylcyclobutyl)(6-(4-(trifluoromethoxy)benzyl)-2-azaspiro[3.4]octan-2-yl)methanone;
(rac)-((1s,3s)-3-Hydroxy-3-methylcyclobutyl)(6-(3-(trifluoromethoxy)benzyl)-2-azaspiro[3.4]octan-2-yl)methanone;
(rac)-((1s,3s)-3-Hydroxy-3-methylcyclobutyl)(6-(3-isopropylbenzyl)-2-azaspiro[3.4]octan-2-yl)methanone;
(rac)-(6-(4-(Difluoromethyl)benzyl)-2-azaspiro[3.4]octan-2-yl)((1s,3s)-3-hydroxy-3-methylcyclobutyl)methanone;
(rac)-(6-(4-(Difluoromethoxy)benzyl)-2-azaspiro[3.4]octan-2-yl)((1s,3s)-3-hydroxy-3-methylcyclobutyl)methanone;
((1s,3s)-3-Hydroxy-3-methylcyclobutyl)(6-(2-methylbenzyl)-2-azaspiro[3.3]heptan-2-yl)methanone;
((1s,3s)-3-Hydroxy-3-methylcyclobutyl)(6-(4-isopropylbenzyl)-2-azaspiro[3.3]heptan-2-yl)methanone;
((1s,3s)-3-Hydroxy-3-methylcyclobutyl)(6-(3-isopropylbenzyl)-2-azaspiro[3.3]heptan-2-yl)methanone;
((1s,3s)-3-Hydroxy-3-methylcyclobutyl)(6-(2-isopropylbenzyl)-2-azaspiro[3.3]heptan-2-yl)methanone;
(6-(3,4-Dimethylbenzyl)-2-azaspiro[3.3]heptan-2-yl)((1s,3s)-3-hydroxy-3-methylcyclobutyl)methanone;
((1s,3s)-3-Hydroxy-3-methylcyclobutyl)(6-(4-methyl-3-(trifluoromethyl)benzyl)-2-azaspiro[3.3]heptan-2-yl)methanone;

(6-((4-(tert-Butyl)pyridin-2-yl)methyl)-2-azaspiro[3.3]heptan-2-yl)((1s,3s)-3-hydroxy-3-methylcyclobutyl)methanone;

((1s,3s)-3-Hydroxy-3-methylcyclobutyl)(6-((6-methoxypyridin-2-yl)methyl)-2-azaspiro[3.3]heptan-2-yl)methanone;

((1s,3s)-3-Hydroxy-3-methylcyclobutyl)(6-(4-methoxybenzyl)-2-azaspiro[3.3]heptan-2-yl)methanone;

((1s,3s)-3-Hydroxy-3-methylcyclobutyl)(6-(3-(trifluoromethyl)benzyl)-2-azaspiro[3.3]heptan-2-yl)methanone;

((1s,3s)-3-Hydroxy-3-methylcyclobutyl)(6-(3-(trifluoromethoxy)benzyl)-2-azaspiro[3.3]heptan-2-yl)methanone;

((1s,3s)-3-Hydroxy-3-methylcyclobutyl)(6-(4-(trifluoromethyl)benzyl)-2-azaspiro[3.3]heptan-2-yl)methanone;

((1s,3s)-3-Hydroxy-3-methylcyclobutyl)(6-(2-(trifluoromethoxy)benzyl)-2-azaspiro[3.3]heptan-2-yl)methanone;

((1s,3s)-3-Hydroxy-3-methylcyclobutyl)(6-(3-methoxybenzyl)-2-azaspiro[3.3]heptan-2-yl)methanone;

((1s,3s)-3-Hydroxy-3-methylcyclobutyl)(6-(quinolin-2-ylmethyl)-2-azaspiro[3.3]heptan-2-yl)methanone;

((1s,3s)-3-Hydroxy-3-methylcyclobutyl)(6-(2-(trifluoromethyl)benzyl)-2-azaspiro[3.3]heptan-2-yl)methanone;

(rac)-(6-(4-Cyclopropylbenzyl)-2-azaspiro[3.4]octan-2-yl)((1s,3s)-3-hydroxy-3-methylcyclobutyl)methanone;

(rac)-(6-(3-Cyclopropylbenzyl)-2-azaspiro[3.4]octan-2-yl)((1s,3s)-3-hydroxy-3-methylcyclobutyl)methanone;

(6-(4-Cyclopropyl-3-methylbenzyl)-2-azaspiro[3.3]heptan-2-yl)((1s,3s)-3-hydroxy-3-methylcyclobutyl)methanone;

(rac)-((1s,3s)-3-Hydroxy-3-methylcyclobutyl)(6-(2-methyl-4-(trifluoromethyl)benzyl)-2-azaspiro[3.4]octan-2-yl)methanone;

(rac)-((1s,3s)-3-Hydroxy-3-methylcyclobutyl)(6-(3-methyl-4-(trifluoromethyl)benzyl)-2-azaspiro[3.4]octan-2-yl)methanone;

(rac)-((1s,3s)-3-Hydroxy-3-methylcyclobutyl)(6-(4-methoxybenzyl)-2-azaspiro[3.4]octan-2-yl)methanone;

((1s,3s)-3-Hydroxy-3-methylcyclobutyl)(6-(pyridin-4-ylmethyl)-2-azaspiro[3.3]heptan-2-yl)methanone;

(6-(2-Cyclopropyl-3-methylbenzyl)-2-azaspiro[3.3]heptan-2-yl)((1s,3s)-3-hydroxy-3-methylcyclobutyl)methanone;

(6-(2-(tert-Butyl)benzyl)-2-azaspiro[3.3]heptan-2-yl)((1s,3s)-3-hydroxy-3-methylcyclobutyl)methanone;

((1s,3s)-3-Hydroxy-3-methylcyclobutyl)(6-(3-methyl-2-(trifluoromethyl)benzyl)-2-azaspiro[3.3]heptan-2-yl)methanone;

((1s,3s)-3-Hydroxy-3-methylcyclobutyl)(6-(2-isopropyl-3-(trifluoromethyl)benzyl)-2-azaspiro[3.3]heptan-2-yl)methanone;

((1s,3s)-3-Hydroxy-3-methylcyclobutyl)(6-(5-methyl-2-(trifluoromethyl)benzyl)-2-azaspiro[3.3]heptan-2-yl)methanone;

((1s,3s)-3-Hydroxy-3-methylcyclobutyl)(6-(3-methyl-4-(trifluoromethyl)benzyl)-2-azaspiro[3.3]heptan-2-yl)methanone;

((1s,3s)-3-Hydroxy-3-methylcyclobutyl)(6-(4-methyl-2-(trifluoromethyl)benzyl)-2-azaspiro[3.3]heptan-2-yl)methanone;

((1s,3s)-3-Hydroxy-3-methylcyclobutyl)(6-((1-methyl-3-(trifluoromethyl)-1H-pyrazol-5-yl)methyl)-2-azaspiro[3.3]heptan-2-yl)methanone;

((1s,3s)-3-Hydroxy-3-methylcyclobutyl)(6-((1-methyl-1H-indazol-6-yl)methyl)-2-azaspiro[3.3]heptan-2-yl)methanone;

((1s,3s)-3-Hydroxy-3-methylcyclobutyl)(6-(2-methoxybenzyl)-2-azaspiro[3.3]heptan-2-yl)methanone;

((1s,3s)-3-Hydroxy-3-methylcyclobutyl)(6-(4-methoxy-2-(trifluoromethyl)benzyl)-2-azaspiro[3.3]heptan-2-yl)methanone;

(6-(3-Cyclopropylbenzyl)-2-azaspiro[3.3]heptan-2-yl)((1s,3s)-3-hydroxy-3-methylcyclobutyl)methanone;

(6-(4-Cyclopropylbenzyl)-2-azaspiro[3.3]heptan-2-yl)((1s,3s)-3-hydroxy-3-methylcyclobutyl)methanone;

((1s,3s)-3-Hydroxy-3-methylcyclobutyl)(6-(4-(trifluoromethoxy)benzyl)-2-azaspiro[3.3]heptan-2-yl)methanone;

(6-(4-(Difluoromethoxy)benzyl)-2-azaspiro[3.3]heptan-2-yl)((1s,3s)-3-hydroxy-3-methylcyclobutyl)methanone;

(6-(3-Ethylbenzyl)-2-azaspiro[3.3]heptan-2-yl)((1s,3s)-3-hydroxy-3-methylcyclobutyl)methanone;

((1s,3s)-3-Hydroxy-3-methylcyclobutyl)(6-((6-(trifluoromethyl)pyridin-2-yl)methyl)-2-azaspiro[3.3]heptan-2-yl)methanone;

((1s,3s)-3-Hydroxy-3-methylcyclobutyl)(6-((1-methyl-1H-pyrrolo[2,3-b]pyridin-6-yl)methyl)-2-azaspiro[3.3]heptan-2-yl)methanone;

((1s,3s)-3-Hydroxy-3-methylcyclobutyl)(6-((1-methyl-3-(trifluoromethyl)-1H-pyrazol-4-yl)methyl)-2-azaspiro[3.3]heptan-2-yl)methanone;

((1s,3s)-3-Hydroxy-3-methylcyclobutyl)(6-(2-methyl-6-(trifluoromethyl)benzyl)-2-azaspiro[3.3]heptan-2-yl)methanone;

(6-(3-Fluoro-2-methylbenzyl)-2-azaspiro[3.3]heptan-2-yl)((1s,3s)-3-hydroxy-3-methylcyclobutyl)methanone;

(6-(4-Fluoro-3-methylbenzyl)-2-azaspiro[3.3]heptan-2-yl)((1s,3s)-3-hydroxy-3-methylcyclobutyl)methanone;

(6-(3-Fluoro-4-methylbenzyl)-2-azaspiro[3.3]heptan-2-yl)((1s,3s)-3-hydroxy-3-methylcyclobutyl)methanone;

(6-(2-Fluoro-4-methylbenzyl)-2-azaspiro[3.3]heptan-2-yl)((1s,3s)-3-hydroxy-3-methylcyclobutyl)methanone;

(6-(3-(Difluoromethyl)benzyl)-2-azaspiro[3.3]heptan-2-yl)((1s,3s)-3-hydroxy-3-methylcyclobutyl)methanone;

(6-(4-(Difluoromethyl)benzyl)-2-azaspiro[3.3]heptan-2-yl)((1s,3s)-3-hydroxy-3-methylcyclobutyl)methanone;

(6-((6-(tert-Butyl)pyridin-2-yl)methyl)-2-azaspiro[3.3]heptan-2-yl)((1s,3s)-3-hydroxy-3-methylcyclobutyl)methanone;

(rac)-(6-Benzyl-2-azaspiro[3.4]octan-2-yl)((1s,3s)-3-hydroxy-3-methylcyclobutyl)methanone;

(7-Benzyl-2-azaspiro[3.5]nonan-2-yl)((1s,3s)-3-hydroxy-3-methylcyclobutyl)methanone;

((1s,3s)-3-Hydroxy-3-methylcyclobutyl)(7-(2-methylbenzyl)-2-azaspiro[3.5]nonan-2-yl)methanone;

((1s,3s)-3-Hydroxy-3-methylcyclobutyl)(6-((3-(trifluoromethyl)-1H-pyrazol-1-yl)methyl)-2-azaspiro[3.3]heptan-2-yl)methanone;

((1s,3s)-3-Hydroxy-3-methylcyclobutyl)(6-(o-tolyloxy)-2-azaspiro[3.3]heptan-2-yl)methanone;

((1s,3s)-3-Hydroxy-3-methylcyclobutyl)(7-(3-methyl-4-(trifluoromethyl)phenoxy)-2-azaspiro[3.5]nonan-2-yl)methanone;

(rac)-(6-(4-(tert-Butyl)phenoxy)-2-azaspiro[3.4]octan-2-yl)((1s,3s)-3-hydroxy-3-methylcyclobutyl)methanone;

((1s,3s)-3-Hydroxy-3-methylcyclobutyl)(7-(3-isopropylphenoxy)-2-azaspiro[3.5]nonan-2-yl)methanone;
((1s,3s)-3-Hydroxy-3-methylcyclobutyl)(7-(4-isopropylphenoxy)-2-azaspiro[3.5]nonan-2-yl)methanone;
(rac)-(6-(3-(tert-Butyl)phenoxy)-2-azaspiro[3.4]octan-2-yl)((1s,3s)-3-hydroxy-3-methylcyclobutyl)methanone;
(6-(3-(tert-Butyl)phenoxy)-2-azaspiro[3.3]heptan-2-yl)((1s,3s)-3-hydroxy-3-methylcyclobutyl)methanone;
((1s,3s)-3-Hydroxy-3-methylcyclobutyl)(2-(p-tolyloxy)-7-azaspiro[3.5]nonan-7-yl)methanone;
(6-(4-(tert-Butyl)phenoxy)-2-azaspiro[3.3]heptan-2-yl)((1s,3s)-3-hydroxy-3-methylcyclobutyl)methanone;
((1s,3s)-3-Hydroxy-3-methylcyclobutyl)(6-(3-methyl-4-(trifluoromethyl)phenoxy)-2-azaspiro[3.3]heptan-2-yl)methanone;
((1s,3s)-3-Hydroxy-3-methylcyclobutyl)(6-(4-methyl-3-(trifluoromethyl)phenoxy)-2-azaspiro[3.3]heptan-2-yl)methanone;
((1s,3s)-3-Hydroxy-3-methylcyclobutyl)(6-(2-methyl-4-(trifluoromethyl)phenoxy)-2-azaspiro[3.3]heptan-2-yl)methanone;
((1s,3s)-3-Hydroxy-3-methylcyclobutyl)(6-(3-methyl-2-(trifluoromethyl)phenoxy)-2-azaspiro[3.3]heptan-2-yl)methanone;
((1s,3s)-3-Hydroxy-3-methylcyclobutyl)(6-(3-isopropyl-2-(trifluoromethyl)phenoxy)-2-azaspiro[3.3]heptan-2-yl)methanone;
((1s,3s)-3-Hydroxy-3-methylcyclobutyl)(6-(2-methyl-3-(trifluoromethyl)phenoxy)-2-azaspiro[3.3]heptan-2-yl)methanone;
(rac)-((1s,3s)-3-Hydroxy-3-methylcyclobutyl)(6-(2-methyl-3-(trifluoromethyl)phenoxy)-2-azaspiro[3.4]octan-2-yl)methanone;
(rac)-((1s,3s)-3-Hydroxy-3-methylcyclobutyl)(6-(3-methyl-4-(trifluoromethyl)phenoxy)-2-azaspiro[3.4]octan-2-yl)methanone;
(rac)-((1s,3s)-3-Hydroxy-3-methylcyclobutyl)(6-(2-methyl-4-(trifluoromethyl)phenoxy)-2-azaspiro[3.4]octan-2-yl)methanone;
(rac)-((1s,3s)-3-Hydroxy-3-methylcyclobutyl)(6-(4-methyl-3-(trifluoromethyl)phenoxy)-2-azaspiro[3.4]octan-2-yl)methanone;
(7-(3-(tert-Butyl)phenoxy)-2-azaspiro[3.5]nonan-2-yl)((1s,3s)-3-hydroxy-3-methylcyclobutyl)methanone;
((1s,3s)-3-Hydroxy-3-methylcyclobutyl)(7-(2-methyl-4-(trifluoromethyl)phenoxy)-2-azaspiro[3.5]nonan-2-yl)methanone;
((1s,3s)-3-Hydroxy-3-methylcyclobutyl)(7-(4-methyl-3-(trifluoromethyl)phenoxy)-2-azaspiro[3.5]nonan-2-yl)methanone;
(7-(4-(tert-Butyl)phenoxy)-2-azaspiro[3.5]nonan-2-yl)((1s,3s)-3-hydroxy-3-methylcyclobutyl)methanone;
(7-(4-Cyclopropylphenoxy)-2-azaspiro[3.5]nonan-2-yl)((1s,3s)-3-hydroxy-3-methylcyclobutyl)methanone;
((1s,3s)-3-Hydroxy-3-methylcyclobutyl)(7-(4-(trifluoromethoxy)phenoxy)-2-azaspiro[3.5]nonan-2-yl)methanone;
((1s,3s)-3-Hydroxy-3-methylcyclobutyl)(7-(3-(trifluoromethoxy)phenoxy)-2-azaspiro[3.5]nonan-2-yl)methanone;
(7-(3-Cyclopropylphenoxy)-2-azaspiro[3.5]nonan-2-yl)((1s,3s)-3-hydroxy-3-methylcyclobutyl)methanone;
((1s,3s)-3-Hydroxy-3-methylcyclobutyl)(7-(2-isopropylphenoxy)-2-azaspiro[3.5]nonan-2-yl)methanone;
((1s,3s)-3-Hydroxy-3-methylcyclobutyl)(7-(3-isopropylphenyl)-7-methoxy-2-azaspiro[3.5]nonan-2-yl)methanone;
((1s,3s)-3-Hydroxy-3-methylcyclobutyl)(6-(3-methyl-5-(trifluoromethyl)phenyl)-2-azaspiro[3.3]heptan-2-yl)methanone;
((1s,3s)-3-Hydroxy-3-methylcyclobutyl)(6-(1-methyl-1H-pyrrolo[2,3-b]pyridin-5-yl)-2-azaspiro[3.3]heptan-2-yl)methanone;
((1s,3s)-3-Hydroxy-3-methylcyclobutyl)(6-(1-methyl-1H-pyrrolo[2,3-b]pyridin-6-yl)-2-azaspiro[3.3]heptan-2-yl)methanone;
(6-Benzyl-6-methoxy-2-azaspiro[3.3]heptan-2-yl)((1s,3s)-3-hydroxy-3-methylcyclobutyl)methanone;
(6-(2-Cyclopropylbenzyl)-2-azaspiro[3.3]heptan-2-yl)((1s,3s)-3-hydroxy-3-methylcyclobutyl)methanone;
(6-(4-Cyclopropoxybenzyl)-2-azaspiro[3.3]heptan-2-yl)((1s,3s)-3-hydroxy-3-methylcyclobutyl)methanone;
(6-(4-Fluoro-2-methylbenzyl)-2-azaspiro[3.3]heptan-2-yl)((1s,3s)-3-hydroxy-3-methylcyclobutyl)methanone;
(6-(2-(Difluoromethyl)-4-methoxybenzyl)-2-azaspiro[3.3]heptan-2-yl)((1s,3s)-3-hydroxy-3-methylcyclobutyl)methanone;
(6-(4-(Difluoromethyl)-2-methoxybenzyl)-2-azaspiro[3.3]heptan-2-yl)((1s,3s)-3-hydroxy-3-methylcyclobutyl)methanone;
((1s,3s)-3-Hydroxy-3-methylcyclobutyl)(6-(3-methoxy-4-(trifluoromethyl)benzyl)-2-azaspiro[3.3]heptan-2-yl)methanone;
((1s,3s)-3-Hydroxy-3-methylcyclobutyl)(6-((5-methyl-6-(trifluoromethyl)pyridin-2-yl)methyl)-2-azaspiro[3.3]heptan-2-yl)methanone;
((1s,3s)-3-Hydroxy-3-methylcyclobutyl)(6-((6-methyl-5-(trifluoromethyl)pyridin-2-yl)methyl)-2-azaspiro[3.3]heptan-2-yl)methanone;
((1s,3s)-3-Hydroxy-3-methylcyclobutyl)(6-((6-isopropoxy-5-methylpyridin-2-yl)methyl)-2-azaspiro[3.3]heptan-2-yl)methanone;
(6-((5-(Difluoromethoxy)-6-methylpyridin-2-yl)methyl)-2-azaspiro[3.3]heptan-2-yl)((1s,3s)-3-hydroxy-3-methylcyclobutyl)methanone;
((1s,3s)-3-Hydroxy-3-methylcyclobutyl)(6-((6-methoxy-5-(trifluoromethyl)pyridin-2-yl)methyl)-2-azaspiro[3.3]heptan-2-yl)methanone;
((1s,3s)-3-Hydroxy-3-methylcyclobutyl)(6-((6-isopropoxy-5-(trifluoromethyl)pyridin-2-yl)methyl)-2-azaspiro[3.3]heptan-2-yl)methanone;
((1s,3s)-3-Hydroxy-3-methylcyclobutyl)(6-((1-methyl-5-(trifluoromethyl)-1H-pyrazol-3-yl)methyl)-2-azaspiro[3.3]heptan-2-yl)methanone;
((1s,3s)-3-Hydroxy-3-methylcyclobutyl)(6-(pyrazolo[1,5-a]pyridin-6-ylmethyl)-2-azaspiro[3.3]heptan-2-yl)methanone;
((1s,3s)-3-Hydroxy-3-methylcyclobutyl)(6-(pyrazolo[1,5-a]pyridin-7-ylmethyl)-2-azaspiro[3.3]heptan-2-yl)methanone;
(6-((1H-Pyrrolo[2,3-b]pyridin-1-yl)methyl)-2-azaspiro[3.3]heptan-2-yl)((1s,3s)-3-hydroxy-3-methylcyclobutyl)methanone;
((1s,3s)-3-Hydroxy-3-methylcyclobutyl)(6-((2-methyl-1H-pyrrolo[2,3-b]pyridin-1-yl)methyl)-2-azaspiro[3.3]heptan-2-yl)methanone;
((1s,3s)-3-Hydroxy-3-methylcyclobutyl)(6-((6-methyl-1H-pyrrolo[2,3-b]pyridin-1-yl)methyl)-2-azaspiro[3.3]heptan-2-yl)methanone;
((1s,3s)-3-Hydroxy-3-methylcyclobutyl)(6-((1-isopropyl-1H-pyrrolo[2,3-b]pyridin-6-yl)methyl)-2-azaspiro[3.3]heptan-2-yl)methanone;

((1s,3s)-3-Hydroxy-3-methylcyclobutyl)(6-((6-isopropyl-1H-pyrrolo[2,3-b]pyridin-1-yl)methyl)-2-azaspiro[3.3]heptan-2-yl)methanone;

(6-((1,3-Dimethyl-1H-pyrrolo[2,3-b]pyridin-6-yl)methyl)-2-azaspiro[3.3]heptan-2-yl)((1s,3s)-3-hydroxy-3-methylcyclobutyl)methanone;

(6-((1,2-Dimethyl-1H-pyrrolo[2,3-b]pyridin-6-yl)methyl)-2-azaspiro[3.3]heptan-2-yl)((1s,3s)-3-hydroxy-3-methylcyclobutyl)methanone;

(6-((3-Fluoro-1-methyl-1H-pyrrolo[2,3-b]pyridin-6-yl)methyl)-2-azaspiro[3.3]heptan-2-yl)((1s,3s)-3-hydroxy-3-methylcyclobutyl)methanone;

((1s,3s)-3-Hydroxy-3-methylcyclobutyl)(6-((2-(trifluoromethyl)-1H-pyrrolo[2,3-b]pyridin-1-yl)methyl)-2-azaspiro[3.3]heptan-2-yl)methanone;

((1s,3s)-3-Hydroxy-3-methylcyclobutyl)(6-((6-(trifluoromethyl)-1H-pyrrolo[2,3-b]pyridin-1-yl)methyl)-2-azaspiro[3.3]heptan-2-yl)methanone;

((1s,3s)-3-Hydroxy-3-methylcyclobutyl)(6-((1-methyl-3-(trifluoromethyl)-1H-pyrrolo[2,3-b]pyridin-6-yl)methyl)-2-azaspiro[3.3]heptan-2-yl)methanone;

((1s,3s)-3-Hydroxy-3-methylcyclobutyl)(6-((1-(2,2,2-trifluoroethyl)-1H-pyrrolo[2,3-b]pyridin-6-yl)methyl)-2-azaspiro[3.3]heptan-2-yl)methanone;

((1s,3s)-3-Hydroxy-3-methylcyclobutyl)(6-((1-methyl-1H-pyrrolo[3,2-c]pyridin-6-yl)methyl)-2-azaspiro[3.3]heptan-2-yl)methanone;

((1s,3s)-3-Hydroxy-3-methylcyclobutyl)(6-((1-methyl-1H-indazol-7-yl)methyl)-2-azaspiro[3.3]heptan-2-yl)methanone;

(6-((1,4-Dimethyl-1H-indazol-6-yl)methyl)-2-azaspiro[3.3]heptan-2-yl)((1s,3s)-3-hydroxy-3-methylcyclobutyl)methanone;

(6-((1,5-Dimethyl-1H-indazol-6-yl)methyl)-2-azaspiro[3.3]heptan-2-yl)((1s,3s)-3-hydroxy-3-methylcyclobutyl)methanone;

(6-((1,3-Dimethyl-1H-indazol-6-yl)methyl)-2-azaspiro[3.3]heptan-2-yl)((1s,3s)-3-hydroxy-3-methylcyclobutyl)methanone;

(6-((4-Fluoro-1-methyl-1H-indazol-6-yl)methyl)-2-azaspiro[3.3]heptan-2-yl)((1s,3s)-3-hydroxy-3-methylcyclobutyl)methanone;

(6-((5-Fluoro-1-methyl-1H-indazol-6-yl)methyl)-2-azaspiro[3.3]heptan-2-yl)((1s,3s)-3-hydroxy-3-methylcyclobutyl)methanone;

(6-((7-Fluoro-1-methyl-1H-indazol-6-yl)methyl)-2-azaspiro[3.3]heptan-2-yl)((1s,3s)-3-hydroxy-3-methylcyclobutyl)methanone;

((1s,3s)-3-Hydroxy-3-methylcyclobutyl)(6-((1-isopropyl-1H-indazol-6-yl)methyl)-2-azaspiro[3.3]heptan-2-yl)methanone;

((1s,3s)-3-Hydroxy-3-methylcyclobutyl)(6-((1-(2,2,2-trifluoroethyl)-1H-indazol-6-yl)methyl)-2-azaspiro[3.3]heptan-2-yl)methanone;

((1s,3s)-3-Hydroxy-3-methylcyclobutyl)(6-((2-isopropyl-2H-indazol-6-yl)methyl)-2-azaspiro[3.3]heptan-2-yl)methanone;

((1s,3s)-3-Hydroxy-3-methylcyclobutyl)(6-((6-methyl-5-(trifluoromethyl)pyridin-2-yl)oxy)-2-azaspiro[3.3]heptan-2-yl)methanone;

((1s,3*S)-3-Hydroxy-3-methylcyclobutyl)(6-((*R)-1-phenylethyl)-2-azaspiro[3.3]heptan-2-yl)methanone;

((1s,3*R)-3-Hydroxy-3-methylcyclobutyl)(6-((*S)-1-phenylethyl)-2-azaspiro[3.3]heptan-2-yl)methanone;

((1s,3*S)-3-Hydroxy-3-methylcyclobutyl)(6-((*R)-1-(6-methyl-5-(trifluoromethyl)pyridin-2-yl)ethyl)-2-azaspiro[3.3]heptan-2-yl)methanone;

((1s,3*R)-3-Hydroxy-3-methylcyclobutyl)(6-((*S)-1-(6-methyl-5-(trifluoromethyl)pyridin-2-yl)ethyl)-2-azaspiro[3.3]heptan-2-yl)methanone;

((1s,3*S)-3-Hydroxy-3-methylcyclobutyl)(6-((*R)-1-(1-methyl-1H-indazol-6-yl)ethyl)-2-azaspiro[3.3]heptan-2-yl)methanone;

((1s,3*R)-3-Hydroxy-3-methylcyclobutyl)(6-((*S)-1-(1-methyl-1H-indazol-6-yl)ethyl)-2-azaspiro[3.3]heptan-2-yl)methanone;

(rac)-((1s,3s)-3-Hydroxy-3-methylcyclobutyl)(6-(1-(pyrazolo[1,5-a]pyridin-7-yl)ethyl)-2-azaspiro[3.3]heptan-2-yl)methanone;

(6-(Difluoro(1-methyl-1H-pyrrolo[2,3-b]pyridin-6-yl)methyl)-2-azaspiro[3.3]heptan-2-yl)((1s,3s)-3-hydroxy-3-methylcyclobutyl)methanone;

((1s,3*S)-3-Hydroxy-3-methylcyclobutyl)((6*R)-6-(3-isopropylphenyl)-1-methyl-2-azaspiro[3.4]octan-2-yl)methanone;

(rac)-((1s,3s)-3-(Difluoromethyl)-3-hydroxycyclobutyl)(6-(3-isopropylphenyl)-2-azaspiro[3.4]octan-2-yl)methanone;

(rac)-(6-(4-(1,1-Difluoroethyl)phenyl)-2-azaspiro[3.4]octan-2-yl)((1s,3s)-3-hydroxy-3-methylcyclobutyl)methanone;

((*S)-6-(2,4-Dimethylphenyl)-2-azaspiro[3.4]octan-2-yl)((1s,3*R)-3-hydroxy-3-methylcyclobutyl)methanone;

((*R)-6-(2,4-Dimethylphenyl)-2-azaspiro[3.4]octan-2-yl)((1s,3*S)-3-hydroxy-3-methylcyclobutyl)methanone;

(rac)-(6-(2,3-Dihydrobenzofuran-6-yl)-2-azaspiro[3.4]octan-2-yl)((1s,3s)-3-hydroxy-3-methylcyclobutyl)methanone;

(rac)-((1s,3s)-3-Hydroxy-3-methylcyclobutyl)(6-(pyrazolo[1,5-a]pyridin-4-yl)-2-azaspiro[3.4]octan-2-yl)methanone;

(rac)-((1s,3s)-3-Hydroxy-3-methylcyclobutyl)(6-(pyrazolo[1,5-a]pyridin-2-yl)-2-azaspiro[3.4]octan-2-yl)methanone;

(rac)-((1s,3s)-3-Hydroxy-3-methylcyclobutyl)(6-(1-methyl-1H-indazol-4-yl)-2-azaspiro[3.4]octan-2-yl)methanone;

(rac)-((1s,3s)-3-Hydroxy-3-methylcyclobutyl)(6-(imidazo[1,2-a]pyridin-8-yl)-2-azaspiro[3.4]octan-2-yl)methanone;

(rac)-((1s,3s)-3-Hydroxy-3-methylcyclobutyl)(6-(imidazo[1,2-a]pyridin-7-yl)-2-azaspiro[3.4]octan-2-yl)methanone;

(rac)-((1s,3s)-3-Hydroxy-3-methylcyclobutyl)(6-(imidazo[1,5-a]pyridin-1-yl)-2-azaspiro[3.4]octan-2-yl)methanone;

(rac)-((1s,3s)-3-Hydroxy-3-methylcyclobutyl)(6-(5,6,7,8-tetrahydroimidazo[1,5-a]pyridin-1-yl)-2-azaspiro[3.4]octan-2-yl)methanone;

(rac)-((1s,3s)-3-Hydroxy-3-methylcyclobutyl)(6-(4,5,6,7-tetrahydropyrazolo[1,5-a]pyridin-2-yl)-2-azaspiro[3.4]octan-2-yl)methanone;

(rac)-(6-(3-Cyclopropyl-4-methylphenoxy)-2-azaspiro[3.4]octan-2-yl)((1s,3s)-3-hydroxy-3-methylcyclobutyl)methanone;

(rac)-(6-(3-Cyclopropyl-2-methylphenoxy)-2-azaspiro[3.4]octan-2-yl)((1s,3s)-3-hydroxy-3-methylcyclobutyl)methanone;

(rac)-(6-(3-Cyclopropyl-2-fluorophenoxy)-2-azaspiro[3.4]octan-2-yl)((1s,3s)-3-hydroxy-3-methylcyclobutyl)methanone;

(rac)-(6-(3-Cyclopropyl-4-fluorophenoxy)-2-azaspiro[3.4]octan-2-yl)((1s,3s)-3-hydroxy-3-methylcyclobutyl)methanone;

(rac)-((1s,3s)-3-Hydroxy-3-methylcyclobutyl)(6-((5-methyl-6-(trifluoromethyl)pyridin-2-yl)oxy)-2-azaspiro[3.4]octan-2-yl)methanone;

((1s,3*S)-3-Hydroxy-3-methylcyclobutyl)((*R)-6-((*R)-1-phenylethyl)-2-azaspiro[3.4]octan-2-yl)methanone;

((1s,3*R)-3-Hydroxy-3-methylcyclobutyl)((*S)-6-((*R)-1-phenylethyl)-2-azaspiro[3.4]octan-2-yl)methanone;

((1s,3*R)-3-Hydroxy-3-methylcyclobutyl)((*S)-6-((*S)-1-phenylethyl)-2-azaspiro[3.4]octan-2-yl)methanone;

(7-Fluoro-7-phenyl-2-azaspiro[3.5]nonan-2-yl)((1s,3s)-3-hydroxy-3-methylcyclobutyl)methanone;

(7-Fluoro-7-(1-methyl-1H-pyrrolo[2,3-b]pyridin-6-yl)-2-azaspiro[3.5]nonan-2-yl)((1s,3s)-3-hydroxy-3-methylcyclobutyl)methanone;

((1s,3s)-3-Hydroxy-3-methylcyclobutyl)(7-methoxy-7-phenyl-2-azaspiro[3.5]nonan-2-yl)methanone;

((1s,3s)-3-Hydroxy-3-methylcyclobutyl)(7-methoxy-7-(o-tolyl)-2-azaspiro[3.5]nonan-2-yl)methanone;

(7-(3,5-Dimethylphenyl)-7-methoxy-2-azaspiro[3.5]nonan-2-yl)((1s,3s)-3-hydroxy-3-methylcyclobutyl)methanone;

((1s,3s)-3-Hydroxy-3-methylcyclobutyl)(7-(3-(1-methyl-1H-imidazol-4-yl)phenyl)-2-azaspiro[3.5]nonan-2-yl)methanone;

(7-(4-(1H-Pyrazol-1-yl)phenyl)-2-azaspiro[3.5]nonan-2-yl)((1s,3s)-3-hydroxy-3-methylcyclobutyl)methanone;

(7-(3-(1H-Pyrazol-1-yl)phenyl)-2-azaspiro[3.5]nonan-2-yl)((1s,3s)-3-hydroxy-3-methylcyclobutyl)methanone;

((1*S,4r,7*S)-7-(3,5-Dimethylphenyl)-1-methyl-2-azaspiro[3.5]nonan-2-yl)((1s,3*R)-3-hydroxy-3-methylcyclobutyl)methanone;

((1*R,4r,7*R)-7-(3,5-Dimethylphenyl)-1-methyl-2-azaspiro[3.5]nonan-2-yl)((1s,3*S)-3-hydroxy-3-methylcyclobutyl)methanone;

((1*S,4s,7*R)-7-(3,5-Dimethylphenyl)-1-methyl-2-azaspiro[3.5]nonan-2-yl)((1s,3*R)-3-hydroxy-3-methylcyclobutyl)methanone;

((1*R,4s,7*S)-7-(3,5-Dimethylphenyl)-1-methyl-2-azaspiro[3.5]nonan-2-yl)((1s,3*S)-3-hydroxy-3-methylcyclobutyl)methanone;

(7-(3-Fluoro-5-methylphenyl)-2-azaspiro[3.5]nonan-2-yl)((1s,3s)-3-hydroxy-3-methylcyclobutyl)methanone;

(7-(4-Fluoro-3-methylphenyl)-2-azaspiro[3.5]nonan-2-yl)((1s,3s)-3-hydroxy-3-methylcyclobutyl)methanone;

(7-(2-Fluoro-5-methylphenyl)-2-azaspiro[3.5]nonan-2-yl)((1s,3s)-3-hydroxy-3-methylcyclobutyl)methanone;

(7-(2-Fluoro-3-methylphenyl)-2-azaspiro[3.5]nonan-2-yl)((1s,3s)-3-hydroxy-3-methylcyclobutyl)methanone;

(7-(2-Fluoro-6-methylphenyl)-2-azaspiro[3.5]nonan-2-yl)((1s,3s)-3-hydroxy-3-methylcyclobutyl)methanone;

(7-(4-Fluoro-2-methylphenyl)-2-azaspiro[3.5]nonan-2-yl)((1s,3s)-3-hydroxy-3-methylcyclobutyl)methanone;

(7-(5-Fluoro-2-methylphenyl)-2-azaspiro[3.5]nonan-2-yl)((1s,3s)-3-hydroxy-3-methylcyclobutyl)methanone;

(7-(3-Fluoro-2-methylphenyl)-2-azaspiro[3.5]nonan-2-yl)((1s,3s)-3-hydroxy-3-methylcyclobutyl)methanone;

(7-(3-Ethoxy-4-methylphenyl)-2-azaspiro[3.5]nonan-2-yl)((1s,3s)-3-hydroxy-3-methylcyclobutyl)methanone;

(7-(3-Ethoxy-2-methylphenyl)-2-azaspiro[3.5]nonan-2-yl)((1s,3s)-3-hydroxy-3-methylcyclobutyl)methanone;

((1s,3s)-3-Hydroxy-3-methylcyclobutyl)(7-(3-isopropoxy-2-methylphenyl)-2-azaspiro[3.5]nonan-2-yl)methanone;

((1s,3s)-3-Hydroxy-3-methylcyclobutyl)(7-(5-methoxy-2-methylphenyl)-2-azaspiro[3.5]nonan-2-yl)methanone;

(7-(3-Cyclopropoxy-2-methylphenyl)-2-azaspiro[3.5]nonan-2-yl)((1s,3s)-3-hydroxy-3-methylcyclobutyl)methanone;

(7-(3-Ethoxy-5-fluorophenyl)-2-azaspiro[3.5]nonan-2-yl)((1s,3s)-3-hydroxy-3-methylcyclobutyl)methanone;

(7-(2-Fluoro-3-methoxyphenyl)-2-azaspiro[3.5]nonan-2-yl)((1s,3s)-3-hydroxy-3-methylcyclobutyl)methanone;

(7-(2-Chloro-3-methoxyphenyl)-2-azaspiro[3.5]nonan-2-yl)((1s,3s)-3-hydroxy-3-methylcyclobutyl)methanone;

(7-(2,3-Difluoro-5-methoxyphenyl)-2-azaspiro[3.5]nonan-2-yl)((1s,3s)-3-hydroxy-3-methylcyclobutyl)methanone;

(7-(2,5-Difluoro-3-methoxyphenyl)-2-azaspiro[3.5]nonan-2-yl)((1s,3s)-3-hydroxy-3-methylcyclobutyl)methanone;

(7-(3-Fluoro-5-methoxy-4-methylphenyl)-2-azaspiro[3.5]nonan-2-yl)((1s,3s)-3-hydroxy-3-methylcyclobutyl)methanone;

((1s,3s)-3-Hydroxy-3-methylcyclobutyl)(7-(6-(1-(trifluoromethyl)cyclopropyl)pyridin-2-yl)-2-azaspiro[3.5]nonan-2-yl)methanone;

((1s,3s)-3-Hydroxy-3-methylcyclobutyl)(7-(6-(1-methylcyclopropyl)pyridin-2-yl)-2-azaspiro[3.5]nonan-2-yl)methanone;

((1s,3s)-3-Hydroxy-3-methylcyclobutyl)(7-(6-isopropyl-5-methylpyridin-2-yl)-2-azaspiro[3.5]nonan-2-yl)methanone;

((1s,3s)-3-Hydroxy-3-methylcyclobutyl)(7-(6-isopropoxy-4-methylpyridin-2-yl)-2-azaspiro[3.5]nonan-2-yl)methanone;

((1s,3s)-3-Hydroxy-3-methylcyclobutyl)(7-(4-methoxy-6-methylpyridin-2-yl)-2-azaspiro[3.5]nonan-2-yl)methanone;

((1s,3s)-3-Hydroxy-3-methylcyclobutyl)(7-(2-isopropoxy-3-methylpyridin-4-yl)-2-azaspiro[3.5]nonan-2-yl)methanone;

(7-(6-(tert-Butyl)pyrazin-2-yl)-2-azaspiro[3.5]nonan-2-yl)((1s,3s)-3-hydroxy-3-methylcyclobutyl)methanone;

(7-(4-(tert-Butyl)pyrimidin-2-yl)-2-azaspiro[3.5]nonan-2-yl)((1s,3s)-3-hydroxy-3-methylcyclobutyl)methanone;

(7-(1-(tert-Butyl)-1H-pyrazol-3-yl)-2-azaspiro[3.5]nonan-2-yl)((1s,3s)-3-hydroxy-3-methylcyclobutyl)methanone;

((1s,3s)-3-Hydroxy-3-methylcyclobutyl)(7-(1-phenyl-1H-pyrazol-3-yl)-2-azaspiro[3.5]nonan-2-yl)methanone;

(7-(1-(tert-Butyl)-1H-imidazol-4-yl)-2-azaspiro[3.5]nonan-2-yl)((1s,3s)-3-hydroxy-3-methylcyclobutyl)methanone;

(7-(3-(tert-Butyl)isoxazol-5-yl)-2-azaspiro[3.5]nonan-2-yl)((1s,3s)-3-hydroxy-3-methylcyclobutyl)methanone;

((1s,3s)-3-Hydroxy-3-methylcyclobutyl)(7-(1-methyl-1H-pyrrolo[2,3-b]pyridin-3-yl)-2-azaspiro[3.5]nonan-2-yl)methanone;

((1s,3s)-3-Hydroxy-3-methylcyclobutyl)(7-(1-methyl-1H-pyrrolo[2,3-b]pyridin-6-yl)-2-azaspiro[3.5]nonan-2-yl)methanone;

((1s,3s)-3-Hydroxy-3-methylcyclobutyl)(7-(1-isopropyl-1H-pyrrolo[2,3-b]pyridin-6-yl)-2-azaspiro[3.5]nonan-2-yl)methanone;

((1s,3s)-3-Hydroxy-3-methylcyclobutyl)(7-(1-methyl-3-(trifluoromethyl)-1H-pyrrolo[2,3-b]pyridin-6-yl)-2-azaspiro[3.5]nonan-2-yl)methanone;

((1s,3s)-3-Hydroxy-3-methylcyclobutyl)(7-(1-(2,2,2-trifluoroethyl)-1H-pyrrolo[2,3-b]pyridin-6-yl)-2-azaspiro[3.5]nonan-2-yl)methanone;

((1s,3s)-3-Hydroxy-3-methylcyclobutyl)(7-(pyrazolo[1,5-a]pyridin-2-yl)-2-azaspiro[3.5]nonan-2-yl)methanone;
((1s,3s)-3-Hydroxy-3-methylcyclobutyl)(7-(pyrazolo[1,5-a]pyridin-7-yl)-2-azaspiro[3.5]nonan-2-yl)methanone;
((1s,3s)-3-Hydroxy-3-methylcyclobutyl)(7-(imidazo[1,2-a]pyridin-5-yl)-2-azaspiro[3.5]nonan-2-yl)methanone;
((1s,3s)-3-Hydroxy-3-methylcyclobutyl)(7-(imidazo[1,2-a]pyridin-2-yl)-2-azaspiro[3.5]nonan-2-yl)methanone;
((1s,3s)-3-Hydroxy-3-methylcyclobutyl)(7-(imidazo[1,2-a]pyridin-3-yl)-2-azaspiro[3.5]nonan-2-yl)methanone;
((1s,3s)-3-Hydroxy-3-methylcyclobutyl)(7-(pyrrolo[1,2-b]pyridazin-3-yl)-2-azaspiro[3.5]nonan-2-yl)methanone;
((1s,3s)-3-Hydroxy-3-methylcyclobutyl)(7-(pyrazolo[1,5-a]pyridin-3-yl)-2-azaspiro[3.5]nonan-2-yl)methanone;
((1s,3s)-3-Hydroxy-3-methylcyclobutyl)(7-(4,5,6,7-tetrahydropyrazolo[1,5-a]pyridin-2-yl)-2-azaspiro[3.5]nonan-2-yl)methanone;
((1s,3s)-3-Hydroxy-3-methylcyclobutyl)(7-(5,6,7,8-tetrahydroimidazo[1,2-a]pyridin-2-yl)-2-azaspiro[3.5]nonan-2-yl)methanone;
((1s,3s)-3-Hydroxy-3-methylcyclobutyl)(7-(4-methylbenzyl)-2-azaspiro[3.5]nonan-2-yl)methanone;
(7-(2-Fluoro-3-methylbenzyl)-2-azaspiro[3.5]nonan-2-yl)((1s,3s)-3-hydroxy-3-methylcyclobutyl)methanone;
(7-(4-Fluoro-3-methylbenzyl)-2-azaspiro[3.5]nonan-2-yl)((1s,3s)-3-hydroxy-3-methylcyclobutyl)methanone;
(7-((1H-Pyrrolo[2,3-b]pyridin-1-yl)methyl)-2-azaspiro[3.5]nonan-2-yl)((1s,3s)-3-hydroxy-3-methylcyclobutyl)methanone;
((1s,3s)-3-Hydroxy-3-methylcyclobutyl)(7-((1-methyl-1H-pyrrolo[2,3-b]pyridin-6-yl)methyl)-2-azaspiro[3.5]nonan-2-yl)methanone;
((1s,3s)-3-Hydroxy-3-methylcyclobutyl)(7-((1-methyl-1H-indazol-6-yl)methyl)-2-azaspiro[3.5]nonan-2-yl)methanone;
((1s,3s)-3-Hydroxy-3-methylcyclobutyl)(7-((1-methyl-1H-pyrazolo[3,4-b]pyridin-6-yl)methyl)-2-azaspiro[3.5]nonan-2-yl)methanone;
((1s,3s)-3-Hydroxy-3-methylcyclobutyl)(7-(p-tolyloxy)-2-azaspiro[3.5]nonan-2-yl)methanone;
(7-(3,4-Dimethylphenoxy)-2-azaspiro[3.5]nonan-2-yl)((1s,3s)-3-hydroxy-3-methylcyclobutyl)methanone;
(7-(2,3-Dimethylphenoxy)-2-azaspiro[3.5]nonan-2-yl)((1s,3s)-3-hydroxy-3-methylcyclobutyl)methanone;
((1s,3s)-3-Hydroxy-3-methylcyclobutyl)(7-(3-methoxy-5-methylphenoxy)-2-azaspiro[3.5]nonan-2-yl)methanone;
((1s,3s)-3-Hydroxy-3-methylcyclobutyl)(7-(3-methoxy-4-methylphenoxy)-2-azaspiro[3.5]nonan-2-yl)methanone;
((1s,3s)-3-Hydroxy-3-methylcyclobutyl)(7-(3-methoxy-2-methylphenoxy)-2-azaspiro[3.5]nonan-2-yl)methanone;
(7-(2-Chloro-5-methylphenoxy)-2-azaspiro[3.5]nonan-2-yl)((1s,3s)-3-hydroxy-3-methylcyclobutyl)methanone;
(7-(3-Chloro-4-methylphenoxy)-2-azaspiro[3.5]nonan-2-yl)((1s,3s)-3-hydroxy-3-methylcyclobutyl)methanone;
(7-(4-Chloro-2-methylphenoxy)-2-azaspiro[3.5]nonan-2-yl)((1s,3s)-3-hydroxy-3-methylcyclobutyl)methanone;
(7-(3-Chloro-2-methylphenoxy)-2-azaspiro[3.5]nonan-2-yl)((1s,3s)-3-hydroxy-3-methylcyclobutyl)methanone;
(7-(4-Chloro-3-methoxyphenoxy)-2-azaspiro[3.5]nonan-2-yl)((1s,3s)-3-hydroxy-3-methylcyclobutyl)methanone;
(7-(4-Cyclopropyl-3-fluorophenoxy)-2-azaspiro[3.5]nonan-2-yl)((1s,3s)-3-hydroxy-3-methylcyclobutyl)methanone;
((1s,3s)-3-Hydroxy-3-methylcyclobutyl)(7-(2-methyl-5-(trifluoromethyl)phenoxy)-2-azaspiro[3.5]nonan-2-yl)methanone;
((1s,3s)-3-Hydroxy-3-methylcyclobutyl)(7-((5-(trifluoromethyl)pyridin-2-yl)oxy)-2-azaspiro[3.5]nonan-2-yl)methanone;
((1s,3s)-3-Hydroxy-3-methylcyclobutyl)(7-((4-(trifluoromethyl)pyridin-2-yl)oxy)-2-azaspiro[3.5]nonan-2-yl)methanone;
((1s,3s)-3-Hydroxy-3-methylcyclobutyl)(7-methyl-7-((5-(trifluoromethyl)pyridin-2-yl)oxy)-2-azaspiro[3.5]nonan-2-yl)methanone;
(7-Ethyl-7-((5-(trifluoromethyl)pyridin-2-yl)oxy)-2-azaspiro[3.5]nonan-2-yl)((1s,3s)-3-hydroxy-3-methylcyclobutyl)methanone;
((1s,3s)-3-Hydroxy-3-methylcyclobutyl)(7-((6-(trifluoromethyl)pyridin-2-yl)oxy)-2-azaspiro[3.5]nonan-2-yl)methanone;
(7-((5-(1,1-Difluoroethyl)pyridin-2-yl)oxy)-2-azaspiro[3.5]nonan-2-yl)((1s,3s)-3-hydroxy-3-methylcyclobutyl)methanone;
(7-((5-(Difluoromethyl)pyridin-2-yl)oxy)-2-azaspiro[3.5]nonan-2-yl)((1s,3s)-3-hydroxy-3-methylcyclobutyl)methanone;
((1s,3s)-3-Hydroxy-3-methylcyclobutyl)(7-((6-(trifluoromethyl)pyridin-3-yl)oxy)-2-azaspiro[3.5]nonan-2-yl)methanone;
(7-((6-(tert-Butyl)pyridin-2-yl)oxy)-2-azaspiro[3.5]nonan-2-yl)((1s,3s)-3-hydroxy-3-methylcyclobutyl)methanone;
(7-((5-Cyclopropylpyridin-2-yl)oxy)-2-azaspiro[3.5]nonan-2-yl)((1s,3s)-3-hydroxy-3-methylcyclobutyl)methanone;
((1s,3s)-3-Hydroxy-3-methylcyclobutyl)(7-((5-(trifluoromethoxy)pyridin-2-yl)oxy)-2-azaspiro[3.5]nonan-2-yl)methanone;
(7-((5,6-Dimethylpyridin-2-yl)oxy)-2-azaspiro[3.5]nonan-2-yl)((1s,3s)-3-hydroxy-3-methylcyclobutyl)methanone;
(7-((3,6-Dimethylpyridin-2-yl)oxy)-2-azaspiro[3.5]nonan-2-yl)((1s,3s)-3-hydroxy-3-methylcyclobutyl)methanone;
(7-((3,5-Dimethylpyridin-2-yl)oxy)-2-azaspiro[3.5]nonan-2-yl)((1s,3s)-3-hydroxy-3-methylcyclobutyl)methanone;
(7-((3-Fluoro-6-methylpyridin-2-yl)oxy)-2-azaspiro[3.5]nonan-2-yl)((1s,3s)-3-hydroxy-3-methylcyclobutyl)methanone;
(7-((3-Fluoro-5-methylpyridin-2-yl)oxy)-2-azaspiro[3.5]nonan-2-yl)((1s,3s)-3-hydroxy-3-methylcyclobutyl)methanone;
(7-((5-Ethyl-3-fluoropyridin-2-yl)oxy)-2-azaspiro[3.5]nonan-2-yl)((1s,3s)-3-hydroxy-3-methylcyclobutyl)methanone;
(7-((5-Chloro-6-methylpyridin-2-yl)oxy)-2-azaspiro[3.5]nonan-2-yl)((1s,3s)-3-hydroxy-3-methylcyclobutyl)methanone;
(7-((3-Chloro-6-methylpyridin-2-yl)oxy)-2-azaspiro[3.5]nonan-2-yl)((1s,3s)-3-hydroxy-3-methylcyclobutyl)methanone;

(7-((3-Chloro-5-methylpyridin-2-yl)oxy)-2-azaspiro[3.5]
nonan-2-yl)((1s,3s)-3-hydroxy-3-methylcyclobutyl)
methanone;
(7-((5-Chloro-3-methylpyridin-2-yl)oxy)-2-azaspiro[3.5]
nonan-2-yl)((1s,3s)-3-hydroxy-3-methylcyclobutyl)
methanone;
(7-((5-(Difluoromethyl)-6-methylpyridin-2-yl)oxy)-2-
azaspiro[3.5]nonan-2-yl)((1s,3s)-3-hydroxy-3-methyl-
cyclobutyl)methanone;
(7-((6-(Difluoromethyl)-5-ethylpyridin-2-yl)oxy)-2-
azaspiro[3.5]nonan-2-yl)((1s,3s)-3-hydroxy-3-methyl-
cyclobutyl)methanone;
(7-((5-(Difluoromethyl)-6-ethylpyridin-2-yl)oxy)-2-
azaspiro[3.5]nonan-2-yl)((1s,3s)-3-hydroxy-3-methyl-
cyclobutyl)methanone;
(7-((3-(Difluoromethyl)-6-ethylpyridin-2-yl)oxy)-2-
azaspiro[3.5]nonan-2-yl)((1s,3s)-3-hydroxy-3-methyl-
cyclobutyl)methanone;
((1s,3s)-3-Hydroxy-3-methylcyclobutyl)(7-((4-methyl-5-
(trifluoromethyl)pyridin-2-yl)oxy)-2-azaspiro[3.5]
nonan-2-yl)methanone;
((1s,3s)-3-Hydroxy-3-methylcyclobutyl)(7-((6-methyl-3-
(trifluoromethyl)pyridin-2-yl)oxy)-2-azaspiro[3.5]
nonan-2-yl)methanone;
((1s,3*R)-3-Hydroxy-3-methylcyclobutyl)((6*S,7*S)-6-
methyl-7-((6-methyl-5-(trifluoromethyl)pyridin-2-yl)
oxy)-2-azaspiro[3.5]nonan-2-yl)methanone;
((1s,3*S)-3-Hydroxy-3-methylcyclobutyl)((6*R,7*R)-6-
methyl-7-((6-methyl-5-(trifluoromethyl)pyridin-2-yl)
oxy)-2-azaspiro[3.5]nonan-2-yl)methanone;
((1s,3s)-3-Hydroxy-3-methylcyclobutyl)(7-((3-methyl-5-
(trifluoromethyl)pyridin-2-yl)oxy)-2-azaspiro[3.5]
nonan-2-yl)methanone;
((1s,3s)-3-Hydroxy-3-methylcyclobutyl)(7-((6-methyl-4-
(trifluoromethyl)pyridin-2-yl)oxy)-2-azaspiro[3.5]
nonan-2-yl)methanone;
((1s,3s)-3-Hydroxy-3-methylcyclobutyl)(7-((6-methyl-5-
(trifluoromethyl)pyridin-2-yl)oxy)-2-azaspiro[3.5]
nonan-2-yl)methanone;
((1s,3s)-3-Hydroxy-3-methylcyclobutyl)(7-((3-methyl-6-
(trifluoromethyl)pyridin-2-yl)oxy)-2-azaspiro[3.5]
nonan-2-yl)methanone;
(7-((5-Ethyl-6-(trifluoromethyl)pyridin-2-yl)oxy)-2-
azaspiro[3.5]nonan-2-yl)((1s,3s)-3-hydroxy-3-methyl-
cyclobutyl)methanone;
((1s,3s)-3-Hydroxy-3-methylcyclobutyl)(7-((5-methyl-6-
(trifluoromethyl)pyridin-2-yl)oxy)-2-azaspiro[3.5]
nonan-2-yl)methanone;
((1r,3s)-3-Ethyl-3-hydroxycyclobutyl)(7-((5-methyl-6-
(trifluoromethyl)pyridin-2-yl)oxy)-2-azaspiro[3.5]
nonan-2-yl)methanone;
((1s,3s)-3-(Difluoromethyl)-3-hydroxycyclobutyl)(7-((5-
methyl-6-(trifluoromethyl)pyridin-2-yl)oxy)-2-
azaspiro[3.5]nonan-2-yl)methanone;
(7-((5-Ethyl-6-methoxypyridin-2-yl)oxy)-2-azaspiro[3.5]
nonan-2-yl)((1s,3s)-3-hydroxy-3-methylcyclobutyl)
methanone;
(7-((5-Cyclopropyl-6-methoxypyridin-2-yl)oxy)-2-
azaspiro[3.5]nonan-2-yl)((1s,3s)-3-hydroxy-3-methyl-
cyclobutyl)methanone;
((1s,3s)-3-Hydroxy-3-methylcyclobutyl)(7-((6-methoxy-
5-methylpyridin-2-yl)oxy)-2-azaspiro[3.5]nonan-2-yl)
methanone;
(7-((3-Fluoro-5-(trifluoromethyl)pyridin-2-yl)oxy)-2-
azaspiro[3.5]nonan-2-yl)((1s,3s)-3-hydroxy-3-methyl-
cyclobutyl)methanone;

((1s,3s)-3-Hydroxy-3-methylcyclobutyl)(7-((6-methoxy-
5-(trifluoromethyl)pyridin-2-yl)oxy)-2-azaspiro[3.5]
nonan-2-yl)methanone;
(7-((6-Ethoxy-5-(trifluoromethyl)pyridin-2-yl)oxy)-2-
azaspiro[3.5]nonan-2-yl)((1s,3s)-3-hydroxy-3-methyl-
cyclobutyl)methanone;
(7-((5-Chloro-4-methoxypyridin-2-yl)oxy)-2-azaspiro
[3.5]nonan-2-yl)((1s,3s)-3-hydroxy-3-methylcy-
clobutyl)methanone;
(7-((5-Chloro-6-methoxypyridin-2-yl)oxy)-2-azaspiro
[3.5]nonan-2-yl)((1s,3s)-3-hydroxy-3-methylcy-
clobutyl)methanone;
(7-((3-Chloro-6-methoxypyridin-2-yl)oxy)-2-azaspiro
[3.5]nonan-2-yl)((1s,3s)-3-hydroxy-3-methylcy-
clobutyl)methanone;
(7-((5-Chloro-3-methoxypyridin-2-yl)oxy)-2-azaspiro
[3.5]nonan-2-yl)((1s,3s)-3-hydroxy-3-methylcy-
clobutyl)methanone;
(7-((3-Chloro-4-methoxypyridin-2-yl)oxy)-2-azaspiro
[3.5]nonan-2-yl)((1s,3s)-3-hydroxy-3-methylcy-
clobutyl)methanone;
(7-((4,6-Dimethyl-5-(trifluoromethyl)pyridin-2-yl)oxy)-
2-azaspiro[3.5]nonan-2-yl)((1s,3s)-3-hydroxy-3-meth-
ylcyclobutyl)methanone;
(7-((3,6-Dimethyl-5-(trifluoromethyl)pyridin-2-yl)oxy)-
2-azaspiro[3.5]nonan-2-yl)((1s,3s)-3-hydroxy-3-meth-
ylcyclobutyl)methanone;
((1s,3s)-3-Hydroxy-3-methylcyclobutyl)(7-((5-(trifluo-
romethyl)pyrimidin-2-yl)oxy)-2-azaspiro[3.5]nonan-
2-yl)methanone;
(7-((6,7-Dihydro-5H-cyclopenta[b]pyridin-2-yl)oxy)-2-
azaspiro[3.5]nonan-2-yl)((1s,3s)-3-hydroxy-3-methyl-
cyclobutyl)methanone;
((1s,3s)-3-Hydroxy-3-methylcyclobutyl)(7-((1-methyl-
1H-pyrrolo[2,3-b]pyridin-6-yl)oxy)-2-azaspiro[3.5]
nonan-2-yl)methanone;
(7-((1,4-Dimethyl-1H-pyrrolo[2,3-b]pyridin-6-yl)oxy)-2-
azaspiro[3.5]nonan-2-yl)((1s,3s)-3-hydroxy-3-methyl-
cyclobutyl)methanone;
(7-((1,3-Dimethyl-1H-pyrrolo[2,3-b]pyridin-6-yl)oxy)-2-
azaspiro[3.5]nonan-2-yl)((1s,3s)-3-hydroxy-3-methyl-
cyclobutyl)methanone;
(7-((1,2-Dimethyl-1H-pyrrolo[2,3-b]pyridin-6-yl)oxy)-2-
azaspiro[3.5]nonan-2-yl)((1s,3s)-3-hydroxy-3-methyl-
cyclobutyl)methanone;
(7-((1,5-Dimethyl-1H-pyrrolo[2,3-b]pyridin-6-yl)oxy)-2-
azaspiro[3.5]nonan-2-yl)((1s,3s)-3-hydroxy-3-methyl-
cyclobutyl)methanone;
(7-((3-Fluoro-1-methyl-1H-pyrrolo[2,3-b]pyridin-6-yl)
oxy)-2-azaspiro[3.5]nonan-2-yl)((1s,3s)-3-hydroxy-3-
methylcyclobutyl)methanone;
(7-((1-Ethyl-3-fluoro-1H-pyrrolo[2,3-b]pyridin-6-yl)
oxy)-2-azaspiro[3.5]nonan-2-yl)((1s,3s)-3-hydroxy-3-
methylcyclobutyl)methanone;
((1s,3s)-3-Hydroxy-3-methylcyclobutyl)(7-((1-methyl-3-
(trifluoromethyl)-1H-pyrrolo[2,3-b]pyridin-6-yl)oxy)-
2-azaspiro[3.5]nonan-2-yl)methanone;
((1s,3s)-3-Hydroxy-3-methylcyclobutyl)(7-((1-methyl-
1H-pyrazolo[3,4-b]pyridin-6-yl)oxy)-2-azaspiro[3.5]
nonan-2-yl)methanone;
((1s,3s)-3-Hydroxy-3-methylcyclobutyl)(2-(3-methoxy-
5-methylphenyl)-7-azaspiro[3.5]nonan-7-yl)metha-
none;
((1s,3s)-3-Hydroxy-3-methylcyclobutyl)(2-(2-methyl-4-
(trifluoromethyl)phenoxy)-7-azaspiro[3.5]nonan-7-yl)
methanone;

((1s,3s)-3-Hydroxy-3-methylcyclobutyl)(2-(3-methyl-4-(trifluoromethyl)phenoxy)-7-azaspiro[3.5]nonan-7-yl)methanone;

((1s,3s)-3-Hydroxy-3-methylcyclobutyl)(2-((3-methyl-5-(trifluoromethyl)pyridin-2-yl)oxy)-7-azaspiro[3.5]nonan-7-yl)methanone; and ((1s,3s)-3-Hydroxy-3-methylcyclobutyl)(2-((6-methyl-5-(trifluoromethyl)pyridin-2-yl)oxy)-7-azaspiro[3.5]nonan-7-yl)methanone;

and pharmaceutically acceptable salts, isotopes, N-oxides, solvates, and stereoisomers thereof.

19. A compound selected from:

((*S)-6-(3-Cyclopropyl-2-fluorophenyl)-2-azaspiro[3.4]octan-2-yl)((1s,3*R)-3-hydroxy-3-methylcyclobutyl)methanone;

((1s,3*R)-3-Hydroxy-3-methylcyclobutyl)((*S)-6-(4-(trifluoromethyl)phenyl)-2-azaspiro[3.4]octan-2-yl)methanone;

(7-(3,5-Dimethylphenyl)-2-azaspiro[3.5]nonan-2-yl)((1s,3s)-3-hydroxy-3-methylcyclobutyl)methanone;

((1s,3s)-3-Hydroxy-3-methylcyclobutyl)(7-(3-methoxy-5-methylphenyl)-2-azaspiro[3.5]nonan-2-yl)methanone; and ((*S)-6-(4-Chloro-3-methylphenyl)-2-azaspiro[3.4]octan-2-yl)((1s,3*R)-3-hydroxy-3-methylcyclobutyl)methanone;

and pharmaceutically acceptable salts, isotopes, N-oxides, solvates, and stereoisomers thereof.

20. A pharmaceutical composition comprising: (A) a compound of claim 1, or a pharmaceutically acceptable salt, isotope, N-oxide, solvate, or stereoisomer thereof; and (B) a pharmaceutically acceptable excipient.

21. A method of treating a disease, disorder, or condition mediated by MGL receptor activity in a subject diagnosed with or suffering therefrom, comprising administering to the subject a therapeutically effective amount of a compound of claim 1, or a pharmaceutically acceptable salt, isotope, N-oxide, solvate, or stereoisomer thereof.

22. The method of claim 21, wherein the disease, disorder, or condition is pain, a psychiatric condition, a neurological condition, cancer, or an eye condition.

23. The method of claim 21, wherein the disease, disorder or condition is depression, major depressive disorder, treatment resistant depression, anxious depression, autism spectrum disorders, Asperger syndrome, bipolar disorder, or inflammatory pain.

* * * * *